US011672826B2

(12) United States Patent
Wong

(10) Patent No.: US 11,672,826 B2

(45) Date of Patent: Jun. 13, 2023

(54) METHODS OF TREATING AGING-RELATED DISORDERS

(71) Applicant: HCW Biologics, Inc., Miramar, FL (US)

(72) Inventor: Hing Wong, Miramar, FL (US)

(73) Assignee: HCW Biologics, Inc., Miramar, FL (US)

(*) Notice: Subject to any disclaimer, the term of this patent is extended or adjusted under 35 U.S.C. 154(b) by 603 days.

(21) Appl. No.: 16/557,875

(22) Filed: Aug. 30, 2019

(65) Prior Publication Data

US 2021/0060064 A1 Mar. 4, 2021

Related U.S. Application Data

(60) Provisional application No. 62/881,039, filed on Jul. 31, 2019, provisional application No. 62/881,088, filed on Jul. 31, 2019, provisional application No. 62/817,244, filed on Mar. 12, 2019, provisional application No. 62/817,241, filed on Mar. 12, 2019, provisional application No. 62/817,230, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/725,038, filed on Aug. 30, 2018, provisional application No. 62/725,010, filed on Aug. 30, 2018, provisional application No. 62/725,043, filed on Aug. 30, 2018, provisional application No. 62/724,969, filed on Aug. 30, 2018.

(51) Int. Cl.

| | |
|---|---|
| ***C07K 14/715*** | (2006.01) |
| ***A61K 35/17*** | (2015.01) |
| ***C07K 14/705*** | (2006.01) |
| ***C07K 16/22*** | (2006.01) |
| ***C07K 16/24*** | (2006.01) |
| ***C07K 16/28*** | (2006.01) |
| ***C07K 16/46*** | (2006.01) |

(52) U.S. Cl.

CPC ........ *A61K 35/17* (2013.01); *C07K 14/70503* (2013.01); *C07K 14/7155* (2013.01); *C07K 16/22* (2013.01); *C07K 16/244* (2013.01); *C07K 16/2863* (2013.01); *C07K 16/468* (2013.01); *C07K 2317/24* (2013.01); *C07K 2317/52* (2013.01); *C07K 2317/569* (2013.01); *C07K 2317/622* (2013.01)

(58) Field of Classification Search

None

See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,741,604 | B2 | 6/2014 | Campbell et al. |
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |

(Continued)

FOREIGN PATENT DOCUMENTS

| | | | |
|---|---|---|---|
| CN | 102153653 | | 8/2011 |
| EP | 1245676 | A1 | 10/2002 |

(Continued)

OTHER PUBLICATIONS

Li et al. (Annu. Rev. Immunol. 2006. 24:99-146). (Year: 2006).*
McCarron et al. (J Clin Invest. 2014;124(10):4375-4386). (Year: 2014).*
Wallace et al. (JCI Insight. 2018;3(7): e99863). (Year: 2018).*
Voelker et al., J Am Soc Nephrol 28: 953-962, 2017). (Year: 2017).*
Abbott et al., "Genomic organization, exact localization, and tissue expression of the human CD26 (dipeptidyl peptidase IV) gene," Immunogentics, Sep. 1994, 40(5):331-338.

(Continued)

*Primary Examiner* — Zachary S Skelding

(74) *Attorney, Agent, or Firm* — Fish & Richardson P.C.

(57) ABSTRACT

Provided herein are methods of treating an aging-related disease or condition in a subject in need thereof, killing or reducing the number of senescent cells in a subject in need thereof, improving the texture and/or appearance of skin and/or hair in a subject in need thereof, and assisting in the treatment of obesity in a subject in need thereof, that include administering to the subject a therapeutically effective amount of one or more natural killer (NK) cell activating agent(s) and/or a therapeutically effective number of activated NK cells.

46 Claims, 150 Drawing Sheets

Specification includes a Sequence Listing.

(56) References Cited

U.S. PATENT DOCUMENTS

| | | |
|---|---|---|
| 9,273,136 B2 | 3/2016 | Rader et al. |
| 9,371,395 B2 | 6/2016 | Takahashi et al. |
| 9,441,034 B2 | 9/2016 | Sivakumar et al. |
| 9,505,843 B2 | 11/2016 | Kim et al. |
| 9,617,345 B2 | 4/2017 | Berne et al. |
| 9,701,758 B2 | 7/2017 | Cooper et al. |
| 2001/0044427 A1 | 11/2001 | Mazel et al. |
| 2003/0219441 A1 | 11/2003 | Thorpe et al. |
| 2005/0014224 A1 | 1/2005 | Collins et al. |
| 2006/0159655 A1 | 7/2006 | Collins et al. |
| 2007/0160579 A1 | 7/2007 | Schmitz et al. |
| 2009/0148942 A1 | 6/2009 | McDonagh et al. |
| 2012/0171197 A1 | 7/2012 | Eriksson et al. |
| 2013/0274446 A1 | 10/2013 | Kumagai et al. |
| 2014/0242077 A1 | 8/2014 | Choi |
| 2015/0218274 A1 | 8/2015 | Sabatos-Peyton et al. |
| 2015/0259429 A1 | 9/2015 | Benaroch et al. |
| 2016/0340413 A1 | 11/2016 | Duemer et al. |
| 2016/0367664 A1 | 12/2016 | Wang et al. |
| 2017/0051063 A1 | 2/2017 | Baum et al. |
| 2017/0198042 A1 | 7/2017 | Williams et al. |
| 2017/0283499 A1 | 10/2017 | Delhem et al. |
| 2018/0200366 A1 | 7/2018 | Wong |
| 2020/0071374 A1 | 3/2020 | Wong |
| 2020/0190174 A1 | 6/2020 | Wong |
| 2021/0070825 A1 | 3/2021 | Wong |
| 2021/0070826 A1 | 3/2021 | Wong |
| 2021/0100840 A1 | 4/2021 | Wong et al. |
| 2021/0137981 A1 | 5/2021 | Wong |
| 2021/0268022 A1 | 9/2021 | Wong et al. |
| 2021/0277054 A1 | 9/2021 | Wong et al. |
| 2021/0338724 A1 | 11/2021 | Wong |
| 2022/0073578 A1 | 3/2022 | Wong et al. |

FOREIGN PATENT DOCUMENTS

| | | |
|---|---|---|
| EP | 2537933 | 12/2012 |
| EP | 3029069 | 6/2016 |
| EP | 3348276 | 7/2018 |
| KR | 2016/0127688 | 11/2016 |
| KR | 101778439 | 9/2017 |
| WO | WO 1995/015341 | 6/1995 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047473 | 3/2020 |

OTHER PUBLICATIONS

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Februaiy 2004, 13(2):412-421.

Ait-Oufella el al., "Natural regulatory T cells control the development of atherosclerosis in mice," Nature Medicine, Feb. 5, 2006, 12:178-180.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

Bennett et al., "Erratum: Killing the old: cell senescence in atherosclerosis," Nature Reviews Cardiology, Jan. 12, 2017, 14(3):132.

Bennett et al., "Killing the old: cell senescence in atherosclerosis," Nature Reviews Cardiology, Dec. 12, 2016, 14(1):8-9, 2 pages.

Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.

Bhat et al., "Astrocyte Senescence as a Component of Alzheimer's Disease," PLoS One, Sep. 12, 2012, 7(9):e45069, 10 pages.

Biran et al., "Senescent cells communicate via intercellular protein transfer," Genes & Development, Apr. 8, 2015, 29(8):791-802, 13 pages.

Borea et al., "Pharmacology of Adenosine Receptors: The State of the Art," Physiological Reviews, May 31, 2918, 98(3):1591-1625.

Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.

Boyman et al., "Selective Stimulation of T Cell Subsets with Antibody-Cytokine Immune Complexes," Science, Mar. 31, 2006, 311(5769):1924-1927.

Broxmeyer et al., "Modulation of Hematopoietic Chemokine Effects In Vitro and In Vivo by DPP-4/CD26," Stem Cells and Development, Mar. 4, 2016, 25(8):575-585.

Bmnstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.

Bmnstein et al., "Umbilical cord blood-derived T regulatory cells to prevent GVHD:kinetics, toxicity profile, and clinical effect," Blood, Feb. 25, 2016, 127(8):1044-1051.

Buhling et al., "Functional role of CD26 on human B lymphocytes," Immunology Letters, Feb. 1995, 45(1-2):47-51.

Bussian et al., "Clearance of senescent glial cells prevents tandependent pathology and cognitive decline," Nature, Sep. 19, 2018, 562(7728):578-582, 21 pages.

Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.

Cao, "Self-regulation and cross-regulation of pattern-recognition receptor signaling in health and disease," Nature Reviews Immunology, Dec. 29, 2015, 16(1):35-50.

Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.

Catania et al., "The tumor-targeting immunocytokine F16-IL2 in combination with doxombicin: dose escalation in patients with

(56) References Cited

OTHER PUBLICATIONS advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chen et al., "Sterile inflammation: sensing and reacting to damage," Nature Reviews Immunology, Nov. 19, 2010, 10(12):826-837.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chong et al., "CD36 initiates the secretory phenotype during the establishment of cellular senescence," EMBO Rep., May 18, 2018, 19(6):e45274, 13 pages.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Crews et al., "Molecular mechanisms of neurodegeneration in Alzheimer's disease," Human Molecular Genetics, Apr. 22, 2010, 19(R1):R12-R20, 9 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healingthrough Secretion of PDGF-AA," Developmental Cell, Dec. 22, 2014, 31(6):722-733.
Di lanni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Eisenhut et al., "Ion Channels in Inflammation," Pflugers Archive, Jan. 29, 2011, 461(4):401-421.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.

(56) References Cited

OTHER PUBLICATIONS

Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Gutschmidt et al., "A quantitative histochemical study of dipeptidyl peptidase IV (DPP IV)," Histochemistry, 1981, 73(2):285-304.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hynes et al., "In vitro analysis of cell metabolism using a long-decay pH-sensitive lanthanide probe and extracellular acidification assay," Analytical biochemistry, Jul. 1, 2009, 390(1):21-28.
Iihoshi et al., "Aclambicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Janeway, "Approaching the Asymptote? Evolution and Revolution in Immunology," Cold Spring Harbor Symposia on Quantitative Biology, 1989, 54 Pt 1:1-13.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kim et al., "Identification of senescent cell surface targetable protein DPP4," Genes & Development, 2017, 31(15):1529-1534.
Kim et al., "SCAMP4 enhances the senescent cell secretome," Genes & Development, 2018, 32(13-14):909-914.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kritsilis et al., "Ageing, Cellular Senescence and Neurodegenerative Disease," International Journal of Molecular Sciences, Sep. 27, 2018, 19(10):2937, 37 pages.
Kumagai et al., "Monitoring of glutamate-induced excitotoxicity by mitochondrial oxygen consumption," Synapse, Jan. 2019, 73(1):e22067, 24 Pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lan et al., "RNA-associated autoantigens activate B cells by combined B cell antigen receptor/Toll-like receptor 7 engagement," The Journal of Experimental Medicine, Oct. 31, 2005, 202(9):1171-1177.
Li et al., "A Novel I L2-based Irrmunotherapeutic Protein Prevents the Development of Atherosclerosis in ApoE−/mice and LDLR−/−mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.

(56) References Cited

OTHER PUBLICATIONS

Liton et al., "Cellular senescence in the glaucomatous outflow pathway," Experimental Gerontology, Aug.-Sep. 2005, 40(8-9):745-748.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maganto-Garcia et al., "Dynamic Changes in Regulatory T Cells Are Linked to Levels of Diet-Induced Hypercholesterolemia," Circulation, Jun. 20, 2011, 124:185-195.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Mentlein et al., "Dipeptidyl-peptidase IV (CD26)-role in the inactivation of regulatory peptides," Regulatory Peptides, Nov. 30, 1999, 85(1):9-24.
Michelet et al., "Metabolic reprogramming of natural killer cells in obesity limits antitumor responses," Nature Immunology, Nov. 12, 2018, 19(12):1330-1340.
Milanovic et al., "Senescence-associated reprogramming promotes cancer sternness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Successful adoptive transfer and in vivo expansion of human haploidentical NK cells in patients with cancer," Blood, Apr. 15, 2005, 105(8):3051-3057.
Minamino et al., "A cmcial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Myung et al., "Evidence of DNA damage in Alzheimer disease: phosphorylation of histone H2AX in astrocytes," Age, Apr. 23, 2008, 30(4):209-215.
Nayyar et al., "Overcoming Resistance to Natural Killer Cell Based Immunotherapies for Solid Tumors," Frontiers in Oncology, 2019, 9: DOI:10.3389/fonc.2019.00051.
Nelson et al., "A senescent cell bystander effect: senescence-induced senescence," Aging Cell, Feb. 9, 2012, 11(2):345-349.
Nishida et al., "CD26 is a potential therapeutic target by humanized monoclonal antibody for the treatment of multiple myeloma," Blood Cancer Journal, Oct. 22, 2018, 8(11):99, 17 pages.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.

(56) References Cited

OTHER PUBLICATIONS

PCT International Preliminary Report on Patentability in International Appln. No. PCT/US2019/049158, dated Mar. 11, 2021, 8 pages.
PCT International Search Report and Written Opinion in International Appln. No. PCT/US2020/035598, dated Feb. 18, 2021, 12 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
PCT International Search Report and Written Opinion in International Appln. No. PCTUS2020/038717, dated Oct. 16, 2020, 17 pages.
Pittayapruek et al., "Role of Matrix Metalloproteinases in Photoaging and Photocarcinogenesis," International Journal of Molecular Sciences, 2016, 17(6):868, 20 pages.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovims disease in immunosuppressed patients," Journal of Clinical Oncology, May 26, 2019, 37(15 Suppl.):7008, 2 pages.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 973-979, 15 pages.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rubinstein et al., "Converting IL-15 to a superagonist by binding to soluble IL-15Rα," Proceedings of the National Academy of Sciences U.S.A., Jun. 13, 2006, 103(24):9166-9171.
Ruscetti et al., "NK cell-mediated cytotoxicity contributes to tumor control by a cytostatic dmg combination," Science, Dec. 21, 2018, 362(6421):1416-1422, 8 pages.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Betal during Renal Fibrosis in Diabetes," American Journal of Nephrology, Sep. 25, 2009, 30:481-490.
Sharma et al., "Regulatory T Cells License Macrophage Pro Resolving Functions During Atherosclerosis Regression," Circulation Research, Apr. 27, 2020, 127:335-353.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Antitumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tanaka et al., "Cloning and functional expression of the T cell activation antigen CD26," Journal of Immunology, Jul. 15, 1992, 149(2):481-486.

(56) References Cited

OTHER PUBLICATIONS

Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody as Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Walsh et al., "Inflammasomes in the CNS," Nature Reviews Neuroscience, Jan. 8, 2014, 15(2):84-97, 14 pages.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiss et al., "Formyl-Peptide Receptors in Infection, Inflammation, and Cancer," Trends in Immunology, Oct. 2018, 39(10):815-829, 15 pages.
Wiemann et al., "Hepatocyte telomere shortening and senescence are general markers of human liver cirrhosis," The FASEB Journal, Jul. 2002, 16(9):935-942.
Wiley et al., "Mitochondrial Dysfunction Induces Senescence with a Distinct Secretory Phenotype," Cell Metabolism, Feb. 9, 2016, 23(2):303-314.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex stmeture," Elife, May 5, 2015, 4:e05505, 16 pages.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Mikayama et al., "Molecular cloning and functional expression of a cDNA encoding glycosylation-inhibiting factor," Proc. Natl. Acad. Sci. USA, Nov. 1, 1993, 90(21):10056-10060.
Voet et al., Biochemistry, John Wiley & Sons, Inc., 1990, pp. 126-128 and 228-234, 12 pages.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.

(56) References Cited

OTHER PUBLICATIONS

Baker et al., "Effects of conjugated linoleic acid (CLA) on tissue composition parameters in a murine cachexia model," The FASEB Journal, Mar. 2006, 20(4), 2 pages (Abstract Only).
Berry et al., "Cancer Anorexia and Cachexia: Screening in an Ambulatory Infusion Service and Nutrition Consultation," Clin J Oncol Nurs., 2018, 22(1):63-68.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chen et al., "Circulating levels of resistin and risk of type 2 diabetes in men and women: results from two prospective cohorts," Diabetes Care, Feb. 2009, 32(2):329-334.
Cosgrove et al., "Usher protein functions in hair cells and photoreceptors," Int J Biochem Cell Biol., Jan. 2014, 46:80-89.
Helman et al., "Effects of ageing and senescence on pancreatic β-cell function," Diabetes Obes Metab., Sep. 2016, 18(Suppl. 1):58-62.
Jeon et al., "Local clearance of senescent cells attenuates the development of post-traumatic osteoarthritis and creates a pro-regenerative environment," Nat Med., Jun. 2017, 23(6):775-781.
Kim et al., "Insulin resistance, inflammation, and nonalcoholic fatty liver disease in non-obese adults without metabolic syndrome components," Hepatol Int., Jun. 2013, 7(2):586-591.
Kuyinu et al., "Animal models of osteoarthritis: classification, update, and measurement of outcomes," J Orthop SurgRes., Feb. 2, 2016, 11:19, 27 pages.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Price et al., "Comparison of collagenase-cleaved articular cartilage collagen in mice in the naturally occurring STR/ort model of osteoarthritis and in collagen-induced arthntis," Osteoarthntis Cartilage, Mar. 2002, 10(3):172-179.
Sousa-Victor et al., "Geroconversion of aged muscle stem cells under regenerative pressure," Cell Cycle, Oct. 15, 2014, 13(20):3183-3190.
Xu et al., "Celecoxib attenuates cachectic events in mice by modulating the expression of vascular endothelial growth factor," Mol Med Rep., Jan. 2015, 11(1):289-294.
PCT International Preliminary Report on Patentability in International Appln. No. PCT/US2020/038717, dated Dec. 30, 2021, 9 pages.
U.S. Appl. No. 16/556,040, filed Aug. 29, 2019, Wong.
U.S. Appl. No. 16/557,822, filed Aug. 30, 2019, Wong.
Akbari et al., "Design, expression and evaluation of a novel humanized single chain antibody against epidermal growth factor receptor (EGFR)," Protein Expression and Purification, Nov. 1, 2016, 127, 26 pages.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker et al. "Clearance of p16 Ink4a-positive senescent cells delays ageing-associated disorders," Nature, Nov. 2011, 479(7372), 13 pages.
Borgerding et al., "B-lymphoma cells escape rituximab-triggered elimination by NK cells through increased HLA class I expression," Experimental Hematology, Mar. 1, 2010, 38(3):213-21.
Bourgeois et al., "Regulation of cellular senescence via the FOXO 4□p53 axis," FEBS Letters, Jun. 2018, 592(12):2083-97.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Chalan et al., "Expression of Lectin-Like Transcript 1, the Ligand for CD161, in Rheumatoid Arthritis," PLoS ONE, 2015, 10(7):e0132436.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chichili et al., "Linkers in the structural biology of protein-protein interactions," Protein Science, Feb. 2013, 22(2):153-67.
Chinta et al., Cellular senescence is induced by the environmental neurotoxin paraquat and contributes to neuropathology linked to Parkinson's disease, Cell Reports, Jan. 23, 2018, 22(4):930-40.
Ciaglia et al., "Recognitionby natural killer cells of N6□isopentenyladenosine□treated human glioma cell lines," International Journal of Cancer, Jan. 1, 2018, 142(1):176-90.
Cichocki et al., "GSK3 inhibition drives maturation of NK cells and enhances their antitumor activity," Cancer Research, Oct. 15, 2017, 77(20):5664-75.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
Deyev et al., "Design of multivalent complexes using the barnase·barstar module," Nature Biotechnology, Dec. 2003, 21(12):1486-92.
DiGiammarino et al., "Design and generation of DVD-Ig™ molecules for dual-specific targeting," InTherapeutic Proteins, 2012, Humana Press, Totowa, NJ., 145-56.
Docagne et al., "A soluble transforming growth factor-β (TGF-β) type I receptor mimics TGF-β responses," Journal of Biological Chemistry, Dec. 7, 2001, 276(49):46243-50.
Drees et al., "Soluble production of a biologically active single-chain antibody against murine PD-L1 in *Escherichia coli*," Protein Expression and Purification, Feb. 1, 2014, 94:60-6.
Edwardraja et al., "Redesigning of anti□c□met single chain Fv antibody for the cytoplasmic folding and its structural analysis," Biotechnology and Bioengineering, Jun. 15, 2010, 106(3):367-75.
Elgueta et al., "Molecular mechanism and function of CD40/CD40L engagement in the immune system," Immunological Reviews, 2009, 229(1):152-172 doi.org/10.1111/j.1600-065X.2009.00782.x.
Farr et al., "Targeting cellular senescence prevents age-related bone loss in mice," Nature Medicine, Sep. 2017, 23(9):1072.
Garber, "Bispecific antibodies rise again," Nature Reviews Drug Discovery, 2014, 13:799-801.

(56) References Cited

OTHER PUBLICATIONS

Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunologic Research, Jul. 1, 2015, 62(3):377-85.
Gibbs et al., "Identification of the factor VIIa binding site on tissue factor by homologous loop swap and alanine scanning mutagenesis," Biochemistry, Nov. 1, 1994, 33(47):14003-10.
"Guo et al., ""Immunobiology of the IL-15-IL-15R complex as an antitumor and antiviral agent,"" 2017, Cytokine & Growth Factor Reviews, 38:10-21".
Haile et al., "Soluble CD80 Restores T Cell Activation and Overcomes Tumor Cell Programmed Death Ligand 1-Mediated Immune Suppression," J. Immunol., 2013, 191(5):2829-2836.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145 DOI:1O.1O16/S0022-1759(99)OO220-3.
Heng et al., Sophea, et al. "Multiple soluble TGF-β receptors in addition to soluble endoglin are elevated in preeclamptic serum and they synergistically inhibit TGF-β signalling." Placenta, 2017 57: 320 (1 page).
Hombach et al., "Generation of the single chain antibody fragment conserves the idiotypic profile of the anti□CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Hudak et al., "Glycocalyx engineering reveals a Siglec-based mechanism for NK cell immunoevasion," Nature Chemical Biology, Jan. 2014, 10(1), 20 pages.
Hughes et al., "Transfer of a TCR gene derived from a patient with a marked antitumor response conveys highly active T-cell effector functions," Human Gene Therapy, Apr. 1, 2005, 16(4):457-72.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Jakob et al., Structure reveals function of the dual variable domain immunoglobulin (DVD-Ig™) molecule, Mabs, May 1, 2013,Taylor & Francis, 5(3):358-63.
Jeannin et al., "Soluble CD86 Is a Costimulatory Moleculefor Human T Lymphocytes," Immunity, 2000, 13(3):303-312.
Kain et al., "The identification of the endogenous ligands of natural killer T cells reveals the presence of mammalian α-linked glycosylceramides," Immunity, Oct. 16, 2014, 41(4):543-54.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kirchhofer et al., "The tissue factor region that interacts with substrates factor IX and factor X," Biochemistry, Jun. 27, 2000, 39(25):7380-7.
Klein et al., "Design and characterization of structured protein linkers with differing flexibilities," Protein Engineering, Design & Selection, 2014, 27(10):325-30.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Krizhanovsky et al., "Senescence of activated stellate cells limits liver fibrosis," Cell, Aug. 22, 2008, 134(4):657-67.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Maeda et al., "Original Ligand for LTβR Is LIGHT: Insight into Evolution of the LT/LTβR System," J Immunol., 2018, 201(1):202-214.
Mandelboim et al., "Recognition of haemagglutinins on virus-infected cells by NKp46 activates lysis by human NK cells," Nature, Feb. 2001, 409(6823):1055.
Masoumi et al., "The role of hypoxia as the driving force for non-erythroid production of globin chains in preeclamptic placentas," Placenta. 2017;57:320.
Menshawy et al., "CD58; leucocyte function adhesion-3 (LFA-3) could be used as a differentiating marker between immune and non-immune thyroid disorders," Comparative Clinical Pathology, 2018, 27(3), 721-727.
Miah et al., "KIR2DL4 differentially signals downstream functions in human NK cells through distinct structural modules," The Journal of Immunology, Mar. 1, 2008, 180(5):2922-32.
Miller et al., ""Soluble CD70: a novel immunotherapeutic agent for experimental glioblastoma,"" J Neurosurg., 2010, 113(2):280-285.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Muller et al., "Antibody fusions with immunomodulatory proteins for cancer therapy," Pharmacology and Therapeutics, 2015, 154:57-66.
Mujić-Delić et al., "GPCR-targeting nanobodies: attractive research tools, diagnostics, and therapeutics," Trends in Pharmacological Sciences, May 1, 2014, 35(5):247-55.
Muyldermans et al., "Recognition of antigens by single-domain antibody fragments: the superfluous luxmy of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Nag et al., "Soluble MHC II-peptide complexes induce antigen-specific apoptosis in T cells," Cellular Immunology, May 25, 1996, 170(1):25-33.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
O'Sullivan et al., "Natural Killer Cell Memory," Immunity, 2015, 43:634-645.

(56) References Cited

OTHER PUBLICATIONS

Ovadya et al., "Strategies targeting cellular senescence," The Journal of Clinical Investigation, Apr. 2, 2018, 128(4):1247-54.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
PCT International Search Report and Written Opinion in International Appln. No. PCT/US2019/048881, dated Nov. 9, 2019, 16 pages.
PCT International Search Report and Written Opinion in International Appln. No. PCT/US2019/048930, dated Nov. 20, 2019, 18 pages.
PCT International Search Report and Written Opinion in International Appln. No. PCT/US2019/049158, dated Jan. 20, 2020, 18 pages.
PCT International Search Report and Written Opinion in International Appln. No. PCT/US2019/04912, dated Jun. 23, 2020, 20 pages.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Priyanka et al., "Linkers in the structural biology of protein-protein interactions," Protein Sci., 2013, 22(2):153-167.
Rahbarizadeh et al., "Nanobody; an old concept and new vehicle for immunotargeting," Immunological Investigations, Jan. 1, 2011, 40(3):299-338.
Ranganathan et al., "Pinpointing the putative heparin/sialic acid-binding residues in the 'sushi' domain 7 of factor H: a molecular modeling study," Pacific Symposium on Biocomputing 2000, 5:152-164.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rogge et al., "Antibodies to the IL-12 receptor β2 chain mark human Th1 but not Th2 cells in vitro and in vivo," The Journal of Immunology, Apr. 1, 1999, 162(7):3926-32.
Rossi et al., "Complex and defined biostmetures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Sagiv et al., "Granule exocytosis mediates immune surveillance of senescent cells," Oncogene, 2013, 32(15):1971-1977.
Sandusky et al., "Regulation of 2B4 (CD244)□mediated NK cell activation by ligand□induced receptor modulation," European Journal of Immunology, Dec. 2006, 36(12):3268-76.
Schullek et al., "Key ligand interface residues in tissue factor contribute independently to factor VIIa binding," Journal of Biological Chemistry, Jul. 29, 1994, 269(30):19399-403.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Spiess et al., "Alternative molecular formats and therapeutic applications for bispecific antibodies," Molecular Immunology, Oct. 1, 2015, 67(2):95-106.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara□Hanaoka et al., "Functional characterization of DNAM□1 (CD226) interaction with its ligands PVR (CD155) and nectin□2 (PRR□2/CD112)," International Immunology, Apr. 1, 2004, 16(4):533-8.
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Vincke et al., "Introduction to heavy chain antibodies and derived Nanobodies," Single Domain Antibodies, Humana Press, Totowa, NJ, 2012, pp. 15-26.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weiner et al., "Antibody-based immunotherapy of cancer," Cell, Mar. 16, 2012, 148(6):1081-4.
Wesolowski et al., "Single domain antibodies: promising experimental and therapeutic tools in infection and immunity," Medical Microbiology and Immunology. Aug. 1, 2009, 198(3):157-74.
Witkowsa et al., "Soluble intercellular adhesion molecule□1 (sICAM□1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "Senolytics improve physical function and increase lifespan in old age," Nature Medicine, Aug. 2018, 24(8):1246.
Xu et al., "Transplanted senescent cells induce an osteoarthritis-like condition in mice," The Journals of Gerontology: Series A, Jun. 1, 2017, 72(6):780-5.
Yigit et al., "A combination of an anti-SLAMF6 antibody and ibrutinib efficiently abrogates expansion of chronic lymphocytic leukemia cells," Oncotarget, May 3, 2016, 7(18):26346.
Yung et al., "A selective transforming growth factor-β ligand trap attenuates pulmonary hypertension," American Journal of Respiratory and Critical Care Medicine, Nov. 1, 2016, 194(9):1140-51.
Zwaagstra et al., "Engineering and therapeutic application of single-chain bivalent TGF-β family traps," Molecular Cancer Therapeutics, Jul. 1, 2012, 11(7):1477-87.
Bork, "Powers and Pitfalls in Sequence Analysis: The 70% Hurdle," Genome Research, 2000, 10:398-400.
Bowie et al., "Deciphering the Message in Protein Sequences: Tolerance to Amino Acid Substitutions," Science, 1990, 247:1306-1310.

(56) References Cited

OTHER PUBLICATIONS

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Greenspan et al., "Defining epitopes: Its not as easy as it seems," Nature Biotechnology, 1999, 17:936-937.
Lazar et al., "Transforming Growth Factor Alpha: Mutation of Aspartic Acid 47 and Leucine 48 Results in Different Biological Activities," Mol. Cell. Biol., 1988, 8:1247-1252.
PCT International Search Report and Written Opinion in International Appln. No. PCT/US2021/029920, dated Oct. 6, 2021, 21 pages.
PCT International Search Report and Written Opinion in International Appln. No. PCT/US2021/035285, dated Oct. 18, 2021, 14 pages.
Chandrudu et al., "Chemical methods for peptide and protein production," Molecules, 2013, 18(4):4373-4388.
Tam et al., "Methods and strategies of peptide ligation," Peptide Science: Original Research on Biomolecules, 2001, 60(3):194-205.
Huang et al., "Targeting the vasculature of colorectal carcinoma with a fused protein of (RGD) 3-tTF" The Scientific World Journal, 2013(637086): 1-11, 2013.
PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
PCT International Preliminary Report on Patentability in International Appln. No. PCT/US2021/029920, dated Nov. 10, 2022, 11 pages.

* cited by examiner

* Statistically significant from High Fat Diet untreated Group

* Statistically significant from High fat diet untreated Group

CD + PBS | WD + PBS | WD + TGFRt15-TGFRs | WD + 2t2 | WD + 21t15-TGFRs

* Statistically significant from Control Normal Diet Group

SEQUENCE LISTING

<160> NUMBER OF SEQ ID NOS: 334

<210> SEQ ID NO 1
<211> LENGTH: 251
<212> TYPE: PRT
<213> ORGANISM: Homo sapiens
<220> FEATURE:
<221> NAME/KEY: source
<223> OTHER INFORMATION: /note="CD25"

<400> SEQUENCE: 1

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250
```

<210> SEQ ID NO 2
<211> LENGTH: 753
<212> TYPE: DNA
<213> ORGANISM: Homo sapiens
<220> FEATURE:
<221> NAME/KEY: source
<223> OTHER INFORMATION: /note="CD25"

<400> SEQUENCE: 2

```
gagctctgtg acgatgaccc gccagagatc ccacacgcca cattcaaagc catggcctac      60

aaggaaggaa ccatgttgaa ctgtgaatgc aagagaggtt tccgcagaat aaaaagcggg     120

tcactctata tgctctgtac aggaaactct agccactcgt cctgggacaa ccaatgtcaa     180

tgcacaagct ctgccactcg gaacacaacg aaacaagtga cacctcaacc tgaagaacag     240
```

```
aaagaaagga aaaccacaga aatgcaaagt ccaatgcagc cagtggacca agcgagcctt    300

ccaggtcact gcagggaacc tccaccatgg gaaaatgaag ccacagagag aatttatcat    360

ttcgtggtgg ggcagatggt ttattatcag tgcgtccagg gatacagggc tctacacaga    420

ggtcctgctg agagcgtctg caaaatgacc cacgggaaga caaggtggac ccagccccag    480

ctcatatgca caggtgaaat ggagaccagt cagtttccag gtgaagagaa gcctcaggca    540

agccccgaag gccgtcctga gagtgagact tcctgcctcg tcacaacaac agattttcaa    600

atacagacag aaatggctgc aaccatggag acgtccatat ttacaacaga gtaccaggta    660

gcagtggccg gctgtgtttt cctgctgatc agcgtcctcc tcctgagtgg gctcacctgg    720

cagcggagac agaggaagag tagaagaaca atc                                 753
```

<210> SEQ ID NO 3
<211> LENGTH: 199
<212> TYPE: PRT
<213> ORGANISM: Homo sapiens
<220> FEATURE:
<221> NAME/KEY: source
<223> OTHER INFORMATION: /note="CD69"

<400> SEQUENCE: 3

```
Met Ser Ser Glu Asn Cys Phe Val Ala Glu Asn Ser Ser Leu His Pro
1               5                   10                  15

Glu Ser Gly Gln Glu Asn Asp Ala Thr Ser Pro His Phe Ser Thr Arg
            20                  25                  30

His Glu Gly Ser Phe Gln Val Pro Val Leu Cys Ala Val Met Asn Val
        35                  40                  45

Val Phe Ile Thr Ile Leu Ile Ile Ala Leu Ile Ala Leu Ser Val Gly
    50                  55                  60

Gln Tyr Asn Cys Pro Gly Gln Tyr Thr Phe Ser Met Pro Ser Asp Ser
65                  70                  75                  80

His Val Ser Ser Cys Ser Glu Asp Trp Val Gly Tyr Gln Arg Lys Cys
                85                  90                  95

Tyr Phe Ile Ser Thr Val Lys Arg Ser Trp Thr Ser Ala Gln Asn Ala
            100                 105                 110

Cys Ser Glu His Gly Ala Thr Leu Ala Val Ile Asp Ser Glu Lys Asp
        115                 120                 125

Met Asn Phe Leu Lys Arg Tyr Ala Gly Arg Glu Glu His Trp Val Gly
    130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
        195
```

<210> SEQ ID NO 4
<211> LENGTH: 600
<212> TYPE: DNA
<213> ORGANISM: Homo sapiens
<220> FEATURE:
<221> NAME/KEY: source
<223> OTHER INFORMATION: /note="CD69"

<400> SEQUENCE: 4

```
atgagctctg aaaattgttt cgtagcagag aacagctctt tgcatccgga gagtggacaa     60

gaaaatgatg ccaccagtcc ccatttctca acacgtcatg aagggtcctt ccaagttcct    120

gtcctgtgtg ctgtaatgaa tgtggtcttc atcaccattt taatcatagc tctcattgcc    180

ttatcagtgg gccaatacaa ttgtccaggc caatacacat tctcaatgcc atcagacagc    240

catgtttctt catgctctga ggactgggtt ggctaccaga ggaaatgcta ctttatttct    300

actgtgaaga ggagctggac ttcagcccaa aatgcttgtt ctgaacatgg tgctactctt    360

gctgtcattg attctgaaaa ggacatgaac tttctaaaac gatacgcagg tagagaggaa    420

cactgggttg gactgaaaaa ggaacctggt cacccatgga agtggtcaaa tggcaaagaa    480

tttaacaact ggttcaacgt tacagggtct gacaagtgtg tttttctgaa aaacacagag    540

gtcagcagca tggaatgtga gaagaattta tactggatat gtaacaaacc ttacaaataa    600
```

```
<210> SEQ ID NO 5
<211> LENGTH: 77
<212> TYPE: PRT
<213> ORGANISM: Homo sapiens
<220> FEATURE:
<221> NAME/KEY: source
<223> OTHER INFORMATION: /note="CD59"

<400> SEQUENCE: 5

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn
65                  70                  75


<210> SEQ ID NO 6
<211> LENGTH: 387
<212> TYPE: DNA
<213> ORGANISM: Homo sapiens
<220> FEATURE:
<221> NAME/KEY: source
<223> OTHER INFORMATION: /note="CD59"

<400> SEQUENCE: 6

atgggaatcc aaggagggtc tgtcctgttc gggctgctgc tcgtcctggc tgtcttctgc     60

cattcaggtc atagcctgca gtgctacaac tgtcctaacc caactgctga ctgcaaaaca    120

gccgtcaatt gttcatctga ttttgatgcg tgtctcatta ccaaagctgg gttacaagtg    180

tataacaagt gttggaagtt tgagcattgc aatttcaacg acgtcacaac ccgcttgagg    240

gaaaatgagc taacgtacta ctgctgcaag aaggacctgt gtaactttaa cgaacagctt    300

gaaaatggtg ggacatcctt atcagagaaa acagttcttc tgctggtgac tccatttctg    360

gcagcagcct ggagccttca tccctaa                                        387


<210> SEQ ID NO 7
<211> LENGTH: 311
<212> TYPE: PRT
<213> ORGANISM: Homo sapiens
<220> FEATURE:
<221> NAME/KEY: source
```

<223> OTHER INFORMATION: /note="CD352"

<400> SEQUENCE: 7

Gln Ser Ser Leu Thr Pro Leu Met Val Asn Gly Ile Leu Gly Glu Ser
1 5 10 15

Val Thr Leu Pro Leu Glu Phe Pro Ala Gly Glu Lys Val Asn Phe Ile
20 25 30

Thr Trp Leu Phe Asn Glu Thr Ser Leu Ala Phe Ile Val Pro His Glu
35 40 45

Thr Lys Ser Pro Glu Ile His Val Thr Asn Pro Lys Gln Gly Lys Arg
50 55 60

Leu Asn Phe Thr Gln Ser Tyr Ser Leu Gln Leu Ser Asn Leu Lys Met
65 70 75 80

Glu Asp Thr Gly Ser Tyr Arg Ala Gln Ile Ser Thr Lys Thr Ser Ala
85 90 95

Lys Leu Ser Ser Tyr Thr Leu Arg Ile Leu Arg Gln Leu Arg Asn Ile
100 105 110

Gln Val Thr Asn His Ser Gln Leu Phe Gln Asn Met Thr Cys Glu Leu
115 120 125

His Leu Thr Cys Ser Val Glu Asp Ala Asp Asp Asn Val Ser Phe Arg
130 135 140

Trp Glu Ala Leu Gly Asn Thr Leu Ser Ser Gln Pro Asn Leu Thr Val
145 150 155 160

Ser Trp Asp Pro Arg Ile Ser Ser Glu Gln Asp Tyr Thr Cys Ile Ala
165 170 175

Glu Asn Ala Val Ser Asn Leu Ser Phe Ser Val Ser Ala Gln Lys Leu
180 185 190

Cys Glu Asp Val Lys Ile Gln Tyr Thr Asp Thr Lys Met Ile Leu Phe
195 200 205

Met Val Ser Gly Ile Cys Ile Val Phe Gly Phe Ile Ile Leu Leu Leu
210 215 220

Leu Val Leu Arg Lys Arg Arg Asp Ser Leu Ser Leu Ser Thr Gln Arg
225 230 235 240

Thr Gln Gly Pro Ala Glu Ser Ala Arg Asn Leu Glu Tyr Val Ser Val
245 250 255

Ser Pro Thr Asn Asn Thr Val Tyr Ala Ser Val Thr His Ser Asn Arg
260 265 270

Glu Thr Glu Ile Trp Thr Pro Arg Glu Asn Asp Thr Ile Thr Ile Tyr
275 280 285

Ser Thr Ile Asn His Ser Lys Glu Ser Lys Pro Thr Phe Ser Arg Ala
290 295 300

Thr Ala Leu Asp Asn Val Val
305 310

<210> SEQ ID NO 8
<211> LENGTH: 996
<212> TYPE: DNA
<213> ORGANISM: Homo sapiens
<220> FEATURE:
<221> NAME/KEY: source
<223> OTHER INFORMATION: /note="CD59"

<400> SEQUENCE: 8
atgttgtggc tgttccaatc gctcctgttt gtcttctgct ttggcccagg gaatgtagtt 60
tcacaaagca gcttaacccc attgatggtg aacgggattc tgggggagtc agtaactctt 120

```
ccccctggagt ttcctgcagg agagaaggtc aacttcatca cttggctttt caatgaaaca    180

tctcttgcct tcatagtacc ccatgaaacc aaaagtccag aaatccacgt gactaatccg    240

aaacagggaa agcgactgaa cttcacccag tcctactccc tgcaactcag caacctgaag    300

atggaagaca caggctctta cagagcccag atatccacaa agacctctgc aaagctgtcc    360

agttacactc tgaggatatt aagacaactg aggaacatac aagttaccaa tcacagtcag    420

ctatttcaga atatgacctg tgagctccat ctgacttgct ctgtggagga tgcagatgac    480

aatgtctcat tcagatggga ggccttggga aacacacttt caagtcagcc aaacctcact    540

gtctcctggg accccaggat ttccagtgaa caggactaca cctgcatagc agagaatgct    600

gtcagtaatt tatccttctc tgtctctgcc cagaagcttt gcgaagatgt taaaattcaa    660

tatacagata ccaaaatgat tctgtttatg gtttctggga tatgcatagt cttcggtttc    720

atcatactgc tgttacttgt tttgaggaaa agaagagatt ccctatcttt gtctactcag    780

cgaacacagg gccccgagtc cgcaaggaac ctagagtatg tttcagtgtc tccaacgaac    840

aacactgtgt atgcttcagt cactcattca aacagggaaa cagaaatctg gacacctaga    900

gaaaatgata ctatcacaat ttactccaca attaatcatt ccaaagagag taaacccact    960

ttttccaggg caactgccct tgacaatgtc gtgtaa                              996


<210> SEQ ID NO 9
<211> LENGTH: 231
<212> TYPE: PRT
<213> ORGANISM: Homo sapiens
<220> FEATURE:
<221> NAME/KEY: source
<223> OTHER INFORMATION: /note="NKp80"

<400> SEQUENCE: 9

Met Gln Asp Glu Glu Arg Tyr Met Thr Leu Asn Val Gln Ser Lys Lys
1               5                   10                  15

Arg Ser Ser Ala Gln Thr Ser Gln Leu Thr Phe Lys Asp Tyr Ser Val
            20                  25                  30

Thr Leu His Trp Tyr Lys Ile Leu Leu Gly Ile Ser Gly Thr Val Asn
        35                  40                  45

Gly Ile Leu Thr Leu Thr Leu Ile Ser Leu Ile Leu Leu Val Ser Gln
    50                  55                  60

Gly Val Leu Leu Lys Cys Gln Lys Gly Ser Cys Ser Asn Ala Thr Gln
65                  70                  75                  80

Tyr Glu Asp Thr Gly Asp Leu Lys Val Asn Asn Gly Thr Arg Arg Asn
                85                  90                  95

Ile Ser Asn Lys Asp Leu Cys Ala Ser Arg Ser Ala Asp Gln Thr Val
            100                 105                 110

Leu Cys Gln Ser Glu Trp Leu Lys Tyr Gln Gly Lys Cys Tyr Trp Phe
        115                 120                 125

Ser Asn Glu Met Lys Ser Trp Ser Asp Ser Tyr Val Tyr Cys Leu Glu
    130                 135                 140

Arg Lys Ser His Leu Leu Ile Ile His Asp Gln Leu Glu Met Ala Phe
145                 150                 155                 160

Ile Gln Lys Asn Leu Arg Gln Leu Asn Tyr Val Trp Ile Gly Leu Asn
                165                 170                 175

Phe Thr Ser Leu Lys Met Thr Trp Thr Trp Val Asp Gly Ser Pro Ile
            180                 185                 190

Asp Ser Lys Ile Phe Phe Ile Lys Gly Pro Ala Lys Glu Asn Ser Cys
        195                 200                 205
```

```
Ala Ala Ile Lys Glu Ser Lys Ile Phe Ser Glu Thr Cys Ser Ser Val
    210                 215                 220

Phe Lys Trp Ile Cys Gln Tyr
225                 230


<210> SEQ ID NO 10
<211> LENGTH: 546
<212> TYPE: DNA
<213> ORGANISM: Homo sapiens
<220> FEATURE:
<221> NAME/KEY: source
<223> OTHER INFORMATION: /note="Npk80"

<400> SEQUENCE: 10

atgcaagatg aagaaagata catgacattg aatgtacagt caaagaaaag gagttctgcc      60

caaacatctc aacttacatt taaagattat tcagtgacgt tgcactggta taaaatctta     120

ctgggaatat ctggaaccgt gaatggtatt ctcactttga ctttgatctc cttgatcctg     180

ttggtactat gccaatcaga atggctcaaa taccaaggga agtgttattg gttctctaat     240

gagatgaaaa gctggagtga cagttatgtg tattgtttgg aaagaaaatc tcatctacta     300

atcatacatg accaacttga aatggctttt atacagaaaa acctaagaca attaaactac     360

gtatggattg ggcttaactt tacctccttg aaaatgacat ggacttgggt ggatggttct     420

ccaatagatt caaagatatt cttcataaag ggaccagcta aagaaaacag ctgtgctgcc     480

attaaggaaa gcaaaatttt ctctgaaacc tgcagcagtg ttttcaaatg gatttgtcag     540

tattag                                                                546


<210> SEQ ID NO 11
<211> LENGTH: 318
<212> TYPE: PRT
<213> ORGANISM: Homo sapiens
<220> FEATURE:
<221> NAME/KEY: source
<223> OTHER INFORMATION: /note="DNAM-1"

<400> SEQUENCE: 11

Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
        35                  40                  45

His Gly Met Val Ile Arg Lys Pro Tyr Ala Glu Arg Val Tyr Phe Leu
    50                  55                  60

Asn Ser Thr Met Ala Ser Asn Asn Met Thr Leu Phe Phe Arg Asn Ala
65                  70                  75                  80

Ser Glu Asp Asp Val Gly Tyr Tyr Ser Cys Ser Leu Tyr Thr Tyr Pro
                85                  90                  95

Gln Gly Thr Trp Gln Lys Val Ile Gln Val Val Gln Ser Asp Ser Phe
            100                 105                 110

Glu Ala Ala Val Pro Ser Asn Ser His Ile Val Ser Glu Pro Gly Lys
        115                 120                 125

Asn Val Thr Leu Thr Cys Gln Pro Gln Met Thr Trp Pro Val Gln Ala
    130                 135                 140

Val Arg Trp Glu Lys Ile Gln Pro Arg Gln Ile Asp Leu Leu Thr Tyr
145                 150                 155                 160
```

```
Cys Asn Leu Val His Gly Arg Asn Phe Thr Ser Lys Phe Pro Arg Gln
                165                 170                 175

Ile Val Ser Asn Cys Ser His Gly Arg Trp Ser Val Ile Val Ile Pro
            180                 185                 190

Asp Val Thr Val Ser Asp Ser Gly Leu Tyr Arg Cys Tyr Leu Gln Ala
        195                 200                 205

Ser Ala Gly Glu Asn Glu Thr Phe Val Met Arg Leu Thr Val Ala Glu
    210                 215                 220

Gly Lys Thr Asp Asn Gln Tyr Thr Leu Phe Val Ala Gly Gly Thr Val
225                 230                 235                 240

Leu Leu Leu Leu Phe Val Ile Ser Ile Thr Thr Ile Ile Val Ile Phe
                245                 250                 255

Leu Asn Arg Arg Arg Arg Arg Glu Arg Arg Asp Leu Phe Thr Glu Ser
            260                 265                 270

Trp Asp Thr Gln Lys Ala Pro Asn Asn Tyr Arg Ser Pro Ile Ser Thr
        275                 280                 285

Ser Gln Pro Thr Asn Gln Ser Met Asp Asp Thr Arg Glu Asp Ile Tyr
    290                 295                 300

Val Asn Tyr Pro Thr Phe Ser Arg Arg Pro Lys Thr Arg Val
305                 310                 315


<210> SEQ ID NO 12
<211> LENGTH: 1011
<212> TYPE: DNA
<213> ORGANISM: Homo sapiens
<220> FEATURE:
<221> NAME/KEY: source
<223> OTHER INFORMATION: /note="DNAM-1"

<400> SEQUENCE: 12

atggattatc ctactttact tttggctctt cttcatgtat acagagctct atgtgaagag      60

gtgctttggc atacatcagt tccctttgcc gagaacatgt ctctagaatg tgtgtatcca     120

tcaatgggca tcttaacaca ggtggagtgg ttcaagatcg ggacccagca ggattccata     180

gccattttca gccctactca tggcatggtc ataaggaagc cctatgctga gagggtttac     240

tttttgaatt caacgatggc ttccaataac atgactcttt tctttcggaa tgcctctgaa     300

gatgatgttg gctactattc ctgctctctt tacacttacc cacagggaac ttggcagaag     360

gtgatacagg tggttcagtc agatagtttt gaggcagctg tgccatcaaa tagccacatt     420

gtttcggaac ctggaaagaa tgtcacactc acttgtcagc ctcagatgac gtggcctgtg     480

caggcagtga ggtgggaaaa gatccagccc cgtcagatcg acctcttaac ttactgcaac     540

ttggtccatg gcagaaattt cacctccaag ttcccaagac aaatagtgag caactgcagc     600

cacggaaggt ggagcgtcat cgtcatcccc gatgtcacag tctcagactc ggggctttac     660

cgctgctact tgcaggccag cgcaggagaa aacgaaacct tcgtgatgag attgactgta     720

gccgagggta aaaccgataa ccaatatacc ctctttgtgg ctggagggac agttttattg     780

ttgttgtttg ttatctcaat taccaccatc attgtcattt tccttaacag aaggagaagg     840

agagagagaa gagatctatt tacagagtcc tgggatacac agaaggcacc caataactat     900

agaagtccca tctctaccag tcaacctacc aatcaatcca tggatgatac aagagaggat     960

atttatgtca actatccaac cttctctcgc agaccaaaga ctagagttta a             1011


<210> SEQ ID NO 13
<211> LENGTH: 347
<212> TYPE: PRT
```

```
<213> ORGANISM: Homo sapiens
<220> FEATURE:
<221> NAME/KEY: source
<223> OTHER INFORMATION: /note="HB4"

<400> SEQUENCE: 13

Gly Lys Gly Cys Gln Gly Ser Ala Asp His Val Val Ser Ile Ser Gly
1               5                   10                  15

Val Pro Leu Gln Leu Gln Pro Asn Ser Ile Gln Thr Lys Val Asp Ser
            20                  25                  30

Ile Ala Trp Lys Lys Leu Leu Pro Ser Gln Asn Gly Phe His His Ile
        35                  40                  45

Leu Lys Trp Glu Asn Gly Ser Leu Pro Ser Asn Thr Ser Asn Asp Arg
    50                  55                  60

Phe Ser Phe Ile Val Lys Asn Leu Ser Leu Leu Ile Lys Ala Ala Gln
65                  70                  75                  80

Gln Gln Asp Ser Gly Leu Tyr Cys Leu Glu Val Thr Ser Ile Ser Gly
                85                  90                  95

Lys Val Gln Thr Ala Thr Phe Gln Val Phe Val Phe Asp Lys Val Glu
            100                 105                 110

Lys Pro Arg Leu Gln Gly Gln Gly Lys Ile Leu Asp Arg Gly Arg Cys
        115                 120                 125

Gln Val Ala Leu Ser Cys Leu Val Ser Arg Asp Gly Asn Val Ser Tyr
    130                 135                 140

Ala Trp Tyr Arg Gly Ser Lys Leu Ile Gln Thr Ala Gly Asn Leu Thr
145                 150                 155                 160

Tyr Leu Asp Glu Glu Val Asp Ile Asn Gly Thr His Thr Tyr Thr Cys
                165                 170                 175

Asn Val Ser Asn Pro Val Ser Trp Glu Ser His Thr Leu Asn Leu Thr
            180                 185                 190

Gln Asp Cys Gln Asn Ala His Gln Glu Phe Arg Phe Trp Pro Phe Leu
        195                 200                 205

Val Ile Ile Val Ile Leu Ser Ala Leu Phe Leu Gly Thr Leu Ala Cys
    210                 215                 220

Phe Cys Val Trp Arg Arg Lys Arg Lys Glu Lys Gln Ser Glu Thr Ser
225                 230                 235                 240

Pro Lys Glu Phe Leu Thr Ile Tyr Glu Asp Val Lys Asp Leu Lys Thr
                245                 250                 255

Arg Arg Asn His Glu Gln Glu Gln Thr Phe Pro Gly Gly Gly Ser Thr
            260                 265                 270

Ile Tyr Ser Met Ile Gln Ser Gln Ser Ser Ala Pro Thr Ser Gln Glu
        275                 280                 285

Pro Ala Tyr Thr Leu Tyr Ser Leu Ile Gln Pro Ser Arg Lys Ser Gly
    290                 295                 300

Ser Arg Lys Arg Asn His Ser Pro Ser Phe Asn Ser Thr Ile Tyr Glu
305                 310                 315                 320

Val Ile Gly Lys Ser Gln Pro Lys Ala Gln Asn Pro Ala Arg Leu Ser
                325                 330                 335

Arg Lys Glu Leu Glu Asn Phe Asp Val Tyr Ser
            340                 345


<210> SEQ ID NO 14
<211> LENGTH: 1098
<212> TYPE: DNA
<213> ORGANISM: Homo sapiens
<220> FEATURE:
```

<221> NAME/KEY: source
<223> OTHER INFORMATION: /note="HB4"

<400> SEQUENCE: 14

```
atgctggggc aagtggtcac cctcatactc ctcctgctcc tcaaggtgta tcagggcaaa      60

ggatgccagg gatcagctga ccatgtggtt agcatctcgg gagtgcctct tcagttacaa     120

ccaaacagca tacagacgaa ggttgacagc attgcatgga agaagttgct gccctcacaa     180

aatggatttc atcacatatt gaagtgggag aatggctctt tgccttccaa tacttccaat     240

gatagattca gttttatagt caagaacttg agtcttctca tcaaggcagc tcagcagcag     300

gacagtggcc tctactgcct ggaggtcacc agtatatctg gaaaagttca gacagccacg     360

ttccaggttt ttgtatttga taaagttgag aaaccccgcc tacaggggca ggggaagatc     420

ctggacagag ggagatgcca agtggctctg tcttgcttgg tctccaggga tggcaatgtg     480

tcctatgctt ggtacagagg gagcaagctg atccagacag cagggaacct cacctacctg     540

gacgaggagg ttgacattaa tggcactcac acatatacct gcaatgtcag caatcctgtt     600

agctgggaaa gccacaccct gaatctcact caggactgtc agaatgccca tcaggaattc     660

agattttggc cgtttttggt gatcatcgtg attctaagcg cactgttcct tggcaccctt     720

gcctgcttct gtgtgtggag gagaaagagg aaggagaagc agtcagagac cagtcccaag     780

gaatttttga caatttacga agatgtcaag gatctgaaaa ccaggagaaa tcacgagcag     840

gagcagactt ttcctggagg ggggagcacc atctactcta tgatccagtc ccagtcttct     900

gctcccacgt cacaagaacc tgcatataca ttatattcat taattcagcc ttccaggaag     960

tctggatcca ggaagaggaa ccacagccct tccttcaata gcactatcta tgaagtgatt    1020

ggaaagagtc aacctaaagc ccagaaccct gctcgattga gccgcaaaga gctggagaac    1080

tttgatgttt attcctag                                                  1098
```

<210> SEQ ID NO 15
<211> LENGTH: 183
<212> TYPE: PRT
<213> ORGANISM: Homo sapiens
<220> FEATURE:
<221> NAME/KEY: source
<223> OTHER INFORMATION: /note="NK-p30"

<400> SEQUENCE: 15

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly Ala Gly Thr Val Leu Leu Leu Arg Ala Gly Phe
        115                 120                 125

Tyr Ala Val Ser Phe Leu Ser Val Ala Val Gly Ser Thr Val Tyr Tyr
```

130 135 140

Gln Gly Lys Cys Leu Thr Trp Lys Gly Pro Arg Arg Gln Leu Pro Ala
145 150 155 160

Val Val Pro Ala Pro Leu Pro Pro Pro Cys Gly Ser Ser Ala His Leu
165 170 175

Leu Pro Pro Val Pro Gly Gly
180

<210> SEQ ID NO 16
<211> LENGTH: 573
<212> TYPE: DNA
<213> ORGANISM: Homo sapiens
<220> FEATURE:
<221> NAME/KEY: source
<223> OTHER INFORMATION: /note="NKp30"

<400> SEQUENCE: 16
atggcctgga tgctgttgct catcttgatc atggtccatc caggatcctg tgctctctgg 60
gtgtcccagc cccctgagat tcgtaccctg gaaggatcct ctgccttcct gccctgctcc 120
ttcaatgcca gccaagggag actggccatt ggctccgtca cgtggttccg agatgaggtg 180
gttccaggga aggaggtgag gaatggaacc ccagagttca ggggccgcct ggccccactt 240
gcttcttccc gtttcctcca tgaccaccag gctgagctgc acatccggga cgtgcgaggc 300
catgacgcca gcatctacgt gtgcagagtg gaggtgctgg gccttggtgt cgggacaggg 360
aatgggactc ggctggtggt ggagaaagaa catcctcagc taggggctgg tacagtcctc 420
ctccttcggg ctggattcta tgctgtcagc tttctctctg tggccgtggg cagcaccgtc 480
tattaccagg gcaaatgcca ctgtcacatg ggaacacact gccactcctc agatgggccc 540
cgaggagtga ttccagagcc cagatgtccc tag 573

<210> SEQ ID NO 17
<211> LENGTH: 255
<212> TYPE: PRT
<213> ORGANISM: Homo sapiens
<220> FEATURE:
<221> NAME/KEY: source
<223> OTHER INFORMATION: /note="NKp44"

<400> SEQUENCE: 17

Gln Ser Lys Ala Gln Val Leu Gln Ser Val Ala Gly Gln Thr Leu Thr
1 5 10 15

Val Arg Cys Gln Tyr Pro Pro Thr Gly Ser Leu Tyr Glu Lys Lys Gly
20 25 30

Trp Cys Lys Glu Ala Ser Ala Leu Val Cys Ile Arg Leu Val Thr Ser
35 40 45

Ser Lys Pro Arg Thr Met Ala Trp Thr Ser Arg Phe Thr Ile Trp Asp
50 55 60

Asp Pro Asp Ala Gly Phe Phe Thr Val Thr Met Thr Asp Leu Arg Glu
65 70 75 80

Glu Asp Ser Gly His Tyr Trp Cys Arg Ile Tyr Arg Pro Ser Asp Asn
85 90 95

Ser Val Ser Lys Ser Val Arg Phe Tyr Leu Val Val Ser Pro Ala Ser
100 105 110

Ala Ser Thr Gln Thr Ser Trp Thr Pro Arg Asp Leu Val Ser Ser Gln
115 120 125

Thr Gln Thr Gln Ser Cys Val Pro Pro Thr Ala Gly Ala Arg Gln Ala
130 135 140

```
Pro Glu Ser Pro Ser Thr Ile Pro Val Pro Ser Gln Pro Gln Asn Ser
145                 150                 155                 160

Thr Leu Arg Pro Gly Pro Ala Ala Pro Ile Ala Leu Val Pro Val Phe
                165                 170                 175

Cys Gly Leu Leu Val Ala Lys Ser Leu Val Leu Ser Ala Leu Leu Val
            180                 185                 190

Trp Trp Gly Asp Ile Trp Trp Lys Thr Met Met Glu Leu Arg Ser Leu
        195                 200                 205

Asp Thr Gln Lys Ala Thr Cys His Leu Gln Gln Val Thr Asp Leu Pro
    210                 215                 220

Trp Thr Ser Val Ser Ser Pro Val Glu Arg Glu Ile Leu Tyr His Thr
225                 230                 235                 240

Val Ala Arg Thr Lys Ile Ser Asp Asp Asp Asp Glu His Thr Leu
                245                 250                 255


<210> SEQ ID NO 18
<211> LENGTH: 777
<212> TYPE: DNA
<213> ORGANISM: Homo sapiens
<220> FEATURE:
<221> NAME/KEY: source
<223> OTHER INFORMATION: /note="NKp44"

<400> SEQUENCE: 18

atggcctggc gagccctaca cccactgcta ctgctgctgc tgctgttccc aggctctcag      60

gcacaatcca aggctcaggt acttcaaagt gtggcagggc agacgctaac cgtgagatgc     120

cagtacccgc ccacgggcag tctctacgag aagaaaggct ggtgtaagga ggcttcagca     180

cttgtgtgca tcaggttagt caccagctcc aagcccagga cgatggcttg gacctctcga     240

ttcacaatct gggacgaccc tgatgctggc ttcttcactg tcaccatgac tgatctgaga     300

gaggaagact caggacatta ctggtgtaga atctaccgcc cttctgacaa ctctgtctct     360

aagtccgtca gattctatct ggtggtatct ccagcctctg cctccacaca gacctcctgg     420

actccccgcg acctggtctc ttcacagacc cagacccaga gctgtgtgcc tcccactgca     480

ggagccagac aagcccctga gtctccatct accatccctg tcccttcaca gccacagaac     540

tccacgctcc gccctggccc tgcagccccc attgccctgg tgcctgtgtt ctgtggactc     600

ctcgtagcca agagcctggt gctgtcagcc ctgctcgtct ggtgggtttt aaggaatcgg     660

cacatgcagc atcaagggag gtctctgctg cacccagctc agcccaggcc ccaggcccat     720

agacacttcc cactgagcca cagggcacca gggggacat atggtggaaa accatga         777


<210> SEQ ID NO 19
<211> LENGTH: 283
<212> TYPE: PRT
<213> ORGANISM: Homo sapiens
<220> FEATURE:
<221> NAME/KEY: source
<223> OTHER INFORMATION: /note="NKp46"

<400> SEQUENCE: 19

Gln Gln Gln Thr Leu Pro Lys Pro Phe Ile Trp Ala Glu Pro His Phe
1               5                   10                  15

Met Val Pro Lys Glu Lys Gln Val Thr Ile Cys Cys Gln Gly Asn Tyr
            20                  25                  30

Gly Ala Val Glu Tyr Gln Leu His Phe Glu Gly Ser Leu Phe Ala Val
        35                  40                  45
```

```
Asp Arg Pro Lys Pro Pro Glu Arg Ile Asn Lys Val Gln Phe Tyr Ile
    50                  55                  60

Pro Asp Met Asn Ser Arg Met Ala Gly Gln Tyr Ser Cys Ile Tyr Arg
65                  70                  75                  80

Val Gly Glu Leu Trp Ser Glu Pro Ser Asn Leu Leu Asp Leu Val Val
                85                  90                  95

Thr Glu Met Tyr Asp Thr Pro Thr Leu Ser Val His Pro Gly Pro Glu
            100                 105                 110

Val Ile Ser Gly Glu Lys Val Thr Phe Tyr Cys Arg Leu Asp Thr Ala
        115                 120                 125

Thr Ser Met Phe Leu Leu Leu Lys Glu Gly Arg Ser Ser His Val Gln
    130                 135                 140

Arg Gly Tyr Gly Lys Val Gln Ala Glu Phe Pro Leu Gly Pro Val Thr
145                 150                 155                 160

Thr Ala His Arg Gly Thr Tyr Arg Cys Phe Gly Ser Tyr Asn Asn His
                165                 170                 175

Ala Trp Ser Phe Pro Ser Glu Pro Val Lys Leu Leu Val Thr Gly Asp
            180                 185                 190

Ile Glu Asn Thr Ser Leu Ala Pro Glu Asp Pro Thr Phe Pro Ala Asp
        195                 200                 205

Thr Trp Gly Thr Tyr Leu Leu Thr Thr Glu Thr Gly Leu Gln Lys Asp
    210                 215                 220

His Ala Leu Trp Asp His Thr Ala Gln Asn Leu Leu Arg Met Gly Leu
225                 230                 235                 240

Ala Phe Leu Val Leu Val Ala Leu Val Trp Phe Leu Val Glu Asp Trp
                245                 250                 255

Leu Ser Arg Lys Arg Thr Arg Glu Arg Ala Ser Arg Ala Ser Thr Trp
            260                 265                 270

Glu Gly Arg Arg Arg Leu Asn Thr Gln Thr Leu
        275                 280
```

<210> SEQ ID NO 20
<211> LENGTH: 777
<212> TYPE: DNA
<213> ORGANISM: Homo sapiens
<220> FEATURE:
<221> NAME/KEY: source
<223> OTHER INFORMATION: /note="NKp46"

<400> SEQUENCE: 20

```
atggcctggc gagccctaca cccactgcta ctgctgctgc tgctgttccc aggctctcag     60

gcacaatcca aggctcaggt acttcaaagt gtggcagggc agacgctaac cgtgagatgc    120

cagtacccgc ccacgggcag tctctacgag aagaaaggct ggtgtaagga ggcttcagca    180

cttgtgtgca tcaggttagt caccagctcc aagcccagga cgatggcttg gacctctcga    240

ttcacaatct gggacgaccc tgatgctggc ttcttcactg tcaccatgac tgatctgaga    300

gaggaagact caggacatta ctggtgtaga atctaccgcc cttctgacaa ctctgtctct    360

aagtccgtca gattctatct ggtggtatct ccagcctctg cctccacaca gacctcctgg    420

actccccgcg acctggtctc ttcacagacc cagacccaga gctgtgtgcc tcccactgca    480

ggagccagac aagcccctga gtctccatct accatccctg tcccttcaca gccacagaac    540

tccacgctcc gccctggccc tgcagccccc attgccctgg tgcctgtgtt ctgtggactc    600

ctcgtagcca agagcctggt gctgtcagcc ctgctcgtct ggtgggtttt aaggaatcgg    660

cacatgcagc atcaagggag gtctctgctg cacccagctc agcccaggcc ccaggcccat    720
```

agacacttcc cactgagcca cagggcacca ggggggacat atggtggaaa accatga 777

<210> SEQ ID NO 21
<211> LENGTH: 216
<212> TYPE: PRT
<213> ORGANISM: Homo sapiens
<220> FEATURE:
<221> NAME/KEY: source
<223> OTHER INFORMATION: /note="NKG2D"

<400> SEQUENCE: 21

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215
```

<210> SEQ ID NO 22
<211> LENGTH: 651
<212> TYPE: DNA
<213> ORGANISM: Homo sapiens
<220> FEATURE:
<221> NAME/KEY: source
<223> OTHER INFORMATION: /note="NKG2D"

<400> SEQUENCE: 22

```
atggggtgga ttcgtggtcg gaggtctcga cacagctggg agatgagtga atttcataat      60

tataacttgg atctgaagaa gagtgatttt tcaacacgat ggcaaaagca aagatgtcca     120

gtagtcaaaa gcaaatgtag agaaaatgca tctccatttt ttttctgctg cttcatcgct     180

gtagccatgg gaatccgttt cattattatg gtaacaatat ggagtgctgt attcctaaac     240

tcattattca accaagaagt tcaaattccc ttgaccgaaa gttactgtgg cccatgtcct     300

aaaaactgga tatgttacaa aaataactgc taccaatttt ttgatgagag taaaaactgg     360
```

-continued

```
tatgagagcc aggcttcttg tatgtctcaa aatgccagcc ttctgaaagt atacagcaaa    420

gaggaccagg atttacttaa actggtgaag tcatatcatt ggatgggact agtacacatt    480

ccaacaaatg gatcttggca gtgggaagat ggctccattc tctcacccaa cctactaaca    540

ataattgaaa tgcagaaggg agactgtgca ctctatgcct cgagctttaa aggctatata    600

gaaaactgtt caactccaaa tacgtacatc tgcatgcaaa ggactgtgta a             651
```

```
<210> SEQ ID NO 23
<211> LENGTH: 359
<212> TYPE: PRT
<213> ORGANISM: Homo sapiens
<220> FEATURE:
<221> NAME/KEY: source
<223> OTHER INFORMATION: /note="CD16"

<400> SEQUENCE: 23

Met Ala Glu Gly Thr Leu Trp Gln Ile Leu Cys Val Ser Ser Asp Ala
1               5                   10                  15

Gln Pro Gln Thr Phe Glu Gly Val Lys Gly Ala Asp Pro Pro Thr Leu
            20                  25                  30

Pro Pro Gly Ser Phe Leu Pro Gly Pro Val Leu Trp Trp Gly Ser Leu
        35                  40                  45

Ala Arg Leu Gln Thr Glu Lys Ser Asp Glu Val Ser Arg Lys Gly Asn
    50                  55                  60

Trp Trp Val Thr Glu Met Gly Gly Gly Ala Gly Glu Arg Leu Phe Thr
65                  70                  75                  80

Ser Ser Cys Leu Val Gly Leu Val Pro Leu Gly Leu Arg Ile Ser Leu
                85                  90                  95

Val Thr Cys Pro Leu Gln Cys Gly Ile Met Trp Gln Leu Leu Leu Pro
            100                 105                 110

Thr Ala Leu Leu Leu Leu Val Ser Ala Gly Met Arg Thr Glu Asp Leu
        115                 120                 125

Pro Lys Ala Val Val Phe Leu Glu Pro Gln Trp Tyr Arg Val Leu Glu
    130                 135                 140

Lys Asp Ser Val Thr Leu Lys Cys Gln Gly Ala Tyr Ser Pro Glu Asp
145                 150                 155                 160

Asn Ser Thr Gln Trp Phe His Asn Glu Ser Leu Ile Ser Ser Gln Ala
                165                 170                 175

Ser Ser Tyr Phe Ile Asp Ala Ala Thr Val Asp Asp Ser Gly Glu Tyr
            180                 185                 190

Arg Cys Gln Thr Asn Leu Ser Thr Leu Ser Asp Pro Val Gln Leu Glu
        195                 200                 205

Val His Ile Gly Trp Leu Leu Leu Gln Ala Pro Arg Trp Val Phe Lys
    210                 215                 220

Glu Glu Asp Pro Ile His Leu Arg Cys His Ser Trp Lys Asn Thr Ala
225                 230                 235                 240

Leu His Lys Val Thr Tyr Leu Gln Asn Gly Lys Gly Arg Lys Tyr Phe
                245                 250                 255

His His Asn Ser Asp Phe Tyr Ile Pro Lys Ala Thr Leu Lys Asp Ser
            260                 265                 270

Gly Ser Tyr Phe Cys Arg Gly Leu Phe Gly Ser Lys Asn Val Ser Ser
        275                 280                 285

Glu Thr Val Asn Ile Thr Ile Thr Gln Gly Leu Ala Val Ser Thr Ile
    290                 295                 300

Ser Ser Phe Phe Pro Pro Gly Tyr Gln Val Ser Phe Cys Leu Val Met
```

-continued

```
305                 310                 315                 320

Val Leu Leu Phe Ala Val Asp Thr Gly Leu Tyr Phe Ser Val Lys Thr
                325                 330                 335

Asn Ile Arg Ser Ser Thr Arg Asp Trp Lys Asp His Lys Phe Lys Trp
            340                 345                 350

Arg Lys Asp Pro Gln Asp Lys
        355


<210> SEQ ID NO 24
<211> LENGTH: 1080
<212> TYPE: DNA
<213> ORGANISM: Homo sapiens
<220> FEATURE:
<221> NAME/KEY: source
<223> OTHER INFORMATION: /note="CD16"

<400> SEQUENCE: 24

atggctgagg gcacactctg gcagattctg tgtgtgtcct cagatgctca gccacagacc     60

tttgagggag taaagggggc agacccaccc accttgcctc caggctcttt ccttcctggt    120

cctgttctat ggtggggctc ccttgccaga cttcagactg agaagtcaga tgaagtttca    180

agaaaaggaa attggtgggt gacagagatg ggtggagggg ctggggaaag gctgtttact    240

tcctcctgtc tagtcggttt ggtcccttta gggctccgga tatctttggt gacttgtcca    300

ctccagtgtg gcatcatgtg gcagctgctc ctcccaactg ctctgctact tctagtttca    360

gctggcatgc ggactgaaga tctcccaaag gctgtggtgt tcctggagcc tcaatggtac    420

agggtgctcg agaaggacag tgtgactctg aagtgccagg gagcctactc ccctgaggac    480

aattccacac agtggtttca caatgagagc ctcatctcaa gccaggcctc gagctacttc    540

attgacgctg ccacagtcga cgacagtgga gagtacaggt gccagacaaa cctctccacc    600

ctcagtgacc cggtgcagct agaagtccat atcggctggc tgttgctcca ggcccctcgg    660

tgggtgttca aggaggaaga ccctattcac ctgaggtgtc acagctggaa gaacactgct    720

ctgcataagg tcacatattt acagaatggc aaaggcagga agtattttca tcataattct    780

gacttctaca ttccaaaagc cacactcaaa gacagcggct cctacttctg cagggggctt    840

tttgggagta aaaatgtgtc ttcagagact gtgaacatca ccatcactca aggtttggca    900

gtgtcaacca tctcatcatt ctttccacct gggtaccaag tctctttctg cttggtgatg    960

gtactccttt ttgcagtgga cacaggacta tatttctctg tgaagacaaa cattcgaagc   1020

tcaacaagag actggaagga ccataaattt aaatggagaa aggaccctca agacaaatga   1080


<210> SEQ ID NO 25
<211> LENGTH: 233
<212> TYPE: PRT
<213> ORGANISM: Homo sapiens
<220> FEATURE:
<221> NAME/KEY: source
<223> OTHER INFORMATION: /note="CD16"

<400> SEQUENCE: 25

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
```

```
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 26
<211> LENGTH: 702
<212> TYPE: DNA
<213> ORGANISM: Homo sapiens
<220> FEATURE:
<221> NAME/KEY: source
<223> OTHER INFORMATION: /note="CD16"

<400> SEQUENCE: 26

```
atgtggcagc tgctcctccc aactgctctg ctacttctag tttcagctgg catgcggact      60

gaagatctcc caaaggctgt ggtgttcctg gagcctcaat ggtacagcgt gcttgagaag     120

gacagtgtga ctctgaagtg ccagggagcc tactcccctg aggacaattc cacacagtgg     180

tttcacaatg agaacctcat ctcaagccag gcctcgagct acttcattga cgctgccaca     240

gtcaacgaca gtggagagta caggtgccag acaaacctct ccaccctcag tgacccggtg     300

cagctagaag tccatatcgg ctggctgttg ctccaggccc ctcggtgggt gttcaaggag     360

gaagacccta ttcacctgag gtgtcacagc tggaagaaca ctgctctgca taaggtcaca     420

tatttacaga atggcaaaga caggaagtat tttcatcata attctgactt ccacattcca     480

aaagccacac tcaaagatag cggctcctac ttctgcaggg ggcttgttgg gagtaaaaat     540

gtgtcttcag agactgtgaa catcaccatc actcaaggtt tggcagtgtc aaccatctca     600

tcattctctc cacctgggta ccaagtctct ttctgcttgg tgatggtact cctttttgca     660

gtggacacag gactatattt ctctgtgaag acaaacattt ga                         702
```

<210> SEQ ID NO 27
<211> LENGTH: 304
<212> TYPE: PRT
<213> ORGANISM: Homo sapiens
<220> FEATURE:
<221> NAME/KEY: source
<223> OTHER INFORMATION: /note="KIR2DS1"

<400> SEQUENCE: 27

Met Ser Leu Thr Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Met Phe Asn Asp Thr Leu Arg Leu Ile Gly Glu His His Asp Gly Val
65                  70                  75                  80

Ser Lys Ala Asn Phe Ser Ile Ser Arg Met Lys Gln Asp Leu Ala Gly
                85                  90                  95

Thr Tyr Arg Cys Tyr Gly Ser Val Thr His Ser Pro Tyr Gln Val Ser
            100                 105                 110

Ala Pro Ser Asp Pro Leu Asp Ile Val Ile Ile Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Thr Lys
                165                 170                 175

Val Asn Gly Thr Phe Gln Ala Asn Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 28
<211> LENGTH: 915
<212> TYPE: DNA
<213> ORGANISM: Homo sapiens
<220> FEATURE:
<221> NAME/KEY: source
<223> OTHER INFORMATION: /note="KIR2DS1"

<400> SEQUENCE: 28
atgtcgctca cggtcgtcag catggcgtgt gttgggttct tcttgctgca gggggcctgg     60
ccacatgagg gagtccacag aaaaccttcc ctcctggccc acccaggtcg cctggtgaaa    120
tcagaagaga cagtcatcct gcaatgttgg tcagatgtca tgtttgaaca cttccttctg    180
cacagagagg ggatgtttaa cgacactttg cgcctcattg gagaacacca tgatggggtc    240
tccaaggcca acttctccat cagtcgcatg aagcaagacc tggcagggac ctacagatgc    300

```
tacggttctg ttactcactc cccctatcag ttgtcagctc ccagtgaccc tctggacatc    360

gtgatcatag gtctatatga gaaaccttct ctctcagccc agccgggccc cacggttctg    420

gcaggagaga atgtgacctt gtcctgcagc tcccggagct cctatgacat gtaccatcta    480

tccagggaag gggaggccca tgaacgtagg ctccctgcag ggaccaaggt caacggaaca    540

ttccaggcca actttcctct gggccctgcc acccatggag ggacctacag atgcttcggc    600

tctttccgtg actctccata cgagtggtca aagtcaagtg acccactgct tgtttctgtc    660

acaggaaacc cttcaaatag ttggccttca cccactgaac caagctccga aaccggtaac    720

cccagacacc tacatgttct gattgggacc tcagtggtca aaatcccttt caccatcctc    780

ctcttctttc tccttcatcg ctggtgctcc gacaaaaaaa atgctgctgt aatggaccaa    840

gagcctgcag ggaacagaac agtgaacagc gaggattctg atgaacaaga ccatcaggag    900

gtgtcatacg cataa                                                      915
```

```
<210> SEQ ID NO 29
<211> LENGTH: 304
<212> TYPE: PRT
<213> ORGANISM: Homo sapiens
<220> FEATURE:
<221> NAME/KEY: source
<223> OTHER INFORMATION: /note="KIR2DS2"

<400> SEQUENCE: 29

Met Ser Leu Met Val Val Ser Met Val Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240
```

-continued

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asn Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 30
<211> LENGTH: 1026
<212> TYPE: DNA
<213> ORGANISM: Homo sapiens
<220> FEATURE:
<221> NAME/KEY: source
<223> OTHER INFORMATION: /note="KIR2DS2"

<400> SEQUENCE: 30
atgtcgctca tggtcgtcag catggcgtgt gttgggttct tcttgctgca gggggcctgg 60
ccacatgagg gagtccacag aaaaccttcc ctcctggccc acccaggtcc cctggtgaaa 120
tcagaagaga cagtcatcct gcaatgttgg tcagatgtca ggtttgagca cttccttctg 180
cacagagagg ggaagtataa ggacactttg cacctcattg gagagcacca tgatggggtc 240
tccaaggcca acttctccat cggtcccatg atgcaagacc ttgcagggac ctacagatgc 300
tacggttctg ttactcactc cccctatcag ttgtcagctc ccagtgaccc tctggacatc 360
gtcatcacag gtctatatga gaaaccttct ctctcagccc agccgggccc cacggttttg 420
gcaggagaga gcgtgacctt gtcctgcagc tcccggagct cctatgacat gtaccatcta 480
tccagggagg gggaggccca tgaacgtagg ttctctgcag ggcccaaggt caacggaaca 540
ttccaggccg actttcctct gggccctgcc acccacggag gaacctacag atgcttcggc 600
tctttccgtg actctcccta tgagtggtca aactcgagtg acccactgct tgtttctgtc 660
acaggaaacc cttcaaatag ttggccttca cccactgaac caagctccaa aaccggtaac 720
cccagacacc tgcatgttct gattgggacc tcagtggtca aaatcccttt caccatcctc 780
ctcttctttc tccttcatcg ctggtgctcc aacaaaaaaa atgctgctgt aatggaccaa 840
gagcctgcag ggaacagaac agtgaacagc gaggactctg atgaacaaga ccctcaggag 900
gtgacataca cacagttgaa tcactgcgtt ttcacacaga gaaaaatcac tcgcccttct 960
cagaggccca agacaccccc aacagatatc atcgtgtaca cggaacttcc aaatgctgag 1020
tccaga 1026

<210> SEQ ID NO 31
<211> LENGTH: 304
<212> TYPE: PRT
<213> ORGANISM: Homo sapiens
<220> FEATURE:
<221> NAME/KEY: source
<223> OTHER INFORMATION: /note="KIR2DS3"

<400> SEQUENCE: 31

Met Ser Leu Met Val Ile Ser Met Ala Cys Val Gly Phe Phe Trp Leu
1               5                   10                  15

Gln Gly Ala Trp Pro His Glu Gly Phe Arg Arg Lys Pro Ser Leu Leu
            20                  25                  30

Ala His Pro Gly Arg Leu Val Lys Ser Glu Glu Thr Val Ile Leu Gln
        35                  40                  45

```
Cys Trp Ser Asp Val Met Phe Glu His Phe Leu Leu His Arg Glu Gly
    50                  55                  60

Thr Phe Asn Asp Thr Leu Arg Leu Ile Gly Glu His Ile Asp Gly Val
65                  70                  75                  80

Ser Lys Ala Asn Phe Ser Ile Gly Arg Met Arg Gln Asp Leu Ala Gly
                85                  90                  95

Thr Tyr Arg Cys Tyr Gly Ser Val Pro His Ser Pro Tyr Gln Phe Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Trp Ser Ser Tyr Asp Met Tyr His Leu
145                 150                 155                 160

Ser Thr Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr Gln
            180                 185                 190

Gly Gly Thr Tyr Arg Cys Phe Gly Ser Phe His Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Leu Pro
                245                 250                 255

Phe Thr Ile Leu Leu Phe Phe Leu Leu His Arg Trp Cys Ser Asp Lys
            260                 265                 270

Lys Asn Ala Ser Val Met Asp Gln Gly Pro Ala Gly Asn Arg Thr Val
        275                 280                 285

Asn Arg Glu Asp Ser Asp Glu Gln Asp His Gln Glu Val Ser Tyr Ala
    290                 295                 300
```

<210> SEQ ID NO 32
<211> LENGTH: 915
<212> TYPE: DNA
<213> ORGANISM: Homo sapiens
<220> FEATURE:
<221> NAME/KEY: source
<223> OTHER INFORMATION: /note="KIR2DS3"

<400> SEQUENCE: 32

```
atgtcgctca tggtcatcag catggcatgt gttgggttct tctggctgca gggggcctgg      60

ccacatgagg gattccgcag aaaaccttcc ctcctggccc acccaggtcg cctggtgaaa     120

tcagaagaga cagtcatcct gcaatgttgg tcagatgtca tgtttgagca cttccttctg     180

cacagagagg ggacgtttaa cgacactttg cgcctcattg gagagcacat tgatggggtc     240

tccaaggcca acttctccat cggtcgcatg aggcaagacc tggcagggac ctacagatgc     300

tacggttctg ttcctcactc cccctatcag ttttcagctc ccagtgaccc tctggacatc     360

gtgatcacag gtctatatga gaaaccttct ctctcagccc agccgggccc cacggttctg     420

gcaggagaga gcgtgacctt gtcctgcagc tcctggagct cctatgacat gtaccatcta     480

tccacggagg gggaggccca tgaacgtagg ttctctgcag ggcccaaggt caacggaaca     540

ttccaggccg actttcctct gggccctgcc acccaaggag gaacctacag atgcttcggc     600
```

-continued

```
tctttccatg actctcccta cgagtggtca aagtcaagtg acccactgct tgtttctgtc    660

acaggaaacc cttcaaatag ttggccttca cccactgaac caagctccaa aaccggtaac    720

cccagacacc tacacgttct gattgggacc tcagtggtca aactcccttt caccatcctc    780

ctcttctttc tccttcatcg ctggtgctcc gacaaaaaaa atgcatctgt aatggaccaa    840

gggcctgcgg ggaacagaac agtgaacagg gaggattctg atgaacagga ccatcaggag    900

gtgtcatacg cataa                                                      915


<210> SEQ ID NO 33
<211> LENGTH: 354
<212> TYPE: PRT
<213> ORGANISM: Homo sapiens
<220> FEATURE:
<221> NAME/KEY: source
<223> OTHER INFORMATION: /note="KIR2DL4"

<400> SEQUENCE: 33

His Val Gly Gly Gln Asp Lys Pro Phe Cys Ser Ala Trp Pro Ser Ala
1               5                   10                  15

Val Val Pro Gln Gly Gly His Ala Thr Leu Arg Cys His Cys Arg Arg
            20                  25                  30

Gly Phe Asn Ile Phe Thr Leu Tyr Lys Lys Asp Gly Val Pro Val Pro
        35                  40                  45

Glu Leu Tyr Asn Arg Ile Phe Trp Asn Ser Phe Leu Ile Ser Pro Val
    50                  55                  60

Thr Pro Ala His Ala Gly Thr Tyr Arg Cys Arg Gly Phe His Pro His
65                  70                  75                  80

Ser Pro Thr Glu Trp Ser Ala Pro Ser Asn Pro Leu Val Ile Met Val
                85                  90                  95

Thr Gly Leu Tyr Glu Lys Pro Ser Leu Thr Ala Arg Pro Gly Pro Thr
            100                 105                 110

Val Arg Ala Gly Glu Asn Val Thr Leu Ser Cys Ser Ser Gln Ser Ser
        115                 120                 125

Phe Asp Ile Tyr His Leu Ser Arg Glu Gly Glu Ala His Glu Leu Arg
    130                 135                 140

Leu Pro Ala Val Pro Ser Ile Asn Gly Thr Phe Gln Ala Asp Phe Pro
145                 150                 155                 160

Leu Gly Pro Ala Thr His Gly Glu Thr Tyr Arg Cys Phe Gly Ser Phe
                165                 170                 175

His Gly Ser Pro Tyr Glu Trp Ser Asp Pro Ser Asp Pro Leu Pro Val
            180                 185                 190

Ser Val Thr Gly Asn Pro Ser Ser Ser Trp Pro Ser Pro Thr Glu Pro
        195                 200                 205

Ser Phe Lys Thr Gly Ile Ala Arg His Leu His Ala Val Ile Arg Tyr
    210                 215                 220

Ser Val Ala Ile Ile Leu Phe Thr Ile Leu Pro Phe Phe Leu Leu His
225                 230                 235                 240

Arg Trp Cys Ser Lys Lys Lys Asn Ala Ala Val Met Asn Gln Glu Pro
                245                 250                 255

Ala Gly His Arg Thr Val Asn Arg Glu Asp Ser Asp Glu Gln Asp Pro
            260                 265                 270

Gln Glu Val Thr Tyr Ala Gln Leu Asp His Cys Ile Phe Thr Gln Arg
        275                 280                 285

Lys Ile Thr Gly Pro Ser Gln Arg Ser Lys Arg Pro Ser Thr Asp Thr
    290                 295                 300
```

Ser Val Cys Ile Glu Leu Pro Asn Ala Glu Pro Arg Ala Leu Ser Pro
305 310 315 320

Ala His Glu His His Ser Gln Ala Leu Met Gly Ser Ser Arg Glu Thr
325 330 335

Thr Ala Leu Ser Gln Thr Gln Leu Ala Ser Ser Asn Val Pro Ala Ala
340 345 350

Gly Ile

<210> SEQ ID NO 34
<211> LENGTH: 1251
<212> TYPE: DNA
<213> ORGANISM: Homo sapiens
<220> FEATURE:
<221> NAME/KEY: source
<223> OTHER INFORMATION: /note="KIR2DL4"

<400> SEQUENCE: 34
atgtcccctt cacatgttgt ggtcaatgtg tcaactgcac gatccgggcc cctcaccaca 60
tcctctgcac cggtcagtcg agccgagtca ctgcgtcctg gcagcagaag ctgcaccatg 120
tccatgtcac ccacggtcat catcctggca tgtcttgggt tcttcttgga ccagagtgtg 180
tgggcacacg tgggtggtca ggacaagccc ttctgctctg cctggcccag cgctgtggtg 240
cctcaaggag gacacgtgac tcttcggtgt cactatcgtc gtgggtttaa catcttcacg 300
ctgtacaaga aagatggggt ccctgtccct gagctctaca acagaatatt ctggaacagt 360
ttcctcatta gccctgtgac cccagcacac gcagggacct acagatgtcg aggttttcac 420
ccgcactccc ccactgagtg gtcggcaccc agcaaccccc tggtgatcat ggtcacaggt 480
ctatatgaga aaccttcgct tacagcccgg ccgggcccca cggttcgcgc aggagagaac 540
gtgaccttgt cctgcagctc ccagagctcc tttgacatct accatctatc cagggagggg 600
gaagcccatg aacttaggct ccctgcagtg cccagcatca atggaacatt ccaggccgac 660
ttccctctgg gtcctgccac ccacggagag acctacagat gcttcggctc tttccatgga 720
tctccctacg agtggtcaga cccgagtgac ccactgcctg tttctgtcac aggaaaccct 780
tctagtagtt ggccttcacc cactgaacca agcttcaaaa ctggtatcgc cagacacctg 840
catgctgtga ttaggtactc agtggccatc atcctcttta ccatccttcc cttctttctc 900
cttcatcgct ggtgctccaa aaaaaaagat gctgctgtaa tgaaccaaga gcctgcggga 960
cacagaacag tgaacaggga ggactctgat gaacaagacc ctcaggaggt gacatacgca 1020
cagttggatc actgcatttt cacacagaga aaaatcactg gcccttctca gaggagcaag 1080
agaccctcaa cagataccag cgtgtgtata gaacttccaa atgctgagcc cagagcgttg 1140
tctcctgccc atgagcacca cagtcaggcc ttgatgggat cttctaggga gacaacagcc 1200
ctgtctcaaa cccagcttgc cagctctaat gtaccagcag ctggaatctg a 1251

<210> SEQ ID NO 35
<211> LENGTH: 218
<212> TYPE: PRT
<213> ORGANISM: Homo sapiens
<220> FEATURE:
<221> NAME/KEY: source
<223> OTHER INFORMATION: /note="KIR2DS4"

<400> SEQUENCE: 35

Gln Glu Gly Val His Arg Lys Pro Ser Phe Leu Ala Leu Pro Gly His
1 5 10 15

```
Leu Val Lys Ser Glu Glu Thr Val Ile Leu Gln Cys Trp Ser Asp Val
            20                  25                  30

Met Phe Glu His Phe Leu Leu His Arg Glu Gly Lys Phe Asn Asn Thr
        35                  40                  45

Leu His Leu Ile Gly Glu His His Asp Gly Val Ser Lys Ala Asn Phe
    50                  55                  60

Ser Ile Gly Pro Met Met Pro Val Leu Ala Gly Thr Tyr Arg Cys Tyr
65                  70                  75                  80

Ser Ser Val Pro His Ser Pro Tyr Gln Leu Ser Ala Pro Ser Asp Pro
                85                  90                  95

Leu Asp Met Val Ile Ile Gly Leu Tyr Glu Lys Pro Ser Leu Ser Ala
            100                 105                 110

Gln Pro Gly Pro Thr Val Gln Ala Gly Glu Asn Val Ser Leu Ser Cys
        115                 120                 125

Ser Ser Ile Tyr Pro Gly Arg Gly Arg Pro Met Asn Val Gly Ser Leu
    130                 135                 140

Gln Cys Ala Ala Ser Thr Glu His Ser Arg Pro Thr Phe Leu Trp Ala
145                 150                 155                 160

Leu Pro Pro Thr Glu Gly Pro Thr Asp Ala Ser Ala Leu Ser Val Thr
                165                 170                 175

Leu Pro Thr Ser Gly Gln Thr Arg Val Ile His Cys Leu Phe Pro Ser
            180                 185                 190

Gln Glu Thr Leu Gln Ile Val Gly Leu His Pro Leu Asn Gln Ala Pro
        195                 200                 205

Lys Pro Val Thr Pro Asp Thr Tyr Met Phe
    210                 215
```

<210> SEQ ID NO 36
<211> LENGTH: 893
<212> TYPE: DNA
<213> ORGANISM: Homo sapiens
<220> FEATURE:
<221> NAME/KEY: source
<223> OTHER INFORMATION: /note="KIR2DS4"

<400> SEQUENCE: 36

```
atgtcgctca tggtcatcat catggcgtgt gttgggttct tcttgctgca gggggcctgg      60

ccacaggagg gagtccacag aaaaccttcc ttcctggccc tcccaggtca cctggtgaaa     120

tcagaagaga cagtcatcct gcaatgttgg tcggatgtca tgtttgagca cttccttctg     180

cacagagagg ggaagtttaa caacactttg cacctcattg gagagcacca tgatggggtt     240

tccaaggcca acttctccat tggtcccatg atgcctgtcc ttgcaggaac ctacagatgc     300

tacggttctg ttcctcactc cccctatcag ttgtcagctc ccagtgaccc tctggacatg     360

gtgatcatag gtctatatga gaaaccttct ctctcagccc agccgggccc cacggttcag     420

gcaggagaga atgtgacctt gtcctgcagc tccatctatc cagggaaggg gaggcccatg     480

aacgtaggct ccctgcagtg cgcagcatca acggaacatt ccaggccgac tttcctctgg     540

gccctgccac ccacggaggg acctacagat gcttcggctc tttccgtgac gctccctacg     600

agtggtcaaa ctcgagtgat ccactgcttg tttccgtcac aggaaaccct tcaaatagtt     660

ggccttcacc cactgaacca agctccaaaa ccggtaaccc cagacaccta catgttctga     720

ttgggacctc agtggtcaaa atccctttca ccatcctcct cttctttctc cttcatcgct     780

ggtgctccga caaaaaaaat gctgctgtaa tggaccaaga gcctgcaggg aacagaacag     840

tgaacagcga ggattctgat gaacaagacc atcaggaggt gtcatacgca taa            893
```

<210> SEQ ID NO 37
<211> LENGTH: 283
<212> TYPE: PRT
<213> ORGANISM: Homo sapiens
<220> FEATURE:
<221> NAME/KEY: source
<223> OTHER INFORMATION: /note="KIR2DS5"

<400> SEQUENCE: 37

```
His Glu Gly Phe Arg Arg Lys Pro Ser Leu Leu Ala His Pro Gly Pro
1               5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Thr Phe Asn His Thr
        35                  40                  45

Leu Arg Leu Ile Gly Glu His Ile Asp Gly Val Ser Lys Gly Asn Phe
    50                  55                  60

Ser Ile Gly Arg Met Thr Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Leu Pro Ala Gly Thr Lys Val Asn Gly Thr Phe
145                 150                 155                 160

Gln Ala Asp Phe Pro Leu Asp Pro Ala Thr His Gly Gly Thr Tyr Arg
                165                 170                 175

Cys Phe Gly Ser Phe Arg Asp Ser Pro Tyr Glu Trp Ser Lys Ser Ser
            180                 185                 190

Asp Pro Leu Leu Val Ser Val Thr Gly Asn Thr Ser Asn Ser Trp Pro
        195                 200                 205

Ser Pro Thr Glu Pro Ser Ser Lys Thr Gly Asn Pro Arg His Leu His
    210                 215                 220

Val Leu Ile Gly Thr Ser Val Val Lys Leu Pro Phe Thr Ile Leu Leu
225                 230                 235                 240

Phe Phe Leu Leu His Arg Trp Cys Ser Asn Lys Lys Asn Ala Ser Val
                245                 250                 255

Met Asp Gln Gly Pro Ala Gly Asn Arg Thr Val Asn Arg Glu Asp Ser
            260                 265                 270

Asp Glu Gln Asp His Gln Glu Val Ser Tyr Ala
        275                 280
```

<210> SEQ ID NO 38
<211> LENGTH: 915
<212> TYPE: DNA
<213> ORGANISM: Homo sapiens
<220> FEATURE:
<221> NAME/KEY: source
<223> OTHER INFORMATION: /note="KIR2DS"

<400> SEQUENCE: 38

```
atgtcgctca tggtcatcag catggcgtgt gttgcgttct tcttgctgca gggggcctgg     60
```

ccacatgagg gattccgcag aaaaccttcc ctcctggccc acccaggtcc cctggtgaaa 120
tcagaagaga cagtcatcct gcaatgttgg tcagatgtca tgtttgagca cttccttctg 180
cacagagagg ggacgtttaa ccacactttg cgcctcattg gagagcacat tgatggggtc 240
tccaagggca acttctccat cggtcgcatg acacaagacc tggcagggac ctacagatgc 300
tacggttctg ttactcactc cccctatcag ttgtcagcgc ccagtgaccc tctggacatc 360
gtgatcacag gtctatatga gaaaccttct ctctcagccc agccgggccc cacggttctg 420
gcaggagaga gcgtgacctt gtcctgcagc tcccggagct cctatgacat gtaccatcta 480
tccagggaag gggaggccca tgaacgtagg ctccctgcag ggcccaaggt caacagaaca 540
ttccaggccg actttcctct ggaccctgcc acccacggag ggacctacag atgcttcggc 600
tctttccgtg actctccata cgagtggtca aagtcaagtg acccactgct tgtttctgtc 660
acaggaaact cttcaaatag ttggccttca cccactgaac caagctccga aaccggtaac 720
cccagacacc tacacgttct gattgggacc tcagtggtca aactcccttt caccatcctc 780
ctcttctttc tccttcatcg ctggtgctcc aacaaaaaaa atgcatctgt aatggaccaa 840
gggcctgcgg ggaacagaac agtgaacagg gaggattctg atgaacagga ccatcaggag 900
gtgtcatacg cataa 915

<210> SEQ ID NO 39
<211> LENGTH: 361
<212> TYPE: PRT
<213> ORGANISM: Homo sapiens
<220> FEATURE:
<221> NAME/KEY: source
<223> OTHER INFORMATION: /note="KIR3DS1"

<400> SEQUENCE: 39

His Met Gly Gly Gln Asp Lys Pro Phe Leu Ser Ala Trp Pro Ser Ala
1 5 10 15

Val Val Pro Arg Gly Gly His Val Thr Leu Arg Cys His Tyr Arg His
20 25 30

Arg Phe Asn Asn Phe Met Leu Tyr Lys Glu Asp Arg Ile His Val Pro
35 40 45

Ile Phe His Gly Arg Ile Phe Gln Glu Gly Phe Asn Met Ser Pro Val
50 55 60

Thr Thr Ala His Ala Gly Asn Tyr Thr Cys Arg Gly Ser His Pro His
65 70 75 80

Ser Pro Thr Gly Trp Ser Ala Pro Ser Asn Pro Met Val Ile Met Val
85 90 95

Thr Gly Asn His Arg Lys Pro Ser Leu Leu Ala His Pro Gly Pro Leu
100 105 110

Val Lys Ser Gly Glu Arg Val Ile Leu Gln Cys Trp Ser Asp Ile Met
115 120 125

Phe Glu His Phe Phe Leu His Lys Glu Gly Ile Ser Lys Asp Pro Ser
130 135 140

Arg Leu Val Gly Gln Ile His Asp Gly Val Ser Lys Ala Asn Phe Ser
145 150 155 160

Ile Gly Ser Met Met Arg Ala Leu Ala Gly Thr Tyr Arg Cys Tyr Gly
165 170 175

Ser Val Thr His Thr Pro Tyr Gln Leu Ser Ala Pro Ser Asp Pro Leu
180 185 190

Asp Ile Val Val Thr Gly Leu Tyr Glu Lys Pro Ser Leu Ser Ala Gln
195 200 205

```
Pro Gly Pro Lys Val Gln Ala Gly Glu Ser Val Thr Leu Ser Cys Ser
    210                 215                 220

Ser Arg Ser Ser Tyr Asp Met Tyr His Leu Ser Arg Glu Gly Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Asn Leu Arg His Leu His Ile
305                 310                 315                 320

Leu Ile Gly Thr Ser Val Val Lys Ile Pro Phe Thr Ile Leu Leu Phe
                325                 330                 335

Phe Leu Leu His Arg Trp Cys Ser Asn Lys Lys Lys Cys Cys Cys Asn
            340                 345                 350

Gly Pro Arg Ala Cys Arg Glu Gln Lys
        355                 360
```

<210> SEQ ID NO 40
<211> LENGTH: 1149
<212> TYPE: DNA
<213> ORGANISM: Homo sapiens
<220> FEATURE:
<221> NAME/KEY: source
<223> OTHER INFORMATION: /note="KIR3DS1"

<400> SEQUENCE: 40

```
atgttgctca tggtcgtcag catggcgtgt gttgggttgt tcttggtcca gagggccggt     60

ccacacatgg gtggtcagga caagcccttc ctgtctgcct ggcccagcgc tgtggtgcct    120

cgcggaggac acgtgactct tcggtgtcac tatcgtcata ggtttaacaa tttcatgcta    180

tacaaagaag acagaatcca cgttcccatc ttccatggca gaatattcca ggagggcttc    240

aacatgagcc ctgtgaccac agcacatgca gggaactaca catgtcgggg ttcacaccca    300

cactccccca ctgggtggtc ggcacccagc aaccccatgg tgatcatggt cacaggaaac    360

cacagaaaac cttccctcct ggcccaccca ggtcccctgg tgaaatcagg agagagagtc    420

atcctgcaat gttggtcaga tatcatgttt gagcacttct ttctgcacaa agagtggatc    480

tctaaggacc cctcacgcct cgttggacag atccatgatg gggtctccaa ggccaatttc    540

tccatcggtt ccatgatgcg tgcccttgca gggacctaca gatgctacgg ttctgttact    600

cacacccct atcagttgtc agctcccagt gatcccctgg acatcgtggt cacaggtcta    660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaacctcag acacctgcac   1020

attctgattg ggacctcagt ggtcaaaatc cctttcacca tcctcctctt ctttctcctt   1080

catcgctggt gctccaacaa aaaaaaatgc tgctgtaatg gaccaagagc ctgcagggaa   1140
```

cagaagtga 1149

<210> SEQ ID NO 41
<211> LENGTH: 231
<212> TYPE: PRT
<213> ORGANISM: Homo sapiens
<220> FEATURE:
<221> NAME/KEY: source
<223> OTHER INFORMATION: /note="NKG2C"

<400> SEQUENCE: 41

```
Met Ser Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Met Lys Phe Leu Ala Ser Ile Leu Pro Ser Ser Trp Ile Gly Val Phe
                165                 170                 175

Arg Asn Ser Ser His His Pro Trp Val Thr Ile Asn Gly Leu Ala Phe
            180                 185                 190

Lys His Lys Ile Lys Asp Ser Asp Asn Ala Glu Leu Asn Cys Ala Val
        195                 200                 205

Leu Gln Val Asn Arg Leu Lys Ser Ala Gln Cys Gly Ser Ser Met Ile
    210                 215                 220

Tyr His Cys Lys His Lys Leu
225                 230
```

<210> SEQ ID NO 42
<211> LENGTH: 696
<212> TYPE: DNA
<213> ORGANISM: Homo sapiens
<220> FEATURE:
<221> NAME/KEY: source
<223> OTHER INFORMATION: /note="NKG2C"

<400> SEQUENCE: 42

```
atgaataaac aaagaggaac cttctcagaa gtgagtctgg cccaggaccc aaagcggcag     60

caaaggaaac ctaaaggcaa taaaagctcc atttcaggaa ccgaacagga aatattccaa    120

gtagaattaa atcttcaaaa tccttccctg aatcatcaag ggattgataa aatatatgac    180

tgccaaggtt tactgccacc tccagagaag ctcactgccg aggtcctagg aatcatttgc    240

attgtcctga tggccactgt gttaaaaaca atagttctta ttcctttcct ggagcagaac    300
```

```
aatttttccc cgaatacaag aacgcagaaa gcacgtcatt gtggccattg tcctgaggag    360

tggattacat attccaacag ttgttattac attggtaagg aaagaagaac ttgggaagag    420

agtttgctgg cctgtacttc gaagaactcc agtctgcttt ctatagataa tgaagaagaa    480

atgaaatttc tggccagcat tttaccttcc tcatggattg gtgtgtttcg taacagcagt    540

catcatccat gggtgacaat aaatggtttg gctttcaaac ataagataaa agactcagat    600

aatgctgaac ttaactgtgc agtgctacaa gtaaatcgac ttaaatcagc ccagtgtgga    660

tcttcaatga tatatcattg taagcataag ctttag                              696


<210> SEQ ID NO 43
<211> LENGTH: 354
<212> TYPE: PRT
<213> ORGANISM: Homo sapiens
<220> FEATURE:
<221> NAME/KEY: source
<223> OTHER INFORMATION: /note="CCR7"

<400> SEQUENCE: 43

Gln Asp Glu Val Thr Asp Asp Tyr Ile Gly Asp Asn Thr Thr Val Asp
1               5                   10                  15

Tyr Thr Leu Phe Glu Ser Leu Cys Ser Lys Lys Asp Val Arg Asn Phe
            20                  25                  30

Lys Ala Trp Phe Leu Pro Ile Met Tyr Ser Ile Ile Cys Phe Val Gly
        35                  40                  45

Leu Leu Gly Asn Gly Leu Val Val Leu Thr Tyr Ile Tyr Phe Lys Arg
    50                  55                  60

Leu Lys Thr Met Thr Asp Thr Tyr Leu Leu Asn Leu Ala Val Ala Asp
65                  70                  75                  80

Ile Leu Phe Leu Leu Thr Leu Pro Phe Trp Ala Tyr Ser Ala Ala Lys
                85                  90                  95

Ser Trp Val Phe Gly Val His Phe Cys Lys Leu Ile Phe Ala Ile Tyr
            100                 105                 110

Lys Met Ser Phe Phe Ser Gly Met Leu Leu Leu Leu Cys Ile Ser Ile
        115                 120                 125

Asp Arg Tyr Val Ala Ile Val Gln Ala Val Ser Ala His Arg His Arg
    130                 135                 140

Ala Arg Val Leu Leu Ile Ser Lys Leu Ser Cys Val Gly Ile Trp Ile
145                 150                 155                 160

Leu Ala Thr Val Leu Ser Ile Pro Glu Leu Leu Tyr Ser Asp Leu Gln
                165                 170                 175

Arg Ser Ser Ser Glu Gln Ala Met Arg Cys Ser Leu Ile Thr Glu His
            180                 185                 190

Val Glu Ala Phe Ile Thr Ile Gln Val Ala Gln Met Val Ile Gly Phe
        195                 200                 205

Leu Val Pro Leu Leu Ala Met Ser Phe Cys Tyr Leu Val Ile Ile Arg
    210                 215                 220

Thr Leu Leu Gln Ala Arg Asn Phe Glu Arg Asn Lys Ala Ile Lys Val
225                 230                 235                 240

Ile Ile Ala Val Val Val Val Phe Ile Val Phe Gln Leu Pro Tyr Asn
                245                 250                 255

Gly Val Val Leu Ala Gln Thr Val Ala Asn Phe Asn Ile Thr Ser Ser
            260                 265                 270

Thr Cys Glu Leu Ser Lys Gln Leu Asn Ile Ala Tyr Asp Val Thr Tyr
        275                 280                 285
```

```
Ser Leu Ala Cys Val Arg Cys Cys Val Asn Pro Phe Leu Tyr Ala Phe
    290                 295                 300

Ile Gly Val Lys Phe Arg Asn Asp Leu Phe Lys Leu Phe Lys Asp Leu
305                 310                 315                 320

Gly Cys Leu Ser Gln Glu Gln Leu Arg Gln Trp Ser Ser Cys Arg His
                325                 330                 335

Ile Arg Arg Ser Ser Met Ser Val Glu Ala Glu Thr Thr Thr Thr Phe
            340                 345                 350

Ser Pro


<210> SEQ ID NO 44
<211> LENGTH: 1137
<212> TYPE: DNA
<213> ORGANISM: Homo sapiens
<220> FEATURE:
<221> NAME/KEY: source
<223> OTHER INFORMATION: /note="CCR7"

<400> SEQUENCE: 44

atggacctgg ggaaaccaat gaaaagcgtg ctggtggtgg ctctccttgt cattttccag     60

gtatgcctgt gtcaagatga ggtcacggac gattacatcg gagacaacac cacagtggac    120

tacactttgt tcgagtcttt gtgctccaag aaggacgtgc ggaactttaa agcctggttc    180

ctccctatca tgtactccat catttgtttc gtgggcctac tgggcaatgg gctggtcgtg    240

ttgacctata tctatttcaa gaggctcaag accatgaccg atacctacct gctcaacctg    300

gcggtggcag acatcctctt cctcctgacc cttcccttct gggcctacag cgcggccaag    360

tcctgggtct tcggtgtcca cttttgcaag ctcatctttg ccatctacaa gatgagcttc    420

ttcagtggca tgctcctact tctttgcatc agcattgacc gctacgtggc catcgtccag    480

gctgtctcag ctcaccgcca ccgtgcccgc gtccttctca tcagcaagct gtcctgtgtg    540

ggcatctgga tactagccac agtgctctcc atcccagagc tcctgtacag tgacctccag    600

aggagcagca gtgagcaagc gatgcgatgc tctctcatca cagagcatgt ggaggccttt    660

atcaccatcc aggtggccca gatggtgatc ggctttctgg tcccccctgct ggccatgagc    720

ttctgttacc ttgtcatcat ccgcaccctg ctccaggcac gcaactttga gcgcaacaag    780

gccatcaagg tgatcatcgc tgtggtcgtg gtcttcatag tcttccagct gccctacaat    840

ggggtggtcc tggcccagac ggtggccaac ttcaacatca ccagtagcac ctgtgagctc    900

agtaagcaac tcaacatcgc ctacgacgtc acctacagcc tggcctgcgt ccgctgctgc    960

gtcaaccctt tcttgtacgc cttcatcggc gtcaagttcc gcaacgatct cttcaagctc   1020

ttcaaggacc tgggctgcct cagccaggag cagctccggc agtggtcttc ctgtcggcac   1080

atccggcgct cctccatgag tgtggaggcc gagaccacca ccaccttctc cccatag      1137


<210> SEQ ID NO 45
<211> LENGTH: 368
<212> TYPE: PRT
<213> ORGANISM: Homo sapiens
<220> FEATURE:
<221> NAME/KEY: source
<223> OTHER INFORMATION: /note="CXCR3"

<400> SEQUENCE: 45

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
```

```
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365
```

<210> SEQ ID NO 46
<211> LENGTH: 1248
<212> TYPE: DNA
<213> ORGANISM: Homo sapiens
<220> FEATURE:
<221> NAME/KEY: source
<223> OTHER INFORMATION: /note="CXCR3"

<400> SEQUENCE: 46

```
atggagttga ggaagtacgg ccctggaaga ctggcgggga cagttatagg aggagctgct      60

cagagtaaat cacagactaa atcagactca atcacaaaag agttcctgcc aggcctttac     120
```

-continued

```
acagcccctt cctccccgtt cccgccctca caggtgagtg accaccaagt gctaaatgac    180

gccgaggttg ccgccctcct ggagaacttc agctcttcct atgactatgg agaaaacgag    240

agtgactcgt gctgtacctc ccgccctgc ccacaggact tcagcctgaa cttcgaccgg    300

gccttcctgc cagccctcta cagcctcctc tttctgctgg ggctgctggg caacggcgcg    360

gtggcagccg tgctgctgag ccggcggaca gccctgagca gcaccgacac cttcctgctc    420

cacctagctg tagcagacac gctgctggtg ctgacactgc cgctctgggc agtggacgct    480

gccgtccagt gggtctttgg ctctggcctc tgcaaagtgg caggtgccct cttcaacatc    540

aacttctacg caggagccct cctgctggcc tgcatcagct ttgaccgcta cctgaacata    600

gttcatgcca cccagctcta ccgccggggg cccccggccc gcgtgaccct cacctgcctg    660

gctgtctggg ggctctgcct gcttttcgcc ctcccagact tcatcttcct gtcggcccac    720

cacgacgagc gcctcaacgc cacccactgc caatacaact tcccacaggt gggccgcacg    780

gctctgcggg tgctgcagct ggtggctggc tttctgctgc ccctgctggt catggcctac    840

tgctatgccc acatcctggc cgtgctgctg gtttccaggg gccagcggcg cctgcgggcc    900

atgcggctgg tggtggtggt cgtggtggcc tttgccctct gctggacccc ctatcacctg    960

gtggtgctgg tggacatcct catggacctg ggcgctttgg cccgcaactg tggccgagaa    1020

agcagggtag acgtggccaa gtcggtcacc tcaggcctgg gctacatgca ctgctgcctc    1080

aacccgctgc tctatgcctt tgtaggggtc aagttccggg agcggatgtg gatgctgctc    1140

ttgcgcctgg gctgccccaa ccagagaggg ctccagaggc agccatcgtc ttcccgccgg    1200

gattcatcct ggtctgagac ctcagaggcc tcctactcgg gcttgtga                1248
```

<210> SEQ ID NO 47
<211> LENGTH: 344
<212> TYPE: PRT
<213> ORGANISM: Homo sapiens
<220> FEATURE:
<221> NAME/KEY: source
<223> OTHER INFORMATION: /note="L-selectin"

<400> SEQUENCE: 47

```
Asp Phe Leu Ala His His Gly Thr Asp Cys Trp Thr Tyr His Tyr Ser
1               5                   10                  15

Glu Lys Pro Met Asn Trp Gln Arg Ala Arg Arg Phe Cys Arg Asp Asn
            20                  25                  30

Tyr Thr Asp Leu Val Ala Ile Gln Asn Lys Ala Glu Ile Glu Tyr Leu
        35                  40                  45

Glu Lys Thr Leu Pro Phe Ser Arg Ser Tyr Tyr Trp Ile Gly Ile Arg
    50                  55                  60

Lys Ile Gly Gly Ile Trp Thr Trp Val Gly Thr Asn Lys Ser Leu Thr
65                  70                  75                  80

Glu Glu Ala Glu Asn Trp Gly Asp Gly Glu Pro Asn Asn Lys Lys Asn
                85                  90                  95

Lys Glu Asp Cys Val Glu Ile Tyr Ile Lys Arg Asn Lys Asp Ala Gly
            100                 105                 110

Lys Trp Asn Asp Asp Ala Cys His Lys Leu Lys Ala Ala Leu Cys Tyr
        115                 120                 125

Thr Ala Ser Cys Gln Pro Trp Ser Cys Ser Gly His Gly Glu Cys Val
    130                 135                 140

Glu Ile Ile Asn Asn Tyr Thr Cys Asn Cys Asp Val Gly Tyr Tyr Gly
145                 150                 155                 160
```

```
Pro Gln Cys Gln Phe Val Ile Gln Cys Glu Pro Leu Glu Ala Pro Glu
                165                 170                 175

Leu Gly Thr Met Asp Cys Thr His Pro Leu Gly Asn Phe Ser Phe Ser
            180                 185                 190

Ser Gln Cys Ala Phe Ser Cys Ser Glu Gly Thr Asn Leu Thr Gly Ile
        195                 200                 205

Glu Glu Thr Thr Cys Gly Pro Phe Gly Asn Trp Ser Ser Pro Glu Pro
    210                 215                 220

Thr Cys Gln Val Ile Gln Cys Glu Pro Leu Ser Ala Pro Asp Leu Gly
225                 230                 235                 240

Ile Met Asn Cys Ser His Pro Leu Ala Ser Phe Ser Phe Thr Ser Ala
                245                 250                 255

Cys Thr Phe Ile Cys Ser Glu Gly Thr Glu Leu Ile Gly Lys Lys Lys
            260                 265                 270

Thr Ile Cys Glu Ser Ser Gly Ile Trp Ser Asn Pro Ser Pro Ile Cys
        275                 280                 285

Gln Lys Leu Asp Lys Ser Phe Ser Met Ile Lys Glu Gly Asp Tyr Asn
    290                 295                 300

Pro Leu Phe Ile Pro Val Ala Val Met Val Thr Ala Phe Ser Gly Leu
305                 310                 315                 320

Ala Phe Ile Ile Trp Leu Ala Arg Arg Leu Lys Lys Gly Lys Lys Ser
                325                 330                 335

Lys Arg Ser Met Asn Asp Pro Tyr
            340
```

<210> SEQ ID NO 48
<211> LENGTH: 1158
<212> TYPE: DNA
<213> ORGANISM: Homo sapiens
<220> FEATURE:
<221> NAME/KEY: source
<223> OTHER INFORMATION: /note="L-selectin"

<400> SEQUENCE: 48

```
atgggctgca gaagaactag agaaggacca agcaaagcca tgatatttcc atggaaatgt     60

cagagcaccc agagggactt atggaacatc ttcaagttgt gggggtggac aatgctctgt    120

tgtgatttcc tggcacatca tggaaccgac tgctggactt accattattc tgaaaaaccc    180

atgaactggc aaagggctag aagattctgc cgagacaatt acacagattt agttgccata    240

caaaacaagg cggaaattga gtatctggag aagactctgc ctttcagtcg ttcttactac    300

tggataggaa tccggaagat aggaggaata tggacgtggg tgggaaccaa caaatctctt    360

actgaagaag cagagaactg gggagatggt gagcccaaca acaagaagaa caaggaggac    420

tgcgtggaga tctatatcaa gagaaacaaa gatgcaggca aatggaacga tgacgcctgc    480

cacaaactaa aggcagccct ctgttacaca gcttcttgcc agccctggtc atgcagtggc    540

catggagaat gtgtagaaat catcaataat tacacctgca actgtgatgt ggggtactat    600

gggccccagt gtcagtttgt gattcagtgt gagcctttgg aggccccaga gctgggtacc    660

atggactgta ctcacccttt gggaaacttc agcttcagct cacagtgtgc cttcagctgc    720

tctgaaggaa caaacttaac tgggattgaa gaaaccacct gtggaccatt tggaaactgg    780

tcatctccag aaccaacctg tcaagtgatt cagtgtgagc ctctatcagc accagatttg    840

gggatcatga actgtagcca tcccctggcc agcttcagct ttacctctgc atgtaccttc    900

atctgctcag aaggaactga gttaattggg aagaagaaaa ccatttgtga atcatctgga    960
```

```
atctggtcaa atcctagtcc aatatgtcaa aaattggaca aaagtttctc aatgattaag   1020

gagggtgatt ataacccccct cttcattcca gtggcagtca tggttactgc attctctggg   1080

ttggcattta tcatttggct ggcaaggaga ttaaaaaaag gcaagaaatc caagagaagt   1140

atgaatgacc catattaa                                                 1158


<210> SEQ ID NO 49
<211> LENGTH: 350
<212> TYPE: PRT
<213> ORGANISM: Homo sapiens
<220> FEATURE:
<221> NAME/KEY: source
<223> OTHER INFORMATION: /note="CXCR1"
<220> FEATURE:
<221> NAME/KEY: MOD_RES
<222> LOCATION: (31)..(31)
<223> OTHER INFORMATION: Any amino acid

<400> SEQUENCE: 49

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Xaa Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
```

-continued

```
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350


<210> SEQ ID NO 50
<211> LENGTH: 1053
<212> TYPE: DNA
<213> ORGANISM: Homo sapiens
<220> FEATURE:
<221> NAME/KEY: source
<223> OTHER INFORMATION: /note="CXCR1"

<400> SEQUENCE: 50

atgtcaaata ttacagatcc acagatgtgg gattttgatg atctaaattt cactggcatg     60

ccacctgcag atgaagatta cagcccctgt atgctagaaa ctgagacact caacaagtat    120

gttgtgatca tcgcctatgc cctagtgttc ctgctgagcc tgctgggaaa ctccctggtg    180

atgctggtca tcttatacag cagggtcggc cgctccgtca ctgatgtcta cctgctgaac    240

ctggccttgg ccgacctact ctttgccctg accttgccca tctgggccgc ctccaaggtg    300

aatggctgga tttttggcac attcctgtgc aaggtggtct cactcctgaa ggaagtcaac    360

ttctacagtg gcatcctgct gttggcctgc atcagtgtgg accgttacct ggccattgtc    420

catgccacac gcacactgac ccagaagcgt cacttggtca agtttgtttg tcttggctgc    480

tggggactgt ctatgaatct gtccctgccc ttcttccttt tccgccaggc ttaccatcca    540

aacaattcca gtccagtttg ctatgaggtc ctgggaaatg acacagcaaa atggcggatg    600

gtgttgcgga tcctgcctca cacctttggc ttcatcgtgc cgctgtttgt catgctgttc    660

tgctatggat tcaccctgcg tacactgttt aaggcccaca tggggcagaa gcaccgagcc    720

atgagggtca tctttgctgt cgtcctcatc ttcctgcttt gctggctgcc ctacaacctg    780

gtcctgctgg cagacaccct catgaggacc caggtgatcc aggagagctg tgagcgccgc    840

aacaacatcg gccgggccct ggatgccact gagattctgg gatttctcca tagctgcctc    900

aaccccatca tctacgcctt catcggccaa aattttcgcc atggattcct caagatcctg    960

gctatgcatg gcctggtcag caaggagttc ttggcacgtc atcgtgttac ctcctacact   1020

tcttcgtctg tcaatgtctc ttccaacctc tga                                1053


<210> SEQ ID NO 51
<211> LENGTH: 360
<212> TYPE: PRT
<213> ORGANISM: Homo sapiens
<220> FEATURE:
<221> NAME/KEY: source
<223> OTHER INFORMATION: /note="CXCR2"

<400> SEQUENCE: 51

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
```

```
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360
```

<210> SEQ ID NO 52
<211> LENGTH: 1083
<212> TYPE: DNA
<213> ORGANISM: Homo sapiens
<220> FEATURE:
<221> NAME/KEY: source
<223> OTHER INFORMATION: /note="CXCR2"

<400> SEQUENCE: 52

```
atggaagatt ttaacatgga gagtgacagc tttgaagatt tctggaaagg tgaagatctt      60

agtaattaca gttacagctc taccctgccc ccttttctac tagatgccgc cccatgtgaa     120

ccagaatccc tggaaatcaa caagtatttt gtggtcatta tctatgccct ggtattcctg     180

ctgagcctgc tgggaaactc cctcgtgatg ctggtcatct tatacagcag ggtcggccgc     240

tccgtcactg atgtctacct gctgaaccta gccttggccg acctactctt tgccctgacc     300
```

-continued

```
ttgcccatct gggccgcctc caaggtgaat ggctggattt ttggcacatt cctgtgcaag    360

gtggtctcac tcctgaagga agtcaacttc tatagtggca tcctgctact ggcctgcatc    420

agtgtggacc gttacctggc cattgtccat gccacacgca cactgaccca gaagcgctac    480

ttggtcaaat tcatatgtct cagcatctgg ggtctgtcct tgctcctggc cctgcctgtc    540

ttacttttcc gaaggaccgt ctactcatcc aatgttagcc cagcctgcta tgaggacatg    600

ggcaacaata cagcaaactg gcggatgctg ttacggatcc tgccccagtc ctttggcttc    660

atcgtgccac tgctgatcat gctgttctgc tacggattca ccctgcgtac gctgtttaag    720

gcccacatgg ggcagaagca ccgggccatg cgggtcatct ttgctgtcgt cctcatcttc    780

ctgctctgct ggctgcccta caacctggtc ctgctggcag acaccctcat gaggacccag    840

gtgatccagg agacctgtga gcgccgcaat cacatcgacc gggctctgga tgccaccgag    900

attctgggca tccttcacag ctgcctcaac cccctcatct acgccttcat tggccagaag    960

tttcgccatg gactcctcaa gattctagct atacatggct tgatcagcaa ggactccctg   1020

cccaaagaca gcaggccttc ctttgttggc tcttcttcag ggcacacttc cactactctc   1080

taa                                                                 1083
```

<210> SEQ ID NO 53
<211> LENGTH: 355
<212> TYPE: PRT
<213> ORGANISM: Homo sapiens
<220> FEATURE:
<221> NAME/KEY: source
<223> OTHER INFORMATION: /note="CXC3CR1"

<400> SEQUENCE: 53

```
Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205
```

-continued

```
Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355
```

<210> SEQ ID NO 54
<211> LENGTH: 1068
<212> TYPE: DNA
<213> ORGANISM: Homo sapiens
<220> FEATURE:
<221> NAME/KEY: source
<223> OTHER INFORMATION: /note="CXC3CR1"

<400> SEQUENCE: 54

```
atggatcagt tccctgaatc agtgacagaa aactttgagt acgatgattt ggctgaggcc      60

tgttatattg ggacatcgt ggtctttggg actgtgttcc tgtccatatt ctactccgtc     120

atctttgcca ttggcctggt gggaaatttg ttggtagtgt ttgccctcac caacagcaag     180

aagcccaaga gtgtcaccga catttacctc ctgaacctgg ccttgtctga tctgctgttt     240

gtagccactt tgcccttctg gactcactat ttgataaatg aaaagggcct ccacaatgcc     300

atgtgcaaat tcactaccgc cttcttcttc atcggctttt ttggaagcat attcttcatc     360

accgtcatca gcattgatag gtacctggcc atcgtcctgg ccgccaactc catgaacaac     420

cggaccgtgc agcatggcgt caccatcagc ctaggcgtct gggcagcagc cattttggtg     480

gcagcacccc agttcatgtt cacaaagcag aaagaaaatg aatgccttgg tgactacccc     540

gaggtcctcc aggaaatctg gcccgtgctc cgcaatgtgg aaacaaattt tcttggcttc     600

ctactccccc tgctcattat gagttattgc tacttcagaa tcatccagac gctgttttcc     660

tgcaagaacc acaagaaagc caaagccatt aaactgatcc ttctggtggt catcgtgttt     720

ttcctcttct ggacacccta caacgttatg attttcctgg agacgcttaa gctctatgac     780

ttctttccca gttgtgacat gaggaaggat ctgaggctgg ccctcagtgt gactgagacg     840

gttgcattta gccattgttg cctgaatcct ctcatctatg catttgctgg ggagaagttc     900

agaagatacc tttaccacct gtatgggaaa tgcctggctg tcctgtgtgg gcgctcagtc     960

cacgttgatt tctcctcatc tgaatcacaa aggagcaggc atggaagtgt tctgagcagc    1020

aattttactt accacacgag tgatggagat gcattgctcc ttctctga                1068
```

<210> SEQ ID NO 55

<211> LENGTH: 373
<212> TYPE: PRT
<213> ORGANISM: Homo sapiens
<220> FEATURE:
<221> NAME/KEY: source
<223> OTHER INFORMATION: /note="ChemR23"

<400> SEQUENCE: 55

```
Met Arg Met Glu Asp Glu Asp Tyr Asn Thr Ser Ile Ser Tyr Gly Asp
1               5                   10                  15

Glu Tyr Pro Asp Tyr Leu Asp Ser Ile Val Val Leu Glu Asp Leu Ser
            20                  25                  30

Pro Leu Glu Ala Arg Val Thr Arg Ile Phe Leu Val Val Val Tyr Ser
        35                  40                  45

Ile Val Cys Phe Leu Gly Ile Leu Gly Asn Gly Leu Val Ile Ile Ile
    50                  55                  60

Ala Thr Phe Lys Met Lys Lys Thr Val Asn Met Val Trp Phe Leu Asn
65                  70                  75                  80

Leu Ala Val Ala Asp Phe Leu Phe Asn Val Phe Leu Pro Ile His Ile
                85                  90                  95

Thr Tyr Ala Ala Met Asp Tyr His Trp Val Phe Gly Thr Ala Met Cys
            100                 105                 110

Lys Ile Ser Asn Phe Leu Leu Ile His Asn Met Phe Thr Ser Val Phe
        115                 120                 125

Leu Leu Thr Ile Ile Ser Ser Asp Arg Cys Ile Ser Val Leu Leu Pro
    130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
            180                 185                 190

Phe Ser Leu Ser Thr Pro Gly Ser Ser Ser Trp Pro Thr His Ser Gln
        195                 200                 205

Met Asp Pro Val Gly Tyr Ser Arg His Met Val Val Thr Val Thr Arg
    210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Ile Val Thr Ile Ile Ile Thr Phe Phe Leu Cys
            260                 265                 270

Trp Cys Pro Tyr His Thr Leu Asn Leu Leu Glu Leu His His Thr Ala
        275                 280                 285

Met Pro Gly Ser Val Phe Ser Leu Gly Leu Pro Leu Ala Thr Ala Leu
    290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
            340                 345                 350

Phe Thr Lys Met Ser Ser Met Asn Glu Arg Thr Ser Met Asn Glu Arg
        355                 360                 365

Glu Thr Gly Met Leu
```

370

<210> SEQ ID NO 56
<211> LENGTH: 1122
<212> TYPE: DNA
<213> ORGANISM: Homo sapiens
<220> FEATURE:
<221> NAME/KEY: source
<223> OTHER INFORMATION: /note="ChemR23"

<400> SEQUENCE: 56
atgagaatgg aggatgaaga ttacaacact tccatcagtt acggtgatga ataccctgat 60
tatttagact ccattgtggt tttggaggac ttatccccct tggaagccag ggtgaccagg 120
atcttcctgg tggtggtcta cagcatcgtc tgcttcctcg ggattctggg caatggtctg 180
gtgatcatca ttgccacctt caagatgaag aagacagtga acatggtctg gttcctcaac 240
ctggcagtgg cagatttcct gttcaacgtc ttcctcccaa tccatatcac ctatgccgcc 300
atggactacc actgggtttt cgggacagcc atgtgcaaga tcagcaactt ccttctcatc 360
cacaacatgt tcaccagcgt cttcctgctg accatcatca gctctgaccg ctgcatctct 420
gtgctcctcc ctgtctggtc ccagaaccac cgcagcgttc gcctggctta catggcctgc 480
atggtcatct gggtcctggc tttcttcttg agttccccat ctctcgtctt ccgggacaca 540
gccaacctgc atgggaaaat atcctgcttc aacaacttca gcctgtccac acctgggtct 600
tcctcgtggc ccactcactc ccaaatggac cctgtggggt atagccggca catggtggtg 660
actgtcaccc gcttcctctg tggcttcctg gtcccagtcc tcatcatcac agcttgctac 720
ctcaccatcg tgtgcaaact gcagcgcaac cgcctggcca agaccaagaa gcccttcaag 780
attattgtga ccatcatcat taccttcttc ctctgctggt gcccctacca cacactcaac 840
ctcctagagc tccaccacac tgccatgcct ggctctgtct tcagcctggg tttgcccctg 900
gccactgccc ttgccattgc caacagctgc atgaacccca ttctgtatgt tttcatgggt 960
caggacttca agaagttcaa ggtggccctc ttctctcgcc tggtcaatgc tctaagtgaa 1020
gatacaggcc actcttccta ccccagccat agaagcttta ccaagatgtc atcaatgaat 1080
gagaggactt ctatgaatga gagggagacc ggcatgcttt ga 1122

<210> SEQ ID NO 57
<211> LENGTH: 352
<212> TYPE: PRT
<213> ORGANISM: Homo sapiens
<220> FEATURE:
<221> NAME/KEY: source
<223> OTHER INFORMATION: /note="CXCR4"

<400> SEQUENCE: 57

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

```
Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350
```

<210> SEQ ID NO 58
<211> LENGTH: 1071
<212> TYPE: DNA
<213> ORGANISM: Homo sapiens
<220> FEATURE:
<221> NAME/KEY: source
<223> OTHER INFORMATION: /note="CXCR4"

<400> SEQUENCE: 58

```
atgtccattc ctttgcctct tttgcagata tacacttcag ataactacac cgaggaaatg      60

ggctcagggg actatgactc catgaaggaa ccctgtttcc gtgaagaaaa tgctaatttc     120

aataaaatct tcctgcccac catctactcc atcatcttct taactggcat tgtgggcaat     180

ggattggtca tcctggtcat gggttaccag aagaaactga gaagcatgac ggacaagtac     240

aggctgcacc tgtcagtggc cgacctcctc tttgtcatca cgcttccctt ctgggcagtt     300

gatgccgtgg caaactggta ctttgggaac ttcctatgca aggcagtcca tgtcatctac     360

acagtcaacc tctacagcag tgtcctcatc ctggccttca tcagtctgga ccgctacctg     420

gccatcgtcc acgccaccaa cagtcagagg ccaaggaagc tgttggctga aaaggtggtc     480

tatgttggcg tctggatccc tgccctcctg ctgactattc ccgacttcat ctttgccaac     540

gtcagtgagg cagatgacag atatatctgt gaccgcttct accccaatga cttgtgggtg     600
```

-continued

```
gttgtgttcc agtttcagca catcatggtt ggccttatcc tgcctggtat tgtcatcctg    660

tcctgctatt gcattatcat ctccaagctg tcacactcca agggccacca gaagcgcaag    720

gccctcaaga ccacagtcat cctcatcctg gctttcttcg cctgttggct gccttactac    780

attgggatca gcatcgactc cttcatcctc ctggaaatca tcaagcaagg gtgtgagttt    840

gagaacactg tgcacaagtg gatttccatc accgaggccc tagctttctt ccactgttgt    900

ctgaacccca tcctctatgc tttccttgga gccaaattta aaacctctgc ccagcacgca    960

ctcacctctg tgagcagagg gtccagcctc aagatcctct ccaaaggaaa gcgaggtgga   1020

cattcatctg tttccactga gtctgagtct tcaagttttc actccagcta a            1071
```

<210> SEQ ID NO 59
<211> LENGTH: 352
<212> TYPE: PRT
<213> ORGANISM: Homo sapiens
<220> FEATURE:
<221> NAME/KEY: source
<223> OTHER INFORMATION: /note="CCR5"

<400> SEQUENCE: 59

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270
```

-continued

```
Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 60
<211> LENGTH: 1059
<212> TYPE: DNA
<213> ORGANISM: Homo sapiens
<220> FEATURE:
<221> NAME/KEY: source
<223> OTHER INFORMATION: /note="CCR5"

<400> SEQUENCE: 60

```
atggattatc aagtgtcaag tccaatctat gacatcaatt attatacatc ggagccctgc      60

caaaaaatca atgtgaagca aatcgcagcc cgcctcctgc ctccgctcta ctcactggtg     120

ttcatctttg gttttgtggg caacatgctg gtcatcctca tcctgataaa ctgcaaaagg     180

ctgaagagca tgactgacat ctacctgctc aacctggcca tctctgacct gtttttcctt     240

cttactgtcc ccttctgggc tcactatgct gccgcccagt gggactttgg aaatacaatg     300

tgtcaactct tgacagggct ctattttata ggcttcttct ctggaatctt cttcatcatc     360

ctcctgacaa tcgataggta cctggctgtc gtccatgctg tgtttgcttt aaaagccagg     420

acggtcacct ttggggtggt gacaagtgtg atcacttggg tggtggctgt gtttgcgtct     480

ctcccaggaa tcatctttac cagatctcaa aaagaaggtc ttcattacac ctgcagctct     540

cattttccat acagtcagta tcaattctgg aagaatttcc agacattaaa gatagtcatc     600

ttggggctgg tcctgccgct gcttgtcatg gtcatctgct actcgggaat cctaaaaact     660

ctgcttcggt gtcgaaatga gaagaagagg cacagggctg tgaggcttat cttcaccatc     720

atgattgttt attttctctt ctgggctccc tacaacattg tccttctcct gaacaccttc     780

caggaattct ttggcctgaa taattgcagt agctctaaca ggttggacca agctatgcag     840

gtgacagaga ctcttgggat gacgcactgc tgcatcaacc ccatcatcta tgcctttgtc     900

ggggagaagt tcagaaacta cctcttagtc ttcttccaaa agcacattgc caaacgcttc     960

tgcaaatgct gttctatttt ccagcaagag gctcccgagc gagcaagctc agtttacacc    1020

cgatccactg gggagcagga aatatctgtg ggcttgtga                           1059
```

<210> SEQ ID NO 61
<211> LENGTH: 398
<212> TYPE: PRT
<213> ORGANISM: Homo sapiens
<220> FEATURE:
<221> NAME/KEY: source
<223> OTHER INFORMATION: /note="S1P5"

<400> SEQUENCE: 61

```
Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30
```

-continued

```
Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395
```

<210> SEQ ID NO 62
<211> LENGTH: 1197
<212> TYPE: DNA
<213> ORGANISM: Homo sapiens
<220> FEATURE:
<221> NAME/KEY: source
<223> OTHER INFORMATION: /note="S1P5"

<400> SEQUENCE: 62
atggagtcgg ggctgctgcg gccggcgccg gtgagcgagg tcatcgtcct gcattacaac 60
tacaccggca agctccgcgg tgcgcgctac cagccgggtg ccggcctgcg cgccgacgcc 120
gtggtgtgcc tggcggtgtg cgccttcatc gtgctagaga atctagccgt gttgttggtg 180
ctcggacgcc acccgcgctt ccacgctccc atgttcctgc tcctgggcag cctcacgttg 240
tcggatctgc tggcaggcgc cgcctacgcc gccaacatcc tactgtcggg gccgctcacg 300
ctgaaactgt cccccgcgct ctggttcgca cgggagggag gcgtcttcgt ggcactcact 360
gcgtccgtgc tgagcctcct ggccatcgcg ctggagcgca gcctcaccat ggcgcgcagg 420
gggcccgcgc ccgtctccag tcgggggcgc acgctggcga tggcagccgc ggcctggggc 480
gtgtcgctgc tcctcgggct cctgccagcg ctgggctgga attgcctggg tcgcctggac 540
gcttgctcca ctgtcttgcc gctctacgcc aaggcctacg tgctcttctg cgtgctcgcc 600
ttcgtgggca tcctggccgc tatctgtgca ctctacgcgc gcatctactg ccaggtacgc 660
gccaacgcgc ggcgcctgcc ggcacggccc gggactgcgg ggaccacctc gacccgggcg 720
cgtcgcaagc cgcgctcgct ggccttgctg cgcacgctca gcgtggtgct cctggccttt 780
gtggcatgtt ggggcccct cttcctgctg ctgttgctcg acgtggcgtg cccggcgcgc 840
acctgtcctg tactcctgca ggccgatccc ttcctgggac tggccatggc caactcactt 900
ctgaacccca tcatctacac gctcaccaac cgcgacctgc gccacgcgct cctgcgcctg 960
gtctgctgcg gacgccactc ctgcggcaga gacccgagtg gctcccagca gtcggcgagc 1020
gcggctgagg cttccggggg cctgcgccgc tgcctgcccc cgggccttga tgggagcttc 1080
agcggctcgg agcgctcatc gccccagcgc gacgggctgg acaccagcgg ctccacaggc 1140
agccccggtg cacccacagc cgcccggact ctggtatcag aaccggctgc agactga 1197

<210> SEQ ID NO 63
<211> LENGTH: 951
<212> TYPE: PRT
<213> ORGANISM: Homo sapiens
<220> FEATURE:
<221> NAME/KEY: source
<223> OTHER INFORMATION: /note="cKit"

<400> SEQUENCE: 63

Gln Pro Ser Val Ser Pro Gly Glu Pro Ser Pro Pro Ser Ile His Pro
1 5 10 15

Gly Lys Ser Asp Leu Ile Val Arg Val Gly Asp Glu Ile Arg Leu Leu
20 25 30

Cys Thr Asp Pro Gly Phe Val Lys Trp Thr Phe Glu Ile Leu Asp Glu
35 40 45

Thr Asn Glu Asn Lys Gln Asn Glu Trp Ile Thr Glu Lys Ala Glu Ala
50 55 60

Thr Asn Thr Gly Lys Tyr Thr Cys Thr Asn Lys His Gly Leu Ser Asn
65 70 75 80

Ser Ile Tyr Val Phe Val Arg Asp Pro Ala Lys Leu Phe Leu Val Asp
85 90 95

Arg Ser Leu Tyr Gly Lys Glu Asp Asn Asp Thr Leu Val Arg Cys Pro
100 105 110

Leu Thr Asp Pro Glu Val Thr Asn Tyr Ser Leu Lys Gly Cys Gln Gly
115 120 125

Lys Pro Leu Pro Lys Asp Leu Arg Phe Ile Pro Asp Pro Lys Ala Gly
130 135 140

```
Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
            180                 185                 190

Lys Ala Ser Tyr Leu Leu Arg Glu Gly Glu Glu Phe Thr Val Thr Cys
        195                 200                 205

Thr Ile Lys Asp Val Ser Ser Ser Val Tyr Ser Thr Trp Lys Arg Glu
    210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
            260                 265                 270

Ser Ala Asn Val Thr Thr Thr Leu Glu Val Val Asp Lys Gly Phe Ile
        275                 280                 285

Asn Ile Phe Pro Met Ile Asn Thr Thr Val Phe Val Asn Asp Gly Glu
    290                 295                 300

Asn Val Asp Leu Ile Val Glu Tyr Glu Ala Phe Pro Lys Pro Glu His
305                 310                 315                 320

Gln Gln Trp Ile Tyr Met Asn Arg Thr Phe Thr Asp Lys Trp Glu Asp
                325                 330                 335

Tyr Pro Lys Ser Glu Asn Glu Ser Asn Ile Arg Tyr Val Ser Glu Leu
            340                 345                 350

His Leu Thr Arg Leu Lys Gly Thr Glu Gly Gly Thr Tyr Thr Phe Leu
        355                 360                 365

Val Ser Asn Ser Asp Val Asn Ala Ala Ile Ala Phe Asn Val Tyr Val
    370                 375                 380

Asn Thr Lys Pro Glu Ile Leu Thr Tyr Asp Arg Leu Val Asn Gly Met
385                 390                 395                 400

Leu Gln Cys Val Ala Ala Gly Phe Pro Glu Pro Thr Ile Asp Trp Tyr
                405                 410                 415

Phe Cys Pro Gly Thr Glu Gln Arg Cys Ser Ala Ser Val Leu Pro Val
            420                 425                 430

Asp Val Gln Thr Leu Asn Ser Ser Gly Pro Pro Phe Gly Lys Leu Val
        435                 440                 445

Val Gln Ser Ser Ile Asp Ser Ser Ala Phe Lys His Asn Gly Thr Val
    450                 455                 460

Glu Cys Lys Ala Tyr Asn Asp Val Gly Lys Thr Ser Ala Tyr Phe Asn
465                 470                 475                 480

Phe Ala Phe Lys Gly Asn Asn Lys Glu Gln Ile His Pro His Thr Leu
                485                 490                 495

Phe Thr Pro Leu Leu Ile Gly Phe Val Ile Val Ala Gly Met Met Cys
            500                 505                 510

Ile Ile Val Met Ile Leu Thr Tyr Lys Tyr Leu Gln Lys Pro Met Tyr
        515                 520                 525

Glu Val Gln Trp Lys Val Val Glu Glu Ile Asn Gly Asn Asn Tyr Val
    530                 535                 540

Tyr Ile Asp Pro Thr Gln Leu Pro Tyr Asp His Lys Trp Glu Phe Pro
545                 550                 555                 560

Arg Asn Arg Leu Ser Phe Gly Lys Thr Leu Gly Ala Gly Ala Phe Gly
```

```
                565                 570                 575

Lys Val Val Glu Ala Thr Ala Tyr Gly Leu Ile Lys Ser Asp Ala Ala
            580                 585                 590

Met Thr Val Ala Val Lys Met Leu Lys Pro Ser Ala His Leu Thr Glu
        595                 600                 605

Arg Glu Ala Leu Met Ser Glu Leu Lys Val Leu Ser Tyr Leu Gly Asn
    610                 615                 620

His Met Asn Ile Val Asn Leu Leu Gly Ala Cys Thr Ile Gly Gly Pro
625                 630                 635                 640

Thr Leu Val Ile Thr Glu Tyr Cys Cys Tyr Gly Asp Leu Leu Asn Phe
                645                 650                 655

Leu Arg Arg Lys Arg Asp Ser Phe Ile Cys Ser Lys Gln Glu Asp His
            660                 665                 670

Ala Glu Ala Ala Leu Tyr Lys Asn Leu Leu His Ser Lys Glu Ser Ser
        675                 680                 685

Cys Ser Asp Ser Thr Asn Glu Tyr Met Asp Met Lys Pro Gly Val Ser
    690                 695                 700

Tyr Val Val Pro Thr Lys Ala Asp Lys Arg Arg Ser Val Arg Ile Gly
705                 710                 715                 720

Ser Tyr Ile Glu Arg Asp Val Thr Pro Ala Ile Met Glu Asp Asp Glu
                725                 730                 735

Leu Ala Leu Asp Leu Glu Asp Leu Leu Ser Phe Ser Tyr Gln Val Ala
            740                 745                 750

Lys Gly Met Ala Phe Leu Ala Ser Lys Asn Cys Ile His Arg Asp Leu
        755                 760                 765

Ala Ala Arg Asn Ile Leu Leu Thr His Gly Arg Ile Thr Lys Ile Cys
    770                 775                 780

Asp Phe Gly Leu Ala Arg Asp Ile Lys Asn Asp Ser Asn Tyr Val Val
785                 790                 795                 800

Lys Gly Asn Ala Arg Leu Pro Val Lys Trp Met Ala Pro Glu Ser Ile
                805                 810                 815

Phe Asn Cys Val Tyr Thr Phe Glu Ser Asp Val Trp Ser Tyr Gly Ile
            820                 825                 830

Phe Leu Trp Glu Leu Phe Ser Leu Gly Ser Ser Pro Tyr Pro Gly Met
        835                 840                 845

Pro Val Asp Ser Lys Phe Tyr Lys Met Ile Lys Glu Gly Phe Arg Met
    850                 855                 860

Leu Ser Pro Glu His Ala Pro Ala Glu Met Tyr Asp Ile Met Lys Thr
865                 870                 875                 880

Cys Trp Asp Ala Asp Pro Leu Lys Arg Pro Thr Phe Lys Gln Ile Val
                885                 890                 895

Gln Leu Ile Glu Lys Gln Ile Ser Glu Ser Thr Asn His Ile Tyr Ser
            900                 905                 910

Asn Leu Ala Asn Cys Ser Pro Asn Arg Gln Lys Pro Val Val Asp His
        915                 920                 925

Ser Val Arg Ile Asn Ser Val Gly Ser Thr Ala Ser Ser Ser Gln Pro
    930                 935                 940

Leu Leu Val His Asp Asp Val
945                 950
```

<210> SEQ ID NO 64
<211> LENGTH: 2931
<212> TYPE: DNA
<213> ORGANISM: Homo sapiens
<220> FEATURE:
<221> NAME/KEY: source
<223> OTHER INFORMATION: /note="cKit"

<400> SEQUENCE: 64

```
atgagaggcg ctcgcggcgc ctgggatttt ctctgcgttc tgctcctact gcttcgcgtc     60

cagacaggct cttctcaacc atctgtgagt ccaggggaac cgtctccacc atccatccat    120

ccaggaaaat cagacttaat agtccgcgtg ggcgacgaga ttaggctgtt atgcactgat    180

ccgggctttg tcaaatggac ttttgagatc ctggatgaaa cgaatgagaa taagcagaat    240

gaatggatca cggaaaaggc agaagccacc aacaccggca aatacacgtg caccaacaaa    300

cacggcttaa gcaattccat ttatgtgttt gttagagatc ctgccaagct tttccttgtt    360

gaccgctcct tgtatgggaa agaagacaac gacacgctgg tccgctgtcc tctcacagac    420

ccagaagtga ccaattattc cctcaagggg tgccagggga agcctcttcc caaggacttg    480

aggtttattc ctgaccccaa ggcgggcatc atgatcaaaa gtgtgaaacg cgcctaccat    540

cggctctgtc tgcattgttc tgtggaccag gagggcaagt cagtgctgtc ggaaaaattc    600

atcctgaaag tgaggccagc cttcaaagct gtgcctgttg tgtctgtgtc caaagcaagc    660

tatcttctta gggaagggga agaattcaca gtgacgtgca caataaaaga tgtgtctagt    720

tctgtgtact caacgtggaa aagagaaaac agtcagacta aactacagga gaaatataat    780

agctggcatc acggtgactt caattatgaa cgtcaggcaa cgttgactat cagttcagcg    840

agagttaatg attctggagt gttcatgtgt tatgccaata atacttttgg atcagcaaat    900

gtcacaacaa ccttggaagt agtagataaa ggattcatta atatcttccc catgataaac    960

actacagtat ttgtaaacga tggagaaaat gtagatttga ttgttgaata tgaagcattc   1020

cccaaacctg aacaccagca gtggatctat atgaacagaa ccttcactga taaatgggaa   1080

gattatccca agtctgagaa tgaaagtaat atcagatacg taagtgaact tcatctaacg   1140

agattaaaag gcaccgaagg aggcacttac acattcctag tgtccaattc tgacgtcaat   1200

gctgccatag catttaatgt ttatgtgaat acaaaaccag aaatcctgac ttacgacagg   1260

ctcgtgaatg gcatgctcca atgtgtggca gcaggattcc cagagcccac aatagattgg   1320

tatttttgtc caggaactga gcagagatgc tctgcttctg tactgccagt ggatgtgcag   1380

acactaaact catctgggcc accgtttgga aagctagtgg ttcagagttc tatagattct   1440

agtgcattca agcacaatgg cacggttgaa tgtaaggctt acaacgatgt gggcaagact   1500

tctgcctatt ttaactttgc atttaaaggt aacaacaaag agcaaatcca tccccacacc   1560

ctgttcactc ctttgctgat tggtttcgta atcgtagctg gcatgatgtg cattattgtg   1620

atgattctga cctacaaata tttacagaaa cccatgtatg aagtacagtg gaaggttgtt   1680

gaggagataa atggaaacaa ttatgtttac atagacccaa cacaacttcc ttatgatcac   1740

aaatgggagt ttcccagaaa caggctgagt tttgggaaaa ccctgggtgc tggagctttc   1800

gggaaggttg ttgaggcaac tgcttatggc ttaattaagt cagatgcggc catgactgtc   1860

gctgtaaaga tgctcaagcc gagtgcccat ttgacagaac gggaagccct catgtctgaa   1920

ctcaaagtcc tgagttacct tggtaatcac atgaatattg tgaatctact tggagcctgc   1980

accattggag ggcccaccct ggtcattaca gaatattgtt gctatggtga tcttttgaat   2040

tttttgagaa gaaaacgtga ttcatttatt tgttcaaagc aggaagatca tgcagaagct   2100

gcactttata agaatcttct gcattcaaag gagtcttcct gcagcgatag tactaatgag   2160

tacatggaca tgaaacctgg agtttcttat gttgtcccaa ccaaggccga caaaaggaga   2220
```

```
tctgtgagaa taggctcata catagaaaga gatgtgactc ccgccatcat ggaggatgac   2280

gagttggccc tagacttaga agacttgctg agcttttctt accaggtggc aaagggcatg   2340

gctttcctcg cctccaagaa ttgtattcac agagacttgg cagccagaaa tatcctcctt   2400

actcatggtc ggatcacaaa gatttgtgat tttggtctag ccagagacat caagaatgat   2460

tctaattatg tggttaaagg aaacgctcga ctacctgtga agtggatggc acctgaaagc   2520

attttcaact gtgtatacac gtttgaaagt gacgtctggt cctatgggat tttctttgg   2580

gagctgttct ctttaggaag cagcccctat cctggaatgc cggtcgattc taagttctac   2640

aagatgatca aggaaggctt ccggatgctc agccctgaac acgcacctgc tgaaatgtat   2700

gacataatga agacttgctg ggatgcagat cccctaaaaa gaccaacatt caagcaaatt   2760

gttcagctaa ttgagaagca gatttcagag agcaccaatc atatttactc caacttagca   2820

aactgcagcc ccaaccgaca gaagcccgtg gtagaccatt ctgtgcggat caattctgtc   2880

ggcagcaccg cttcctcctc ccagcctctg cttgtgcacg acgatgtctg a            2931
```

<210> SEQ ID NO 65
<211> LENGTH: 2549
<212> TYPE: PRT
<213> ORGANISM: Homo sapiens
<220> FEATURE:
<221> NAME/KEY: source
<223> OTHER INFORMATION: /note="mTor"

<400> SEQUENCE: 65

```
Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
```

-continued

```
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655
```

```
Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                1005

Arg Glu  Phe Leu Phe Gln Gln  Leu Gly Met Leu Val  Ser Phe Val
    1010                1015                1020

Lys Ser  His Ile Arg Pro Tyr  Met Asp Glu Ile Val  Thr Leu Met
    1025                1030                1035

Arg Glu  Phe Trp Val Met Asn  Thr Ser Ile Gln Ser  Thr Ile Ile
    1040                1045                1050

Leu Leu  Ile Glu Gln Ile Val  Val Ala Leu Gly Gly  Glu Phe Lys
    1055                1060                1065
```

```
Leu Tyr  Leu Pro Gln Leu Ile  Pro His Met Leu Arg  Val Phe Met
    1070                 1075                 1080

His Asp  Asn Ser Pro Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110

Leu Leu  Pro Pro Ile Val Lys  Leu Phe Asp Ala Pro  Glu Ala Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185

Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Gly  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
    1340                 1345                 1350

Thr Gln  Thr Leu Leu Asn Leu  Ala Glu Phe Met Glu  His Ser Asp
    1355                 1360                 1365

Lys Gly  Pro Leu Pro Leu Arg  Asp Asp Asn Gly Ile  Val Leu Leu
    1370                 1375                 1380

Gly Glu  Arg Ala Ala Lys Cys  Arg Ala Tyr Ala Lys  Ala Leu His
    1385                 1390                 1395

Tyr Lys  Glu Leu Glu Phe Gln  Lys Gly Pro Thr Pro  Ala Ile Leu
    1400                 1405                 1410

Glu Ser  Leu Ile Ser Ile Asn  Asn Lys Leu Gln Gln  Pro Glu Ala
    1415                 1420                 1425

Ala Ala  Gly Val Leu Glu Tyr  Ala Met Lys His Phe  Gly Glu Leu
    1430                 1435                 1440

Glu Ile  Gln Ala Thr Trp Tyr  Glu Lys Leu His Glu  Trp Glu Asp
    1445                 1450                 1455

Ala Leu  Val Ala Tyr Asp Lys  Lys Met Asp Thr Asn  Lys Asp Asp
```

```
1460                1465                1470

Pro Glu Leu Met Leu Gly Arg Met Arg Cys Leu Glu Ala Leu Gly
    1475                1480                1485

Glu Trp Gly Gln Leu His Gln Gln Cys Cys Glu Lys Trp Thr Leu
    1490                1495                1500

Val Asn Asp Glu Thr Gln Ala Lys Met Ala Arg Met Ala Ala Ala
    1505                1510                1515

Ala Ala Trp Gly Leu Gly Gln Trp Asp Ser Met Glu Glu Tyr Thr
    1520                1525                1530

Cys Met Ile Pro Arg Asp Thr His Asp Gly Ala Phe Tyr Arg Ala
    1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
    1565                1570                1575

Ala Gly Glu Ser Tyr Ser Arg Ala Tyr Gly Ala Met Val Ser Cys
    1580                1585                1590

His Met Leu Ser Glu Leu Glu Glu Val Ile Gln Tyr Lys Leu Val
    1595                1600                1605

Pro Glu Arg Arg Glu Ile Ile Arg Gln Ile Trp Trp Glu Arg Leu
    1610                1615                1620

Gln Gly Cys Gln Arg Ile Val Glu Asp Trp Gln Lys Ile Leu Met
    1625                1630                1635

Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Val His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860
```

```
Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905

Leu Trp Phe Asp Tyr Gly His Trp Pro Asp Val Asn Glu Ala Leu
    1910                1915                1920

Val Glu Gly Val Lys Ala Ile Gln Ile Asp Thr Trp Leu Gln Val
    1925                1930                1935

Ile Pro Gln Leu Ile Ala Arg Ile Asp Thr Pro Arg Pro Leu Val
    1940                1945                1950

Gly Arg Leu Ile His Gln Leu Leu Thr Asp Ile Gly Arg Tyr His
    1955                1960                1965

Pro Gln Ala Leu Ile Tyr Pro Leu Thr Val Ala Ser Lys Ser Thr
    1970                1975                1980

Thr Thr Ala Arg His Asn Ala Ala Asn Lys Ile Leu Lys Asn Met
    1985                1990                1995

Cys Glu His Ser Asn Thr Leu Val Gln Gln Ala Met Met Val Ser
    2000                2005                2010

Glu Glu Leu Ile Arg Val Ala Ile Leu Trp His Glu Met Trp His
    2015                2020                2025

Glu Gly Leu Glu Glu Ala Ser Arg Leu Tyr Phe Gly Glu Arg Asn
    2030                2035                2040

Val Lys Gly Met Phe Glu Val Leu Glu Pro Leu His Ala Met Met
    2045                2050                2055

Glu Arg Gly Pro Gln Thr Leu Lys Glu Thr Ser Phe Asn Gln Ala
    2060                2065                2070

Tyr Gly Arg Asp Leu Met Glu Ala Gln Glu Trp Cys Arg Lys Tyr
    2075                2080                2085

Met Lys Ser Gly Asn Val Lys Asp Leu Thr Gln Ala Trp Asp Leu
    2090                2095                2100

Tyr Tyr His Val Phe Arg Arg Ile Ser Lys Gln Leu Pro Gln Leu
    2105                2110                2115

Thr Ser Leu Glu Leu Gln Tyr Val Ser Pro Lys Leu Leu Met Cys
    2120                2125                2130

Arg Asp Leu Glu Leu Ala Val Pro Gly Thr Tyr Asp Pro Asn Gln
    2135                2140                2145

Pro Ile Ile Arg Ile Gln Ser Ile Ala Pro Ser Leu Gln Val Ile
    2150                2155                2160

Thr Ser Lys Gln Arg Pro Arg Lys Leu Thr Leu Met Gly Ser Asn
    2165                2170                2175

Gly His Glu Phe Val Phe Leu Leu Lys Gly His Glu Asp Leu Arg
    2180                2185                2190

Gln Asp Glu Arg Val Met Gln Leu Phe Gly Leu Val Asn Thr Leu
    2195                2200                2205

Leu Ala Asn Asp Pro Thr Ser Leu Arg Lys Asn Leu Ser Ile Gln
    2210                2215                2220

Arg Tyr Ala Val Ile Pro Leu Ser Thr Asn Ser Gly Leu Ile Gly
    2225                2230                2235

Trp Val Pro His Cys Asp Thr Leu His Ala Leu Ile Arg Asp Tyr
    2240                2245                2250
```

```
Arg Glu  Lys Lys Lys Ile Leu  Leu Asn Ile Glu His  Arg Ile Met
    2255                 2260                 2265

Leu Arg  Met Ala Pro Asp Tyr  Asp His Leu Thr Leu  Met Gln Lys
    2270                 2275                 2280

Val Glu  Val Phe Glu His Ala  Val Asn Asn Thr Ala  Gly Asp Asp
    2285                 2290                 2295

Leu Ala  Lys Leu Leu Trp Leu  Lys Ser Pro Ser Ser  Glu Val Trp
    2300                 2305                 2310

Phe Asp  Arg Arg Thr Asn Tyr  Thr Arg Ser Leu Ala  Val Met Ser
    2315                 2320                 2325

Met Val  Gly Tyr Ile Leu Gly  Leu Gly Asp Arg His  Pro Ser Asn
    2330                 2335                 2340

Leu Met  Leu Asp Arg Leu Ser  Gly Lys Ile Leu His  Ile Asp Phe
    2345                 2350                 2355

Gly Asp  Cys Phe Glu Val Ala  Met Thr Arg Glu Lys  Phe Pro Glu
    2360                 2365                 2370

Lys Ile  Pro Phe Arg Leu Thr  Arg Met Leu Thr Asn  Ala Met Glu
    2375                 2380                 2385

Val Thr  Gly Leu Asp Gly Asn  Tyr Arg Ile Thr Cys  His Thr Val
    2390                 2395                 2400

Met Glu  Val Leu Arg Glu His  Lys Asp Ser Val Met  Ala Val Leu
    2405                 2410                 2415

Glu Ala  Phe Val Tyr Asp Pro  Leu Leu Asn Trp Arg  Leu Met Asp
    2420                 2425                 2430

Thr Asn  Thr Lys Gly Asn Lys  Arg Ser Arg Thr Arg  Thr Asp Ser
    2435                 2440                 2445

Tyr Ser  Ala Gly Gln Ser Val  Glu Ile Leu Asp Gly  Val Glu Leu
    2450                 2455                 2460

Gly Glu  Pro Ala His Lys Lys  Thr Gly Thr Thr Val  Pro Glu Ser
    2465                 2470                 2475

Ile His  Ser Phe Ile Gly Asp  Gly Leu Val Lys Pro  Glu Ala Leu
    2480                 2485                 2490

Asn Lys  Lys Ala Ile Gln Ile  Ile Asn Arg Val Arg  Asp Lys Leu
    2495                 2500                 2505

Thr Gly  Arg Asp Phe Ser His  Asp Asp Thr Leu Asp  Val Pro Thr
    2510                 2515                 2520

Gln Val  Glu Leu Leu Ile Lys  Gln Ala Thr Ser His  Glu Asn Leu
    2525                 2530                 2535

Cys Gln  Cys Tyr Ile Gly Trp  Cys Pro Phe Trp
    2540                 2545
```

<210> SEQ ID NO 66
<211> LENGTH: 7650
<212> TYPE: DNA
<213> ORGANISM: Homo sapiens
<220> FEATURE:
<221> NAME/KEY: source
<223> OTHER INFORMATION: /note="mTor"

<400> SEQUENCE: 66

```
atgcttggaa ccggacctgc cgccgccacc accgctgcca ccacatctag caatgtgagc     60

gtcctgcagc agtttgccag tggcctaaag agccggaatg aggaaaccag ggccaaagcc    120

gccaaggagc tccagcacta tgtcaccatg gaactccgag agatgagtca agaggagtct    180

actcgcttct atgaccaact gaaccatcac atttttgaat tggtttccag ctcagatgcc    240
```

-continued

```
aatgagagga aaggtggcat cttggccata gctagcctca taggagtgga aggtgggaat    300
gccacccgaa ttggcagatt tgccaactat cttcggaacc tcctcccctc caatgaccca    360
gttgtcatgg aaatggcatc caaggccatt ggccgtcttg ccatggcagg ggacactttt    420
accgctgagt acgtggaatt tgaggtgaag cgagccctgg aatggctggg tgctgaccgc    480
aatgagggcc ggagacatgc agctgtcctg gttctccgtg agctggccat cagcgtccct    540
accttcttct tccagcaagt gcaacccttc tttgacaaca tttttgtggc cgtgtgggac    600
cccaaacagg ccatccgtga gggagctgta gccgcccttc gtgcctgtct gattctcaca    660
acccagcgtg agccgaagga gatgcagaag cctcagtggt acaggcacac atttgaagaa    720
gcagagaagg gatttgatga gaccttggcc aaagagaagg gcatgaatcg ggatgatcgg    780
atccatggag ccttgttgat ccttaacgag ctggtccgaa tcagcagcat ggagggagag    840
cgtctgagag aagaaatgga agaaatcaca cagcagcagc tggtacacga caagtactgc    900
aaagatctca tgggcttcgg aacaaaacct cgtcacatta ccccttcac cagtttccag    960
gctgtacagc cccagcagtc aaatgccttg gtggggctgc tggggtacag ctctcaccaa   1020
ggcctcatgg gatttgggac ctcccccagt ccagctaagt ccaccctggt ggagagccgg   1080
tgttgcagag acttgatgga ggagaaattt gatcaggtgt gccagtgggt gctgaaatgc   1140
aggaatagca agaactcgct gatccaaatg acaatcctta atttgttgcc ccgcttggct   1200
gcattccgac cttctgcctt cacagatacc cagtatctcc aagataccat gaaccatgtc   1260
ctaagctgtg tcaagaagga gaaggaacgt acagcggcct tccaagccct ggggctactt   1320
tctgtggctg tgaggtctga gtttaaggtc tatttgcctc gcgtgctgga catcatccga   1380
gcggccctgc ccccaaagga cttcgcccat aagaggcaga aggcaatgca ggtggatgcc   1440
acagtcttca cttgcatcag catgctggct cgagcaatgg ggccaggcat ccagcaggat   1500
atcaaggagc tgctggagcc catgctggca gtgggactaa gccctgccct cactgcagtg   1560
ctctacgacc tgagccgtca gattccacag ctaaagaagg acattcaaga tgggctactg   1620
aaaatgctgt ccctggtcct tatgcacaaa ccccttcgcc acccaggcat gcccaagggc   1680
ctggcccatc agctggcctc tcctggcctc acgaccctcc ctgaggccag cgatgtgggc   1740
agcatcactc ttgccctccg aacgcttggc agctttgaat ttgaaggcca ctctctgacc   1800
caatttgttc gccactgtgc ggatcatttc ctgaacagtg agcacaagga gatccgcatg   1860
gaggctgccc gcacctgctc ccgcctgctc acaccctcca tccacctcat cagtggccat   1920
gctcatgtgg ttagccagac cgcagtgcaa gtggtggcag atgtgcttag caaactgctc   1980
gtagttggga taacagatcc tgaccctgac attcgctact gtgtcttggc gtccctggac   2040
gagcgctttg atgcacacct ggcccaggcg gagaacttgc aggccttgtt tgtggctctg   2100
aatgaccagg tgtttgagat ccgggagctg gccatctgca ctgtgggccg actcagtagc   2160
atgaaccctg cctttgtcat gcctttcctg cgcaagatgc tcatccagat tttgacagag   2220
ttggagcaca gtgggattgg aagaatcaaa gagcagagtg cccgcatgct ggggcacctg   2280
gtctccaatg ccccccgact catccgcccc tacatggagc ctattctgaa ggcattaatt   2340
ttgaaactga aagatccaga ccctgatcca aacccaggtg tgatcaataa tgtcctggca   2400
acaataggag aattggcaca ggttagtggc ctggaaatga ggaaatgggt tgatgaactt   2460
tttattatca tcatggacat gctccaggat tcctctttgt tggccaaaag gcaggtggct   2520
ctgtggaccc tgggacagtt ggtggccagc actggctatg tagtagagcc ctacaggaag   2580
taccctactt tgcttgaggt gctactgaat tttctgaaga ctgagcagaa ccagggtaca   2640
```

```
cgcagagagg ccatccgtgt gttagggctt ttaggggctt tggatcctta caagcacaaa   2700
gtgaacattg gcatgataga ccagtcccgg gatgcctctg ctgtcagcct gtcagaatcc   2760
aagtcaagtc aggattcctc tgactatagc actagtgaaa tgctggtcaa catgggaaac   2820
ttgcctctgg atgagttcta cccagctgtg tccatggtgg ccctgatgcg gatcttccga   2880
gaccagtcac tctctcatca tcacaccatg gttgtccagg ccatcacctt catcttcaag   2940
tccctgggac tcaaatgtgt gcagttcctg ccccaggtca tgcccacgtt ccttaacgtc   3000
attcgagtct gtgatggggc catccgggaa tttttgttcc agcagctggg aatgttggtg   3060
tcctttgtga agagccacat cagaccttat atggatgaaa tagtcaccct catgagagaa   3120
ttctgggtca tgaacacctc aattcagagc acgatcattc ttctcattga gcaaattgtg   3180
gtagctcttg gggtgaatt taagctctac ctgccccagc tgatcccaca catgctgcgt    3240
gtcttcatgc atgacaacag cccaggccgc attgtctcta tcaagttact ggctgcaatc   3300
cagctgtttg gcgccaacct ggatgactac ctgcatttac tgctgcctcc tattgttaag   3360
ttgtttgatg cccctgaagc tccactgcca tctcgaaagg cagcgctaga gactgtggac   3420
cgcctgacgg agtccctgga tttcactgac tatgcctccc ggatcattca ccctattgtt   3480
cgaacactgg accagagccc agaactgcgc tccacagcca tggacacgct gtcttcactt   3540
gtttttcagc tggggaagaa gtaccaaatt ttcattccaa tggtgaataa agttctggtg   3600
cgacaccgaa tcaatcatca gcgctatgat gtgctcatct gcagaattgt caagggatac   3660
acacttgctg atgaagagga ggatcctttg atttaccagc atcggatgct taggagtggc   3720
caaggggatg cattggctag tggaccagtg gaaacaggac ccatgaagaa actgcacgtc   3780
agcaccatca acctccaaaa ggcctggggc gctgccagga gggtctccaa agatgactgg   3840
ctggaatggc tgagacggct gagcctggag ctgctgaagg actcatcatc gccctccctg   3900
cgctcctgct gggccctggc acaggcctac aacccgatgg ccagggatct cttcaatgct   3960
gcatttgtgt cctgctggtc tgaactgaat gaagatcaac aggatgagct catcagaagc   4020
atcgagttgg ccctcacctc acaagacatc gctgaagtca cacagaccct cttaaacttg   4080
gctgaattca tggaacacag tgacaagggc cccctgccac tgagagatga caatggcatt   4140
gttctgctgg gtgagagagc tgccaagtgc cgagcatatg ccaaagcact acactacaaa   4200
gaactggagt tccagaaagg ccccacccct gccattctag aatctctcat cagcattaat   4260
aataagctac agcagccgga ggcagcggcc ggagtgttag aatatgccat gaaacacttt   4320
ggagagctgg agatccaggc tacctggtat gagaaactgc acgagtggga ggatgccctt   4380
gtggcctatg acaagaaaat ggacaccaac aaggacgacc cagagctgat gctgggccgc   4440
atgcgctgcc tcgaggcctt gggggaatgg ggtcaactcc accagcagtg ctgtgaaaag   4500
tggaccctgg ttaatgatga gacccaagcc aagatggccc ggatggctgc tgcagctgca   4560
tggggtttag gtcagtggga cagcatggaa gaatacacct gtatgatccc tcgggacacc   4620
catgatgggg cattttatag agctgtgctg gcactgcatc aggacctctt ctccttggca   4680
caacagtgca ttgacaaggc cagggacctg ctggatgctg aattaactgc gatggcagga   4740
gagagttaca gtcgggcata tggggccatg gtttcttgcc acatgctgtc cgagctggag   4800
gaggttatcc agtacaaact tgtccccgag cgacgagaga tcatccgcca gatctggtgg   4860
gagagactgc agggctgcca gcgtatcgta gaggactggc agaaaatcct tatggtgcgg   4920
tcccttgtgg tcagccctca tgaagacatg agaacctggc tcaagtatgc aagcctgtgc   4980
```

-continued

```
ggcaagagtg gcaggctggc tcttgctcat aaaactttag tgttgctcct gggagttgat   5040
ccgtctcggc aacttgacca tcctctgcca acagttcacc ctcaggtgac ctatgcctac   5100
atgaaaaaca tgtggaagag tgcccgcaag atcgatgcct tccagcacat gcagcatttt   5160
gtccagacca tgcagcaaca ggcccagcat gccatcgcta ctgaggacca gcagcataag   5220
caggaactgc acaagctcat ggcccgatgc ttcctgaaac ttggagagtg gcagctgaat   5280
ctacagggca tcaatgagag cacaatcccc aaagtgctgc agtactacag cgccgccaca   5340
gagcacgacc gcagctggta caaggcctgg catgcgtggg cagtgatgaa cttcgaagct   5400
gtgctacact acaaacatca gaaccaagcc cgcgatgaga agaagaaact gcgtcatgcc   5460
agcggggcca acatcaccaa cgccaccact gccgccacca cggccgccac tgccaccacc   5520
actgccagca ccgagggcag caacagtgag agcgaggccg agagcaccga gaacagcccc   5580
accccatcgc cgctgcagaa gaaggtcact gaggatctgt ccaaaaccct cctgatgtac   5640
acggtgcctg ccgtccaggg cttcttccgt tccatctcct tgtcacgagg caacaacctc   5700
caggatacac tcagagttct caccttatgg tttgattatg gtcactggcc agatgtcaat   5760
gaggccttag tggagggggt gaaagccatc cagattgata cctggctaca ggttatacct   5820
cagctcattg caagaattga tacgcccaga cccttggtgg gacgtctcat tcaccagctt   5880
ctcacagaca ttggtcggta ccacccccag gccctcatct acccactgac agtggcttct   5940
aagtctacca cgacagcccg gcacaatgca gccaacaaga ttctgaagaa catgtgtgag   6000
cacagcaaca ccctggtcca gcaggccatg atggtgagcg aggagctgat ccgagtggcc   6060
atcctctggc atgagatgtg gcatgaaggc ctggaagagg catctcgttt gtactttggg   6120
gaaaggaacg tgaaaggcat gtttgaggtg ctggagccct tgcatgctat gatggaacgg   6180
ggcccccaga ctctgaagga aacatccttt aatcaggcct atggtcgaga tttaatggag   6240
gcccaagagt ggtgcaggaa gtacatgaaa tcagggaatg tcaaggacct cacccaagcc   6300
tgggacctct attatcatgt gttccgacga atctcaaagc agctgcctca gctcacatcc   6360
ttagagctgc aatatgtttc cccaaaactt ctgatgtgcc gggaccttga attggctgtg   6420
ccaggaacat atgaccccaa ccagccaatc attcgcattc agtccatagc accgtctttg   6480
caagtcatca catccaagca gaggccccgg aaattgacac ttatgggcag caacggacat   6540
gagtttgttt tccttctaaa aggccatgaa gatctgcgcc aggatgagcg tgtgatgcag   6600
ctcttcggcc tggttaacac ccttctggcc aatgacccaa catctcttcg gaaaaacctc   6660
agcatccaga gatacgctgt catcccttta tcgaccaact cgggcctcat tggctgggtt   6720
ccccactgtg acacactgca cgccctcatc cgggactaca gggagaagaa gaagatcctt   6780
ctcaacatcg agcatcgcat catgttgcgg atggctccgg actatgacca cttgactctg   6840
atgcagaagg tggaggtgtt tgagcatgcc gtcaataata cagctgggga cgacctggcc   6900
aagctgctgt ggctgaaaag ccccagctcc gaggtgtggt ttgaccgaag aaccaattat   6960
acccgttctt tagcggtcat gtcaatggtt gggtatattt taggcctggg agatagacac   7020
ccatccaacc tgatgctgga ccgtctgagt gggaagatcc tgcacattga ctttggggac   7080
tgctttgagg ttgctatgac ccgagagaag tttccagaga agattccatt tagactaaca   7140
agaatgttga ccaatgctat ggaggttaca ggcctggatg gcaactacag aatcacatgc   7200
cacacagtga tggaggtgct gcgagagcac aaggacagtg tcatggccgt gctggaagcc   7260
tttgtctatg accccttgct gaactggagg ctgatggaca caaataccaa aggcaacaag   7320
cgatcccgaa cgaggacgga ttcctactct gctggccagt cagtcgaaat tttggacggt   7380
```

```
gtggaacttg gagagccagc ccataagaaa acggggacca cagtgccaga atctattcat   7440

tctttcattg gagacggttt ggtgaaacca gaggccctaa ataagaaagc tatccagatt   7500

attaacaggg ttcgagataa gctcactggt cgggacttct ctcatgatga cactttggat   7560

gttccaacgc aagttgagct gctcatcaaa caagcgacat cccatgaaaa cctctgccag   7620

tgctatattg gctggtgccc tttctggtaa                                    7650


<210> SEQ ID NO 67
<211> LENGTH: 1147
<212> TYPE: PRT
<213> ORGANISM: Homo sapiens
<220> FEATURE:
<221> NAME/KEY: source
<223> OTHER INFORMATION: /note="SREBP1"

<400> SEQUENCE: 67

Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
            20                  25                  30

Leu Gln Leu Ile Asn Asn Gln Asp Ser Asp Phe Pro Gly Leu Phe Asp
        35                  40                  45

Pro Pro Tyr Ala Gly Ser Gly Ala Gly Gly Thr Asp Pro Ala Ser Pro
    50                  55                  60

Asp Thr Ser Ser Pro Gly Ser Leu Ser Pro Pro Pro Ala Thr Leu Ser
65                  70                  75                  80

Ser Ser Leu Glu Ala Phe Leu Ser Gly Pro Gln Ala Ala Pro Ser Pro
                85                  90                  95

Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125

Leu Ser Ile Leu Gln Thr Pro Thr Pro Gln Pro Leu Pro Gly Ala Leu
    130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
        195                 200                 205

Val Pro Gln Gln Leu Leu Thr Val Thr Ala Ala Pro Thr Ala Ala Pro
    210                 215                 220

Val Thr Thr Thr Val Thr Ser Gln Ile Gln Gln Val Pro Val Leu Leu
225                 230                 235                 240

Gln Pro His Phe Ile Lys Ala Asp Ser Leu Leu Leu Thr Ala Met Lys
                245                 250                 255

Thr Asp Gly Ala Thr Val Lys Ala Ala Gly Leu Ser Pro Leu Val Ser
            260                 265                 270

Gly Thr Thr Val Gln Thr Gly Pro Leu Pro Thr Leu Val Ser Gly Gly
        275                 280                 285

Thr Ile Leu Ala Thr Val Pro Leu Val Val Asp Ala Glu Lys Leu Pro
    290                 295                 300
```

-continued

Ile Asn Arg Leu Ala Ala Gly Ser Lys Ala Pro Ala Ser Ala Gln Ser
305 310 315 320

Arg Gly Glu Lys Arg Thr Ala His Asn Ala Ile Glu Lys Arg Tyr Arg
325 330 335

Ser Ser Ile Asn Asp Lys Ile Ile Glu Leu Lys Asp Leu Val Val Gly
340 345 350

Thr Glu Ala Lys Leu Asn Lys Ser Ala Val Leu Arg Lys Ala Ile Asp
355 360 365

Tyr Ile Arg Phe Leu Gln His Ser Asn Gln Lys Leu Lys Gln Glu Asn
370 375 380

Leu Ser Leu Arg Thr Ala Val His Lys Ser Lys Ser Leu Lys Asp Leu
385 390 395 400

Val Ser Ala Cys Gly Ser Gly Gly Asn Thr Asp Val Leu Met Glu Gly
405 410 415

Val Lys Thr Glu Val Glu Asp Thr Leu Thr Pro Pro Pro Ser Asp Ala
420 425 430

Gly Ser Pro Phe Gln Ser Ser Pro Leu Ser Leu Gly Ser Arg Gly Ser
435 440 445

Gly Ser Gly Gly Ser Gly Ser Asp Ser Glu Pro Asp Ser Pro Val Phe
450 455 460

Glu Asp Ser Lys Ala Lys Pro Glu Gln Arg Pro Ser Leu His Ser Arg
465 470 475 480

Gly Met Leu Asp Arg Ser Arg Leu Ala Leu Cys Thr Leu Val Phe Leu
485 490 495

Cys Leu Ser Cys Asn Pro Leu Ala Ser Leu Leu Gly Ala Arg Gly Leu
500 505 510

Pro Ser Pro Ser Asp Thr Thr Ser Val Tyr His Ser Pro Gly Arg Asn
515 520 525

Val Leu Gly Thr Glu Ser Arg Asp Gly Pro Gly Trp Ala Gln Trp Leu
530 535 540

Leu Pro Pro Val Val Trp Leu Leu Asn Gly Leu Leu Val Leu Val Ser
545 550 555 560

Leu Val Leu Leu Phe Val Tyr Gly Glu Pro Val Thr Arg Pro His Ser
565 570 575

Gly Pro Ala Val Tyr Phe Trp Arg His Arg Lys Gln Ala Asp Leu Asp
580 585 590

Leu Ala Arg Gly Asp Phe Ala Gln Ala Ala Gln Gln Leu Trp Leu Ala
595 600 605

Leu Arg Ala Leu Gly Arg Pro Leu Pro Thr Ser His Leu Asp Leu Ala
610 615 620

Cys Ser Leu Leu Trp Asn Leu Ile Arg His Leu Leu Gln Arg Leu Trp
625 630 635 640

Val Gly Arg Trp Leu Ala Gly Arg Ala Gly Gly Leu Gln Gln Asp Cys
645 650 655

Ala Leu Arg Val Asp Ala Ser Ala Ser Ala Arg Asp Ala Ala Leu Val
660 665 670

Tyr His Lys Leu His Gln Leu His Thr Met Gly Lys His Thr Gly Gly
675 680 685

His Leu Thr Ala Thr Asn Leu Ala Leu Ser Ala Leu Asn Leu Ala Glu
690 695 700

Cys Ala Gly Asp Ala Val Ser Val Ala Thr Leu Ala Glu Ile Tyr Val
705 710 715 720

Ala Ala Ala Leu Arg Val Lys Thr Ser Leu Pro Arg Ala Leu His Phe

-continued

```
                725                 730                 735

Leu Thr Arg Phe Phe Leu Ser Ser Ala Arg Gln Ala Cys Leu Ala Gln
            740                 745                 750

Ser Gly Ser Val Pro Pro Ala Met Gln Trp Leu Cys His Pro Val Gly
        755                 760                 765

His Arg Phe Phe Val Asp Gly Asp Trp Ser Val Leu Ser Thr Pro Trp
    770                 775                 780

Glu Ser Leu Tyr Ser Leu Ala Gly Asn Pro Val Asp Pro Leu Ala Gln
785                 790                 795                 800

Val Thr Gln Leu Phe Arg Glu His Leu Leu Glu Arg Ala Leu Asn Cys
                805                 810                 815

Val Thr Gln Pro Asn Pro Ser Pro Gly Ser Ala Asp Gly Asp Lys Glu
            820                 825                 830

Phe Ser Asp Ala Leu Gly Tyr Leu Gln Leu Leu Asn Ser Cys Ser Asp
        835                 840                 845

Ala Ala Gly Ala Pro Ala Tyr Ser Phe Ser Ile Ser Ser Ser Met Ala
    850                 855                 860

Thr Thr Thr Gly Val Asp Pro Val Ala Lys Trp Trp Ala Ser Leu Thr
865                 870                 875                 880

Ala Val Val Ile His Trp Leu Arg Arg Asp Glu Glu Ala Ala Glu Arg
                885                 890                 895

Leu Cys Pro Leu Val Glu His Leu Pro Arg Val Leu Gln Glu Ser Glu
            900                 905                 910

Arg Pro Leu Pro Arg Ala Ala Leu His Ser Phe Lys Ala Ala Arg Ala
        915                 920                 925

Leu Leu Gly Cys Ala Lys Ala Glu Ser Gly Pro Ala Ser Leu Thr Ile
    930                 935                 940

Cys Glu Lys Ala Ser Gly Tyr Leu Gln Asp Ser Leu Ala Thr Thr Pro
945                 950                 955                 960

Ala Ser Ser Ser Ile Asp Lys Ala Val Gln Leu Phe Leu Cys Asp Leu
                965                 970                 975

Leu Leu Val Val Arg Thr Ser Leu Trp Arg Gln Gln Gln Pro Pro Ala
            980                 985                 990

Pro Ala Pro Ala Ala Gln Gly Thr  Ser Ser Arg Pro Gln  Ala Ser Ala
        995                 1000                1005

Leu Glu  Leu Arg Gly Phe Gln  Arg Asp Leu Ser Ser  Leu Arg Arg
    1010                1015                1020

Leu Ala  Gln Ser Phe Arg Pro  Ala Met Arg Arg Val  Phe Leu His
    1025                1030                1035

Glu Ala  Thr Ala Arg Leu Met  Ala Gly Ala Ser Pro  Thr Arg Thr
    1040                1045                1050

His Gln  Leu Leu Asp Arg Ser  Leu Arg Arg Arg Ala  Gly Pro Gly
    1055                1060                1065

Gly Lys  Gly Gly Ala Val Ala  Glu Leu Glu Pro Arg  Pro Thr Arg
    1070                1075                1080

Arg Glu  His Ala Glu Ala Leu  Leu Leu Ala Ser Cys  Tyr Leu Pro
    1085                1090                1095

Pro Gly  Phe Leu Ser Ala Pro  Gly Gln Arg Val Gly  Met Leu Ala
    1100                1105                1110

Glu Ala  Ala Arg Thr Leu Glu  Lys Leu Gly Asp Arg  Arg Leu Leu
    1115                1120                1125

His Asp  Cys Gln Gln Met Leu  Met Arg Leu Gly Gly  Gly Thr Thr
    1130                1135                1140
```

Val Thr Ser Ser
1145

<210> SEQ ID NO 68
<211> LENGTH: 3444
<212> TYPE: DNA
<213> ORGANISM: Homo sapiens
<220> FEATURE:
<221> NAME/KEY: source
<223> OTHER INFORMATION: /note="SREBP1"

<400> SEQUENCE: 68
atggacgagc cacccttcag cgaggcggct ttggagcagg cgctgggcga gccgtgcgat 60
ctggacgcgg cgctgctgac cgacatcgaa gacatgcttc agcttatcaa caaccaagac 120
agtgacttcc ctggcctatt tgacccaccc tatgctggga gtggggcagg gggcacagac 180
cctgccagcc ccgataccag ctccccaggc agcttgtctc cacctcctgc cacattgagc 240
tcctctcttg aagccttcct gagcgggccg caggcagcgc cctcacccct gtcccctccc 300
cagcctgcac ccactccatt gaagatgtac ccgtccatgc ccgctttctc ccctgggcct 360
ggtatcaagg aagagtcagt gccactgagc atcctgcaga cccccacccc acagcccctg 420
ccaggggccc tcctgccaca gagcttccca gccccagccc caccgcagtt cagctccacc 480
cctgtgttag gctaccccag ccctccggga ggcttctcta caggaagccc tcccgggaac 540
acccagcagc cgctgcctgg cctgccactg gcttccccgc caggggtccc gcccgtctcc 600
ttgcacaccc aggtccagag tgtggtcccc cagcagctac tgacagtcac agctgccccc 660
acggcagccc ctgtaacgac cactgtgacc tcgcagatcc agcaggtccc ggtcctgctg 720
cagccccact tcatcaaggc agactcgctg cttctgacag ccatgaagac agacggagcc 780
actgtgaagg cggcaggtct cagtcccctg gtctctggca ccactgtgca gacagggcct 840
ttgccgaccc tggtgagtgg cggaaccatc ttggcaacag tcccactggt cgtagatgcg 900
gagaagctgc ctatcaaccg gctcgcagct ggcagcaagg ccccggcctc tgcccagagc 960
cgtggagaga agcgcacagc ccacaacgcc attgagaagc gctaccgctc ctccatcaat 1020
gacaaaatca ttgagctcaa ggatctggtg gtgggcactg aggcaaagct gaataaatct 1080
gctgtcttgc gcaaggccat cgactacatt cgctttctgc aacacagcaa ccagaaactc 1140
aagcaggaga acctaagtct gcgcactgct gtccacaaaa gcaaatctct gaaggatctg 1200
gtgtcggcct gtggcagtgg agggaacaca gacgtgctca tggagggcgt gaagactgag 1260
gtggaggaca cactgacccc acccccctcg gatgctggct cacctttcca gagcagcccc 1320
ttgtcccttg gcagcagggg cagtggcagc ggtggcagtg gcagtgactc ggagcctgac 1380
agcccagtct ttgaggacag caaggcaaag ccagagcagc ggccgtctct gcacagccgg 1440
ggcatgctgg accgctcccg cctggccctg tgcacgctcg tcttcctctg cctgtcctgc 1500
aaccccttgg cctccttgct gggggcccgg gggcttccca gcccctcaga taccaccagc 1560
gtctaccata gccctgggcg caacgtgctg ggcaccgaga gcagagatgg ccctggctgg 1620
gcccagtggc tgctgccccc agtggtctgg ctgctcaatg ggctgttggt gctcgtctcc 1680
ttggtgcttc tctttgtcta cggtgagcca gtcacacggc cccactcagg ccccgccgtg 1740
tacttctgga ggcatcgcaa gcaggctgac ctggacctgg cccggggaga ctttgcccag 1800
gctgcccagc agctgtggct ggccctgcgg gcactgggcc ggcccctgcc cacctcccac 1860
ctggacctgg cttgtagcct cctctggaac ctcatccgtc acctgctgca gcgtctctgg 1920

```
gtgggccgct ggctggcagg ccgggcaggg ggcctgcagc aggactgtgc tctgcgagtg   1980

gatgctagcg ccagcgcccg agacgcagcc ctggtctacc ataagctgca ccagctgcac   2040

accatgggga agcacacagg cgggcacctc actgccacca acctggcgct gagtgccctg   2100

aacctggcag agtgtgcagg ggatgccgtg tctgtggcga cgctggccga gatctatgtg   2160

gcggctgcat tgagagtgaa gaccagtctc ccacgggcct tgcattttct gacacgcttc   2220

ttcctgagca gtgcccgcca ggcctgcctg gcacagagtg gctcagtgcc tcctgccatg   2280

cagtggctct gccaccccgt gggccaccgt ttcttcgtgg atggggactg gtccgtgctc   2340

agtaccccat gggagagcct gtacagcttg gccgggaacc cagtggaccc cctggcccag   2400

gtgactcagc tattccggga acatctctta gagcgagcac tgaactgtgt gacccagccc   2460

aaccccagcc ctgggtcagc tgatggggac aaggaattct cggatgccct cgggtacctg   2520

cagctgctga acagctgttc tgatgctgcg gggggctcctg cctacagctt ctccatcagt   2580

tccagcatgg ccaccaccac cggcgtagac ccggtggcca agtggtgggc ctctctgaca   2640

gctgtggtga tccactggct gcggcgggat gaggaggcgg ctgagcggct gtgcccgctg   2700

gtggagcacc tgccccgggt gctgcaggag tctgagagac ccctgcccag ggcagctctg   2760

cactccttca aggctgcccg ggccctgctg ggctgtgcca aggcagagtc tggtccagcc   2820

agcctgacca tctgtgagaa ggccagtggg tacctgcagg acagcctggc taccacacca   2880

gccagcagct ccattgacaa ggccgtgcag ctgttcctgt gtgacctgct tcttgtggtg   2940

cgcaccagcc tgtggcggca gcagcagccc ccggccccgg ccccagcagc ccagggcacc   3000

agcagcaggc cccaggcttc cgcccttgag ctgcgtggct tccaacggga cctgagcagc   3060

ctgaggcggc tggcacagag cttccggccc gccatgcgga gggtgttcct acatgaggcc   3120

acggcccggc tgatggcggg ggccagcccc acacggacac accagctcct cgaccgcagt   3180

ctgaggcggc gggcaggccc cggtggcaaa ggaggcgcgg tggcggagct ggagccgcgg   3240

cccacgcggc gggagcacgc ggaggccttg ctgctggcct cctgctacct gcccccggc   3300

ttcctgtcgg cgcccgggca gcgcgtgggc atgctggctg aggcggcgcg cacactcgag   3360

aagcttggcg atcgccggct gctgcacgac tgtcagcaga tgctcatgcg cctgggcggt   3420

gggaccactg tcacttccag ctag                                          3444
```

<210> SEQ ID NO 69
<211> LENGTH: 138
<212> TYPE: PRT
<213> ORGANISM: Homo sapiens
<220> FEATURE:
<221> NAME/KEY: source
<223> OTHER INFORMATION: /note="Interferon-gamma"

<400> SEQUENCE: 69

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
```

```
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
    130                 135
```

<210> SEQ ID NO 70
<211> LENGTH: 414
<212> TYPE: DNA
<213> ORGANISM: Homo sapiens
<220> FEATURE:
<221> NAME/KEY: source
<223> OTHER INFORMATION: /note="Interferon-gamma"

<400> SEQUENCE: 70

```
caggacccat atgtaaaaga agcagaaaac cttaagaaat attttaatgc aggtcattca      60

gatgtagcgg ataatggaac tcttttctta ggcattttga agaattggaa agaggagagt     120

gacagaaaaa taatgcagag ccaaattgtc tccttttact tcaaactttt taaaaacttt     180

aaagatgacc agagcatcca aaagagtgtg gagaccatca aggaagacat gaatgtcaag     240

tttttcaata gcaacaaaaa gaaacgagat gacttcgaaa agctgactaa ttattcggta     300

actgacttga atgtccaacg caaagcaata catgaactca tccaagtgat ggctgaactg     360

tcgccagcag ctaaaacagg gaagcgaaaa aggagtcaga tgctgtttcg aggt           414
```

<210> SEQ ID NO 71
<211> LENGTH: 227
<212> TYPE: PRT
<213> ORGANISM: Homo sapiens
<220> FEATURE:
<221> NAME/KEY: source
<223> OTHER INFORMATION: /note="Granzyme B"

<400> SEQUENCE: 71

```
Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175
```

-continued

```
Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 72
<211> LENGTH: 681
<212> TYPE: DNA
<213> ORGANISM: Homo sapiens
<220> FEATURE:
<221> NAME/KEY: source
<223> OTHER INFORMATION: /note="Granzyme B"

<400> SEQUENCE: 72

atcatcgggg gacatgaggc caagccccac tcccgcccct acatggctta tcttatgatc      60

tgggatcaga agtctctgaa gaggtgcggt ggcttcctga tacgagacga cttcgtgctg     120

acagctgctc actgttgggg aagctccata aatgtcacct tgggggccca caatatcaaa     180

gaacaggagc cgacccagca gtttatccct gtgaaaagac ccatccccca tccagcctat     240

aatcctaaga acttctccaa cgacatcatg ctactgcagc tggagagaaa ggccaagcgg     300

accagagctg tgcagcccct caggctacct agcaacaagg cccaggtgaa gccagggcag     360

acatgcagtg tggccggctg ggggcagacg gccccctgg gaaaacactc acacacacta     420

caagaggtga agatgacagt gcaggaagat cgaaagtgcg aatctgactt acgccattat     480

tacgacagta ccattgagtt gtgcgtgggg gacccagaga ttaaaaagac ttcctttaag     540

ggggactctg gaggccctct tgtgtgtaac aaggtggccc agggcattgt ctcctatgga     600

cgaaacaatg gcatgcctcc acgagcctgc accaaagtct caagctttgt acactggata     660

aagaaaacca tgaaacgcta c                                               681


<210> SEQ ID NO 73
<211> LENGTH: 268
<212> TYPE: PRT
<213> ORGANISM: Homo sapiens
<220> FEATURE:
<221> NAME/KEY: source
<223> OTHER INFORMATION: /note="PD-1"

<400> SEQUENCE: 73

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110
```

Gln Ile Lys Glu Ser Leu Arg Ala Glu Leu Arg Val Thr Glu Arg Arg
115 120 125

Ala Glu Val Pro Thr Ala His Pro Ser Pro Ser Pro Arg Pro Ala Gly
130 135 140

Gln Phe Gln Thr Leu Val Val Gly Val Val Gly Gly Leu Leu Gly Ser
145 150 155 160

Leu Val Leu Leu Val Trp Val Leu Ala Val Ile Cys Ser Arg Ala Ala
165 170 175

Arg Gly Thr Ile Gly Ala Arg Arg Thr Gly Gln Pro Leu Lys Glu Asp
180 185 190

Pro Ser Ala Val Pro Val Phe Ser Val Asp Tyr Gly Glu Leu Asp Phe
195 200 205

Gln Trp Arg Glu Lys Thr Pro Glu Pro Pro Val Pro Cys Val Pro Glu
210 215 220

Gln Thr Glu Tyr Ala Thr Ile Val Phe Pro Ser Gly Met Gly Thr Ser
225 230 235 240

Ser Pro Ala Arg Arg Gly Ser Ala Asp Gly Pro Arg Ser Ala Gln Pro
245 250 255

Leu Arg Pro Glu Asp Gly His Cys Ser Trp Pro Leu
260 265

<210> SEQ ID NO 74
<211> LENGTH: 272
<212> TYPE: PRT
<213> ORGANISM: Homo sapiens
<220> FEATURE:
<221> NAME/KEY: source
<223> OTHER INFORMATION: /note="PD-L1"

<400> SEQUENCE: 74

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile

```
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270


<210> SEQ ID NO 75
<211> LENGTH: 223
<212> TYPE: PRT
<213> ORGANISM: Homo sapiens
<220> FEATURE:
<221> NAME/KEY: source
<223> OTHER INFORMATION: /note="TIGIT"

<400> SEQUENCE: 75

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Leu Leu Gly Ala Met Ala Ala Thr
        115                 120                 125

Leu Val Val Ile Cys Thr Ala Val Ile Val Val Val Ala Leu Thr Arg
    130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
            180                 185                 190

Gln Arg Gly Glu Asp Cys Ala Glu Leu His Asp Tyr Phe Asn Val Leu
        195                 200                 205

Ser Tyr Arg Ser Leu Gly Asn Cys Ser Phe Phe Thr Glu Thr Gly
    210                 215                 220


<210> SEQ ID NO 76
<211> LENGTH: 311
<212> TYPE: PRT
<213> ORGANISM: Homo sapiens
<220> FEATURE:
<221> NAME/KEY: source
<223> OTHER INFORMATION: /note="CD1A"

<400> SEQUENCE: 76

Asn Ala Asp Gly Leu Lys Glu Pro Leu Ser Phe His Val Thr Trp Ile
```

```
1               5                   10                  15

Ala Ser Phe Tyr Asn His Ser Trp Lys Gln Asn Leu Val Ser Gly Trp
            20                  25                  30

Leu Ser Asp Leu Gln Thr His Thr Trp Asp Ser Asn Ser Ser Thr Ile
        35                  40                  45

Val Phe Leu Cys Pro Trp Ser Arg Gly Asn Phe Ser Asn Glu Glu Trp
    50                  55                  60

Lys Glu Leu Glu Thr Leu Phe Arg Ile Arg Thr Ile Arg Ser Phe Glu
65                  70                  75                  80

Gly Ile Arg Arg Tyr Ala His Glu Leu Gln Phe Glu Tyr Pro Phe Glu
                85                  90                  95

Ile Gln Val Thr Gly Gly Cys Glu Leu His Ser Gly Lys Val Ser Gly
            100                 105                 110

Ser Phe Leu Gln Leu Ala Tyr Gln Gly Ser Asp Phe Val Ser Phe Gln
        115                 120                 125

Asn Asn Ser Trp Leu Pro Tyr Pro Val Ala Gly Asn Met Ala Lys His
    130                 135                 140

Phe Cys Lys Val Leu Asn Gln Asn Gln His Glu Asn Asp Ile Thr His
145                 150                 155                 160

Asn Leu Leu Ser Asp Thr Cys Pro Arg Phe Ile Leu Gly Leu Leu Asp
                165                 170                 175

Ala Gly Lys Ala His Leu Gln Arg Gln Val Lys Pro Glu Ala Trp Leu
            180                 185                 190

Ser His Gly Pro Ser Pro Gly Pro Gly His Leu Gln Leu Val Cys His
        195                 200                 205

Val Ser Gly Phe Tyr Pro Lys Pro Val Trp Val Met Trp Met Arg Gly
    210                 215                 220

Glu Gln Glu Gln Gln Gly Thr Gln Arg Gly Asp Ile Leu Pro Ser Ala
225                 230                 235                 240

Asp Gly Thr Trp Tyr Leu Arg Ala Thr Leu Glu Val Ala Ala Gly Glu
                245                 250                 255

Ala Ala Asp Leu Ser Cys Arg Val Lys His Ser Ser Leu Glu Gly Gln
            260                 265                 270

Asp Ile Val Leu Tyr Trp Glu His His Ser Ser Val Gly Phe Ile Ile
        275                 280                 285

Leu Ala Val Ile Val Pro Leu Leu Leu Leu Ile Gly Leu Ala Leu Trp
    290                 295                 300

Phe Arg Lys Arg Cys Phe Cys
305                 310
```

<210> SEQ ID NO 77
<211> LENGTH: 279
<212> TYPE: PRT
<213> ORGANISM: Homo sapiens
<220> FEATURE:
<221> NAME/KEY: source
<223> OTHER INFORMATION: /note=“TIM3”

<400> SEQUENCE: 77

```
Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45
```

-continued

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
    210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
            260                 265                 270

Leu Gly Cys Arg Phe Ala Met
        275

<210> SEQ ID NO 78
<211> LENGTH: 133
<212> TYPE: PRT
<213> ORGANISM: Homo sapiens
<220> FEATURE:
<221> NAME/KEY: source
<223> OTHER INFORMATION: /note="IL-2"

<400> SEQUENCE: 78

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

```
Ile Ser Thr Leu Thr
    130


<210> SEQ ID NO 79
<211> LENGTH: 152
<212> TYPE: PRT
<213> ORGANISM: Homo sapiens
<220> FEATURE:
<221> NAME/KEY: source
<223> OTHER INFORMATION: /note="IL-7"

<400> SEQUENCE: 79

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 80
<211> LENGTH: 197
<212> TYPE: PRT
<213> ORGANISM: Homo sapiens
<220> FEATURE:
<221> NAME/KEY: source
<223> OTHER INFORMATION: /note="IL-12alpha"

<400> SEQUENCE: 80

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125
```

```
Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 81
<211> LENGTH: 306
<212> TYPE: PRT
<213> ORGANISM: Homo sapiens
<220> FEATURE:
<221> NAME/KEY: source
<223> OTHER INFORMATION: /note="IL-12beta"

<400> SEQUENCE: 81

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
```

```
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 82
<211> LENGTH: 114
<212> TYPE: PRT
<213> ORGANISM: Homo sapiens
<220> FEATURE:
<221> NAME/KEY: source
<223> OTHER INFORMATION: /note="IL-15"

<400> SEQUENCE: 82

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 83
<211> LENGTH: 133
<212> TYPE: PRT
<213> ORGANISM: Homo sapiens
<220> FEATURE:
<221> NAME/KEY: source
<223> OTHER INFORMATION: /note="IL-21"

<400> SEQUENCE: 83

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130
```

<210> SEQ ID NO 84
<211> LENGTH: 270
<212> TYPE: PRT
<213> ORGANISM: Homo sapiens
<220> FEATURE:
<221> NAME/KEY: source
<223> OTHER INFORMATION: /note="IL-33"

<400> SEQUENCE: 84

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270
```

<210> SEQ ID NO 85
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
```

```
                20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255

Ser Thr Asn Phe Lys Thr Ile Leu Glu Trp Glu Pro Lys Pro Val Asn
            260                 265                 270

Gln Val Tyr Thr Val Gln Ile Ser Thr Lys Ser Gly Asp Trp Lys Ser
        275                 280                 285

Lys Cys Phe Tyr Thr Thr Asp Thr Glu Cys Asp Leu Thr Asp Glu Ile
    290                 295                 300

Val Lys Asp Val Lys Gln Thr Tyr Leu Ala Arg Val Phe Ser Tyr Pro
305                 310                 315                 320

Ala Gly Asn Val Glu Ser Thr Gly Ser Ala Gly Glu Pro Leu Tyr Glu
                325                 330                 335

Asn Ser Pro Glu Phe Thr Pro Tyr Leu Glu Thr Asn Leu Gly Gln Pro
            340                 345                 350

Thr Ile Gln Ser Phe Glu Gln Val Gly Thr Lys Val Asn Val Thr Val
        355                 360                 365

Glu Asp Glu Arg Thr Leu Val Arg Arg Asn Asn Thr Phe Leu Ser Leu
    370                 375                 380

Arg Asp Val Phe Gly Lys Asp Leu Ile Tyr Thr Leu Tyr Tyr Trp Lys
385                 390                 395                 400

Ser Ser Ser Ser Gly Lys Lys Thr Ala Lys Thr Asn Thr Asn Glu Phe
                405                 410                 415

Leu Ile Asp Val Asp Lys Gly Glu Asn Tyr Cys Phe Ser Val Gln Ala
            420                 425                 430

Val Ile Pro Ser Arg Thr Val Asn Arg Lys Ser Thr Asp Ser Pro Val
        435                 440                 445
```

```
Glu Cys Met Gly Gln Glu Lys Gly Glu Phe Arg Glu Val Gln Leu Gln
    450                 455                 460

Gln Ser Gly Pro Glu Leu Val Lys Pro Gly Ala Ser Val Lys Met Ser
465                 470                 475                 480

Cys Lys Ala Ser Gly Tyr Thr Phe Thr Ser Tyr Val Ile Gln Trp Val
                485                 490                 495

Lys Gln Lys Pro Gly Gln Gly Leu Glu Trp Ile Gly Ser Ile Asn Pro
            500                 505                 510

Tyr Asn Asp Tyr Thr Lys Tyr Asn Glu Lys Phe Lys Gly Lys Ala Thr
        515                 520                 525

Leu Thr Ser Asp Lys Ser Ser Ile Thr Ala Tyr Met Glu Phe Ser Ser
    530                 535                 540

Leu Thr Ser Glu Asp Ser Ala Leu Tyr Tyr Cys Ala Arg Trp Gly Asp
545                 550                 555                 560

Gly Asn Tyr Trp Gly Arg Gly Thr Thr Leu Thr Val Ser Ser Gly Gly
                565                 570                 575

Gly Gly Ser Gly Gly Gly Gly Ser Gly Gly Gly Gly Ser Asp Ile Glu
            580                 585                 590

Met Thr Gln Ser Pro Ala Ile Met Ser Ala Ser Leu Gly Glu Arg Val
        595                 600                 605

Thr Met Thr Cys Thr Ala Ser Ser Ser Val Ser Ser Ser Tyr Phe His
    610                 615                 620

Trp Tyr Gln Gln Lys Pro Gly Ser Ser Pro Lys Leu Cys Ile Tyr Ser
625                 630                 635                 640

Thr Ser Asn Leu Ala Ser Gly Val Pro Pro Arg Phe Ser Gly Ser Gly
                645                 650                 655

Ser Thr Ser Tyr Ser Leu Thr Ile Ser Ser Met Glu Ala Glu Asp Ala
            660                 665                 670

Ala Thr Tyr Phe Cys His Gln Tyr His Arg Ser Pro Thr Phe Gly Gly
        675                 680                 685

Gly Thr Lys Leu Glu Thr Lys Arg
    690                 695
```

<210> SEQ ID NO 86
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
cagatcgtgc tgacccaaag ccccgccatc atgagcgcta gccccggtga gaaggtgacc      60

atgacatgct ccgcttccag ctccgtgtcc tacatgaact ggtatcagca gaaaagcgga     120

accagcccca aaaggtggat ctacgacacc agcaagctgg cctccggagt gcccgctcat     180

ttccggggct ctggatccgg caccagctac tctttaacca tttccggcat ggaagctgaa     240

gacgctgcca cctactattg ccagcaatgg agcagcaacc ccttcacatt cggatctggc     300

accaagctcg aaatcaatcg tggaggaggt ggcagcggcg gcggtggatc cggcggagga     360

ggaagccaag ttcaactcca gcagagcggc gctgaactgg cccggcccgg cgcctccgtc     420

aagatgagct gcaaggcttc cggctataca tttactcgtt acacaatgca ttgggtcaag     480

cagaggcccg gtcaaggttt agagtggatc ggatatatca acccttcccg gggctacacc     540
```

-continued

```
aactataacc aaaagttcaa ggataaagcc actttaacca ctgacaagag ctcctccacc    600

gcctacatgc agctgtcctc tttaaccagc gaggactccg ctgtttacta ctgcgctagg    660

tattacgacg accactactg tttagactat tggggacaag gtaccacttt aaccgtcagc    720

agctccggca ccaccaatac cgtggccgct tataacctca catggaagag caccaacttc    780

aagacaattc tggaatggga acccaagccc gtcaatcaag tttacaccgt gcagatctcc    840

accaaatccg gagactggaa gagcaagtgc ttctacacaa cagacaccga gtgtgattta    900

accgacgaaa tcgtcaagga cgtcaagcaa acctatctgg ctcgggtctt ttcctacccc    960

gctggcaatg tcgagtccac cggctccgct ggcgagcctc tctacgagaa ttcccccgaa   1020

ttcacccctt atttagagac caatttaggc cagcctacca tccagagctt cgagcaagtt   1080

ggcaccaagg tgaacgtcac cgtcgaggat gaaaggactt tagtgcggcg gaataacaca   1140

tttttatccc tccgggatgt gttcggcaaa gacctcatct acacactgta ctattggaag   1200

tccagctcct ccggcaaaaa gaccgctaag accaacacca acgagttttt aattgacgtg   1260

gacaaaggcg agaactactg cttcagcgtg caagccgtga tcccttctcg taccgtcaac   1320

cggaagagca cagattcccc cgttgagtgc atgggccaag aaaagggcga gttccgggag   1380

gtccagctgc agcagagcgg acccgaactc gtgaaacccg gtgcttccgt gaaaatgtct   1440

tgtaaggcca gcggatacac cttcacctcc tatgtgatcc agtgggtcaa acagaagccc   1500

ggacaaggtc tcgagtggat cggcagcatc aacccttaca acgactatac caaatacaac   1560

gagaagttta agggaaaggc tactttaacc tccgacaaaa gctccatcac agcctacatg   1620

gagttcagct ctttaacatc cgaggacagc gctctgtact attgcgcccg gtggggcgac   1680

ggcaattact ggggacgggg cacaacactg accgtgagca gcggaggcgg aggctccggc   1740

ggaggcggat ctggcggtgg cggctccgac atcgagatga cccagtcccc cgctatcatg   1800

tccgcctctt taggcgagcg ggtcacaatg acttgtacag cctcctccag cgtctcctcc   1860

tcctacttcc attggtacca acagaaaccc ggaagctccc ctaaactgtg catctacagc   1920

accagcaatc tcgccagcgg cgtgcccct aggttttccg gaagcggaag caccagctac   1980

tctttaacca tctcctccat ggaggctgag gatgccgcca cctacttttg tcaccagtac   2040

caccggtccc ccaccttcgg aggcggcacc aaactggaga caaagagg                2088
```

```
<210> SEQ ID NO 87
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Met Lys Trp Val Thr Phe Ile Ser Leu Leu Phe Leu Phe Ser Ser Ala
1               5                   10                  15

Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ser
        35                  40                  45

Tyr Met Asn Trp Tyr Gln Gln Lys Ser Gly Thr Ser Pro Lys Arg Trp
    50                  55                  60

Ile Tyr Asp Thr Ser Lys Leu Ala Ser Gly Val Pro Ala His Phe Arg
65                  70                  75                  80
```

```
Gly Ser Gly Ser Gly Thr Ser Tyr Ser Leu Thr Ile Ser Gly Met Glu
                85                  90                  95

Ala Glu Asp Ala Ala Thr Tyr Tyr Cys Gln Gln Trp Ser Ser Asn Pro
            100                 105                 110

Phe Thr Phe Gly Ser Gly Thr Lys Leu Glu Ile Asn Arg Gly Gly Gly
        115                 120                 125

Gly Ser Gly Gly Gly Gly Ser Gly Gly Gly Gly Ser Gln Val Gln Leu
    130                 135                 140

Gln Gln Ser Gly Ala Glu Leu Ala Arg Pro Gly Ala Ser Val Lys Met
145                 150                 155                 160

Ser Cys Lys Ala Ser Gly Tyr Thr Phe Thr Arg Tyr Thr Met His Trp
                165                 170                 175

Val Lys Gln Arg Pro Gly Gln Gly Leu Glu Trp Ile Gly Tyr Ile Asn
            180                 185                 190

Pro Ser Arg Gly Tyr Thr Asn Tyr Asn Gln Lys Phe Lys Asp Lys Ala
        195                 200                 205

Thr Leu Thr Thr Asp Lys Ser Ser Ser Thr Ala Tyr Met Gln Leu Ser
    210                 215                 220

Ser Leu Thr Ser Glu Asp Ser Ala Val Tyr Tyr Cys Ala Arg Tyr Tyr
225                 230                 235                 240

Asp Asp His Tyr Cys Leu Asp Tyr Trp Gly Gln Gly Thr Thr Leu Thr
                245                 250                 255

Val Ser Ser Ser Gly Thr Thr Asn Thr Val Ala Ala Tyr Asn Leu Thr
            260                 265                 270

Trp Lys Ser Thr Asn Phe Lys Thr Ile Leu Glu Trp Glu Pro Lys Pro
        275                 280                 285

Val Asn Gln Val Tyr Thr Val Gln Ile Ser Thr Lys Ser Gly Asp Trp
    290                 295                 300

Lys Ser Lys Cys Phe Tyr Thr Thr Asp Thr Glu Cys Asp Leu Thr Asp
305                 310                 315                 320

Glu Ile Val Lys Asp Val Lys Gln Thr Tyr Leu Ala Arg Val Phe Ser
                325                 330                 335

Tyr Pro Ala Gly Asn Val Glu Ser Thr Gly Ser Ala Gly Glu Pro Leu
            340                 345                 350

Tyr Glu Asn Ser Pro Glu Phe Thr Pro Tyr Leu Glu Thr Asn Leu Gly
        355                 360                 365

Gln Pro Thr Ile Gln Ser Phe Glu Gln Val Gly Thr Lys Val Asn Val
    370                 375                 380

Thr Val Glu Asp Glu Arg Thr Leu Val Arg Arg Asn Asn Thr Phe Leu
385                 390                 395                 400

Ser Leu Arg Asp Val Phe Gly Lys Asp Leu Ile Tyr Thr Leu Tyr Tyr
                405                 410                 415

Trp Lys Ser Ser Ser Ser Gly Lys Lys Thr Ala Lys Thr Asn Thr Asn
            420                 425                 430

Glu Phe Leu Ile Asp Val Asp Lys Gly Glu Asn Tyr Cys Phe Ser Val
        435                 440                 445

Gln Ala Val Ile Pro Ser Arg Thr Val Asn Arg Lys Ser Thr Asp Ser
    450                 455                 460

Pro Val Glu Cys Met Gly Gln Glu Lys Gly Glu Phe Arg Glu Val Gln
465                 470                 475                 480

Leu Gln Gln Ser Gly Pro Glu Leu Val Lys Pro Gly Ala Ser Val Lys
                485                 490                 495

Met Ser Cys Lys Ala Ser Gly Tyr Thr Phe Thr Ser Tyr Val Ile Gln
```

```
            500                 505                 510

Trp Val Lys Gln Lys Pro Gly Gln Gly Leu Glu Trp Ile Gly Ser Ile
        515                 520                 525

Asn Pro Tyr Asn Asp Tyr Thr Lys Tyr Asn Glu Lys Phe Lys Gly Lys
    530                 535                 540

Ala Thr Leu Thr Ser Asp Lys Ser Ser Ile Thr Ala Tyr Met Glu Phe
545                 550                 555                 560

Ser Ser Leu Thr Ser Glu Asp Ser Ala Leu Tyr Tyr Cys Ala Arg Trp
                565                 570                 575

Gly Asp Gly Asn Tyr Trp Gly Arg Gly Thr Thr Leu Thr Val Ser Ser
            580                 585                 590

Gly Gly Gly Gly Ser Gly Gly Gly Gly Ser Gly Gly Gly Gly Ser Asp
        595                 600                 605

Ile Glu Met Thr Gln Ser Pro Ala Ile Met Ser Ala Ser Leu Gly Glu
    610                 615                 620

Arg Val Thr Met Thr Cys Thr Ala Ser Ser Ser Val Ser Ser Ser Tyr
625                 630                 635                 640

Phe His Trp Tyr Gln Gln Lys Pro Gly Ser Ser Pro Lys Leu Cys Ile
                645                 650                 655

Tyr Ser Thr Ser Asn Leu Ala Ser Gly Val Pro Pro Arg Phe Ser Gly
            660                 665                 670

Ser Gly Ser Thr Ser Tyr Ser Leu Thr Ile Ser Ser Met Glu Ala Glu
        675                 680                 685

Asp Ala Ala Thr Tyr Phe Cys His Gln Tyr His Arg Ser Pro Thr Phe
    690                 695                 700

Gly Gly Gly Thr Lys Leu Glu Thr Lys Arg
705                 710
```

<210> SEQ ID NO 88
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
atgaagtggg tgaccttcat cagcttatta tttttattca gctccgccta ttcccagatc      60

gtgctgaccc aaagccccgc catcatgagc gctagccccg gtgagaaggt gaccatgaca     120

tgctccgctt ccagctccgt gtcctacatg aactggtatc agcagaaaag cggaaccagc     180

cccaaaaggt ggatctacga caccagcaag ctggcctccg gagtgcccgc tcatttccgg     240

ggctctggat ccggcaccag ctactcttta accatttccg gcatggaagc tgaagacgct     300

gccacctact attgccagca atggagcagc aacccccttca cattcggatc tggcaccaag     360

ctcgaaatca atcgtggagg aggtggcagc ggcggcggtg gatccggcgg aggaggaagc     420

caagttcaac tccagcagag cggcgctgaa ctggcccggc ccggcgcctc cgtcaagatg     480

agctgcaagg cttccggcta tacatttact cgttacacaa tgcattgggt caagcagagg     540

cccggtcaag gtttagagtg gatcggatat atcaaccctt cccggggcta caccaactat     600

aaccaaaagt tcaaggataa agccacttta accactgaca agagctcctc caccgcctac     660

atgcagctgt cctctttaac cagcgaggac tccgctgttt actactgcgc taggtattac     720

gacgaccact actgtttaga ctattgggga caaggtacca ctttaaccgt cagcagctcc     780
```

-continued

```
ggcaccacca ataccgtggc cgcttataac ctcacatgga agagcaccaa cttcaagaca    840

attctggaat gggaacccaa gcccgtcaat caagtttaca ccgtgcagat ctccaccaaa    900

tccggagact ggaagagcaa gtgcttctac acaacagaca ccgagtgtga tttaaccgac    960

gaaatcgtca aggacgtcaa gcaaacctat ctggctcggg tcttttccta ccccgctggc   1020

aatgtcgagt ccaccggctc cgctggcgag cctctctacg agaattcccc cgaattcacc   1080

ccttatttag agaccaattt aggccagcct accatccaga gcttcgagca agttggcacc   1140

aaggtgaacg tcaccgtcga ggatgaaagg actttagtgc ggcggaataa cacattttta   1200

tccctccggg atgtgttcgg caaagacctc atctacacac tgtactattg gaagtccagc   1260

tcctccggca aaaagaccgc taagaccaac accaacgagt ttttaattga cgtggacaaa   1320

ggcgagaact actgcttcag cgtgcaagcc gtgatccctt ctcgtaccgt caaccggaag   1380

agcacagatt cccccgttga gtgcatgggc caagaaaagg gcgagttccg ggaggtccag   1440

ctgcagcaga gcggacccga actcgtgaaa cccggtgctt ccgtgaaaat gtcttgtaag   1500

gccagcggat acaccttcac ctcctatgtg atccagtggg tcaaacagaa gcccggacaa   1560

ggtctcgagt ggatcggcag catcaaccct tacaacgact ataccaaata caacgagaag   1620

tttaagggaa aggctacttt aacctccgac aaaagctcca tcacagccta catggagttc   1680

agctctttaa catccgagga cagcgctctg tactattgcg cccggtgggg cgacggcaat   1740

tactggggac ggggcacaac actgaccgtg agcagcggag gcggaggctc cggcggaggc   1800

ggatctggcg gtggcggctc cgacatcgag atgacccagt cccccgctat catgtccgcc   1860

tctttaggcg agcgggtcac aatgacttgt acagcctcct ccagcgtctc ctcctcctac   1920

ttccattggt accaacagaa acccggaagc tcccctaaac tgtgcatcta cagcaccagc   1980

aatctcgcca gcggcgtgcc ccctaggttt tccggaagcg gaagcaccag ctactcttta   2040

accatctcct ccatggaggc tgaggatgcc gccacctact tttgtcacca gtaccaccgg   2100

tcccccacct tcggaggcgg caccaaactg gagacaaaga gg                      2142
```

<210> SEQ ID NO 89
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

```
Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110
```

-continued

```
Ser Ser Gly Gly Gly Gly Ser Gly Gly Gly Gly Ser Gly Gly Gly Gly
        115                 120                 125

Ser Asp Ile Glu Met Thr Gln Ser Pro Ala Ile Met Ser Ala Ser Leu
    130                 135                 140

Gly Glu Arg Val Thr Met Thr Cys Thr Ala Ser Ser Ser Val Ser Ser
145                 150                 155                 160

Ser Tyr Phe His Trp Tyr Gln Gln Lys Pro Gly Ser Ser Pro Lys Leu
                165                 170                 175

Cys Ile Tyr Ser Thr Ser Asn Leu Ala Ser Gly Val Pro Pro Arg Phe
            180                 185                 190

Ser Gly Ser Gly Ser Thr Ser Tyr Ser Leu Thr Ile Ser Ser Met Glu
        195                 200                 205

Ala Glu Asp Ala Ala Thr Tyr Phe Cys His Gln Tyr His Arg Ser Pro
    210                 215                 220

Thr Phe Gly Gly Gly Thr Lys Leu Glu Thr Lys Arg Ser Gly Thr Thr
225                 230                 235                 240

Asn Thr Val Ala Ala Tyr Asn Leu Thr Trp Lys Ser Thr Asn Phe Lys
                245                 250                 255

Thr Ile Leu Glu Trp Glu Pro Lys Pro Val Asn Gln Val Tyr Thr Val
            260                 265                 270

Gln Ile Ser Thr Lys Ser Gly Asp Trp Lys Ser Lys Cys Phe Tyr Thr
        275                 280                 285

Thr Asp Thr Glu Cys Asp Leu Thr Asp Glu Ile Val Lys Asp Val Lys
    290                 295                 300

Gln Thr Tyr Leu Ala Arg Val Phe Ser Tyr Pro Ala Gly Asn Val Glu
305                 310                 315                 320

Ser Thr Gly Ser Ala Gly Glu Pro Leu Tyr Glu Asn Ser Pro Glu Phe
                325                 330                 335

Thr Pro Tyr Leu Glu Thr Asn Leu Gly Gln Pro Thr Ile Gln Ser Phe
            340                 345                 350

Glu Gln Val Gly Thr Lys Val Asn Val Thr Val Glu Asp Glu Arg Thr
        355                 360                 365

Leu Val Arg Arg Asn Asn Thr Phe Leu Ser Leu Arg Asp Val Phe Gly
    370                 375                 380

Lys Asp Leu Ile Tyr Thr Leu Tyr Tyr Trp Lys Ser Ser Ser Ser Gly
385                 390                 395                 400

Lys Lys Thr Ala Lys Thr Asn Thr Asn Glu Phe Leu Ile Asp Val Asp
                405                 410                 415

Lys Gly Glu Asn Tyr Cys Phe Ser Val Gln Ala Val Ile Pro Ser Arg
            420                 425                 430

Thr Val Asn Arg Lys Ser Thr Asp Ser Pro Val Glu Cys Met Gly Gln
        435                 440                 445

Glu Lys Gly Glu Phe Arg Glu Gln Ile Val Leu Thr Gln Ser Pro Ala
    450                 455                 460

Ile Met Ser Ala Ser Pro Gly Glu Lys Val Thr Met Thr Cys Ser Ala
465                 470                 475                 480

Ser Ser Ser Val Ser Tyr Met Asn Trp Tyr Gln Gln Lys Ser Gly Thr
                485                 490                 495

Ser Pro Lys Arg Trp Ile Tyr Asp Thr Ser Lys Leu Ala Ser Gly Val
            500                 505                 510

Pro Ala His Phe Arg Gly Ser Gly Ser Gly Thr Ser Tyr Ser Leu Thr
        515                 520                 525

Ile Ser Gly Met Glu Ala Glu Asp Ala Ala Thr Tyr Tyr Cys Gln Gln
```

```
    530                 535                 540

Trp Ser Ser Asn Pro Phe Thr Phe Gly Ser Gly Thr Lys Leu Glu Ile
545                 550                 555                 560

Asn Arg Gly Gly Gly Gly Ser Gly Gly Gly Gly Ser Gly Gly Gly Gly
                565                 570                 575

Ser Gln Val Gln Leu Gln Gln Ser Gly Ala Glu Leu Ala Arg Pro Gly
            580                 585                 590

Ala Ser Val Lys Met Ser Cys Lys Ala Ser Gly Tyr Thr Phe Thr Arg
        595                 600                 605

Tyr Thr Met His Trp Val Lys Gln Arg Pro Gly Gln Gly Leu Glu Trp
    610                 615                 620

Ile Gly Tyr Ile Asn Pro Ser Arg Gly Tyr Thr Asn Tyr Asn Gln Lys
625                 630                 635                 640

Phe Lys Asp Lys Ala Thr Leu Thr Thr Asp Lys Ser Ser Ser Thr Ala
                645                 650                 655

Tyr Met Gln Leu Ser Ser Leu Thr Ser Glu Asp Ser Ala Val Tyr Tyr
            660                 665                 670

Cys Ala Arg Tyr Tyr Asp Asp His Tyr Cys Leu Asp Tyr Trp Gly Gln
        675                 680                 685

Gly Thr Thr Leu Thr Val Ser Ser
    690                 695
```

```
<210> SEQ ID NO 90
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90

gtgcagctgc agcagtccgg acccgaactg gtcaagcccg gtgcctccgt gaaaatgtct      60

tgtaaggctt ctggctacac ctttacctcc tacgtcatcc aatgggtgaa gcagaagccc     120

ggtcaaggtc tcgagtggat cggcagcatc aatccctaca acgattacac caagtataac     180

gaaaagttta agggcaaggc cactctgaca agcgacaaga gctccattac cgcctacatg     240

gagttttcct ctttaacttc tgaggactcc gctttatact attgcgctcg ttggggcgat     300

ggcaattatt ggggccgggg aactacttta acagtgagct ccggcggcgg cggaagcgga     360

ggtggaggat ctggcggtgg aggcagcgac atcgagatga cacagtcccc cgctatcatg     420

agcgcctctt taggagaacg tgtgaccatg acttgtacag cttcctccag cgtgagcagc     480

tcctatttcc actggtacca gcagaaaccc ggctcctccc ctaaactgtg tatctactcc     540

acaagcaatt tagctagcgg cgtgcctcct cgttttagcg gctccggcag cacctcttac     600

tctttaacca ttagctctat ggaggccgaa gatgccgcca catacttttg ccatcagtac     660

caccggtccc ctacctttgg cggaggcaca aagctggaga ccaagcggag cggcaccacc     720

aacacagtgg ccgcctacaa tctgacttgg aaatccacca acttcaagac catcctcgag     780

tgggagccca agcccgttaa tcaagtttat accgtgcaga tttccaccaa gagcggcgac     840

tggaaatcca agtgcttcta taccacagac accgagtgcg atctcaccga cgagatcgtc     900

aaagacgtga agcagacata tttagctagg gtgttctcct accccgctgg aaacgtggag     960

agcaccggat ccgctggaga gcctttatac gagaactccc ccgaattcac cccctatctg    1020

gaaaccaatt taggccagcc caccatccag agcttcgaac aagttggcac aaaggtgaac    1080
```

```
gtcaccgtcg aagatgagag gactttagtg cggaggaaca atacattttt atccttacgt   1140

gacgtcttcg gcaaggattt aatctacaca ctgtattact ggaagtctag ctcctccggc   1200

aagaagaccg ccaagaccaa taccaacgaa tttttaattg acgtggacaa gggcgagaac   1260

tactgcttct ccgtgcaagc tgtgatcccc tcccggacag tgaaccggaa gtccaccgac   1320

tcccccgtgg agtgcatggg ccaagagaag ggagagtttc gtgagcagat cgtgctgacc   1380

cagtcccccg ctattatgag cgctagcccc ggtgaaaagg tgactatgac atgcagcgcc   1440

agctcttccg tgagctacat gaactggtat cagcagaagt ccggcaccag ccctaaaagg   1500

tggatctacg acaccagcaa gctggccagc ggcgtccccg ctcactttcg gggctccggc   1560

tccggaacaa gctactctct gaccatcagc ggcatggaag ccgaggatgc cgctacctat   1620

tactgtcagc agtggagctc caaccccttc acctttggat ccggcaccaa gctcgagatt   1680

aatcgtggag gcggaggtag cggaggaggc ggatccggcg gtggaggtag ccaagttcag   1740

ctccagcaaa gcggcgccga actcgctcgg cccggcgctt ccgtgaagat gtcttgtaag   1800

gcctccggct ataccttcac ccggtacaca atgcactggg tcaagcaacg gcccggtcaa   1860

ggtttagagt ggattggcta tatcaacccc tcccggggct ataccaacta caaccagaag   1920

ttcaaggaca aagccaccct caccaccgac aagtccagca gcaccgctta catgcagctg   1980

agctctttaa catccgagga ttccgccgtg tactactgcg ctcggtacta cgacgatcat   2040

tactgcctcg attactgggg ccaaggtacc accttaacag tctcctcc                2088
```

<210> SEQ ID NO 91
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

```
Met Lys Trp Val Thr Phe Ile Ser Leu Leu Phe Leu Phe Ser Ser Ala
1               5                   10                  15

Tyr Ser Val Gln Leu Gln Gln Ser Gly Pro Glu Leu Val Lys Pro Gly
            20                  25                  30

Ala Ser Val Lys Met Ser Cys Lys Ala Ser Gly Tyr Thr Phe Thr Ser
        35                  40                  45

Tyr Val Ile Gln Trp Val Lys Gln Lys Pro Gly Gln Gly Leu Glu Trp
    50                  55                  60

Ile Gly Ser Ile Asn Pro Tyr Asn Asp Tyr Thr Lys Tyr Asn Glu Lys
65                  70                  75                  80

Phe Lys Gly Lys Ala Thr Leu Thr Ser Asp Lys Ser Ser Ile Thr Ala
                85                  90                  95

Tyr Met Glu Phe Ser Ser Leu Thr Ser Glu Asp Ser Ala Leu Tyr Tyr
            100                 105                 110

Cys Ala Arg Trp Gly Asp Gly Asn Tyr Trp Gly Arg Gly Thr Thr Leu
        115                 120                 125

Thr Val Ser Ser Gly Gly Gly Gly Ser Gly Gly Gly Gly Ser Gly Gly
    130                 135                 140

Gly Gly Ser Asp Ile Glu Met Thr Gln Ser Pro Ala Ile Met Ser Ala
145                 150                 155                 160

Ser Leu Gly Glu Arg Val Thr Met Thr Cys Thr Ala Ser Ser Ser Val
                165                 170                 175
```

-continued

```
Ser Ser Ser Tyr Phe His Trp Tyr Gln Gln Lys Pro Gly Ser Ser Pro
            180                 185                 190

Lys Leu Cys Ile Tyr Ser Thr Ser Asn Leu Ala Ser Gly Val Pro Pro
        195                 200                 205

Arg Phe Ser Gly Ser Gly Ser Thr Ser Tyr Ser Leu Thr Ile Ser Ser
    210                 215                 220

Met Glu Ala Glu Asp Ala Ala Thr Tyr Phe Cys His Gln Tyr His Arg
225                 230                 235                 240

Ser Pro Thr Phe Gly Gly Gly Thr Lys Leu Glu Thr Lys Arg Ser Gly
                245                 250                 255

Thr Thr Asn Thr Val Ala Ala Tyr Asn Leu Thr Trp Lys Ser Thr Asn
            260                 265                 270

Phe Lys Thr Ile Leu Glu Trp Glu Pro Lys Pro Val Asn Gln Val Tyr
        275                 280                 285

Thr Val Gln Ile Ser Thr Lys Ser Gly Asp Trp Lys Ser Lys Cys Phe
    290                 295                 300

Tyr Thr Thr Asp Thr Glu Cys Asp Leu Thr Asp Glu Ile Val Lys Asp
305                 310                 315                 320

Val Lys Gln Thr Tyr Leu Ala Arg Val Phe Ser Tyr Pro Ala Gly Asn
                325                 330                 335

Val Glu Ser Thr Gly Ser Ala Gly Glu Pro Leu Tyr Glu Asn Ser Pro
            340                 345                 350

Glu Phe Thr Pro Tyr Leu Glu Thr Asn Leu Gly Gln Pro Thr Ile Gln
        355                 360                 365

Ser Phe Glu Gln Val Gly Thr Lys Val Asn Val Thr Val Glu Asp Glu
    370                 375                 380

Arg Thr Leu Val Arg Arg Asn Asn Thr Phe Leu Ser Leu Arg Asp Val
385                 390                 395                 400

Phe Gly Lys Asp Leu Ile Tyr Thr Leu Tyr Tyr Trp Lys Ser Ser Ser
                405                 410                 415

Ser Gly Lys Lys Thr Ala Lys Thr Asn Thr Asn Glu Phe Leu Ile Asp
            420                 425                 430

Val Asp Lys Gly Glu Asn Tyr Cys Phe Ser Val Gln Ala Val Ile Pro
        435                 440                 445

Ser Arg Thr Val Asn Arg Lys Ser Thr Asp Ser Pro Val Glu Cys Met
    450                 455                 460

Gly Gln Glu Lys Gly Glu Phe Arg Glu Gln Ile Val Leu Thr Gln Ser
465                 470                 475                 480

Pro Ala Ile Met Ser Ala Ser Pro Gly Glu Lys Val Thr Met Thr Cys
                485                 490                 495

Ser Ala Ser Ser Ser Val Ser Tyr Met Asn Trp Tyr Gln Gln Lys Ser
            500                 505                 510

Gly Thr Ser Pro Lys Arg Trp Ile Tyr Asp Thr Ser Lys Leu Ala Ser
        515                 520                 525

Gly Val Pro Ala His Phe Arg Gly Ser Gly Ser Gly Thr Ser Tyr Ser
    530                 535                 540

Leu Thr Ile Ser Gly Met Glu Ala Glu Asp Ala Ala Thr Tyr Tyr Cys
545                 550                 555                 560

Gln Gln Trp Ser Ser Asn Pro Phe Thr Phe Gly Ser Gly Thr Lys Leu
                565                 570                 575

Glu Ile Asn Arg Gly Gly Gly Gly Ser Gly Gly Gly Gly Ser Gly Gly
            580                 585                 590
```

```
Gly Gly Ser Gln Val Gln Leu Gln Gln Ser Gly Ala Glu Leu Ala Arg
        595                 600                 605

Pro Gly Ala Ser Val Lys Met Ser Cys Lys Ala Ser Gly Tyr Thr Phe
    610                 615                 620

Thr Arg Tyr Thr Met His Trp Val Lys Gln Arg Pro Gly Gln Gly Leu
625                 630                 635                 640

Glu Trp Ile Gly Tyr Ile Asn Pro Ser Arg Gly Tyr Thr Asn Tyr Asn
                645                 650                 655

Gln Lys Phe Lys Asp Lys Ala Thr Leu Thr Thr Asp Lys Ser Ser Ser
            660                 665                 670

Thr Ala Tyr Met Gln Leu Ser Ser Leu Thr Ser Glu Asp Ser Ala Val
        675                 680                 685

Tyr Tyr Cys Ala Arg Tyr Tyr Asp Asp His Tyr Cys Leu Asp Tyr Trp
    690                 695                 700

Gly Gln Gly Thr Thr Leu Thr Val Ser Ser
705                 710
```

<210> SEQ ID NO 92
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
atgaaatggg tcaccttcat ctctttactg tttttattta gcagcgccta cagcgtgcag     60

ctgcagcagt ccggacccga actggtcaag cccggtgcct ccgtgaaaat gtcttgtaag    120

gcttctggct acacctttac ctcctacgtc atccaatggg tgaagcagaa gcccggtcaa    180

ggtctcgagt ggatcggcag catcaatccc tacaacgatt acaccaagta taacgaaaag    240

tttaagggca aggccactct gacaagcgac aagagctcca ttaccgccta catggagttt    300

tcctctttaa cttctgagga ctccgcttta tactattgcg ctcgttgggg cgatggcaat    360

tattggggcc ggggaactac tttaacagtg agctccggcg gcggcggaag cggaggtgga    420

ggatctggcg gtggaggcag cgacatcgag atgacacagt cccccgctat catgagcgcc    480

tctttaggag aacgtgtgac catgacttgt acagcttcct ccagcgtgag cagctcctat    540

ttccactggt accagcagaa acccggctcc tcccctaaac tgtgtatcta ctccacaagc    600

aatttagcta gcggcgtgcc tcctcgtttt agcggctccg gcagcacctc ttactcttta    660

accattagct ctatggaggc cgaagatgcc gccacatact tttgccatca gtaccaccgg    720

tcccctacct ttggcggagg cacaaagctg gagaccaagc ggagcggcac caccaacaca    780

gtggccgcct acaatctgac ttggaaatcc accaacttca agaccatcct cgagtgggag    840

cccaagcccg ttaatcaagt ttataccgtg cagatttcca ccaagagcgg cgactggaaa    900

tccaagtgct tctataccac agacaccgag tgcgatctca ccgacgagat cgtcaaagac    960

gtgaagcaga catatttagc tagggtgttc tcctaccccg ctggaaacgt ggagagcacc   1020

ggatccgctg gagagccttt atacgagaac tcccccgaat tcacccccta tctggaaacc   1080

aatttaggcc agcccaccat ccagagcttc gaacaagttg gcacaaaggt gaacgtcacc   1140

gtcgaagatg agaggacttt agtgcggagg aacaatacat tttatccttt acgtgacgtc   1200

ttcggcaagg atttaatcta cacactgtat tactggaagt ctagctcctc cggcaagaag   1260

accgccaaga ccaataccaa cgaattttta attgacgtgg acaagggcga gaactactgc   1320
```

ttctccgtgc aagctgtgat cccctcccgg acagtgaacc ggaagtccac cgactccccc 1380
gtggagtgca tgggccaaga gaagggagag tttcgtgagc agatcgtgct gacccagtcc 1440
cccgctatta tgagcgctag ccccggtgaa aaggtgacta tgacatgcag cgccagctct 1500
tccgtgagct acatgaactg gtatcagcag aagtccggca ccagccctaa aaggtggatc 1560
tacgacacca gcaagctggc cagcggcgtc cccgctcact ttcggggctc cggctccgga 1620
acaagctact ctctgaccat cagcggcatg gaagccgagg atgccgctac ctattactgt 1680
cagcagtgga gctccaaccc cttcaccttt ggatccggca ccaagctcga gattaatcgt 1740
ggaggcggag gtagcggagg aggcggatcc ggcggtggag gtagccaagt tcagctccag 1800
caaagcggcg ccgaactcgc tcggcccggc gcttccgtga agatgtcttg taaggcctcc 1860
ggctatacct tcacccggta cacaatgcac tgggtcaagc aacggcccgg tcaaggttta 1920
gagtggattg gctatatcaa cccctcccgg ggctatacca actacaacca gaagttcaag 1980
gacaaagcca ccctcaccac cgacaagtcc agcagcaccg cttacatgca gctgagctct 2040
ttaacatccg aggattccgc cgtgtactac tgcgctcggt actacgacga tcattactgc 2100
ctcgattact ggggccaagg taccacctta acagtctcct cc 2142

<210> SEQ ID NO 93
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 93

Ser Gly Thr Thr Asn Thr Val Ala Ala Tyr Asn Leu Thr Trp Lys Ser
1 5 10 15

Thr Asn Phe Lys Thr Ile Leu Glu Trp Glu Pro Lys Pro Val Asn Gln
20 25 30

Val Tyr Thr Val Gln Ile Ser Thr Lys Ser Gly Asp Trp Lys Ser Lys
35 40 45

Cys Phe Tyr Thr Thr Asp Thr Glu Cys Asp Leu Thr Asp Glu Ile Val
50 55 60

Lys Asp Val Lys Gln Thr Tyr Leu Ala Arg Val Phe Ser Tyr Pro Ala
65 70 75 80

Gly Asn Val Glu Ser Thr Gly Ser Ala Gly Glu Pro Leu Tyr Glu Asn
85 90 95

Ser Pro Glu Phe Thr Pro Tyr Leu Glu Thr Asn Leu Gly Gln Pro Thr
100 105 110

Ile Gln Ser Phe Glu Gln Val Gly Thr Lys Val Asn Val Thr Val Glu
115 120 125

Asp Glu Arg Thr Leu Val Arg Arg Asn Asn Thr Phe Leu Ser Leu Arg
130 135 140

Asp Val Phe Gly Lys Asp Leu Ile Tyr Thr Leu Tyr Tyr Trp Lys Ser
145 150 155 160

Ser Ser Ser Gly Lys Lys Thr Ala Lys Thr Asn Thr Asn Glu Phe Leu
165 170 175

Ile Asp Val Asp Lys Gly Glu Asn Tyr Cys Phe Ser Val Gln Ala Val
180 185 190

Ile Pro Ser Arg Thr Val Asn Arg Lys Ser Thr Asp Ser Pro Val Glu
195 200 205

Cys Met Gly Gln Glu Lys Gly Glu Phe Arg Glu
    210                 215

<210> SEQ ID NO 94
<211> LENGTH: 657
<212> TYPE: DNA
<213> ORGANISM: Homo sapiens
<220> FEATURE:
<221> NAME/KEY: source
<223> OTHER INFORMATION: /note="Tissue factor"

<400> SEQUENCE: 94
agcggcacaa ccaacacagt cgctgcctat aacctcactt ggaagagcac caacttcaaa 60
accatcctcg aatgggaacc caaacccgtt aaccaagttt acaccgtgca gatcagcacc 120
aagtccggcg actggaagtc caaatgtttc tataccaccg acaccgagtg cgatctcacc 180
gatgagatcg tgaaagatgt gaaacagacc tacctcgccc gggtgtttag ctaccccgcc 240
ggcaatgtgg agagcactgg ttccgctggc gagcctttat acgagaacag ccccgaattt 300
accccttacc tcgagaccaa tttaggacag cccaccatcc aaagctttga gcaagttggc 360
acaaaggtga atgtgacagt ggaggacgag cggactttag tgcggcggaa caacaccttt 420
ctcagcctcc gggatgtgtt cggcaaagat ttaatctaca cactgtatta ctggaagtcc 480
tcttcctccg gcaagaagac agctaaaacc aacacaaacg agtttttaat cgacgtggat 540
aaaggcgaaa actactgttt cagcgtgcaa gctgtgatcc cctcccggac cgtgaatagg 600
aaaagcaccg atagccccgt tgagtgcatg ggccaagaaa agggcgagtt ccgggag 657

<210> SEQ ID NO 95
<211> LENGTH: 223
<212> TYPE: PRT
<213> ORGANISM: Mus musculus
<220> FEATURE:
<221> NAME/KEY: source
<223> OTHER INFORMATION: /note="Tissue factor"

<400> SEQUENCE: 95

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
180 185 190

Val Gln Ala Met Ile Phe Ser Arg Lys Thr Asn Gln Asn Ser Pro Gly
195 200 205

Ser Ser Thr Val Cys Thr Glu Gln Trp Lys Ser Phe Leu Gly Glu
210 215 220

<210> SEQ ID NO 96
<211> LENGTH: 224
<212> TYPE: PRT
<213> ORGANISM: Rattus rattus
<220> FEATURE:
<221> NAME/KEY: source
<223> OTHER INFORMATION: /note="Tissue factor"

<400> SEQUENCE: 96

Ala Gly Thr Pro Pro Gly Lys Ala Phe Asn Leu Thr Trp Ile Ser Thr
1 5 10 15

Asp Phe Lys Thr Ile Leu Glu Trp Gln Pro Lys Pro Thr Asn Tyr Thr
20 25 30

Tyr Thr Val Gln Ile Ser Asp Arg Ser Arg Asn Trp Lys Tyr Lys Cys
35 40 45

Thr Gly Thr Thr Asp Thr Glu Cys Asp Leu Thr Asp Glu Ile Val Lys
50 55 60

Asp Val Asn Trp Thr Tyr Glu Ala Arg Val Leu Ser Val Pro Trp Arg
65 70 75 80

Asn Ser Thr His Gly Lys Glu Thr Leu Phe Gly Thr His Gly Glu Glu
85 90 95

Pro Pro Phe Thr Asn Ala Arg Lys Phe Leu Pro Tyr Arg Asp Thr Lys
100 105 110

Ile Gly Gln Pro Val Ile Gln Lys Tyr Glu Gln Gly Gly Thr Lys Leu
115 120 125

Lys Val Thr Val Lys Asp Ser Phe Thr Leu Val Arg Lys Asn Gly Thr
130 135 140

Phe Leu Thr Leu Arg Gln Val Phe Gly Asn Asp Leu Gly Tyr Ile Leu
145 150 155 160

Thr Tyr Arg Lys Asp Ser Ser Thr Gly Arg Lys Thr Asn Thr Thr His
165 170 175

Thr Asn Glu Phe Leu Ile Asp Val Glu Lys Gly Val Ser Tyr Cys Phe
180 185 190

Phe Ala Gln Ala Val Ile Phe Ser Arg Lys Thr Asn His Lys Ser Pro
195 200 205

Glu Ser Ile Thr Lys Cys Thr Glu Gln Trp Lys Ser Val Leu Gly Glu
210 215 220

<210> SEQ ID NO 97
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 97

Ser Gly Thr Thr Asn Thr Val Ala Ala Tyr Asn Leu Thr Trp Lys Ser
1 5 10 15

Thr Asn Phe Ala Thr Ala Leu Glu Trp Glu Pro Lys Pro Val Asn Gln
20 25 30

Val Tyr Thr Val Gln Ile Ser Thr Lys Ser Gly Asp Trp Lys Ser Lys
35 40 45

Cys Phe Tyr Thr Thr Asp Thr Glu Cys Ala Leu Thr Asp Glu Ile Val
50 55 60

Lys Asp Val Lys Gln Thr Tyr Leu Ala Arg Val Phe Ser Tyr Pro Ala
65 70 75 80

Gly Asn Val Glu Ser Thr Gly Ser Ala Gly Glu Pro Leu Tyr Glu Asn
85 90 95

Ser Pro Glu Phe Thr Pro Tyr Leu Glu Thr Asn Leu Gly Gln Pro Thr
100 105 110

Ile Gln Ser Phe Glu Gln Val Gly Thr Lys Val Asn Val Thr Val Glu
115 120 125

Asp Glu Arg Thr Leu Val Ala Arg Asn Asn Thr Ala Leu Ser Leu Arg
130 135 140

Asp Val Phe Gly Lys Asp Leu Ile Tyr Thr Leu Tyr Tyr Trp Lys Ser
145 150 155 160

Ser Ser Ser Gly Lys Lys Thr Ala Lys Thr Asn Thr Asn Glu Phe Leu
165 170 175

Ile Asp Val Asp Lys Gly Glu Asn Tyr Cys Phe Ser Val Gln Ala Val
180 185 190

Ile Pro Ser Arg Thr Val Asn Arg Lys Ser Thr Asp Ser Pro Val Glu
195 200 205

Cys Met Gly Gln Glu Lys Gly Glu Phe Arg Glu
210 215

<210> SEQ ID NO 98
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 98

Ser Gly Thr Thr Asn Thr Val Ala Ala Tyr Asn Leu Thr Trp Lys Ser
1 5 10 15

Thr Asn Phe Ala Thr Ala Leu Glu Trp Glu Pro Lys Pro Val Asn Gln
20 25 30

Val Tyr Thr Val Gln Ile Ser Thr Lys Ser Gly Asp Ala Lys Ser Lys
35 40 45

Cys Phe Tyr Thr Thr Asp Thr Glu Cys Ala Leu Thr Asp Glu Ile Val
50 55 60

Lys Asp Val Lys Gln Thr Tyr Leu Ala Arg Val Phe Ser Tyr Pro Ala
65 70 75 80

Gly Asn Val Glu Ser Thr Gly Ser Ala Gly Glu Pro Leu Ala Glu Asn
85 90 95

Ser Pro Glu Phe Thr Pro Tyr Leu Glu Thr Asn Leu Gly Gln Pro Thr
100 105 110

Ile Gln Ser Phe Glu Gln Val Gly Thr Lys Val Asn Val Thr Val Glu
115 120 125

Asp Glu Arg Thr Leu Val Ala Arg Asn Asn Thr Ala Leu Ser Leu Arg
130 135 140

Asp Val Phe Gly Lys Asp Leu Ile Tyr Thr Leu Tyr Tyr Trp Lys Ser
145 150 155 160

Ser Ser Ser Gly Lys Lys Thr Ala Lys Thr Asn Thr Asn Glu Phe Leu

```
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215


<210> SEQ ID NO 99
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Gly Gly Ser
1


<210> SEQ ID NO 100
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Gly Gly Gly Ser
1               5


<210> SEQ ID NO 101
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Gly Ser Gly
1


<210> SEQ ID NO 102
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Gly Gly Gly Ser Gly Gly Gly Gly Ser Gly Gly Gly Gly Ser
1               5                   10                  15


<210> SEQ ID NO 103
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 103
ggcggtggag gatccggagg aggtggctcc ggcggcggag gatct 45

<210> SEQ ID NO 104
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

Gly Gly Gly Ser Gly Gly Gly Ser
1 5

<210> SEQ ID NO 105
<211> LENGTH: 133
<212> TYPE: PRT
<213> ORGANISM: Homo sapiens
<220> FEATURE:
<221> NAME/KEY: source
<223> OTHER INFORMATION: /note="IL-3"

<400> SEQUENCE: 105

Ala Pro Met Thr Gln Thr Thr Pro Leu Lys Thr Ser Trp Val Asn Cys
1 5 10 15

Ser Asn Met Ile Asp Glu Ile Ile Thr His Leu Lys Gln Pro Pro Leu
20 25 30

Pro Leu Leu Asp Phe Asn Asn Leu Asn Gly Glu Asp Gln Asp Ile Leu
35 40 45

Met Glu Asn Asn Leu Arg Arg Pro Asn Leu Glu Ala Phe Asn Arg Ala
50 55 60

Val Lys Ser Leu Gln Asn Ala Ser Ala Ile Glu Ser Ile Leu Lys Asn
65 70 75 80

Leu Leu Pro Cys Leu Pro Leu Ala Thr Ala Ala Pro Thr Arg His Pro
85 90 95

Ile His Ile Lys Asp Gly Asp Trp Asn Glu Phe Arg Arg Lys Leu Thr
100 105 110

Phe Tyr Leu Lys Thr Leu Glu Asn Ala Gln Ala Gln Gln Thr Thr Leu
115 120 125

Ser Leu Ala Ile Phe
130

<210> SEQ ID NO 106
<211> LENGTH: 79
<212> TYPE: PRT
<213> ORGANISM: Homo sapiens
<220> FEATURE:
<221> NAME/KEY: source
<223> OTHER INFORMATION: /note="IL-8"

<400> SEQUENCE: 106

Glu Gly Ala Val Leu Pro Arg Ser Ala Lys Glu Leu Arg Cys Gln Cys
1 5 10 15

Ile Lys Thr Tyr Ser Lys Pro Phe His Pro Lys Phe Ile Lys Glu Leu
20 25 30

Arg Val Ile Glu Ser Gly Pro His Cys Ala Asn Thr Glu Ile Ile Val
35 40 45

```
Lys Leu Ser Asp Gly Arg Glu Leu Cys Leu Asp Pro Lys Glu Asn Trp
    50                  55                  60

Val Gln Arg Val Val Glu Lys Phe Leu Lys Arg Ala Glu Asn Ser
65                  70                  75


<210> SEQ ID NO 107
<211> LENGTH: 160
<212> TYPE: PRT
<213> ORGANISM: Homo sapiens
<220> FEATURE:
<221> NAME/KEY: source
<223> OTHER INFORMATION: /note="IL-10"

<400> SEQUENCE: 107

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 108
<211> LENGTH: 132
<212> TYPE: PRT
<213> ORGANISM: Homo sapiens
<220> FEATURE:
<221> NAME/KEY: source
<223> OTHER INFORMATION: /note="IL-17"

<400> SEQUENCE: 108

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110
```

Glu Lys Ile Leu Val Ser Val Gly Cys Thr Cys Val Thr Pro Ile Val
115 120 125

His His Val Ala
130

<210> SEQ ID NO 109
<211> LENGTH: 157
<212> TYPE: PRT
<213> ORGANISM: Homo sapiens
<220> FEATURE:
<221> NAME/KEY: source
<223> OTHER INFORMATION: /note="IL-18"

<400> SEQUENCE: 109

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Ser Val Pro Gly His Asp Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 110
<211> LENGTH: 352
<212> TYPE: PRT
<213> ORGANISM: Homo sapiens
<220> FEATURE:
<221> NAME/KEY: source
<223> OTHER INFORMATION: /note="PDGF-DD"

<400> SEQUENCE: 110

Arg Asp Thr Ser Ala Thr Pro Gln Ser Ala Ser Ile Lys Ala Leu Arg
1 5 10 15

Asn Ala Asn Leu Arg Arg Asp Glu Ser Asn His Leu Thr Asp Leu Tyr
20 25 30

Arg Arg Asp Glu Thr Ile Gln Val Lys Gly Asn Gly Tyr Val Gln Ser
35 40 45

Pro Arg Phe Pro Asn Ser Tyr Pro Arg Asn Leu Leu Leu Thr Trp Arg
50 55 60

Leu His Ser Gln Glu Asn Thr Arg Ile Gln Leu Val Phe Asp Asn Gln
65 70 75 80

Phe Gly Leu Glu Glu Ala Glu Asn Asp Ile Cys Arg Tyr Asp Phe Val
85 90 95

Glu Val Glu Asp Ile Ser Glu Thr Ser Thr Ile Ile Arg Gly Arg Trp
100 105 110

Cys Gly His Lys Glu Val Pro Pro Arg Ile Lys Ser Arg Thr Asn Gln
115 120 125

Ile Lys Ile Thr Phe Lys Ser Asp Asp Tyr Phe Val Ala Lys Pro Gly
130 135 140

Phe Lys Ile Tyr Tyr Ser Leu Leu Glu Asp Phe Gln Pro Ala Ala Ala
145 150 155 160

Ser Glu Thr Asn Trp Glu Ser Val Thr Ser Ser Ile Ser Gly Val Ser
165 170 175

Tyr Asn Ser Pro Ser Val Thr Asp Pro Thr Leu Ile Ala Asp Ala Leu
180 185 190

Asp Lys Lys Ile Ala Glu Phe Asp Thr Val Glu Asp Leu Leu Lys Tyr
195 200 205

Phe Asn Pro Glu Ser Trp Gln Glu Asp Leu Glu Asn Met Tyr Leu Asp
210 215 220

Thr Pro Arg Tyr Arg Gly Arg Ser Tyr His Asp Arg Lys Ser Lys Val
225 230 235 240

Asp Leu Asp Arg Leu Asn Asp Asp Ala Lys Arg Tyr Ser Cys Thr Pro
245 250 255

Arg Asn Tyr Ser Val Asn Ile Arg Glu Glu Leu Lys Leu Ala Asn Val
260 265 270

Val Phe Phe Pro Arg Cys Leu Leu Val Gln Arg Cys Gly Gly Asn Cys
275 280 285

Gly Cys Gly Thr Val Asn Trp Arg Ser Cys Thr Cys Asn Ser Gly Lys
290 295 300

Thr Val Lys Lys Tyr His Glu Val Leu Gln Phe Glu Pro Gly His Ile
305 310 315 320

Lys Arg Arg Gly Arg Ala Lys Thr Met Ala Leu Val Asp Ile Gln Leu
325 330 335

Asp His His Glu Arg Cys Asp Cys Ile Cys Ser Ser Arg Pro Pro Arg
340 345 350

<210> SEQ ID NO 111
<211> LENGTH: 248
<212> TYPE: PRT
<213> ORGANISM: Homo sapiens
<220> FEATURE:
<221> NAME/KEY: source
<223> OTHER INFORMATION: /note="SCF"

<400> SEQUENCE: 111

Glu Gly Ile Cys Arg Asn Arg Val Thr Asn Asn Val Lys Asp Val Thr
1 5 10 15

Lys Leu Val Ala Asn Leu Pro Lys Asp Tyr Met Ile Thr Leu Lys Tyr
20 25 30

Val Pro Gly Met Asp Val Leu Pro Ser His Cys Trp Ile Ser Glu Met
35 40 45

Val Val Gln Leu Ser Asp Ser Leu Thr Asp Leu Leu Asp Lys Phe Ser
50 55 60

Asn Ile Ser Glu Gly Leu Ser Asn Tyr Ser Ile Ile Asp Lys Leu Val
65 70 75 80

Asn Ile Val Asp Asp Leu Val Glu Cys Val Lys Glu Asn Ser Ser Lys
85 90 95

Asp Leu Lys Lys Ser Phe Lys Ser Pro Glu Pro Arg Leu Phe Thr Pro
100 105 110

Glu Glu Phe Phe Arg Ile Phe Asn Arg Ser Ile Asp Ala Phe Lys Asp
115 120 125

```
Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245


<210> SEQ ID NO 112
<211> LENGTH: 209
<212> TYPE: PRT
<213> ORGANISM: Homo sapiens
<220> FEATURE:
<221> NAME/KEY: source
<223> OTHER INFORMATION: /note="FLT3L"

<400> SEQUENCE: 112

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
            180                 185                 190

Glu Gln Val Pro Pro Val Pro Ser Pro Gln Asp Leu Leu Leu Val Glu
        195                 200                 205

His


<210> SEQ ID NO 113
```

<211> LENGTH: 65
<212> TYPE: PRT
<213> ORGANISM: Homo sapiens
<220> FEATURE:
<221> NAME/KEY: source
<223> OTHER INFORMATION: /note="IL15Ralpha"

<400> SEQUENCE: 113

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 114
<211> LENGTH: 195
<212> TYPE: DNA
<213> ORGANISM: Homo sapiens
<220> FEATURE:
<221> NAME/KEY: source
<223> OTHER INFORMATION: /note="IL15Ralpha"

<400> SEQUENCE: 114
attacatgcc cccctcccat gagcgtggag cacgccgaca tctgggtgaa gagctatagc      60
ctctacagcc gggagaggta tatctgtaac agcggcttca agaggaaggc cggcaccagc     120
agcctcaccg agtgcgtgct gaataaggct accaacgtgg ctcactggac aacaccctct     180
ttaaagtgca tccgg                                                      195

<210> SEQ ID NO 115
<211> LENGTH: 114
<212> TYPE: PRT
<213> ORGANISM: Homo sapiens
<220> FEATURE:
<221> NAME/KEY: source
<223> OTHER INFORMATION: /note="IL-15"

<400> SEQUENCE: 115

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 116

<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 116
aactgggtga acgtcatcag cgatttaaag aagatcgaag atttaattca gtccatgcat 60
atcgacgcca ctttatacac agaatccgac gtgcacccct cttgtaaggt gaccgccatg 120
aaatgttttt tactggagct gcaagttatc tctttagaga gcggagacgc tagcatccac 180
gacaccgtgg agaatttaat cattttagcc aataactctt tatccagcaa cggcaacgtg 240
acagagtccg gctgcaagga gtgcgaagag ctggaggaga agaacatcaa ggagtttctg 300
caatcctttg tgcacattgt ccagatgttc atcaatacct cc 342

<210> SEQ ID NO 117
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 117

Met Lys Trp Val Thr Phe Ile Ser Leu Leu Phe Leu Phe Ser Ser Ala
1               5                   10                  15

Tyr Ser

<210> SEQ ID NO 118
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 118
atgaaatggg tgacctttat ttctttactg ttcctcttta gcagcgccta ctcc 54

<210> SEQ ID NO 119
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 119
atgaagtggg tcacatttat ctctttactg ttcctcttct ccagcgccta cagc 54

<210> SEQ ID NO 120
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 120
atgaaatggg tgacctttat ttctttactg ttcctcttta gcagcgccta ctcc 54

<210> SEQ ID NO 121
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 121

Met Lys Cys Leu Leu Tyr Leu Ala Phe Leu Phe Leu Gly Val Asn Cys
1 5 10 15

<210> SEQ ID NO 122
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 122

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

Phe Leu Phe Leu Ala Gly Arg Ser Cys Gly
50 55

<210> SEQ ID NO 123
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 123

Met Pro Asn His Gln Ser Gly Ser Pro Thr Gly Ser Ser Asp Leu Leu
1 5 10 15

Leu Ser Gly Lys Lys Gln Arg Pro His Leu Ala Leu Arg Arg Lys Arg
20 25 30

Arg Arg Glu Met Arg Lys Ile Asn Arg Lys Val Arg Arg Met Asn Leu
35 40 45

Ala Pro Ile Lys Glu Lys Thr Ala Trp Gln His Leu Gln Ala Leu Ile
50 55 60

Ser Glu Ala Glu Glu Val Leu Lys Thr Ser Gln Thr Pro Gln Asn Ser
65 70 75 80

Leu Thr Leu Phe Leu Ala Leu Leu Ser Val Leu Gly Pro Pro Val Thr
85 90 95

Gly

<210> SEQ ID NO 124
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 124

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 125
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Signal sequence"

<400> SEQUENCE: 125

Met Lys Cys Leu Leu Tyr Leu Ala Phe Leu Phe Leu Gly Val Asn Cys
1               5                   10                  15

<210> SEQ ID NO 126
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Gly Leu Asn Asp Ile Phe Glu Ala Gln Lys Ile Glu Trp His Glu
1               5                   10                  15

<210> SEQ ID NO 127
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 128
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 128

Glu Glu Glu Glu Glu Glu
1               5

<210> SEQ ID NO 129
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 129

Gly Ala Pro Val Pro Tyr Pro Asp Pro Leu Glu Pro Arg
1 5 10

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 130

Asp Tyr Lys Asp Asp Asp Asp Lys
1 5

<210> SEQ ID NO 131
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 131

Tyr Pro Tyr Asp Val Pro Asp Tyr Ala
1 5

<210> SEQ ID NO 132
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 132

His His His His His
1 5

<210> SEQ ID NO 133
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 133

His His His His His His
1 5

<210> SEQ ID NO 134
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 134

His His His His His His His
1 5

<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

His His His His His His His His
1 5

<210> SEQ ID NO 136
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 136

His His His His His His His His His
1 5

<210> SEQ ID NO 137
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 137

His His His His His His His His His His
1 5 10

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 138

Glu Gln Lys Leu Ile Ser Glu Glu Asp Leu
1 5 10

<210> SEQ ID NO 139
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Thr Lys Glu Asn Pro Arg Ser Asn Gln Glu Glu Ser Tyr Asp Asp Asn 1 5 10 15

Glu Ser

<210> SEQ ID NO 140
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Lys Glu Thr Ala Ala Ala Lys Phe Glu Arg Gln His Met Asp Ser
1 5 10 15

<210> SEQ ID NO 141
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

Met Asp Glu Lys Thr Thr Gly Trp Arg Gly Gly His Val Val Glu Gly
1 5 10 15

Leu Ala Gly Glu Leu Glu Gln Leu Arg Ala Arg Leu Glu His His Pro
20 25 30

Gln Gly Gln Arg Glu Pro
35

<210> SEQ ID NO 142
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Ser Leu Ala Glu Leu Leu Asn Ala Gly Leu Gly Gly Ser
1 5 10

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 143

Thr Gln Asp Pro Ser Arg Val Gly
1 5

<210> SEQ ID NO 144
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Pro Asp Arg Val Arg Ala Val Ser His Trp Ser Ser
1               5                   10

<210> SEQ ID NO 145
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

Trp Ser His Pro Gln Phe Glu Lys
1               5

<210> SEQ ID NO 146
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

Cys Cys Pro Gly Cys Cys
1               5

<210> SEQ ID NO 147
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 147

Glu Val His Thr Asn Gln Asp Pro Leu Asp
1               5                   10

<210> SEQ ID NO 148
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Gly Lys Pro Ile Pro Asn Pro Leu Leu Gly Leu Asp Ser Thr
1               5                   10

<210> SEQ ID NO 149
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Tyr Thr Asp Ile Glu Met Asn Arg Leu Gly Lys

```
1               5                   10


<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Asp Leu Tyr Asp Asp Asp Asp Lys
1               5


<210> SEQ ID NO 151
<211> LENGTH: 241
<212> TYPE: PRT
<213> ORGANISM: Homo sapiens
<220> FEATURE:
<221> NAME/KEY: source
<223> OTHER INFORMATION: /note="CD3"

<400> SEQUENCE: 151

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser


<210> SEQ ID NO 152
<211> LENGTH: 723
<212> TYPE: DNA
```

-continued

```
<213> ORGANISM: Homo sapiens
<220> FEATURE:
<221> NAME/KEY: source
<223> OTHER INFORMATION: /note="CD3"

<400> SEQUENCE: 152

cagatcgtgc tgacccaaag ccccgccatc atgagcgcta gccccggtga gaaggtgacc     60

atgacatgct ccgcttccag ctccgtgtcc tacatgaact ggtatcagca gaaaagcgga    120

accagcccca aaaggtggat ctacgacacc agcaagctgg cctccggagt gcccgctcat    180

ttccggggct ctggatccgg caccagctac tctttaacca tttccggcat ggaagctgaa    240

gacgctgcca cctactattg ccagcaatgg agcagcaacc ccttcacatt cggatctggc    300

accaagctcg aaatcaatcg tggaggaggt ggcagcggcg gcggtggatc cggcggagga    360

ggaagccaag ttcaactcca gcagagcggc gctgaactgg cccggcccgg cgcctccgtc    420

aagatgagct gcaaggcttc cggctataca tttactcgtt acacaatgca ttgggtcaag    480

cagaggcccg gtcaaggttt agagtggatc ggatatatca acccttcccg gggctacacc    540

aactataacc aaaagttcaa ggataaagcc actttaacca ctgacaagag ctcctccacc    600

gcctacatgc agctgtcctc tttaaccagc gaggactccg ctgtttacta ctgcgctagg    660

tattacgacg accactactg tttagactat tggggacaag gtaccacttt aaccgtcagc    720

agc                                                                  723


<210> SEQ ID NO 153
<211> LENGTH: 236
<212> TYPE: PRT
<213> ORGANISM: Homo sapiens
<220> FEATURE:
<221> NAME/KEY: source
<223> OTHER INFORMATION: /note="CD28"

<400> SEQUENCE: 153

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Ile Glu Met Thr Gln Ser Pro Ala Ile Met Ser Ala Ser Leu
    130                 135                 140

Gly Glu Arg Val Thr Met Thr Cys Thr Ala Ser Ser Ser Val Ser Ser
145                 150                 155                 160

Ser Tyr Phe His Trp Tyr Gln Gln Lys Pro Gly Ser Ser Pro Lys Leu
                165                 170                 175

Cys Ile Tyr Ser Thr Ser Asn Leu Ala Ser Gly Val Pro Pro Arg Phe
            180                 185                 190
```

```
Ser Gly Ser Gly Ser Thr Ser Tyr Ser Leu Thr Ile Ser Ser Met Glu
        195                 200                 205

Ala Glu Asp Ala Ala Thr Tyr Phe Cys His Gln Tyr His Arg Ser Pro
    210                 215                 220

Thr Phe Gly Gly Gly Thr Lys Leu Glu Thr Lys Arg
225                 230                 235


<210> SEQ ID NO 154
<211> LENGTH: 708
<212> TYPE: DNA
<213> ORGANISM: Homo sapiens
<220> FEATURE:
<221> NAME/KEY: source
<223> OTHER INFORMATION: /note="CD28"

<400> SEQUENCE: 154

gtccagctgc agcagagcgg acccgaactc gtgaaacccg gtgcttccgt gaaaatgtct     60

tgtaaggcca gcggatacac cttcacctcc tatgtgatcc agtgggtcaa acagaagccc    120

ggacaaggtc tcgagtggat cggcagcatc aacccttaca acgactatac caaatacaac    180

gagaagttta agggaaaggc tactttaacc tccgacaaaa gctccatcac agcctacatg    240

gagttcagct ctttaacatc cgaggacagc gctctgtact attgcgcccg gtggggcgac    300

ggcaattact ggggacgggg cacaacactg accgtgagca gcggaggcgg aggctccggc    360

ggaggcggat ctggcggtgg cggctccgac atcgagatga cccagtcccc cgctatcatg    420

tccgcctctt taggcgagcg ggtcacaatg acttgtacag cctcctccag cgtctcctcc    480

tcctacttcc attggtacca acagaaaccc ggaagctccc ctaaactgtg catctacagc    540

accagcaatc tcgccagcgg cgtgccccct aggttttccg gaagcggaag caccagctac    600

tctttaacca tctcctccat ggaggctgag gatgccgcca cctacttttg tcaccagtac    660

caccggtccc ccaccttcgg aggcggcacc aaactggaga caaagagg                  708


<210> SEQ ID NO 155
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 3t28 sequence"

<400> SEQUENCE: 155

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Gly Ser Gln Val Gln Leu Gln Gln
```

```
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255

Ser Thr Asn Phe Lys Thr Ile Leu Glu Trp Glu Pro Lys Pro Val Asn
            260                 265                 270

Gln Val Tyr Thr Val Gln Ile Ser Thr Lys Ser Gly Asp Trp Lys Ser
        275                 280                 285

Lys Cys Phe Tyr Thr Thr Asp Thr Glu Cys Asp Leu Thr Asp Glu Ile
    290                 295                 300

Val Lys Asp Val Lys Gln Thr Tyr Leu Ala Arg Val Phe Ser Tyr Pro
305                 310                 315                 320

Ala Gly Asn Val Glu Ser Thr Gly Ser Ala Gly Glu Pro Leu Tyr Glu
                325                 330                 335

Asn Ser Pro Glu Phe Thr Pro Tyr Leu Glu Thr Asn Leu Gly Gln Pro
            340                 345                 350

Thr Ile Gln Ser Phe Glu Gln Val Gly Thr Lys Val Asn Val Thr Val
        355                 360                 365

Glu Asp Glu Arg Thr Leu Val Arg Arg Asn Asn Thr Phe Leu Ser Leu
    370                 375                 380

Arg Asp Val Phe Gly Lys Asp Leu Ile Tyr Thr Leu Tyr Tyr Trp Lys
385                 390                 395                 400

Ser Ser Ser Ser Gly Lys Lys Thr Ala Lys Thr Asn Thr Asn Glu Phe
                405                 410                 415

Leu Ile Asp Val Asp Lys Gly Glu Asn Tyr Cys Phe Ser Val Gln Ala
            420                 425                 430

Val Ile Pro Ser Arg Thr Val Asn Arg Lys Ser Thr Asp Ser Pro Val
        435                 440                 445

Glu Cys Met Gly Gln Glu Lys Gly Glu Phe Arg Glu Val Gln Leu Gln
    450                 455                 460

Gln Ser Gly Pro Glu Leu Val Lys Pro Gly Ala Ser Val Lys Met Ser
465                 470                 475                 480

Cys Lys Ala Ser Gly Tyr Thr Phe Thr Ser Tyr Val Ile Gln Trp Val
                485                 490                 495

Lys Gln Lys Pro Gly Gln Gly Leu Glu Trp Ile Gly Ser Ile Asn Pro
            500                 505                 510

Tyr Asn Asp Tyr Thr Lys Tyr Asn Glu Lys Phe Lys Gly Lys Ala Thr
        515                 520                 525

Leu Thr Ser Asp Lys Ser Ser Ile Thr Ala Tyr Met Glu Phe Ser Ser
    530                 535                 540
```

```
Leu Thr Ser Glu Asp Ser Ala Leu Tyr Tyr Cys Ala Arg Trp Gly Asp
545                 550                 555                 560

Gly Asn Tyr Trp Gly Arg Gly Thr Thr Leu Thr Val Ser Ser Gly Gly
                565                 570                 575

Gly Gly Ser Gly Gly Gly Gly Ser Gly Gly Gly Gly Ser Asp Ile Glu
            580                 585                 590

Met Thr Gln Ser Pro Ala Ile Met Ser Ala Ser Leu Gly Glu Arg Val
        595                 600                 605

Thr Met Thr Cys Thr Ala Ser Ser Ser Val Ser Ser Ser Tyr Phe His
    610                 615                 620

Trp Tyr Gln Gln Lys Pro Gly Ser Ser Pro Lys Leu Cys Ile Tyr Ser
625                 630                 635                 640

Thr Ser Asn Leu Ala Ser Gly Val Pro Pro Arg Phe Ser Gly Ser Gly
                645                 650                 655

Ser Thr Ser Tyr Ser Leu Thr Ile Ser Ser Met Glu Ala Glu Asp Ala
            660                 665                 670

Ala Thr Tyr Phe Cys His Gln Tyr His Arg Ser Pro Thr Phe Gly Gly
        675                 680                 685

Gly Thr Lys Leu Glu Thr Lys Arg
    690                 695


<210> SEQ ID NO 156
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 3t28 sequence"

<400> SEQUENCE: 156

cagatcgtgc tgacccaaag ccccgccatc atgagcgcta gccccggtga gaaggtgacc     60

atgacatgct ccgcttccag ctccgtgtcc tacatgaact ggtatcagca gaaaagcgga    120

accagcccca aaaggtggat ctacgacacc agcaagctgg cctccggagt gcccgctcat    180

ttccggggct ctggatccgg caccagctac tctttaacca tttccggcat ggaagctgaa    240

gacgctgcca cctactattg ccagcaatgg agcagcaacc ccttcacatt cggatctggc    300

accaagctcg aaatcaatcg tggaggaggt ggcagcggcg gcggtggatc cggcggagga    360

ggaagccaag ttcaactcca gcagagcggc gctgaactgg cccggcccgg cgcctccgtc    420

aagatgagct gcaaggcttc cggctataca tttactcgtt acacaatgca ttgggtcaag    480

cagaggcccg gtcaaggttt agagtggatc ggatatatca acccttcccg gggctacacc    540

aactataacc aaaagttcaa ggataaagcc actttaacca ctgacaagag ctcctccacc    600

gcctacatgc agctgtcctc tttaaccagc gaggactccg ctgtttacta ctgcgctagg    660

tattacgacg accactactg tttagactat tggggacaag gtaccacttt aaccgtcagc    720

agctccggca ccaccaatac cgtggccgct tataacctca catggaagag caccaacttc    780

aagacaattc tggaatggga acccaagccc gtcaatcaag tttacaccgt gcagatctcc    840

accaaatccg gagactggaa gagcaagtgc ttctacacaa cagacaccga gtgtgattta    900

accgacgaaa tcgtcaagga cgtcaagcaa acctatctgg ctcgggtctt ttcctacccc    960

gctggcaatg tcgagtccac cggctccgct ggcgagcctc tctacgagaa ttcccccgaa   1020

ttcacccctt atttagagac caatttaggc cagcctacca tccagagctt cgagcaagtt   1080
```

-continued

```
ggcaccaagg tgaacgtcac cgtcgaggat gaaaggactt tagtgcggcg gaataacaca   1140
tttttatccc tccgggatgt gttcggcaaa gacctcatct acacactgta ctattggaag   1200
tccagctcct ccggcaaaaa gaccgctaag accaacacca acgagttttt aattgacgtg   1260
gacaaaggcg agaactactg cttcagcgtg caagccgtga tcccttctcg taccgtcaac   1320
cggaagagca cagattcccc cgttgagtgc atgggccaag aaaagggcga gttccgggag   1380
gtccagctgc agcagagcgg acccgaactc gtgaaacccg gtgcttccgt gaaaatgtct   1440
tgtaaggcca gcggatacac cttcacctcc tatgtgatcc agtgggtcaa acagaagccc   1500
ggacaaggtc tcgagtggat cggcagcatc aacccttaca acgactatac caaatacaac   1560
gagaagttta agggaaaggc tactttaacc tccgacaaaa gctccatcac agcctacatg   1620
gagttcagct ctttaacatc cgaggacagc gctctgtact attgcgcccg gtggggcgac   1680
ggcaattact ggggacgggg cacaacactg accgtgagca gcggaggcgg aggctccggc   1740
ggaggcggat ctggcggtgg cggctccgac atcgagatga cccagtcccc cgctatcatg   1800
tccgcctctt taggcgagcg ggtcacaatg acttgtacag cctcctccag cgtctcctcc   1860
tcctacttcc attggtacca acagaaaccc ggaagctccc ctaaactgtg catctacagc   1920
accagcaatc tcgccagcgg cgtgccccct aggttttccg gaagcggaag caccagctac   1980
tctttaacca tctcctccat ggaggctgag gatgccgcca cctacttttg tcaccagtac   2040
caccggtccc ccaccttcgg aggcggcacc aaactggaga caaagagg                2088
```

<210> SEQ ID NO 157
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 3t28 sequence"

<400> SEQUENCE: 157

```
Met Lys Trp Val Thr Phe Ile Ser Leu Leu Phe Leu Phe Ser Ser Ala
1               5                   10                  15

Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ser
        35                  40                  45

Tyr Met Asn Trp Tyr Gln Gln Lys Ser Gly Thr Ser Pro Lys Arg Trp
    50                  55                  60

Ile Tyr Asp Thr Ser Lys Leu Ala Ser Gly Val Pro Ala His Phe Arg
65                  70                  75                  80

Gly Ser Gly Ser Gly Thr Ser Tyr Ser Leu Thr Ile Ser Gly Met Glu
                85                  90                  95

Ala Glu Asp Ala Ala Thr Tyr Tyr Cys Gln Gln Trp Ser Ser Asn Pro
            100                 105                 110

Phe Thr Phe Gly Ser Gly Thr Lys Leu Glu Ile Asn Arg Gly Gly Gly
        115                 120                 125

Gly Ser Gly Gly Gly Gly Ser Gly Gly Gly Gly Ser Gln Val Gln Leu
    130                 135                 140

Gln Gln Ser Gly Ala Glu Leu Ala Arg Pro Gly Ala Ser Val Lys Met
145                 150                 155                 160

Ser Cys Lys Ala Ser Gly Tyr Thr Phe Thr Arg Tyr Thr Met His Trp
                165                 170                 175
```

```
Val Lys Gln Arg Pro Gly Gln Gly Leu Glu Trp Ile Gly Tyr Ile Asn
            180                 185                 190

Pro Ser Arg Gly Tyr Thr Asn Tyr Asn Gln Lys Phe Lys Asp Lys Ala
        195                 200                 205

Thr Leu Thr Thr Asp Lys Ser Ser Ser Thr Ala Tyr Met Gln Leu Ser
    210                 215                 220

Ser Leu Thr Ser Glu Asp Ser Ala Val Tyr Tyr Cys Ala Arg Tyr Tyr
225                 230                 235                 240

Asp Asp His Tyr Cys Leu Asp Tyr Trp Gly Gln Gly Thr Thr Leu Thr
                245                 250                 255

Val Ser Ser Ser Gly Thr Thr Asn Thr Val Ala Ala Tyr Asn Leu Thr
            260                 265                 270

Trp Lys Ser Thr Asn Phe Lys Thr Ile Leu Glu Trp Glu Pro Lys Pro
        275                 280                 285

Val Asn Gln Val Tyr Thr Val Gln Ile Ser Thr Lys Ser Gly Asp Trp
    290                 295                 300

Lys Ser Lys Cys Phe Tyr Thr Thr Asp Thr Glu Cys Asp Leu Thr Asp
305                 310                 315                 320

Glu Ile Val Lys Asp Val Lys Gln Thr Tyr Leu Ala Arg Val Phe Ser
                325                 330                 335

Tyr Pro Ala Gly Asn Val Glu Ser Thr Gly Ser Ala Gly Glu Pro Leu
            340                 345                 350

Tyr Glu Asn Ser Pro Glu Phe Thr Pro Tyr Leu Glu Thr Asn Leu Gly
        355                 360                 365

Gln Pro Thr Ile Gln Ser Phe Glu Gln Val Gly Thr Lys Val Asn Val
    370                 375                 380

Thr Val Glu Asp Glu Arg Thr Leu Val Arg Arg Asn Asn Thr Phe Leu
385                 390                 395                 400

Ser Leu Arg Asp Val Phe Gly Lys Asp Leu Ile Tyr Thr Leu Tyr Tyr
                405                 410                 415

Trp Lys Ser Ser Ser Ser Gly Lys Lys Thr Ala Lys Thr Asn Thr Asn
            420                 425                 430

Glu Phe Leu Ile Asp Val Asp Lys Gly Glu Asn Tyr Cys Phe Ser Val
        435                 440                 445

Gln Ala Val Ile Pro Ser Arg Thr Val Asn Arg Lys Ser Thr Asp Ser
    450                 455                 460

Pro Val Glu Cys Met Gly Gln Glu Lys Gly Glu Phe Arg Glu Val Gln
465                 470                 475                 480

Leu Gln Gln Ser Gly Pro Glu Leu Val Lys Pro Gly Ala Ser Val Lys
                485                 490                 495

Met Ser Cys Lys Ala Ser Gly Tyr Thr Phe Thr Ser Tyr Val Ile Gln
            500                 505                 510

Trp Val Lys Gln Lys Pro Gly Gln Gly Leu Glu Trp Ile Gly Ser Ile
        515                 520                 525

Asn Pro Tyr Asn Asp Tyr Thr Lys Tyr Asn Glu Lys Phe Lys Gly Lys
    530                 535                 540

Ala Thr Leu Thr Ser Asp Lys Ser Ser Ile Thr Ala Tyr Met Glu Phe
545                 550                 555                 560

Ser Ser Leu Thr Ser Glu Asp Ser Ala Leu Tyr Tyr Cys Ala Arg Trp
                565                 570                 575

Gly Asp Gly Asn Tyr Trp Gly Arg Gly Thr Thr Leu Thr Val Ser Ser
            580                 585                 590

Gly Gly Gly Gly Ser Gly Gly Gly Gly Ser Gly Gly Gly Gly Ser Asp
```

```
        595                 600                 605

Ile Glu Met Thr Gln Ser Pro Ala Ile Met Ser Ala Ser Leu Gly Glu
    610                 615                 620

Arg Val Thr Met Thr Cys Thr Ala Ser Ser Ser Val Ser Ser Ser Tyr
625                 630                 635                 640

Phe His Trp Tyr Gln Gln Lys Pro Gly Ser Ser Pro Lys Leu Cys Ile
                645                 650                 655

Tyr Ser Thr Ser Asn Leu Ala Ser Gly Val Pro Pro Arg Phe Ser Gly
            660                 665                 670

Ser Gly Ser Thr Ser Tyr Ser Leu Thr Ile Ser Ser Met Glu Ala Glu
        675                 680                 685

Asp Ala Ala Thr Tyr Phe Cys His Gln Tyr His Arg Ser Pro Thr Phe
    690                 695                 700

Gly Gly Gly Thr Lys Leu Glu Thr Lys Arg
705                 710


<210> SEQ ID NO 158
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 3t28 sequence"

<400> SEQUENCE: 158

atgaagtggg tgaccttcat cagcttatta tttttattca gctccgccta ttcccagatc     60

gtgctgaccc aaagccccgc catcatgagc gctagccccg gtgagaaggt gaccatgaca    120

tgctccgctt ccagctccgt gtcctacatg aactggtatc agcagaaaag cggaaccagc    180

cccaaaaggt ggatctacga caccagcaag ctggcctccg gagtgcccgc tcatttccgg    240

ggctctggat ccggcaccag ctactcttta accatttccg gcatggaagc tgaagacgct    300

gccacctact attgccagca atggagcagc aacccccttca cattcggatc tggcaccaag    360

ctcgaaatca atcgtggagg aggtggcagc ggcggcggtg gatccggcgg aggaggaagc    420

caagttcaac tccagcagag cggcgctgaa ctggcccggc ccggcgcctc cgtcaagatg    480

agctgcaagg cttccggcta tacatttact cgttacacaa tgcattgggt caagcagagg    540

cccggtcaag gtttagagtg gatcggatat atcaaccctt cccggggcta caccaactat    600

aaccaaaagt tcaaggataa agccacttta accactgaca agagctcctc caccgcctac    660

atgcagctgt cctctttaac cagcgaggac tccgctgttt actactgcgc taggtattac    720

gacgaccact actgtttaga ctattgggga caaggtacca ctttaaccgt cagcagctcc    780

ggcaccacca ataccgtggc cgcttataac ctcacatgga agagcaccaa cttcaagaca    840

attctggaat gggaacccaa gcccgtcaat caagtttaca ccgtgcagat ctccaccaaa    900

tccggagact ggaagagcaa gtgcttctac acaacagaca ccgagtgtga tttaaccgac    960

gaaatcgtca aggacgtcaa gcaaacctat ctggctcggg tcttttccta ccccgctggc   1020

aatgtcgagt ccaccggctc cgctggcgag cctctctacg agaattcccc cgaattcacc   1080

ccttatttag agaccaattt aggccagcct accatccaga gcttcgagca agttggcacc   1140

aaggtgaacg tcaccgtcga ggatgaaagg actttagtgc ggcggaataa cacattttta   1200

tccctccggg atgtgttcgg caaagacctc atctacacac tgtactattg gaagtccagc   1260

tcctccggca aaaagaccgc taagaccaac accaacgagt ttttaattga cgtggacaaa   1320
```

ggcgagaact actgcttcag cgtgcaagcc gtgatccctt ctcgtaccgt caaccggaag 1380
agcacagatt cccccgttga gtgcatgggc caagaaaagg gcgagttccg ggaggtccag 1440
ctgcagcaga gcggacccga actcgtgaaa cccggtgctt ccgtgaaaat gtcttgtaag 1500
gccagcggat acaccttcac ctcctatgtg atccagtggg tcaaacagaa gcccggacaa 1560
ggtctcgagt ggatcggcag catcaaccct tacaacgact ataccaaata caacgagaag 1620
tttaagggaa aggctacttt aacctccgac aaaagctcca tcacagccta catggagttc 1680
agctctttaa catccgagga cagcgctctg tactattgcg cccggtgggg cgacggcaat 1740
tactggggac ggggcacaac actgaccgtg agcagcggag gcggaggctc cggcggaggc 1800
ggatctggcg gtggcggctc cgacatcgag atgacccagt cccccgctat catgtccgcc 1860
tctttaggcg agcgggtcac aatgacttgt acagcctcct ccagcgtctc ctcctcctac 1920
ttccattggt accaacagaa acccggaagc tcccctaaac tgtgcatcta cagcaccagc 1980
aatctcgcca gcggcgtgcc ccctaggttt tccggaagcg gaagcaccag ctactcttta 2040
accatctcct ccatggaggc tgaggatgcc gccacctact tttgtcacca gtaccaccgg 2100
tcccccacct tcggaggcgg caccaaactg gagacaaaga gg 2142

<210> SEQ ID NO 159
<211> LENGTH: 399
<212> TYPE: DNA
<213> ORGANISM: Homo sapiens
<220> FEATURE:
<221> NAME/KEY: source
<223> OTHER INFORMATION: /note="IL-2"

<400> SEQUENCE: 159
gcacctactt caagttctac aaagaaaaca cagctacaac tggagcattt actgctggat 60
ttacagatga ttttgaatgg aattaataat tacaagaatc ccaaactcac caggatgctc 120
acatttaagt tttacatgcc caagaaggcc acagaactga aacatcttca gtgtctagaa 180
gaagaactca aacctctgga ggaagtgcta aatttagctc aaagcaaaaa ctttcactta 240
agacccaggg acttaatcag caatatcaac gtaatagttc tggaactaaa gggatctgaa 300
acaacattca tgtgtgaata tgctgatgag acagcaacca ttgtagaatt tctgaacaga 360
tggattacct tttgtcaaag catcatctca acactaact 399

<210> SEQ ID NO 160
<211> LENGTH: 399
<212> TYPE: DNA
<213> ORGANISM: Homo sapiens
<220> FEATURE:
<221> NAME/KEY: source
<223> OTHER INFORMATION: /note="IL-2"

<400> SEQUENCE: 160
gcccccacct cctcctccac caagaagacc cagctgcagc tggagcattt actgctggat 60
ttacagatga ttttaaacgg catcaacaac tacaagaacc ccaagctgac tcgtatgctg 120
accttcaagt tctacatgcc caagaaggcc accgagctga agcatttaca gtgtttagag 180
gaggagctga agcccctcga ggaggtgctg aatttagccc agtccaagaa tttccattta 240
aggccccggg atttaatcag caacatcaac gtgatcgttt tagagctgaa gggctccgag 300
accaccttca tgtgcgagta cgccgacgag accgccacca tcgtggagtt tttaaatcgt 360
tggatcacct tctgccagtc catcatctcc actttaacc 399

<210> SEQ ID NO 161
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 2t2 sequence"

<400> SEQUENCE: 161

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Ala Pro Thr Ser Ser Ser Thr Lys Lys Thr Gln Leu Gln Leu Glu His
        355                 360                 365
```

```
Leu Leu Leu Asp Leu Gln Met Ile Leu Asn Gly Ile Asn Asn Tyr Lys
    370                 375                 380

Asn Pro Lys Leu Thr Arg Met Leu Thr Phe Lys Phe Tyr Met Pro Lys
385                 390                 395                 400

Lys Ala Thr Glu Leu Lys His Leu Gln Cys Leu Glu Glu Glu Leu Lys
                405                 410                 415

Pro Leu Glu Glu Val Leu Asn Leu Ala Gln Ser Lys Asn Phe His Leu
            420                 425                 430

Arg Pro Arg Asp Leu Ile Ser Asn Ile Asn Val Ile Val Leu Glu Leu
        435                 440                 445

Lys Gly Ser Glu Thr Thr Phe Met Cys Glu Tyr Ala Asp Glu Thr Ala
    450                 455                 460

Thr Ile Val Glu Phe Leu Asn Arg Trp Ile Thr Phe Cys Gln Ser Ile
465                 470                 475                 480

Ile Ser Thr Leu Thr
                485


<210> SEQ ID NO 162
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 2t2 sequence"

<400> SEQUENCE: 162

gcccccacct cctcctccac caagaagacc cagctgcagc tggagcattt actgctggat     60

ttacagatga ttttaaacgg catcaacaac tacaagaacc ccaagctgac tcgtatgctg    120

accttcaagt tctacatgcc caagaaggcc accgagctga agcatttaca gtgtttagag    180

gaggagctga agcccctcga ggaggtgctg aatttagccc agtccaagaa tttccattta    240

aggccccggg atttaatcag caacatcaac gtgatcgttt tagagctgaa gggctccgag    300

accaccttca tgtgcgagta cgccgacgag accgccacca tcgtggagtt tttaaatcgt    360

tggatcacct tctgccagtc catcatctcc actttaacca gcggcacaac caacacagtc    420

gctgcctata acctcacttg gaagagcacc aacttcaaaa ccatcctcga atgggaaccc    480

aaacccgtta accaagttta caccgtgcag atcagcacca agtccggcga ctggaagtcc    540

aaatgtttct ataccaccga caccgagtgc gatctcaccg atgagatcgt gaaagatgtg    600

aaacagacct acctcgcccg ggtgtttagc taccccgccg gcaatgtgga gagcactggt    660

tccgctggcg agcctttata cgagaacagc cccgaattta ccccttacct cgagaccaat    720

ttaggacagc ccaccatcca aagctttgag caagttggca caaaggtgaa tgtgacagtg    780

gaggacgagc ggactttagt gcggcggaac aacacctttc tcagcctccg ggatgtgttc    840

ggcaaagatt taatctacac actgtattac tggaagtcct cttcctccgg caagaagaca    900

gctaaaacca acacaaacga gtttttaatc gacgtggata aaggcgaaaa ctactgtttc    960

agcgtgcaag ctgtgatccc ctcccggacc gtgaatagga aaagcaccga tagccccgtt   1020

gagtgcatgg gccaagaaaa gggcgagttc cgggaggcac ctacttcaag ttctacaaag   1080

aaaacacagc tacaactgga gcatttactg ctggatttac agatgatttt gaatggaatt   1140

aataattaca agaatcccaa actcaccagg atgctcacat ttaagtttta catgcccaag   1200

aaggccacag aactgaaaca tcttcagtgt ctagaagaag aactcaaacc tctggaggaa   1260
```

```
gtgctaaatt tagctcaaag caaaaacttt cacttaagac ccagggactt aatcagcaat   1320

atcaacgtaa tagttctgga actaaaggga tctgaaacaa cattcatgtg tgaatatgct   1380

gatgagacag caaccattgt agaatttctg aacagatgga ttacctttttg tcaaagcatc   1440

atctcaacac taact                                                    1455


<210> SEQ ID NO 163
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 2t2 sequence"

<400> SEQUENCE: 163

Met Lys Trp Val Thr Phe Ile Ser Leu Leu Phe Leu Phe Ser Ser Ala
1               5                   10                  15

Tyr Ser Ala Pro Thr Ser Ser Ser Thr Lys Lys Thr Gln Leu Gln Leu
            20                  25                  30

Glu His Leu Leu Leu Asp Leu Gln Met Ile Leu Asn Gly Ile Asn Asn
        35                  40                  45

Tyr Lys Asn Pro Lys Leu Thr Arg Met Leu Thr Phe Lys Phe Tyr Met
    50                  55                  60

Pro Lys Lys Ala Thr Glu Leu Lys His Leu Gln Cys Leu Glu Glu Glu
65                  70                  75                  80

Leu Lys Pro Leu Glu Glu Val Leu Asn Leu Ala Gln Ser Lys Asn Phe
                85                  90                  95

His Leu Arg Pro Arg Asp Leu Ile Ser Asn Ile Asn Val Ile Val Leu
            100                 105                 110

Glu Leu Lys Gly Ser Glu Thr Thr Phe Met Cys Glu Tyr Ala Asp Glu
        115                 120                 125

Thr Ala Thr Ile Val Glu Phe Leu Asn Arg Trp Ile Thr Phe Cys Gln
    130                 135                 140

Ser Ile Ile Ser Thr Leu Thr Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Ser Gly Lys Lys Thr Ala Lys
305                 310                 315                 320
```

```
Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Ala Pro Thr Ser Ser Ser Thr Lys Lys Thr Gln Leu Gln Leu
    370                 375                 380

Glu His Leu Leu Leu Asp Leu Gln Met Ile Leu Asn Gly Ile Asn Asn
385                 390                 395                 400

Tyr Lys Asn Pro Lys Leu Thr Arg Met Leu Thr Phe Lys Phe Tyr Met
                405                 410                 415

Pro Lys Lys Ala Thr Glu Leu Lys His Leu Gln Cys Leu Glu Glu Glu
            420                 425                 430

Leu Lys Pro Leu Glu Glu Val Leu Asn Leu Ala Gln Ser Lys Asn Phe
        435                 440                 445

His Leu Arg Pro Arg Asp Leu Ile Ser Asn Ile Asn Val Ile Val Leu
    450                 455                 460

Glu Leu Lys Gly Ser Glu Thr Thr Phe Met Cys Glu Tyr Ala Asp Glu
465                 470                 475                 480

Thr Ala Thr Ile Val Glu Phe Leu Asn Arg Trp Ile Thr Phe Cys Gln
                485                 490                 495

Ser Ile Ile Ser Thr Leu Thr
            500


<210> SEQ ID NO 164
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 2t2 sequence"

<400> SEQUENCE: 164

atgaagtggg tgaccttcat cagcctgctg ttcctgttct ccagcgccta ctccgccccc     60

acctcctcct ccaccaagaa gacccagctg cagctggagc atttactgct ggatttacag    120

atgattttaa acggcatcaa caactacaag aaccccaagc tgactcgtat gctgaccttc    180

aagttctaca tgcccaagaa ggccaccgag ctgaagcatt tacagtgttt agaggaggag    240

ctgaagcccc tcgaggaggt gctgaattta gcccagtcca agaatttcca tttaaggccc    300

cgggatttaa tcagcaacat caacgtgatc gttttagagc tgaagggctc cgagaccacc    360

ttcatgtgcg agtacgccga cgagaccgcc accatcgtgg agtttttaaa tcgttggatc    420

accttctgcc agtccatcat ctccacttta accagcggca caaccaacac agtcgctgcc    480

tataacctca cttggaagag caccaacttc aaaaccatcc tcgaatggga acccaaaccc    540

gttaaccaag tttacaccgt gcagatcagc accaagtccg gcgactggaa gtccaaatgt    600

ttctatacca ccgacaccga gtgcgatctc accgatgaga tcgtgaaaga tgtgaaacag    660

acctacctcg cccgggtgtt tagctacccc gccggcaatg tggagagcac tggttccgct    720

ggcgagcctt tatacgagaa cagccccgaa tttacccctt acctcgagac caatttagga    780

cagcccacca tccaaagctt tgagcaagtt ggcacaaagg tgaatgtgac agtggaggac    840

gagcggactt tagtgcggcg gaacaacacc tttctcagcc tccgggatgt gttcggcaaa    900
```

gatttaatct acacactgta ttactggaag tcctcttcct ccggcaagaa gacagctaaa 960
accaacacaa acgagttttt aatcgacgtg gataaaggcg aaaactactg tttcagcgtg 1020
caagctgtga tcccctcccg gaccgtgaat aggaaaagca ccgatagccc cgttgagtgc 1080
atgggccaag aaaagggcga gttccgggag gcacctactt caagttctac aaagaaaaca 1140
cagctacaac tggagcattt actgctggat ttacagatga ttttgaatgg aattaataat 1200
tacaagaatc ccaaactcac caggatgctc acatttaagt tttacatgcc caagaaggcc 1260
acagaactga aacatcttca gtgtctagaa gaagaactca aacctctgga ggaagtgcta 1320
aatttagctc aaagcaaaaa ctttcactta agacccaggg acttaatcag caatatcaac 1380
gtaatagttc tggaactaaa gggatctgaa acaacattca tgtgtgaata tgctgatgag 1440
acagcaacca ttgtagaatt tctgaacaga tggattacct tttgtcaaag catcatctca 1500
acactaact 1509

<210> SEQ ID NO 165
<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 165
aactgggtga acgtgatcag cgatttaaag aagatcgagg atttaatcca gagcatgcac 60
atcgacgcca ctctgtacac tgagagcgac gtgcacccta gctgcaaggt gactgccatg 120
aagtgctttt tactggagct gcaagttatc tctttagaga gcggcgatgc cagcatccac 180
gacactgtgg agaatttaat cattttagcc aacaactctt taagcagcaa cggcaacgtg 240
acagagagcg gctgcaagga gtgcgaggag ctggaggaga agaacatcaa ggagttttta 300
cagagcttcg tgcacatcgt gcagatgttc atcaacacta gc 342

<210> SEQ ID NO 166
<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 166
aactgggtga acgtcatcag cgatttaaag aagatcgaag atttaattca gtccatgcat 60
atcgacgcca ctttatacac agaatccgac gtgcacccct cttgtaaggt gaccgccatg 120
aaatgttttt tactggagct gcaagttatc tctttagaga gcggagacgc tagcatccac 180
gacaccgtgg agaatttaat cattttagcc aataactctt tatccagcaa cggcaacgtg 240
acagagtccg gctgcaagga gtgcgaagag ctggaggaga agaacatcaa ggagtttctg 300
caatcctttg tgcacattgt ccagatgttc atcaatacct cc 342

<210> SEQ ID NO 167
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 15t15 sequence"

<400> SEQUENCE: 167

-continued

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Thr Thr Asn Thr Val Ala Ala Tyr Asn Leu Thr Trp
        115                 120                 125

Lys Ser Thr Asn Phe Lys Thr Ile Leu Glu Trp Glu Pro Lys Pro Val
    130                 135                 140

Asn Gln Val Tyr Thr Val Gln Ile Ser Thr Lys Ser Gly Asp Trp Lys
145                 150                 155                 160

Ser Lys Cys Phe Tyr Thr Thr Asp Thr Glu Cys Asp Leu Thr Asp Glu
                165                 170                 175

Ile Val Lys Asp Val Lys Gln Thr Tyr Leu Ala Arg Val Phe Ser Tyr
            180                 185                 190

Pro Ala Gly Asn Val Glu Ser Thr Gly Ser Ala Gly Glu Pro Leu Tyr
        195                 200                 205

Glu Asn Ser Pro Glu Phe Thr Pro Tyr Leu Glu Thr Asn Leu Gly Gln
    210                 215                 220

Pro Thr Ile Gln Ser Phe Glu Gln Val Gly Thr Lys Val Asn Val Thr
225                 230                 235                 240

Val Glu Asp Glu Arg Thr Leu Val Arg Arg Asn Asn Thr Phe Leu Ser
                245                 250                 255

Leu Arg Asp Val Phe Gly Lys Asp Leu Ile Tyr Thr Leu Tyr Tyr Trp
            260                 265                 270

Lys Ser Ser Ser Ser Gly Lys Lys Thr Ala Lys Thr Asn Thr Asn Glu
        275                 280                 285

Phe Leu Ile Asp Val Asp Lys Gly Glu Asn Tyr Cys Phe Ser Val Gln
    290                 295                 300

Ala Val Ile Pro Ser Arg Thr Val Asn Arg Lys Ser Thr Asp Ser Pro
305                 310                 315                 320

Val Glu Cys Met Gly Gln Glu Lys Gly Glu Phe Arg Glu Asn Trp Val
                325                 330                 335

Asn Val Ile Ser Asp Leu Lys Lys Ile Glu Asp Leu Ile Gln Ser Met
            340                 345                 350

His Ile Asp Ala Thr Leu Tyr Thr Glu Ser Asp Val His Pro Ser Cys
        355                 360                 365

Lys Val Thr Ala Met Lys Cys Phe Leu Leu Glu Leu Gln Val Ile Ser
    370                 375                 380

Leu Glu Ser Gly Asp Ala Ser Ile His Asp Thr Val Glu Asn Leu Ile
385                 390                 395                 400

Ile Leu Ala Asn Asn Ser Leu Ser Ser Asn Gly Asn Val Thr Glu Ser
                405                 410                 415
```

Gly Cys Lys Glu Cys Glu Glu Leu Glu Glu Lys Asn Ile Lys Glu Phe
420 425 430

Leu Gln Ser Phe Val His Ile Val Gln Met Phe Ile Asn Thr Ser
435 440 445

<210> SEQ ID NO 168
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 15t15 sequence"

<400> SEQUENCE: 168
aactgggtga acgtgatcag cgatttaaag aagatcgagg atttaatcca gagcatgcac 60
atcgacgcca ctctgtacac tgagagcgac gtgcacccta gctgcaaggt gactgccatg 120
aagtgctttt tactggagct gcaagttatc tctttagaga gcggcgatgc cagcatccac 180
gacactgtgg agaatttaat cattttagcc aacaactctt taagcagcaa cggcaacgtg 240
acagagagcg gctgcaagga gtgcgaggag ctggaggaga agaacatcaa ggagttttta 300
cagagcttcg tgcacatcgt gcagatgttc atcaacacta gcagcggcac aaccaacaca 360
gtcgctgcct ataacctcac ttggaagagc accaacttca aaaccatcct cgaatgggaa 420
cccaaacccg ttaaccaagt ttacaccgtg cagatcagca ccaagtccgg cgactggaag 480
tccaaatgtt tctataccac cgacaccgag tgcgatctca ccgatgagat cgtgaaagat 540
gtgaaacaga cctacctcgc ccgggtgttt agctaccccg ccggcaatgt ggagagcact 600
ggttccgctg gcgagccttt atacgagaac agccccgaat ttacccctta cctcgagacc 660
aatttaggac agcccaccat ccaaagcttt gagcaagttg gcacaaaggt gaatgtgaca 720
gtggaggacg agcggacttt agtgcggcgg aacaacacct ttctcagcct ccgggatgtg 780
ttcggcaaag atttaatcta cacactgtat tactggaagt cctcttcctc cggcaagaag 840
acagctaaaa ccaacacaaa cgagttttta atcgacgtgg ataaaggcga aaactactgt 900
ttcagcgtgc aagctgtgat cccctcccgg accgtgaata ggaaaagcac cgatagcccc 960
gttgagtgca tgggccaaga aaagggcgag ttccgggaga actgggtgaa cgtcatcagc 1020
gatttaaaga agatcgaaga tttaattcag tccatgcata tcgacgccac tttatacaca 1080
gaatccgacg tgcacccctc ttgtaaggtg accgccatga aatgtttttt actggagctg 1140
caagttatct ctttagagag cggagacgct agcatccacg acaccgtgga gaatttaatc 1200
attttagcca ataactcttt atccagcaac ggcaacgtga cagagtccgg ctgcaaggag 1260
tgcgaagagc tggaggagaa gaacatcaag gagtttctgc aatcctttgt gcacattgtc 1320
cagatgttca tcaatacctc c 1341

<210> SEQ ID NO 169
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 15t15 sequence"

<400> SEQUENCE: 169

Met Lys Trp Val Thr Phe Ile Ser Leu Leu Phe Leu Phe Ser Ser Ala
1 5 10 15

-continued

```
Tyr Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Thr Thr Asn Thr Val Ala Ala Tyr Asn Leu
    130                 135                 140

Thr Trp Lys Ser Thr Asn Phe Lys Thr Ile Leu Glu Trp Glu Pro Lys
145                 150                 155                 160

Pro Val Asn Gln Val Tyr Thr Val Gln Ile Ser Thr Lys Ser Gly Asp
                165                 170                 175

Trp Lys Ser Lys Cys Phe Tyr Thr Thr Asp Thr Glu Cys Asp Leu Thr
            180                 185                 190

Asp Glu Ile Val Lys Asp Val Lys Gln Thr Tyr Leu Ala Arg Val Phe
        195                 200                 205

Ser Tyr Pro Ala Gly Asn Val Glu Ser Thr Gly Ser Ala Gly Glu Pro
    210                 215                 220

Leu Tyr Glu Asn Ser Pro Glu Phe Thr Pro Tyr Leu Glu Thr Asn Leu
225                 230                 235                 240

Gly Gln Pro Thr Ile Gln Ser Phe Glu Gln Val Gly Thr Lys Val Asn
                245                 250                 255

Val Thr Val Glu Asp Glu Arg Thr Leu Val Arg Arg Asn Asn Thr Phe
            260                 265                 270

Leu Ser Leu Arg Asp Val Phe Gly Lys Asp Leu Ile Tyr Thr Leu Tyr
        275                 280                 285

Tyr Trp Lys Ser Ser Ser Ser Gly Lys Lys Thr Ala Lys Thr Asn Thr
    290                 295                 300

Asn Glu Phe Leu Ile Asp Val Asp Lys Gly Glu Asn Tyr Cys Phe Ser
305                 310                 315                 320

Val Gln Ala Val Ile Pro Ser Arg Thr Val Asn Arg Lys Ser Thr Asp
                325                 330                 335

Ser Pro Val Glu Cys Met Gly Gln Glu Lys Gly Glu Phe Arg Glu Asn
            340                 345                 350

Trp Val Asn Val Ile Ser Asp Leu Lys Lys Ile Glu Asp Leu Ile Gln
        355                 360                 365

Ser Met His Ile Asp Ala Thr Leu Tyr Thr Glu Ser Asp Val His Pro
    370                 375                 380

Ser Cys Lys Val Thr Ala Met Lys Cys Phe Leu Leu Glu Leu Gln Val
385                 390                 395                 400

Ile Ser Leu Glu Ser Gly Asp Ala Ser Ile His Asp Thr Val Glu Asn
                405                 410                 415

Leu Ile Ile Leu Ala Asn Asn Ser Leu Ser Ser Asn Gly Asn Val Thr
            420                 425                 430

Glu Ser Gly Cys Lys Glu Cys Glu Glu Leu Glu Glu Lys Asn Ile Lys
```

-continued

```
        435                 440                 445

Glu Phe Leu Gln Ser Phe Val His Ile Val Gln Met Phe Ile Asn Thr
    450                 455                 460

Ser
465


<210> SEQ ID NO 170
<211> LENGTH: 1395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 15t15 sequence"

<400> SEQUENCE: 170

atgaagtggg tgaccttcat cagcctgctg ttcctgttct ccagcgccta ctccaactgg      60

gtgaacgtga tcagcgattt aaagaagatc gaggatttaa tccagagcat gcacatcgac     120

gccactctgt acactgagag cgacgtgcac cctagctgca aggtgactgc catgaagtgc     180

tttttactgg agctgcaagt tatctcttta gagagcggcg atgccagcat ccacgacact     240

gtggagaatt taatcatttt agccaacaac tctttaagca gcaacggcaa cgtgacagag     300

agcggctgca aggagtgcga ggagctggag gagaagaaca tcaaggagtt tttacagagc     360

ttcgtgcaca tcgtgcagat gttcatcaac actagcagcg gcacaaccaa cacagtcgct     420

gcctataacc tcacttggaa gagcaccaac ttcaaaacca tcctcgaatg ggaacccaaa     480

cccgttaacc aagtttacac cgtgcagatc agcaccaagt ccggcgactg gaagtccaaa     540

tgtttctata ccaccgacac cgagtgcgat ctcaccgatg agatcgtgaa agatgtgaaa     600

cagacctacc tcgcccgggt gtttagctac cccgccggca atgtggagag cactggttcc     660

gctggcgagc ctttatacga gaacagcccc gaatttaccc cttacctcga gaccaattta     720

ggacagccca ccatccaaag ctttgagcaa gttggcacaa aggtgaatgt gacagtggag     780

gacgagcgga ctttagtgcg gcggaacaac acctttctca gcctccggga tgtgttcggc     840

aaagatttaa tctacacact gtattactgg aagtcctctt cctccggcaa gaagacagct     900

aaaaccaaca caaacgagtt tttaatcgac gtggataaag gcgaaaacta ctgtttcagc     960

gtgcaagctg tgatcccctc ccggaccgtg aataggaaaa gcaccgatag ccccgttgag    1020

tgcatgggcc aagaaaaggg cgagttccgg gagaactggg tgaacgtcat cagcgattta    1080

aagaagatcg aagatttaat tcagtccatg catatcgacg ccactttata cacagaatcc    1140

gacgtgcacc cctcttgtaa ggtgaccgcc atgaaatgtt ttttactgga gctgcaagtt    1200

atctctttag agagcggaga cgctagcatc cacgacaccg tggagaattt aatcatttta    1260

gccaataact ctttatccag caacggcaac gtgacagagt ccggctgcaa ggagtgcgaa    1320

gagctggagg agaagaacat caaggagttt ctgcaatcct ttgtgcacat tgtccagatg    1380

ttcatcaata cctcc                                                    1395


<210> SEQ ID NO 171
<211> LENGTH: 471
<212> TYPE: DNA
<213> ORGANISM: Homo sapiens
<220> FEATURE:
<221> NAME/KEY: source
<223> OTHER INFORMATION: /note="IL-18"

<400> SEQUENCE: 171
```

```
tacttcggca aactggaatc caagctgagc gtgatccgga atttaaacga ccaagttctg     60

tttatcgatc aaggtaaccg gcctctgttc gaggacatga ccgactccga ttgccgggac    120

aatgcccccc ggaccatctt cattatctcc atgtacaagg acagccagcc ccggggcatg    180

gctgtgacaa ttagcgtgaa gtgtgagaaa atcagcactt tatcttgtga gaacaagatc    240

atctccttta aggaaatgaa ccccccccgat aacatcaagg acaccaagtc cgatatcatc    300

ttcttccagc ggtccgtgcc cggtcacgat aacaagatgc agttcgaatc ctcctcctac    360

gagggctact ttttagcttg tgaaaaggag agggatttat tcaagctgat cctcaagaag    420

gaggacgagc tgggcgatcg ttccatcatg ttcaccgtcc aaaacgagga t             471
```

```
<210> SEQ ID NO 172
<211> LENGTH: 918
<212> TYPE: DNA
<213> ORGANISM: Homo sapiens
<220> FEATURE:
<221> NAME/KEY: source
<223> OTHER INFORMATION: /note="IL12Beta"

<400> SEQUENCE: 172

atttgggaac tgaagaagga cgtctacgtg gtcgaactgg actggtatcc cgatgctccc     60

ggcgaaatgg tggtgctcac ttgtgacacc cccgaagaag acggcatcac ttggaccctc    120

gatcagagca gcgaggtgct gggctccgga aagaccctca caatccaagt taaggagttc    180

ggagacgctg gccaatacac atgccacaag ggaggcgagg tgctcagcca ttccttatta    240

ttattacaca agaaggaaga cggaatctgg tccaccgaca ttttaaaaga tcagaaggag    300

cccaagaata agaccttttt aaggtgtgag gccaaaaact acagcggtcg tttcacttgt    360

tggtggctga ccaccatttc caccgattta accttctccg tgaaaagcag ccggggaagc    420

tccgaccctc aaggtgtgac atgtggagcc gctaccctca gcgctgagag ggttcgtggc    480

gataacaagg aatacgagta cagcgtggag tgccaagaag atagcgcttg tcccgctgcc    540

gaagaatctt tacccattga ggtgatggtg gacgccgtgc acaaactcaa gtacgagaac    600

tacacctcct ccttctttat ccgggacatc attaagcccg atcctcctaa gaatttacag    660

ctgaagcctc tcaaaaatag ccggcaagtt gaggtctctt gggaatatcc cgacacttgg    720

agcacacccc acagctactt ctctttaacc ttttgtgtgc aagttcaagg taaaagcaag    780

cgggagaaga aagaccgggt gtttaccgac aaaaccagcg ccaccgtcat ctgtcggaag    840

aacgcctcca tcagcgtgag ggctcaagat cgttattact ccagcagctg gtccgagtgg    900

gccagcgtgc cttgttcc                                                  918
```

```
<210> SEQ ID NO 173
<211> LENGTH: 591
<212> TYPE: DNA
<213> ORGANISM: Homo sapiens
<220> FEATURE:
<221> NAME/KEY: source
<223> OTHER INFORMATION: /note="IL-12alpha"

<400> SEQUENCE: 173

cgtaacctcc ccgtggctac ccccgatccc ggaatgttcc cttgtttaca ccacagccag     60

aatttactga gggccgtgag caacatgctg cagaaagcta ggcagacttt agaattttac    120

ccttgcacca gcgaggagat cgaccatgaa gatatcacca aggacaagac atccaccgtg    180

gaggcttgtt tacctctgga gctgacaaag aacgagtctt gtctcaactc tcgtgaaacc    240

agcttcatca caaatggctc ttgtttagct tcccggaaga cctcctttat gatggcttta    300
```

tgcctcagct ccatctacga ggatttaaag atgtaccaag tggagttcaa gaccatgaac 360
gccaagctgc tcatggaccc taaacggcag atctttttag accagaacat gctggctgtg 420
attgatgagc tgatgcaagc tttaaacttc aactccgaga ccgtccctca gaagtcctcc 480
ctcgaggagc ccgattttta caagacaaag atcaaactgt gcattttact ccacgccttt 540
aggatccggg ccgtgaccat tgaccgggtc atgagctatt taaacgccag c 591

<210> SEQ ID NO 174
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 18t15-12s sequence"

<400> SEQUENCE: 174

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Ser Val Pro Gly His Asp Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp Ser Gly Thr
145 150 155 160

Thr Asn Thr Val Ala Ala Tyr Asn Leu Thr Trp Lys Ser Thr Asn Phe
165 170 175

Lys Thr Ile Leu Glu Trp Glu Pro Lys Pro Val Asn Gln Val Tyr Thr
180 185 190

Val Gln Ile Ser Thr Lys Ser Gly Asp Trp Lys Ser Lys Cys Phe Tyr
195 200 205

Thr Thr Asp Thr Glu Cys Asp Leu Thr Asp Glu Ile Val Lys Asp Val
210 215 220

Lys Gln Thr Tyr Leu Ala Arg Val Phe Ser Tyr Pro Ala Gly Asn Val
225 230 235 240

Glu Ser Thr Gly Ser Ala Gly Glu Pro Leu Tyr Glu Asn Ser Pro Glu
245 250 255

Phe Thr Pro Tyr Leu Glu Thr Asn Leu Gly Gln Pro Thr Ile Gln Ser
260 265 270

Phe Glu Gln Val Gly Thr Lys Val Asn Val Thr Val Glu Asp Glu Arg
275 280 285

Thr Leu Val Arg Arg Asn Asn Thr Phe Leu Ser Leu Arg Asp Val Phe
290 295 300

```
Gly Lys Asp Leu Ile Tyr Thr Leu Tyr Tyr Trp Lys Ser Ser Ser Ser
305                 310                 315                 320

Gly Lys Lys Thr Ala Lys Thr Asn Thr Asn Glu Phe Leu Ile Asp Val
                325                 330                 335

Asp Lys Gly Glu Asn Tyr Cys Phe Ser Val Gln Ala Val Ile Pro Ser
            340                 345                 350

Arg Thr Val Asn Arg Lys Ser Thr Asp Ser Pro Val Glu Cys Met Gly
        355                 360                 365

Gln Glu Lys Gly Glu Phe Arg Glu Asn Trp Val Asn Val Ile Ser Asp
    370                 375                 380

Leu Lys Lys Ile Glu Asp Leu Ile Gln Ser Met His Ile Asp Ala Thr
385                 390                 395                 400

Leu Tyr Thr Glu Ser Asp Val His Pro Ser Cys Lys Val Thr Ala Met
                405                 410                 415

Lys Cys Phe Leu Leu Glu Leu Gln Val Ile Ser Leu Glu Ser Gly Asp
            420                 425                 430

Ala Ser Ile His Asp Thr Val Glu Asn Leu Ile Ile Leu Ala Asn Asn
        435                 440                 445

Ser Leu Ser Ser Asn Gly Asn Val Thr Glu Ser Gly Cys Lys Glu Cys
    450                 455                 460

Glu Glu Leu Glu Glu Lys Asn Ile Lys Glu Phe Leu Gln Ser Phe Val
465                 470                 475                 480

His Ile Val Gln Met Phe Ile Asn Thr Ser
                485                 490


<210> SEQ ID NO 175
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 175

tacttcggca aactggaatc caagctgagc gtgatccgga atttaaacga ccaagttctg     60

tttatcgatc aaggtaaccg gcctctgttc gaggacatga ccgactccga ttgccgggac    120

aatgcccccc ggaccatctt cattatctcc atgtacaagg acagccagcc ccggggcatg    180

gctgtgacaa ttagcgtgaa gtgtgagaaa atcagcactt tatcttgtga gaacaagatc    240

atctccttta aggaaatgaa cccccccgat aacatcaagg acaccaagtc cgatatcatc    300

ttcttccagc ggtccgtgcc cggtcacgat aacaagatgc agttcgaatc ctcctcctac    360

gagggctact tttagcttg tgaaaaggag agggatttat tcaagctgat cctcaagaag    420

gaggacgagc tgggcgatcg ttccatcatg ttcaccgtcc aaaacgagga tagcggcaca    480

accaacacag tcgctgccta taacctcact tggaagagca ccaacttcaa aaccatcctc    540

gaatgggaac ccaaacccgt taaccaagtt tacaccgtgc agatcagcac caagtccggc    600

gactggaagt ccaaatgttt ctataccacc gacaccgagt gcgatctcac cgatgagatc    660

gtgaaagatg tgaaacagac ctacctcgcc cgggtgttta gctaccccgc cggcaatgtg    720

gagagcactg gttccgctgg cgagccttta tacgagaaca gccccgaatt taccccttac    780

ctcgagacca atttaggaca gcccaccatc caaagctttg agcaagttgg cacaaaggtg    840

aatgtgacag tggaggacga gcggacttta gtgcggcgga acaacacctt tctcagcctc    900
```

```
cgggatgtgt tcggcaaaga tttaatctac acactgtatt actggaagtc ctcttcctcc    960

ggcaagaaga cagctaaaac caacacaaac gagtttttaa tcgacgtgga taaaggcgaa   1020

aactactgtt tcagcgtgca agctgtgatc cctcccggga ccgtgaatag gaaaagcacc   1080

gatagccccg ttgagtgcat gggccaagaa aagggcgagt tccgggagaa ctgggtgaac   1140

gtcatcagcg atttaaagaa gatcgaagat ttaattcagt ccatgcatat cgacgccact   1200

ttatacacag aatccgacgt gcacccctct tgtaaggtga ccgccatgaa atgtttttta   1260

ctggagctgc aagttatctc tttagagagc ggagacgcta gcatccacga caccgtggag   1320

aatttaatca ttttagccaa taactcttta tccagcaacg gcaacgtgac agagtccggc   1380

tgcaaggagt gcgaagagct ggaggagaag aacatcaagg agtttctgca atcctttgtg   1440

cacattgtcc agatgttcat caatacctcc                                    1470


<210> SEQ ID NO 176
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 176

Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ser
                165                 170                 175

Gly Thr Thr Asn Thr Val Ala Ala Tyr Asn Leu Thr Trp Lys Ser Thr
            180                 185                 190

Asn Phe Lys Thr Ile Leu Glu Trp Glu Pro Lys Pro Val Asn Gln Val
        195                 200                 205

Tyr Thr Val Gln Ile Ser Thr Lys Ser Gly Asp Trp Lys Ser Lys Cys
    210                 215                 220

Phe Tyr Thr Thr Asp Thr Glu Cys Asp Leu Thr Asp Glu Ile Val Lys
225                 230                 235                 240

Asp Val Lys Gln Thr Tyr Leu Ala Arg Val Phe Ser Tyr Pro Ala Gly
                245                 250                 255
```

```
Asn Val Glu Ser Thr Gly Ser Ala Gly Glu Pro Leu Tyr Glu Asn Ser
            260                 265                 270

Pro Glu Phe Thr Pro Tyr Leu Glu Thr Asn Leu Gly Gln Pro Thr Ile
        275                 280                 285

Gln Ser Phe Glu Gln Val Gly Thr Lys Val Asn Val Thr Val Glu Asp
    290                 295                 300

Glu Arg Thr Leu Val Arg Arg Asn Asn Thr Phe Leu Ser Leu Arg Asp
305                 310                 315                 320

Val Phe Gly Lys Asp Leu Ile Tyr Thr Leu Tyr Tyr Trp Lys Ser Ser
                325                 330                 335

Ser Ser Gly Lys Lys Thr Ala Lys Thr Asn Thr Asn Glu Phe Leu Ile
            340                 345                 350

Asp Val Asp Lys Gly Glu Asn Tyr Cys Phe Ser Val Gln Ala Val Ile
        355                 360                 365

Pro Ser Arg Thr Val Asn Arg Lys Ser Thr Asp Ser Pro Val Glu Cys
    370                 375                 380

Met Gly Gln Glu Lys Gly Glu Phe Arg Glu Asn Trp Val Asn Val Ile
385                 390                 395                 400

Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
    450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
            500                 505
```

<210> SEQ ID NO 177
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 18t15-12s sequence"

<400> SEQUENCE: 177

```
atgaagtggg tcacatttat ctctttactg ttcctcttct ccagcgccta cagctacttc      60

ggcaaactgg aatccaagct gagcgtgatc cggaatttaa acgaccaagt tctgtttatc     120

gatcaaggta accggcctct gttcgaggac atgaccgact ccgattgccg ggacaatgcc     180

ccccggacca tcttcattat ctccatgtac aaggacagcc agccccgggg catggctgtg     240

acaattagcg tgaagtgtga gaaaatcagc actttatctt gtgagaacaa gatcatctcc     300

tttaaggaaa tgaacccccc cgataacatc aaggacacca agtccgatat catcttcttc     360

cagcggtccg tgcccggtca cgataacaag atgcagttcg aatcctcctc ctacgagggc     420

tactttttag cttgtgaaaa ggagagggat ttattcaagc tgatcctcaa gaaggaggac     480

gagctgggcg atcgttccat catgttcacc gtccaaaacg aggatagcgg cacaaccaac     540
```

-continued

```
acagtcgctg cctataacct cacttggaag agcaccaact tcaaaaccat cctcgaatgg    600

gaacccaaac ccgttaacca agtttacacc gtgcagatca gcaccaagtc cggcgactgg    660

aagtccaaat gtttctatac caccgacacc gagtgcgatc tcaccgatga gatcgtgaaa    720

gatgtgaaac agacctacct cgcccgggtg tttagctacc ccgccggcaa tgtggagagc    780

actggttccg ctggcgagcc tttatacgag aacagccccg aatttacccc ttacctcgag    840

accaatttag gacagcccac catccaaagc tttgagcaag ttggcacaaa ggtgaatgtg    900

acagtggagg acgagcggac tttagtgcgg cggaacaaca cctttctcag cctccgggat    960

gtgttcggca aagatttaat ctacacactg tattactgga agtcctcttc ctccggcaag   1020

aagacagcta aaaccaacac aaacgagttt ttaatcgacg tggataaagg cgaaaactac   1080

tgtttcagcg tgcaagctgt gatcccctcc cggaccgtga ataggaaaag caccgatagc   1140

cccgttgagt gcatgggcca agaaaagggc gagttccggg agaactgggt gaacgtcatc   1200

agcgatttaa agaagatcga agatttaatt cagtccatgc atatcgacgc cactttatac   1260

acagaatccg acgtgcaccc ctcttgtaag gtgaccgcca tgaaatgttt tttactggag   1320

ctgcaagtta tctctttaga gagcggagac gctagcatcc acgacaccgt ggagaattta   1380

atcattttag ccaataactc tttatccagc aacggcaacg tgacagagtc cggctgcaag   1440

gagtgcgaag agctggagga gaagaacatc aaggagtttc tgcaatcctt tgtgcacatt   1500

gtccagatgt tcatcaatac ctcc                                          1524
```

```
<210> SEQ ID NO 178
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 178

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175
```

-continued

```
Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Pro Met Ser Val Glu
        515                 520                 525

His Ala Asp Ile Trp Val Lys Ser Tyr Ser Leu Tyr Ser Arg Glu Arg
    530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg
            580
```

<210> SEQ ID NO 179
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic 18t15-12s sequence"

<400> SEQUENCE: 179

```
atttgggaac tgaagaagga cgtctacgtg gtcgaactgg actggtatcc cgatgctccc     60

ggcgaaatgg tggtgctcac ttgtgacacc cccgaagaag acggcatcac ttggaccctc    120

gatcagagca gcgaggtgct gggctccgga aagaccctca caatccaagt taaggagttc    180

ggagacgctg gccaatacac atgccacaag ggaggcgagg tgctcagcca ttccttatta    240

ttattacaca agaaggaaga cggaatctgg tccaccgaca ttttaaaaga tcagaaggag    300

cccaagaata agaccttttt aaggtgtgag gccaaaaact acagcggtcg tttcacttgt    360

tggtggctga ccaccatttc caccgattta accttctccg tgaaaagcag ccggggaagc    420

tccgaccctc aaggtgtgac atgtggagcc gctaccctca gcgctgagag ggttcgtggc    480

gataacaagg aatacgagta cagcgtggag tgccaagaag atagcgcttg tcccgctgcc    540

gaagaatctt tacccattga ggtgatggtg gacgccgtgc acaaactcaa gtacgagaac    600

tacacctcct ccttctttat ccgggacatc attaagcccg atcctcctaa gaatttacag    660

ctgaagcctc tcaaaaatag ccggcaagtt gaggtctctt gggaatatcc cgacacttgg    720

agcacacccc acagctactt ctctttaacc ttttgtgtgc aagttcaagg taaaagcaag    780

cgggagaaga aagaccgggt gtttaccgac aaaaccagcg ccaccgtcat ctgtcggaag    840

aacgcctcca tcagcgtgag ggctcaagat cgttattact ccagcagctg gtccgagtgg    900

gccagcgtgc cttgttccgg cggtggagga tccggaggag gtggctccgg cggcggagga    960

tctcgtaacc tccccgtggc tacccccgat cccggaatgt tcccttgttt acaccacagc   1020

cagaatttac tgagggccgt gagcaacatg ctgcagaaag ctaggcagac tttagaattt   1080

tacccttgca ccagcgagga gatcgaccat gaagatatca ccaaggacaa gacatccacc   1140

gtggaggctt gtttacctct ggagctgaca aagaacgagt cttgtctcaa ctctcgtgaa   1200

accagcttca tcacaaatgg ctcttgttta gcttcccgga agacctcctt tatgatggct   1260

ttatgcctca gctccatcta cgaggattta aagatgtacc aagtggagtt caagaccatg   1320

aacgccaagc tgctcatgga ccctaaacgg cagatctttt tagaccagaa catgctggct   1380

gtgattgatg agctgatgca agctttaaac ttcaactccg agaccgtccc tcagaagtcc   1440

tccctcgagg agcccgattt ttacaagaca aagatcaaac tgtgcatttt actccacgcc   1500

tttaggatcc gggccgtgac cattgaccgg gtcatgagct atttaaacgc cagcattaca   1560

tgcccccctc ccatgagcgt ggagcacgcc gacatctggg tgaagagcta tagcctctac   1620

agccgggaga ggtatatctg taacagcggc ttcaagagga aggccggcac cagcagcctc   1680

accgagtgcg tgctgaataa ggctaccaac gtggctcact ggacaacacc ctctttaaag   1740

tgcatccgg                                                           1749
```

<210> SEQ ID NO 180
<211> LENGTH: 601
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic 18t15-12s sequence"

<400> SEQUENCE: 180

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Gly Ser Gly Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400
```

```
Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg
        595                 600


<210> SEQ ID NO 181
<211> LENGTH: 1803
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 181

atgaaatggg tgacctttat ttctttactg ttcctcttta gcagcgccta ctccatttgg      60

gaactgaaga aggacgtcta cgtggtcgaa ctggactggt atcccgatgc tcccggcgaa     120

atggtggtgc tcacttgtga cacccccgaa gaagacggca tcacttggac cctcgatcag     180

agcagcgagg tgctgggctc cggaaagacc ctcacaatcc aagttaagga gttcggagac     240

gctggccaat acacatgcca caagggaggc gaggtgctca gccattcctt attattatta     300

cacaagaagg aagacggaat ctggtccacc gacattttaa aagatcagaa ggagcccaag     360

aataagacct ttttaaggtg tgaggccaaa aactacagcg gtcgtttcac ttgttggtgg     420

ctgaccacca tttccaccga tttaaccttc tccgtgaaaa gcagccgggg aagctccgac     480

cctcaaggtg tgacatgtgg agccgctacc ctcagcgctg agagggttcg tggcgataac     540

aaggaatacg agtacagcgt ggagtgccaa gaagatagcg cttgtcccgc tgccgaagaa     600

tctttaccca ttgaggtgat ggtggacgcc gtgcacaaac tcaagtacga gaactacacc     660

tcctccttct ttatccggga catcattaag cccgatcctc ctaagaattt acagctgaag     720

cctctcaaaa atagccggca agttgaggtc tcttgggaat atcccgacac ttggagcaca     780

ccccacagct acttctcttt aacctttgt gtgcaagttc aaggtaaaag caagcgggag      840
```

-continued

```
aagaaagacc gggtgtttac cgacaaaacc agcgccaccg tcatctgtcg gaagaacgcc    900

tccatcagcg tgagggctca agatcgttat tactccagca gctggtccga gtgggccagc    960

gtgccttgtt ccggcggtgg aggatccgga ggaggtggct ccggcggcgg aggatctcgt   1020

aacctccccg tggctacccc cgatcccgga atgttccctt gtttacacca cagccagaat   1080

ttactgaggg ccgtgagcaa catgctgcag aaagctaggc agactttaga attttaccct   1140

tgcaccagcg aggagatcga ccatgaagat atcaccaagg acaagacatc caccgtggag   1200

gcttgtttac ctctggagct gacaaagaac gagtcttgtc tcaactctcg tgaaaccagc   1260

ttcatcacaa atggctcttg tttagcttcc cggaagacct cctttatgat ggctttatgc   1320

ctcagctcca tctacgagga tttaaagatg taccaagtgg agttcaagac catgaacgcc   1380

aagctgctca tggaccctaa acggcagatc tttttagacc agaacatgct ggctgtgatt   1440

gatgagctga tgcaagcttt aaacttcaac tccgagaccg tccctcagaa gtcctccctc   1500

gaggagcccg atttttacaa gacaaagatc aaactgtgca ttttactcca cgcctttagg   1560

atccgggccg tgaccattga ccgggtcatg agctatttaa acgccagcat tacatgcccc   1620

cctcccatga gcgtggagca cgccgacatc tgggtgaaga gctatagcct ctacagccgg   1680

gagaggtata tctgtaacag cggcttcaag aggaaggccg gcaccagcag cctcaccgag   1740

tgcgtgctga ataaggctac caacgtggct cactggacaa caccctcttt aaagtgcatc   1800

cgg                                                                 1803
```

<210> SEQ ID NO 182
<211> LENGTH: 399
<212> TYPE: DNA
<213> ORGANISM: Homo sapiens
<220> FEATURE:
<221> NAME/KEY: source
<223> OTHER INFORMATION: /note="IL-21"

<400> SEQUENCE: 182

```
cagggccagg acaggcacat gatccggatg aggcagctca tcgacatcgt cgaccagctg     60

aagaactacg tgaacgacct ggtgcccgag tttctgcctg cccccgagga cgtggagacc    120

aactgcgagt ggtccgcctt ctcctgcttt cagaaggccc agctgaagtc cgccaacacc    180

ggcaacaacg agcggatcat caacgtgagc atcaagaagc tgaagcggaa gcctccctcc    240

acaaacgccg gcaggaggca gaagcacagg ctgacctgcc ccagctgtga ctcctacgag    300

aagaagcccc ccaaggagtt cctggagagg ttcaagtccc tgctgcagaa gatgatccat    360

cagcacctgt cctccaggac ccacggctcc gaggactcc                           399
```

<210> SEQ ID NO 183
<211> LENGTH: 136
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 183

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45
```

-continued

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 184
<211> LENGTH: 136
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 184

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 185
<211> LENGTH: 408
<212> TYPE: DNA
<213> ORGANISM: Homo sapiens
<220> FEATURE:
<221> NAME/KEY: source
<223> OTHER INFORMATION: /note="TGFRbetaRII"

<400> SEQUENCE: 185 atccccccc atgtgcaaaa gagcgtgaac aacgatatga tcgtgaccga caacaacggc 60
gccgtgaagt ttccccagct ctgcaagttc tgcgatgtca ggttcagcac ctgcgataat 120
cagaagtcct gcatgtccaa ctgcacgatc acctccatct gcgagaagcc ccaagaagtg 180
tgcgtggccg tgtggcggaa aaatgacgag aacatcaccc tggagaccgt gtgtcacgac 240
cccaagctcc cttatcacga cttcattctg gaggacgctg cctcccccaa atgcatcatg 300
aaggagaaga agaagcccgg agagaccttc tttatgtgtt cctgtagcag cgacgagtgt 360
aacgacaaca tcatcttcag cgaagagtac aacaccagca accctgat 408

<210> SEQ ID NO 186
<211> LENGTH: 408
<212> TYPE: DNA
<213> ORGANISM: Homo sapiens
<220> FEATURE:
<221> NAME/KEY: source
<223> OTHER INFORMATION: /note="TGFRbetaRII"

<400> SEQUENCE: 186
attcctcccc acgtgcagaa gagcgtgaat aatgacatga tcgtgaccga taacaatggc 60
gccgtgaaat ttccccagct gtgcaaattc tgcgatgtga ggttttccac ctgcgacaac 120
cagaagtcct gtatgagcaa ctgcacaatc acctccatct gtgagaagcc tcaggaggtg 180
tgcgtggctg tctggcggaa gaatgacgag aatatcaccc tggaaaccgt ctgccacgat 240
cccaagctgc cctaccacga tttcatcctg gaagacgccg ccagccctaa gtgcatcatg 300
aaagagaaaa agaagcctgg cgagaccttt ttcatgtgct cctgcagcag cgacgaatgc 360
aacgacaata tcatctttag cgaggaatac aataccagca accccgac 408

<210> SEQ ID NO 187
<211> LENGTH: 861
<212> TYPE: DNA
<213> ORGANISM: Homo sapiens
<220> FEATURE:
<221> NAME/KEY: source
<223> OTHER INFORMATION: /note="TGFRbetaRII"

<400> SEQUENCE: 187
atcccccccc atgtgcaaaa gagcgtgaac aacgatatga tcgtgaccga caacaacggc 60
gccgtgaagt ttccccagct ctgcaagttc tgcgatgtca ggttcagcac ctgcgataat 120
cagaagtcct gcatgtccaa ctgcacgatc acctccatct gcgagaagcc ccaagaagtg 180
tgcgtggccg tgtggcggaa aaatgacgag aacatcaccc tggagaccgt gtgtcacgac 240
cccaagctcc cttatcacga cttcattctg gaggacgctg cctcccccaa atgcatcatg 300
aaggagaaga agaagcccgg agagaccttc tttatgtgtt cctgtagcag cgacgagtgt 360
aacgacaaca tcatcttcag cgaagagtac aacaccagca accctgatgg aggtggcgga 420
tccggaggtg gaggttctgg tggaggtggg agtattcctc cccacgtgca gaagagcgtg 480
aataatgaca tgatcgtgac cgataacaat ggcgccgtga aatttcccca gctgtgcaaa 540
ttctgcgatg tgaggttttc cacctgcgac aaccagaagt cctgtatgag caactgcaca 600
atcacctcca tctgtgagaa gcctcaggag gtgtgcgtgg ctgtctggcg gaagaatgac 660
gagaatatca ccctggaaac cgtctgccac gatcccaagc tgccctacca cgatttcatc 720
ctggaagacg ccgccagccc taagtgcatc atgaaagaga aaaagaagcc tggcgagacc 780
tttttcatgt gctcctgcag cagcgacgaa tgcaacgaca atatcatctt tagcgaggaa 840
tacaatacca gcaaccccga c 861

<210> SEQ ID NO 188
<211> LENGTH: 287
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 188

-continued

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285
```

<210> SEQ ID NO 189
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 189

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
```

```
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Asn Trp Val Asn Val Ile Ser Asp Leu Lys Lys Ile Glu Asp Leu Ile
        355                 360                 365

Gln Ser Met His Ile Asp Ala Thr Leu Tyr Thr Glu Ser Asp Val His
    370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
                405                 410                 415

Asn Leu Ile Ile Leu Ala Asn Asn Ser Leu Ser Ser Asn Gly Asn Val
            420                 425                 430

Thr Glu Ser Gly Cys Lys Glu Cys Glu Glu Leu Glu Glu Lys Asn Ile
        435                 440                 445

Lys Glu Phe Leu Gln Ser Phe Val His Ile Val Gln Met Phe Ile Asn
    450                 455                 460

Thr Ser
465
```

<210> SEQ ID NO 190

<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 190

```
cagggccagg acaggcacat gatccggatg aggcagctca tcgacatcgt cgaccagctg      60

aagaactacg tgaacgacct ggtgcccgag tttctgcctg cccccgagga cgtggagacc     120

aactgcgagt ggtccgcctt ctcctgcttt cagaaggccc agctgaagtc cgccaacacc     180

ggcaacaacg agcggatcat caacgtgagc atcaagaagc tgaagcggaa gcctccctcc     240

acaaacgccg gcaggaggca gaagcacagg ctgacctgcc ccagctgtga ctcctacgag     300

aagaagcccc ccaaggagtt cctggagagg ttcaagtccc tgctgcagaa gatgatccat     360

cagcacctgt cctccaggac ccacggctcc gaggactcct ccggcaccac caataccgtg     420

gccgcttata acctcacatg gaagagcacc aacttcaaga caattctgga atgggaaccc     480

aagcccgtca atcaagttta caccgtgcag atctccacca aatccggaga ctggaagagc     540

aagtgcttct acacaacaga caccgagtgt gatttaaccg acgaaatcgt caaggacgtc     600

aagcaaacct atctggctcg ggtcttttcc taccccgctg gcaatgtcga gtccaccggc     660

tccgctggcg agcctctcta cgagaattcc cccgaattca ccccttattt agagaccaat     720

ttaggccagc ctaccatcca gagcttcgag caagttggca ccaaggtgaa cgtcaccgtc     780

gaggatgaaa ggactttagt gcggcggaat aacacatttt tatccctccg ggatgtgttc     840

ggcaaagacc tcatctacac actgtactat tggaagtcca gctcctccgg caaaaagacc     900

gctaagacca acaccaacga gtttttaatt gacgtggaca aaggcgagaa ctactgcttc     960

agcgtgcaag ccgtgatccc ttctcgtacc gtcaaccgga agagcacaga ttcccccgtt    1020

gagtgcatgg gccaagaaaa gggcgagttc cgggagaact gggtgaacgt catcagcgat    1080

ttaaagaaga tcgaagattt aattcagtcc atgcatatcg acgccacttt atacacagaa    1140

tccgacgtgc acccctcttg taaggtgacc gccatgaaat gtttttttact ggagctgcaa    1200

gttatctctt tagagagcgg agacgctagc atccacgaca ccgtggagaa tttaatcatt    1260

ttagccaata actctttatc cagcaacggc aacgtgacag agtccggctg caaggagtgc    1320

gaagagctgg aggagaagaa catcaaggag tttctgcaat cctttgtgca cattgtccag    1380

atgttcatca atacctcc                                                  1398
```

<210> SEQ ID NO 191
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 191

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45
```

```
Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
```

465 470 475 480

Ile Asn Thr Ser

<210> SEQ ID NO 192
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 192
atgaagtggg tgaccttcat cagcctgctg ttcctgttct ccagcgccta ctcccagggc 60
caggacaggc acatgatccg gatgaggcag ctcatcgaca tcgtcgacca gctgaagaac 120
tacgtgaacg acctggtgcc cgagtttctg cctgcccccg aggacgtgga gaccaactgc 180
gagtggtccg ccttctcctg ctttcagaag gcccagctga agtccgccaa caccggcaac 240
aacgagcgga tcatcaacgt gagcatcaag aagctgaagc ggaagcctcc ctccacaaac 300
gccggcagga ggcagaagca caggctgacc tgccccagct gtgactccta cgagaagaag 360
ccccccaagg agttcctgga gaggttcaag tccctgctgc agaagatgat ccatcagcac 420
ctgtcctcca ggacccacgg ctccgaggac tcctccggca ccaccaatac cgtggccgct 480
tataacctca catggaagag caccaacttc aagacaattc tggaatggga acccaagccc 540
gtcaatcaag tttacaccgt gcagatctcc accaaatccg gagactggaa gagcaagtgc 600
ttctacacaa cagacaccga gtgtgattta accgacgaaa tcgtcaagga cgtcaagcaa 660
acctatctgg ctcgggtctt ttcctacccc gctggcaatg tcgagtccac cggctccgct 720
ggcgagcctc tctacgagaa ttcccccgaa ttcacccctt atttagagac caatttaggc 780
cagcctacca tccagagctt cgagcaagtt ggcaccaagg tgaacgtcac cgtcgaggat 840
gaaaggactt tagtgcggcg gaataacaca tttttatccc tccgggatgt gttcggcaaa 900
gacctcatct acacactgta ctattggaag tccagctcct ccggcaaaaa gaccgctaag 960
accaacacca acgagttttt aattgacgtg gacaaaggcg agaactactg cttcagcgtg 1020
caagccgtga tcccttctcg taccgtcaac cggaagagca cagattcccc cgttgagtgc 1080
atgggccaag aaaagggcga gttccgggag aactgggtga acgtcatcag cgatttaaag 1140
aagatcgaag atttaattca gtccatgcat atcgacgcca ctttatacac agaatccgac 1200
gtgcacccct cttgtaaggt gaccgccatg aaatgttttt tactggagct gcaagttatc 1260
tctttagaga gcggagacgc tagcatccac gacaccgtgg agaatttaat cattttagcc 1320
aataactctt tatccagcaa cggcaacgtg acagagtccg gctgcaagga gtgcgaagag 1380
ctggaggaga agaacatcaa ggagtttctg caatcctttg tgcacattgt ccagatgttc 1440
atcaatacct cc 1452

<210> SEQ ID NO 193
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 193

Ile Pro Pro His Val Gln Lys Ser Val Asn Asn Asp Met Ile Val Thr

-continued

```
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350
```

<210> SEQ ID NO 194
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 194

```
atccccccc atgtgcaaaa gagcgtgaac aacgatatga tcgtgaccga caacaacggc     60
```

-continued

```
gccgtgaagt ttccccagct ctgcaagttc tgcgatgtca ggttcagcac ctgcgataat    120

cagaagtcct gcatgtccaa ctgcacgatc acctccatct gcgagaagcc ccaagaagtg    180

tgcgtggccg tgtggcggaa aaatgacgag aacatcaccc tggagaccgt gtgtcacgac    240

cccaagctcc cttatcacga cttcattctg gaggacgctg cctcccccaa atgcatcatg    300

aaggagaaga agaagcccgg agagaccttc tttatgtgtt cctgtagcag cgacgagtgt    360

aacgacaaca tcatcttcag cgaagagtac aacaccagca accctgatgg aggtggcgga    420

tccggaggtg gaggttctgg tggaggtggg agtattcctc cccacgtgca gaagagcgtg    480

aataatgaca tgatcgtgac cgataacaat ggcgccgtga aatttcccca gctgtgcaaa    540

ttctgcgatg tgaggttttc cacctgcgac aaccagaagt cctgtatgag caactgcaca    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga catcacgtgt cctcctccta tgtccgtgga acacgcagac    900

atctgggtca agagctacag cttgtactcc agggagcggt acatttgtaa ctctggtttc    960

aagcgtaaag ccggcacgtc cagcctgacg gagtgcgtgt tgaacaaggc cacgaatgtc   1020

gcccactgga caaccccccag tctcaaatgt attaga                            1056
```

<210> SEQ ID NO 195
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 195

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175
```

```
Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg
    370
```

<210> SEQ ID NO 196
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs21 sequence"

<400> SEQUENCE: 196

```
atgaagtggg tgaccttcat cagcctgctg ttcctgttct ccagcgccta ctccatcccc      60

ccccatgtgc aaaagagcgt gaacaacgat atgatcgtga ccgacaacaa cggcgccgtg     120

aagtttcccc agctctgcaa gttctgcgat gtcaggttca gcacctgcga taatcagaag     180

tcctgcatgt ccaactgcac gatcacctcc atctgcgaga agccccaaga agtgtgcgtg     240

gccgtgtggc ggaaaaatga cgagaacatc accctggaga ccgtgtgtca cgaccccaag     300

ctcccttatc acgacttcat tctggaggac gctgcctccc ccaaatgcat catgaaggag     360

aagaagaagc ccggagagac cttctttatg tgttcctgta gcagcgacga gtgtaacgac     420

aacatcatct tcagcgaaga gtacaacacc agcaaccctg atggaggtgg cggatccgga     480

ggtggaggtt ctggtggagg tgggagtatt cctccccacg tgcagaagag cgtgaataat     540

gacatgatcg tgaccgataa caatggcgcc gtgaaatttc cccagctgtg caaattctgc     600

gatgtgaggt tttccacctg cgacaaccag aagtcctgta tgagcaactg cacaatcacc     660

tccatctgtg agaagcctca ggaggtgtgc gtggctgtct ggcggaagaa tgacgagaat     720

atcaccctgg aaaccgtctg ccacgatccc aagctgccct accacgattt catcctggaa     780

gacgccgcca gccctaagtg catcatgaaa gagaaaaaga agcctggcga gacctttttc     840
```

atgtgctcct gcagcagcga cgaatgcaac gacaatatca tctttagcga ggaatacaat 900
accagcaacc ccgacatcac gtgtcctcct cctatgtccg tggaacacgc agacatctgg 960
gtcaagagct acagcttgta ctccagggag cggtacattt gtaactctgg tttcaagcgt 1020
aaagccggca cgtccagcct gacggagtgc gtgttgaaca aggccacgaa tgtcgcccac 1080
tggacaaccc ccagtctcaa atgtattaga 1110

<210> SEQ ID NO 197
<211> LENGTH: 399
<212> TYPE: DNA
<213> ORGANISM: Homo sapiens
<220> FEATURE:
<221> NAME/KEY: source
<223> OTHER INFORMATION: /note="IL21"

<400> SEQUENCE: 197
caaggtcaag atcgccacat gattagaatg cgtcaactta tagatattgt tgatcagctg 60
aaaaattatg tgaatgactt ggtccctgaa tttctgccag ctccagaaga tgtagagaca 120
aactgtgagt ggtcagcttt ttcctgtttt cagaaggccc aactaaagtc agcaaataca 180
ggaaacaatg aaaggataat caatgtatca attaaaaagc tgaagaggaa accaccttcc 240
acaaatgcag ggagaagaca gaaacacaga ctaacatgcc cttcatgtga ttcttatgag 300
aaaaaaccac ccaaagaatt cctagaaaga ttcaaatcac ttctccaaaa gatgattcat 360
cagcatctgt cctctagaac acacggaagt gaagattcc 399

<210> SEQ ID NO 198
<211> LENGTH: 456
<212> TYPE: DNA
<213> ORGANISM: Homo sapiens
<220> FEATURE:
<221> NAME/KEY: source
<223> OTHER INFORMATION: /note="IL7"

<400> SEQUENCE: 198
gattgtgata ttgaaggtaa agatggcaaa caatatgaga gtgttctaat ggtcagcatc 60
gatcaattat tggacagcat gaaagaaatt ggtagcaatt gcctgaataa tgaatttaac 120
ttttttaaaa gacatatctg tgatgctaat aaggaaggta tgtttttatt ccgtgctgct 180
cgcaagttga ggcaatttct taaaatgaat agcactggtg attttgatct ccacttatta 240
aaagtttcag aaggcacaac aatactgttg aactgcactg gccaggttaa aggaagaaaa 300
ccagctgccc tgggtgaagc ccaaccaaca aagagtttgg aagaaaataa atctttaaag 360
gaacagaaaa aactgaatga cttgtgtttc ctaaagagac tattacaaga gataaaaact 420
tgttggaata aaattttgat gggcactaaa gaacac 456

<210> SEQ ID NO 199
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-7s sequence"

<400> SEQUENCE: 199

Gln Gly Gln Asp Arg His Met Ile Arg Met Arg Gln Leu Ile Asp Ile
1 5 10 15

Val Asp Gln Leu Lys Asn Tyr Val Asn Asp Leu Val Pro Glu Phe Leu
20 25 30

```
Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Asn Trp Val Asn Val Ile Ser Asp Leu Lys Lys Ile Glu Asp Leu Ile
        355                 360                 365

Gln Ser Met His Ile Asp Ala Thr Leu Tyr Thr Glu Ser Asp Val His
    370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
                405                 410                 415

Asn Leu Ile Ile Leu Ala Asn Asn Ser Leu Ser Ser Asn Gly Asn Val
            420                 425                 430

Thr Glu Ser Gly Cys Lys Glu Cys Glu Glu Leu Glu Glu Lys Asn Ile
        435                 440                 445
```

-continued

Lys Glu Phe Leu Gln Ser Phe Val His Ile Val Gln Met Phe Ile Asn
    450                 455                 460

Thr Ser
465

<210> SEQ ID NO 200
<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-7s sequence"

<400> SEQUENCE: 200
caaggtcaag atcgccacat gattagaatg cgtcaactta tagatattgt tgatcagctg 60
aaaaattatg tgaatgactt ggtccctgaa tttctgccag ctccagaaga tgtagagaca 120
aactgtgagt ggtcagcttt ttcctgtttt cagaaggccc aactaaagtc agcaaataca 180
ggaaacaatg aaaggataat caatgtatca attaaaaagc tgaagaggaa accaccttcc 240
acaaatgcag ggagaagaca gaaacacaga ctaacatgcc cttcatgtga ttcttatgag 300
aaaaaaccac ccaaagaatt cctagaaaga ttcaaatcac ttctccaaaa gatgattcat 360
cagcatctgt cctctagaac acacggaagt gaagattcct caggcactac aaatactgtg 420
gcagcatata atttaacttg gaaatcaact aatttcaaga caattttgga gtgggaaccc 480
aaacccgtca atcaagtcta cactgttcaa ataagcacta agtcaggaga ttggaaaagc 540
aaatgctttt acacaacaga cacagagtgt gacctcaccg acgagattgt gaaggatgtg 600
aagcagacgt acttggcacg ggtcttctcc tacccggcag ggaatgtgga gagcaccggt 660
tctgctgggg agcctctgta tgagaactcc ccagagttca caccttacct ggagacaaac 720
ctcggacagc caacaattca gagttttgaa caggtgggaa caaaagtgaa tgtgaccgta 780
gaagatgaac ggactttagt cagaaggaac aacactttcc taagcctccg ggatgttttt 840
ggcaaggact taatttatac actttattat tggaaatctt caagttcagg aaagaaaaca 900
gccaaaacaa acactaatga gtttttgatt gatgtggata aaggagaaaa ctactgtttc 960
agtgttcaag cagtgattcc ctcccgaaca gttaaccgga agagtacaga cagcccggta 1020
gagtgtatgg gccaggagaa aggggaattc agagaaaact gggtgaacgt catcagcgat 1080
ttaaagaaga tcgaagattt aattcagtcc atgcatatcg acgccacttt atacacagaa 1140
tccgacgtgc acccctcttg taaggtgacc gccatgaaat gtttttttact ggagctgcaa 1200 gttatctctt tagagagcgg agacgctagc atccacgaca ccgtggagaa tttaatcatt 1260
ttagccaata actctttatc cagcaacggc aacgtgacag agtccggctg caaggagtgc 1320
gaagagctgg aggagaagaa catcaaggag tttctgcaat cctttgtgca cattgtccag 1380
atgttcatca atacctcc 1398

<210> SEQ ID NO 201
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-7s sequence"

<400> SEQUENCE: 201

Met Gly Val Lys Val Leu Phe Ala Leu Ile Cys Ile Ala Val Ala Glu

```
1               5                   10                  15

Ala Gln Gly Gln Asp Arg His Met Ile Arg Met Arg Gln Leu Ile Asp
            20                  25                  30

Ile Val Asp Gln Leu Lys Asn Tyr Val Asn Asp Leu Val Pro Glu Phe
        35                  40                  45

Leu Pro Ala Pro Glu Asp Val Glu Thr Asn Cys Glu Trp Ser Ala Phe
    50                  55                  60

Ser Cys Phe Gln Lys Ala Gln Leu Lys Ser Ala Asn Thr Gly Asn Asn
65                  70                  75                  80

Glu Arg Ile Ile Asn Val Ser Ile Lys Lys Leu Lys Arg Lys Pro Pro
                85                  90                  95

Ser Thr Asn Ala Gly Arg Arg Gln Lys His Arg Leu Thr Cys Pro Ser
            100                 105                 110

Cys Asp Ser Tyr Glu Lys Lys Pro Pro Lys Glu Phe Leu Glu Arg Phe
        115                 120                 125

Lys Ser Leu Leu Gln Lys Met Ile His Gln His Leu Ser Ser Arg Thr
    130                 135                 140

His Gly Ser Glu Asp Ser Ser Gly Thr Thr Asn Thr Val Ala Ala Tyr
145                 150                 155                 160

Asn Leu Thr Trp Lys Ser Thr Asn Phe Lys Thr Ile Leu Glu Trp Glu
                165                 170                 175

Pro Lys Pro Val Asn Gln Val Tyr Thr Val Gln Ile Ser Thr Lys Ser
            180                 185                 190

Gly Asp Trp Lys Ser Lys Cys Phe Tyr Thr Thr Asp Thr Glu Cys Asp
        195                 200                 205

Leu Thr Asp Glu Ile Val Lys Asp Val Lys Gln Thr Tyr Leu Ala Arg
    210                 215                 220

Val Phe Ser Tyr Pro Ala Gly Asn Val Glu Ser Thr Gly Ser Ala Gly
225                 230                 235                 240

Glu Pro Leu Tyr Glu Asn Ser Pro Glu Phe Thr Pro Tyr Leu Glu Thr
                245                 250                 255

Asn Leu Gly Gln Pro Thr Ile Gln Ser Phe Glu Gln Val Gly Thr Lys
            260                 265                 270

Val Asn Val Thr Val Glu Asp Glu Arg Thr Leu Val Arg Arg Asn Asn
        275                 280                 285

Thr Phe Leu Ser Leu Arg Asp Val Phe Gly Lys Asp Leu Ile Tyr Thr
    290                 295                 300

Leu Tyr Tyr Trp Lys Ser Ser Ser Ser Gly Lys Lys Thr Ala Lys Thr
305                 310                 315                 320

Asn Thr Asn Glu Phe Leu Ile Asp Val Asp Lys Gly Glu Asn Tyr Cys
                325                 330                 335

Phe Ser Val Gln Ala Val Ile Pro Ser Arg Thr Val Asn Arg Lys Ser
            340                 345                 350

Thr Asp Ser Pro Val Glu Cys Met Gly Gln Glu Lys Gly Glu Phe Arg
        355                 360                 365

Glu Asn Trp Val Asn Val Ile Ser Asp Leu Lys Lys Ile Glu Asp Leu
    370                 375                 380

Ile Gln Ser Met His Ile Asp Ala Thr Leu Tyr Thr Glu Ser Asp Val
385                 390                 395                 400

His Pro Ser Cys Lys Val Thr Ala Met Lys Cys Phe Leu Leu Glu Leu
                405                 410                 415

Gln Val Ile Ser Leu Glu Ser Gly Asp Ala Ser Ile His Asp Thr Val
            420                 425                 430
```

```
Glu Asn Leu Ile Ile Leu Ala Asn Asn Ser Leu Ser Ser Asn Gly Asn
        435                 440                 445

Val Thr Glu Ser Gly Cys Lys Glu Cys Glu Glu Leu Glu Glu Lys Asn
    450                 455                 460

Ile Lys Glu Phe Leu Gln Ser Phe Val His Ile Val Gln Met Phe Ile
465                 470                 475                 480

Asn Thr Ser


<210> SEQ ID NO 202
<211> LENGTH: 1449
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 202

atgggagtga aagttctttt tgcccttatt tgtattgctg tggccgaggc ccaaggtcaa     60

gatcgccaca tgattagaat gcgtcaactt atagatattg ttgatcagct gaaaaattat    120

gtgaatgact tggtccctga atttctgcca gctccagaag atgtagagac aaactgtgag    180

tggtcagctt tttcctgttt tcagaaggcc caactaaagt cagcaaatac aggaaacaat    240

gaaaggataa tcaatgtatc aattaaaaag ctgaagagga aaccaccttc cacaaatgca    300

gggagaagac agaaacacag actaacatgc ccttcatgtg attcttatga gaaaaaacca    360

cccaaagaat tcctagaaag attcaaatca cttctccaaa agatgattca tcagcatctg    420

tcctctagaa cacacggaag tgaagattcc tcaggcacta caaatactgt ggcagcatat    480

aatttaactt ggaaatcaac taatttcaag acaattttgg agtgggaacc caaacccgtc    540

aatcaagtct acactgttca aataagcact aagtcaggag attggaaaag caaatgcttt    600

tacacaacag acacagagtg tgacctcacc gacgagattg tgaaggatgt gaagcagacg    660

tacttggcac gggtcttctc ctacccggca gggaatgtgg agagcaccgg ttctgctggg    720

gagcctctgt atgagaactc cccagagttc acaccttacc tggagacaaa cctcggacag    780

ccaacaattc agagttttga acaggtggga acaaaagtga atgtgaccgt agaagatgaa    840

cggactttag tcagaaggaa caacactttc ctaagcctcc gggatgtttt tggcaaggac    900

ttaatttata cactttatta ttggaaatct tcaagttcag gaaagaaaac agccaaaaca    960

aacactaatg agtttttgat tgatgtggat aaaggagaaa actactgttt cagtgttcaa   1020

gcagtgattc cctcccgaac agttaaccgg aagagtacag acagcccggt agagtgtatg   1080

ggccaggaga aaggggaatt cagagaaaac tgggtgaacg tcatcagcga tttaaagaag   1140

atcgaagatt taattcagtc catgcatatc gacgccactt tatacacaga atccgacgtg   1200

cacccctctt gtaaggtgac cgccatgaaa tgtttttttac tggagctgca agttatctct   1260

ttagagagcg gagacgctag catccacgac accgtggaga atttaatcat tttagccaat   1320

aactctttat ccagcaacgg caacgtgaca gagtccggct gcaaggagtg cgaagagctg   1380

gaggagaaga acatcaagga gtttctgcaa tcctttgtgc acattgtcca gatgttcatc   1440

aatacctcc                                                          1449


<210> SEQ ID NO 203
<211> LENGTH: 217
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic 21t15-7s sequence"

<400> SEQUENCE: 203

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ile Thr Cys Pro Pro Pro Met Ser
145                 150                 155                 160

Val Glu His Ala Asp Ile Trp Val Lys Ser Tyr Ser Leu Tyr Ser Arg
                165                 170                 175

Glu Arg Tyr Ile Cys Asn Ser Gly Phe Lys Arg Lys Ala Gly Thr Ser
            180                 185                 190

Ser Leu Thr Glu Cys Val Leu Asn Lys Ala Thr Asn Val Ala His Trp
        195                 200                 205

Thr Thr Pro Ser Leu Lys Cys Ile Arg
    210                 215
```

<210> SEQ ID NO 204
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-7s sequence"

<400> SEQUENCE: 204

```
gattgtgata ttgaaggtaa agatggcaaa caatatgaga gtgttctaat ggtcagcatc     60

gatcaattat tggacagcat gaaagaaatt ggtagcaatt gcctgaataa tgaatttaac    120

ttttttaaaa gacatatctg tgatgctaat aaggaaggta tgtttttatt ccgtgctgct    180

cgcaagttga ggcaatttct taaaatgaat agcactggtg attttgatct ccacttatta    240

aaagtttcag aaggcacaac aatactgttg aactgcactg gccaggttaa aggaagaaaa    300

ccagctgccc tgggtgaagc ccaaccaaca aagagtttgg aagaaaataa atctttaaag    360

gaacagaaaa aactgaatga cttgtgtttc ctaaagagac tattacaaga gataaaaact    420

tgttggaata aaattttgat gggcactaaa gaacacatca cgtgccctcc ccccatgtcc    480

gtggaacacg cagacatctg ggtcaagagc tacagcttgt actccaggga gcggtacatt    540
```

```
tgtaactctg gtttcaagcg taaagccggc acgtccagcc tgacggagtg cgtgttgaac    600

aaggccacga atgtcgccca ctggacaacc cccagtctca aatgcattag a             651


<210> SEQ ID NO 205
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 205

Met Gly Val Lys Val Leu Phe Ala Leu Ile Cys Ile Ala Val Ala Glu
1               5                   10                  15

Ala Asp Cys Asp Ile Glu Gly Lys Asp Gly Lys Gln Tyr Glu Ser Val
            20                  25                  30

Leu Met Val Ser Ile Asp Gln Leu Leu Asp Ser Met Lys Glu Ile Gly
        35                  40                  45

Ser Asn Cys Leu Asn Asn Glu Phe Asn Phe Phe Lys Arg His Ile Cys
    50                  55                  60

Asp Ala Asn Lys Glu Gly Met Phe Leu Phe Arg Ala Ala Arg Lys Leu
65                  70                  75                  80

Arg Gln Phe Leu Lys Met Asn Ser Thr Gly Asp Phe Asp Leu His Leu
                85                  90                  95

Leu Lys Val Ser Glu Gly Thr Thr Ile Leu Leu Asn Cys Thr Gly Gln
            100                 105                 110

Val Lys Gly Arg Lys Pro Ala Ala Leu Gly Glu Ala Gln Pro Thr Lys
        115                 120                 125

Ser Leu Glu Glu Asn Lys Ser Leu Lys Glu Gln Lys Lys Leu Asn Asp
    130                 135                 140

Leu Cys Phe Leu Lys Arg Leu Leu Gln Glu Ile Lys Thr Cys Trp Asn
145                 150                 155                 160

Lys Ile Leu Met Gly Thr Lys Glu His Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg
225                 230


<210> SEQ ID NO 206
<211> LENGTH: 702
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 206

atgggagtga aagttctttt tgcccttatt tgtattgctg tggccgaggc cgattgtgat     60

attgaaggta aagatggcaa acaatatgag agtgttctaa tggtcagcat cgatcaatta    120

ttggacagca tgaaagaaat tggtagcaat tgcctgaata atgaatttaa ctttttttaaa    180
```

```
agacatatct gtgatgctaa taaggaaggt atgtttttat tccgtgctgc tcgcaagttg    240

aggcaatttc ttaaaatgaa tagcactggt gattttgatc tccacttatt aaaagtttca    300

gaaggcacaa caatactgtt gaactgcact ggccaggtta aaggaagaaa accagctgcc    360

ctgggtgaag cccaaccaac aaagagtttg gaagaaaata aatctttaaa ggaacagaaa    420

aaactgaatg acttgtgttt cctaaagaga ctattacaag agataaaaac ttgttggaat    480

aaaattttga tgggcactaa agaacacatc acgtgccctc cccccatgtc cgtggaacac    540

gcagacatct gggtcaagag ctacagcttg tactccaggg agcggtacat ttgtaactct    600

ggtttcaagc gtaaagccgg cacgtccagc ctgacggagt gcgtgttgaa caaggccacg    660

aatgtcgccc actggacaac ccccagtctc aaatgcatta ga                       702
```

<210> SEQ ID NO 207
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 207

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
                165                 170                 175

Trp Glu Pro Lys Pro Val Asn Gln Val Tyr Thr Val Gln Ile Ser Thr
            180                 185                 190

Lys Ser Gly Asp Trp Lys Ser Lys Cys Phe Tyr Thr Thr Asp Thr Glu
        195                 200                 205

Cys Asp Leu Thr Asp Glu Ile Val Lys Asp Val Lys Gln Thr Tyr Leu
    210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Glu Gln Val Gly
```

-continued

```
            260                 265                 270

Thr Lys Val Asn Val Thr Val Glu Asp Glu Arg Thr Leu Val Arg Arg
        275                 280                 285

Asn Asn Thr Phe Leu Ser Leu Arg Asp Val Phe Gly Lys Asp Leu Ile
    290                 295                 300

Tyr Thr Leu Tyr Tyr Trp Lys Ser Ser Ser Ser Gly Lys Lys Thr Ala
305                 310                 315                 320

Lys Thr Asn Thr Asn Glu Phe Leu Ile Asp Val Asp Lys Gly Glu Asn
                325                 330                 335

Tyr Cys Phe Ser Val Gln Ala Val Ile Pro Ser Arg Thr Val Asn Arg
            340                 345                 350

Lys Ser Thr Asp Ser Pro Val Glu Cys Met Gly Gln Glu Lys Gly Glu
        355                 360                 365

Phe Arg Glu Asn Trp Val Asn Val Ile Ser Asp Leu Lys Lys Ile Glu
    370                 375                 380

Asp Leu Ile Gln Ser Met His Ile Asp Ala Thr Leu Tyr Thr Glu Ser
385                 390                 395                 400

Asp Val His Pro Ser Cys Lys Val Thr Ala Met Lys Cys Phe Leu Leu
                405                 410                 415

Glu Leu Gln Val Ile Ser Leu Glu Ser Gly Asp Ala Ser Ile His Asp
            420                 425                 430

Thr Val Glu Asn Leu Ile Ile Leu Ala Asn Asn Ser Leu Ser Ser Asn
        435                 440                 445

Gly Asn Val Thr Glu Ser Gly Cys Lys Glu Cys Glu Glu Leu Glu Glu
    450                 455                 460

Lys Asn Ile Lys Glu Phe Leu Gln Ser Phe Val His Ile Val Gln Met
465                 470                 475                 480

Phe Ile Asn Thr Ser
                485
```

<210> SEQ ID NO 208
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 208

```
gattgcgaca tcgagggcaa ggacggcaag cagtacgaga gcgtgctgat ggtgtccatc     60

gaccagctgc tggacagcat gaaggagatc ggctccaact gcctcaacaa cgagttcaac    120

ttcttcaagc ggcacatctg cgacgccaac aaggagggca tgttcctgtt cagggccgcc    180

aggaaactgc ggcagttcct gaagatgaac tccaccggcg acttcgacct gcacctgctg    240

aaggtgtccg agggcaccac catcctgctg aactgcaccg gacaggtgaa gggccggaaa    300

cctgctgctc tgggagaggc ccaacccacc aagagcctgg aggagaacaa gtccctgaag    360

gagcagaaga agctgaacga cctgtgcttc ctgaagaggc tgctgcagga gatcaagacc    420

tgctggaaca agatcctgat gggcaccaag gagcatagcg gcacaaccaa cacagtcgct    480

gcctataacc tcacttggaa gagcaccaac ttcaaaacca tcctcgaatg ggaacccaaa    540

cccgttaacc aagtttacac cgtgcagatc agcaccaagt ccggcgactg gaagtccaaa    600

tgtttctata ccaccgacac cgagtgcgat ctcaccgatg agatcgtgaa agatgtgaaa    660

cagacctacc tcgcccgggt gtttagctac cccgccggca atgtggagag cactggttcc    720
```

```
gctggcgagc ctttatacga gaacagcccc gaatttaccc cttacctcga gaccaattta    780

ggacagccca ccatccaaag ctttgagcaa gttggcacaa aggtgaatgt gacagtggag    840

gacgagcgga ctttagtgcg gcggaacaac acctttctca gcctccggga tgtgttcggc    900

aaagatttaa tctacacact gtattactgg aagtcctctt cctccggcaa gaagacagct    960

aaaaccaaca caaacgagtt tttaatcgac gtggataaag gcgaaaacta ctgtttcagc   1020

gtgcaagctg tgatcccctc ccggaccgtg aataggaaaa gcaccgatag ccccgttgag   1080

tgcatgggcc aagaaaaggg cgagttccgg gagaactggg tgaacgtcat cagcgattta   1140

aagaagatcg aagatttaat tcagtccatg catatcgacg ccactttata cacagaatcc   1200

gacgtgcacc cctcttgtaa ggtgaccgcc atgaaatgtt ttttactgga gctgcaagtt   1260

atctctttag agagcggaga cgctagcatc cacgacaccg tggagaattt aatcatttta   1320

gccaataact ctttatccag caacggcaac gtgacagagt ccggctgcaa ggagtgcgaa   1380

gagctggagg agaagaacat caaggagttt ctgcaatcct ttgtgcacat tgtccagatg   1440

ttcatcaata cctcc                                                    1455
```

<210> SEQ ID NO 209
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 209

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
```

```
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365

Asn Arg Lys Ser Thr Asp Ser Pro Val Glu Cys Met Gly Gln Glu Lys
    370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
        435                 440                 445

His Asp Thr Val Glu Asn Leu Ile Ile Leu Ala Asn Asn Ser Leu Ser
    450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500


<210> SEQ ID NO 210
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 210

atgaagtggg tgaccttcat cagcctgctg ttcctgttct ccagcgccta ctccgattgc      60

gacatcgagg gcaaggacgg caagcagtac gagagcgtgc tgatggtgtc catcgaccag     120

ctgctggaca gcatgaagga gatcggctcc aactgcctca acaacgagtt caacttcttc     180

aagcggcaca tctgcgacgc caacaaggag ggcatgttcc tgttcagggc cgccaggaaa     240

ctgcggcagt tcctgaagat gaactccacc ggcgacttcg acctgcacct gctgaaggtg     300

tccgagggca ccaccatcct gctgaactgc accggacagg tgaagggccg gaaacctgct     360
```

```
gctctgggag aggcccaacc caccaagagc ctggaggaga acaagtccct gaaggagcag    420
aagaagctga acgacctgtg cttcctgaag aggctgctgc aggagatcaa gacctgctgg    480
aacaagatcc tgatgggcac caaggagcat agcggcacaa ccaacacagt cgctgcctat    540
aacctcactt ggaagagcac caacttcaaa accatcctcg aatgggaacc caaacccgtt    600
aaccaagttt acaccgtgca gatcagcacc aagtccggcg actggaagtc caaatgtttc    660
tataccaccg acaccgagtg cgatctcacc gatgagatcg tgaaagatgt gaaacagacc    720
tacctcgccc gggtgtttag ctaccccgcc ggcaatgtgg agagcactgg ttccgctggc    780
gagcctttat acgagaacag ccccgaattt accccttacc tcgagaccaa tttaggacag    840
cccaccatcc aaagctttga gcaagttggc acaaaggtga atgtgacagt ggaggacgag    900
cggactttag tgcggcggaa caacaccttt ctcagcctcc gggatgtgtt cggcaaagat    960
ttaatctaca cactgtatta ctggaagtcc tcttcctccg gcaagaagac agctaaaacc   1020
aacacaaacg agtttttaat cgacgtggat aaaggcgaaa actactgttt cagcgtgcaa   1080
gctgtgatcc cctcccggac cgtgaatagg aaaagcaccg atagccccgt tgagtgcatg   1140
ggccaagaaa agggcgagtt ccgggagaac tgggtgaacg tcatcagcga tttaaagaag   1200
atcgaagatt taattcagtc catgcatatc gacgccactt tatacacaga atccgacgtg   1260
cacccctctt gtaaggtgac cgccatgaaa tgtttttttac tggagctgca agttatctct   1320
ttagagagcg gagacgctag catccacgac accgtggaga atttaatcat tttagccaat   1380
aactctttat ccagcaacgg caacgtgaca gagtccggct gcaaggagtg cgaagagctg   1440
gaggagaaga acatcaagga gtttctgcaa tcctttgtgc acattgtcca gatgttcatc   1500
aatacctcc                                                            1509
```

<210> SEQ ID NO 211
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 211

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Pro Met Ser Val Glu His
    130                 135                 140
```

```
Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg
        195
```

<210> SEQ ID NO 212
<211> LENGTH: 594
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 212

```
cagggccagg acaggcacat gatccggatg aggcagctca tcgacatcgt cgaccagctg     60

aagaactacg tgaacgacct ggtgcccgag tttctgcctg cccccgagga cgtggagacc    120

aactgcgagt ggtccgcctt ctcctgcttt cagaaggccc agctgaagtc cgccaacacc    180

ggcaacaacg agcggatcat caacgtgagc atcaagaagc tgaagcggaa gcctccctcc    240

acaaacgccg gcaggaggca gaagcacagg ctgacctgcc ccagctgtga ctcctacgag    300

aagaagcccc ccaaggagtt cctggagagg ttcaagtccc tgctgcagaa gatgatccat    360

cagcacctgt cctccaggac ccacggctcc gaggactcca ttacatgccc ccctcccatg    420

agcgtggagc acgccgacat ctgggtgaag agctatagcc tctacagccg ggagaggtat    480

atctgtaaca gcggcttcaa gaggaaggcc ggcaccagca gcctcaccga gtgcgtgctg    540

aataaggcta ccaacgtggc tcactggaca acaccctctt taaagtgcat ccgg          594
```

<210> SEQ ID NO 213
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 213

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
```

```
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg
    210                 215


<210> SEQ ID NO 214
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 214

atgaagtggg tgaccttcat cagcctgctg ttcctgttct ccagcgccta ctcccagggc      60

caggacaggc acatgatccg gatgaggcag ctcatcgaca tcgtcgacca gctgaagaac     120

tacgtgaacg acctggtgcc cgagtttctg cctgccccccg aggacgtgga gaccaactgc    180

gagtggtccg ccttctcctg ctttcagaag gcccagctga agtccgccaa caccggcaac     240

aacgagcgga tcatcaacgt gagcatcaag aagctgaagc ggaagcctcc ctccacaaac     300

gccggcagga ggcagaagca caggctgacc tgccccagct gtgactccta cgagaagaag     360

ccccccaagg agttcctgga gaggttcaag tccctgctgc agaagatgat ccatcagcac     420

ctgtcctcca ggacccacgg ctccgaggac tccattacat gcccccctcc catgagcgtg     480

gagcacgccg acatctgggt gaagagctat agcctctaca gccgggagag gtatatctgt     540

aacagcggct tcaagaggaa ggccggcacc agcagcctca ccgagtgcgt gctgaataag     600

gctaccaacg tggctcactg gacaacaccc tctttaaagt gcatccgg                  648


<210> SEQ ID NO 215
<211> LENGTH: 108
<212> TYPE: PRT
<213> ORGANISM: Homo sapiens
<220> FEATURE:
<221> NAME/KEY: source
<223> OTHER INFORMATION: /note="CD16"

<400> SEQUENCE: 215

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80
```

```
Glu Ala Asp Tyr Tyr Cys Asn Ser Arg Asp Ser Ser Gly Asn His Val
                85                  90                  95

Val Phe Gly Gly Gly Thr Lys Leu Thr Val Gly His
            100                 105
```

<210> SEQ ID NO 216
<211> LENGTH: 324
<212> TYPE: DNA
<213> ORGANISM: Homo sapiens
<220> FEATURE:
<221> NAME/KEY: source
<223> OTHER INFORMATION: /note="CD16"

<400> SEQUENCE: 216

```
tccgagctga cccaggaccc tgctgtgtcc gtggctctgg gccagaccgt gaggatcacc      60

tgccagggcg actccctgag gtcctactac gcctcctggt accagcagaa gcccggccag     120

gctcctgtgc tggtgatcta cggcaagaac aacaggccct ccggcatccc tgacaggttc     180

tccggatcct cctccggcaa caccgcctcc ctgaccatca caggcgctca ggccgaggac     240

gaggctgact actactgcaa ctccagggac tcctccggca accatgtggt gttcggcggc     300

ggcaccaagc tgaccgtggg ccat                                           324
```

<210> SEQ ID NO 217
<211> LENGTH: 117
<212> TYPE: PRT
<213> ORGANISM: Homo sapiens
<220> FEATURE:
<221> NAME/KEY: source
<223> OTHER INFORMATION: /note="CD16"

<400> SEQUENCE: 217

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
            100                 105                 110

Val Thr Val Ser Arg
        115
```

<210> SEQ ID NO 218
<211> LENGTH: 351
<212> TYPE: DNA
<213> ORGANISM: Homo sapiens
<220> FEATURE:
<221> NAME/KEY: source
<223> OTHER INFORMATION: /note="CD16"

<400> SEQUENCE: 218

```
gaggtgcagc tggtggagtc cggaggagga gtggtgaggc ctggaggctc cctgaggctg      60

agctgtgctg cctccggctt caccttcgac gactacggca tgtcctgggt gaggcaggct     120
```

```
cctggaaagg gcctggagtg ggtgtccggc atcaactgga acggcggatc caccggctac    180

gccgattccg tgaagggcag gttcaccatc agcagggaca acgccaagaa ctccctgtac    240

ctgcagatga actccctgag ggccgaggac accgccgtgt actactgcgc caggggcagg    300

tccctgctgt tcgactactg gggacagggc accctggtga ccgtgtccag g             351


<210> SEQ ID NO 219

<400> SEQUENCE: 219

000


<210> SEQ ID NO 220

<400> SEQUENCE: 220

000


<210> SEQ ID NO 221

<400> SEQUENCE: 221

000


<210> SEQ ID NO 222

<400> SEQUENCE: 222

000


<210> SEQ ID NO 223
<211> LENGTH: 823
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 223

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160
```

-continued

```
Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Pro Met Ser Val Glu
        515                 520                 525

His Ala Asp Ile Trp Val Lys Ser Tyr Ser Leu Tyr Ser Arg Glu Arg
    530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg Ser Glu Leu Thr Gln Asp Pro Ala Val
```

```
            580                 585                 590

Ser Val Ala Leu Gly Gln Thr Val Arg Ile Thr Cys Gln Gly Asp Ser
        595                 600                 605

Leu Arg Ser Tyr Tyr Ala Ser Trp Tyr Gln Gln Lys Pro Gly Gln Ala
    610                 615                 620

Pro Val Leu Val Ile Tyr Gly Lys Asn Asn Arg Pro Ser Gly Ile Pro
625                 630                 635                 640

Asp Arg Phe Ser Gly Ser Ser Ser Gly Asn Thr Ala Ser Leu Thr Ile
                645                 650                 655

Thr Gly Ala Gln Ala Glu Asp Glu Ala Asp Tyr Tyr Cys Asn Ser Arg
            660                 665                 670

Asp Ser Ser Gly Asn His Val Val Phe Gly Gly Gly Thr Lys Leu Thr
        675                 680                 685

Val Gly His Gly Gly Gly Gly Ser Gly Gly Gly Gly Ser Gly Gly Gly
    690                 695                 700

Gly Ser Glu Val Gln Leu Val Glu Ser Gly Gly Gly Val Val Arg Pro
705                 710                 715                 720

Gly Gly Ser Leu Arg Leu Ser Cys Ala Ala Ser Gly Phe Thr Phe Asp
                725                 730                 735

Asp Tyr Gly Met Ser Trp Val Arg Gln Ala Pro Gly Lys Gly Leu Glu
            740                 745                 750

Trp Val Ser Gly Ile Asn Trp Asn Gly Gly Ser Thr Gly Tyr Ala Asp
        755                 760                 765

Ser Val Lys Gly Arg Phe Thr Ile Ser Arg Asp Asn Ala Lys Asn Ser
    770                 775                 780

Leu Tyr Leu Gln Met Asn Ser Leu Arg Ala Glu Asp Thr Ala Val Tyr
785                 790                 795                 800

Tyr Cys Ala Arg Gly Arg Ser Leu Leu Phe Asp Tyr Trp Gly Gln Gly
                805                 810                 815

Thr Leu Val Thr Val Ser Arg
            820


<210> SEQ ID NO 224
<211> LENGTH: 2469
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 224

atttgggaac tgaagaagga cgtctacgtg gtcgaactgg actggtatcc cgatgctccc      60

ggcgaaatgg tggtgctcac ttgtgacacc cccgaagaag acggcatcac ttggaccctc     120

gatcagagca gcgaggtgct gggctccgga aagaccctca caatccaagt taaggagttc     180

ggagacgctg gccaatacac atgccacaag ggaggcgagg tgctcagcca ttccttatta     240

ttattacaca agaaggaaga cggaatctgg tccaccgaca ttttaaaaga tcagaaggag     300

cccaagaata agaccttttt aaggtgtgag gccaaaaact acagcggtcg tttcacttgt     360

tggtggctga ccaccatttc caccgattta accttctccg tgaaaagcag ccggggaagc     420

tccgaccctc aaggtgtgac atgtggagcc gctaccctca gcgctgagag ggttcgtggc     480

gataacaagg aatacgagta cagcgtggag tgccaagaag atagcgcttg tcccgctgcc     540

gaagaatctt tacccattga ggtgatggtg gacgccgtgc acaaactcaa gtacgagaac     600
```

-continued

```
tacacctcct ccttctttat ccgggacatc attaagcccg atcctcctaa gaatttacag    660

ctgaagcctc tcaaaaatag ccggcaagtt gaggtctctt gggaatatcc cgacacttgg    720

agcacacccc acagctactt ctctttaacc ttttgtgtgc aagttcaagg taaaagcaag    780

cgggagaaga aagaccgggt gtttaccgac aaaaccagcg ccaccgtcat ctgtcggaag    840

aacgcctcca tcagcgtgag ggctcaagat cgttattact ccagcagctg gtccgagtgg    900

gccagcgtgc cttgttccgg cggtggagga tccggaggag gtggctccgg cggcggagga    960

tctcgtaacc tccccgtggc tacccccgat cccggaatgt tcccttgttt acaccacagc   1020

cagaatttac tgagggccgt gagcaacatg ctgcagaaag ctaggcagac tttagaattt   1080

tacccttgca ccagcgagga gatcgaccat gaagatatca ccaaggacaa gacatccacc   1140

gtggaggctt gtttacctct ggagctgaca aagaacgagt cttgtctcaa ctctcgtgaa   1200

accagcttca tcacaaatgg ctcttgttta gcttcccgga agacctcctt tatgatggct   1260

ttatgcctca gctccatcta cgaggattta aagatgtacc aagtggagtt caagaccatg   1320

aacgccaagc tgctcatgga ccctaaacgg cagatctttt tagaccagaa catgctggct   1380

gtgattgatg agctgatgca agctttaaac ttcaactccg agaccgtccc tcagaagtcc   1440

tccctcgagg agcccgattt ttacaagaca aagatcaaac tgtgcatttt actccacgcc   1500

tttaggatcc gggccgtgac cattgaccgg gtcatgagct atttaaacgc cagcattaca   1560

tgcccccctc ccatgagcgt ggagcacgcc gacatctggg tgaagagcta tagcctctac   1620

agccgggaga ggtatatctg taacagcggc ttcaagagga aggccggcac cagcagcctc   1680

accgagtgcg tgctgaataa ggctaccaac gtggctcact ggacaacacc ctctttaaag   1740

tgcatccggt ccgagctgac ccaggaccct gctgtgtccg tggctctggg ccagaccgtg   1800

aggatcacct gccagggcga ctccctgagg tcctactacg cctcctggta ccagcagaag   1860

cccggccagg ctcctgtgct ggtgatctac ggcaagaaca acaggccctc cggcatccct   1920

gacaggttct ccggatcctc ctccggcaac accgcctccc tgaccatcac aggcgctcag   1980

gccgaggacg aggctgacta ctactgcaac tccagggact cctccggcaa ccatgtggtg   2040

ttcggcggcg gcaccaagct gaccgtgggc catggcggcg gcggctccgg aggcggcggc   2100

agcggcggag gaggatccga ggtgcagctg gtggagtccg gaggaggagt ggtgaggcct   2160

ggaggctccc tgaggctgag ctgtgctgcc tccggcttca ccttcgacga ctacggcatg   2220

tcctgggtga ggcaggctcc tggaaagggc ctggagtggg tgtccggcat caactggaac   2280

ggcggatcca ccggctacgc cgattccgtg aagggcaggt tcaccatcag cagggacaac   2340

gccaagaact ccctgtacct gcagatgaac tccctgaggg ccgaggacac cgccgtgtac   2400

tactgcgcca ggggcaggtc cctgctgttc gactactggg gacagggcac cctggtgacc   2460

gtgtccagg                                                           2469
```

<210> SEQ ID NO 225
<211> LENGTH: 841
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic 18t15-12s16 sequence"

<400> SEQUENCE: 225

```
Met Lys Trp Val Thr Phe Ile Ser Leu Leu Phe Leu Phe Ser Ser Ala
1               5                   10                  15
```

-continued

```
Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Gly Ser Gly Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
```

```
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg Ser Glu Leu Thr Gln Asp Pro
        595                 600                 605

Ala Val Ser Val Ala Leu Gly Gln Thr Val Arg Ile Thr Cys Gln Gly
    610                 615                 620

Asp Ser Leu Arg Ser Tyr Tyr Ala Ser Trp Tyr Gln Gln Lys Pro Gly
625                 630                 635                 640

Gln Ala Pro Val Leu Val Ile Tyr Gly Lys Asn Asn Arg Pro Ser Gly
                645                 650                 655

Ile Pro Asp Arg Phe Ser Gly Ser Ser Ser Gly Asn Thr Ala Ser Leu
            660                 665                 670

Thr Ile Thr Gly Ala Gln Ala Glu Asp Glu Ala Asp Tyr Tyr Cys Asn
        675                 680                 685

Ser Arg Asp Ser Ser Gly Asn His Val Val Phe Gly Gly Gly Thr Lys
    690                 695                 700

Leu Thr Val Gly His Gly Gly Gly Gly Ser Gly Gly Gly Gly Ser Gly
705                 710                 715                 720

Gly Gly Gly Ser Glu Val Gln Leu Val Glu Ser Gly Gly Gly Val Val
                725                 730                 735

Arg Pro Gly Gly Ser Leu Arg Leu Ser Cys Ala Ala Ser Gly Phe Thr
            740                 745                 750

Phe Asp Asp Tyr Gly Met Ser Trp Val Arg Gln Ala Pro Gly Lys Gly
        755                 760                 765

Leu Glu Trp Val Ser Gly Ile Asn Trp Asn Gly Gly Ser Thr Gly Tyr
    770                 775                 780

Ala Asp Ser Val Lys Gly Arg Phe Thr Ile Ser Arg Asp Asn Ala Lys
785                 790                 795                 800

Asn Ser Leu Tyr Leu Gln Met Asn Ser Leu Arg Ala Glu Asp Thr Ala
                805                 810                 815

Val Tyr Tyr Cys Ala Arg Gly Arg Ser Leu Leu Phe Asp Tyr Trp Gly
            820                 825                 830

Gln Gly Thr Leu Val Thr Val Ser Arg
        835                 840
```

<210> SEQ ID NO 226

<211> LENGTH: 2523
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 18t15-12s16 sequence"

<400> SEQUENCE: 226

```
atgaaatggg tgacctttat ttctttactg ttcctcttta gcagcgccta ctccatttgg     60
gaactgaaga aggacgtcta cgtggtcgaa ctggactggt atcccgatgc tcccggcgaa    120
atggtggtgc tcacttgtga cacccccgaa gaagacggca tcacttggac cctcgatcag    180
agcagcgagg tgctgggctc cggaaagacc ctcacaatcc aagttaagga gttcggagac    240
gctggccaat acacatgcca caagggaggc gaggtgctca gccattcctt attattatta    300
cacaagaagg aagacggaat ctggtccacc gacattttaa aagatcagaa ggagcccaag    360
aataagacct ttttaaggtg tgaggccaaa aactacagcg gtcgtttcac ttgttggtgg    420
ctgaccacca tttccaccga tttaaccttc tccgtgaaaa gcagccgggg aagctccgac    480
cctcaaggtg tgacatgtgg agccgctacc ctcagcgctg agagggttcg tggcgataac    540
aaggaatacg agtacagcgt ggagtgccaa gaagatagcg cttgtcccgc tgccgaagaa    600
tctttaccca ttgaggtgat ggtggacgcc gtgcacaaac tcaagtacga gaactacacc    660
tcctccttct ttatccggga catcattaag cccgatcctc ctaagaattt acagctgaag    720
cctctcaaaa atagccggca agttgaggtc tcttgggaat atcccgacac ttggagcaca    780
ccccacagct acttctcttt aacctttgt gtgcaagttc aaggtaaaag caagcgggag     840
aagaaagacc gggtgtttac cgacaaaacc agcgccaccg tcatctgtcg gaagaacgcc    900
tccatcagcg tgagggctca agatcgttat tactccagca gctggtccga gtgggccagc    960
gtgccttgtt ccggcggtgg aggatccgga ggaggtggct ccggcggcgg aggatctcgt   1020
aacctccccg tggctacccc cgatcccgga atgttccctt gtttacacca cagccagaat   1080
ttactgaggg ccgtgagcaa catgctgcag aaagctaggc agactttaga attttaccct   1140
tgcaccagcg aggagatcga ccatgaagat atcaccaagg acaagacatc caccgtggag   1200
gcttgtttac ctctggagct gacaaagaac gagtcttgtc tcaactctcg tgaaaccagc   1260
ttcatcacaa atggctcttg tttagcttcc cggaagacct cctttatgat ggctttatgc   1320
ctcagctcca tctacgagga tttaaagatg taccaagtgg agttcaagac catgaacgcc   1380
aagctgctca tggaccctaa acggcagatc tttttagacc agaacatgct ggctgtgatt   1440
gatgagctga tgcaagcttt aaacttcaac tccgagaccg tccctcagaa gtcctccctc   1500
gaggagcccg atttttacaa gacaaagatc aaactgtgca ttttactcca cgcctttagg   1560
atccgggccg tgaccattga ccgggtcatg agctatttaa acgccagcat tacatgcccc   1620
cctcccatga gcgtggagca cgccgacatc tgggtgaaga gctatagcct ctacagccgg   1680
gagaggtata tctgtaacag cggcttcaag aggaaggccg gcaccagcag cctcaccgag   1740
tgcgtgctga ataaggctac caacgtggct cactggacaa caccctcttt aaagtgcatc   1800
cggtccgagc tgacccagga ccctgctgtg tccgtggctc tgggccagac cgtgaggatc   1860
acctgccagg gcgactccct gaggtcctac tacgcctcct ggtaccagca gaagcccggc   1920
caggctcctg tgctggtgat ctacggcaag aacaacaggc cctccggcat ccctgacagg   1980
ttctccggat cctcctccgg caacaccgcc tccctgacca tcacaggcgc tcaggccgag   2040
gacgaggctg actactactg caactccagg gactcctccg gcaaccatgt ggtgttcggc   2100
```

ggcggcacca agctgaccgt gggccatggc ggcggcggct ccggaggcgg cggcagcggc 2160
ggaggaggat ccgaggtgca gctggtggag tccggaggag gagtggtgag gcctggaggc 2220
tccctgaggc tgagctgtgc tgcctccggc ttcaccttcg acgactacgg catgtcctgg 2280
gtgaggcagg ctcctggaaa gggcctggag tgggtgtccg gcatcaactg gaacggcgga 2340
tccaccggct acgccgattc cgtgaagggc aggttcacca tcagcaggga caacgccaag 2400
aactccctgt acctgcagat gaactccctg agggccgagg acaccgccgt gtactactgc 2460
gccaggggca ggtccctgct gttcgactac tggggacagg gcaccctggt gaccgtgtcc 2520
agg 2523

<210> SEQ ID NO 227
<211> LENGTH: 456
<212> TYPE: DNA
<213> ORGANISM: Homo sapiens
<220> FEATURE:
<221> NAME/KEY: source
<223> OTHER INFORMATION: /note="IL7"

<400> SEQUENCE: 227
gattgcgaca tcgagggcaa ggacggcaag cagtacgaga gcgtgctgat ggtgtccatc 60
gaccagctgc tggacagcat gaaggagatc ggctccaact gcctcaacaa cgagttcaac 120
ttcttcaagc ggcacatctg cgacgccaac aaggagggca tgttcctgtt cagggccgcc 180
aggaaactgc ggcagttcct gaagatgaac tccaccggcg acttcgacct gcacctgctg 240
aaggtgtccg agggcaccac catcctgctg aactgcaccg gacaggtgaa gggccggaaa 300
cctgctgctc tgggagaggc ccaacccacc aagagcctgg aggagaacaa gtccctgaag 360
gagcagaaga agctgaacga cctgtgcttc ctgaagaggc tgctgcagga gatcaagacc 420
tgctggaaca agatcctgat gggcaccaag gagcat 456

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232
<211> LENGTH: 438
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 232

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Val Val Arg Pro Gly Gly Ser Leu Arg Leu Ser
    130                 135                 140

Cys Ala Ala Ser Gly Phe Thr Phe Asp Asp Tyr Gly Met Ser Trp Val
145                 150                 155                 160

Arg Gln Ala Pro Gly Lys Gly Leu Glu Trp Val Ser Gly Ile Asn Trp
                165                 170                 175

Asn Gly Gly Ser Thr Gly Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Gly Arg Ser
    210                 215                 220

Leu Leu Phe Asp Tyr Trp Gly Gln Gly Thr Leu Val Thr Val Ser Arg
225                 230                 235                 240

Ile Thr Cys Pro Pro Pro Met Ser Val Glu His Ala Asp Ile Trp Val
                245                 250                 255

Lys Ser Tyr Ser Leu Tyr Ser Arg Glu Arg Tyr Ile Cys Asn Ser Gly
            260                 265                 270

Phe Lys Arg Lys Ala Gly Thr Ser Ser Leu Thr Glu Cys Val Leu Asn
        275                 280                 285

Lys Ala Thr Asn Val Ala His Trp Thr Thr Pro Ser Leu Lys Cys Ile
    290                 295                 300

Arg Gln Gly Gln Asp Arg His Met Ile Arg Met Arg Gln Leu Ile Asp
305                 310                 315                 320

Ile Val Asp Gln Leu Lys Asn Tyr Val Asn Asp Leu Val Pro Glu Phe
                325                 330                 335

Leu Pro Ala Pro Glu Asp Val Glu Thr Asn Cys Glu Trp Ser Ala Phe
            340                 345                 350

Ser Cys Phe Gln Lys Ala Gln Leu Lys Ser Ala Asn Thr Gly Asn Asn
        355                 360                 365

Glu Arg Ile Ile Asn Val Ser Ile Lys Lys Leu Lys Arg Lys Pro Pro
    370                 375                 380

Ser Thr Asn Ala Gly Arg Arg Gln Lys His Arg Leu Thr Cys Pro Ser
385                 390                 395                 400
```

Cys Asp Ser Tyr Glu Lys Lys Pro Pro Lys Glu Phe Leu Glu Arg Phe
405 410 415

Lys Ser Leu Leu Gln Lys Met Ile His Gln His Leu Ser Ser Arg Thr
420 425 430

His Gly Ser Glu Asp Ser
435

<210> SEQ ID NO 233
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 233
tccgagctga cccaggaccc tgctgtgtcc gtggctctgg gccagaccgt gaggatcacc 60
tgccagggcg actccctgag gtcctactac gcctcctggt accagcagaa gcccggccag 120
gctcctgtgc tggtgatcta cggcaagaac aacaggccct ccggcatccc tgacaggttc 180
tccggatcct cctccggcaa caccgcctcc ctgaccatca caggcgctca ggccgaggac 240
gaggctgact actactgcaa ctccagggac tcctccggca accatgtggt gttcggcggc 300
ggcaccaagc tgaccgtggg ccatggcggc ggcggctccg gaggcggcgg cagcggcgga 360
ggaggatccg aggtgcagct ggtggagtcc ggaggaggag tggtgaggcc tggaggctcc 420
ctgaggctga gctgtgctgc ctccggcttc accttcgacg actacggcat gtcctgggtg 480
aggcaggctc ctggaaaggg cctggagtgg gtgtccggca tcaactggaa cggcggatcc 540
accggctacg ccgattccgt gaagggcagg ttcaccatca gcagggacaa cgccaagaac 600
tccctgtacc tgcagatgaa ctccctgagg gccgaggaca ccgccgtgta ctactgcgcc 660
aggggcaggt ccctgctgtt cgactactgg ggacagggca ccctggtgac cgtgtccagg 720
attacatgcc cccctcccat gagcgtggag cacgccgaca tctgggtgaa gagctatagc 780
ctctacagcc gggagaggta tatctgtaac agcggcttca agaggaaggc cggcaccagc 840
agcctcaccg agtgcgtgct gaataaggct accaacgtgg ctcactggac aacaccctct 900
ttaaagtgca tccggcaggg ccaggacagg cacatgatcc ggatgaggca gctcatcgac 960
atcgtcgacc agctgaagaa ctacgtgaac gacctggtgc ccgagtttct gcctgccccc 1020
gaggacgtgg agaccaactg cgagtggtcc gccttctcct gctttcagaa ggcccagctg 1080
aagtccgcca acaccggcaa caacgagcgg atcatcaacg tgagcatcaa gaagctgaag 1140
cggaagcctc cctccacaaa cgccggcagg aggcagaagc acaggctgac ctgccccagc 1200
tgtgactcct acgagaagaa gccccccaag gagttcctgg agaggttcaa gtccctgctg 1260
cagaagatga tccatcagca cctgtcctcc aggacccacg gctccgagga ctcc 1314

<210> SEQ ID NO 234
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 234

Met Lys Trp Val Thr Phe Ile Ser Leu Leu Phe Leu Phe Ser Ser Ala

-continued

```
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr
        35                  40                  45

Ala Ser Trp Tyr Gln Gln Lys Pro Gly Gln Ala Pro Val Leu Val Ile
    50                  55                  60

Tyr Gly Lys Asn Asn Arg Pro Ser Gly Ile Pro Asp Arg Phe Ser Gly
65                  70                  75                  80

Ser Ser Ser Gly Asn Thr Ala Ser Leu Thr Ile Thr Gly Ala Gln Ala
                85                  90                  95

Glu Asp Glu Ala Asp Tyr Tyr Cys Asn Ser Arg Asp Ser Ser Gly Asn
            100                 105                 110

His Val Val Phe Gly Gly Gly Thr Lys Leu Thr Val Gly His Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Val Val Arg Pro Gly Gly Ser Leu Arg
145                 150                 155                 160

Leu Ser Cys Ala Ala Ser Gly Phe Thr Phe Asp Asp Tyr Gly Met Ser
                165                 170                 175

Trp Val Arg Gln Ala Pro Gly Lys Gly Leu Glu Trp Val Ser Gly Ile
            180                 185                 190

Asn Trp Asn Gly Gly Ser Thr Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg Gly
225                 230                 235                 240

Arg Ser Leu Leu Phe Asp Tyr Trp Gly Gln Gly Thr Leu Val Thr Val
                245                 250                 255

Ser Arg Ile Thr Cys Pro Pro Pro Met Ser Val Glu His Ala Asp Ile
            260                 265                 270

Trp Val Lys Ser Tyr Ser Leu Tyr Ser Arg Glu Arg Tyr Ile Cys Asn
        275                 280                 285

Ser Gly Phe Lys Arg Lys Ala Gly Thr Ser Ser Leu Thr Glu Cys Val
    290                 295                 300

Leu Asn Lys Ala Thr Asn Val Ala His Trp Thr Thr Pro Ser Leu Lys
305                 310                 315                 320

Cys Ile Arg Gln Gly Gln Asp Arg His Met Ile Arg Met Arg Gln Leu
                325                 330                 335

Ile Asp Ile Val Asp Gln Leu Lys Asn Tyr Val Asn Asp Leu Val Pro
            340                 345                 350

Glu Phe Leu Pro Ala Pro Glu Asp Val Glu Thr Asn Cys Glu Trp Ser
        355                 360                 365

Ala Phe Ser Cys Phe Gln Lys Ala Gln Leu Lys Ser Ala Asn Thr Gly
    370                 375                 380

Asn Asn Glu Arg Ile Ile Asn Val Ser Ile Lys Lys Leu Lys Arg Lys
385                 390                 395                 400

Pro Pro Ser Thr Asn Ala Gly Arg Arg Gln Lys His Arg Leu Thr Cys
                405                 410                 415

Pro Ser Cys Asp Ser Tyr Glu Lys Lys Pro Pro Lys Glu Phe Leu Glu
            420                 425                 430
```

Arg Phe Lys Ser Leu Leu Gln Lys Met Ile His Gln His Leu Ser Ser
435 440 445

Arg Thr His Gly Ser Glu Asp Ser
450 455

<210> SEQ ID NO 235
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 235
atgaagtggg tgaccttcat cagcctgctg ttcctgttct ccagcgccta ctcctccgag 60
ctgacccagg accctgctgt gtccgtggct ctgggccaga ccgtgaggat cacctgccag 120
ggcgactccc tgaggtccta ctacgcctcc tggtaccagc agaagcccgg ccaggctcct 180
gtgctggtga tctacggcaa gaacaacagg ccctccggca tccctgacag gttctccgga 240
tcctcctccg gcaacaccgc ctccctgacc atcacaggcg ctcaggccga ggacgaggct 300
gactactact gcaactccag ggactcctcc ggcaaccatg tggtgttcgg cggcggcacc 360
aagctgaccg tgggccatgg cggcggcggc tccggaggcg gcggcagcgg cggaggagga 420
tccgaggtgc agctggtgga gtccggagga ggagtggtga ggcctggagg ctccctgagg 480
ctgagctgtg ctgcctccgg cttcaccttc gacgactacg gcatgtcctg ggtgaggcag 540
gctcctggaa agggcctgga gtgggtgtcc ggcatcaact ggaacggcgg atccaccggc 600
tacgccgatt ccgtgaaggg caggttcacc atcagcaggg acaacgccaa gaactccctg 660
tacctgcaga tgaactccct gagggccgag gacaccgccg tgtactactg cgccaggggc 720
aggtccctgc tgttcgacta ctggggacag ggcaccctgg tgaccgtgtc caggattaca 780
tgcccccctc ccatgagcgt ggagcacgcc gacatctggg tgaagagcta tagcctctac 840
agccgggaga ggtatatctg taacagcggc ttcaagagga aggccggcac cagcagcctc 900
accgagtgcg tgctgaataa ggctaccaac gtggctcact ggacaacacc ctctttaaag 960
tgcatccggc agggccagga caggcacatg atccggatga ggcagctcat cgacatcgtc 1020
gaccagctga agaactacgt gaacgacctg gtgcccgagt ttctgcctgc ccccgaggac 1080
gtggagacca actgcgagtg gtccgccttc tcctgctttc agaaggccca gctgaagtcc 1140
gccaacaccg gcaacaacga gcggatcatc aacgtgagca tcaagaagct gaagcggaag 1200
cctccctcca caaacgccgg caggaggcag aagcacaggc tgacctgccc cagctgtgac 1260
tcctacgaga agaagccccc caaggagttc ctggagaggt tcaagtccct gctgcagaag 1320
atgatccatc agcacctgtc ctccaggacc cacggctccg aggactcc 1368

<210> SEQ ID NO 236
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 236

Ile Pro Pro His Val Gln Lys Ser Val Asn Asn Asp Met Ile Val Thr
1 5 10 15

```
Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ser
        275                 280                 285

Gly Thr Thr Asn Thr Val Ala Ala Tyr Asn Leu Thr Trp Lys Ser Thr
    290                 295                 300

Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
            340                 345                 350

Asp Val Lys Gln Thr Tyr Leu Ala Arg Val Phe Ser Tyr Pro Ala Gly
        355                 360                 365

Asn Val Glu Ser Thr Gly Ser Ala Gly Glu Pro Leu Tyr Glu Asn Ser
    370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
            420                 425                 430
```

```
Val Phe Gly Lys Asp Leu Ile Tyr Thr Leu Tyr Tyr Trp Lys Ser Ser
        435                 440                 445

Ser Ser Gly Lys Lys Thr Ala Lys Thr Asn Thr Asn Glu Phe Leu Ile
    450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
                485                 490                 495

Met Gly Gln Glu Lys Gly Glu Phe Arg Glu Asn Trp Val Asn Val Ile
            500                 505                 510

Ser Asp Leu Lys Lys Ile Glu Asp Leu Ile Gln Ser Met His Ile Asp
        515                 520                 525

Ala Thr Leu Tyr Thr Glu Ser Asp Val His Pro Ser Cys Lys Val Thr
    530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
        595                 600                 605

Phe Val His Ile Val Gln Met Phe Ile Asn Thr Ser
    610                 615                 620
```

<210> SEQ ID NO 237
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 237

```
atcccccccc atgtgcaaaa gagcgtgaac aacgatatga tcgtgaccga caacaacggc     60

gccgtgaagt ttccccagct ctgcaagttc tgcgatgtca ggttcagcac ctgcgataat    120

cagaagtcct gcatgtccaa ctgcagcatc acctccatct gcgagaagcc ccaagaagtg    180

tgcgtggccg tgtggcggaa aaatgacgag aacatcaccc tggagaccgt gtgtcacgac    240

cccaagctcc cttatcacga cttcattctg gaggacgctg cctcccccaa atgcatcatg    300

aaggagaaga agaagcccgg agagaccttc tttatgtgtt cctgtagcag cgacgagtgt    360

aacgacaaca tcatcttcag cgaagagtac aacaccagca accctgatgg aggtggcgga    420

tccggaggtg gaggttctgg tggaggtggg agtattcctc cccacgtgca gaagagcgtg    480

aataatgaca tgatcgtgac cgataacaat ggcgccgtga aatttcccca gctgtgcaaa    540

ttctgcgatg tgaggttttc cacctgcgac aaccagaagt cctgtatgag caactgctcc    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga cagcggcaca accaacacag tcgctgccta taacctcact    900

tggaagagca ccaacttcaa aaccatcctc gaatgggaac ccaaacccgt taaccaagtt    960
```

```
tacaccgtgc agatcagcac caagtccggc gactggaagt ccaaatgttt ctataccacc   1020

gacaccgagt gcgatctcac cgatgagatc gtgaaagatg tgaaacagac ctacctcgcc   1080

cgggtgttta gctaccccgc cggcaatgtg gagagcactg gttccgctgg cgagccttta   1140

tacgagaaca gccccgaatt taccccttac ctcgagacca atttaggaca gcccaccatc   1200

caaagctttg agcaagttgg cacaaaggtg aatgtgacag tggaggacga gcggacttta   1260

gtgcggcgga acaacacctt tctcagcctc cgggatgtgt tcggcaaaga tttaatctac   1320

acactgtatt actggaagtc ctcttcctcc ggcaagaaga cagctaaaac caacacaaac   1380

gagtttttaa tcgacgtgga taaaggcgaa aactactgtt tcagcgtgca agctgtgatc   1440

ccctcccgga ccgtgaatag gaaaagcacc gatagccccg ttgagtgcat gggccaagaa   1500

aagggcgagt tccgggagaa ctgggtgaac gtcatcagcg atttaaagaa gatcgaagat   1560

ttaattcagt ccatgcatat cgacgccact ttatacacag aatccgacgt gcacccctct   1620

tgtaaggtga ccgccatgaa atgtttttta ctggagctgc aagttatctc tttagagagc   1680

ggagacgcta gcatccacga caccgtggag aatttaatca ttttagccaa taactcttta   1740

tccagcaacg gcaacgtgac agagtccggc tgcaaggagt gcgaagagct ggaggagaag   1800

aacatcaagg agtttctgca atcctttgtg cacattgtcc agatgttcat caatacctcc   1860
```

<210> SEQ ID NO 238
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 238

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190
```

-continued

```
Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
    370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
            420                 425                 430

Glu Asp Glu Arg Thr Leu Val Arg Arg Asn Asn Thr Phe Leu Ser Leu
        435                 440                 445

Arg Asp Val Phe Gly Lys Asp Leu Ile Tyr Thr Leu Tyr Tyr Trp Lys
    450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
    530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
```

610 615 620

Gln Ser Phe Val His Ile Val Gln Met Phe Ile Asn Thr Ser
625 630 635

<210> SEQ ID NO 239
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 239
atgaagtggg tgaccttcat cagcctgctg ttcctgttct ccagcgccta ctccatcccc 60
ccccatgtgc aaaagagcgt gaacaacgat atgatcgtga ccgacaacaa cggcgccgtg 120
aagtttcccc agctctgcaa gttctgcgat gtcaggttca gcacctgcga taatcagaag 180
tcctgcatgt ccaactgcag catcacctcc atctgcgaga agccccaaga agtgtgcgtg 240
gccgtgtggc ggaaaaatga cgagaacatc accctggaga ccgtgtgtca cgaccccaag 300
ctcccttatc acgacttcat tctggaggac gctgcctccc ccaaatgcat catgaaggag 360
aagaagaagc ccggagagac cttctttatg tgttcctgta gcagcgacga gtgtaacgac 420
aacatcatct tcagcgaaga gtacaacacc agcaaccctg atggaggtgg cggatccgga 480
ggtggaggtt ctggtggagg tgggagtatt cctccccacg tgcagaagag cgtgaataat 540
gacatgatcg tgaccgataa caatggcgcc gtgaaatttc cccagctgtg caaattctgc 600
gatgtgaggt tttccacctg cgacaaccag aagtcctgta tgagcaactg ctccatcacc 660
tccatctgtg agaagcctca ggaggtgtgc gtggctgtct ggcggaagaa tgacgagaat 720
atcaccctgg aaaccgtctg ccacgatccc aagctgccct accacgattt catcctggaa 780
gacgccgcca gccctaagtg catcatgaaa gagaaaaaga agcctggcga gacctttttc 840
atgtgctcct gcagcagcga cgaatgcaac gacaatatca tctttagcga ggaatacaat 900
accagcaacc ccgacagcgg cacaaccaac acagtcgctg cctataacct cacttggaag 960
agcaccaact tcaaaaccat cctcgaatgg gaacccaaac ccgttaacca agtttacacc 1020
gtgcagatca gcaccaagtc cggcgactgg aagtccaaat gtttctatac caccgacacc 1080
gagtgcgatc tcaccgatga gatcgtgaaa gatgtgaaac agacctacct cgcccgggtg 1140
tttagctacc ccgccggcaa tgtggagagc actggttccg ctggcgagcc tttatacgag 1200
aacagccccg aatttacccc ttacctcgag accaatttag gacagcccac catccaaagc 1260
tttgagcaag ttggcacaaa ggtgaatgtg acagtggagg acgagcggac tttagtgcgg 1320
cggaacaaca cctttctcag cctccgggat gtgttcggca aagatttaat ctacacactg 1380
tattactgga agtcctcttc ctccggcaag aagacagcta aaaccaacac aaacgagttt 1440
ttaatcgacg tggataaagg cgaaaactac tgtttcagcg tgcaagctgt gatcccctcc 1500
cggaccgtga ataggaaaag caccgatagc cccgttgagt gcatgggcca agaaaagggc 1560
gagttccggg agaactgggt gaacgtcatc agcgatttaa agaagatcga agatttaatt 1620
cagtccatgc atatcgacgc cactttatac acagaatccg acgtgcaccc ctcttgtaag 1680
gtgaccgcca tgaaatgttt tttactggag ctgcaagtta tctctttaga gagcggagac 1740
gctagcatcc acgacaccgt ggagaattta atcattttag ccaataactc tttatccagc 1800
aacggcaacg tgacagagtc cggctgcaag gagtgcgaag agctggagga gaagaacatc 1860
aaggagtttc tgcaatcctt tgtgcacatt gtccagatgt tcatcaatac ctcc 1914

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 250

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ile Thr Cys Pro Pro Pro
                165                 170                 175

Met Ser Val Glu His Ala Asp Ile Trp Val Lys Ser Tyr Ser Leu Tyr
            180                 185                 190

Ser Arg Glu Arg Tyr Ile Cys Asn Ser Gly Phe Lys Arg Lys Ala Gly
        195                 200                 205

Thr Ser Ser Leu Thr Glu Cys Val Leu Asn Lys Ala Thr Asn Val Ala
    210                 215                 220

His Trp Thr Thr Pro Ser Leu Lys Cys Ile Arg
225                 230                 235
```

<210> SEQ ID NO 251
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 251

```
atgaagtggg tgaccttcat cagcctgctg ttcctgttct ccagcgccta ctccgattgc     60

gacatcgagg gcaaggacgg caagcagtac gagagcgtgc tgatggtgtc catcgaccag    120

ctgctggaca gcatgaagga gatcggctcc aactgcctca acaacgagtt caacttcttc    180

aagcggcaca tctgcgacgc caacaaggag ggcatgttcc tgttcagggc cgccaggaaa    240

ctgcggcagt tcctgaagat gaactccacc ggcgacttcg acctgcacct gctgaaggtg    300

tccgagggca ccaccatcct gctgaactgc accggacagg tgaagggccg gaaacctgct    360

gctctgggag aggcccaacc caccaagagc ctggaggaga acaagtccct gaaggagcag    420

aagaagctga acgacctgtg cttcctgaag aggctgctgc aggagatcaa gacctgctgg    480

aacaagatcc tgatgggcac caaggagcat attacatgcc cccctcccat gagcgtggag    540
```

cacgccgaca tctgggtgaa gagctatagc ctctacagcc gggagaggta tatctgtaac 600
agcggcttca agaggaaggc cggcaccagc agcctcaccg agtgcgtgct gaataaggct 660
accaacgtgg ctcactggac aacaccctct ttaaagtgca tccgg 705

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs sequence"

<400> SEQUENCE: 257
atcccccccc atgtgcaaaa gagcgtgaac aacgatatga tcgtgaccga caacaacggc 60
gccgtgaagt ttccccagct ctgcaagttc tgcgatgtca ggttcagcac ctgcgataat 120
cagaagtcct gcatgtccaa ctgcagcatc acctccatct gcgagaagcc ccaagaagtg 180
tgcgtggccg tgtggcggaa aaatgacgag aacatcaccc tggagaccgt gtgtcacgac 240
cccaagctcc cttatcacga cttcattctg gaggacgctg cctcccccaa atgcatcatg 300
aaggagaaga agaagcccgg agagaccttc tttatgtgtt cctgtagcag cgacgagtgt 360
aacgacaaca tcatcttcag cgaagagtac aacaccagca accctgatgg aggtggcgga 420
tccggaggtg gaggttctgg tggaggtggg agtattcctc cccacgtgca gaagagcgtg 480
aataatgaca tgatcgtgac cgataacaat ggcgccgtga aatttcccca gctgtgcaaa 540
ttctgcgatg tgaggttttc cacctgcgac aaccagaagt cctgtatgag caactgctcc 600
atcacctcca tctgtgagaa gcctcaggag gtgtgcgtgg ctgtctggcg gaagaatgac 660
gagaatatca ccctggaaac cgtctgccac gatcccaagc tgccctacca cgatttcatc 720
ctggaagacg ccgccagccc taagtgcatc atgaaagaga aaaagaagcc tggcgagacc 780
tttttcatgt gctcctgcag cagcgacgaa tgcaacgaca atatcatctt tagcgaggaa 840
tacaatacca gcaaccccga cattacatgc ccccctccca tgagcgtgga gcacgccgac 900
atctgggtga agagctatag cctctacagc cgggagaggt atatctgtaa cagcggcttc 960
aagaggaagg ccggcaccag cagcctcacc gagtgcgtgc tgaataaggc taccaacgtg 1020
gctcactgga caacaccctc tttaaagtgc atccgg 1056

<210> SEQ ID NO 258

<400> SEQUENCE: 258

000

<210> SEQ ID NO 259
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic TGFRt15-TGFRs sequence"

<400> SEQUENCE: 259
atgaagtggg tgaccttcat cagcctgctg ttcctgttct ccagcgccta ctccatcccc 60
ccccatgtgc aaaagagcgt gaacaacgat atgatcgtga ccgacaacaa cggcgccgtg 120
aagtttcccc agctctgcaa gttctgcgat gtcaggttca gcacctgcga taatcagaag 180
tcctgcatgt ccaactgcag catcacctcc atctgcgaga agccccaaga agtgtgcgtg 240
gccgtgtggc ggaaaaatga cgagaacatc accctggaga ccgtgtgtca cgaccccaag 300
ctcccttatc acgacttcat tctggaggac gctgcctccc ccaaatgcat catgaaggag 360
aagaagaagc ccggagagac cttctttatg tgttcctgta gcagcgacga gtgtaacgac 420
aacatcatct tcagcgaaga gtacaacacc agcaaccctg atggaggtgg cggatccgga 480
ggtggaggtt ctggtggagg tgggagtatt cctccccacg tgcagaagag cgtgaataat 540
gacatgatcg tgaccgataa caatggcgcc gtgaaatttc cccagctgtg caaattctgc 600
gatgtgaggt tttccacctg cgacaaccag aagtcctgta tgagcaactg ctccatcacc 660
tccatctgtg agaagcctca ggaggtgtgc gtggctgtct ggcggaagaa tgacgagaat 720
atcaccctgg aaaccgtctg ccacgatccc aagctgccct accacgattt catcctggaa 780
gacgccgcca gccctaagtg catcatgaaa gagaaaaaga agcctggcga gacctttttc 840
atgtgctcct gcagcagcga cgaatgcaac gacaatatca tctttagcga ggaatacaat 900
accagcaacc ccgacattac atgccccct cccatgagcg tggagcacgc cgacatctgg 960
gtgaagagct atagcctcta cagccgggag aggtatatct gtaacagcgg cttcaagagg 1020
aaggccggca ccagcagcct caccgagtgc gtgctgaata aggctaccaa cgtggctcac 1080
tggacaacac cctctttaaa gtgcatccgg 1110

<210> SEQ ID NO 260
<211> LENGTH: 184
<212> TYPE: PRT
<213> ORGANISM: Homo sapiens
<220> FEATURE:
<221> NAME/KEY: source
<223> OTHER INFORMATION: /note="CD137"

<400> SEQUENCE: 260

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180
```

<210> SEQ ID NO 261
<211> LENGTH: 552
<212> TYPE: DNA
<213> ORGANISM: Homo sapiens
<220> FEATURE:
<221> NAME/KEY: source
<223> OTHER INFORMATION: /note="CD137"

<400> SEQUENCE: 261

```
cgcgagggtc ccgagctttc gcccgacgat cccgccggcc tcttggacct gcggcagggc     60

atgtttgcgc agctggtggc ccaaaatgtt ctgctgatcg atgggcccct gagctggtac    120

agtgacccag gcctggcagg cgtgtccctg acgggggggcc tgagctacaa agaggacacg    180

aaggagctgg tggtggccaa ggctggagtc tactatgtct tctttcaact agagctgcgg    240

cgcgtggtgg ccggcgaggg ctcaggctcc gtttcacttg cgctgcacct gcagccactg    300

cgctctgctg ctggggccgc cgccctggct ttgaccgtgg acctgccacc cgcctcctcc    360

gaggctcgga actcggcctt cggtttccag ggccgcttgc tgcacctgag tgccggccag    420

cgcctgggcg tccatcttca cactgaggcc agggcacgcc atgcctggca gcttacccag    480

ggcgccacag tcttgggact cttccgggtg acccccgaaa tcccagccgg actcccttca    540

ccgaggtcgg aa                                                         552
```

<210> SEQ ID NO 262
<211> LENGTH: 165
<212> TYPE: PRT
<213> ORGANISM: Homo sapiens
<220> FEATURE:
<221> NAME/KEY: source
<223> OTHER INFORMATION: /note="CD137"

<400> SEQUENCE: 262

```
Asp Pro Ala Gly Leu Leu Asp Leu Arg Gln Gly Met Phe Ala Gln Leu
```

```
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile
                165
```

<210> SEQ ID NO 263
<211> LENGTH: 495
<212> TYPE: DNA
<213> ORGANISM: Homo sapiens
<220> FEATURE:
<221> NAME/KEY: source
<223> OTHER INFORMATION: /note="CD137"

<400> SEQUENCE: 263

```
gatcccgccg gcctcttgga cctgcggcag ggcatgtttg cgcagctggt ggcccaaaat     60

gttctgctga tcgatgggcc cctgagctgg tacagtgacc caggcctggc aggcgtgtcc    120

ctgacggggg gcctgagcta caaagaggac acgaaggagc tggtggtggc caaggctgga    180

gtctactatg tcttctttca actagagctg cggcgcgtgg tggccggcga gggctcaggc    240

tccgtttcac ttgcgctgca cctgcagcca ctgcgctctg ctgctggggc cgccgccctg    300

gctttgaccg tggacctgcc acccgcctcc tccgaggctc ggaactcggc cttcggtttc    360

cagggccgct tgctgcacct gagtgccggc cagcgcctgg gcgtccatct tcacactgag    420

gccagggcac gccatgcctg gcagcttacc cagggcgcca cagtcttggg actcttccgg    480

gtgacccccg aaatc                                                     495
```

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268
<211> LENGTH: 397
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21CD137 sequence"

<400> SEQUENCE: 268

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Gly Ser Gly Gly Gly Gly Ser
        195                 200                 205

Gly Gly Gly Gly Ser Arg Glu Gly Pro Glu Leu Ser Pro Asp Asp Pro
    210                 215                 220

Ala Gly Leu Leu Asp Leu Arg Gln Gly Met Phe Ala Gln Leu Val Ala
225                 230                 235                 240

Gln Asn Val Leu Leu Ile Asp Gly Pro Leu Ser Trp Tyr Ser Asp Pro
                245                 250                 255

Gly Leu Ala Gly Val Ser Leu Thr Gly Gly Leu Ser Tyr Lys Glu Asp
            260                 265                 270

Thr Lys Glu Leu Val Val Ala Lys Ala Gly Val Tyr Tyr Val Phe Phe
        275                 280                 285

Gln Leu Glu Leu Arg Arg Val Val Ala Gly Glu Gly Ser Gly Ser Val
    290                 295                 300
```

-continued

```
Ser Leu Ala Leu His Leu Gln Pro Leu Arg Ser Ala Ala Gly Ala Ala
305                 310                 315                 320

Ala Leu Ala Leu Thr Val Asp Leu Pro Pro Ala Ser Ser Glu Ala Arg
                325                 330                 335

Asn Ser Ala Phe Gly Phe Gln Gly Arg Leu Leu His Leu Ser Ala Gly
            340                 345                 350

Gln Arg Leu Gly Val His Leu His Thr Glu Ala Arg Ala Arg His Ala
        355                 360                 365

Trp Gln Leu Thr Gln Gly Ala Thr Val Leu Gly Leu Phe Arg Val Thr
    370                 375                 380

Pro Glu Ile Pro Ala Gly Leu Pro Ser Pro Arg Ser Glu
385                 390                 395
```

```
<210> SEQ ID NO 269
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21CD137 sequence"

<400> SEQUENCE: 269

cagggccagg acaggcacat gatccggatg aggcagctca tcgacatcgt cgaccagctg     60

aagaactacg tgaacgacct ggtgcccgag tttctgcctg cccccgagga cgtggagacc    120

aactgcgagt ggtccgcctt ctcctgcttt cagaaggccc agctgaagtc cgccaacacc    180

ggcaacaacg agcggatcat caacgtgagc atcaagaagc tgaagcggaa gcctccctcc    240

acaaacgccg gcaggaggca gaagcacagg ctgacctgcc ccagctgtga ctcctacgag    300

aagaagcccc ccaaggagtt cctggagagg ttcaagtccc tgctgcagaa gatgatccat    360

cagcacctgt cctccaggac ccacggctcc gaggactcca ttacatgccc ccctcccatg    420

agcgtggagc acgccgacat ctgggtgaag agctatagcc tctacagccg ggagaggtat    480

atctgtaaca gcggcttcaa gaggaaggcc ggcaccagca gcctcaccga gtgcgtgctg    540

aataaggcta ccaacgtggc tcactggaca acaccctctt taaagtgcat ccggggcggt    600

ggaggatccg gaggaggtgg ctccggcggc ggaggatctc gcgagggtcc cgagctttcg    660

cccgacgatc ccgccggcct cttggacctg cggcagggca tgtttgcgca gctggtggcc    720

caaaatgttc tgctgatcga tgggcccctg agctggtaca gtgacccagg cctggcaggc    780

gtgtccctga cggggggcct gagctacaaa gaggacacga aggagctggt ggtggccaag    840

gctggagtct actatgtctt ctttcaacta gagctgcggc gcgtggtggc cggcgagggc    900

tcaggctccg tttcacttgc gctgcacctg cagccactgc gctctgctgc tggggccgcc    960

gccctggctt tgaccgtgga cctgccaccc gcctcctccg aggctcggaa ctcggccttc   1020

ggtttccagg gccgcttgct gcacctgagt gccggccagc gcctgggcgt ccatcttcac   1080

actgaggcca gggcacgcca tgcctggcag cttacccagg gcgccacagt cttgggactc   1140

ttccgggtga cccccgaaat cccagccgga ctcccttcac cgaggtcgga a            1191
```

```
<210> SEQ ID NO 270
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21CD137 sequence"
```

<400> SEQUENCE: 270

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Gly Ser Gly Gly Gly
    210                 215                 220

Gly Ser Gly Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
                245                 250                 255

Val Ala Gln Asn Val Leu Leu Ile Asp Gly Pro Leu Ser Trp Tyr Ser
            260                 265                 270

Asp Pro Gly Leu Ala Gly Val Ser Leu Thr Gly Gly Leu Ser Tyr Lys
        275                 280                 285

Glu Asp Thr Lys Glu Leu Val Val Ala Lys Ala Gly Val Tyr Tyr Val
    290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
                325                 330                 335

Ala Ala Ala Leu Ala Leu Thr Val Asp Leu Pro Pro Ala Ser Ser Glu
            340                 345                 350

Ala Arg Asn Ser Ala Phe Gly Phe Gln Gly Arg Leu Leu His Leu Ser
        355                 360                 365

Ala Gly Gln Arg Leu Gly Val His Leu His Thr Glu Ala Arg Ala Arg
    370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu 405 410 415

<210> SEQ ID NO 271
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21CD137 sequence"

<400> SEQUENCE: 271
atgaagtggg tgaccttcat cagcctgctg ttcctgttct ccagcgccta ctcccagggc 60
caggacaggc acatgatccg gatgaggcag ctcatcgaca tcgtcgacca gctgaagaac 120
tacgtgaacg acctggtgcc cgagtttctg cctgcccccg aggacgtgga gaccaactgc 180
gagtggtccg ccttctcctg ctttcagaag gcccagctga agtccgccaa caccggcaac 240
aacgagcgga tcatcaacgt gagcatcaag aagctgaagc ggaagcctcc ctccacaaac 300
gccggcagga ggcagaagca caggctgacc tgccccagct gtgactccta cgagaagaag 360
ccccccaagg agttcctgga gaggttcaag tccctgctgc agaagatgat ccatcagcac 420
ctgtcctcca ggacccacgg ctccgaggac tccattacat gccccccctcc catgagcgtg 480 gagcacgccg acatctgggt gaagagctat agcctctaca gccgggagag gtatatctgt 540
aacagcggct tcaagaggaa ggccggcacc agcagcctca ccgagtgcgt gctgaataag 600
gctaccaacg tggctcactg gacaacaccc tctttaaagt gcatccgggg cggtggagga 660
tccggaggag gtggctccgg cggcggagga tctcgcgagg gtcccgagct ttcgcccgac 720
gatcccgccg gcctcttgga cctgcggcag ggcatgtttg cgcagctggt ggcccaaaat 780
gttctgctga tcgatgggcc cctgagctgg tacagtgacc caggcctggc aggcgtgtcc 840
ctgacggggg gcctgagcta caaagaggac acgaaggagc tggtggtggc caaggctgga 900
gtctactatg tcttctttca actagagctg cggcgcgtgg tggccggcga gggctcaggc 960
tccgtttcac ttgcgctgca cctgcagcca ctgcgctctg ctgctggggc cgccgccctg 1020
gctttgaccg tggacctgcc acccgcctcc tccgaggctc ggaactcggc cttcggtttc 1080
cagggccgct tgctgcacct gagtgccggc cagcgcctgg gcgtccatct tcacactgag 1140
gccagggcac gccatgcctg gcagcttacc cagggcgcca cagtcttggg actcttccgg 1200
gtgacccccg aaatcccagc cggactccct tcaccgaggt cggaa 1245

<210> SEQ ID NO 272
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21CD137 sequence"

<400> SEQUENCE: 272

Gln Gly Gln Asp Arg His Met Ile Arg Met Arg Gln Leu Ile Asp Ile
1 5 10 15

Val Asp Gln Leu Lys Asn Tyr Val Asn Asp Leu Val Pro Glu Phe Leu
20 25 30

Pro Ala Pro Glu Asp Val Glu Thr Asn Cys Glu Trp Ser Ala Phe Ser
35 40 45

Cys Phe Gln Lys Ala Gln Leu Lys Ser Ala Asn Thr Gly Asn Asn Glu
50 55 60

```
Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Gly Ser Gly Gly Gly Gly Ser
        195                 200                 205

Gly Gly Gly Gly Ser Asp Pro Ala Gly Leu Leu Asp Leu Arg Gln Gly
    210                 215                 220

Met Phe Ala Gln Leu Val Ala Gln Asn Val Leu Leu Ile Asp Gly Pro
225                 230                 235                 240

Leu Ser Trp Tyr Ser Asp Pro Gly Leu Ala Gly Val Ser Leu Thr Gly
                245                 250                 255

Gly Leu Ser Tyr Lys Glu Asp Thr Lys Glu Leu Val Val Ala Lys Ala
            260                 265                 270

Gly Val Tyr Tyr Val Phe Phe Gln Leu Glu Leu Arg Arg Val Val Ala
        275                 280                 285

Gly Glu Gly Ser Gly Ser Val Ser Leu Ala Leu His Leu Gln Pro Leu
    290                 295                 300

Arg Ser Ala Ala Gly Ala Ala Ala Leu Ala Leu Thr Val Asp Leu Pro
305                 310                 315                 320

Pro Ala Ser Ser Glu Ala Arg Asn Ser Ala Phe Gly Phe Gln Gly Arg
                325                 330                 335

Leu Leu His Leu Ser Ala Gly Gln Arg Leu Gly Val His Leu His Thr
            340                 345                 350

Glu Ala Arg Ala Arg His Ala Trp Gln Leu Thr Gln Gly Ala Thr Val
        355                 360                 365

Leu Gly Leu Phe Arg Val Thr Pro Glu Ile
    370                 375
```

<210> SEQ ID NO 273
<211> LENGTH: 1134
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21CD137 sequence"

<400> SEQUENCE: 273

```
cagggccagg acaggcacat gatccggatg aggcagctca tcgacatcgt cgaccagctg     60

aagaactacg tgaacgacct ggtgcccgag tttctgcctg cccccgagga cgtggagacc    120

aactgcgagt ggtccgcctt ctcctgcttt cagaaggccc agctgaagtc cgccaacacc    180
```

-continued

```
ggcaacaacg agcggatcat caacgtgagc atcaagaagc tgaagcggaa gcctccctcc    240

acaaacgccg gcaggaggca gaagcacagg ctgacctgcc ccagctgtga ctcctacgag    300

aagaagcccc ccaaggagtt cctggagagg ttcaagtccc tgctgcagaa gatgatccat    360

cagcacctgt cctccaggac ccacggctcc gaggactcca ttacatgccc ccctcccatg    420

agcgtggagc acgccgacat ctgggtgaag agctatagcc tctacagccg ggagaggtat    480

atctgtaaca gcggcttcaa gaggaaggcc ggcaccagca gcctcaccga gtgcgtgctg    540

aataaggcta ccaacgtggc tcactggaca acaccctctt taaagtgcat ccggggcggt    600

ggaggatccg gaggaggtgg ctccggcggc ggaggatctg atcccgccgg cctcttggac    660

ctgcggcagg gcatgtttgc gcagctggtg gcccaaaatg ttctgctgat cgatgggccc    720

ctgagctggt acagtgaccc aggcctggca ggcgtgtccc tgacgggggg cctgagctac    780

aaagaggaca cgaaggagct ggtggtggcc aaggctggag tctactatgt cttctttcaa    840

ctagagctgc ggcgcgtggt ggccggcgag ggctcaggct ccgtttcact tgcgctgcac    900

ctgcagccac tgcgctctgc tgctggggcc gccgccctgg ctttgaccgt ggacctgcca    960

cccgcctcct ccgaggctcg gaactcggcc ttcggtttcc agggccgctt gctgcacctg   1020

agtgccggcc agcgcctggg cgtccatctt cacactgagg ccagggcacg ccatgcctgg   1080

cagcttaccc agggcgccac agtcttggga ctcttccggg tgacccccga aatc         1134
```

```
<210> SEQ ID NO 274
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21CD137 sequence"

<400> SEQUENCE: 274

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190
```

```
Leu Thr Glu Cys Val Leu Asn Lys Ala Thr Asn Val Ala His Trp Thr
        195                 200                 205

Thr Pro Ser Leu Lys Cys Ile Arg Gly Gly Gly Gly Ser Gly Gly Gly
    210                 215                 220

Gly Ser Gly Gly Gly Gly Ser Asp Pro Ala Gly Leu Leu Asp Leu Arg
225                 230                 235                 240

Gln Gly Met Phe Ala Gln Leu Val Ala Gln Asn Val Leu Leu Ile Asp
                245                 250                 255

Gly Pro Leu Ser Trp Tyr Ser Asp Pro Gly Leu Ala Gly Val Ser Leu
            260                 265                 270

Thr Gly Gly Leu Ser Tyr Lys Glu Asp Thr Lys Glu Leu Val Val Ala
        275                 280                 285

Lys Ala Gly Val Tyr Tyr Val Phe Phe Gln Leu Glu Leu Arg Arg Val
    290                 295                 300

Val Ala Gly Glu Gly Ser Gly Ser Val Ser Leu Ala Leu His Leu Gln
305                 310                 315                 320

Pro Leu Arg Ser Ala Ala Gly Ala Ala Ala Leu Ala Leu Thr Val Asp
                325                 330                 335

Leu Pro Pro Ala Ser Ser Glu Ala Arg Asn Ser Ala Phe Gly Phe Gln
            340                 345                 350

Gly Arg Leu Leu His Leu Ser Ala Gly Gln Arg Leu Gly Val His Leu
        355                 360                 365

His Thr Glu Ala Arg Ala Arg His Ala Trp Gln Leu Thr Gln Gly Ala
    370                 375                 380

Thr Val Leu Gly Leu Phe Arg Val Thr Pro Glu Ile
385                 390                 395
```

```
<210> SEQ ID NO 275
<211> LENGTH: 1188
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21CD137 sequence"

<400> SEQUENCE: 275

atgaagtggg tgaccttcat cagcctgctg ttcctgttct ccagcgccta ctcccagggc      60

caggacaggc acatgatccg gatgaggcag ctcatcgaca tcgtcgacca gctgaagaac     120

tacgtgaacg acctggtgcc cgagtttctg cctgcccccg aggacgtgga gaccaactgc     180

gagtggtccg ccttctcctg ctttcagaag gcccagctga agtccgccaa caccggcaac     240

aacgagcgga tcatcaacgt gagcatcaag aagctgaagc ggaagcctcc ctccacaaac     300

gccggcagga ggcagaagca caggctgacc tgccccagct gtgactccta cgagaagaag     360

ccccccaagg agttcctgga gaggttcaag tccctgctgc agaagatgat ccatcagcac     420

ctgtcctcca ggacccacgg ctccgaggac tccattacat gccccccctcc catgagcgtg     480

gagcacgccg acatctgggt gaagagctat agcctctaca gccgggagag gtatatctgt     540

aacagcggct tcaagaggaa ggccggcacc agcagcctca ccgagtgcgt gctgaataag     600

gctaccaacg tggctcactg gacaacaccc tctttaaagt gcatccgggg cggtggagga     660

tccggaggag gtggctccgg cggcggagga tctgatcccg ccggcctctt ggacctgcgg     720

cagggcatgt ttgcgcagct ggtggcccaa aatgttctgc tgatcgatgg gccccctgagc     780

tggtacagtg acccaggcct ggcaggcgtg tccctgacgg ggggcctgag ctacaaagag     840
```

-continued

```
gacacgaagg agctggtggt ggccaaggct ggagtctact atgtcttctt tcaactagag    900
ctgcggcgcg tggtggccgg cgagggctca ggctccgttt cacttgcgct gcacctgcag    960
ccactgcgct ctgctgctgg ggccgccgcc ctggctttga ccgtggacct gccacccgcc   1020
tcctccgagg ctcggaactc ggccttcggt ttccagggcc gcttgctgca cctgagtgcc   1080
ggccagcgcc tgggcgtcca tcttcacact gaggccaggg cacgccatgc ctggcagctt   1140
acccagggcg ccacagtctt gggactcttc cgggtgaccc ccgaaatc               1188
```

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs21 sequence"

<400> SEQUENCE: 300

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240
```

```
Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Gln Gly Gln Asp Arg His Met Ile Arg Met Arg Gln Leu Ile Asp Ile
        355                 360                 365

Val Asp Gln Leu Lys Asn Tyr Val Asn Asp Leu Val Pro Glu Phe Leu
    370                 375                 380

Pro Ala Pro Glu Asp Val Glu Thr Asn Cys Glu Trp Ser Ala Phe Ser
385                 390                 395                 400

Cys Phe Gln Lys Ala Gln Leu Lys Ser Ala Asn Thr Gly Asn Asn Glu
                405                 410                 415

Arg Ile Ile Asn Val Ser Ile Lys Lys Leu Lys Arg Lys Pro Pro Ser
            420                 425                 430

Thr Asn Ala Gly Arg Arg Gln Lys His Arg Leu Thr Cys Pro Ser Cys
        435                 440                 445

Asp Ser Tyr Glu Lys Lys Pro Pro Lys Glu Phe Leu Glu Arg Phe Lys
    450                 455                 460

Ser Leu Leu Gln Lys Met Ile His Gln His Leu Ser Ser Arg Thr His
465                 470                 475                 480

Gly Ser Glu Asp Ser
                485
```

<210> SEQ ID NO 301
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs21 sequence"

<400> SEQUENCE: 301

```
atcccccccc atgtgcaaaa gagcgtgaac aacgatatga tcgtgaccga caacaacggc      60

gccgtgaagt ttccccagct ctgcaagttc tgcgatgtca ggttcagcac ctgcgataat     120

cagaagtcct gcatgtccaa ctgcagcatc acctccatct gcgagaagcc ccaagaagtg     180

tgcgtggccg tgtggcggaa aaatgacgag aacatcaccc tggagaccgt gtgtcacgac     240

cccaagctcc cttatcacga cttcattctg gaggacgctg cctcccccaa atgcatcatg     300

aaggagaaga agaagcccgg agagaccttc tttatgtgtt cctgtagcag cgacgagtgt     360

aacgacaaca tcatcttcag cgaagagtac aacaccagca accctgatgg aggtggcgga     420

tccggaggtg gaggttctgg tggaggtggg agtattcctc cccacgtgca gaagagcgtg     480

aataatgaca tgatcgtgac cgataacaat ggcgccgtga aatttcccca gctgtgcaaa     540
```

-continued

```
ttctgcgatg tgaggttttc cacctgcgac aaccagaagt cctgtatgag caactgctcc    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga cattacatgc ccccctccca tgagcgtgga gcacgccgac    900

atctgggtga agagctatag cctctacagc cgggagaggt atatctgtaa cagcggcttc    960

aagaggaagg ccggcaccag cagcctcacc gagtgcgtgc tgaataaggc taccaacgtg   1020

gctcactgga caacaccctc tttaaagtgc atccggcagg gccaggacag gcacatgatc   1080

cggatgaggc agctcatcga catcgtcgac cagctgaaga actacgtgaa cgacctggtg   1140

cccgagtttc tgcctgcccc cgaggacgtg gagaccaact gcgagtggtc cgccttctcc   1200

tgctttcaga aggcccagct gaagtccgcc aacaccggca acaacgagcg gatcatcaac   1260

gtgagcatca agaagctgaa gcggaagcct ccctccacaa acgccggcag gaggcagaag   1320

cacaggctga cctgccccag ctgtgactcc tacgagaaga agcccccca ggagttcctg    1380

gagaggttca agtccctgct gcagaagatg atccatcagc acctgtcctc caggacccac   1440

ggctccgagg actcc                                                    1455
```

<210> SEQ ID NO 302
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs21 sequence"

<400> SEQUENCE: 302

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190
```

```
Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Gln Gly Gln Asp Arg His Met Ile Arg Met Arg Gln Leu Ile
    370                 375                 380

Asp Ile Val Asp Gln Leu Lys Asn Tyr Val Asn Asp Leu Val Pro Glu
385                 390                 395                 400

Phe Leu Pro Ala Pro Glu Asp Val Glu Thr Asn Cys Glu Trp Ser Ala
                405                 410                 415

Phe Ser Cys Phe Gln Lys Ala Gln Leu Lys Ser Ala Asn Thr Gly Asn
            420                 425                 430

Asn Glu Arg Ile Ile Asn Val Ser Ile Lys Lys Leu Lys Arg Lys Pro
        435                 440                 445

Pro Ser Thr Asn Ala Gly Arg Arg Gln Lys His Arg Leu Thr Cys Pro
    450                 455                 460

Ser Cys Asp Ser Tyr Glu Lys Lys Pro Pro Lys Glu Phe Leu Glu Arg
465                 470                 475                 480

Phe Lys Ser Leu Leu Gln Lys Met Ile His Gln His Leu Ser Ser Arg
                485                 490                 495

Thr His Gly Ser Glu Asp Ser
            500
```

<210> SEQ ID NO 303
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs21 sequence"

<400> SEQUENCE: 303

```
atgaagtggg tgaccttcat cagcctgctg ttcctgttct ccagcgccta ctccatcccc      60

ccccatgtgc aaaagagcgt gaacaacgat atgatcgtga ccgacaacaa cggcgccgtg     120

aagtttcccc agctctgcaa gttctgcgat gtcaggttca gcacctgcga taatcagaag     180
```

-continued

```
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccggagagac cttctttatg tgttcctgta gcagcgacga gtgtaacgac    420
aacatcatct tcagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga agcctggcga gacctttttc    840
atgtgctcct gcagcagcga cgaatgcaac gacaatatca tctttagcga ggaatacaat    900
accagcaacc ccgacattac atgccccct cccatgagcg tggagcacgc cgacatctgg    960
gtgaagagct atagcctcta cagccgggag aggtatatct gtaacagcgg cttcaagagg   1020
aaggccggca ccagcagcct caccgagtgc gtgctgaata aggctaccaa cgtggctcac   1080
tggacaacac cctctttaaa gtgcatccgg cagggccagg acaggcacat gatccggatg   1140
aggcagctca tcgacatcgt cgaccagctg aagaactacg tgaacgacct ggtgcccgag   1200
tttctgcctg cccccgagga cgtggagacc aactgcgagt ggtccgcctt ctcctgcttt   1260
cagaaggccc agctgaagtc cgccaacacc ggcaacaacg agcggatcat caacgtgagc   1320
atcaagaagc tgaagcggaa gcctccctcc acaaacgccg gcaggaggca gaagcacagg   1380
ctgacctgcc ccagctgtga ctcctacgag aagaagcccc ccaaggagtt cctggagagg   1440
ttcaagtccc tgctgcagaa gatgatccat cagcacctgt cctccaggac ccacggctcc   1500
gaggactcc                                                           1509
```

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs16 sequence"

<400> SEQUENCE: 308

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Ser Glu Leu Thr Gln Asp Pro Ala Val Ser Val Ala Leu Gly Gln Thr
        355                 360                 365

Val Arg Ile Thr Cys Gln Gly Asp Ser Leu Arg Ser Tyr Tyr Ala Ser
    370                 375                 380
```

```
Trp Tyr Gln Gln Lys Pro Gly Gln Ala Pro Val Leu Val Ile Tyr Gly
385                 390                 395                 400

Lys Asn Asn Arg Pro Ser Gly Ile Pro Asp Arg Phe Ser Gly Ser Ser
                405                 410                 415

Ser Gly Asn Thr Ala Ser Leu Thr Ile Thr Gly Ala Gln Ala Glu Asp
            420                 425                 430

Glu Ala Asp Tyr Tyr Cys Asn Ser Arg Asp Ser Ser Gly Asn His Val
        435                 440                 445

Val Phe Gly Gly Gly Thr Lys Leu Thr Val Gly His Gly Gly Gly Gly
    450                 455                 460

Ser Gly Gly Gly Gly Ser Gly Gly Gly Gly Ser Glu Val Gln Leu Val
465                 470                 475                 480

Glu Ser Gly Gly Gly Val Val Arg Pro Gly Gly Ser Leu Arg Leu Ser
                485                 490                 495

Cys Ala Ala Ser Gly Phe Thr Phe Asp Asp Tyr Gly Met Ser Trp Val
            500                 505                 510

Arg Gln Ala Pro Gly Lys Gly Leu Glu Trp Val Ser Gly Ile Asn Trp
        515                 520                 525

Asn Gly Gly Ser Thr Gly Tyr Ala Asp Ser Val Lys Gly Arg Phe Thr
    530                 535                 540

Ile Ser Arg Asp Asn Ala Lys Asn Ser Leu Tyr Leu Gln Met Asn Ser
545                 550                 555                 560

Leu Arg Ala Glu Asp Thr Ala Val Tyr Tyr Cys Ala Arg Gly Arg Ser
                565                 570                 575

Leu Leu Phe Asp Tyr Trp Gly Gln Gly Thr Leu Val Thr Val Ser Arg
            580                 585                 590
```

<210> SEQ ID NO 309
<211> LENGTH: 1776
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs16 sequence"

<400> SEQUENCE: 309

```
atcccccccc atgtgcaaaa gagcgtgaac aacgatatga tcgtgaccga caacaacggc      60

gccgtgaagt ttccccagct ctgcaagttc tgcgatgtca ggttcagcac ctgcgataat     120

cagaagtcct gcatgtccaa ctgcagcatc acctccatct gcgagaagcc ccaagaagtg     180

tgcgtggccg tgtggcggaa aaatgacgag aacatcaccc tggagaccgt gtgtcacgac     240

cccaagctcc cttatcacga cttcattctg gaggacgctg cctcccccaa atgcatcatg     300

aaggagaaga agaagcccgg agagaccttc tttatgtgtt cctgtagcag cgacgagtgt     360

aacgacaaca tcatcttcag cgaagagtac aacaccagca accctgatgg aggtggcgga     420

tccggaggtg gaggttctgg tggaggtggg agtattcctc cccacgtgca gaagagcgtg     480

aataatgaca tgatcgtgac cgataacaat ggcgccgtga aatttcccca gctgtgcaaa     540

ttctgcgatg tgaggttttc cacctgcgac aaccagaagt cctgtatgag caactgctcc     600

atcacctcca tctgtgagaa gcctcaggag gtgtgcgtgg ctgtctggcg gaagaatgac     660

gagaatatca ccctggaaac cgtctgccac gatcccaagc tgccctacca cgatttcatc     720

ctggaagacg ccgccagccc taagtgcatc atgaaagaga aaaagaagcc tggcgagacc     780

tttttcatgt gctcctgcag cagcgacgaa tgcaacgaca atatcatctt tagcgaggaa     840
```

-continued

```
tacaatacca gcaaccccga cattacatgc ccccctccca tgagcgtgga gcacgccgac    900

atctgggtga agagctatag cctctacagc cgggagaggt atatctgtaa cagcggcttc    960

aagaggaagg ccggcaccag cagcctcacc gagtgcgtgc tgaataaggc taccaacgtg   1020

gctcactgga caacaccctc tttaaagtgc atccggtccg agctgaccca ggaccctgct   1080

gtgtccgtgg ctctgggcca gaccgtgagg atcacctgcc agggcgactc cctgaggtcc   1140

tactacgcct cctggtacca gcagaagccc ggccaggctc ctgtgctggt gatctacggc   1200

aagaacaaca ggccctccgg catccctgac aggttctccg gatcctcctc cggcaacacc   1260

gcctccctga ccatcacagg cgctcaggcc gaggacgagg ctgactacta ctgcaactcc   1320

agggactcct ccggcaacca tgtggtgttc ggcggcggca ccaagctgac cgtgggccat   1380

ggcggcggcg gctccggagg cggcggcagc ggcggaggag gatccgaggt gcagctggtg   1440

gagtccggag gaggagtggt gaggcctgga ggctccctga ggctgagctg tgctgcctcc   1500

ggcttcacct tcgacgacta cggcatgtcc tgggtgaggc aggctcctgg aaagggcctg   1560

gagtgggtgt ccggcatcaa ctggaacggc ggatccaccg gctacgccga ttccgtgaag   1620

ggcaggttca ccatcagcag ggacaacgcc aagaactccc tgtacctgca gatgaactcc   1680

ctgagggccg aggacaccgc cgtgtactac tgcgccaggg gcaggtccct gctgttcgac   1740

tactggggac agggcaccct ggtgaccgtg tccagg                             1776
```

<210> SEQ ID NO 310
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 310

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190
```

```
Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Ser Glu Leu Thr Gln Asp Pro Ala Val Ser Val Ala Leu Gly
    370                 375                 380

Gln Thr Val Arg Ile Thr Cys Gln Gly Asp Ser Leu Arg Ser Tyr Tyr
385                 390                 395                 400

Ala Ser Trp Tyr Gln Gln Lys Pro Gly Gln Ala Pro Val Leu Val Ile
                405                 410                 415

Tyr Gly Lys Asn Asn Arg Pro Ser Gly Ile Pro Asp Arg Phe Ser Gly
            420                 425                 430

Ser Ser Ser Gly Asn Thr Ala Ser Leu Thr Ile Thr Gly Ala Gln Ala
        435                 440                 445

Glu Asp Glu Ala Asp Tyr Tyr Cys Asn Ser Arg Asp Ser Ser Gly Asn
    450                 455                 460

His Val Val Phe Gly Gly Gly Thr Lys Leu Thr Val Gly His Gly Gly
465                 470                 475                 480

Gly Gly Ser Gly Gly Gly Gly Ser Gly Gly Gly Gly Ser Glu Val Gln
                485                 490                 495

Leu Val Glu Ser Gly Gly Gly Val Val Arg Pro Gly Gly Ser Leu Arg
            500                 505                 510

Leu Ser Cys Ala Ala Ser Gly Phe Thr Phe Asp Asp Tyr Gly Met Ser
        515                 520                 525

Trp Val Arg Gln Ala Pro Gly Lys Gly Leu Glu Trp Val Ser Gly Ile
    530                 535                 540

Asn Trp Asn Gly Gly Ser Thr Gly Tyr Ala Asp Ser Val Lys Gly Arg
545                 550                 555                 560

Phe Thr Ile Ser Arg Asp Asn Ala Lys Asn Ser Leu Tyr Leu Gln Met
                565                 570                 575

Asn Ser Leu Arg Ala Glu Asp Thr Ala Val Tyr Tyr Cys Ala Arg Gly
            580                 585                 590

Arg Ser Leu Leu Phe Asp Tyr Trp Gly Gln Gly Thr Leu Val Thr Val
        595                 600                 605
```

Ser Arg
610

<210> SEQ ID NO 311
<211> LENGTH: 1830
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs16 sequence"

<400> SEQUENCE: 311
atgaagtggg tgaccttcat cagcctgctg ttcctgttct ccagcgccta ctccatcccc 60
ccccatgtgc aaaagagcgt gaacaacgat atgatcgtga ccgacaacaa cggcgccgtg 120
aagtttcccc agctctgcaa gttctgcgat gtcaggttca gcacctgcga taatcagaag 180
tcctgcatgt ccaactgcag catcacctcc atctgcgaga agccccaaga agtgtgcgtg 240
gccgtgtggc ggaaaaatga cgagaacatc accctggaga ccgtgtgtca cgaccccaag 300 ctccccttatc acgacttcat tctggaggac gctgcctccc ccaaatgcat catgaaggag 360
aagaagaagc ccggagagac cttctttatg tgttcctgta gcagcgacga gtgtaacgac 420
aacatcatct tcagcgaaga gtacaacacc agcaaccctg atggaggtgg cggatccgga 480
ggtggaggtt ctggtggagg tgggagtatt cctccccacg tgcagaagag cgtgaataat 540
gacatgatcg tgaccgataa caatggcgcc gtgaaatttc cccagctgtg caaattctgc 600
gatgtgaggt tttccacctg cgacaaccag aagtcctgta tgagcaactg ctccatcacc 660
tccatctgtg agaagcctca ggaggtgtgc gtggctgtct ggcggaagaa tgacgagaat 720
atcaccctgg aaaccgtctg ccacgatccc aagctgccct accacgattt catcctggaa 780
gacgccgcca gccctaagtg catcatgaaa gagaaaaaga agcctggcga gacctttttc 840
atgtgctcct gcagcagcga cgaatgcaac gacaatatca tctttagcga ggaatacaat 900
accagcaacc ccgacattac atgccccccct cccatgagcg tggagcacgc cgacatctgg 960
gtgaagagct atagcctcta cagccgggag aggtatatct gtaacagcgg cttcaagagg 1020
aaggccggca ccagcagcct caccgagtgc gtgctgaata aggctaccaa cgtggctcac 1080
tggacaacac cctctttaaa gtgcatccgg tccgagctga cccaggaccc tgctgtgtcc 1140
gtggctctgg gccagaccgt gaggatcacc tgccagggcg actccctgag gtcctactac 1200
gcctcctggt accagcagaa gcccggccag gctcctgtgc tggtgatcta cggcaagaac 1260
aacaggccct ccggcatccc tgacaggttc tccggatcct cctccggcaa caccgcctcc 1320
ctgaccatca caggcgctca ggccgaggac gaggctgact actactgcaa ctccagggac 1380
tcctccggca accatgtggt gttcggcggc ggcaccaagc tgaccgtggg ccatggcggc 1440
ggcggctccg gaggcggcgg cagcggcgga ggaggatccg aggtgcagct ggtggagtcc 1500
ggaggaggag tggtgaggcc tggaggctcc ctgaggctga gctgtgctgc ctccggcttc 1560
accttcgacg actacggcat gtcctgggtg aggcaggctc ctggaaaggg cctggagtgg 1620
gtgtccggca tcaactggaa cggcggatcc accggctacg ccgattccgt gaagggcagg 1680
ttcaccatca gcagggacaa cgccaagaac tccctgtacc tgcagatgaa ctccctgagg 1740
gccgaggaca ccgccgtgta ctactgcgcc aggggcaggt ccctgctgtt cgactactgg 1800
ggacagggca ccctggtgac cgtgtccagg 1830

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316
<211> LENGTH: 551
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 316

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220
```

```
Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Gly Gly Gly Gly Ser Gly Gly Gly Gly Ser Gly Gly Gly Gly Ser Arg
        355                 360                 365

Glu Gly Pro Glu Leu Ser Pro Asp Asp Pro Ala Gly Leu Leu Asp Leu
    370                 375                 380

Arg Gln Gly Met Phe Ala Gln Leu Val Ala Gln Asn Val Leu Leu Ile
385                 390                 395                 400

Asp Gly Pro Leu Ser Trp Tyr Ser Asp Pro Gly Leu Ala Gly Val Ser
                405                 410                 415

Leu Thr Gly Gly Leu Ser Tyr Lys Glu Asp Thr Lys Glu Leu Val Val
            420                 425                 430

Ala Lys Ala Gly Val Tyr Tyr Val Phe Phe Gln Leu Glu Leu Arg Arg
        435                 440                 445

Val Val Ala Gly Glu Gly Ser Gly Ser Val Ser Leu Ala Leu His Leu
    450                 455                 460

Gln Pro Leu Arg Ser Ala Ala Gly Ala Ala Ala Leu Ala Leu Thr Val
465                 470                 475                 480

Asp Leu Pro Pro Ala Ser Ser Glu Ala Arg Asn Ser Ala Phe Gly Phe
                485                 490                 495

Gln Gly Arg Leu Leu His Leu Ser Ala Gly Gln Arg Leu Gly Val His
            500                 505                 510

Leu His Thr Glu Ala Arg Ala Arg His Ala Trp Gln Leu Thr Gln Gly
        515                 520                 525

Ala Thr Val Leu Gly Leu Phe Arg Val Thr Pro Glu Ile Pro Ala Gly
    530                 535                 540

Leu Pro Ser Pro Arg Ser Glu
545                 550
```

<210> SEQ ID NO 317
<211> LENGTH: 1653
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 317

```
atcccccccc atgtgcaaaa gagcgtgaac aacgatatga tcgtgaccga caacaacggc      60

gccgtgaagt ttccccagct ctgcaagttc tgcgatgtca ggttcagcac ctgcgataat     120
```

-continued

```
cagaagtcct gcatgtccaa ctgcagcatc acctccatct gcgagaagcc ccaagaagtg    180

tgcgtggccg tgtggcggaa aaatgacgag aacatcaccc tggagaccgt gtgtcacgac    240

cccaagctcc cttatcacga cttcattctg gaggacgctg cctcccccaa atgcatcatg    300

aaggagaaga agaagcccgg agagaccttc tttatgtgtt cctgtagcag cgacgagtgt    360

aacgacaaca tcatcttcag cgaagagtac aacaccagca accctgatgg aggtggcgga    420

tccggaggtg gaggttctgg tggaggtggg agtattcctc cccacgtgca gaagagcgtg    480

aataatgaca tgatcgtgac cgataacaat ggcgccgtga aatttcccca gctgtgcaaa    540

ttctgcgatg tgaggttttc cacctgcgac aaccagaagt cctgtatgag caactgctcc    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga cattacatgc ccccctccca tgagcgtgga gcacgccgac    900

atctgggtga agagctatag cctctacagc cgggagaggt atatctgtaa cagcggcttc    960

aagaggaagg ccggcaccag cagcctcacc gagtgcgtgc tgaataaggc taccaacgtg   1020

gctcactgga caacaccctc tttaaagtgc atccggggcg gtggaggatc cggaggaggt   1080

ggctccggcg gcggaggatc tcgcgagggt cccgagcttt cgcccgacga tcccgccggc   1140

ctcttggacc tgcggcaggg catgtttgcg cagctggtgg cccaaaatgt tctgctgatc   1200

gatgggcccc tgagctggta cagtgaccca ggcctggcag gcgtgtccct gacgggggc    1260

ctgagctaca aagaggacac gaaggagctg gtggtggcca aggctggagt ctactatgtc   1320

ttctttcaac tagagctgcg gcgcgtggtg gccggcgagg gctcaggctc cgtttcactt   1380

gcgctgcacc tgcagccact gcgctctgct gctggggccg ccgccctggc tttgaccgtg   1440

gacctgccac ccgcctcctc cgaggctcgg aactcggcct tcggtttcca gggccgcttg   1500

ctgcacctga gtgccggcca gcgcctgggc gtccatcttc acactgaggc cagggcacgc   1560

catgcctggc agcttaccca gggcgccaca gtcttgggac tcttccgggt gacccccgaa   1620

atcccagccg gactcccttc accgaggtcg gaa                                 1653
```

```
<210> SEQ ID NO 318
<211> LENGTH: 569
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs137 sequence"

<400> SEQUENCE: 318

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80
```

```
Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Gly Gly Gly Gly Ser Gly Gly Gly Gly Ser Gly Gly Gly Gly
    370                 375                 380

Ser Arg Glu Gly Pro Glu Leu Ser Pro Asp Asp Pro Ala Gly Leu Leu
385                 390                 395                 400

Asp Leu Arg Gln Gly Met Phe Ala Gln Leu Val Ala Gln Asn Val Leu
                405                 410                 415

Leu Ile Asp Gly Pro Leu Ser Trp Tyr Ser Asp Pro Gly Leu Ala Gly
            420                 425                 430

Val Ser Leu Thr Gly Gly Leu Ser Tyr Lys Glu Asp Thr Lys Glu Leu
        435                 440                 445

Val Val Ala Lys Ala Gly Val Tyr Tyr Val Phe Phe Gln Leu Glu Leu
    450                 455                 460

Arg Arg Val Val Ala Gly Glu Gly Ser Gly Ser Val Ser Leu Ala Leu
465                 470                 475                 480

His Leu Gln Pro Leu Arg Ser Ala Ala Gly Ala Ala Ala Leu Ala Leu
                485                 490                 495
```

```
Thr Val Asp Leu Pro Pro Ala Ser Ser Glu Ala Arg Asn Ser Ala Phe
            500                 505                 510

Gly Phe Gln Gly Arg Leu Leu His Leu Ser Ala Gly Gln Arg Leu Gly
        515                 520                 525

Val His Leu His Thr Glu Ala Arg Ala Arg His Ala Trp Gln Leu Thr
    530                 535                 540

Gln Gly Ala Thr Val Leu Gly Leu Phe Arg Val Thr Pro Glu Ile Pro
545                 550                 555                 560

Ala Gly Leu Pro Ser Pro Arg Ser Glu
                565


<210> SEQ ID NO 319
<211> LENGTH: 1707
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs137 sequence"

<400> SEQUENCE: 319

atgaagtggg tgaccttcat cagcctgctg ttcctgttct ccagcgccta ctccatcccc     60

ccccatgtgc aaaagagcgt gaacaacgat atgatcgtga ccgacaacaa cggcgccgtg    120

aagtttcccc agctctgcaa gttctgcgat gtcaggttca gcacctgcga taatcagaag    180

tcctgcatgt ccaactgcag catcacctcc atctgcgaga agccccaaga agtgtgcgtg    240

gccgtgtggc ggaaaaatga cgagaacatc accctggaga ccgtgtgtca cgaccccaag    300

ctcccttatc acgacttcat tctggaggac gctgcctccc ccaaatgcat catgaaggag    360

aagaagaagc ccggagagac cttctttatg tgttcctgta gcagcgacga gtgtaacgac    420

aacatcatct tcagcgaaga gtacaacacc agcaaccctg atggaggtgg cggatccgga    480

ggtggaggtt ctggtggagg tgggagtatt cctccccacg tgcagaagag cgtgaataat    540

gacatgatcg tgaccgataa caatggcgcc gtgaaatttc cccagctgtg caaattctgc    600

gatgtgaggt tttccacctg cgacaaccag aagtcctgta tgagcaactg ctccatcacc    660

tccatctgtg agaagcctca ggaggtgtgc gtggctgtct ggcggaagaa tgacgagaat    720

atcaccctgg aaaccgtctg ccacgatccc aagctgccct accacgattt catcctggaa    780

gacgccgcca gccctaagtg catcatgaaa gagaaaaaga agcctggcga gacctttttc    840

atgtgctcct gcagcagcga cgaatgcaac gacaatatca tctttagcga ggaatacaat    900

accagcaacc ccgacattac atgccccct cccatgagcg tggagcacgc cgacatctgg    960

gtgaagagct atagcctcta cagccgggag aggtatatct gtaacagcgg cttcaagagg   1020

aaggccggca ccagcagcct caccgagtgc gtgctgaata aggctaccaa cgtggctcac   1080

tggacaacac cctctttaaa gtgcatccgg ggcggtggag gatccggagg aggtggctcc   1140

ggcggcggag gatctcgcga gggtcccgag ctttcgcccg acgatcccgc cggcctcttg   1200

gacctgcggc agggcatgtt tgcgcagctg gtggcccaaa atgttctgct gatcgatggg   1260

cccctgagct ggtacagtga cccaggcctg gcaggcgtgt ccctgacggg gggcctgagc   1320

tacaaagagg acacgaagga gctggtggtg gccaaggctg gagtctacta tgtcttcttt   1380

caactagagc tgcggcgcgt ggtggccggc gagggctcag gctccgtttc acttgcgctg   1440

cacctgcagc cactgcgctc tgctgctggg gccgccgccc tggctttgac cgtggacctg   1500

ccacccgcct cctccgaggc tcggaactcg gccttcggtt tccagggccg cttgctgcac   1560
```

-continued

```
ctgagtgccg gccagcgcct gggcgtccat cttcacactg aggccagggc acgccatgcc   1620

tggcagctta cccagggcgc cacagtcttg ggactcttcc gggtgacccc cgaaatccca   1680

gccggactcc cttcaccgag gtcggaa                                       1707
```

<210> SEQ ID NO 320
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 18s sequence"

<400> SEQUENCE: 320

```
atgaagtggg tcacatttat ctctttactg ttcctcttct ccagcgccta cagctacttc     60

ggcaaactgg aatccaagct gagcgtgatc cggaatttaa acgaccaagt tctgtttatc    120

gatcaaggta accggcctct gttcgaggac atgaccgact ccgattgccg ggacaatgcc    180

ccccggacca tcttcattat ctccatgtac aaggacagcc agccccgggg catggctgtg    240

acaattagcg tgaagtgtga gaaaatcagc actttatctt gtgagaacaa gatcatctcc    300

tttaaggaaa tgaacccccc cgataacatc aaggacacca agtccgatat catcttcttc    360

cagcggtccg tgcccggtca cgataacaag atgcagttcg aatcctcctc ctacgagggc    420

tactttttag cttgtgaaaa ggagagggat ttattcaagc tgatcctcaa gaaggaggac    480

gagctgggcg atcgttccat catgttcacc gtccaaaacg aggatattac atgccccccct    540

cccatgagcg tggagcacgc cgacatctgg gtgaagagct atagcctcta cagccgggag    600

aggtatatct gtaacagcgg cttcaagagg aaggccggca ccagcagcct caccgagtgc    660

gtgctgaata aggctaccaa cgtggctcac tggacaacac cctctttaaa gtgcatccgg    720
```

<210> SEQ ID NO 321
<211> LENGTH: 2607
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 12t15 sequence"

<400> SEQUENCE: 321

```
atgaaatggg tgacctttat ttctttactg ttcctcttta gcagcgccta ctccatttgg     60

gaactgaaga aggacgtcta cgtggtcgaa ctggactggt atcccgatgc tcccggcgaa    120

atggtggtgc tcacttgtga cacccccgaa gaagacggca tcacttggac cctcgatcag    180

agcagcgagg tgctgggctc cggaaagacc ctcacaatcc aagttaagga gttcggagac    240

gctggccaat acacatgcca caagggaggc gaggtgctca gccattcctt attattatta    300

cacaagaagg aagacggaat ctggtccacc gacattttaa aagatcagaa ggagcccaag    360

aataagacct ttttaaggtg tgaggccaaa aactacagcg gtcgtttcac ttgttggtgg    420

ctgaccacca tttccaccga tttaaccttc tccgtgaaaa gcagccgggg aagctccgac    480

cctcaaggtg tgacatgtgg agccgctacc ctcagcgctg agagggttcg tggcgataac    540

aaggaatacg agtacagcgt ggagtgccaa gaagatagcg cttgtcccgc tgccgaagaa    600

tctttaccca ttgaggtgat ggtggacgcc gtgcacaaac tcaagtacga gaactacacc    660

tcctccttct ttatccggga catcattaag cccgatcctc ctaagaattt acagctgaag    720

cctctcaaaa atagccggca agttgaggtc tcttgggaat atcccgacac ttggagcaca    780
```

ccccacagct acttctcttt aaccttttgt gtgcaagttc aaggtaaaag caagcgggag 840
aagaaagacc gggtgtttac cgacaaaacc agcgccaccg tcatctgtcg gaagaacgcc 900
tccatcagcg tgagggctca agatcgttat tactccagca gctggtccga gtgggccagc 960
gtgccttgtt ccggcggtgg aggatccgga ggaggtggct ccggcggcgg aggatctcgt 1020
aacctccccg tggctacccc cgatcccgga atgttccctt gtttacacca cagccagaat 1080
ttactgaggg ccgtgagcaa catgctgcag aaagctaggc agactttaga attttaccct 1140
tgcaccagcg aggagatcga ccatgaagat atcaccaagg acaagacatc caccgtggag 1200
gcttgtttac ctctggagct gacaaagaac gagtcttgtc tcaactctcg tgaaaccagc 1260
ttcatcacaa atggctcttg tttagcttcc cggaagacct cctttatgat ggctttatgc 1320
ctcagctcca tctacgagga tttaaagatg taccaagtgg agttcaagac catgaacgcc 1380
aagctgctca tggaccctaa acggcagatc tttttagacc agaacatgct ggctgtgatt 1440
gatgagctga tgcaagcttt aaacttcaac tccgagaccg tccctcagaa gtcctccctc 1500
gaggagcccg atttttacaa gacaaagatc aaactgtgca ttttactcca cgcctttagg 1560
atccgggccg tgaccattga ccgggtcatg agctatttaa acgccagcag cggcacaacc 1620
aacacagtcg ctgcctataa cctcacttgg aagagcacca acttcaaaac catcctcgaa 1680
tgggaaccca aacccgttaa ccaagtttac accgtgcaga tcagcaccaa gtccggcgac 1740
tggaagtcca aatgtttcta taccaccgac accgagtgcg atctcaccga tgagatcgtg 1800
aaagatgtga aacagaccta cctcgcccgg gtgtttagct accccgccgg caatgtggag 1860
agcactggtt ccgctggcga gcctttatac gagaacagcc ccgaatttac cccttacctc 1920
gagaccaatt taggacagcc caccatccaa agctttgagc aagttggcac aaaggtgaat 1980
gtgacagtgg aggacgagcg gactttagtg cggcggaaca acacctttct cagcctccgg 2040
gatgtgttcg gcaaagattt aatctacaca ctgtattact ggaagtcctc ttcctccggc 2100
aagaagacag ctaaaaccaa cacaaacgag tttttaatcg acgtggataa aggcgaaaac 2160
tactgtttca gcgtgcaagc tgtgatcccc tcccggaccg tgaataggaa aagcaccgat 2220
agccccgttg agtgcatggg ccaagaaaag ggcgagttcc gggagaactg ggtgaacgtc 2280
atcagcgatt taaagaagat cgaagattta attcagtcca tgcatatcga cgccacttta 2340
tacacagaat ccgacgtgca cccctcttgt aaggtgaccg ccatgaaatg ttttttactg 2400
gagctgcaag ttatctcttt agagagcgga gacgctagca tccacgacac cgtggagaat 2460
ttaatcattt tagccaataa ctctttatcc agcaacggca acgtgacaga gtccggctgc 2520
aaggagtgcg aagagctgga ggagaagaac atcaaggagt ttctgcaatc ctttgtgcac 2580
attgtccaga tgttcatcaa tacctcc 2607

<210> SEQ ID NO 322
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 18s sequence"

<400> SEQUENCE: 322

Met Lys Trp Val Thr Phe Ile Ser Leu Leu Phe Leu Phe Ser Ser Ala
1 5 10 15

Tyr Ser Tyr Phe Gly Lys Leu Glu Ser Lys Leu Ser Val Ile Arg Asn

```
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ile
                165                 170                 175

Thr Cys Pro Pro Pro Met Ser Val Glu His Ala Asp Ile Trp Val Lys
            180                 185                 190

Ser Tyr Ser Leu Tyr Ser Arg Glu Arg Tyr Ile Cys Asn Ser Gly Phe
        195                 200                 205

Lys Arg Lys Ala Gly Thr Ser Ser Leu Thr Glu Cys Val Leu Asn Lys
    210                 215                 220

Ala Thr Asn Val Ala His Trp Thr Thr Pro Ser Leu Lys Cys Ile Arg
225                 230                 235                 240


<210> SEQ ID NO 323
<211> LENGTH: 869
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 12t15 sequence"

<400> SEQUENCE: 323

Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140
```

```
Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Gly Ser Gly Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ser Gly Thr Thr Asn Thr Val Ala
    530                 535                 540

Ala Tyr Asn Leu Thr Trp Lys Ser Thr Asn Phe Lys Thr Ile Leu Glu
545                 550                 555                 560
```

```
Trp Glu Pro Lys Pro Val Asn Gln Val Tyr Thr Val Gln Ile Ser Thr
                565                 570                 575

Lys Ser Gly Asp Trp Lys Ser Lys Cys Phe Tyr Thr Thr Asp Thr Glu
            580                 585                 590

Cys Asp Leu Thr Asp Glu Ile Val Lys Asp Val Lys Gln Thr Tyr Leu
        595                 600                 605

Ala Arg Val Phe Ser Tyr Pro Ala Gly Asn Val Glu Ser Thr Gly Ser
    610                 615                 620

Ala Gly Glu Pro Leu Tyr Glu Asn Ser Pro Glu Phe Thr Pro Tyr Leu
625                 630                 635                 640

Glu Thr Asn Leu Gly Gln Pro Thr Ile Gln Ser Phe Glu Gln Val Gly
                645                 650                 655

Thr Lys Val Asn Val Thr Val Glu Asp Glu Arg Thr Leu Val Arg Arg
            660                 665                 670

Asn Asn Thr Phe Leu Ser Leu Arg Asp Val Phe Gly Lys Asp Leu Ile
        675                 680                 685

Tyr Thr Leu Tyr Tyr Trp Lys Ser Ser Ser Ser Gly Lys Lys Thr Ala
    690                 695                 700

Lys Thr Asn Thr Asn Glu Phe Leu Ile Asp Val Asp Lys Gly Glu Asn
705                 710                 715                 720

Tyr Cys Phe Ser Val Gln Ala Val Ile Pro Ser Arg Thr Val Asn Arg
                725                 730                 735

Lys Ser Thr Asp Ser Pro Val Glu Cys Met Gly Gln Glu Lys Gly Glu
            740                 745                 750

Phe Arg Glu Asn Trp Val Asn Val Ile Ser Asp Leu Lys Lys Ile Glu
        755                 760                 765

Asp Leu Ile Gln Ser Met His Ile Asp Ala Thr Leu Tyr Thr Glu Ser
    770                 775                 780

Asp Val His Pro Ser Cys Lys Val Thr Ala Met Lys Cys Phe Leu Leu
785                 790                 795                 800

Glu Leu Gln Val Ile Ser Leu Glu Ser Gly Asp Ala Ser Ile His Asp
                805                 810                 815

Thr Val Glu Asn Leu Ile Ile Leu Ala Asn Asn Ser Leu Ser Ser Asn
            820                 825                 830

Gly Asn Val Thr Glu Ser Gly Cys Lys Glu Cys Glu Glu Leu Glu Glu
        835                 840                 845

Lys Asn Ile Lys Glu Phe Leu Gln Ser Phe Val His Ile Val Gln Met
    850                 855                 860

Phe Ile Asn Thr Ser
865
```

<210> SEQ ID NO 324
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15 sequence"

<400> SEQUENCE: 324

```
atgaagtggg tgaccttcat cagcctgctg ttcctgttct ccagcgccta ctcccagggc      60

caggacaggc acatgatccg gatgaggcag ctcatcgaca tcgtcgacca gctgaagaac     120

tacgtgaacg acctggtgcc cgagtttctg cctgcccccg aggacgtgga gaccaactgc     180

gagtggtccg ccttctcctg ctttcagaag gcccagctga agtccgccaa caccggcaac     240
```

```
aacgagcgga tcatcaacgt gagcatcaag aagctgaagc ggaagcctcc ctccacaaac    300

gccggcagga ggcagaagca caggctgacc tgccccagct gtgactccta cgagaagaag    360

ccccccaagg agttcctgga gaggttcaag tccctgctgc agaagatgat ccatcagcac    420

ctgtcctcca ggacccacgg ctccgaggac tcctccggca ccaccaatac cgtggccgct    480

tataacctca catggaagag caccaacttc gcgacagctc tggaatggga acccaagccc    540

gtcaatcaag tttacaccgt gcagatctcc accaaatccg gagactggaa gagcaagtgc    600

ttctacacaa cagacaccga gtgtgcttta accgacgaaa tcgtcaagga cgtcaagcaa    660

acctatctgg ctcgggtctt ttcctacccc gctggcaatg tcgagtccac cggctccgct    720

ggcgagcctc tctacgagaa ttcccccgaa ttcacccctt atttagagac caatttaggc    780

cagcctacca tccagagctt cgagcaagtt ggcaccaagg tgaacgtcac cgtcgaggat    840

gaaaggactt tagtggcgcg gaataacaca gctttatccc tccgggatgt gttcggcaaa    900

gacctcatct acacactgta ctattggaag tccagctcct ccggcaaaaa gaccgctaag    960

accaacacca acgagttttt aattgacgtg gacaaaggcg agaactactg cttcagcgtg   1020

caagccgtga tcccttctcg taccgtcaac cggaagagca cagattcccc cgttgagtgc   1080

atgggccaag aaaagggcga gttccgggag aactgggtga acgtcatcag cgatttaaag   1140

aagatcgaag atttaattca gtccatgcat atcgacgcca ctttatacac agaatccgac   1200

gtgcacccct cttgtaaggt gaccgccatg aaatgttttt tactggagct gcaagttatc   1260

tctttagaga gcggagacgc tagcatccac gacaccgtgg agaatttaat cattttagcc   1320

aataactctt tatccagcaa cggcaacgtg acagagtccg gctgcaagga gtgcgaagag   1380

ctggaggaga agaacatcaa ggagtttctg caatcctttg tgcacattgt ccagatgttc   1440

atcaatacct cc                                                        1452
```

<210> SEQ ID NO 325
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15 sequence"

<400> SEQUENCE: 325

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125
```

```
Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Ala Thr Ala Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Ala Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Ala Arg Asn
        275                 280                 285

Asn Thr Ala Leu Ser Leu Arg Asp Val Phe Gly Lys Asp Leu Ile Tyr
    290                 295                 300

Thr Leu Tyr Tyr Trp Lys Ser Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
465                 470                 475                 480

Ile Asn Thr Ser
```

<210> SEQ ID NO 326
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence: Synthetic CD28tCD3 sequence"

<400> SEQUENCE: 326
atgaaatggg tcaccttcat ctctttactg tttttattta gcagcgccta cagcgtgcag 60
ctgcagcagt ccggacccga actggtcaag cccggtgcct ccgtgaaaat gtcttgtaag 120
gcttctggct acacctttac ctcctacgtc atccaatggg tgaagcagaa gcccggtcaa 180
ggtctcgagt ggatcggcag catcaatccc tacaacgatt acaccaagta taacgaaaag 240
tttaagggca aggccactct gacaagcgac aagagctcca ttaccgccta catggagttt 300
tcctctttaa cttctgagga ctccgcttta tactattgcg ctcgttgggg cgatggcaat 360
tattggggcc ggggaactac tttaacagtg agctccggcg gcggcggaag cggaggtgga 420
ggatctggcg gtggaggcag cgacatcgag atgacacagt cccccgctat catgagcgcc 480
tctttaggag aacgtgtgac catgacttgt acagcttcct ccagcgtgag cagctcctat 540
ttccactggt accagcagaa acccggctcc tcccctaaac tgtgtatcta ctccacaagc 600
aatttagcta gcggcgtgcc tcctcgtttt agcggctccg gcagcacctc ttactcttta 660
accattagct ctatggaggc cgaagatgcc gccacatact tttgccatca gtaccaccgg 720
tcccctacct ttggcggagg cacaaagctg gagaccaagc ggagcggcac caccaacaca 780
gtggccgcct acaatctgac ttggaaatcc accaacttca agaccatcct cgagtgggag 840
cccaagcccg ttaatcaagt ttataccgtg cagatttcca ccaagagcgg cgactggaaa 900
tccaagtgct tctataccac agacaccgag tgcgatctca ccgacgagat cgtcaaagac 960
gtgaagcaga catatttagc tagggtgttc tcctaccccg ctggaaacgt ggagagcacc 1020
ggatccgctg gagagccttt atacgagaac tcccccgaat tcacccccta tctggaaacc 1080
aatttaggcc agcccaccat ccagagcttc gaacaagttg gcacaaaggt gaacgtcacc 1140
gtcgaagatg agaggacttt agtgcggagg aacaatacat tttatccttt acgtgacgtc 1200
ttcggcaagg atttaatcta cacactgtat tactggaagt ctagctcctc cggcaagaag 1260
accgccaaga ccaataccaa cgaattttta attgacgtgg acaagggcga gaactactgc 1320
ttctccgtgc aagctgtgat cccctcccgg acagtgaacc ggaagtccac cgactccccc 1380
gtggagtgca tgggccaaga gaagggagag tttcgtgagc agatcgtgct gacccagtcc 1440
cccgctatta tgagcgctag ccccggtgaa aaggtgacta tgacatgcag cgccagctct 1500
tccgtgagct acatgaactg gtatcagcag aagtccggca ccagccctaa aaggtggatc 1560
tacgacacca gcaagctggc cagcggcgtc cccgctcact ttcggggctc cggctccgga 1620
acaagctact ctctgaccat cagcggcatg gaagccgagg atgccgctac ctattactgt 1680
cagcagtgga gctccaaccc cttcaccttt ggatccggca ccaagctcga gattaatcgt 1740
ggaggcggag gtagcggagg aggcggatcc ggcggtggag gtagccaagt tcagctccag 1800
caaagcggcg ccgaactcgc tcggcccggc gcttccgtga agatgtcttg taaggcctcc 1860
ggctatacct tcacccggta cacaatgcac tgggtcaagc aacggcccgg tcaaggttta 1920
gagtggattg gctatatcaa cccctcccgg ggctatacca actacaacca gaagttcaag 1980
gacaaagcca ccctcaccac cgacaagtcc agcagcaccg cttacatgca gctgagctct 2040
ttaacatccg aggattccgc cgtgtactac tgcgctcggt actacgacga tcattactgc 2100
ctcgattact ggggccaagg taccacctta acagtctcct cc 2142

<210> SEQ ID NO 327
<211> LENGTH: 714
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic CD28tCD3 sequence"

<400> SEQUENCE: 327

```
Met Lys Trp Val Thr Phe Ile Ser Leu Leu Phe Leu Phe Ser Ser Ala
1               5                   10                  15

Tyr Ser Val Gln Leu Gln Gln Ser Gly Pro Glu Leu Val Lys Pro Gly
            20                  25                  30

Ala Ser Val Lys Met Ser Cys Lys Ala Ser Gly Tyr Thr Phe Thr Ser
        35                  40                  45

Tyr Val Ile Gln Trp Val Lys Gln Lys Pro Gly Gln Gly Leu Glu Trp
    50                  55                  60

Ile Gly Ser Ile Asn Pro Tyr Asn Asp Tyr Thr Lys Tyr Asn Glu Lys
65                  70                  75                  80

Phe Lys Gly Lys Ala Thr Leu Thr Ser Asp Lys Ser Ser Ile Thr Ala
                85                  90                  95

Tyr Met Glu Phe Ser Ser Leu Thr Ser Glu Asp Ser Ala Leu Tyr Tyr
            100                 105                 110

Cys Ala Arg Trp Gly Asp Gly Asn Tyr Trp Gly Arg Gly Thr Thr Leu
        115                 120                 125

Thr Val Ser Ser Gly Gly Gly Gly Ser Gly Gly Gly Gly Ser Gly Gly
    130                 135                 140

Gly Gly Ser Asp Ile Glu Met Thr Gln Ser Pro Ala Ile Met Ser Ala
145                 150                 155                 160

Ser Leu Gly Glu Arg Val Thr Met Thr Cys Thr Ala Ser Ser Ser Val
                165                 170                 175

Ser Ser Ser Tyr Phe His Trp Tyr Gln Gln Lys Pro Gly Ser Ser Pro
            180                 185                 190

Lys Leu Cys Ile Tyr Ser Thr Ser Asn Leu Ala Ser Gly Val Pro Pro
        195                 200                 205

Arg Phe Ser Gly Ser Gly Ser Thr Ser Tyr Ser Leu Thr Ile Ser Ser
    210                 215                 220

Met Glu Ala Glu Asp Ala Ala Thr Tyr Phe Cys His Gln Tyr His Arg
225                 230                 235                 240

Ser Pro Thr Phe Gly Gly Gly Thr Lys Leu Glu Thr Lys Arg Ser Gly
                245                 250                 255

Thr Thr Asn Thr Val Ala Ala Tyr Asn Leu Thr Trp Lys Ser Thr Asn
            260                 265                 270

Phe Lys Thr Ile Leu Glu Trp Glu Pro Lys Pro Val Asn Gln Val Tyr
        275                 280                 285

Thr Val Gln Ile Ser Thr Lys Ser Gly Asp Trp Lys Ser Lys Cys Phe
    290                 295                 300

Tyr Thr Thr Asp Thr Glu Cys Asp Leu Thr Asp Glu Ile Val Lys Asp
305                 310                 315                 320

Val Lys Gln Thr Tyr Leu Ala Arg Val Phe Ser Tyr Pro Ala Gly Asn
                325                 330                 335

Val Glu Ser Thr Gly Ser Ala Gly Glu Pro Leu Tyr Glu Asn Ser Pro
            340                 345                 350

Glu Phe Thr Pro Tyr Leu Glu Thr Asn Leu Gly Gln Pro Thr Ile Gln
        355                 360                 365

Ser Phe Glu Gln Val Gly Thr Lys Val Asn Val Thr Val Glu Asp Glu
    370                 375                 380

Arg Thr Leu Val Arg Arg Asn Asn Thr Phe Leu Ser Leu Arg Asp Val
```

```
385                 390                 395                 400

Phe Gly Lys Asp Leu Ile Tyr Thr Leu Tyr Tyr Trp Lys Ser Ser Ser
                405                 410                 415

Ser Gly Lys Lys Thr Ala Lys Thr Asn Thr Asn Glu Phe Leu Ile Asp
            420                 425                 430

Val Asp Lys Gly Glu Asn Tyr Cys Phe Ser Val Gln Ala Val Ile Pro
        435                 440                 445

Ser Arg Thr Val Asn Arg Lys Ser Thr Asp Ser Pro Val Glu Cys Met
    450                 455                 460

Gly Gln Glu Lys Gly Glu Phe Arg Glu Gln Ile Val Leu Thr Gln Ser
465                 470                 475                 480

Pro Ala Ile Met Ser Ala Ser Pro Gly Glu Lys Val Thr Met Thr Cys
                485                 490                 495

Ser Ala Ser Ser Ser Val Ser Tyr Met Asn Trp Tyr Gln Gln Lys Ser
            500                 505                 510

Gly Thr Ser Pro Lys Arg Trp Ile Tyr Asp Thr Ser Lys Leu Ala Ser
        515                 520                 525

Gly Val Pro Ala His Phe Arg Gly Ser Gly Ser Gly Thr Ser Tyr Ser
    530                 535                 540

Leu Thr Ile Ser Gly Met Glu Ala Glu Asp Ala Ala Thr Tyr Tyr Cys
545                 550                 555                 560

Gln Gln Trp Ser Ser Asn Pro Phe Thr Phe Gly Ser Gly Thr Lys Leu
                565                 570                 575

Glu Ile Asn Arg Gly Gly Gly Gly Ser Gly Gly Gly Gly Ser Gly Gly
            580                 585                 590

Gly Gly Ser Gln Val Gln Leu Gln Gln Ser Gly Ala Glu Leu Ala Arg
        595                 600                 605

Pro Gly Ala Ser Val Lys Met Ser Cys Lys Ala Ser Gly Tyr Thr Phe
    610                 615                 620

Thr Arg Tyr Thr Met His Trp Val Lys Gln Arg Pro Gly Gln Gly Leu
625                 630                 635                 640

Glu Trp Ile Gly Tyr Ile Asn Pro Ser Arg Gly Tyr Thr Asn Tyr Asn
                645                 650                 655

Gln Lys Phe Lys Asp Lys Ala Thr Leu Thr Thr Asp Lys Ser Ser Ser
            660                 665                 670

Thr Ala Tyr Met Gln Leu Ser Ser Leu Thr Ser Glu Asp Ser Ala Val
        675                 680                 685

Tyr Tyr Cys Ala Arg Tyr Tyr Asp Asp His Tyr Cys Leu Asp Tyr Trp
    690                 695                 700

Gly Gln Gly Thr Thr Leu Thr Val Ser Ser
705                 710


<210> SEQ ID NO 328
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Signal sequence"

<400> SEQUENCE: 328

Met Gly Val Lys Val Leu Phe Ala Leu Ile Cys Ile Ala Val Ala Glu
1               5                   10                  15

Ala
```

<210> SEQ ID NO 329
<211> LENGTH: 454
<212> TYPE: PRT
<213> ORGANISM: Homo sapiens
<220> FEATURE:
<221> NAME/KEY: source
<223> OTHER INFORMATION: /note="Myc"

<400> SEQUENCE: 329

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365
```

```
Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450
```

<210> SEQ ID NO 330
<211> LENGTH: 1365
<212> TYPE: DNA
<213> ORGANISM: Homo sapiens
<220> FEATURE:
<221> NAME/KEY: source
<223> OTHER INFORMATION: /note="Myc"

<400> SEQUENCE: 330

```
ctggattttt ttcgggtagt ggaaaaccag cagcctcccg cgacgatgcc cctcaacgtt     60
agcttcacca acaggaacta tgacctcgac tacgactcgg tgcagccgta tttctactgc    120
gacgaggagg agaacttcta ccagcagcag cagcagagcg agctgcagcc cccggcgccc    180
agcgaggata tctggaagaa attcgagctg ctgcccaccc cgcccctgtc ccctagccgc    240
cgctccgggc tctgctcgcc ctcctacgtt gcggtcacac ccttctccct tcggggagac    300
aacgacggcg gtggcgggag cttctccacg gccgaccagc tggagatggt gaccgagctg    360
ctgggaggag acatggtgaa ccagagtttc atctgcgacc cggacgacga gaccttcatc    420
aaaaacatca tcatccagga ctgtatgtgg agcggcttct cggccgccgc caagctcgtc    480
tcagagaagc tggcctccta ccaggctgcg cgcaaagaca gcggcagccc gaaccccgcc    540
cgcggccaca gcgtctgctc cacctccagc ttgtacctgc aggatctgag cgccgccgcc    600
tcagagtgca tcgacccctc ggtggtcttc ccctaccctc tcaacgacag cagctcgccc    660
aagtcctgcg cctcgcaaga ctccagcgcc ttctctccgt cctcggattc tctgctctcc    720
tcgacggagt cctccccgca gggcagcccc gagcccctgg tgctccatga ggagacaccg    780
cccaccacca gcagcgactc tgaggaggaa caagaagatg aggaagaaat cgatgttgtt    840
tctgtggaaa agaggcaggc tcctggcaaa aggtcagagt ctggatcacc ttctgctgga    900
ggccacagca aacctcctca cagcccactg gtcctcaaga ggtgccacgt ctccacacat    960
cagcacaact acgcagcgcc tccctccact cggaaggact atcctgctgc caagagggtc   1020
aagttggaca gtgtcagagt cctgagacag atcagcaaca accgaaaatg caccagcccc   1080
aggtcctcgg acaccgagga gaatgtcaag aggcgaacac acaacgtctt ggagcgccag   1140
aggaggaacg agctaaaacg gagctttttt gccctgcgtg accagatccc ggagttggaa   1200
aacaatgaaa aggcccccaa ggtagttatc cttaaaaaag ccacagcata catcctgtcc   1260
gtccaagcag aggagcaaaa gctcatttct gaagaggact tgttgcggaa acgacgagaa   1320
cagttgaaac acaaacttga acagctacgg aactcttgtg cgtaa                   1365
```

<210> SEQ ID NO 331
<211> LENGTH: 1245

<212> TYPE: DNA
<213> ORGANISM: Homo sapiens
<220> FEATURE:
<221> NAME/KEY: source
<223> OTHER INFORMATION: /note="21s137L"

<400> SEQUENCE: 331

```
atgaagtggg tgaccttcat cagcctgctg ttcctgttct ccagcgccta ctcccagggc     60

caggacaggc acatgatccg gatgaggcag ctcatcgaca tcgtcgacca gctgaagaac    120

tacgtgaacg acctggtgcc cgagtttctg cctgcccccg aggacgtgga gaccaactgc    180

gagtggtccg ccttctcctg ctttcagaag gcccagctga agtccgccaa caccggcaac    240

aacgagcgga tcatcaacgt gagcatcaag aagctgaagc ggaagcctcc ctccacaaac    300

gccggcagga ggcagaagca caggctgacc tgccccagct gtgactccta cgagaagaag    360

ccccccaagg agttcctgga gaggttcaag tccctgctgc agaagatgat ccatcagcac    420

ctgtcctcca ggacccacgg ctccgaggac tccattacat gcccccctcc catgagcgtg    480

gagcacgccg acatctgggt gaagagctat agcctctaca gccgggagag gtatatctgt    540

aacagcggct tcaagaggaa ggccggcacc agcagcctca ccgagtgcgt gctgaataag    600

gctaccaacg tggctcactg gacaacaccc tctttaaagt gcatccgggg cggtggagga    660

tccggaggag gtggctccgg cggcggagga tctcgcgagg gtcccgagct ttcgcccgac    720

gatcccgccg gcctcttgga cctgcggcag ggcatgtttg cgcagctggt ggcccaaaat    780

gttctgctga tcgatgggcc cctgagctgg tacagtgacc caggcctggc aggcgtgtcc    840

ctgacggggg gcctgagcta caaagaggac acgaaggagc tggtggtggc caaggctgga    900

gtctactatg tcttctttca actagagctg cggcgcgtgg tggccggcga gggctcaggc    960

tccgtttcac ttgcgctgca cctgcagcca ctgcgctctg ctgctggggc cgccgccctg   1020

gctttgaccg tggacctgcc acccgcctcc tccgaggctc ggaactcggc cttcggtttc   1080

cagggccgct tgctgcacct gagtgccggc cagcgcctgg gcgtccatct tcacactgag   1140

gccagggcac gccatgcctg gcagcttacc cagggcgcca cagtcttggg actcttccgg   1200

gtgacccccg aaatcccagc cggactccct tcaccgaggt cggaa                   1245
```

<210> SEQ ID NO 332
<211> LENGTH: 415
<212> TYPE: PRT
<213> ORGANISM: Homo sapiens
<220> FEATURE:
<221> NAME/KEY: source
<223> OTHER INFORMATION: /note="21s137L"

<400> SEQUENCE: 332

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95
```

```
Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Gly Ser Gly Gly Gly
    210                 215                 220

Gly Ser Gly Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
                245                 250                 255

Val Ala Gln Asn Val Leu Leu Ile Asp Gly Pro Leu Ser Trp Tyr Ser
            260                 265                 270

Asp Pro Gly Leu Ala Gly Val Ser Leu Thr Gly Gly Leu Ser Tyr Lys
        275                 280                 285

Glu Asp Thr Lys Glu Leu Val Val Ala Lys Ala Gly Val Tyr Tyr Val
    290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
                325                 330                 335

Ala Ala Ala Leu Ala Leu Thr Val Asp Leu Pro Pro Ala Ser Ser Glu
            340                 345                 350

Ala Arg Asn Ser Ala Phe Gly Phe Gln Gly Arg Leu Leu His Leu Ser
        355                 360                 365

Ala Gly Gln Arg Leu Gly Val His Leu His Thr Glu Ala Arg Ala Arg
    370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu
                405                 410                 415
```

<210> SEQ ID NO 333
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 333
ggtgggtata atggg 15

<210> SEQ ID NO 334
<211> LENGTH: 25
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 334

attattttat tttaaaaaat ttgtg                                           25
```

METHODS OF TREATING AGING-RELATED DISORDERS

CROSS-REFERENCE TO RELATED APPLICATIONS

This application claims priority to: U.S. Patent Application Ser. No. 62/816,683, filed Mar. 11, 2019; U.S. Patent Application Ser. No. 62/725,038, filed Aug. 30, 2018; U.S. Patent Application Ser. No. 62/817,244, filed Mar. 12, 2019; U.S. Patent Application Ser. No. 62/881,039, filed Jul. 31, 2019; U.S. Patent Application Ser. No. 62/724,969, filed Aug. 30, 2018; U.S. Patent Application Ser. No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; and U.S. Patent Application Ser. No. 62/881,088, filed Jul. 31, 2019, each of which is incorporated hereby reference in its entirety.

TECHNICAL FIELD

The present disclosure relates to the field of immunology and cell biology.

BACKGROUND

Senescence is a form of irreversible growth arrest accompanied by phenotypic changes, resistance to apoptosis, and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence tissue hemostasis, disease, and aging through their secretory phenotype. Senescence is considered as a physiologic process and is important in promoting wound healing, tissue homeostasis, regeneration, and regulation of fibrosis. For instance, transient induction of senescent cells is observed during would healing and contributes to wound resolution. Senescence also plays a role in tumor suppression. The accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on the observation that senescent cells accumulate in aged tissue. The use of transgenic models has enabled the detection of senescent cells systematically in many aging-related disorders. Strategies to selectively eliminate senescent cells have demonstrated that senescent cells play a causal role in aging-related disorders.

SUMMARY

The present invention is based on the discovery that administration of NK cell activating agents to a mammal having a cancer resulted in a tumor inhibition and administration of NK cell activating agents to a diabetic animal model demonstrated improved skin and hair appearance and texture, and decreased blood glucose levels. In view of this discovery provided herein are methods of treating an aging-related disease or condition in a subject in need thereof that include administering to a subject identified as having an aging-related disease or condition a therapeutically effective amount of one or more natural killer (NK) cell activating agent (s) and/or a therapeutically effective number of activated NK cells. Also provided herein are methods of killing or reducing the number of senescent cells in a subject in need thereof that include administering to the subject a therapeutically effective amount of one or more NK cell activating agent(s) and/or or a therapeutically effective number of activated NK cells. Also provided herein are methods of improving the texture and/or appearance of skin and/or hair in a subject in need thereof over a period of time that include administering to the subject a therapeutically effective amount of one or more natural killer (NK) cell activating agent(s) and/or a therapeutically effective number of activated NK cells. Also provided herein are methods of assisting in the treatment of obesity in a subject in need thereof over a period of time that include administering to the subject a therapeutically effective amount of one or more natural killer (NK) cell activating agent(s) and/or a therapeutically effective number of activated NK cells.

Provided herein are methods of treating an aging-related disease or condition in a subject in need thereof that include administering to a subject identified as having an aging-related disease or condition a therapeutically effective amount of one or more natural killer (NK) cell activating agent(s).

Also provided herein are methods of killing or reducing the number of senescent cells in a subject in need thereof that include administering to the subject a therapeutically effective amount of one or more NK cell activating agent(s). In some embodiments of any of the methods described herein, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of any of the methods described herein, the senescent cancer cells are chemotherapy-induced senescent cells or radiation-induced senescent cells. In some embodiments of any of the methods described herein, the subject has been identified or diagnosed as having an aging-related disease or condition.

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the autoimmune disease is type-1 diabetes.

In some embodiments of any of the methods described herein, the metabolic disease is selected from the group of: obesity, a lipodystrophy, and type-2 diabetes mellitus.

In some embodiments of any of the methods described herein, the neurodegenerative disease is selected from the group of: Alzheimer's disease, Parkinson's disease, and dementia.

In some embodiments of any of the methods described herein, the cardiovascular disease is selected from the group of: coronary artery disease, atherosclerosis, and pulmonary arterial hypertension.

In some embodiments of any of the methods described herein, the skin disease is selected from the group of: wound healing, alopecia, wrinkles, senile lentigo, skin thinning, xeroderma pigmentosum, and dyskeratosis congenita.

In some embodiments of any of the methods described herein, the progeria disease is selected from the group of: progeria and Hutchinson-Gilford Progeria Syndrome.

In some embodiments of any of the methods described herein, the fragility disease is selected from the group of: frailty, responsiveness to vaccination, osteoporosis, and sarcopenia.

In some embodiments of any of the methods described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the methods described herein, the aging-related disease or condition is type-2 diabetes or atherosclerosis.

In some embodiments of any of the methods described herein, the administering results in a decrease in the number of senescent cells in a target tissue in the subject. In some embodiments of any of the methods described herein, the target tissue is selected from the group of: adipose tissue, pancreatic tissue, liver tissue, lung tissue, vasculature, bone tissue, central nervous system (CNS) tissue, eye tissue, skin tissue, muscle tissue, and secondary lympho-organ tissue.

In some embodiments of any of the methods described herein, the administering results in an increase in the expression levels of CD25, CD69, mTORC1, SREBP1, IFN-γ, and granzyme B in activated NK cells.

Also provided herein are methods of treating an aging-related disease or condition in a subject in need thereof that include administering to a subject identified as having an aging-related disease or condition a therapeutically effective number of activated NK cells.

Also provided herein are methods of killing or reducing the number of senescent cells in a subject in need thereof that include administering to the subject a therapeutically effective number of activated NK cells. In some embodiments of any of the methods described herein, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of any of the methods described herein, the senescent cancer cells are chemotherapy-induced senescent cells or radiation-induced senescent cells. In some embodiments of any of the methods described herein, the subject has been identified or diagnosed as having an aging-related disease or condition.

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the autoimmune disease is type-1 diabetes.

In some embodiments of any of the methods described herein, the metabolic disease is selected from the group of: obesity, a lipodystrophy, and type-2 diabetes mellitus.

In some embodiments of any of the methods described herein, the neurodegenerative disease is selected from the group of: Alzheimer's disease, Parkinson's disease, and dementia.

In some embodiments of any of the methods described herein, the cardiovascular disease is selected from the group of: coronary artery disease, atherosclerosis, and pulmonary arterial hypertension.

In some embodiments of any of the methods described herein, the skin disease is selected from the group of: wound healing, alopecia, wrinkles, senile lentigo, skin thinning, xeroderma pigmentosum, and dyskeratosis congenita.

In some embodiments of any of the methods described herein, the progeria disease is selected from the group of: progeria and Hutchinson-Gilford Progeria Syndrome.

In some embodiments of any of the methods described herein, the fragility disease is selected from the group of: frailty, responsiveness to vaccination, osteoporosis, and sarcopenia.

In some embodiments of any of the methods described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject. Some embodiments of any of the methods described herein further include introducing a nucleic acid that encodes a chimeric antigen receptor or a recombinant T cell receptor into the resting NK cell or the activated NK cell prior to administration to the subject.

Also provided herein are methods of improving the texture and/or appearance of skin and/or hair in a subject in need thereof over a period of time that include administering to the subject a therapeutically effective amount of one or more natural killer (NK) cell activating agent(s).

Also provided herein are methods of improving the texture and/or appearance of skin and/or hair in a subject in need thereof over a period of time that include administering to the subject a therapeutically effective number of activated NK cells. Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject.

In some embodiments of any of the methods described herein, the method provides for an improvement in the texture and/or appearance of skin of the subject over the period of time. In some embodiments of any of the methods described herein, the method results in a decrease in the rate of formation of wrinkles in the skin of the subject over the period of time. In some embodiments of any of the methods described herein, the method results in an improvement in the coloration of skin of the subject over the period of time. In some embodiments of any of the methods described herein, the method results in an improvement in the texture of skin of the subject over the period of time. In some embodiments of any of the methods described herein, the method provides for an improvement in the texture and/or appearance of hair of the subject over the period of time. In some embodiments of any of the methods described herein, the method results in a decrease in the rate of formation of gray hair in the subject over the period of time. In some embodiments of any of the methods described herein, the method results in a decrease in the number of gray hairs of the subject over the period of time. In some embodiments of any of the methods described herein, the method results in a decrease in the rate of hair loss in the subject over time. In some embodiments of any of the methods described herein, the method results in an improvement in the texture of hair of the subject over the period of time.

In some embodiments of any of the methods described herein, the period of time is between about one month and about 10 years. In some embodiments of any of the methods described herein, the method results in a decrease in the number of senescent dermal fibroblasts in the skin of the subject over the period of time.

Also provided herein are methods of assisting in the treatment of obesity in a subject in need thereof over a period of time that include administering to the subject a therapeutically effective amount of one or more natural killer (NK) cell activating agent(s).

Also provided herein are methods of assisting in the treatment of obesity in a subject in need thereof over a period of time that include administering to the subject a therapeutically effective number of activated NK cells. Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject.

In some embodiments of any of the methods described herein, the method results in a decrease in the mass of the subject over the period of time. In some embodiments of any of the methods described herein, the method results in a decrease in the body mass index (BMI) of the subject over the period of time. In some embodiments of any of the methods described herein, the method results in a decrease in the rate of progression from pre-diabetes to type-2 diabetes in the subject. In some embodiments of any of the methods described herein, the method results in a decrease in fasting serum glucose level in the subject. In some embodiments of any of the methods described herein, the method results in an increase in insulin sensitivity in the subject. In some embodiments of any of the methods described herein, the method results in a decrease in the severity of atherosclerosis in the subject. In some embodiments of any of the methods described herein, the period of time is between about two weeks and about 10 years.

In some embodiments of any of the methods described herein, at least one of the one or more NK cell activating agent(s) results in activation of one or more of: a receptor for IL-2, a receptor for IL-7, a receptor for IL-12, a receptor for IL-15, a receptor for IL-18, a receptor for IL-21, a receptor for IL-33, CD16, CD69, CD25, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1.

In some embodiments of any of the methods described herein, the at least one of the one or more NK cell activating agent(s) that results in activation of a receptor for IL-2 is a soluble IL-2 or an agonistic antibody that binds specifically to an IL-2 receptor.

In some embodiments of any of the methods described herein, the at least one of the one or more NK cell activating agent(s) that results in activation of a receptor for IL-7 is a soluble IL-7 or an agonistic antibody that binds specifically to an IL-7 receptor.

In some embodiments of any of the methods described herein, the at least one of the one or more NK cell activating agent(s) that results in activation of a receptor for IL-12 is a soluble IL-12 or an agonistic antibody that binds specifically to an IL-12 receptor.

In some embodiments of any of the methods described herein, the at least one of the one or more NK cell activating agent(s) that results in activation of a receptor for IL-15 is a soluble IL-15 or an agonistic antibody that binds specifically to an IL-15 receptor.

In some embodiments of any of the methods described herein, the at least one of the one or more NK cell activating agent(s) that results in activation of a receptor for IL-21 is a soluble IL-21 or an agonistic antibody that binds specifically to an IL-21 receptor.

In some embodiments of any of the methods described herein, the at least one of the one or more NK cell activating agent(s) that results in activation of a receptor for IL-33 is a soluble IL-33 or an agonistic antibody that binds specifically to an IL-33 receptor.

In some embodiments of any of the methods described herein, the at least one of the one or more NK cell activating agent(s) that results in activation of a receptor for CD16 is an agonistic antibody that binds specifically to a CD16.

In some embodiments of any of the methods described herein, the at least one of the one or more NK cell activating agent(s) that results in activation of a receptor for CD69 is an agonistic antibody that binds specifically to a CD69.

In some embodiments of any of the methods described herein, the at least one of the one or more NK cell activating agent(s) that results in activation of a receptor for CD25 or CD59 is an agonistic antibody that binds specifically to CD25 or CD59.

In some embodiments of any of the methods described herein, the at least one of the one or more NK cell activating agent(s) that results in activation of a receptor for CD352 is an agonistic antibody that binds specifically to a CD352.

In some embodiments of any of the methods described herein, the at least one of the one or more NK cell activating agent(s) that results in activation of a receptor for NKp80 is an agonistic antibody that binds specifically to an NKp80.

In some embodiments of any of the methods described herein, the at least one of the one or more NK cell activating agent(s) that results in activation of a receptor for DNAM-1 is an agonistic antibody that binds specifically to a DNAM-1.

In some embodiments of any of the methods described herein, the at least one of the one or more NK cell activating agent(s) that results in activation of a receptor for 2B4 is an agonistic antibody that binds specifically to a 2B4.

In some embodiments of any of the methods described herein, the at least one of the one or more NK cell activating agent(s) that results in activation of a receptor for NKp30 is an agonistic antibody that binds specifically to an NKp30.

In some embodiments of any of the methods described herein, the at least one of the one or more NK cell activating agent(s) that results in activation of a receptor for NKp44 is an agonistic antibody that binds specifically to an NKp44.

In some embodiments of any of the methods described herein, the at least one of the one or more NK cell activating agent(s) that results in activation of a receptor for NKp46 is an agonistic antibody that binds specifically to an NKp46.

In some embodiments of any of the methods described herein, the at least one of the one or more NK cell activating agent(s) that results in activation of a receptor for NKG2D is an agonistic antibody that binds specifically to an NKG2D.

In some embodiments of any of the methods described herein, the at least one of the one or more NK cell activating agent(s) that results in activation of a receptor for KIR2DS1 is an agonistic antibody that binds specifically to a KIR2DS1.

In some embodiments of any of the methods described herein, the at least one of the one or more NK cell activating agent(s) that results in activation of a receptor for KIR2DS2/3 is an agonistic antibody that binds specifically to a KIR2DS2/3.

In some embodiments of any of the methods described herein, the at least one of the one or more NK cell activating agent(s) that results in activation of a receptor for KIR2DL4 is an agonistic antibody that binds specifically to a KIR2DL4.

In some embodiments of any of the methods described herein, the at least one of the one or more NK cell activating agent(s) that results in activation of a receptor for KIR2DS4 is an agonistic antibody that binds specifically to a KIR2DS4.

In some embodiments of any of the methods described herein, the at least one of the one or more NK cell activating agent(s) that results in activation of a receptor for KIR2DS5 is an agonistic antibody that binds specifically to a KIR2DS5.

In some embodiments of any of the methods described herein, the at least one of the one or more NK cell activating agent(s) that results in activation of a receptor for KIR3DS1 is an agonistic antibody that binds specifically to a KIR3DS1.

In some embodiments of any of the methods described herein, at least one of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2. In some embodiments of any of the methods described herein, the at least one of the one or more NK cell activating agent(s) that results in a decrease in the activation of PD-1 is an antagonistic antibody that binds specifically to PD-1, a soluble PD-1, a soluble PD-L1, or an antibody that binds specifically to PD-L1. In some embodiments of any of the methods described herein, at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

In some embodiments of any of the methods described herein, at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

In some embodiments of any of the methods described herein, at least one of the one or more NK cell activating agent(s) that results in a decrease in the activation of CD1 is an antagonistic antibody that binds specifically to CD1, a soluble CD1, or an antibody that binds specifically to a ligand of CD1.

In some embodiments of any of the methods described herein, at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

In some embodiments of any of the methods described herein, at least one of the one or more NK cell activating agent(s) that results in a decrease in the activation of Siglec-7 is an antagonistic antibody that binds specifically to Siglec-7 or an antibody that binds specifically to a ligand of Siglec-7.

In some embodiments of any of the methods described herein, at least one of the one or more NK cell activating agent(s) that results in a decrease in the activation of IRP60 is an antagonistic antibody that binds specifically to IRP60 or an antibody that binds specifically to a ligand of IRP60.

In some embodiments of any of the methods described herein, at least one of the one or more NK cell activating agent(s) that results in a decrease in the activation of Tactile is an antagonistic antibody that binds specifically to Tactile or an antibody that binds specifically to a ligand of Tactile.

In some embodiments of any of the methods described herein, at least one of the one or more NK cell activating agent(s) that results in a decrease in the activation of IL1R8 is an antagonistic antibody that binds specifically to IL1R8 or an antibody that binds specifically to a ligand of IL1R8.

In some embodiments of any of the methods described herein, at least one of the one or more NK cell activating agent(s) that results in a decrease in the activation of NKG2A/KLRD1 is an antagonistic antibody that binds specifically to NKG2A/KLRD1 or an antibody that binds specifically to a ligand of NKG2A/KLRD1.

In some embodiments of any of the methods described herein, at least one of the one or more NK cell activating agent(s) that results in a decrease in the activation of KIR2DL1 is an antagonistic antibody that binds specifically to KIR2DL1 or an antibody that binds specifically to a ligand of KIR2DL1.

In some embodiments of any of the methods described herein, at least one of the one or more NK cell activating agent(s) that results in a decrease in the activation of KIR2DL2/3 is an antagonistic antibody that binds specifically to KIR2DL2/3 or an antibody that binds specifically to a ligand of KIR2DL2/3.

In some embodiments of any of the methods described herein, at least one of the one or more NK cell activating agent(s) that results in a decrease in the activation of KIR2DL5 is an antagonistic antibody that binds specifically to KIR2DL5 or an antibody that binds specifically to a ligand of KIR2DL5.

In some embodiments of any of the methods described herein, at least one of the one or more NK cell activating agent(s) that results in a decrease in the activation of KIR3DL1 is an antagonistic antibody that binds specifically to KIR3DL1 or an antibody that binds specifically to a ligand of KIR3DL1.

In some embodiments of any of the methods described herein, at least one of the one or more NK cell activating agent(s) that results in a decrease in the activation of KIR3DL2 is an antagonistic antibody that binds specifically to KIR3DL2 or an antibody that binds specifically to a ligand of KIR3DL2.

In some embodiments of any of the methods described herein, at least one of the one or more NK cell activating agent(s) that results in a decrease in the activation of ILT2/LIR-1 is an antagonistic antibody that binds specifically to ILT2/LIR-1 or an antibody that binds specifically to a ligand of ILT2/LIR-1.

In some embodiments of any of the methods described herein, at least one of the one or more NK cell activating agent(s) that results in a decrease in the activation of LAG-2 is an antagonistic antibody that binds specifically to LAG-2 or an antibody that binds specifically to a ligand of LAG-2.

In some embodiments of any of the methods described herein, at least one of the one or more NK cell activating agent(s) is a single-chain chimeric polypeptide that includes: (i) a first target-binding domain; (ii) a soluble tissue factor domain; and (iii) a second target-binding domain. In some embodiments of any of the methods described herein, the first target-binding domain and the soluble tissue factor domain directly abut each other. In some embodiments of any of the methods described herein, the single-chain chimeric polypeptide further includes a linker sequence between the first target-binding domain and the soluble tissue factor domain. In some embodiments of any of the methods described herein, the soluble tissue factor domain and the second target-binding domain directly abut each other. In some embodiments of any of the methods described herein, the single-chain chimeric polypeptide further includes a linker sequence between the soluble tissue factor domain and the second target-binding domain. In some embodiments of any of the methods described herein, the first target-binding domain and the second target-binding domain directly abut each other. In some embodiments of any of the methods described herein, the single-chain chimeric polypeptide further includes a linker sequence between the first target-binding domain and the second target-binding domain. In some embodiments of any of the methods described herein, the second target-binding domain and the soluble tissue factor domain directly abut each other. In some embodiments of any of the methods described herein, the single-chain chimeric polypeptide further includes a linker sequence between the second target-binding domain and the soluble tissue factor domain.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each an antigen-binding domain. In some embodiments of any of the methods described herein, the antigen-binding domain includes a scFv or a single domain antibody.

In some embodiments of any of the methods described herein, one or both of the first target-binding domain and the second target-binding domain bind to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble interleukin or cytokine receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain. In some embodiments of any of the methods described herein, the soluble human tissue factor domain includes a sequence that is at least 80% identical to SEQ ID NO: 93. In some embodiments of any of the methods described herein, the soluble human tissue factor domain includes a sequence that is at least 90% identical to SEQ ID NO: 93. In some embodiments of any of the methods described herein, the soluble human tissue factor domain includes a sequence that is at least 95% identical to SEQ ID NO: 93. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding Factor VIIa. In some embodiments of any of the methods described herein, the soluble tissue factor domain does not convert inactive Factor X into Factor Xa. In some embodiments of any of the methods described herein, the single-chain chimeric polypeptide does not blood stimulate coagulation in a mammal. In some embodiments of any of the methods described herein, the single-chain chimeric polypeptide further includes one or more additional target-binding domains at its N- and/or C-terminus.

In some embodiments of any of the methods described herein, the single-chain chimeric polypeptide includes one or more additional target-binding domains at its N-terminus. In some embodiments of any of the methods described herein, one or more additional target-binding domains directly abuts the first target-binding domain, the second target-binding domain, or the soluble tissue factor domain. In some embodiments of any of the methods described herein, the single-chain chimeric polypeptide further includes a linker sequence between one of the at least one additional target-binding domains and the first target-binding domain, the second target-binding domain, or the soluble tissue factor domain.

In some embodiments of any of the methods described herein, the single-chain chimeric polypeptide includes one or more additional target-binding domains at its C-terminus. In some embodiments of any of the methods described herein, one of the one or more additional target-binding domains directly abuts the first target-binding domain, the second target-binding domain, or the soluble tissue factor domain. In some embodiments of any of the methods described herein, the single-chain chimeric polypeptide further includes a linker sequence between one of the at least one additional target-binding domains and the first target-binding domain, the second target-binding domain, or the soluble tissue factor domain.

In some embodiments of any of the methods described herein, the single-chain chimeric polypeptide includes one or more additional target binding domains at its N-terminus and the C-terminus. In some embodiments of any of the methods described herein, one of the one or more additional antigen binding domains at the N-terminus directly abuts the first target-binding domain, the second target-binding domain, or the soluble tissue factor domain. In some embodiments of any of the methods described herein, the single-chain chimeric polypeptide further includes a linker sequence between one of the one or more additional antigen-binding domains at the N-terminus and the first target-binding domain, the second target-binding domain, or the soluble tissue factor domain. In some embodiments of any of the methods described herein, one of the one or more additional antigen binding domains at the C-terminus directly abuts the first target-binding domain, the second target-binding domain, or the soluble tissue factor domain. In some embodiments of any of the methods described herein, the single-chain chimeric polypeptide further includes a linker sequence between one of the one or more additional antigen-binding domains at the C-terminus and the first target-binding domain, the second target-binding domain, or the soluble tissue factor domain.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence.

In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv or a single domain antibody.

In some embodiments of any of the methods described herein, one or more of the first target-binding domain, the second target-binding domain, and the one or more target-binding domains bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or more of the first target-binding domain, the second target-binding domain, and the one or more additional target-binding domains is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or more of the first target-binding domain, the second target-binding domain, and the one or more additional target-binding domains is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, at least one of the one or more NK cell activating agent(s) is a multi-chain chimeric polypeptide that includes: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some embodiments of any of the methods described herein, the first target-binding domain and the soluble tissue factor domain directly abut each other in the first chimeric polypeptide. In some embodiments of any of the methods described herein, the first chimeric polypeptide further includes a linker sequence between the first target-binding domain and the soluble tissue factor domain in the first chimeric polypeptide. In some embodiments of any of the methods described herein, the soluble tissue factor domain and the first domain of the pair of affinity domains directly abut each other in the first chimeric polypeptide. In some embodiments of any of the methods described herein, the first chimeric polypeptide further includes a linker sequence between the soluble tissue factor domain and the first domain of the pair of affinity domains in the first chimeric polypeptide. In some embodiments of any of the methods described herein, the second domain of the pair of affinity domains and the second target-binding domain directly abut each other in the second chimeric polypeptide. In some embodiments of any of the methods described herein, the second chimeric polypeptide further includes a linker sequence between the second domain of the pair of affinity domains and the second target-binding domain in the second chimeric polypeptide.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain includes a scFv or a single domain antibody.

In some embodiments of any of the methods described herein, one or both of the first target-binding domain and the second target-binding domain bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the first chimeric polypeptide further includes one or more additional target-binding domain(s), where at least one of the one or more additional antigen-binding domain(s) is positioned between the soluble tissue factor domain and the first domain of the pair of affinity domains. In some embodiments of any of the methods described herein, the first chimeric polypeptide further includes a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

In some embodiments of any of the methods described herein, the first chimeric polypeptide further includes one or more additional target-binding domains at the N-terminal and/or C-terminal end of the first chimeric polypeptide. In some embodiments of any of the methods described herein, at least one of the one or more additional target-binding domains directly abuts the first domain of the pair of affinity domains in the first chimeric polypeptide. In some embodiments of any of the methods described herein, the first chimeric polypeptide further includes a linker sequence between the at least one of the one or more additional target-binding domains and the first domain of the pair of affinity domains. In some embodiments of any of the methods described herein, the at least one of the one or more additional target-binding domains directly abuts the first target-binding domain in the first chimeric polypeptide. In some embodiments of any of the methods described herein, the first chimeric polypeptide further includes a linker sequence between the at least one of the one or more additional target-binding domains and the first target-binding domain.

In some embodiments of any of the methods described herein, at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide. In some embodiments of any of the methods described herein, the at least one additional target-binding domain of the one or more additional target-binding domains disposed at the N-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one additional target-binding domain of the one or more additional target-binding domains disposed at the C-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one of the one or more additional target-binding domains positioned between the soluble tissue factor domain and the first domain of the pair of affinity domains, directly abuts the soluble tissue factor domain and/or the first domain of the pair of affinity domains. In some embodiments of any of the methods described herein, the first chimeric polypeptide further includes a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

In some embodiments of any of the methods described herein, the second chimeric polypeptide further includes one or more additional target-binding domains at the N-terminal end or the C-terminal end of the second chimeric polypeptide. In some embodiments of any of the methods described herein, at least one of the one or more additional target-binding domains directly abuts the second domain of the pair of affinity domains in the second chimeric polypeptide. In some embodiments of any of the methods described herein, the second chimeric polypeptide further includes a linker sequence between at least one of the one or more additional target-binding domains and the second domain of the pair of affinity domains in the second chimeric polypeptide. In some embodiments of any of the methods described herein, at least one of the one or more additional target-binding domains directly abuts the second target-binding domain in the second chimeric polypeptide. In some embodiments of any of the methods described herein, the second chimeric polypeptide further includes a linker sequence between at least one of the one or more additional target-binding domains and the second target-binding domain in the second chimeric polypeptide.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence.

In some embodiments of any of the methods described herein, the first target-binding domain, the second target-binding domain, and the one or more additional target-binding domains bind specifically to different antigens. In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv.

In some embodiments of any of the methods described herein, one or more of the first target-binding domain, the second target-binding domain, and the one or more target-binding domains bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or more of the first target-binding domain, the second target-binding domain, and the one or more additional target-binding domains is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or more of the first target-binding domain, the second target-binding domain, and the one or more additional target-binding domains is a soluble interleukin or cytokine receptor. In some embodiments of any of the methods described herein, the soluble receptor a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain. In some embodiments of any of the methods described herein, the soluble human tissue factor domain includes a sequence that is at least 80% identical to SEQ ID NO: 93. In some embodiments of any of the methods described herein, the soluble human tissue factor domain includes a sequence that is at least 90% identical to SEQ ID NO: 93. In some embodiments of any of the methods described herein, the soluble human tissue factor domain includes a sequence that is at least 95% identical to SEQ ID NO: 93.

In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding to Factor VIIa. In some embodiments of any of the methods described herein, the soluble tissue factor domain does not convert inactive Factor X into Factor Xa. In some embodiments of any of the methods described herein, the multi-chain chimeric polypeptide does not stimulate blood coagulation in a mammal. In some embodiments of any of the methods described herein, the pair of affinity domains is a sushi domain from an alpha chain of human IL-15 receptor (IL-15Rα) and a soluble IL-15. In some embodiments of any of the methods described herein, the soluble IL-15 has a D8N or D8A amino acid substitution. In some embodiments of any of the methods described herein, the human IL-15Rα is a mature full-length IL-15Rα.

In some embodiments of any of the methods described herein, the pair of affinity domains is selected from the group of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

In some embodiments of any of the methods described herein, at least one of the one or more NK cell activating agent(s) is a multi-chain chimeric polypeptide that includes: (a) a first and second chimeric polypeptides, where each includes: (i) a first target-binding domain; (ii) a Fc domain; and (iii) a first domain of a pair of affinity domains; and (b) a third and fourth chimeric polypeptide, where each includes: (i) a second domain of a pair of affinity domains; and (ii) a second target-binding domain, where the first and second chimeric polypeptides and the third and fourth chimeric polypeptides associate through the binding of the first domain and the second domain of the pair of affinity domains, and the first and second chimeric polypeptides associate through their Fc domains.

In some embodiments of any of the methods described herein, the first target-binding domain and the Fc domain directly abut each other in the first and second chimeric polypeptides. In some embodiments of any of the methods described herein, the first and second chimeric polypeptides further include a linker sequence between the first target-binding domain and the Fc domain in the first and second chimeric polypeptides. In some embodiments of any of the methods described herein, the Fc domain and the first domain of the pair of affinity domains directly abut each other in the first and second chimeric polypeptides. In some embodiments of any of the methods described herein, the first chimeric polypeptide further includes a linker sequence between the Fc domain and the first domain of the pair of affinity domains in the first and second chimeric polypeptides.

In some embodiments of any of the methods described herein, the second domain of the pair of affinity domains and the second target-binding domain directly abut each other in the third and fourth chimeric polypeptides. In some embodiments of any of the methods described herein, the third and fourth chimeric polypeptides further include a linker sequence between the second domain of the pair of affinity domains and the second target-binding domain in the third and fourth chimeric polypeptides.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens. In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain includes a scFv or a single domain antibody.

In some embodiments of any of the methods described herein, one or both of the first target-binding domain and the second target-binding domain bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain that does not stimulate blood coagulation. In some embodiments of any of the methods described herein, the soluble tissue factor domain comprises or consists of a sequence from a wildtype soluble human tissue factor.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "activated NK cell" is a NK cell demonstrating increased expression levels of two or more (e.g., three, four, five, or six) of CD25, CD69, MTOR-C1, SREBP, IFN-γ, and a granzyme (e.g., granzyme B), e.g., as compared to a resting NK cell. Exemplary methods for identifying the expression levels of CD25, CD69, MTOR-C1, SREBP, IFN-γ, and a granzyme (e.g., granzyme B) are described herein.

A "resting NK cell" is a NK cell that has a reduced expression of two or more (e.g., three, four, five, or six) of CD25, CD69, MTOR-C1, SREBP, IFN-γ, and a granzyme (e.g., granzyme B), e.g., as compared to an activated NK cell.

An "NK cell activating agent" is an agent that induces or promotes (alone or in combination with additional NK cell activating agents) a resting NK cell to develop into an activated NK cell. Non-limiting examples and aspects of NK cell activating agents are described herein.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein to refers to a single protein chain.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1\times10^{-7}$ M (e.g., less than $1\times10^{-8}$ M, less than $1\times10^{-9}$M, less than $1\times10^{-10}$ M, or less than $1\times10^{-11}$M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of a composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1A shows the spleen weight of mice treated with increasing dosage of the exemplary multi-chain polypeptide as compared to mice treated with the control solution. FIG. 1B shows the percentages of immune cell types present in the spleen of mice treated with increasing dosage of the exemplary multi-chain polypeptide as compared to mice treated with the control solution.

FIG. 2A shows the spleen weight over a period of 92 hours in mice treated with 3 mg/kg of the exemplary multi-chain polypeptide. FIG. 2B shows the percentages of immune cell types present in the spleen over a period of 92 hours in mice treated with 3 mg/kg of the exemplary multi-chain polypeptide.

FIG. 3A shows the expression of Ki67 in $CD4^+$ T cells, $CD8^+$ T cells, natural killer (NK) cells, and $CD19^+$ B cells at various time points post-treatment with the multi-chain polypeptide. FIG. 3B shows the expression of Granzyme B in $CD4^+$ T cells, $CD8^+$ T cells, natural killer (NK) cells, and $CD19^+$ B cells at various time points post-treatment with the multi-chain polypeptide.

FIG. 5A shows the percentages of the different cell types in each control and experimental group. FIG. 5B shows the proliferation rate of the of the different cell types in each control and experimental group.

FIG. 9A shows chemotherapy induction of senescent B16F10 cells visualized using SA β-gal staining. FIGS. 9B-9F show expression of p21, IL6, DPP4, RATE1E, and ULBP1 over time in the chemotherapy-induced senescent B16F10 cells.

FIG. 10A shows colony formation by chemotherapy-induced senescent B16F10 cells. FIGS. 10B and 10C show expression of Oct4 mRNA and Notch4 mRNA by chemotherapy-induced senescent B16F10 cells as compared to control B16F10 cells. FIGS. 10D-10F show percentage of chemotherapy-induced senescent B16F10 cells double-positive for two out of the three stem cell markers including CD44, CD24, and CD133.

FIG. 11A shows the results of a migration assay comparing chemotherapy-induced senescent cells with stem cell properties (B16F10-SNC-CSC) with control B16F10 cells. FIGS. 11B and 11C show the results of an invasion assay comparing chemotherapy-induced senescent cells with stem cell properties (B16F10-SNC-CSC) with control B16F10 cells.

FIG. 12A shows an exemplary schematic of a process of obtaining in vitro expanded NK cells. FIG.

12 B shows cytotoxicity of the expanded NK cells against chemotherapy-induced senescent cells with stem cell properties (B16F10-SNC-CSC) or control B16F10 cells.

Figure 13A:
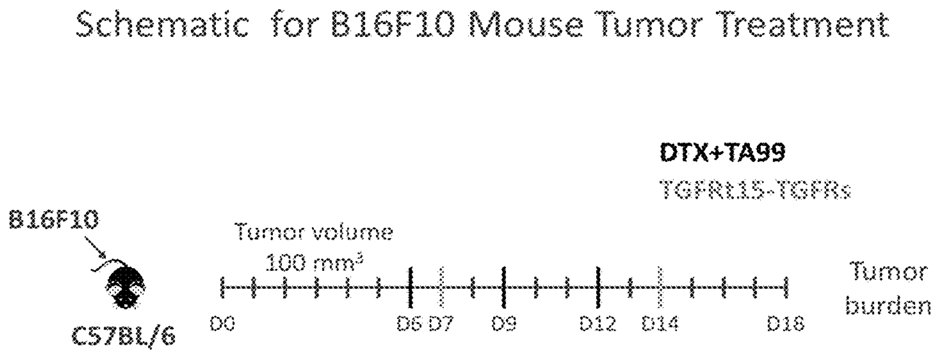
Figure 13B:
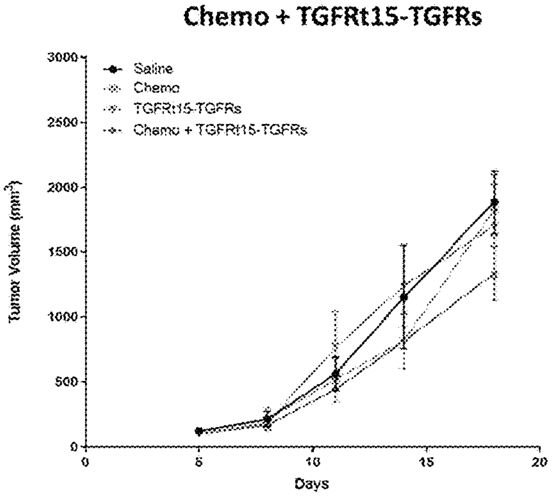
Figure 13C:
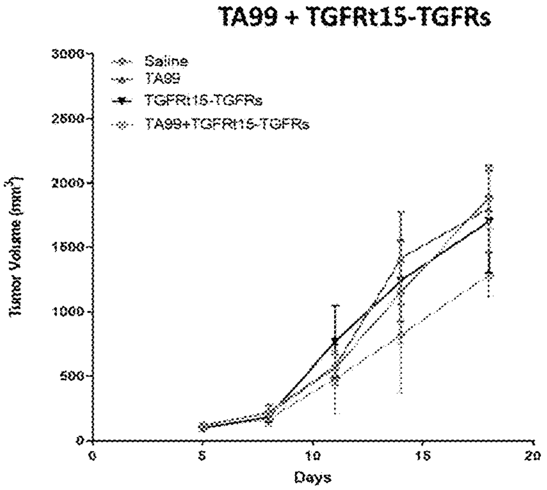

FIGS. 13A-13C show results of combination treatment using a mouse melanoma model. FIG. 13A shows an exemplary schematic for treating melanoma in a mouse model. FIGS. 13B and 13C show the change in tumor volume over time with combination treatments including TGFRt15-TGFRs as compared to chemotherapy or TA99 treatment alone.

Figure 14:
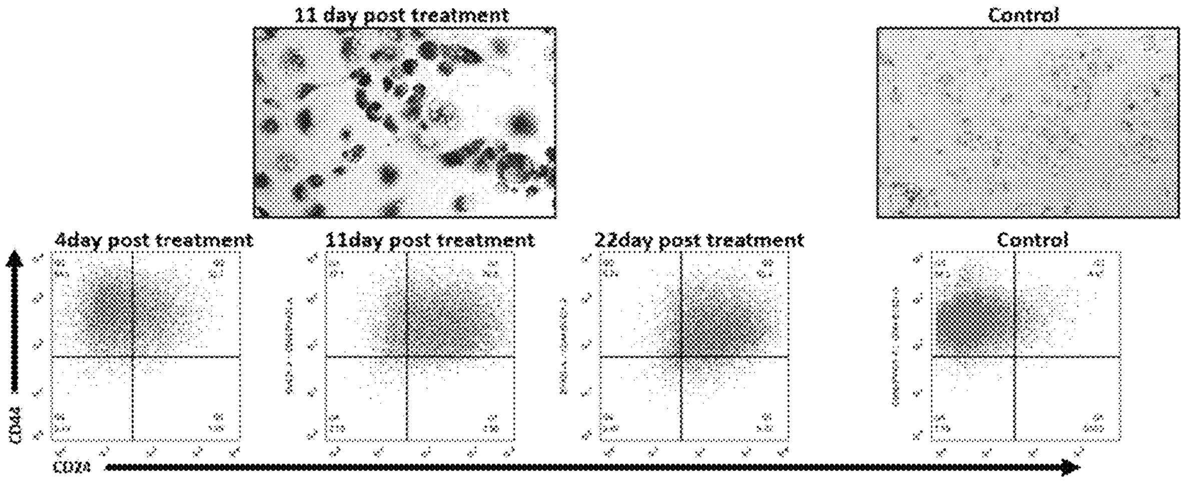

FIG. 14 shows induction of senescence in the human pancreatic tumor cell line SW1990 and expression of CD44 and CD24 in senescent SW1990 cells as compared to control SW1990 cells.

Figure 15:
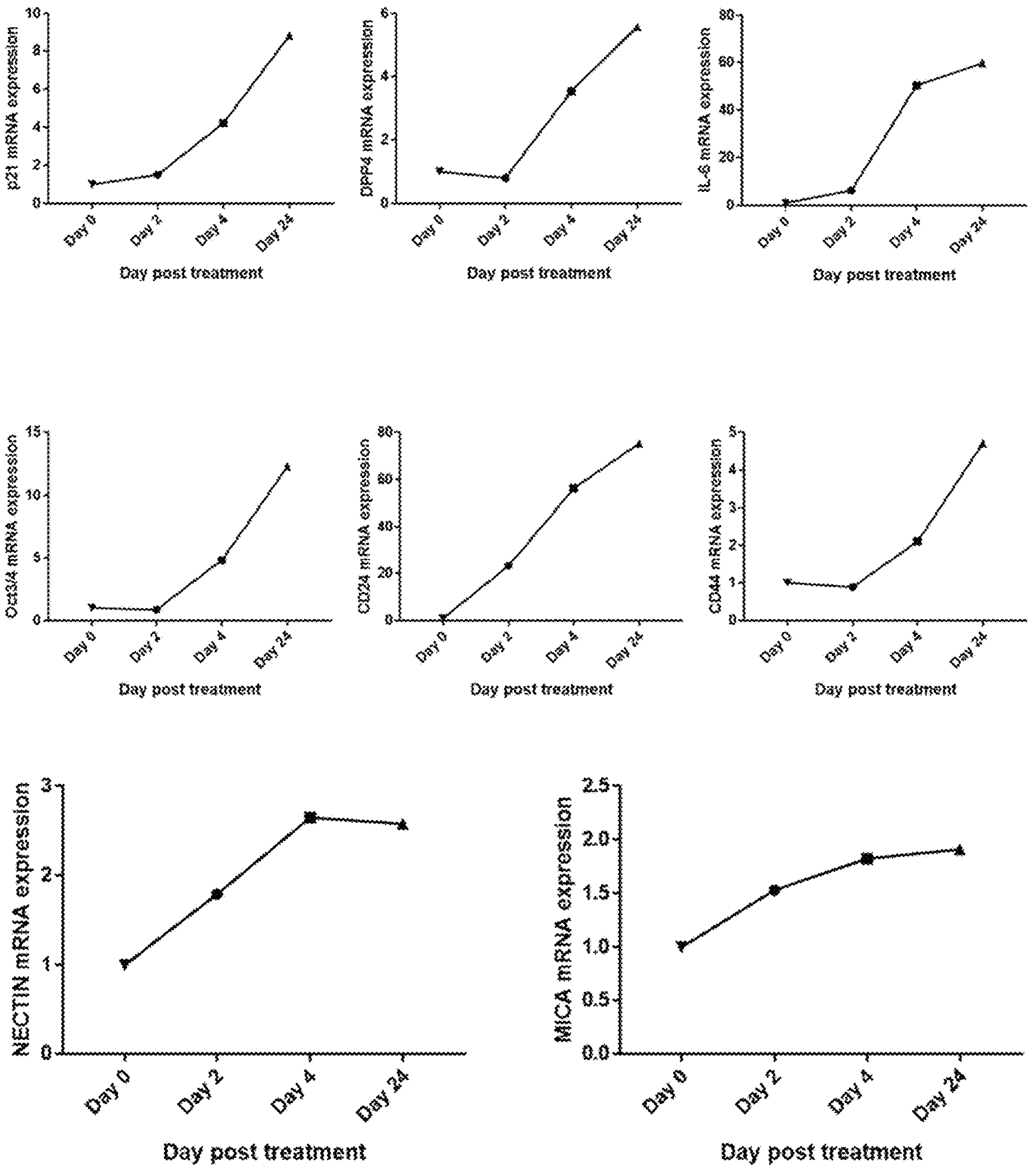

FIG. 15 shows expression of senescent markers by chemotherapy-induced senescent SW1990 cells.

Figure 16:
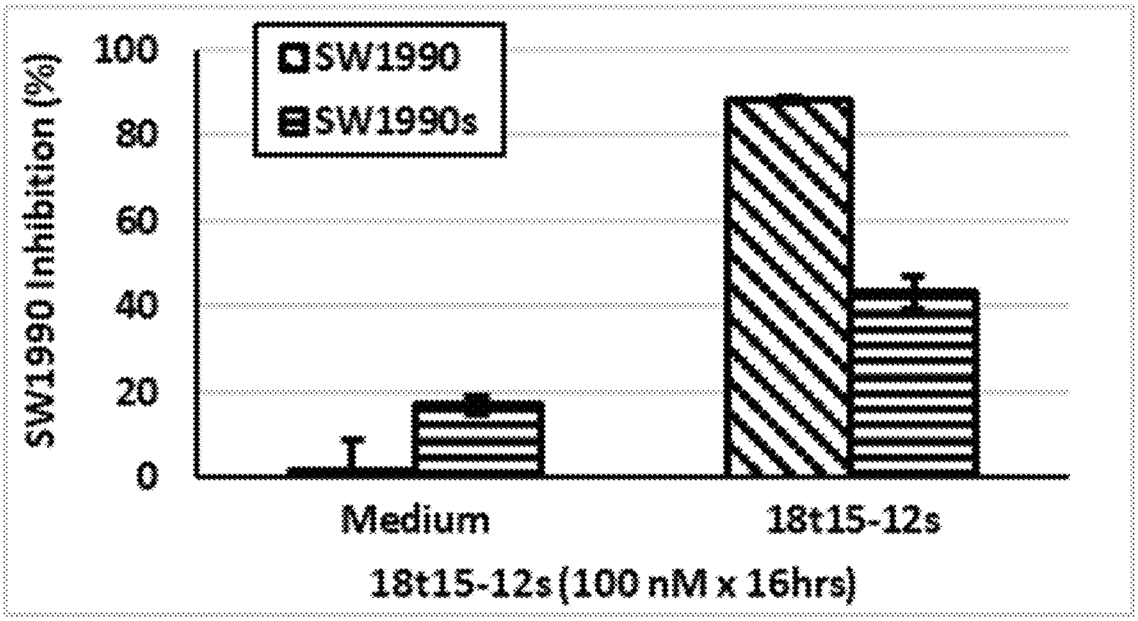

FIG. 16 shows the cytotoxicity of in vitro activated human NK cells against chemotherapy-induced senescent SW1990 cells or control SW1990 cells.

Figure 17:
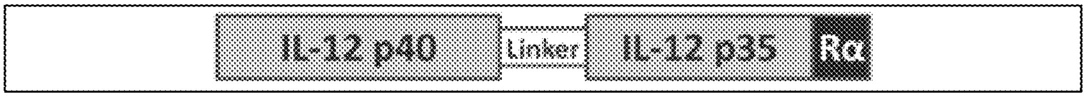

FIG. 17 shows a schematic diagram of an exemplary IL-12/IL-15RαSu DNA construct.

Figure 18:

FIG. 18 shows a schematic diagram of an exemplary IL-18/TF/IL-15 DNA construct.

Figure 19:
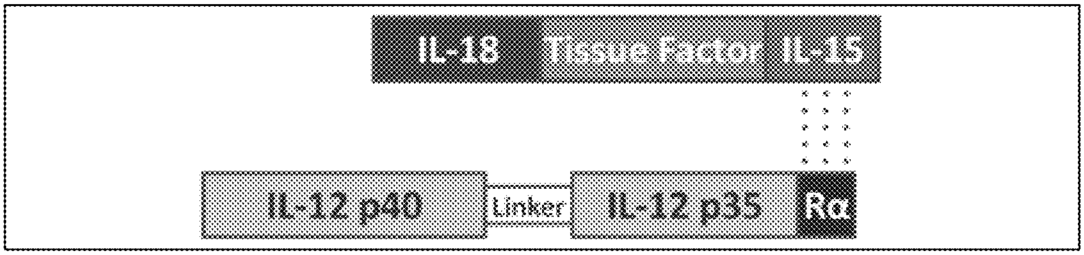

FIG. 19 shows a schematic diagram of the interaction between the exemplary IL-12/IL-15RαSu and IL-18/TF/IL-15 DNA constructs.

Figure 20:
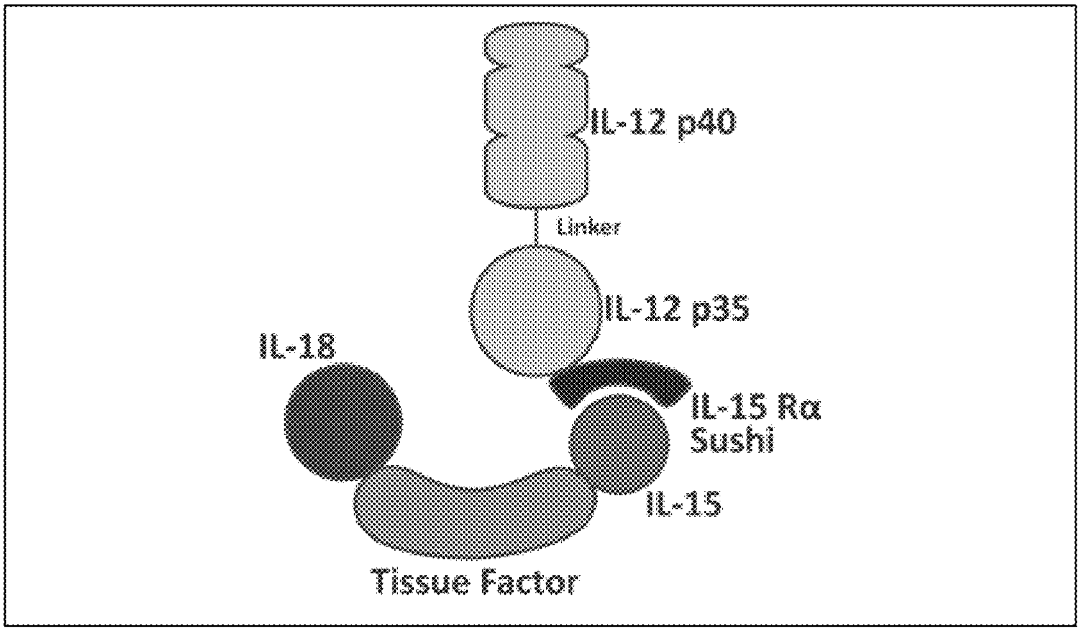

FIG. 20 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

Figure 21:
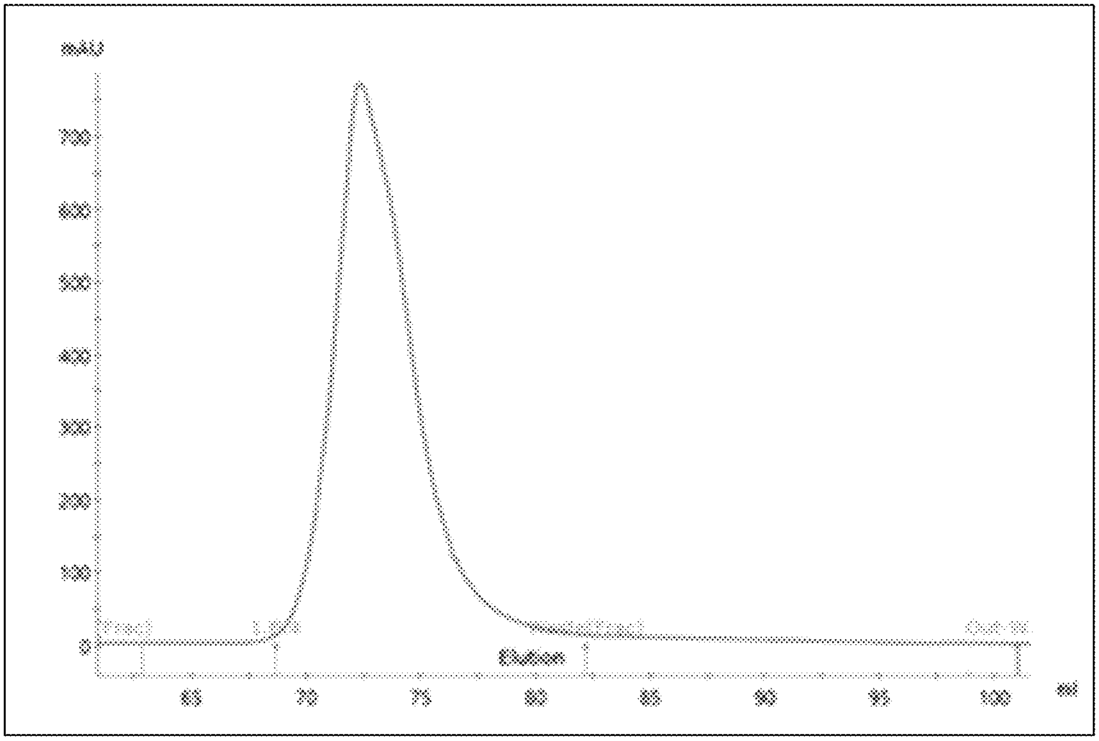

FIG. 21 shows a chromatograph of 18t15-12s purification elution from an anti-TF antibody affinity column.

Figure 22:
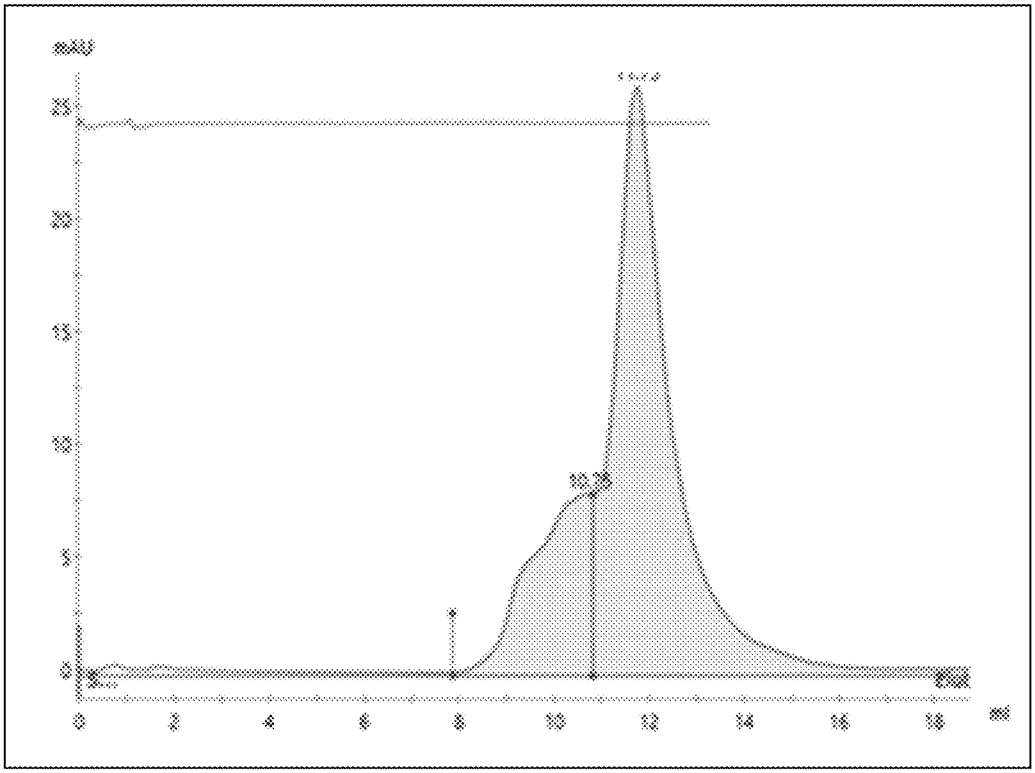

FIG. 22 shows an exemplary chromatographic profile of anti-TF Ab/SEC-purified 18t15-12s protein following elution on an analytical size exclusion column, demonstrating separation of monomeric multiprotein 18t15-12s complexes from protein aggregates.

Figure 23:
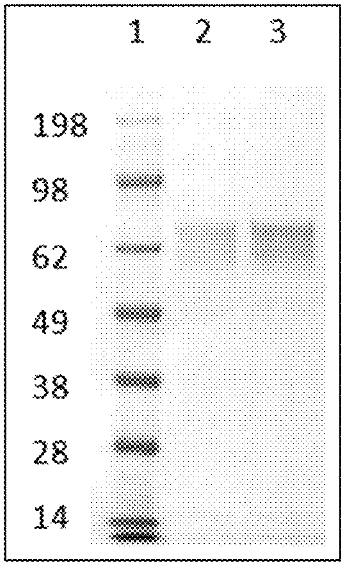

FIG. 23 shows an example of a 4-12% SDS-PAGE of the 18t15-12s complex following disulfide bond reduction. Lane 1: SeeBlue Plus2 marker; Lane 2: anti-TF Ab-purified 18t15-12s (0.5 μg); Lane 3: anti-TF Ab-purified 18t15-12s (1 μg).

Figure 24:
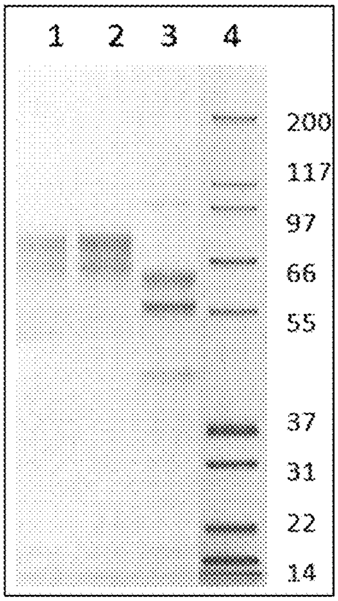

FIG. 24 shows SDS PAGE analysis of deglycosylated and non-deglycosylated 18t15-12s. Lane 1: anti-TF Ab-purified 18t15-12s (0.5 μg), non-deglycosylated; Lane 2: anti-TF Ab-purified 18t15-12s (1 μg), non-deglycosylated; Lane 3: 18t15-12s (1 μg), deglycosylated, Lane 4: Mark12 unstained maker.

Figure 25:
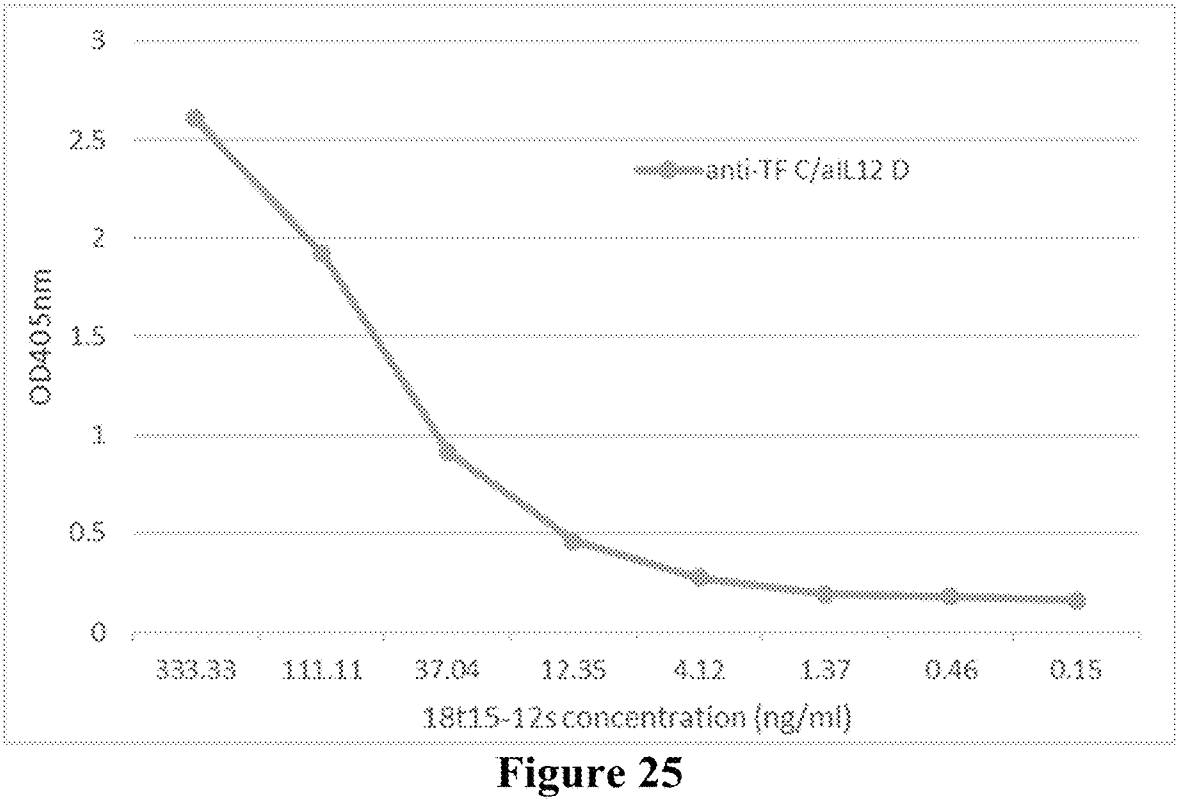

FIG. 25 shows a sandwich ELISA for the 18t15-12s complex, comprising an anti-human tissue factor antibody capture and a biotinylated anti-human IL-12 detection antibody (BAF 219).

Figure 26:
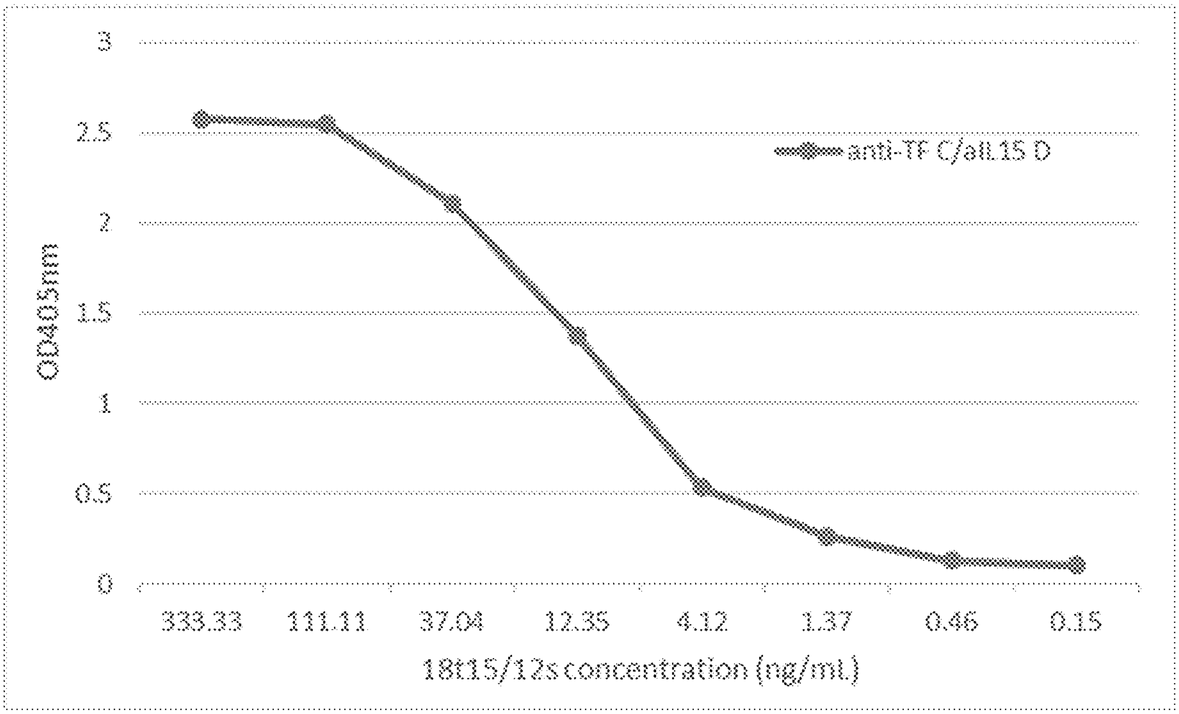

FIG. 26 shows a sandwich ELISA for the 18t15-12s complex, comprising an anti-human tissue factor antibody capture and a biotinylated anti-human IL-15 detection antibody (BAM 247).

Figure 27:
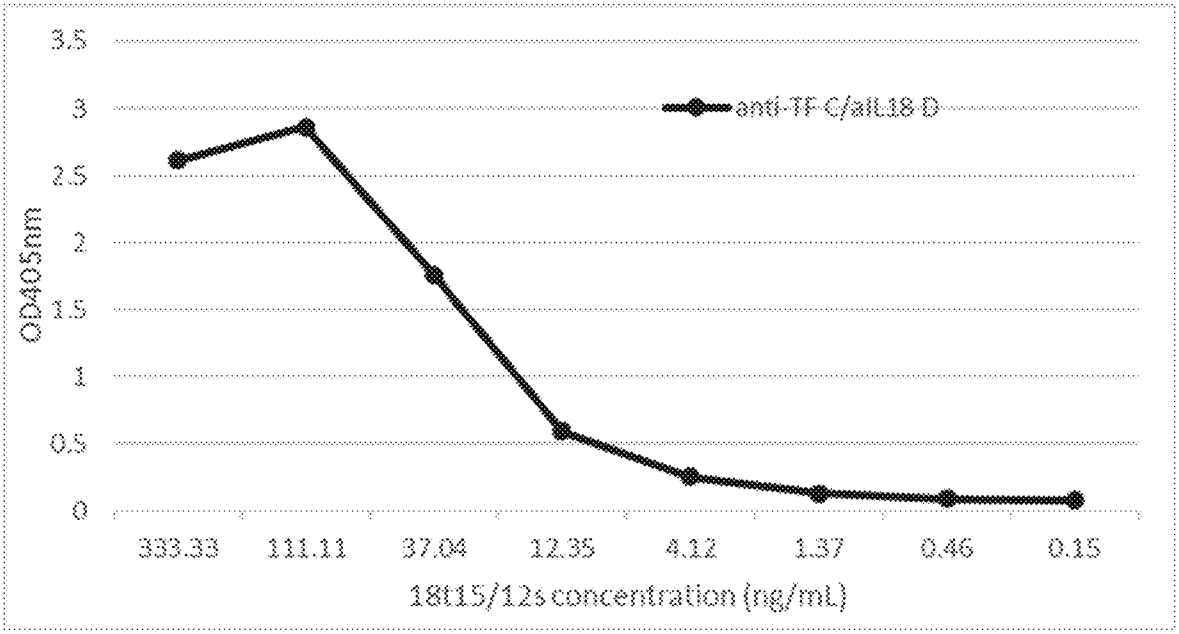

FIG. 27 shows a sandwich ELISA for the 18t15-12s complex, comprising an anti-human tissue factor antibody capture and a biotinylated anti-human IL-18 detection antibody (D045-6).

Figure 28:
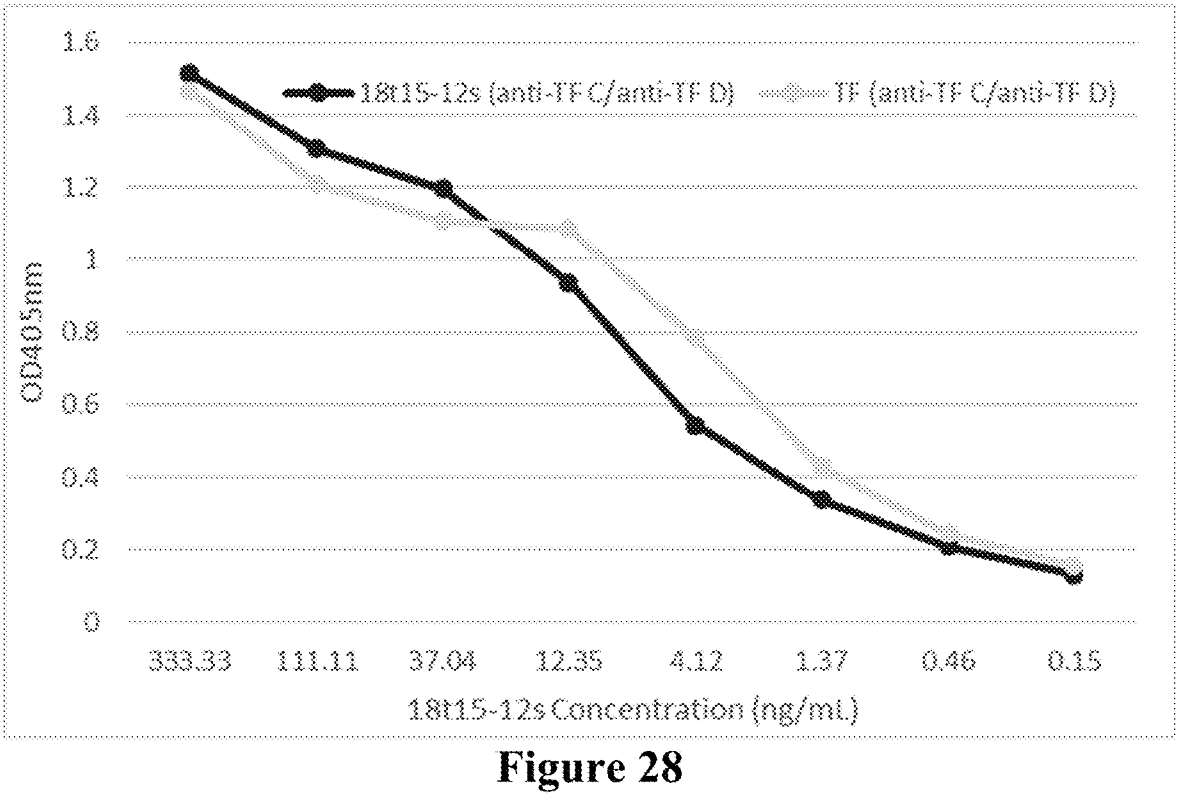

FIG. 28 shows a sandwich ELISA for the 18t15-12s complex, comprising an anti-human tissue factor (143) capture antibody and an anti-human tissue factor detection antibody.

Figure 29:
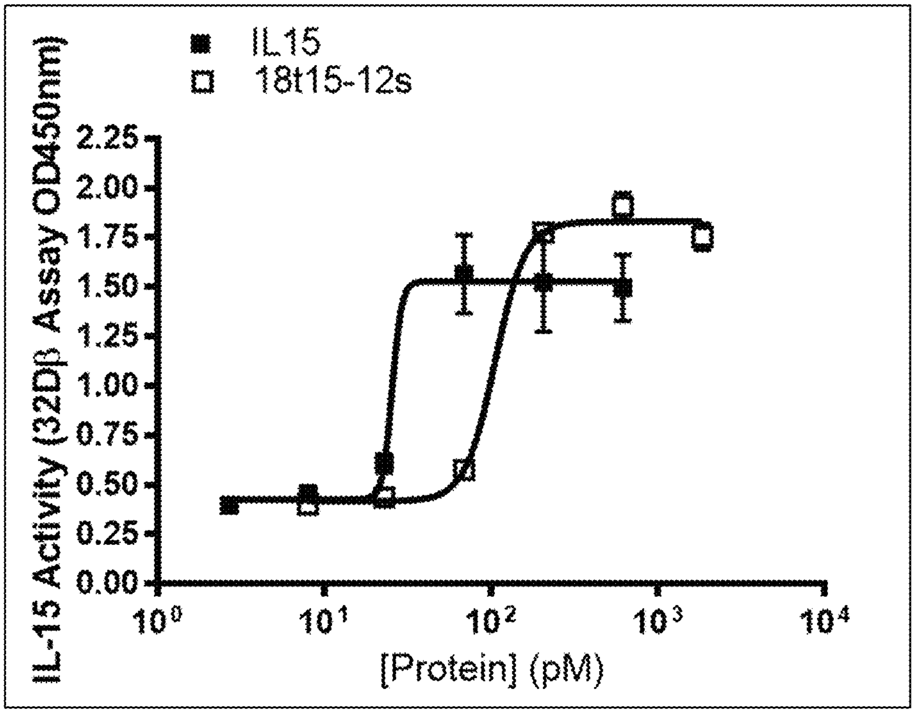

FIG. 29 shows proliferation of IL-15-dependent 32Dβ cells mediated by the 18t15-12s complex (open squares) and recombinant IL-15 (black squares).

Figure 30:
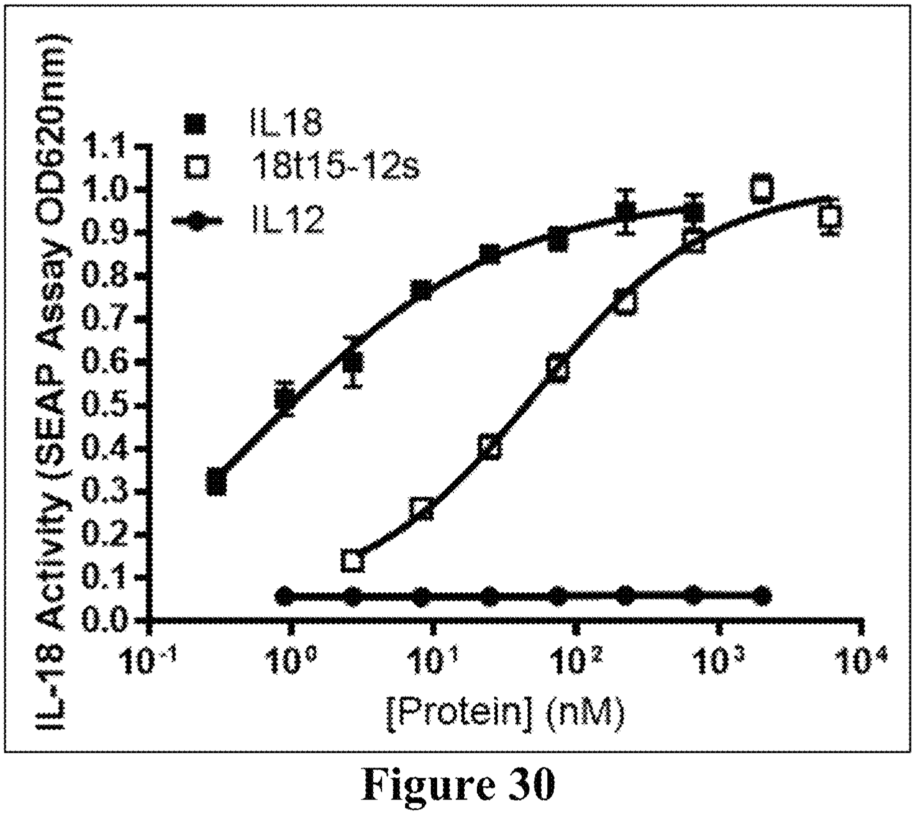

FIG. 30 shows biological activity of IL-18 within the 18t15-12s complex (open squares), where recombinant IL-18 (black squares) and recombinant IL-12 (black circles) serve as positive and negative controls, respectively.

Figure 31:
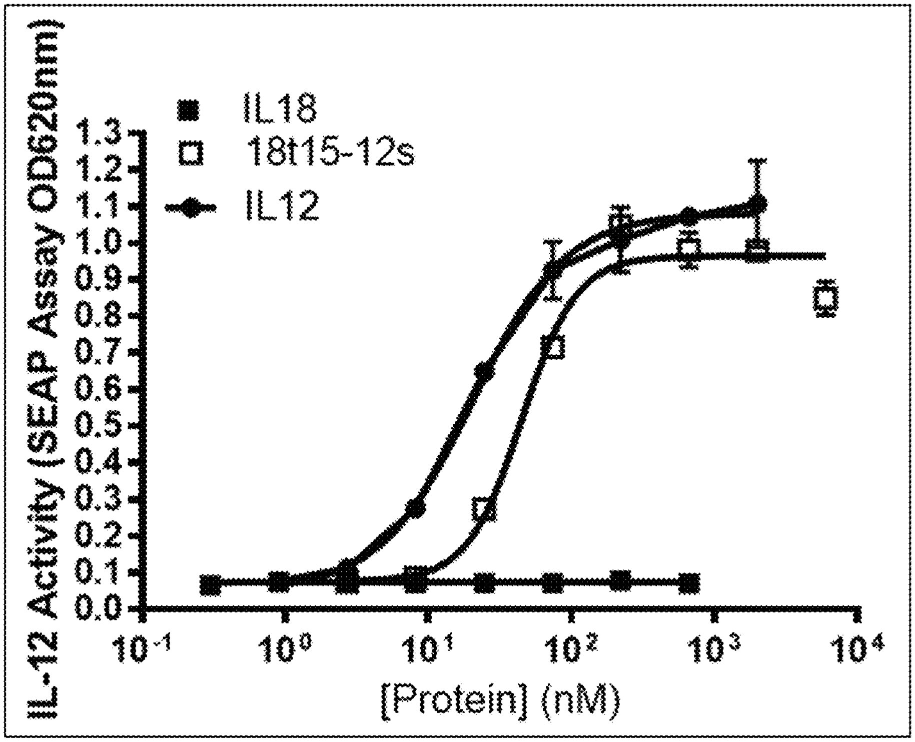

FIG. 31 shows biological activity of IL-12 within the 18t15-12s complex (open squares), where recombinant IL-12 (black circles) and recombinant IL-18 (open squares) serve as positive and negative controls, respectively.

Figure 32A:
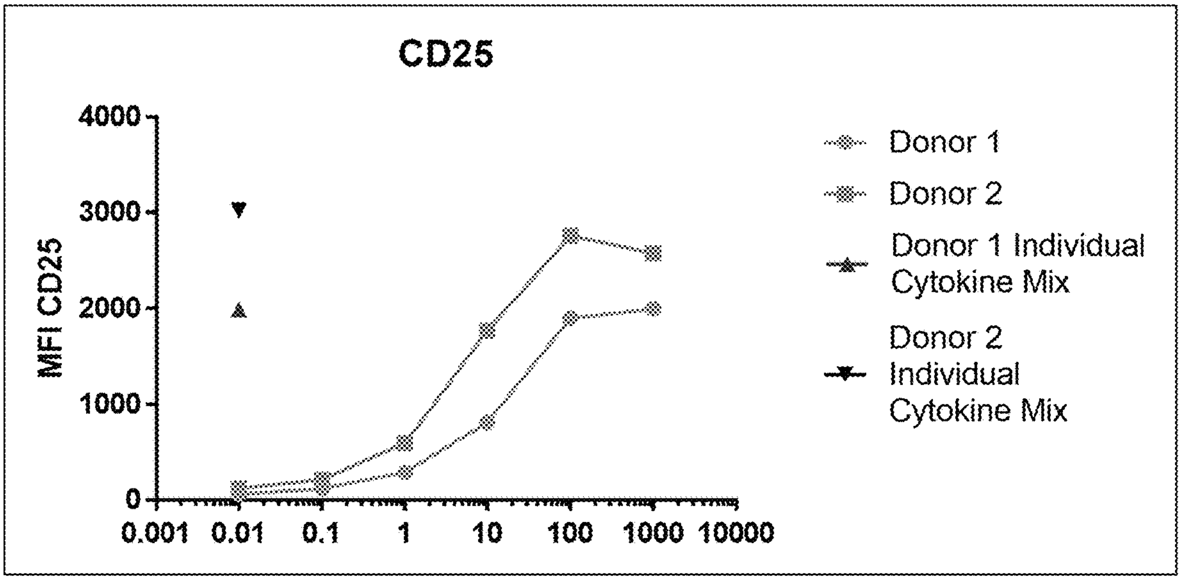
Figure 32B:
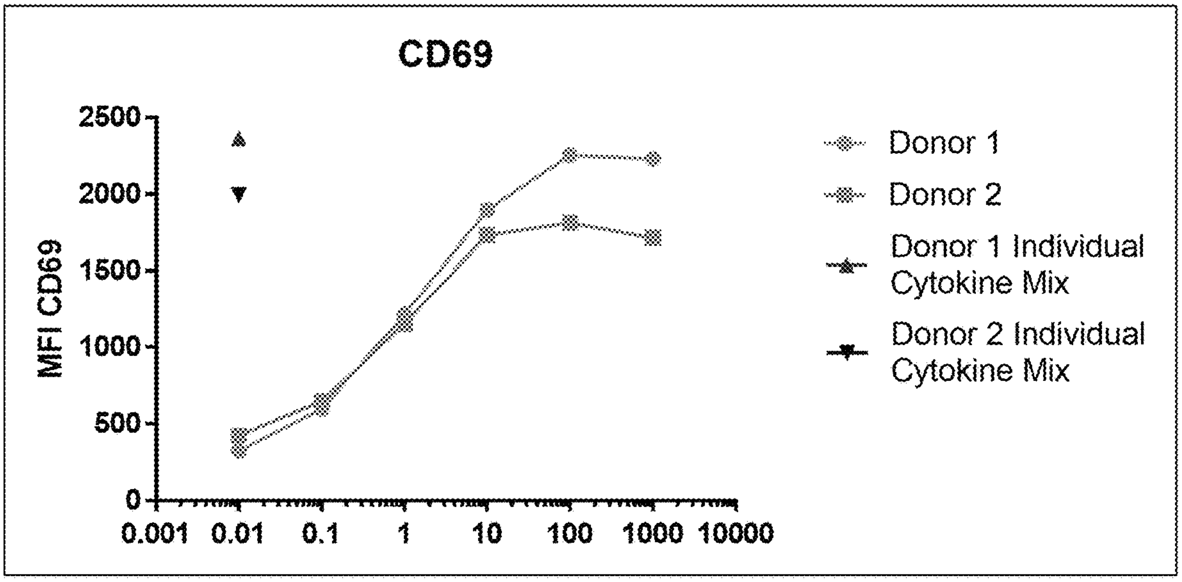

FIGS. 32A and 32B show cell-surface expression of CD25 on NK cells induced by the 18t15-12s complex and cell-surface CD69 expression of NK cells induced by the 18t15-12s complex.

Figure 33:
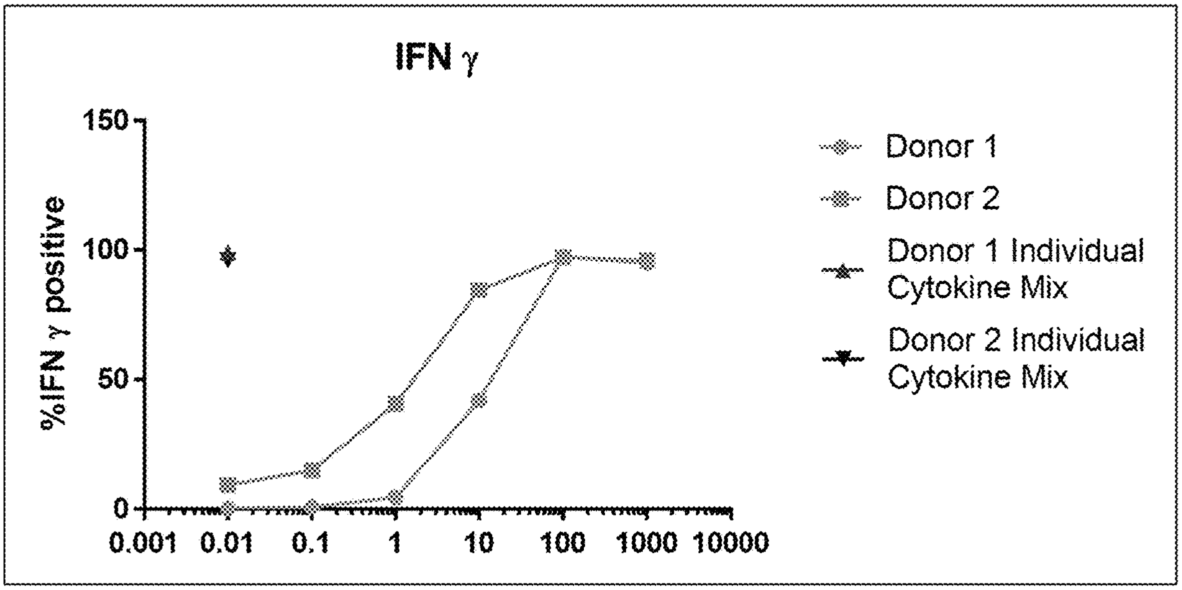

FIG. 33 shows a flow cytometry graph of intracellular IFN-γ expression of NK cells induced by the 18t15-12s complex.

Figure 34:
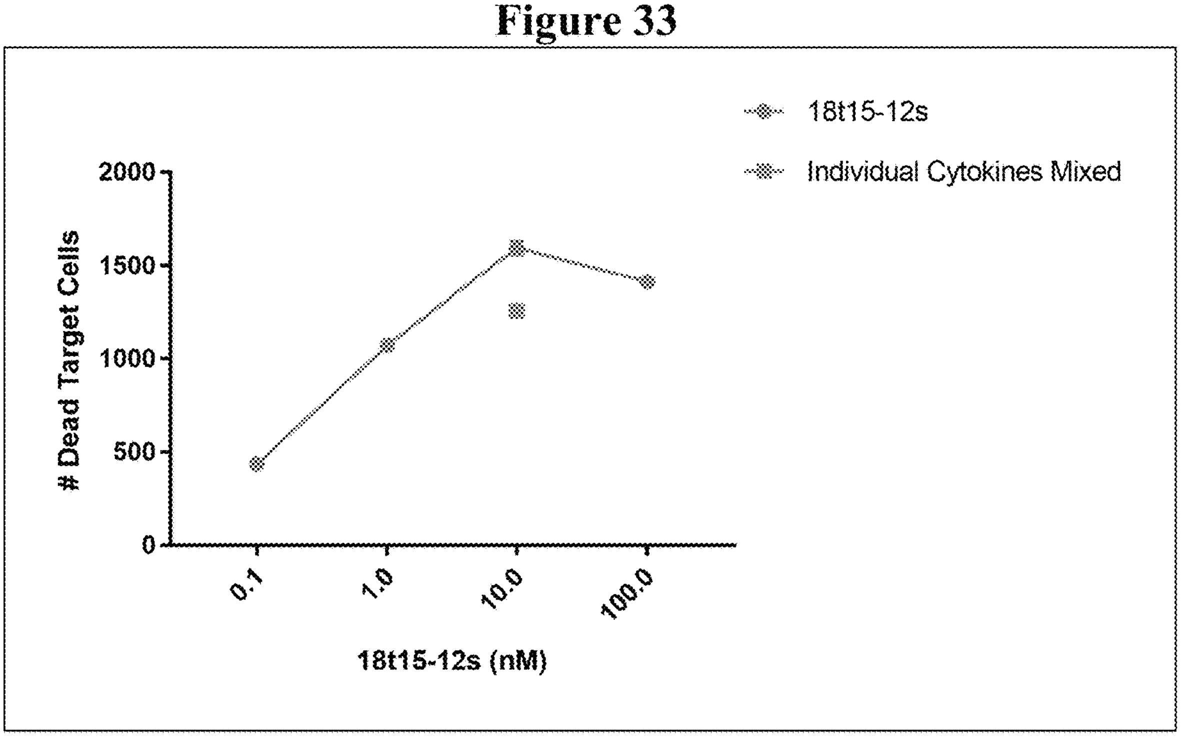

FIG. 34 shows cytotoxicity of 18t15-12s induced human NK cells against K562 cells.

Figure 35:
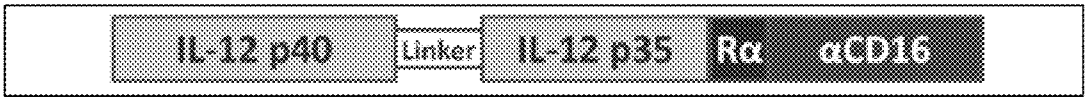

FIG. 35 shows a schematic diagram of an exemplary IL-12/IL-15RαSu/αCD16 DNA construct.

Figure 36:

FIG. 36 shows a schematic diagram of an exemplary IL-18/TF/IL-15 DNA construct.

Figure 37:
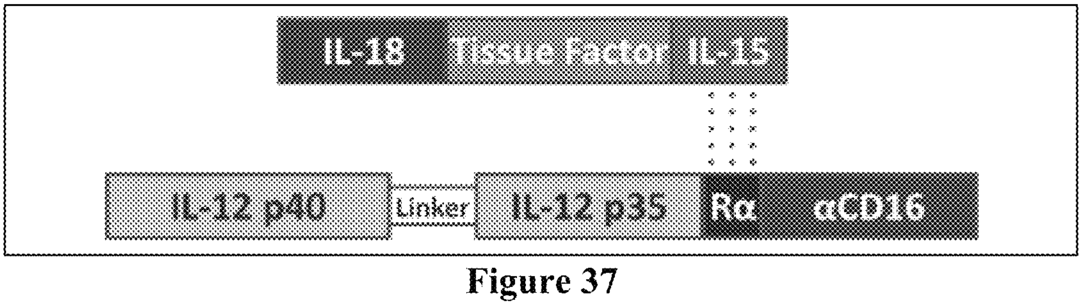

FIG. 37 shows a schematic diagram of the interaction between the exemplary IL-12/IL-15RαSu/αCD16scFv and IL-18/TF/IL-15 DNA constructs.

Figure 38:
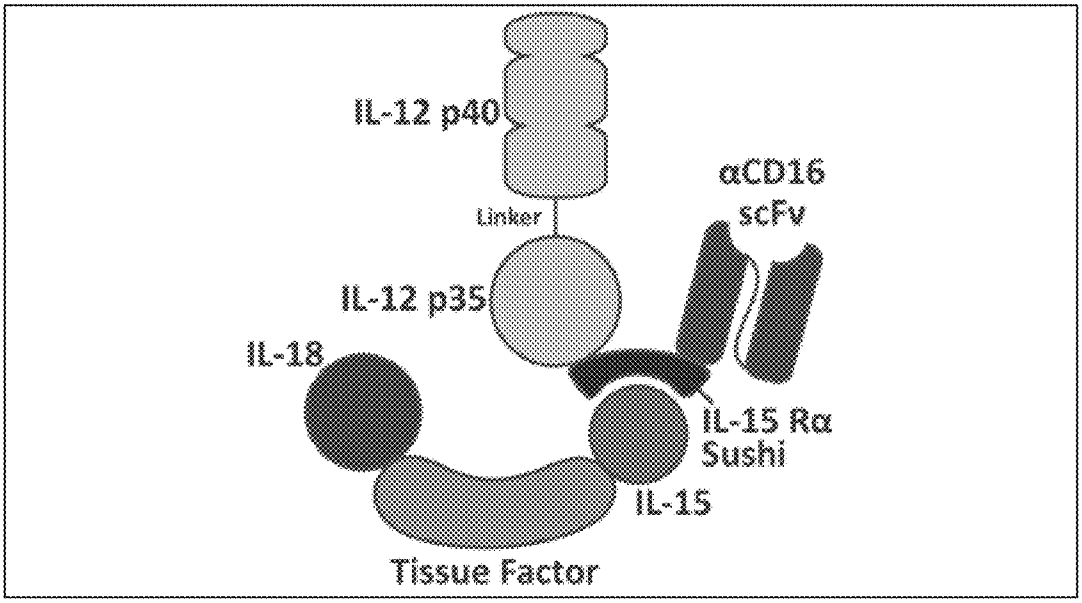

FIG. 38 shows a schematic diagram of an exemplary 18t15-12s/αCD16 protein complex.

Figure 39:
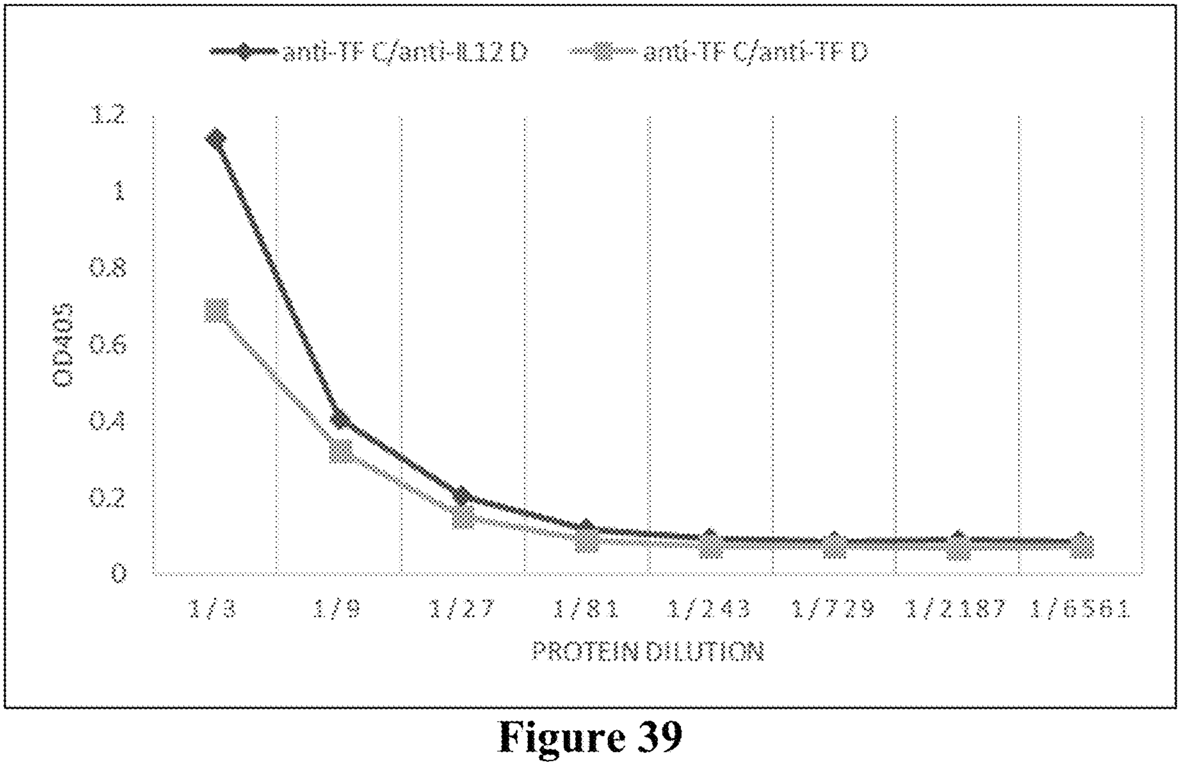

FIG. 39 shows a sandwich ELISA for the 18t15-12s16 complex, comprising an anti-human tissue factor antibody capture antibody and a biotinylated anti-human IL-12 (BAF 219) (dark line) or an anti-human tissue factor detection antibody (light line).

Figure 40:

FIG. 40 shows a schematic diagram of an exemplary TGFβRII/IL-15RαSu DNA construct.

Figure 41:

FIG. 41 shows a schematic diagram of an exemplary IL-21/TF/IL-15 construct.

Figure 42:
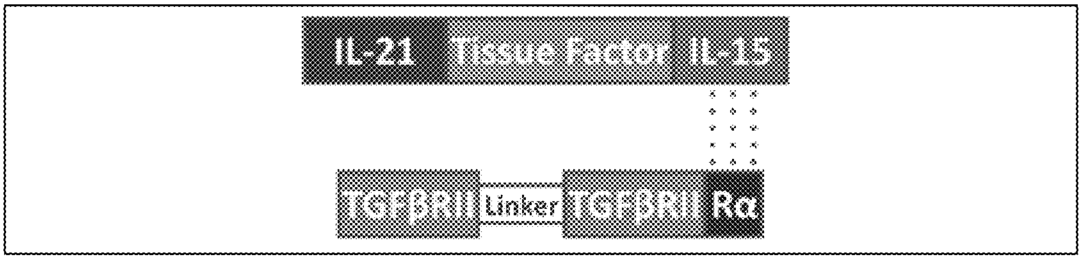

FIG. 42 shows a schematic diagram of the interaction between the exemplary IL-IL-21/TF/IL-15 and TGFβRII/IL-15RαSu constructs.

Figure 43:
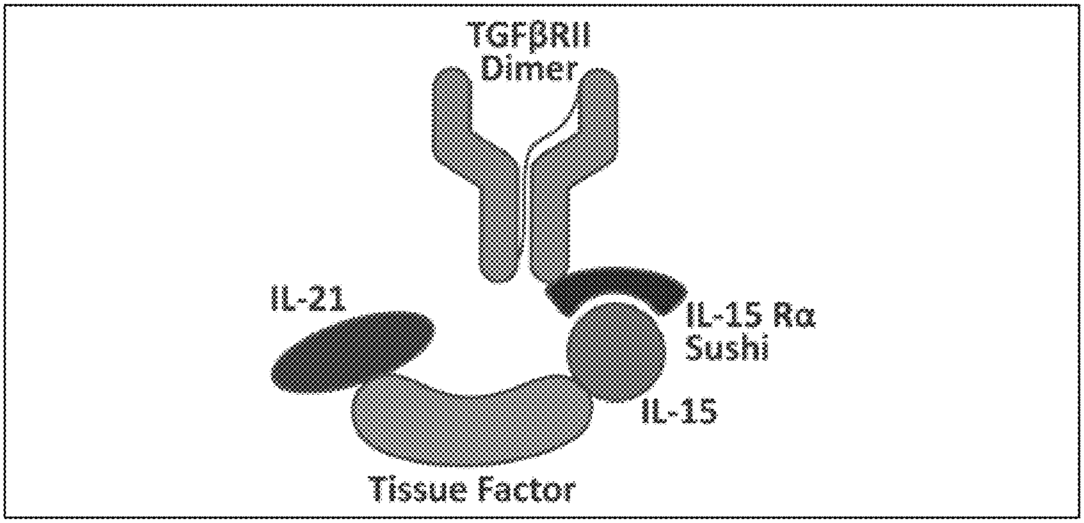

FIG. 43 shows a schematic diagram of the interaction between the exemplary TGFβRII/IL-15RαSu and IL-21/TF/IL-15 fusion proteins, resulting in an IL-21/TF/IL-15/TGFβRII/IL-15RαSu complex (21t15-TGFRs).

Figure 44:
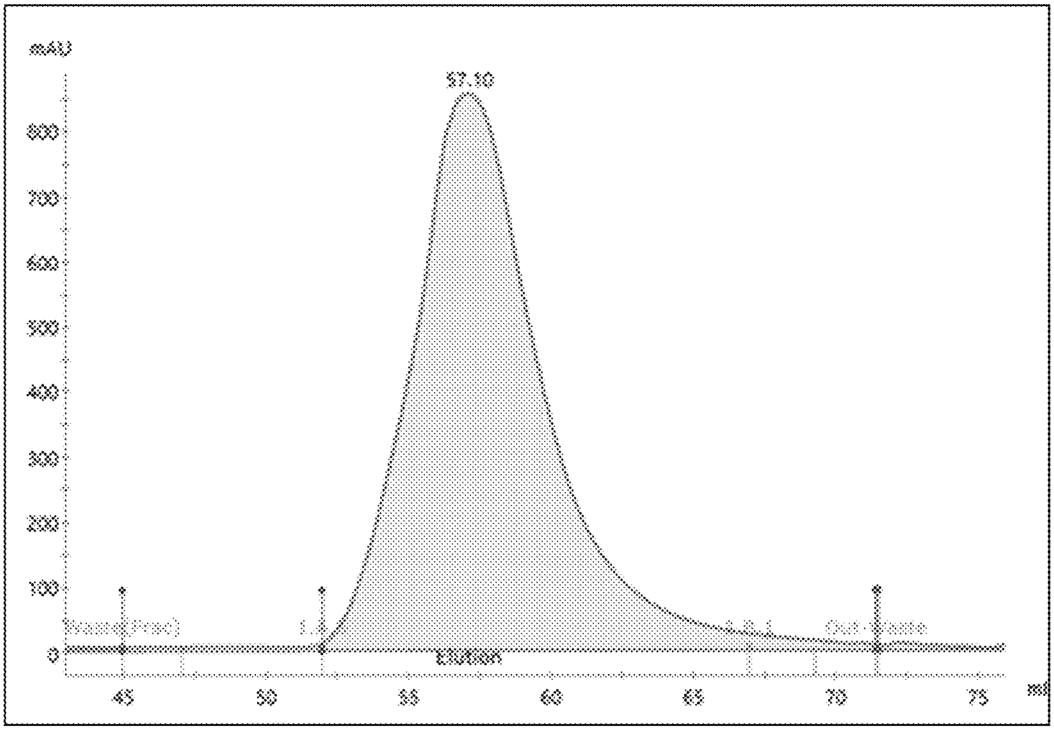

FIG. 44 shows a chromatograph of 21t15-TGFRs purification elution from an anti-TF antibody affinity column.

Figure 45:
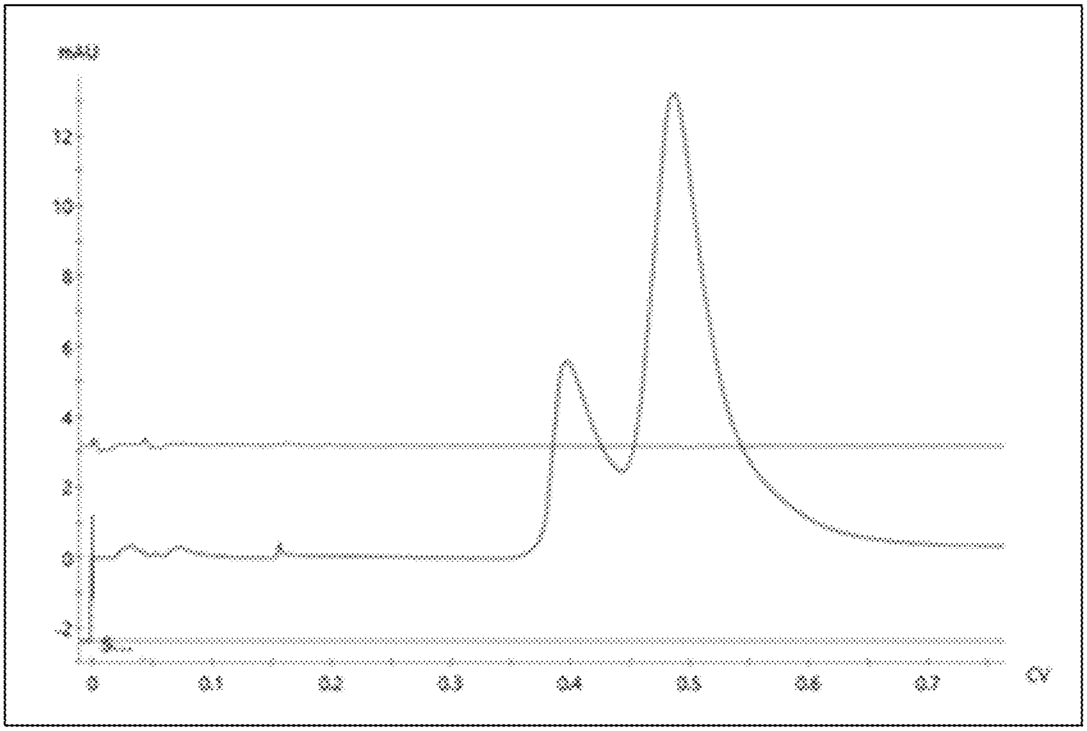
Figure 46:
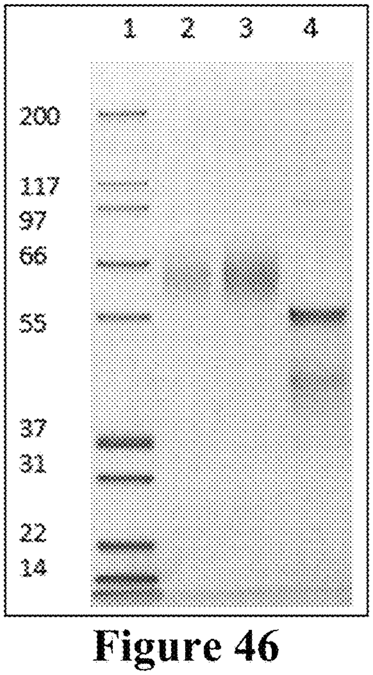

FIG. 45 shows an exemplary 21t15-TGFRs size exclusion chromatograph showing a main protein peak and a high molecular weight peak FIG. 46 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 μg); Lane 3: 21t15-TGFRs (1 μg); Lane 4: 21t15-TGFRs, deglycosylated (1 μg), wherein the MW was the expected size of 53 kDa and 39.08 kDa.

Figure 47:
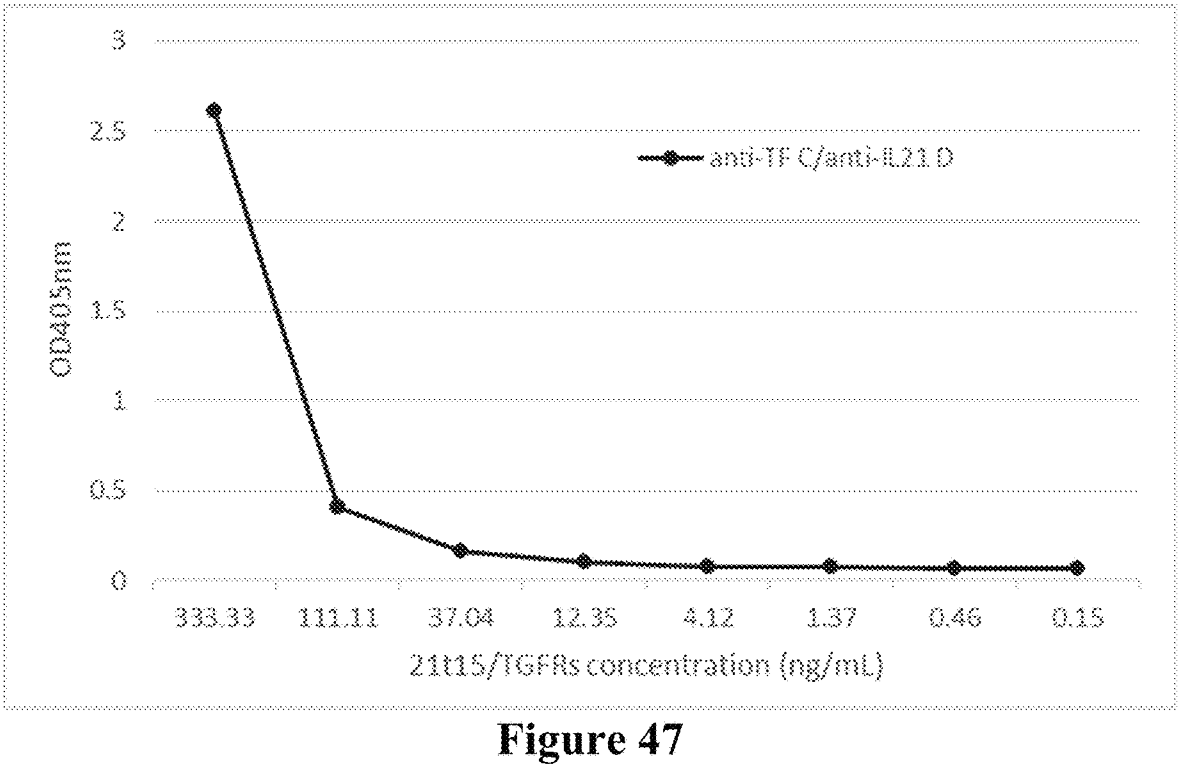

FIG. 47 shows a sandwich ELISA for the 21t15-TGFRs complex, comprising an anti-human tissue factor capture and a biotinylated anti-human IL-21 detection antibody (13-7218-81, BioLegend).

Figure 48:
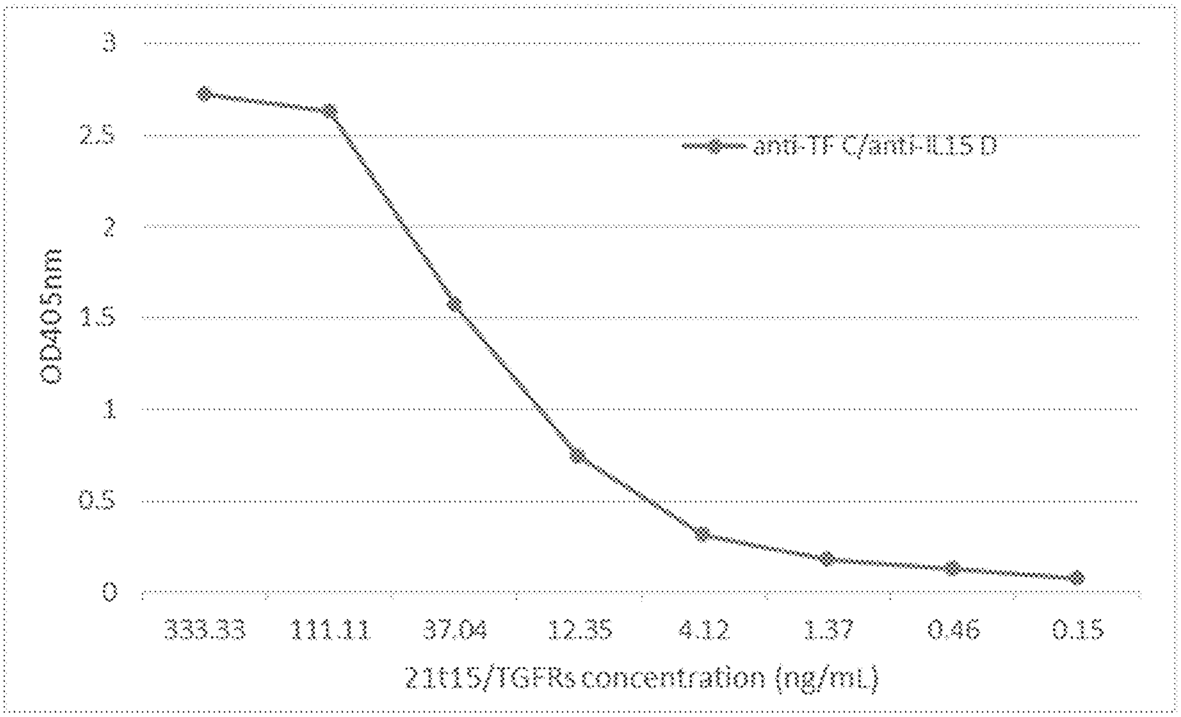

FIG. 48 shows a sandwich ELISA for the 21t15-TGFRs complex, comprising an anti-human tissue factor antibody capture and a biotinylated anti-human IL-15 detection antibody (BAM 247, R&D Systems).

Figure 49:
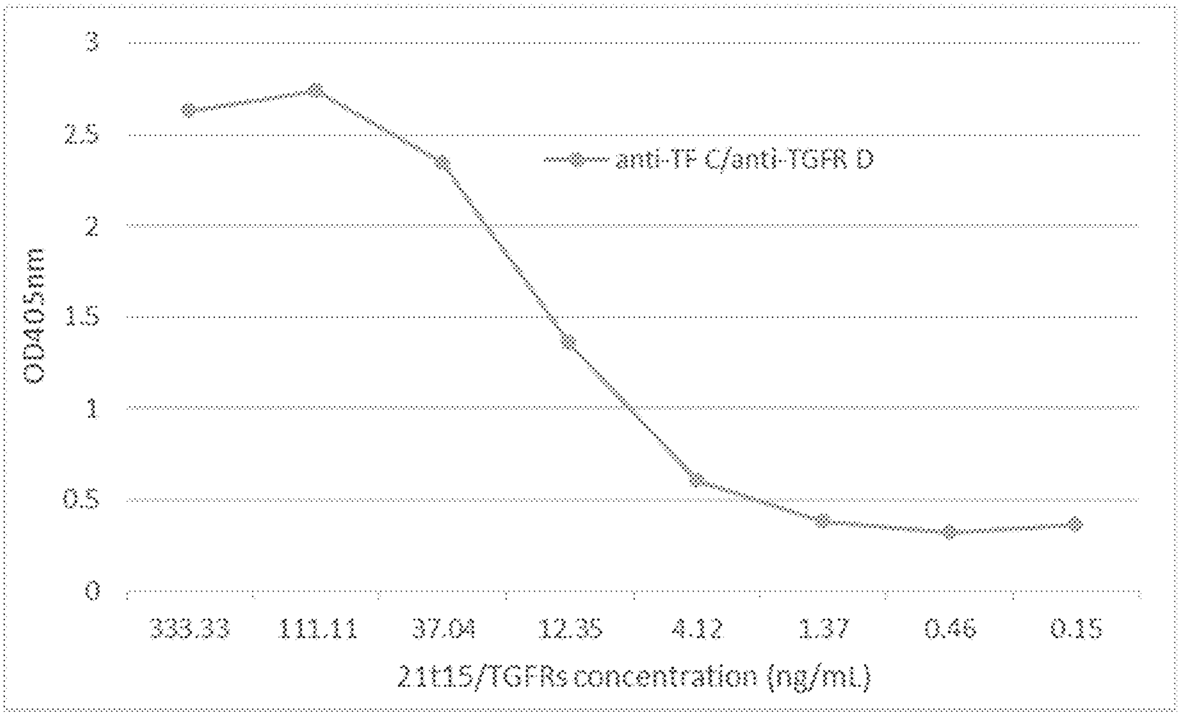

FIG. 49 shows a sandwich ELISA for the 21t15-TGFRs complex, comprising an anti-human tissue factor antibody capture and a biotinylated anti-human TGFβRII detection antibody (BAF241, R&D Systems).

Figure 50:
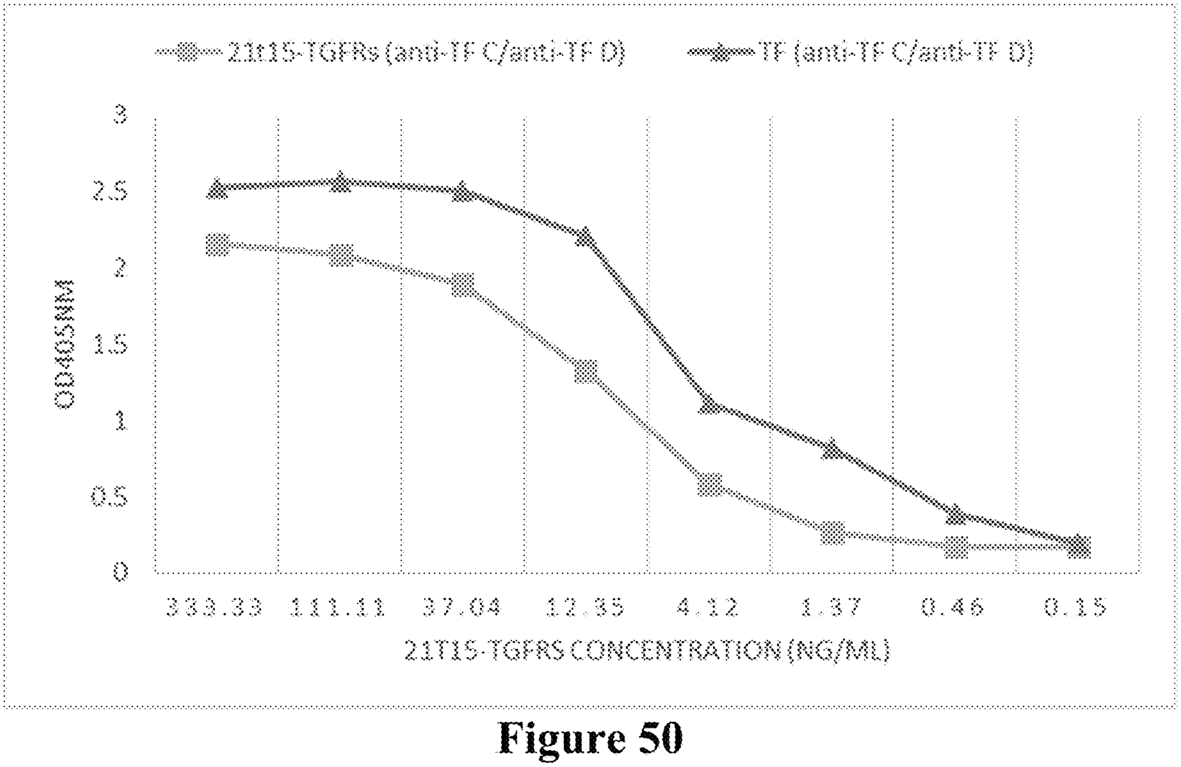

FIG. 50 shows a sandwich ELISA for the 21t15-TGFRs complex, comprising an anti-human tissue factor (143) capture antibody and an anti-human tissue factor detection antibody.

Figure 51:
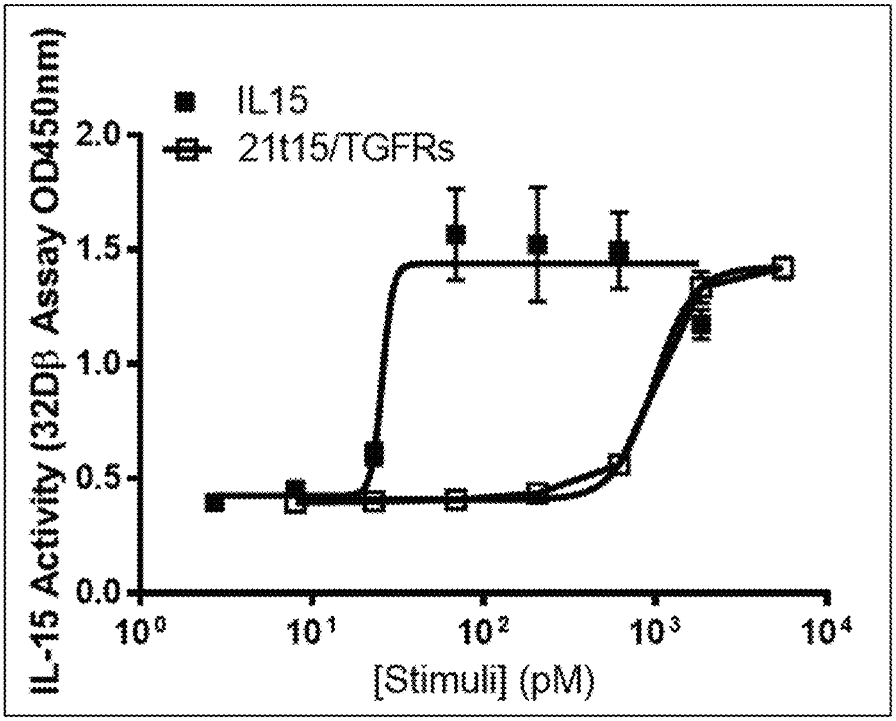

FIG. 51 shows IL-15-dependent proliferation of 32Dβ cells mediated by the 21t15-TGFRs complex (open squares) compared to IL-15 (black squares).

Figure 52:
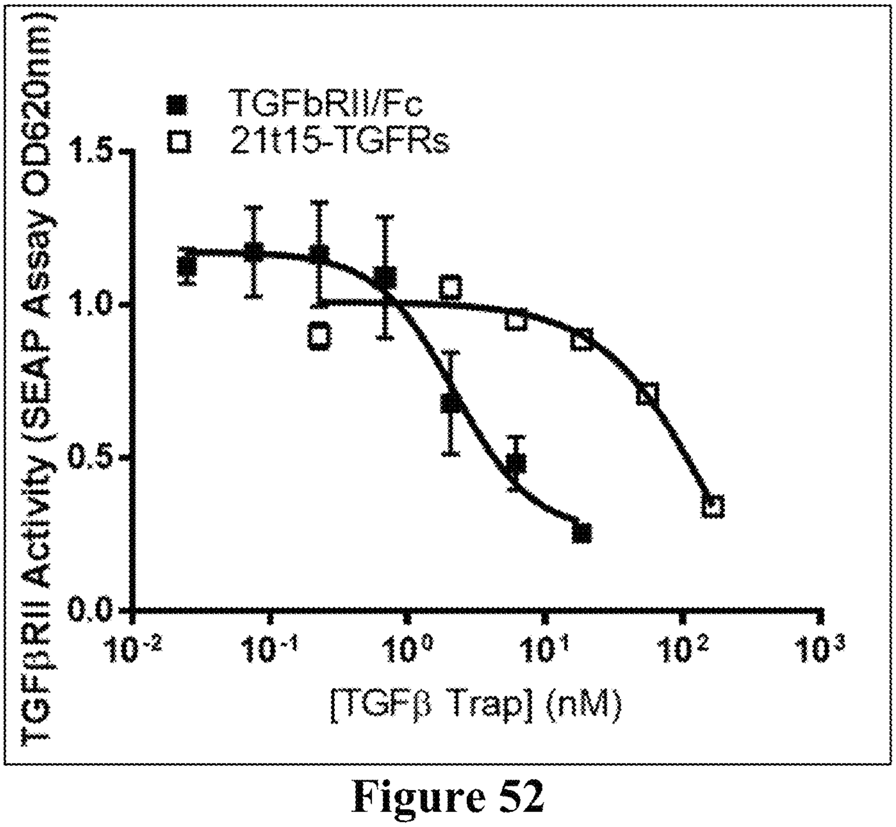

FIG. 52 shows biological activity of the TGFβRII domain within the 21t15-TGFRs complex (open squares). TGFβRII/Fc (black squares) served as a positive control.

Figure 53:
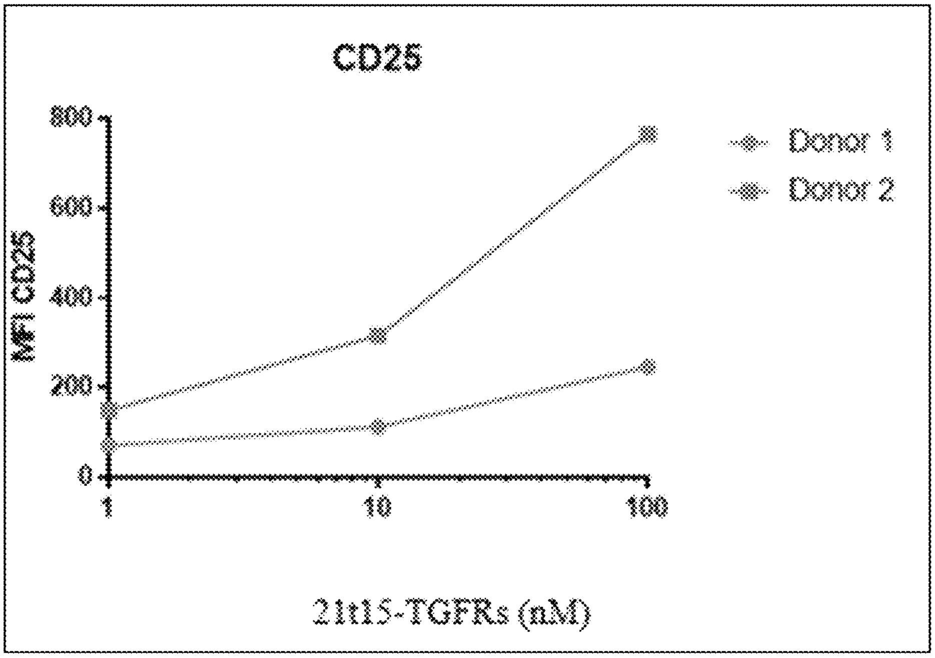

FIG. 53 shows a flow cytometry graph of cell-surface CD25 expression of NK cells induced by the 21t15-TGFRs complex.

Figure 54:
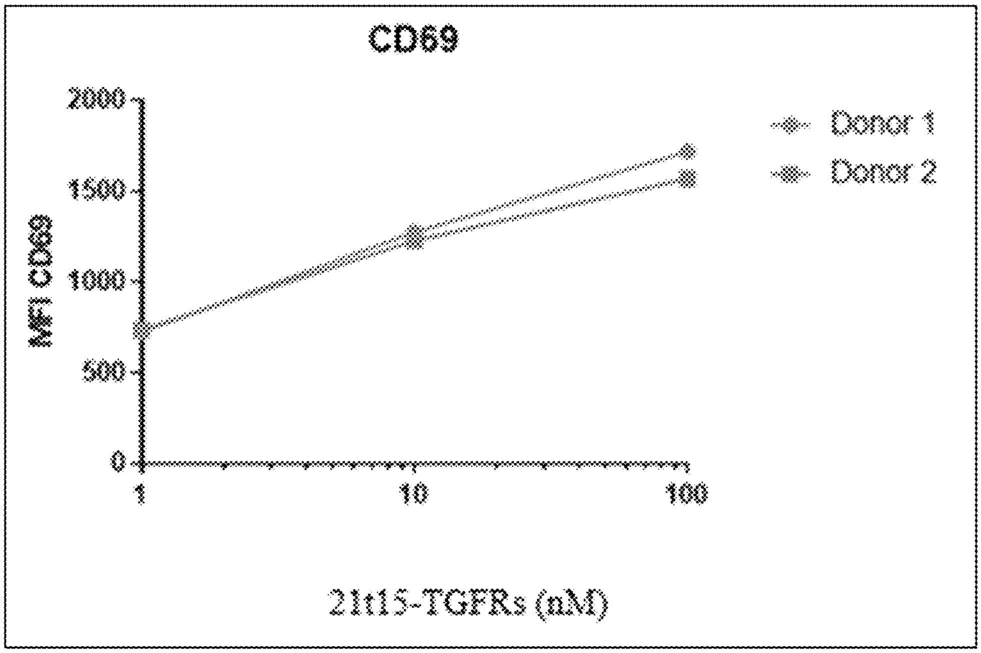

FIG. 54 shows a flow cytometry graph of cell-surface CD69 expression of NK cells induced by the 21t15-TGFRs complex.

Figure 55:
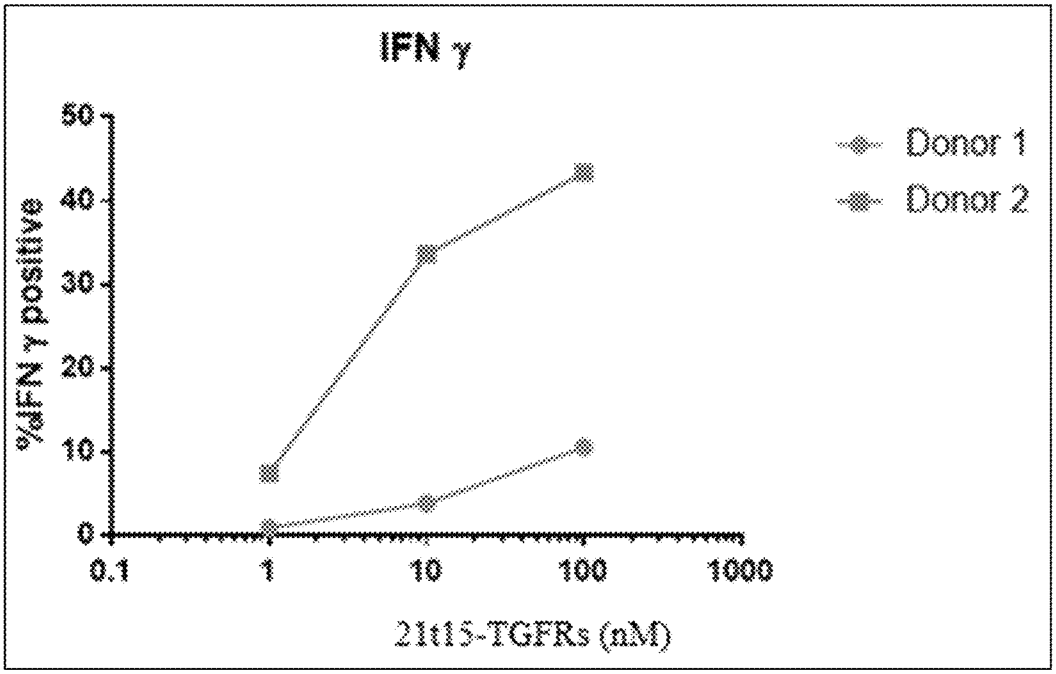

FIG. 55 shows a flow cytometry graph of intracellular IFN-γ expression of NK cells induced by the 21t15-TGFRs complex.

Figure 56:
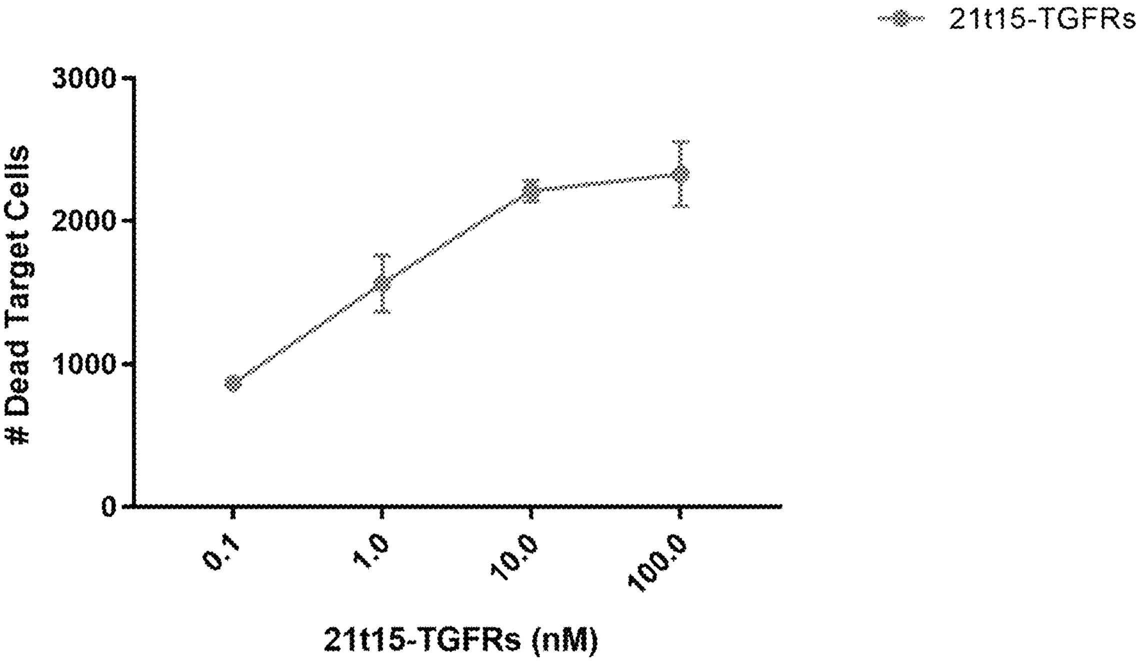

FIG. 56 shows cytotoxicity of 21t15-TGFRs-induced human NK cells against K562 cells.

Figure 57:
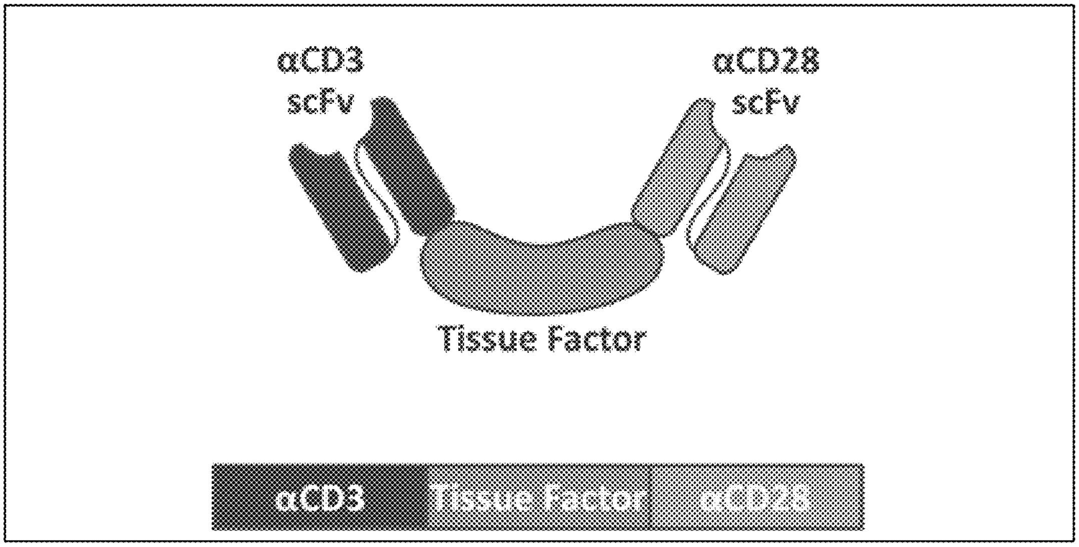

FIG. 57 are schematic diagrams of an exemplary αCD3scFv/TF/αCD28scFv single-chain chimeric polypeptide.

Figure 58:
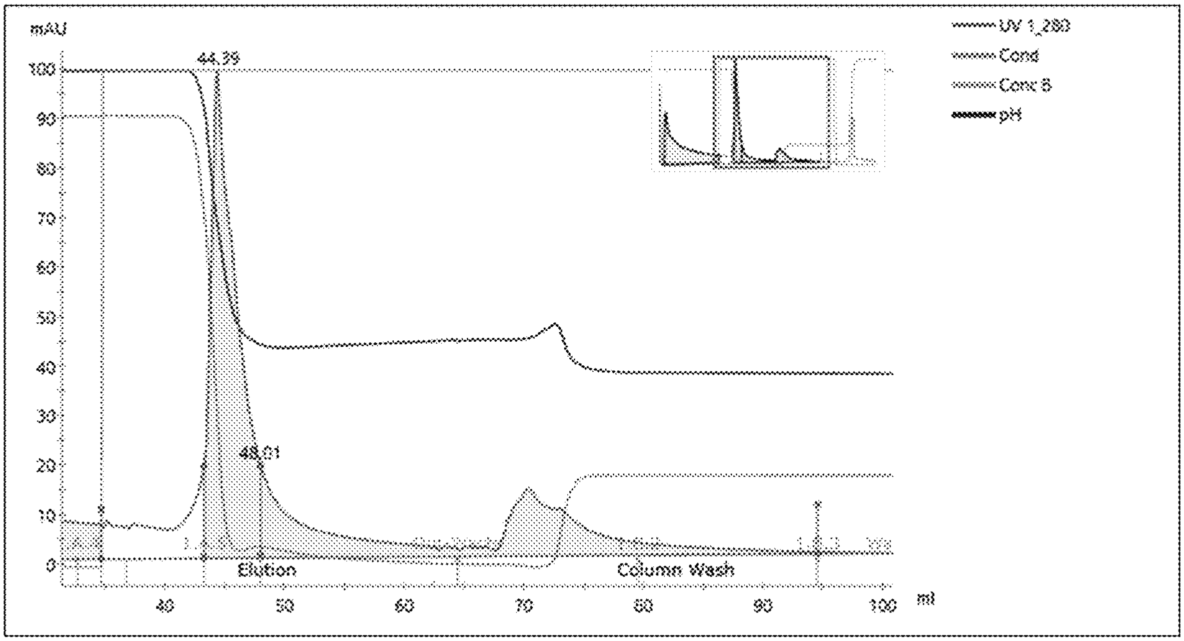

FIG. 58 is a chromatograph showing the elution of an exemplary αCD3scFv/TF/αCD28scFv single-chain chimeric polypeptide from an anti-tissue factor affinity column.

Figure 59:
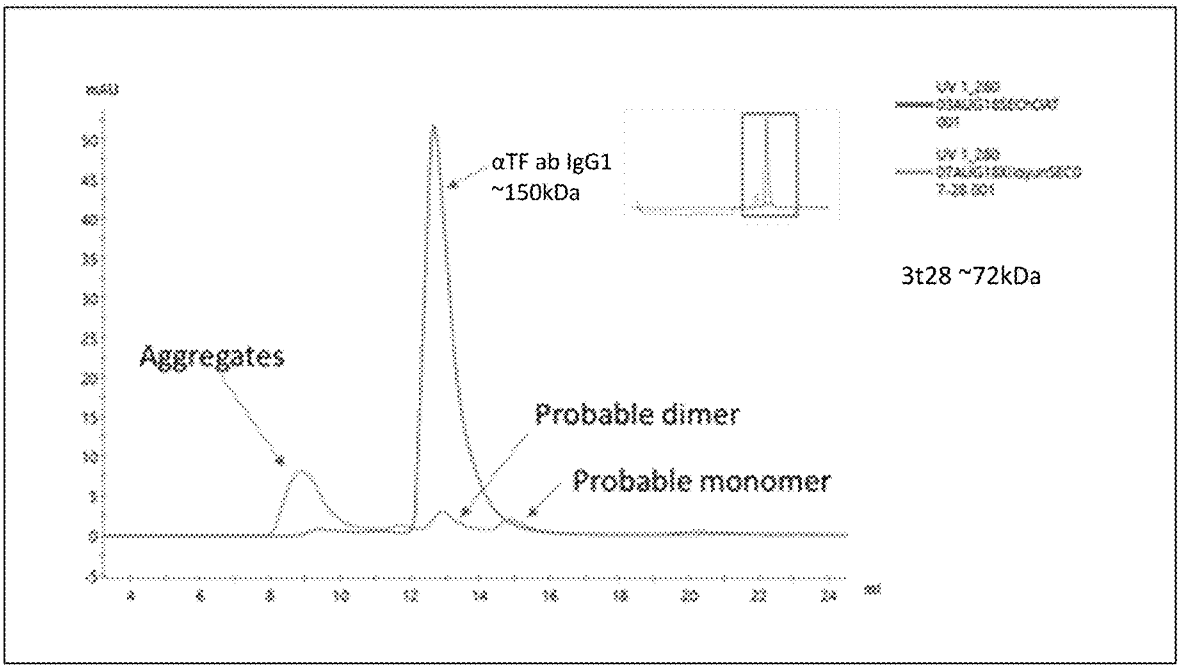

FIG. 59 is a chromatograph showing the elution of a Superdex 200 Increase 10/300 GL gel filtration column loaded with an exemplary αCD3scFv/TF/αCD28scFv single-chain chimeric polypeptide.

Figure 60:
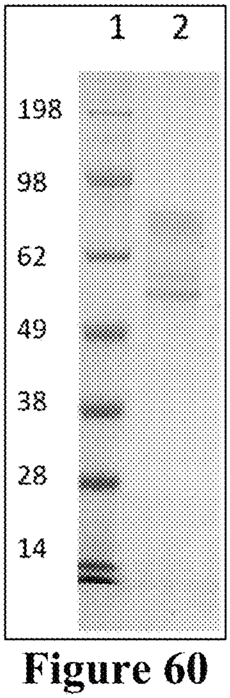

FIG. 60 is a sodium dodecyl sulfate polyacrylamide gel (4-12% NuPage Bis-Tris gel) of an exemplary αCD3scFv/TF/αCD28scFv single-chain chimeric polypeptide purified using an anti-tissue factor affinity column.

Figure 61:
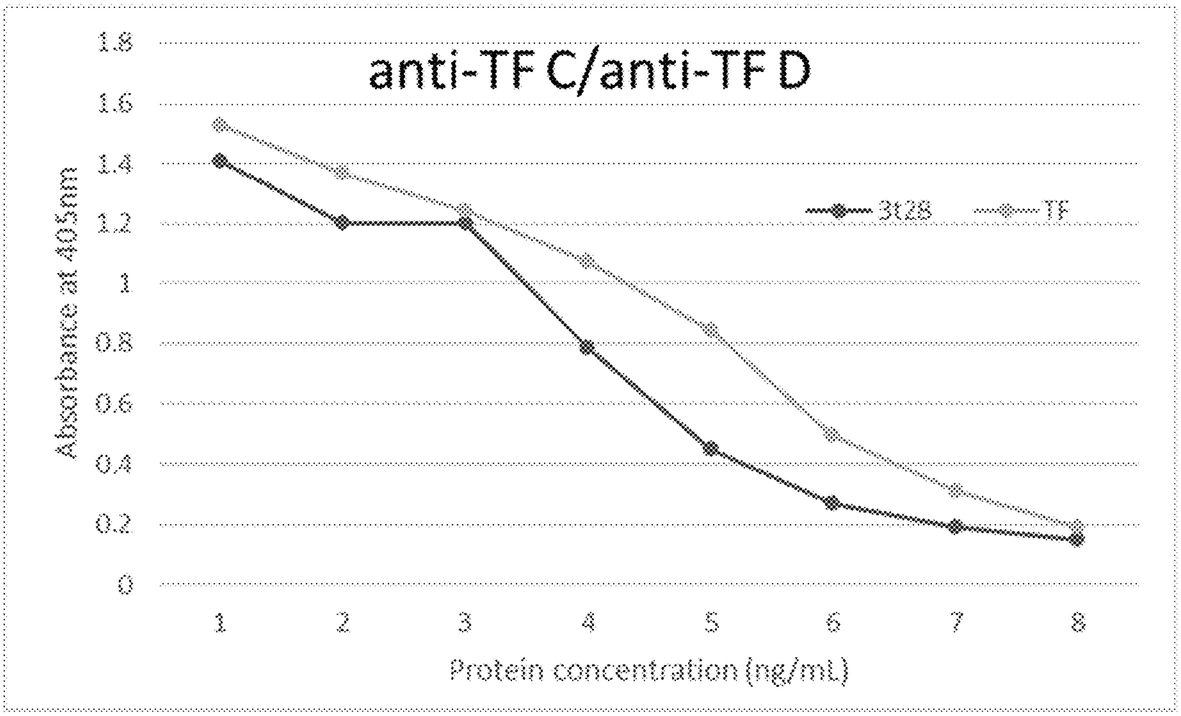

FIG. 61 is a graph showing the ELISA quantitation of an exemplary αCD3scFv/TF/αCD28scFv single-chain chimeric polypeptide performed using the methods described in Example 1. Purified tissue factor was used as the control.

Figure 62:
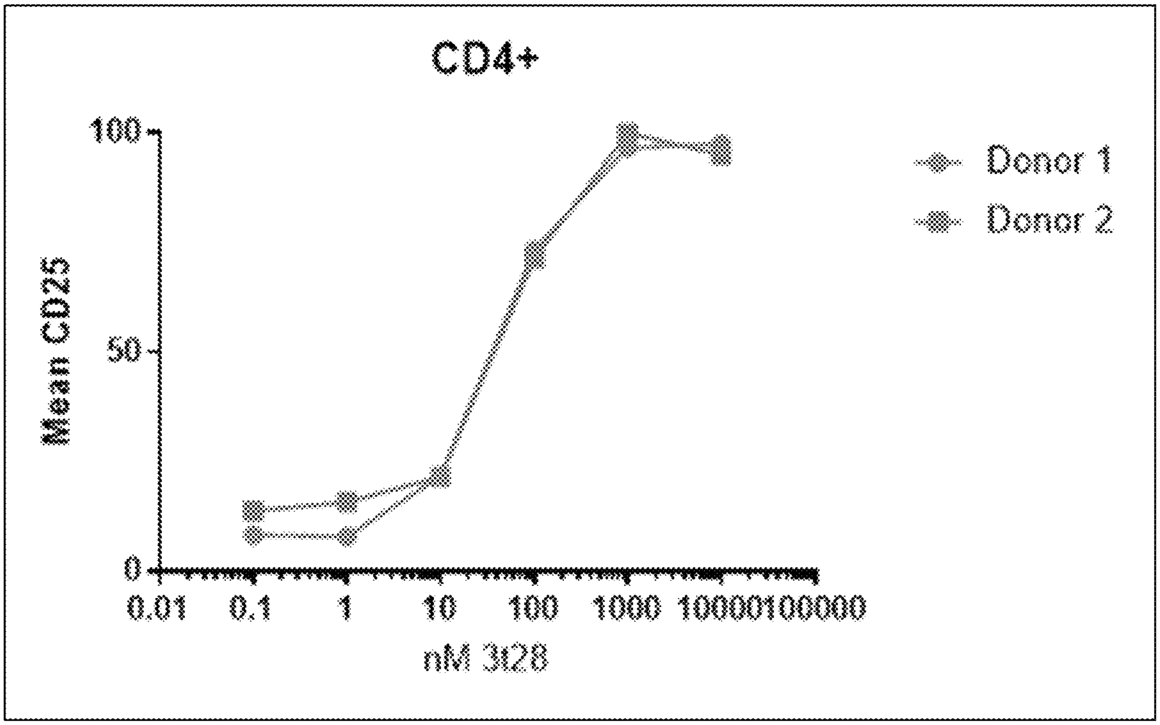

FIG. 62 is a graph showing the ability of an exemplary αCD3scFv/TF/αCD28scFv single-chain chimeric polypeptide to stimulate CD25 expression in $CD4^+$ T-cells isolated from blood from two donors. The experiments were performed as described in Example 2.

Figure 63:
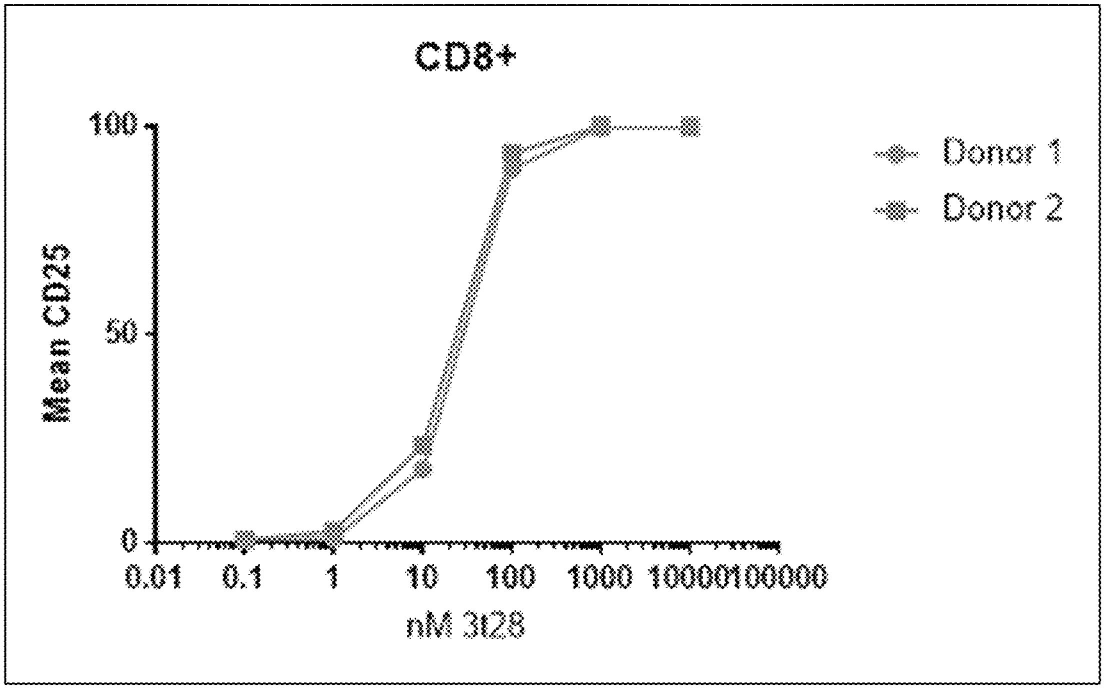

FIG. 63 is a graph showing the ability of an exemplary αCD3scFv/TF/αCD28scFv single-chain chimeric polypeptide to stimulate CD25 expression in $CD8^+$ T-cells isolated from blood from two donors. The experiments were performed as described in Example 2.

Figure 64:
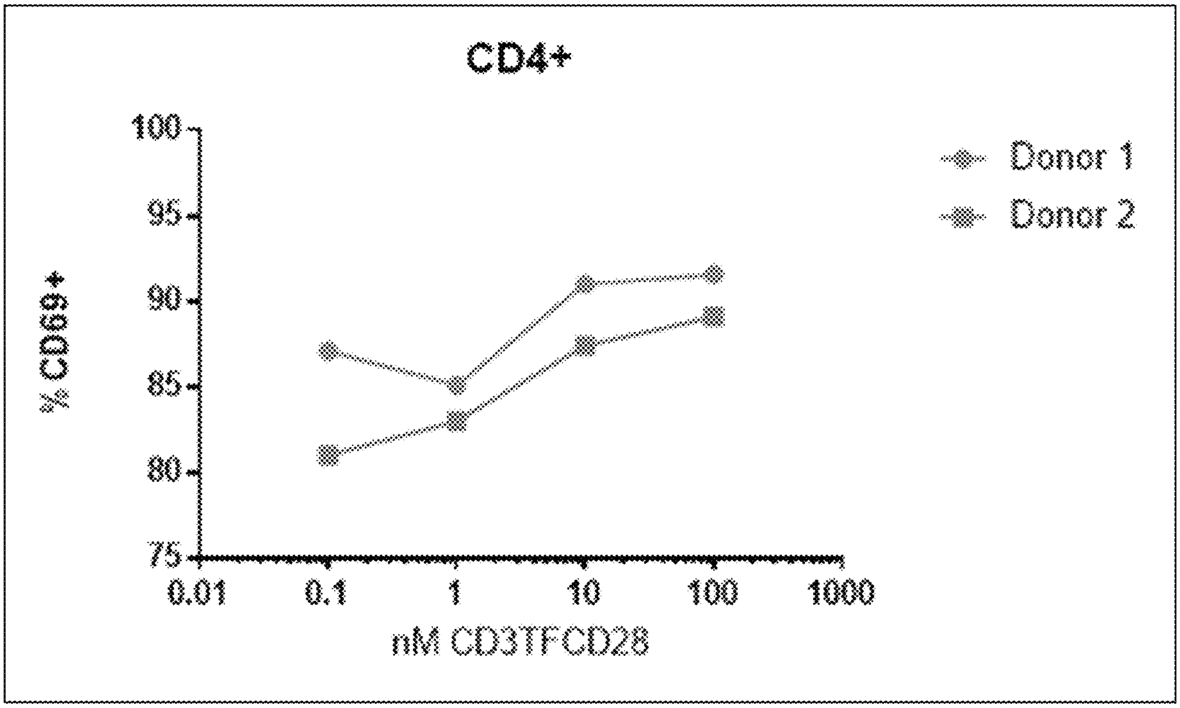

FIG. 64 is a graph showing the ability of an exemplary αCD3scFv/TF/αCD28scFv single-chain chimeric polypeptide to stimulate CD69 expression in $CD4^+$ T-cells isolated from blood from two donors. The experiments were performed as described in Example 2.

Figure 65:

FIG. 65 shows a schematic diagram of an exemplary IL-7/IL-15RαSu DNA construct.

Figure 66:

FIG. 66 shows a schematic diagram of an exemplary IL-21/TF/IL-15 DNA construct.

Figure 67:
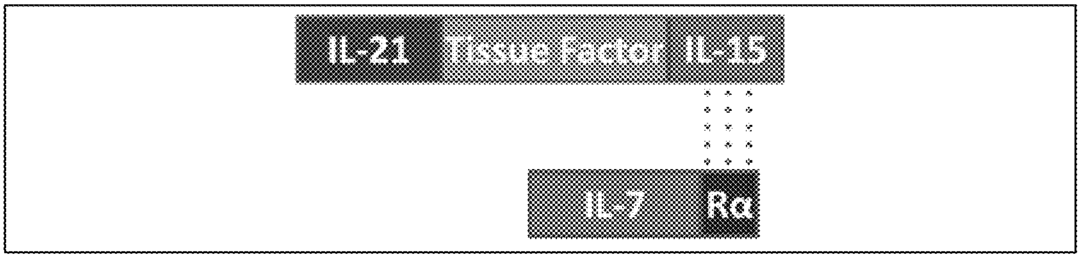

FIG. 67 shows a schematic diagram of the interaction between the exemplary IL-7/IL-15RαSu and IL-21/TF/IL-15 DNA constructs.

Figure 68:
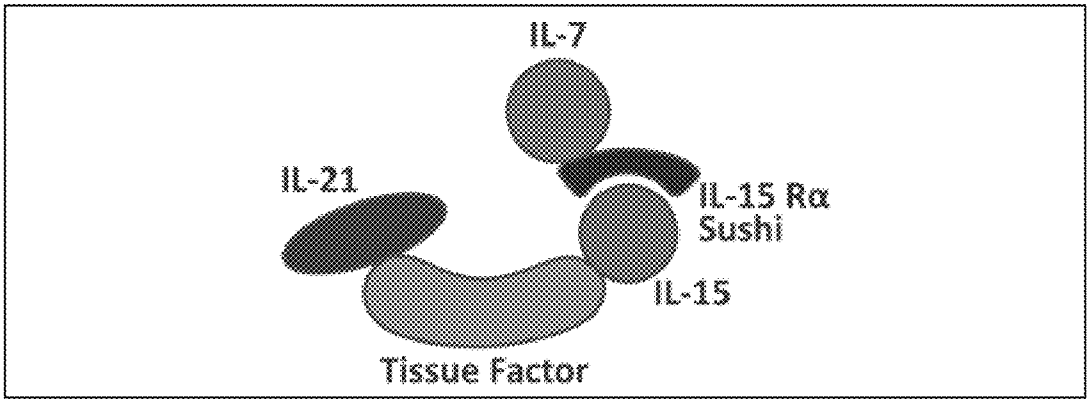

FIG. 68 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

Figure 69:
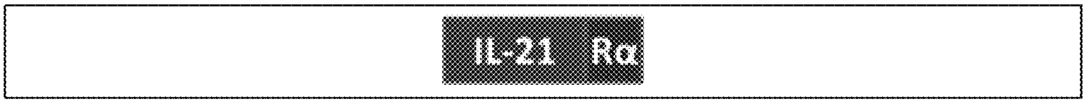

FIG. 69 shows a schematic diagram of an exemplary IL-21/IL-15RαSu DNA construct.

Figure 70:
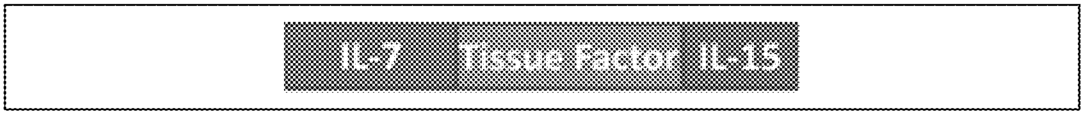

FIG. 70 shows a schematic diagram of an exemplary IL-7/TF/IL-15 DNA construct.

Figure 71:
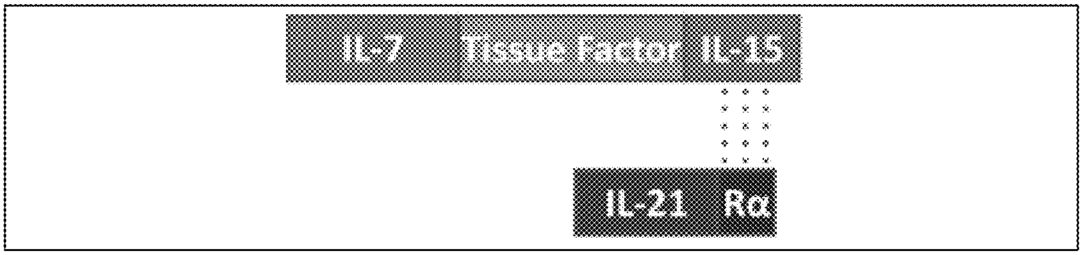

FIG. 71 shows a schematic diagram of the interaction between the exemplary IL-21/IL-15RαSu and IL-7/TF/IL-15 DNA constructs.

Figure 72:
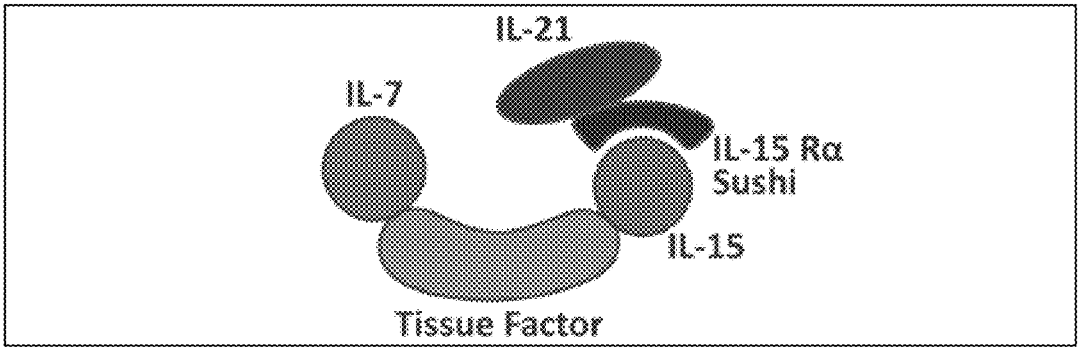

FIG. 72 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

Figure 73:
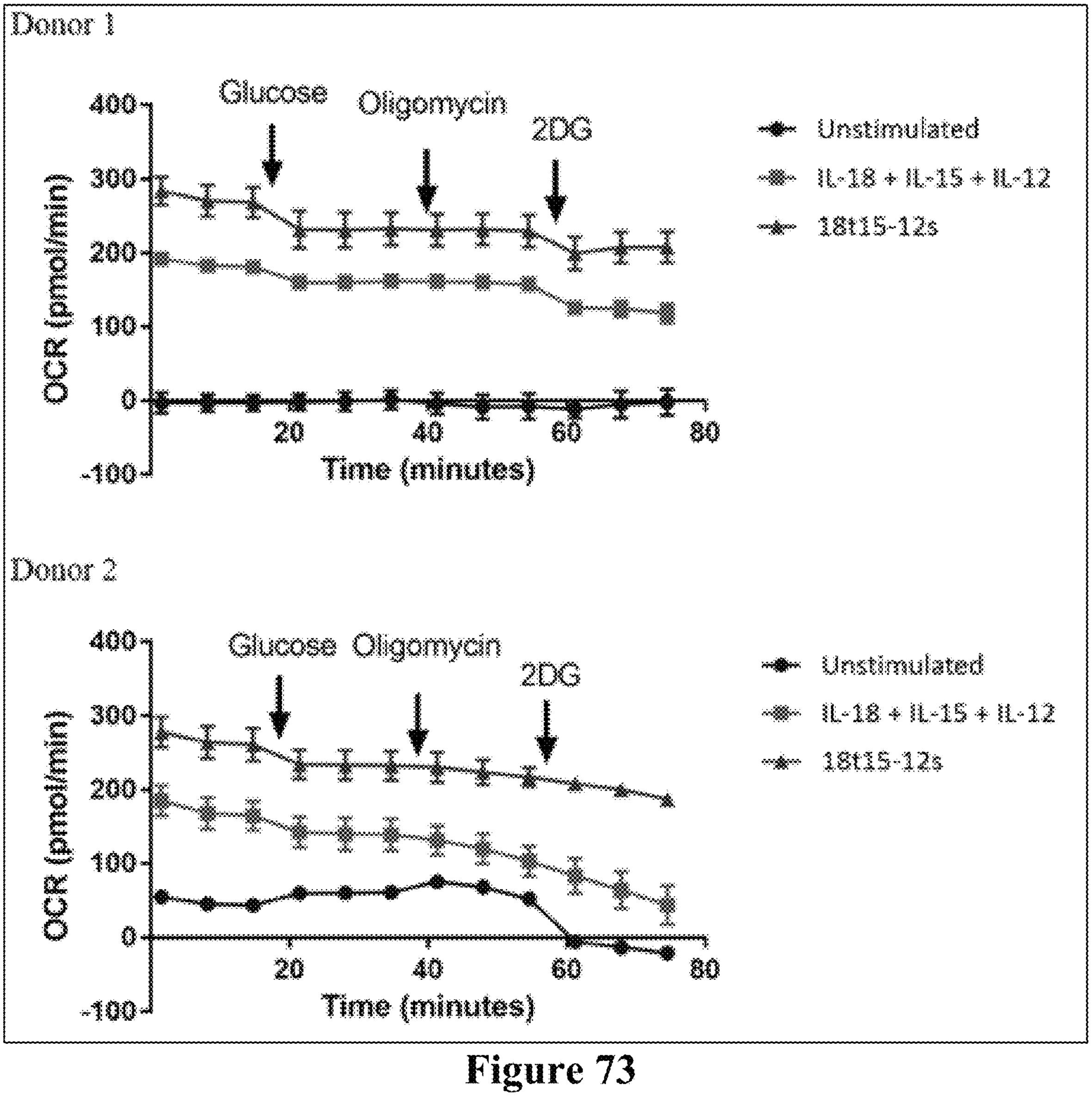

FIG. 73 shows the oxygen consumption rate (OCR) in pmoles/min for human NK cells isolated from blood ($2\times10^6$ cells/mL) of two different donors.

Figure 74:
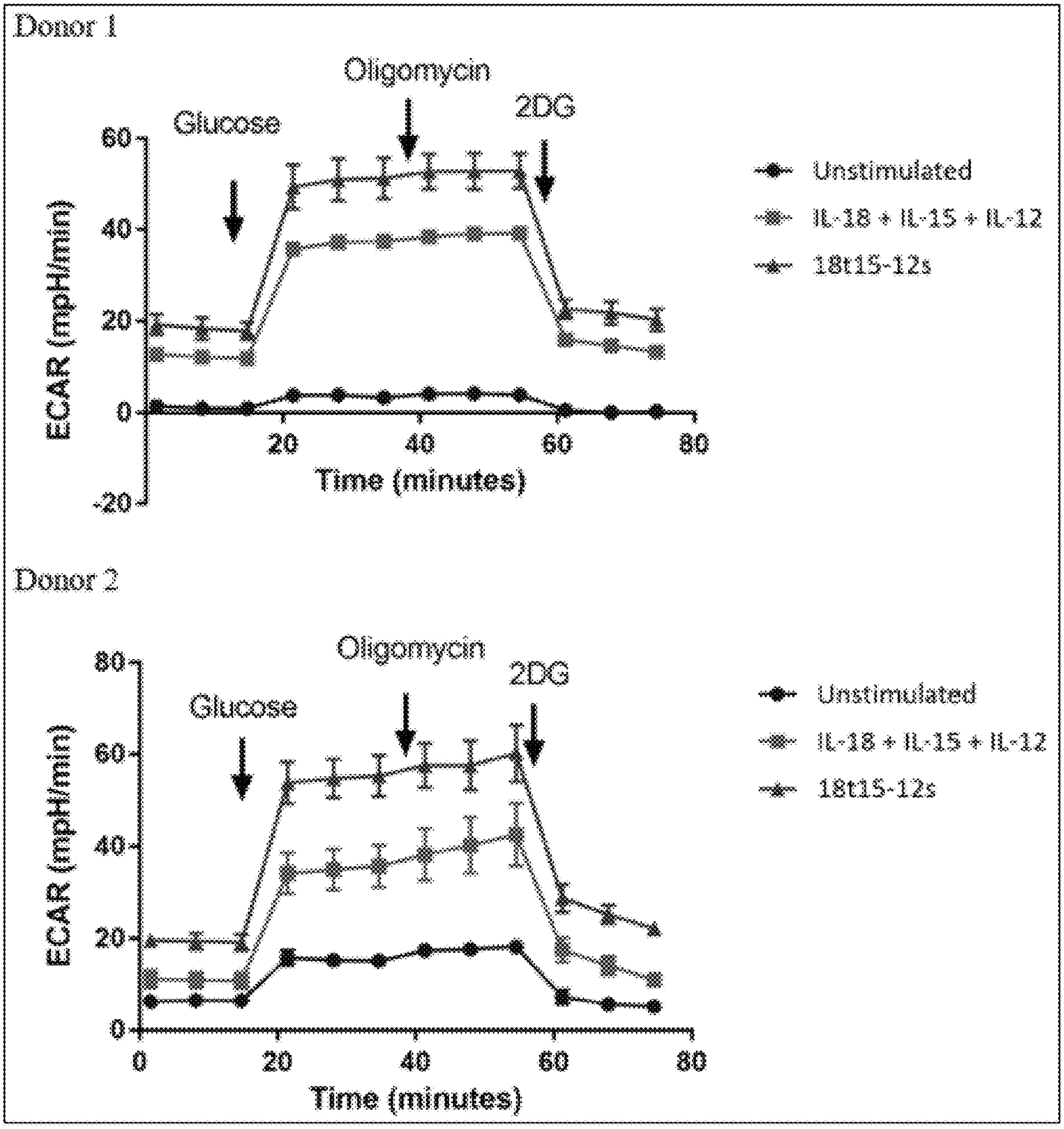

FIG. 74 shows the extracellular acidification rate (ECAR) in mpH/minute for human NK cells isolated from blood ($2\times10^6$ cells/mL) of two different donors.

Figure 75:
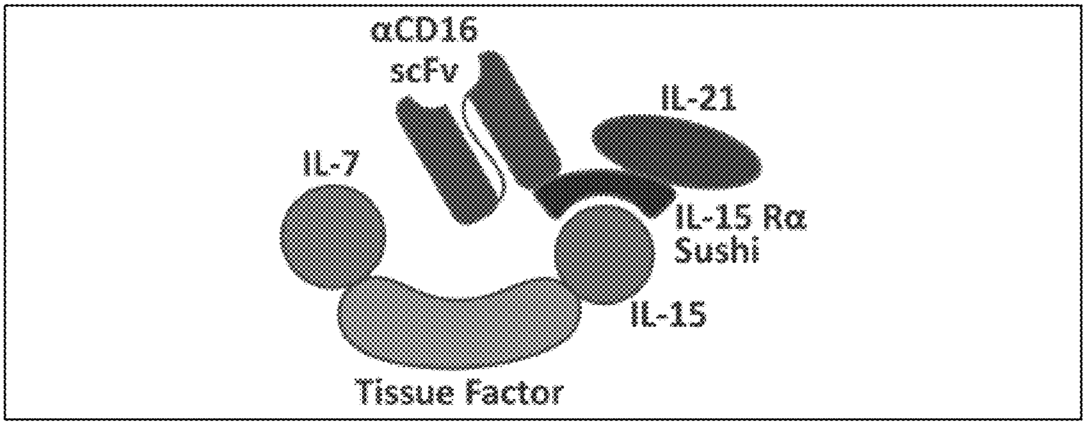

FIG. 75 shows a schematic of the 7t15-16s21 construct.

Figure 76:
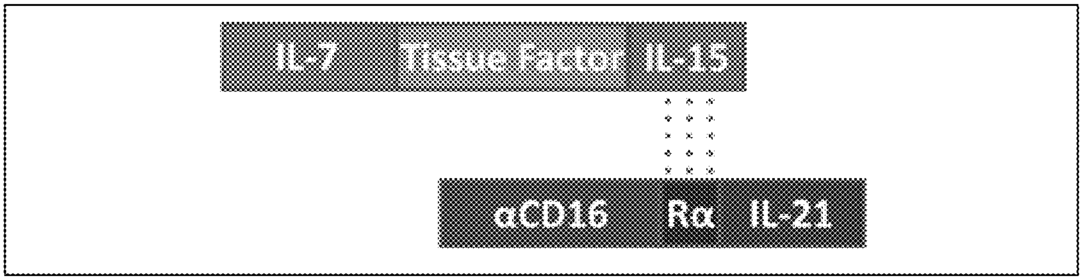

FIG. 76 shows an additional schematic of the 7t15-16s21 construct.

Figure 77A:
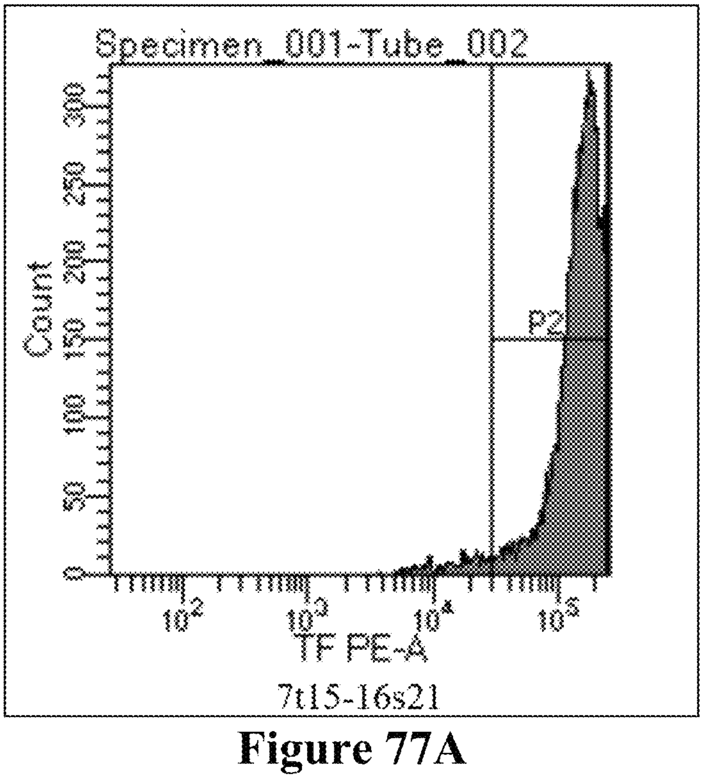
Figure 77B:
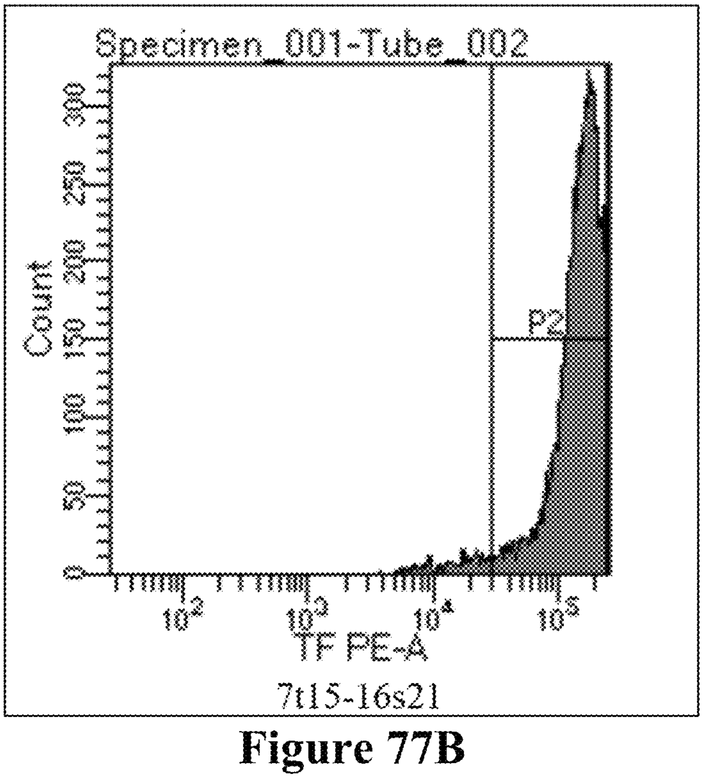

FIGS. 77A and 77B show binding of 7t15-16s21 to CHO cells expressing human CD16b as compared to a control protein.

Figure 78A:
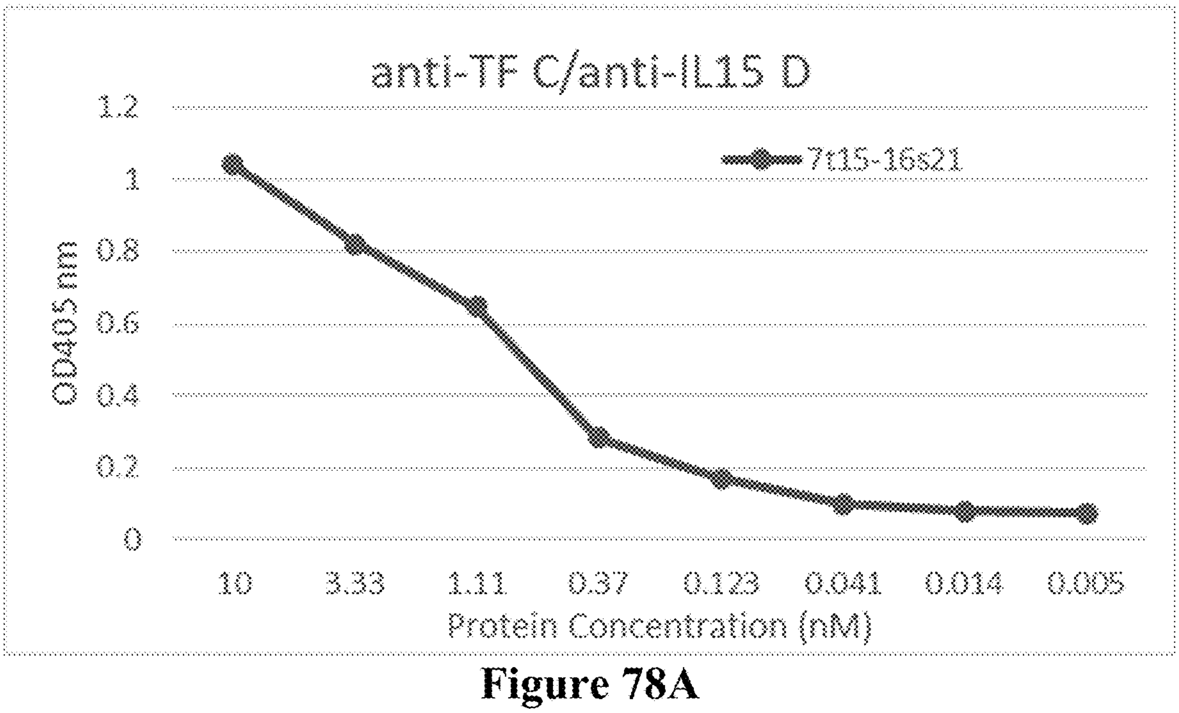
Figure 78B:
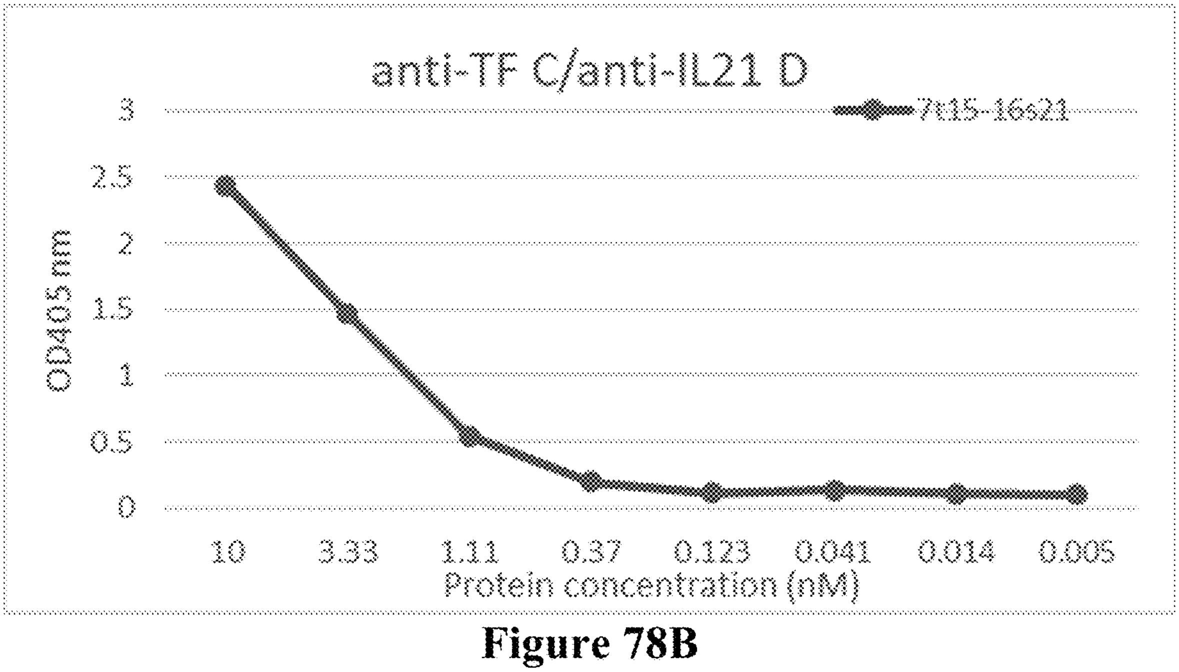
Figure 78C:
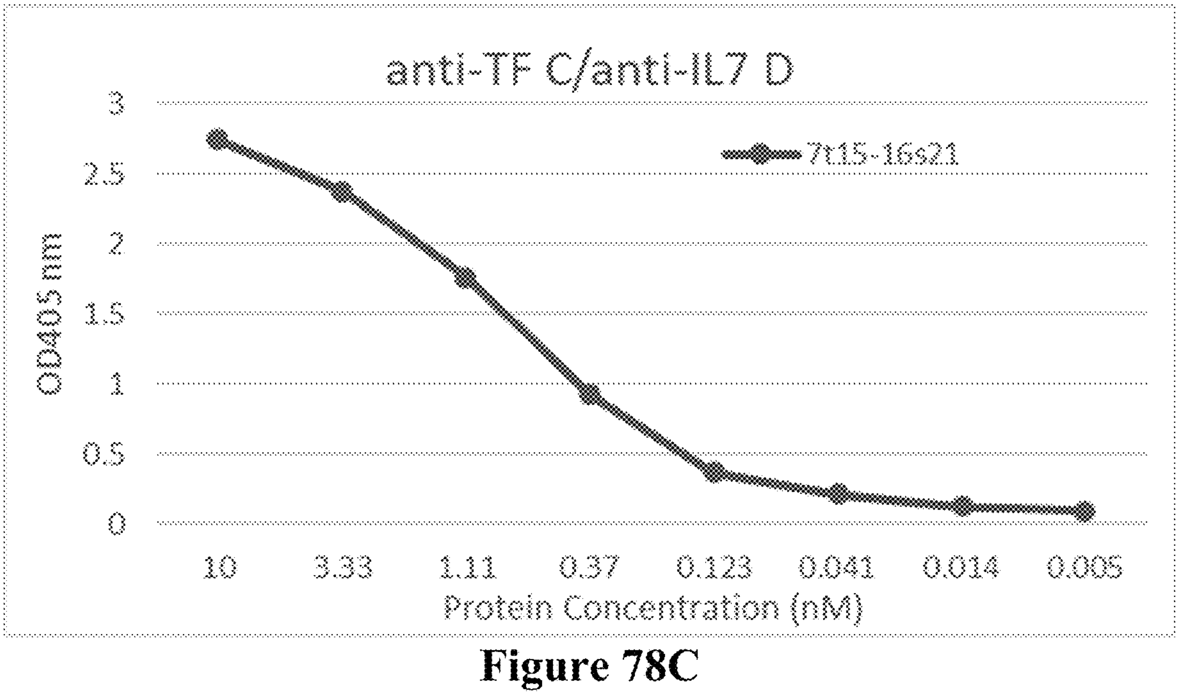

FIGS. 78A-78C are results from ELISA experiments using antibodies against IL-15, IL-21, and IL-7 in detecting 7t15-16s21.

Figure 79:
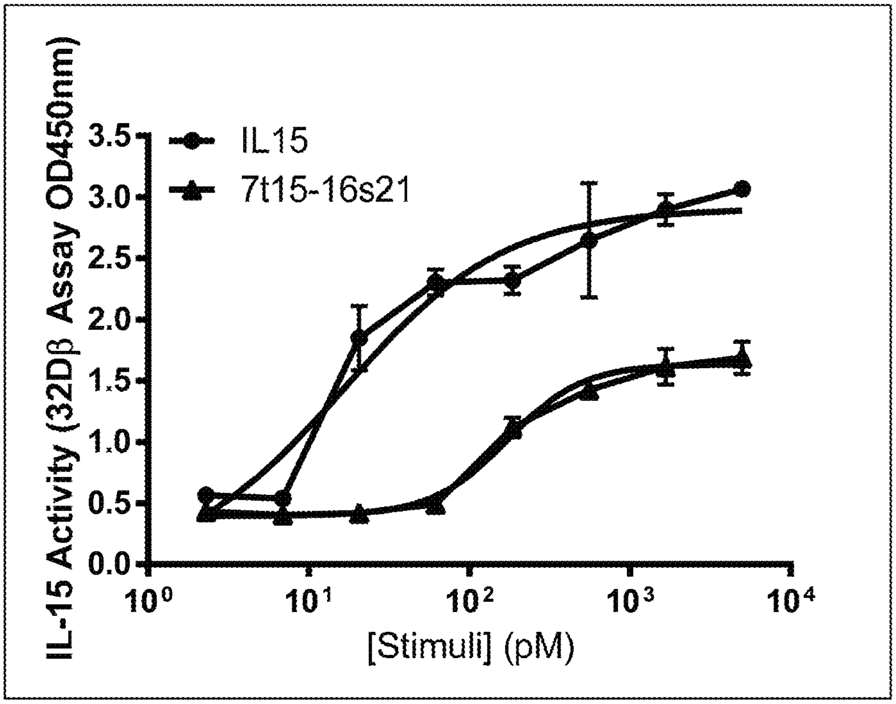

FIG. 79 shows results of the 32Dβ cell proliferation assay with 7t15-16s21 or recombinant IL-15.

Figure 80:
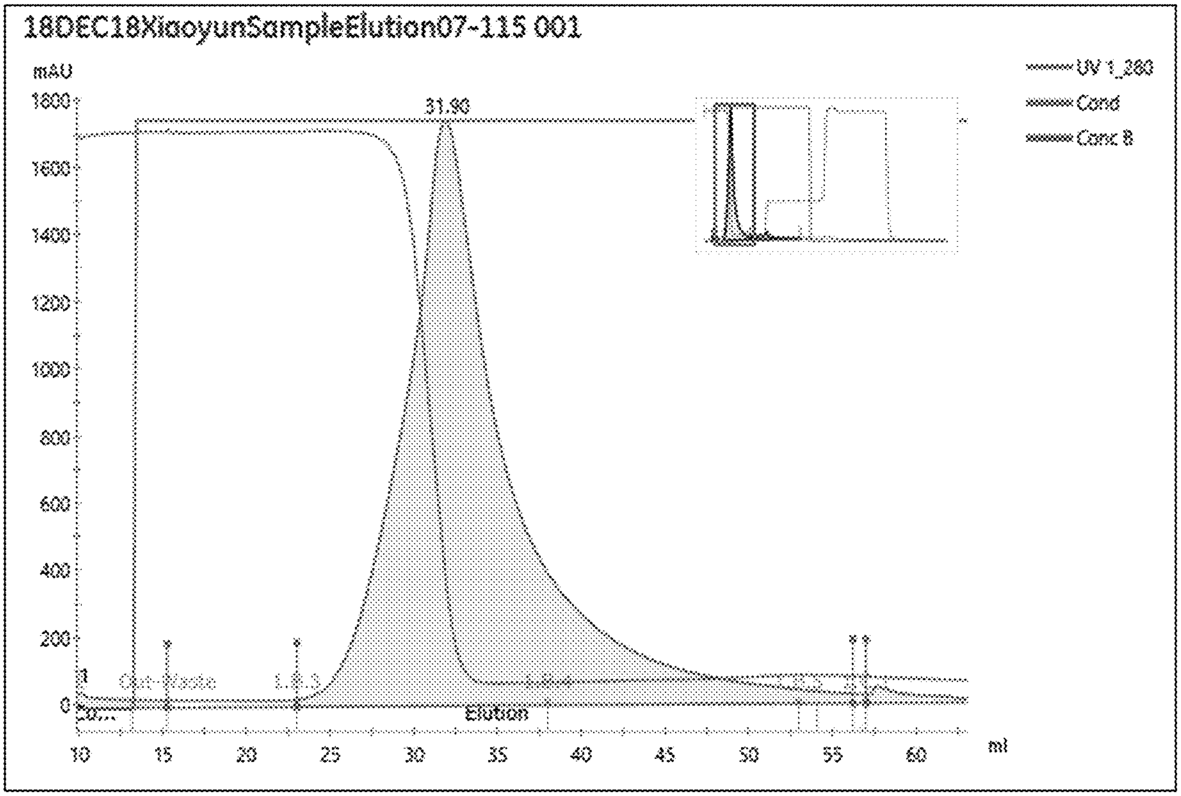

FIG. 80 shows the chromatographic profile of 7t15-16s21 protein containing cell culture supernatant following binding and elution on anti-TF antibody resin.

Figure 81:
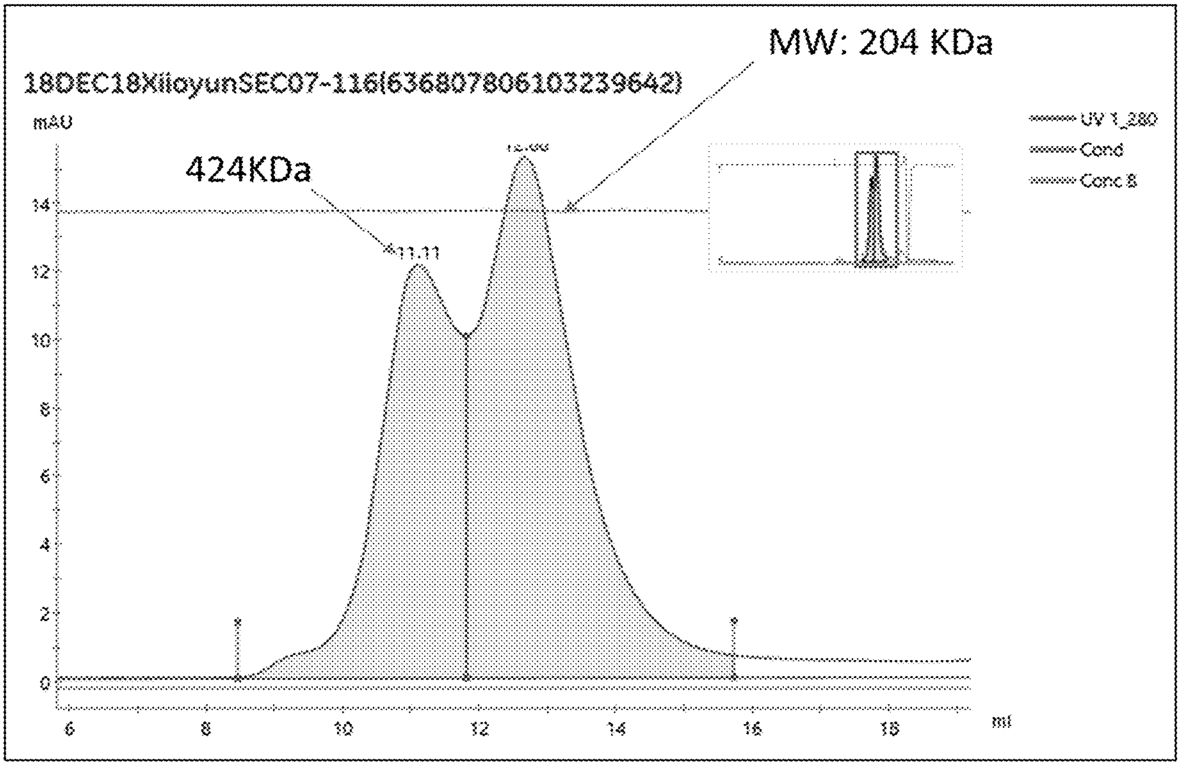

FIG. 81 shows the analytical SEC Profile of 7t15-16s21.

Figure 82:
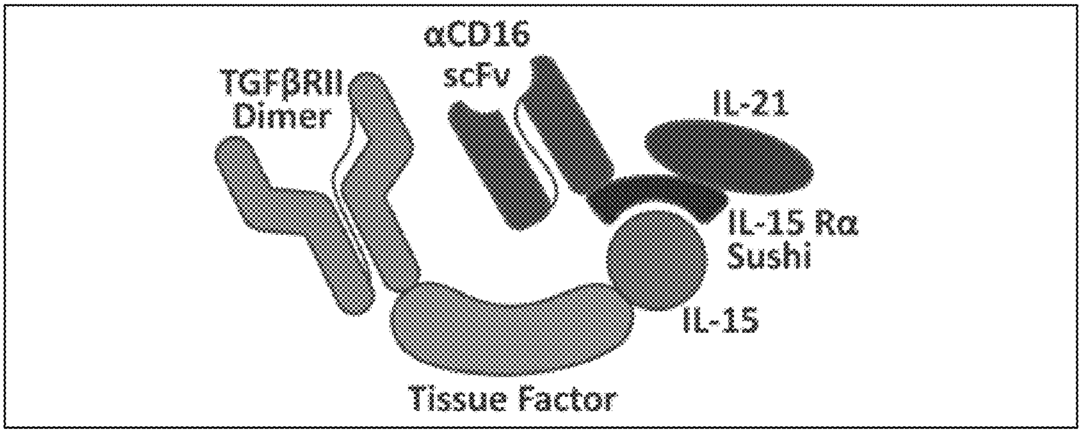

FIG. 82 shows a schematic of the TGFRt15-16s21 construct.

Figure 83:
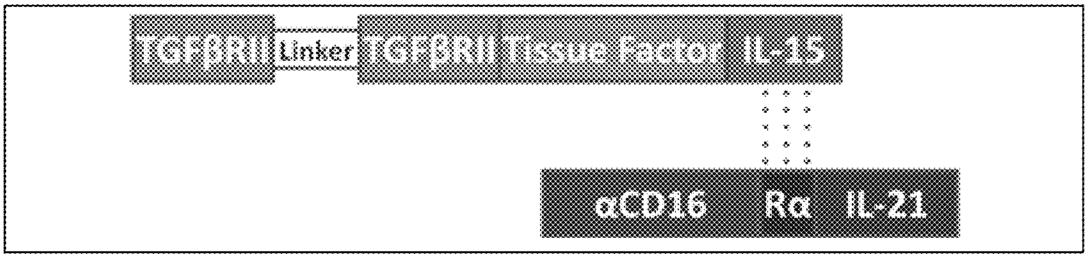

FIG. 83 shows an additional schematic of the TGFRt15-16s21 construct.

Figure 84A:
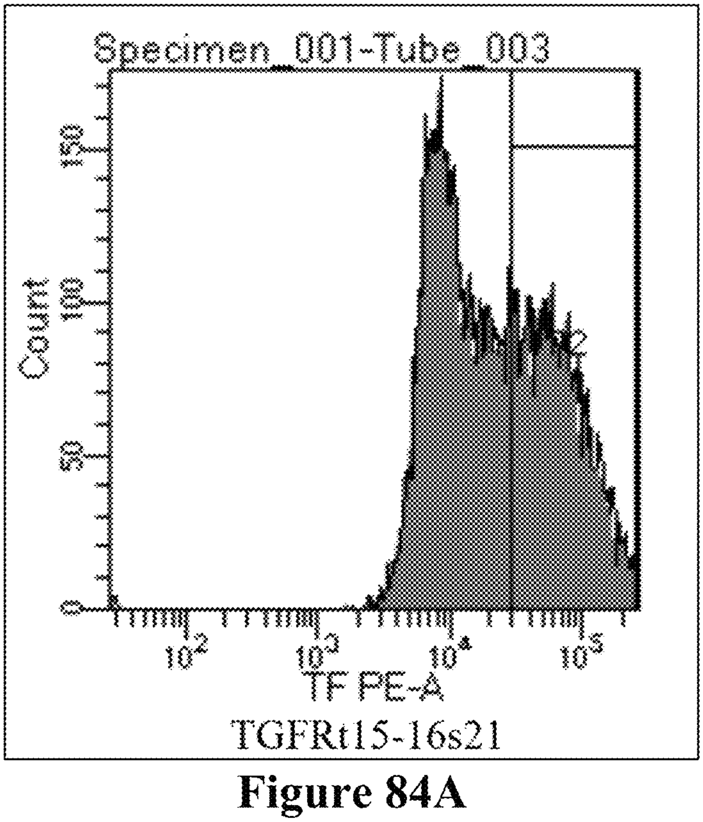
Figure 84B:
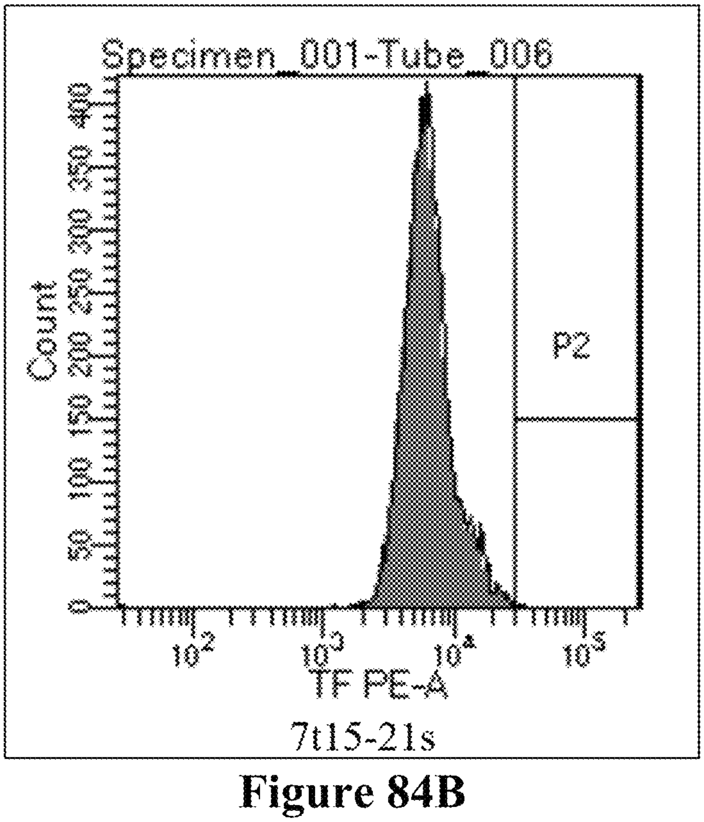

FIGS. 84A and 84B show binding affinity of TGFRT15-16521 and 7t15-21s with CHO cells expressing human CD16b. FIG. 84A shows binding affinity of TGFRT15-16S21 with CHO cells expressing human CD16b. FIG. 84B shows binding affinity of 7t15-21s with CHO cells expressing human CD16b.

Figure 85:
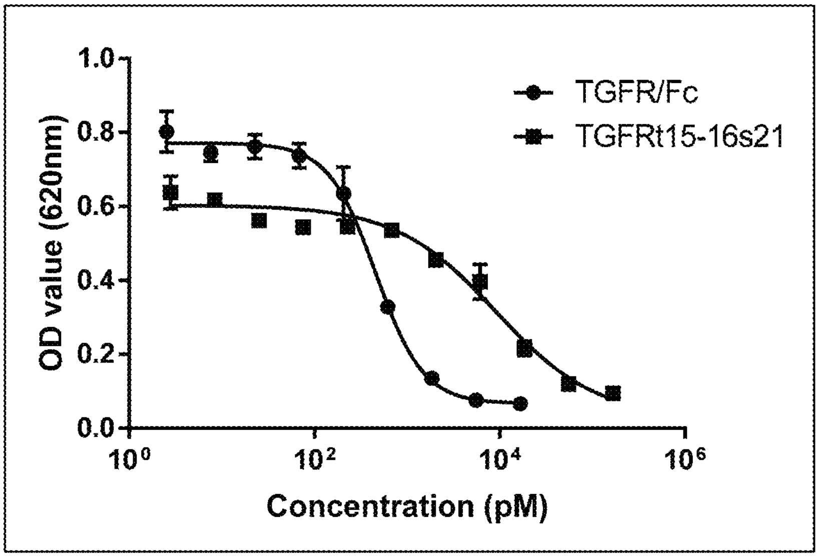

FIG. 85 shows results of TGFβ1 inhibition by TGFRt15-16s21 and TGFR-Fc.

Figure 86:
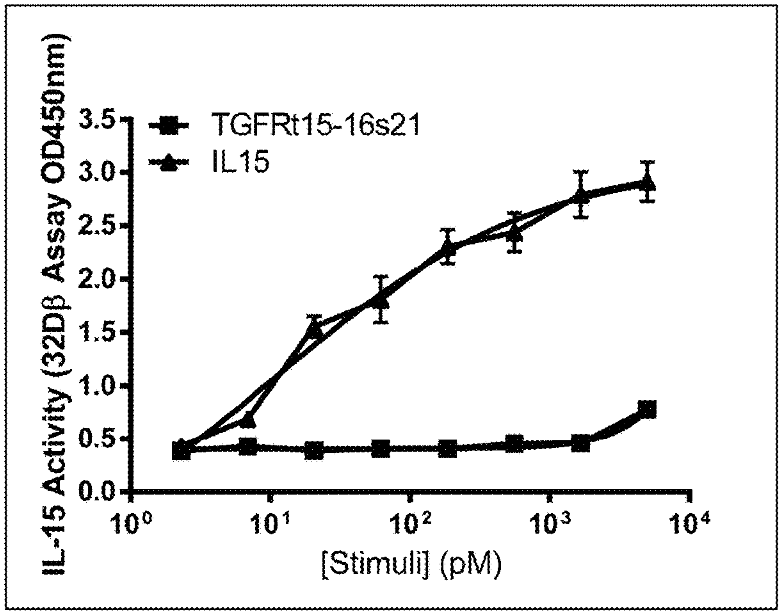

FIG. 86 shows results of 32Dβ cell proliferation assay with TGFRt15-16s21 or recombinant IL-15.

Figure 87A:
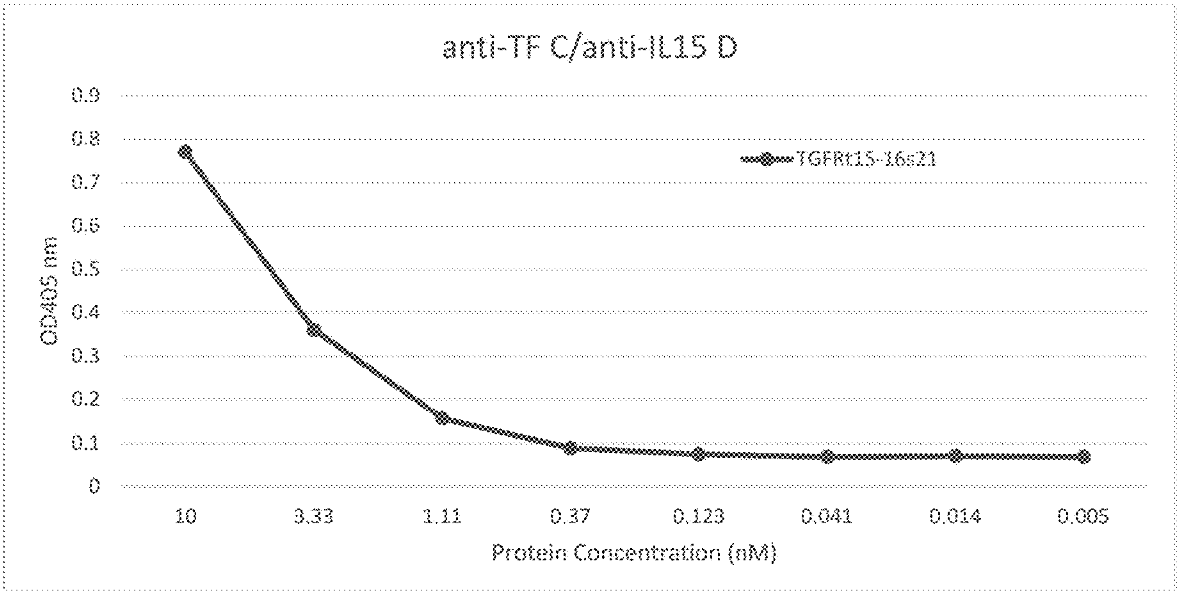
Figure 87B:
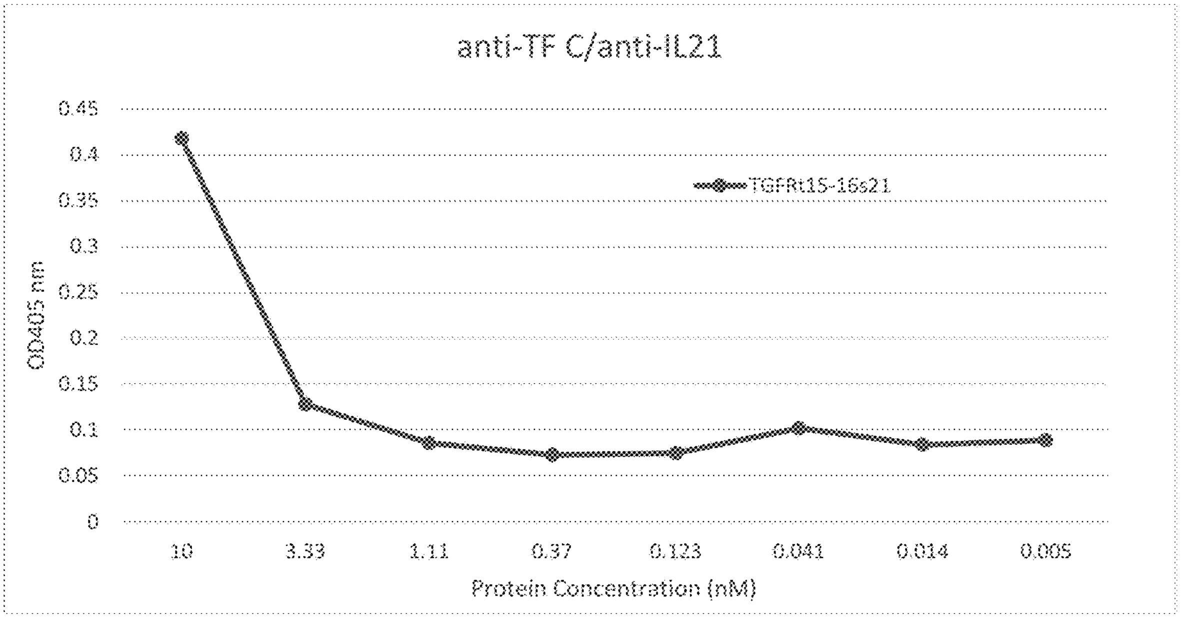
Figure 87C:
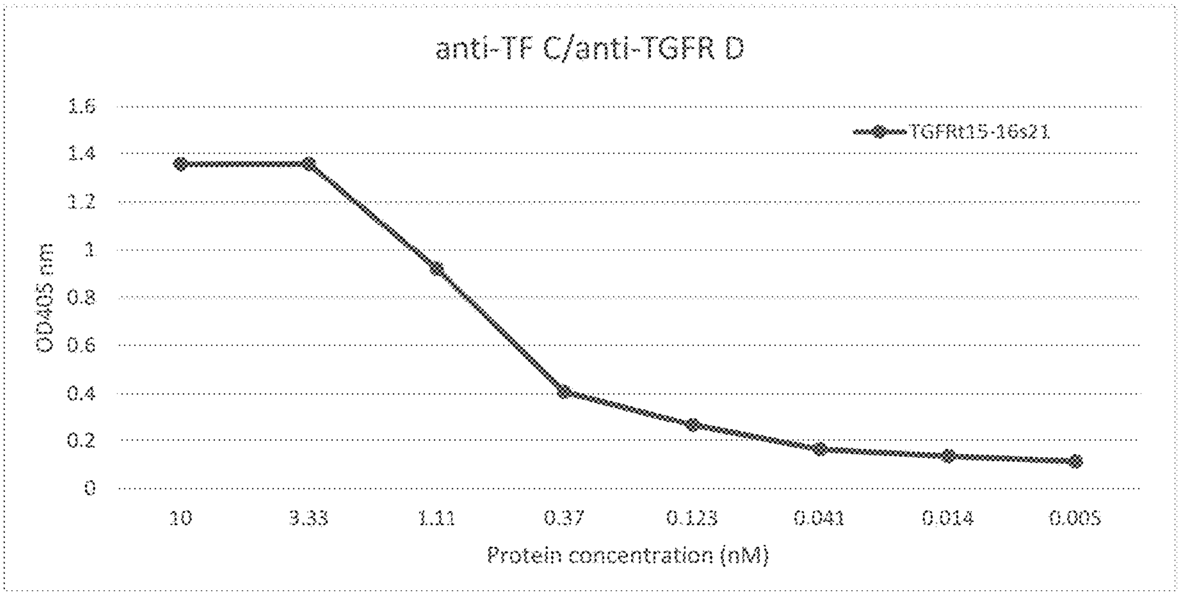

FIGS. 87A-87C show results of detecting IL-15, IL-21, and TGFβRII in TGFRt15-16s21 with corresponding antibodies using ELISA.

Figure 88:
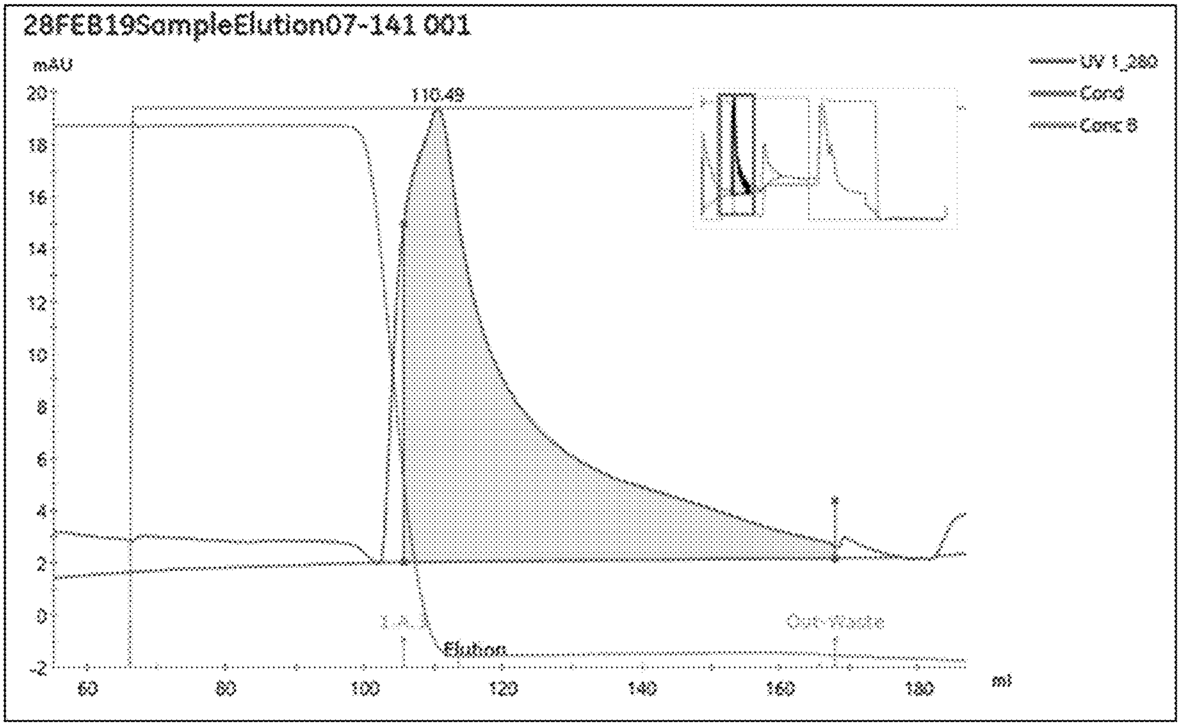

FIG. 88 shows the chromatographic profile of TGFRt15-16s21 protein containing cell culture supernatant following binding and elution on anti-TF antibody resin.

Figure 89:
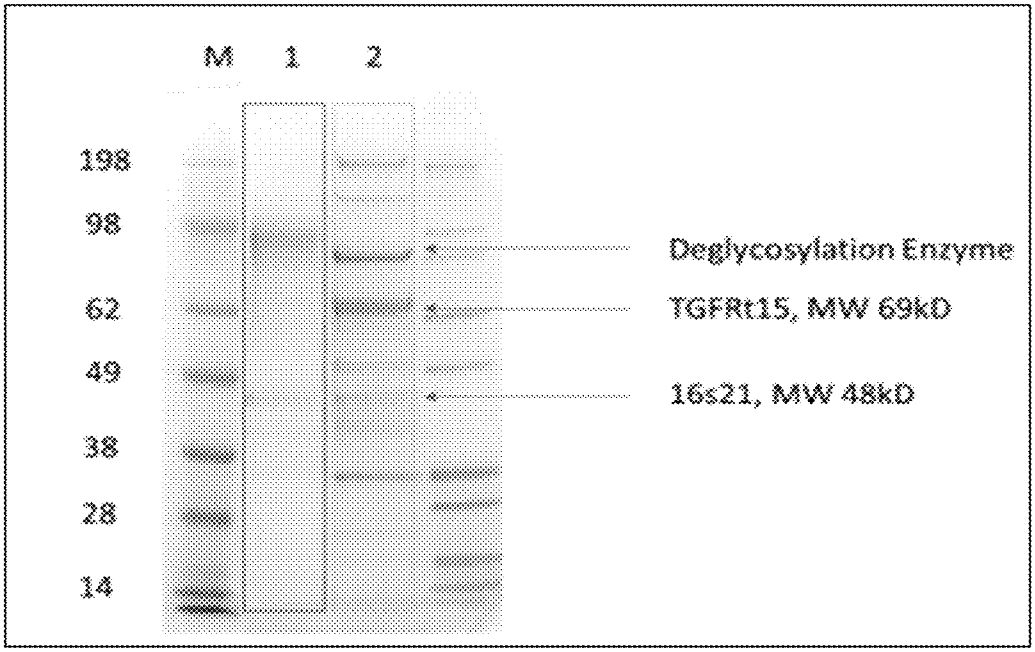

FIG. 89 shows results of a reduced SDS-PAGE analysis of TGFRt15-16s21.

Figure 90:
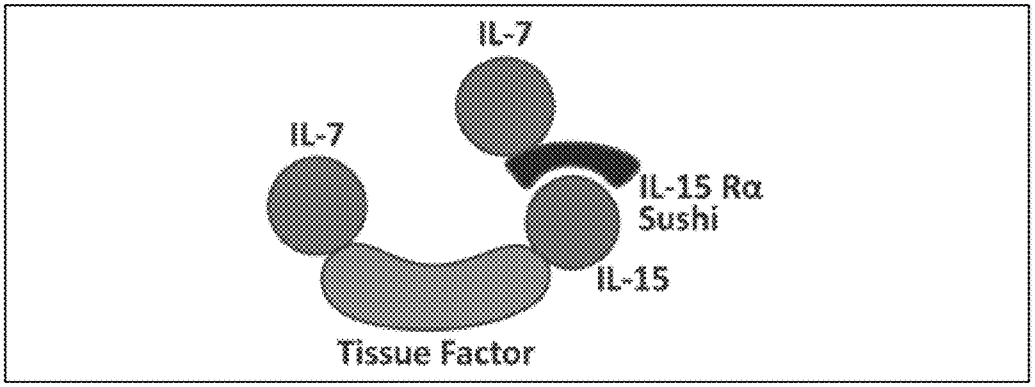

FIG. 90 shows a schematic of the 7t15-7s construct.

Figure 91:
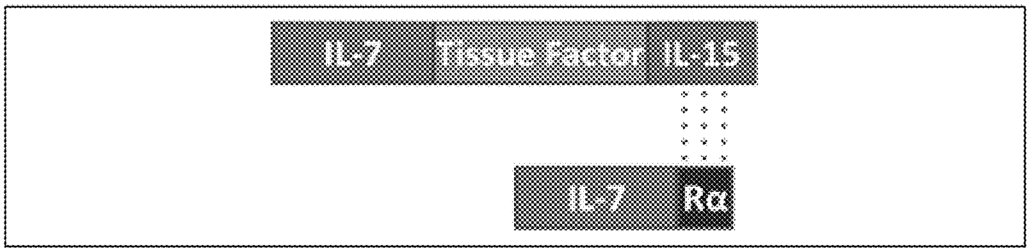

FIG. 91 shows an additional schematic of the 7t15-7s construct.

Figure 92:
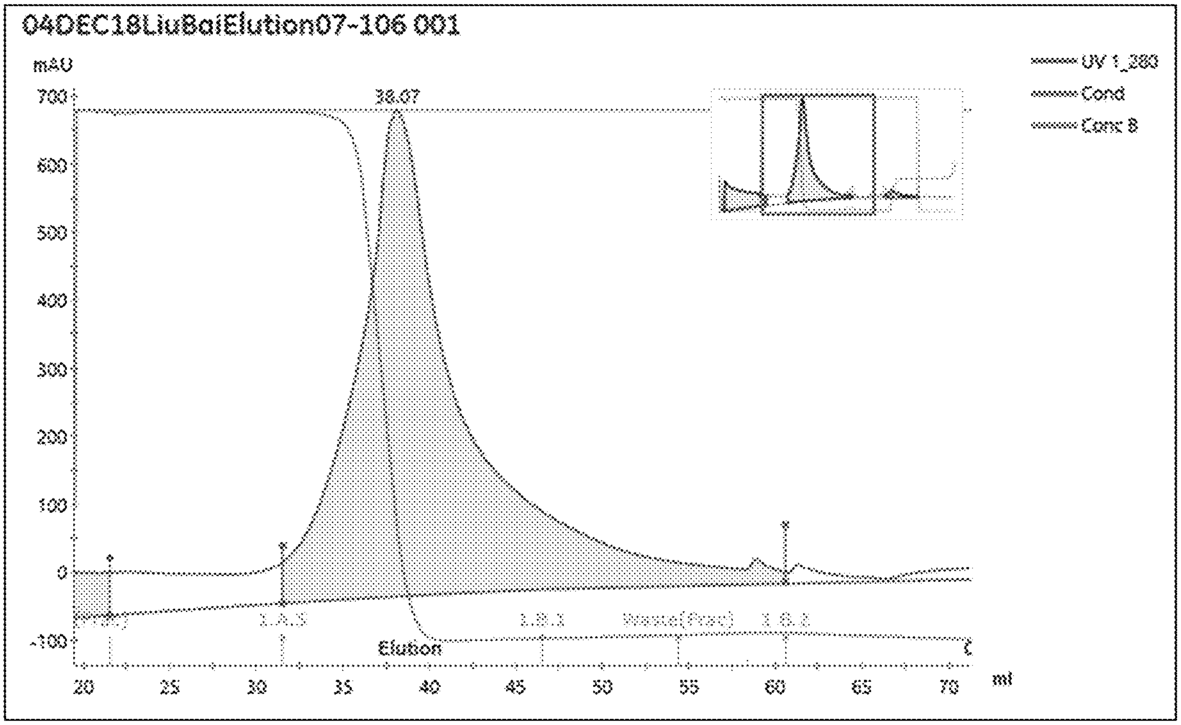

FIG. 92 shows the chromatographic profile of 7t15-7s protein containing cell culture supernatant following binding and elution on anti-TF antibody resin.

Figure 93:
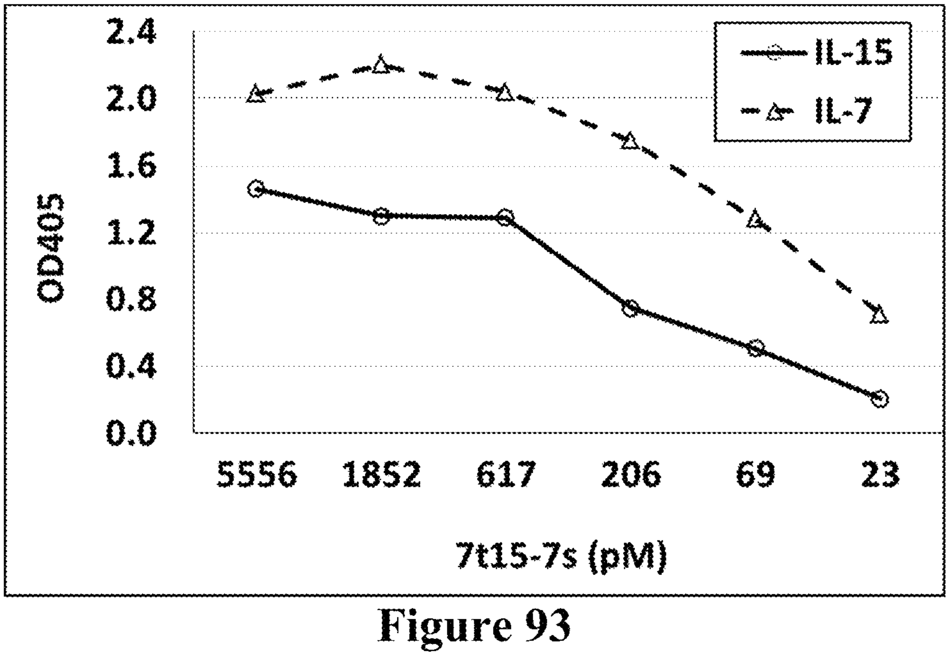

FIG. 93 shows detection of TF, IL-15 and IL-7 in 7t15-7s using ELISA.

Figure 94A:
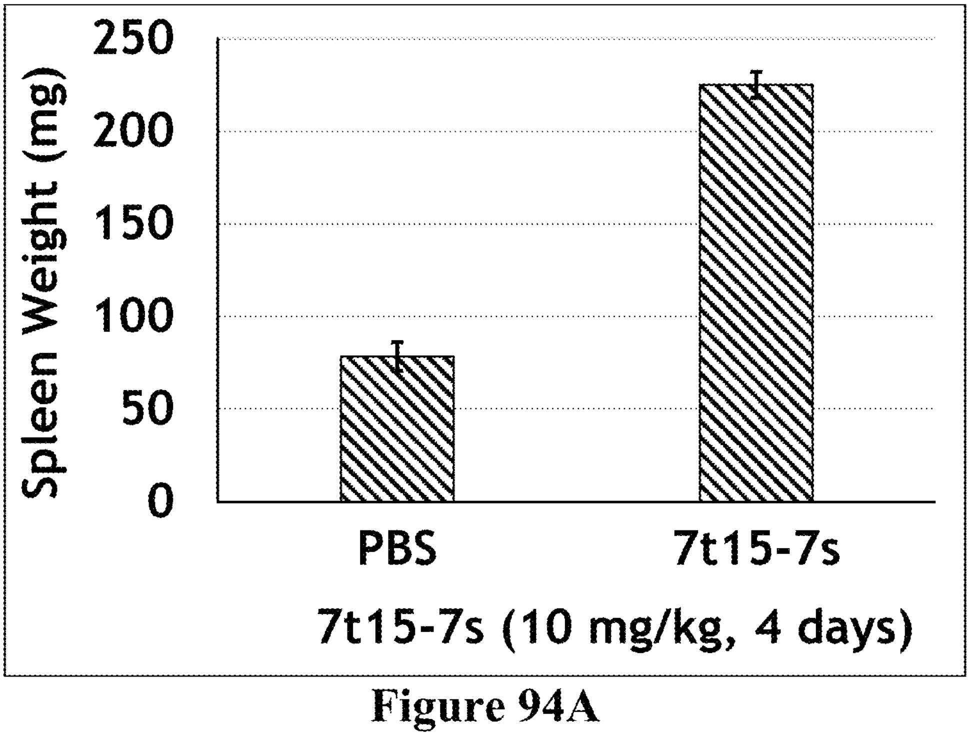
Figure 94B:
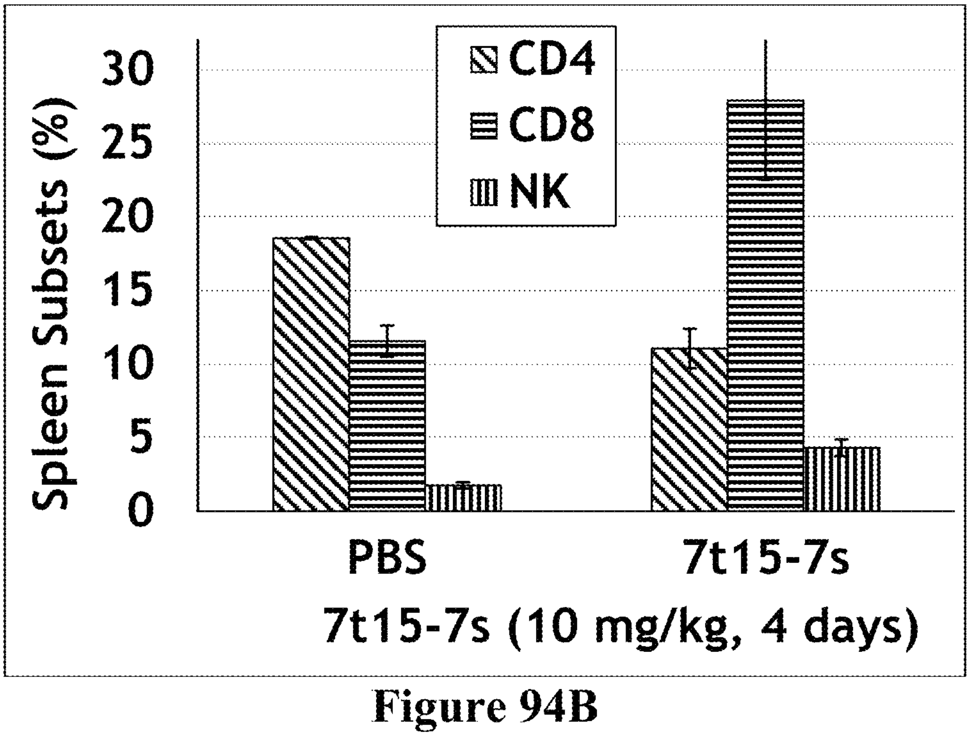

FIGS. 94A and 94B show spleen weight and the percentages of immune cell types in 7t15-7s-treated and control-treated mice. FIG. 94A shows spleen weight in mice treated with 7t15-7s as compared to PBS control. FIG. 94B shows the percentage of $CD4^+$ T cells, $CD8^+$ T cells, and NK cells in mice treated with 7t15-7s as compared to PBS control.

Figure 95:
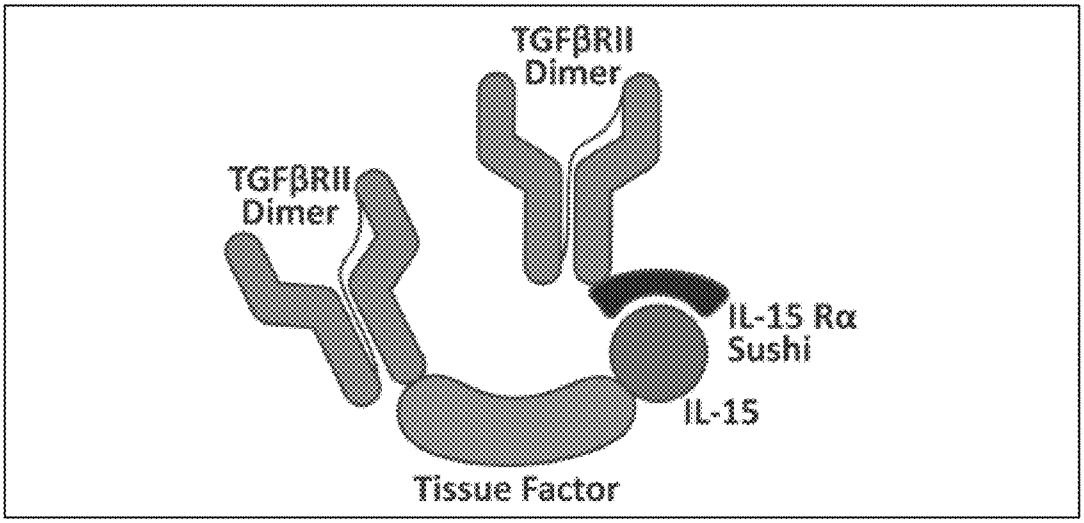

FIG. 95 shows a schematic of the TGFRt15-TGFRs construct.

Figure 96:
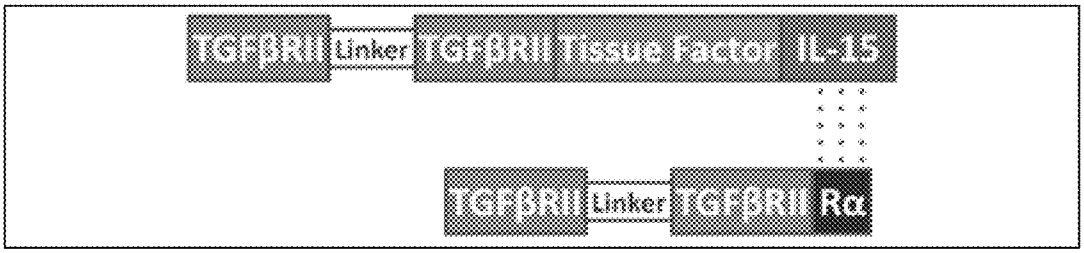

FIG. 96 shows an additional schematic of the TGFRt15-TGFRs construct.

Figure 97:
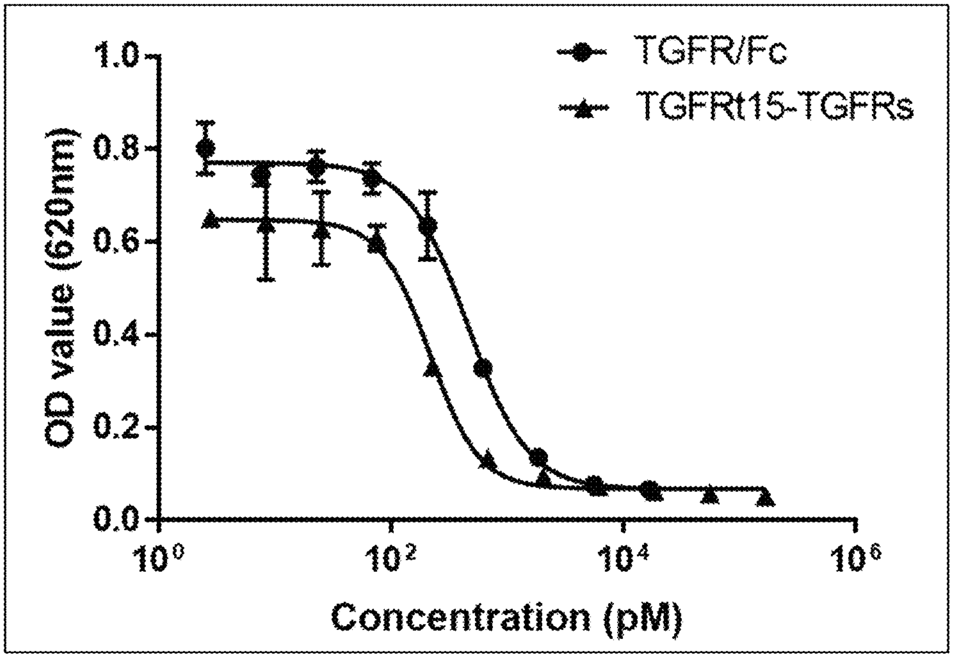

FIG. 97 shows results of TGFβ1 inhibition by TGFRt15-TGFRs and TGFR-Fc.

Figure 98:
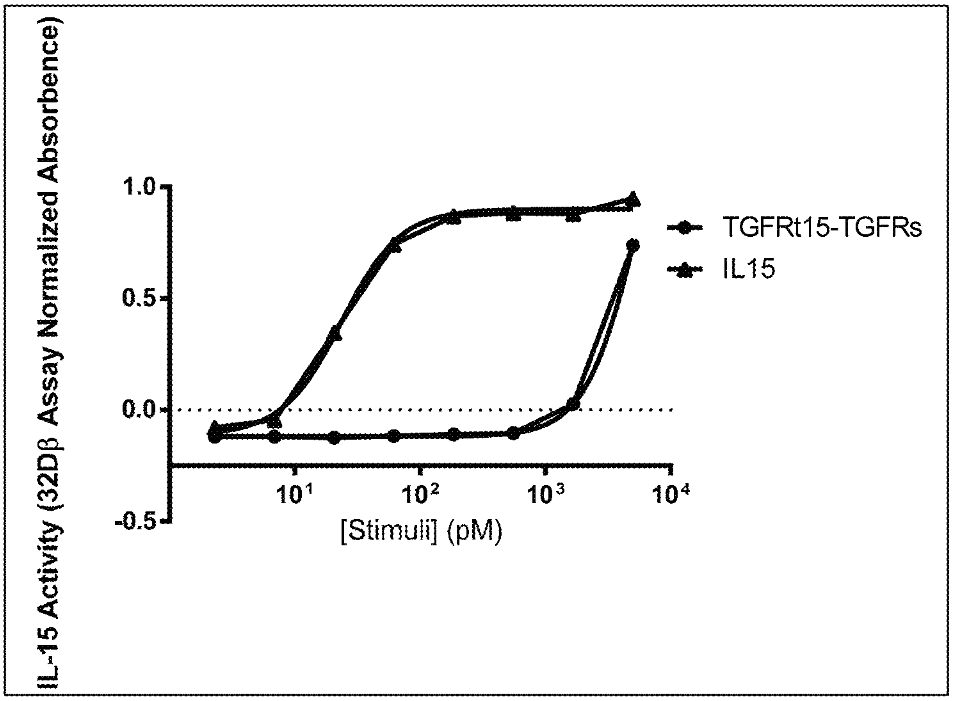

FIG. 98 shows results of 32Dβ cell proliferation assay with TGFRt15-TGFRs or recombinant IL-15

Figure 99A:
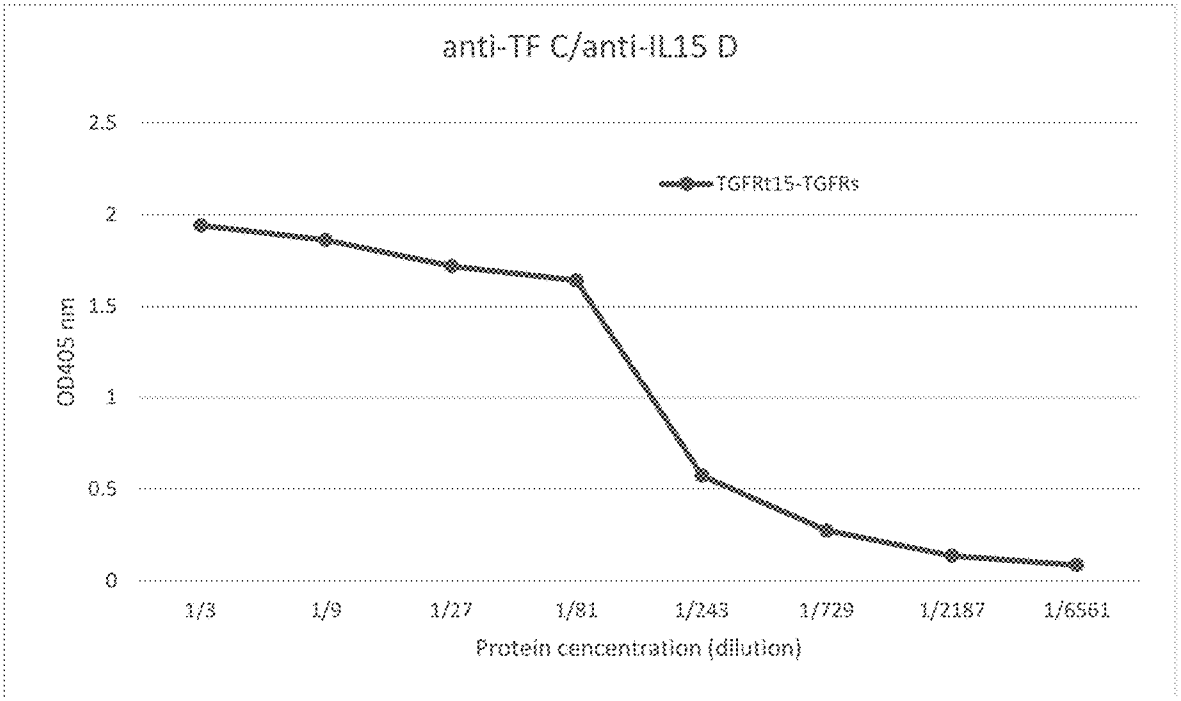
Figure 99B:
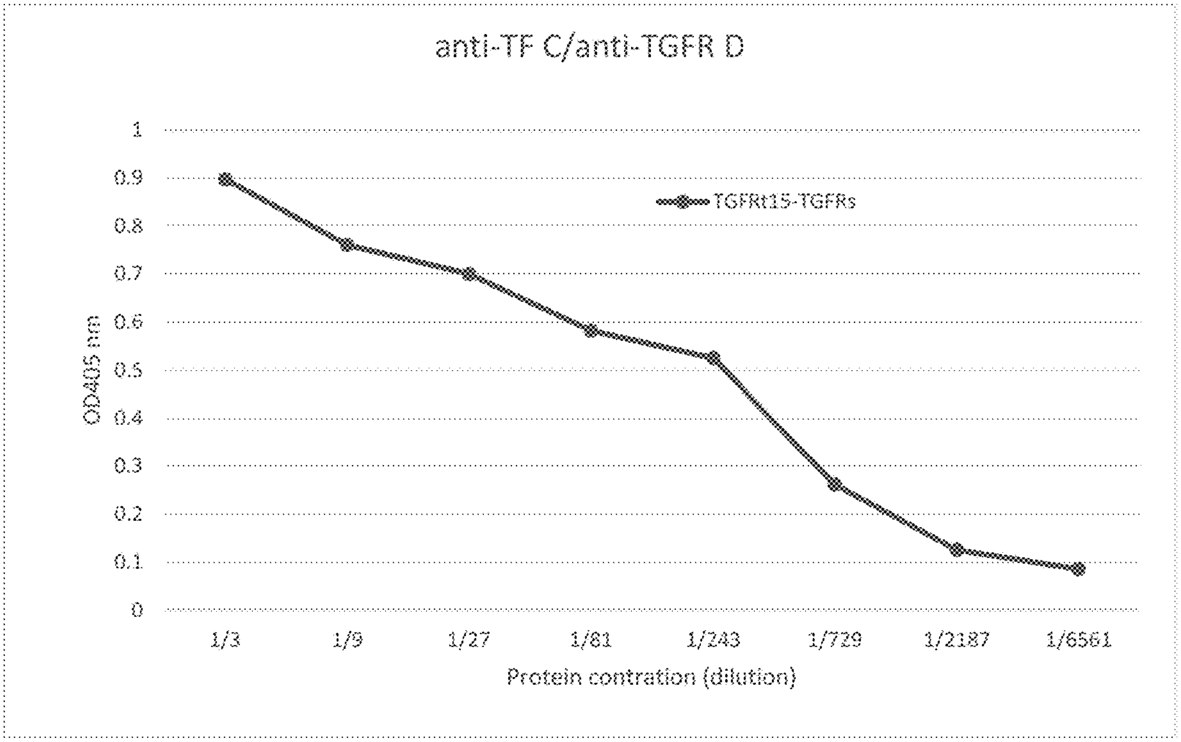

FIGS. 99A and 99B show results of detecting IL-15 and TGFβRII in TGFRt15-TGFRs with corresponding antibodies using ELISA.

Figure 100:
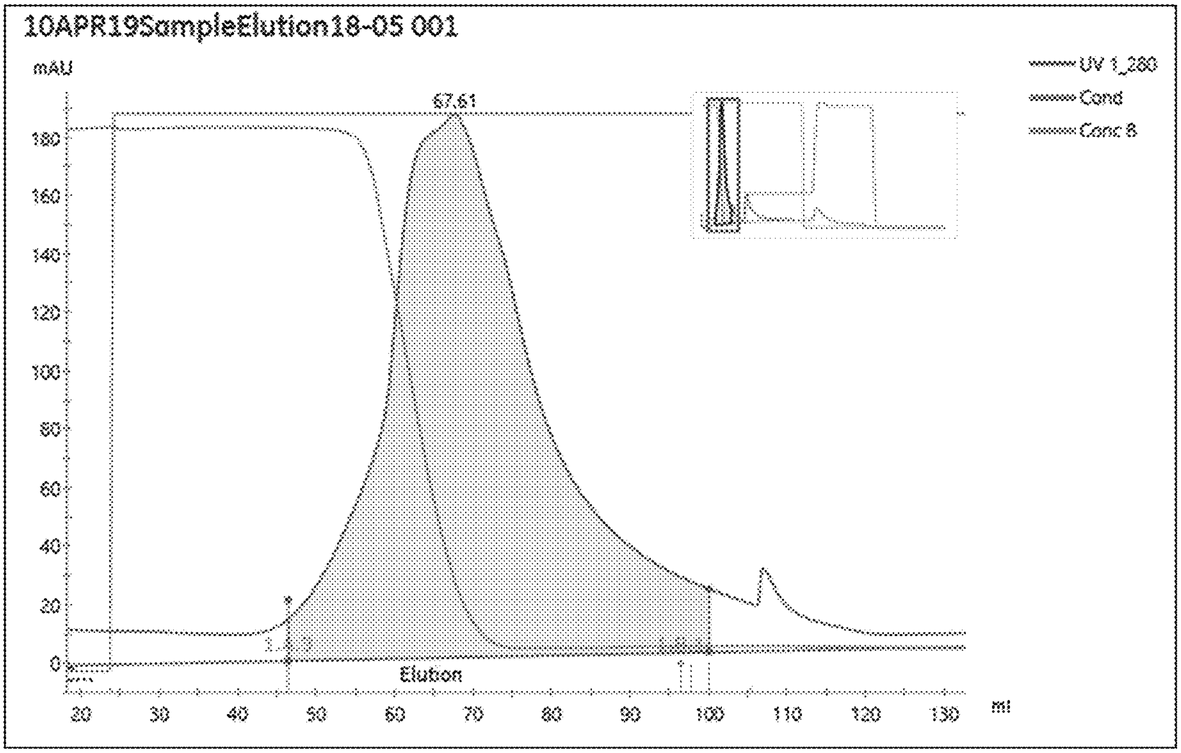

FIG. 100 is a line graph showing the chromatographic profile of TGFRt15-TGFRs protein containing cell culture supernatant following binding and elution on anti-TF antibody resin.

Figure 101:
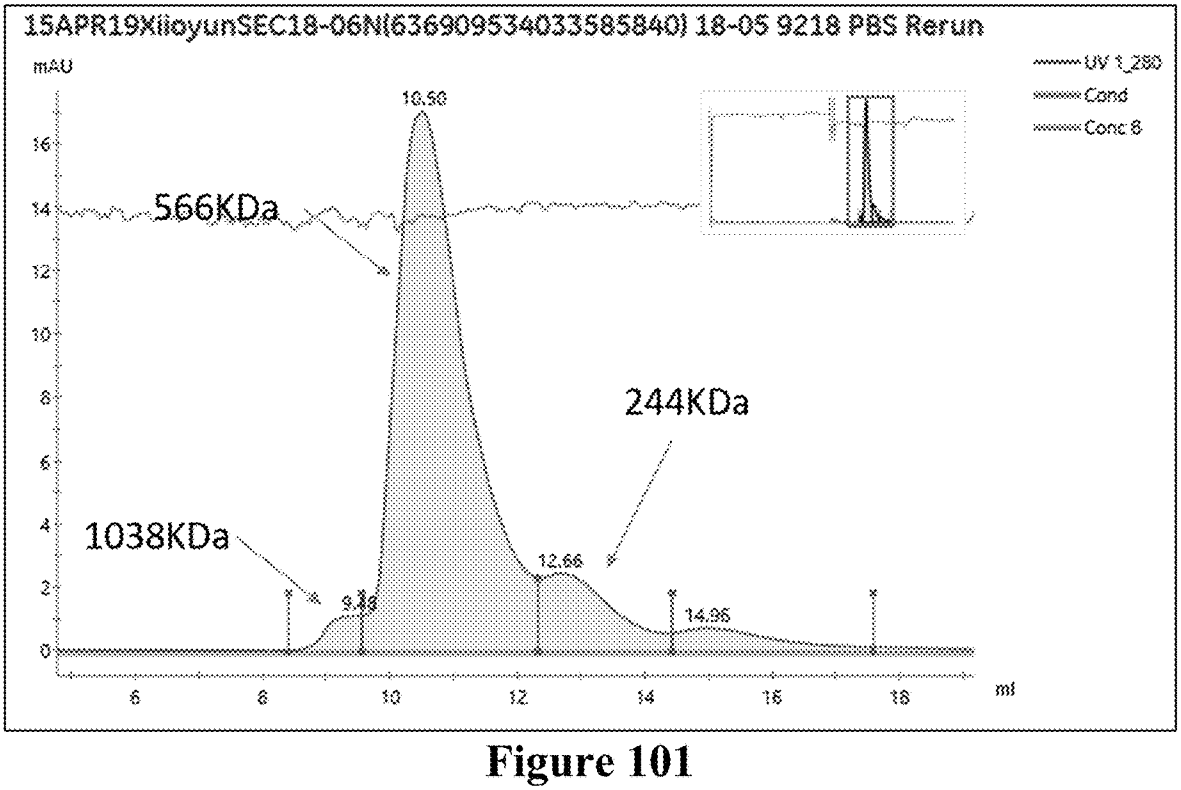

FIG. 101 shows the analytical SEC profile of TGFRt15-TGFRs.

Figure 102:
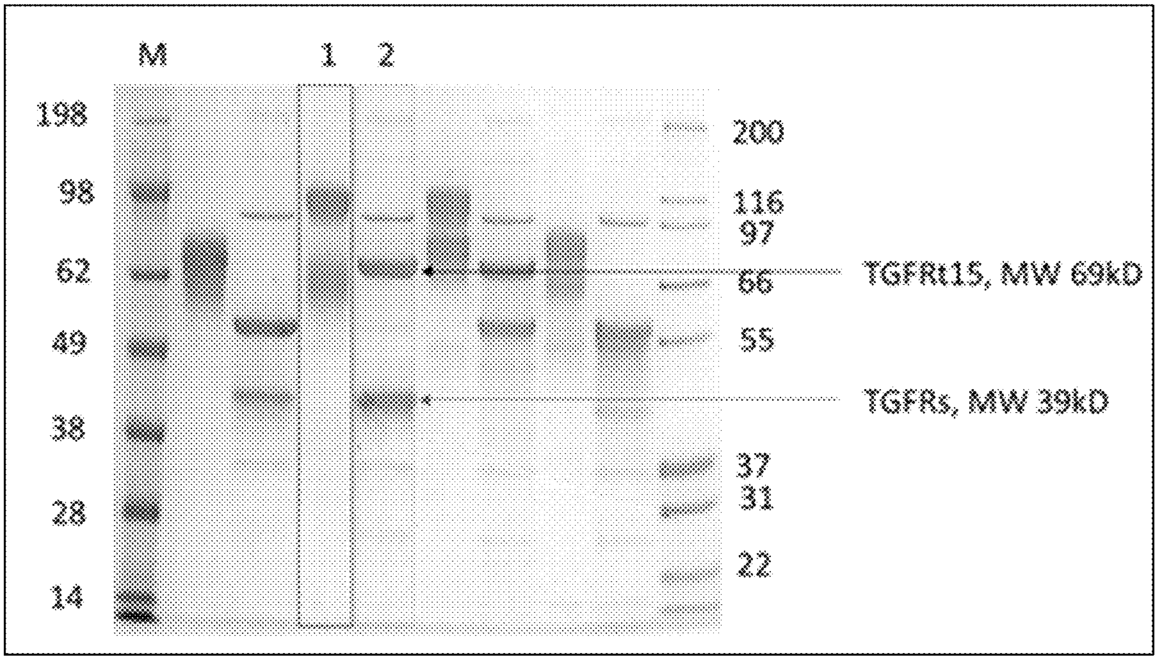

FIG. 102 shows TGFRt15-TGFRs before and after deglycosylation as analyzed by reduced SDS-PAGE.

Figure 103A:
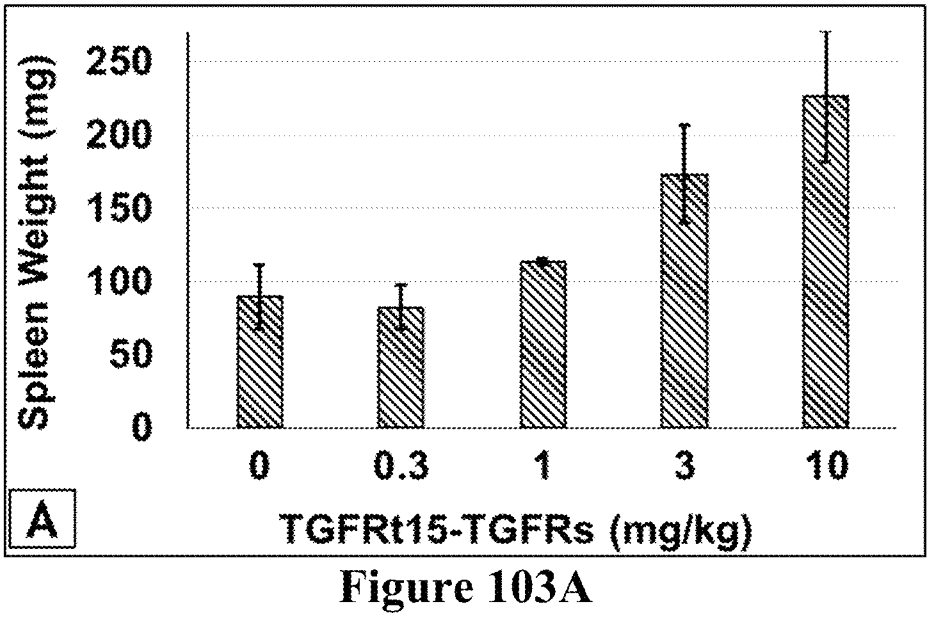
Figure 103B:
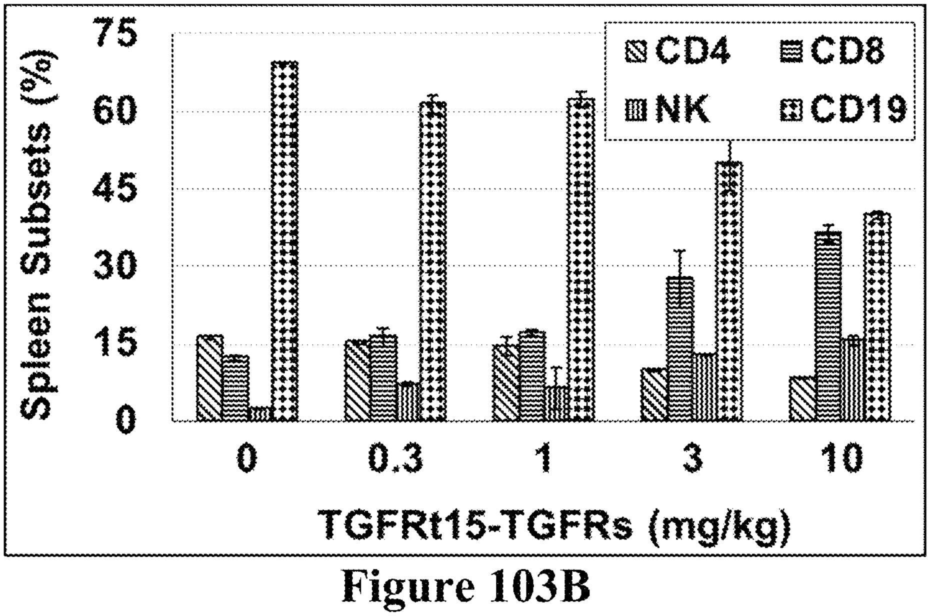

FIGS. 103A and 103B show spleen weight and the percentages of immune cell types in TGFRt15-TGFRs-treated and control-treated mice. FIG. 103A shows spleen weight in mice treated with TGFRt15-TGFRs as compared to PBS control. FIG. 103B shows the percentage of $CD4^+$ T cells, $CD8^+$ T cells, and NK cells in mice treated with TGFRt15-TGFRs as compared to PBS control.

Figure 104A:
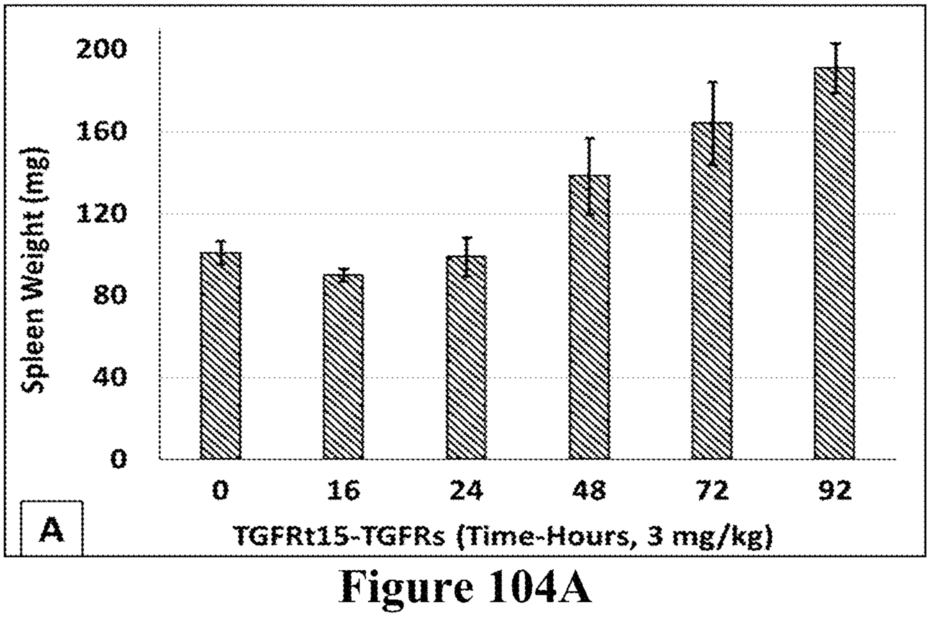
Figure 104B:
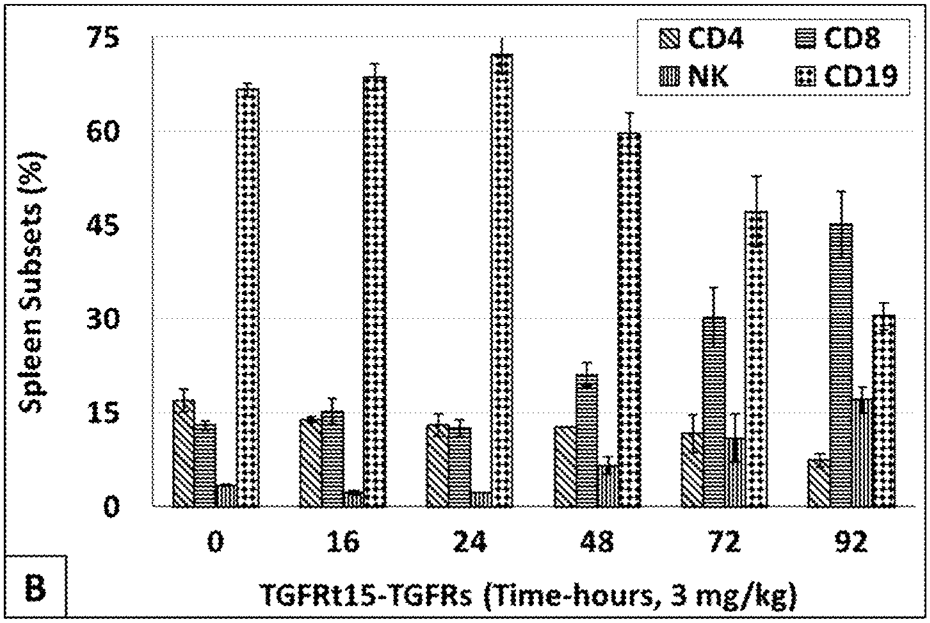

FIGS. 104A and 104B show the spleen weight and immunostimulation over 92 hours in mice treated with TGFRt15-TGFRs. FIG. 104A shows spleen weight of mice treated with TGFRt15-TGFRs at 16, 24, 48, 72, and 92 hours after treatment. FIG. 104B shows the percentages of immune cells in mice treated with TGFRt15-TGFRs at 16, 24, 48, 72, and 92 hours after treatment.

Figure 105A:
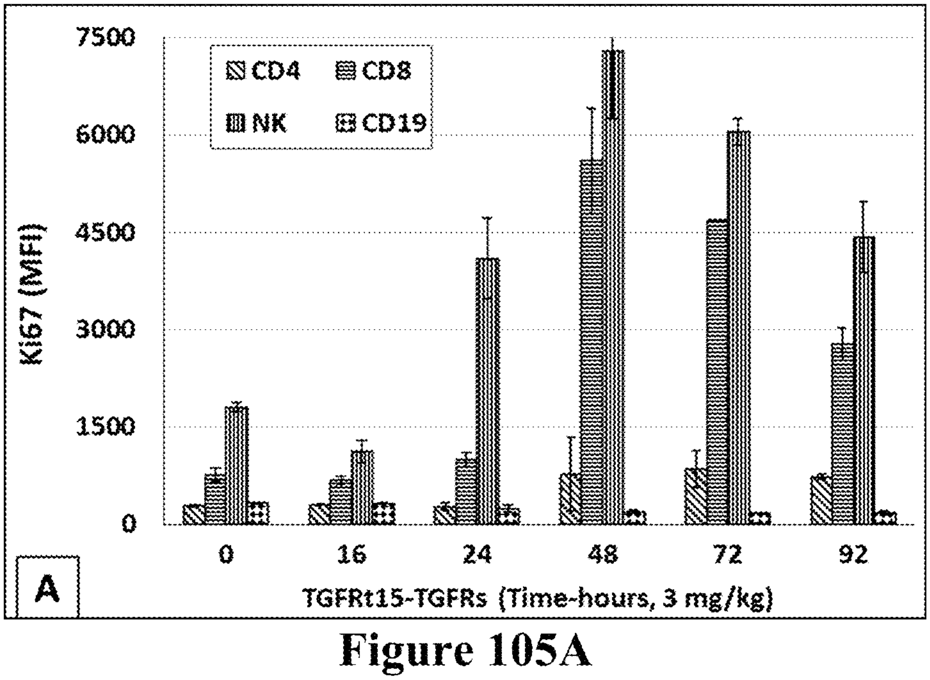
Figure 105B:
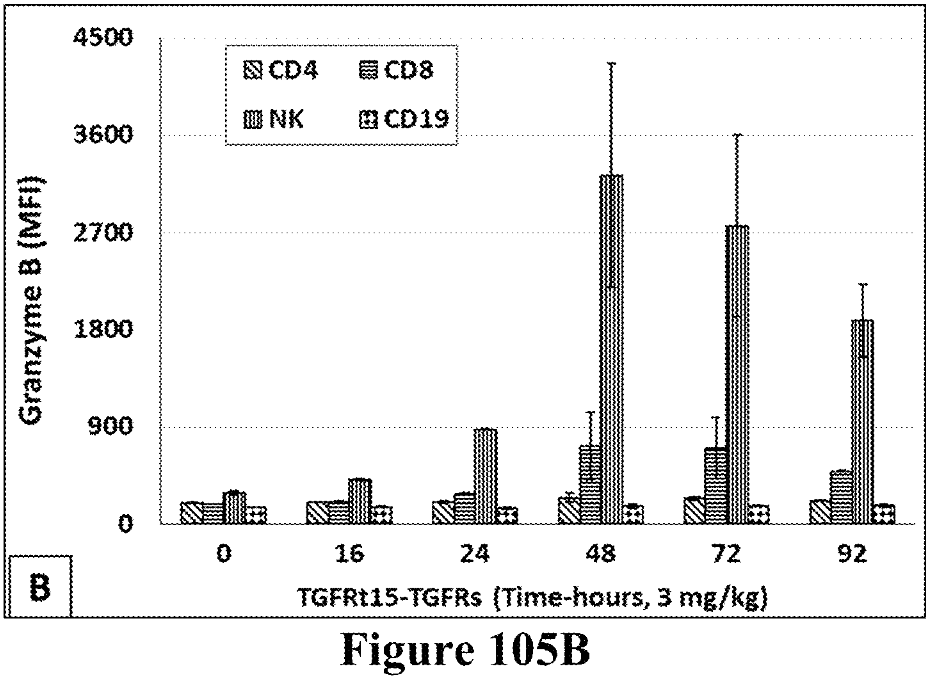

FIGS. 105A and 105B show Ki67 and Granzyme B expression in mice treated with TGFRt15-TGFRs over time.

Figure 106:
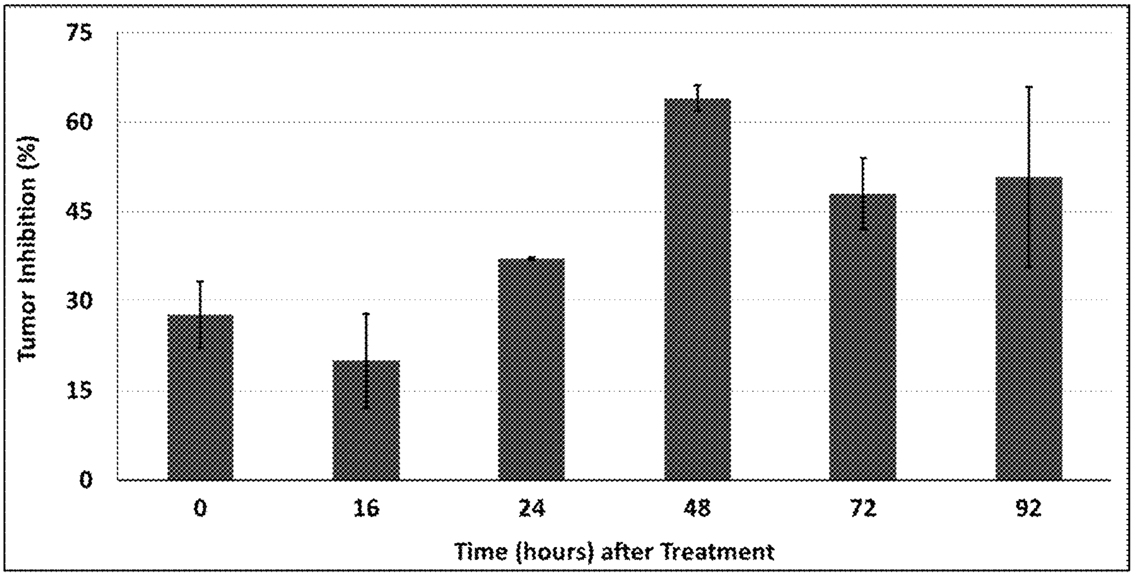

FIG. 106 shows enhancement of cytotoxicity of splenocytes by TGFRt15-TGFRs in C57BL/6 Mice.

Figure 107:
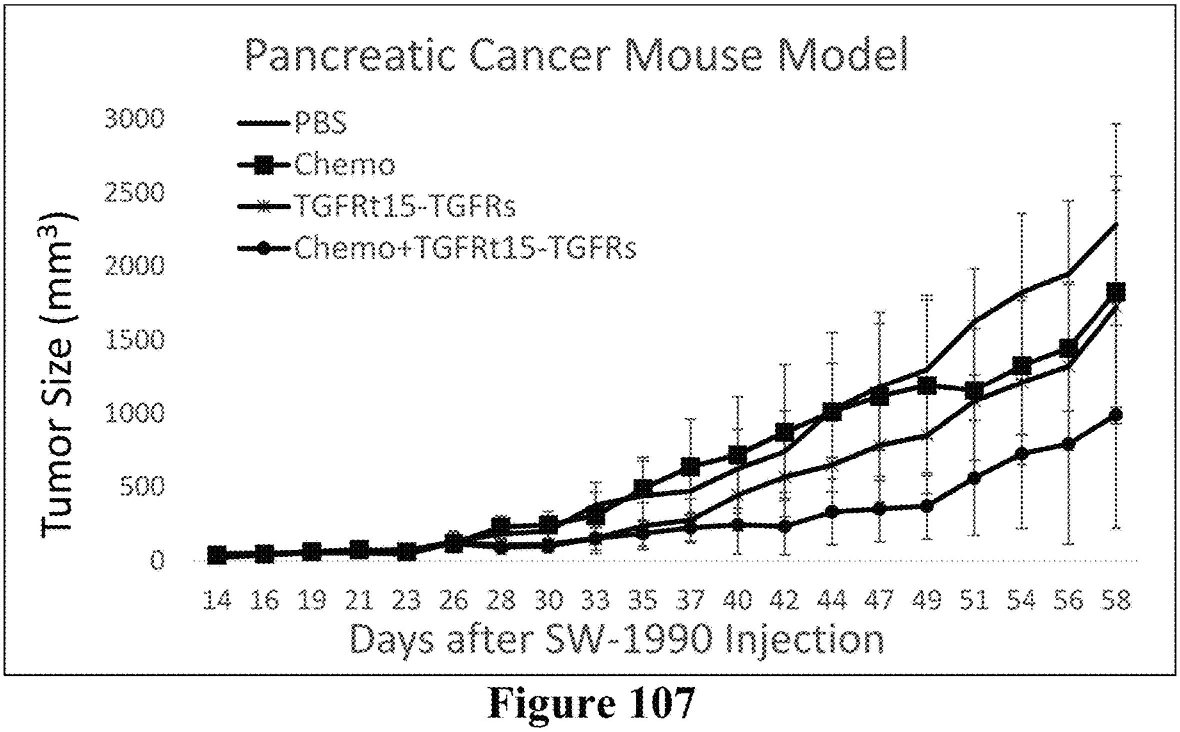

FIG. 107 shows changes in tumor size in response to PBS treatment, chemotherapy alone, TGFRt15-TGFRs alone, or chemotherapy and TGFRt15-TGFRs combination, in a pancreatic cancer mouse model.

Figure 108:
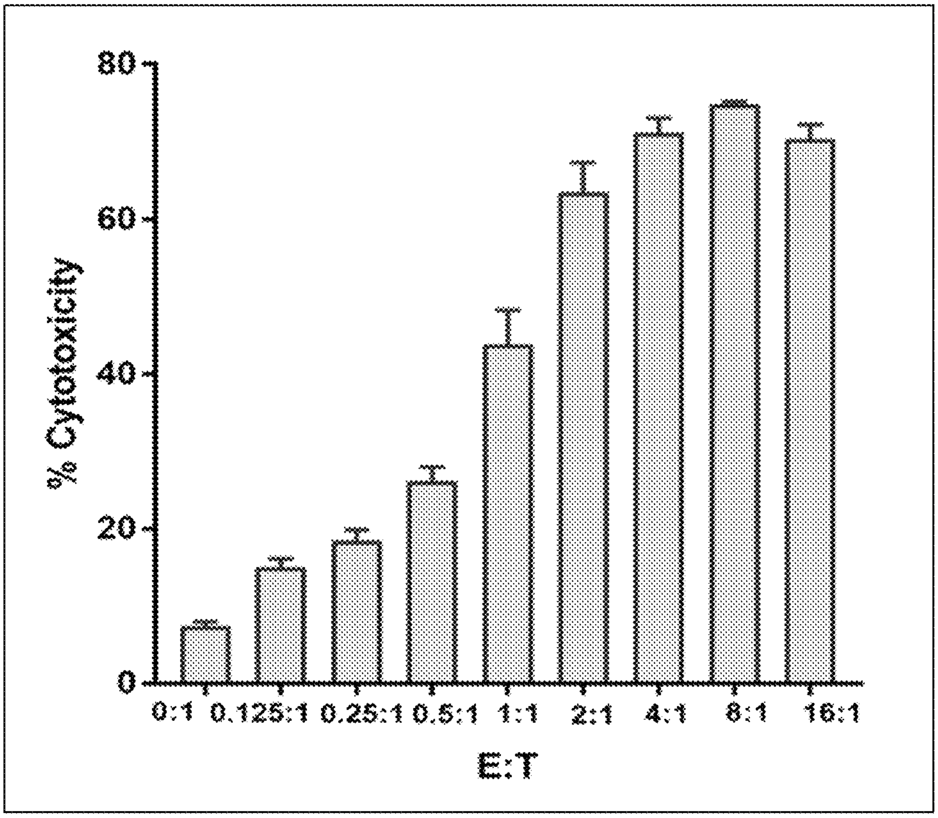

FIG. 108 shows the cytotoxicity of NK cells isolated from mice treated with TGFRt15-TGFRs.

Figure 109:
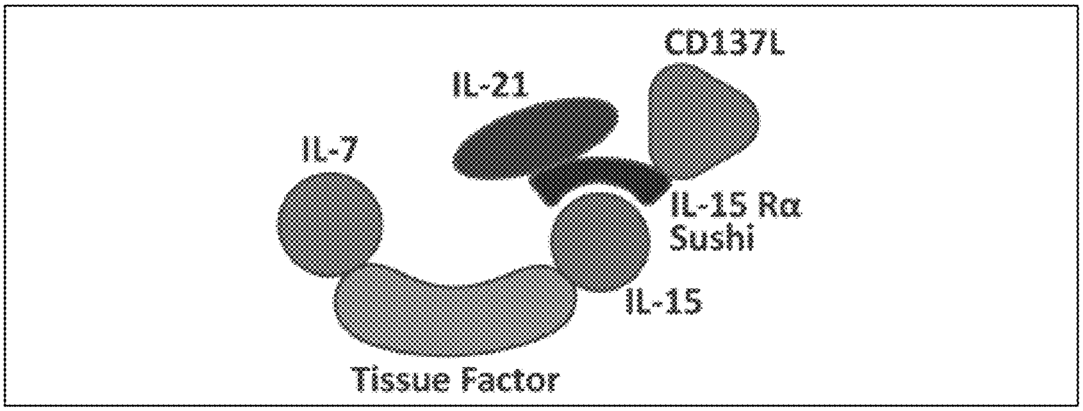

FIG. 109 shows a schematic of the 7t15-21s137L (long version) construct.

Figure 110:
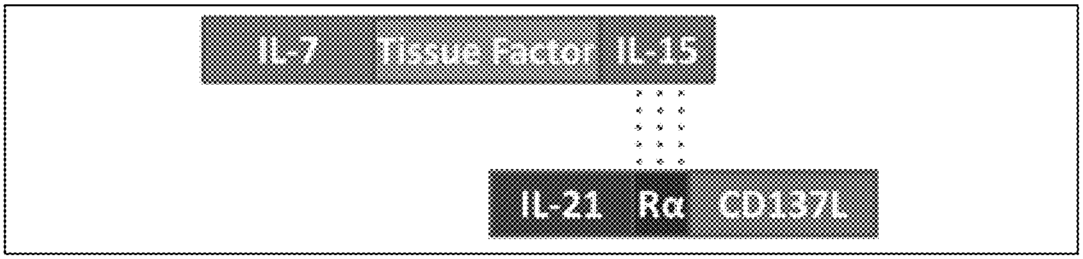

FIG. 110 shows an additional schematic of the 7t15-21s137L (long version) construct.

Figure 111:
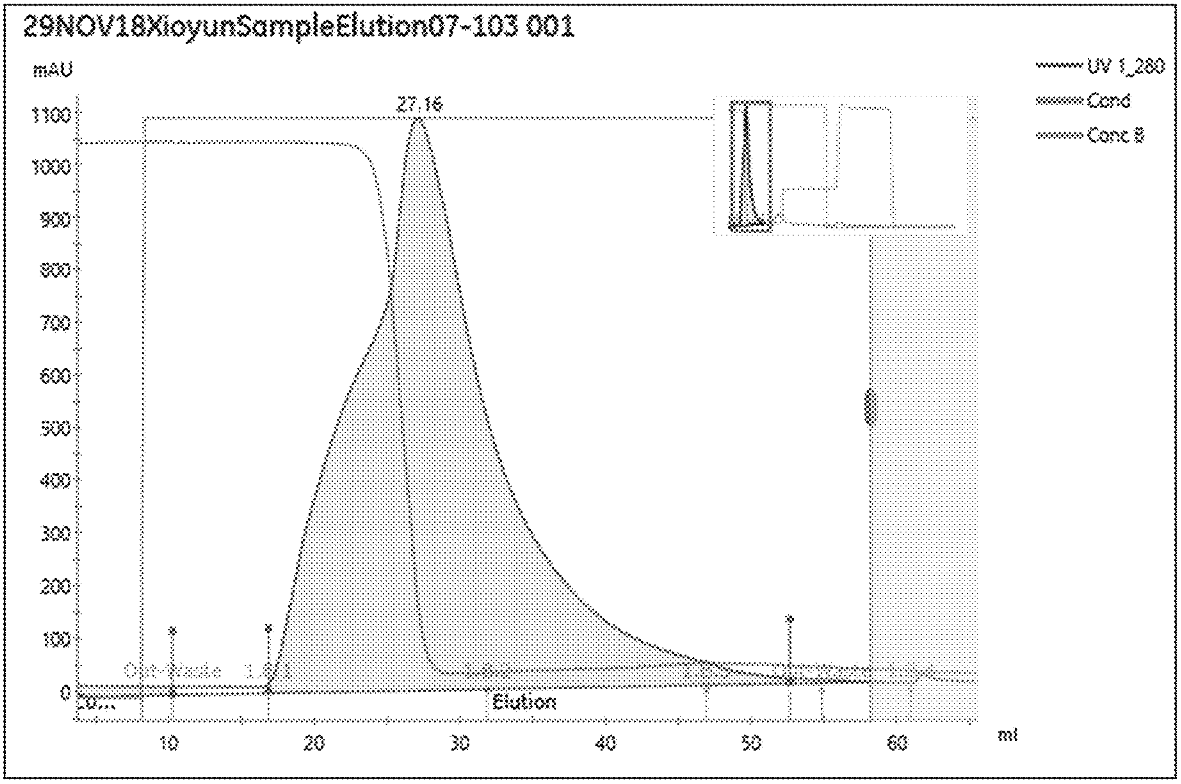

FIG. 111 is a line graph showing the chromatographic profile of 7t15-21s137L (long version) protein containing cell culture supernatant following binding and elution on anti-TF antibody resin.

Figure 112:
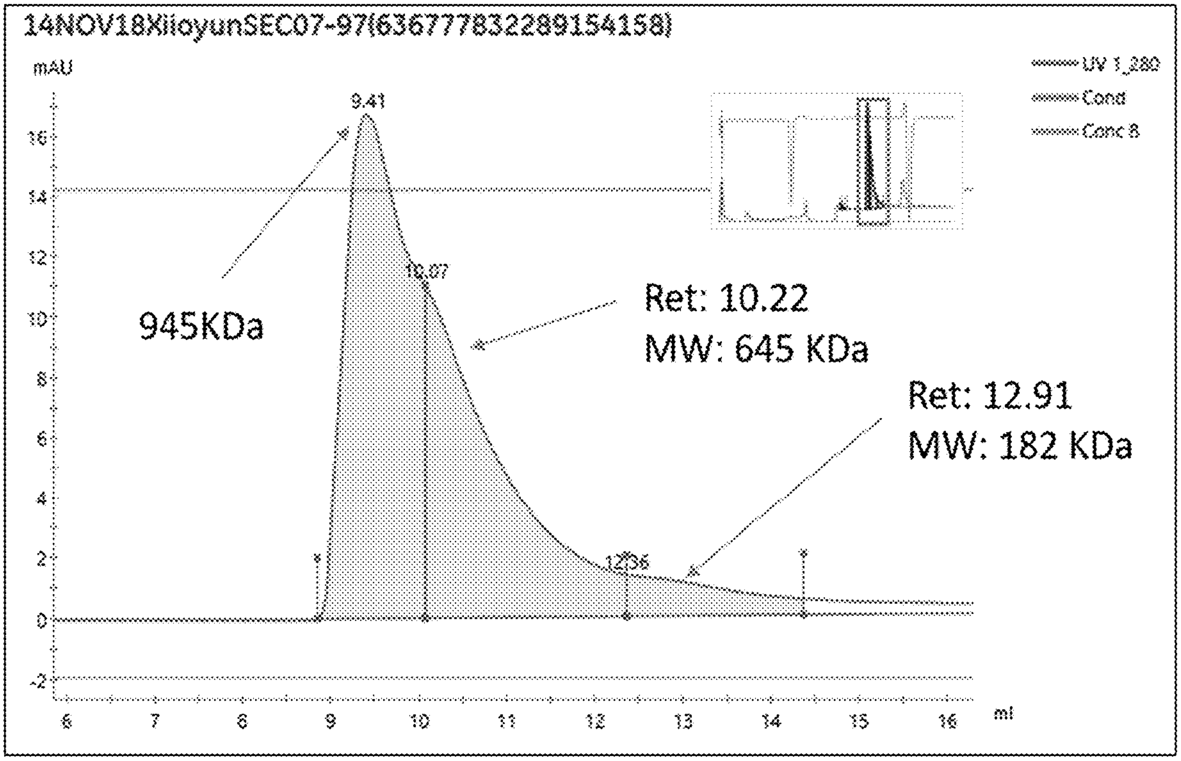

FIG. 112 shows the analytical SEC profile of 7t15-21s137L (long version).

Figure 113:
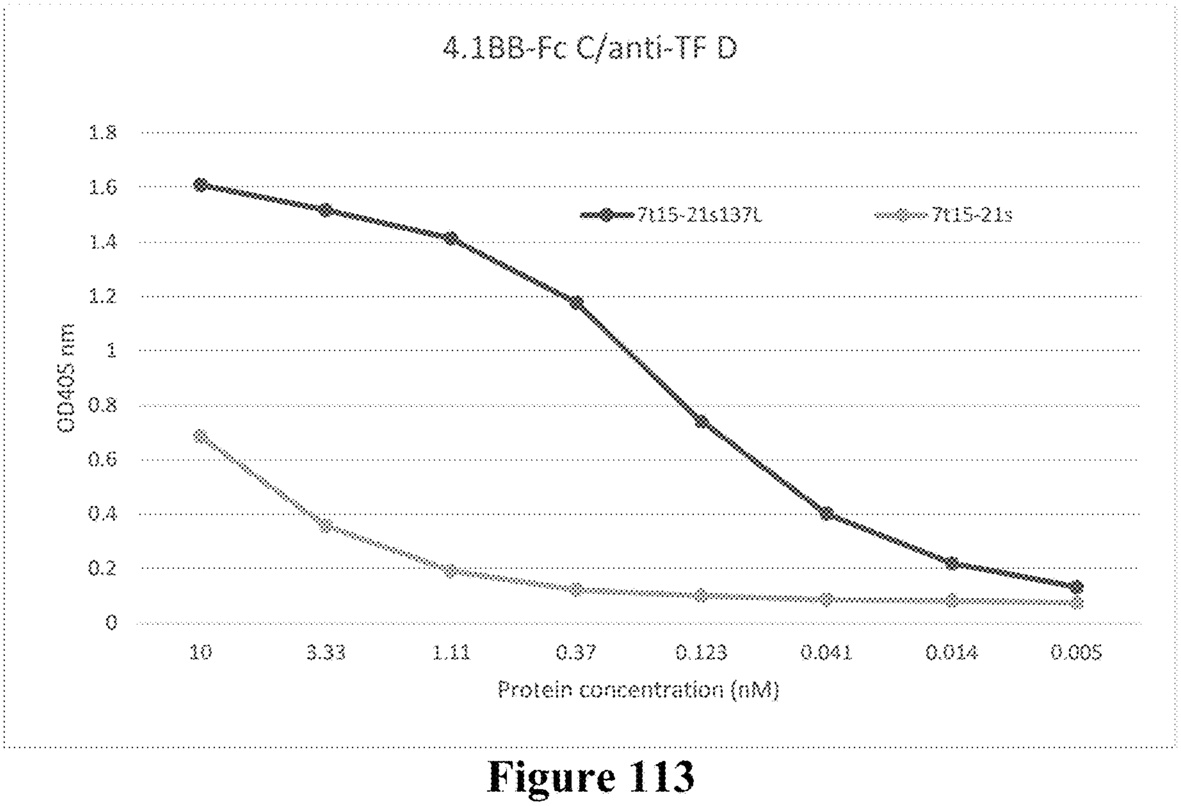

FIG. 113 shows binding of 7t15-21s137L (short version) to CD137L (4.1BBL)

Figure 114A:
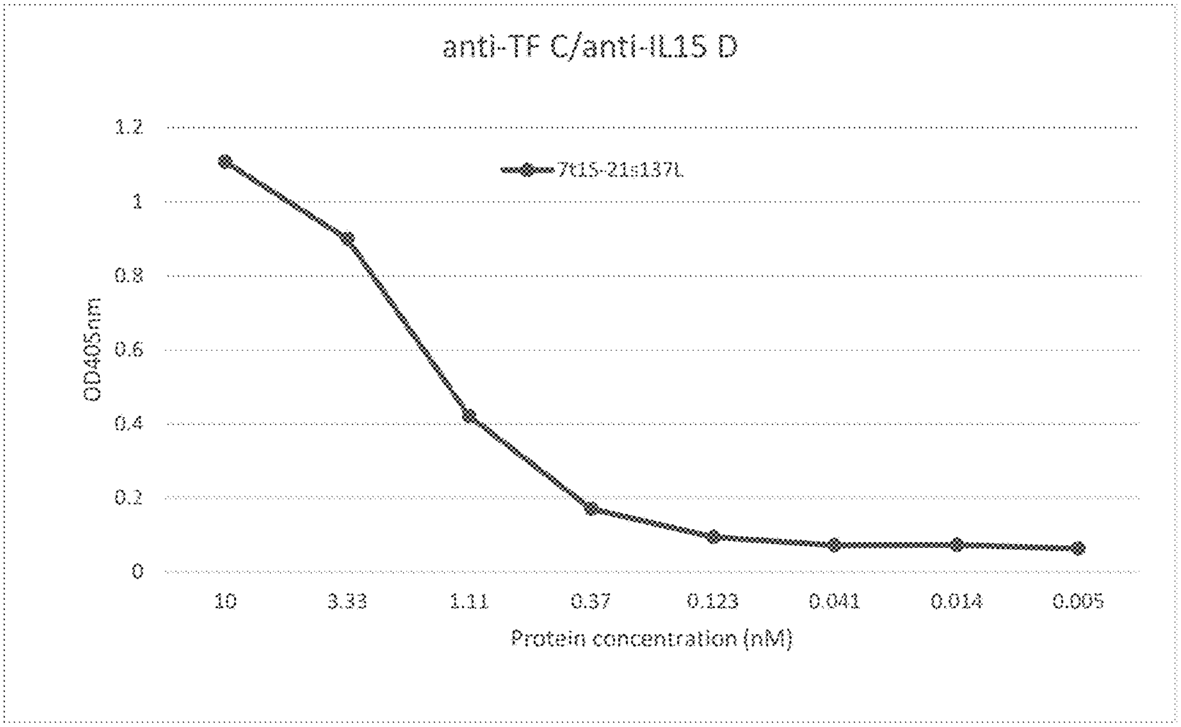
Figure 114B:
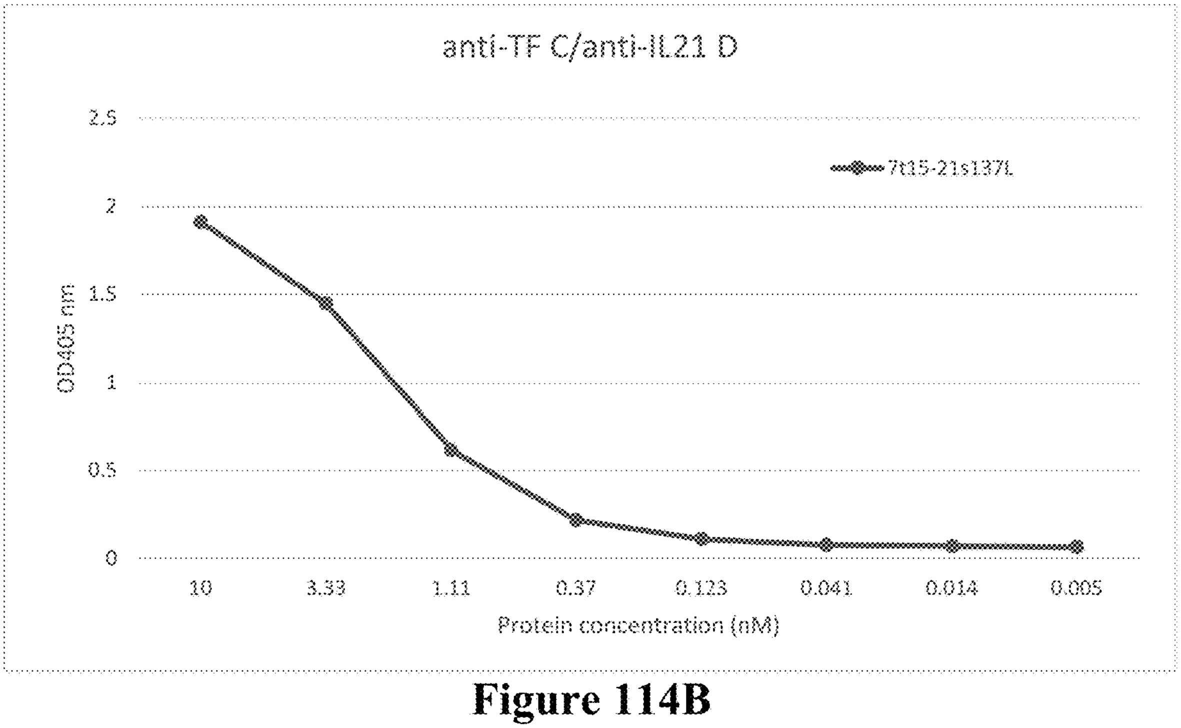
Figure 114C:
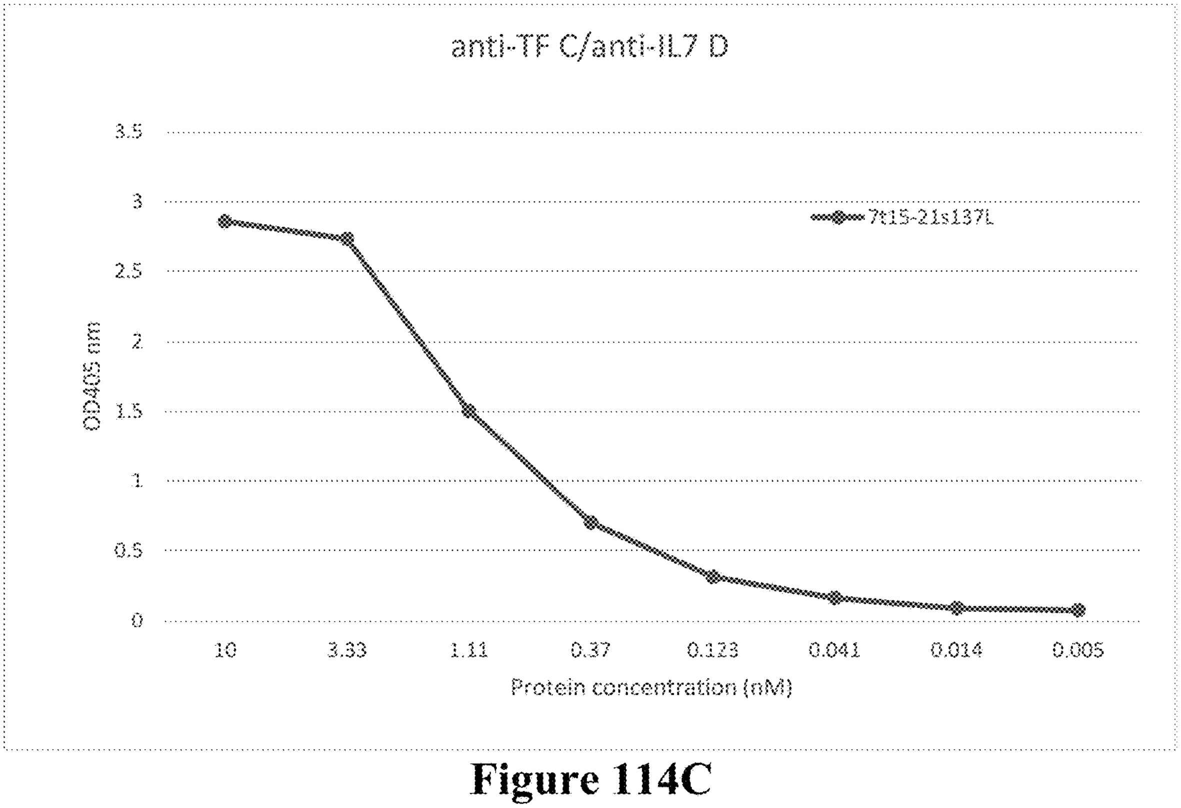

FIGS. 114A-114C show detection of IL-15, IL21, and IL7 in 7t15-21s137L (short version) with ELISA. FIG. 114A shows detection of IL-15 in 7t15-21s137L (short version) with ELISA. FIG. 114B shows detection of IL21 in 7t15-21s137L (short version) with ELISA. FIG. 114C shows detection of IL7 in 7t15-21s137L (short version) with ELISA.

Figure 115:
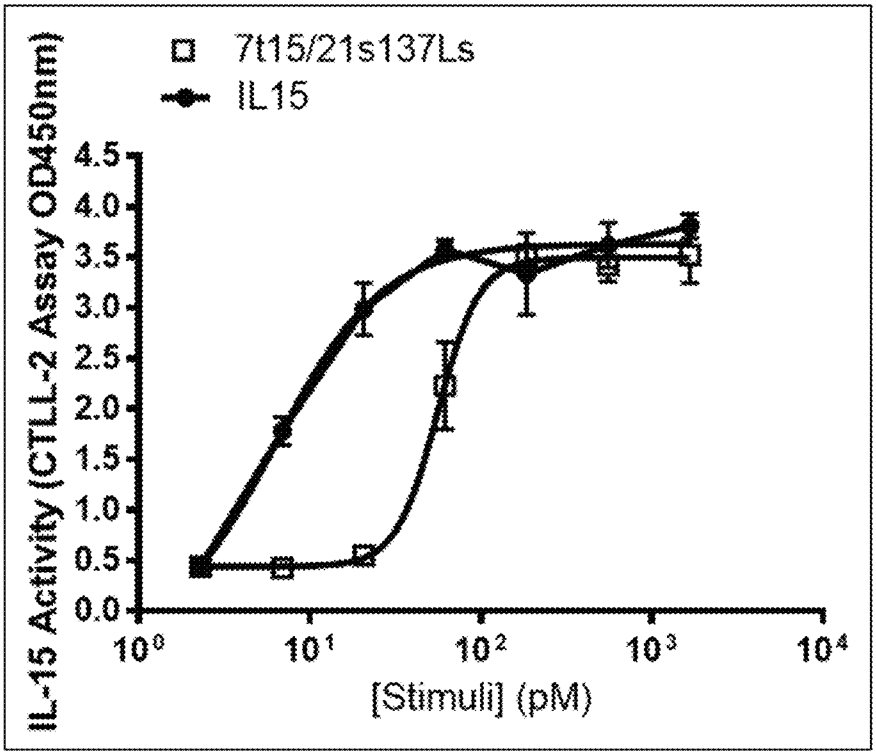

FIG. 115 shows results from a CTLL-2 cell proliferation assay.

Figure 116:
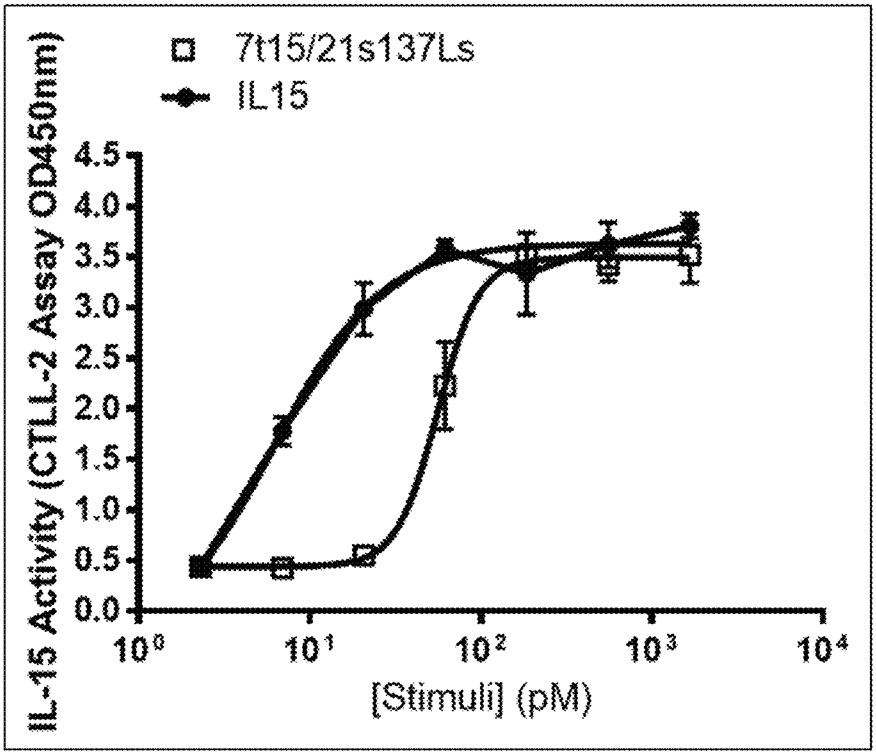

FIG. 116 shows the activity of 7t15-1s137L (short version) in promoting IL21R containing B9 cell proliferation.

Figure 117:
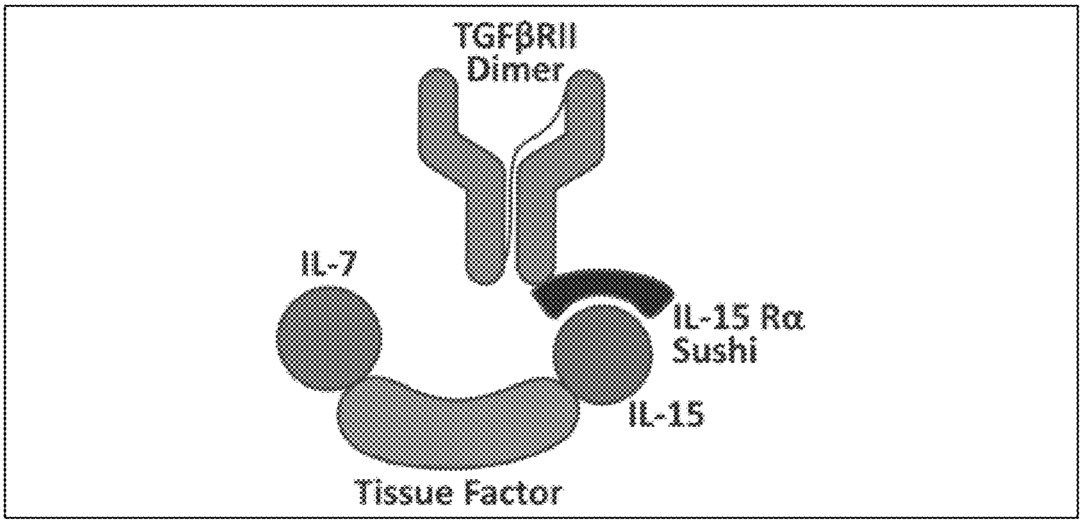

FIG. 117 shows a schematic of the 7t15-TGFRs construct.

Figure 118:
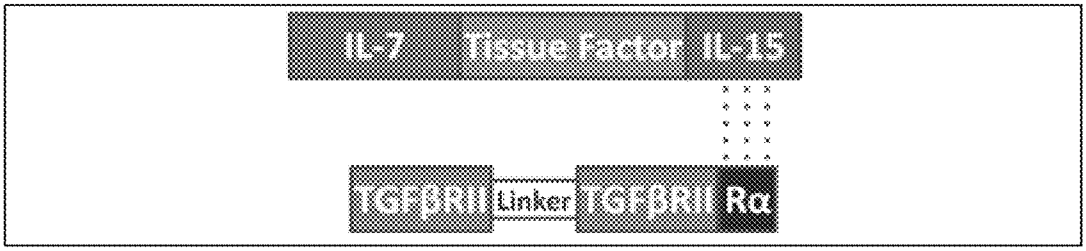

FIG. 118 shows an additional schematic of the 7t15-TGFRs construct.

Figure 119:
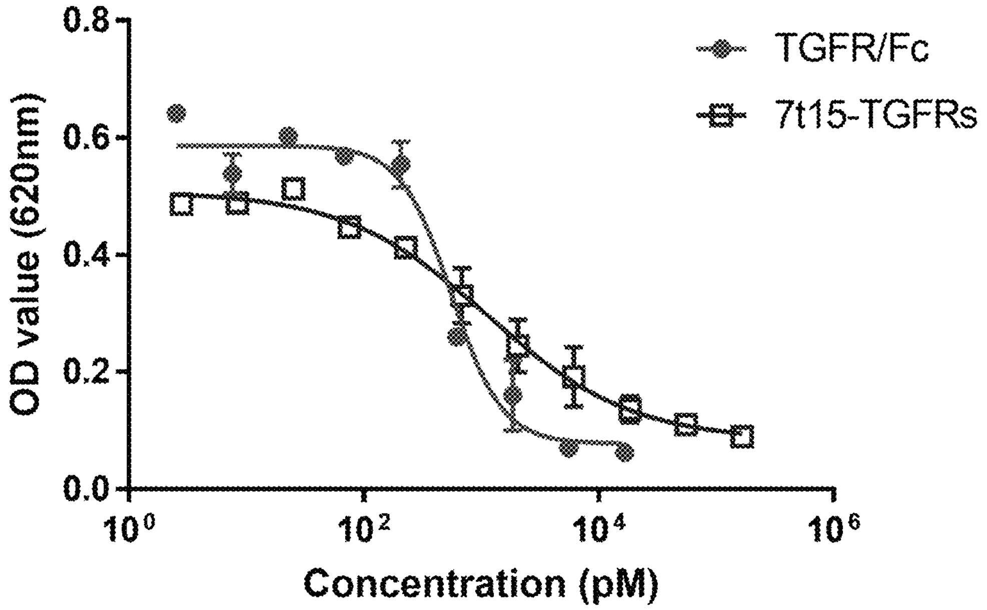

FIG. 119 shows results of TGFβ1 inhibition by 7t15-TGFRs and TGFR-Fc.

Figure 120A:
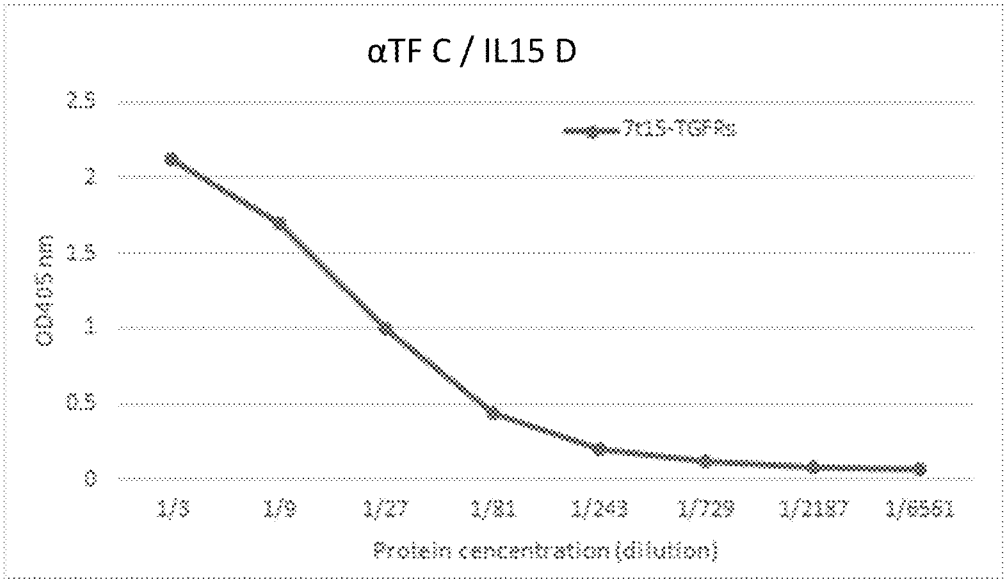
Figure 120B:
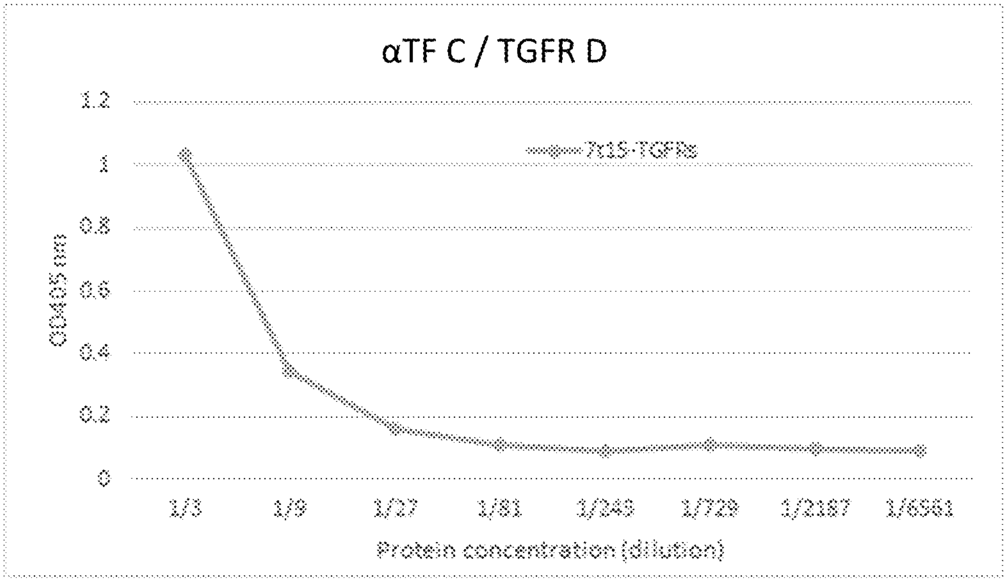
Figure 120C:
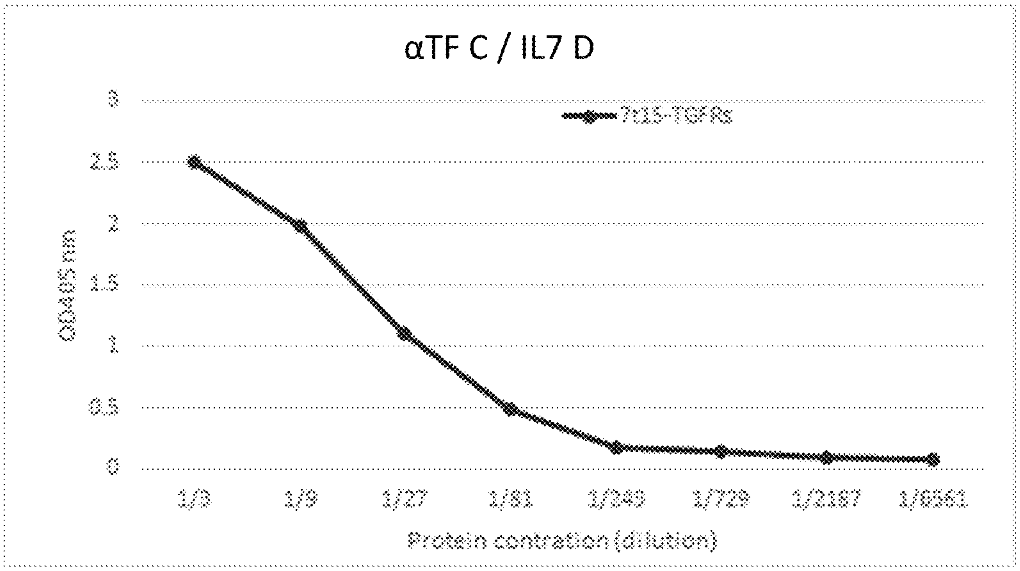

FIGS. 120A-120C show detection of IL-15, TGFβRII, and IL-7 in 7t15-TGFRs with ELISA.

Figure 121:
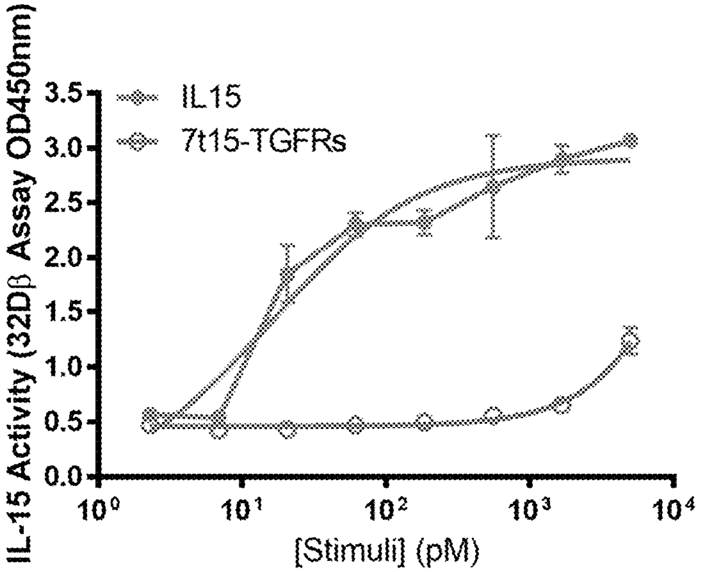

FIG. 121 shows results of a 32Dβ cell proliferation assay with 7t15-TGFRs or recombinant IL-15.

Figure 122:
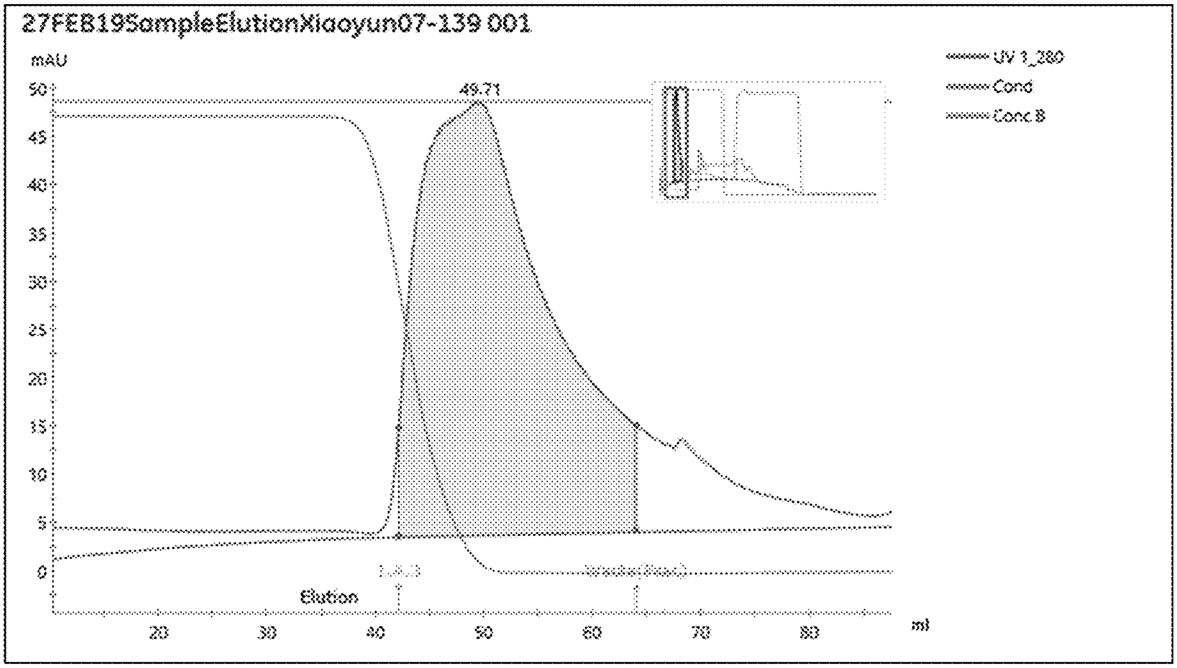

FIG. 122 is a line graph showing the chromatographic profile of 7t15-TGFRs protein containing cell culture supernatant following binding and elution on anti-TF antibody resin.

Figure 123:
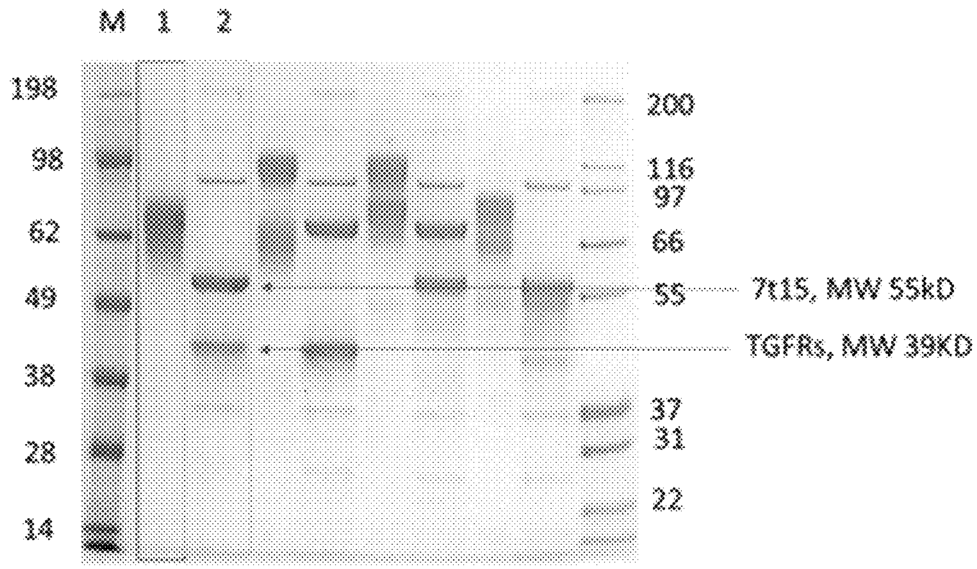

FIG. 123 shows 7t15-TGFRs before and after deglycosylation as analyzed using reduced SDS-PAGE.

Figure 124:
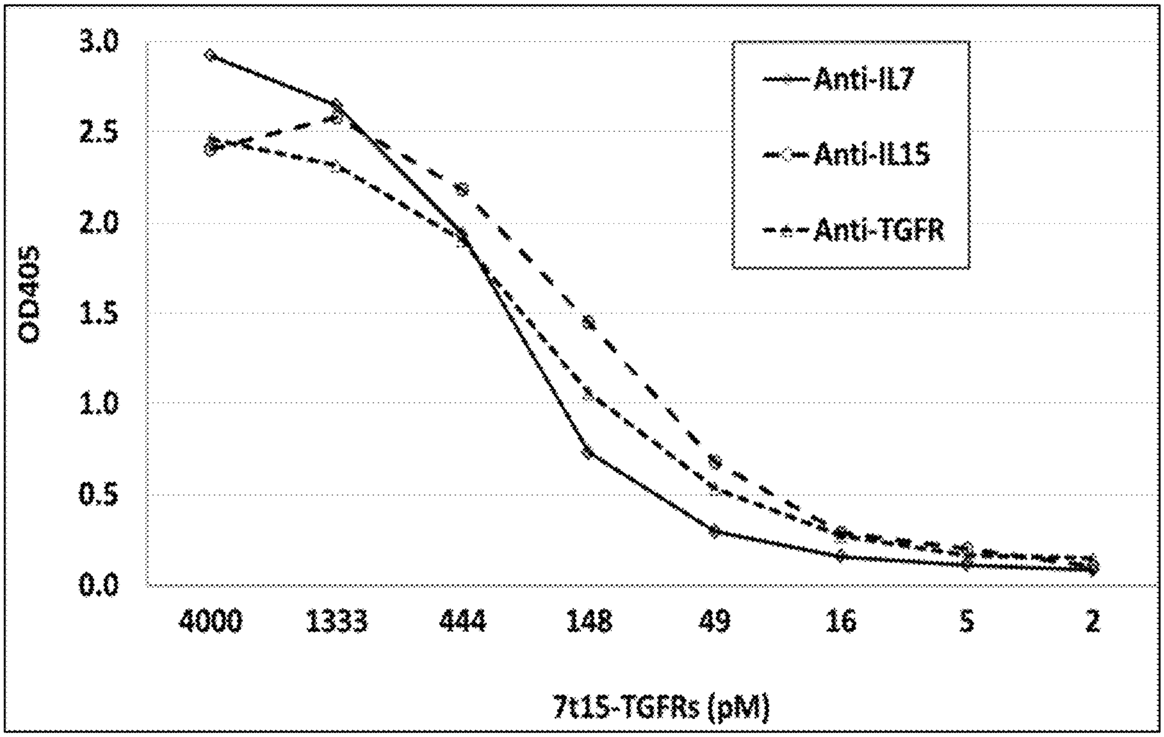

FIG. 124 shows ELISA detection of IL-7, IL-15 and TGFβRII in the 7t15-TGFRs protein.

Figure 125A:
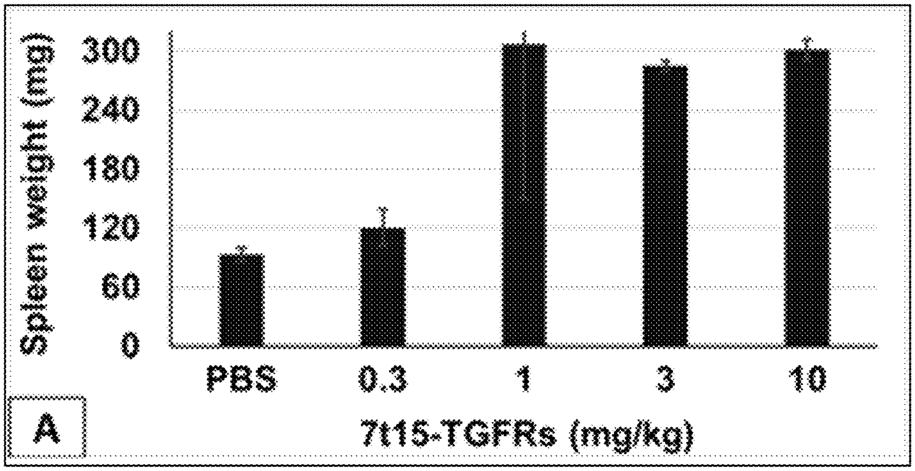
Figure 125B:
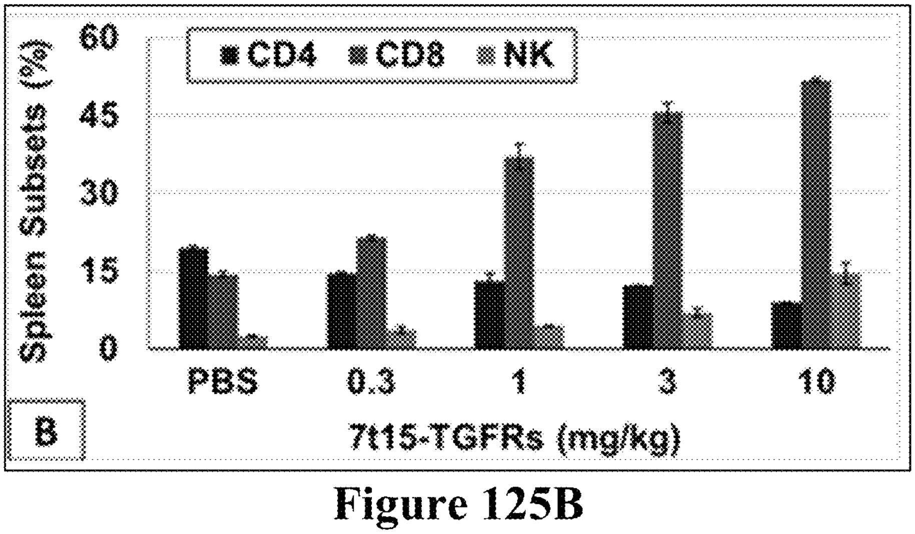

FIGS. 125A and 125B show spleen weight and the percentages of immune cell types in 7t15-TGFRs-treated and control-treated mice. FIG. 125A shows spleen weight in mice treated with 7t15-TGFRs at various dosages, as compared to PBS control. FIG. 125B shows the percentage of $CD4^+$ T cells, $CD8^+$ T cells, and NK cells in mice treated with 7t15-TGFRs at various dosages, as compared to PBS control.

Figure 126A:
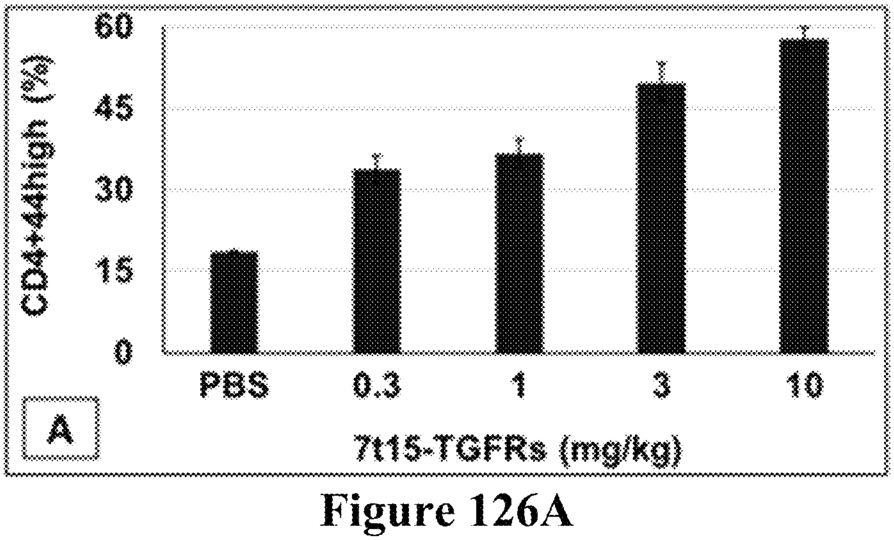
Figure 126B:
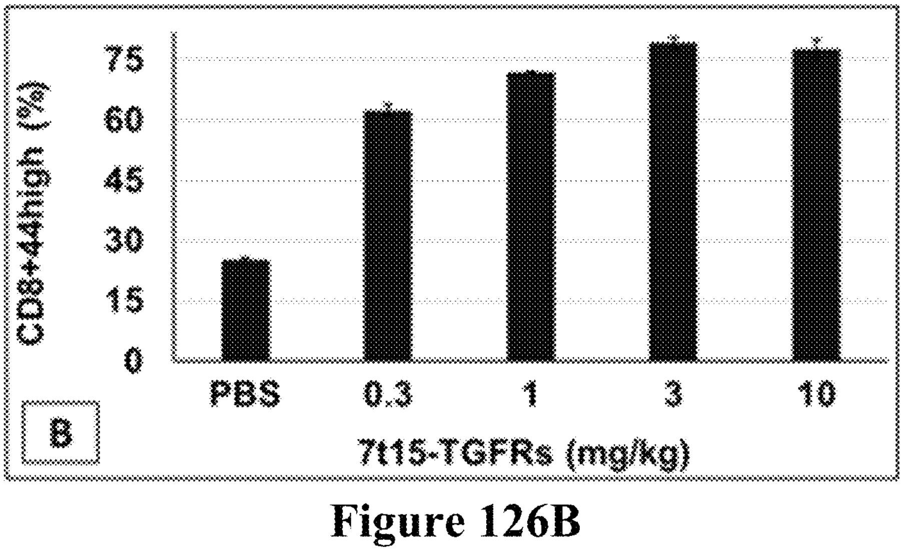

FIGS. 126A and 126B show upregulation of CD44 expression of $CD4^+$ and $CD8^+$ T cells by 7t15-TGFRs in C57BL/6 mice.

Figure 127A:
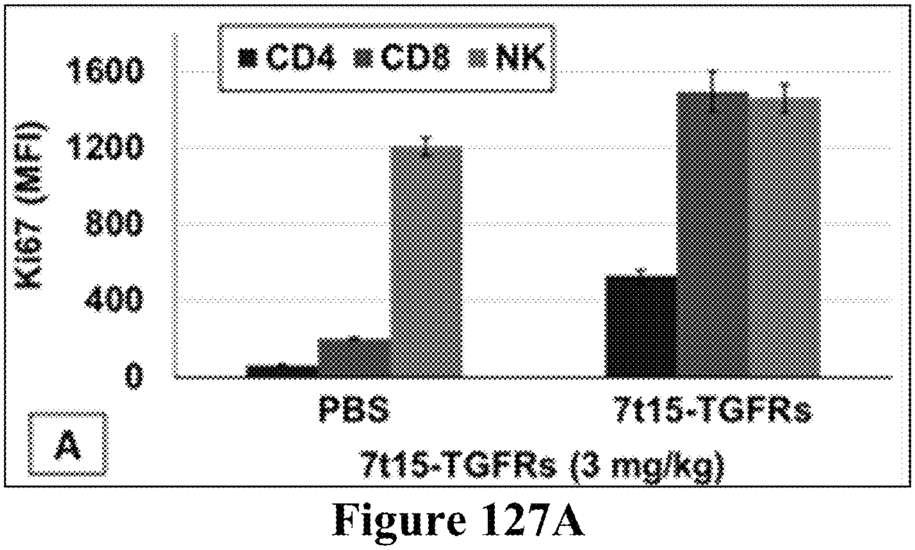
Figure 127B:
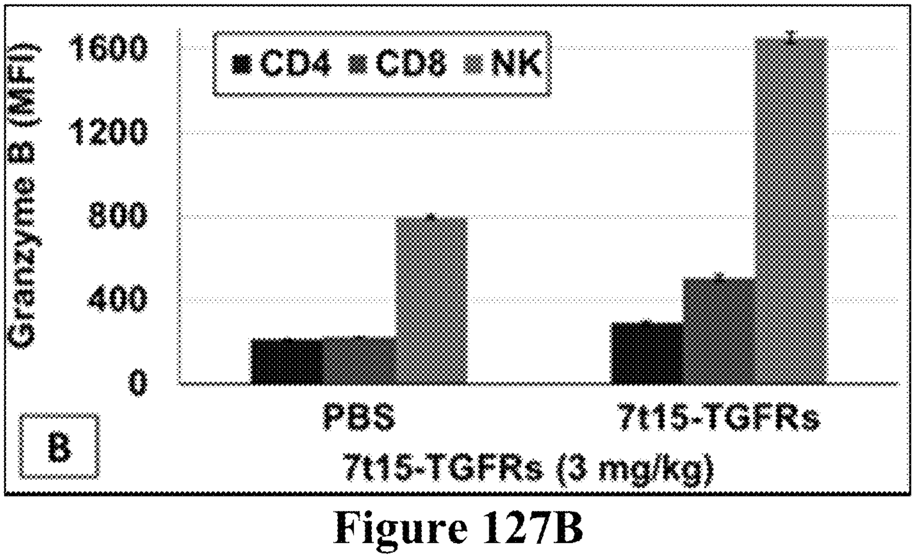

FIGS. 127A and 127B show upregulation of Ki67 expression and Granzyme B expression of $CD8^+$ T cells and NK Cells by 7t15-TGFRs in C57BL/6 mice.

Figure 128:
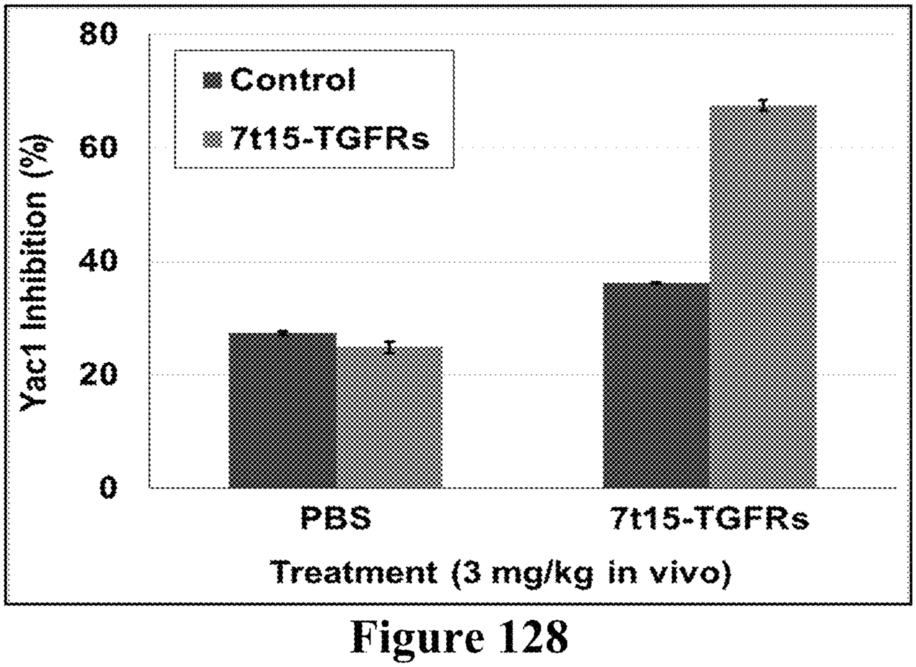

FIG. 128 shows enhancement of cytotoxicity of splenocytes by 7t15-TGFRs in C57BL/6 mice.

Figure 129:
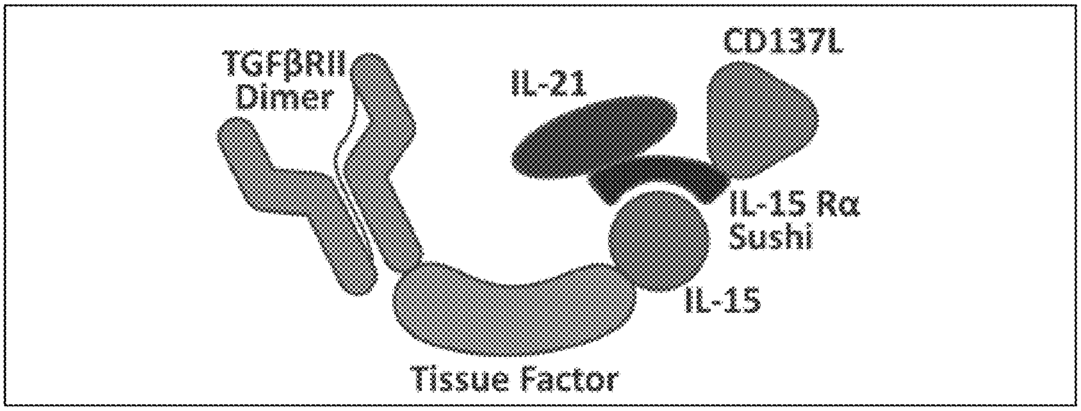

FIG. 129 shows a schematic of the TGFRt15-21s137L construct.

Figure 130:
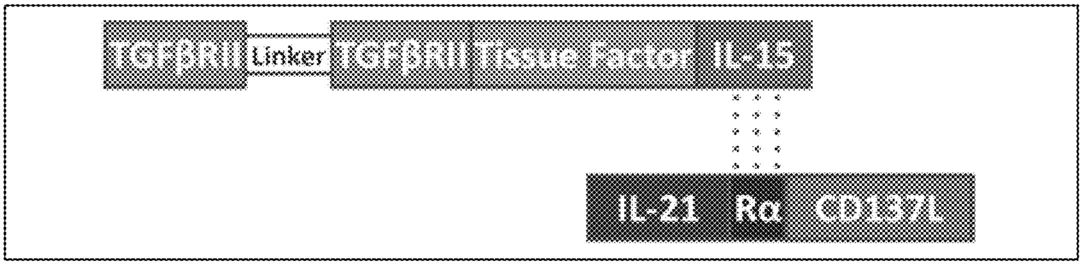

FIG. 130 shows an additional schematic of the TGFRt15-21s137L construct.

Figure 131:
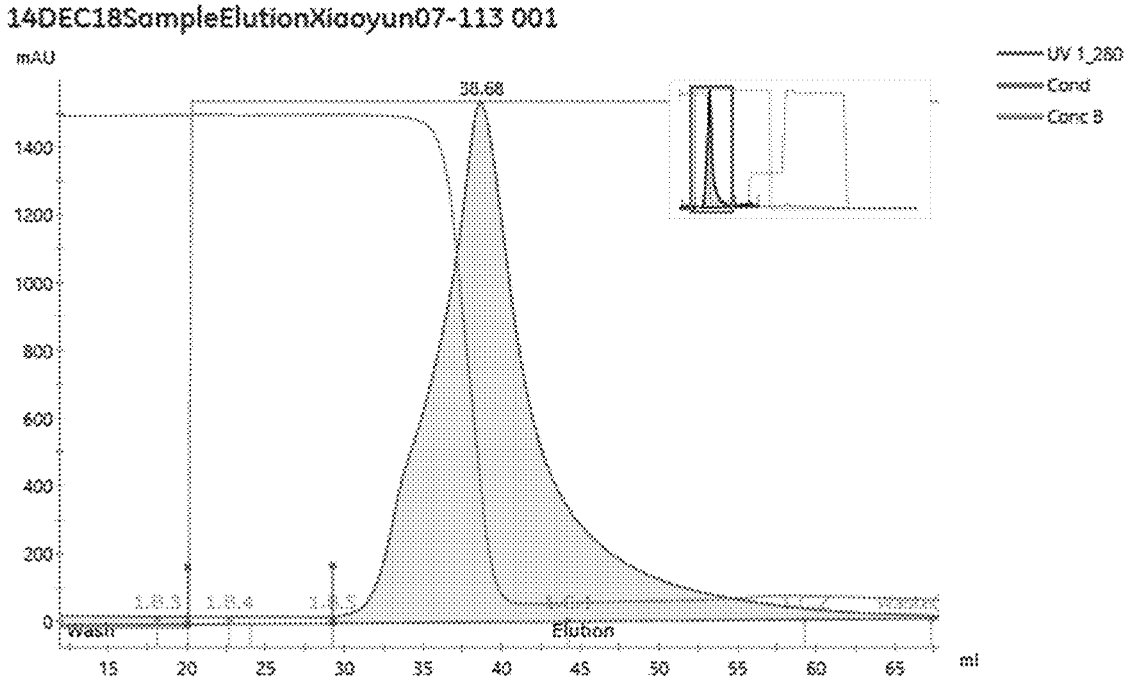

FIG. 131 is a line graph showing the chromatographic profile of TGFRt15-21s137L protein containing cell culture supernatant following binding and elution on anti-TF antibody resin.

Figure 132:
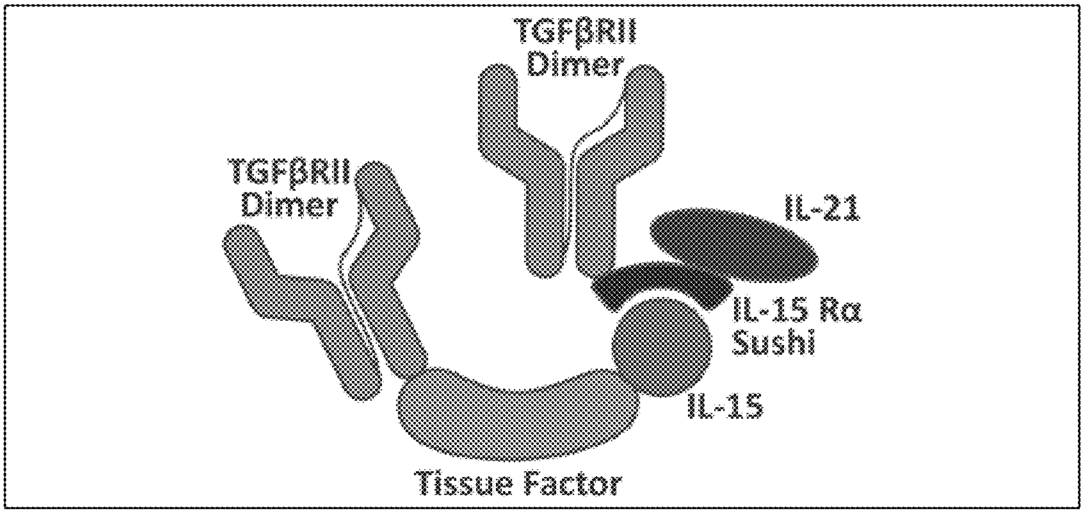

FIG. 132 shows a schematic of the TGFRt15-TGFRs21 construct.

Figure 133:
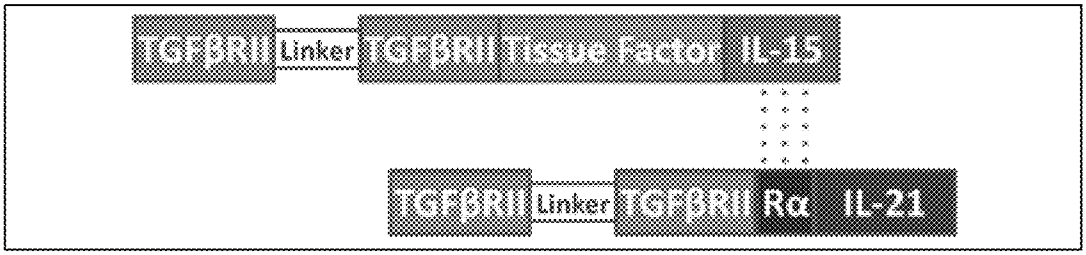

FIG. 133 shows an additional schematic of the TGFRt15-TGFRs21 construct.

Figure 134:
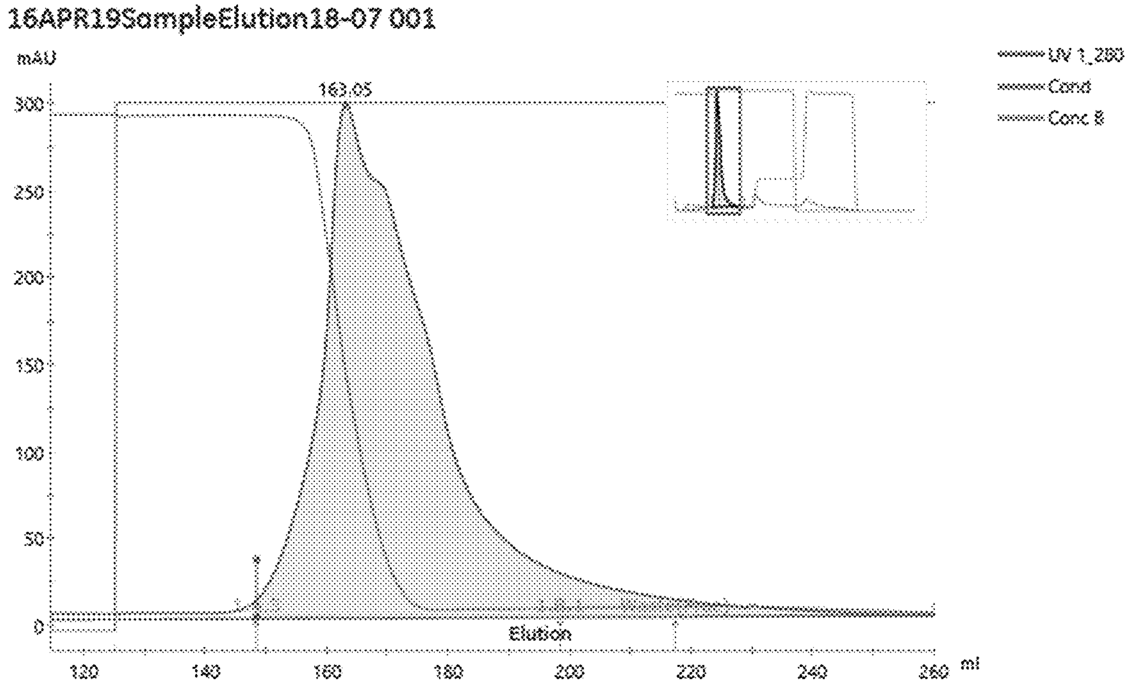

FIG. 134 is a line graph showing the chromatographic profile of TGFRt15-TGFRs21 protein containing cell culture supernatant following binding and elution on anti-TF antibody resin.

Figure 135:
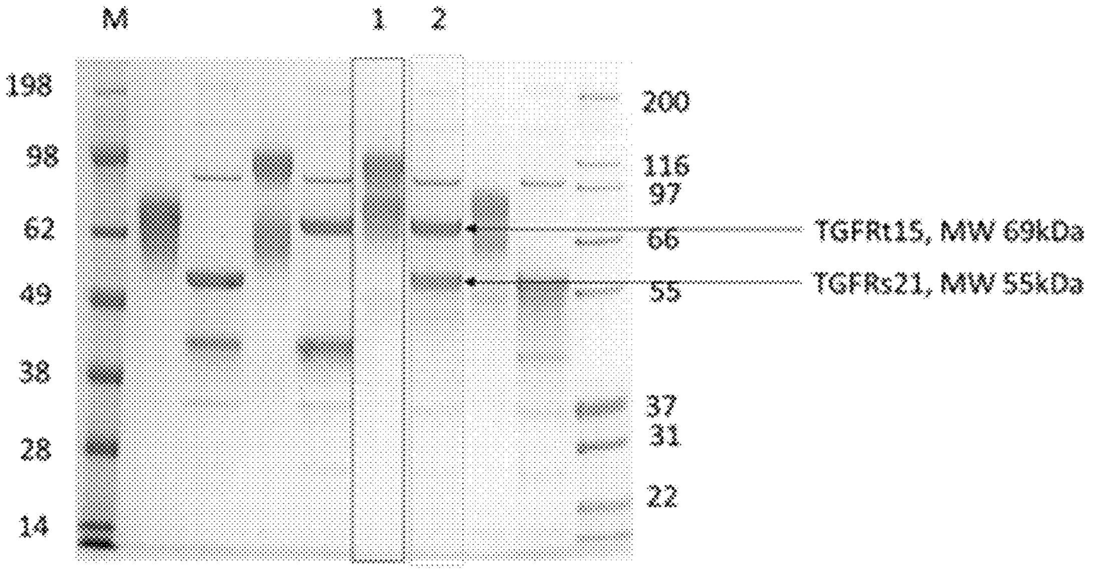

FIG. 135 shows TGFRt15-TGFRs21 before and after deglycosylation as analyzed by reduced SDS-PAGE.

Figure 136A:
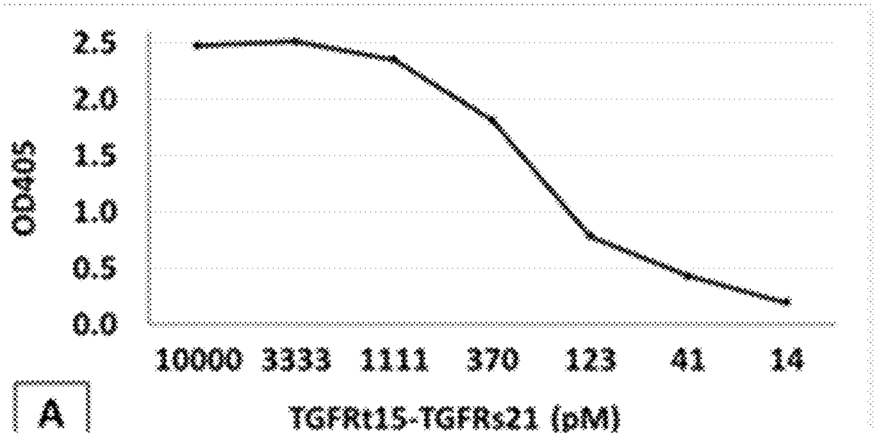
Figure 136B:
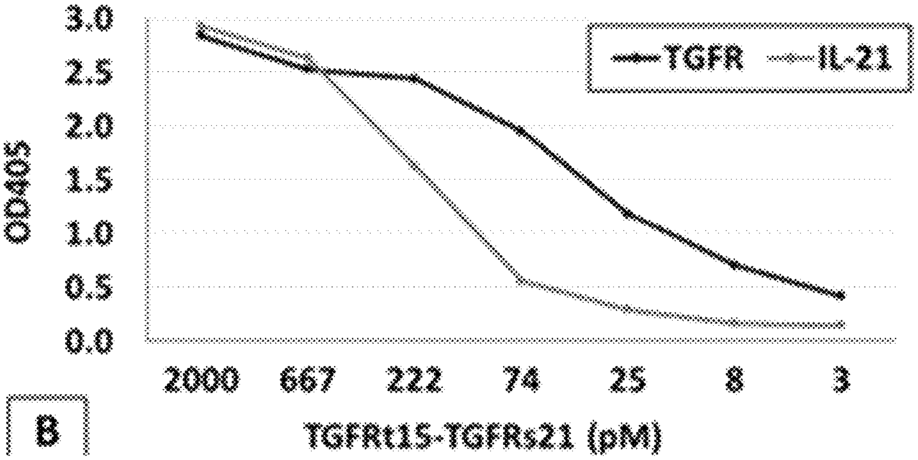

FIGS. 136A and 136B show detection of components of TGFRt15-TGFRs21 using ELISA.

Figure 137A:
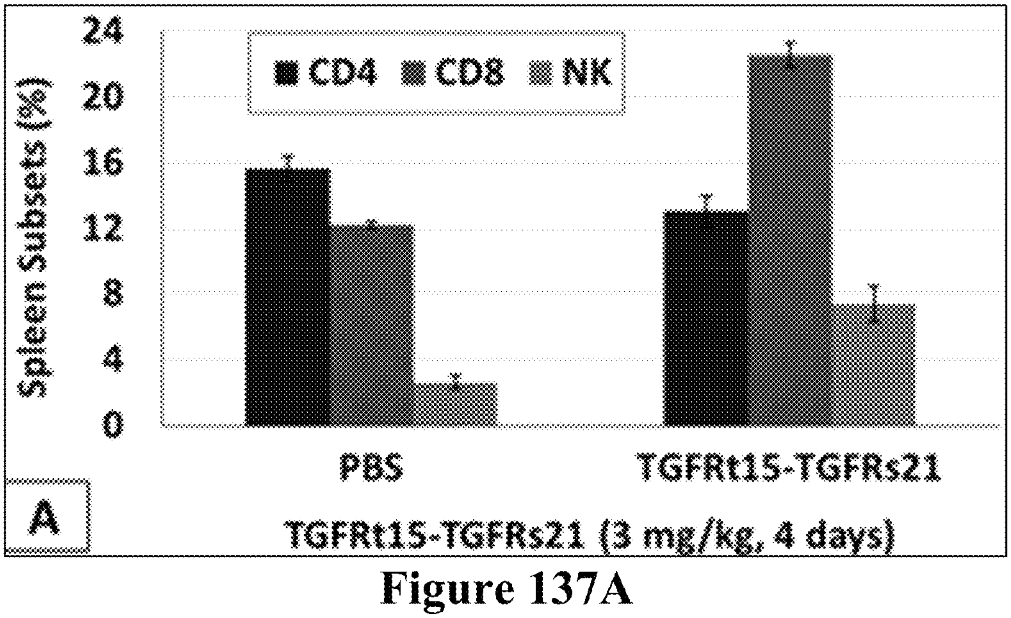
Figure 137B:
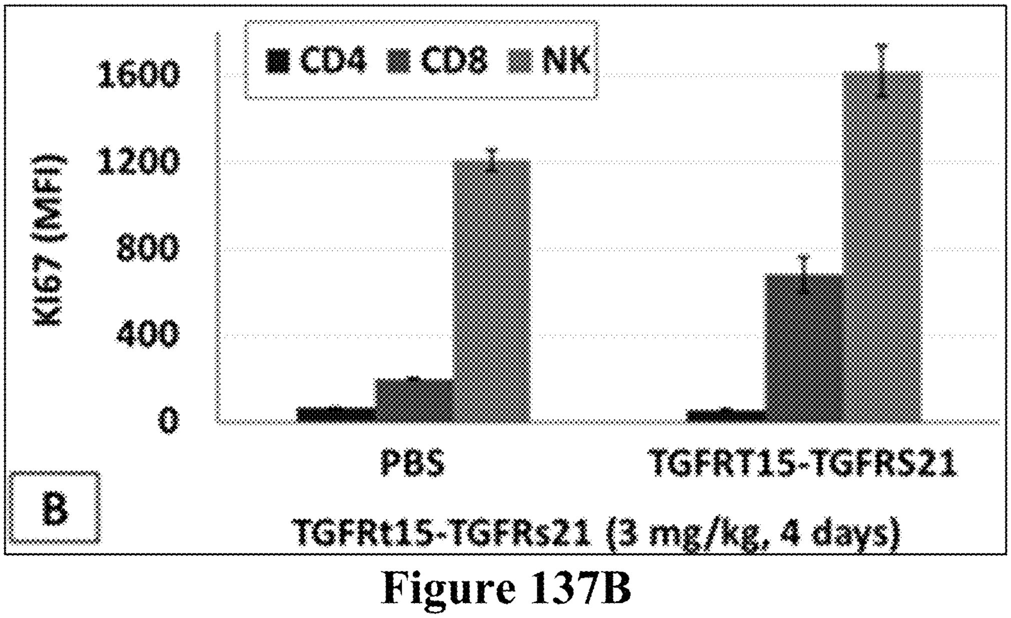

FIGS. 137A and 137B show the percentages and proliferation of $CD4^+$ T cells, $CD8^+$ T cells, and natural killer (NK) cells present in the spleen of control-treated and TGFRt15-TGFRs21-treated mice.

Figure 138:
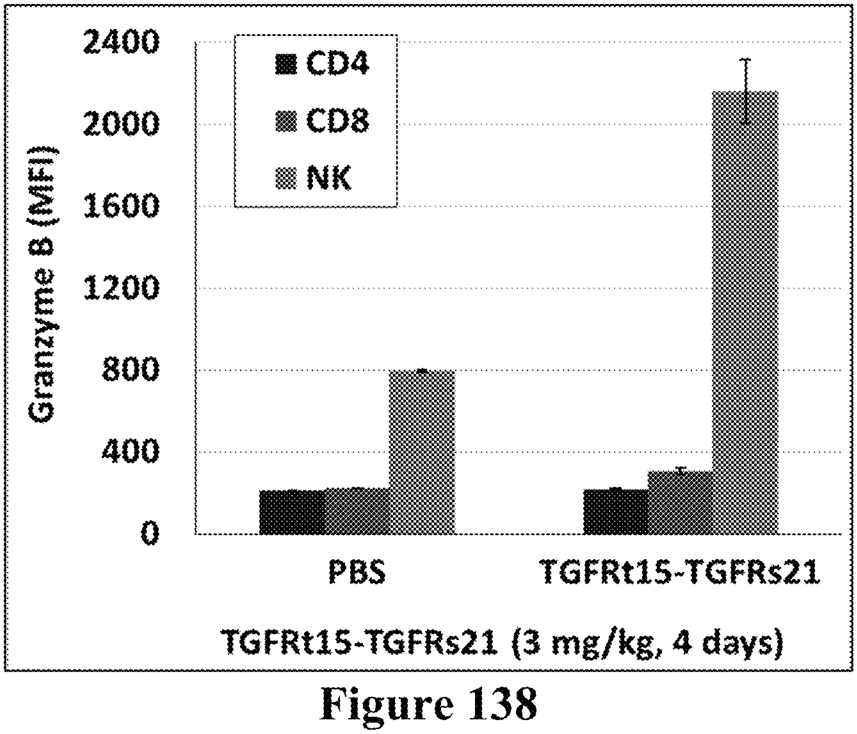

FIG. 138 shows upregulation of Granzyme B expression of splenocytes in mice treated with TGFRt15-TGFRs21.

Figure 139:
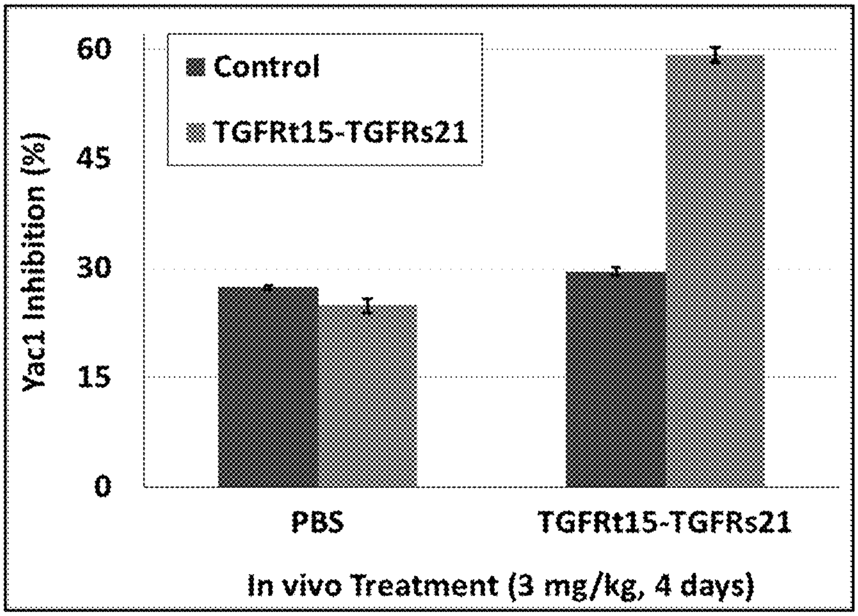

FIG. 139 shows enhancement of cytotoxicity of splenocytes by TGFRt15-TGFRs21 in C57BL/6 Mice.

Figure 140:
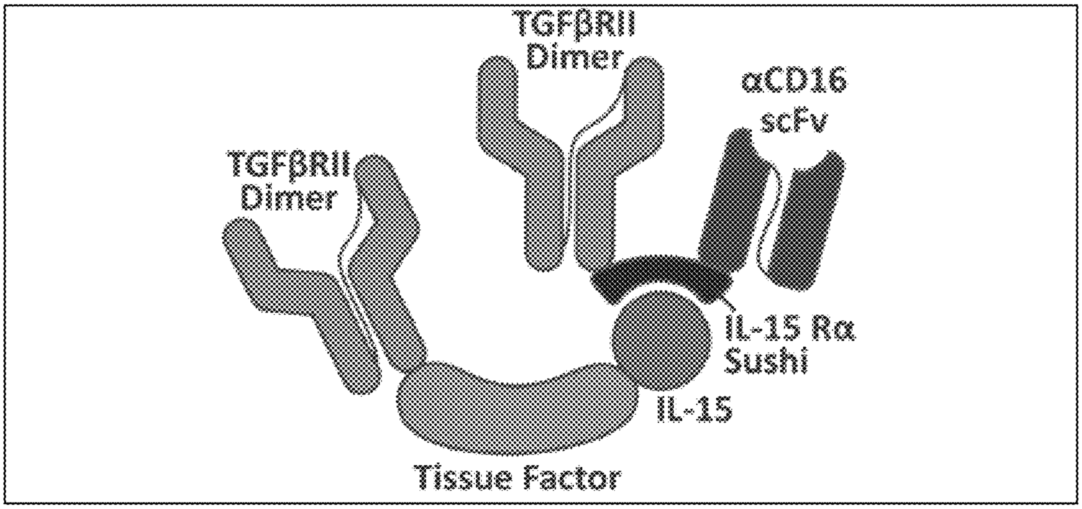

FIG. 140 shows a schematic of the TGFRt15-TGFRs16 construct.

Figure 141:
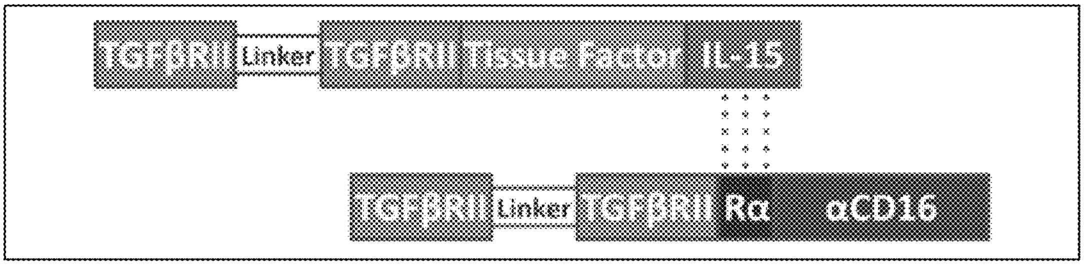

FIG. 141 shows an additional schematic of the TGFRt15-TGFRs16 construct.

Figure 142:
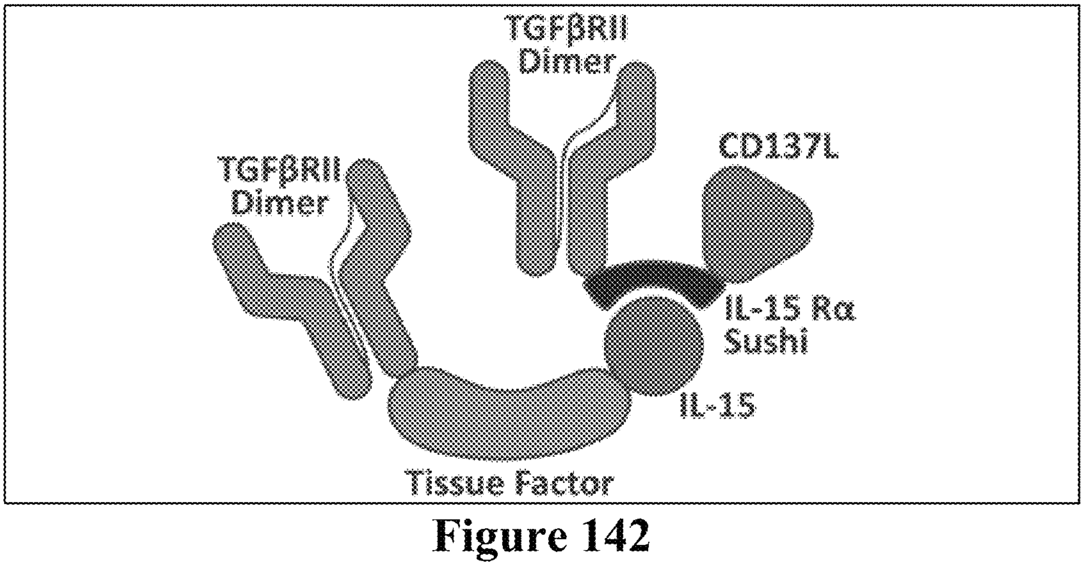

FIG. 142 shows a schematic of the TGFRt15-TGFRs137L construct.

Figure 143:
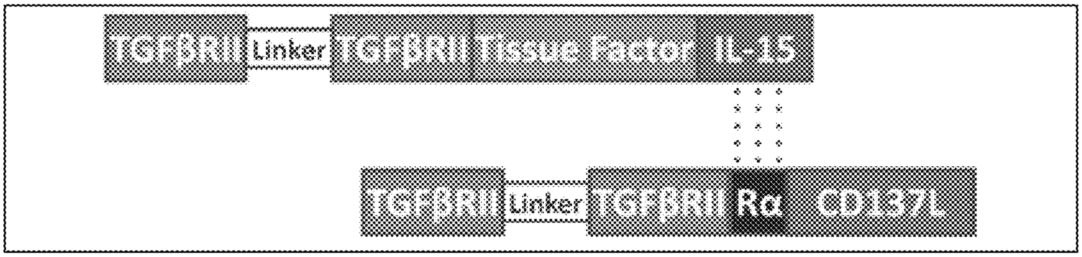

FIG. 143 shows an additional schematic of the TGFRt15-TGFRs137L construct.

Figure 144:
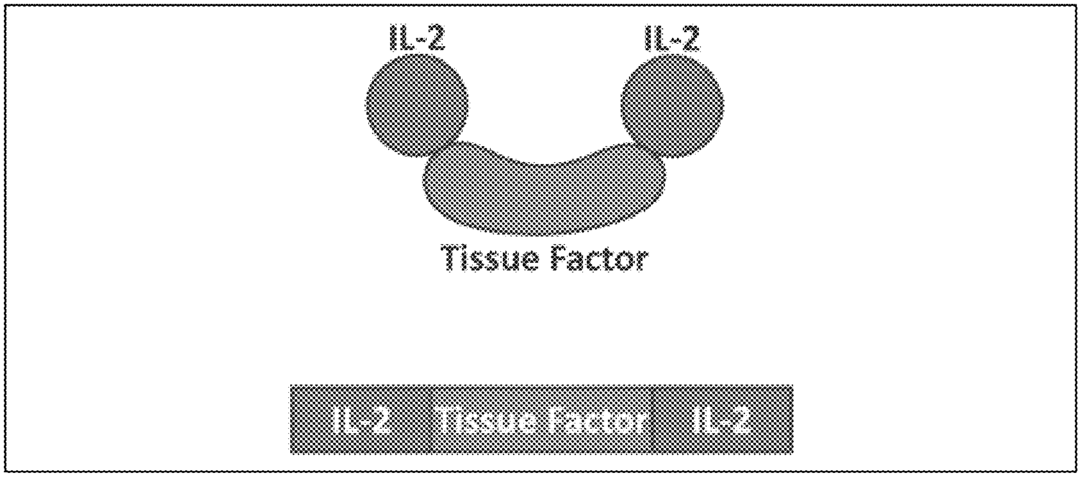

FIG. 144 are schematic diagrams of an exemplary 2t2 single-chain chimeric polypeptide.

Figure 145:
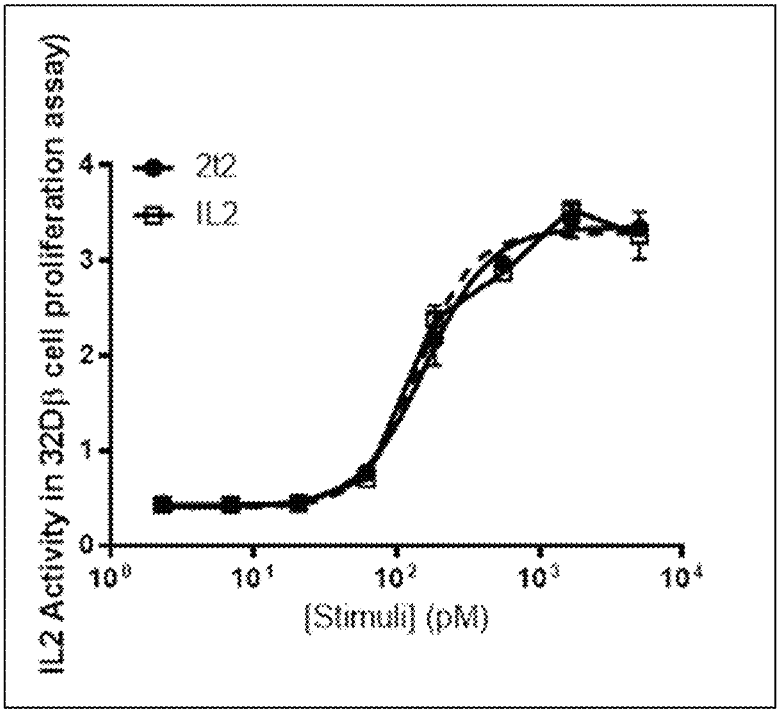

FIG. 145 shows IL-2 activity in 2t2 as compared to recombinant IL-2 using a 32Dβ cell proliferation assay.

Figure 146:
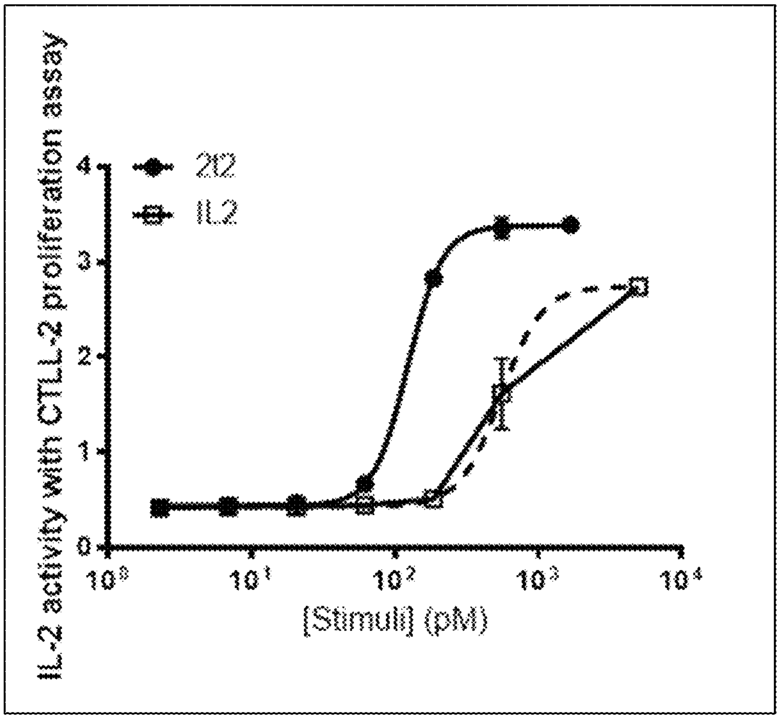

FIG. 146 shows IL-2 activity in 2t2 as compared to recombinant IL-2 using a CTLL-2 cell proliferation assay.

Figure 147:
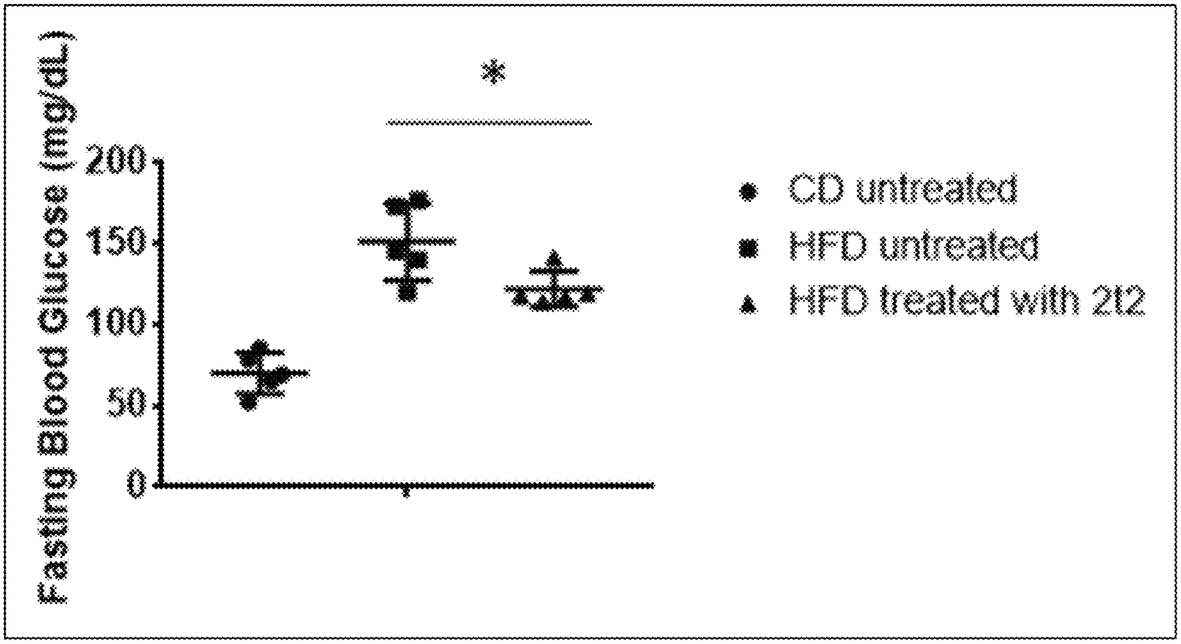

FIG. 147 shows the fasting blood glucose levels in $ApoE^{-/-}$ mice fed with standard chow or a high fat diet and treated with a PBS control (untreated) or with 2t2.

Figure 148:
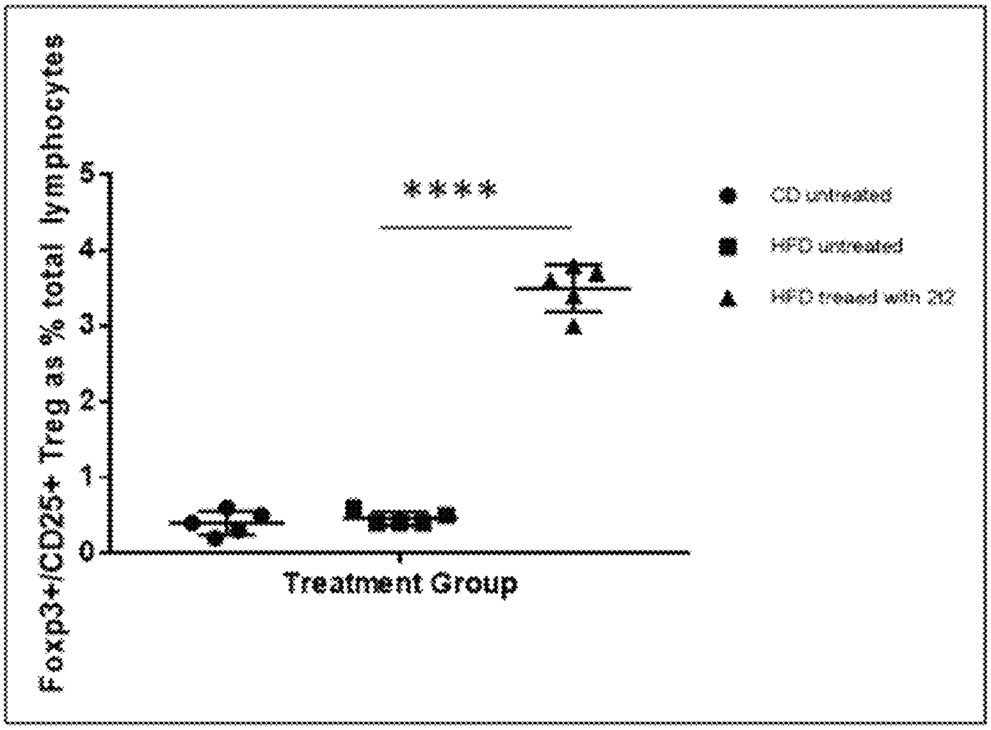

FIG. 148 shows the ratio of $CD4^+CD25^+$ $FoxP3^+$ T regulatory cells in blood lymphocytes from $ApoE^{-/-}$ mice fed with standard chow or a high fat diet and treated with a PBS control (untreated) or with 2t2.

Figure 149:
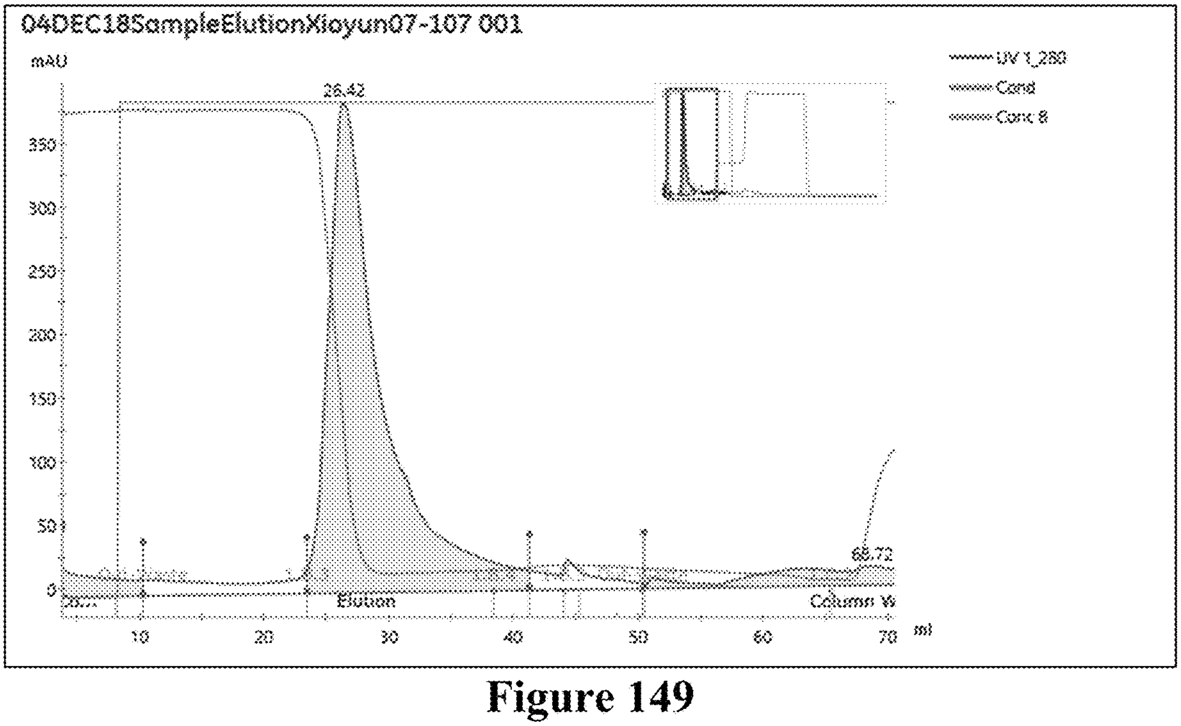

FIG. 149 is a line graph showing the chromatographic profile of 2t2 protein containing cell culture supernatant following binding and elution on anti-TF antibody resin.

Figure 150:
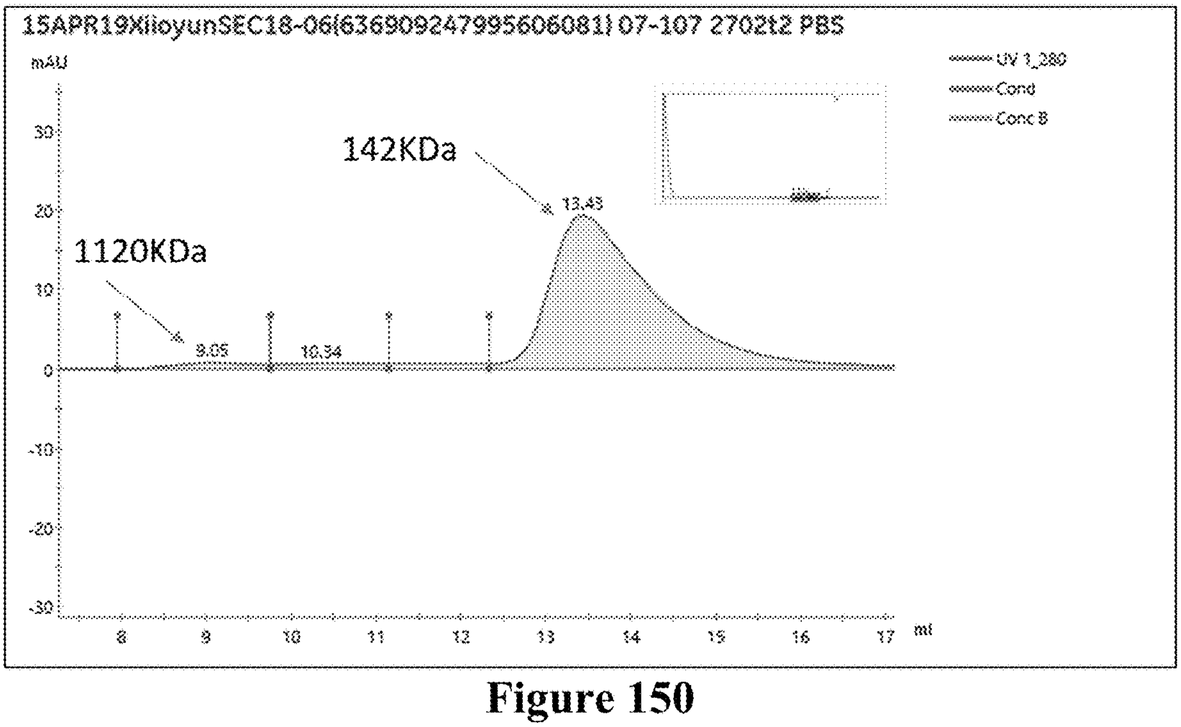

FIG. 150 shows an analytical SEC profile of 2t2.

Figure 151A:
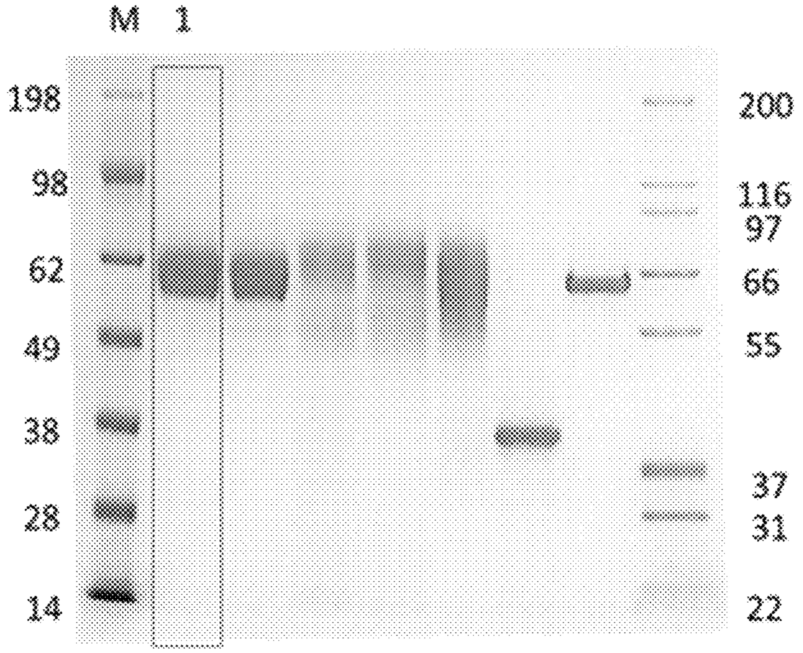
Figure 151B:
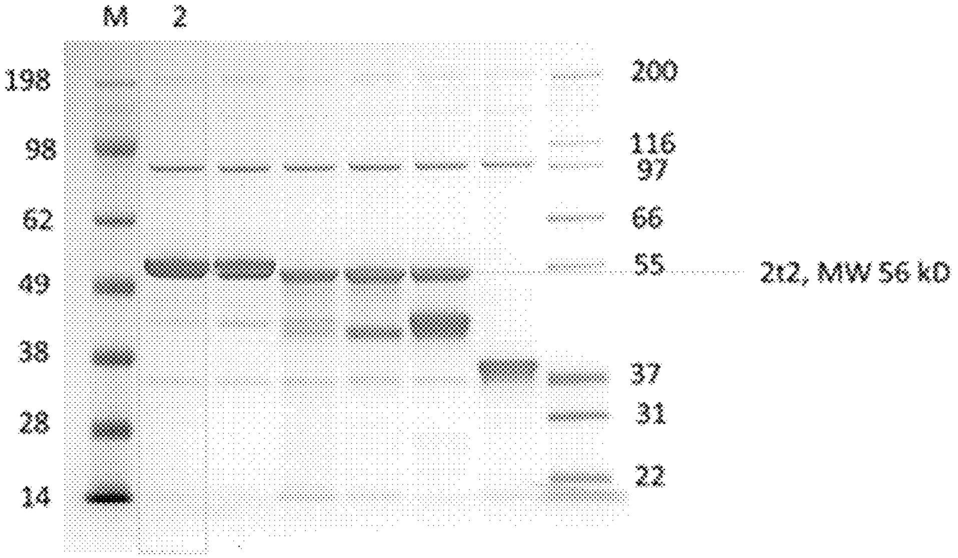

FIGS. 151A and 151B show reduced SDS-PAGE analysis of 2t2 before and after deglycosylation. FIG. 151A shows reduced SDS-PAGE analysis of 2t2 before deglycosylation. FIG. 151B shows reduced SDS-PAGE analysis of 2t2 after deglycosylation.

Figure 152A:
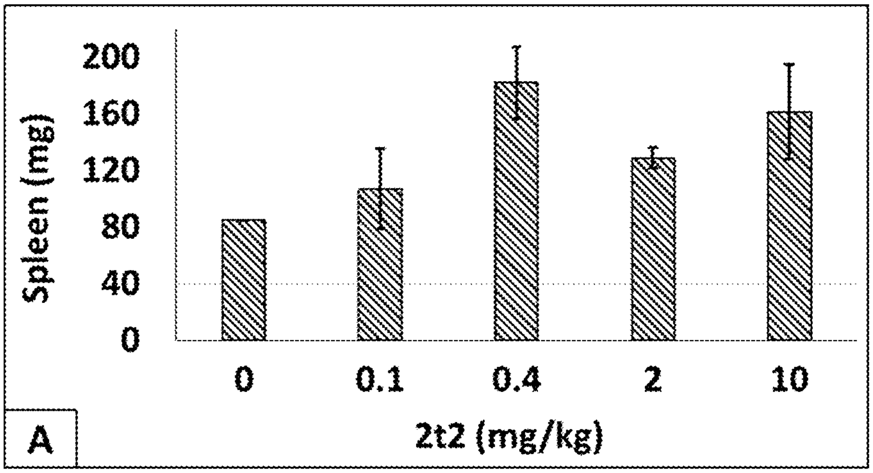
Figure 152B:
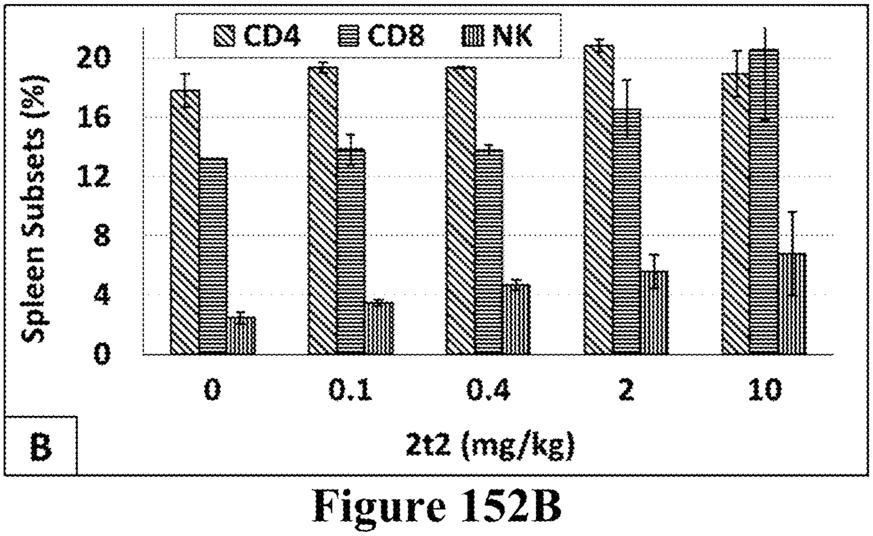

FIGS. 152A and 152B show results of immunostimulation in C57BL/6 mice using 2t2. FIG. 152A shows spleen weight following treatment with 2t2. FIG. 152B shows the percentages of immune cell types following 2t2 treatment.

Figure 153:
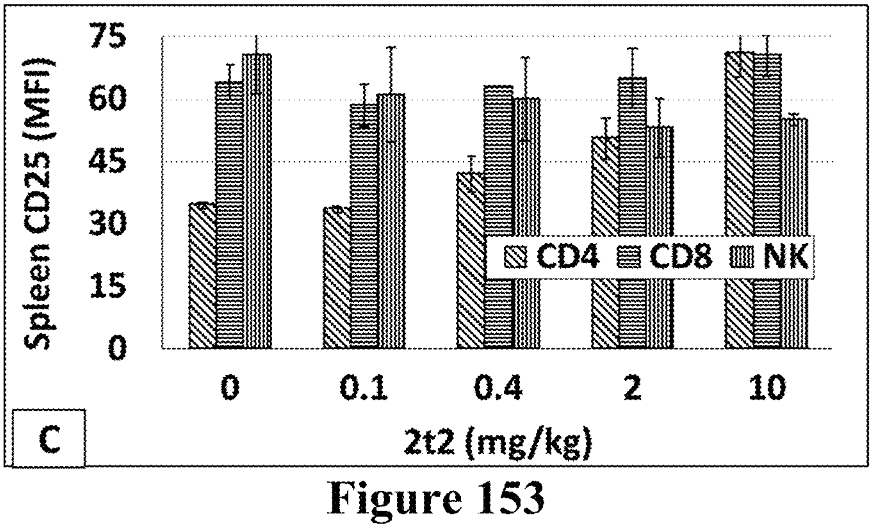

FIG. 153 shows upregulation of CD25 expression of $CD4^+$ T cells in mice treated with 2t2.

Figure 154:
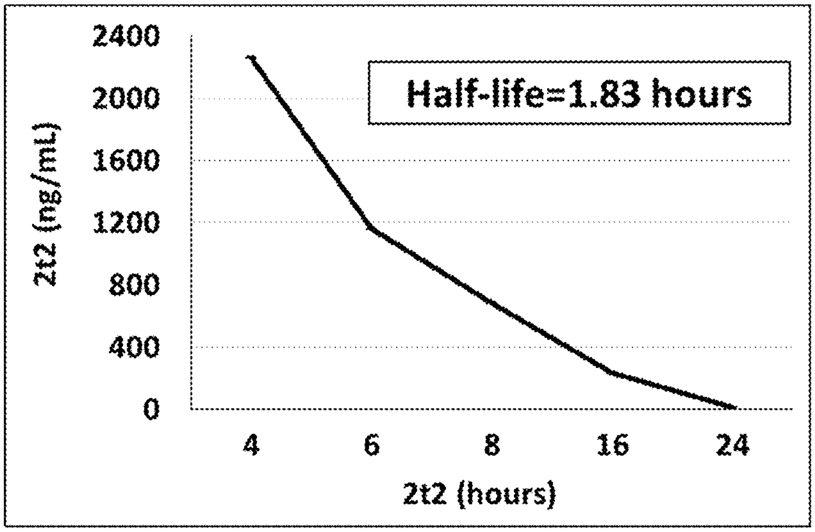

FIG. 154 shows the pharmacokinetics of 2t2 in C57BL/6 mice.

Figure 155A:
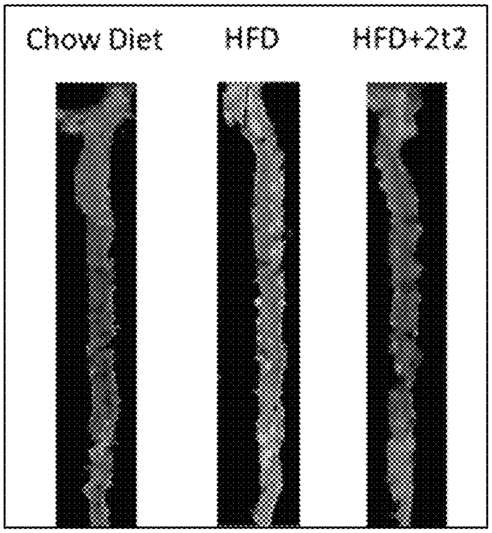
Figure 155B:
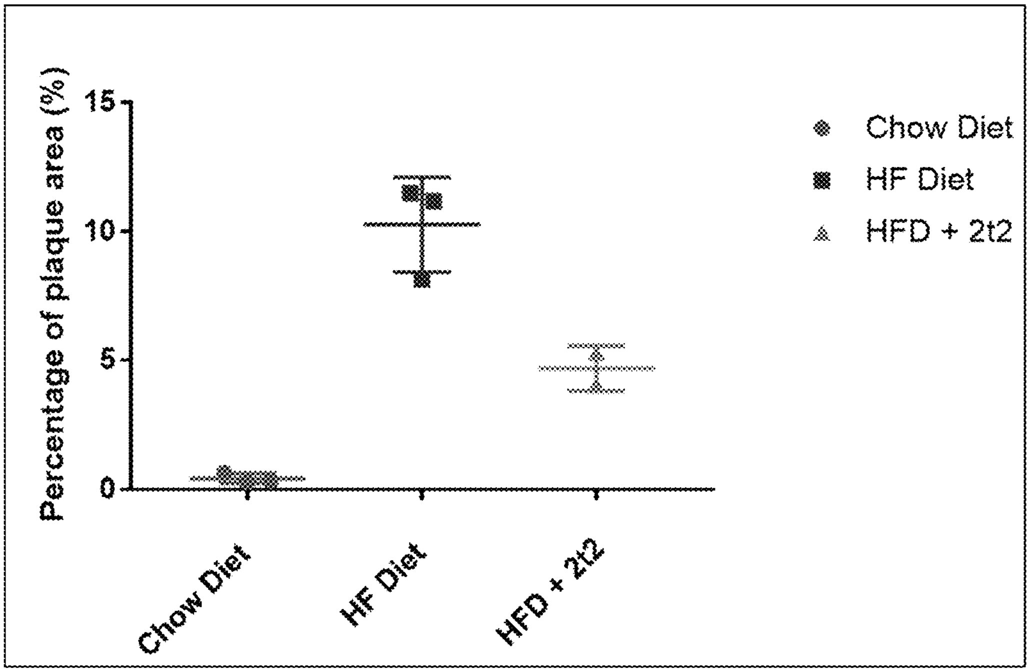

FIGS. 155A and 155B show effects of 2t2 in attenuating the formation of high fat-induced atherosclerotic plaques in $ApoE^{-/-}$ mice. FIG. 155A shows a representative view of atherosclerotic plaques from $ApoE^{-/-}$ mice fed with standard chow or a high fat diet and treated with either PBS control or 2t2. FIG. 155B shows the results of quantitative analysis of atherosclerotic plaques of each group.

Figure 156:
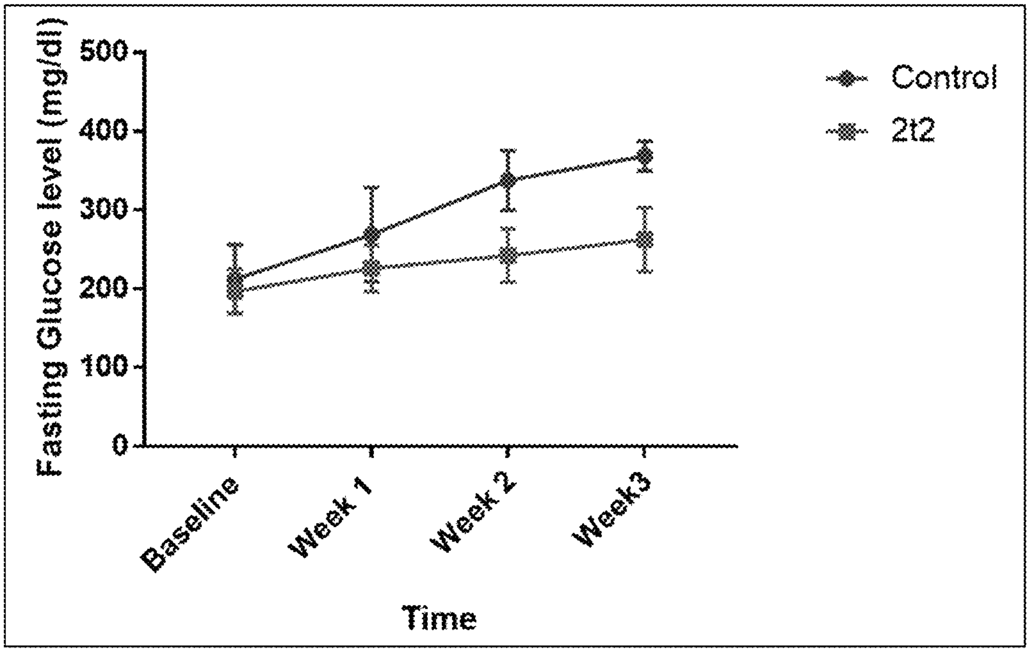

FIG. 156 shows fasting glucose levels in 2t2 treated-mice as compared to control-treated mice.

Figure 157:
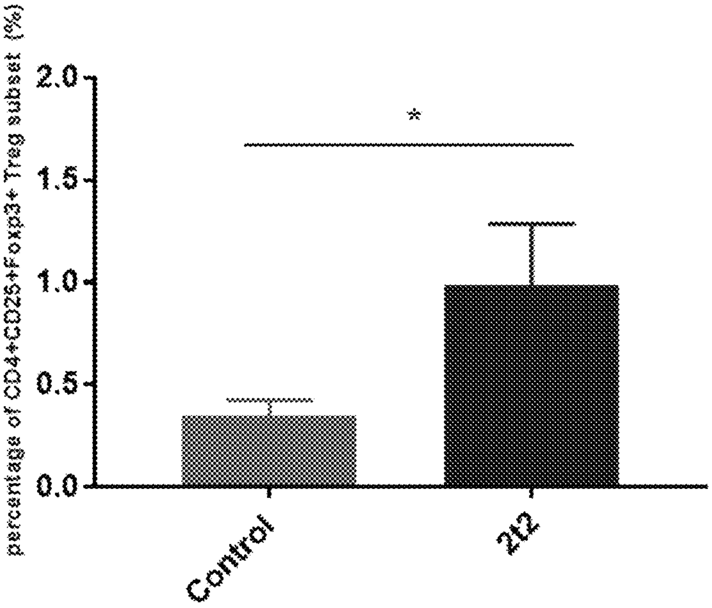

FIG. 157 shows the percentage of $CD4^+CD25^+$ $FoxP3^+$ Tregs in blood lymphocytes from mice treated with 2t2 and control-treated mice.

Figure 158:
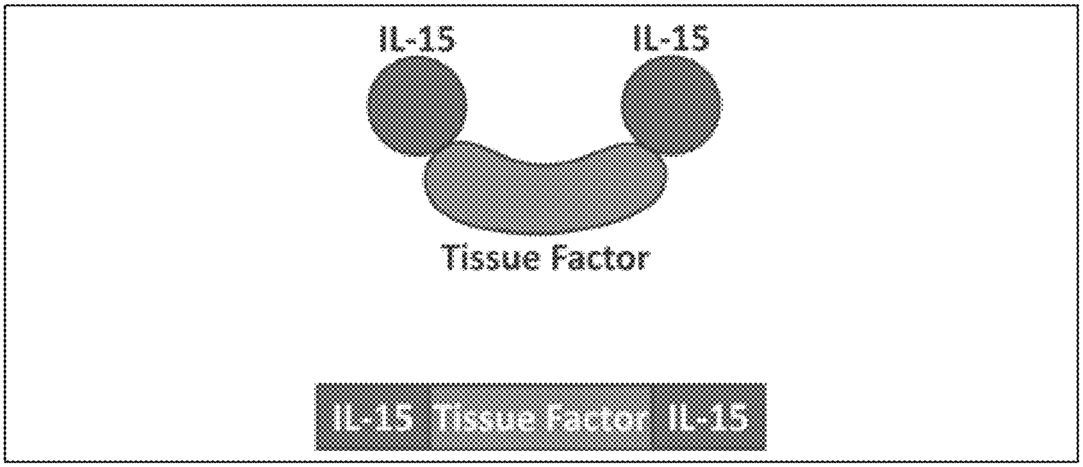

FIG. 158 are schematic diagrams of an exemplary 15t15 single-chain chimeric polypeptide.

Figure 159:
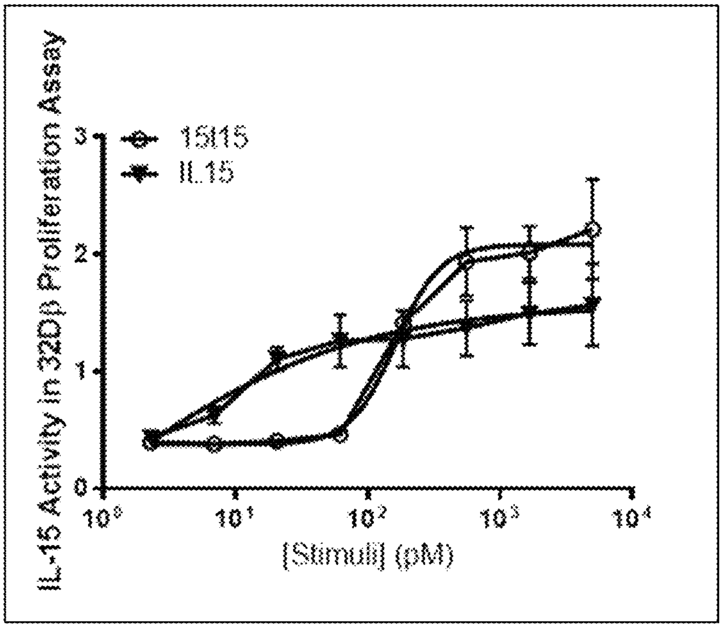

FIG. 159 shows the IL-15 activity of 15t15 as compared to recombinant IL-15 in a 32Dβ cell proliferation assay.

Figure 160:
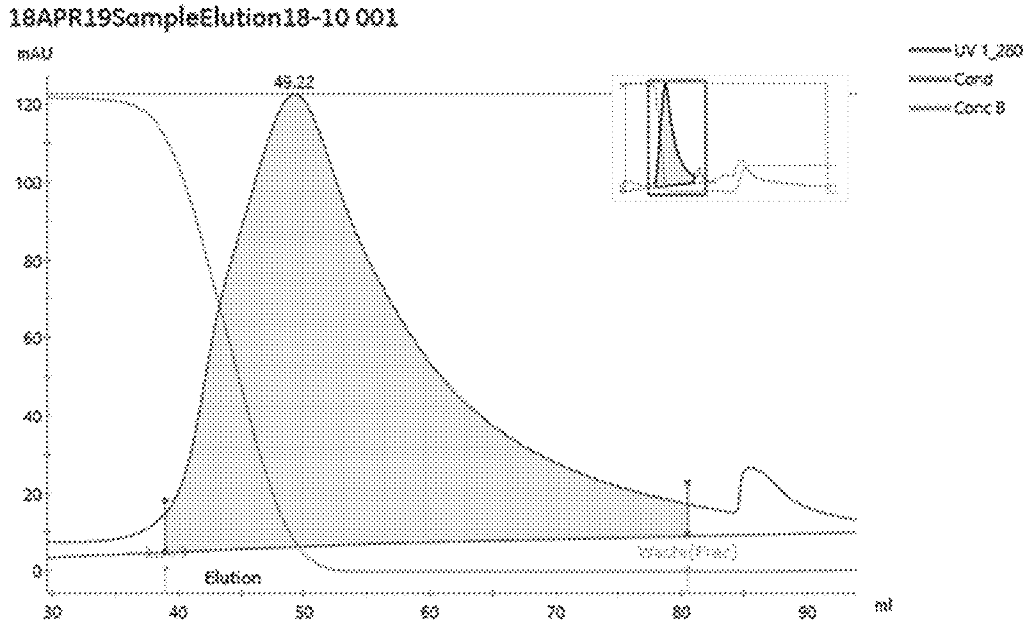

FIG. 160 is a line graph showing the chromatographic profile of 15t15 protein containing cell culture supernatant following binding and elution on anti-TF antibody resin.

Figure 161A:
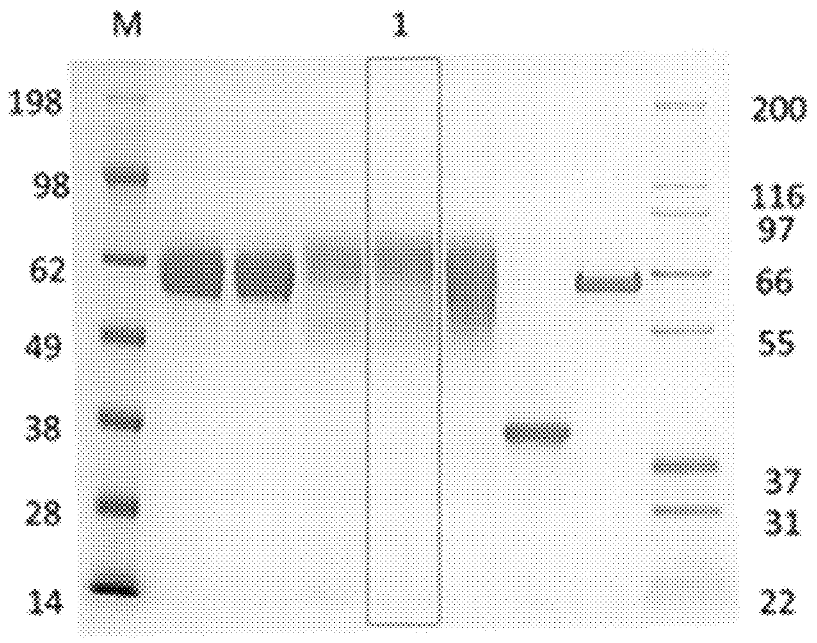
Figure 161B:
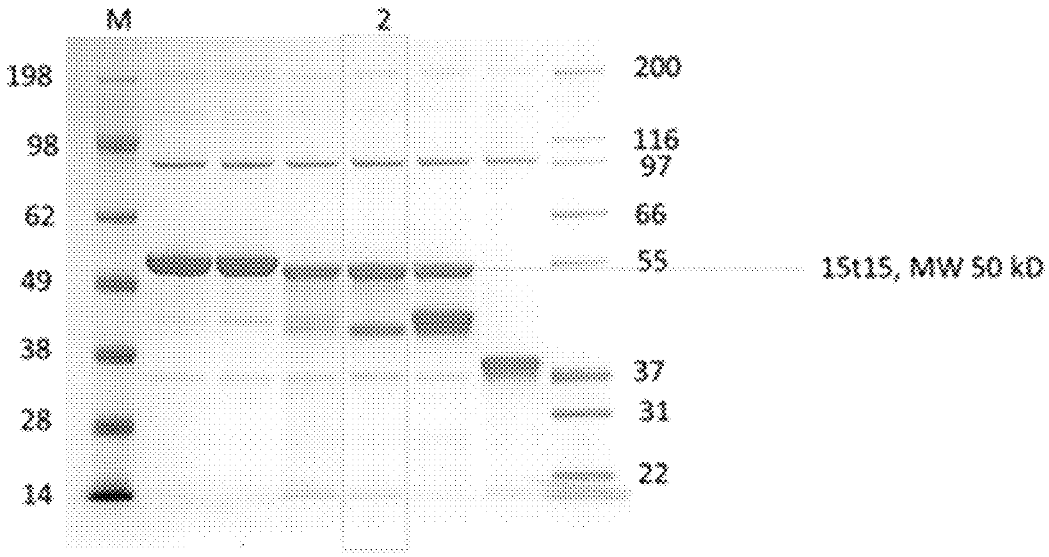

FIGS. 161A and 161B show reduced SDS-PAGE analysis of 15t15 before and after deglycosylation. FIG. 161A shows reduced SDS-PAGE analysis of 15t15 before deglycosylation. FIG. 161B shows reduced SDS-PAGE analysis of 15t15 after deglycosylation.

Figure 162A:
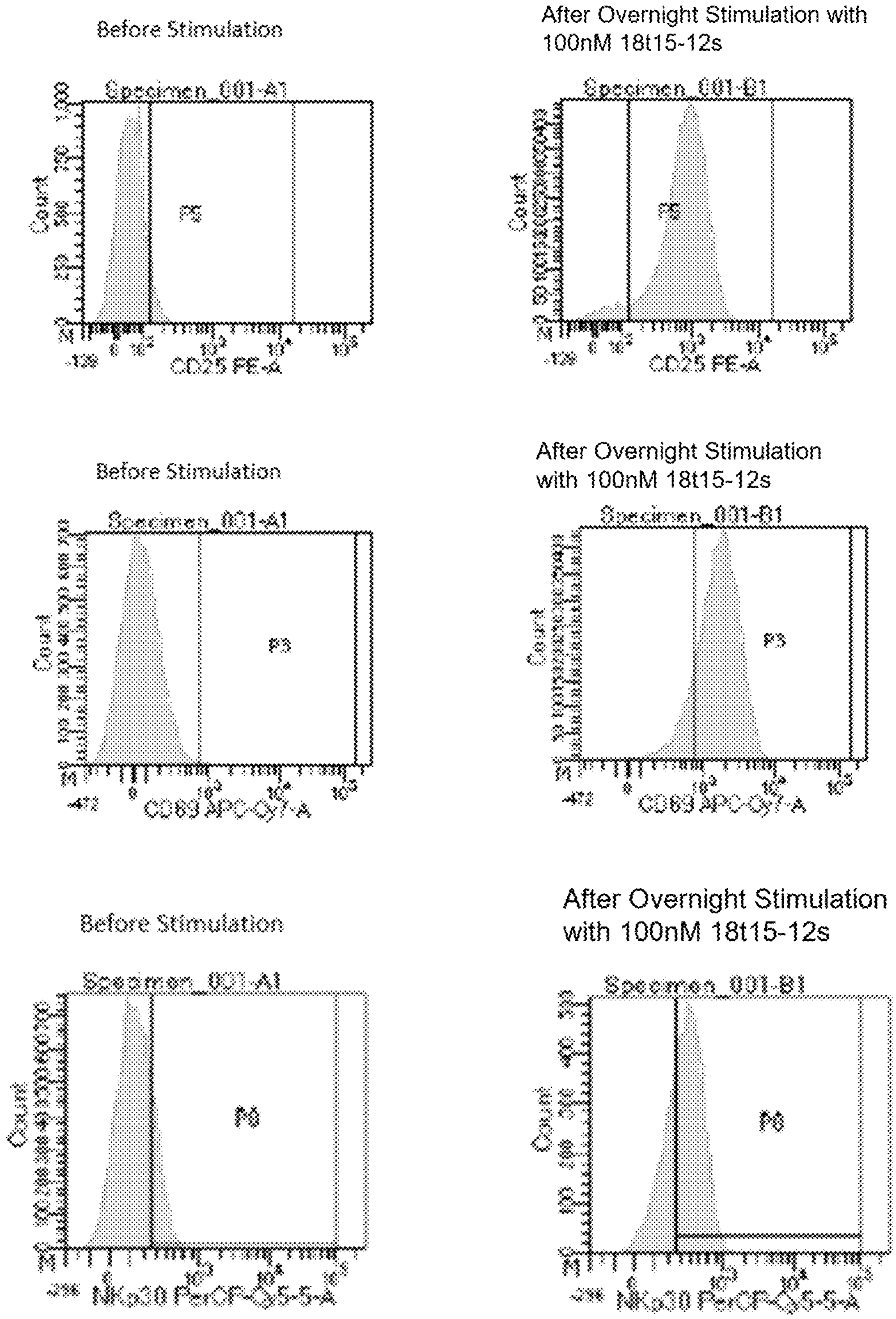
Figure 162B:
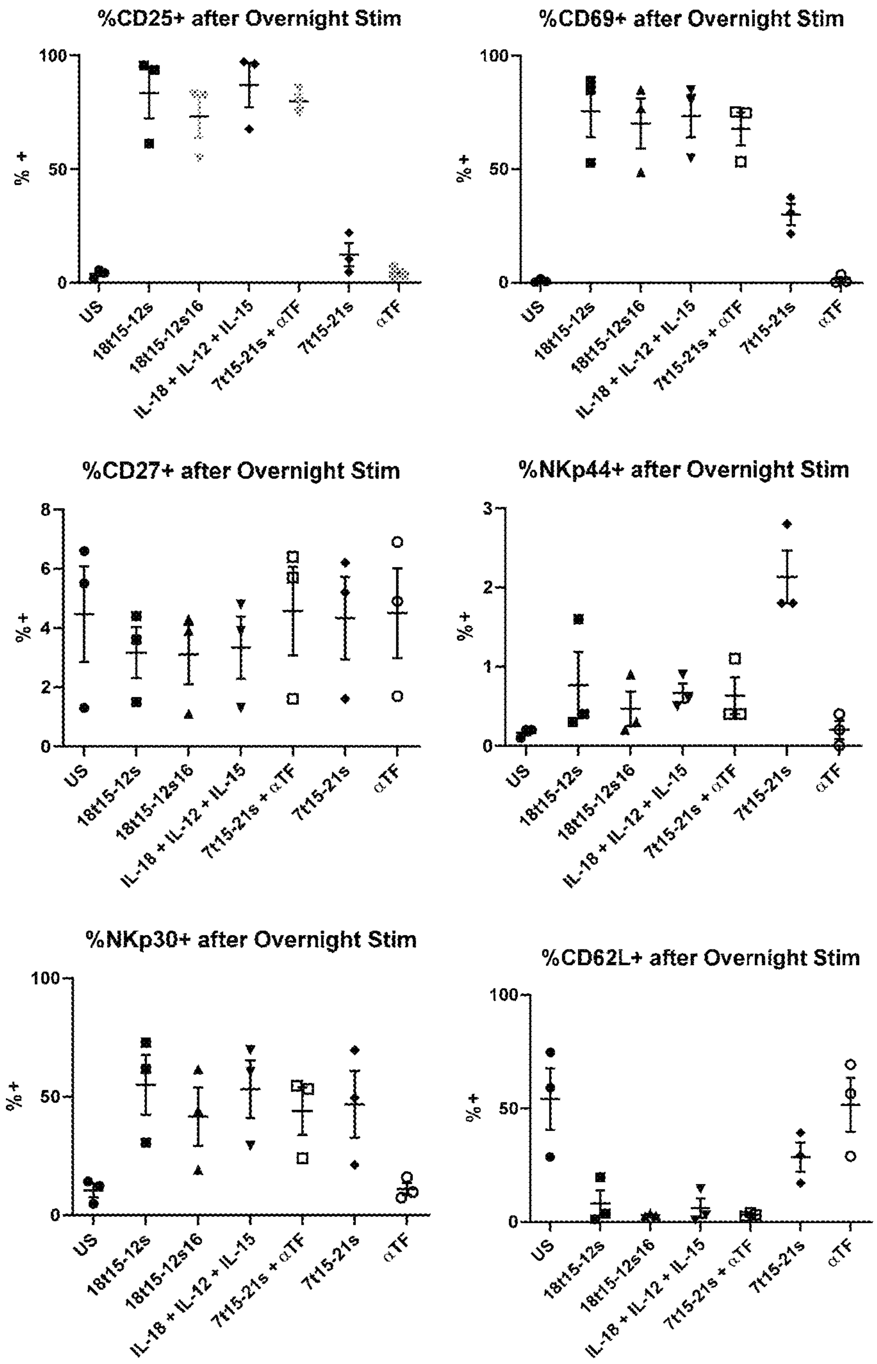

FIGS. 162A and 162B is a set of histograms (FIG. 162A) and a set of graphs (FIG. 162B) showing the change in the surface phenotype of NK cells after stimulation with 18t15-12s, 18t15-12s16, and 7t15-21s+anti-TF antibody.

Figure 163:
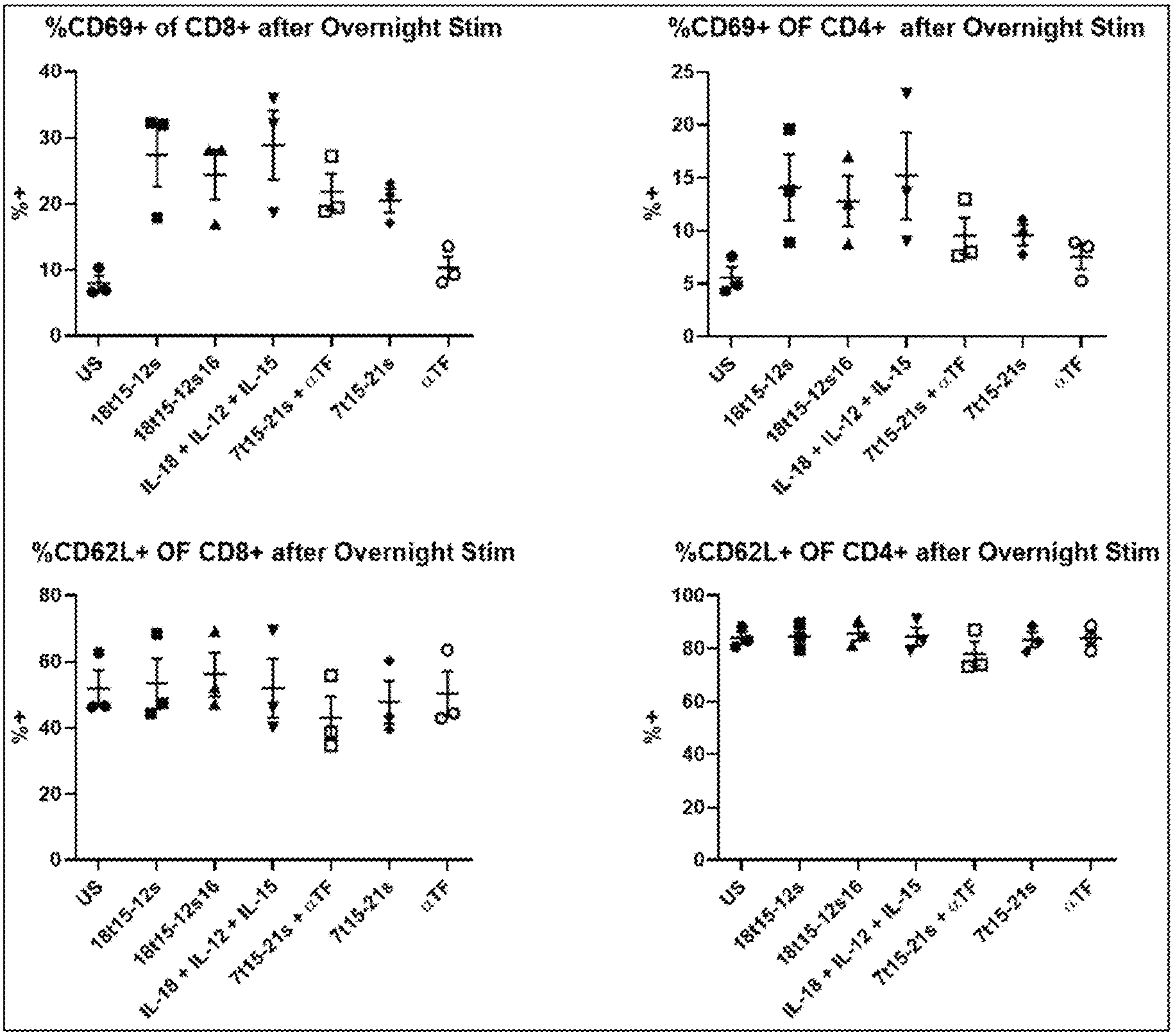

FIG. 163 is a set of graphs showing changes in the surface phenotype of lymphocyte populations after stimulation with 18t15-12s, 18t15-12s16, and 7t15-21s.

Figure 164:
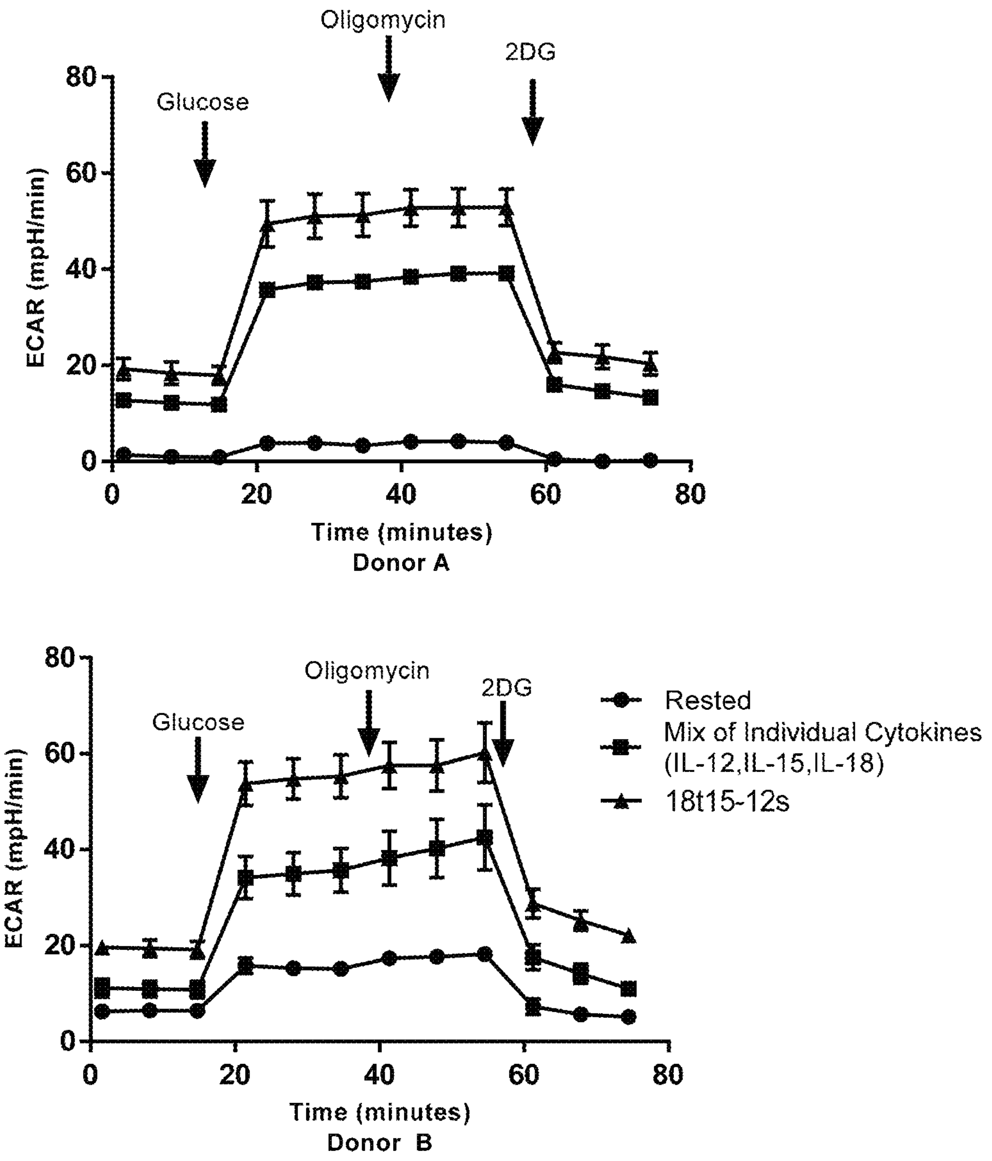

FIG. 164 is a set of graphs showing an increase in glycolysis in NK cells following treatment with 18t15-12s.

Figure 165:
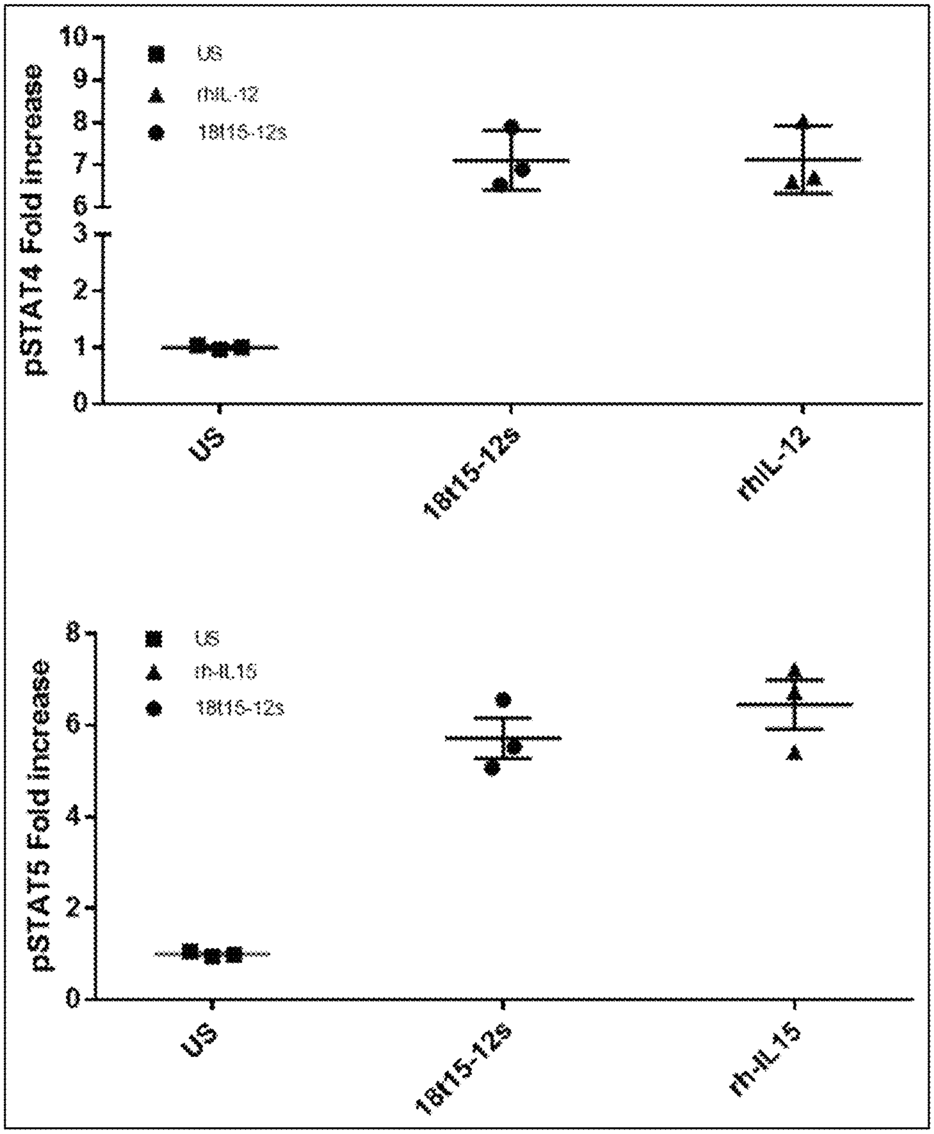

FIG. 165 is a set of graphs showing an increase in phospho-STAT4 and phospho-STAT5 levels in NK cells after stimulation with 18t15-12s.

Figure 166:
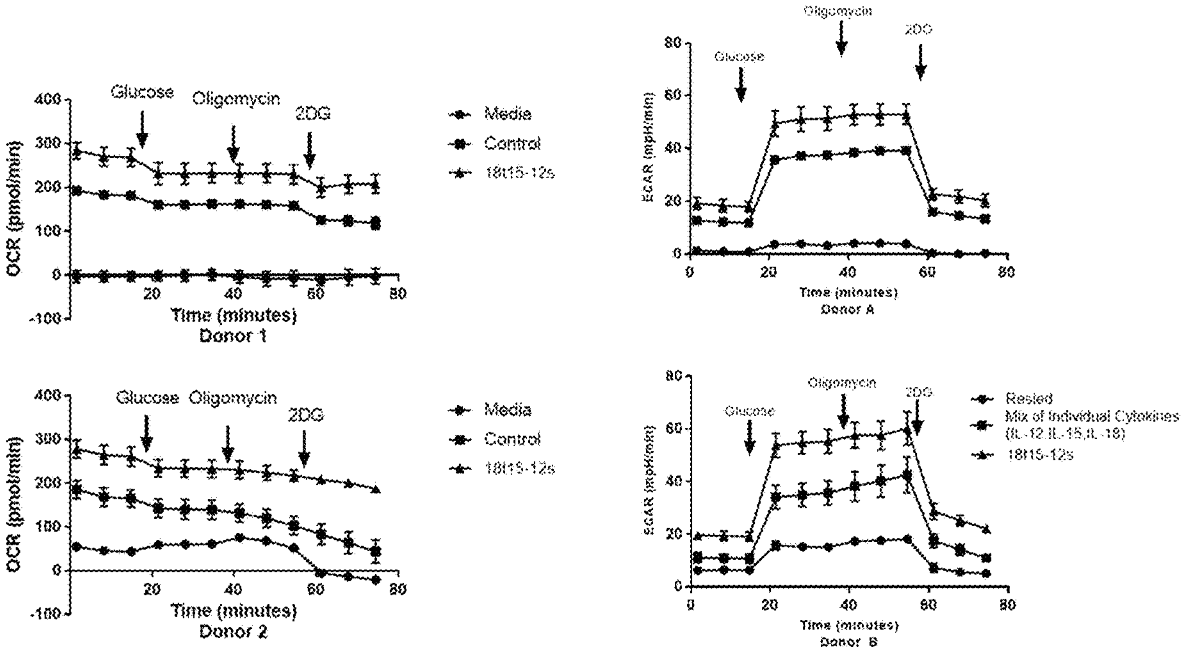

FIG. 166 is a set of graphs showing that overnight stimulation of NK cells with 18t15-12s enhances cell metabolism.

Figure 167A:
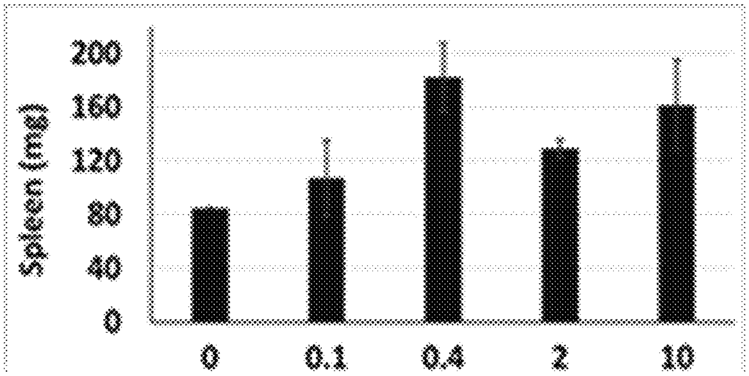
Figure 167B:
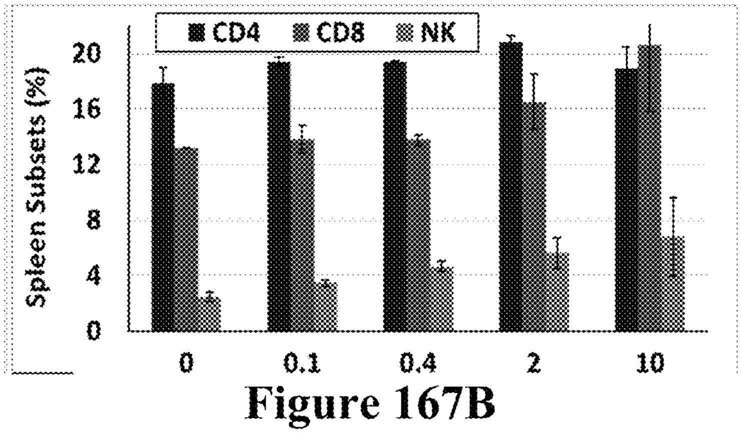
Figure 167C:
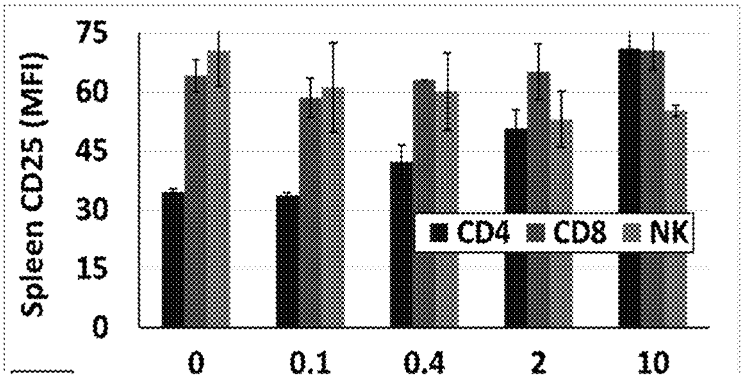

FIG. 167A-C is a set of graphs showing immunostimulation in C57BL/6 mice following treatment with 2t2.

Figure 168A:
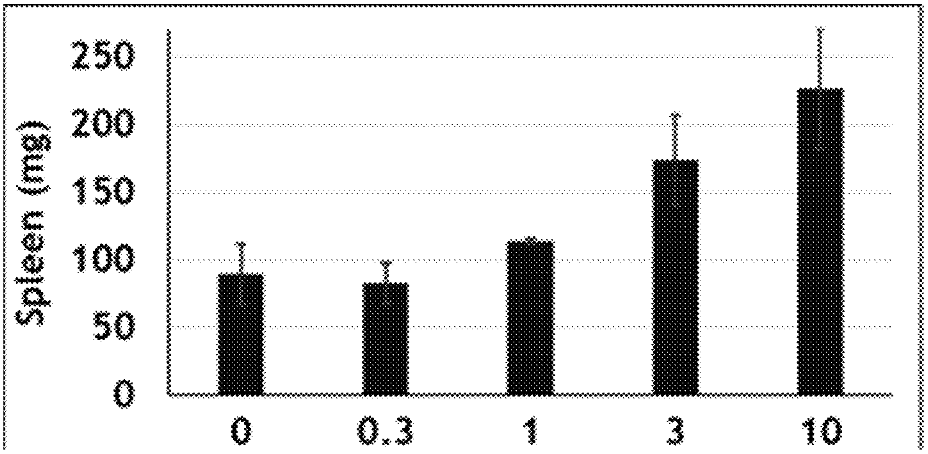
Figure 168B:
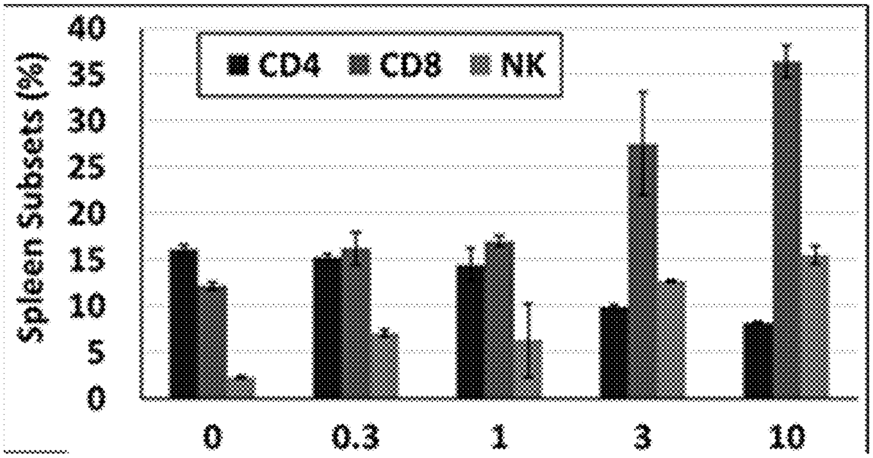

FIG. 168A-B is a set of graphs showing immunostimulation in C57BL/6 mice following treatment with TGFRt15-TGFRs.

Figure 169A:
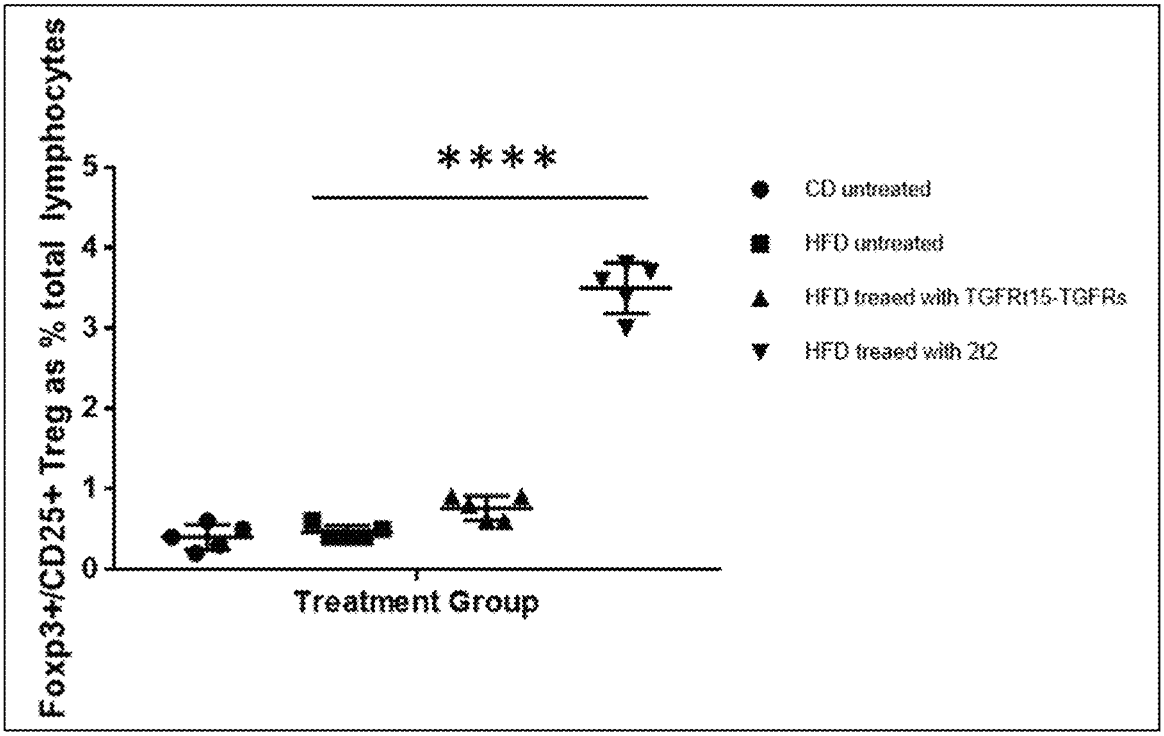
Figure 169B:
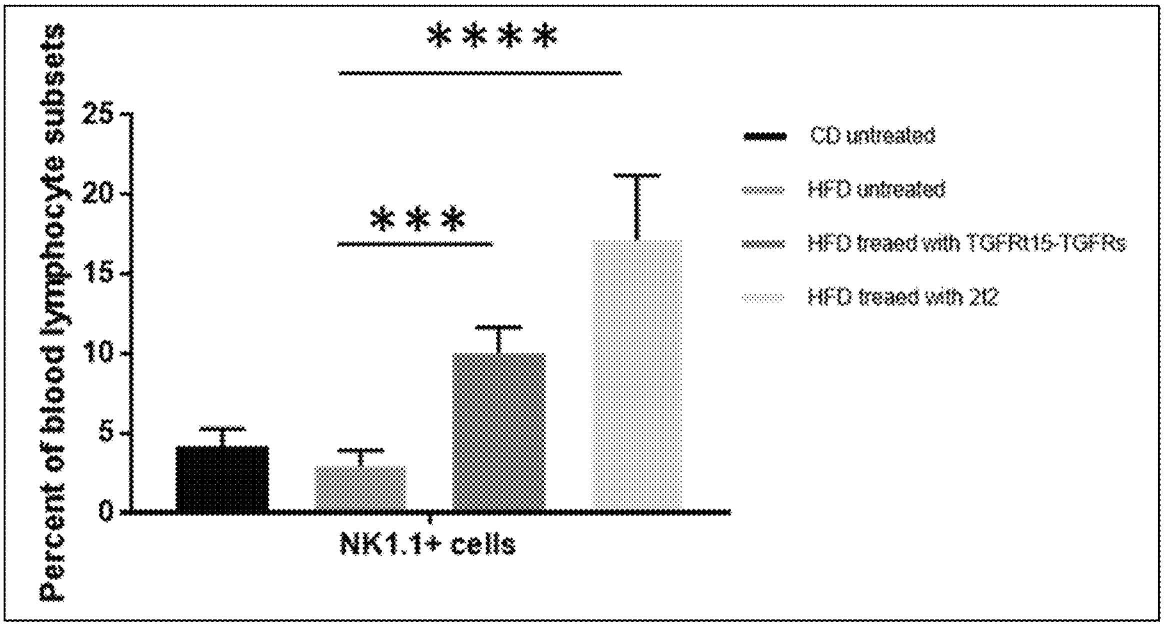
Figure 169C:
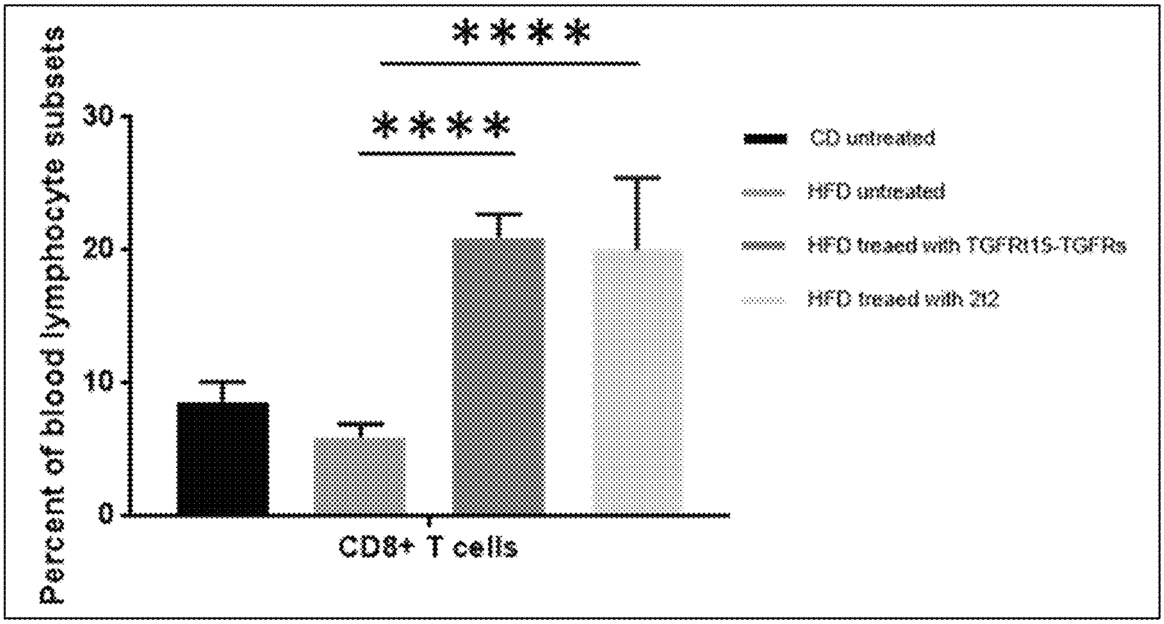

FIG. 169A-C is a set of graphs showing in vivo stimulation of Tregs, NK cells, and $CD8^+$ T cells in $ApoE^{-/-}$ mice fed with a Western diet and treated with TGFRt15-TGFRs or 2t2.

Figure 170A:
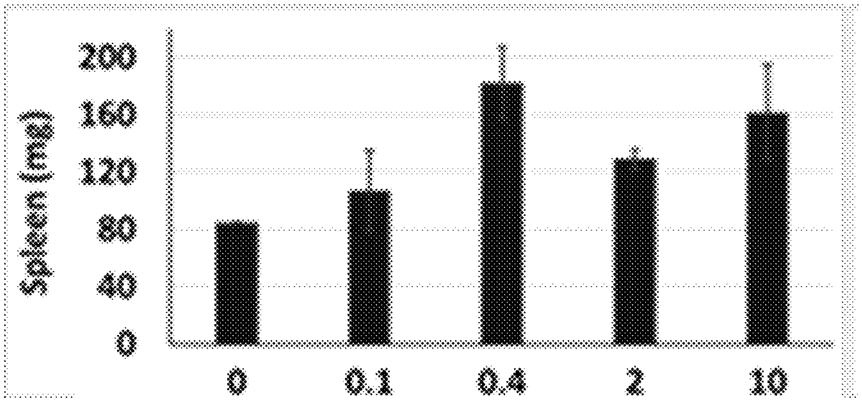
Figure 170B:
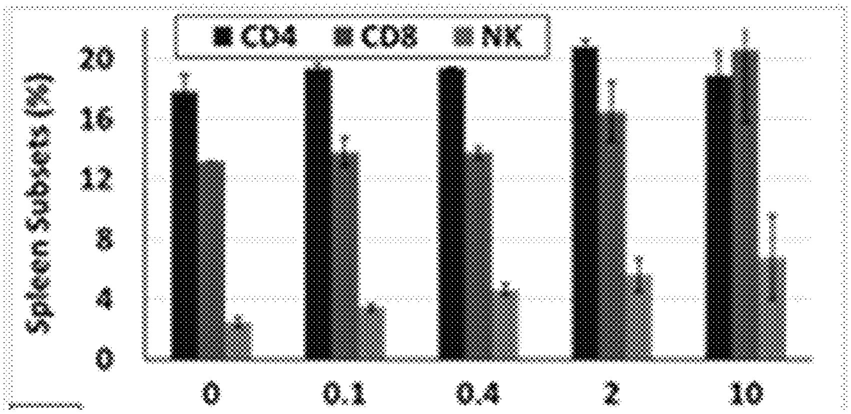

FIG. 170A-B is a set of graphs showing induction of splenocyte proliferation by 2t2 in C57BL/6 mice.

Figure 171A:
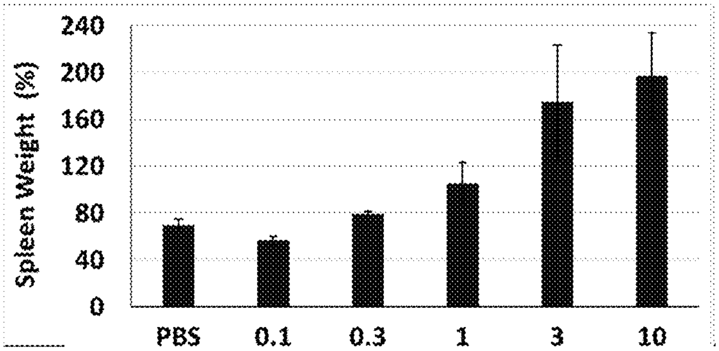
Figure 171B:
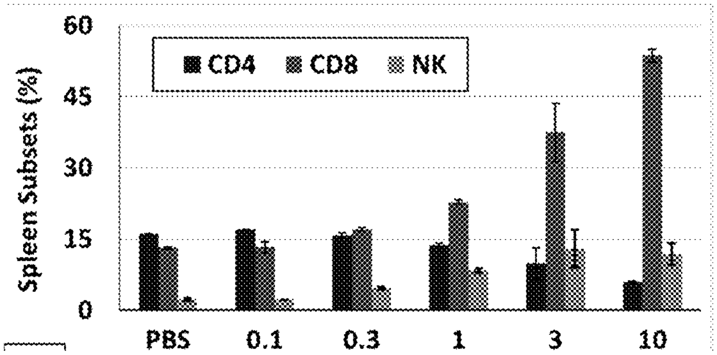
Figure 171C:
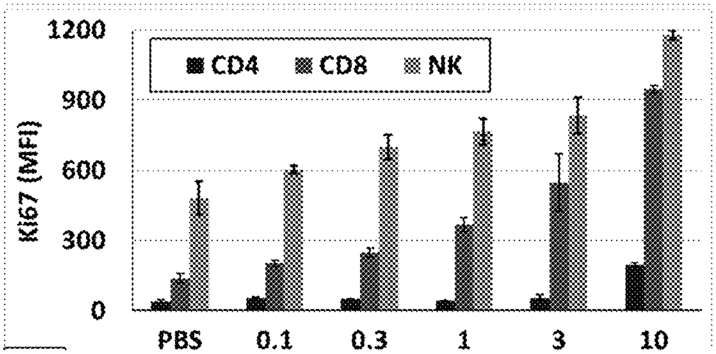

FIG. 171A-C is a set of graphs showing immunostimulation in C57BL/6 mice following treatment with TGFRt15-TGFRs.

Figure 172A:
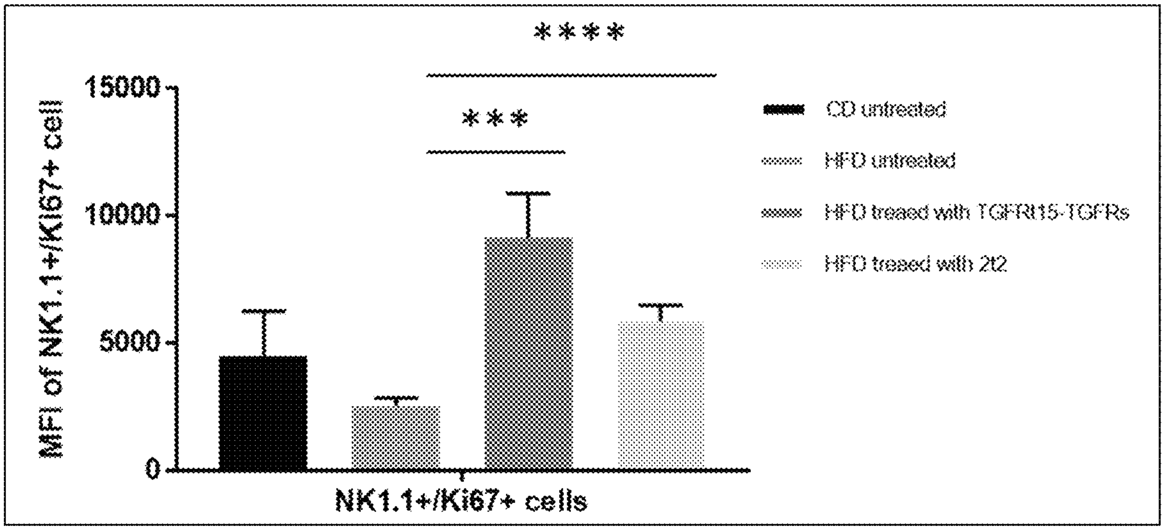
Figure 172B:
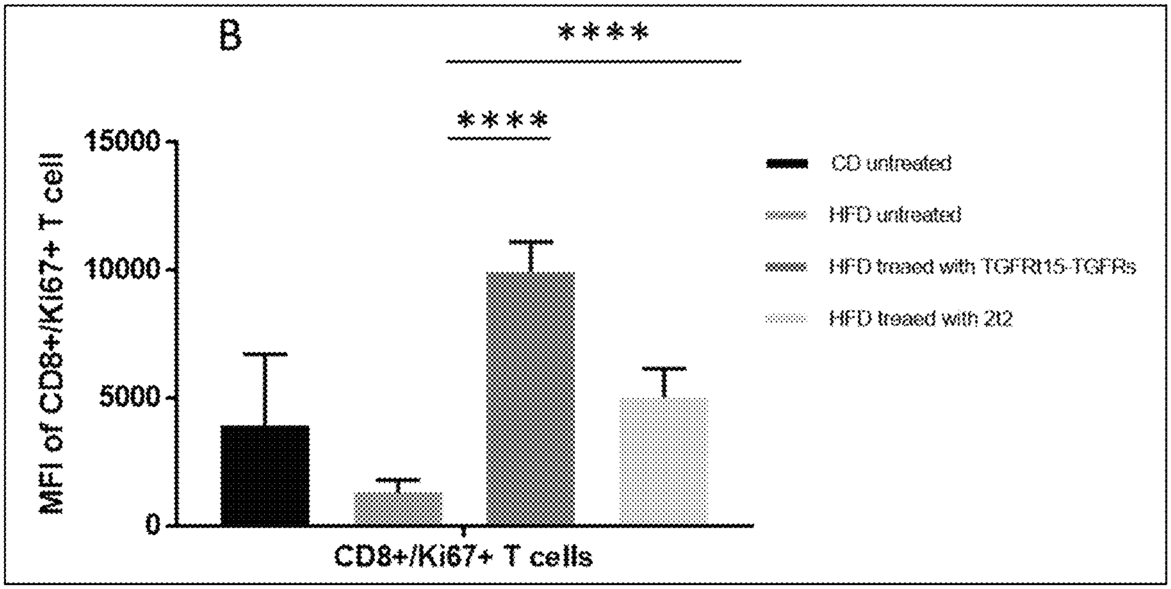

FIG. 172A-B is a set of graphs showing in vivo induction of proliferation of NK cells and $CD8^+$ T cells in $ApoE^{-/-}$ mice fed with a Western diet and treated with TGFRt15-TGFRs or 2t2.

Figure 173:
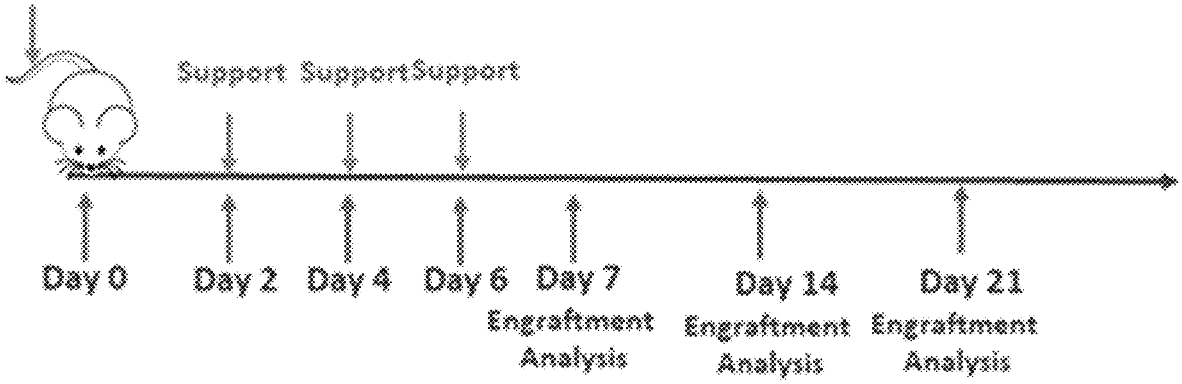
Figure 173:
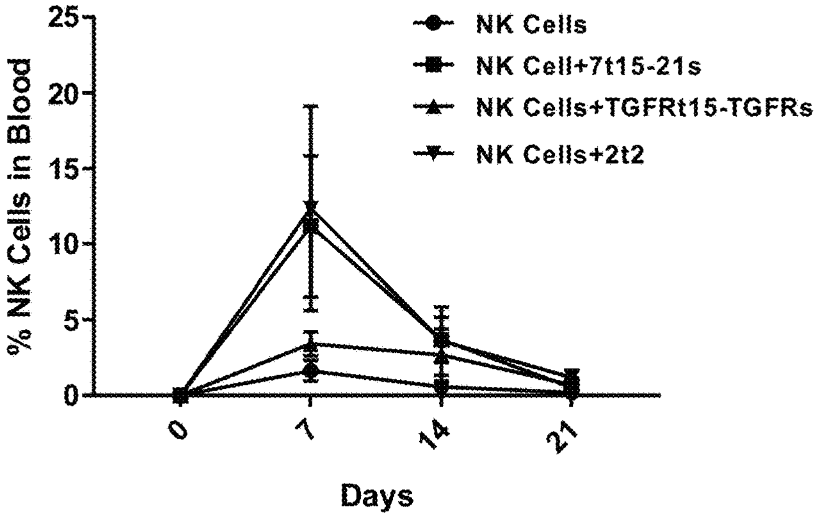

FIG. 173 is a schematic and a set of graphs showing the persistence of 7t15-21s and anti-TF antibody-expanded NK cells in NSG mice following treatment with 7t15-21, TGFRt15-TGFRs or 2t2.

Figure 174A:
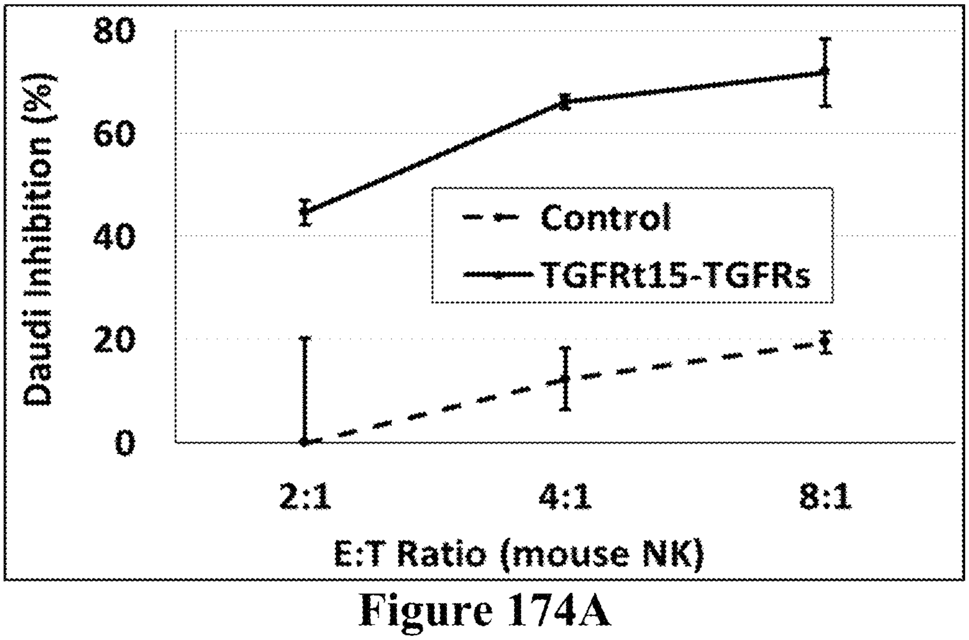
Figure 174B:
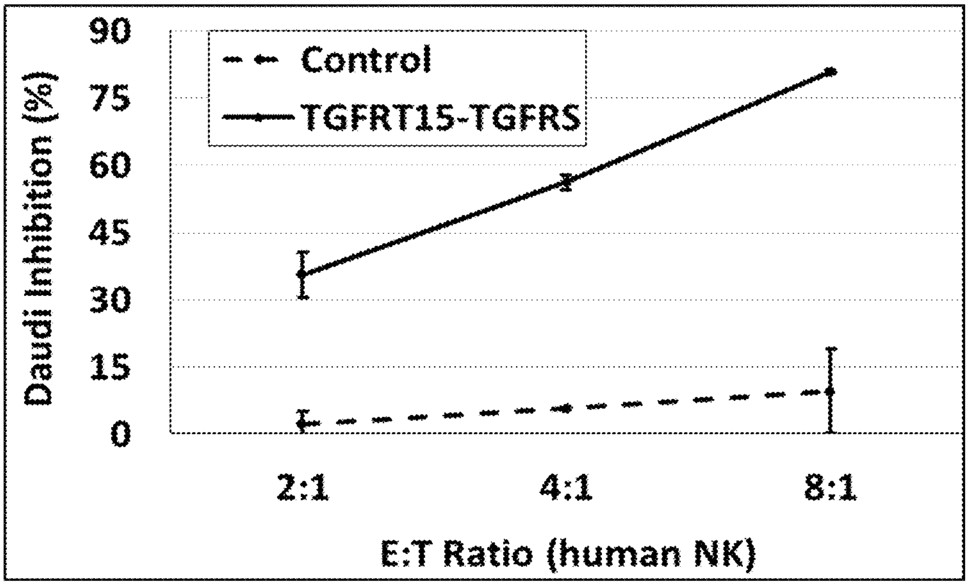

FIG. 174A-B is a set of graphs showing enhancement of cytotoxicity of NK cells following treatment of NK cells with TGFRt15-TGFRs.

Figure 175A:
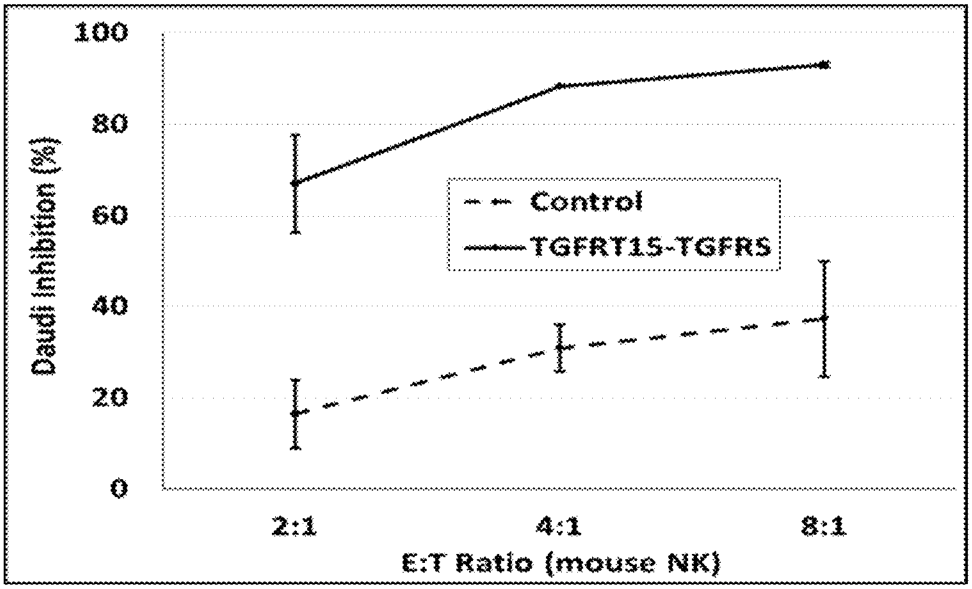
Figure 175B:
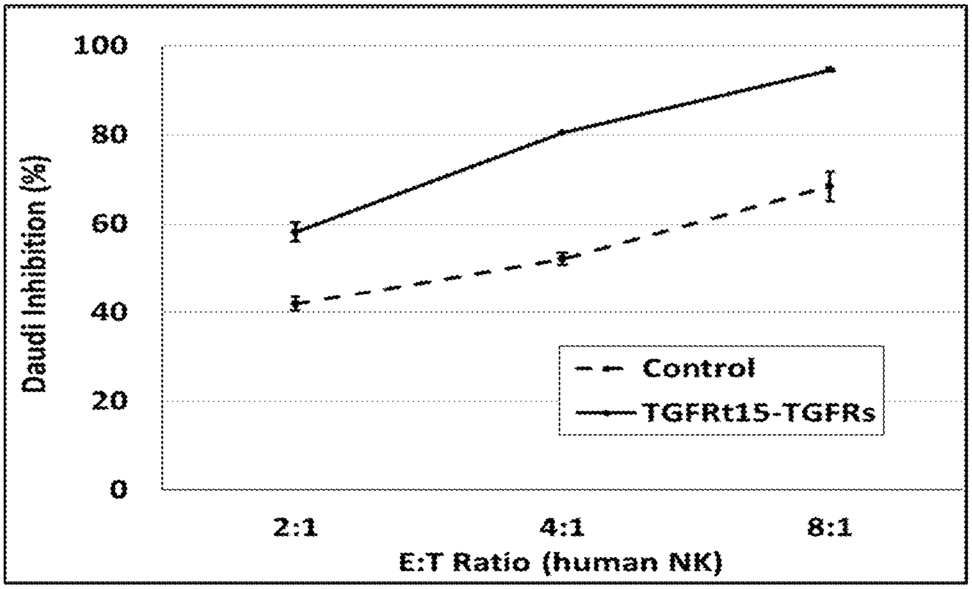

FIG. 175A-B is a set of graphs showing enhancement of ADCC activity of NK cells following treatment of NK cells with TGFRt15-TGFRs.

Figure 176:
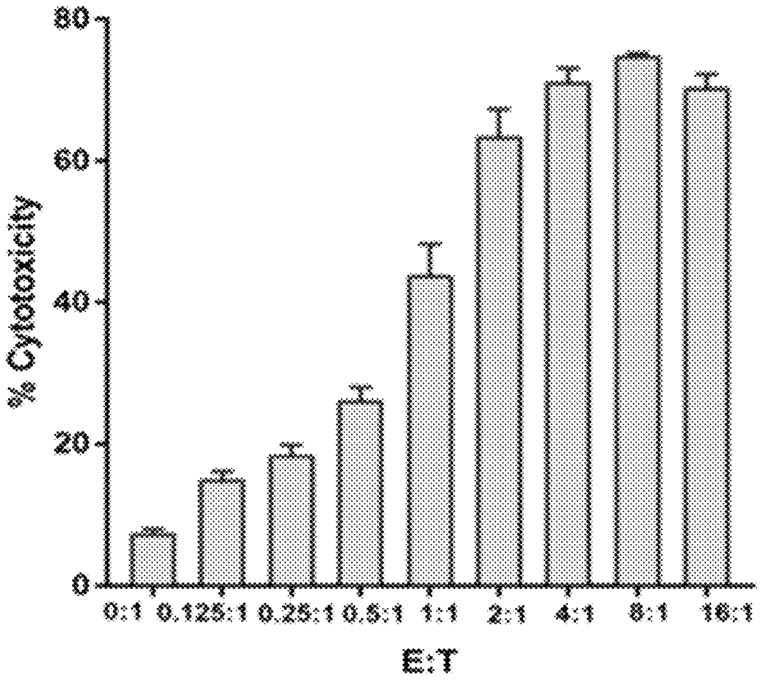

FIG. 176 is a graph of in vitro killing of senescent B16F10 melanoma cells by TGFRt15-TGFRs/2t2-activated mouse NK cells.

FIG. 177A-H is a set of graphs showing antitumor activity of TGFRt15-TGFRs plus anti-TRP1 antibody (TA99) in combination with chemotherapy in a melanoma mouse model.

Figure 178A:
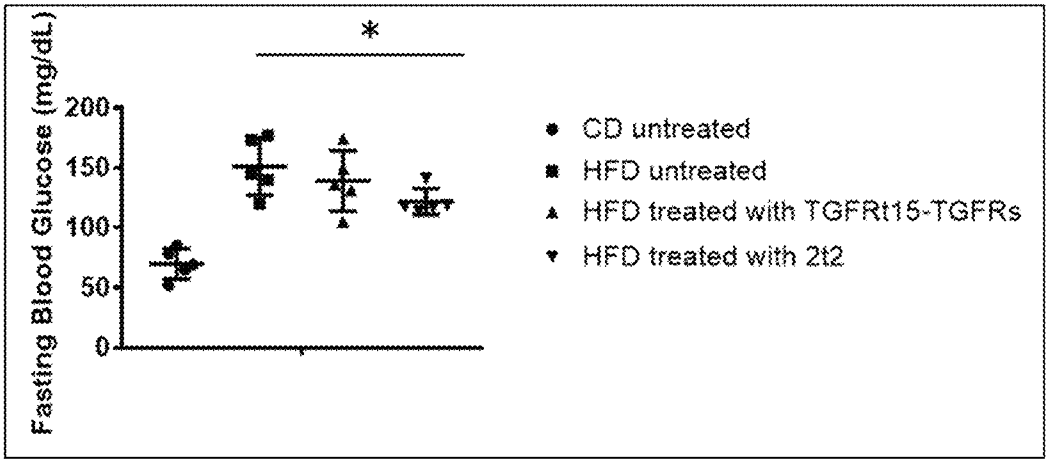
Figure 178B:
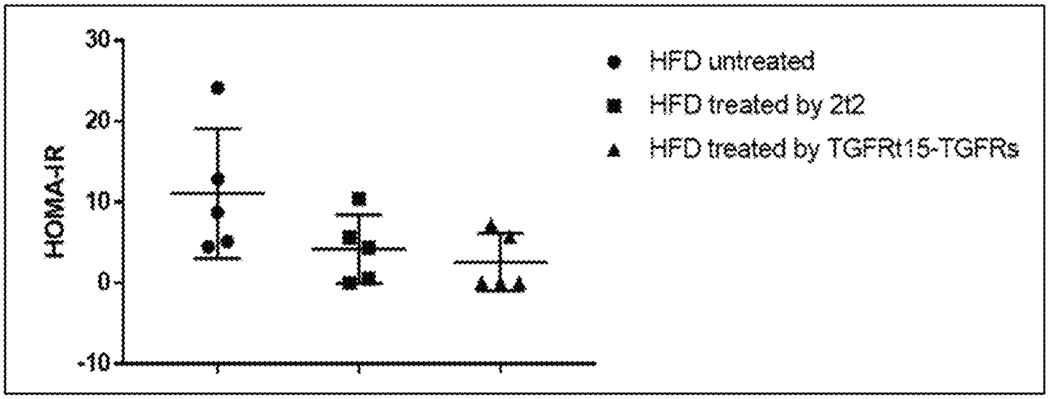
Figure 178C:
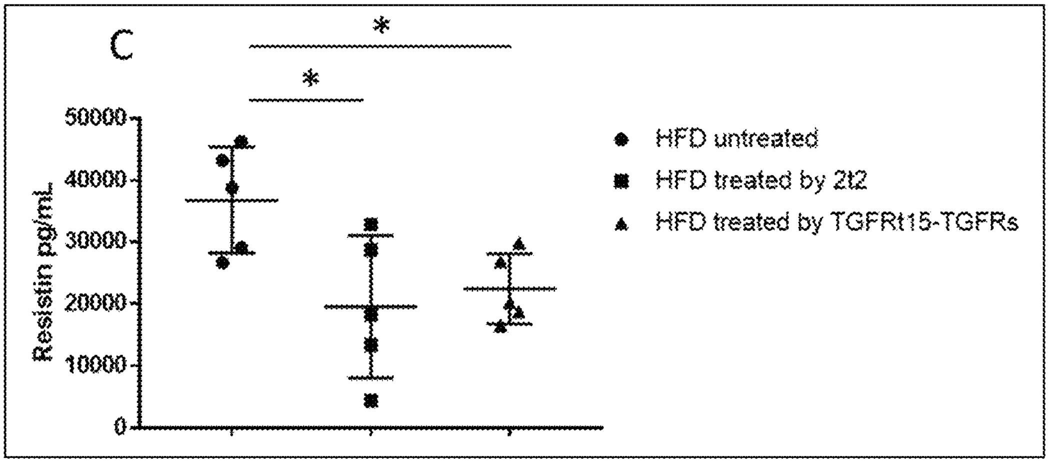

FIG. 178A-C is a set of graphs showing amelioration of the Western diet-induced hyperglycemia in $ApoE^{-/-}$ mice by 2t2.

Figure 179:
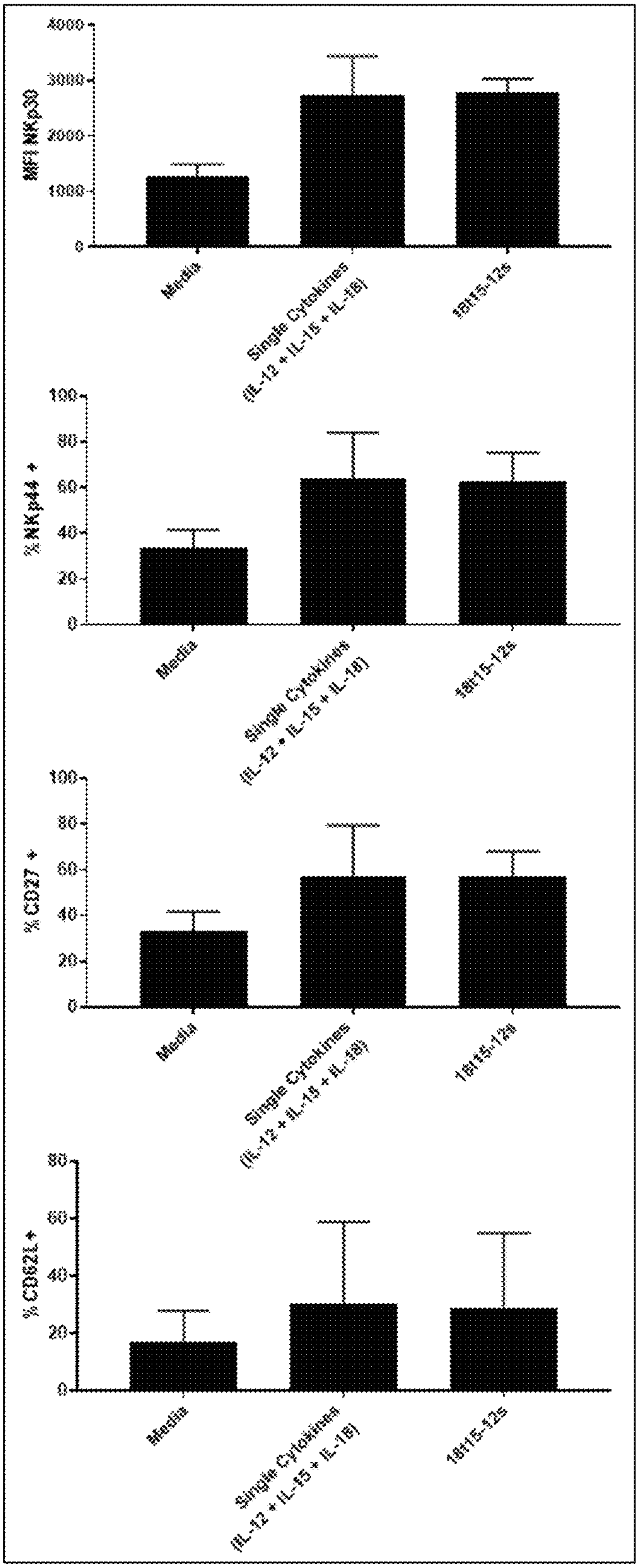

FIG. 179 is a set of graphs showing cell surface staining summarizing the differentiation of NK cells into cytokine-induced memory like NK cells (CIML-NK Cells) after stimulation with 18t15-12s and cultured in rhIL-15.

Figure 180:
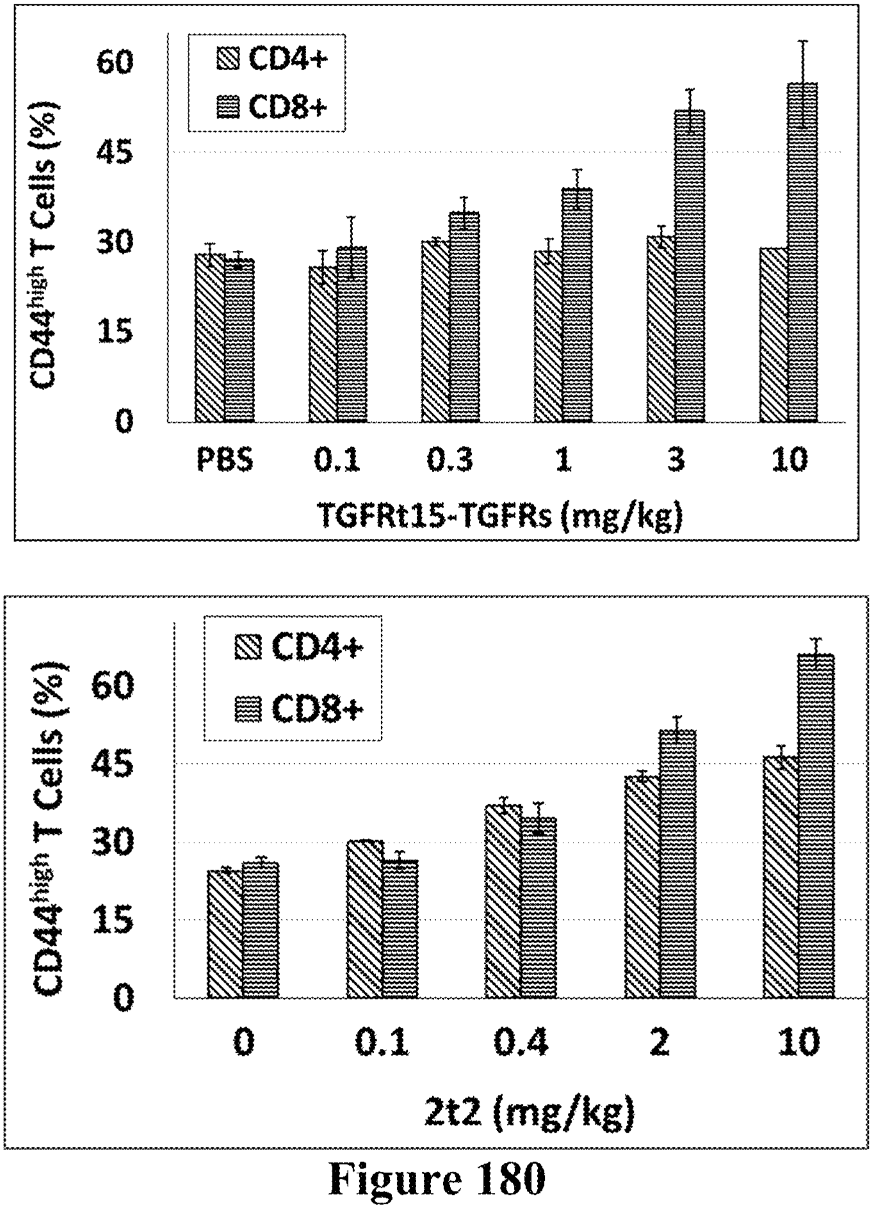

FIG. 180 shows upregulation of CD44 memory T cells. The upper panel shows upregulation of CD44 memory T cells upon treatment with TGFRt15-TGFRs. The lower panel shows upregulation of CD44 memory T cells upon treatment with 2t2.

Figure 181A:
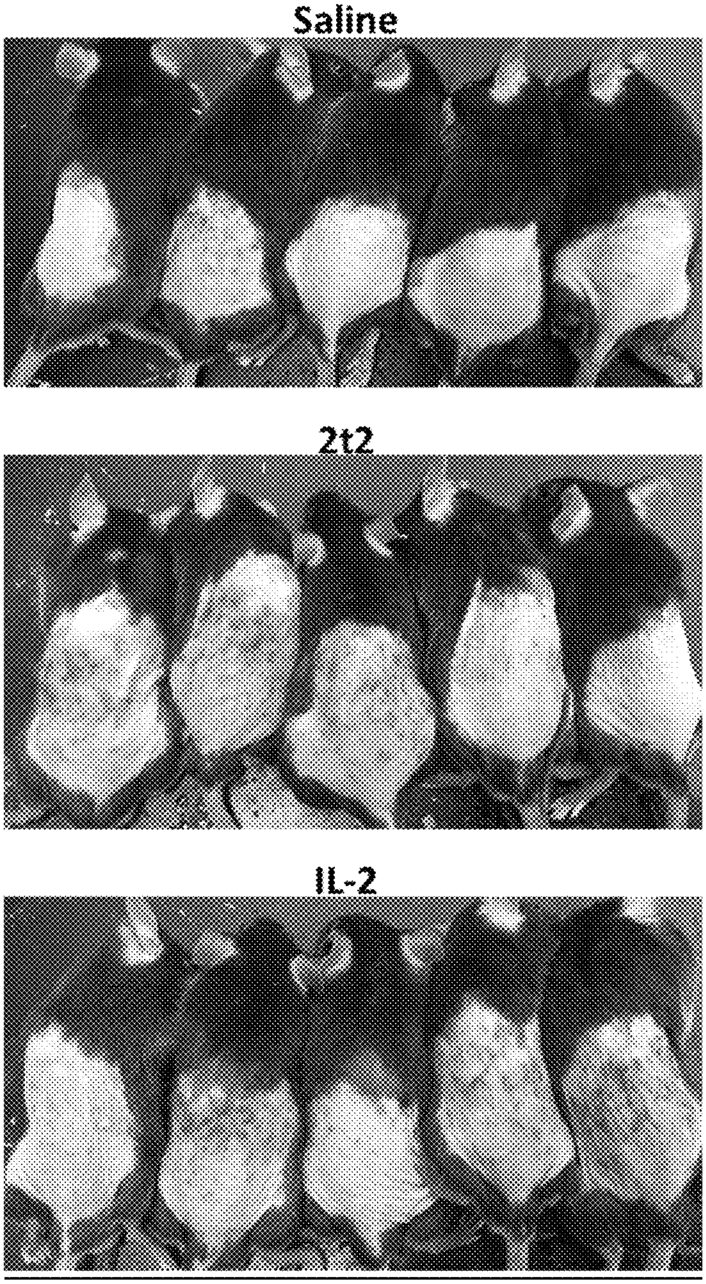
Figure 181B:
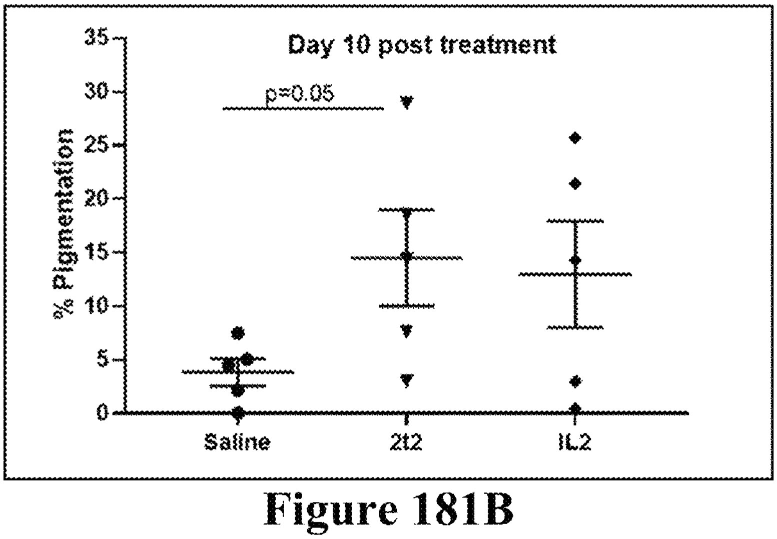

FIGS. 181A and 181B show improvement in hair regrowth following depilation in mice treated with 2t2 or IL-2. FIG. 181A shows skin pigmentation 10 days after depilation in PBS-, 2t2-, or IL-2-treated mice. FIG. 181B shows percent pigmentation in PBS-, 2t2-, or IL-2-treated mice as analyzed using the ImageJ software.

Figure 182:
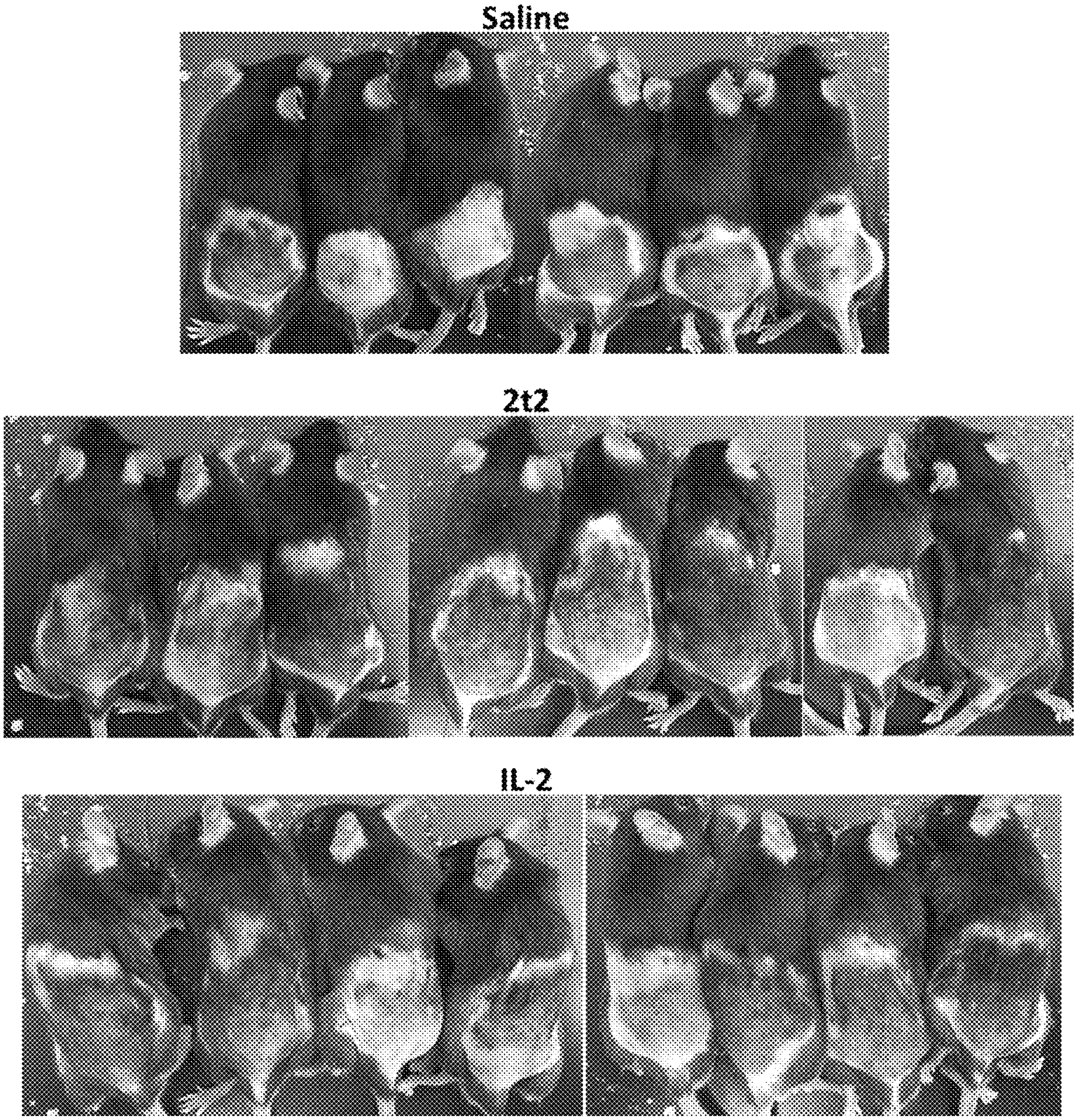

FIG. 182 shows skin pigmentation 14 days after depilation in PBS-, 2t2-, or IL-2-treated mice.

Figure 183:
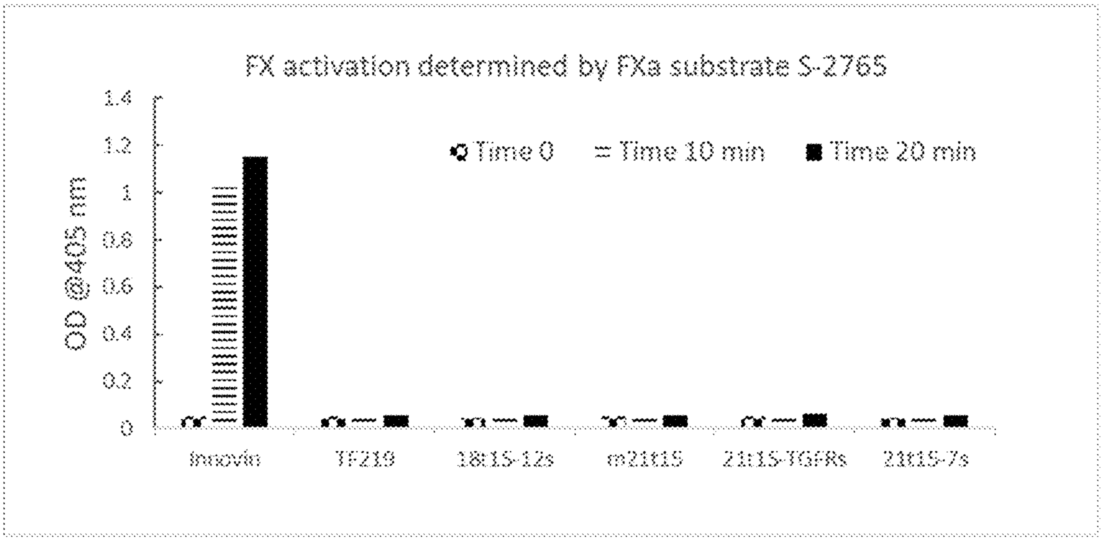

FIG. 183 shows a graph of Factor X (FX) activation following treatment with single-chain or multi-chain chimeric polypeptides.

Figure 184:
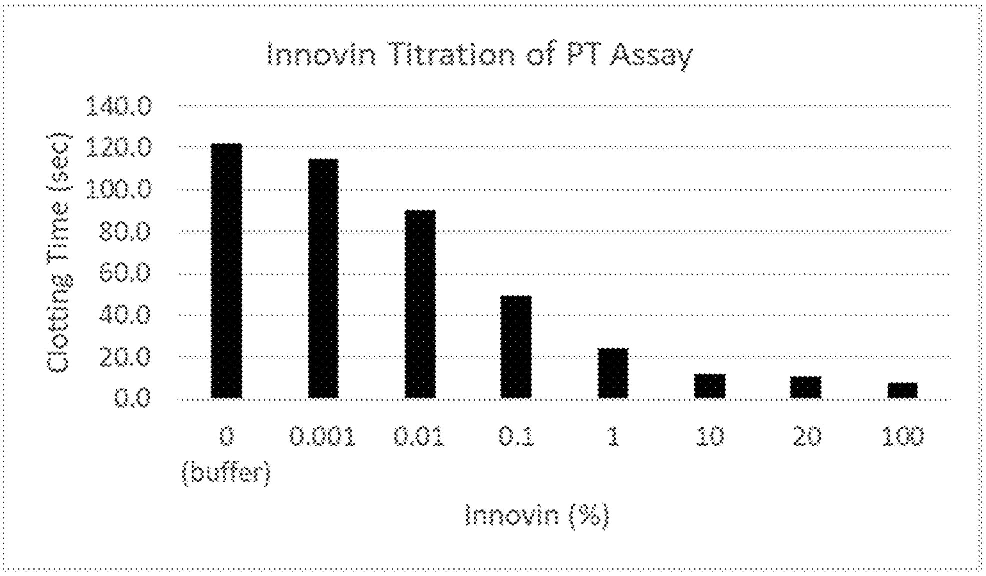

FIG. 184 shows clotting time for a buffer with varying concentrations of Innovin in a prothrombin time (PT) test.

Figure 185:
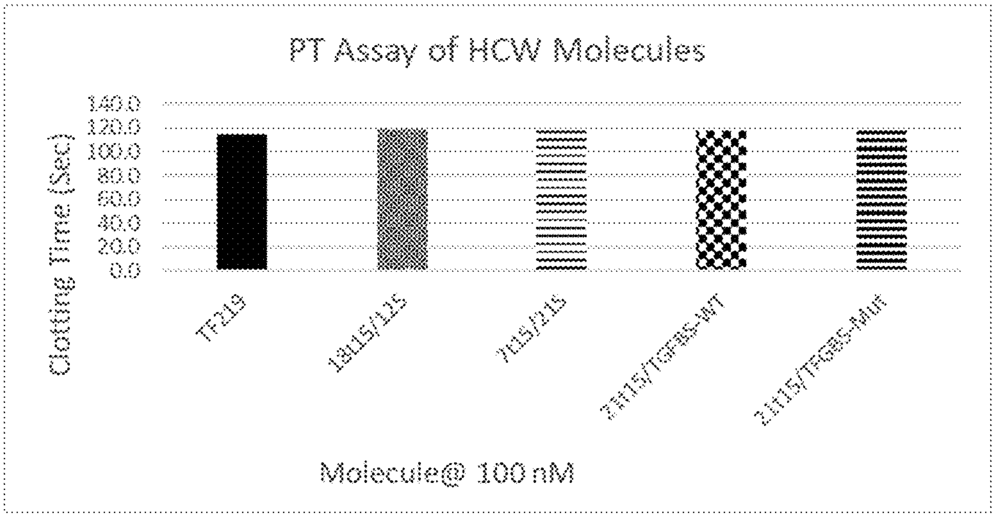

FIG. 185 shows clotting time for multi-chain chimeric polypeptides in a PT Assay.

Figure 186:
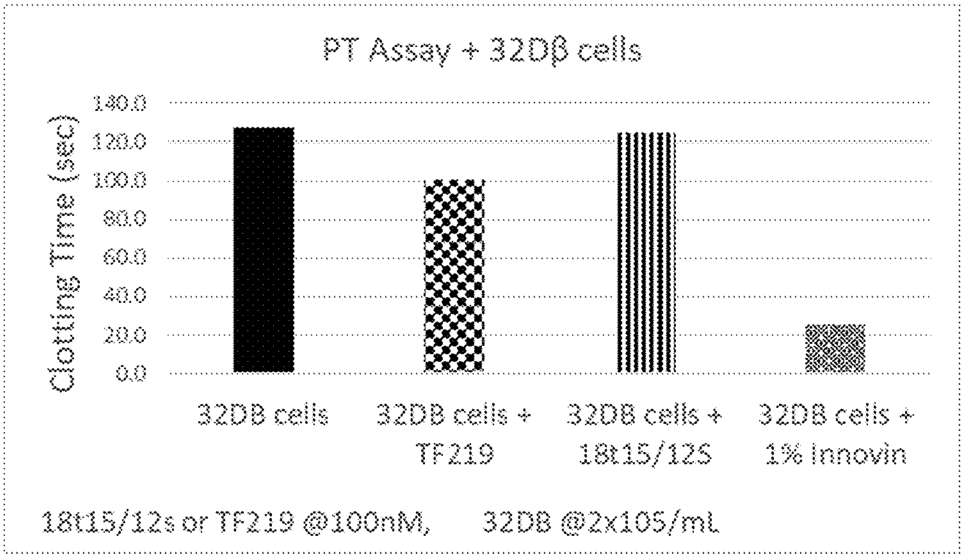

FIG. 186 shows clotting time of the multi-chain chimeric polypeptides in a PT assay when mixed with 32DB cells.

Figure 187:
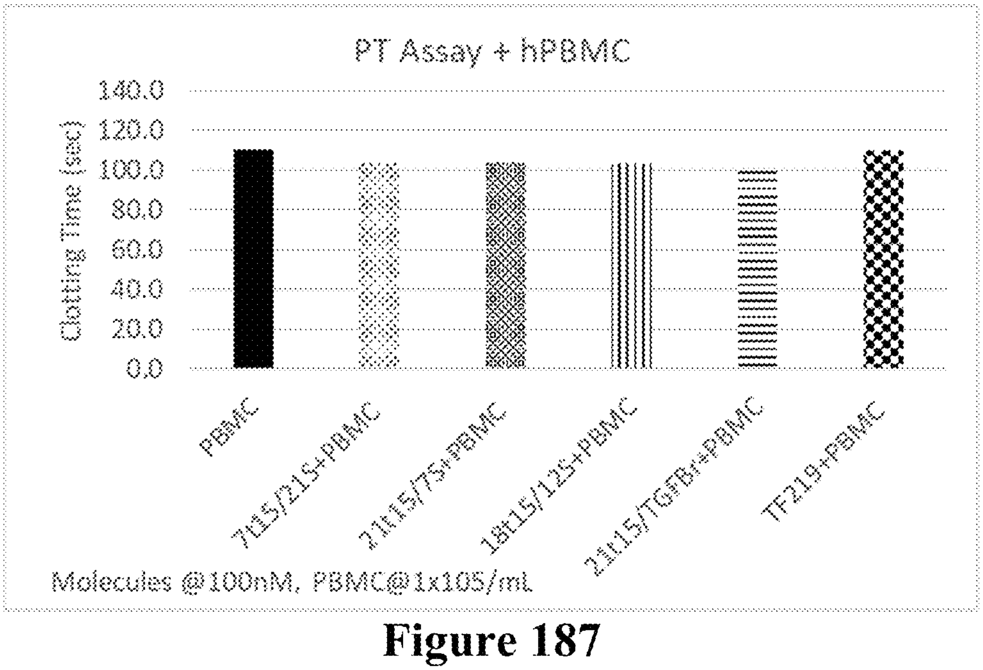

FIG. 187 shows clotting time of multi-chain chimeric polypeptides in a PT assay when mixed with human PBMC.

Figure 188:
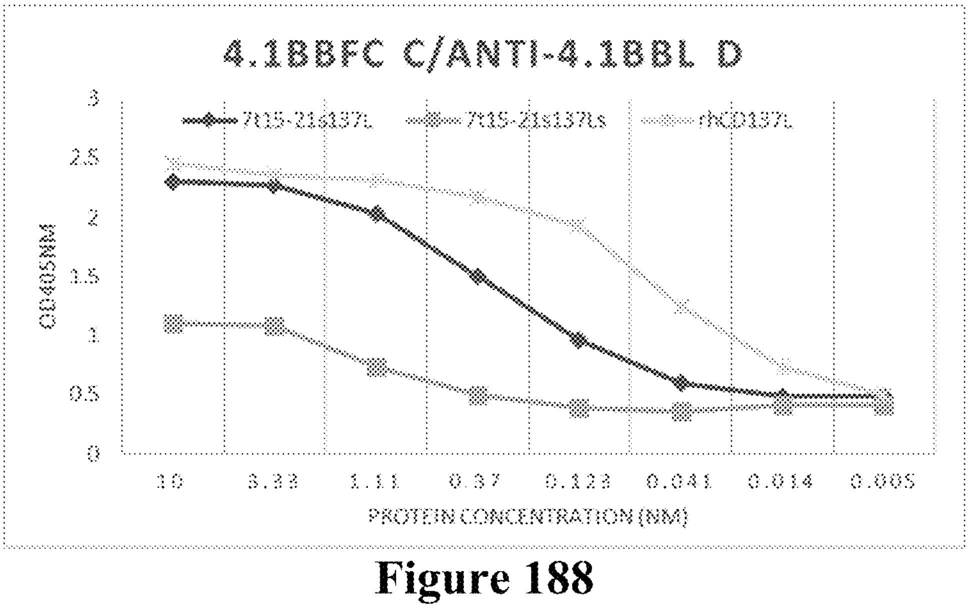
Figure 189A:
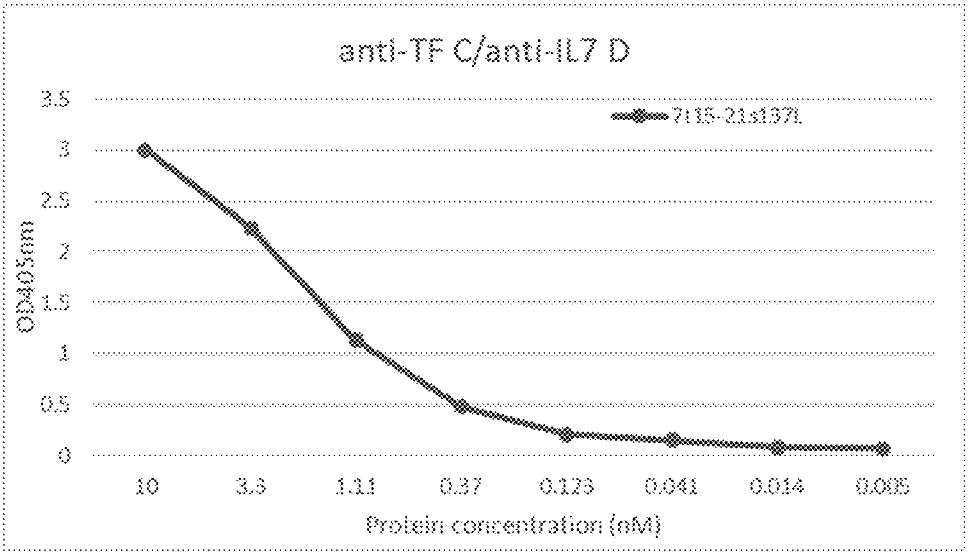
Figure 189B:
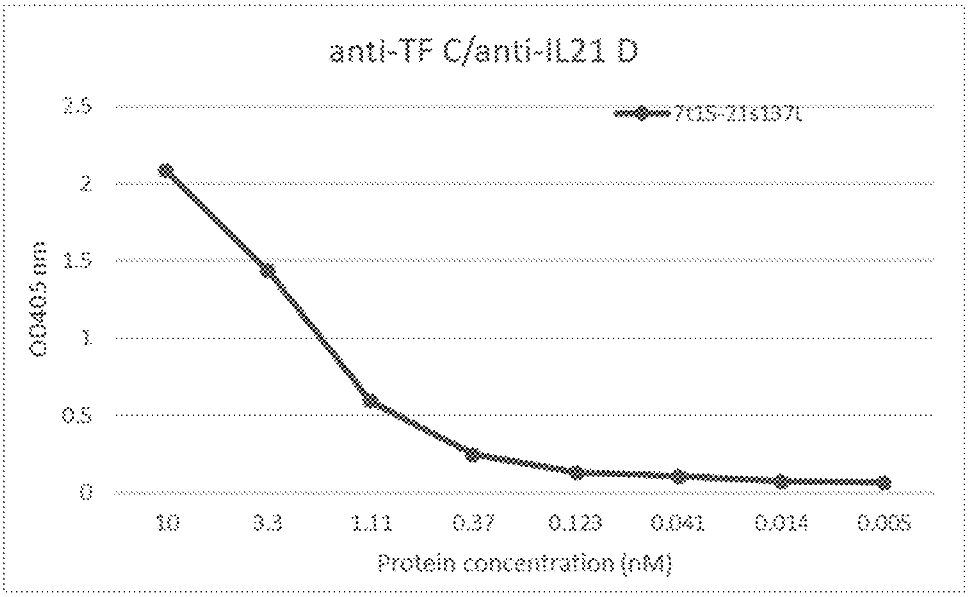
Figure 189C:
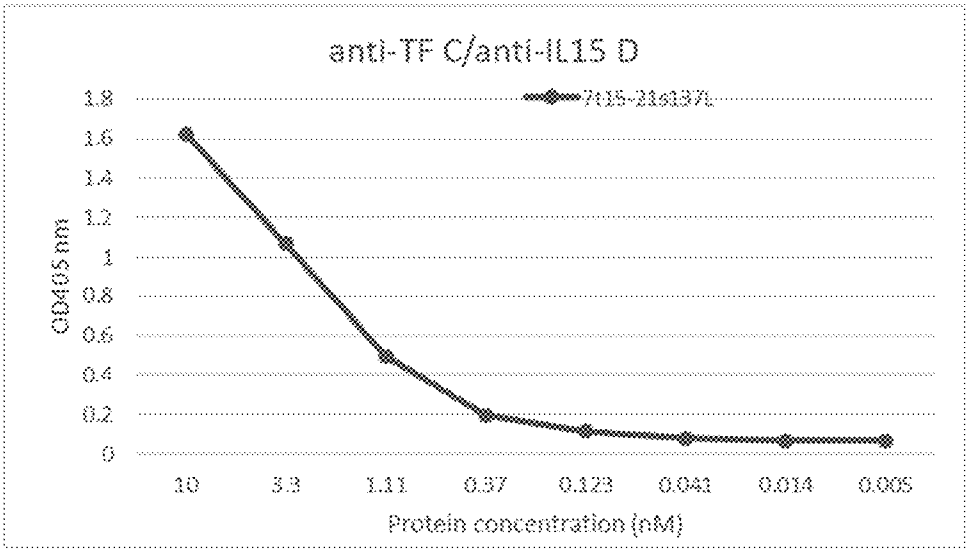
Figure 189D:
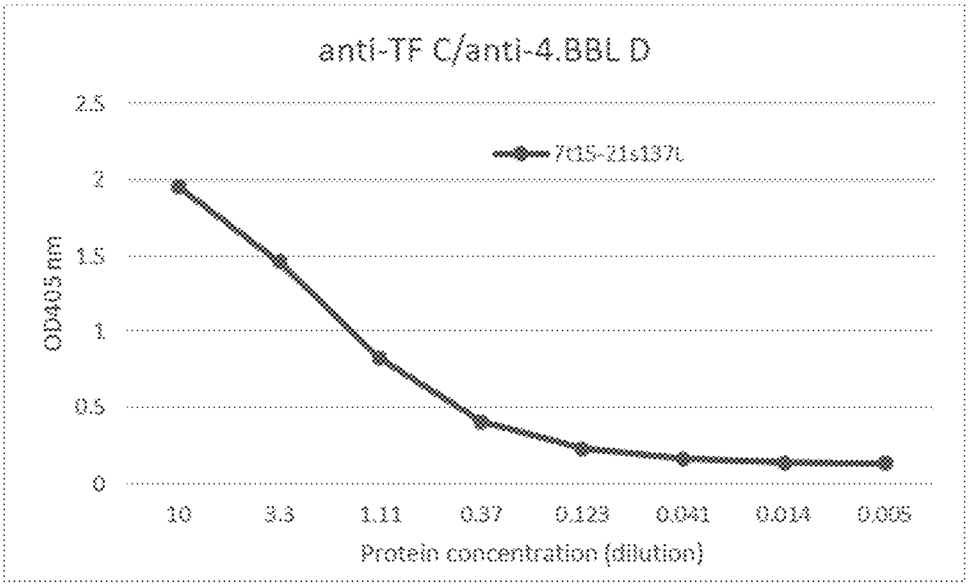

FIG. 188 shows binding of 7t15-21s137L (long version) and 7t15-21s137L (short version) to CD137 (4.1BB).

FIG. 189A-189D show detection of IL7, IL21, IL15, and 4.1BBL in 7t15-21s137L (long version) by the respective antibodies using ELISA.

Figure 190:
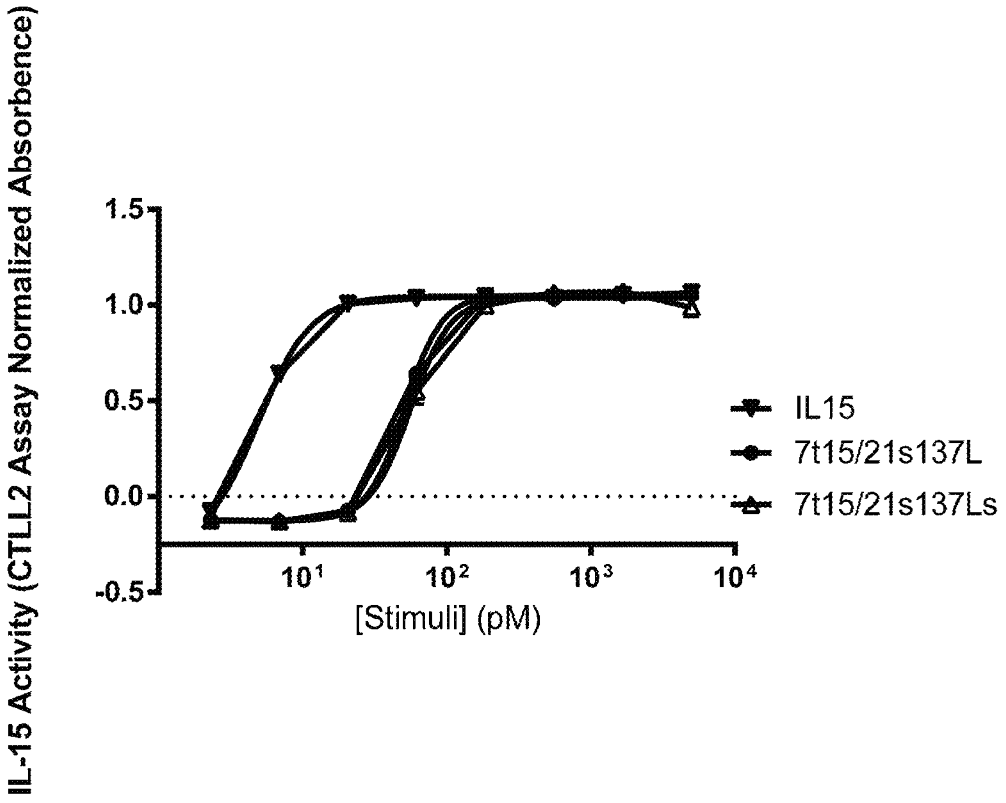

FIG. 190 shows IL-15 activity of 7t15-21s137L (long version) and 7t15-21s137L (short version) as evaluated by a IL2Rαβγ-containing CTLL2 cell proliferation assay.

Figure 191A:
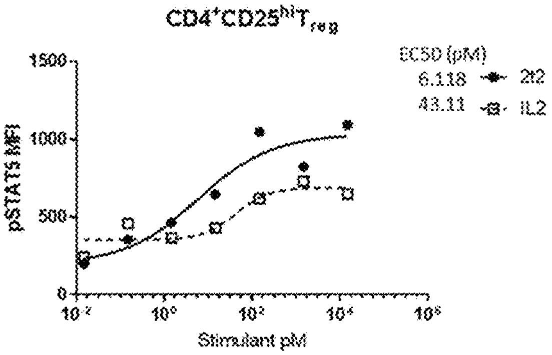
Figure 191B:
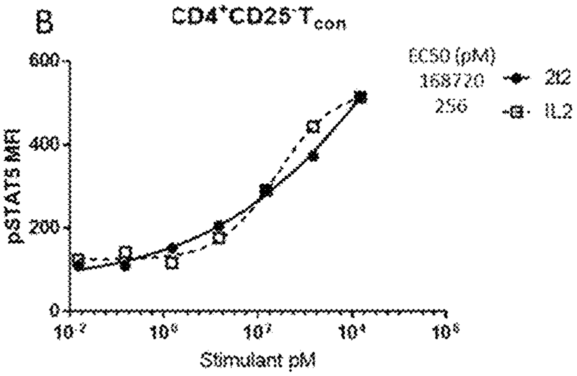
Figure 191C:
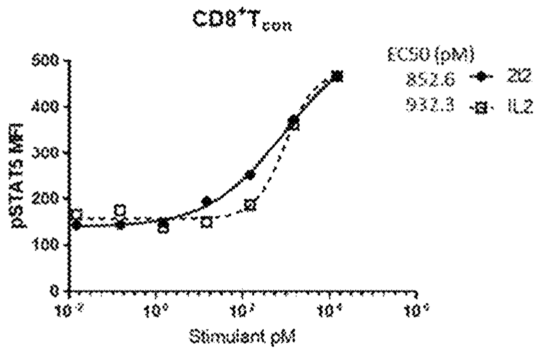

FIGS. 191A-191C show human blood lymphocyte pStat5a responses in $CD4^{+}CD25^{-}T_{reg}$ cells, $CD4^{+}CD25^{-}$ $T_{con}$ cells, or in $CD8^{+}$ $T_{con}$ cells in response to 2t2 or IL2 treatment. FIG. 191A shows pSTAT5 responses in $CD4^{+}$ $CD25^{hi}T_{reg}$ cells. Figure C191B shows pSTAT5 responses in $CD4^{+}CD25^{-}T_{con}$ cells. FIG. 191C shows pSTAT5 responses in $CD8^{+}$ $T_{con}$ cells.

Figure 192A:
Figure 192B:
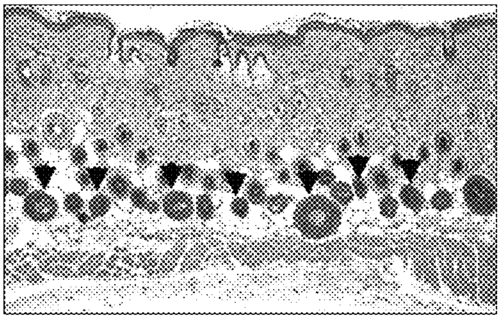
Figure 192C:
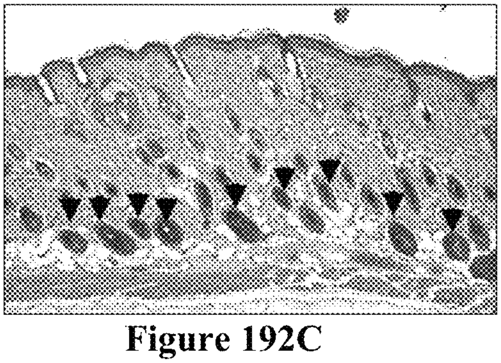
Figure 192D:
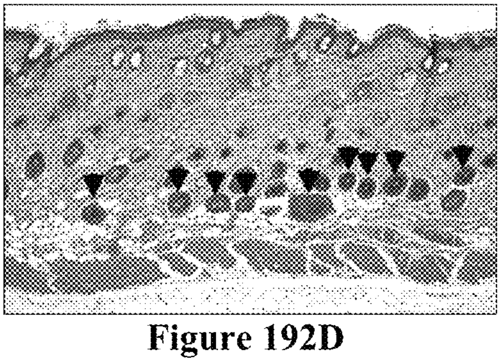
Figure 192E:
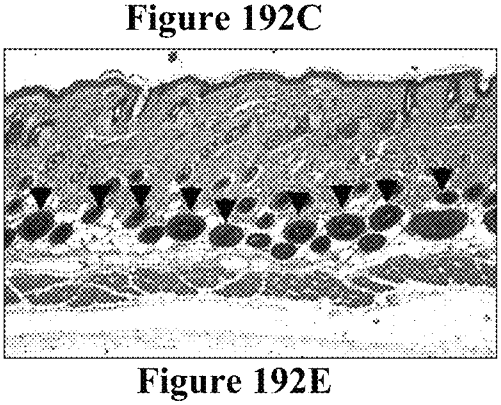

FIGS. 192A-192E is a set of imaging showing that treatment with an IL-2 based molecule (2t2) can induce formation of hair follicles following depilation in mouse model. FIG. 192A is an image from a control mouse—only depilation done after hair was shaved, FIG. 192B is an image from a mouse where depilation was followed by low dose IL-2 (1 mg/kg) administration, and FIGS. 192C-192E show images from mice where depilation was followed by 2t2 at 0.3 mg/kg, (FIG. 192C), 1 mg/kg (FIG. 192D), and (FIG. 192E) 3 mg/kg. Black arrows indicate anagen-phase hair follicles that will later extend into dermis and facilitate hair growth.

Figure 193:
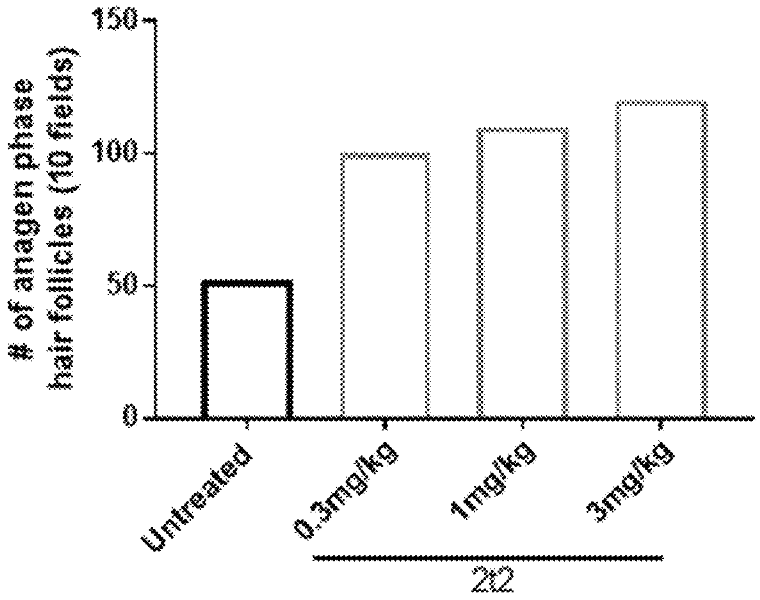

FIG. 193 shows the total number of anagen phase hair follicles counted per 10 fields for each treatment group.

Figure 194:
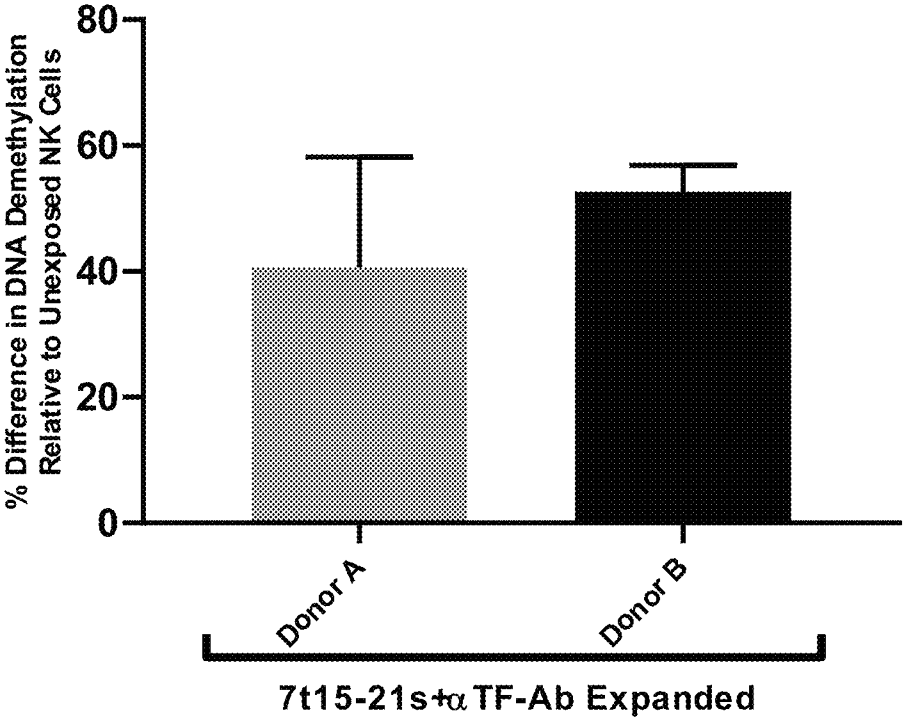

FIG. 194 is a graph showing the percentage different in DNA demethylation in NK cells (relative to unexposed NK cells) from two different donors following expansion with 7t15-21s+anti-tissue factor (TF)-antibody (IgG1) (50 nM).

DETAILED DESCRIPTION

Provided herein are methods of treating an aging-related disease or condition in a subject in need thereof that include administering to a subject identified as having an aging-related disease or condition a therapeutically effective amount of one or more natural killer (NK) cell activating agent(s) and/or a therapeutically effective number of activated NK cells. Also provided herein are methods of killing or reducing the number of senescent cells in a subject in need thereof that include administering to the subject a therapeutically effective amount of one or more NK cell activating agent(s) and/or a therapeutically effective number of activated NK cells. Also provided herein are methods of improving the texture and/or appearance of skin and/or hair in a subject in need thereof over a period of time that include administering to the subject a therapeutically effective amount of one or more natural killer (NK) cell activating agent(s) and/or a therapeutically effective number of activated NK cells. Also provided herein are methods of assisting in the treatment of obesity in a subject in need thereof over a period of time that include administering to the subject a therapeutically effective amount of one or more natural killer (NK) cell activating agent(s) and/or a therapeutically effective number of activated NK cells.

Activated NK Cells

Some embodiments of any of the methods described herein can include administering to a subject (e.g., any of the exemplary subjects described herein) a therapeutically effective number of activated NK cells (e.g., human activated NK cells). An activated NK cell is an NK cell (e.g., a human NK cell) that has increased expression levels of two or more (e.g., three, four, five, or six) of CD25, CD69, MTOR-C1, SREBP1, IFN-γ, and a granzyme (e.g., granzyme B), e.g., as compared to a resting NK cell (e.g., a human resting NK cell). For example, an activated NK cell can have at least a 10% increase (e.g., at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) in the expression levels of two of more (e.g., three, four, five, or six) of CD25, CD69, MTOR-C1, SREBP1, IFN-γ, and a granzyme (e.g., granzyme B), e.g., as compared to a resting NK cell (e.g., a human activated NK cell).

In some embodiments, an activated NK cell can optionally further can have at least a 10% increase (e.g., at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) in the expression levels of two of more (e.g., 3, 4, 5, 6, 7, 8, 9, 10, 11, 12, 13, 14, 15, 16, 17, 18, 19, 20, 21, 22, 23, 24, 25, 26, 27, 28, or 29) of CD25, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, e.g., as compared to a resting NK cell (e.g., a human activated NK cell).

For example, an activated NK cell (e.g., a human activated NK cell) can have about a 10% increase to about a 500% increase, about a 10% increase to about a 450% increase, about a 10% increase to about a 400% increase, about a 10% increase to about a 350% increase, about a 10% increase to about a 300% increase, about a 10% increase to about a 280% increase, about a 10% increase to about a 260% increase, about a 10% increase to about a 240% increase, about a 10% increase to about a 220% increase, about a 10% increase to about a 200% increase, about a 10% increase to about a 180% increase, about a 10% increase to about a 160% increase, about a 10% increase to about a 140% increase, about a 10% increase to about a 120% increase, about a 10% increase to about a 100% increase, about a 10% increase to about a 80% increase, about a 10% increase to about a 60% increase, about a 10% increase to about a 40% increase, about a 10% increase to about a 20% increase, a 20% increase to about a 500% increase, about a 20% increase to about a 450% increase, about a 20% increase to about a 400% increase, about a 20% increase to about a 350% increase, about a 20% increase to about a 300% increase, about a 20% increase to about a 280% increase, about a 20% increase to about a 260% increase, about a 20% increase to about a 240% increase, about a 20% increase to about a 220% increase, about a 20% increase to about a 200% increase, about a 20% increase to about a 180% increase, about a 20% increase to about a 160% increase, about a 20% increase to about a 140% increase, about a 20% increase to about a 120% increase, about a 20% increase to about a 100% increase, about a 20% increase to about a 80% increase, about a 20% increase to about a 60% increase, about a 20% increase to about a 40% increase, a 40% increase to about a 500% increase, about a 40% increase to about a 450% increase, about a 40% increase to about a 400% increase, about a 40% increase to about a 350% increase, about a 40% increase to about a 300% increase, about a 40% increase to about a 280% increase, about a 40% increase to about a 260% increase, about a 40% increase to about a 240% increase, about a 40% increase to about a 220% increase, about a 40% increase to about a 200% increase, about a 40% increase to about a 180% increase, about a 40% increase to about a 160% increase, about a 40% increase to about a 140% increase, about a 40% increase to about a 120% increase, about a 40% increase to about a 100% increase, about a 40% increase to about a 80% increase, about a 40% increase to about a 60% increase, a 60% increase to about a 500% increase, about a 60% increase to about a 450% increase, about a 60% increase to about a 400% increase, about a 60% increase to about a 350% increase, about a 60% increase to about a 300% increase, about a 60% increase to about a 280% increase, about a 60% increase to about a 260% increase, about a 60% increase to about a 240% increase, about a 60% increase to about a 220% increase, about a 60% increase to about a 200% increase, about a 60% increase to about a 180% increase, about a 60% increase to about a 160% increase, about a 60% increase to about a 140% increase, about a 60% increase to about a 120% increase, about a 60% increase to about a 100% increase, about a 60% increase to about a 80% increase, a 80% increase to about a 500% increase, about a 80% increase to about a 450% increase, about a 80% increase to about a 400% increase, about a 80% increase to about a 350% increase, about a 80% increase to about a 300% increase, about a 80% increase to about a 280% increase, about a 80% increase to about a 260% increase, about a 80% increase to about a 240% increase, about a 80% increase to about a 220% increase, about a 80% increase to about a 200% increase, about a 80% increase to about a 180% increase, about a 80% increase to about a 160% increase, about a 80% increase to about a 140% increase, about a 80% increase to about a 120% increase, about a 80% increase to about a 100% increase, a 100% increase to about a 500% increase, about a 100% increase to about a 450% increase, about a 100% increase to about a 400% increase, about a 100% increase to about a 350% increase, about a 100% increase to about a 300% increase, about a 100% increase to about a 280% increase, about a 100% increase to about a 260% increase, about a 100% increase to about a 240% increase, about a 100% increase to about a 220% increase, about a 100% increase to about a 200% increase, about a 100% increase to about a 180% increase, about a 100% increase to about a 160% increase, about a 100% increase to about a 140% increase, about a 100% increase to about a 120% increase, a 120% increase to about a 500% increase, about a 120% increase to about a 450% increase, about a 120% increase to about a 400% increase, about a 120% increase to about a 350% increase, about a 120% increase to about a 300% increase, about a 120% increase to about a 280% increase, about a 120% increase to about a 260% increase, about a 120% increase to about a 240% increase, about a 120% increase to about a 220% increase, about a 120% increase to about a 200% increase, about a 120% increase to about a 180% increase, about a 120% increase to about a 160% increase, about a 120% increase to about a 140% increase, a 140% increase to about a 500% increase, about a 140% increase to about a 450% increase, about a 140% increase to about a 400% increase, about a 140% increase to about a 350% increase, about a 140% increase to about a 300% increase, about a 140% increase to about a 280% increase, about a 140% increase to about a 260% increase, about a 140% increase to about a 240% increase, about a 140% increase to about a 220% increase, about a 140% increase to about a 200% increase, about a 140% increase to about a 180% increase, about a 140% increase to about a 160% increase, a 160% increase to about a 500% increase, about a 160% increase to about a 450% increase, about a 160% increase to about a 400% increase, about a 160% increase to about a 350% increase, about a 160% increase to about a 300% increase, about a 160% increase to about a 280% increase, about a 160% increase to about a 260% increase, about a 160% increase to about a 240% increase, about a 160% increase to about a 220% increase, about a 160% increase to about a 200% increase, about a 160% increase to about a 180% increase, a 180% increase to about a 500% increase, about a 180% increase to about a 450% increase, about a 180% increase to about a 400% increase, about a 180% increase to about a 350% increase, about a 180% increase to about a 300% increase, about a 180% increase to about a 280% increase, about a 180% increase to about a 260% increase, about a 180% increase to about a 240% increase, about a 180% increase to about a 220% increase, about a 180% increase to about a 200% increase, a 200% increase to about a 500% increase, about a 200% increase to about a 450% increase, about a 200% increase to about a 400% increase, about a 200% increase to about a 350% increase, about a 200% increase to about a 300% increase, about a 200% increase to about a 280% increase, about a 200% increase to about a 260% increase, about a 200% increase to about a 240% increase, about a 200% increase to about a 220% increase, a 220% increase to about a 500% increase, about a 220% increase to about a 450% increase, about a 220% increase to about a 400% increase, about a 220% increase to about a 350% increase, about a 220% increase to about a 300% increase, about a 220% increase to about a 280% increase, about a 220% increase to about a 260% increase, about a 220% increase to about a 240% increase, a 240% increase to about a 500% increase, about a 240% increase to about a 450% increase, about a 240% increase to about a 400% increase, about a 240% increase to about a 350% increase, about a 240% increase to about a 300% increase, about a 240% increase to about a 280% increase, about a 240% increase to about a 260% increase, a 260% increase to about a 500% increase, about a 260% increase to about a 450% increase, about a 260% increase to about a 400% increase, about a 260% increase to about a 350% increase, about a 260% increase to about a 300% increase, about a 260% increase to about a 280% increase, a 280% increase to about a 500% increase, about a 280% increase to about a 450% increase, about a 280% increase to about a 400% increase, about a 280% increase to about a 350% increase, about a 280% increase to about a 300% increase, a 300% increase to about a 500% increase, about a 300% increase to about a 450% increase, about a 300% increase to about a 400% increase, about a 300% increase to about a 350% increase, a 350% increase to about a 500% increase, about a 350% increase to about a 450% increase, about a 350% increase to about a 400% increase, a 400% increase to about a 500% increase, about a 400% increase to about a 450% increase, or a 400% increase to about a 500% increase, in the expression levels of two of more (e.g., three, four, five, or six) of CD25, CD69, mTORC1, SREBP1, IFN-γ, and a granzyme (e.g., granzyme B), e.g., as compared to a resting NK cell (e.g., a human resting NK cell).

In some embodiments, an activated NK cell can further have about a 10% increase to about a 500% increase (e.g., or any of the subranges of this range described herein) in the expression levels of two of more (e.g., 3, 4, 5, 6, 7, 8, 9, 10, 11, 12, 13, 14, 15, 16, 17, 18, 19, 20, 21, 22, 23, 24, 25, 26, 27, 28, or 29) of CD25, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, e.g., as compared to a resting NK cell (e.g., a human activated NK cell).

Non-limiting examples of assays that can be used to determining the expression level of CD25, CD69, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, MYC, SREBP1, IFN-γ, and a granzyme (e.g., granzyme B) include, e.g., immunoblotting, fluorescence-assisted cell sorting, enzyme-linked immunosorbent assays, and RT-PCR.

Non-limiting examples of commercial ELISA assays that can be used to determine the expression level of CD25 are available from Diaclone, Covalab Biotechnology, and Caltag Medsystems. The protein and cDNA sequences for mature human CD25 are shown below.

```
Mature Human CD25 Protein
                                          (SEQ ID NO: 1)
elcdddppe iphatfkama ykegtmlnce ckrgfrriks

gslymlctgn sshsswdnqc qctssatrnt tkqvtpqpee

qkerkttemq spmqpvdqas lpghcreppp weneateriy

hfvvgqmvyy qcvqgyralh rgpaesvckm thgktrwtqp

qlictgemet sqfpgeekpq aspegrpese tsclvtttdf

qiqtemaatm etsiftteyq vavagcvfll isvlllsglt

wqrrqrksrr ti

Human CD25 cDNA
                                          (SEQ ID NO: 2)
gagctctg tgacgatgac ccgccagaga tcccacacgc

cacattcaaa gccatggcct acaaggaagg aaccatgttg

aactgtgaat gcaagagagg tttccgcaga ataaaaagcg

ggtcactcta tatgctctgt acaggaaact ctagccactc

gtcctgggac aaccaatgtc aatgcacaag ctctgccact

cggaacacaa cgaaacaagt gacacctcaa cctgaagaac

agaaagaaag gaaaaccaca gaaatgcaaa gtccaatgca
```

-continued

```
gccagtggac caagcgagcc ttccaggtca ctgcagggaa

cctccaccat gggaaaatga agccacagag agaatttatc

atttcgtggt ggggcagatg gtttattatc agtgcgtcca

gggatacagg gctctacaca gaggtcctgc tgagagcgtc

tgcaaaatga cccacgggaa gacaaggtgg acccagcccc

agctcatatg cacaggtgaa atggagacca gtcagtttcc

aggtgaagag aagcctcagg caagccccga aggccgtcct

gagagtgaga cttcctgcct cgtcacaaca acagattttc

aaatacagac agaaatggct gcaaccatgg agacgtccat

atttacaaca gagtaccagg tagcagtggc cggctgtgtt

ttcctgctga tcagcgtcct cctcctgagt gggctcacct

ggcagcggag acagaggaag agtagaagaa caatc
```

Non-limiting examples of commercial ELISA assays that can be used to determine the expression level of CD69 are available from RayBiotech, Novus Biologicals, and Aviscera Bioscience. The protein and cDNA sequences for mature human CD69 are shown below.

```
Mature Human CD69 Protein
                                          (SEQ ID NO: 3)
mssencfvae nsslhpesgq endatsphfs trhegsfqvp

vlcavmnvvf itiliialia lsvgqyncpg qytfsmpsds

hvsscsedwv gyqrkcyfis tvkrswtsaq nacsehgatl

avidsekdmn flkryagree hwvglkkepg hpwkwsngke

fnnwfnvtgs dkcvflknte vssmeceknl ywicnkpyk

Human CD69 cDNA
                                          (SEQ ID NO: 4)
atgagctctg aaaattgttt cgtagcagag aacagctctt

tgcatccgga gagtggacaa gaaaatgatg ccaccagtcc

ccatttctca acacgtcatg aagggtcctt ccaagttcct

gtcctgtgtg ctgtaatgaa tgtggtcttc atcaccattt

taatcatagc tctcattgcc ttatcagtgg gccaatacaa

ttgtccaggc caatacacat tctcaatgcc atcagacagc

catgtttctt catgctctga ggactgggtt ggctaccaga

ggaaatgcta ctttatttct actgtgaaga ggagctggac

ttcagcccaa aatgcttgtt ctgaacatgg tgctactctt

gctgtcattg attctgaaaa ggacatgaac tttctaaaac

gatacgcagg tagagaggaa cactgggttg gactgaaaaa

ggaacctggt cacccatgga agtggtcaaa tggcaaagaa

tttaacaact ggttcaacgt tacagggtct gacaagtgtg

tttttctgaa aaacacagag gtcagcagca tggaatgtga

gaagaattta tactggatat gtaacaaacc ttacaaataa
```

The protein and cDNA sequences for mature human CD59 are shown below.

Mature Human CD59 Protein
(SEQ ID NO: 5)
```
lqcyncpnptadckt avncssdfda clitkaglqv ynkcwkfehc
nfndvttrlr eneltyycck kdlcnfneql en
```

Human CD59 cDNA
(SEQ ID NO: 6)
```
atgggaatcc aaggagggtc tgtcctgttc gggctgctgc
tcgtcctggc tgtcttctgc cattcaggtc atagcctgca
gtgctacaac tgtcctaacc caactgctga ctgcaaaaca
gccgtcaatt gttcatctga ttttgatgcg tgtctcatta
ccaaagctgg gttacaagtg tataacaagt gttggaagtt
tgagcattgc aatttcaacg acgtcacaac ccgcttgagg
gaaaatgagc taacgtacta ctgctgcaag aaggacctgt
gtaactttaa cgaacagctt gaaaatggtg ggacatcctt
atcagagaaa acagttcttc tgctggtgac tccatttctg
gcagcagcct ggagccttca tccctaa
```

The protein and cDNA sequences for mature human CD352 are shown below.

Mature Human CD352 Protein
(SEQ ID NO: 7)
```
qssltplmv ngilgesvtl plefpagekv nfitwlfnet
slafivphet kspeihvtnp kqgkrinftq syslqlsnlk
medtgsyraq istktsakls sytlrilrql rniqvtnhsq
lfqnmtcelh ltcsvedadd nvsfrwealg ntlssqpnlt
vswdprisse qdytciaena vsnlsfsysa qklcedvkiq
ytdtkmilfm vsgicivfgf iillllvlrk rrdslslstq
rtqgpaesar nleyvsyspt nntvyasvth snreteiwtp
rendtitiys tinhskeskp tfsrataldn vv
```

Human CD352 cDNA
(SEQ ID NO: 8)
```
atgttgtggc tgttccaatc gctcctgttt gtcttctgct
ttggcccagg gaatgtagtt tcacaaagca gcttaacccc
attgatggtg aacgggattc tgggggagtc agtaactctt
cccctggagt ttcctgcagg agagaaggtc aacttcatca
cttggctttt caatgaaaca tctcttgcct tcatagtacc
ccatgaaacc aaaagtccag aaatccacgt gactaatccg
aaacagggaa agcgactgaa cttcacccag tcctactccc
tgcaactcag caacctgaag atggaagaca caggctctta
cagagcccag atatccacaa agacctctgc aaagctgtcc
agttacactc tgaggatatt aagacaactg aggaacatac
aagttaccaa tcacagtcag ctatttcaga atatgacctg
tgagctccat ctgacttgct ctgtggagga tgcagatgac
```

-continued
```
aatgtctcat tcagatggga ggccttggga aacacacttt
caagtcagcc aaacctcact gtctcctggg accccaggat
ttccagtgaa caggactaca cctgcatagc agagaatgct
gtcagtaatt tatccttctc tgtctctgcc cagaagcttt
gcgaagatgt taaaattcaa tatacagata ccaaaatgat
tctgtttatg gtttctggga tatgcatagt cttcggtttc
atcatactgc tgttacttgt tttgaggaaa agaagagatt
ccctatcttt gtctactcag cgaacacagg gccccgagtc
cgcaaggaac ctagagtatg tttcagtgtc tccaacgaac
aacactgtgt atgcttcagt cactcattca aacagggaaa
cagaaatctg gacacctaga gaaaatgata ctatcacaat
ttactccaca attaatcatt ccaaagagag taaacccact
ttttccaggg caactgccct tgacaatgtc gtgtaa
```

The protein and cDNA sequences for mature human NKp80 are shown below.

Mature Human NKp80 Protein
(SEQ ID NO: 9)
```
mqdeerymtl nvqskkrssa qtsqltfkdy svtlhwykil
lgisgtvngi ltltlislil lvsqgvllkc qkgscsnatq
yedtgdlkvn ngtrrnisnk dlcasrsadq tvlcqsewlk
yqgkcywfsn emkswsdsyv yclerkshll iihdqlemaf
iqknlrqlny vwiglnftsl kmtwtwvdgs pidskiffik
gpakenscaa ikeskifset cssvfkwicq y
```

Human NKp80 cDNA
(SEQ ID NO: 10)
```
atgcaagatg aagaaagata catgacattg aatgtacagt
caaagaaaag gagttctgcc caaacatctc aacttacatt
taaagattat tcagtgacgt tgcactggta taaaatctta
ctgggaatat ctggaaccgt gaatggtatt ctcactttga
ctttgatctc cttgatcctg ttggtactat gccaatcaga
atggctcaaa taccaaggga agtgttattg gttctctaat
gagatgaaaa gctggagtga cagttatgtg tattgtttgg
aaagaaaatc tcatctacta atcatacatg accaacttga
aatggctttt atacagaaaa acctaagaca attaaactac
gtatggattg ggcttaactt tacctccttg aaaatgacat
ggacttgggt ggatggttct ccaatagatt caaagatatt
cttcataaag ggaccagcta aagaaaacag ctgtgctgcc
attaaggaaa gcaaaatttt ctctgaaacc tgcagcagtg
ttttcaaatg gatttgtcag tattag
```

The protein and cDNA sequences for mature human DNAM-1 are shown below.

Mature Human DNAM-1 Protein (SEQ ID NO: 11)

ee vlwhtsvpfa enmslecvyp smgiltqvew fkigtqqdsi aifspthgmv irkpyaervy flnstmasnn mtlffrnase ddvgyyscsl ytypqgtwqk viqvvqsdsf eaavpsnshi vsepgknvtl tcqpqmtwpv qavrwekiqp rqidlltycn lvhgrnftsk fprqivsncs hgrwsvivip dvtvsdsgly rcylqasage netfvmrltv aegktdnqyt lfvaggtvll llfvisitti ivifln rrrr rerrdlftes wdtqkapnny rspistsgpt nqsmddtred iyvnyptfsr rpktrv Human DNAM-1 cDNA (SEQ ID NO: 12)

atggattatc ctactttact tttggctctt cttcatgtat acagagctct atgtgaagag gtgctttggc atacatcagt tccctttgcc gagaacatgt ctctagaatg tgtgtatcca tcaatgggca tcttaacaca ggtggagtgg ttcaagatcg ggacccagca ggattccata gccattttca gccctactca tggcatggtc ataaggaagc cctatgctga gagggtttac tttttgaatt caacgatggc ttccaataac atgactcttt tctttcggaa tgcctctgaa gatgatgttg gctactattc ctgctctctt tacacttacc cacagggaac ttggcagaag gtgatacagg tggttcagtc agatagtttt gaggcagctg tgccatcaaa tagccacatt gtttcggaac ctggaaagaa tgtcacactc acttgtcagc ctcagatgac gtggcctgtg caggcagtga ggtgggaaaa gatccagccc cgtcagatcg acctcttaac ttactgcaac ttggtccatg gcagaaattt cacctccaag ttcccaagac aaatagtgag caactgcagc cacggaaggt ggagcgtcat cgtcatcccc gatgtcacag tctcagactc ggggctttac cgctgctact tgcaggccag cgcaggagaa aacgaaacct tcgtgatgag attgactgta gccgagggta aaaccgataa ccaatatacc ctctttgtgg ctggagggac agttttattg ttgttgtttg ttatctcaat taccaccatc attgtcattt tccttaacag aaggagaagg agagagagaa gagatctatt tacagagtcc tgggatacac agaaggcacc caataactat agaagtccca tctctaccag tcaacctacc aatcaatcca tggatgatac aagagaggat atttatgtca actatccaac cttctctcgc agaccaaaga ctagagttta a The protein and cDNA sequences for mature human 2B4 are shown below.

Mature Human 2B4 Protein (SEQ ID NO: 13)

gk gcqgsadhvv sisgvplqlq pnsiqtkvds iawkkllpsq ngfhhilkwe ngslpsntsn drfsfivknl sllikaaqqq dsglyclevt sisgkvqtat fqvfvfdkve kprlqgqgki ldrgrcqval sclvsrdgnv syawyrgskl iqtagnltyl deevdingth tytcnvsnpv sweshtlnlt qdcqnahqef rfwpflviiv ilsalflgtl acfcvwrrkr kekqsetspk efltiyedvk dlktrrnheq eqtfpgggst iysmiqsqss aptsqepayt lysliqpsrk sgsrkrnhsp sfnstiyevi gksqpkaqnp arlsrkelen fdvys Human 2B4 cDNA (SEQ ID NO: 14)

atgctggggc aagtggtcac cctcatactc ctcctgctcc tcaaggtgta tcagggcaaa ggatgccagg gatcagctga ccatgtggtt agcatctcgg gagtgcctct tcagttacaa ccaaacagca tacagacgaa ggttgacagc attgcatgga agaagttgct gccctcacaa aatggatttc atcacatatt gaagtgggag aatggctctt tgccttccaa tacttccaat gatagattca gttttatagt caagaacttg agtcttctca tcaaggcagc tcagcagcag gacagtggcc tctactgcct ggaggtcacc agtatatctg gaaaagttca gacagccacg ttccaggttt ttgtatttga taaagttgag aaaccccgcc tacaggggca ggggaagatc ctggacagag ggagatgcca agtggctctg tcttgcttgg tctccaggga tggcaatgtg tcctatgctt ggtacagagg gagcaagctg atccagacag cagggaacct cacctacctg gacgaggagg ttgacattaa tggcactcac acatatacct gcaatgtcag caatcctgtt agctgggaaa gccacaccct gaatctcact caggactgtc agaatgccca tcaggaattc agattttggc cgtttttggt gatcatcgtg attctaagcg cactgttcct tggcaccctt gcctgcttct gtgtgtggag gagaaagagg aaggagaagc agtcagagac cagtcccaag gaatttttga caatttacga agatgtcaag gatctgaaaa ccaggagaaa tcacgagcag gagcagactt ttcctggagg ggggagcacc atctactcta tgatccagtc ccagtcttct gctcccacgt cacaagaacc tgcatataca ttatattcat taattcagcc ttccaggaag tctggatcca ggaagaggaa ccacagccct tccttcaata gcactatcta tgaagtgatt ggaaagagtc aacctaaagc ccagaaccct gctcgattga gccgcaaaga gctggagaac tttgatgttt attcctag The protein and cDNA sequences for mature human NKp30 are shown below.

```
Mature Human NKp30 Protein
                                                  (SEQ ID NO: 15)
lw vsqppeirtl egssaflpcs fnasqgrlai gsvtwfrdev

vpgkevrngt pefrgrlapl assrflhdhq aelhirdvrg

hdasiyvcrv evlglgvgtg ngtrlvveke hpqlgagtvl

llragfyavs flsvavgstv yyqgkcltwk gprrqlpavv

paplpppcgs sahllppvpg g
```

```
Human NKp30 cDNA
                                                  (SEQ ID NO: 16)
atggcctgga tgctgttgct catcttgatc atggtccatc

caggatcctg tgctctctgg gtgtcccagc cccctgagat

tcgtaccctg gaaggatcct ctgccttcct gccctgctcc

ttcaatgcca gccaagggag actggccatt ggctccgtca

cgtggttccg agatgaggtg gttccaggga aggaggtgag

gaatggaacc ccagagttca ggggccgcct ggccccactt

gcttcttccc gtttcctcca tgaccaccag gctgagctgc

acatccggga cgtgcgaggc catgacgcca gcatctacgt

gtgcagagtg gaggtgctgg gccttggtgt cgggacaggg

aatgggactc ggctggtggt ggagaaagaa catcctcagc

taggggctgg tacagtcctc ctccttcggg ctggattcta

tgctgtcagc tttctctctg tggccgtggg cagcaccgtc

tattaccagg gcaaatgcca ctgtcacatg ggaacacact

gccactcctc agatgggccc cgaggagtga ttccagagcc

cagatgtccc tag
```

The protein and cDNA sequences for mature human NKp44 are shown below.

```
Mature Human NKp44 Protein
                                                  (SEQ ID NO: 17)
qskaqvlqs vagqtltvrc qypptgslye kkgwckeasa

lvcirlvtss kprtmawtsr ftiwddpdag fftvtmtdlr

eedsghywcr iyrpsdnsvs ksvrfylvvs pasastqtsw

tprdlvssqt qtqscvppta garqapesps tipvpsqpqn

stlrpgpaap ialvpvfcgl lvakslvlsa llvwwgdiww

ktmmelrsld tqkatchlqg vtdlpwtsvs spvereilyh

tvartkisdd ddehtl
```

```
Human NKp44 cDNA
                                                  (SEQ ID NO: 18)
atggcctggc gagccctaca cccactgcta ctgctgctgc

tgctgttccc aggctctcag gcacaatcca aggctcaggt

acttcaaagt gtggcagggc agacgctaac cgtgagatgc

cagtacccgc ccacgggcag tctctacgag aagaaaggct

ggtgtaagga ggcttcagca cttgtgtgca tcaggttagt
```

-continued

```
caccagctcc aagcccagga cgatggcttg gacctctcga

ttcacaatct gggacgaccc tgatgctggc ttcttcactg

tcaccatgac tgatctgaga gaggaagact caggacatta

ctggtgtaga atctaccgcc cttctgacaa ctctgtctct

aagtccgtca gattctatct ggtggtatct ccagcctctg

cctccacaca gacctcctgg actccccgcg acctggtctc

ttcacagacc cagacccaga gctgtgtgcc tcccactgca

ggagccagac aagcccctga gtctccatct accatccctg

tcccttcaca gccacagaac tccacgctcc gccctggccc

tgcagccccc attgccctgg tgcctgtgtt ctgtggactc

ctcgtagcca agagcctggt gctgtcagcc ctgctcgtct

ggtgggtttt aaggaatcgg cacatgcagc atcaagggag

gtctctgctg cacccagctc agcccaggcc ccaggcccat

agacacttcc cactgagcca cagggcacca ggggggacat

atggtggaaa accatga
```

The protein and cDNA sequences for mature human NKp46 are shown below.

```
Mature Human NKp46 Protein
                                                  (SEQ ID NO: 19)
qqqtlpkpf iwaephfmvp kekqvticcq gnygaveyql

hfegslfavd rpkpperink vqfyipdmns rmagqysciy

rvgelwseps nlldlvvtem ydtptlsvhp gpevisgekv

tfycrldtat smflllkegr sshvqrgygk vqaefplgpv

ttahrgtyrc fgsynnhaws fpsepvkllv tgdientsla

pedptfpadt wgtyllttet glqkdhalwd htagnllrmg

laflvlvalv wflvedwlsr krtrerasra stwegrrrln

tqtl
```

```
Human NKp46 cDNA
                                                  (SEQ ID NO: 20)
atggcctggc gagccctaca cccactgcta ctgctgctgc

tgctgttccc aggctctcag gcacaatcca aggctcaggt

acttcaaagt gtggcagggc agacgctaac cgtgagatgc

cagtacccgc ccacgggcag tctctacgag aagaaaggct

ggtgtaagga ggcttcagca cttgtgtgca tcaggttagt

caccagctcc aagcccagga cgatggcttg gacctctcga

ttcacaatct gggacgaccc tgatgctggc ttcttcactg

tcaccatgac tgatctgaga gaggaagact caggacatta

ctggtgtaga atctaccgcc cttctgacaa ctctgtctct

aagtccgtca gattctatct ggtggtatct ccagcctctg

cctccacaca gacctcctgg actccccgcg acctggtctc

ttcacagacc cagacccaga gctgtgtgcc tcccactgca

ggagccagac aagcccctga gtctccatct accatccctg
```

-continued

```
tcccttcaca gccacagaac tccacgctcc gccctggccc
tgcagccccc attgccctgg tgcctgtgtt ctgtggactc
ctcgtagcca agagcctggt gctgtcagcc ctgctcgtct
ggtgggtttt aaggaatcgg cacatgcagc atcaagggag
gtctctgctg cacccagctc agcccaggcc ccaggcccat
agacacttcc cactgagcca cagggcacca ggggggacat
atggtggaaa accatga
```

The protein and cDNA sequences for mature human NKG2D are shown below.

```
Mature Human NKG2D Protein
                                 (SEQ ID NO: 21)
mgwirgrrsr hswemsefhn ynldlkksdf strwqkqrcp
vvkskcrena spfffccfia vamgirfiim vaiwsavfln
slfnqevqip ltesycgpcp knwicyknnc yqffdesknw
yesqascmsq nasllkvysk edqdllklvk syhwmglvhi
ptngswqwed gsilspnllt iiemqkgdca lyassfkgyi
encstpntyi cmqrtv
```

```
Human NKG2D cDNA
                                 (SEQ ID NO: 22)
atggggtgga ttcgtggtcg gaggtctcga cacagctggg
agatgagtga atttcataat tataacttgg atctgaagaa
gagtgatttt tcaacacgat ggcaaaagca aagatgtcca
gtagtcaaaa gcaaatgtag agaaaatgca tctccatttt
ttttctgctg cttcatcgct gtagccatgg gaatccgttt
cattattatg gtaacaatat ggagtgctgt attcctaaac
tcattattca accaagaagt tcaaattccc ttgaccgaaa
gttactgtgg cccatgtcct aaaaactgga tatgttacaa
aaataactgc taccaatttt ttgatgagag taaaaactgg
tatgagagcc aggcttcttg tatgtctcaa aatgccagcc
ttctgaaagt atacagcaaa gaggaccagg atttacttaa
actggtgaag tcatatcatt ggatgggact agtacacatt
ccaacaaatg gatcttggca gtgggaagat ggctccattc
tctcacccaa cctactaaca ataattgaaa tgcagaaggg
agactgtgca ctctatgcct cgagctttaa aggctatata
gaaaactgtt caactccaaa tacgtacatc tgcatgcaaa
ggactgtgta a
```

The protein and cDNA sequences for mature human CD16a are shown below.

```
Mature Human CD16a Protein
                                 (SEQ ID NO: 23)
maegtlwqil cvssdaqpqt fegvkgadpp tlppgsflpg
pvlwwgslar lqteksdevs rkgnwwvtem gggagerlft
ssclvglvpl glrislvtcp lqcgimwqll lptallllvs
```

-continued

```
agmrtedlpk avvflepqwy rvlekdsvtl kcqgaysped
nstqwfhnes lissqassyf idaatvddsg eyrcqtnlst
lsdpvglevh igwlllqapr wvfkeedpih lrchswknta
lhkvtylqng kgrkyfhhns dfyipkatlk dsgsyfcrgl
fgsknvsset vnititqgla vstissffpp gyqvsfclvm
vllfavdtgl yfsvktnirs strdwkdhkf kwrkdpqdk
```

```
Human CD16a cDNA
                                 (SEQ ID NO: 24)
atggctgagggcacactctggcagattctgtgtgtgtcctcagatgctca
gccacagacctttgagggagtaaaggggggcagacccacccaccttgcctc
caggctctttccttcctggtcctgttctatggtggggctcccttgccaga
cttcagactgagaagtcagatgaagtttcaagaaaaggaaattggtgggt
gacagagatgggtggaggggctggggaaaggctgtttacttcctcctgtc
tagtcggtttggtccctttagggctccggatatctttggtgacttgtcca
ctccagtgtggcatcatgtggcagctgctcctcccaactgctctgctact
tctagtttcagctggcatgcggactgaagatctcccaaaggctgtggtgt
tcctggagcctcaatggtacagggtgctcgagaaggacagtgtgactctg
aagtgccagggagcctactcccctgaggacaattccacacagtggtttca
caatgagagcctcatctcaagccaggcctcgagctacttcattgacgctg
ccacagtcgacgacagtggagagtacaggtgccagacaaacctctccacc
ctcagtgacccggtgcagctagaagtccatatcggctggctgttgctcca
ggcccctcggtgggtgttcaaggaggaagaccctattcacctgaggtgtc
acagctggaagaacactgctctgcataaggtcacatatttacagaatggc
aaaggcaggaagtattttcatcataattctgacttctacattccaaaagc
cacactcaaagacagcggctcctacttctgcagggggctttttgggagta
aaaatgtgtcttcagagactgtgaacatcaccatcactcaaggtttggca
gtgtcaaccatctcatcattctttccacctgggtaccaagtctctttctg
cttggtgatggtactcctttttgcagtggacacaggactatatttctctg
tgaagacaaacattcgaagctcaacaagagactggaaggaccataaattt
aaatggagaaaggaccctcaagacaaatga
```

The protein and cDNA sequences for mature human CD16b are shown below.

```
Mature Human CD16b Protein
                                 (SEQ ID NO: 25)
mwqlllptal lllvsagmrt edlpkavvfl epqwysvlek
dsvtlkcqga yspednstqw fhneslissq assyfidaat
vndsgeyrcq tnlstlsdpv qlevhigwll lqaprwvfke
edpihlrchs wkntalhkvt ylqngkdrky fhhnsdfhip
katlkdsgsy fcrglvgskn vssetvniti tqglaystis
sfsppgyqvs fclvmvllfa vdtglyfsvk tni
```

-continued

Human CD16b cDNA (SEQ ID NO: 26)

atgtggcagctgctcctcccaactgctctgctacttctagtttcagctgg catgcggactgaagatctcccaaaggctgtggtgttcctggagcctcaat ggtacagcgtgcttgagaaggacagtgtgactctgaagtgccagggagcc tactcccctgaggacaattccacacagtggtttcacaatgagaacctcat ctcaagccaggcctcgagctacttcattgacgctgccacagtcaacgaca gtggagagtacaggtgccagacaaacctctccaccctcagtgacccggtg cagctagaagtccatatcggctggctgttgctccaggcccctcggtgggt gttcaaggaggaagaccctattcacctgaggtgtcacagctggaagaaca ctgctctgcataaggtcacatatttacagaatggcaaagacaggaagtat tttcatcataattctgacttccacattccaaaagccacactcaaagatag cggctcctacttctgcagggggcttgttgggagtaaaaatgtgtcttcag agactgtgaacatcaccatcactcaaggtttggcagtgtcaaccatctca tcattctctccacctgggtaccaagtctctttctgcttggtgatggtact ccttttttgcagtggacacaggactatatttctctgtgaagacaaacattt ga The protein and cDNA sequences for mature human KIR2DS1 are shown below.

Human KIR2DS1 Protein (SEQ ID NO: 27)

msltvvsmac vgffllqgaw phegvhrkps llahpgrlvk seetvilqcw sdvmfehfll hregmfndtl rligehhdgv skanfsisrm kqdlagtyrc ygsvthspyq vsapsdpldi viiglyekps lsaqpgptvl agesvtlscs srssydmyhl sregeaherr lpagtkvngt fqanfplgpa thggtyrcfg sfrdspyews kssdpllvsv tgnpsnswps ptepssetgn prhlhvligt svvkipftil lfflhrwcs dkknaavmdq epagnrtvns edsdeqdhqe vsya Human KIR2DS1 cDNA (SEQ ID NO: 28)

atgtcgctcacggtcgtcagcatggcgtgtgttgggttcttcttgctgca gggggcctggccacatgagggagtccacagaaaccttccctcctggccc acccaggtcgcctggtgaaatcagaagagacagtcatcctgcaatgttgg tcagatgtcatgtttgaacacttccttctgcacagagaggggatgtttaa cgacactttgcgcctcattggagaacaccatgatggggtctccaaggcca acttctccatcagtcgcatgaagcaagacctggcagggacctacagatgc tacggttctgttactcactcccccctatcagttgtcagctcccagtgaccc tctggacatcgtgatcataggtctatatgagaaaccttctctctcagccc agccgggccccacggttctggcaggagagaatgtgaccttgtcctgcagc tcccggagctcctatgacatgtaccatctatccagggaaggggaggccca tgaacgtaggctccctgcagggaccaaggtcaacggaacattccaggcca actttcctctgggccctgccacccatggagggacctacagatgcttcggc -continued tctttccgtgactctccatacgagtggtcaaagtcaagtgacccactgct tgtttctgtcacaggaaacccttcaaatagttggccttcacccactgaac caagctccgaaaccggtaaccccagacacctacatgttctgattgggacc tcagtggtcaaaatccctttcaccatcctcctcttctttctccttcatcg ctggtgctccgacaaaaaaaatgctgctgtaatggaccaagagcctgcag ggaacagaacagtgaacagcgaggattctgatgaacaagaccatcaggag gtgtcatacgcataa The protein and cDNA sequences for mature human KIR2DS2 are shown below.

Human KIR2DS2 Protein (SEQ ID NO: 29)

mslmvvsmvc vgffllqgaw phegvhrkps llahpgplvk seetvilqcw sdvrfehfll hregkykdtl hligehhdgv skanfsigpm mqdlagtyrc ygsvthspyq lsapsdpldi vitglyekps lsaqpgptvl agesvtlscs srssydmyhl sregeaherr fsagpkvngt fqadfplgpa thggtyrcfg sfrdspyews nssdpllvsv tgnpsnswps ptepssktgn prhlhvligt svvkipftil lfflhrwcs nkknaavmdq epagnrtvns edsdeqdhqe vsya Human KIR2DS2 cDNA (SEQ ID NO: 30)

atgtcgctcatggtcgtcagcatggcgtgtgttgggttcttcttgctgca gggggcctggccacatgagggagtccacagaaaccttccctcctggccc acccaggtcccctggtgaaatcagaagagacagtcatcctgcaatgttgg tcagatgtcaggtttgagcacttccttctgcacagagaggggaagtataa ggacactttgcacctcattggagagcaccatgatggggtctccaaggcca acttctccatcggtcccatgatgcaagaccttgcagggacctacagatgc tacggttctgttactcactcccccctatcagttgtcagctcccagtgaccc tctggacatcgtcatcacaggtctatatgagaaaccttctctctcagccc agccgggccccacggttttggcaggagagagcgtgaccttgtcctgcagc tcccggagctcctatgacatgtaccatctatccagggagggggaggccca tgaacgtaggttctctgcagggcccaaggtcaacggaacattccaggccg actttcctctgggccctgccacccacggaggaacctacagatgcttcggc tctttccgtgactctccctatgagtggtcaaactcgagtgacccactgct tgtttctgtcacaggaaacccttcaaatagttggccttcacccactgaac caagctccaaaaccggtaaccccagacacctgcatgttctgattgggacc tcagtggtcaaaatccctttcaccatcctcctcttctttctccttcatcg ctggtgctccaacaaaaaaaatgctgctgtaatggaccaagagcctgcag ggaacagaacagtgaacagcgaggactctgatgaacaagaccctcaggag gtgacatacacacagttgaatcactgcgttttcacacagagaaaaatcac tcgcccttctcagaggcccaagacacccccaacagatatcatcgtgtaca cggaacttccaaatgctgagtccaga The protein and cDNA sequences for mature human KIR2DS3 are shown below.

Mature Human KIR2DS3 Protein
(SEQ ID NO: 31)
mslmvismac vgffwlqgaw phegfrrkps llahpgrlvk
seetvilqcw sdvmfehfll hregtfndtl rligehidgv
skanfsigrm rqdlagtyrc ygsvphspyq fsapsdpldi
vitglyekps lsaqpgptvl agesvtlscs swssydmyhl
stegeaherr fsagpkvngt fqadfplgpa tqggtyrcfg
sfhdspyews kssdpllvsv tgnpsnswps ptepssktgn
prhlhvligt svvklpftil lffllhrwcs dkknasvmdq
gpagnrtvnr edsdeqdhqe vsya Human KIR2DS3 cDNA
(SEQ ID NO: 32)
atgtcgctcatggtcatcagcatggcatgtgttgggttcttctggctgca
gggggcctggccacatgagggattccgcagaaaaccttccctcctggccc
acccaggtcgcctggtgaaatcagaagagacagtcatcctgcaatgttgg
tcagatgtcatgtttgagcacttccttctgcacagagaggggacgtttaa
cgacactttgcgcctcattggagagcacattgatggggtctccaaggcca
acttctccatcggtcgcatgaggcaagacctggcagggacctacagatgc
tacggttctgttcctcactcccctatcagttttcagctcccagtgaccc
tctggacatcgtgatcacaggtctatatgagaaaccttctctctcagccc
agccgggccccacggttctggcaggagagagcgtgaccttgtcctgcagc
tcctggagctcctatgacatgtaccatctatccacggagggggaggccca
tgaacgtaggttctctgcagggcccaaggtcaacggaacattccaggccg
actttcctctgggccctgccacccaaggaggaacctacagatgcttcggc
tctttccatgactctccctacgagtggtcaaagtcaagtgacccactgct
tgtttctgtcacaggaaacccttcaaatagttggccttcacccactgaac
caagctccaaaaccggtaaccccagacacctacacgttctgattgggacc
tcagtggtcaaactccctttcaccatcctcctcttctttctccttcatcg
ctggtgctccgacaaaaaaaatgcatctgtaatggaccaagggcctgcgg
ggaacagaacagtgaacagggaggattctgatgaacaggaccatcaggag
gtgtcatacgcataa The protein and cDNA sequences for mature human KIR2DL4 are shown below.

Mature Human KIR2DL4 Protein
(SEQ ID NO: 33)
hvggqdk pfcsawpsav vpqgghatlr chcrrgfnif
tlykkdgvpv pelynrifwn sflispvtpa hagtyrcrgf
hphsptewsa psnplvimvt glyekpslta rpgptvrage
nvtlscssqs sfdiyhlsre geahelrlpa vpsingtfqa
dfplgpathg etyrcfgsfh gspyewsdps dplpvsvtgn
pssswpspte psfktgiarh lhavirysva iilftilpff -continued
llhrwcskkk naavmnqepa ghrtvnreds degdpgevty
agldhciftg rkitgpsqrs krpstdtsvc ielpnaepra
lspahehhsq almgssrett alsqtqlass nvpaagi Human KIR2DL4 cDNA
(SEQ ID NO: 34)
atgtccccttcacatgttgtggtcaatgtgtcaactgcacgatccgggcc
cctcaccacatcctctgcaccggtcagtcgagccgagtcactgcgtcctg
gcagcagaagctgcaccatgtccatgtcacccacggtcatcatcctggca
tgtcttgggtcttcttggaccagagtgtgtgggcacacgtgggtggtca
ggacaagcccttctgctctgcctggcccagcgctgtggtgcctcaaggag
gacacgtgactcttcggtgtcactatcgtcgtgggtttaacatcttcacg
ctgtacaagaaagatggggtccctgtccctgagctctacaacagaatatt
ctggaacagtttcctcattagccctgtgaccccagcacacgcagggacct
acagatgtcgaggttttcacccgcactcccccactgagtggtcggcaccc
agcaacccccctggtgatcatggtcacaggtctatatgagaaaccttcgct
tacagcccggccgggccccacggttcgcgcaggagagaacgtgaccttgt
cctgcagctcccagagctcctttgacatctaccatctatccagggagggg
gaagcccatgaacttaggctccctgcagtgcccagcatcaatggaacatt
ccaggccgacttccctctgggtcctgccacccacggagagacctacagat
gcttcggctctttccatggatctccctacgagtggtcagacccgagtgac
ccactgcctgtttctgtcacaggaaacccttctagtagttggccttcacc
cactgaaccaagcttcaaaactggtatcgccagacacctgcatgctgtga
ttaggtactcagtggccatcatcctctttaccatccttcccttctttctc
cttcatcgctggtgctccaaaaaaaaagatgctgctgtaatgaaccaaga
gcctgcgggacacagaacagtgaacagggaggactctgatgaacaagacc
ctcaggaggtgacatacgcacagttggatcactgcattttcacacagaga
aaaatcactggcccttctcagaggagcaagagaccctcaacagataccag
cgtgtgtatagaacttccaaatgctgagcccagagcgttgtctcctgccc
atgagcaccacagtcaggccttgatgggatcttctagggagacaacagcc
ctgtctcaaacccagcttgccagctctaatgtaccagcagctggaatctg
a The protein and cDNA sequences for mature human KIR2DS4 are shown below.

Mature Human KIR2DS4 Protein
(SEQ ID NO: 35)
qegvhrkps flalpghlvk seetvilqcw sdvmfehfll
hregkfnntl hligehhdgv skanfsigpm mpvlagtyrc
yssvphspyq lsapsdpldm viiglyekps lsaqpgptvg
agenvslscs siypgrgrpm nvgslqcaas tehsrptflw
alpptegptd asalsvtlpt sgqtrvihcl fpsgetlgiv
glhpinqapk pvtpdtymf -continued Human KIR2DS4 cDNA
(SEQ ID NO: 36)

atgtcgctcatggtcatcatcatggcgtgtgttgggttcttcttgctgca
gggggcctggccacaggagggagtccacagaaaaccttccttcctggccc
tcccaggtcacctggtgaaatcagaagagacagtcatcctgcaatgttgg
tcggatgtcatgtttgagcacttccttctgcacagagaggggaagtttaa
caacactttgcacctcattggagagcaccatgatggggtttccaaggcca
acttctccattggtcccatgatgcctgtccttgcaggaacctacagatgc
tacggttctgttcctcactcccccctatcagttgtcagctcccagtgaccc
tctggacatggtgatcataggtctatatgagaaaccttctctctcagccc
agccgggccccacggttcaggcaggagagaatgtgaccttgtcctgcagc
tccatctatccagggaaggggaggcccatgaacgtaggctccctgcagtg
cgcagcatcaacggaacattccaggccgactttcctctgggccctgccac
ccacggagggacctacagatgcttcggctctttccgtgacgctccctacg
agtggtcaaactcgagtgatccactgcttgtttccgtcacaggaaaccct
tcaaatagttggccttcacccactgaaccaagctccaaaaccggtaaccc
cagacacctacatgttctgattgggacctcagtggtcaaaatccctttca
ccatcctcctcttctttctccttcatcgctggtgctccgacaaaaaaaat
gctgctgtaatggaccaagagcctgcagggaacagaacagtgaacagcga
ggattctgatgaacaagaccatcaggaggtgtcatacgcataa The protein and cDNA sequences for mature human KIR2DS5 are shown below.

Mature Human KIR2DS5
(SEQ ID NO: 37)

hegfrrkps llahpgplvk seetvilqcw sdvmfehfll
hregtfnhtl rligehidgv skgnfsigrm tqdlagtyrc
ygsvthspyq lsapsdpldi vitglyekps lsaqpgptvl
agesvtlscs srssydmyhl sregeaherr lpagtkvngt
fqadfpldpa thggtyrcfg sfrdspyews kssdpllvsv
tgntsnswps ptepssktgn prhlhvligt svvklpftil
lffllhrwcs nkknasvmdq gpagnrtvnr edsdeqdhqe
vsya Human KIR2DS5 cDNA
(SEQ ID NO: 38)

atgtcgctcatggtcatcagcatggcgtgtgttgcgttcttcttgctgca
gggggcctggccacatgagggattccgcagaaaaccttccctcctggccc
acccaggtcccctggtgaaatcagaagagacagtcatcctgcaatgttgg
tcagatgtcatgtttgagcacttccttctgcacagagaggggacgtttaa
ccacactttgcgcctcattggagagcacattgatggggtctccaagggca
acttctccatcggtcgcatgacacaagacctggcagggacctacagatgc
tacggttctgttactcactcccccctatcagttgtcagcgcccagtgaccc
tctggacatcgtgatcacaggtctatatgagaaaccttctctctcagccc
agccgggccccacggttctggcaggagagagcgtgaccttgtcctgcagc
tcccggagctcctatgacatgtaccatctatccagggaagggggaggccca
tgaacgtaggctccctgcagggcccaaggtcaacagaacattccaggccg
actttcctctggaccctgccacccacggagggacctacagatgcttcggc
tctttccgtgactctccatacgagtggtcaaagtcaagtgacccactgct
tgtttctgtcacaggaaactcttcaaatagttggccttcacccactgaac
caagctccgaaaccggtaaccccagacacctacacgttctgattgggacc
tcagtggtcaaactccctttcaccatcctcctcttctttctccttcatcg
ctggtgctccaacaaaaaaaatgcatctgtaatggaccaagggcctgcgg
ggaacagaacagtgaacagggaggattctgatgaacaggaccatcaggag
gtgtcatacgcataa The protein and cDNA sequences for mature human KIR3DS1 are shown below.

Mature Human KIR3DS1 cDNA
(SEQ ID NO: 39)

hmggqdkpf lsawpsavvp rgghvtlrch yrhrfnnfml
ykedrihvpi fhgrifqegf nmspvttaha gnytcrgshp
hsptgwsaps npmvimvtgn hrkpsllahp gplvksgerv
ilqcwsdimf ehfflhkegi skdpsrlvgq ihdgvskanf
sigsmmrala gtyrcygsvt htpyqlsaps dpldivvtgl
yekpslsaqp gpkvqagesv tlscssrssy dmyhlsregg
aherrlpavr kvnrtfqadf plgpathggt yrcfgsfrhs
pyewsdpsdp llvsvtgnps sswpspteps sksgnlrhlh
iligtsvvki pftillffll hrwcsnkkkc ccngpracre
qk Human KIR3DS1 cDNA
(SEQ ID NO: 40)

atgttgctcatggtcgtcagcatggcgtgtgttgggttgttcttggtcca
gagggccggtccacacatgggtggtcaggacaagcccttcctgtctgcct
ggcccagcgctgtggtgcctcgcggaggacacgtgactcttcggtgtcac
tatcgtcataggtttaacaatttcatgctatacaaagaagacagaatcca
cgttcccatcttccatggcagaatattccaggagggcttcaacatgagcc
ctgtgaccacagcacatgcagggaactacacatgtcggggttcacaccca
cactcccccactgggtggtcggcacccagcaaccccatggtgatcatggt
cacaggaaaccacagaaaaccttccctcctggcccacccaggtcccctgg
tgaaatcaggagagagagtcatcctgcaatgttggtcagatatcatgttt
gagcacttctttctgcacaaagagtggatctctaaggacccctcacgcct
cgttggacagatccatgatggggtctccaaggccaatttctccatcggtt
ccatgatgcgtgcccttgcagggacctacagatgctacggttctgttact
cacacccccctatcagttgtcagctcccagtgatcccctggacatcgtggt
cacaggtctatatgagaaaccttctctctcagcccagccgggccccaagg
ttcaggcaggagagagcgtgaccttgtcctgtagctcccggagctcctat
gacatgtaccatctatccagggagggggggagcccatgaacgtaggctccc -continued tgcagtgcgcaaggtcaacagaacattccaggcagatttccctctgggcc
ctgccacccacggagggacctacagatgcttcggctctttccgtcactct
ccctacgagtggtcagacccgagtgacccactgcttgtttctgtcacagg
aaacccttcaagtagttggccttcacccacagaaccaagctccaaatctg
gtaacctcagacacctgcacattctgattgggacctcagtggtcaaaatc
cctttcaccatcctcctcttctttctccttcatcgctggtgctccaacaa
aaaaaaatgctgctgtaatggaccaagagcctgcagggaacagaagtga The protein and cDNA sequences for mature human NKG2C are shown below.

Mature Human NKG2C Protein
(SEQ ID NO: 41)
mskqrgtfse vslaqdpkrq qrkpkgnkss isgteqeifq
velnlqnpsl nhqgidkiyd cqgllpppek ltaevlgiic
ivlmatvlkt ivlipfleqn nsspntrtqk arhcghcpee
witysnscyy igkerrtwee sllactskns sllsidneee
mkflasilps swigvfrnss hhpwvtingl afkhkikdsd
naelncavlq vnrlksaqcg ssmiyhckhk l Human NKG2C cDNA
(SEQ ID NO: 42)
atgaataaacaaagaggaaccttctcagaagtgagtctggcccaggaccc
aaagcggcagcaaaggaaacctaaaggcaataaaagctccatttcaggaa
ccgaacaggaaatattccaagtagaattaaatcttcaaaatccttccctg
aatcatcaagggattgataaaatatatgactgccaaggtttactgccacc
tccagagaagctcactgccgaggtcctaggaatcatttgcattgtcctga
tggccactgtgttaaaaacaatagttcttattcctttcctggagcagaac
aatttttccccgaatacaagaacgcagaaagcacgtcattgtggccattg
tcctgaggagtggattacatattccaacagttgttattacattggtaagg
aaagaagaacttgggaagagagtttgctggcctgtacttcgaagaactcc
agtctgctttctatagataatgaagaagaaatgaaatttctggccagcat
tttaccttcctcatggattggtgtgtttcgtaacagcagtcatcatccat
gggtgacaataaatggtttggctttcaaacataagataaaagactcagat
aatgctgaacttaactgtgcagtgctacaagtaaatcgacttaaatcagc
ccagtgtggatcttcaatgatatatcattgtaagcataagctttag The protein and cDNA sequences for mature human CCR7 are shown below.

Mature Human CCR7 Protein
(SEQ ID NO: 43)
qdevtd dyigdnttvd ytlfeslcsk kdvrnfkawf
lpimysiicf vgllgnglvv ltyiyfkrlk tmtdtyllnl
avadilfllt lpfwaysaak swvfgvhfck lifaiykmsf
fsgmllllci sidryvaivq avsahrhrar vllisklscv
giwilatvls ipellysdlq rssseqamrc slitehveaf
itiqvaqmvi gflvpllams fcylviirtl lqarnfernk
aikviiavvv vfivfqlpyn gvvlaqtvan fnitsstcel
skqlniaydv tyslacvrcc vnpflyafig vkfrndlfkl
fkdlgclsqe qlrqwsscrh irrssmsvea ettttfsp Human CCR7 cDNA
(SEQ ID NO: 44)
atggacctggggaaaccaatgaaaagcgtgctggtggtggctctccttgt
cattttccaggtatgcctgtgtcaagatgaggtcacggacgattacatcg
gagacaacaccacagtggactacactttgttcgagtctttgtgctccaag
aaggacgtgcggaactttaaagcctggttcctccctatcatgtactccat
catttgtttcgtgggcctactgggcaatgggctggtcgtgttgacctata
tctatttcaagaggctcaagaccatgaccgatacctacctgctcaacctg
gcggtggcagacatcctcttcctcctgacccttcccttctgggcctacag
cgcggccaagtcctgggtcttcggtgtccacttttgcaagctcatctttg
ccatctacaagatgagcttcttcagtggcatgctcctacttctttgcatc
agcattgaccgctacgtggccatcgtccaggctgtctcagctcaccgcca
ccgtgcccgcgtccttctcatcagcaagctgtcctgtgtgggcatctgga
tactagccacagtgctctccatcccagagctcctgtacagtgacctccag
aggagcagcagtgagcaagcgatgcgatgctctctcatcacagagcatgt
ggaggcctttatcaccatccaggtggcccagatggtgatcggctttctgg
tccccctgctggccatgagcttctgttaccttgtcatcatccgcaccctg
ctccaggcacgcaactttgagcgcaacaaggccatcaaggtgatcatcgc
tgtggtcgtggtcttcatagtcttccagctgccctacaatggggtggtcc
tggcccagacggtggccaacttcaacatcaccagtagcacctgtgagctc
agtaagcaactcaacatcgcctacgacgtcacctacagcctggcctgcgt
ccgctgctgcgtcaaccctttcttgtacgccttcatcggcgtcaagttcc
gcaacgatctcttcaagctcttcaaggacctgggctgcctcagccaggag
cagctccggcagtggtcttcctgtcggcacatccggcgctcctccatgag
tgtggaggccgagaccaccaccaccttctccccatag The protein and cDNA sequences for mature human CXCR3 are shown below.

Mature Human CXCR3 Protein
(SEQ ID NO: 45)
mvlevsdhqv lndaevaall enfsssydyg enesdsccts
ppcpqdfsln fdraflpaly sllfllgllg ngavaavlls
rrtalsstdt fllhlavadt llvltlplwa vdaavqwvfg
sglckvagal fninfyagal llacisfdry lnivhatqly
rrgpparvtl tclavwglcl lfalpdfifl sahhderlna
thcqynfpqv grtalrvlql vagfllpllv maycyahila
vllvsrgqrr lramrlvvvv vvafalcwtp yhlvvlvdil
mdlgalarnc gresrvdvak svtsglgymh cclnpllyaf -continued vgvkfrermw mlllrlgcpn qrglqrqpss srrdsswset seasysgl Human CXCR3 cDNA (SEQ ID NO: 46)

atggagttgaggaagtacggccctggaagactggcggggacagttatagg aggagctgctcagagtaaatcacagactaaatcagactcaatcacaaaag agttcctgccaggcctttacacagccccttcctccccgttcccgccctca caggtgagtgaccaccaagtgctaaatgacgccgaggttgccgccctcct ggagaacttcagctcttcctatgactatggagaaaacgagagtgactcgt gctgtacctccccgccctgcccacaggacttcagcctgaacttcgaccgg gccttcctgccagccctctacagcctcctctttctgctggggctgctggg caacggcgcggtggcagccgtgctgctgagccggcggacagccctgagca gcaccgacaccttcctgctccacctagctgtagcagacacgctgctggtg ctgacactgccgctctgggcagtggacgctgccgtccagtgggtctttgg ctctggcctctgcaaagtggcaggtgccctcttcaacatcaacttctacg caggagccctcctgctggcctgcatcagctttgaccgctacctgaacata gttcatgccacccagctctaccgccgggggcccccggcccgcgtgaccct cacctgcctggctgtctggggctctgcctgcttttcgccctcccagact tcatcttcctgtcggcccaccacgacgagcgcctcaacgccacccactgc caatacaacttcccacaggtgggccgcacggctctgcgggtgctgcagct ggtggctggctttctgctgcccctgctggtcatggcctactgctatgccc acatcctggccgtgctgctggtttccaggggccagcggcgcctgcgggcc atgcggctggtggtggtggtcgtggtggcctttgccctctgctggacccc ctatcacctggtggtgctggtggacatcctcatggacctgggcgctttgg cccgcaactgtggccgagaaagcagggtagacgtggccaagtcggtcacc tcaggcctgggctacatgcactgctgcctcaacccgctgctctatgcctt tgtaggggtcaagttccgggagcggatgtggatgctgctcttgcgcctgg gctgccccaaccagagagggctccagaggcagccatcgtcttcccgccgg gattcatcctggtctgagacctcagaggcctcctactcgggcttgtga The protein and cDNA sequences for mature human L-selectin are shown below.

Mature Human L-Selectin Protein (SEQ ID NO: 47)

df lahhgtdcwt yhysekpmnw qrarrfcrdn ytdlvaiqnk aeieylektl pfsrsyywig irkiggiwtw vgtnksltee aenwgdgepn nkknkedcve iyikrnkdag kwnddachkl kaalcytasc qpwscsghge cveiinnytc ncdvgyygpq cqfviqcepl eapelgtmdc thplgnfsfs sqcafscseg tnltgieett cgpfgnwssp eptcqviqce plsapdlgim ncshplasfs ftsactfics egteligkkk ticessgiws npspicqkld ksfsmikegd ynplfipvav mvtafsglaf iiwlarrlkk gkkskrsmnd py -continued Human L-Selectin cDNA (SEQ ID NO: 48)

atgggctgcagaagaactagagaaggaccaagcaaagccatgatatttcc atggaaatgtcagagcacccagagggacttatggaacatcttcaagttgt gggggtggacaatgctctgttgtgatttcctggcacatcatggaaccgac tgctggacttaccattattctgaaaaacccatgaactggcaaagggctag aagattctgccgagacaattacacagatttagttgccatacaaaacaagg cggaaattgagtatctggagaagactctgcctttcagtcgttcttactac tggataggaatccggaagataggaggaatatggacgtgggtgggaaccaa caaatctcttactgaagaagcagagaactggggagatggtgagcccaaca acaagaagaacaaggaggactgcgtggagatctatatcaagagaaacaaa gatgcaggcaaatggaacgatgacgcctgccacaaactaaaggcagccct ctgttacacagcttcttgccagccctggtcatgcagtggccatggagaat gtgtagaaatcatcaataattacacctgcaactgtgatgtggggtactat gggccccagtgtcagtttgtgattcagtgtgagcctttggaggccccaga gctgggtaccatggactgtactcaccctttgggaaacttcagcttcagct cacagtgtgccttcagctgctctgaaggaacaaacttaactgggattgaa gaaaccacctgtggaccatttggaaactggtcatctccagaaccaacctg tcaagtgattcagtgtgagcctctatcagcaccagatttggggatcatga actgtagccatcccctggccagcttcagctttacctctgcatgtaccttc atctgctcagaaggaactgagttaattgggaagaagaaaaccatttgtga atcatctggaatctggtcaaatcctagtccaatatgtcaaaaattggaca aaagtttctcaatgattaaggagggtgattataacccccctcttcattcca gtggcagtcatggttactgcattctctgggttggcatttatcatttggct ggcaaggagattaaaaaaaggcaagaaatccaagagaagtatgaatgacc catattaa The protein and cDNA sequences for mature human CXCR1 are shown below.

Mature Human CXCR1 Protein (SEQ ID NO: 49)

msnitdpqmw dfddlnftgm ppadedyspc xletetlnky vviiayalvf llsllgnslv mlvilysrvg rsvtdvylln laladllfal tlpiwaaskv ngwifgtflc kvvsllkevn fysgilllac isvdrylaiv hatrtltqkr hlvkfvclgc wglsmnlslp fflfrqayhp nnsspvcyev lgndtakwrm vlrilphtfg fivplfvmlf cygftlrtlf kahmgqkhra mrvifavvli fllcwlpynl vlladtlmrt qviqescerr nnigraldat eilgflhscl npiiyafigq nfrhgflkil amhglvskef larhrvtsyt sssvnvssnl Human CXCR1 cDNA (SEQ ID NO: 50)

atgtcaaatattacagatccacagatgtgggattttgatgatctaaattt cactggcatgccacctgcagatgaagattacagcccctgtatgctagaaa -continued ctgagacactcaacaagtatgttgtgatcatcgcctatgccctagtgttc ctgctgagcctgctgggaaactccctggtgatgctggtcatcttatacag cagggtcggccgctccgtcactgatgtctacctgctgaacctggccttgg ccgacctactctttgccctgaccttgcccatctgggccgcctccaaggtg aatggctggattttttggcacattcctgtgcaaggtggtctcactcctgaa ggaagtcaacttctacagtggcatcctgctgttggcctgcatcagtgtgg accgttacctggccattgtccatgccacacgcacactgacccagaagcgt cacttggtcaagtttgtttgtcttggctgctggggactgtctatgaatct gtccctgcccttcttccttttccgccaggcttaccatccaaacaattcca gtccagtttgctatgaggtcctgggaaatgacacagcaaaatggcggatg gtgttgcggatcctgcctcacacctttggcttcatcgtgccgctgtttgt catgctgttctgctatggattcaccctgcgtacactgtttaaggcccaca tggggcagaagcaccgagccatgagggtcatctttgctgtcgtcctcatc ttcctgctttgctggctgccctacaacctggtcctgctggcagacaccct catgaggacccaggtgatccaggagagctgtgagcgccgcaacaacatcg gccgggccctggatgccactgagattctgggatttctccatagctgcctc aaccccatcatctacgccttcatcggccaaaatttcgccatggattcct caagatcctggctatgcatggcctggtcagcaaggagttcttggcacgtc atcgtgttacctcctacacttcttcgtctgtcaatgtctcttccaacctc tga The protein and cDNA sequences for mature human CXCR2 are shown below.

Mature Human CXCR2 Protein (SEQ ID NO: 51)

medfnmesds fedfwkgedl snysysstlp pflldaapce pesleinkyf vviiyalvfl lsllgnslvm lvilysrvgr svtdvyllnl aladllfalt lpiwaaskvn gwifgtflck vvsllkevnf ysgillacl svdrylaivh atrtltqkry lvkficlsiw glslllalpv llfrrtvyss nvspacyedm gnntanwrml lrilpqsfgf ivpllimlfc ygftlrtlfk ahmgqkhram rvifavvlif llcwlpynlv lladtlmrtq viqetcerrn hidraldate ilgilhscln pliyafigqk frhgllkila ihgliskdsl pkdsrpsfvg sssghtsttl Human CXCR2 cDNA (SEQ ID NO: 52)

atggaagattttaacatggagagtgacagctttgaagatttctggaaagg tgaagatcttagtaattacagttacagctctaccctgcccccttttctac tagatgccgccccatgtgaaccagaatccctggaaatcaacaagtatttt gtggtcattatctatgccctggtattcctgctgagcctgctgggaaactc cctcgtgatgctggtcatcttatacagcagggtcggccgctccgtcactg atgtctacctgctgaacctagccttggccgacctactctttgccctgacc ttgcccatctgggccgcctccaaggtgaatggctggattttttggcacatt cctgtgcaaggtggtctcactcctgaaggaagtcaacttctatagtggca tcctgctactggcctgcatcagtgtggaccgttacctggccattgtccat gccacacgcacactgacccagaagcgctacttggtcaaattcatatgtct cagcatctggggtctgtccttgctcctggccctgcctgtcttacttttcc gaaggaccgtctactcatccaatgttagcccagcctgctatgaggacatg ggcaacaatacagcaaactggcggatgctgttacggatcctgccccagtc ctttggcttcatcgtgccactgctgatcatgctgttctgctacggattca ccctgcgtacgctgtttaaggcccacatggggcagaagcaccgggccatg cgggtcatctttgctgtcgtcctcatcttcctgctctgctggctgcccta caacctggtcctgctggcagacaccctcatgaggacccaggtgatccagg agacctgtgagcgccgcaatcacatcgaccgggctctggatgccaccgag attctgggcatccttcacagctgcctcaacccccctcatctacgccttcat tggccagaagtttcgccatggactcctcaagattctagctatacatggct tgatcagcaaggactccctgcccaaagacagcaggccttcctttgttggc tcttcttcagggcacacttccactactctctaa The protein and cDNA sequences for mature human CX3CR1 are shown below.

Mature Human CX3CR1 Protein (SEQ ID NO: 53)

mdqfpesvte nfeyddlaea cyigdivvfg tvflsifysv ifaiglvgnl lvvfaltnsk kpksvtdiyl lnlalsdllf vatlpfwthy linekglhna mckfttafff igffgsiffi tvisidryla ivlaansmnn rtvqhgvtis lgvwaaailv aapqfmftkq keneclgdyp evlqeiwpvl rnvetnflgf llpllimsyc yfriiqtlfs cknhkkakai klillvvivf flfwtpynvm ifletlklyd ffpscdmrkd lrlalsvtet vafshcclnp liyafagekf rrylyhlygk clavlcgrsv hvdfsssesq rsrhgsvlss nftyhtsdgd allll Human CX3CR1 cDNA (SEQ ID NO: 54)

atggatcagttccctgaatcagtgacagaaaactttgagtacgatgattt ggctgaggcctgttatattggggacatcgtggtctttgggactgtgttcc tgtccatattctactccgtcatctttgccattggcctggtgggaaatttg ttggtagtgtttgccctcaccaacagcaagaagcccaagagtgtcaccga catttacctcctgaacctggccttgtctgatctgctgtttgtagccactt tgcccttctggactcactatttgataaatgaaaagggcctccacaatgcc atgtgcaaattcactaccgccttcttcttcatcggcttttttggaagcat attcttcatcaccgtcatcagcattgataggtacctggccatcgtcctgg ccgccaactccatgaacaaccggaccgtgcagcatggcgtcaccatcagc ctaggcgtctgggcagcagccattttggtggcagcaccccagttcatgtt cacaaagcagaaagaaaatgaatgccttggtgactaccccgaggtcctcc aggaaatctggcccgtgctccgcaatgtggaaacaaattttcttggcttc -continued ctactccccctgctcattatgagttattgctacttcagaatcatccagac gctgttttcctgcaagaaccacaagaaagccaaagccattaaactgatcc ttctggtggtcatcgtgtttttcctcttctggacaccctacaacgttatg attttcctggagacgcttaagctctatgacttctttcccagttgtgacat gaggaaggatctgaggctggccctcagtgtgactgagacggttgcattta gccattgttgcctgaatcctctcatctatgcatttgctggggagaagttc agaagatacctttaccacctgtatgggaaatgcctggctgtcctgtgtgg gcgctcagtccacgttgatttctcctcatctgaatcacaaaggagcaggc atggaagtgttctgagcagcaattttacttaccacacgagtgatggagat gcattgctccttctctga The protein and cDNA sequences for mature human ChemR23 are shown below.

Mature Human ChemR23 Protein
(SEQ ID NO: 55)

mrmededynt sisygdeypd yldsivvled lsplearvtr iflvvvysiv cflgilgngl viiiatfkmk ktvnmvwfln lavadflfnv flpihityaa mdyhwvfgta mckisnflli hnmftsvfll tiissdrcis vllpvwsqnh rsvrlaymac mviwvlaffl sspslvfrdt anlhgkiscf nnfslstpgs sswpthsqmd pvgysrhmvv tvtrflcgfl vpvliitacy ltivcklqrn rlaktkkpfk iivtiiitff lcwcpyhtln llelhhtamp gsvfslglpl atalaiansc mnpilyvfmg qdfkkfkval fsrlvnalse dtghssypsh rsftkmssmn ertsmneret gml Human ChemR23 cDNA
(SEQ ID NO: 56)

atgagaatggaggatgaagattacaacacttccatcagttacggtgatga ataccctgattatttagactccattgtggttttggaggacttatccccct tggaagccagggtgaccaggatcttcctggtggtggtctacagcatcgtc tgcttcctcgggattctgggcaatggtctggtgatcatcattgccacctt caagatgaagaagacagtgaacatggtctggttcctcaacctggcagtgg cagatttcctgttcaacgtcttcctcccaatccatatcacctatgccgcc atggactaccactgggttttcgggacagccatgtgcaagatcagcaactt ccttctcatccacaacatgttcaccagcgtcttcctgctgaccatcatca gctctgaccgctgcatctctgtgctcctccctgtctggtcccagaaccac cgcagcgttcgcctggcttacatggcctgcatggtcatctgggtcctggc tttcttcttgagttccccatctctcgtcttccgggacacagccaacctgc atgggaaaatatcctgcttcaacaacttcagcctgtccacacctgggtct tcctcgtggcccactcactcccaaatggaccctgtggggtatagccggca catggtggtgactgtcacccgcttcctctgtggcttcctggtcccagtcc tcatcatcacagcttgctacctcaccatcgtgtgcaaactgcagcgcaac cgcctggccaagaccaagaagcccttcaagattattgtgaccatcatcat -continued taccttcttcctctgctggtgcccctaccacacactcaacctcctagagc tccaccacactgccatgcctggctctgtcttcagcctgggtttgcccctg gccactgcccttgccattgccaacagctgcatgaaccccattctgtatgt tttcatgggtcaggacttcaagaagttcaaggtggccctcttctctcgcc tggtcaatgctctaagtgaagatacaggccactcttcctaccccagccat agaagctttaccaagatgtcatcaatgaatgagaggacttctatgaatga gagggagaccggcatgctttga The protein and cDNA sequences for mature human CXCR4 are shown below.

Mature Human CXCR4 Protein
(SEQ ID NO: 57)

megisiytsd nyteemgsgd ydsmkepcfr eenanfnkif lptiysiifl tgivgnglvi lvmgyqkklr smtdkyrlhl svadllfvit lpfwavdava nwyfgnflck avhviytvnl yssvlilafi sldrylaivh atnsgrprkl laekvvyvgv wipallltip dfifanvsea ddryicdrfy pndlwvvvfq fqhimvglil pgivilscyc iiisklshsk ghqkrkalkt tvililaffa cwlpyyigis idsfilleii kqgcefentv hkwisiteal affhcclnpi lyaflgakfk tsaqhaltsv srgsslkils kgkrgghssv stesesssfh ss Human CXCR4 cDNA
(SEQ ID NO: 58)

atgtccattcctttgcctcttttgcagatatacacttcagataactacac cgaggaaatgggctcaggggactatgactccatgaaggaaccctgtttcc gtgaagaaaatgctaatttcaataaaatcttcctgcccaccatctactcc atcatcttcttaactggcattgtgggcaatggattggtcatcctggtcat gggttaccagaagaaactgagaagcatgacggacaagtacaggctgcacc tgtcagtggccgacctcctctttgtcatcacgcttcccttctgggcagtt gatgccgtggcaaactggtactttgggaacttcctatgcaaggcagtcca tgtcatctacacagtcaacctctacagcagtgtcctcatcctggccttca tcagtctggaccgctacctggccatcgtccacgccaccaacagtcagagg ccaaggaagctgttggctgaaaaggtggtctatgttggcgtctggatccc tgccctcctgctgactattcccgacttcatctttgccaacgtcagtgagg cagatgacagatatatctgtgaccgcttctaccccaatgacttgtgggtg gttgtgttccagtttcagcacatcatggttggccttatcctgcctggtat tgtcatcctgtcctgctattgcattatcatctccaagctgtcacactcca agggccaccagaagcgcaaggccctcaagaccacagtcatcctcatcctg gctttcttcgcctgttggctgccttactacattgggatcagcatcgactc cttcatcctcctggaaatcatcaagcaagggtgtgagtttgagaacactg tgcacaagtggatttccatcaccgaggccctagctttcttccactgttgt ctgaaccccatcctctatgctttccttggagccaaatttaaaacctctgc ccagcacgcactcacctctgtgagcagagggtccagcctcaagatcctct -continued ccaaaggaaagcgaggtggacattcatctgtttccactgagtctgagtct tcaagttttcactccagctaa The protein and cDNA sequences for mature human CCR5 are shown below.

Mature Human CCR5 Protein (SEQ ID NO: 59)

mdyqvsspiy dinyytsepc qkinvkqiaa rllpplyslv fifgfvgnml vililinckr lksmtdiyll nlaisdlffl ltvpfwahya aaqwdfgntm cqlltglyfi gffsgiffii lltidrylav vhavfalkar tvtfgvvtsv itwvvavfas lpgiiftrsq keglhytcss hfpysqyqfw knfqtlkivi lglvlpllvm vicysgilkt llrcrnekkr hravrlifti mivyflfwap ynivlllntf qeffglnncs ssnrldqamq vtetlgmthc cinpiiyafv gekfrnyllv ffqkhiakrf ckccsifqqe aperassvyt rstgeqeisv gl Human CCR5 cDNA (SEQ ID NO: 60)

atggattatcaagtgtcaagtccaatctatgacatcaattattatacatc ggagccctgccaaaaaatcaatgtgaagcaaatcgcagcccgcctcctgc ctccgctctactcactggtgttcatctttggttttgtgggcaacatgctg gtcatcctcatcctgataaactgcaaaaggctgaagagcatgactgacat ctacctgctcaacctggccatctctgacctgtttttccttcttactgtcc ccttctgggctcactatgctgccgcccagtgggactttggaaatacaatg tgtcaactcttgacagggctctattttataggcttcttctctggaatctt cttcatcatcctcctgacaatcgataggtacctggctgtcgtccatgctg tgtttgctttaaaagccaggacggtcacctttggggtggtgacaagtgtg atcacttgggtggtggctgtgtttgcgtctctcccaggaatcatctttac cagatctcaaaaagaaggtcttcattacacctgcagctctcattttccat acagtcagtatcaattctggaagaatttccagacattaaagatagtcatc ttggggctggtcctgccgctgcttgtcatggtcatctgctactcgggaat cctaaaaactctgcttcggtgtcgaaatgagaagaagaggcacagggctg tgaggcttatcttcaccatcatgattgtttattttctcttctgggctccc tacaacattgtccttctcctgaacaccttccaggaattctttggcctgaa taattgcagtagctctaacaggttggaccaagctatgcaggtgacagaga ctcttgggatgacgcactgctgcatcaaccccatcatctatgcctttgtc ggggagaagttcagaaactacctcttagtcttcttccaaaagcacattgc caaacgcttctgcaaatgctgttctattttccagcaagaggctcccgagc gagcaagctcagtttacacccgatccactggggagcaggaaatatctgtg ggcttgtga The protein and cDNA sequences for mature human SIP5 are shown below.

Mature Human S1P5 Protein (SEQ ID NO: 61)

mesgllrpap vsevivlhyn ytgklrgary qpgaglrada vvclavcafi vlenlavllv lgrhprfhap mflllgsltl sdllagaaya anillsgplt lklspalwfa reggvfvalt asvlsllaia lersltmarr gpapvssrgr tlamaaaawg vslllgllpa lgwnclgrld acstvlplya kayvlfcvla fvgilaaica lyariycqvr anarrlparp gtagttstra rrkprslall rtlsvvllaf vacwgplfll llldvacpar tcpvllqadp flglamansl lnpiiytltn rdlrhallrl vccgrhscgr dpsgsqqsas aaeasgglrr clppgldgsf sgserrsspqr dgldtsgstg spgaptaart lvsepaad Human S1P5 cDNA (SEQ ID NO: 62)

atggagtcggggctgctgcggccggcgccggtgagcgaggtcatcgtcct gcattacaactacaccggcaagctccgcggtgcgcgctaccagccgggtg ccggcctgcgcgccgacgccgtggtgtgcctggcggtgtgcgccttcatc gtgctagagaatctagccgtgttgttggtgctcggacgccacccgcgctt ccacgctcccatgttcctgctcctgggcagcctcacgttgtcggatctgc tggcaggcgccgcctacgccgccaacatcctactgtcggggccgctcacg ctgaaactgtcccccgcgctctggttcgcacgggagggaggcgtcttcgt ggcactcactgcgtccgtgctgagcctcctggccatcgcgctggagcgca gcctcaccatggcgcgcagggggcccgcgcccgtctccagtcgggggcgc acgctggcgatggcagccgcggcctggggcgtgtcgctgctcctcgggct cctgccagcgctgggctggaattgcctgggtcgcctggacgcttgctcca ctgtcttgccgctctacgccaaggcctacgtgctcttctgcgtgctcgcc ttcgtgggcatcctggccgctatctgtgcactctacgcgcgcatctactg ccaggtacgcgccaacgcgcggcgcctgccggcacggcccgggactgcgg ggaccacctcgacccgggcgcgtcgcaagccgcgctcgctggccttgctg cgcacgctcagcgtggtgctcctggcctttgtggcatgttggggcccccct cttcctgctgctgttgctcgacgtggcgtgcccggcgcgcacctgtcctg tactcctgcaggccgatcccttcctgggactggccatggccaactcactt ctgaaccccatcatctacacgctcaccaaccgcgacctgcgccacgcgct cctgcgcctggtctgctgcggacgccactcctgcggcagagacccgagtg gctcccagcagtcggcgagcgcggctgaggcttccgggggcctgcgccgc tgcctgcccccgggccttgatgggagcttcagcggctcggagcgctcatc gccccagcgcgacgggctggacaccagcggctccacaggcagccccggtg cacccacagccgcccggactctggtatcagaaccggctgcagactga The protein and cDNA sequences for mature human C-kit are shown below.

Mature Human C-kit Protein (SEQ ID NO: 63)

qpsvs pgepsppsih pgksdlivrv gdeirllctd pgfvkwtfei
ldetnenkqn ewitekaeat ntgkytctnk hglsnsiyvf
vrdpaklflv drslygkedn dtlvrcpltd pevtnyslkg
cqgkplpkdl rfipdpkagi miksvkrayh rlclhcsvdq
egksvlsekf ilkvrpafka vpvvsvskas yllregeeft
vtctikdvss svystwkren sqtklqekyn swhhgdfnye
rqatltissa rvndsgvfmc yanntfgsan vtttlevvdk
gfinifpmin ttvfvndgen vdliveyeaf pkpehqqwiy
mnrtftdkwe dypksenesn iryvselhlt rlkgteggty
tflvsnsdvn aaiafnvyvn tkpeiltydr lvngmlqcva
agfpeptidw yfcpgteqrc sasvlpvdvq tlnssgppfg
klvvqssids safkhngtve ckayndvgkt sayfnfafkg
nnkeqihpht lftplligfv ivagmmciiv miltykylqk
pmyevqwkvv eeingnnyvy idptqlpydh kwefprnrls
fgktlgagaf gkvveatayg liksdaamtv avkmlkpsah
lterealmse lkvlsylgnh mnivnllgac tiggptlvit
eyccygdlln flrrkrdsfi cskqedhaea alyknllhsk
esscsdstne ymdmkpgvsy vvptkadkrr svrigsyier
dvtpaimedd elaldledll sfsyqvakgm aflaskncih
rdlaarnill thgritkicd fglardiknd snyvvkgnar
lpvkwmapes ifncvytfes dvwsygiflw elfslgsspy
pgmpvdskfy kmikegfrml spehapaemy dimktcwdad
plkrptfkqi vqliekqise stnhiysnla ncspnrqkpv
vdhsvrinsv gstasssqpl lvhddv Human C-kit cDNA (SEQ ID NO: 64)

atgagaggcgctcgcggcgcctgggattttctctgcgttctgctcctact
gcttcgcgtccagacaggctcttctcaaccatctgtgagtccaggggaac
cgtctccaccatccatccatccaggaaaatcagacttaatagtccgcgtg
ggcgacgagattaggctgttatgcactgatccgggctttgtcaaatggac
ttttgagatcctggatgaaacgaatgagaataagcagaatgaatggatca
cggaaaaggcagaagccaccaacaccggcaaatacacgtgcaccaacaaa
cacggcttaagcaattccatttatgtgtttgttagagatcctgccaagct
ttttcttgttgaccgctccttgtatgggaaagaagacaacgacacgctgg
tccgctgtcctctcacagacccagaagtgaccaattattccctcaagggg
tgccaggggaagcctcttcccaaggacttgaggtttattcctgaccccaa
ggcgggcatcatgatcaaaagtgtgaaacgcgcctaccatcggctctgtc
tgcattgttctgtggaccaggagggcaagtcagtgctgtcggaaaaattc
atcctgaaagtgaggccagccttcaaagctgtgcctgttgtgtctgtgtc -continued caaagcaagctatcttcttagggaaggggaagaattcacagtgacgtgca
caataaaagatgtgtctagttctgtgtactcaacgtggaaaagagaaaac
agtcagactaaactacaggagaaatataatagctggcatcacggtgactt
caattatgaacgtcaggcaacgttgactatcagttcagcgagagttaatg
attctggagtgttcatgtgttatgccaataatacttttggatcagcaaat
gtcacaacaaccttggaagtagtagataaaggattcattaatatcttccc
catgataaacactacagtatttgtaaacgatggagaaaatgtagatttga
ttgttgaatatgaagcattccccaaacctgaacaccagcagtggatctat
atgaacagaaccttcactgataaatgggaagattatcccaagtctgagaa
tgaaagtaatatcagatacgtaagtgaacttcatctaacgagattaaaag
gcaccgaaggaggcacttacacattcctagtgtccaattctgacgtcaat
gctgccatagcatttaatgtttatgtgaatacaaaaccagaaatcctgac
ttacgacaggctcgtgaatggcatgctccaatgtgtggcagcaggattcc
cagagcccacaatagattggtattttgtccaggaactgagcagagatgc
tctgcttctgtactgccagtggatgtgcagacactaaactcatctgggcc
accgtttggaaagctagtggttcagagttctatagattctagtgcattca
agcacaatggcacggttgaatgtaaggcttacaacgatgtgggcaagact
tctgcctattttaactttgcatttaaaggtaacaacaaagagcaaatcca
tccccacaccctgttcactcctttgctgattggtttcgtaatcgtagctg
gcatgatgtgcattattgtgatgattctgacctacaaatatttacagaaa
cccatgtatgaagtacagtggaaggttgttgaggagataaatggaaacaa
ttatgtttacatagacccaacacaacttccttatgatcacaaatgggagt
ttcccagaaacaggctgagttttgggaaaaccctgggtgctggagctttc
gggaaggttgttgaggcaactgcttatggcttaattaagtcagatgcggc
catgactgtcgctgtaaagatgctcaagccgagtgcccatttgacagaac
gggaagccctcatgtctgaactcaaagtcctgagttaccttggtaatcac
atgaatattgtgaatctacttggagcctgcaccattggagggcccaccct
ggtcattacagaatattgttgctatggtgatcttttgaatttttttgagaa
gaaaaacgtgattcatttatttgttcaaagcaggaagatcatgcagaagct
gcactttataagaatcttctgcattcaaaggagtcttcctgcagcgatag
tactaatgagtacatggacatgaaacctggagtttcttatgttgtcccaa
ccaaggccgacaaaaggagatctgtgagaataggctcatacatagaaaga
gatgtgactcccgccatcatggaggatgacgagttggccctagacttaga
agacttgctgagcttttcttaccaggtggcaaagggcatggctttcctcg
cctccaagaattgtattcacagagacttggcagccagaaatatcctcctt
actcatggtcggatcacaaagatttgtgattttggtctagccagagacat
caagaatgattctaattatgtggttaaaggaaacgctcgactacctgtga
agtggatggcacctgaaagcattttcaactgtgtatacacgtttgaaagt
gacgtctggtcctatgggatttttctttgggagctgttctctttaggaag
cagcccctatcctggaatgccggtcgattctaagttctacaagatgatca -continued aggaaggcttccggatgctcagccctgaacacgcacctgctgaaatgtat gacataatgaagacttgctgggatgcagatcccctaaaaagaccaacatt caagcaaattgttcagctaattgagaagcagatttcagagagcaccaatc atatttactccaacttagcaaactgcagccccaaccgacagaagcccgtg gtagaccattctgtgcggatcaattctgtcggcagcaccgcttcctcctc ccagcctctgcttgtgcacgacgatgtctga The protein and cDNA sequences for mature human mTOR are shown below.

Mature Human mTOR Protein (SEQ ID NO: 65)

mlgtgpaaat taattssnvs vlqqfasglk srneetraka akelqhyvtm elremsqees trfydqlnhh ifelvsssda nerkggilai asligveggn atrigrfany lrnllpsndp vvmemaskai grlamagdtf taeyvefevk ralewlgadr negrrhaavl vlrelaisvp tfffqqvqpf fdnifvavwd pkqairegav aalraclilt tqrepkemqk pqwyrhtfee aekgfdetla kekgmnrddr ihgallilne lvrissmege rlreemeeit qqqlvhdkyc kdlmgfgtkp rhitpftsfq avqpqqsnal vgllgysshq glmgfgtsps pakstlvesr ccrdlmeekf dqvcqwvlkc rnsknsliqm tilnllprla afrpsaftdt qylqdtmnhv lscvkkeker taafqalgll svavrsefkv ylprvldiir aalppkdfah krqkamqvda tvftcismla ramgpgiqqd ikellepmla vglspaltav lydlsrqipq lkkdiqdgll kmlslvlmhk plrhpgmpkg lahglaspgl ttlpeasdvg sitlalrtlg sfefeghslt qfvrhcadhf lnsehkeirm eaartcsrll tpsihlisgh ahvvsqtavq vvadvlskll vvgitdpdpd irycvlasld erfdahlaqa enlqalfval ndqvfeirel aictvgrlss mnpafvmpfl rkmliqilte lehsgigrik eqsarmlghl vsnaprlirp ymepilkali lklkdpdpdp npgvinnvla tigelaqvsg lemrkwvdel fiiimdmlqd ssllakrqva lwtlgqlvas tgyvvepyrk yptllevlln flkteqnqgt rreairvlgl lgaldpykhk vnigmidqsr dasavslses kssqdssdys tsemlvnmgn lpldefypav smvalmrifr dqslshhhtm vvqaitfifk slglkcvqfl pqvmptflnv irvcdgaire flfqqlgmlv sfvkshirpy mdeivtlmre fwvmntsiqs tiilliegiv valggefkly lpqliphmlr vfmhdnspgr ivsikllaai qlfganlddy lhlllppivk lfdapeaplp srkaaletvd rltesldftd yasriihpiv rtldqspelr stamdtlssl vfqlgkkyqi fipmvnkvlv rhrinhqryd vlicrivkgy tladeeedpl iyqhrmlrsg -continued qgdalasgpv etgpmkklhv stinlqkawg aarrvskddw lewlrrlsle llkdssspsl rscwalaqay npmardlfna afvscwseln edqqdelirs ielaltsqdi aevtqtllnl aefmehsdkg plplrddngi vllgeraakc rayakalhyk elefqkgptp aileslisin nklqqpeaaa gvleyamkhf geleiqatwy eklhewedal vaydkkmdtn kddpelmlgr mrclealgew gqlhqqccek wtlvndetqa kmarmaaaaa wglgqwdsme eytcmiprdt hdgafyravl alhqdlfsla qqcidkardl ldaeltamag esysraygam vschmlsele eviqyklype rreiirqiww erlqgcqriv edwqkilmvr slvvsphedm rtwlkyaslc gksgrlalah ktlvlllgvd psrqldhplp tvhpqvtyay mknmwksark idafqhmqhf vqtmqqqaqh aiatedqqhk qelhklmarc flklgewqln lqginestip kvlqyysaat ehdrswykaw hawavmnfea vlhykhqnqa rdekkklrha sganitnatt aattaatatt tastegsnse seaestensp tpsplqkkvt edlsktllmy tvpavqgffr sislsrgnnl qdtlrvltlw fdyghwpdvn ealvegvkai qidtwlqvip qliaridtpr plvgrlihql ltdigryhpq aliypltvas kstttarhna ankilknmce hsntlvqqam mvseelirva ilwhemwheg leeasrlyfg ernvkgmfev leplhammer gpqtlketsf nqaygrdlme aqewcrkymk sgnvkdltqa wdlyyhvfrr iskqlpqlts lelgyvspkl lmcrdlelav pgtydpnqpi iriqsiapsl qvitskqrpr kltlmgsngh efvfllkghe dlrqdervmq lfglvntlla ndptslrknl siqryavipl stnsgligwv phcdtlhali rdyrekkkil lniehrimlr mapdydhltl mqkvevfeha vnntagddla kllwlkspss evwfdrrtny trslavmsmv gyilglgdrh psnlmldrls gkilhidfgd cfevamtrek fpekipfrlt rmltnamevt gldgnyritc htvmevlreh kdsvmavlea fvydpllnwr lmdtntkgnk rsrtrtdsys agqsveildg velgepahkk tgttvpesih sfigdglvkp ealnkkaiqi inrvrdkltg rdfshddtld vptqvellik qatshenlcq cyigwcpfw Human mTOR cDNA (SEQ ID NO: 66)

atgcttgga accggacctg ccgccgccac caccgctgcc accacatcta gcaatgtgag cgtcctgcag cagtttgcca gtggcctaaa gagccggaat gaggaaacca gggccaaagc cgccaaggag ctccagcact atgtcaccat ggaactccga gagatgagtc aagaggagtc tactcgcttc tatgaccaac tgaaccatca catttttgaa ttggtttcca gctcagatgc caatgagagg aaaggtggca tcttggccat agctagcctc -continued ataggagtgg aaggtgggaa tgccacccga attggcagat
ttgccaacta tcttcggaac ctcctcccct ccaatgaccc
agttgtcatg gaaatggcat ccaaggccat tggccgtctt
gccatggcag gggacacttt taccgctgag tacgtggaat
ttgaggtgaa gcgagccctg gaatggctgg gtgctgaccg
caatgagggc cggagacatg cagctgtcct ggttctccgt
gagctggcca tcagcgtccc taccttcttc ttccagcaag
tgcaaccctt ctttgacaac atttttgtgg ccgtgtggga
ccccaaacag gccatccgtg agggagctgt agccgccctt
cgtgcctgtc tgattctcac aacccagcgt gagccgaagg
agatgcagaa gcctcagtgg tacaggcaca catttgaaga
agcagagaag ggatttgatg agaccttggc caaagagaag
ggcatgaatc gggatgatcg gatccatgga gccttgttga
tccttaacga gctggtccga atcagcagca tggaggggaga
gcgtctgaga gaagaaatgg aagaaatcac acagcagcag
ctggtacacg acaagtactg caaagatctc atgggcttcg
gaacaaaacc tcgtcacatt accccccttca ccagtttcca
ggctgtacag ccccagcagt caaatgcctt ggtggggctg
ctggggtaca gctctcacca aggcctcatg ggatttggga
cctcccccag tccagctaag tccaccctgg tggagagccg
gtgttgcaga gacttgatgg aggagaaatt tgatcaggtg
tgccagtggg tgctgaaatg caggaatagc aagaactcgc
tgatccaaat gacaatcctt aatttgttgc cccgcttggc
tgcattccga ccttctgcct tcacagatac ccagtatctc
caagatacca tgaaccatgt cctaagctgt gtcaagaagg
agaaggaacg tacagcggcc ttccaagccc tggggctact
ttctgtggct gtgaggtctg agtttaaggt ctatttgcct
cgcgtgctgg acatcatccg agcggccctg cccccaaagg
acttcgccca taagaggcag aaggcaatgc aggtggatgc
cacagtcttc acttgcatca gcatgctggc tcgagcaatg
gggccaggca tccagcagga tatcaaggag ctgctggagc
ccatgctggc agtgggacta agccctgccc tcactgcagt
gctctacgac ctgagccgtc agattccaca gctaaagaag
gacattcaag atgggctact gaaaatgctg tccctggtcc
ttatgcacaa accccttcgc cacccaggca tgcccaaggg
cctggcccat cagctggcct ctcctggcct cacgaccctc
cctgaggcca gcgatgtggg cagcatcact cttgccctcc
gaacgcttgg cagctttgaa tttgaaggcc actctctgac
ccaatttgtt cgccactgtg cggatcattt cctgaacagt
gagcacaagg agatccgcat ggaggctgcc cgcacctgct -continued cccgcctgct cacaccctcc atccacctca tcagtggcca
tgctcatgtg gttagccaga ccgcagtgca agtggtggca
gatgtgctta gcaaactgct cgtagttggg ataacagatc
ctgaccctga cattcgctac tgtgtcttgg cgtccctgga
cgagcgcttt gatgcacacc tggcccaggc ggagaacttg
caggccttgt ttgtggctct gaatgaccag gtgtttgaga
tccgggagct ggccatctgc actgtgggcc gactcagtag
catgaaccct gcctttgtca tgcctttcct gcgcaagatg
ctcatccaga ttttgacaga gttggagcac agtgggattg
gaagaatcaa agagcagagt gcccgcatgc tggggcacct
ggtctccaat gccccccgac tcatccgccc ctacatggag
cctattctga aggcattaat tttgaaactg aaagatccag
accctgatcc aaacccaggt gtgatcaata atgtcctggc
aacaatagga gaattggcac aggttagtgg cctggaaatg
aggaaatggg ttgatgaact tttattatc atcatggaca
tgctccagga ttcctctttg ttggccaaaa ggcaggtggc
tctgtggacc ctgggacagt tggtggccag cactggctat
gtagtagagc cctacaggaa gtaccctact ttgcttgagg
tgctactgaa ttttctgaag actgagcaga accagggtac
acgcagagag gccatccgtg tgttagggct tttaggggct
ttggatcctt acaagcacaa agtgaacatt ggcatgatag
accagtcccg ggatgcctct gctgtcagcc tgtcagaatc
caagtcaagt caggattcct ctgactatag cactagtgaa
atgctggtca acatgggaaa cttgcctctg gatgagttct
acccagctgt gtccatggtg gccctgatgc ggatcttccg
agaccagtca ctctctcatc atcacaccat ggttgtccag
gccatcacct tcatcttcaa gtccctggga ctcaaatgtg
tgcagttcct gccccaggtc atgcccacgt tccttaacgt
cattcgagtc tgtgatgggg ccatccggga atttttgttc
cagcagctgg gaatgttggt gtcctttgtg aagagccaca
tcagacctta tatggatgaa atagtcaccc tcatgagaga
attctgggtc atgaacacct caattcagag cacgatcatt
cttctcattg agcaaattgt ggtagctctt gggggtgaat
ttaagctcta cctgccccag ctgatcccac acatgctgcg
tgtcttcatg catgacaaca gcccaggccg cattgtctct
atcaagttac tggctgcaat ccagctgttt ggcgccaacc
tggatgacta cctgcattta ctgctgcctc ctattgttaa
gttgtttgat gcccctgaag ctccactgcc atctcgaaag
gcagcgctag agactgtgga ccgcctgacg gagtccctgg
atttcactga ctatgcctcc cggatcattc accctattgt
tcgaacactg gaccagagcc cagaactgcg ctccacagcc -continued atggacacgc tgtcttcact tgtttttcag ctggggaaga
agtaccaaat tttcattcca atggtgaata aagttctggt
gcgacaccga atcaatcatc agcgctatga tgtgctcatc
tgcagaattg tcaagggata cacacttgct gatgaagagg
aggatccttt gatttaccag catcggatgc ttaggagtgg
ccaaggggat gcattggcta gtggaccagt ggaaacagga
cccatgaaga aactgcacgt cagcaccatc aacctccaaa
aggcctgggg cgctgccagg agggtctcca aagatgactg
gctggaatgg ctgagacggc tgagcctgga gctgctgaag
gactcatcat cgccctccct gcgctcctgc tgggccctgg
cacaggccta caacccgatg gccagggatc tcttcaatgc
tgcatttgtg tcctgctggt ctgaactgaa tgaagatcaa
caggatgagc tcatcagaag catcgagttg gccctcacct
cacaagacat cgctgaagtc acacagaccc tcttaaactt
ggctgaattc atggaacaca gtgacaaggg ccccctgcca
ctgagagatg acaatggcat tgttctgctg ggtgagagag
ctgccaagtg ccgagcatat gccaaagcac tacactacaa
agaactggag ttccagaaag gccccacccc tgccattcta
gaatctctca tcagcattaa taataagcta cagcagccgg
aggcagcggc cggagtgtta gaatatgcca tgaaacactt
tggagagctg gagatccagg ctacctggta tgagaaactg
cacgagtggg aggatgccct tgtggcctat gacaagaaaa
tggacaccaa caaggacgac ccagagctga tgctgggccg
catgcgctgc ctcgaggcct tgggggaatg gggtcaactc
caccagcagt gctgtgaaaa gtggaccctg gttaatgatg
agacccaagc caagatggcc cggatggctg ctgcagctgc
atggggttta ggtcagtggg acagcatgga agaatacacc
tgtatgatcc ctcgggacac ccatgatggg gcattttata
gagctgtgct ggcactgcat caggacctct tctccttggc
acaacagtgc attgacaagg ccagggacct gctggatgct
gaattaactg cgatggcagg agagagttac agtcgggcat
atggggccat ggtttcttgc cacatgctgt ccgagctgga
ggaggttatc cagtacaaac ttgtccccga gcgacgagag
atcatccgcc agatctggtg ggagagactg cagggctgcc
agcgtatcgt agaggactgg cagaaaatcc ttatggtgcg
gtcccttgtg gtcagccctc atgaagacat gagaacctgg
ctcaagtatg caagcctgtg cggcaagagt ggcaggctgg
ctcttgctca taaaacttta gtgttgctcc tgggagttga
tccgtctcgg caacttgacc atcctctgcc aacagttcac
cctcaggtga cctatgccta catgaaaaac atgtggaaga -continued gtgcccgcaa gatcgatgcc ttccagcaca tgcagcattt
tgtccagacc atgcagcaac aggcccagca tgccatcgct
actgaggacc agcagcataa gcaggaactg cacaagctca
tggcccgatg cttcctgaaa cttggagagt ggcagctgaa
tctacagggc atcaatgaga gcacaatccc caaagtgctg
cagtactaca gcgccgccac agagcacgac cgcagctggt
acaaggcctg gcatgcgtgg gcagtgatga acttcgaagc
tgtgctacac tacaaacatc agaaccaagc ccgcgatgag
aagaagaaac tgcgtcatgc cagcggggcc aacatcacca
acgccaccac tgccgccacc acggccgcca ctgccaccac
cactgccagc accgagggca gcaacagtga gagcgaggcc
gagagcaccg agaacagccc caccccatcg ccgctgcaga
agaaggtcac tgaggatctg tccaaaaccc tcctgatgta
cacggtgcct gccgtccagg gcttcttccg ttccatctcc
ttgtcacgag gcaacaacct ccaggataca ctcagagttc
tcaccttatg gtttgattat ggtcactggc cagatgtcaa
tgaggcctta gtggaggggg tgaaagccat ccagattgat
acctggctac aggttatacc tcagctcatt gcaagaattg
atacgcccag acccttggtg ggacgtctca ttcaccagct
tctcacagac attggtcggt accaccccca ggccctcatc
tacccactga cagtggcttc taagtctacc acgacagccc
ggcacaatgc agccaacaag attctgaaga acatgtgtga
gcacagcaac accctggtcc agcaggccat gatggtgagc
gaggagctga tccgagtggc catcctctgg catgagatgt
ggcatgaagg cctggaagag gcatctcgtt tgtactttgg
ggaaaggaac gtgaaaggca tgtttgaggt gctggagccc
ttgcatgcta tgatggaacg gggcccccag actctgaagg
aaacatcctt taatcaggcc tatggtcgag atttaatgga
ggcccaagag tggtgcagga agtacatgaa atcagggaat
gtcaaggacc tcacccaagc ctgggacctc tattatcatg
tgttccgacg aatctcaaag cagctgcctc agctcacatc
cttagagctg caatatgttt ccccaaaact tctgatgtgc
cgggaccttg aattggctgt gccaggaaca tatgacccca
accagccaat cattcgcatt cagtccatag caccgtcttt
gcaagtcatc acatccaagc agaggccccg gaaattgaca
cttatgggca gcaacggaca tgagtttgtt ttccttctaa
aaggccatga agatctgcgc caggatgagc gtgtgatgca
gctcttcggc ctggttaaca cccttctggc caatgaccca
acatctcttc ggaaaaacct cagcatccag agatacgctg
tcatcccttt atcgaccaac tcgggcctca ttggctgggt
tccccactgt gacacactgc acgccctcat ccgggactac -continued agggagaaga agaagatcct tctcaacatc gagcatcgca
tcatgttgcg gatggctccg gactatgacc acttgactct
gatgcagaag gtggaggtgt ttgagcatgc cgtcaataat
acagctgggg acgacctggc caagctgctg tggctgaaaa
gccccagctc cgaggtgtgg tttgaccgaa gaaccaatta
tacccgttct ttagcggtca tgtcaatggt tgggtatatt
ttaggcctgg gagatagaca cccatccaac ctgatgctgg
accgtctgag tgggaagatc ctgcacattg actttgggga
ctgctttgag gttgctatga cccgagagaa gtttccagag
aagattccat ttagactaac aagaatgttg accaatgcta
tggaggttac aggcctggat ggcaactaca gaatcacatg
ccacacagtg atggaggtgc tgcgagagca caaggacagt
gtcatggccg tgctggaagc ctttgtctat gaccccttgc
tgaactggag gctgatggac acaaatacca aaggcaacaa
gcgatcccga acgaggacgg attcctactc tgctggccag
tcagtcgaaa ttttggacgg tgtggaactt ggagagccag
cccataagaa aacggggacc acagtgccag aatctattca
ttctttcatt ggagacggtt tggtgaaacc agaggcccta
aataagaaag ctatccagat tattaacagg gttcgagata
agctcactgg tcgggacttc tctcatgatg acactttgga
tgttccaacg caagttgagc tgctcatcaa acaagcgaca
tcccatgaaa acctctgcca gtgctatatt ggctggtgcc
ctttctggta a Non-limiting examples of commercial ELISA assays that can be used to determine the expression level of SREBP1 are available from Novus Biologicals and Abcam. The protein and cDNA sequences for mature human SREBP1 are shown below.

Mature Human SREBP1 Protein
(SEQ ID NO: 67)
MDEPPFSEAALEQALGEPCDLDAALLTDIEDMLQLINNQDSDFPGLFDPP
YAGSGAGGTDPASPDTSSPGSLSPPPATLSSSLEAFLSGPQAAPSPLSPP
QPAPTPLKMYPSMPAFSPGPGIKEESVPLSILQTPTPQPLPGALLPQSFP
APAPPQFSSTPVLGYPSPPGGFSTGSPPGNTQQPLPGLPLASPPGVPPVS
LHTQVQSVVPQQLLTVTAAPTAAPVTTTVTSQIQQVPVLLQPHFIKADSL
LLTAMKTDGATVKAAGLSPLVSGTTVQTGPLPTLVSGGTILATVPLVVDA
EKLPINRLAAGSKAPASAQSRGEKRTAHNAIEKRYRSSINDKIIELKDLV
VGTEAKLNKSAVLRKAIDYIRFLQHSNQKLKQENLSLRTAVHKSKSLKDL
VSACGSGGNTDVLMEGVKTEVEDTLTPPPSDAGSPFQSSPLSLGSRGSGS
GGSGSDSEPDSPVFEDSKAKPEQRPSLHSRGMLDRSRLALCTLVFLCLSC
NPLASLLGARGLPSPSDTTSVYHSPGRNVLGTESRDGPGWAQWLLPPVVW
LLNGLLVLVSLVLLFVYGEPVTRPHSGPAVYFWRHRKQADLDLARGDFAQ -continued AAQQLWLALRALGRPLPTSHLDLACSLLWNLIRHLLQRLWVGRWLAGRAG
GLQQDCALRVDASASARDAALVYHKLHQLHTMGKHTGGHLTATNLALSAL
NLAECAGDAVSVATLAEIYVAAALRVKTSLPRALHFLTRFFLSSARQACL
AQSGSVPPAMQWLCHPVGHRFFVDGDWSVLSTPWESLYSLAGNPVDPLAQ
VTQLFREHLLERALNCVTQPNPSPGSADGDKEFSDALGYLQLLNSCSDAA
GAPAYSFSISSSMATTTGVDPVAKWWASLTAVVIHWLRRDEEAAERLCPL
VEHLPRVLQESERPLPRAALHSFKAARALLGCAKAESGPASLTICEKASG
YLQDSLATTPASSSIDKAVQLFLCDLLLVVRTSLWRQQQPPAPAPAAQGT
SSRPQASALELRGFQRDLSSLRRLAQSFRPAMRRVFLHEATARLMAGASP
TRTHQLLDRSLRRRAGPGGKGGAVAELEPRPTRREHAEALLLASCYLPPG
FLSAPGQRVGMLAEAARTLEKLGDRRLLHDCQQMLMRLGGGTTVTSS Human SREBP1 cDNA
(SEQ ID NO: 68)
atggacgagccacccttcagcgaggcggctttggagcaggcgctgggcga
gccgtgcgatctggacgcggcgctgctgaccgacatcgaagacatgcttc
agcttatcaacaaccaagacagtgacttccctggcctatttgacccaccc
tatgctgggagtggggcagggggcacagaccctgccagccccgataccag
ctccccaggcagcttgtctccacctcctgccacattgagctcctctcttg
aagccttcctgagcgggccgcaggcagcgccctcacccctgtcccctccc
cagcctgcacccactccattgaagatgtacccgtccatgcccgctttctc
ccctgggcctggtatcaaggaagagtcagtgccactgagcatcctgcaga
cccccaccccacagcccctgccaggggccctcctgccacagagcttccca
gccccagccccaccgcagttcagctccacccctgtgttaggctaccccag
ccctccgggaggcttctctacaggaagccctcccgggaacacccagcagc
cgctgcctggcctgccactggcttccccgccaggggtcccgcccgtctcc
ttgcacacccaggtccagagtgtggtcccccagcagctactgacagtcac
agctgcccccacggcagcccctgtaacgaccactgtgacctcgcagatcc
agcaggtcccggtcctgctgcagccccacttcatcaaggcagactcgctg
cttctgacagccatgaagacagacggagccactgtgaaggcggcaggtct
cagtcccctggtctctggcaccactgtgcagacagggcctttgccgaccc
tggtgagtggcggaaccatcttggcaacagtcccactggtcgtagatgcg
gagaagctgcctatcaaccggctcgcagctggcagcaaggccccggcctc
tgcccagagccgtggagagaagcgcacagcccacaacgccattgagaagc
gctaccgctcctccatcaatgacaaaatcattgagctcaaggatctggtg
gtgggcactgaggcaaagctgaataaatctgctgtcttgcgcaaggccat
cgactacattcgctttctgcaacacagcaaccagaaactcaagcaggaga
acctaagtctgcgcactgctgtccacaaaagcaaatctctgaaggatctg
gtgtcggcctgtggcagtggagggaacacagacgtgctcatggagggcgt
gaagactgaggtggaggacacactgaccccacccccctcggatgctggct
cacctttccagagcagccccttgtcccttggcagcaggggcagtggcagc
ggtggcagtggcagtgactcggagcctgacagcccagtctttgaggacag -continued

```
caaggcaaagccagagcagcggccgtctctgcacagccggggcatgctgg
accgctcccgcctggccctgtgcacgctcgtcttcctctgcctgtcctgc
aaccccttggcctccttgctggggggcccggggggcttcccagcccctcaga
taccaccagcgtctaccatagccctgggcgcaacgtgctgggcaccgaga
gcagagatggccctggctgggcccagtggctgctgcccccagtggtctgg
ctgctcaatgggctgttggtgctcgtctccttggtgcttctctttgtcta
cggtgagccagtcacacggccccactcaggccccgccgtgtacttctgga
ggcatcgcaagcaggctgacctggacctggcccggggagactttgcccag
gctgcccagcagctgtggctggccctgcgggcactgggccggcccctgcc
cacctcccacctggacctggcttgtagcctcctctggaacctcatccgtc
acctgctgcagcgtctctgggtgggccgctggctggcaggccgggcaggg
ggcctgcagcaggactgtgctctgcgagtggatgctagcgccagcgcccg
agacgcagccctggtctaccataagctgcaccagctgcacaccatgggga
agcacacaggcgggcacctcactgccaccaacctggcgctgagtgccctg
aacctggcagagtgtgcaggggatgccgtgtctgtggcgacgctggccga
gatctatgtggcggctgcattgagagtgaagaccagtctcccacgggcct
tgcattttctgacacgcttcttcctgagcagtgcccgccaggcctgcctg
gcacagagtggctcagtgcctcctgccatgcagtggctctgccaccccgt
gggccaccgtttcttcgtggatggggactggtccgtgctcagtaccccat
gggagagcctgtacagcttggccgggaacccagtggacccccctggcccag
gtgactcagctattccgggaacatctcttagagcgagcactgaactgtgt
gacccagcccaaccccagccctgggtcagctgatggggacaaggaattct
cggatgccctcgggtacctgcagctgctgaacagctgttctgatgctgcg
ggggctcctgcctacagcttctccatcagttccagcatggccaccaccac
cggcgtagacccggtggccaagtggtgggcctctctgacagctgtggtga
tccactggctgcggcgggatgaggaggcggctgagcggctgtgcccgctg
gtggagcacctgccccgggtgctgcaggagtctgagagaccccctgcccag
ggcagctctgcactccttcaaggctgcccgggccctgctgggctgtgcca
aggcagagtctggtccagccagcctgaccatctgtgagaaggccagtggg
tacctgcaggacagcctggctaccacaccagccagcagctccattgacaa
ggccgtgcagctgttcctgtgtgacctgcttcttgtggtgcgcaccagcc
tgtggcggcagcagcagcccccggccccggccccagcagcccagggcacc
agcagcaggccccaggcttccgcccttgagctgcgtggcttccaacggga
cctgagcagcctgaggcggctggcacagagcttccggcccgccatgcgga
gggtgttcctacatgaggccacggcccggctgatggcgggggccagcccc
acacggacacaccagctcctcgaccgcagtctgaggcggcgggcaggccc
cggtggcaaaggaggcgcggtggcggagctggagccgcggcccacgcggc
gggagcacgcggaggccttgctgctggcctcctgctacctgccccccggc
ttcctgtcggcgcccgggcagcgcgtgggcatgctggctgaggcggcgcg
cacactcgagaagcttggcgatcgccggctgctgcacgactgtcagcaga
tgctcatgcgcctgggcggtgggaccactgtcacttccagctag
```

Non-limiting examples of commercial ELISA assays that can be used to determine the expression level of IFN-γ are available from R&D Systems, Thermo Fisher Scientific, Abcam, Enzo Life Sciences, and RayBiotech. The protein and cDNA sequences for mature human IFN-γ are shown below.

```
Mature Human IFN-γ
                                        (SEQ ID NO: 69)
qdpyvke aenlkkyfna ghsdvadngt lflgilknwk
eesdrkimqs qivsfyfklf knfkddqsiq ksvetikedm
nvkffnsnkk krddfekltn ysvtdlnvqr kaiheliqvm
aelspaaktg krkrsqmlfr g

Human IFN-γ cDNA
                                        (SEQ ID NO: 70)
caggac ccatatgtaa aagaagcaga aaaccttaag
aaatatttta atgcaggtca ttcagatgta gcggataatg
gaactctttt cttaggcatt ttgaagaatt ggaaagagga
gagtgacaga aaaataatgc agagccaaat tgtctccttt
tacttcaaac tttttaaaaa ctttaaagat gaccagagca
tccaaaagag tgtggagacc atcaaggaag acatgaatgt
caagtttttc aatagcaaca aaaagaaacg agatgacttc
gaaaagctga ctaattattc ggtaactgac ttgaatgtcc
aacgcaaagc aatacatgaa ctcatccaag tgatggctga
actgtcgcca gcagctaaaa cagggaagcg aaaaaggagt
cagatgctgt ttcgaggt
```

Non-limiting examples of commercial ELISA assays that can be used to determine the expression level of granzyme B are available from RayBiotech, Thermo Fisher Scientific, and R&D Systems. The protein and cDNA sequences for mature human granzyme B are shown below.

```
Mature Human Granzyme B
                                        (SEQ ID NO: 71)
iiggheakph srpymaylmi wdqkslkrcg gflirddfvl
taahcwgssi nvtlgahnik eqeptqqfip vkrpiphpay
npknfsndim llqlerkakr travqplrlp snkaqvkpgq
tcsvagwgqt aplgkhshtl gevkmtvqed rkcesdlrhy
ydstielcvg dpeikktsfk gdsggplvcn kvaqgivsyg
rnngmpprac tkvssfvhwi kktmkry

Human Granzyme B cDNA
                                        (SEQ ID NO: 72)
atcatcgggg gacatgaggc caagccccac tcccgcccct
acatggctta tcttatgatc tgggatcaga agtctctgaa
gaggtgcggt ggcttcctga tacgagacga cttcgtgctg
acagctgctc actgttgggg aagctccata aatgtcacct
tgggggccca caatatcaaa gaacaggagc cgacccagca
gtttatccct gtgaaaagac ccatccccca tccagcctat
aatcctaaga acttctccaa cgacatcatg ctactgcagc
```

-continued tggagagaaa ggccaagcgg accagagctg tgcagcccct caggctacct agcaacaagg cccaggtgaa gccagggcag acatgcagtg tggccggctg ggggcagacg gcccccctgg gaaaacactc acacacacta caagaggtga agatgacagt gcaggaagat cgaaagtgcg aatctgactt acgccattat tacgacagta ccattgagtt gtgcgtgggg gacccagaga ttaaaaagac ttcctttaag gggactctg gaggccctct tgtgtgtaac aaggtggccc agggcattgt ctcctatgga cgaaacaatg gcatgcctcc acgagcctgc accaaagtct caagctttgt acactggata aagaaaacca tgaaacgcta c Non-limiting examples of commercial ELISA assays that can be used to determine the expression level of MYC are available from Invitrogen, LSBio, Biocodon Technologies, and Elisa Genie. The protein and cDNA sequences for mature human MYC are shown below.

Human Myc Protien (SEQ ID NO: 329)

mdffrvvenq qppatmplnv sftnrnydld ydsvqpyfyc deeenfyqqq qqselqppap sediwkkfel lptpplspsr rsglcspsyv avtpfslrgd ndggggsfst adqlemvtel lggdmvngsf icdpddetfi kniiiqdcmw sgfsaaaklv seklasyqaa rkdsgspnpa rghsvcstss lylqdlsaaa secidpsvvf pyplndsssp kscasqdssa fspssdslls stesspqgsp eplvlheetp pttssdseee qedeeeidvv svekrqapgk rsesgspsag ghskpphspl vlkrchvsth qhnyaappst rkdypaakrv kldsvrvlrq isnnrkctsp rssdteenvk rrthnvlerq rrnelkrsff alrdqipele nnekapkvvi lkkatayils vqaeeqklis eedllrkrre qlkhkleqlr nsca Human Myc cDNA (SEQ ID NO: 330)

ctggatt tttttcgggt agtggaaaac cagcagcctc ccgcgacgat gcccctcaac gttagcttca ccaacaggaa ctatgacctc gactacgact cggtgcagcc gtatttctac tgcgacgagg aggagaactt ctaccagcag cagcagcaga gcgagctgca gcccccggcg cccagcgagg atatctggaa gaaattcgag ctgctgccca ccccgcccct gtcccctagc cgccgctccg ggctctgctc gccctcctac gttgcggtca cacccttctc ccttcgggga gacaacgacg gcggtggcgg gagcttctcc acggccgacc agctggagat ggtgaccgag ctgctgggag gagacatggt gaaccagagt ttcatctgcg acccggacga cgagaccttc atcaaaaaca tcatcatcca -continued ggactgtatg tggagcggct tctcggccgc cgccaagctc gtctcagaga agctggcctc ctaccaggct gcgcgcaaag acagcggcag cccgaacccc gcccgcggcc acagcgtctg ctccacctcc agcttgtacc tgcaggatct gagcgccgcc gcctcagagt gcatcgaccc ctcggtggtc ttcccctacc ctctcaacga cagcagctcg cccaagtcct gcgcctcgca agactccagc gccttctctc cgtcctcgga ttctctgctc tcctcgacgg agtcctcccc gcagggcagc cccgagcccc tggtgctcca tgaggagaca ccgcccacca ccagcagcga ctctgaggag gaacaagaag atgaggaaga aatcgatgtt gtttctgtgg aaaagaggca ggctcctggc aaaaggtcag agtctggatc accttctgct ggaggccaca gcaaacctcc tcacagccca ctggtcctca agaggtgcca cgtctccaca catcagcaca actacgcagc gcctccctcc actcggaagg actatcctgc tgccaagagg gtcaagttgg acagtgtcag agtcctgaga cagatcagca acaaccgaaa atgcaccagc cccaggtcct cggacaccga ggagaatgtc aagaggcgaa cacacaacgt cttggagcgc cagaggagga acgagctaaa acggagcttt tttgccctgc gtgaccagat cccggagttg gaaaacaatg aaaaggcccc caaggtagtt atccttaaaa aagccacagc atacatcctg tccgtccaag cagaggagca aaagctcatt tctgaagagg acttgttgcg gaaacgacga gaacagttga aacacaaact tgaacagcta cggaactctt gtgcgtaa In some embodiments, activated NK cells (e.g., human activated NK cells) can show increased (e.g., at least a 10% increase, at least a 20% increase, at least a 30% increase, at least a 40% increase, at least a 50% increase, at least a 60% increase, at least a 70% increase, at least 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) ability to kill senescent cells (e.g., any of the senescent cells described herein) in a subject (e.g., any of the subjects described herein) or in vitro as compared to resting NK cells (e.g., human resting NK cells).

In some embodiments, activated NK cells (e.g., human activated NK cells) can show about a 10% increase to about a 500% increase (or any of the subranges of this range described herein) ability to kill senescent cells (e.g., any of the senescent cells described herein) in a subject (e.g., any of the subjects described herein) or in vivo as compared to resting NK cells (e.g., human resting NK cells).

In some embodiments, activated NK cells (e.g., human activated NK cells) can show increased (e.g., at least a 10% increase, at least a 20% increase, at least a 30% increase, at least a 40% increase, at least a 50% increase, at least a 60% increase, at least a 70% increase, at least 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) cytotoxic activity in a contact-cytotoxicity assay in the presence of an antibody that binds specifically to an antigen present on a senescent or target cell, e.g., as compared to a resting NK cell (e.g., human resting NK cells).

In some embodiments, activated NK cells (e.g., human activated NK cells) can show increased (e.g., about a 10% increase to about a 500% increase, or any of the subranges of this range described herein) cytotoxic activity in a contact-cytotoxicity assay in the presence of an antibody that binds specifically to an antigen present on a senescent or target cell, e.g., as compared to a resting NK cell (e.g., human resting NK cells).

In some embodiments, an activated NK cell can be produced by a method that includes obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is an autologous NK cell obtained from the subject. In some examples of these methods, the resting NK cell is an haploidentical resting NK cells. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and optionally further administering a therapeutically effective amount of the activated NK cells to a subject, e.g., any of the subjects described herein).

In some embodiments of these methods, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days.

NK Cell Activating Agents

Provided herein are methods that include the use or administration of one or more NK cell activating agents. In some embodiments, an NK cell activating agent can be a protein. In some embodiments, an NK cell activating agent can be a single-chain chimeric polypeptide (e.g. any of the single-chain chimeric polypeptides described herein), a multi-chain chimeric polypeptide (e.g. any of the multi-chain chimeric polypeptides described herein, e.g., the exemplary type A and type B multi-chain chimeric polypeptides described herein), an antibody, a recombinant cytokine or an interleukin (e.g. any of the recombinant cytokines or interleukins described herein), and a soluble interleukin or cytokine receptor (e.g. any of the soluble interleukin or cytokine receptors described herein). In some embodiments, the NK cell activating agent can be a small molecule (e.g., a glycogen synthase kinase-3 (GSK3) inhibitor, e.g., CHIR99021 as described in Cichocki et al., *Cancer Res.* 77:5664-5675, 2017) or an aptamer.

In some embodiments of any of the one or more NK cell activating agents provided herein, at least one of the one or more NK cell activating agent(s) results in activation of one or more (e.g., two, three, four, five, six, seven, or eight) of: a receptor for IL-2, a receptor for IL-7, a receptor for IL-12, a receptor for IL-15, a receptor for IL-18, a receptor for IL-21, a receptor for IL-33, CD16, CD69, CD25, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1 (e.g., in an immune cell, e.g., a human immune cell, e.g., a human NK cell) as compared to the level of activation in the absence of the one or more NK cell activating agent(s).

In some embodiments, the at least one of the one or more NK cell activating agent(s) that results in activation of a receptor for IL-2 is a soluble IL-2 or an agonistic antibody that binds specifically to an IL-2 receptor.

In some embodiments, the at least one of the one or more NK cell activating agent(s) that results in activation of a receptor for IL-7 is a soluble IL-7 or an agonistic antibody that binds specifically to an IL-7 receptor.

In some embodiments, the at least one of the one or more NK cell activating agent(s) that results in activation of a receptor for IL-12 is a soluble IL-12 or an agonistic antibody that binds specifically to an IL-12 receptor.

In some embodiments, the at least one of the one or more NK cell activating agent(s) that results in activation of a receptor for IL-15 is a soluble IL-15 or an agonistic antibody that binds specifically to an IL-15 receptor.

In some embodiments, the at least one of the one or more NK cell activating agent(s) that results in activation of a receptor for IL-21 is a soluble IL-21 or an agonistic antibody that binds specifically to an IL-21 receptor.

In some embodiments, the at least one of the one or more NK cell activating agent(s) that results in activation of a receptor for IL-33 is a soluble IL-33 or an agonistic antibody that binds specifically to an IL-33 receptor.

In some embodiments, the at least one of the one or more NK cell activating agent(s) that results in activation of CD16 is an agonistic antibody that binds specifically to CD16.

In some embodiments, the at least one of the one or more NK cell activating agent(s) that results in activation of CD69 is an agonistic antibody that binds specifically to CD69.

In some embodiments, the at least one of the one or more NK cell activating agent(s) that results in activation of CD25, CD59 is an agonistic antibody that binds specifically to CD25, CD59.

In some embodiments, the at least one of the one or more NK cell activating agent(s) that results in activation of CD352 is an agonistic antibody that binds specifically to CD352.

In some embodiments, the at least one of the one or more NK cell activating agent(s) that results in activation of NKp80 is an agonistic antibody that binds specifically to NKp80.

In some embodiments, the at least one of the one or more NK cell activating agent(s) that results in activation of DNAM-1 is an agonistic antibody that binds specifically to DNAM-1.

In some embodiments, the at least one of the one or more NK cell activating agent(s) that results in activation of 2B4 is an agonistic antibody that binds specifically to 2B4.

In some embodiments, the at least one of the one or more NK cell activating agent(s) that results in activation of NKp30 is an agonistic antibody that binds specifically to NKp30.

In some embodiments, the at least one of the one or more NK cell activating agent(s) that results in activation of NKp44 is an agonistic antibody that binds specifically to NKp44.

In some embodiments, the at least one of the one or more NK cell activating agent(s) that results in activation of NKp46 is an agonistic antibody that binds specifically to NKp46.

In some embodiments, the at least one of the one or more NK cell activating agent(s) that results in activation of NKG2D is an agonistic antibody that binds specifically to NKG2D.

In some embodiments, the at least one of the one or more NK cell activating agent(s) that results in activation of KIR2DS1 is an agonistic antibody that binds specifically to KIT2DS1.

In some embodiments, the at least one of the one or more NK cell activating agent(s) that results in activation of KIR2DS2/3 is an agonistic antibody that binds specifically to KIT2DS2/3.

In some embodiments, the at least one of the one or more NK cell activating agent(s) that results in activation of KIR2DL4 is an agonistic antibody that binds specifically to KIT2DL4.

In some embodiments, the at least one of the one or more NK cell activating agent(s) that results in activation of KIR2DS4 is an agonistic antibody that binds specifically to KIT2DS4.

In some embodiments, the at least one of the one or more NK cell activating agent(s) that results in activation of KIR2DS5 is an agonistic antibody that binds specifically to KIT2DS5.

In some embodiments, the at least one of the one or more NK cell activating agent(s) that results in activation of KIR3DS1 is an agonistic antibody that binds specifically to KIT3DS1.

In some embodiments of any of the one or more NK cell activating agents provided herein, at least one (e.g., two, three, four, or five) of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2 (e.g., in an immune cell, e.g., a human immune cell, e.g., a human NK cell) as compared to the level of activation in the absence of the one or more NK cell activating agent(s).

In some embodiments, the at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

In some embodiments, the at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

In some embodiments, the at least one of the one or more NK cell activating agent(s) that results in a decrease in the activation of CD1 is an antagonistic antibody that binds specifically to CD1, a soluble CD1, or an antibody that binds specifically to a ligand of CD1.

In some embodiments, the at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

In some embodiments, the at least one of the one or more NK cell activating agent(s) that results in a decrease in the activation of Siglec-7 is an antagonistic antibody that binds specifically to Siglec-7, a soluble Siglec-7, or an antibody that binds specifically to a ligand of Siglec-7.

In some embodiments, the at least one of the one or more NK cell activating agent(s) that results in a decrease in the activation of IRP-60 is an antagonistic antibody that binds specifically to IRP-60, a soluble IRP-60, or an antibody that binds specifically to a ligand of IRP-60.

In some embodiments, the at least one of the one or more NK cell activating agent(s) that results in a decrease in the activation of Tactile is an antagonistic antibody that binds specifically to Tactile, a soluble Tactile, or an antibody that binds specifically to a ligand of Tactile.

In some embodiments, the at least one of the one or more NK cell activating agent(s) that results in a decrease in the activation of IL1R8 is an antagonistic antibody that binds specifically to IL1R8, a soluble IL1R8, or an antibody that binds specifically to a ligand of IL1R8.

In some embodiments, the at least one of the one or more NK cell activating agent(s) that results in a decrease in the activation of NKG2A/KLRD1 is an antagonistic antibody that binds specifically to NKG2A/KLRD1, a soluble NKG2A/KLRD1, or an antibody that binds specifically to a ligand of NKG2A/KLRD1.

In some embodiments, the at least one of the one or more NK cell activating agent(s) that results in a decrease in the activation of KIR2DL1 is an antagonistic antibody that binds specifically to KIR2DL1, a soluble KIR2DL1, or an antibody that binds specifically to a ligand of KIR2DL1.

In some embodiments, the at least one of the one or more NK cell activating agent(s) that results in a decrease in the activation of KIR2DL2/3 is an antagonistic antibody that binds specifically to KIR2DL2/3, a soluble KIR2DL2/3, or an antibody that binds specifically to a ligand of KIR2DL2/3.

In some embodiments, the at least one of the one or more NK cell activating agent(s) that results in a decrease in the activation of KIR2DL5 is an antagonistic antibody that binds specifically to KIR2DL5, a soluble KIR2DL5, or an antibody that binds specifically to a ligand of KIR2DL5.

In some embodiments, the at least one of the one or more NK cell activating agent(s) that results in a decrease in the activation of KIR3DL1 is an antagonistic antibody that binds specifically to KIR3DL1, a soluble KIR3DL1, or an antibody that binds specifically to a ligand of KIR3DL1.

In some embodiments, the at least one of the one or more NK cell activating agent(s) that results in a decrease in the activation of KIR3DL2 is an antagonistic antibody that binds specifically to KIR3DL2, a soluble KIR3DL2, or an antibody that binds specifically to a ligand of KIR3DL2.

In some embodiments, the at least one of the one or more NK cell activating agent(s) that results in a decrease in the activation of ILT2/LIR-1 is an antagonistic antibody that binds specifically to ILT2/LIR-1, a soluble ILT2/LIR-1, or an antibody that binds specifically to a ligand of ILT2/LIR-1.

In some embodiments, the at least one of the one or more NK cell activating agent(s) that results in a decrease in the activation of LAG2 is an antagonistic antibody that binds specifically to LAG2, a soluble LAG2, or an antibody that binds specifically to a ligand of LAG2.

Non-limiting examples of NK cell activating agents are described below and can be used in any combination.

In some examples, an NK cell activating agents can be a soluble PD-1, a soluble PD-L1, a soluble TIGIT, a soluble CD1, or a soluble TIM-3. Non-limiting examples of soluble PD-1, PD-L1, TIGIT, CD1, and TIM-3 are provided below.

Human Soluble PD-1
(SEQ ID NO: 73)

pgwfldspdr pwnpptfspa llvvtegdna tftcsfsnts esfvlnwyrm spsnqtdkla afpedrsqpg qdcrfrvtql -continued pngrdfhmsv vrarrndsgt ylcgaislap kaqikeslra elrvterrae vptahpspsp rpagqfqtlv vgvvggllgs lvllvwvlav icsraargti garrtgqplk edpsavpvfs vdygeldfqw rektpeppvp cvpeqteyat ivfpsgmgts sparrgsadg prsaqplrpe dghcswpl Human Soluble PD-L1
(SEQ ID NO: 74)

ftvtvpkdlyvv eygsnmtiec kfpvekqldl aalivyweme dkniiqfvhg eedlkvqhss yrqrarllkd qlslgnaalq itdvklqdag vyrcmisygg adykritvkv napynkinqr ilvvdpvtse heltcqaegy pkaeviwtss dhqvlsgktt ttnskreekl fnvtstlrin tttneifyct frrldpeenh taelvipelp lahppnerth lvilgaillc lgvaltfifr lrkgrmmdvk kcgiqdtnsk kqsdthleet Human Soluble TIGIT
(SEQ ID NO: 75)

mmtgtiett gnisaekggs iilqchlsst taqvtqvnwe qqdqllaicn adlgwhisps fkdrvapgpg lgltlqsltv ndtgeyfciy htypdgtytg riflevless vaehgarfqi pllgamaatl vvictavivv valtrkkkal rihsvegdlr rksagqeews psapsppgsc vqaeaapagl cgeqrgedca elhdyfnvls yrslgncsff tetg Human Soluble CD1A
(SEQ ID NO: 76)

nadglkeplsfhvt wiasfynhsw kqnlvsgwls dlqthtwdsn sstivflcpw srgnfsneew keletlfrir tirsfegirr yahelqfeyp feiqvtggce lhsgkvsgsf lqlayqgsdf vsfqnnswlp ypvagnmakh fckvlnqnqh endithnlls dtcprfilgl ldagkahlqr qvkpeawlsh gpspgpghlq lvchvsgfyp kpvwvmwmrg eqeqqgtqrg dilpsadgtw ylratlevaa geaadlscrv khsslegqdi vlywehhssv gfiilavivp lllliglalw frkrcfc Human Soluble TIM3
(SEQ ID NO: 77)

seveyraev gqnaylpcfy tpaapgnlvp vcwgkgacpv fecgnvvlrt derdvnywts rywlngdfrk gdvsltienv tladsgiycc riqipgimnd ekfnlklvik pakvtpaptr qrdftaafpr mlttrghgpa etqtlgslpd inltqistla nelrdsrlan dlrdsgatir igiyigagic aglalalifg alifkwyshs kekiqnlsli slanlppsgl anavaegirs eeniytieen vyeveepney ycyvssrqqp sqplgcrfam In some embodiments, a soluble PD-1 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 73.

In some embodiments, a soluble PD-L1 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 74.

In some embodiments, a soluble TIGIT protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 75.

In some embodiments, a soluble CD1A protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 76.

In some embodiments, a soluble TIM3 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 77.

Recombinant Antibodies

In some examples, NK activating agent can be: an agonistic antibody that binds specifically to an IL-2 receptor (see, e.g., those described in Gaulton et al., *Clinical Immunology and Immunopathology* 36(1):18-29, 1985), an agonistic antibody that binds specifically to an IL-7 receptor, an agonistic antibody that binds specifically to IL-12 receptor (see, e.g., those described in Rogge et al., *J. Immunol.* 162(7): 3926-3932, 1999), an agonistic antibody that binds specifically to IL-15 receptor, an agonistic antibody that binds specifically to IL-21 receptor (see, e.g., those described in U.S. Patent Application Publication No. 2006/159655), an agonistic antibody that binds specifically to IL-33 receptor (see, e.g., those described in U.S. Patent Application Publication No. 2007/160579), an antagonistic antibody that binds specifically to PD-1 (see, e.g., those described in U.S. Pat. No. 7,521,051), an antibody that binds specifically to PD-L1 (see, e.g., those described in U.S. Pat. No. 8,217,149), an antibody that binds specifically to TGF-β, an antagonistic antibody that binds specifically to TGF-β receptor (see, e.g., those described in European Patent Application Publication No. 1245676 A1), an antagonistic antibody that binds specifically to TIGIT (see, e.g., those described in WO 2017/053748), an antibody that binds specifically to a ligand of TIGIT (see, e.g., those described in WO 2011/127324), an antagonistic antibody that binds specifically to CD1 (see, e.g., those described in Szalay et al., *J. Immunol.* 162(12):6955-6958, 1999), an antibody that binds specifically to a ligand of CD1 (see, e.g., those described in Kain et al., *Immunity* 41(4):543-554, 2014), an antagonistic antibody that binds specifically to TIM-3 (see, e.g., those described in U.S. Patent Application Publication No. 2015/218274), an antibody that binds specifically to a ligand of TIM-3 (see, e.g., those described in U.S. Patent Application Publication No. 2017/283499), an agonistic antibody that binds specifically to CD69 (see, e.g., those described in Moretta et al., Journal of Experimental Medicine 174:1393, 1991), an agonistic antibody that binds specifically to CD25, CD59, an agonistic antibody that binds specifically to CD352 (see, e.g., those described in Yigit et al., *Oncotarget* 7:26346-26360, 2016), an agonistic antibody that binds specifically to NKp80 (see, e.g., those described in Peipp et al., *Oncotarget* 6:32075-32088, 2015), an agonistic antibody that binds specifically to DNAM-1, an agonistic antibody that binds specifically to 2B4 (see, e.g., those described in Sandusky et al., *European J. Immunol.* 36:3268-3276, 2006), an agonistic antibody that binds specifically to NKp30 (see, e.g., those described in Kellner et al., *OncoImmunology* 5:1-12, 2016), an agonistic antibody that binds specifically to NKp44, an agonistic antibody that binds specifically to NKp46 (see, e.g., those described in Xiong et al., *J. Clin. Invest.* 123:4264-4272, 2013), an agonistic antibody that binds specifically to NKG2D (see, e.g., those described in Kellner et al., *OncoImmunology* 5:1-12, 2016), an agonistic antibody that binds specifically to KIR2DS1 (see, e.g., those described in Xiong et al., *J. Clin. Invest.* 123:4264-4272, 2013), an agonistic antibody that binds specifically to KIR2Ds2/3 (see, e.g., those described in Borgerding et al., *Exp. Hematology* 38:213-221, 2010), an agonistic antibody that binds specifically to KIR2DL4 (see, e.g., those described in Miah et al., *J. Immunol.* 180:2922-32, 2008), an agonistic antibody that binds specifically to KIR2DS4 (see, e.g., those described in Czaja et al., *Genes and Immunity* 15:33-37, 2014), an agonistic antibody that binds specifically to KIR2DS5 (see, e.g., those described in Czaja et al., *Genes and Immunity* 15:33-37, 2014), an agonistic antibody that binds specifically to KIR3DS1 (see, e.g., those described in Czaja et al., *Genes and Immunity* 15:33-37, 2014), an antagonistic antibody that binds specifically to Siglec-7 (see, e.g., those described in Hudak et al., *Nature Chemical Biology* 10:69-75, 2014), an antagonistic antibody that binds specifically to IRP60 (see, e.g., those described in Bachelet et al., *J. Biol. Chem.* 281:27190-27196, 2006), an antagonistic antibody that binds specifically to Tactile (see, e.g., those described in Brooks et al., *Eur. J. Cancer* 61 (Suppl. 1):S189, 2016), an antagonistic antibody that binds specifically to IL1R8 (see, e.g., those described in Molgora et al., *Frontiers Immunol.* 7:1, 2016), an antagonistic antibody that binds specifically to NKG2A/KLRD1 (see, e.g., those described in Kim et al., *Infection Immunity* 76:5873-5882, 2008), an antagonistic antibody that binds specifically to KIR2DL1 (see, e.g., those described in Weiner et al., *Cell* 148:1081-1084, 2012), an antagonistic antibody that binds specifically to KIR2DL2/3 (see, e.g., those described in Weiner et al., *Cell* 148:1081-1084, 2012), an antagonistic antibody that binds specifically to KIR2DL5 (see, e.g., those described in U.S. Pat. No. 9,067,997), and an antagonistic antibody that binds specifically KIR3DL1 (see, e.g., those described in U.S. Pat. No. 9,067,997), an antagonistic antibody that binds specifically to KIR3DL2 (see, e.g., those described in U.S. Pat. No. 9,067,997), an antagonistic antibody that binds specifically to ILT2/LIR-1 (see, e.g., those described in U.S. Pat. No. 8,133,485), and an antagonistic antibody that binds specifically to LAG-2.

A recombinant antibody that is an NK cell activating agent can be any of exemplary types of antibodies (e.g., a human or humanized antibody) or any of the exemplary antibody fragments described herein. A recombinant antibody that is an NK cell activating agent can include, e.g., any of the antigen-binding domains described herein.

Recombinant Interleukins or Cytokines

In some examples, NK activating agents can be, e.g., a soluble IL-2, a soluble IL-7, a soluble IL-12, a soluble IL-15, a soluble IL-21, and a soluble IL-33. Non-limiting examples of soluble IL-12, IL-15, IL-21, and IL-33. are provided below.

Human Soluble IL-2

(SEQ ID NO: 78)

aptsssstkkt qlqlehllld lqmilnginn yknpkltrml tfkfympkka telkhlqcle eelkpleevl nlaqsknfhl rprdlisnin vivlelkgse ttfmceyade tativeflnr witfcgsiis tlt Human Soluble IL-7

(SEQ ID NO: 79)

dcdiegkdgkqyesv lmvsidqlld smkeigsncl nnefnffkrh icdankegmf lfraarklrq flkmnstgdf dlhllkvseg ttillnctgq vkgrkpaalg eaqptkslee nkslkeqkkl ndlcflkrll qeiktcwnki lmgtkeh Human Soluble IL-12 subunit alpha (SEQ ID NO: 80)

rnlpvatp dpgmfpclhh sqnllravsn mlqkarqtle fypctseeid heditkdkts tveaclplel tknesclnsr etsfitngsc lasrktsfmm alclssiyed lkmyqvefkt mnakllmdpk rqifldqnml avidelmqal nfnsetvpqk ssleepdfyk tkiklcillh afriravtid rvmsylnas Human Soluble IL-12 subunit beta (SEQ ID NO: 81)

iwelkkdv yvveldwypd apgemvvltc dtpeedgitw tldqssevlg sgktltiqvk efgdagqytc hkggevlshs llllhkkedg iwstdilkdq kepknktflr ceaknysgrf tcwwlttist dltfsvkssr gssdpqgvtc gaatlsaerv rgdnkeyeys vecqedsacp aaeeslpiev mvdavhklky enytssffir diikpdppkn lqlkplknsr qvevsweypd twstphsyfs ltfcvqvqgk skrekkdrvf tdktsatvic rknasisvra qdryysssws ewasvpcs Human Soluble IL-15

(SEQ ID NO: 82)

Nwvnvisdlkki edliqsmhid atlytesdvh psckvtamkc fllelqvisl esgdasihdt venliilann slssngnvte sgckeceele eknikeflqs fvhivqmfin ts Human Soluble IL-21

(SEQ ID NO: 83)

qgqdrhmi rmrqlidivd qlknyvndlv peflpapedv etncewsafs cfqkaqlksa ntgnneriin vsikklkrkp pstnagrrqk hrltcpscds yekkppkefl erfksllqkm ihqhlssrth gseds -continued Human Soluble IL-33

(SEQ ID NO: 84)

mkpkmkystn kistakwknt askalcfklg ksqqkakevc pmyfmklrsg lmikkeacyf rrettkrpsl ktgrkhkrhl vlaacqqqst vecfafgisg vqkytralhd ssitgispit eylaslstyn dqsitfaled esyeiyvedl kkdekkdkvl lsyyesqhps nesgdgvdgk mlmvtlsptk dfwlhannke hsvelhkcek plpdqaffvl hnmhsncvsf ecktdpgvfi gvkdnhlali kvdssenlct enilfklset In some embodiments, a soluble IL-2 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 78.

In some embodiments, a soluble IL-7 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 79.

In some embodiments, a soluble IL-2 protein includes a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 80 and a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 81.

In some embodiments, a soluble IL-15 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 82.

In some embodiments, a soluble IL-21 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 83.

In some embodiments, a soluble IL-33 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 84.

Soluble Cytokine or Interleukin Receptors

In some examples of any of the soluble cytokine or interleukin receptors described herein, the soluble cytokine or interleukin receptors can be a soluble TGF-β receptor. In some examples, the soluble TGF-β receptor is a soluble TGF-β receptor I (TGF-βRI) (see, e.g., those described in Docagne et al., *Journal of Biological Chemistry* 276(49): 46243-46250, 2001), a soluble TGF-β receptor II (TGF-βRII) (see, e.g., those described in Yung et al., *Am. J. Resp. Crit. Care Med.* 194(9):1140-1151, 2016), a soluble TGF-βRIII (see, e.g., those described in Heng et al., *Placenta*

57:320, 2017). In some examples, the soluble TGF-β receptor is a receptor "trap" for TGF-β (see, e.g., those described in Zwaagstra et al., *Mol. Cancer Ther.* 11(7):1477-1487, 2012, and those described in De Crescenzo et al. *Transforming Growth Factor-β* in *Cancer Therapy, Volume II*, pp 671-684).

Additional examples of soluble cytokine or soluble interleukin receptors are known in the art.

Single Chain Chimeric Polypeptides

Non-limiting examples of NK cell activating agents are single-chain chimeric polypeptides that include: (i) a first target-binding domain (e.g., any of the target-binding domains described herein or known in the art), (ii) a soluble tissue factor domain (e.g., any of the exemplary soluble tissue factor domains described herein or known in the art), and (iii) as second target-binding domain (e.g., any of the target-binding domains described herein or known in the art).

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to

```
                                                (SEQ ID NO: 85)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL

TDEIVKDVKQTYLARVFSYPAGNVESTGSAGEPLYENSPEFTPYLETNLG

QPTIQSFEQVGTKVNVTVEDERTLVRRNNTFLSLRDVFGKDLIYTLYYWK

SSSSGKKTAKTNTNEFLIDVDKGENYCFSVQAVIPSRTVNRKSTDSPVEC

MGQEKGEFREVQLQQSGPELVKPGASVKMSCKASGYTFTSYVIQWVKQKP

GQGLEWIGSINPYNDYTKYNEKFKGKATLTSDKSSITAYMEFSSLTSEDS

ALYYCARWGDGNYWGRGTTLTVSSGGGGSGGGGSGGGGSDIEMTQSPAIM

SASLGERVTMTCTASSSVSSSYFHWYQQKPGSSPKLCIYSTSNLASGVPP

RFSGSGSTSYSLTISSMEAEDAATYFCHQYHRSPTFGGGTKLETKR.
```

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to

```
                                                (SEQ ID NO: 86)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGGACAAG

GTACCACTTTAACCGTCAGCAGCTCCGGCACCACCAATACCGTGGCCGCT

TATAACCTCACATGGAAGAGCACCAACTTCAAGACAATTCTGGAATGGGA

ACCCAAGCCCGTCAATCAAGTTTACACCGTGCAGATCTCCACCAAATCCG
```

-continued

```
GAGACTGGAAGAGCAAGTGCTTCTACACAACAGACACCGAGTGTGATTTA

ACCGACGAAATCGTCAAGGACGTCAAGCAAACCTATCTGGCTCGGGTCTT

TTCCTACCCCGCTGGCAATGTCGAGTCCACCGGCTCCGCTGGCGAGCCTC

TCTACGAGAATTCCCCCGAATTCACCCCTTATTTAGAGACCAATTTAGGC

CAGCCTACCATCCAGAGCTTCGAGCAAGTTGGCACCAAGGTGAACGTCAC

CGTCGAGGATGAAAGGACTTTAGTGCGGCGGAATAACACATTTTTATCCC

TCCGGGATGTGTTCGGCAAAGACCTCATCTACACACTGTACTATTGGAAG

TCCAGCTCCTCCGGCAAAAAGACCGCTAAGACCAACACCAACGAGTTTTT

AATTGACGTGGACAAAGGCGAGAACTACTGCTTCAGCGTGCAAGCCGTGA

TCCCTTCTCGTACCGTCAACCGGAAGAGCACAGATTCCCCCGTTGAGTGC

ATGGGCCAAGAAAAGGGCGAGTTCCGGGAGGTCCAGCTGCAGCAGAGCGG

ACCCGAACTCGTGAAACCCGGTGCTTCCGTGAAAATGTCTTGTAAGGCCA

GCGGATACACCTTCACCTCCTATGTGATCCAGTGGGTCAAACAGAAGCCC

GGACAAGGTCTCGAGTGGATCGGCAGCATCAACCCTTACAACGACTATAC

CAAATACAACGAGAAGTTTAAGGGAAAGGCTACTTTAACCTCCGACAAAA

GCTCCATCACAGCCTACATGGAGTTCAGCTCTTTAACATCCGAGGACAGC

GCTCTGTACTATTGCGCCCGGTGGGGCGACGGCAATTACTGGGGACGGGG

CACAACACTGACCGTGAGCAGCGGAGGCGGAGGCTCCGGCGGAGGCGGAT

CTGGCGGTGGCGGCTCCGACATCGAGATGACCCAGTCCCCCGCTATCATG

TCCGCCTCTTTAGGCGAGCGGGTCACAATGACTTGTACAGCCTCCTCCAG

CGTCTCCTCCTCCTACTTCCATTGGTACCAACAGAAACCCGGAAGCTCCC

CTAAACTGTGCATCTACAGCACCAGCAATCTCGCCAGCGGCGTGCCCCCT

AGGTTTTCCGGAAGCGGAAGCACCAGCTACTCTTTAACCATCTCCTCCAT

GGAGGCTGAGGATGCCGCCACCTACTTTTGTCACCAGTACCACCGGTCCC

CCACCTTCGGAGGCGGCACCAAACTGGAGACAAAGAGG.
```

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to

```
                                                (SEQ ID NO: 87)
MKWVTFISLLFLFSSAYSQIVLTQSPAIMSASPGEKVTMTCSASSSVSYM

NWYQQKSGTSPKRWIYDTSKLASGVPAHFRGSGSGTSYSLTISGMEAEDA

ATYYCQQWSSNPFTFGSGTKLEINRGGGGSGGGGSGGGGSQVQLQQSGAE

LARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWG

QGTTLTVSSSGTTNTVAAYNLTWKSTNFKTILEWEPKPVNQVYTVQISTK

SGDWKSKCFYTTDTECDLTDEIVKDVKQTYLARVFSYPAGNVESTGSAGE

PLYENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFSVQA

VIPSRTVNRKSTDSPVECMGQEKGEFREVQLQQSGPELVKPGASVKMSCK

ASGYTFTSYVIQWVKQKPGQGLEWIGSINPYNDYTKYNEKFKGKATLTSD
```

-continued

KSSITAYMEFSSLTSEDSALYYCARWGDGNYWGRGTTLTVSSGGGGSGGG

GSGGGGSDIEMTQSPAIMSASLGERVTMTCTASSSVSSSYFHWYQQKPGS

SPKLCIYSTSNLASGVPPRFSGSGSTSYSLTISSMEAEDAATYFCHQYHR

SPTFGGGTKLETKR.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 88)

ATGAAGTGGGTGACCTTCATCAGCTTATTATTTTTATTCAGCTCCGCCTA

TTCCCAGATCGTGCTGACCCAAAGCCCCGCCATCATGAGCGCTAGCCCCG

GTGAGAAGGTGACCATGACATGCTCCGCTTCCAGCTCCGTGTCCTACATG

AACTGGTATCAGCAGAAAAGCGGAACCAGCCCCAAAAGGTGGATCTACGA

CACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGCT

GCCACCTACTATTGCCAGCAATGGAGCAGCAACCCCTTCACATTCGGATC

TGGCACCAAGCTCGAAATCAATCGTGGAGGAGGTGGCAGCGGCGGCGGTG

GATCCGGCGGAGGAGGAAGCCAAGTTCAACTCCAGCAGAGCGGCGCTGAA

CTGGCCCGGCCCGGCGCCTCCGTCAAGATGAGCTGCAAGGCTTCCGGCTA

TACATTTACTCGTTACACAATGCATTGGGTCAAGCAGAGGCCCGGTCAAG

GTTTAGAGTGGATCGGATATATCAACCCTTCCCGGGGCTACACCAACTAT

AACCAAAAGTTCAAGGATAAAGCCACTTTAACCACTGACAAGAGCTCCTC

CACCGCCTACATGCAGCTGTCCTCTTTAACCAGCGAGGACTCCGCTGTTT

ACTACTGCGCTAGGTATTACGACGACCACTACTGTTTAGACTATTGGGGA

CAAGGTACCACTTTAACCGTCAGCAGCTCCGGCACCACCAATACCGTGGC

CGCTTATAACCTCACATGGAAGAGCACCAACTTCAAGACAATTCTGGAAT

GGGAACCCAAGCCCGTCAATCAAGTTTACACCGTGCAGATCTCCACCAAA

TCCGGAGACTGGAAGAGCAAGTGCTTCTACACAACAGACACCGAGTGTGA

TTTAACCGACGAAATCGTCAAGGACGTCAAGCAAACCTATCTGGCTCGGG

TCTTTTCCTACCCCGCTGGCAATGTCGAGTCCACCGGCTCCGCTGGCGAG

CCTCTCTACGAGAATTCCCCCGAATTCACCCCTTATTTAGAGACCAATTT

AGGCCAGCCTACCATCCAGAGCTTCGAGCAAGTTGGCACCAAGGTGAACG

TCACCGTCGAGGATGAAAGGACTTTAGTGCGGCGGAATAACACATTTTTA

TCCCTCCGGGATGTGTTCGGCAAAGACCTCATCTACACACTGTACTATTG

GAAGTCCAGCTCCTCCGGCAAAAAGACCGCTAAGACCAACACCAACGAGT

TTTTAATTGACGTGGACAAAGGCGAGAACTACTGCTTCAGCGTGCAAGCC

GTGATCCCTTCTCGTACCGTCAACCGGAAGAGCACAGATTCCCCCGTTGA

GTGCATGGGCCAAGAAAAGGGCGAGTTCCGGGAGGTCCAGCTGCAGCAGA

GCGGACCCGAACTCGTGAAACCCGGTGCTTCCGTGAAAATGTCTTGTAAG

GCCAGCGGATACACCTTCACCTCCTATGTGATCCAGTGGGTCAAACAGAA

-continued

GCCCGGACAAGGTCTCGAGTGGATCGGCAGCATCAACCCTTACAACGACT

ATACCAAATACAACGAGAAGTTTAAGGGAAAGGCTACTTTAACCTCCGAC

AAAAGCTCCATCACAGCCTACATGGAGTTCAGCTCTTTAACATCCGAGGA

CAGCGCTCTGTACTATTGCGCCCGGTGGGGCGACGGCAATTACTGGGGAC

GGGGCACAACACTGACCGTGAGCAGCGGAGGCGGAGGCTCCGGCGGAGGC

GGATCTGGCGGTGGCGGCTCCGACATCGAGATGACCCAGTCCCCCGCTAT

CATGTCCGCCTCTTTAGGCGAGCGGGTCACAATGACTTGTACAGCCTCCT

CCAGCGTCTCCTCCTCCTACTTCCATTGGTACCAACAGAAACCCGGAAGC

TCCCCTAAACTGTGCATCTACAGCACCAGCAATCTCGCCAGCGGCGTGCC

CCCTAGGTTTTCCGGAAGCGGAAGCACCAGCTACTCTTTAACCATCTCCT

CCATGGAGGCTGAGGATGCCGCCACCTACTTTTGTCACCAGTACCACCGG

TCCCCCACCTTCGGAGGCGGCACCAAACTGGAGACAAAGAGG.

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 89)

VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKRSGTTNTVAAYNLTW

KSTNFKTILEWEPKPVNQVYTVQISTKSGDWKSKCFYTTDTECDLTDEIV

KDVKQTYLARVFSYPAGNVESTGSAGEPLYENSPEFTPYLETNLGQPTIQ

SFEQVGTKVNVTVEDERTLVRRNNTFLSLRDVFGKDLIYTLYYWKSSSSG

KKTAKTNTNEFLIDVDKGENYCFSVQAVIPSRTVNRKSTDSPVECMGQEK

GEFREQIVLTQSPAIMSASPGEKVTMTCSASSSVSYMNWYQQKSGTSPKR

WIYDTSKLASGVPAHFRGSGSGTSYSLTISGMEAEDAATYYCQQWSSNPF

TFGSGTKLEINRGGGGSGGGGSGGGGSQVQLQQSGAELARPGASVKMSCK

ASGYTFTRYTMHWVKQRPGQGLEWIGYINPSRGYTNYNQKFKDKATLTTD

KSSSTAYMQLSSLTSEDSAVYYCARYYDDHYCLDYWGQGTTLTVSS.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 90)

GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

-continued

CACTCTGACAAGCGACAAGAGCTCCATTACCGCCTACATGGAGTTTTCCT
CTTTAACTTCTGAGGACTCCGCTTTATACTATTGCGCTCGTTGGGGCGAT
GGCAATTATTGGGGCCGGGGAACTACTTTAACAGTGAGCTCCGGCGGCGG
CGGAAGCGGAGGTGGAGGATCTGGCGGTGGAGGCAGCGACATCGAGATGA
CACAGTCCCCCGCTATCATGAGCGCCTCTTTAGGAGAACGTGTGACCATG
ACTTGTACAGCTTCCTCCAGCGTGAGCAGCTCCTATTTCCACTGGTACCA
GCAGAAACCCGGCTCCTCCCCTAAACTGTGTATCTACTCCACAAGCAATT
TAGCTAGCGGCGTGCCTCCTCGTTTTAGCGGCTCCGGCAGCACCTCTTAC
TCTTTAACCATTAGCTCTATGGAGGCCGAAGATGCCGCCACATACTTTTG
CCATCAGTACCACCGGTCCCCTACCTTTGGCGGAGGCACAAAGCTGGAGA
CCAAGCGGAGCGGCACCACCAACACAGTGGCCGCCTACAATCTGACTTGG
AAATCCACCAACTTCAAGACCATCCTCGAGTGGGAGCCCAAGCCCGTTAA
TCAAGTTTATACCGTGCAGATTTCCACCAAGAGCGGCGACTGGAAATCCA
AGTGCTTCTATACCACAGACACCGAGTGCGATCTCACCGACGAGATCGTC
AAAGACGTGAAGCAGACATATTTAGCTAGGGTGTTCTCCTACCCCGCTGG
AAACGTGGAGAGCACCGGATCCGCTGGAGAGCCTTTATACGAGAACTCCC
CCGAATTCACCCCCTATCTGGAAACCAATTTAGGCCAGCCCACCATCCAG
AGCTTCGAACAAGTTGGCACAAAGGTGAACGTCACCGTCGAAGATGAGAG
GACTTTAGTGCGGAGGAACAATACATTTTTATCCTTACGTGACGTCTTCG
GCAAGGATTTAATCTACACACTGTATTACTGGAAGTCTAGCTCCTCCGGC
AAGAAGACCGCCAAGACCAATACCAACGAATTTTTAATTGACGTGGACAA
GGGCGAGAACTACTGCTTCTCCGTGCAAGCTGTGATCCCCTCCCGGACAG
TGAACCGGAAGTCCACCGACTCCCCCGTGGAGTGCATGGGCCAAGAGAAG
GGAGAGTTTCGTGAGCAGATCGTGCTGACCCAGTCCCCCGCTATTATGAG
CGCTAGCCCCGGTGAAAAGGTGACTATGACATGCAGCGCCAGCTCTTCCG
TGAGCTACATGAACTGGTATCAGCAGAAGTCCGGCACCAGCCCTAAAAGG
TGGATCTACGACACCAGCAAGCTGGCCAGCGGCGTCCCCGCTCACTTTCG
GGGCTCCGGCTCCGGAACAAGCTACTCTCTGACCATCAGCGGCATGGAAG
CCGAGGATGCCGCTACCTATTACTGTCAGCAGTGGAGCTCCAACCCCTTC
ACCTTTGGATCCGGCACCAAGCTCGAGATTAATCGTGGAGGCGGAGGTAG
CGGAGGAGGCGGATCCGGCGGTGGAGGTAGCCAAGTTCAGCTCCAGCAAA
GCGGCGCCGAACTCGCTCGGCCCGGCGCTTCCGTGAAGATGTCTTGTAAG
GCCTCCGGCTATACCTTCACCCGGTACACAATGCACTGGGTCAAGCAACG
GCCCGGTCAAGGTTTAGAGTGGATTGGCTATATCAACCCCTCCCGGGGCT
ATACCAACTACAACCAGAAGTTCAAGGACAAAGCCACCCTCACCACCGAC
AAGTCCAGCAGCACCGCTTACATGCAGCTGAGCTCTTTAACATCCGAGGA
TTCCGCCGTGTACTACTGCGCTCGGTACTACGACGATCATTACTGCCTCG
ATTACTGGGGCCAAGGTACCACCTTAACAGTCTCCTCC.

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 91)

MKWVTFISLLFLFSSAYSVQLQQSGPELVKPGASVKMSCKASGYTFTSYV
IQWVKQKPGQGLEWIGSINPYNDYTKYNEKFKGKATLTSDKSSITAYMEF
SSLTSEDSALYYCARWGDGNYWGRGTTLTVSSGGGGSGGGGSGGGGSDIE
MTQSPAIMSASLGERVTMTCTASSSVSSSYFHWYQQKPGSSPKLCIYSTS
NLASGVPPRFSGSGSTSYSLTISSMEAEDAATYFCHQYHRSPTFGGGTKL
ETKRSGTTNTVAAYNLTWKSTNFKTILEWEPKPVNQVYTVQISTKSGDWK
SKCFYTTDTECDLTDEIVKDVKQTYLARVFSYPAGNVESTGSAGEPLYEN
SPEFTPYLETNLGQPTIQSFEQVGTKVNVTVEDERTLVRRNNTFLSLRDV
FGKDLIYTLYYWKSSSSGKKTAKTNTNEFLIDVDKGENYCFSVQAVIPSR
TVNRKSTDSPVECMGQEKGEFREQIVLTQSPAIMSASPGEKVTMTCSASS
SVSYMNWYQQKSGTSPKRWIYDTSKLASGVPAHFRGSGSGTSYSLTISGM
EAEDAATYYCQQWSSNPFTFGSGTKLEINRGGGGSGGGGSGGGGSQVQLQ
QSGAELARPGASVKMSCKASGYTFTRYTMHWVKQRPGQGLEWIGYINPSR
GYTNYNQKFKDKATLTTDKSSSTAYMQLSSLTSEDSAVYYCARYYDDHYC
LDYWGQGTTLTVSS.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 92)

ATGAAATGGGTCACCTTCATCTCTTTACTGTTTTTATTTAGCAGCGCCTA
CAGCGTGCAGCTGCAGCAGTCCGGACCCGAACTGGTCAAGCCCGGTGCCT
CCGTGAAAATGTCTTGTAAGGCTTCTGGCTACACCTTTACCTCCTACGTC
ATCCAATGGGTGAAGCAGAAGCCCGGTCAAGGTCTCGAGTGGATCGGCAG
CATCAATCCCTACAACGATTACACCAAGTATAACGAAAAGTTTAAGGGCA
AGGCCACTCTGACAAGCGACAAGAGCTCCATTACCGCCTACATGGAGTTT
TCCTCTTTAACTTCTGAGGACTCCGCTTTATACTATTGCGCTCGTTGGGG
CGATGGCAATTATTGGGGCCGGGGAACTACTTTAACAGTGAGCTCCGGCG
GCGGCGGAAGCGGAGGTGGAGGATCTGGCGGTGGAGGCAGCGACATCGAG
ATGACACAGTCCCCCGCTATCATGAGCGCCTCTTTAGGAGAACGTGTGAC
CATGACTTGTACAGCTTCCTCCAGCGTGAGCAGCTCCTATTTCCACTGGT
ACCAGCAGAAACCCGGCTCCTCCCCTAAACTGTGTATCTACTCCACAAGC
AATTTAGCTAGCGGCGTGCCTCCTCGTTTTAGCGGCTCCGGCAGCACCTC
TTACTCTTTAACCATTAGCTCTATGGAGGCCGAAGATGCCGCCACATACT
TTTGCCATCAGTACCACCGGTCCCCTACCTTTGGCGGAGGCACAAAGCTG
GAGACCAAGCGGAGCGGCACCACCAACACAGTGGCCGCCTACAATCTGAC
TTGGAAATCCACCAACTTCAAGACCATCCTCGAGTGGGAGCCCAAGCCCG
TTAATCAAGTTTATACCGTGCAGATTTCCACCAAGAGCGGCGACTGGAAA
TCCAAGTGCTTCTATACCACAGACACCGAGTGCGATCTCACCGACGAGAT
CGTCAAAGACGTGAAGCAGACATATTTAGCTAGGGTGTTCTCCTACCCCG

-continued

```
CTGGAAACGTGGAGAGCACCGGATCCGCTGGAGAGCCTTTATACGAGAAC
TCCCCCGAATTCACCCCCTATCTGGAAACCAATTTAGGCCAGCCCACCAT
CCAGAGCTTCGAACAAGTTGGCACAAAGGTGAACGTCACCGTCGAAGATG
AGAGGACTTTAGTGCGGAGGAACAATACATTTTTATCCTTACGTGACGTC
TTCGGCAAGGATTTAATCTACACACTGTATTACTGGAAGTCTAGCTCCTC
CGGCAAGAAGACCGCCAAGACCAATACCAACGAATTTTTAATTGACGTGG
ACAAGGGCGAGAACTACTGCTTCTCCGTGCAAGCTGTGATCCCCTCCCGG
ACAGTGAACCGGAAGTCCACCGACTCCCCCGTGGAGTGCATGGGCCAAGA
GAAGGGAGAGTTTCGTGAGCAGATCGTGCTGACCCAGTCCCCCGCTATTA
TGAGCGCTAGCCCCGGTGAAAAGGTGACTATGACATGCAGCGCCAGCTCT
TCCGTGAGCTACATGAACTGGTATCAGCAGAAGTCCGGCACCAGCCCTAA
AAGGTGGATCTACGACACCAGCAAGCTGGCCAGCGGCGTCCCCGCTCACT
TTCGGGGCTCCGGCTCCGGAACAAGCTACTCTCTGACCATCAGCGGCATG
GAAGCCGAGGATGCCGCTACCTATTACTGTCAGCAGTGGAGCTCCAACCC
CTTCACCTTTGGATCCGGCACCAAGCTCGAGATTAATCGTGGAGGCGGAG
GTAGCGGAGGAGGCGGATCCGGCGGTGGAGGTAGCCAAGTTCAGCTCCAG
CAAAGCGGCGCCGAACTCGCTCGGCCCGGCGCTTCCGTGAAGATGTCTTG
TAAGGCCTCCGGCTATACCTTCACCCGGTACACAATGCACTGGGTCAAGC
AACGGCCCGGTCAAGGTTTAGAGTGGATTGGCTATATCAACCCCTCCCGG
GGCTATACCAACTACAACCAGAAGTTCAAGGACAAAGCCACCCTCACCAC
CGACAAGTCCAGCAGCACCGCTTACATGCAGCTGAGCTCTTTAACATCCG
AGGATTCCGCCGTGTACTACTGCGCTCGGTACTACGACGATCATTACTGC
CTCGATTACTGGGGCCAAGGTACCACCTTAACAGTCTCCTCC.
```

Some embodiments of any of the single-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptides can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide can directly abut the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein or known in the art). In some embodiments, the single-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the single-chain chimeric polypeptides described herein, the first target-binding domain (e.g., any of the target-binding domains described herein), the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Multi-Chain Chimeric Polypeptides—Type A

Non-limiting examples of NK cell activating agents are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more additional target-binding domains is an antigen-binding domain. In some embodiments, the first target-binding domain, the second target-binding domain, and the one or more additional target-binding domains are each an antigen-binding domain (e.g., a scFv or a single-domain antibody).

In some embodiments of any of the multi-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain (e.g., any of the target-binding domains described herein, the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain (e.g., any of the target-binding domains described herein), the second target-binding domain (e.g., any of the target-binding domains described herein), and the one or more additional binding domains (e.g., any of the target-binding described herein) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Multi-Chain Chimeric Polypeptides—Type B

Non-limiting examples of NK cell activating agents are multi-chain chimeric polypeptides that include: (a) a first and second chimeric polypeptide each including: (i) a first target-binding domain; (ii) a Fc domain; and (iii) a first domain of a pair of affinity domains; and (b) a third and fourth chimeric polypeptide each including: (i) a second domain of a pair of affinity domains; and (ii) a second target-binding domain, where the first and second chimeric polypeptides and the third and fourth chimeric polypeptides associate through the binding of the first domain and the second domain of the pair of affinity domains, and the first and second chimeric polypeptides associate through their Fc domains.

In some embodiments of any of the multi-chain chimeric polypeptides described herein, the first target-binding domain (e.g., any of the first target-binding domains described herein) and the Fc domain (e.g., any of the exemplary Fc domains described herein) directly abut each other in the first and second chimeric polypeptides. In some embodiments of any of the multi-chain chimeric polypeptides described herein, the first and second chimeric polypeptides further comprise a linker sequence (e.g., any of the exemplary linker sequences described herein or known in the art) between the first target-binding domain (e.g., any of the exemplary first target-binding domains described herein) and the Fc domain (e.g., any of the exemplary Fc domains described herein) in the first and second chimeric polypeptides.

In some embodiments of any of the multi-chain chimeric polypeptides described herein, the Fc domain (e.g., any of the exemplary Fc domains described herein) and the first domain of the pair of affinity domains (e.g., any of the exemplary first domains of any of the exemplary pairs of affinity domains described herein) directly abut each other in the first and second chimeric polypeptide. In some embodiments of any of the multi-chain chimeric polypeptides described herein, the first and second chimeric polypeptide further comprises a linker sequence (e.g., any of the exemplary linker sequences described herein or known in the art) between the Fc domain (e.g., any of the exemplary Fc domains described herein) and the first domain of the pair of affinity domains (e.g., any of the exemplary first domains of any of the exemplary pairs of affinity domains described herein) in the first and second chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the third and fourth chimeric polypeptide. In some embodiments of any of the multi-chain chimeric polypeptides described herein, the third and fourth chimeric polypeptide further comprise a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the third and fourth chimeric polypeptide.

In some embodiments of any of the multi-chain chimeric polypeptides described herein, the first target-binding domain and the second target-binding domain bind specifically to the same antigen. In some embodiments of any of the multi-chain chimeric polypeptides described herein, the first target-binding domain and the second target-binding domain bind specifically to the same epitope. In some embodiments of any of the multi-chain chimeric polypeptides described herein, the first target-binding domain and the second target-binding domain include the same amino acid sequence. In some embodiments of any of the multi-chain chimeric polypeptides described herein, the first target-binding domain and the second target-binding domain bind specifically to different antigens. In some embodiments of any of the multi-chain chimeric polypeptides described herein, one or both of the first target-binding domain and the second target-binding domain is an antigen-binding domain (e.g., any of the exemplary second target-binding domains described herein). In some embodiments of any of the multi-chain chimeric polypeptides described herein, the first target-binding domain and the second target-binding domain are each antigen-binding domains (e.g., any of the exemplary second target-binding domains described herein). In some embodiments of any of the multi-chain chimeric polypeptides described herein, the antigen-binding domain (e.g., any of the exemplary second target-binding domains described herein) includes a scFv or a single domain antibody.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain and the second target-binding domain can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain and the second target-binding domain is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and PE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the Ile-$^{154}$-Arg$^{152}$ bond in the short linker region between the EGF2 and the protease domain. This cleavage results in the light and heavy chains being held together by a single disulfide bond of Cys$^{135}$ and Cys$^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of His$^{193}$, Asp$^{242}$, and Ser$^{344}$, and binding of a single $Ca^{2+}$ ion within the FVIIa protease domain is critical for its catalytic activity. Proteolytic activation of FVII to FVIIa frees the newly formed amino terminus at Ile$^{153}$ to fold back and be inserted into the activation pocket forming a salt bridge with the carboxylate of Asp$^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from $Asp^{58}$ onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

Exemplary Soluble Human Tissue Factor Domain
(SEQ ID NO: 93)

SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE

Exemplary Nucleic Acid Encoding Soluble Human Tissue Factor Domain
(SEQ ID NO: 94)

AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG

-continued

Exemplary Soluble Mouse Tissue Factor Domain (SEQ ID NO: 95)

```
agipekafnltwistdfktilewqpkptnytytvqisdrsrnwknkcfst

tdtecdltdeivkdvtwayeakvlsvprrnsvhgdgdqlvihgeeppftn

apkflpyrdtnlggpviqqfeqdgrklnvvvkdsltlvrkngtfltlrqv

fgkdlgyiityrkgsstgkktnitntnefsidveegvsycffvqamifsr

ktnqnspgsstvcteqwksflge
```

Exemplary Soluble Rat Tissue Factor Domain (SEQ ID NO: 96)

```
Agtppgkafnltwistdfktilewqpkptnytytvqisdrsrnwkykctg

ttdtecdltdeivkdvnwtyearvlsvpwrnsthgketlfgthgeeppft

narkflpyrdtkigqpviqkyeqggtklkvtvkdsftlvrkngtfltlrq

vfgndlgyiltyrkdsstgrktntthtneflidvekgvsycffaqavifs

rktnhkspesitkcteqwksvlge
```

Exemplary Mutant Soluble Human Tissue Factor Domain (SEQ ID NO: 97)

```
SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE
```

Exemplary Mutant Soluble Human Tissue Factor Domain (SEQ ID NO: 98)

```
SGTTNTVAAYNLTWKSTNFATALEWEPKPVNQVYTVQISTKSGDAKSKCF

YTTDTECALTDEIVKDVKQTYLARVFSYPAGNVESTGSAGEPLAENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE
```

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 93, 95, 96, 97 or 98. In some embodiments, a soluble tissue factor domain can include a sequence of SEQ ID NO: 93, 95, 96, 97, or 98, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 97 or SEQ ID NO: 98.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 94.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., *Protein Engineering, Design & Selection* 27(10):325-330, 2014; Priyanka et al., *Protein Sci.* 22(2):153-167, 2013. In some examples, the linker sequence is a synthetic linker sequence.

In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) (SEQ ID NO: 99) sequences, e.g., 1, 2, 3, 4, 5, 6, 7, 8, 9, or 10 or more GGGS (SEQ ID NO: 99) sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS (SEQ ID NO: 100) sequences. In some embodiments, the linker has one or more Gly-Gly-Ser-Gly (GGSG) (SEQ ID NO: 101) sequences, e.g., 1, 2, 3, 4, 5, 6, 7, 8, 9, or 10 or more GGSG (SEQ ID NO: 101) sequences.

In some embodiments, the linker sequence can comprise or consist of GGGGSGGGGSGGGGS (SEQ ID NO: 102). In some embodiments, the linker sequence can be encoded by a nucleic acid comprising or consisting of: GGCGGTG-GAGGATCCGGAGGAGGTGGCTCCGGCGGCGGAG-GATCT (SEQ ID NO: 103). In some embodiments, the linker sequence can comprise or consist of: GGGSGGGS (SEQ ID NO: 104), Target-Binding Domains In some embodiments of any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$M, less than $1\times10^{-8}$M, less than $1\times10^{-9}$M, less than $1\times10^{-10}$ M, less than $1\times10^{-11}$M, less than $1\times10^{-12}$M, or less than $1\times10^{-13}$ M. In some embodiments, the antigen-binding protein construct provided herein can bind to an identifying antigen with a $K_D$ of about $1\times10^{-3}$M to about $1\times10^{-5}$ M, about $1\times10^{-4}$M to about $1\times10^{-6}$M, about $1\times10^{-5}$M to about $1\times10^{-7}$M, about $1\times10^{-6}$M to about $1\times10^{-8}$M, about $1\times10^{-7}$M to about $1\times10^{-9}$M, about $1\times10^{-8}$M to about $1\times10^{-10}$ M, or about $1\times10^{-9}$M to about $1\times10^{-11}$M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain or multi-chain chimeric polypeptides described herein, the first target-binding domain and the second target-binding domain bind specifically to the same antigen. In some embodiments of these single-chain or multi-chain chimeric polypeptides, the first target-binding domain and the second target-binding domain bind specifically to the same epitope. In some embodiments of these single-chain or multi-chain chimeric polypeptides, the first target-binding domain and the second target-binding domain include the same amino acid sequence.

In some embodiments of any of the single-chain or multi-chain chimeric polypeptides described herein, the first target-binding domain and the second target-binding domain bind specifically to different antigens.

In some embodiments of any of the single-chain or multi-chain chimeric polypeptides described herein, one or both of the first target-binding domain and the second target-binding domain is an antigen-binding domain. In some embodiments of any of the single-chain or multi-chain chimeric polypeptides described herein, the first target-binding domain and the second target-binding domain are each antigen-binding domains. In some embodiments of any of the single-chain or multi-chain chimeric polypeptides described herein, the antigen-binding domain includes or is a scFv or a single domain antibody (e.g., a $V_{aH}H$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3):377-385, 2015), CD26 (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3):367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No.

9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the single-chain or multi-chain chimeric polypeptides described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain or multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014*; Muyldermans, J. Biotechnol.* 74:277-302, 2001; Muyldermans et al., *Trends Biochem. Sci.* 26:230-235, 2001*; Muyldermans, Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain or multi-chain chimeric polypeptides described herein are both VHH domains, or at least one antigen-binding domain is a VHH domain. In some embodiments, each of the antigen-binding domains in the single-chain or multi-chain chimeric polypeptides described herein are both VNAR domains, or at least one antigen-binding domain is a VNAR domain. In some embodiments, each of the antigen-binding domains in the single-chain or multi-chain chimeric polypeptides described herein are both scFv domains, or at least one antigen-binding domain is a scFv domain.

In some embodiments, two or more of polypeptides present in the single-chain or multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a 1mmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain (CHO of the heavy chain, in addition to the heavy and light chain variable domains of the Fv fragment.

A "$F(ab')_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, *Nature Reviews Drug Discovery* 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain or multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, and SCF. Non-limiting examples of soluble IL-2, IL-3, IL-7, IL-8, IL-10, IL-15, IL-17, IL-18, IL-21, PDGF-DD, and SCF are provided below.

Human Soluble IL-3

(SEQ ID NO: 105)

apmtqttplkt swvncsnmid eiithlkqpp lplldfnnln gedqdilmen nlrrpnleaf nravkslqna saiesilknl lpclplataa ptrhpihikd gdwnefrrkl tfylktlena qaqqttlsla if Human Soluble IL-8

(SEQ ID NO: 106)

egavlprsak elrcqcikty skpfhpkfik elrviesgph canteiivkl sdgrelcldp kenwvqrvve kflkraens Human Soluble IL-10

(SEQ ID NO: 107)

spgqgtqsensc thfpgnlpnm lrdlrdafsr vktffqmkdq ldnlllkesl ledfkgylgc qalsemiqfy leevmpqaen qdpdikahvn slgenlktlr lrlrrchrfl pcenkskave qvknafnklq ekgiykamse fdifinyiea ymtmkirn Human Soluble IL-17

(SEQ ID NO: 108)

gitiprn pgcpnsedkn fprtvmvnln ihnrntntnp krssdyynrs tspwnlhrne dperypsviw eakcrhlgci nadgnvdyhm nsvpiqqeil vlrrepphcp nsfrlekilv svgctcvtpi vhhva Human Soluble IL-18

(SEQ ID NO: 109)

yfgklesklsvirn lndqvlfidq gnrplfedmt dsdcrdnapr tifiismykd sqprgmavti svkcekistl scenkiisfk emnppdnikd tksdiiffqr svpghdnkmq fesssyegyf lacekerdlf klilkkedel gdrsimftvq ned Human Soluble PDGF-DD (SEQ ID NO: 110)

rdtsatpqsasi kalrnanlrr desnhltdly rrdetiqvkg ngyvqsprfp nsyprnlllt wrlhsqentr iqlvfdnqfg leeaendicr ydfvevedis etstiirgrw cghkevppri ksrtnqikit fksddyfvak pgfkiyysll edfqpaaase tnwesvtssi sgvsynspsv tdptliadal dkkiaefdtv edllkyfnpe swqedlenmy ldtpryrgrs yhdrkskvdl drlnddakry sctprnysvn ireelklanv vffprcllvq rcggncgcgt vnwrsctcns gktvkkyhev lqfepghikr rgraktmalv diqldhherc dcicssrppr Human Soluble SCF (SEQ ID NO: 111)

egicrnrvtnnvkdv tklvanlpkd ymitlkyvpg mdvlpshcwi semvvqlsds ltdlldkfsn iseglsnysi idklvnivdd lvecvkenss kdlkksfksp eprlftpeef frifnrsida fkdfvvaset sdcvvsstls pekdsrvsvt kpfmlppvaa -continued sslrndssss nrkaknppgd sslhwaamal palfsliigf afgalywkkr qpsltraven iqineednei smlqekeref qev Human Soluble FLT3L (SEQ ID NO: 112)

tqdcsfqhspissd favkirelsd yllqdypvtv asnlqdeelc gglwrlvlaq rwmerlktva gskmqgller vnteihfvtk cafqpppscl rfvqtnisrl lqetseqlva lkpwitrqnf srclelqcqp dsstlpppws prpleatapt apqppllll llpvglllla aawclhwqrt rrrtprpgeq vppvpspqdl llveh Additional examples of soluble interleukin proteins and soluble cytokine proteins are known in the art.

Soluble Receptor

In some embodiments of any of the single-chain or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-β RII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017), a soluble NKG2D (see, e.g., Cosman et al., *Immunity* 14(2):123-133, 2001; Costa et al., *Front. Immunol.*, Vol. 9, Article 1150, May 29, 2018; doi: 10.3389/fimmu.2018.01150), a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

Additional examples of soluble interleukin receptors and soluble cytokine receptors are known in the art.

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL-15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL-15 has a D8N or D8A amino acid substitution. In some embodiments in which one member of the pair of affinity domains is an alpha chain of human IL-15 receptor (IL-15Rα), the human IL-15Rα is a mature full-length IL-15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103:6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$M, less than $1\times10^{-9}$ M, less than $1\times10^{-10}$ M, less than $1\times10^{-11}$ M, less than $1\times10^{-12}$M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$M to about $1\times10^{-7}$ M, about $1\times10^{-6}$ M to about $1\times10^{-8}$ M, about $1\times10^{-7}$ M to about $1\times10^{-9}$M, about $1\times10^{-8}$M to about $1\times10^{-10}$ M, about $1\times10^{-9}$M to about $1\times10^{-11}$M, about $1\times10^{-10}$ M to about $1\times10^{-12}$M, about $1\times10^{-11}$M to about $1\times10^{-13}$M, about $1\times10^{-4}$ M to about $1\times10^{-5}$M, about $1\times10^{-5}$M to about $1\times10^{-6}$ M, about $1\times10^{-6}$ M to about $1\times10^{-7}$ M, about $1\times10^{-7}$ M to about $1\times10^{-8}$M, about $1\times10^{-8}$M to about $1\times10^{-9}$M, about $1\times10^{-9}$M to about $1\times10^{-10}$ M, about $1\times10^{-10}$ M to about $1\times10^{-11}$ about $1\times10^{-11}$M to about $1\times10^{-12}$M, or about $1\times10^{-12}$M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL-15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL-15Rα).

A non-limiting example of a sushi domain from an alpha chain of IL-15 receptor alpha (IL-15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSR-ERYICNSGFKRKAGTSSLTECVLNKATNVAH WTTPSLKCIR (SEQ ID NO: 113). In some embodiments, a sushi domain from an alpha chain of IL-15Rα can be encoded by a nucleic acid including

```
                                         (SEQ ID NO: 114)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDATLYTESDVHPSCKVTAMKCFLLELQVISLESGD ASIHDTVENLIILANNSLSSNGNVTESGCKECEELEEKNIKEFLQSFVHIVQMFINT S (SEQ ID NO: 115). In some embodiments, a soluble IL-15 can be encoded by a nucleic acid including the sequence of

```
                                          (SEQ ID NO: 116)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC.
```

Signal Sequence

In some embodiments, a single-chain chimeric polypeptide comprises a signal sequence at its N-terminal end. In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MKWVTFISLLFLFSSAYS (SEQ ID NO: 117). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence encoded by the nucleic acid sequence

```
                                          (SEQ ID NO: 118)
ATGAAATGGGTGACCTTTATTTCTTTACTGTTCCTCTTTAGCAGCGCCTA

CTCC,
```

-continued

```
                                          (SEQ ID NO: 119)
ATGAAGTGGGTCACATTTATCTCTTTACTGTTCCTCTTCTCCAGCGCCTA

CAGC,
or

                                          (SEQ ID NO: 120)
ATGAAATGGGTGACCTTTATTTCTTTACTGTTCCTCTTTAGCAGCGCCTA

CTCC.
```

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MKCLLYLAFLFLGVNC (SEQ ID NO: 121). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MGQIVTMFEALPHIIDEVINIVIIVLIIITSIKAVYNFATCGILALVSFLFLAGRSCG (SEQ ID NO: 122). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence: MPNHQSGSPTGSSDLLLSGKKQRPHLALRRKRRREMRKINRKVRRMNLAPIKEK TAWQHLQALISEAEEVLKTSQTPQNSLTLFLALLSVLGPPVTG (SEQ ID NO: 123). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MDSKGSSQKGSRLLLLLVVSNLLLCQGVVS (SEQ ID NO: 124). Those of ordinary skill in the art will be aware of other appropriate signal sequences for use in a first chimeric polypeptide and/or a second chimeric polypeptide of multi-chain chimeric polypeptides, or single-chain chimeric polypeptides described herein.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 125) can include one or more additional amino acids at the N-terminus or C-terminus, while still retaining the ability to direct the a first chimeric polypeptide of a multi-chain chimeric polypeptide, a second chimeric polypeptide of the multi-chain chimeric polypeptide, or both, or a single-chain chimeric polypeptide, to the secretory pathway.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence that directs the multi-chain chimeric polypeptide into the extracellular space. Such embodiments are useful in producing single-chain or multi-chain chimeric polypeptides that are relatively easy to be isolated and/or purified.

Peptide Tags

In some embodiments, a single-chain chimeric polypeptide includes a peptide tag (e.g., at the N-terminal end or the C-terminal end of the chimeric polypeptide). In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both, or a single-chain chimeric polypeptide, includes two or more peptide tags.

Exemplary peptide tags that can be included in a first chimeric polypeptide of a multi-chain chimeric polypeptide, a second chimeric polypeptide of the multi-chain chimeric polypeptide, or both, or a single-chain chimeric polypeptide include, without limitation, AviTag (GLNDIFEAQKIEWHE; SEQ ID NO: 126), a calmodulin-tag (KRRWKKNFIAVSAANRFKKISSSGAL; SEQ ID NO: 127), a polyglutamate tag (EEEEEE; SEQ ID NO: 128), an E-tag (GAPVPYPDPLEPR; SEQ ID NO: 129), a FLAG-tag (DYKDDDDK; SEQ ID NO: 130), an HA-tag, a peptide from hemagglutinin (YPYDVPDYA; SEQ ID NO: 131), a his-tag (HEIHHH (SEQ ID NO: 132); HHHHHH (SEQ ID NO: 133); HHHHHHH (SEQ ID NO: 134); HHHHHHHH (SEQ ID NO: 135); HHHHHHHHH (SEQ ID NO: 136); or HHHHHHHHHH (SEQ ID NO: 137)), a myc-tag (EQKLISEEDL; SEQ ID NO: 138), NE-tag (TKENPRSNQEESYDDNES; SEQ ID NO: 139), S-tag, (KETAAAKFERQHMDS; SEQ ID NO: 140), SBP-tag (MDEKTTGWRGGHVVEGLAGELEQLRARLEHHPQGQREP; SEQ ID NO: 141), Softag 1 (SLAELLNAGLGGS; SEQ ID NO: 142), Softag 3 (TQDPSRVG; SEQ ID NO: 143), Spot-tag (PDRVRAVSHWSS; SEQ ID NO: 144), Strep-tag (WSHPQFEK; SEQ ID NO: 145), TC tag (CCPGCC; SEQ ID NO: 146), Ty tag (EVHTNQDPLD; SEQ ID NO: 147), V5 tag (GKPIPNPLLGLDST; SEQ ID NO: 148), VSV-tag (YTDIEMNRLGK; SEQ ID NO: 149), and Xpress tag (DLYDDDDK; SEQ ID NO: 150). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both, or a single-chain chimeric polypeptide can be used in any of a variety of applications related to the multi-chain or single-chain chimeric polypeptide, respectively. For example, a peptide tag can be used in the purification of a multi-chain or single-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both, or a single-chain chimeric polypeptide, can include a myc tag; the multi-chain chimeric polypeptide that includes the myc-tagged first chimeric polypeptide, the myc-tagged second chimeric polypeptide, or both, or the myc-tagged single-chain chimeric polypeptide can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both, or a single-chain chimeric polypeptide, can include a histidine tag; the multi-chain chimeric polypeptide that includes the histidine-tagged first chimeric polypeptide, the histidine-tagged second chimeric polypeptide, or both, or the histidine-tagged single-chain chimeric polypeptide can be purified using a nickel or cobalt chelate. Those of ordinary skill in the art will be aware of other suitable tags and agents that bind those tags for use in purifying a single-chain or multi-chain chimeric polypeptide. In some embodiments, a peptide tag is removed from the first chimeric polypeptide and/or the second chimeric polypeptide of the multi-chain chimeric polypeptide, or the single-chain chimeric polypeptide after purification. In some embodiments, a peptide tag is not removed from the first chimeric polypeptide and/or the second chimeric polypeptide of the multi-chain chimeric polypeptide, or the single-chain chimeric polypeptide, after purification.

Peptide tags that can be included in a first chimeric polypeptide of a multi-chain chimeric polypeptide, a second chimeric polypeptide of the multi-chain chimeric polypeptide, or both, or a single-chain chimeric polypeptide, can be used, for example, in immunoprecipitation of the multi-chain chimeric polypeptide or single-chain chimeric polypeptide, respectively, imaging of the multi-chain chimeric polypeptide or single-chain chimeric polypeptide, respectively (e.g., via Western blotting, ELISA, flow cytometry, and/or immunocytochemistry), and/or solubilization of the multi-chain chimeric polypeptide or single-chain chimeric polypeptide, respectively.

In some embodiments, a first chimeric polypeptide of a multi-chain chimeric polypeptide, a second chimeric polypeptide of the multi-chain chimeric polypeptide, or both, or a single-chain chimeric polypeptide, includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both, or a single-chain chimeric polypeptide, can be of any suitable length. For example, peptide tags can be 5, 6, 7, 8, 9, 10, 11, 12, 13, 14, 15, 16, 17, 18, 19, 20, or more amino acids in length. In embodiments in which a single-chain or multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 138) can include one or more additional amino acids (e.g., at the N-terminus and/or the C-terminus of the peptide tag), while still retaining the ability to be bound by an antibody (e.g., 9E10).

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
QIVLTQSPAIMSASPGEKVTMTCSASSSVSYMNWYQQKSGTSPKRWIYDT
SKLASGVPAHFRGSGSGTSYSLTISGMEAEDAATYYCQQWSSNPFTFGSG
TKLEINRGGGGSGGGGSGGGGSQVQLQQSGAELARPGASVKMSCKASGYT
FTRYTMHWVKQRPGQGLEWIGYINPSRGYTNYNQKFKDKATLTTDKSSST
AYMQLSSLTSEDSAVYYCARYYDDHYCLDYWGQGTTLTVSS.

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
CAGATCGTGCTGACCCAAAGCCCCGCCATCATGAGCGCTAGCCCCGGTGA
GAAGGTGACCATGACATGCTCCGCTTCCAGCTCCGTGTCCTACATGAACT
GGTATCAGCAGAAAAGCGGAACCAGCCCCAAAAGGTGGATCTACGACACC
AGCAAGCTGGCCTCCGGAGTGCCCGCTCATTTCCGGGGCTCTGGATCCGG

-continued

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGGACAAG

GTACCACTTTAACCGTCAGCAGC.

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 153)

VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKR.

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 154)

GTCCAGCTGCAGCAGAGCGGACCCGAACTCGTGAAACCCGGTGCTTCCGT

GAAAATGTCTTGTAAGGCCAGCGGATACACCTTCACCTCCTATGTGATCC

AGTGGGTCAAACAGAAGCCCGGACAAGGTCTCGAGTGGATCGGCAGCATC

AACCCTTACAACGACTATACCAAATACAACGAGAAGTTTAAGGGAAAGGC

TACTTTAACCTCCGACAAAAGCTCCATCACAGCCTACATGGAGTTCAGCT

CTTTAACATCCGAGGACAGCGCTCTGTACTATTGCGCCCGGTGGGGCGAC

GGCAATTACTGGGGACGGGGCACAACACTGACCGTGAGCAGCGGAGGCGG

AGGCTCCGGCGGAGGCGGATCTGGCGGTGGCGGCTCCGACATCGAGATGA

CCCAGTCCCCCGCTATCATGTCCGCCTCTTTAGGCGAGCGGGTCACAATG

ACTTGTACAGCCTCCTCCAGCGTCTCCTCCTCCTACTTCCATTGGTACCA

ACAGAAACCCGGAAGCTCCCCTAAACTGTGCATCTACAGCACCAGCAATC

TCGCCAGCGGCGTGCCCCCTAGGTTTTCCGGAAGCGGAAGCACCAGCTAC

-continued

TCTTTAACCATCTCCTCCATGGAGGCTGAGGATGCCGCCACCTACTTTTG

TCACCAGTACCACCGGTCCCCCACCTTCGGAGGCGGCACCAAACTGGAGA

CAAAGAGG.

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 155)

QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL

TDEIVKDVKQTYLARVFSYPAGNVESTGSAGEPLYENSPEFTPYLETNLG

QPTIQSFEQVGTKVNVTVEDERTLVRRNNTFLSLRDVFGKDLIYTLYYWK

SSSSGKKTAKTNTNEFLIDVDKGENYCFSVQAVIPSRTVNRKSTDSPVEC

MGQEKGEFREVQLQQSGPELVKPGASVKMSCKASGYTFTSYVIQWVKQKP

GQGLEWIGSINPYNDYTKYNEKFKGKATLTSDKSSITAYMEFSSLTSEDS

ALYYCARWGDGNYWGRGTTLTVSSGGGGSGGGGSGGGGSDIEMTQSPAIM

SASLGERVTMTCTASSSVSSSYFHWYQQKPGSSPKLCIYSTSNLASGVPP

RFSGSGSTSYSLTISSMEAEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 156)

CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

-continued

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGGACAAG

GTACCACTTTAACCGTCAGCAGCTCCGGCACCACCAATACCGTGGCCGCT

TATAACCTCACATGGAAGAGCACCAACTTCAAGACAATTCTGGAATGGGA

ACCCAAGCCCGTCAATCAAGTTTACACCGTGCAGATCTCCACCAAATCCG

GAGACTGGAAGAGCAAGTGCTTCTACACAACAGACACCGAGTGTGATTTA

ACCGACGAAATCGTCAAGGACGTCAAGCAAACCTATCTGGCTCGGGTCTT

TTCCTACCCCGCTGGCAATGTCGAGTCCACCGGCTCCGCTGGCGAGCCTC

TCTACGAGAATTCCCCCGAATTCACCCCTTATTTAGAGACCAATTTAGGC

CAGCCTACCATCCAGAGCTTCGAGCAAGTTGGCACCAAGGTGAACGTCAC

CGTCGAGGATGAAAGGACTTTAGTGCGGCGGAATAACACATTTTTATCCC

TCCGGGATGTGTTCGGCAAAGACCTCATCTACACACTGTACTATTGGAAG

TCCAGCTCCTCCGGCAAAAAGACCGCTAAGACCAACACCAACGAGTTTTT

AATTGACGTGGACAAAGGCGAGAACTACTGCTTCAGCGTGCAAGCCGTGA

TCCCTTCTCGTACCGTCAACCGGAAGAGCACAGATTCCCCCGTTGAGTGC

ATGGGCCAAGAAAAGGGCGAGTTCCGGGAGGTCCAGCTGCAGCAGAGCGG

ACCCGAACTCGTGAAACCCGGTGCTTCCGTGAAAATGTCTTGTAAGGCCA

GCGGATACACCTTCACCTCCTATGTGATCCAGTGGGTCAAACAGAAGCCC

GGACAAGGTCTCGAGTGGATCGGCAGCATCAACCCTTACAACGACTATAC

CAAATACAACGAGAAGTTTAAGGGAAAGGCTACTTTAACCTCCGACAAAA

GCTCCATCACAGCCTACATGGAGTTCAGCTCTTTAACATCCGAGGACAGC

GCTCTGTACTATTGCGCCCGGTGGGGCGACGGCAATTACTGGGGACGGGG

CACAACACTGACCGTGAGCAGCGGAGGCGGAGGCTCCGGCGGAGGCGGAT

CTGGCGGTGGCGGCTCCGACATCGAGATGACCCAGTCCCCCGCTATCATG

TCCGCCTCTTTAGGCGAGCGGGTCACAATGACTTGTACAGCCTCCTCCAG

CGTCTCCTCCTCCTACTTCCATTGGTACCAACAGAAACCCGGAAGCTCCC

CTAAACTGTGCATCTACAGCACCAGCAATCTCGCCAGCGGCGTGCCCCCT

AGGTTTTCCGGAAGCGGAAGCACCAGCTACTCTTTAACCATCTCCTCCAT

GGAGGCTGAGGATGCCGCCACCTACTTTTGTCACCAGTACCACCGGTCCC

CCACCTTCGGAGGCGGCACCAAACTGGAGACAAAGAGG.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)

MKWVTFISLLFLFSSAYSQIVLTQSPAIMSASPGEKVTMTCSASSSVSYM

NWYQQKSGTSPKRWIYDTSKLASGVPAHFRGSGSGTSYSLTISGMEAEDA

ATYYCQQWSSNPFTFGSGTKLEINRGGGGSGGGGSGGGGSQVQLQQSGAE

LARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWG

QGTTLTVSSSGTTNTVAAYNLTWKSTNFKTILEWEPKPVNQVYTVQISTK

SGDWKSKCFYTTDTECDLTDEIVKDVKQTYLARVFSYPAGNVESTGSAGE

PLYENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFSVQA

VIPSRTVNRKSTDSPVECMGQEKGEFREVQLQQSGPELVKPGASVKMSCK

ASGYTFTSYVIQWVKQKPGQGLEWIGSINPYNDYTKYNEKFKGKATLTSD

KSSITAYMEFSSLTSEDSALYYCARWGDGNYWGRGTTLTVSSGGGGSGGG

GSGGGGSDIEMTQSPAIMSASLGERVTMTCTASSSVSSSYFHWYQQKPGS

SPKLCIYSTSNLASGVPPRFSGSGSTSYSLTISSMEAEDAATYFCHQYHR

SPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)

ATGAAGTGGGTGACCTTCATCAGCTTATTATTTTTATTCAGCTCCGCCTA

TTCCCAGATCGTGCTGACCCAAAGCCCCGCCATCATGAGCGCTAGCCCCG

GTGAGAAGGTGACCATGACATGCTCCGCTTCCAGCTCCGTGTCCTACATG

AACTGGTATCAGCAGAAAAGCGGAACCAGCCCCAAAAGGTGGATCTACGA

CACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGCT

GCCACCTACTATTGCCAGCAATGGAGCAGCAACCCCTTCACATTCGGATC

TGGCACCAAGCTCGAAATCAATCGTGGAGGAGGTGGCAGCGGCGGCGGTG

GATCCGGCGGAGGAGGAAGCCAAGTTCAACTCCAGCAGAGCGGCGCTGAA

CTGGCCCGGCCCGGCGCCTCCGTCAAGATGAGCTGCAAGGCTTCCGGCTA

TACATTTACTCGTTACACAATGCATTGGGTCAAGCAGAGGCCCGGTCAAG

GTTTAGAGTGGATCGGATATATCAACCCTTCCCGGGGCTACACCAACTAT

AACCAAAAGTTCAAGGATAAAGCCACTTTAACCACTGACAAGAGCTCCTC

CACCGCCTACATGCAGCTGTCCTCTTTAACCAGCGAGGACTCCGCTGTTT

ACTACTGCGCTAGGTATTACGACGACCACTACTGTTTAGACTATTGGGGA

CAAGGTACCACTTTAACCGTCAGCAGCTCCGGCACCACCAATACCGTGGC

CGCTTATAACCTCACATGGAAGAGCACCAACTTCAAGACAATTCTGGAAT

GGGAACCCAAGCCCGTCAATCAAGTTTACACCGTGCAGATCTCCACCAAA

TCCGGAGACTGGAAGAGCAAGTGCTTCTACACAACAGACACCGAGTGTGA

-continued

TTTAACCGACGAAATCGTCAAGGACGTCAAGCAAACCTATCTGGCTCGGG

TCTTTTCCTACCCCGCTGGCAATGTCGAGTCCACCGGCTCCGCTGGCGAG

CCTCTCTACGAGAATTCCCCCGAATTCACCCCTTATTTAGAGACCAATTT

AGGCCAGCCTACCATCCAGAGCTTCGAGCAAGTTGGCACCAAGGTGAACG

TCACCGTCGAGGATGAAAGGACTTTAGTGCGGCGGAATAACACATTTTTA

TCCCTCCGGGATGTGTTCGGCAAAGACCTCATCTACACACTGTACTATTG

GAAGTCCAGCTCCTCCGGCAAAAAGACCGCTAAGACCAACACCAACGAGT

TTTTAATTGACGTGGACAAAGGCGAGAACTACTGCTTCAGCGTGCAAGCC

GTGATCCCTTCTCGTACCGTCAACCGGAAGAGCACAGATTCCCCCGTTGA

GTGCATGGGCCAAGAAAAGGGCGAGTTCCGGGAGGTCCAGCTGCAGCAGA

GCGGACCCGAACTCGTGAAACCCGGTGCTTCCGTGAAAATGTCTTGTAAG

GCCAGCGGATACACCTTCACCTCCTATGTGATCCAGTGGGTCAAACAGAA

GCCCGGACAAGGTCTCGAGTGGATCGGCAGCATCAACCCTTACAACGACT

ATACCAAATACAACGAGAAGTTTAAGGGAAAGGCTACTTTAACCTCCGAC

AAAAGCTCCATCACAGCCTACATGGAGTTCAGCTCTTTAACATCCGAGGA

CAGCGCTCTGTACTATTGCGCCCGGTGGGGCGACGGCAATTACTGGGGAC

GGGGCACAACACTGACCGTGAGCAGCGGAGGCGGAGGCTCCGGCGGAGGC

GGATCTGGCGGTGGCGGCTCCGACATCGAGATGACCCAGTCCCCCGCTAT

CATGTCCGCCTCTTTAGGCGAGCGGGTCACAATGACTTGTACAGCCTCCT

CCAGCGTCTCCTCCTCCTACTTCCATTGGTACCAACAGAAACCCGGAAGC

TCCCCTAAACTGTGCATCTACAGCACCAGCAATCTCGCCAGCGGCGTGCC

CCCTAGGTTTTCCGGAAGCGGAAGCACCAGCTACTCTTTAACCATCTCCT

CCATGGAGGCTGAGGATGCCGCCACCTACTTTTGTCACCAGTACCACCGG

TCCCCCACCTTCGGAGGCGGCACCAAACTGGAGACAAAGAGG.

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)

GCACCTACTTCAAGTTCTACAAAGAAAACACAGCTACAACTGGAGCATTT

ACTGCTGGATTTACAGATGATTTTGAATGGAATTAATAATTACAAGAATC

CCAAACTCACCAGGATGCTCACATTTAAGTTTTACATGCCCAAGAAGGCC

ACAGAACTGAAACATCTTCAGTGTCTAGAAGAAGAACTCAAACCTCTGGA

GGAAGTGCTAAATTTAGCTCAAAGCAAAAACTTTCACTTAAGACCCAGGG

ACTTAATCAGCAATATCAACGTAATAGTTCTGGAACTAAAGGGATCTGAA

ACAACATTCATGTGTGAATATGCTGATGAGACAGCAACCATTGTAGAATT

TCTGAACAGATGGATTACCTTTTGTCAAAGCATCATCTCAACACTAACT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)

GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLTSGTTNTVAAYNLTWKST
NFKTILEWEPKPVNQVYTVQISTKSGDWKSKCFYTTDTECDLTDEIVKDV
KQTYLARVFSYPAGNVESTGSAGEPLYENSPEFTPYLETNLGQPTIQSFE
QVGTKVNVTVEDERTLVRRNNTFLSLRDVFGKDLIYTLYYWKSSSSGKKT
AKTNTNEFLIDVDKGENYCFSVQAVIPSRTVNRKSTDSPVECMGQEKGEF
REAPTSSSTKKTQLQLEHLLLDLQMILNGINNYKNPKLTRMLTFKFYMPK
KATELKHLQCLEEELKPLEEVLNLAQSKNFHLRPRDLISNINVIVLELKG
SETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)

GCCCCCACCTCCTCCTCCACCAAGAAGACCCAGCTGCAGCTGGAGCATTT
ACTGCTGGATTTACAGATGATTTTAAACGGCATCAACAACTACAAGAACC
CCAAGCTGACTCGTATGCTGACCTTCAAGTTCTACATGCCCAAGAAGGCC
ACCGAGCTGAAGCATTTACAGTGTTTAGAGGAGGAGCTGAAGCCCCTCGA
GGAGGTGCTGAATTTAGCCCAGTCCAAGAATTTCCATTTAAGGCCCCGGG
ATTTAATCAGCAACATCAACGTGATCGTTTTAGAGCTGAAGGGCTCCGAG
ACCACCTTCATGTGCGAGTACGCCGACGAGACCGCCACCATCGTGGAGTT
TTTAAATCGTTGGATCACCTTCTGCCAGTCCATCATCTCCACTTTAACCA
GCGGCACAACCAACACAGTCGCTGCCTATAACCTCACTTGGAAGAGCACC
AACTTCAAAACCATCCTCGAATGGGAACCCAAACCCGTTAACCAAGTTTA
CACCGTGCAGATCAGCACCAAGTCCGGCGACTGGAAGTCCAAATGTTTCT
ATACCACCGACACCGAGTGCGATCTCACCGATGAGATCGTGAAAGATGTG
AAACAGACCTACCTCGCCCGGGTGTTTAGCTACCCCGCCGGCAATGTGGA
GAGCACTGGTTCCGCTGGCGAGCCTTTATACGAGAACAGCCCCGAATTTA
CCCCTTACCTCGAGACCAATTTAGGACAGCCCACCATCCAAAGCTTTGAG
CAAGTTGGCACAAAGGTGAATGTGACAGTGGAGGACGAGCGGACTTTAGT
GCGGCGGAACAACACCTTTCTCAGCCTCCGGGATGTGTTCGGCAAAGATT
TAATCTACACACTGTATTACTGGAAGTCCTCTTCCTCCGGCAAGAAGACA
GCTAAAACCAACACAAACGAGTTTTTAATCGACGTGGATAAAGGCGAAAA
CTACTGTTTCAGCGTGCAAGCTGTGATCCCCTCCCGGACCGTGAATAGGA
AAAGCACCGATAGCCCCGTTGAGTGCATGGGCCAAGAAAAGGGCGAGTTC
CGGGAGGCACCTACTTCAAGTTCTACAAAGAAAACACAGCTACAACTGGA

-continued

GCATTTACTGCTGGATTTACAGATGATTTTGAATGGAATTAATAATTACA
AGAATCCCAAACTCACCAGGATGCTCACATTTAAGTTTTACATGCCCAAG
AAGGCCACAGAACTGAAACATCTTCAGTGTCTAGAAGAAGAACTCAAACC
TCTGGAGGAAGTGCTAAATTTAGCTCAAAGCAAAAACTTTCACTTAAGAC
CCAGGGACTTAATCAGCAATATCAACGTAATAGTTCTGGAACTAAAGGGA
TCTGAAACAACATTCATGTGTGAATATGCTGATGAGACAGCAACCATTGT
AGAATTTCTGAACAGATGGATTACCTTTTGTCAAAGCATCATCTCAACAC
TAACT.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)

MKWVTFISLLFLFSSAYSAPTSSSTKKTQLQLEHLLLDLQMILNGINNYK
NPKLTRMLTFKFYMPKKATELKHLQCLEEELKPLEEVLNLAQSKNFHLRP
RDLISNINVIVLELKGSETTFMCEYADETATIVEFLNRWITFCQSIISTL
TSGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSPE
FTPYLETNLGQPTIQSFEQVGTKVNVTVEDERTLVRRNNTFLSLRDVFGK
DLIYTLYYWKSSSSGKKTAKTNTNEFLIDVDKGENYCFSVQAVIPSRTVN
RKSTDSPVECMGQEKGEFREAPTSSSTKKTQLQLEHLLLDLQMILNGINN
YKNPKLTRMLTFKFYMPKKATELKHLQCLEEELKPLEEVLNLAQSKNFHL
RPRDLISNINVIVLELKGSETTFMCEYADETATIVEFLNRWITFCQSIIS
TLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCTA
CTCCGCCCCCACCTCCTCCTCCACCAAGAAGACCCAGCTGCAGCTGGAGC
ATTTACTGCTGGATTTACAGATGATTTTAAACGGCATCAACAACTACAAG
AACCCCAAGCTGACTCGTATGCTGACCTTCAAGTTCTACATGCCCAAGAA
GGCCACCGAGCTGAAGCATTTACAGTGTTTAGAGGAGGAGCTGAAGCCCC
TCGAGGAGGTGCTGAATTTAGCCCAGTCCAAGAATTTCCATTTAAGGCCC
CGGGATTTAATCAGCAACATCAACGTGATCGTTTTAGAGCTGAAGGGCTC
CGAGACCACCTTCATGTGCGAGTACGCCGACGAGACCGCCACCATCGTGG
AGTTTTTAAATCGTTGGATCACCTTCTGCCAGTCCATCATCTCCACTTTA

-continued

ACCAGCGGCACAACCAACACAGTCGCTGCCTATAACCTCACTTGGAAGAG

CACCAACTTCAAAACCATCCTCGAATGGGAACCCAAACCCGTTAACCAAG

TTTACACCGTGCAGATCAGCACCAAGTCCGGCGACTGGAAGTCCAAATGT

TTCTATACCACCGACACCGAGTGCGATCTCACCGATGAGATCGTGAAAGA

TGTGAAACAGACCTACCTCGCCCGGGTGTTTAGCTACCCCGCCGGCAATG

TGGAGAGCACTGGTTCCGCTGGCGAGCCTTTATACGAGAACAGCCCCGAA

TTTACCCCTTACCTCGAGACCAATTTAGGACAGCCCACCATCCAAAGCTT

TGAGCAAGTTGGCACAAAGGTGAATGTGACAGTGGAGGACGAGCGGACTT

TAGTGCGGCGGAACAACACCTTTCTCAGCCTCCGGGATGTGTTCGGCAAA

GATTTAATCTACACACTGTATTACTGGAAGTCCTCTTCCTCCGGCAAGAA

GACAGCTAAAACCAACACAAACGAGTTTTTAATCGACGTGGATAAAGGCG

AAAACTACTGTTTCAGCGTGCAAGCTGTGATCCCCTCCCGGACCGTGAAT

AGGAAAAGCACCGATAGCCCCGTTGAGTGCATGGGCCAAGAAAAGGGCGA

GTTCCGGGAGGCACCTACTTCAAGTTCTACAAAGAAAACACAGCTACAAC

TGGAGCATTTACTGCTGGATTTACAGATGATTTTGAATGGAATTAATAAT

TACAAGAATCCCAAACTCACCAGGATGCTCACATTTAAGTTTTACATGCC

CAAGAAGGCCACAGAACTGAAACATCTTCAGTGTCTAGAAGAAGAACTCA

AACCTCTGGAGGAAGTGCTAAATTTAGCTCAAAGCAAAAACTTTCACTTA

AGACCCAGGGACTTAATCAGCAATATCAACGTAATAGTTCTGGAACTAAA

GGGATCTGAAACAACATTCATGTGTGAATATGCTGATGAGACAGCAACCA

TTGTAGAATTTCTGAACAGATGGATTACCTTTTGTCAAAGCATCATCTCA

ACACTAACT.

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-15 protein. A non-limiting example of an IL-15 protein that binds specifically to an IL-15 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)

AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)

AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)
NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTSSGTTNTVAAYNLTWKSTNFKTILEWEPKPVNQVYTV
QISTKSGDWKSKCFYTTDTECDLTDEIVKDVKQTYLARVFSYPAGNVEST
GSAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENYC
FSVQAVIPSRTVNRKSTDSPVECMGQEKGEFRENWVNVISDLKKIEDLIQ
SMHIDATLYTESDVHPSCKVTAMKCFLLELQVISLESGDASIHDTVENLI
ILANNSLSSNGNVTESGCKECEELEEKNIKEFLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)
AACTGGGTGAACGTGATCAGCGATTTAAAGAAGATCGAGGATTTAATCCA
GAGCATGCACATCGACGCCACTCTGTACACTGAGAGCGACGTGCACCCTA
GCTGCAAGGTGACTGCCATGAAGTGCTTTTTACTGGAGCTGCAAGTTATC
TCTTTAGAGAGCGGCGATGCCAGCATCCACGACACTGTGGAGAATTTAAT
CATTTTAGCCAACAACTCTTTAAGCAGCAACGGCAACGTGACAGAGAGCG
GCTGCAAGGAGTGCGAGGAGCTGGAGGAGAAGAACATCAAGGAGTTTTTA
CAGAGCTTCGTGCACATCGTGCAGATGTTCATCAACACTAGCAGCGGCAC
AACCAACACAGTCGCTGCCTATAACCTCACTTGGAAGAGCACCAACTTCA
AAACCATCCTCGAATGGGAACCCAAACCCGTTAACCAAGTTTACACCGTG
CAGATCAGCACCAAGTCCGGCGACTGGAAGTCCAAATGTTTCTATACCAC
CGACACCGAGTGCGATCTCACCGATGAGATCGTGAAAGATGTGAAACAGA
CCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTA
CCTCGAGACCAATTTAGGACAGCCCACCATCCAAAGCTTTGAGCAAGTTG
GCACAAAGGTGAATGTGACAGTGGAGGACGAGCGGACTTTAGTGCGGCGG
AACAACACCTTTCTCAGCCTCCGGGATGTGTTCGGCAAAGATTTAATCTA
CACACTGTATTACTGGAAGTCCTCTTCCTCCGGCAAGAAGACAGCTAAAA
CCAACACAAACGAGTTTTTAATCGACGTGGATAAAGGCGAAAACTACTGT
TTCAGCGTGCAAGCTGTGATCCCCTCCCGGACCGTGAATAGGAAAAGCAC
CGATAGCCCCGTTGAGTGCATGGGCCAAGAAAAGGGCGAGTTCCGGGAGA
ACTGGGTGAACGTCATCAGCGATTTAAAGAAGATCGAAGATTTAATTCAG
TCCATGCATATCGACGCCACTTTATACACAGAATCCGACGTGCACCCCTC
TTGTAAGGTGACCGCCATGAAATGTTTTTTACTGGAGCTGCAAGTTATCT
CTTTAGAGAGCGGAGACGCTAGCATCCACGACACCGTGGAGAATTTAATC
ATTTTAGCCAATAACTCTTTATCCAGCAACGGCAACGTGACAGAGTCCGG

-continued
CTGCAAGGAGTGCGAAGAGCTGGAGGAGAAGAACATCAAGGAGTTTCTGC
AATCCTTTGTGCACATTGTCCAGATGTTCATCAATACCTCC.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)
MKWVTFISLLFLFSSAYSNWVNVISDLKKIEDLIQSMHIDATLYTESDVH
PSCKVTAMKCFLLELQVISLESGDASIHDTVENLIILANNSLSSNGNVTE
SGCKECEELEEKNIKEFLQSFVHIVQMFINTSSGTTNTVAAYNLTWKSTN
FKTILEWEPKPVNQVYTVQISTKSGDWKSKCFYTTDTECDLTDEIVKDVK
QTYLARVFSYPAGNVESTGSAGEPLYENSPEFTPYLETNLGQPTIQSFEQ
VGTKVNVTVEDERTLVRRNNTFLSLRDVFGKDLIYTLYYWKSSSSGKKTA
KTNTNEFLIDVDKGENYCFSVQAVIPSRTVNRKSTDSPVECMGQEKGEFR
ENWVNVISDLKKIEDLIQSMIIIDATLYTESDVHPSCKVTAMKCFLLELQ
VISLESGDASIHDTVENLIILANNSLSSNGNVTESGCKECEELEEKNIKE
FLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)
ATGAAGTGGGTGACCTTCATCAGCCTGCTGTTCCTGTTCTCCAGCGCCTA
CTCCAACTGGGTGAACGTGATCAGCGATTTAAAGAAGATCGAGGATTTAA
TCCAGAGCATGCACATCGACGCCACTCTGTACACTGAGAGCGACGTGCAC
CCTAGCTGCAAGGTGACTGCCATGAAGTGCTTTTTACTGGAGCTGCAAGT
TATCTCTTTAGAGAGCGGCGATGCCAGCATCCACGACACTGTGGAGAATT
TAATCATTTTAGCCAACAACTCTTTAAGCAGCAACGGCAACGTGACAGAG
AGCGGCTGCAAGGAGTGCGAGGAGCTGGAGGAGAAGAACATCAAGGAGTT
TTTACAGAGCTTCGTGCACATCGTGCAGATGTTCATCAACACTAGCAGCG
GCACAACCAACACAGTCGCTGCCTATAACCTCACTTGGAAGAGCACCAAC
TTCAAAACCATCCTCGAATGGGAACCCAAACCCGTTAACCAAGTTTACAC
CGTGCAGATCAGCACCAAGTCCGGCGACTGGAAGTCCAAATGTTTCTATA
CCACCGACACCGAGTGCGATCTCACCGATGAGATCGTGAAAGATGTGAAA
CAGACCTACCTCGCCCGGGTGTTTAGCTACCCCGCCGGCAATGTGGAGAG
CACTGGTTCCGCTGGCGAGCCTTTATACGAGAACAGCCCCGAATTTACCC
CTTACCTCGAGACCAATTTAGGACAGCCCACCATCCAAAGCTTTGAGCAA
GTTGGCACAAAGGTGAATGTGACAGTGGAGGACGAGCGGACTTTAGTGCG
GCGGAACAACACCTTTCTCAGCCTCCGGGATGTGTTCGGCAAAGATTTAA

-continued

```
TCTACACACTGTATTACTGGAAGTCCTCTTCCTCCGGCAAGAAGACAGCT

AAAACCAACACAAACGAGTTTTTAATCGACGTGGATAAAGGCGAAAACTA

CTGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCGG

GAGAACTGGGTGAACGTCATCAGCGATTTAAAGAAGATCGAAGATTTAAT

TCAGTCCATGCATATCGACGCCACTTTATACACAGAATCCGACGTGCACC

CCTCTTGTAAGGTGACCGCCATGAAATGTTTTTTACTGGAGCTGCAAGTT

ATCTCTTTAGAGAGCGGAGACGCTAGCATCCACGACACCGTGGAGAATTT

AATCATTTTAGCCAATAACTCTTTATCCAGCAACGGCAACGTGACAGAGT

CCGGCTGCAAGGAGTGCGAAGAGCTGGAGGAGAAGAACATCAAGGAGTTT

CTGCAATCCTTTGTGCACATTGTCCAGATGTTCATCAATACCTCC.
```

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 109)
YFGKLESKLSVIRNLNDQVLFIDQGNRPLFEDMTDSDCRDNAPRTIFIIS
MYKDSQPRGMAVTISVKCEKISTLSCENKIISFKEMNPPDNIKDTKSDII
FFQRSVPGHDNKMQFESSSYEGYFLACEKERDLFKLILKKEDELGDRSIM
FTVQNED.
```

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 171)
TACTTCGGCAAACTGGAATCCAAGCTGAGCGTGATCCGGAATTTAAACGA
CCAAGTTCTGTTTATCGATCAAGGTAACCGGCCTCTGTTCGAGGACATGA
CCGACTCCGATTGCCGGGACAATGCCCCCCGGACCATCTTCATTATCTCC
ATGTACAAGGACAGCCAGCCCCGGGGCATGGCTGTGACAATTAGCGTGAA
GTGTGAGAAAATCAGCACTTTATCTTGTGAGAACAAGATCATCTCCTTTA
AGGAAATGAACCCCCCCGATAACATCAAGGACACCAAGTCCGATATCATC
TTCTTCCAGCGGTCCGTGCCCGGTCACGATAACAAGATGCAGTTCGAATC
CTCCTCCTACGAGGGCTACTTTTTAGCTTGTGAAAAGGAGAGGGATTTAT
TCAAGCTGATCCTCAAGAAGGAGGACGAGCTGGGCGATCGTTCCATCATG
TTCACCGTCCAAAACGAGGAT.
```

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12a (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 102).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEW
ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATTTGGGAACTGAAGAAGGACGTCTACGTGGTCGAACTGGACTGGTATCC
CGATGCTCCCGGCGAAATGGTGGTGCTCACTTGTGACACCCCCGAAGAAG
ACGGCATCACTTGGACCCTCGATCAGAGCAGCGAGGTGCTGGGCTCCGGA
AAGACCCTCACAATCCAAGTTAAGGAGTTCGGAGACGCTGGCCAATACAC
ATGCCACAAGGGAGGCGAGGTGCTCAGCCATTCCTTATTATTATTACACA
AGAAGGAAGACGGAATCTGGTCCACCGACATTTTAAAAGATCAGAAGGAG
CCCAAGAATAAGACCTTTTTAAGGTGTGAGGCCAAAAACTACAGCGGTCG
TTTCACTTGTTGGTGGCTGACCACCATTTCCACCGATTTAACCTTCTCCG
TGAAAAGCAGCCGGGGAAGCTCCGACCCTCAAGGTGTGACATGTGGAGCC
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC

-continued

TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
RNLPVATPDPGMFPCLHHSQNLLRAVSNMLQKARQTLEFYPCTSEEIDHED
ITKDKTSTVEACLPLELTKNESCLNSRETSFITNGSCLASRKTSFMMALCL
SSIYEDLKMYQVEFKTMNAKLLMDPKRQIFLDQNMLAVIDELMQALNFNSE
TVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
CGTAACCTCCCCGTGGCTACCCCCGATCCCGGAATGTTCCCTTGTTTACAC
CACAGCCAGAATTTACTGAGGGCCGTGAGCAACATGCTGCAGAAAGCTAGG
CAGACTTTAGAATTTTACCCTTGCACCAGCGAGGAGATCGACCATGAAGAT
ATCACCAAGGACAAGACATCCACCGTGGAGGCTTGTTTACCTCTGGAGCTG
ACAAAGAACGAGTCTTGTCTCAACTCTCGTGAAACCAGCTTCATCACAAAT
GGCTCTTGTTTAGCTTCCCGGAAGACCTCCTTTATGATGGCTTTATGCCTC
AGCTCCATCTACGAGGATTTAAAGATGTACCAAGTGGAGTTCAAGACCATG
AACGCCAAGCTGCTCATGGACCCTAAACGGCAGATCTTTTTAGACCAGAAC
ATGCTGGCTGTGATTGATGAGCTGATGCAAGCTTTAAACTTCAACTCCGAG
ACCGTCCCTCAGAAGTCCTCCCTCGAGGAGCCCGATTTTTACAAGACAAAG
ATCAAACTGTGCATTTTACTCCACGCCTTTAGGATCCGGGCCGTGACCATT
GACCGGGTCATGAGCTATTTAAACGCCAGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
YFGKLESKLSVIRNLNDQVLFIDQGNRPLFEDMTDSDCRDNAPRTIFIISM
YKDSQPRGMAVTISVKCEKISTLSCENKIISFKEMNPPDNIKDTKSDIIFF

-continued

QRSVPGHDNKMQFESSSYEGYFLACEKERDLFKLILKKEDELGDRSIMFTV

QNEDSGTTNTVAAYNLTWKSTNFKTILEWEPKPVNQVYTVQISTKSGDWKS

KCFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVNR

KSTDSPVECMGQEKGEFRENWVNVISDLKKIEDLIQSMHIDATLYTESDVH

PSCKVTAMKCFLLELQVISLESGDASIHDTVENLIILANNSLSSNGNVTES

GCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)

TACTTCGGCAAACTGGAATCCAAGCTGAGCGTGATCCGGAATTTAAACGAC

CAAGTTCTGTTTATCGATCAAGGTAACCGGCCTCTGTTCGAGGACATGACC

GACTCCGATTGCCGGGACAATGCCCCCCGGACCATCTTCATTATCTCCATG

TACAAGGACAGCCAGCCCCGGGGCATGGCTGTGACAATTAGCGTGAAGTGT

GAGAAAATCAGCACTTTATCTTGTGAGAACAAGATCATCTCCTTTAAGGAA

ATGAACCCCCCCGATAACATCAAGGACACCAAGTCCGATATCATCTTCTTC

CAGCGGTCCGTGCCCGGTCACGATAACAAGATGCAGTTCGAATCCTCCTCC

TACGAGGGCTACTTTTTAGCTTGTGAAAAGGAGAGGGATTTATTCAAGCTG

ATCCTCAAGAAGGAGGACGAGCTGGGCGATCGTTCCATCATGTTCACCGTC

CAAAACGAGGATAGCGGCACAACCAACACAGTCGCTGCCTATAACCTCACT

TGGAAGAGCACCAACTTCAAAACCATCCTCGAATGGGAACCCAAACCCGTT

AACCAAGTTTACACCGTGCAGATCAGCACCAAGTCCGGCGACTGGAAGTCC

AAATGTTTCTATACCACCGACACCGAGTGCGATCTCACCGATGAGATCGTG

AAAGATGTGAAACAGACCTACCTCGCCCGGGTGTTTAGCTACCCCGCCGGC

AATGTGGAGAGCACTGGTTCCGCTGGCGAGCCTTTATACGAGAACAGCCCC

GAATTTACCCCTTACCTCGAGACCAATTTAGGACAGCCCACCATCCAAAGC

TTTGAGCAAGTTGGCACAAAGGTGAATGTGACAGTGGAGGACGAGCGGACT

TTAGTGCGGCGGAACAACACCTTTCTCAGCCTCCGGGATGTGTTCGGCAAA

GATTTAATCTACACACTGTATTACTGGAAGTCCTCTTCCTCCGGCAAGAAG

ACAGCTAAAACCAACACAAACGAGTTTTTAATCGACGTGGATAAAGGCGAA

AACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTTC

CGGGAGAACTGGGTGAACGTCATCAGCGATTTAAAGAAGATCGAAGATTTA

ATTCAGTCCATGCATATCGACGCCACTTTATACACAGAATCCGACGTGCAC

CCCTCTTGTAAGGTGACCGCCATGAAATGTTTTTTACTGGAGCTGCAAGTT

ATCTCTTTAGAGAGCGGAGACGCTAGCATCCACGACACCGTGGAGAATTTA

ATCATTTTAGCCAATAACTCTTTATCCAGCAACGGCAACGTGACAGAGTCC

-continued

GGCTGCAAGGAGTGCGAAGAGCTGGAGGAGAAGAACATCAAGGAGTTTCTG

CAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)

MKWVTFISLLFLFSSAYSYFGKLESKLSVIRNLNDQVLFIDQGNRPLFEDM

TDSDCRDNAPRTIFIISMYKDSQPRGMAVTISVKCEKISTLSCENKIISFK

EMNPPDNIKDTKSDIIFFQRSVPGHDNKMQFESSSYEGYFLACEKERDLFK

LILKKEDELGDRSIMFTVQNEDSGTTNTVAAYNLTWKSTNFKTILEWEPKP

VNQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDER

TLVRRNNTFLSLRDVFGKDLIYTLYYWKSSSSGKKTAKTNTNEFLIDVDKG

ENYCFSVQAVIPSRTVNRKSTDSPVECMGQEKGEFRENWVNVISDLKKIED

LIQSMHIDATLYTESDVHPSCKVTAMKCFLLELQVISLESGDASIHDTVEN

LIILANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)

ATGAAGTGGGTCACATTTATCTCTTTACTGTTCCTCTTCTCCAGCGCCTAC

AGCTACTTCGGCAAACTGGAATCCAAGCTGAGCGTGATCCGGAATTTAAAC

GACCAAGTTCTGTTTATCGATCAAGGTAACCGGCCTCTGTTCGAGGACATG

ACCGACTCCGATTGCCGGGACAATGCCCCCCGGACCATCTTCATTATCTCC

ATGTACAAGGACAGCCAGCCCCGGGGCATGGCTGTGACAATTAGCGTGAAG

TGTGAGAAAATCAGCACTTTATCTTGTGAGAACAAGATCATCTCCTTTAAG

GAAATGAACCCCCCCGATAACATCAAGGACACCAAGTCCGATATCATCTTC

TTCCAGCGGTCCGTGCCCGGTCACGATAACAAGATGCAGTTCGAATCCTCC

TCCTACGAGGGCTACTTTTTAGCTTGTGAAAAGGAGAGGGATTTATTCAAG

CTGATCCTCAAGAAGGAGGACGAGCTGGGCGATCGTTCCATCATGTTCACC

GTCCAAAACGAGGATAGCGGCACAACCAACACAGTCGCTGCCTATAACCTC

ACTTGGAAGAGCACCAACTTCAAAACCATCCTCGAATGGGAACCCAAACCC

GTTAACCAAGTTTACACCGTGCAGATCAGCACCAAGTCCGGCGACTGGAAG

TCCAAATGTTTCTATACCACCGACACCGAGTGCGATCTCACCGATGAGATC

GTGAAAGATGTGAAACAGACCTACCTCGCCCGGGTGTTTAGCTACCCCGCC

GGCAATGTGGAGAGCACTGGTTCCGCTGGCGAGCCTTTATACGAGAACAGC

-continued

CCCGAATTTACCCCTTACCTCGAGACCAATTTAGGACAGCCCACCATCCAA

AGCTTTGAGCAAGTTGGCACAAAGGTGAATGTGACAGTGGAGGACGAGCGG

ACTTTAGTGCGGCGGAACAACACCTTTCTCAGCCTCCGGGATGTGTTCGGC

AAAGATTTAATCTACACACTGTATTACTGGAAGTCCTCTTCCTCCGGCAAG

AAGACAGCTAAAACCAACACAAACGAGTTTTTAATCGACGTGGATAAAGGC

GAAAACTACTGTTTCAGCGTGCAAGCTGTGATCCCCTCCCGGACCGTGAAT

AGGAAAAGCACCGATAGCCCCGTTGAGTGCATGGGCCAAGAAAAGGGCGAG

TTCCGGGAGAACTGGGTGAACGTCATCAGCGATTTAAAGAAGATCGAAGAT

TTAATTCAGTCCATGCATATCGACGCCACTTTATACACAGAATCCGACGTG

CACCCCTCTTGTAAGGTGACCGCCATGAAATGTTTTTACTGGAGCTGCAA

GTTATCTCTTTAGAGAGCGGAGACGCTAGCATCCACGACACCGTGGAGAAT

TTAATCATTTTAGCCAATAACTCTTTATCCAGCAACGGCAACGTGACAGAG

TCCGGCTGCAAGGAGTGCGAAGAGCTGGAGGAGAAGAACATCAAGGAGTTT

CTGCAATCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 178)

IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS

GGGGSGGGGSGGGGSRNLPVATPDPGMFPCLHEISQNLLRAVSNMLQKARQ

TLEFYPCTSEEIDHEDITKDKTSTVEACLPLELTKNESCLNSRETSFITNG

SCLASRKTSFMMALCLSSIYEDLKMYQVEFKTMNAKLLMDPKRQIFLDQNM

LAVIDELMQALNFNSETVPQKSSLEEPDFYKTKIKLCILLHAFRIRAVTID

RVMSYLNASITCPPPMSVEHADIWVKSYSLYSRERYICNSGFKRKAGTSSL

TECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)

ATTTGGGAACTGAAGAAGGACGTCTACGTGGTCGAACTGGACTGGTATCCC

GATGCTCCCGGCGAAATGGTGGTGCTCACTTGTGACACCCCCGAAGAAGAC

GGCATCACTTGGACCCTCGATCAGAGCAGCGAGGTGCTGGGCTCCGGAAAG

-continued

ACCCTCACAATCCAAGTTAAGGAGTTCGGAGACGCTGGCCAATACACATGC

CACAAGGGAGGCGAGGTGCTCAGCCATTCCTTATTATTATTACACAAGAAG

GAAGACGGAATCTGGTCCACCGACATTTTAAAAGATCAGAAGGAGCCCAAG

AATAAGACCTTTTTAAGGTGTGAGGCCAAAAACTACAGCGGTCGTTTCACT

TGTTGGTGGCTGACCACCATTTCCACCGATTTAACCTTCTCCGTGAAAAGC

AGCCGGGGAAGCTCCGACCCTCAAGGTGTGACATGTGGAGCCGCTACCCTC

AGCGCTGAGAGGGTTCGTGGCGATAACAAGGAATACGAGTACAGCGTGGAG

TGCCAAGAAGATAGCGCTTGTCCCGCTGCCGAAGAATCTTTACCCATTGAG

GTGATGGTGGACGCCGTGCACAAACTCAAGTACGAGAACTACACCTCCTCC

TTCTTTATCCGGGACATCATTAAGCCCGATCCTCCTAAGAATTTACAGCTG

AAGCCTCTCAAAAATAGCCGGCAAGTTGAGGTCTCTTGGGAATATCCCGAC

ACTTGGAGCACACCCCACAGCTACTTCTCTTTAACCTTTTGTGTGCAAGTT

CAAGGTAAAAGCAAGCGGGAGAAGAAAGACCGGGTGTTTACCGACAAAACC

AGCGCCACCGTCATCTGTCGGAAGAACGCCTCCATCAGCGTGAGGGCTCAA

GATCGTTATTACTCCAGCAGCTGGTCCGAGTGGGCCAGCGTGCCTTGTTCC

GGCGGTGGAGGATCCGGAGGAGGTGGCTCCGGCGGCGGAGGATCTCGTAAC

CTCCCCGTGGCTACCCCCGATCCCGGAATGTTCCCTTGTTTACACCACAGC

CAGAATTTACTGAGGGCCGTGAGCAACATGCTGCAGAAAGCTAGGCAGACT

TTAGAATTTTACCCTTGCACCAGCGAGGAGATCGACCATGAAGATATCACC

AAGGACAAGACATCCACCGTGGAGGCTTGTTTACCTCTGGAGCTGACAAAG

AACGAGTCTTGTCTCAACTCTCGTGAAACCAGCTTCATCACAAATGGCTCT

TGTTTAGCTTCCCGGAAGACCTCCTTTATGATGGCTTTATGCCTCAGCTCC

ATCTACGAGGATTTAAAGATGTACCAAGTGGAGTTCAAGACCATGAACGCC

AAGCTGCTCATGGACCCTAAACGGCAGATCTTTTTAGACCAGAACATGCTG

GCTGTGATTGATGAGCTGATGCAAGCTTTAAACTTCAACTCCGAGACCGTC

CCTCAGAAGTCCTCCCTCGAGGAGCCCGATTTTTACAAGACAAAGATCAAA

CTGTGCATTTTACTCCACGCCTTTAGGATCCGGGCCGTGACCATTGACCGG

GTCATGAGCTATTTAAACGCCAGCATTACATGCCCCCCTCCCATGAGCGTG

GAGCACGCCGACATCTGGGTGAAGAGCTATAGCCTCTACAGCCGGGAGAGG

TATATCTGTAACAGCGGCTTCAAGAGGAAGGCCGGCACCAGCAGCCTCACC

GAGTGCGTGCTGAATAAGGCTACCAACGTGGCTCACTGGACAACACCCTCT

TTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 180)

MKWVTFISLLFLFSSAYSIWELKKDVYVVELDWYPDAPGEMVVLTCDTPEE

DGITWTLDQSSEVLGSGKTLTIQVKEFGDAGQYTCHKGGEVLSHSLLLLHK

-continued

KEDGIWSTDILKDQKEPKNKTFLRCEAKNYSGRFTCWWLTTISTDLTFSVK

SSRGSSDPQGVTCGAATLSAERVRGDNKEYEYSVECQEDSACPAAEESLPI

EVMVDAVHKLKYENYTSSFFIRDIIKPDPPKNLQLKPLKNSRQVEVSWEYP

DTWSTPHSYFSLTFCVQVQGKSKREKKDRVFTDKTSATVICRKNASISVRA

QDRYYSSSWSEWASVPCSGGGGSGGGGSGGGGSRNLPVATPDPGMFPCLHH

SQNLLRAVSNMLQKARQTLEFYPCTSEEIDHEDITKDKTSTVEACLPLELT

KNESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKTKI

KLCILLHAFRIRAVTIDRVMSYLNASITCPPPMSVEHADIWVKSYSLYSRE

RYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 181)

ATGAAATGGGTGACCTTTATTTCTTTACTGTTCCTCTTTAGCAGCGCCTAC

TCCATTTGGGAACTGAAGAAGGACGTCTACGTGGTCGAACTGGACTGGTAT

CCCGATGCTCCCGGCGAAATGGTGGTGCTCACTTGTGACACCCCCGAAGAA

GACGGCATCACTTGGACCCTCGATCAGAGCAGCGAGGTGCTGGGCTCCGGA

AAGACCCTCACAATCCAAGTTAAGGAGTTCGGAGACGCTGGCCAATACACA

TGCCACAAGGGAGGCGAGGTGCTCAGCCATTCCTTATTATTATTACACAAG

AAGGAAGACGGAATCTGGTCCACCGACATTTTAAAAGATCAGAAGGAGCCC

AAGAATAAGACCTTTTTAAGGTGTGAGGCCAAAAACTACAGCGGTCGTTTC

ACTTGTTGGTGGCTGACCACCATTTCCACCGATTTAACCTTCTCCGTGAAA

AGCAGCCGGGGAAGCTCCGACCCTCAAGGTGTGACATGTGGAGCCGCTACC

CTCAGCGCTGAGAGGGTTCGTGGCGATAACAAGGAATACGAGTACAGCGTG

GAGTGCCAAGAAGATAGCGCTTGTCCCGCTGCCGAAGAATCTTTACCCATT

GAGGTGATGGTGGACGCCGTGCACAAACTCAAGTACGAGAACTACACCTCC

TCCTTCTTTATCCGGGACATCATTAAGCCCGATCCTCCTAAGAATTTACAG

CTGAAGCCTCTCAAAAATAGCCGGCAAGTTGAGGTCTCTTGGGAATATCCC

GACACTTGGAGCACACCCCACAGCTACTTCTCTTTAACCTTTTGTGTGCAA

GTTCAAGGTAAAAGCAAGCGGGAGAAGAAAGACCGGGTGTTTACCGACAAA

ACCAGCGCCACCGTCATCTGTCGGAAGAACGCCTCCATCAGCGTGAGGGCT

CAAGATCGTTATTACTCCAGCAGCTGGTCCGAGTGGGCCAGCGTGCCTTGT

TCCGGCGGTGGAGGATCCGGAGGAGGTGGCTCCGGCGGCGGAGGATCTCGT

AACCTCCCCGTGGCTACCCCCGATCCCGGAATGTTCCCTTGTTTACACCAC

AGCCAGAATTTACTGAGGGCCGTGAGCAACATGCTGCAGAAAGCTAGGCAG

ACTTTAGAATTTTACCCTTGCACCAGCGAGGAGATCGACCATGAAGATATC

ACCAAGGACAAGACATCCACCGTGGAGGCTTGTTTACCTCTGGAGCTGACA

AAGAACGAGTCTTGTCTCAACTCTCGTGAAACCAGCTTCATCACAAATGGC

TCTTGTTTAGCTTCCCGGAAGACCTCCTTTATGATGGCTTTATGCCTCAGC

TCCATCTACGAGGATTTAAAGATGTACCAAGTGGAGTTCAAGACCATGAAC

GCCAAGCTGCTCATGGACCCTAAACGGCAGATCTTTTTAGACCAGAACATG

CTGGCTGTGATTGATGAGCTGATGCAAGCTTTAAACTTCAACTCCGAGACC

GTCCCTCAGAAGTCCTCCCTCGAGGAGCCCGATTTTTACAAGACAAAGATC

AAACTGTGCATTTTACTCCACGCCTTTAGGATCCGGGCCGTGACCATTGAC

CGGGTCATGAGCTATTTAAACGCCAGCATTACATGCCCCCCTCCCATGAGC

GTGGAGCACGCCGACATCTGGGTGAAGAGCTATAGCCTCTACAGCCGGGAG

AGGTATATCTGTAACAGCGGCTTCAAGAGGAAGGCCGGCACCAGCAGCCTC

ACCGAGTGCGTGCTGAATAAGGCTACCAACGTGGCTCACTGGACAACACCC

TCTTTAAAGTGCATCCGG.

Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGFRβRII receptor). In some embodiments of these multi-chain chimeric polypeptides, the first target-binding domain and the second target-binding domain are each independently a soluble IL-21 or a soluble TGF-β receptor (e.g., a soluble TGFRβRII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC.

In some embodiments of these multi-chain chimeric polypeptides, the second target-binding domain includes a soluble TGF-β receptor (e.g., a soluble TGFRβRII receptor (e.g., a soluble human TGFRβRII receptor)). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)

ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCACA
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCCCCCCAAATGCA
TCATGAAGGAGAAGAAGAAGCCCGGAGAGACCTTCTTTATGTGTTCCTG
TAGCAGCGACGAGTGTAACGACAACATCATCTTCAGCGAAGAGTACAAC
ACCAGCAACCCTGATGGAGGTGGCGGATCCGGAGGTGGAGGTTCTGGTG
GAGGTGGGAGTATTCCTCCCCACGTGCAGAAGAGCGTGAATAATGACAT
GATCGTGACCGATAACAATGGCGCCGTGAAATTTCCCCAGCTGTGCAAA
TTCTGCGATGTGAGGTTTTCCACCTGCGACAACCAGAAGTCCTGTATGA
GCAACTGCACAATCACCTCCATCTGTGAGAAGCCTCAGGAGGTGTGCGT
GGCTGTCTGGCGGAAGAATGACGAGAATATCACCCTGGAAACCGTCTGC
CACGATCCCAAGCTGCCCTACCACGATTTCATCCTGGAAGACGCCGCCA
GCCCTAAGTGCATCATGAAAGAGAAAAAGAAGCCTGGCGAGACCTTTTT
CATGTGCTCCTGCAGCAGCGACGAATGCAACGACAATATCATCTTTAGC
GAGGAATACAATACCAGCAACCCCGAC.

In some embodiments of these multi-chain chimeric polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHFILEDAAS
PKCIMKEKKKPGETFFMCSCSSDECNDNIIFSEEYNTSNPD.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 189)

QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSSGTTNTVAAYNLTW
KSTNFKTILEWEPKPVNQVYTVQISTKSGDWKSKCFYTTDTECDLTDEI
VKDVKQTYLARVFSYPAGNVESTGSAGEPLYENSPEFTPYETNLGQPTI
QSFEQVGTKVNVTVEDERTLVRRNNTFLSLRDVFGKDLIYTLYYWKSSS
SGKKTAKTNTNEFLIDVDKGENYCFSVQAVIPSRTVNRKSTDSPVECMG
QEKGEFRENWVNVISDLKKIEDLIQSMHIDATLYTESDVHPSCKVTAMK
CFLLELQVISLESGDASIHDTVENLIILANNSLSSNGNVTESGCKECEE
LEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 190)

CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCTCCGGCACCACCAATACCGTGGCCGCTTATAACCTCACATGG
AAGAGCACCAACTTCAAGACAATTCTGGAATGGGAACCCAAGCCCGTCA
ATCAAGTTTACACCGTGCAGATCTCCACCAAATCCGGAGACTGGAAGAG
CAAGTGCTTCTACACAACAGACACCGAGTGTGATTTAACCGACGAAATC

-continued

GTCAAGGACGTCAAGCAAACCTATCTGGCTCGGGTCTTTTCCTACCCCG

CTGGCAATGTCGAGTCCACCGGCTCCGCTGGCGAGCCTCTCTACGAGAA

TTCCCCCGAATTCACCCCTTATTTAGAGACCAATTTAGGCCAGCCTACC

ATCCAGAGCTTCGAGCAAGTTGGCACCAAGGTGAACGTCACCGTCGAGG

ATGAAAGGACTTTAGTGCGGCGGAATAACACATTTTTATCCCTCCGGGA

TGTGTTCGGCAAAGACCTCATCTACACACTGTACTATTGGAAGTCCAGC

TCCTCCGGCAAAAAGACCGCTAAGACCAACACCAACGAGTTTTTAATTG

ACGTGGACAAAGGCGAGAACTACTGCTTCAGCGTGCAAGCCGTGATCCC

TTCTCGTACCGTCAACCGGAAGAGCACAGATTCCCCCGTTGAGTGCATG

GGCCAAGAAAAGGGCGAGTTCCGGGAGAACTGGGTGAACGTCATCAGCG

ATTTAAAGAAGATCGAAGATTTAATTCAGTCCATGCATATCGACGCCAC

TTTATACACAGAATCCGACGTGCACCCCTCTTGTAAGGTGACCGCCATG

AAATGTTTTTTACTGGAGCTGCAAGTTATCTCTTTAGAGAGCGGAGACG

CTAGCATCCACGACACCGTGGAGAATTTAATCATTTTAGCCAATAACTC

TTTATCCAGCAACGGCAACGTGACAGAGTCCGGCTGCAAGGAGTGCGAA

GAGCTGGAGGAGAAGAACATCAAGGAGTTTCTGCAATCCTTTGTGCACA

TTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 191)

MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSSGTTNTVAAYNLTWKSTNFKTILEWEPKPVNQVYTVQISTKSGDW

KSKCFYTTDTECDLTDEIVKDVKQTYLARVFSYPAGNVESTGSAGEPLY

ENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAV

IPSRTVNRKSTDSPVECMGQEKGEFRENWVNVISDLKKIEDLIQSMHID

ATLYTESDVHPSCKVTAMKCFLLELQVISLESGDASIHDTVENLIILAN

NSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 192)

ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

-continued

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCTCCGGCACCACCAATACCGTGGCCGCTTATAACCTCA

CATGGAAGAGCACCAACTTCAAGACAATTCTGGAATGGGAACCCAAGCC

CGTCAATCAAGTTTACACCGTGCAGATCTCCACCAAATCCGGAGACTGG

AAGAGCAAGTGCTTCTACACAACAGACACCGAGTGTGATTTAACCGACG

AAATCGTCAAGGACGTCAAGCAAACCTATCTGGCTCGGGTCTTTTCCTA

CCCCGCTGGCAATGTCGAGTCCACCGGCTCCGCTGGCGAGCCTCTCTAC

GAGAATTCCCCCGAATTCACCCCTTATTTAGAGACCAATTTAGGCCAGC

CTACCATCCAGAGCTTCGAGCAAGTTGGCACCAAGGTGAACGTCACCGT

CGAGGATGAAAGGACTTTAGTGCGGCGGAATAACACATTTTTATCCCTC

CGGGATGTGTTCGGCAAAGACCTCATCTACACACTGTACTATTGGAAGT

CCAGCTCCTCCGGCAAAAAGACCGCTAAGACCAACACCAACGAGTTTTT

AATTGACGTGGACAAAGGCGAGAACTACTGCTTCAGCGTGCAAGCCGTG

ATCCCTTCTCGTACCGTCAACCGGAAGAGCACAGATTCCCCCGTTGAGT

GCATGGGCCAAGAAAAGGGCGAGTTCCGGGAGAACTGGGTGAACGTCAT

CAGCGATTTAAAGAAGATCGAAGATTTAATTCAGTCCATGCATATCGAC

GCCACTTTATACACAGAATCCGACGTGCACCCCTCTTGTAAGGTGACCG

CCATGAAATGTTTTTTACTGGAGCTGCAAGTTATCTCTTTAGAGAGCGG

AGACGCTAGCATCCACGACACCGTGGAGAATTTAATCATTTTAGCCAAT

AACTCTTTATCCAGCAACGGCAACGTGACAGAGTCCGGCTGCAAGGAGT

GCGAAGAGCTGGAGGAGAAGAACATCAAGGAGTTTCTGCAATCCTTTGT

GCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

-continued

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 194)

ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

ACGATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCACAATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGACATC

ACGTGTCCTCCTCCTATGTCCGTGGAACACGCAGACATCTGGGTCAAG

AGCTACAGCTTGTACTCCAGGGAGCGGTACATTTGTAACTCTGGTTTC

AAGCGTAAAGCCGGCACGTCCAGCCTGACGGAGTGCGTGTTGAACAAG

GCCACGAATGTCGCCCACTGGACAACCCCCAGTCTCAAATGTATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

-continued

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 196)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCACGATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCACAATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATCACGTGTCCTCCTC

CTATGTCCGTGGAACACGCAGACATCTGGGTCAAGAGCTACAGCTTGTA

CTCCAGGGAGCGGTACATTTGTAACTCTGGTTTCAAGCGTAAAGCCGGC

ACGTCCAGCCTGACGGAGTGCGTGTTGAACAAGGCCACGAATGTCGCCC

ACTGGACAACCCCCAGTCTCAAATGTATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
CAAGGTCAAGATCGCCACATGATTAGAATGCGTCAACTTATAGATAT

TGTTGATCAGCTGAAAAATTATGTGAATGACTTGGTCCCTGAATTTC

TGCCAGCTCCAGAAGATGTAGAGACAAACTGTGAGTGGTCAGCTTTT

TCCTGTTTTCAGAAGGCCCAACTAAAGTCAGCAAATACAGGAAACAA

TGAAAGGATAATCAATGTATCAATTAAAAAGCTGAAGAGGAAACCAC

CTTCCACAAATGCAGGGAGAAGACAGAAACACAGACTAACATGCCCT

TCATGTGATTCTTATGAGAAAAAACCACCCAAAGAATTCCTAGAAAG

ATTCAAATCACTTCTCCAAAAGATGATTCATCAGCATCTGTCCTCTA

GAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGA

CATCGTCGACCAGCTGAAGAACTACGTGAACGACCTGGTGCCCG

AGTTTCTGCCTGCCCCCGAGGACGTGGAGACCAACTGCGAGTGG

TCCGCCTTCTCCTGCTTTCAGAAGGCCCAGCTGAAGTCCGCCAA

CACCGGCAACAACGAGCGGATCATCAACGTGAGCATCAAGAAGC

TGAAGCGGAAGCCTCCCTCCACAAACGCCGGCAGGAGGCAGAAG

CACAGGCTGACCTGCCCCAGCTGTGACTCCTACGAGAAGAAGCC

CCCCAAGGAGTTCCTGGAGAGGTTCAAGTCCCTGCTGCAGAAGA

TGATCCATCAGCACCTGTCCTCCAGGACCCACGGCTCCGAGGAC

TCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNFFK
RHICDANKEGMFLFRAARKLRQFLKMNSTGDFDLHLLKVSEGT
TILLNCTGQVKGRKPAALGEAQPTKSLEENKSLKEQKKLNDLC
FLKRLLQEIKTCWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
GATTGTGATATTGAAGGTAAAGATGGCAAACAATATGAGAGTGT
TCTAATGGTCAGCATCGATCAATTATTGGACAGCATGAAAGAAA
TTGGTAGCAATTGCCTGAATAATGAATTTAACTTTTTTAAAAGA
CATATCTGTGATGCTAATAAGGAAGGTATGTTTTTATTCCGTGC
TGCTCGCAAGTTGAGGCAATTTCTTAAAATGAATAGCACTGGTG
ATTTTGATCTCCACTTATTAAAAGTTTCAGAAGGCACAACAATA
CTGTTGAACTGCACTGGCCAGGTTAAAGGAAGAAAACCAGCTGC
CCTGGGTGAAGCCCAACCAACAAAGAGTTTGGAAGAAAATAAAT
CTTTAAAGGAACAGAAAAAACTGAATGACTTGTGTTTCCTAAAG
AGACTATTACAAGAGATAAAAACTTGTTGGAATAAAATTTTGAT
GGGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 199)
QGQDRHMIRMRQLIDIVDQLKNYVNDLVPEFLPAPEDVETNCE
WSAFSCFQKAQLKSANTGNNERIINVSIKKLKRKPPSTNAGRR
QKHRLTCPSCDSYEKKPPKEFLERFKSLLQKMIHQHLSSRTHG
SEDSSGTTNTVAAYNLTWKSTNFKTILEWEPKPVNQVYTVQIS
TKSGDWKSKCFYTTDTECDLTDEIVKDVKQTYLARVFSYPAGN
VESTESTGSAGEPLYENSPEFTPYLETNLGQPTIQSFEQVGTK
VNVTVEDERTLVRRNNTFLSLRDVFGKDLIYTLYYWKSSSSGK
KTAKTNTNEFLIDVDKGENYCFSVQAVIPSRTVNRKSTDSPVE
CMGQEKGEFRENWVNVISDLKKIEDLIQSMHIDATLYTESDVH
PSCKVTAMKCFLLELQVISLESGDASIHDTVENLIILLANNSL
SSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 200)
CAAGGTCAAGATCGCCACATGATTAGAATGCGTCAACTTATAGAT
ATTGTTGATCAGCTGAAAAATTATGTGAATGACTTGGTCCCTGAA
TTTCTGCCAGCTCCAGAAGATGTAGAGACAAACTGTGAGTGGTCA
GCTTTTTCCTGTTTTCAGAAGGCCCAACTAAAGTCAGCAAATACA
GGAAACAATGAAAGGATAATCAATGTATCAATTAAAAAGCTGAAG
AGGAAACCACCTTCCACAAATGCAGGGAGAAGACAGAAACACAGA
CTAACATGCCCTTCATGTGATTCTTATGAGAAAAAACCACCCAAA
GAATTCCTAGAAAGATTCAAATCACTTCTCCAAAAGATGATTCAT
CAGCATCTGTCCTCTAGAACACACGGAAGTGAAGATTCCTCAGGC
ACTACAAATACTGTGGCAGCATATAATTTAACTTGGAAATCAACT
AATTTCAAGACAATTTTGGAGTGGGAACCCAAACCCGTCAATCAA
GTCTACACTGTTCAAATAAGCACTAAGTCAGGAGATTGGAAAAGC
AAATGCTTTTACACAACAGACACAGAGTGTGACCTCACCGACGAG
ATTGTGAAGGATGTGAAGCAGACGTACTTGGCACGGGTCTTCTCC
TACCCGGCAGGGAATGTGGAGAGCACCGGTTCTGCTGGGGAGCCT
CTGTATGAGAACTCCCCAGAGTTCACACCTTACCTGGAGACAAAC
CTCGGACAGCCAACAATTCAGAGTTTTGAACAGGTGGGAACAAAA
GTGAATGTGACCGTAGAAGATGAACGGACTTTAGTCAGAAGGAAC
AACACTTTCCTAAGCCTCCGGGATGTTTTTGGCAAGGACTTAATT
TATACACTTTATTATTGGAAATCTTCAAGTTCAGGAAAGAAAACA
GCCAAAACAAACACTAATGAGTTTTTGATTGATGTGGATAAAGGA
GAAAACTACTGTTTCAGTGTTCAAGCAGTGATTCCCTCCCGAACA
GTTAACCGGAAGAGTACAGACAGCCCGGTAGAGTGTATGGGCCAG
GAGAAAGGGGAATTCAGAGAAAACTGGGTGAACGTCATCAGCGAT
TTAAAGAAGATCGAAGATTTAATTCAGTCCATGCATATCGACGCC
ACTTTATACACAGAATCCGACGTGCACCCCTCTTGTAAGGTGACC
GCCATGAAATGTTTTTTACTGGAGCTGCAAGTTATCTCTTTAGAG
AGCGGAGACGCTAGCATCCACGACACCGTGGAGAATTTAATCATT
TTAGCCAATAACTCTTTATCCAGCAACGGCAACGTGACAGAGTCC
GGCTGCAAGGAGTGCGAAGAGCTGGAGGAGAAGAACATCAAGGAG
TTTCTGCAATCCTTTGTGCACATTGTCCAGATGTTCATCAATACC
TCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 201)
MGVKVLFALICIAVAEAQGQDRHMIRMRQLIDIVDQLKNYVNDLVPE
FLPAPEDTVETNCEWSAFSCFQKAQLKSANTGNNERIINVSIKKLKR
KPPSTNAGRRQKHRLCPSCDSYEKKPPKEFLERFKSLLQKMIHQHLS
SRTHGSEDSSGTTNTVAAYNLTWKSTNFKTILEWEPKPVNQVYTVQI
STKSGDWKSKCFYTTDTECDLTDEIVKDVKVKQTYLARVFSYPAGNV
ESTGSAGEPLYENSPEFTPYLETNLGQPTIQSFEQVGTKVNVTVEDE
RTLVRRNNTFLSLRDVFGKDLIYTLYYWKSSSSGKKTAKTNTNEFLI
DVDKGENYCFSVQAVIPSRTVNRKSTDSPVECMGQEKGEFRENWVNV
ISDLKKIEDLIQSMHIDATLYTESDVHPSCKVTAMKCFLLELQVISL
ESGDASIHDTVENLIILANNSLSSNGNVTESGCKECEELEEKNIKEF
LQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)
ATGGGAGTGAAAGTTCTTTTTGCCCTTATTTGTATTGCTGTGGC
CGAGGCCCAAGGTCAAGATCGCCACATGATTAGAATGCGTCAACTTAT
AGATATTGTTGATCAGCTGAAAAATTATGTGAATGACTTGGTCCCTGA
ATTTCTGCCAGCTCCAGAAGATGTAGAGACAAACTGTGAGTGGTCAGC
TTTTTCCTGTTTTCAGAAGGCCCAACTAAAGTCAGCAAATACAGGAAA
CAATGAAAGGATAATCAATGTATCAATTAAAAAGCTGAAGAGGAAACC
ACCTTCCACAAATGCAGGGAGAAGACAGAAACACAGACTAACATGCCC
TTCATGTGATTCTTATGAGAAAAAACCACCCAAAGAATTCCTAGAAAG
ATTCAAATCACTTCTCCAAAAGATGATTCATCAGCATCTGTCCTCTAG
AACACACGGAAGTGAAGATTCCTCAGGCACTACAAATACTGTGGCAGC
ATATAATTTAACTTGGAAATCAACTAATTTCAAGACAATTTTGGAGTG
GGAACCCAAACCCGTCAATCAAGTCTACACTGTTCAAATAAGCACTAA
GTCAGGAGATTGGAAAAGCAAATGCTTTTACACAACAGACACAGAGTG
TGACCTCACCGACGAGATTGTGAAGGATGTGAAGCAGACGTACTTGGC
ACGGGTCTTCTCCTACCCGGCAGGGAATGTGGAGAGCACCGGTTCTGC
TGGGGAGCCTCTGTATGAGAACTCCCCAGAGTTCACACCTTACCTGGA
GACAAACCTCGGACAGCCAACAATTCAGAGTTTTGAACAGGTGGGAAC
AAAAGTGAATGTGACCGTAGAAGATGAACGGACTTTAGTCAGAAGGAA
CAACACTTTCCTAAGCCTCCGGGATGTTTTTGGCAAGGACTTAATTTA
TACACTTTATTATTGGAAATCTTCAAGTTCAGGAAAGAAAACAGCCAA
AACAAACACTAATGAGTTTTTGATTGATGTGGATAAAGGAGAAAACTA
CTGTTTCAGTGTTCAAGCAGTGATTCCCTCCCGAACAGTTAACCGGAA
GAGTACAGACAGCCCGGTAGAGTGTATGGGCCAGGAGAAAGGGGAATT

-continued

CAGAGAAAACTGGGTGAACGTCATCAGCGATTTAAAGAAGATCGAAGA
TTTAATTCAGTCCATGCATATCGACGCCACTTTATACACAGAATCCGA
CGTGCACCCCTCTTGTAAGGTGACCGCCATGAAATGTTTTTTACTGGA
GCTGCAAGTTATCTCTTTAGAGAGCGGAGACGCTAGCATCCACGACAC
CGTGGAGAATTTAATCATTTTAGCCAATAACTCTTTATCCAGCAACGG
CAACGTGACAGAGTCCGGCTGCAAGGAGTGCGAAGAGCTGGAGGAGAA
GAACATCAAGGAGTTTCTGCAATCCTTTGTGCACATTGTCCAGATGTT
CATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)
DCDIEGKDGKQYESVLMVSIDQLLDSMKEIGSNCLNNENFFKRHIC
DANKEGMFLFRAARKLRQFLKMNSTGDFDLHLLKVSEGTTILLNCT
GQVKGRKPAALGEAQPTKSLEENKSLKEQKKLNDLCFLKRLLQEIK
TCWNKILMGTKEHITCPPPMSVEHADIWVKSYSLYSRERYICNSGF
KRKAGTSSLTECVLNKATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 204)
GATTGTGATATTGAAGGTAAAGATGGCAAACAATATGAGAGTGTTC
TAATGGTCAGCATCGATCAATTATTGGACAGCATGAAAGAAATTGG
TAGCAATTGCCTGAATAATGAATTTAACTTTTTTAAAAGACATATC
TGTGATGCTAATAAGGAAGGTATGTTTTTATTCCGTGCTGCTCGCA
AGTTGAGGCAATTTCTTAAAATGAATAGCACTGGTGATTTTGATCT
CCACTTATTAAAAGTTTCAGAAGGCACAACAATACTGTTGAACTGC
ACTGGCCAGGTTAAAGGAAGAAAACCAGCTGCCCTGGGTGAAGCCC
AACCAACAAAGAGTTTGGAAGAAAATAAATCTTTAAAGGAACAGAA
AAAACTGAATGACTTGTGTTTCCTAAAGAGACTATTACAAGAGATA
AAAACTTGTTGGAATAAAATTTTGATGGGCACTAAAGAACACATCA
CGTGCCCTCCCCCCATGTCCGTGGAACACGCAGACATCTGGGTCAA
GAGCTACAGCTTGTACTCCAGGGAGCGGTACATTTGTAACTCTGGT
TTCAAGCGTAAAGCCGGCACGTCCAGCCTGACGGAGTGCGTGTTGA
ACAAGGCCACGAATGTCGCCCACTGGACAACCCCCAGTCTCAAATG
CATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 205)

```
MGVKVLFALICIAVAEADCDIEGKDGKQYESVLMVSIDQLLDSMKEIGS

NCLNNEFNFFKRHICDANKEGMFLFRAARKLRQFLKMNSTGDFDLHLLK

VSEGTTILLNCTGQVKGRKPAALGEAQPTKSLEENKSLKEQKKLNDLCF

LKRLLQEIKTCWNKILMGTKEHITCPPPMSVEHADIWVKSYSLYSRERY

ICNSGFKRKAGTSSLTECVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 206)

```
ATGGGAGTGAAAGTTCTTTTTGCCCTTATTTGTATTGCTGTGGCCGAG

GCCGATTGTGATATTGAAGGTAAAGATGGCAAACAATATGAGAGTGTT

CTAATGGTCAGCATCGATCAATTATTGGACAGCATGAAAGAAATTGGT

AGCAATTGCCTGAATAATGAATTTAACTTTTTTAAAAGACATATCTGT

GATGCTAATAAGGAAGGTATGTTTTTATTCCGTGCTGCTCGCAAGTTG

AGGCAATTTCTTAAAATGAATAGCACTGGTGATTTTGATCTCCACTTA

TTAAAAGTTTCAGAAGGCACAACAATACTGTTGAACTGCACTGGCCAG

GTTAAAGGAAGAAAACCAGCTGCCCTGGGTGAAGCCCAACCAACAAAG

AGTTTGGAAGAAAATAAATCTTTAAAGGAACAGAAAAAACTGAATGAC

TTGTGTTTCCTAAAGAGACTATTACAAGAGATAAAAACTTGTTGGAAT

AAAATTTTGATGGGCACTAAAGAACACATCACGTGCCCTCCCCCCATG

TCCGTGGAACACGCAGACATCTGGGTCAAGAGCTACAGCTTGTACTCC

AGGGAGCGGTACATTTGTAACTCTGGTTTCAAGCGTAAAGCCGGCACG

TCCAGCCTGACGGAGTGCGTGTTGAACAAGGCCACGAATGTCGCCCAC

TGGACAACCCCCAGTCTCAAATGCATTAGA.
```

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)

```
QGQDRHMIRMRQLIDIVDQLKNYVNDLVPEFLPAPEDVETNCEWSAFS

CLKSANTGNNERIINVSIKKLKRKPPSTNAGRRQKHRLTCPSCDSYEK

kPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)

CAAGGTCAAGATCGCCACATGATTAGAATGCGTCAACTTATAGATAT

TGTTGATCAGCTGAAAAATTATGTGAATGACTTGGTCCCTGAATTTC

TGCCAGCTCCAGAAGATGTAGAGACAAACTGTGAGTGGTCAGCTTTT

TCCTGTTTTCAGAAGGCCCAACTAAAGTCAGCAAATACAGGAAACAA

TGAAAGGATAATCAATGTATCAATTAAAAAGCTGAAGAGGAAACCAC

CTTCCACAAATGCAGGGAGAAGACAGAAACACAGACTAACATGCCCT

TCATGTGATTCTTATGAGAAAAAACCACCCAAAGAATTCCTAGAAAG

ATTCAAATCACTTCTCCAAAAGATGATTCATCAGCATCTGTCCTCTA

GAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

CAGGGCCAGGACAGGCACATGATCCGGATGAGGCAGCTCATCGACAT

CGTCGACCAGCTGAAGAACTACGTGAACGACCTGGTGCCCGAGTTTCTGCC

TGCCCCCGAGGACGTGGAGACCAACTGCGAGTGGTCCGCCTTCTCCTGCTT

TCAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCGG

CAGGAGGCAGAAGCACAGGCTGACCTGCCCCAGCTGTGACTCCTACGAGAA

GAAGCCCCCCAAGGAGTTCCTGGAGAGGTTCAAGTCCCTGCTGCAGAAGAT

GATCCATCAGCACCTGTCCTCCAGGACCCACGGCTCCGAGGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)

DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)

GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)

DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVFGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

-continued

GAAGAGGCTGCTGCAGGAGATCAAGACCTGCTGGAACAAGATCCTGATG
GGCACCAAGGAGCATAGCGGCACAACCAACACAGTCGCTGCCTATAACC
TCACTTGGAAGAGCACCAACTTCAAAACCATCCTCGAATGGGAACCCAA
ACCCGTTAACCAAGTTTACACCGTGCAGATCAGCACCAAGTCCGGCGAC
TGGAAGTCCAAATGTTTCTATACCACCGACACCGAGTGCGATCTCACCG
ATGAGATCGTGAAAGATGTGAAACAGACCTACCTCGCCCGGGTGTTTAG
CTACCCCGCCGGCAATGTGGAGAGCACTGGTTCCGCTGGCGAGCCTTTA
TACGAGAACAGCCCCGAATTTACCCCTTACCTCGAGACCAATTTAGGAC
AGCCCACCATCCAAAGCTTTGAGCAAGTTGGCACAAAGGTGAATGTGAC
AGTGGAGGACGAGCGGACTTTAGTGCGGCGGAACAACACCTTTCTCAGC
CTCCGGGATGTGTTCGGCAAAGATTTAATCTACACACTGTATTACTGGA
AGTCCTCTTCCTCCGGCAAGAAGACAGCTAAAACCAACACAAACGAGTT
TTTAATCGACGTGGATAAAGGCGAAAACTACTGTTTCAGCGTGCAAGCT
GTGATCCCCTCCCGGACCGTGAATAGGAAAAGCACCGATAGCCCCGTTG
AGTGCATGGGCCAAGAAAAGGGCGAGTTCCGGGAGAACTGGGTGAACGT
CATCAGCGATTTAAAGAAGATCGAAGATTTAATTCAGTCCATGCATATC
GACGCCACTTTATACACAGAATCCGACGTGCACCCCTCTTGTAAGGTGA
CCGCCATGAAATGTTTTTTACTGGAGCTGCAAGTTATCTCTTTAGAGAG
CGGAGACGCTAGCATCCACGACACCGTGGAGAATTTAATCATTTTAGCC
AATAACTCTTTATCCAGCAACGGCAACGTGACAGAGTCCGGCTGCAAGG
AGTGCGAAGAGCTGGAGGAGAAGAACATCAAGGAGTTTCTGCAATCCTT
TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIG
SNCLNNEFNFFKRHICDANKEGMFLFRAARKLRQFLKMNSTGDFDLHLL
KVSEGTTILLNCTGQVKGRKPAALGEAQPTKSLEENKSLKEQKKLNDLC
FLKRLLQEIKTCWNKILMGTKEHSGTTNTVAAYNLTWKSTNFKTILEWE
PKPVNQVYTVQISTKSGDWKSKCFYTTDTECDLTDEIVKDVKQTYLARV
FSYPAGNVESTGSAGEPLYENSPEFTPYLETNLGQPTIQSFEQVGTKVN
VTVEDERTLVRRNNTFLSLRDVFGKDLIYTLYYWKSSSSGKKTAKTNTN
EFLIDVDKGENYCFSVQAVIPSRTVNRKSTDSPVECMGQEKGEFRENWV
NVISDLKKIEDLIQSMHIDATLYTESDVHPSCKVTAMKCFLLELQVISL
ESGDASIHDTVENLIILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCT
ACTCCGATTGCGACATCGAGGGCAAGGACGGCAAGCAGTACGAGAGCGT
GCTGATGGTGTCCATCGACCAGCTGCTGGACAGCATGAAGGAGATCGGC
TCCAACTGCCTCAACAACGAGTTCAACTTCTTCAAGCGGCACATCTGCG
ACGCCAACAAGGAGGGCATGTTCCTGTTCAGGGCCGCCAGGAAACTGCG
GCAGTTCCTGAAGATGAACTCCACCGGCGACTTCGACCTGCACCTGCTG
AAGGTGTCCGAGGGCACCACCATCCTGCTGAACTGCACCGGACAGGTGA
AGGGCCGGAAACCTGCTGCTCTGGGAGAGGCCCAACCCACCAAGAGCCT
GGAGGAGAACAAGTCCCTGAAGGAGCAGAAGAAGCTGAACGACCTGTGC
TTCCTGAAGAGGCTGCTGCAGGAGATCAAGACCTGCTGGAACAAGATCC
TGATGGGCACCAAGGAGCATAGCGGCACAACCAACACAGTCGCTGCCTA
TAACCTCACTTGGAAGAGCACCAACTTCAAAACCATCCTCGAATGGGAA
CCCAAACCCGTTAACCAAGTTTACACCGTGCAGATCAGCACCAAGTCCG
GCGACTGGAAGTCCAAATGTTTCTATACCACCGACACCGAGTGCGATCT
CACCGATGAGATCGTGAAAGATGTGAAACAGACCTACCTCGCCCGGGTG
TTTAGCTACCCCGCCGGCAATGTGGAGAGCACTGGTTCCGCTGGCGAGC
CTTTATACGAGAACAGCCCCGAATTTACCCCTTACCTCGAGACCAATTT
AGGACAGCCCACCATCCAAAGCTTTGAGCAAGTTGGCACAAAGGTGAAT
GTGACAGTGGAGGACGAGCGGACTTTAGTGCGGCGGAACAACACCTTTC
TCAGCCTCCGGGATGTGTTCGGCAAAGATTTAATCTACACACTGTATTA
CTGGAAGTCCTCTTCCTCCGGCAAGAAGACAGCTAAAACCAACACAAAC
GAGTTTTTAATCGACGTGGATAAAGGCGAAAACTACTGTTTCAGCGTGC
AAGCTGTGATCCCCTCCCGGACCGTGAATAGGAAAAGCACCGATAGCCC
CGTTGAGTGCATGGGCCAAGAAAAGGGCGAGTTCCGGGAGAACTGGGTG
AACGTCATCAGCGATTTAAAGAAGATCGAAGATTTAATTCAGTCCATGC
ATATCGACGCCACTTTATACACAGAATCCGACGTGCACCCCTCTTGTAA
GGTGACCGCCATGAAATGTTTTTTACTGGAGCTGCAAGTTATCTCTTTA
GAGAGCGGAGACGCTAGCATCCACGACACCGTGGAGAATTTAATCATTT
TAGCCAATAACTCTTTATCCAGCAACGGCAACGTGACAGAGTCCGGCTG
CAAGGAGTGCGAAGAGCTGGAGGAGAAGAACATCAAGGAGTTTCTGCAA
TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 211)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 212)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 213)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 214)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGG.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein)

between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12a (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-120 (p40) and the sequence of soluble human IL-12α (p35). In some examples of these multi-chain chimeric polypeptides, the linker sequence comprises GGGGSGGGGSGGGGS (SEQ ID NO: 102).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEW
ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATTTGGGAACTGAAGAAGGACGTCTACGTGGTCGAACTGGACTGGTATCC
CGATGCTCCCGGCGAAATGGTGGTGCTCACTTGTGACACCCCCGAAGAAG
ACGGCATCACTTGGACCCTCGATCAGAGCAGCGAGGTGCTGGGCTCCGGA
AAGACCCTCACAATCCAAGTTAAGGAGTTCGGAGACGCTGGCCAATACAC
ATGCCACAAGGGAGGCGAGGTGCTCAGCCATTCCTTATTATTATTACACA
AGAAGGAAGACGGAATCTGGTCCACCGACATTTTAAAAGATCAGAAGGAG
CCCAAGAATAAGACCTTTTTAAGGTGTGAGGCCAAAAACTACAGCGGTCG
TTTCACTTGTTGGTGGCTGACCACCATTTCCACCGATTTAACCTTCTCCG
TGAAAAGCAGCCGGGGAAGCTCCGACCCTCAAGGTGTGACATGTGGAGCC
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA

-continued
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC
TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
RNLPVATPDPGMFPCLEIRSQNLLRAVSNMLQKARQTLEFYPCTSEEIDH
EDITKDKTSTVEACLPLELTKNESCLNSRETSFITNGSCLASRKTSFMMA
LCLSSIYEDLKMYQVEFKTMNAKLLMDPKRQIFLDQNMLAVIDELMQALN
FNSETVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
CGTAACCTCCCCGTGGCTACCCCCGATCCCGGAATGTTCCCTTGTTTACA
CCACAGCCAGAATTTACTGAGGGCCGTGAGCAACATGCTGCAGAAAGCTA
GGCAGACTTTAGAATTTTACCCTTGCACCAGCGAGGAGATCGACCATGAA
GATATCACCAAGGACAAGACATCCACCGTGGAGGCTTGTTTACCTCTGGA
GCTGACAAAGAACGAGTCTTGTCTCAACTCTCGTGAAACCAGCTTCATCA
CAAATGGCTCTTGTTTAGCTTCCCGGAAGACCTCCTTTATGATGGCTTTA
TGCCTCAGCTCCATCTACGAGGATTTAAAGATGTACCAAGTGGAGTTCAA
GACCATGAACGCCAAGCTGCTCATGGACCCTAAACGGCAGATCTTTTTAG
ACCAGAACATGCTGGCTGTGATTGATGAGCTGATGCAAGCTTTAAACTTC
AACTCCGAGACCGTCCCTCAGAAGTCCTCCCTCGAGGAGCCCGATTTTTA
CAAGACAAAGATCAAACTGTGCATTTTACTCCACGCCTTTAGGATCCGGG
CCGTGACCATTGACCGGGTCATGAGCTATTTAAACGCCAGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKN
NRPSGIPDRFSGSSSGNTASLTITGAQAEDEADYYCNSRDSSGNHVVFGG
GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGT
GAGGATCACCTGCCAGGGCGACTCCCTGAGGTCCTACTACGCCTCCTGGT
ACCAGCAGAAGCCCGGCCAGGCTCCTGTGCTGGTGATCTACGGCAAGAAC
AACAGGCCCTCCGGCATCCCTGACAGGTTCTCCGGATCCTCCTCCGGCAA
CACCGCCTCCCTGACCATCACAGGCGCTCAGGCCGAGGACGAGGCTGACT
ACTACTGCAACTCCAGGGACTCCTCCGGCAACCATGTGGTGTTCGGCGGC
GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSG
INWNGGSTGYADSVKGRFTISRDNAKNSLYLQMNSLRAEDTAVYYCARGR
SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC
CCTGAGGCTGAGCTGTGCTGCCTCCGGCTTCACCTTCGACGACTACGGCA
TGTCCTGGGTGAGGCAGGCTCCTGGAAAGGGCCTGGAGTGGGTGTCCGGC
ATCAACTGGAACGGCGGATCCACCGGCTACGCCGATTCCGTGAAGGGCAG
GTTCACCATCAGCAGGGACAACGCCAAGAACTCCCTGTACCTGCAGATGA

-continued

ACTCCCTGAGGGCCGAGGACACCGCCGTGTACTACTGCGCCAGGGGCAGG
TCCCTGCTGTTCGACTACTGGGGACAGGGCACCCTGGTGACCGTGTCCAG
G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
YFGKLESKLSVIRNLNDQVLFIDQGNRPLFEDMTDSDCRDNAPRTIFIIS
MYKDSQPRGMAVTISVKCEKISTLSCENKIISFKEMNPPDNIKDTKSDII
FFQRSVPGHDNKMQFESSSYEGYFLACEKERDLFKLILKKEDELGDRSIM
FTVQNEDSGTTNTVAAYNLTWKSTNFKTILEWEPKPVNQVYTVQISTKSG
DWKSKCFYTTDTECDLTDEIVKDVKQTYLARVFSYPAGNVESTGSAGEPL
YENSPEFTPYLETNLGQPTIQSFEQVGTKVNVTVEDERTLVRRNNTFLSL
RDVFGKDLIYTLYYWKSSSSGKKTAKTNTNEFLIDVDKGENYCFSVQAVI
PSRTVNRKSTDSPVECMGQEKGEFRENWVNVISDLKKIEDLIQSMHIDAT
LYTESDVHPSCKVTAMKCFLLELQVISLESGDASIHDTVENLIILANNSL
SSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
TACTTCGGCAAACTGGAATCCAAGCTGAGCGTGATCCGGAATTTAAACGA
CCAAGTTCTGTTTATCGATCAAGGTAACCGGCCTCTGTTCGAGGACATGA
CCGACTCCGATTGCCGGGACAATGCCCCCCGGACCATCTTCATTATCTCC
ATGTACAAGGACAGCCAGCCCCGGGGCATGGCTGTGACAATTAGCGTGAA
GTGTGAGAAAATCAGCACTTTATCTTGTGAGAACAAGATCATCTCCTTTA
AGGAAATGAACCCCCCCGATAACATCAAGGACACCAAGTCCGATATCATC
TTCTTCCAGCGGTCCGTGCCCGGTCACGATAACAAGATGCAGTTCGAATC
CTCCTCCTACGAGGGCTACTTTTTAGCTTGTGAAAAGGAGAGGGATTTAT
TCAAGCTGATCCTCAAGAAGGAGGACGAGCTGGGCGATCGTTCCATCATG
TTCACCGTCCAAAACGAGGATAGCGGCACAACCAACACAGTCGCTGCCTA
TAACCTCACTTGGAAGAGCACCAACTTCAAAACCATCCTCGAATGGGAAC
CCAAACCCGTTAACCAAGTTTACACCGTGCAGATCAGCACCAAGTCCGGC
GACTGGAAGTCCAAATGTTTCTATACCACCGACACCGAGTGCGATCTCAC
CGATGAGATCGTGAAAGATGTGAAACAGACCTACCTCGCCCGGGTGTTTA
GCTACCCCGCCGGCAATGTGGAGAGCACTGGTTCCGCTGGCGAGCCTTTA

-continued

TACGAGAACAGCCCCGAATTTACCCCTTACCTCGAGACCAATTTAGGACA

GCCCACCATCCAAAGCTTTGAGCAAGTTGGCACAAAGGTGAATGTGACAG

TGGAGGACGAGCGGACTTTAGTGCGGCGGAACAACACCTTTCTCAGCCTC

CGGGATGTGTTCGGCAAAGATTTAATCTACACACTGTATTACTGGAAGTC

CTCTTCCTCCGGCAAGAAGACAGCTAAAACCAACACAAACGAGTTTTTAA

TCGACGTGGATAAAGGCGAAAACTACTGTTTCAGCGTGCAAGCTGTGATC

CCCTCCCGGACCGTGAATAGGAAAAGCACCGATAGCCCCGTTGAGTGCAT

GGGCCAAGAAAAGGGCGAGTTCCGGGAGAACTGGGTGAACGTCATCAGCG

ATTTAAAGAAGATCGAAGATTTAATTCAGTCCATGCATATCGACGCCACT

TTATACACAGAATCCGACGTGCACCCCTCTTGTAAGGTGACCGCCATGAA

ATGTTTTTTACTGGAGCTGCAAGTTATCTCTTTAGAGAGCGGAGACGCTA

GCATCCACGACACCGTGGAGAATTTAATCATTTTAGCCAATAACTCTTTA

TCCAGCAACGGCAACGTGACAGAGTCCGGCTGCAAGGAGTGCGAAGAGCT

GGAGGAGAAGAACATCAAGGAGTTTCTGCAATCCTTTGTGCACATTGTCC

AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)

MKWVTFISLLFLFSSAYSYFGKLESKLSVIRNLNDQVLFIDQGNRPLFED

MTDSDCRDNAPRTIFIISMYKDSQPRGMAVTISVKCEKISTLSCENKIIS

FKEMNPPDNIKDTKSDIIFFQRSVPGHDNKMQFESSSYEGYFLACEKERD

LFKLILKKEDELGDRSIMFTVQNEDSGTTNTVAAYNLTWKSTNFKTILEW

EPKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNEF

LIDVDKGENYCFSVQAVIPSRTVNRKSTDSPVECMGQEKGEFRENWVNVI

SDLKKIEDLIQSMHIDATLYTESDVHPSCKVTAMKCFLLELQVISLESGD

ASIHDTVENLIILANNSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)

ATGAAGTGGGTCACATTTATCTCTTTACTGTTCCTCTTCTCCAGCGCCTA

CAGCTACTTCGGCAAACTGGAATCCAAGCTGAGCGTGATCCGGAATTTAA

ACGACCAAGTTCTGTTTATCGATCAAGGTAACCGGCCTCTGTTCGAGGAC

-continued

ATGACCGACTCCGATTGCCGGGACAATGCCCCCCGGACCATCTTCATTAT

CTCCATGTACAAGGACAGCCAGCCCCGGGGCATGGCTGTGACAATTAGCG

TGAAGTGTGAGAAAATCAGCACTTTATCTTGTGAGAACAAGATCATCTCC

TTTAAGGAAATGAACCCCCCCGATAACATCAAGGACACCAAGTCCGATAT

CATCTTCTTCCAGCGGTCCGTGCCCGGTCACGATAACAAGATGCAGTTCG

AATCCTCCTCCTACGAGGGCTACTTTTTAGCTTGTGAAAAGGAGAGGGAT

TTATTCAAGCTGATCCTCAAGAAGGAGGACGAGCTGGGCGATCGTTCCAT

CATGTTCACCGTCCAAAACGAGGATAGCGGCACAACCAACACAGTCGCTG

CCTATAACCTCACTTGGAAGAGCACCAACTTCAAAACCATCCTCGAATGG

GAACCCAAACCCGTTAACCAAGTTTACACCGTGCAGATCAGCACCAAGTC

CGGCGACTGGAAGTCCAAATGTTTCTATACCACCGACACCGAGTGCGATC

TCACCGATGAGATCGTGAAAGATGTGAAACAGACCTACCTCGCCCGGGTG

TTTAGCTACCCCGCCGGCAATGTGGAGAGCACTGGTTCCGCTGGCGAGCC

TTTATACGAGAACAGCCCCGAATTTACCCCTTACCTCGAGACCAATTTAG

GACAGCCCACCATCCAAAGCTTTGAGCAAGTTGGCACAAAGGTGAATGTG

ACAGTGGAGGACGAGCGGACTTTAGTGCGGCGGAACAACACCTTTCTCAG

CCTCCGGGATGTGTTCGGCAAAGATTTAATCTACACACTGTATTACTGGA

AGTCCTCTTCCTCCGGCAAGAAGACAGCTAAAACCAACACAAACGAGTTT

TTAATCGACGTGGATAAAGGCGAAAACTACTGTTTCAGCGTGCAAGCTGT

GATCCCCTCCCGGACCGTGAATAGGAAAAGCACCGATAGCCCCGTTGAGT

GCATGGGCCAAGAAAAGGGCGAGTTCCGGGAGAACTGGGTGAACGTCATC

AGCGATTTAAAGAAGATCGAAGATTTAATTCAGTCCATGCATATCGACGC

CACTTTATACACAGAATCCGACGTGCACCCCTCTTGTAAGGTGACCGCCA

TGAAATGTTTTTTACTGGAGCTGCAAGTTATCTCTTTAGAGAGCGGAGAC

GCTAGCATCCACGACACCGTGGAGAATTTAATCATTTTAGCCAATAACTC

TTTATCCAGCAACGGCAACGTGACAGAGTCCGGCTGCAAGGAGTGCGAAG

AGCTGGAGGAGAAGAACATCAAGGAGTTTCTGCAATCCTTTGTGCACATT

GTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 223)

IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

-continued

ASVPCSGGGGSGGGGSGGGGSRNLPVATPDPGMFPCLHESQNLLRAVSNM
LQKARQTLEFYPCTSEEIDHEDITKDKTSTVEACLPLELTKNESCLNSRE
TSFITNGSCLASRKTSFMMALCLSSIYEDLKMYQVEFKTMNAKLLMDPKR
QIFLDQNMLAVIDELMQALNFNSETVPQKSSLEEPDFYKTKIKLCILLHA
FRIRAVTIDRVMSYLNASITCPPPMSVEHADIWVKSYSLYSRERYICNSG
FKRKAGTSSLTECVLNKATNVAHWTTPSLKCIRSELTQDPAVSVALGQTV
RITCQGDSLRSYYASWYQQKPGQAPVLVIYGKNNRPSGIPDRFSGSSSGN
TASLTITGAQAEDEADYYCNSRDSSGNHVVFGGGTKLTVGHGGGGSGGGG
SGGGGSEVQLVESGGGVVRPGGSLRLSCAASGFTFDDYGMSWVRQAPGKG
LEWVSGINWNGGSTGYADSVKGRFTISRDNAKNSLYLQMNSLRAEDTAVY
YCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 224)
ATTTGGGAACTGAAGAAGGACGTCTACGTGGTCGAACTGGACTGGTATCC
CGATGCTCCCGGCGAAATGGTGGTGCTCACTTGTGACACCCCCGAAGAAG
ACGGCATCACTTGGACCCTCGATCAGAGCAGCGAGGTGCTGGGCTCCGGA
AAGACCCTCACAATCCAAGTTAAGGAGTTCGGAGACGCTGGCCAATACAC
ATGCCACAAGGGAGGCGAGGTGCTCAGCCATTCCTTATTATTATTACACA
AGAAGGAAGACGGAATCTGGTCCACCGACATTTTAAAAGATCAGAAGGAG
CCCAAGAATAAGACCTTTTTAAGGTGTGAGGCCAAAAACTACAGCGGTCG
TTTCACTTGTTGGTGGCTGACCACCATTTCCACCGATTTAACCTTCTCCG
TGAAAAGCAGCCGGGGAAGCTCCGACCCTCAAGGTGTGACATGTGGAGCC
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC
TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCCGGCGGTGGAGGATCCGGAGGAGGTGGCTCCGG
CGGCGGAGGATCTCGTAACCTCCCCGTGGCTACCCCCGATCCCGGAATGT
TCCCTTGTTTACACCACAGCCAGAATTTACTGAGGGCCGTGAGCAACATG
CTGCAGAAAGCTAGGCAGACTTTAGAATTTTACCCTTGCACCAGCGAGGA
GATCGACCATGAAGATATCACCAAGGACAAGACATCCACCGTGGAGGCTT
GTTTACCTCTGGAGCTGACAAAGAACGAGTCTTGTCTCAACTCTCGTGAA

-continued

ACCAGCTTCATCACAAATGGCTCTTGTTTAGCTTCCCGGAAGACCTCCTT
TATGATGGCTTTATGCCTCAGCTCCATCTACGAGGATTTAAAGATGTACC
AAGTGGAGTTCAAGACCATGAACGCCAAGCTGCTCATGGACCCTAAACGG
CAGATCTTTTTAGACCAGAACATGCTGGCTGTGATTGATGAGCTGATGCA
AGCTTTAAACTTCAACTCCGAGACCGTCCCTCAGAAGTCCTCCCTCGAGG
AGCCCGATTTTTACAAGACAAAGATCAAACTGTGCATTTTACTCCACGCC
TTTAGGATCCGGGCCGTGACCATTGACCGGGTCATGAGCTATTTAAACGC
CAGCATTACATGCCCCCCTCCCATGAGCGTGGAGCACGCCGACATCTGGG
TGAAGAGCTATAGCCTCTACAGCCGGGAGAGGTATATCTGTAACAGCGGC
TTCAAGAGGAAGGCCGGCACCAGCAGCCTCACCGAGTGCGTGCTGAATAA
GGCTACCAACGTGGCTCACTGGACAACACCCTCTTTAAAGTGCATCCGGT
CCGAGCTGACCCAGGACCCTGCTGTGTCCGTGGCTCTGGGCCAGACCGTG
AGGATCACCTGCCAGGGCGACTCCCTGAGGTCCTACTACGCCTCCTGGTA
CCAGCAGAAGCCCGGCCAGGCTCCTGTGCTGGTGATCTACGGCAAGAACA
ACAGGCCCTCCGGCATCCCTGACAGGTTCTCCGGATCCTCCTCCGGCAAC
ACCGCCTCCCTGACCATCACAGGCGCTCAGGCCGAGGACGAGGCTGACTA
CTACTGCAACTCCAGGGACTCCTCCGGCAACCATGTGGTGTTCGGCGGCG
GCACCAAGCTGACCGTGGGCCATGGCGGCGGCGGCTCCGGAGGCGGCGGC
AGCGGCGGAGGAGGATCCGAGGTGCAGCTGGTGGAGTCCGGAGGAGGAGT
GGTGAGGCCTGGAGGCTCCCTGAGGCTGAGCTGTGCTGCCTCCGGCTTCA
CCTTCGACGACTACGGCATGTCCTGGGTGAGGCAGGCTCCTGGAAAGGGC
CTGGAGTGGGTGTCCGGCATCAACTGGAACGGCGGATCCACCGGCTACGC
CGATTCCGTGAAGGGCAGGTTCACCATCAGCAGGGACAACGCCAAGAACT
CCCTGTACCTGCAGATGAACTCCCTGAGGGCCGAGGACACCGCCGTGTAC
TACTGCGCCAGGGGCAGGTCCCTGCTGTTCGACTACTGGGGACAGGGCAC
CCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 225)
MKWVTFISLLFLFSSAYSIWELKKDVYVVELDWYPDAPGEMVVLTCDTPE
EDGITWTLDQSSEVLGSGKTLTIQVKEFGDAGQYTCHKGGEVLSHSLLLL
HKKEDGIWSTDILKDQKEPKNKTFLRCEAKNYSGRFTCWWLTTISTDLTF
SVKSSRGSSDPQGVTCGAATLSAERVRGDNKEYEYSVECQEDSACPAAEE
SLPIEVMVDAVHKLKYENYTSSFFIRDIIKPDPPKNLQLKPLKNSRQVEV
SWEYPDTWSTPHSYFSLTFCVQVQGKSKREKKDRVFTDKTSATVICRKNA
SISVRAQDRYYSSSWSEWASVPCSGGGGSGGGGSGGGGSRNLPVATPDPG
MFPCLHHSQNLLRAVSNMLQKARQTLEFYPCTSEEIDHEDITKDKTSTVE

-continued

```
ACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSL

EEPDFYKTKIKLCILLHAFRIRAVTIDRVMSYLNASITCPPPMSVEHADI

WVKSYSLYSRERYICNSGFKRKAGTSSLTECVLNKATNVAHWTTPSLKCI

RSELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVFG

GGTKLTVGHGGGGSGGGGSGGGGSEVQLVESGGGVVRPGGSLRLSCAASG

FTFDDYGMSWVRQAPGKGLEWVSGINWNGGSTGYADSVKGRFTISRDNAK

NSLYLQMNSLRAEDTAVYYCARGRSLLFDYWGQGTLVTVSR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                             (SEQ ID NO: 226)
ATGAAATGGGTGACCTTTATTTCTTTACTGTTCCTCTTTAGCAGCGCCTA

CTCCATTTGGGAACTGAAGAAGGACGTCTACGTGGTCGAACTGGACTGGT

ATCCCGATGCTCCCGGCGAAATGGTGGTGCTCACTTGTGACACCCCCGAA

GAAGACGGCATCACTTGGACCCTCGATCAGAGCAGCGAGGTGCTGGGCTC

CGGAAAGACCCTCACAATCCAAGTTAAGGAGTTCGGAGACGCTGGCCAAT

ACACATGCCACAAGGGAGGCGAGGTGCTCAGCCATTCCTTATTATTATTA

CACAAGAAGGAAGACGGAATCTGGTCCACCGACATTTTAAAAGATCAGAA

GGAGCCCAAGAATAAGACCTTTTTAAGGTGTGAGGCCAAAAACTACAGCG

GTCGTTTCACTTGTTGGTGGCTGACCACCATTTCCACCGATTTAACCTTC

TCCGTGAAAAGCAGCCGGGGAAGCTCCGACCCTCAAGGTGTGACATGTGG

AGCCGCTACCCTCAGCGCTGAGAGGGTTCGTGGCGATAACAAGGAATACG

AGTACAGCGTGGAGTGCCAAGAAGATAGCGCTTGTCCCGCTGCCGAAGAA

TCTTTACCCATTGAGGTGATGGTGGACGCCGTGCACAAACTCAAGTACGA

GAACTACACCTCCTCCTTCTTTATCCGGGACATCATTAAGCCCGATCCTC

CTAAGAATTTACAGCTGAAGCCTCTCAAAAATAGCCGGCAAGTTGAGGTC

TCTTGGGAATATCCCGACACTTGGAGCACACCCCACAGCTACTTCTCTTT

AACCTTTTGTGTGCAAGTTCAAGGTAAAAGCAAGCGGGAGAAGAAAGACC

GGGTGTTTACCGACAAAACCAGCGCCACCGTCATCTGTCGGAAGAACGCC

TCCATCAGCGTGAGGGCTCAAGATCGTTATTACTCCAGCAGCTGGTCCGA

GTGGGCCAGCGTGCCTTGTTCCGGCGGTGGAGGATCCGGAGGAGGTGGCT

CCGGCGGCGGAGGATCTCGTAACCTCCCCGTGGCTACCCCCGATCCCGGA

ATGTTCCCTTGTTTACACCACAGCCAGAATTTACTGAGGGCCGTGAGCAA

CATGCTGCAGAAAGCTAGGCAGACTTTAGAATTTTACCCTTGCACCAGCG

AGGAGATCGACCATGAAGATATCACCAAGGACAAGACATCCACCGTGGAG

GCTTGTTTACCTCTGGAGCTGACAAAGAACGAGTCTTGTCTCAACTCTCG

TGAAACCAGCTTCATCACAAATGGCTCTTGTTTAGCTTCCCGGAAGACCT
```

-continued

```
CCTTTATGATGGCTTTATGCCTCAGCTCCATCTACGAGGATTTAAAGATG

TACCAAGTGGAGTTCAAGACCATGAACGCCAAGCTGCTCATGGACCCTAA

ACGGCAGATCTTTTTAGACCAGAACATGCTGGCTGTGATTGATGAGCTGA

TGCAAGCTTTAAACTTCAACTCCGAGACCGTCCCTCAGAAGTCCTCCCTC

GAGGAGCCCGATTTTTACAAGACAAAGATCAAACTGTGCATTTTACTCCA

CGCCTTTAGGATCCGGGCCGTGACCATTGACCGGGTCATGAGCTATTTAA

ACGCCAGCATTACATGCCCCCCTCCCATGAGCGTGGAGCACGCCGACATC

TGGGTGAAGAGCTATAGCCTCTACAGCCGGGAGAGGTATATCTGTAACAG

CGGCTTCAAGAGGAAGGCCGGCACCAGCAGCCTCACCGAGTGCGTGCTGA

ATAAGGCTACCAACGTGGCTCACTGGACAACACCCTCTTTAAAGTGCATC

CGGTCCGAGCTGACCCAGGACCCTGCTGTGTCCGTGGCTCTGGGCCAGAC

CGTGAGGATCACCTGCCAGGGCGACTCCCTGAGGTCCTACTACGCCTCCT

GGTACCAGCAGAAGCCCGGCCAGGCTCCTGTGCTGGTGATCTACGGCAAG

AACAACAGGCCCTCCGGCATCCCTGACAGGTTCTCCGGATCCTCCTCCGG

CAACACCGCCTCCCTGACCATCACAGGCGCTCAGGCCGAGGACGAGGCTG

ACTACTACTGCAACTCCAGGGACTCCTCCGGCAACCATGTGGTGTTCGGC

GGCGGCACCAAGCTGACCGTGGGCCATGGCGGCGGCGGCTCCGGAGGCGG

CGGCAGCGGCGGAGGAGGATCCGAGGTGCAGCTGGTGGAGTCCGGAGGAG

GAGTGGTGAGGCCTGGAGGCTCCCTGAGGCTGAGCTGTGCTGCCTCCGGC

TTCACCTTCGACGACTACGGCATGTCCTGGGTGAGGCAGGCTCCTGGAAA

GGGCCTGGAGTGGGTGTCCGGCATCAACTGGAACGGCGGATCCACCGGCT

ACGCCGATTCCGTGAAGGGCAGGTTCACCATCAGCAGGGACAACGCCAAG

AACTCCCTGTACCTGCAGATGAACTCCCTGAGGGCCGAGGACACCGCCGT

GTACTACTGCGCCAGGGGCAGGTCCCTGCTGTTCGACTACTGGGGACAGG

GCACCCTGGTGACCGTGTCCAGG.
```

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
GATTGTGATATTGAAGGTAAAGATGGCAAACAATATGAGAGTGTTCTAAT
GGTCAGCATCGATCAATTATTGGACAGCATGAAAGAAATTGGTAGCAATT
GCCTGAATAATGAATTTAACTTTTTTAAAAGACATATCTGTGATGCTAAT
AAGGAAGGTATGTTTTTATTCCGTGCTGCTCGCAAGTTGAGGCAATTTCT
TAAAATGAATAGCACTGGTGATTTTGATCTCCACTTATTAAAAGTTTCAG
AAGGCACAACAATACTGTTGAACTGCACTGGCCAGGTTAAAGGAAGAAAA
CCAGCTGCCCTGGGTGAAGCCCAACCAACAAAGAGTTTGGAAGAAAATAA
ATCTTTAAAGGAACAGAAAAAACTGAATGACTTGTGTTTCCTAAAGAGAC
TATTACAAGAGATAAAAACTTGTTGGAATAAAATTTTGATGGGCACTAAA
GAACAC.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCAT.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
CAAGGTCAAGATCGCCACATGATTAGAATGCGTCAACTTATAGATATTGT
TGATCAGCTGAAAAATTATGTGAATGACTTGGTCCCTGAATTTCTGCCAG
CTCCAGAAGATGTAGAGACAAACTGTGAGTGGTCAGCTTTTTCCTGTTTT
CAGAAGGCCCAACTAAAGTCAGCAAATACAGGAAACAATGAAAGGATAAT
CAATGTATCAATTAAAAAGCTGAAGAGGAAACCACCTTCCACAAATGCAG
GGAGAAGACAGAAACACAGACTAACATGCCCTTCATGTGATTCTTATGAG
AAAAAACCACCCAAAGAATTCCTAGAAAGATTCAAATCACTTCTCCAAAA
GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCC

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKN
NRPSGIPDRFSGSSSGNTASLTITGAQAEDEADYYCNSRDSSGNHVVFGG
GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGT
GAGGATCACCTGCCAGGGCGACTCCCTGAGGTCCTACTACGCCTCCTGGT
ACCAGCAGAAGCCCGGCCAGGCTCCTGTGCTGGTGATCTACGGCAAGAAC
AACAGGCCCTCCGGCATCCCTGACAGGTTCTCCGGATCCTCCTCCGGCAA
CACCGCCTCCCTGACCATCACAGGCGCTCAGGCCGAGGACGAGGCTGACT
ACTACTGCAACTCCAGGGACTCCTCCGGCAACCATGTGGTGTTCGGCGGC
GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSG
INWNGGSTGYADSVKGRFTISRDNAKNSLYLQMNSLRAEDTAVYYCARGR
SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC
CCTGAGGCTGAGCTGTGCTGCCTCCGGCTTCACCTTCGACGACTACGGCA
TGTCCTGGGTGAGGCAGGCTCCTGGAAAGGGCCTGGAGTGGGTGTCCGGC
ATCAACTGGAACGGCGGATCCACCGGCTACGCCGATTCCGTGAAGGGCAG
GTTCACCATCAGCAGGGACAACGCCAAGAACTCCCTGTACCTGCAGATGA
ACTCCCTGAGGGCCGAGGACACCGCCGTGTACTACTGCGCCAGGGGCAGG
TCCCTGCTGTTCGACTACTGGGGACAGGGCACCCTGGTGACCGTGTCCAG
G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
DCDIEGKDGKQYESVLMVSIDQLLDSMKEIGSNCLNNEFNEFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK

-continued

EHSGTTNTVAAYNLTWKSTNFKTILEWEPKPVNQVYTVQISTKSGDWKSK
CFYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVFG
KDLIYTLYYWKSSSSGKKTAKTNTNEFLIDVDKGENYCFSVQAVIPSRTV
NRKSTDSPVECMGQEKGEFRENWVNVISDLKKIEDLIQSMHIDATLYTES
DVHPSCKVTAMKCFLLELQVISLESGDASIHDTVENLIILANNSLSSNGN
VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCATAGCGGCACAACCAACACAGTCGCTGCCTATAACCTCACTTGGAA
GAGCACCAACTTCAAAACCATCCTCGAATGGGAACCCAAACCCGTTAACC
AAGTTTACACCGTGCAGATCAGCACCAAGTCCGGCGACTGGAAGTCCAAA
TGTTTCTATACCACCGACACCGAGTGCGATCTCACCGATGAGATCGTGAA
AGATGTGAAACAGACCTACCTCGCCCGGGTGTTTAGCTACCCCGCCGGCA
ATGTGGAGAGCACTGGTTCCGCTGGCGAGCCTTTATACGAGAACAGCCCC
GAATTTACCCCTTACCTCGAGACCAATTTAGGACAGCCCACCATCCAAAG
CTTTGAGCAAGTTGGCACAAAGGTGAATGTGACAGTGGAGGACGAGCGGA
CTTTAGTGCGGCGGAACAACACCTTTCTCAGCCTCCGGGATGTGTTCGGC
AAAGATTTAATCTACACACTGTATTACTGGAAGTCCTCTTCCTCCGGCAA
GAAGACAGCTAAAACCAACACAAACGAGTTTTTAATCGACGTGGATAAAG
GCGAAAACTACTGTTTCAGCGTGCAAGCTGTGATCCCCTCCCGGACCGTG
AATAGGAAAAGCACCGATAGCCCCGTTGAGTGCATGGGCCAAGAAAAGGG
CGAGTTCCGGGAGAACTGGGTGAACGTCATCAGCGATTTAAAGAAGATCG
AAGATTTAATTCAGTCCATGCATATCGACGCCACTTTATACACAGAATCC
GACGTGCACCCCTCTTGTAAGGTGACCGCCATGAAATGTTTTTTACTGGA
GCTGCAAGTTATCTCTTTAGAGAGCGGAGACGCTAGCATCCACGACACCG
TGGAGAATTTAATCATTTTAGCCAATAACTCTTTATCCAGCAACGGCAAC

-continued

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

-continued

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 232)

SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSRITCPPPMSVE

HADIWVKSYSLYSRERYICNSGFKRKAGTSSLTECVLNKATNVAHWTTPS

LKCIRQGQDRHMIRMRQLIDIVDQLKNYVNDLVPEFLPAPEDVETNCEWS

AFSCFQKAQLKSANTGNNERIINVSIKKLKRKPPSTNAGRRQKHRLTCPS

CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 233)

TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

-continued

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGGATTACATGCCCCCCTCCCATGAGCGTGGAG

CACGCCGACATCTGGGTGAAGAGCTATAGCCTCTACAGCCGGGAGAGGTA

TATCTGTAACAGCGGCTTCAAGAGGAAGGCCGGCACCAGCAGCCTCACCG

AGTGCGTGCTGAATAAGGCTACCAACGTGGCTCACTGGACAACACCCTCT

TTAAAGTGCATCCGGCAGGGCCAGGACAGGCACATGATCCGGATGAGGCA

GCTCATCGACATCGTCGACCAGCTGAAGAACTACGTGAACGACCTGGTGC

CCGAGTTTCTGCCTGCCCCCGAGGACGTGGAGACCAACTGCGAGTGGTCC

GCCTTCTCCTGCTTTCAGAAGGCCCAGCTGAAGTCCGCCAACACCGGCAA

CAACGAGCGGATCATCAACGTGAGCATCAAGAAGCTGAAGCGGAAGCCTC

CCTCCACAAACGCCGGCAGGAGGCAGAAGCACAGGCTGACCTGCCCCAGC

TGTGACTCCTACGAGAAGAAGCCCCCCAAGGAGTTCCTGGAGAGGTTCAA

GTCCCTGCTGCAGAAGATGATCCATCAGCACCTGTCCTCCAGGACCCACG

GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 234)

MKWVTFISLLFLFSSAYSSELTQDPAVSVALGQTVRITCQGDSLRSYYAS

WYQQKPGQAPVLVIYGKNNRPSGIPDRFSGSSSGNTASLTITGAQAEDEA

DYYCNSRDSSGNHVVFGGGTKLTVGHGGGGSGGGGSGGGGSEVQLVESGG

GVVRPGGSLRLSCAASGFTFDDYGMSWVRQAPGKGLEWVSGINWNGGSTG

YADSVKGRFTISRDNAKNSLYLQMNSLRAEDTAVYYCARGRSLLFDYWGQ

GTLVTVSRITCPPPMSVEHADIWVKSYSLYSRERYICNSGFKRKAGTSSL

TECVLNKATNVAHWTTPSLKCIRQGQDRHMIRMRQLIDIVDQLKNYVNDL

VPEFLPAPEDVETNCEWSAFSCFQKAQLKSANTGNNERIINVSIKKLKRK

PPSTNAGRRQKHRLTCPSCDSYEKKPPKEFLERFKSLLQKMIHQHLSSRT

HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 235)

ATGAAGTGGGTGACCTTCATCAGCCTGCTGTTCCTGTTCTCCAGCGCCTA

CTCCTCCGAGCTGACCCAGGACCCTGCTGTGTCCGTGGCTCTGGGCCAGA

CCGTGAGGATCACCTGCCAGGGCGACTCCCTGAGGTCCTACTACGCCTCC

TGGTACCAGCAGAAGCCCGGCCAGGCTCCTGTGCTGGTGATCTACGGCAA

GAACAACAGGCCCTCCGGCATCCCTGACAGGTTCTCCGGATCCTCCTCCG

GCAACACCGCCTCCCTGACCATCACAGGCGCTCAGGCCGAGGACGAGGCT

GACTACTACTGCAACTCCAGGGACTCCTCCGGCAACCATGTGGTGTTCGG

CGGCGGCACCAAGCTGACCGTGGGCCATGGCGGCGGCGGCTCCGGAGGCG

GCGGCAGCGGCGGAGGAGGATCCGAGGTGCAGCTGGTGGAGTCCGGAGGA

GGAGTGGTGAGGCCTGGAGGCTCCCTGAGGCTGAGCTGTGCTGCCTCCGG

CTTCACCTTCGACGACTACGGCATGTCCTGGGTGAGGCAGGCTCCTGGAA

AGGGCCTGGAGTGGGTGTCCGGCATCAACTGGAACGGCGGATCCACCGGC

TACGCCGATTCCGTGAAGGGCAGGTTCACCATCAGCAGGGACAACGCCAA

GAACTCCCTGTACCTGCAGATGAACTCCCTGAGGGCCGAGGACACCGCCG

TGTACTACTGCGCCAGGGGCAGGTCCCTGCTGTTCGACTACTGGGGACAG

GGCACCCTGGTGACCGTGTCCAGGATTACATGCCCCCCTCCCATGAGCGT

GGAGCACGCCGACATCTGGGTGAAGAGCTATAGCCTCTACAGCCGGGAGA

GGTATATCTGTAACAGCGGCTTCAAGAGGAAGGCCGGCACCAGCAGCCTC

ACCGAGTGCGTGCTGAATAAGGCTACCAACGTGGCTCACTGGACAACACC

CTCTTTAAAGTGCATCCGGCAGGGCCAGGACAGGCACATGATCCGGATGA

GGCAGCTCATCGACATCGTCGACCAGCTGAAGAACTACGTGAACGACCTG

GTGCCCGAGTTTCTGCCTGCCCCCGAGGACGTGGAGACCAACTGCGAGTG

GTCCGCCTTCTCCTGCTTTCAGAAGGCCCAGCTGAAGTCCGCCAACACCG

GCAACAACGAGCGGATCATCAACGTGAGCATCAAGAAGCTGAAGCGGAAG

CCTCCCTCCACAAACGCCGGCAGGAGGCAGAAGCACAGGCTGACCTGCCC

CAGCTGTGACTCCTACGAGAAGAAGCCCCCCAAGGAGTTCCTGGAGAGGT

TCAAGTCCCTGCTGCAGAAGATGATCCATCAGCACCTGTCCTCCAGGACC

CACGGCTCCGAGGACTCC.

Exemplary Multi-Chain Chimeric Polypeptides—Type G

In some embodiments of any of the multi-chain chimeric polypeptides described herein, the first target-binding domain and the second targeting-binding domain each independently bind specifically to TGFβ (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble human TGFβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

-continued

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)

QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)

CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

-continued

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)

SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)

TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)

EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC
CCTGAGGCTGAGCTGTGCTGCCTCCGGCTTCACCTTCGACGACTACGGCA
TGTCCTGGGTGAGGCAGGCTCCTGGAAAGGGCCTGGAGTGGGTGTCCGGC
ATCAACTGGAACGGCGGATCCACCGGCTACGCCGATTCCGTGAAGGGCAG
GTTCACCATCAGCAGGGACAACGCCAAGAACTCCCTGTACCTGCAGATGA
ACTCCCTGAGGGCCGAGGACACCGCCGTGTACTACTGCGCCAGGGGCAGG
TCCCTGCTGTTCGACTACTGGGGACAGGGCACCCTGGTGACCGTGTCCAG
G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDSGTTNTVAAYNLT
WKSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPTI
QSFEQVGTKVNVTVEDERTLVRRNNTFLSLRDVFGKDLIYTLYYWKSSSS
GKKTAKTNTNEFLIDVDKGENYCFSVQAVIPSRTVNRKSTDSPVECMGQE
KGEFRENWVNVISDLKKIEDLIQSMHIDATLYTESDVHPSCKVTAMKCFL
LELQVISLESGDASIHDTVENLIILANNSLSSNGNVTESGCKECEELEEK
NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC

-continued

CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACAGCGGCACAACCAACACAGTCGCTGCCTATAACCTCACT
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK

-continued

LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACAGCGGCACAACCAACACAGTCGCTGCCTATAACCT
CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG
TGGATAAAGGCGAAAACTACTGTTTCAGCGTGCAAGCTGTGATCCCCTCC
CGGACCGTGAATAGGAAAAGCACCGATAGCCCCGTTGAGTGCATGGGCCA
AGAAAAGGGCGAGTTCCGGGAGAACTGGGTGAACGTCATCAGCGATTTAA
AGAAGATCGAAGATTTAATTCAGTCCATGCATATCGACGCCACTTTATAC
ACAGAATCCGACGTGCACCCCTCTTGTAAGGTGACCGCCATGAAATGTTT
TTTACTGGAGCTGCAAGTTATCTCTTTAGAGAGCGGAGACGCTAGCATCC
ACGACACCGTGGAGAATTTAATCATTTTAGCCAATAACTCTTTATCCAGC
AACGGCAACGTGACAGAGTCCGGCTGCAAGGAGTGCGAAGAGCTGGAGGA
GAAGAACATCAAGGAGTTTCTGCAATCCTTTGTGCACATTGTCCAGATGT
TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 232)
SELTQDPAVSVALGQTVRITCQGDSLRSYYASWYQQKPGQAPVLVIYGKN
NRPSGIPDRFSGSSSGNTASLTITGAQAEDEADYYCNSRDSSGNHVVFGG
GTKLTVGHGGGGSGGGGSGGGGSEVQLVESGGGVVRPGGSLRLSCAASGF
TFDDYGMSWVRQAPGKGLEWVSGINWNGGSTGYADSVKGRFTISRDNAKN
SLYLQMNSLRAEDTAVYYCARGRSLLFDYWGQGTLVTVSRITCPPPMSVE
HADIWVKSYSLYSRERYICNSGFKRKAGTSSLTECVLNKATNVAHWTTPS
LKCIRQGQDRHMIRMRQLIDIVDQLKNYVNDLVPEFLPAPEDVETNCEWS
AFSCFQKAQLKSANTGNNERIINVSIKKLKRKPPSTNAGRRQKHRLTCPS
CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 233)
TCCGAGCTGACCCAGGACCCTGCTGTGTCCGTGGCTCTGGGCCAGACCGT
GAGGATCACCTGCCAGGGCGACTCCCTGAGGTCCTACTACGCCTCCTGGT
ACCAGCAGAAGCCCGGCCAGGCTCCTGTGCTGGTGATCTACGGCAAGAAC
AACAGGCCCTCCGGCATCCCTGACAGGTTCTCCGGATCCTCCTCCGGCAA

-continued

CACCGCCTCCCTGACCATCACAGGCGCTCAGGCCGAGGACGAGGCTGACT
ACTACTGCAACTCCAGGGACTCCTCCGGCAACCATGTGGTGTTCGGCGGC
GGCACCAAGCTGACCGTGGGCCATGGCGGCGGCGGCTCCGGAGGCGGCGG
CAGCGGCGGAGGAGGATCCGAGGTGCAGCTGGTGGAGTCCGGAGGAGGAG
TGGTGAGGCCTGGAGGCTCCCTGAGGCTGAGCTGTGCTGCCTCCGGCTTC
ACCTTCGACGACTACGGCATGTCCTGGGTGAGGCAGGCTCCTGGAAAGGG
CCTGGAGTGGGTGTCCGGCATCAACTGGAACGGCGGATCCACCGGCTACG
CCGATTCCGTGAAGGGCAGGTTCACCATCAGCAGGGACAACGCCAAGAAC
TCCCTGTACCTGCAGATGAACTCCCTGAGGGCCGAGGACACCGCCGTGTA
CTACTGCGCCAGGGGCAGGTCCCTGCTGTTCGACTACTGGGGACAGGGCA
CCCTGGTGACCGTGTCCAGGATTACATGCCCCCCTCCCATGAGCGTGGAG
CACGCCGACATCTGGGTGAAGAGCTATAGCCTCTACAGCCGGGAGAGGTA
TATCTGTAACAGCGGCTTCAAGAGGAAGGCCGGCACCAGCAGCCTCACCG
AGTGCGTGCTGAATAAGGCTACCAACGTGGCTCACTGGACAACACCCTCT
TTAAAGTGCATCCGGCAGGGCCAGGACAGGCACATGATCCGGATGAGGCA
GCTCATCGACATCGTCGACCAGCTGAAGAACTACGTGAACGACCTGGTGC
CCGAGTTTCTGCCTGCCCCCGAGGACGTGGAGACCAACTGCGAGTGGTCC
GCCTTCTCCTGCTTTCAGAAGGCCCAGCTGAAGTCCGCCAACACCGGCAA
CAACGAGCGGATCATCAACGTGAGCATCAAGAAGCTGAAGCGGAAGCCTC
CCTCCACAAACGCCGGCAGGAGGCAGAAGCACAGGCTGACCTGCCCCAGC
TGTGACTCCTACGAGAAGAAGCCCCCCAAGGAGTTCCTGGAGAGGTTCAA
GTCCCTGCTGCAGAAGATGATCCATCAGCACCTGTCCTCCAGGACCCACG
GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 234)
MKWVTFISLLFLFSSAYSSELTQDPAVSVALGQTVRITCQGDSLRSYYAS
WYQQKPGQAPVLVIYGKNNRPSGIPDRFSGSSSGNTASLTITGAQAEDEA
DYYCNSRDSSGNHVVFGGGTKLTVGHGGGGSGGGGSGGGGSEVQLVESGG
GVVRPGGSLRLSCAASGFTFDDYGMSWVRQAPGKGLEWVSGINWNGGSTG
YADSVKGRFTISRDNAKNSLYLQMNSLRAEDTAVYYCARGRSLLFDYWGQ
GTLVTVSRITCPPPMSVEHADIWVKSYSLYSRERYICNSGFKRKAGTSSL
TECVLNKATNVAHWTTPSLKCIRQGQDRHMIRMRQLIDIVDQLKNYVNDL
VPEFLPAPEDVETNCEWSAFSCFQKAQLKSANTGNNERIINVSIKKLKRK
PPSTNAGRRQKHRLTCPSCDSYEKKPPKEFLERFKSLLQKMIHQHLSSRT
HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 235)
ATGAAGTGGGTGACCTTCATCAGCCTGCTGTTCCTGTTCTCCAGCGCCTA
CTCCTCCGAGCTGACCCAGGACCCTGCTGTGTCCGTGGCTCTGGGCCAGA
CCGTGAGGATCACCTGCCAGGGCGACTCCCTGAGGTCCTACTACGCCTCC
TGGTACCAGCAGAAGCCCGGCCAGGCTCCTGTGCTGGTGATCTACGGCAA
GAACAACAGGCCCTCCGGCATCCCTGACAGGTTCTCCGGATCCTCCTCCG
GCAACACCGCCTCCCTGACCATCACAGGCGCTCAGGCCGAGGACGAGGCT
GACTACTACTGCAACTCCAGGGACTCCTCCGGCAACCATGTGGTGTTCGG
CGGCGGCACCAAGCTGACCGTGGGCCATGGCGGCGGCGGCTCCGGAGGCG
GCGGCAGCGGCGGAGGAGGATCCGAGGTGCAGCTGGTGGAGTCCGGAGGA
GGAGTGGTGAGGCCTGGAGGCTCCCTGAGGCTGAGCTGTGCTGCCTCCGG
CTTCACCTTCGACGACTACGGCATGTCCTGGGTGAGGCAGGCTCCTGGAA
AGGGCCTGGAGTGGGTGTCCGGCATCAACTGGAACGGCGGATCCACCGGC
TACGCCGATTCCGTGAAGGGCAGGTTCACCATCAGCAGGGACAACGCCAA
GAACTCCCTGTACCTGCAGATGAACTCCCTGAGGGCCGAGGACACCGCCG
TGTACTACTGCGCCAGGGGCAGGTCCCTGCTGTTCGACTACTGGGGACAG
GGCACCCTGGTGACCGTGTCCAGGATTACATGCCCCCCTCCCATGAGCGT
GGAGCACGCCGACATCTGGGTGAAGAGCTATAGCCTCTACAGCCGGGAGA
GGTATATCTGTAACAGCGGCTTCAAGAGGAAGGCCGGCACCAGCAGCCTC
ACCGAGTGCGTGCTGAATAAGGCTACCAACGTGGCTCACTGGACAACACC
CTCTTTAAAGTGCATCCGGCAGGGCCAGGACAGGCACATGATCCGGATGA
GGCAGCTCATCGACATCGTCGACCAGCTGAAGAACTACGTGAACGACCTG
GTGCCCGAGTTTCTGCCTGCCCCCGAGGACGTGGAGACCAACTGCGAGTG
GTCCGCCTTCTCCTGCTTTCAGAAGGCCCAGCTGAAGTCCGCCAACACCG
GCAACAACGAGCGGATCATCAACGTGAGCATCAAGAAGCTGAAGCGGAAG
CCTCCCTCCACAAACGCCGGCAGGAGGCAGAAGCACAGGCTGACCTGCCC
CAGCTGTGACTCCTACGAGAAGAAGCCCCCCAAGGAGTTCCTGGAGAGGT
TCAAGTCCCTGCTGCAGAAGATGATCCATCAGCACCTGTCCTCCAGGACC
CACGGCTCCGAGGACTCC.

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

-continued
GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
DCDIEGKDGKQYESVLMVSIDQLLDSMKEIGSNCLNNEFNEFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

-continued

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)
DCDIEGKDGKQYESVLMVSIDQLLDSMKEIGSNCLNNEFNFFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EHITCPPPMSVEHADIWVKSYSLYSRERYICNSGFKRKAGTSSLTECVLN
KATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 204)
GATTGTGATATTGAAGGTAAAGATGGCAAACAATATGAGAGTGTTCTAAT
GGTCAGCATCGATCAATTATTGGACAGCATGAAAGAAATTGGTAGCAATT
GCCTGAATAATGAATTTAACTTTTTTAAAAGACATATCTGTGATGCTAAT
AAGGAAGGTATGTTTTTATTCCGTGCTGCTCGCAAGTTGAGGCAATTTCT
TAAAATGAATAGCACTGGTGATTTTGATCTCCACTTATTAAAAGTTTCAG
AAGGCACAACAATACTGTTGAACTGCACTGGCCAGGTTAAAGGAAGAAAA
CCAGCTGCCCTGGGTGAAGCCCAACCAACAAAGAGTTTGGAAGAAAATAA
ATCTTTAAAGGAACAGAAAAAACTGAATGACTTGTGTTTCCTAAAGAGAC
TATTACAAGAGATAAAAACTTGTTGGAATAAAATTTTGATGGGCACTAAA
GAACACATCACGTGCCCTCCCCCCATGTCCGTGGAACACGCAGACATCTG
GGTCAAGAGCTACAGCTTGTACTCCAGGGAGCGGTACATTTGTAACTCTG
GTTTCAAGCGTAAAGCCGGCACGTCCAGCCTGACGGAGTGCGTGTTGAAC
AAGGCCACGAATGTCGCCCACTGGACAACCCCCAGTCTCAAATGCATTAG
A.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 250)
MKWVTFISLLFLFSSAYSDCDIEGKDGKQYESVLMVSIDQLLDSMKEIGS
NCLNNEFNFFKRHICDANKEGMFLFRAARKLRQFLKMNSTGDFDLHLLKV
SEGTTILLNCTGQVKGRKPAALGEAQPTKSLEENKSLKEQKKLNDLCFLK
RLLQEIKTCWNKILMGTKEHITCPPPMSVEHADIWVKSYSLYSRERYICN
SGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 251)
ATGAAGTGGGTGACCTTCATCAGCCTGCTGTTCCTGTTCTCCAGCGCCTA
CTCCGATTGCGACATCGAGGGCAAGGACGGCAAGCAGTACGAGAGCGTGC
TGATGGTGTCCATCGACCAGCTGCTGGACAGCATGAAGGAGATCGGCTCC
AACTGCCTCAACAACGAGTTCAACTTCTTCAAGCGGCACATCTGCGACGC
CAACAAGGAGGGCATGTTCCTGTTCAGGGCCGCCAGGAAACTGCGGCAGT
TCCTGAAGATGAACTCCACCGGCGACTTCGACCTGCACCTGCTGAAGGTG
TCCGAGGGCACCACCATCCTGCTGAACTGCACCGGACAGGTGAAGGGCCG
GAAACCTGCTGCTCTGGGAGAGGCCCAACCCACCAAGAGCCTGGAGGAGA
ACAAGTCCCTGAAGGAGCAGAAGAAGCTGAACGACCTGTGCTTCCTGAAG
AGGCTGCTGCAGGAGATCAAGACCTGCTGGAACAAGATCCTGATGGGCAC
CAAGGAGCATATTACATGCCCCCCTCCCATGAGCGTGGAGCACGCCGACA
TCTGGGTGAAGAGCTATAGCCTCTACAGCCGGGAGAGGTATATCTGTAAC
AGCGGCTTCAAGAGGAAGGCCGGCACCAGCAGCCTCACCGAGTGCGTGCT
GAATAAGGCTACCAACGTGGCTCACTGGACAACACCCTCTTTAAAGTGCA
TCCGG.

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)

MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)

ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

-continued

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 257)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 259)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNEFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCAT.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 260)
REGPELSPDDPAGLLDLRQGMFAQLVAQNVLLIDGPLSWYSDPGLAGVSL
TGGLSYKEDTKELVVAKAGVYYVFFQLELRRVVAGEGSGSVSLALHLQPL
RSAAGAAALALTVDLPPASSEARNSAFGFQGRLLHLSAGQRLGVHLHTEA
RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 261)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG
ACGGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGG
CCGGCGAGGGCTCAGGCTCCGTTTCACTTGCGCTGCACCTGCAGCCACTG
CGCTCTGCTGCTGGGGCCGCCGCCCTGGCTTTGACCGTGGACCTGCCACC

-continued

CGCCTCCTCCGAGGCTCGGAACTCGGCCTTCGGTTTCCAGGGCCGCTTGC
TGCACCTGAGTGCCGGCCAGCGCCTGGGCGTCCATCTTCACACTGAGGCC
AGGGCACGCCATGCCTGGCAGCTTACCCAGGGCGCCACAGTCTTGGGACT
CTTCCGGGTGACCCCCGAAATCCCAGCCGGACTCCCTTCACCGAGGTCGG
AA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 262)
DPAGLLDLRQGMFAQLVAQNVLLIDGPLSWYSDPGLAGVSLTGGLSYKED
TKELVVAKAGVYYVFFQLELRRVVAGEGSGSVSLALHLQPLRSAAGAAAL
ALTVDLPPASSEARNSAFGFQGRLLHLSAGQRLGVHLHTEARARHAWQLT
QGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 263)
GATCCCGCCGGCCTCTTGGACCTGCGGCAGGGCATGTTTGCGCAGCTGGT
GGCCCAAAATGTTCTGCTGATCGATGGGCCCCTGAGCTGGTACAGTGACC
CAGGCCTGGCAGGCGTGTCCCTGACGGGGGGCCTGAGCTACAAAGAGGAC
ACGAAGGAGCTGGTGGTGGCCAAGGCTGGAGTCTACTATGTCTTCTTTCA
ACTAGAGCTGCGGCGCGTGGTGGCCGGCGAGGGCTCAGGCTCCGTTTCAC
TTGCGCTGCACCTGCAGCCACTGCGCTCTGCTGCTGGGGCCGCCGCCCTG
GCTTTGACCGTGGACCTGCCACCCGCCTCCTCCGAGGCTCGGAACTCGGC
CTTCGGTTTCCAGGGCCGCTTGCTGCACCTGAGTGCCGGCCAGCGCCTGG
GCGTCCATCTTCACACTGAGGCCAGGGCACGCCATGCCTGGCAGCTTACC
CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
DCDIEGKDGKQYESVLMVSIDQLLDSMKEIGSNCLNNEFNEFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK

-continued

EHSGTTNTVAAYNLTWKSTNFKTILEWEPKPVNQVYTVQISTKSGDWKSK
CFYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVFG
KDLIYTLYYWKSSSSGKKTAKTNTNEFLIDVDKGENYCFSVQAVIPSRTV
NRKSTDSPVECMGQEKGEFRENWVNVISDLKKIEDLIQSMHIDATLYTES
DVHPSCKVTAMKCFLLELQVISLESGDASIHDTVENLIILANNSLSSNGN
VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGCGACATCGAGGGCAAGGACGGCAAGCAGTACGAGAGCGTGCTGATG
GTGTCCATCGACCAGCTGCTGGACAGCATGAAGGAGATCGGCTCCAACTGC
CTCAACAACGAGTTCAACTTCTTCAAGCGGCACATCTGCGACGCCAACAAG
GAGGGCATGTTCCTGTTCAGGGCCGCCAGGAAACTGCGGCAGTTCCTGAAG
ATGAACTCCACCGGCGACTTCGACCTGCACCTGCTGAAGGTGTCCGAGGGC
ACCACCATCCTGCTGAACTGCACCGGACAGGTGAAGGGCCGGAAACCTGCT
GCTCTGGGAGAGGCCCAACCCACCAAGAGCCTGGAGGAGAACAAGTCCCTG
AAGGAGCAGAAGAAGCTGAACGACCTGTGCTTCCTGAAGAGGCTGCTGCAG
GAGATCAAGACCTGCTGGAACAAGATCCTGATGGGCACCAAGGAGCATAGC
GGCACAACCAACACAGTCGCTGCCTATAACCTCACTTGGAAGAGCACCAAC
TTCAAAACCATCCTCGAATGGGAACCCAAACCCGTTAACCAAGTTTACACC
GTGCAGATCAGCACCAAGTCCGGCGACTGGAAGTCCAAATGTTTCTATACC
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA
CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC

-continued

GAAGAGCTGGAGGAGAAGAACATCAAGGAGTTTCTGCAATCCTTTGTGCAC
ATTGTCCAGATGTTCATCAATACCTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)
MKWVTFISLLFLFSSAYSDCDIEGKDGKQYESVLMVSIDQLLDSMKEIGSN
CLNNEFNFFKRHICDANKEGMFLFRAARKLRQFLKMNSTGDFDLHLLKVSE
GTTILLNCTGQVKGRKPAALGEAQPTKSLEENKSLKEQKKLNDLCFLKRLL
QEIKTCWNKILMGTKEHSGTTNTVAAYNLTWKSTNFKTILEWEPKPVNQVY
TVQISTKSGDWKSKCFYTTDTECDLTDEIVKDVKQTYLARVFSYPAGNVES
TGSAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENYCF
SVQAVIPSRTVNRKSTDSPVECMGQEKGEFRENWVNVISDLKKIEDLIQSM
HIDATLYTESDVHPSCKVTAMKCFLLELQVISLESGDASIHDTVENLIILA
NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)
ATGAAGTGGGTGACCTTCATCAGCCTGCTGTTCCTGTTCTCCAGCGCCTAC
TCCGATTGCGACATCGAGGGCAAGGACGGCAAGCAGTACGAGAGCGTGCTG
ATGGTGTCCATCGACCAGCTGCTGGACAGCATGAAGGAGATCGGCTCCAAC
TGCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCTG
AAGATGAACTCCACCGGCGACTTCGACCTGCACCTGCTGAAGGTGTCCGAG
GGCACCACCATCCTGCTGAACTGCACCGGACAGGTGAAGGGCCGGAAACCT
GCTGCTCTGGGAGAGGCCCAACCCACCAAGAGCCTGGAGGAGAACAAGTCC
CTGAAGGAGCAGAAGAAGCTGAACGACCTGTGCTTCCTGAAGAGGCTGCTG
CAGGAGATCAAGACCTGCTGGAACAAGATCCTGATGGGCACCAAGGAGCAT
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
ACTGGTTCCGCTGGCGAGCCTTTATACGAGAACAGCCCCGAATTTACCCCT
TACCTCGAGACCAATTTAGGACAGCCCACCATCCAAAGCTTTGAGCAAGTT

-continued

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAGAACTGG

GTGAACGTCATCAGCGATTTAAAGAAGATCGAAGATTTAATTCAGTCCATG

CATATCGACGCCACTTTATACACAGAATCCGACGTGCACCCCTCTTGTAAG

GTGACCGCCATGAAATGTTTTTTACTGGAGCTGCAAGTTATCTCTTTAGAG

AGCGGAGACGCTAGCATCCACGACACCGTGGAGAATTTAATCATTTTAGCC

AATAACTCTTTATCCAGCAACGGCAACGTGACAGAGTCCGGCTGCAAGGAG

TGCGAAGAGCTGGAGGAGAAGAACATCAAGGAGTTTCTGCAATCCTTTGTG

CACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 268)

QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTPSCDSYEKKP

PKEFLERFKSLLQKMIHQHLSSRTHGSEDSITCPPPMSVEHADIWVKSYSL

YSRERYICNSGFKRKAGTSSLTECVLNKATNVAHWTTPSLKCIRGGGGSGG

GGSGGGGSREGPELSPDDPAGLLDLRQGMFAQLVAQNVLLIDGPLSWYSDP

GLAGVSLTGGLSYKEDTKELVVAKAGVYYVFFQLELRRVVAGEGSGSVSLA

LHLQPLRSAAGAAALALTVDLPPASSEARNSAFGFQGRLLHLSAGQRLGVH

LHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 269)

CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCCATTACATGC

-continued

CCCCCTCCCATGAGCGTGGAGCACGCCGACATCTGGGTGAAGAGCTATAGC

CTCTACAGCCGGGAGAGGTATATCTGTAACAGCGGCTTCAAGAGGAAGGCC

GGCACCAGCAGCCTCACCGAGTGCGTGCTGAATAAGGCTACCAACGTGGCT

CACTGGACAACACCCTCTTTAAAGTGCATCCGGGGCGGTGGAGGATCCGGA

GGAGGTGGCTCCGGCGGCGGAGGATCTCGCGAGGGTCCCGAGCTTTCGCCC

GACGATCCCGCCGGCCTCTTGGACCTGCGGCAGGGCATGTTTGCGCAGCTG

GTGGCCCAAAATGTTCTGCTGATCGATGGGCCCCTGAGCTGGTACAGTGAC

CCAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCAA

CTAGAGCTGCGGCGCGTGGTGGCCGGCGAGGGCTCAGGCTCCGTTTCACTT

GCGCTGCACCTGCAGCCACTGCGCTCTGCTGCTGGGGCCGCCGCCCTGGCT

TTGACCGTGGACCTGCCACCCGCCTCCTCCGAGGCTCGGAACTCGGCCTTC

GGTTTCCAGGGCCGCTTGCTGCACCTGAGTGCCGGCCAGCGCCTGGGCGTC

CATCTTCACACTGAGGCCAGGGCACGCCATGCCTGGCAGCTTACCCAGGGC

GCCACAGTCTTGGGACTCTTCCGGGTGACCCCCGAAATCCCAGCCGGACTC

CCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 270)

MKWVTFISLLFLFSSAYSQGQDRHMIRMRQLIDIVDQLKNYVNDLVPEFLP

APEDVETNCEWSAFSCFQKAQLKSANTGNNERIINVSIKKLKRKPPSTNAG

RRQKHRLTCPSCDSYEKKPPKEFLERFKSLLQKMIHQHLSSRTHGSEDSIT

CPPPMSVEHADIWVKSYSLYSRERYICNSGFKRKAGTSSLTECVLNKATNV

AHWTTPSLKCIRGGGGSGGGGSGGGGSREGPELSPDDPAGLLDLRQGMFAQ

LVAQNVLLIDGPLSWYSDPGLAGVSLTGGLSYKEDTKELVVAKAGVYYVFF

QLELRRVVAGEGSGSVSLALHLQPLRSAAGAAALALTVDLPPASSEARNSA

FGFQGRLLHLSAGQRLGVHLHTEARARHAWQLTQGATVLGLFRVTPEIPAG

LPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 271)

ATGAAGTGGGTGACCTTCATCAGCCTGCTGTTCCTGTTCTCCAGCGCCTAC

TCCCAGGGCCAGGACAGGCACATGATCCGGATGAGGCAGCTCATCGACATC

GTCGACCAGCTGAAGAACTACGTGAACGACCTGGTGCCCGAGTTTCTGCCT

-continued

GCCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCATC
AACGTGAGCATCAAGAAGCTGAAGCGGAAGCCTCCCTCCACAAACGCCGGC
AGGAGGCAGAAGCACAGGCTGACCTGCCCCAGCTGTGACTCCTACGAGAAG
AAGCCCCCCAAGGAGTTCCTGGAGAGGTTCAAGTCCCTGCTGCAGAAGATG
ATCCATCAGCACCTGTCCTCCAGGACCCACGGCTCCGAGGACTCCATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGGGGCGGTGGAGGATCC
GGAGGAGGTGGCTCCGGCGGCGGAGGATCTCGCGAGGGTCCCGAGCTTTCG
CCCGACGATCCCGCCGGCCTCTTGGACCTGCGGCAGGGCATGTTTGCGCAG
CTGGTGGCCCAAAATGTTCTGCTGATCGATGGGCCCCTGAGCTGGTACAGT
GACCCAGGCCTGGCAGGCGTGTCCCTGACGGGGGGCCTGAGCTACAAAGAG
GACACGAAGGAGCTGGTGGTGGCCAAGGCTGGAGTCTACTATGTCTTCTTT
CAACTAGAGCTGCGGCGCGTGGTGGCCGGCGAGGGCTCAGGCTCCGTTTCA
CTTGCGCTGCACCTGCAGCCACTGCGCTCTGCTGCTGGGGCCGCCGCCCTG
GCTTTGACCGTGGACCTGCCACCCGCCTCCTCCGAGGCTCGGAACTCGGCC
TTCGGTTTCCAGGGCCGCTTGCTGCACCTGAGTGCCGGCCAGCGCCTGGGC
GTCCATCTTCACACTGAGGCCAGGGCACGCCATGCCTGGCAGCTTACCCAG
GGCGCCACAGTCTTGGGACTCTTCCGGGTGACCCCCGAAATCCCAGCCGGA
CTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 272)
QGQDRHMIRMRQLIDIVDQLKNYVNDLVPEFLPAPEDVETNCEWSAFSCFQ
KAQLKSANTGNNERIINVSIKKLKRKPPSTNAGRRQKHRLTCPSCDSYEKK
PPKEFLERFKSLLQKMIHQHLSSRTHGSEDSITCPPPMSVEHADIWVKSYS
LYSRERYICNSGFKRKAGTSSLTECVLNKATNVAHWTTPSLKCIRGGGGSG
GGGSGGGGSDPAGLLDLRQGMFAQLVAQNVLLIDGPLSWYSDPGLAGVSLT
GGLSYKEDTKELVVAKAGVYYVFFQLELRRVVAGEGSGSVSLALHLQPLRS
AAGAAALALTVDLPPASSEARNSAFGFQGRLLHLSAGQRLGVHLHTEARAR
HAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 273)
CAGGGCCAGGACAGGCACATGATCCGGATGAGGCAGCTCATCGACATCGTC
GACCAGCTGAAGAACTACGTGAACGACCTGGTGCCCGAGTTTCTGCCTGCC
CCCGAGGACGTGGAGACCAACTGCGAGTGGTCCGCCTTCTCCTGCTTTCAG
AAGGCCCAGCTGAAGTCCGCCAACACCGGCAACAACGAGCGGATCATCAAC
GTGAGCATCAAGAAGCTGAAGCGGAAGCCTCCCTCCACAAACGCCGGCAGG
AGGCAGAAGCACAGGCTGACCTGCCCCAGCTGTGACTCCTACGAGAAGAAG
CCCCCCAAGGAGTTCCTGGAGAGGTTCAAGTCCCTGCTGCAGAAGATGATC
CATCAGCACCTGTCCTCCAGGACCCACGGCTCCGAGGACTCCATTACATGC
CCCCCTCCCATGAGCGTGGAGCACGCCGACATCTGGGTGAAGAGCTATAGC
CTCTACAGCCGGGAGAGGTATATCTGTAACAGCGGCTTCAAGAGGAAGGCC
GGCACCAGCAGCCTCACCGAGTGCGTGCTGAATAAGGCTACCAACGTGGCT
CACTGGACAACACCCTCTTTAAAGTGCATCCGGGGCGGTGGAGGATCCGGA
GGAGGTGGCTCCGGCGGCGGAGGATCTGATCCCGCCGGCCTCTTGGACCTG
CGGCAGGGCATGTTTGCGCAGCTGGTGGCCCAAAATGTTCTGCTGATCGAT
GGGCCCCTGAGCTGGTACAGTGACCCAGGCCTGGCAGGCGTGTCCCTGACG
GGGGGCCTGAGCTACAAAGAGGACACGAAGGAGCTGGTGGTGGCCAAGGCT
GGAGTCTACTATGTCTTCTTTCAACTAGAGCTGCGGCGCGTGGTGGCCGGC
GAGGGCTCAGGCTCCGTTTCACTTGCGCTGCACCTGCAGCCACTGCGCTCT
GCTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCTG
AGTGCCGGCCAGCGCCTGGGCGTCCATCTTCACACTGAGGCCAGGGCACGC
CATGCCTGGCAGCTTACCCAGGGCGCCACAGTCTTGGGACTCTTCCGGGTG
ACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 274)
MKWVTFISLLFLFSSAYSQGQDRHMIRMRQLIDIVDQLKNYVNDLVPEFLP
APEDVETNCEWSAFSCFQKAQLKSANTGNNERIINVSIKKLKRKPPSTNAG
RRQKHRLTCPSCDSYEKKPPKEFLERFKSLLQKMIHQHLSSRTHGSEDSIT
CPPPMSVEHADIWVKSYSLYSRERYICNSGFKRKAGTSSLTECVLNKATNV
AHWTTPSLKCIRGGGGSGGGGSGGGGSDPAGLLDLRQGMFAQLVAQNVLLI
DGPLSWYSDPGLAGVSLTGGLSYKEDTKELVVAKAGVYYVFFQLELRRVVA
GEGSGSVSLALHLQPLRSAAGAAALALTVDLPPASSEARNSAFGFQGRLLH
LSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 275)

ATGAAGTGGGTGACCTTCATCAGCCTGCTGTTCCTGTTCTCCAGCGCCTAC

TCCCAGGGCCAGGACAGGCACATGATCCGGATGAGGCAGCTCATCGACATC

GTCGACCAGCTGAAGAACTACGTGAACGACCTGGTGCCCGAGTTTCTGCCT

GCCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCATC

AACGTGAGCATCAAGAAGCTGAAGCGGAAGCCTCCCTCCACAAACGCCGGC

AGGAGGCAGAAGCACAGGCTGACCTGCCCCAGCTGTGACTCCTACGAGAAG

AAGCCCCCCAAGGAGTTCCTGGAGAGGTTCAAGTCCCTGCTGCAGAAGATG

ATCCATCAGCACCTGTCCTCCAGGACCCACGGCTCCGAGGACTCCATTACA

TGCCCCCCTCCCATGAGCGTGGAGCACGCCGACATCTGGGTGAAGAGCTAT

AGCCTCTACAGCCGGGAGAGGTATATCTGTAACAGCGGCTTCAAGAGGAAG

GCCGGCACCAGCAGCCTCACCGAGTGCGTGCTGAATAAGGCTACCAACGTG

GCTCACTGGACAACACCCTCTTTAAAGTGCATCCGGGGCGGTGGAGGATCC

GGAGGAGGTGGCTCCGGCGGCGGAGGATCTGATCCCGCCGGCCTCTTGGAC

CTGCGGCAGGGCATGTTTGCGCAGCTGGTGGCCCAAAATGTTCTGCTGATC

GATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAAG

GCTGGAGTCTACTATGTCTTCTTTCAACTAGAGCTGCGGCGCGTGGTGGCC

GGCGAGGGCTCAGGCTCCGTTTCACTTGCGCTGCACCTGCAGCCACTGCGC

TCTGCTGCTGGGGCCGCCGCCCTGGCTTTGACCGTGGACCTGCCACCCGCC

TCCTCCGAGGCTCGGAACTCGGCCTTCGGTTTCCAGGGCCGCTTGCTGCAC

CTGAGTGCCGGCCAGCGCCTGGGCGTCCATCTTCACACTGAGGCCAGGGCA

CGCCATGCCTGGCAGCTTACCCAGGGCGCCACAGTCTTGGGACTCTTCCGG

GTGACCCCCGAAATC.

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)

DCDIEGKDGKQYESVLMVSIDQLLDSMKEIGSNCLNNEFNEFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)

GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG

-continued

AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA
TAACAATGGCGCCGTGAAATTTCCCCAGCTGTGCAAATTCTGCGATGTGA
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNND1VIVTDNNGAVKFPQLCKFCDVRFSTCDNQKSCMSNCSITS
ICEKPQEVCVAVWRKNDENITLETVCHDPKLPYHDFILEDAASPKCIMKEK
KKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC

-continued

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)

DCDIEGKDGKQYESVLMVSIDQLLDSMKEIGSNCLNNEFNEFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEHS

GTTNTVAAYNLTWKSTNEKTILEWEPKPVNQVYTVQISTKSGDWKSKCEYT

TDTECDLTDEIVKDVKQTYLARVFSYPAGNVESTGSAGEPLYENSPEFTPY

LETNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKSTDS

PVECMGQEKGEFRENWVNVISDLKKIEDLIQSMHIDATLYTESDVHPSCKV

TAMKCFLLELQVISLESGDASIHDTVENLIILANNSLSSNGNVTESGCKEC

EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

-continued

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCATAGC

GGCACAACCAACACAGTCGCTGCCTATAACCTCACTTGGAAGAGCACCAAC

TTCAAAACCATCCTCGAATGGGAACCCAAACCCGTTAACCAAGTTTACACC

GTGCAGATCAGCACCAAGTCCGGCGACTGGAAGTCCAAATGTTTCTATACC

ACCGACACCGAGTGCGATCTCACCGATGAGATCGTGAAAGATGTGAAACAG

ACCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTAC

CTCGAGACCAATTTAGGACAGCCCACCATCCAAAGCTTTGAGCAAGTTGGC

ACAAAGGTGAATGTGACAGTGGAGGACGAGCGGACTTTAGTGCGGCGGAAC

AACACCTTTCTCAGCCTCCGGGATGTGTTCGGCAAAGATTTAATCTACACA

CTGTATTACTGGAAGTCCTCTTCCTCCGGCAAGAAGACAGCTAAAACCAAC

ACAAACGAGTTTTTAATCGACGTGGATAAAGGCGAAAACTACTGTTTCAGC

GTGCAAGCTGTGATCCCCTCCCGGACCGTGAATAGGAAAAGCACCGATAGC

CCCGTTGAGTGCATGGGCCAAGAAAAGGGCGAGTTCCGGGAGAACTGGGTG

AACGTCATCAGCGATTTAAAGAAGATCGAAGATTTAATTCAGTCCATGCAT

ATCGACGCCACTTTATACACAGAATCCGACGTGCACCCCTCTTGTAAGGTG

ACCGCCATGAAATGTTTTTTACTGGAGCTGCAAGTTATCTCTTTAGAGAGC

GGAGACGCTAGCATCCACGACACCGTGGAGAATTTAATCATTTTAGCCAAT

AACTCTTTATCCAGCAACGGCAACGTGACAGAGTCCGGCTGCAAGGAGTGC

GAAGAGCTGGAGGAGAAGAACATCAAGGAGTTTCTGCAATCCTTTGTGCAC

ATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIGSN

CLNNEFNFFKRHICDANKEGMFLFRAARKLRQFLKMNSTGDFDLHLLKVSE

GTTILLNCTGQVKGRKPAALGEAQPTKSLEENKSLKEQKKLNDLCFLKRLL

QEIKTCWNKILMGTKEHSGTTNTVAAYNLTWKSTNFKTILEWEPKPVNQVY

TVQISTKSGDWKSKCFYTTDTECDLTDEIVKDVKQTYLARVFSYPAGNVES

TGSAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENYCF

SVQAVIPSRTVNRKSTDSPVECMGQEKGEFRENWVNVISDLKKIEDLIQSM

HIDATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)
ATGAAGTGGGTGACCTTCATCAGCCTGCTGTTCCTGTTCTCCAGCGCCTAC
TCCGATTGCGACATCGAGGGCAAGGACGGCAAGCAGTACGAGAGCGTGCTG
ATGGTGTCCATCGACCAGCTGCTGGACAGCATGAAGGAGATCGGCTCCAAC
TGCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCTG
AAGATGAACTCCACCGGCGACTTCGACCTGCACCTGCTGAAGGTGTCCGAG
GGCACCACCATCCTGCTGAACTGCACCGGACAGGTGAAGGGCCGGAAACCT
GCTGCTCTGGGAGAGGCCCAACCCACCAAGAGCCTGGAGGAGAACAAGTCC
CTGAAGGAGCAGAAGAAGCTGAACGACCTGTGCTTCCTGAAGAGGCTGCTG
CAGGAGATCAAGACCTGCTGGAACAAGATCCTGATGGGCACCAAGGAGCAT
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
ACTGGTTCCGCTGGCGAGCCTTTATACGAGAACAGCCCCGAATTTACCCCT
TACCTCGAGACCAATTTAGGACAGCCCACCATCCAAAGCTTTGAGCAAGTT
GGCACAAAGGTGAATGTGACAGTGGAGGACGAGCGGACTTTAGTGCGGCGG
AACAACACCTTTCTCAGCCTCCGGGATGTGTTCGGCAAAGATTTAATCTAC
ACACTGTATTACTGGAAGTCCTCTTCCTCCGGCAAGAAGACAGCTAAAACC
AACACAAACGAGTTTTTAATCGACGTGGATAAAGGCGAAAACTACTGTTTC
AGCGTGCAAGCTGTGATCCCCTCCCGGACCGTGAATAGGAAAAGCACCGAT
AGCCCCGTTGAGTGCATGGGCCAAGAAAAGGGCGAGTTCCGGGAGAACTGG
GTGAACGTCATCAGCGATTTAAAGAAGATCGAAGATTTAATTCAGTCCATG
CATATCGACGCCACTTTATACACAGAATCCGACGTGCACCCCTCTTGTAAG
GTGACCGCCATGAAATGTTTTTTACTGGAGCTGCAAGTTATCTCTTTAGAG
AGCGGAGACGCTAGCATCCACGACACCGTGGAGAATTTAATCATTTTAGCC
AATAACTCTTTATCCAGCAACGGCAACGTGACAGAGTCCGGCTGCAAGGAG
TGCGAAGAGCTGGAGGAGAAGAACATCAAGGAGTTTCTGCAATCCTTTGTG
CACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDITCPPPMSVEHADIWVKSY
SLYSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 257)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDI
TCPPPMSVEHADIWVKSYSLYSRERYICNSGFKRKAGTSSLTECVLNKATN
VAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 259)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACATT
ACATGCCCCCCTCCCATGAGCGTGGAGCACGCCGACATCTGGGTGAAGAGC
TATAGCCTCTACAGCCGGGAGAGGTATATCTGTAACAGCGGCTTCAAGAGG
AAGGCCGGCACCAGCAGCCTCACCGAGTGCGTGCTGAATAAGGCTACCAAC
GTGGCTCACTGGACAACACCCTCTTTAAAGTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 183)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 184)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 188)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD.
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGAC.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCFQ
KAQLKSANTGNNERIINVSIKKLKRKPPSTNAGRRQKHRLTCPSCDSYEKK
PPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGTC
GACCAGCTGAAGAACTACGTGAACGACCTGGTGCCCGAGTTTCTGCCTGCC

-continued
CCCGAGGACGTGGAGACCAACTGCGAGTGGTCCGCCTTCTCCTGCTTTCAG
AAGGCCCAGCTGAAGTCCGCCAACACCGGCAACAACGAGCGGATCATCAAC
GTGAGCATCAAGAAGCTGAAGCGGAAGCCTCCCTCCACAAACGCCGGCAGG
AGGCAGAAGCACAGGCTGACCTGCCCCAGCTGTGACTCCTACGAGAAGAAG
CCCCCCAAGGAGTTCCTGGAGAGGTTCAAGTCCCTGCTGCAGAAGATGATC
CATCAGCACCTGTCCTCCAGGACCCACGGCTCCGAGGACTCC.

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 260)
REGPELSPDDPAGLLDLRQGMFAQLVAQNVLLIDGPLSWYSDPGLAGVSLT
GGLSYKEDTKELVVAKAGVYYVFFQLELRRVVAGEGSGSVSLALHLQPLRS
AAGAAALALTVDLPPASSEARNSAFGFQGRLLHLSAGQRLGVHLHTEARAR
HAWQLTQGATVLGLFRVTPEIPAGLPSPRSE.

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 261)
CGCGAGGGTCCCGAGCTTTCGCCCGACGATCCCGCCGGCCTCTTGGACCTG
CGGCAGGGCATGTTTGCGCAGCTGGTGGCCCAAAATGTTCTGCTGATCGAT
GGGCCCCTGAGCTGGTACAGTGACCCAGGCCTGGCAGGCGTGTCCCTGACG
GGGGGCCTGAGCTACAAAGAGGACACGAAGGAGCTGGTGGTGGCCAAGGCT
GGAGTCTACTATGTCTTCTTTCAACTAGAGCTGCGGCGCGTGGTGGCCGGC
GAGGGCTCAGGCTCCGTTTCACTTGCGCTGCACCTGCAGCCACTGCGCTCT
GCTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCTG
AGTGCCGGCCAGCGCCTGGGCGTCCATCTTCACACTGAGGCCAGGGCACGC
CATGCCTGGCAGCTTACCCAGGGCGCCACAGTCTTGGGACTCTTCCGGGTG
ACCCCCGAAATCCCAGCCGGACTCCCTTCACCGAGGTCGGAA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 262)
DPAGLLDLRQGMFAQLVAQNVLLIDGPLSWYSDPGLAGVSLTGGLSYKEDT
KELVVAKAGVYYVFFQLELRRVVAGEGSGSVSLALHLQPLRSAAGAAALAL
TVDLPPASSEARNSAFGFQGRLLHLSAGQRLGVHLHTEARARHAWQLTQGA
TVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 263)
GATCCCGCCGGCCTCTTGGACCTGCGGCAGGGCATGTTTGCGCAGCTGGTG
GCCCAAAATGTTCTGCTGATCGATGGGCCCCTGAGCTGGTACAGTGACCCA
GGCCTGGCAGGCGTGTCCCTGACGGGGGGCCTGAGCTACAAAGAGGACACG
AAGGAGCTGGTGGTGGCCAAGGCTGGAGTCTACTATGTCTTCTTTCAACTA
GAGCTGCGGCGCGTGGTGGCCGGCGAGGGCTCAGGCTCCGTTTCACTTGCG
CTGCACCTGCAGCCACTGCGCTCTGCTGCTGGGGCCGCCGCCCTGGCTTTG
ACCGTGGACCTGCCACCCGCCTCCTCCGAGGCTCGGAACTCGGCCTTCGGT
TTCCAGGGCCGCTTGCTGCACCTGAGTGCCGGCCAGCGCCTGGGCGTCCAT
CTTCACACTGAGGCCAGGGCACGCCATGCCTGGCAGCTTACCCAGGGCGCC
ACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDSGTTNTVAAYNLTWKSTNF
KTILEWEPKPVNQVYTVQISTKSGDWKSKCFYTTDTECDLTDEIVKDVKQT
YLARVFSYPAGNVESTGSAGEPLYENSPEFTPYLETNLGQPTIQSFEQVGT
KVNVTVEDERTLVRRNNTFLSLRDVFGKDLIYTLYYWKSSSSGKKTAKTNT
NEFLIDVDKGENYCFSVQAVIPSRTVNRKSTDSPVECMGQEKGEFRENWVN
VISDLKKIEDLIQSMHIDATLYTESDVHPSCKVTAMKCFLLELQVISLESG
DASIHDTVENLIIILANNSLSSNGNVTESGCKECEELEEKNIKEFLQSFVHI
VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACAGCGGC
ACAACCAACACAGTCGCTGCCTATAACCTCACTTGGAAGAGCACCAACTTC
AAAACCATCCTCGAATGGGAACCCAAACCCGTTAACCAAGTTTACACCGTG
CAGATCAGCACCAAGTCCGGCGACTGGAAGTCCAAATGTTTCTATACCACC
GACACCGAGTGCGATCTCACCGATGAGATCGTGAAAGATGTGAAACAGACC
TACCTCGCCCGGGTGTTTAGCTACCCCGCCGGCAATGTGGAGAGCACTGGT
TCCGCTGGCGAGCCTTTATACGAGAACAGCCCCGAATTTACCCCTTACCTC
GAGACCAATTTAGGACAGCCCACCATCCAAAGCTTTGAGCAAGTTGGCACA
AAGGTGAATGTGACAGTGGAGGACGAGCGGACTTTAGTGCGGCGGAACAAC
ACCTTTCTCAGCCTCCGGGATGTGTTCGGCAAAGATTTAATCTACACACTG
TATTACTGGAAGTCCTCTTCCTCCGGCAAGAAGACAGCTAAAACCAACACA
AACGAGTTTTTAATCGACGTGGATAAAGGCGAAAACTACTGTTTCAGCGTG
CAAGCTGTGATCCCCTCCCGGACCGTGAATAGGAAAAGCACCGATAGCCCC
GTTGAGTGCATGGGCCAAGAAAAGGGCGAGTTCCGGGAGAACTGGGTGAAC
GTCATCAGCGATTTAAAGAAGATCGAAGATTTAATTCAGTCCATGCATATC
GACGCCACTTTATACACAGAATCCGACGTGCACCCCTCTTGTAAGGTGACC
GCCATGAAATGTTTTTTACTGGAGCTGCAAGTTATCTCTTTAGAGAGCGGA
GACGCTAGCATCCACGACACCGTGGAGAATTTAATCATTTTAGCCAATAAC
TCTTTATCCAGCAACGGCAACGTGACAGAGTCCGGCTGCAAGGAGTGCGAA
GAGCTGGAGGAGAAGAACATCAAGGAGTTTCTGCAATCCTTTGTGCACATT
GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCDV
RSTCDNQKSCMSNCSITSICEKPQEVCVAVWRKNDENITLETVCHDPKLPY
HDFILEDAASPKCIMKEKKKPGETFFMCSCSSDECNDNIIFSEEYNTSNPD
GGGGSGGGGSGGGGSIPPHVQKSVNNDMIVTDNNGAVKFPQLCKFCDVRFS
TCDNQKSCMSNCSITSICEKPQEVCVAVWRKNDENITLETVCHDPKLPYHD
FILEDAASPKCIMKEKKKPGETFFMCSCSSDECNDNIIFSEEYNTSNPDSG
TTNTVAAYNLTWKSTNFKTILEWEPKPVNQVYTVQISTKSGDWKSKCFYTT
DTECDLTDEIVKDVKQTYLARVFSYPAGNVESTGSAGEPLYENSPEFTPYL
ETNLGQPTIQSFEQVGTKVNVTVEDERTLVRRNNTFLSLRDVFGKDLIYTL
YYWKSSSSGKKTAKTNTNEFLIDVDKGENYCFSVQAVIPSRTVNRKSTDSP
VECMGQEKGEFRENWVNVISDLKKIEDLIQSMHIDATLYTESDVHPSCKVT
AMKCFLLELQVISLESGDASIHDTVENLIILANNSLSSNGNVTESGCKECE
ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACAGC

-continued

GGCACAACCAACACAGTCGCTGCCTATAACCTCACTTGGAAGAGCACCAAC
TTCAAAACCATCCTCGAATGGGAACCCAAACCCGTTAACCAAGTTTACACC
GTGCAGATCAGCACCAAGTCCGGCGACTGGAAGTCCAAATGTTTCTATACC
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA
CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC
GAAGAGCTGGAGGAGAAGAACATCAAGGAGTTTCTGCAATCCTTTGTGCAC
ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 268)
QGQDRHMIRMRQLIDIVDQLKNYVNDLVPEFLPAPEDVETNCEWSAFSCFQ
KAQLKSANTGNNERIINVSIKKLKRKPPSTNAGRRQKHRLTCPSCDSYEKK
PPKEFLERFKSLLQKMIHQHLSSRTHGSEDSITCPPPMSVEHADIWVKSYS
LYSRERYICNSGFKRKAGTSSLTECVLNKATNVAHWTTPSLKCIRGGGGSG
GGGSGGGGSREGPELSPDDPAGLLDLRQGMFAQLVAQNVLLIDGPLSWYSD
PGLAGVSLTGGLSYKEDTKELVVAKAGVYYVFFQLELRRVVAGEGSGSVSL
ALHLQPLRSAAGAAALALTVDLPPASSEARNSAFGFQGRLLHLSAGQRLGV
HLHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 269)
CAGGGCCAGGACAGGCACATGATCCGGATGAGGCAGCTCATCGACATCGTC
GACCAGCTGAAGAACTACGTGAACGACCTGGTGCCCGAGTTTCTGCCTGCC
CCCGAGGACGTGGAGACCAACTGCGAGTGGTCCGCCTTCTCCTGCTTTCAG
AAGGCCCAGCTGAAGTCCGCCAACACCGGCAACAACGAGCGGATCATCAAC
GTGAGCATCAAGAAGCTGAAGCGGAAGCCTCCCTCCACAAACGCCGGCAGG
AGGCAGAAGCACAGGCTGACCTGCCCCAGCTGTGACTCCTACGAGAAGAAG
CCCCCCAAGGAGTTCCTGGAGAGGTTCAAGTCCCTGCTGCAGAAGATGATC
CATCAGCACCTGTCCTCCAGGACCCACGGCTCCGAGGACTCCATTACATGC
CCCCCTCCCATGAGCGTGGAGCACGCCGACATCTGGGTGAAGAGCTATAGC
CTCTACAGCCGGGAGAGGTATATCTGTAACAGCGGCTTCAAGAGGAAGGCC
GGCACCAGCAGCCTCACCGAGTGCGTGCTGAATAAGGCTACCAACGTGGCT
CACTGGACAACACCCTCTTTAAAGTGCATCCGGGGCGGTGGAGGATCCGGA
GGAGGTGGCTCCGGCGGCGGAGGATCTCGCGAGGGTCCCGAGCTTTCGCCC
GACGATCCCGCCGGCCTCTTGGACCTGCGGCAGGGCATGTTTGCGCAGCTG
GTGGCCCAAAATGTTCTGCTGATCGATGGGCCCCTGAGCTGGTACAGTGAC
CCAGGCCTGGCAGGCGTGTCCCTGACGGGGGGCCTGAGCTACAAAGAGGAC
ACGAAGGAGCTGGTGGTGGCCAAGGCTGGAGTCTACTATGTCTTCTTTCAA
CTAGAGCTGCGGCGCGTGGTGGCCGGCGAGGGCTCAGGCTCCGTTTCACTT
GCGCTGCACCTGCAGCCACTGCGCTCTGCTGCTGGGGCCGCCGCCCTGGCT
TTGACCGTGGACCTGCCACCCGCCTCCTCCGAGGCTCGGAACTCGGCCTTC
GGTTTCCAGGGCCGCTTGCTGCACCTGAGTGCCGGCCAGCGCCTGGGCGTC
CATCTTCACACTGAGGCCAGGGCACGCCATGCCTGGCAGCTTACCCAGGGC
GCCACAGTCTTGGGACTCTTCCGGGTGACCCCCGAAATCCCAGCCGGACTC
CCTTCACCGAGGTCGGAA

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 270)
MKWVTFISLLFLFSSAYSQGQDRHMIRMRQLIDIVDQLKNYVNDLVP
EFLPAPEDVETNCEWSAFSCFQKAQLKSANTGNNERIINVSIKKLKR
KPPSTNAGRRQKHRLTCPSCDSYEKKPPKEFLERFKSLLQKMIHQHL
SSRTHGSEDSITCPPPMSVEHADIWVKSYSLYSRERYICNSGFKRKA
GTSSLTECVLNKATNVAHWTTPSLKCIRGGGGSGGGGSGGGGSREGP
ELSPDDPAGLLDLRQGMFAQLVAQNVLLIDGPLSWYSDPGLAGVSLT
GGLSYKEDTKELVVAKAGVYYVFFQLELRRVVAGEGSGSVSLALHLQ
PLRSAAGAAALALTVDLPPASSEARNSAFGFQGRLLHLSAGQRLGVH
LHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 271)
ATGAAGTGGGTGACCTTCATCAGCCTGCTGTTCCTGTTCTCCAGCGC
CTACTCCCAGGGCCAGGACAGGCACATGATCCGGATGAGGCAGCTCA
TCGACATCGTCGACCAGCTGAAGAACTACGTGAACGACCTGGTGCCC
GAGTTTCTGCCTGCCCCCGAGGACGTGGAGACCAACTGCGAGTGGTC
CGCCTTCTCCTGCTTTCAGAAGGCCCAGCTGAAGTCCGCCAACACCG
GCAACAACGAGCGGATCATCAACGTGAGCATCAAGAAGCTGAAGCGG
AAGCCTCCCTCCACAAACGCCGGCAGGAGGCAGAAGCACAGGCTGAC
CTGCCCCAGCTGTGACTCCTACGAGAAGAAGCCCCCCAAGGAGTTCC
TGGAGAGGTTCAAGTCCCTGCTGCAGAAGATGATCCATCAGCACCTG
TCCTCCAGGACCCACGGCTCCGAGGACTCCATTACATGCCCCCCTCC
CATGAGCGTGGAGCACGCCGACATCTGGGTGAAGAGCTATAGCCTCT
ACAGCCGGGAGAGGTATATCTGTAACAGCGGCTTCAAGAGGAAGGCC
GGCACCAGCAGCCTCACCGAGTGCGTGCTGAATAAGGCTACCAACGT
GGCTCACTGGACAACACCCTCTTTAAAGTGCATCCGGGGCGGTGGAG
GATCCGGAGGAGGTGGCTCCGGCGGCGGAGGATCTCGCGAGGGTCCC
GAGCTTTCGCCCGACGATCCCGCCGGCCTCTTGGACCTGCGGCAGGG
CATGTTTGCGCAGCTGGTGGCCCAAAATGTTCTGCTGATCGATGGGC
CCCTGAGCTGGTACAGTGACCCAGGCCTGGCAGGCGTGTCCCTGACG
GGGGGCCTGAGCTACAAAGAGGACACGAAGGAGCTGGTGGTGGCCAA
GGCTGGAGTCTACTATGTCTTCTTTCAACTAGAGCTGCGGCGCGTGG
TGGCCGGCGAGGGCTCAGGCTCCGTTTCACTTGCGCTGCACCTGCAG
CCACTGCGCTCTGCTGCTGGGGCCGCCGCCCTGGCTTTGACCGTGGA
CCTGCCACCCGCCTCCTCCGAGGCTCGGAACTCGGCCTTCGGTTTCC
AGGGCCGCTTGCTGCACCTGAGTGCCGGCCAGCGCCTGGGCGTCCAT
CTTCACACTGAGGCCAGGGCACGCCATGCCTGGCAGCTTACCCAGGG
CGCCACAGTCTTGGGACTCTTCCGGGTGACCCCCGAAATCCCAGCCG
GACTCCCTTCACCGAGGTCGGAA

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 272)
QGQDRHMIRMRQLIDIVDQLKNYVNDLVPEFLPAPEDVETNCEWSAFS
CFQKAQLKSANTGNNERIINVSIKKLKRKPPSTNAGRRQKHRLTCPSC
DSYEKKPPKEFLERFKSLLQKMIHQHLSSRTHGSEDSITCPPPMSVEH
ADIWVKSYSLYSRERYICNSGFKRKAGTSSLTECVLNKATNVAHWTTP

-continued

SLKCIRGGGGSGGGGSGGGGSDPAGLLDLRQGMFAQLVAQNVLLIDGP

LSWYSDPGLAGVSLTGGLSYKEDTKELVVAKAGVYYVFFQLELRRVVA

GEGSGSVSLALHLQPLRSAAGAAALALTVDLPPASSEARNSAFGFQGR

LLHLSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 273)

CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCCATTACATGCCCCCCTCCCATGAGCGTGGAGCAC

GCCGACATCTGGGTGAAGAGCTATAGCCTCTACAGCCGGGAGAGGTAT

ATCTGTAACAGCGGCTTCAAGAGGAAGGCCGGCACCAGCAGCCTCACC

GAGTGCGTGCTGAATAAGGCTACCAACGTGGCTCACTGGACAACACCC

TCTTTAAAGTGCATCCGGGGCGGTGGAGGATCCGGAGGAGGTGGCTCC

GGCGGCGGAGGATCTGATCCCGCCGGCCTCTTGGACCTGCGGCAGGGC

ATGTTTGCGCAGCTGGTGGCCCAAAATGTTCTGCTGATCGATGGGCCC

CTGAGCTGGTACAGTGACCCAGGCCTGGCAGGCGTGTCCCTGACGGGG

GGCCTGAGCTACAAAGAGGACACGAAGGAGCTGGTGGTGGCCAAGGCT

GGAGTCTACTATGTCTTCTTTCAACTAGAGCTGCGGCGCGTGGTGGCC

GGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCA

CCCGCCTCCTCCGAGGCTCGGAACTCGGCCTTCGGTTTCCAGGGCCGC

TTGCTGCACCTGAGTGCCGGCCAGCGCCTGGGCGTCCATCTTCACACT

GAGGCCAGGGCACGCCATGCCTGGCAGCTTACCCAGGGCGCCACAGTC

TTGGGACTCTTCCGGGTGACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 274)

MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIRGGGGSGGGGSGGGGSDPAGLLDLRQGMFA

QLVAQNVLLIDGPLSWYSDPGLAGVSLTGGLSYKEDTKELVVAKAGVYY

VFFQLELRRVVAGEGSGSVSLALHLQPLRSAAGAAALALTVDLPPASSE

ARNSAFGFQGRLLHLSAGQRLGVHLHTEARARHAWQLTQGATVLGLFRV

TPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 275)

ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTGATCCCGCCGGCCTCTTGGACCTGCGGCAGGGCATGTTTGCG

CAGCTGGTGGCCCAAAATGTTCTGCTGATCGATGGGCCCCTGAGCTGGT

ACAGTGACCCAGGCCTGGCAGGCGTGTCCCTGACGGGGGGCCTGAGCTA

CAAAGAGGACACGAAGGAGCTGGTGGTGGCCAAGGCTGGAGTCTACTAT

GTCTTCTTTCAACTAGAGCTGCGGCGCGTGGTGGCCGGCGAGGGCTCAG

GCTCCGTTTCACTTGCGCTGCACCTGCAGCCACTGCGCTCTGCTGCTGG

GGCCGCCGCCCTGGCTTTGACCGTGGACCTGCCACCCGCCTCCTCCGAG

GCTCGGAACTCGGCCTTCGGTTTCCAGGGCCGCTTGCTGCACCTGAGTG

CCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTG

ACCCCCGAAATC.

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

-continued

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)

ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

CAGGGCCAGGACAGGCACATGATCGGATGAGGCAGCTCATCGACATCGT

CGACCAGCTGAAGAACTACGTGAACGACCTGGTGCCCGAGTTTCTGCCT

GCCCCCGAGGACGTGGAGACCAACTGCGAGTGGTCCGCCTTCTCCTGCT

TTCAGAAGGCCCAGCTGAAGTCCGCCAACACCGGCAACAACGAGCGGAT

-continued

CATCAACGTGAGCATCAAGAAGCTGAAGCGGAAGCCTCCCTCCACAAAC

GCCGGCAGGAGGCAGAAGCACAGGCTGACCTGCCCCAGCTGTGACTCCT

ACGAGAAGAAGCCCCCCAAGGAGTTCCTGGAGAGGTTCAAGTCCCTGCT

GCAGAAGATGATCCATCAGCACCTGTCCTCCAGGACCCACGGCTCCGAG

GACTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)

ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

-continued

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGACAGCGGC

ACAACCAACACAGTCGCTGCCTATAACCTCACTTGGAAGAGCACCAACTTC

AAAACCATCCTCGAATGGGAACCCAAACCCGTTAACCAAGTTTACACCGTG

CAGATCAGCACCAAGTCCGGCGACTGGAAGTCCAAATGTTTCTATACCACC

GACACCGAGTGCGATCTCACCGATGAGATCGTGAAAGATGTGAAACAGACC

TACCTCGCCCGGGTGTTTAGCTACCCCGCCGGCAATGTGGAGAGCACTGGT

TCCGCTGGCGAGCCTTTATACGAGAACAGCCCCGAATTTACCCCTTACCTC

GAGACCAATTTAGGACAGCCCACCATCCAAAGCTTTGAGCAAGTTGGCACA

AAGGTGAATGTGACAGTGGAGGACGAGCGGACTTTAGTGCGGCGGAACAAC

ACCTTTCTCAGCCTCCGGGATGTGTTCGGCAAAGATTTAATCTACACACTG

TATTACTGGAAGTCCTCTTCCTCCGGCAAGAAGACAGCTAAAACCAACACA

AACGAGTTTTTAATCGACGTGGATAAAGGCGAAAACTACTGTTTCAGCGTG

CAAGCTGTGATCCCCTCCCGGACCGTGAATAGGAAAAGCACCGATAGCCCC

GTTGAGTGCATGGGCCAAGAAAAGGGCGAGTTCCGGGAGAACTGGGTGAAC

GTCATCAGCGATTTAAAGAAGATCGAAGATTTAATTCAGTCCATGCATATC

GACGCCACTTTATACACAGAATCCGACGTGCACCCCTCTTGTAAGGTGACC

GCCATGAAATGTTTTTTACTGGAGCTGCAAGTTATCTCTTTAGAGAGCGGA

GACGCTAGCATCCACGACACCGTGGAGAATTTAATCATTTTAGCCAATAAC

TCTTTATCCAGCAACGGCAACGTGACAGAGTCCGGCTGCAAGGAGTGCGAA

GAGCTGGAGGAGAAGAACATCAAGGAGTTTCTGCAATCCTTTGTGCACATT

GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)

MKWVTFISLLFLFSSAYSIPPHVQKSVNNDMIVTDNNGAVKFPQLCKFCDV

RFSTCDNQKSCMSNCSITSICEKPQEVCVAVWRKNDENITLETVCHDPKLP

YHDFILEDAASPKCIMKEKKKPGETFFMCSCSSDECNDNIIFSEEYNTSNP

DGGGGSGGGGSGGGGSIPPHVQKSVNNDMIVTDNNGAVKFPQLCKFCDVRF

STCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPDS

GTTNTVAAYNLTWKSTNFKTILEWEPKPVNQVYTVQISTKSGDWKSKCFYT

TDTECDLTDEIVKDVKQTYLARVFSYPAGNVESTGSAGEPLYENSPEFTPY

-continued

LETNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKSTDS

PVECMGQEKGEFRENWVNVISDLKKIEDLIQSMHIDATLYTESDVHPSCKV

TAMKCFLLELQVISLESGDASIHDTVENLIILANNSLSSNGNVTESGCKEC

EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)

ATGAAGTGGGTGACCTTCATCAGCCTGCTGTTCCTGTTCTCCAGCGCCTAC

TCCATCCCCCCCCATGTGCAAAAGAGCGTGAACAACGATATGATCGTGACC

GACAACAACGGCGCCGTGAAGTTTCCCCAGCTCTGCAAGTTCTGCGATGTC

AGGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAAA

AATGACGAGAACATCACCCTGGAGACCGTGTGTCACGACCCCAAGCTCCCT

TATCACGACTTCATTCTGGAGGACGCTGCCTCCCCCAAATGCATCATGAAG

GAGAAGAAGAAGCCCGGAGAGACCTTCTTTATGTGTTCCTGTAGCAGCGAC

GAGTGTAACGACAACATCATCTTCAGCGAAGAGTACAACACCAGCAACCCT

GATGGAGGTGGCGGATCCGGAGGTGGAGGTTCTGGTGGAGGTGGGAGTATT

CCTCCCCACGTGCAGAAGAGCGTGAATAATGACATGATCGTGACCGATAAC

AATGGCGCCGTGAAATTTCCCCAGCTGTGCAAATTCTGCGATGTGAGGTTT

TCCACCTGCGACAACCAGAAGTCCTGTATGAGCAACTGCTCCATCACCTCC

ATCTGTGAGAAGCCTCAGGAGGTGTGCGTGGCTGTCTGGCGGAAGAATGAC

GAGAATATCACCCTGGAAACCGTCTGCCACGATCCCAAGCTGCCCTACCAC

GATTTCATCCTGGAAGACGCCGCCAGCCCTAAGTGCATCATGAAAGAGAAA

AAGAAGCCTGGCGAGACCTTTTTCATGTGCTCCTGCAGCAGCGACGAATGC

AACGACAATATCATCTTTAGCGAGGAATACAATACCAGCAACCCCGACAGC

GGCACAACCAACACAGTCGCTGCCTATAACCTCACTTGGAAGAGCACCAAC

TTCAAAACCATCCTCGAATGGGAACCCAAACCCGTTAACCAAGTTTACACC

GTGCAGATCAGCACCAAGTCCGGCGACTGGAAGTCCAAATGTTTCTATACC

ACCGACACCGAGTGCGATCTCACCGATGAGATCGTGAAAGATGTGAAACAG

ACCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTAC

CTCGAGACCAATTTAGGACAGCCCACCATCCAAAGCTTTGAGCAAGTTGGC

ACAAAGGTGAATGTGACAGTGGAGGACGAGCGGACTTTAGTGCGGCGGAAC

AACACCTTTCTCAGCCTCCGGGATGTGTTCGGCAAAGATTTAATCTACACA

CTGTATTACTGGAAGTCCTCTTCCTCCGGCAAGAAGACAGCTAAAACCAAC

ACAAACGAGTTTTTAATCGACGTGGATAAAGGCGAAAACTACTGTTTCAGC

-continued

GTGCAAGCTGTGATCCCCTCCCGGACCGTGAATAGGAAAAGCACCGATAGC

CCCGTTGAGTGCATGGGCCAAGAAAAGGGCGAGTTCCGGGAGAACTGGGTG

AACGTCATCAGCGATTTAAAGAAGATCGAAGATTTAATTCAGTCCATGCAT

ATCGACGCCACTTTATACACAGAATCCGACGTGCACCCCTCTTGTAAGGTG

ACCGCCATGAAATGTTTTTTACTGGAGCTGCAAGTTATCTCTTTAGAGAGC

GGAGACGCTAGCATCCACGACACCGTGGAGAATTTAATCATTTTAGCCAAT

AACTCTTTATCCAGCAACGGCAACGTGACAGAGTCCGGCTGCAAGGAGTGC

GAAGAGCTGGAGGAGAAGAACATCAAGGAGTTTCTGCAATCCTTTGTGCAC

ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 300)

IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPDITCPPPMSVEHADIWVKSY

SLYSRERYICNSGFKRKAGTSSLTECVLNKATNVAHWTTPSLKCIRQGQDR

HMIRMRQLIDIVDQLKNYVNDLVPEFLPAPEDVETNCEWSAFSCFQKAQLK

SANTGNNERIINVSIKKLKRKPPSTNAGRRQKHRLTCPSCDSYEKKPPKEF

LERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 301)

ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

-continued

GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGGCAGGGCCAGGACAGG
CACATGATCCGGATGAGGCAGCTCATCGACATCGTCGACCAGCTGAAGAAC
TACGTGAACGACCTGGTGCCCGAGTTTCTGCCTGCCCCCGAGGACGTGGAG
ACCAACTGCGAGTGGTCCGCCTTCTCCTGCTTTCAGAAGGCCCAGCTGAAG
TCCGCCAACACCGGCAACAACGAGCGGATCATCAACGTGAGCATCAAGAAG
CTGAAGCGGAAGCCTCCCTCCACAAACGCCGGCAGGAGGCAGAAGCACAGG
CTGACCTGCCCCAGCTGTGACTCCTACGAGAAGAAGCCCCCCAAGGAGTTC
CTGGAGAGGTTCAAGTCCCTGCTGCAGAAGATGATCCATCAGCACCTGTCC
TCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 302)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDI
TCPPPMSVEHADIWVKSYSLYSRERYICNSGFKRKAGTSSLTECVLNKATN
VAHWTTPSLKCIRQGQDRHMIRMRQLIDIVDQLKNYVNDLVPEFLPAPEDV
ETNCEWSAFSCFQKAQLKSANTGNNERIINVSIKKLKRKPPSTNAGRRQKH
RLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 303)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACATT
ACATGCCCCCCTCCCATGAGCGTGGAGCACGCCGACATCTGGGTGAAGAGC
TATAGCCTCTACAGCCGGGAGAGGTATATCTGTAACAGCGGCTTCAAGAGG
AAGGCCGGCACCAGCAGCCTCACCGAGTGCGTGCTGAATAAGGCTACCAAC
GTGGCTCACTGGACAACACCCTCTTTAAAGTGCATCCGGCAGGGCCAGGAC
AGGCACATGATCCGGATGAGGCAGCTCATCGACATCGTCGACCAGCTGAAG
AACTACGTGAACGACCTGGTGCCCGAGTTTCTGCCTGCCCCCGAGGACGTG
GAGACCAACTGCGAGTGGTCCGCCTTCTCCTGCTTTCAGAAGGCCCAGCTG
AAGTCCGCCAACACCGGCAACAACGAGCGGATCATCAACGTGAGCATCAAG
AAGCTGAAGCGGAAGCCTCCCTCCACAAACGCCGGCAGGAGGCAGAAGCAC
AGGCTGACCTGCCCCAGCTGTGACTCCTACGAGAAGAAGCCCCCCAAGGAG
TTCCTGGAGAGGTTCAAGTCCCTGCTGCAGAAGATGATCCATCAGCACCTG
TCCTCCAGGACCCACGGCTCCGAGGACTCC.

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA
TAACAATGGCGCCGTGAAATTTCCCCAGCTGTGCAAATTCTGCGATGTGA
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC

-continued
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGAC.

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKNN
RPSGIPDRFSGSSSGNTASLTITGAQAEDEADYYCNSRDSSGNHVVFGGGT
KLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGTG
AGGATCACCTGCCAGGGCGACTCCCTGAGGTCCTACTACGCCTCCTGGTAC
CAGCAGAAGCCCGGCCAGGCTCCTGTGCTGGTGATCTACGGCAAGAACAAC
AGGCCCTCCGGCATCCCTGACAGGTTCTCCGGATCCTCCTCCGGCAACACC
GCCTCCCTGACCATCACAGGCGCTCAGGCCGAGGACGAGGCTGACTACTAC
TGCAACTCCAGGGACTCCTCCGGCAACCATGTGGTGTTCGGCGGCGGCACC
AAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSGI
NWNGGSTGYADSVKGRFTISRDNAKNSLYLQMNSLRAEDTAVYYCARGRSL
LFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTCC
CTGAGGCTGAGCTGTGCTGCCTCCGGCTTCACCTTCGACGACTACGGCATG
TCCTGGGTGAGGCAGGCTCCTGGAAAGGGCCTGGAGTGGGTGTCCGGCATC
AACTGGAACGGCGGATCCACCGGCTACGCCGATTCCGTGAAGGGCAGGTTC
ACCATCAGCAGGGACAACGCCAAGAACTCCCTGTACCTGCAGATGAACTCC
CTGAGGGCCGAGGACACCGCCGTGTACTACTGCGCCAGGGGCAGGTCCCTG
CTGTTCGACTACTGGGGACAGGGCACCCTGGTGACCGTGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDSGTTNTVAAYNLTWKSTNF
KTILEWEPKPVNQVYTVQISTKSGDWKSKCFYTTDTECDLTDEIVKDVKQT
YLARVFSYPAGNVESTGSAGEPLYENSPEFTPYLETNLGQPTIQSFEQVGT
KVNVTVEDERTLVRRNNTFLSLRDVFGKDLIYTLYYWKSSSSGKKTAKTNT
NEFLIDVDKGENYCFSVQAVIPSRTVNRKSTDSPVECMGQEKGEFRENWVN
VISDLKKIEDLIQSMHIDATLYTESDVHPSCKVTAMKCFLLELQVISLESG
DASIHDTVENLIILANNSLSSNGNVTESGCKECEELEEKNIKEFLQSFVHI
VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC

-continued

TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACAGCGGC
ACAACCAACACAGTCGCTGCCTATAACCTCACTTGGAAGAGCACCAACTTC
AAAACCATCCTCGAATGGGAACCCAAACCCGTTAACCAAGTTTACACCGTG
CAGATCAGCACCAAGTCCGGCGACTGGAAGTCCAAATGTTTCTATACCACC
GACACCGAGTGCGATCTCACCGATGAGATCGTGAAAGATGTGAAACAGACC
TACCTCGCCCGGGTGTTTAGCTACCCCGCCGGCAATGTGGAGAGCACTGGT
TCCGCTGGCGAGCCTTTATACGAGAACAGCCCCGAATTTACCCCTTACCTC
GAGACCAATTTAGGACAGCCCACCATCCAAAGCTTTGAGCAAGTTGGCACA
AAGGTGAATGTGACAGTGGAGGACGAGCGGACTTTAGTGCGGCGGAACAAC
ACCTTTCTCAGCCTCCGGGATGTGTTCGGCAAAGATTTAATCTACACACTG
TATTACTGGAAGTCCTCTTCCTCCGGCAAGAAGACAGCTAAAACCAACACA
AACGAGTTTTTAATCGACGTGGATAAAGGCGAAAACTACTGTTTCAGCGTG
CAAGCTGTGATCCCCTCCCGGACCGTGAATAGGAAAAGCACCGATAGCCCC
GTTGAGTGCATGGGCCAAGAAAAGGGCGAGTTCCGGGAGAACTGGGTGAAC
GTCATCAGCGATTTAAAGAAGATCGAAGATTTAATTCAGTCCATGCATATC
GACGCCACTTTATACACAGAATCCGACGTGCACCCCTCTTGTAAGGTGACC
GCCATGAAATGTTTTTTACTGGAGCTGCAAGTTATCTCTTTAGAGAGCGGA
GACGCTAGCATCCACGACACCGTGGAGAATTTAATCATTTTAGCCAATAAC
TCTTTATCCAGCAACGGCAACGTGACAGAGTCCGGCTGCAAGGAGTGCGAA
GAGCTGGAGGAGAAGAACATCAAGGAGTTTCTGCAATCCTTTGTGCACATT
GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDS
GTTNTVAAYNLTWKSTNFKTILEWEPKPVNQVYTVQISTKSGDWKSKCFYT
TDTECDLTDEIVKDVKQTYLARVFSYPAGNVESTGSAGEPLYENSPEFTPY
LETNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKSTDS
PVECMGQEKGEFRENWVNVISDLKKIEDLIQSMHIDATLYTESDVHPSCKV
TAMKCFLLELQVISLESGDASIHDTVENLIILANNSLSSNGNVTESGCKEC
EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACAGC
GGCACAACCAACACAGTCGCTGCCTATAACCTCACTTGGAAGAGCACCAAC
TTCAAAACCATCCTCGAATGGGAACCCAAACCCGTTAACCAAGTTTACACC
GTGCAGATCAGCACCAAGTCCGGCGACTGGAAGTCCAAATGTTTCTATACC

-continued
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA
CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC
GAAGAGCTGGAGGAGAAGAACATCAAGGAGTTTCTGCAATCCTTTGTGCAC
ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 308)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDITCPPPMSVEHADIWVKSY
SLYSRERYICNSGFKRKAGTSSLTECVLNKATNVAHWTTPSLKCIRSELTQ
DPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVG
HGGGGSGGGGSGGGGSEVQLVESGGGVVRPGGSLRLSCAASGFTFDDYGMS
WVRQAPGKGLEWVSGINWNGGSTGYADSVKGRFTISRDNAKNSLYLQMNSL
RAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 309)

ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGACATTACA

TGCCCCCCTCCCATGAGCGTGGAGCACGCCGACATCTGGGTGAAGAGCTAT

AGCCTCTACAGCCGGGAGAGGTATATCTGTAACAGCGGCTTCAAGAGGAAG

GCCGGCACCAGCAGCCTCACCGAGTGCGTGCTGAATAAGGCTACCAACGTG

GCTCACTGGACAACACCCTCTTTAAAGTGCATCCGGTCCGAGCTGACCCAG

GACCCTGCTGTGTCCGTGGCTCTGGGCCAGACCGTGAGGATCACCTGCCAG

GGCGACTCCCTGAGGTCCTACTACGCCTCCTGGTACCAGCAGAAGCCCGGC

CAGGCTCCTGTGCTGGTGATCTACGGCAAGAACAACAGGCCCTCCGGCATC

CCTGACAGGTTCTCCGGATCCTCCTCCGGCAACACCGCCTCCCTGACCATC

ACAGGCGCTCAGGCCGAGGACGAGGCTGACTACTACTGCAACTCCAGGGAC

TCCTCCGGCAACCATGTGGTGTTCGGCGGCGGCACCAAGCTGACCGTGGGC

CATGGCGGCGGCGGCTCCGGAGGCGGCGGCAGCGGCGGAGGAGGATCCGAG

GTGCAGCTGGTGGAGTCCGGAGGAGGAGTGGTGAGGCCTGGAGGCTCCCTG

AGGCTGAGCTGTGCTGCCTCCGGCTTCACCTTCGACGACTACGGCATGTCC

TGGGTGAGGCAGGCTCCTGGAAAGGGCCTGGAGTGGGTGTCCGGCATCAAC

TGGAACGGCGGATCCACCGGCTACGCCGATTCCGTGAAGGGCAGGTTCACC

ATCAGCAGGGACAACGCCAAGAACTCCCTGTACCTGCAGATGAACTCCCTG

AGGGCCGAGGACACCGCCGTGTACTACTGCGCCAGGGGCAGGTCCCTGCTG

TTCGACTACTGGGGACAGGGCACCCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 310)

MKWVTFISLLFLFSSAYSIPPHVQKSVNNDMIVTDNNGAVKFPQLCKFCDV

RFSTCDNQKSCMSNCSITSICEKPQEVCVAVWRKNDENITLETVCHDPKLP

YHDFILEDAASPKCIMKEKKKPGETFFMCSCSSDECNDNIIFSEEYNTSNP

DGGGGSGGGGSGGGGSIPPHVQKSVNNDMIVTDNNGAVKFPQLCKFCDVRF

STCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPDI

TCPPPMSVEHADIWVKSYSLYSRERYICNSGFKRKAGTSSLTECVLNKATN

VAHWTTPSLKCIRSELTQDPAVSVALGQTVRITCQGDSLRSYYASWYQQKP

GQAPVLVIYGKNNRPSGIPDRFSGSSSGNTASLTITGAQAEDEADYYCNSR

DSSGNHVVFGGGTKLTVGHGGGGSGGGGSGGGGSEVQLVESGGGVVRPGGS

LRLSCAASGFTFDDYGMSWVRQAPGKGLEWVSGINWNGGSTGYADSVKGRF

TISRDNAKNSLYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 311)

ATGAAGTGGGTGACCTTCATCAGCCTGCTGTTCCTGTTCTCCAGCGCCTAC

TCCATCCCCCCCCATGTGCAAAAGAGCGTGAACAACGATATGATCGTGACC

GACAACAACGGCGCCGTGAAGTTTCCCCAGCTCTGCAAGTTCTGCGATGTC

AGGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAAA

AATGACGAGAACATCACCCTGGAGACCGTGTGTCACGACCCCAAGCTCCCT

TATCACGACTTCATTCTGGAGGACGCTGCCTCCCCCAAATGCATCATGAAG

GAGAAGAAGAAGCCCGGAGAGACCTTCTTTATGTGTTCCTGTAGCAGCGAC

GAGTGTAACGACAACATCATCTTCAGCGAAGAGTACAACACCAGCAACCCT

GATGGAGGTGGCGGATCCGGAGGTGGAGGTTCTGGTGGAGGTGGGAGTATT

CCTCCCCACGTGCAGAAGAGCGTGAATAATGACATGATCGTGACCGATAAC

AATGGCGCCGTGAAATTTCCCCAGCTGTGCAAATTCTGCGATGTGAGGTTT

TCCACCTGCGACAACCAGAAGTCCTGTATGAGCAACTGCTCCATCACCTCC

ATCTGTGAGAAGCCTCAGGAGGTGTGCGTGGCTGTCTGGCGGAAGAATGAC

GAGAATATCACCCTGGAAACCGTCTGCCACGATCCCAAGCTGCCCTACCAC

GATTTCATCCTGGAAGACGCCGCCAGCCCTAAGTGCATCATGAAAGAGAAA

AAGAAGCCTGGCGAGACCTTTTTCATGTGCTCCTGCAGCAGCGACGAATGC

AACGACAATATCATCTTTAGCGAGGAATACAATACCAGCAACCCCGACATT

ACATGCCCCCCTCCCATGAGCGTGGAGCACGCCGACATCTGGGTGAAGAGC

TATAGCCTCTACAGCCGGGAGAGGTATATCTGTAACAGCGGCTTCAAGAGG

AAGGCCGGCACCAGCAGCCTCACCGAGTGCGTGCTGAATAAGGCTACCAAC

GTGGCTCACTGGACAACACCCTCTTTAAAGTGCATCCGGTCCGAGCTGACC

-continued

```
CAGGACCCTGCTGTGTCCGTGGCTCTGGGCCAGACCGTGAGGATCACCTGC
CAGGGCGACTCCCTGAGGTCCTACTACGCCTCCTGGTACCAGCAGAAGCCC
GGCCAGGCTCCTGTGCTGGTGATCTACGGCAAGAACAACAGGCCCTCCGGC
ATCCCTGACAGGTTCTCCGGATCCTCCTCCGGCAACACCGCCTCCCTGACC
ATCACAGGCGCTCAGGCCGAGGACGAGGCTGACTACTACTGCAACTCCAGG
GACTCCTCCGGCAACCATGTGGTGTTCGGCGGCGGCACCAAGCTGACCGTG
GGCCATGGCGGCGGCGGCTCCGGAGGCGGCGGCAGCGGCGGAGGAGGATCC
GAGGTGCAGCTGGTGGAGTCCGGAGGAGGAGTGGTGAGGCCTGGAGGCTCC
CTGAGGCTGAGCTGTGCTGCCTCCGGCTTCACCTTCGACGACTACGGCATG
TCCTGGGTGAGGCAGGCTCCTGGAAAGGGCCTGGAGTGGGTGTCCGGCATC
AACTGGAACGGCGGATCCACCGGCTACGCCGATTCCGTGAAGGGCAGGTTC
ACCATCAGCAGGGACAACGCCAAGAACTCCCTGTACCTGCAGATGAACTCC
CTGAGGGCCGAGGACACCGCCGTGTACTACTGCGCCAGGGGCAGGTCCCTG
CTGTTCGACTACTGGGGACAGGGCACCCTGGTGACCGTGTCCAGG.
```

Exemplary Multi-Chain Chimeric Polypeptides—Type 0

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 183)
IPPHVQKSVNNDMIVTDNNGAVKFPQLCKFCDVRFSTCDNQKSCMNCSITS
ICEKPQEVCVAVWRKNDENITLETVCHDPKLPYHDFILEDAASPKCIMKEK
KKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT
SCEKPQEVCVAVWRKNDENITLETVCHDPKLPYHDFILEDAASPKCIMKEK
KKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA
TAACAATGGCGCCGTGAAATTTCCCCAGCTGTGCAAATTCTGCGATGTGA
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 260)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 261)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 262)
DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 263)
GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

-continued

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

-continued

TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACAGCGGCACAACCAACACAGTCGCTGCCTATAACCTCACT
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE

-continued

NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACAGCGGCACAACCAACACAGTCGCTGCCTATAACCT
CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG

-continued

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 316)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IRGGGGSGGGGSGGGGSREGPELSPDDPAGLLDLRQGMFAQLVAQNVLLI

DGPLSWYSDPGLAGVSLTGGLSYKEDTKELVVAKAGVYYVFFQLELRRVV

AGEGSGSVSLALHLQPLRSAAGAAALALTVDLPPASSEARNSAFGFQGRL

LHLSAGQRLGVHLHTEARARHAWQLTQGATVLGLFRVTPEIPAGLPSPRS

E.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 317)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

-continued

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGGGGCGGTGGAGGATCCGGAGGAG

GTGGCTCCGGCGGCGGAGGATCTCGCGAGGGTCCCGAGCTTTCGCCCGA

CGATCCCGCCGGCCTCTTGGACCTGCGGCAGGGCATGTTTGCGCAGCTG

GTGGCCCAAAATGTTCTGCTGATCGATGGGCCCCTGAGCTGGTACAGTG

ACCCAGGCCTGGCAGGCGTGTCCCTGACGGGGGGCCTGAGCTACAAAGA

GGACACGAAGGAGCTGGTGGTGGCCAAGGCTGGAGTCTACTATGTCTTC

TTTCAACTAGAGCTGCGGCGCGTGGTGGCCGGCGAGGGCTCAGGCTCCG

TTTCACTTGCGCTGCACCTGCAGCCACTGCGCTCTGCTGCTGGGGCCGC

CGCCCTGGCTTTGACCGTGGACCTGCCACCCGCCTCCTCCGAGGCTCGG

AACTCGGCCTTCGGTTTCCAGGGCCGCTTGCTGCACCTGAGTGCCGGCC

AGCGCCTGGGCGTCCATCTTCACACTGAGGCCAGGGCACGCCATGCCTG

GCAGCTTACCCAGGGCGCCACAGTCTTGGGACTCTTCCGGGTGACCCCC

GAAATCCCAGCCGGACTCCCTTCACCGAGGTCGGAA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 318)

MKWVTFISLLFLFSSASIPPHVQKSVNNDMIVTDNNGAVKFPQLCKFCD

VRFSTCDNQKSCMSNCSITSICEKPQEVCVAVWRKNDENITLETVCHDP

KLPYHDFILEDAASPKCIMKEKKKPGETFFMCSCSSDECNDNIIFSEEY

NTSNPDGGGGSGGGGSGGGGSIPPHVQKSVNNDMIVTDNNGAVKFPQLC

KFCDVRFSTCDNQKSCMSNCSITSICEKPQEVCVAVWRKNDENITLETV

CHDPKLPYHDFILEDAASPKCIMKEKKKPGETFFMCSCSSDECNDNIIF

SEEYNTSNPDITCPPPMSVEHADIWVKSYSLYSRERYICNSGFKRKAGT

-continued

SSLTECVLNKATNVAHWTTPSLKCIRGGGGSGGGGSGGGGSREGPELSP

DDPAGLLDLRQGMFAQLVAQNVLLIDGPLSWYSDPGLAGVSLTGGLSYK

EDTKELVVAKAGVYYVFFQLELRRVVAGEGSGSVSLALHLQPLRSAAGA

AALALTVDLPPASSEARNSAFGFQGRLLHLSAGQRLGVHLHTEARARHA

WQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 319)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGGGGCGGTGGAGGATCCGG

AGGAGGTGGCTCCGGCGGCGGAGGATCTCGCGAGGGTCCCGAGCTTTCG

CCCGACGATCCCGCCGGCCTCTTGGACCTGCGGCAGGGCATGTTTGCGC

AGCTGGTGGCCCAAAATGTTCTGCTGATCGATGGGCCCCTGAGCTGGTA

CAGTGACCCAGGCCTGGCAGGCGTGTCCCTGACGGGGGGCCTGAGCTAC

AAAGAGGACACGAAGGAGCTGGTGGTGGCCAAGGCTGGAGTCTACTATG

TCTTCTTTCAACTAGAGCTGCGGCGCGTGGTGGCCGGCGAGGGCTCAGG

CTCCGTTTCACTTGCGCTGCACCTGCAGCCACTGCGCTCTGCTGCTGGG

-continued

GCCGCCGCCCTGGCTTTGACCGTGGACCTGCCACCCGCCTCCTCCGAGG

CTCGGAACTCGGCCTTCGGTTTCCAGGGCCGCTTGCTGCACCTGAGTGC

CGGCCAGCGCCTGGGCGTCCATCTTCACACTGAGGCCAGGGCACGCCAT

GCCTGGCAGCTTACCCAGGGCGCCACAGTCTTGGGACTCTTCCGGGTGA

CCCCCGAAATCCCAGCCGGACTCCCTTCACCGAGGTCGGAA.

Methods of Treating an Aging-Related Disease or Condition

Provided herein are methods of treating an aging-related disease or condition (e.g. any of the exemplary types of aging-related disease or condition described herein or known in the art) in a subject in need thereof that include administering to a subject identified as having an aging-related disease or condition (e.g. any of the exemplary types of aging-related disease or condition described herein or known in the art) a therapeutically effective amount of one or more natural killer (NK) cell activating agent(s) (e.g. any of the natural killer (NK) cell activating agent(s) described herein or known in the art).

Provided herein are methods of treating an aging-related disease or condition (e.g. any of the exemplary types of aging-related disease or condition described herein or known in the art) in a subject in need thereof that include administering to a subject identified as having an aging-related disease or condition (e.g. any of the exemplary types of aging-related disease or condition described herein or known in the art) a therapeutically effective amount of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and optionally further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease.

Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

A non-limiting example of an autoimmune disease is type-1 diabetes.

Non-limiting examples of metabolic disease include: obesity, a lipodystrophy, and type-2 diabetes mellitus.

Non-limiting examples of neurodegenerative disease include: Alzheimer's disease, Parkinson's disease, and dementia.

Non-limiting examples of cardiovascular disease include: coronary artery disease, atherosclerosis, and pulmonary arterial hypertension.

Non-limiting examples of skin disease include: wound healing, alopecia, wrinkles, senile lentigo, skin thinning, xeroderma pigmentosum, and dyskeratosis congenita.

Non-limiting examples of progeria disease include: progeria and Hutchinson-Gilford Progeria Syndrome.

Non-limiting examples of fragility disease include: frailty, responsiveness to vaccination, osteoporosis, and sarcopenia.

In some embodiments of any of the aging-related disease or condition described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the aging-related disease or condition described herein, the aging-related disease or condition is type-2 diabetes or atherosclerosis.

In some embodiments of any of the methods described herein, the subject has been diagnosed or identified as having an aging-related disease or condition (e.g., any of the exemplary aging-related diseases or conditions described herein). Some embodiments of any of the methods described herein can include a step of selecting a subject identified or diagnosed as having an aging-related disease or condition (e.g., any of the exemplary aging-related diseases or conditions described herein).

In some embodiments of these methods, the administering results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) in the number of senescent cells in a target tissue in the subject, e.g., as compared to the number of senescent cells in the target tissue in the subject prior to treatment.

In some embodiments of these methods, the administering results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein) in the levels of IFN-γ, a cytotoxic granule granzyme, and/or perform in the subject, as compared to the levels in a subject prior to treatment or a similar control subject who has not received a treatment.

In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some embodiments, these methods can result in treatment of metabolic disease in the subject. In some embodiments, the treatment of metabolic disease can result in, e.g., one or more (e.g., two, three, four, five, or six) improved glucose tolerance, improved glucose utilization, decreased severity or progression of diabetic osteoarthropathy, decreased severity or progression of skin lesions, decreased severity or progression of ketosis, decreased generation of autoantibodies against islet cells, increased insulin sensitivity, decreased mass, and decreased body mass index. The response of a subject to treatment can be monitored by determining fasting glucose or glucose tolerance according to standard techniques. Typically, in accordance with the method, blood glucose is lowered so as to achieve a blood glucose level characterized by a fasting blood glucose of less than 100 mg/dL or a two-hour 75-g oral glucose tolerance test values of less than 140 mg/dL. In some embodiments, response to treatment may include determining other factors relevant to pre-diabetes, new-onset diabetes, or active diabetes including blood pressure, body mass index, PPARy function, lipid metabolism, glycated hemoglobin (H1c), and renal function.

In some embodiments, these methods can eliminate or reduce the risk, lessen the severity, or delay the outset of the neurodegenerative disease, including biochemical, histologic and/or behavioral symptoms of the disease, its complications and intermediate pathological phenotypes presenting during development of the disease.

In some embodiments, effective treatment of a skin disease can be assessed by any method described herein or known in the art, including inspecting skin conditions that include skin color, moisture, temperature, texture, mobility and turgor, and skin lesions, as compared to the skin conditions prior to treatment.

In some embodiments, effective treatment of an autoimmune disease can be assessed by any method described herein or known in the art, including monitoring full blood count analysis on freshly isolated PBMCs, total Ig levels, and analysis of serum autoantibody titers.

In some embodiments, effective treatment of a fragility disease can be assessed by any method described herein or known in the art, including monitoring bone mineral density, bone architecture and geometry, biomedical markers of bone turnover, vitamin D measurement, Karnofsky performance status and ECOG scores, and responsiveness to vaccination.

Methods of Killing or Reducing the Number of Senescent Cells in a Subject

Provided herein are methods of killing or reducing the number of senescent cells (e.g. any of the exemplary types of senescent cells described herein or known in the art) in a subject in need thereof that include administering to the subject a therapeutically effective amount of one or more NK cell activating agent(s) (e.g. any of the NK cell activating agent(s) described herein or known in the art).

Also provided herein are methods of killing or reducing the number of senescent cells (e.g. any of the exemplary types of senescent cells described herein or known in the art) in a subject in need thereof that include administering to the subject a therapeutically effective amount of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of these methods, senescent cancer cells are chemotherapy-induced senescent cells or radiation-induced senescent cells.

In some embodiments of these methods, the subject has been identified or diagnosed as having an aging-related disease or condition (e.g., any of the aging-related diseases or conditions described herein or known in the art). In some embodiments of any of the aging-related disease or condition described herein, the aging-related disease or condition is selected from the group of: a cancer, an autoimmune disease, a metabolic disease, a neurodegenerative disease, a cardiovascular disease, a skin disease, a progeria disease, and a fragility disease.

Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

A non-limiting example of an autoimmune disease is type-1 diabetes.

Non-limiting examples of metabolic disease include: obesity, a lipodystrophy, and type-2 diabetes mellitus.

Non-limiting examples of neurodegenerative disease include: Alzheimer's disease, Parkinson's disease, and dementia.

Non-limiting examples of cardiovascular disease include: coronary artery disease, atherosclerosis, and pulmonary arterial hypertension.

Non-limiting examples of skin disease include: wound healing, alopecia, wrinkles, senile lentigo, skin thinning, xeroderma pigmentosum, and dyskeratosis congenita.

Non-limiting examples of progeria disease include: progeria and Hutchinson-Gilford Progeria Syndrome.

Non-limiting examples of fragility disease include: frailty, responsiveness to vaccination, osteoporosis, and sarcopenia.

In some embodiments of any of the aging-related disease or condition described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the aging-related disease or condition described herein, the aging-related disease or condition is type-2 diabetes or atherosclerosis.

In some embodiments of these methods, the administering results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 10% decrease to about a 99% decrease (or any of the subranges of this range described herein)) in the number of senescent cells in a target tissue in the subject, e.g., as compared to the number of senescent cells in the target tissue in the subject prior to treatment. In some embodiments of these methods, the target tissue in the subject can be one or more of an adipose tissue, pancreatic tissue, liver tissue, lung tissue, vasculature, bone tissue, central nervous system (CNS) tissue, eye tissue, skin tissue, muscle tissue, and secondary lympho-organ tissue.

In some embodiments of these methods, the administering results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein)) in the levels of IFN-γ, a cytotoxic granule granzyme, and/or perform in the subject, as compared to the levels in a subject prior to treatment or a similar control subject who has not received a treatment.

In some embodiments of these methods, the number of senescent cells in a target tissue (e.g. any of the target tissues described herein) can be determined by performing immunostaining on a biopsy sample. In some embodiments of these methods, the number of senescent cells in a target tissue (e.g. any of the target tissues described herein) can be observed indirectly through an improvement in one or more symptoms of an aging-related disease or condition (e.g. any of the symptoms of an aging-related disease or condition described herein) in a subject.

Senescent Cells

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer metastasis and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113 (15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, *Cell* 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018*; Xu, Nat Med* 24(8): 1246-1256, 2018).

Methods of Improving the Texture and/or Appearance of Skin and/or Hair

Also provided herein are methods of improving the texture and/or appearance of skin and/or hair in a subject in need thereof over a period of time (e.g. any of the periods of time described herein) that include administering to the subject a therapeutically effective amount of one or more natural killer (NK) cell activating agent(s) (e.g. any of the NK cell activating agent(s) described herein or known in the art).

Also provided herein are methods of improving the texture and/or appearance of skin and/or hair in a subject in need thereof over a period of time (e.g. any of the periods of time described herein) that include administering to the subject a therapeutically effective number of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the method provides for an improvement in the texture and/or appearance of skin of the subject over the period of time (e.g. any of periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of formation of wrinkles in the skin of the subject over the period of time (e.g., any of the periods of time described herein), e.g., as compared to the rate of formulation of wrinkles in the subject prior to treatment or the rate of formulation of wrinkles in a similar subject not receiving a treatment.

In some embodiments of these methods, the method results in an improvement in the coloration of skin of the subject over the period of time (e.g. any of the periods of time described herein).

In some embodiments of these methods, the method results in an improvement in the texture of skin of the subject over the period of time (e.g. any of the periods of time described herein).

In some embodiments of these methods, the method provides for an improvement in the texture and/or appearance of hair of the subject over the period of time (e.g. any of the periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of formation of gray hair in the subject over the period of time (e.g. any of the range of time period described herein), e.g., as compared to the rate of formulation of gray hair in the subject prior to treatment or the rate of formulation of gray hair in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the number of gray hairs of the subject over the period of time (e.g. any of the periods of time described herein), e.g., as compared to the number of gray hairs in the subject prior to treatment or the rate of formation of gray hairs in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of hair loss in the subject over the period of time (e.g., any of the periods of time described herein), e.g., as compared to the rate of hair loss in the subject prior to treatment or the rate of hair loss in a similar subject not receiving a treatment.

In some embodiments of these methods, the method results in an improvement in the texture of hair of the subject over the period of time (e.g. any of the periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the number of senescent dermal fibroblasts in the skin of the subject over the period of time (e.g., any of the periods of time described herein), e.g., as compared to the number of senescent dermal cells in the subject prior to treatment or the number of senescent dermal cells in a similar subject not receiving a treatment.

In some embodiments of these methods, improvement in the texture and/or appearance of skin of the subject over the period of time (e.g. any of the periods of time described herein) can be assessed by any method described herein or known in the art, including inspecting the presence, size and shape of skin lesions, skin color and pigmentation, skin moisture, temperature, elasticity, and vascularity.

In some embodiments of these methods, improvement in the texture and/or appearance of hair of the subject over the period of time (e.g., any of periods of time described herein) can be assessed by any method described herein or known in the art.

In some embodiments of these methods, the period of time is, e.g., one month to ten years, one month to nine years, one month to eight years, one month to seven years, one month to six years, one month to five years, one month to four years, one month to three years, one month to two years, one month to eighteen months, one month to twelve months, one month to ten months, one month to eight months, one month to six months, one month to four months, one month to two months, one month to six weeks, six weeks to ten years, six weeks to nine years, six weeks to eight years, six weeks to seven years, six weeks to six years, six weeks to five years, six weeks to four years, six weeks to three years, six weeks to two years, six weeks to eighteen months, six weeks to twelve months, six weeks to ten months, six weeks to eight months, six weeks to six months, six weeks to four months, six weeks to two months, two months to ten years, two months to nine years, two months to eight years, two months to seven years, two months to six years, two months to five years, two months to four years, two months to three years, two months to two years, two months to eighteen months, two months to twelve months, two months to ten months, two months to eight months, two months to six months, two months to four months, four months to ten years, four months to nine years, four months to eight years, four months to seven years, four months to six years, four months to five years, four months to four years, four months to three years, four months to two years, four months to eighteen months, four months to twelve months, four months to ten months, four months to eight months, four months to six months, six months to ten years, six months to nine years, six months to eight years, six months to seven years, six months to six years, six months to five years, six months to four years, six months to three years, six months to two years, six months to eighteen months, six months to twelve months, six months to ten months, six months to eight months, eight months to ten years, eight months to nine years, eight months to eight years, eight months to seven years, eight months to six years, eight months to five years, eight months to four years, eight months to three years, eight months to two years, months to eighteen months, eight months to twelve months, eight months to ten months, ten months to ten years, ten months to nine years, ten months to eight years, ten months to seven years, ten months to six years, ten months to five years, ten months to four years, ten months to three years, ten months to two years, ten months to eighteen months, ten months to twelve months, twelve months to ten years, twelve months to nine years, twelve months to eight years, twelve months to seven years, twelve months to six years, twelve months to five years, twelve months to four years, twelve months to three years, twelve months to two years, twelve months to eighteen months, eighteen months to ten years, eighteen months to nine years, eighteen months to eight years, eighteen months to seven years, eighteen months to six years, eighteen months to five years, eighteen months to four years, eighteen months to three years, eighteen months to two years, two years to ten years, two years to nine years, two years to eight years, two years to seven years, two years to six years, two years to five years, two years to four years, two years to three years, three years to ten years, three years to nine years, three years to eight years, three years to seven years, three years to six years, three years to five years, three years to four years, four years to ten years, four years to nine years, four years to eight years, four years to seven years, four years to six years, four years to five years, five years to ten years, five years to nine years, five years to eight years, five years to seven years, five years to six years, six years to ten years, six years to nine years, six years to eight years, six years to seven years, seven years to ten years, seven years to nine years, seven years to eight years, eight years to ten years, eight years to nine years, or nine years to ten years.

In some embodiments of these methods, the age of the subject is between about 30 to about 35, about 35 to about 40, about 40 to about 45, about 45 to about 50, about 50 to about 55, about 55 to about 60, about 60 to about 65, about 65 to about 70, about 70 to about 75, about 75 to about 80, about 80 to about 85, about 85 to about 90, about 90 to about 95, about 95 to about 100, about 100 to about 105, about 105 to about 110, about 110 to about 115, or about 115 to about 120.

Methods of Assisting in the Treatment of Obesity in a Subject

Provided herein are methods of assisting in the treatment of obesity in a subject in need thereof over a period of time (e.g. any of the range of time period described herein), that include administering to the subject a therapeutically effective amount of one or more natural killer (NK) cell activating agent(s) (e.g. any of the NK cell activating agent(s) described herein or known in the art).

Also provided herein are methods of assisting in the treatment of obesity in a subject in need thereof over a period of time (e.g. any of the range of time period described herein) that include administering to the subject a therapeutically effective number of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the mass of the subject over the period of time (e.g. any of the periods of time described herein), e.g., as compared to the mass of the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the body mass index (BMI) of the subject over the period of time (e.g. any of periods of time described herein), e.g., as compared to the BMI of the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of progression from pre-diabetes to type 2 diabetes in the subject, e.g., as compared to the rate of progression from pre-diabetes to type 2 diabetes in the subject prior to treatment or the rate of progression from pre-diabetes to type 2 diabetes in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in fasting serum glucose level in the subject, e.g., as compared to the fasting serum glucose level in the subject prior to treatment.

In some embodiments of these methods, the method results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein) in insulin sensitivity in the subject, e.g., as compared to the insulin sensitivity in the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the severity of atherosclerosis in the subject, e.g., as compared to the severity of atherosclerosis in the subject prior to treatment.

In some embodiments of these methods, treatment of obesity in the subject over the period of time (e.g. any of the periods of time described herein) can be assessed by any method described herein or known in the art, including, e.g., measurement of body weight and/or body dimensions, total body fat, total or regional adiposity, and body mass index (BMI).

In some embodiments of these methods, the response of a subject to the treatment can be monitored by determining fasting serum glucose level or glucose tolerance according to standard techniques. In some embodiments of these methods, insulin sensitivity can be measured using any method described herein or known in the art, including hyperinsulinemic euglycemic clamp and intravenous glucose tolerance test, homeostasis model assessment (HOMA), and quantitative insulin sensitivity check index (QUICKI).

In some embodiments of these methods, the severity of atherosclerosis in the subject can be measured using any method described herein or known in the art, including cardiac catheterization, Doppler sonography, blood pressure comparison, MUGA/radionuclide angiography, Thallium/myocardial perfusion scan, and computerized tomography.

In some embodiments of these methods, the period of time is one month to ten years (or any of the subranges of this range described herein).

In some embodiments of these methods, the age range for the subject is between about 1 to about 5, about 5 to about 10, about 10 to about 15, about 15 to about 20, about 20 to about 25, about 25 to about 30, about 30 to about 35, about 35 to about 40, about 40 to about 45, about 45 to about 50, about 50 to about 55, about 55 to about 60, about 60 to about 65, about 65 to about 70, about 70 to about 75, about 75 to about 80, about 80 to about 85, about 85 to about 90, about 90 to about 95, about 95 to about 100, about 100 to about 105, about 105 to about 110, about 110 to about 115, or about 115 to about 120.

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as the NK cell activating agent(s) or activated NK cells (e.g., administered as a single formulation or two or more formulations to the subject). In some embodiments, one or more additional therapeutic agents can be administered to the subject prior to administration of the NK cell activating agent(s) or activated NK cells. In some embodiments, one or more additional therapeutic agents can be administered to the subject after administration of the NK cell activating agent(s) or activated NK cells to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include antimetabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1: Immunostimulation in C57BL/6 Mice Using a Multi-Chain Polypeptide Materials and Methods An exemplary multi-chain polypeptide (a type A multi-chain polypeptide described herein) was generated that includes a first polypeptide and a second polypeptide, where the first polypeptide is a soluble fusion of two TGFβRII domains, a human tissue factor 219 fragment, and a human IL-15, and the second polypeptide is a soluble fusion of two TGFβRII domains and the sushi domain of human IL-15Rα chain.

Results

Immunostimulation in C57BL/6 Mice

Figure 1A:
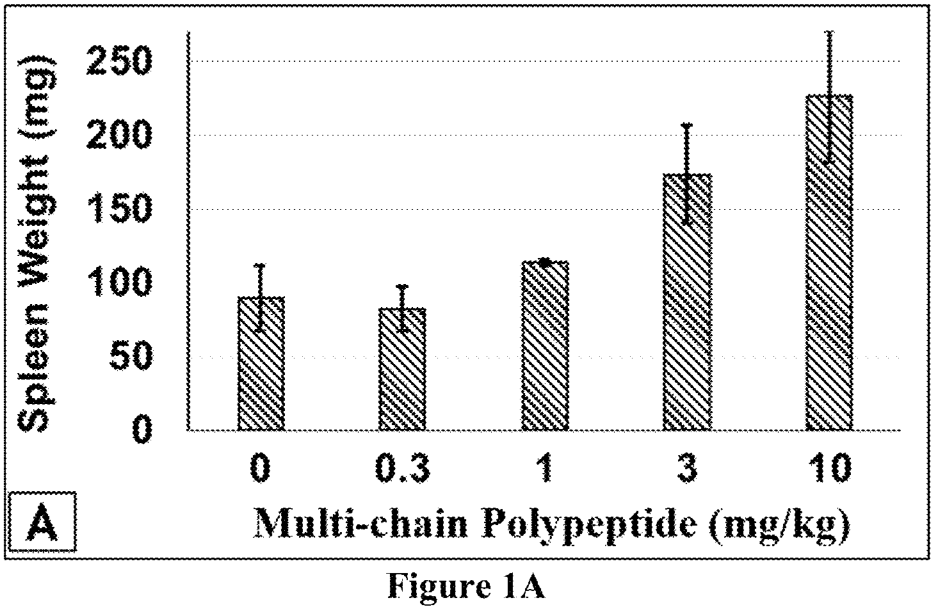
FIGS. 1A-1B show the results of immunostimulation of an exemplary multi-chain polypeptide in C57BL/6 mice.
Figure 1B:
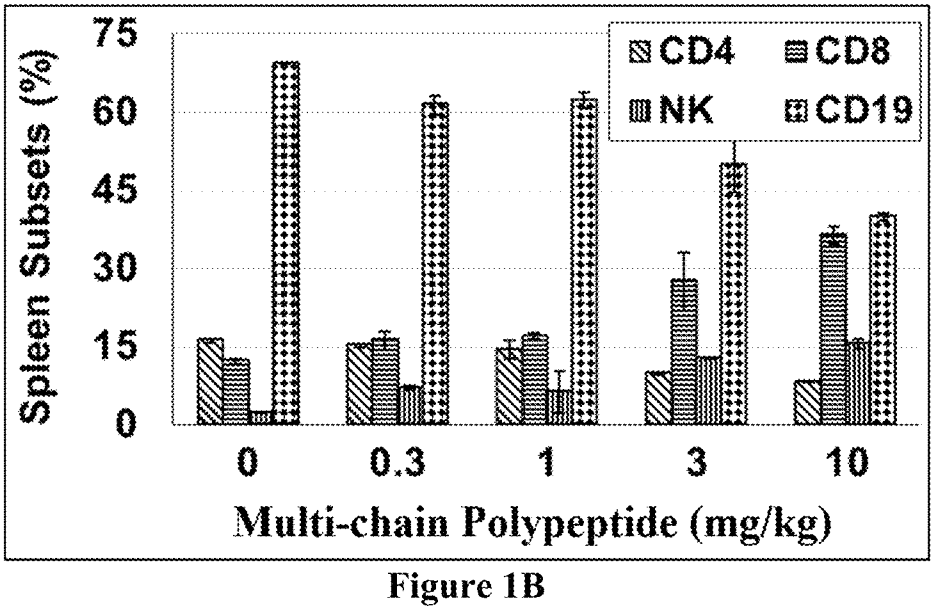

Wild type C57BL/6 mice were treated subcutaneously with either a control PBS solution or with the multi-chain polypeptide at a dosage of 0.3 mg/kg, 1 mg/kg, 3 mg/kg, or 10 mg/kg, respectively. Four days after treatment, spleen weight and the percentages of various immune cell types present in the spleen were evaluated. Specifically, single splenocyte suspensions were generated and stained with fluorochrome-conjugated antibodies including anti-CD4, anti-CD8, anti-NK1.1, and anti-CD19. The percentages of $CD4^+$ T cells, $CD8^+$ T cells, Natural Killer (NK) cells, and $CD19^+$ B cells present in the spleen of mice treated with either the control solution or the multi-chain polypeptide were evaluated using flow cytometry. As shown in FIG. 1A, the spleen weight in mice treated with the multi-chain polypeptide increased with increasing dosage of the multi-chain polypeptide. Moreover, the spleen weight in mice treated with 1 mg/kg, 3 mg/kg, and 10 mg/kg of the multi-chain polypeptide were significantly higher as compared to mice treated with the control solution, respectively. As shown in FIG. 1B, in the spleens of mice treated with the multi-chain polypeptide, the percentages of $CD8^+$ T cells and NK cells both increased with increasing dosage of the multi-chain polypeptide. Specifically, the percentages of $CD8^+$ T cells were higher in mice treated with 0.3 mg/kg, 3 mg/kg, and 10 mg/kg of the multi-chain polypeptide compared to control-treated mice, and the percentages of NK cells were higher in mice treated with 0.3 mg/kg, 1 mg/kg, 3 mg/kg, and 10 mg/kg of the multi-chain polypeptide compared to control-treated mice. These results demonstrate that the exemplary multi-chain polypeptide is able to stimulate immune cells in the spleen, in particular $CD8^+$ T cells and NK cells.

Pharmacokinetics

The pharmacokinetics of the exemplary multi-chain polypeptide were evaluated in wild type C57BL/6 mice. Mice were treated subcutaneously with the multi-chain polypeptide at a dosage of 3 mg/kg. Blood was collected at various time points via tail vein, and serum was prepared. The concentration of the multi-chain polypeptide in the serum was determined with ELISA. Briefly, the multi-chain polypeptide was captured using an anti-human tissue factor antibody, and detected using a biotinylated anti-human TGFβ receptor, a peroxidase conjugated streptavidin, and ABTS substrate. The results showed that the half-life of the exemplary multi-chain polypeptide was 12.66 hours.

Immunostimulation Over Time in C57BL/6 Mice

Figure 2A:
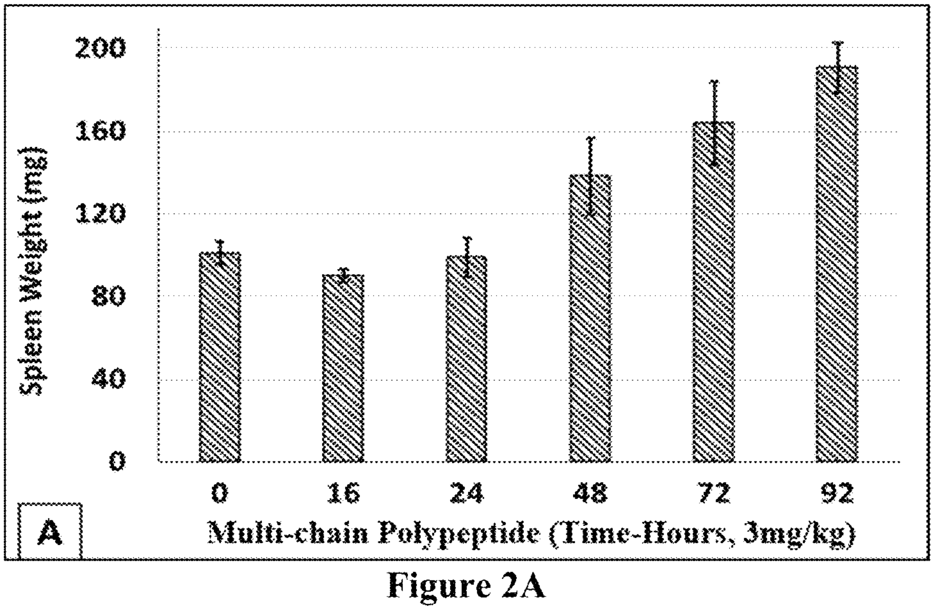
FIGS. 2A-2B show the duration of immunostimulation of an exemplary multi-chain polypeptide in C57BL/6 mice.
Figure 2B:
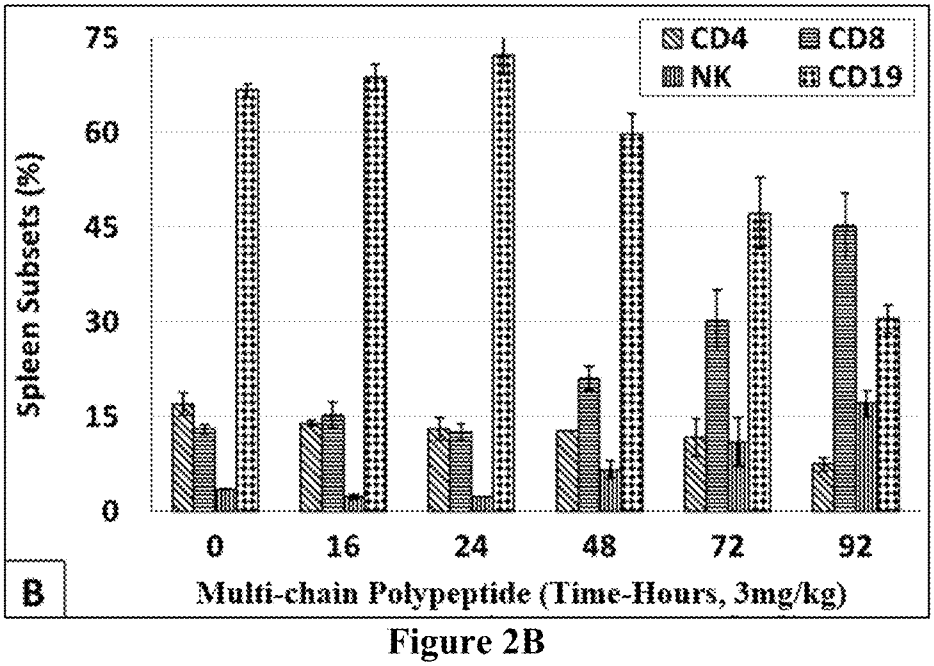

To evaluate the effect of immunostimulation by the multi-chain polypeptide over time, mice were treated with a single dose of the multi-chain polypeptide at 3 mg/kg and the spleen weight and percentages of immune cell types present in the spleen were evaluated immediately upon treatment and at 16, 24, 48, 72, and 92 hours after treatment, using techniques described above. As shown in FIG. 2A, the spleen weight of mice treated with the multi-chain polypeptide increased at 48 hours after treatment, and continued to increase over the next 44 hours. Moreover, as shown in FIG. 2B, in the spleens of mice treated with the multi-chain polypeptide, the percentages of $CD8^+$ T cells and NK cells both increased at 48 hours after treatment and continued to increase over the next 44 hours. These results further demonstrate that the exemplary multi-chain polypeptide is able to stimulate immune cells in the spleen, in particular $CD8^+$ T cells and NK cells, over time.

Figure 3A:
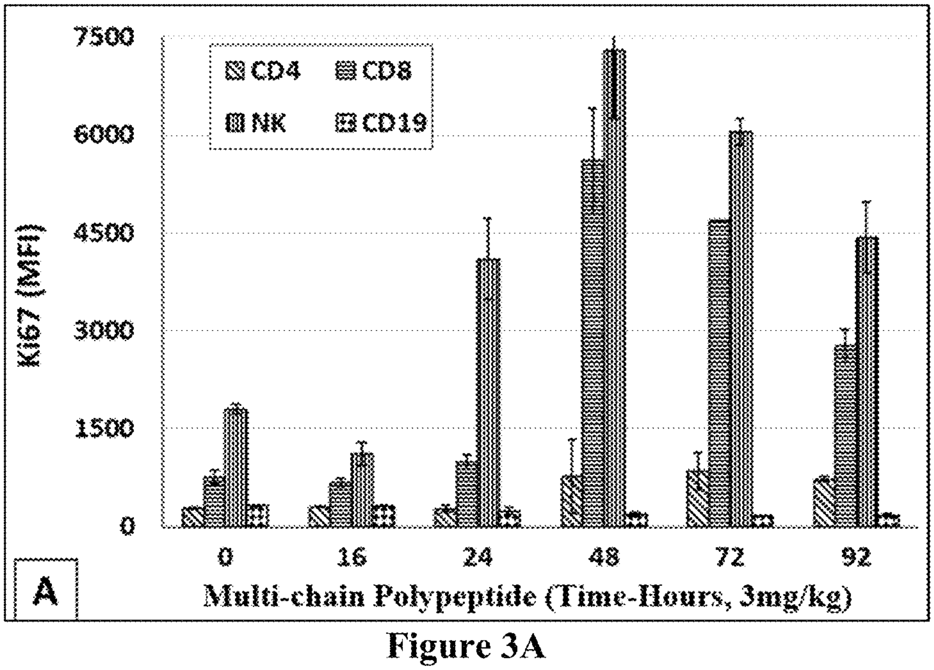
FIGS. 3A-3B show the expression of Ki67 and Granzyme B in immune cells induced by the exemplary multi-chain polypeptide.
Figure 3B:
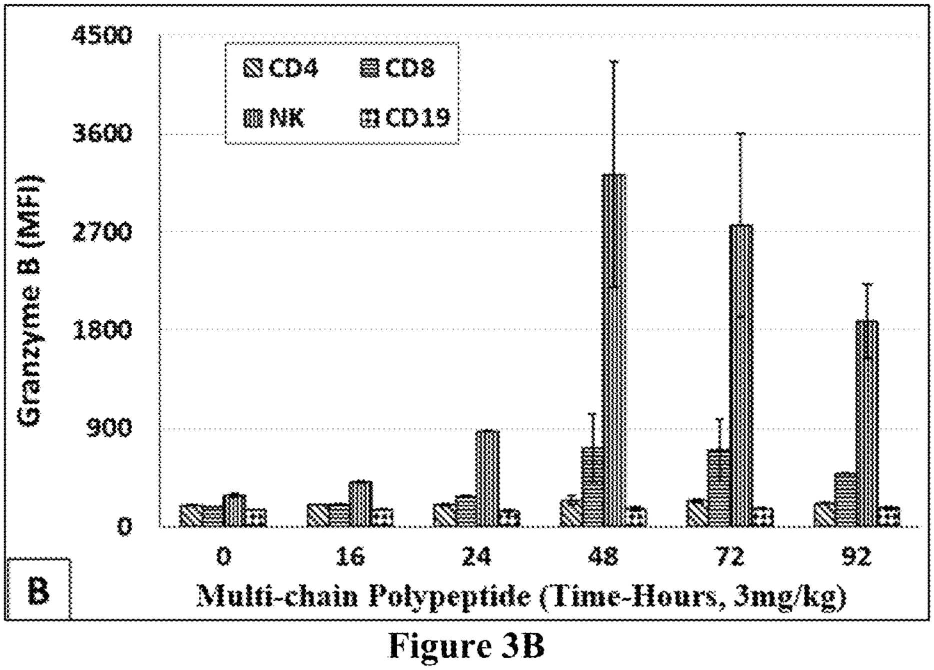

Increased Proliferation and Granzyme B Expression by $CD8^+$ T Cells and NK Cells To evaluate the proliferation and cytotoxic potential of the immune cells induced by the multi-chain polypeptide, mice were treated with a single dose of the multi-chain polypeptide at 3 mg/kg, and the spleens of these mice were evaluated immediately after, and at 16, 24, 48, 72, and 92 hours after treatment. Briefly, single splenocyte suspensions were generated and stained with fluorochrome-conjugated antibodies for the various cell types including anti-CD4, anti-CD8, anti-NK1.1, and anti-CD19, and with an anti-Ki67 antibody (i.e. a cell proliferation marker) and an anti-Granzyme B antibody (i.e. a cytotoxic marker). The mean fluorescent intensity (MFI) of Ki67 and Granzyme B for each immune cell type was analyzed by flow cytometry. As shown in FIGS. 3A and 3B, the expression of Ki67 and Granzyme B by NK cells showed an increase at 24 hours as well as each time point evaluated thereafter as compared to immediately after treatment (0 hours). Moreover, the expression of Ki67 and Granzyme B by $CD8^+$ T cells showed an increase at 48 hours as well as each time point evaluated thereafter as compared to immediately after treatment (0 hours). As such, a single dose of the multi-chain polypeptide resulted in proliferation of $CD8^+$ T cells and NK cells for up to at least 4 days post-treatment.

These results demonstrate that the multi-chain polypeptide not only increased the number of $CD8^+$ T cells and NK cells in the spleen, but also enhanced the proliferation and cytotoxicity of these cells.

Cytotoxicity Against Tumor Cells

Next, the cytotoxicity of the splenocytes activated by the multi-chain polypeptide against tumor cells were evaluated in C57BL/6 mice. Mouse Moloney leukemia cells (Yac-1) were labeled with CellTrace Violet and used as tumor target cells. C57BL/6 mice were treated with a single dose of the multi-chain polypeptide at 3 mg/kg, and splenocytes were prepared at various time points thereafter and used as effector cells. The target tumor cells were mixed with the effector cells at an effector:target (E:T) ratio of 10:1, and incubated at 37° C. for 20 hours. Target cell viability was assessed by analyzing Propidium Iodide (PI)-positive, violet-labeled Yac-1 cells using flow cytometry. The percentage of Yac-1 tumor inhibition was calculated using the formula:

Percentage of Yac-1 tumor inhibition=(1−viable Yac-1 cell number in experimental sample/viable Yac-1 cell number in the sample without splenocytes)×100

Figure 4:
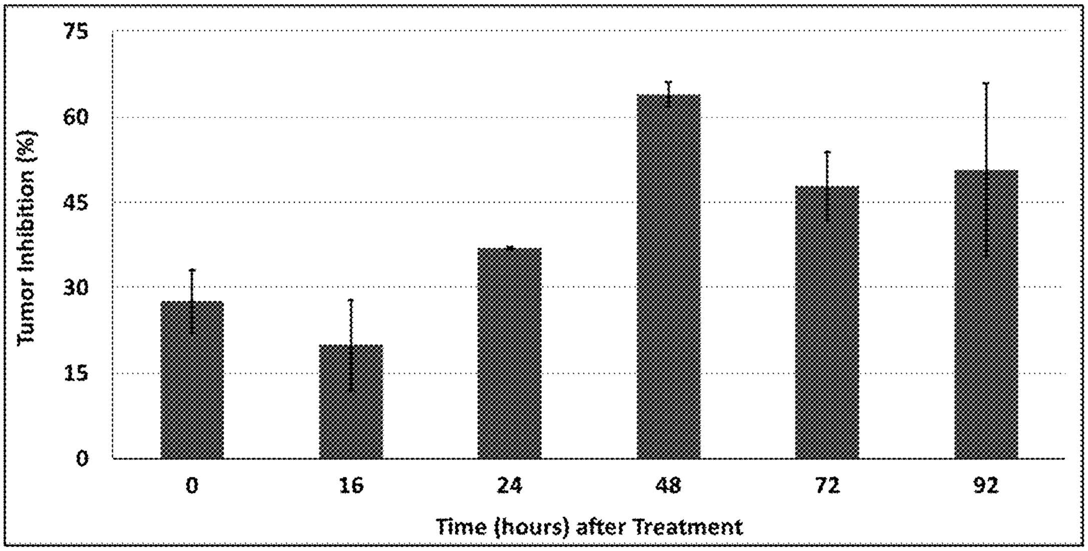
FIG. 4 shows the effect of tumor inhibition by splenocytes prepared from mice treated with an exemplary multi-chain polypeptide at various time points after treatment.

As shown in FIG. 4, splenocytes from mice after 24-hour or more treatment with the multi-chain polypeptide showed increased cytotoxicity against Yac-1 cells as compared to the splenocytes from untreated mice.

Example 2: Immunostimulation in C57BL/6 Mice Using a High Fat Diet-Based Type-2 Diabetes Mouse Model Materials and Methods TGFRt15-TGFRs is a multi-chain chimeric polypeptide (a type A multi-chain chimeric polypeptide described herein) that includes two TGFβ-binding domains which a soluble human TGFβRII dimer (aa24-159). 21t15-TGFRs is a multi-chain chimeric polypeptide (a type A multi-chain chimeric polypeptide described herein) that includes IL-21 and a TGFβ-binding domain. 3t28 is a chimeric polypeptide (a type B chimeric polypeptide described herein) that include two IL-2 polypeptides.

Results

To evaluate the effect of TGFRt15-TGFRs, 2t2, and 21t15-TGFRs in treating Type-2 diabetes, a high fat diet-based Type-2 diabetes mouse model (B6.129P2-ApoE$^{tm1Unc}$/J from The Jackson Laboratory) was used. Mice were fed either a control diet or a high fat diet for 11 weeks. A subset of mice fed with the high fat diet were also treated with TGFRt15-TGFRs, 2t2, or 21t15-TGFRs. Mice fed the control diet, high fat diet, and mice fed with the high fat diet and treated with TGFRt15-TGFRs, 2t2, or 21t15-TGFRs were evaluated 4 days post-treatment. Briefly, single splenocyte suspensions were generated and stained with fluorochrome-conjugated antibodies including anti-CD4, anti-CD8, anti-NK1.1, and anti-CD19. The percentages of CD4$^+$ T cells, CD8$^+$ T cells, Natural Killer (NK) cells, and CD19$^+$ B cells present in the spleen of mice in each group were evaluated using flow cytometry.

Figure 5A:
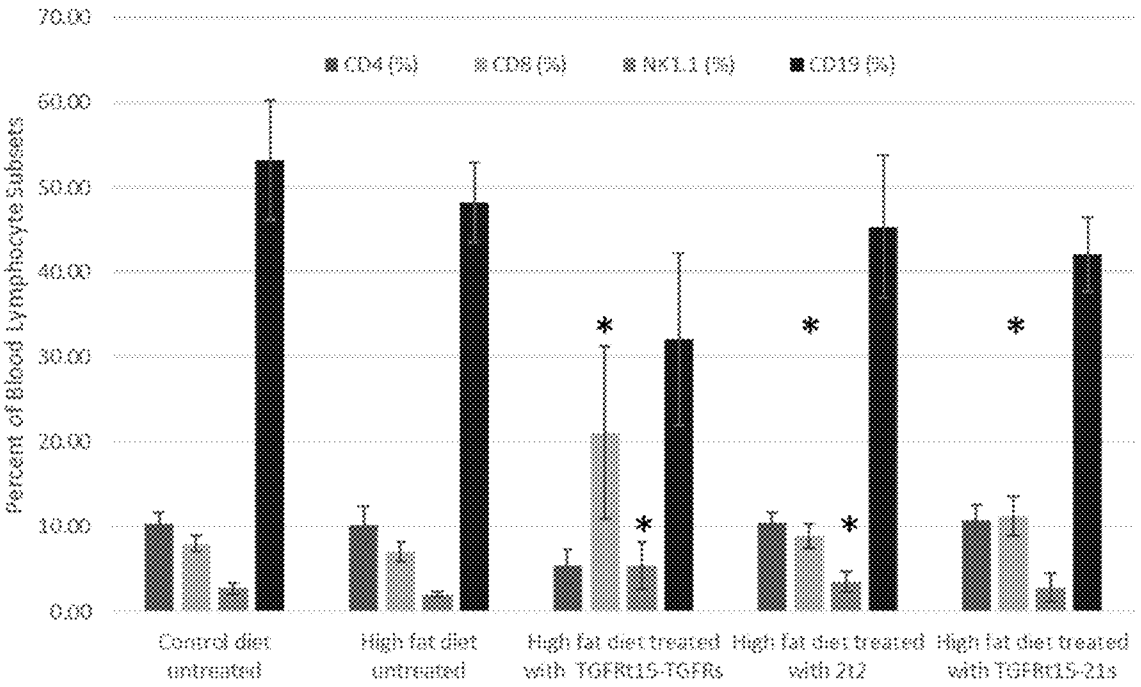
FIGS. 5A-5B show the percentages and the proliferation rate of $CD4^+$ T cells, $CD8^+$ T cells, Natural Killer (NK) cells, and $CD19^+$ B cells in the blood of B6.129P2-$ApoE^{tm1Unc}$/J mice (purchased from The Jackson Laboratory) fed a control diet, a high fat diet and untreated, and mice fed a high fat diet and treated with TGFRt15-TGFRs, 2t2, or 21t15-TGFRs.
Figure 5B:
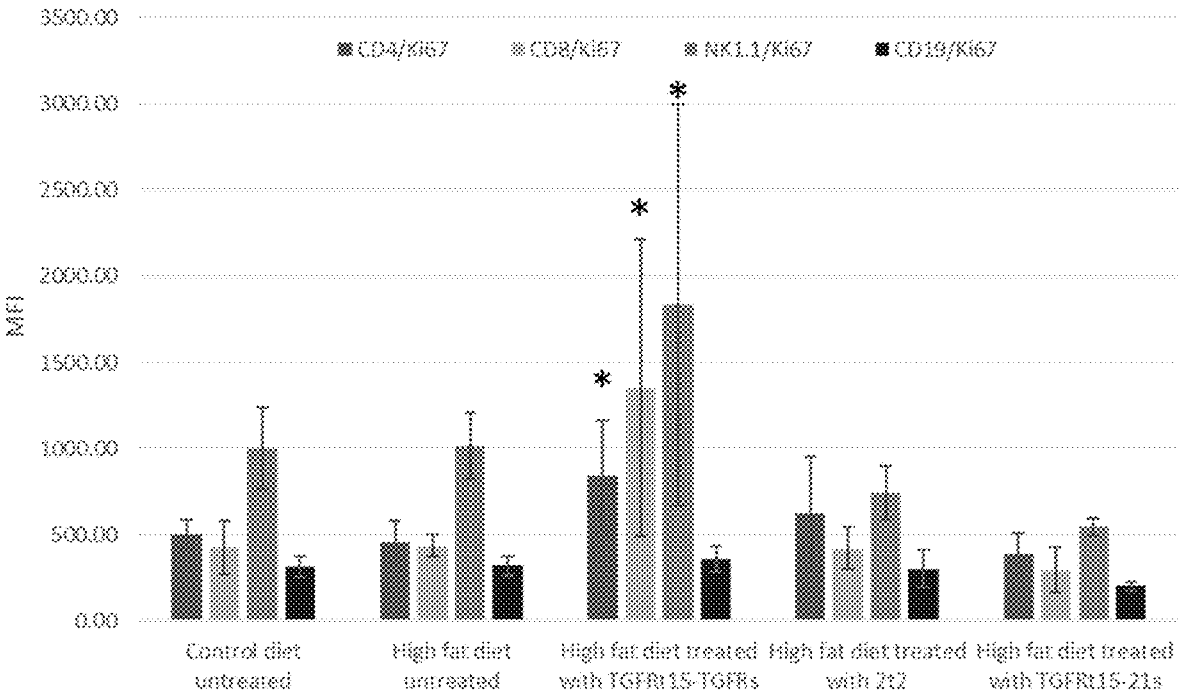

As shown in FIG. 5A, in mice fed a high fat diet, the percentage of NK cells in PBMCs was significantly increased after treatment with TGFRt15-TGFRs or 2t2 compared to untreated mice, but not after treatment with 21t15-TGFRs. Furthermore, the percentage of CD8$^+$ T cells in PBMCs was significantly increased after treatment with TGFRt15-TGFRs, 2t2, or 21t15-TGFRs compared to untreated mice. Moreover, the proliferation of CD4$^+$ T cells, CD8$^+$ T cells, Natural Killer (NK) cells, and CD19$^+$ B cells in PBMCs were also evaluated using an anti-Ki67 antibody. As shown in FIG. 5B, the number of proliferating NK cells, CD4$^+$ T cells, and CD8$^+$ T cells were significantly increased after treatment with TGFRt15-TGFRs, but not after treatment with 2t2 or 21t15-TGFRs.

Figures 6A, 6B, 6C, 6D, 6E:
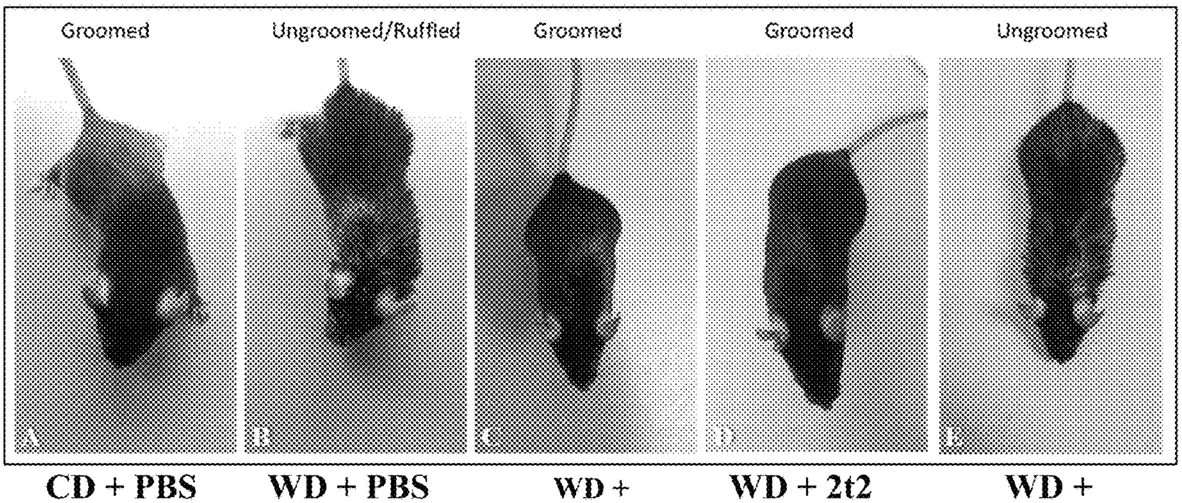
FIGS. 6A-6E show exemplary physical appearance of mice fed either a control or high fat diet and were either untreated or treated with TGFRt15-TGFRs, 2t2, or 21t15-TGFRs.

To examine the effect of TGFRt15-TGFRs, 2t2 and 21t15-TGFRs on the appearance and texture of skin and hair in animals, mice were fed either a control or a high fat diet for 7 weeks, and a subset of the mice fed a high fat diet were also treated with TGFRt15-TGFRs, 2t2 or 21t15-TGFRs. One week post-treatment, the appearance of the mice was evaluated. Mice fed a high fat diet and untreated, or a high diet and treated with 21t15-TGFRs appeared ungroomed and ruffled, and had increased gray hair/hair loss as compared to mice fed a control diet (FIGS. 6A, 6B and 6E). Surprisingly, mice fed a high fat diet that received TGFRt15-TGFRs or 2t2 treatment appeared groomed and healthier (less gray hair/hair loss) (FIGS. 6C and 6D) as compared to mice fed a high fat diet that did not receive TGFRt15-TGFRs or 2t2 treatment (FIG. 6B). Specifically, TGFRt15-TGFRs or 2t2-treated mice showed superior skin and hair appearance and texture as compared to control mice. These results demonstrate that treatment with TGFRt15-TGFRs or 2t2 improves the appearance and texture of skin and hair in mammals.

Figure 7:
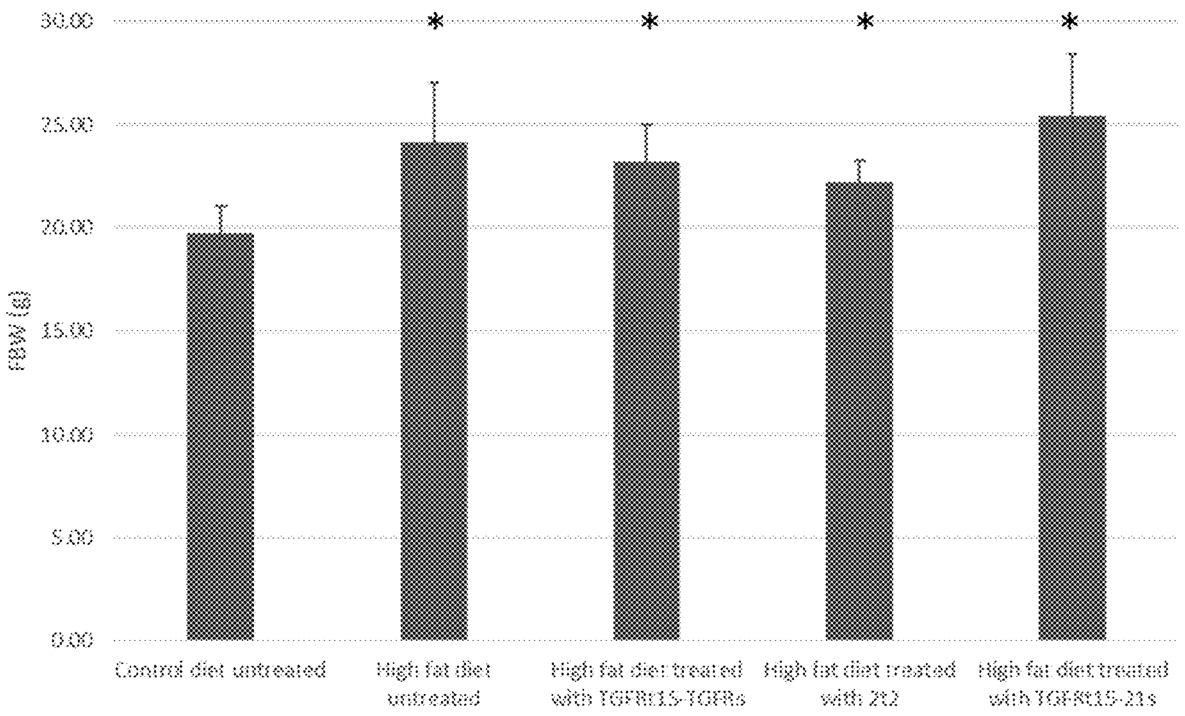
FIG. 7 shows the fasting body weight of mice fed either a control or a high fat diet and were either untreated or treated with TGFRt15-TGFRs, 2t2, or 21t15-TGFRs.

Next, mice were fed either a control or high fat diet for 9 weeks, and a subset of the mice fed a high fat diet were treated with TGFRt15-TGFRs, 2t2, or 21t15-TGFRs. Four days post-treatment, the fasting body weight of mice in each group were measured. The fasting body weight of mice fed with the high fat diet and untreated, as well as mice fed with the high fat diet and treated with 21t15-TGFRs were significantly increased compared to mice fed a control diet. However, the fasting body weight of mice fed a high fat diet and treated with TGFRt15-TGFRs or 2t2 were decreased compared to the other two high fat diet groups mentioned above. The fasting body weight of the mice at the end of the study (9 weeks) is shown in FIG. 7.

Figure 8:
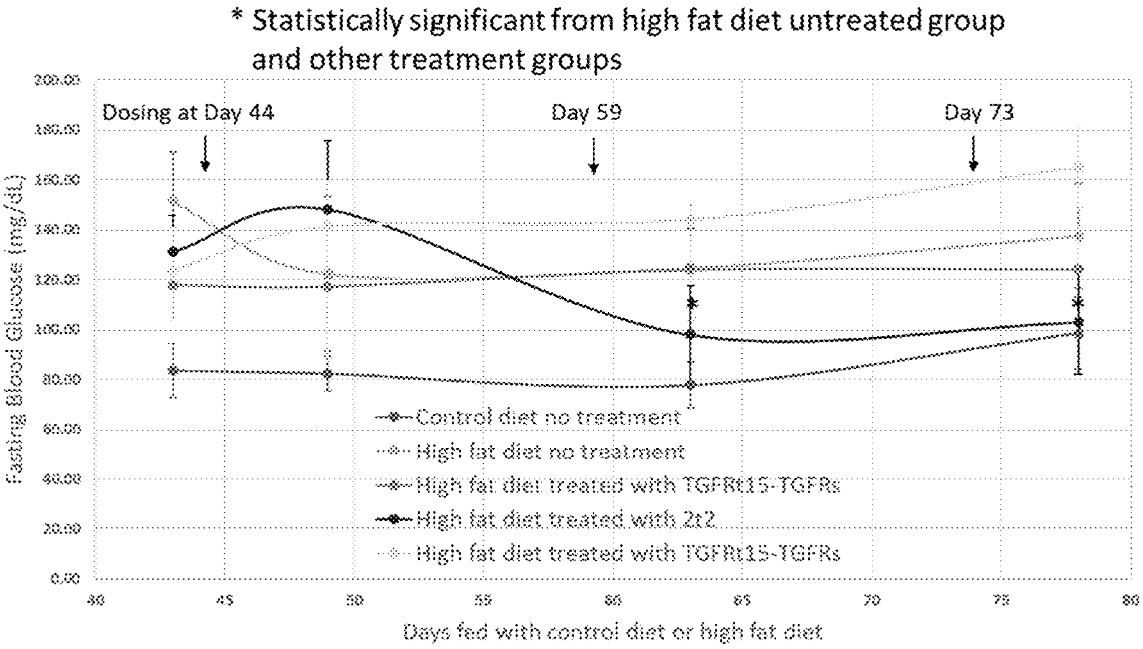
FIG. 8 shows the fasting blood glucose levels of mice fed either a control or a high fat diet and were either untreated or treated with TGFRt15-TGFRs, 2t2, or 21t15-TGFRs.

To evaluate the fasting glucose levels in the mice of each group, mice were fed either a control or a high fat diet and were either untreated or treated with TGFRt15-TGFRs, 2t2, or 21t15-TGFRs on days 44, 59 and 73. The fasting blood glucose in the mice of each group were measured 4 days post-treatment. As shown in FIG. 8, after the second and third doses (on Days 59 and 73, respectively), the fasting blood glucose level was significantly reduced for mice fed a high fat diet and treated with 2t2 (red line) as compared to mice fed a high fat diet but untreated (yellow line). The fasting blood glucose level remained constant for mice fed a high fat diet and treated with TGFRt15-TGFRs (green line), whereas the fasting blood glucose level increased for mice fed a high fat diet and treated with 21t15-TGFRs (blue line).

Example 3: Chemotherapy-Induced Senescent B16F10 Melanoma Cells Express NK Ligands Material and Methods Cellular senescence in B16F10 melanoma cells was induced by treating the cells with docetaxel (7.5 μM, Sigma) for 3 days followed by recovery in complete media for 4 days. Cellular senescence was accessed by staining the cells with senescence-associated 3-galactosidase (SA β-gal). Briefly, B16F10 control and senescence cells (B16F10-SNC) were washed once with PBS, fixed with 0.5% glutaraldehyde (PBS (pH 7.2)), for 30 minutes. Cells were stained in X-gal solution (1 mg/mL X-gal, 0.12 mM K3Fe$[CN]_6$, 0.12 mM K4Fe$[CN]_6$, and 1 mM $MgCl_2$ in PBS at pH 6.0) overnight at 37° C., and were imaged using a Nikon optical light microscope.

Results

Figure 9A:
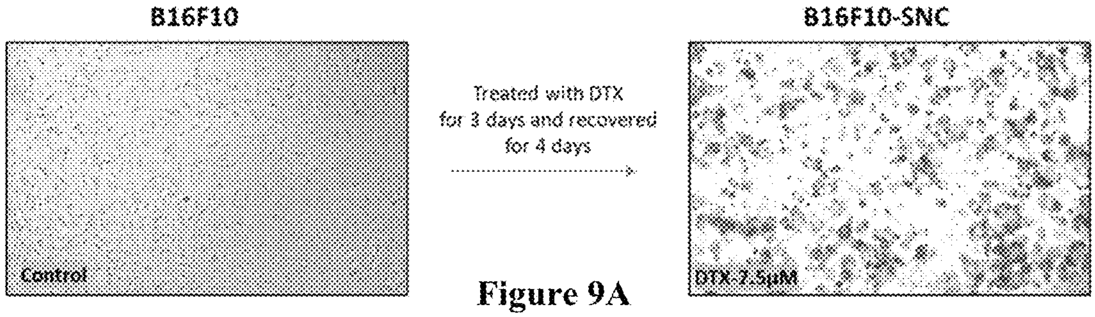
FIGS. 9A-9F show chemotherapy-induced senescent B16F10 cells and expression of senescent genes.
Figure 9B:
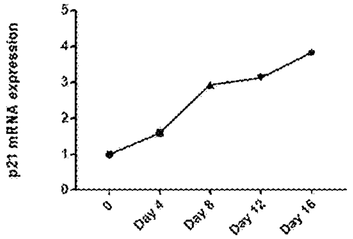
Figure 9C:
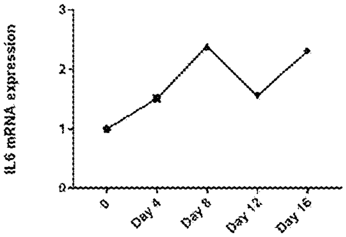
Figure 9D:
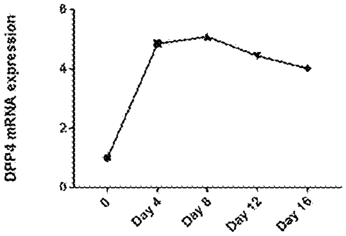
Figure 9E:
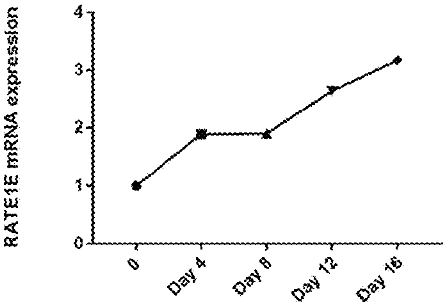
Figure 9F:
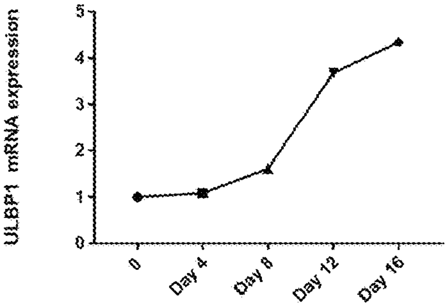

Cellular senescence in B16F10 melanoma cells was induced using chemotherapy as described above. As shown in FIG. 9A, chemotherapy-induced senescent B16F10 cells (B16F10-SNC) were positive for SA β-gal staining, while the control B16F10 cells were not stained. Next, expression of senescence genes was analyzed using RT-qPCR with RNA isolated on day 0 or following senescence induction on days 4, 8, 12 and 16, respectively. The expression levels were normalized to control B16F10 cells. As shown in FIGS. 9B-9D, the expression of p21, IL6 and DPP4 were upregulated in RNA isolated from the senescent cells over the duration of the experiment. Moreover, as shown in FIGS. 9E and 9F, the expression of RATE1E and ULBP1 (NK activating receptor NKG2D ligands) were also induced in senescent cells, with the highest expression level being on day 16. These results demonstrate that the chemotherapy-induced senescent B16F10 cells are subjected to stronger cytotoxicity of activated NK cells than control B16F10 cells.

Figure 10A:
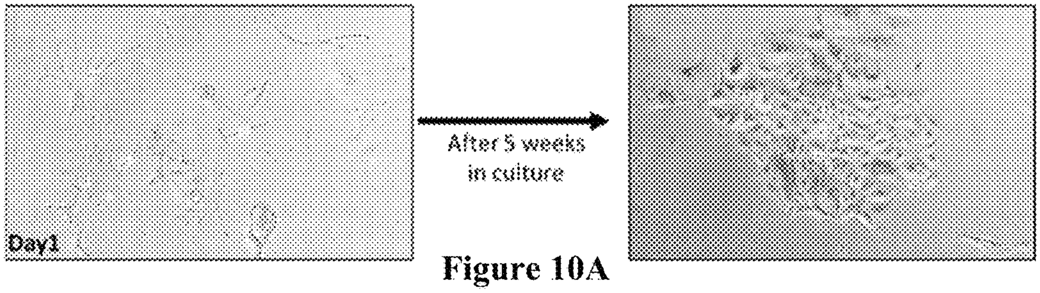
FIGS. 10A-10F show colony formation and expression of stem cell markers by chemotherapy-induced senescent B16F10 cells.
Figure 10B:
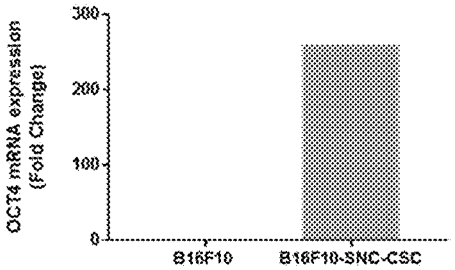
Figure 10C:
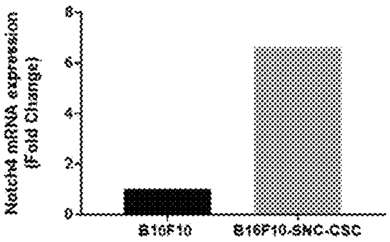
Figure 10D:
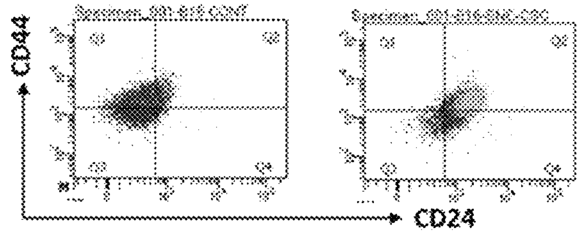
Figure 10D:
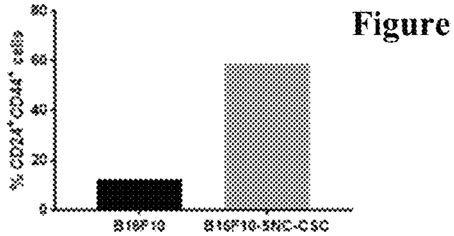
Figure 10E:
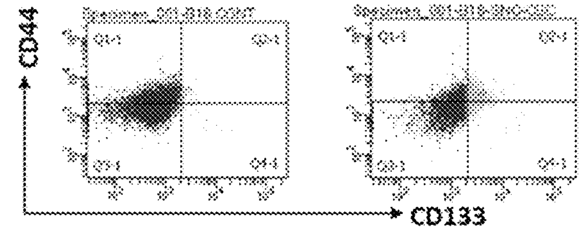
Figure 10E:
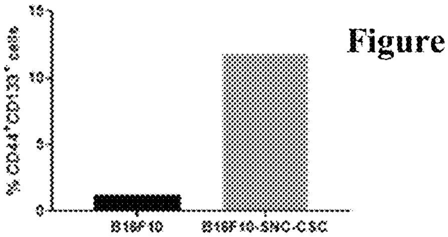
Figure 10F:
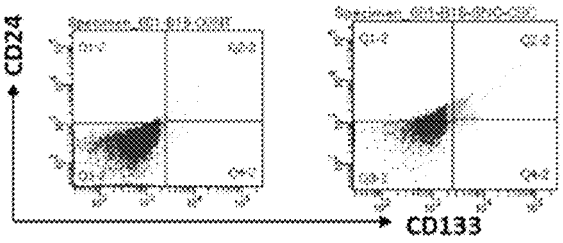
Figure 10F:
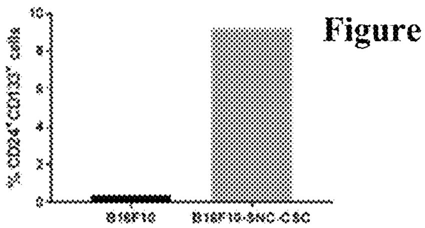

Acquisition of Stem-Cell Properties in Chemotherapy-Induced Senescent B16F10 Melanoma Cells To examine whether chemotherapy-induced senescent B16F10 melanoma cells acquired stem cell properties, a colony formation assay was performed. Briefly, 1000 cells/well were seeded on a six well plate, and the media was changed every third day. As shown in FIG. 10A (images taken at 100× magnification), after 5 weeks in culture the senescent cells were able to form colonies. To evaluate stem cell marker expression by the colonies, RNA was isolated from the colonies and the expression of Oct4 and Notch4 mRNA were determined by RT-qPCR. As compared to control B16F10 cells, chemotherapy-induced senescent B16F10 melanoma cells showed upregulation of Oct4 and Notch 4, which are cancer stem cell markers (FIGS. 10B and 10C). Moreover, cell surface expression of stem cell markers CD44, CD24 and CD133 were evaluated by staining with antibodies against CD44, CD24, and CD133 followed by flow cytometry. As shown in FIGS. 10D-10F, double positive populations ($CD44^+CD24^+$, $CD44^+CD133^+$, and $CD24^+CD133^+$) were increased in the chemotherapy induced senescence stem cells (B16F10-SNC-CSC) compared to control B16F10.

Figure 11A:
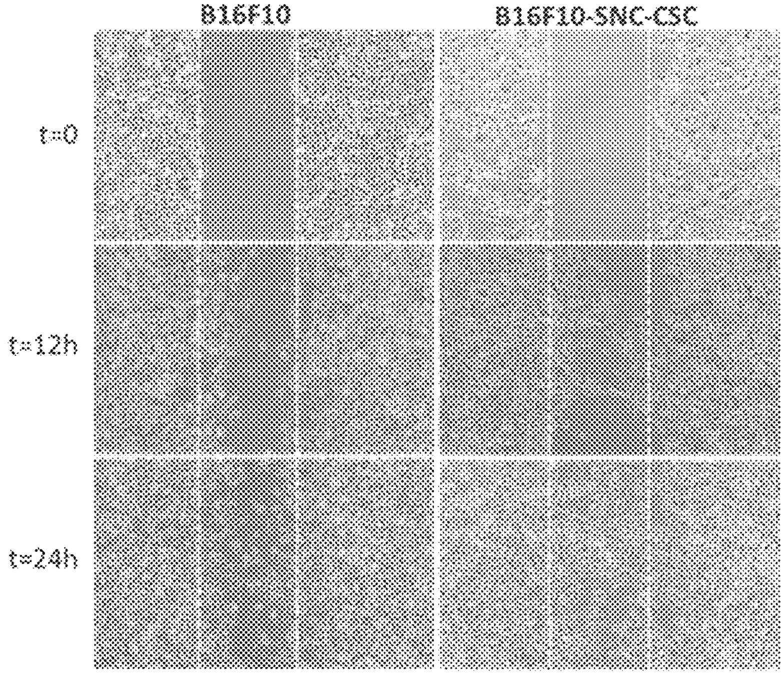
FIGS. 11A-11C show migratory and invasive properties of chemotherapy-induced senescent B16F10 cells.

Chemotherapy-Induced Senescent (CIS) Melanoma Cells with Stem Cell Properties are More "Migratory" and "Invasive" than Control B16F10 Cells The migratory properties of chemotherapy-induced senescent (CIS) melanoma cells with stem cell properties (B16F10-SNC-CSC) were analyzed using a migration assay. Briefly, control B16F10 cells and B16F10-SNC-CSC cells were plated on six well plates and wounded with a p20 pipette tip. Movement of cells were imaged at 0, 12, and 24 hours after. As shown in FIG. 11A, chemotherapy-induced senescent (CIS) melanoma cells with stem cell properties (B16F10-SNC-CSC) were more migratory in the in vitro migration assay, as compared to control B16F10 cells.

Figure 11B:
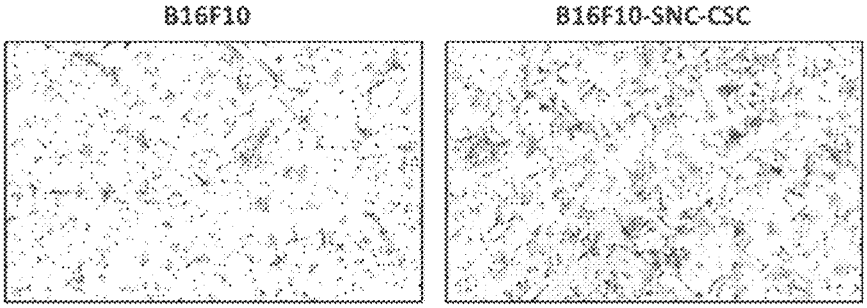
Figure 11C:
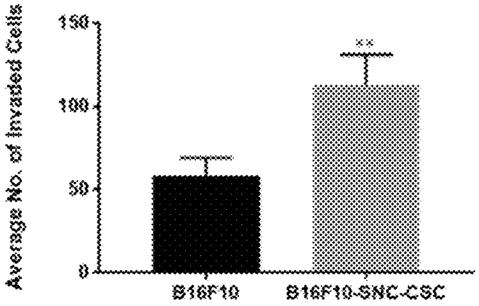

Next, the invasive properties of chemotherapy-induced senescent cells with stem cell properties (B16F10-SNC-CSC) were analyzed using an invasion assay. The invasion assay was carried out on 24-well transwell inserts coated with Matrigel. Briefly, $0.5\times10^6$ control B16F10 cells and B16F10-SNC-CSC cells were seeded in serum-free media onto the upper chamber, and the lower chamber was filled with media supplemented with 10% FBS. After 16 hours of incubation, the cells on the upper surface of the filter were removed, and cells underneath the filter were fixed and stained with a 0.02% crystal violet solution. The number of cells were counted in three fields at 100× magnification. As shown in FIGS. 11B and 11C, chemotherapy-induced senescent cells with stem cell properties were more aggressive in invading the Matrigel coated membrane as compared to control B16F10 cells. These results demonstrate that chemotherapy-induced senescent B16F10 tumor cells are able to regain their proliferation capability, obtain stem-cell features, and have increased migratory abilities and invasiveness for metastasis.

Figure 12A:
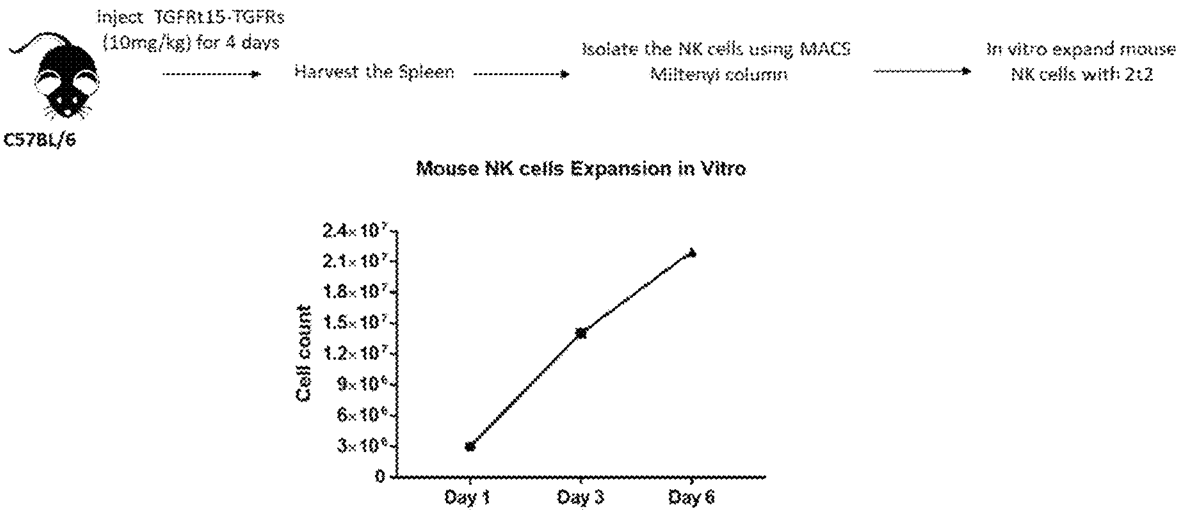
FIGS. 12A and 12B show in vitro expanded NK cells and their cytotoxicity against chemotherapy-induced senescent cells with stem cell properties (B16F10-SNC-CSC) or control B16F10 cells.

Cytotoxic Activity of Mouse NK Cells on Chemotherapy-Induced Senescent Cells with Stem Cell Properties To expand NK cells in vivo, C57BL/6 mice were injected subcutaneously with TGFRt15-TGFRs (10 mg/kg) for 4 days. The spleens from these mice were obtained and NK cells were purified using MACS Miltenyi column. The purified NK cells were then expanded in vitro with 2t2 (FIG. 12A).

Figure 12B:
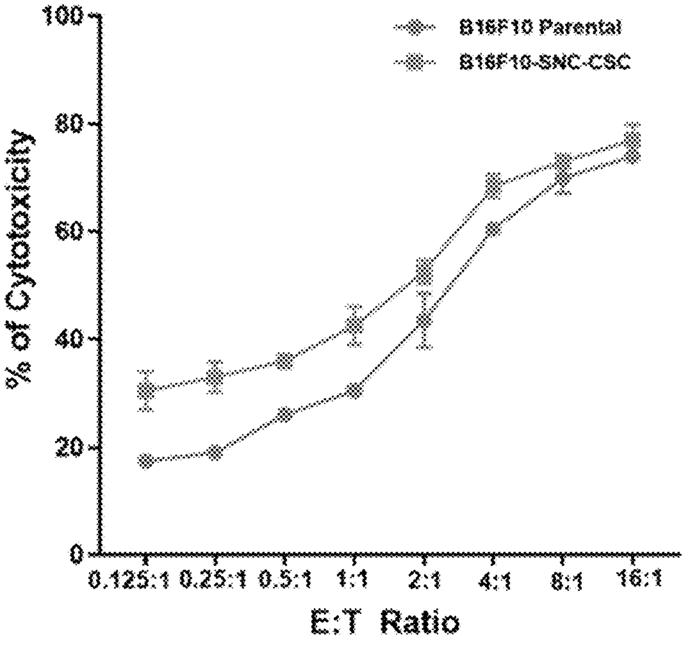

To evaluate the cytotoxicity of the expanded NK cells, chemotherapy-induced senescent stem cells (B16F10-SNC-CSC) or control B16F10 cells were labelled with CellTrace violet and incubated with in vitro activated 2t2 mouse NK cells (isolated from spleen of C57BL/6 mice injected with 10 mg/kg TGFRt15-TGFRs for 4 days) at various E:T ratios for 16 hrs. The B16F10-SNC-CSC and control B16F10 cells were trypsinized, washed and re-suspended in complete media containing a Propidium Iodide (PI) solution, and cytotoxicity was accessed by flow cytometry. As shown in FIG. 12B, NK cells were more effective at killing chemotherapy-induced senescent cells with stem cell properties (B16F10-SNC-CSC), as compared to control B16F10 cells.

Combination Treatment in Melanoma Mouse Model

The effect of TGFRt15-TGFRs in treating melanoma was evaluated in a mouse melanoma model. Briefly, $5\times10^5$ B16F10 cells were injected subcutaneously into C57BL/6 mice. When the tumor volume reached ~100 $mm^3$, mice were treated with docetaxel (chemotherapy) (5 mg/kg) or TA99 (200 μg) either as a single agent or in combination every third day, and TGFRt15-TGFRs (3 mg/kg) was given once a week (FIG. 13A). Mice that received saline, docetaxel (chemotherapy)/TA99 alone, or TGFRt15-TGFRs alone were used as controls. Five mice were tested in each experimental and control group. Tumor volume was measured every third day. As shown in FIGS. 13B and 13C, combinations of TGFRt15-TGFRs with either chemotherapy or TA99 slowed down tumor progression as compared to mice treated with saline or mice treated with chemotherapy or TA99 alone in the syngeneic melanoma mouse model.

Example 4: Chemotherapeutic Induction of Senescence in Human Pancreatic Cell Line SW1990

Materials and Methods

β-Galactosidase Staining:

Confirmation of chemotherapy induced senescence was carried out by standard β-galactosidase staining at pH 6.0 using commercially available kit (Cell Signaling Technology) according to manufacturer's instructions. The following day, the staining solution was removed, and cells were washed with phosphate buffered saline, and 70% glycerol was added to the wells. The β-galactosidase positive cells will be stained blue, while control untreated cells will not stain.

Flow Cytometry:

One million control and senescent cells were obtained and stained using commercially available antibodies to surface markers of stem cells such as anti-CD44 and anti-CD24 antibodies (Biolegend) according to manufacturers' instructions. The cells were then washed and analyzed using the BD Celesta flow cytometer. Cells showing stem cell-like properties will be doubly positive for both CD44 and CD24.

Gene Expression Assay:

One million control and senescent cells were obtained and lysed using Trizol (Thermofisher), followed by RNA purification using an RNA isolation kit (Qiagen). The RNA was quantified and converted to cDNA using a Qiagen cDNA QUANTITECT® kit (kit for cDNA synthesis with integrated removal of genomic DNA contamination). The cDNA was then used as a template for standard Taqman gene expression assays (Thermofisher) to quantify the relative abundance of senescent, stem cell markers as well as NK ligands.

NK Cell Cytotoxicity Assay:

NK cells were isolated from healthy human donors (n=2) using a commercially available NK isolation kit (Stem Cell), and were activated overnight using the cytokine fusion molecule 18t15-12s (100 nM). On the following day, NK cells were washed to remove cytokine molecules and mixed with either CELLTRACE™ Violet (cell proliferation kit for flow cytometry)-labelled control untreated tumor cells or chemotherapy-induced senescent tumor cells at an E:T ratio of 4:1 for 20 hours. On the following day, cells were trypsinized, and complete contents of each well were analyzed using flow cytometry and percent inhibition of cells was analyzed.

Results

Senescence in the human pancreatic tumor cell line SW1990 was induced through treatment with chemotherapeutic drugs Abraxane (Celgene) and Gemcitabine (Sigma Aldrich) for 3 days at 2.5 μM and 6.25 μM, respectively. SW1990 cells that were untreated were used as controls. Media was changed after 3 days and cells were allowed to rest in the culture media for 4 days. As shown in FIG. 14, senescent cells treated with the chemotherapeutic drugs were positive for β-galactosidase staining (blue), while control cells were not stained. Senescent cells and control cells were evaluated for their expression of senescence and stem cell markers at 4 days, 11 days, and 22 days post-treatment. As shown in FIG. 14, senescent cells showed increased double positive staining for CD44 and CD24 over time as compared to the control cells. Moreover, the chemotherapy-induced senescent SW1990 cells were also analyzed for their expression of senescent markers including DPP4, IL6, and p21, stem cell markers including Oct3/4, CD24, and CD44, and NK ligands including Nectin and MICA, on day 0, and days 2, 4, and 24 post-treatment using the gene expression assay described above. As shown in FIG. 15, the expression of all of the markers mentioned showed an increase over time.

Cytotoxicity of In Vitro Activated Human NK Cells

To evaluate the cytotoxicity of in vitro activated human NK Cells (treated with 18t15-12s), senescence in the human pancreatic tumor cell line SW1990 was induced through treatment with chemotherapeutic drugs Abraxane (Celgene) and Gemcitabine (Sigma Aldrich) for 3 days at 2.5 μM and 6.25 μM, respectively. SW1990 cells that were untreated were used as controls. Media was changed after 3 days and cells were allowed to rest in the culture media for 30 days. The culture media was changed every 4 days. Activated NK cells were obtained and their cytotoxicity for chemotherapy-induced senescent tumor cells and untreated control tumor cells were evaluated using the NK cell cytotoxicity assay described above. As shown in FIG. 16, activated NK cells showed increased cytotoxicity against both control SW1990 cells (SW1990) and senescent SW1990 cells (SW1990s).

Example 5: Creation of an IL-12/IL-15RαSu DNA Construct

In a non-limiting example, an IL-12/IL-15RαSu DNA construct was created (FIG. 17). The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 181):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGTGTTTACCGACAAAACCAGCGCCACCGTCATCTGT

CGGAAGAACGCCTCCATCAGCGTGAGGGCTCAAGATCGTTATTACTCCA

GCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC
```

-continued (Human IL-15R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

Example 6: Creation of an IL-18/TF/IL-15 DNA Construct

In a non-limiting example, an IL-18/TF/IL-15 construct was made (FIG. 18) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 177):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

-continued (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 7: Secretion of IL-12/IL-15RαSu and IL-18/TF/IL-15 Fusion Proteins

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s; FIG. 19 and FIG. 20). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 180):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHED

ITKDKTSTVEACLPLELTKNESCLNSRETSFITNGSCLASRKTSFMMALCL

SSIYEDLKMYQVEFKTMNAKLLMDPKRQIFLDQNMLAVIDELMQALNFNSE

TVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKAT

NVAHWTTPSLKCIR

-continued

```
The amino acid sequence of the IL-18/TF/IL-15
fusion protein (including signal peptide sequence)
is as follows (SEQ ID NO: 176):
(Signal peptide)
MKWVTFISLLFLFSSAYS

(Human IL-18)
YFGKLESKLSVIRNLNDQVLFIDQGNRPLFEDMTDSDCRDNAPRTIFIISM

YKDSQPRGMAVTISVKCEKISTLSCENKIISFKEMNPPDNIKDTKSDIIFF

QRSVPGHDNKMQFESSSYEGYFLACEKERDLFKLILKKEDELGDRSIMFTV

QNED

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

In some cases, the leader (signal sequence) peptide is cleaved from the intact polypeptide to generate the mature form that may be soluble or secreted.

Example 8: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 18t15-12s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. FIG. 21 shows that the 18t15-12s complex binds the anti-TF antibody affinity column, wherein TF is an 18t15-12s binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 9: Size Exclusion Chromatography of 18t15-12s

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 2004, of 1 mg/mL of 18t15-12s complex onto the column. The injection was chased with 1.25 column volumes of PBS. The SEC chromatograph is shown in FIG. 22. There is a main 18t15-12s protein peak with a minor high molecular weight peak, likely due to differing degrees of glycosylation of 18t15-12s dimers or aggregates.

Example 10: SDS-PAGE of 18t15-12s

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 23 shows an example SDS gel of anti-TF antibody affinity purified 18t15-12s, with bands at the expected molecular weights (66 kDa and 56 kDa).

Example 11: Glycosylation of 18t15-12s in CHO-K1 Cells

Glycosylation of 18t15-12s in CHO-K1 cells was confirmed using the Protein Deglycosylation Mix II kit (New England Biolabs), according to the manufacturer's instructions. FIG. 24 shows an example SDS PAGE of deglycosylated and non-deglycosylated 18t15-12s. Deglycosylation reduces the molecular weight of 18t15-12s as seen in FIG. 24, lane 4.

Example 12: Recombinant Protein Quantitation of 18t15-12s Complexes

The 18t15-12s complex was detected and quantified using standard sandwich ELISA methods (FIGS. 25-28). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (143), and anti-human tissue factor antibody detection. The I43/anti-TF antibody ELISA was compared to purified tissue factor at similar concentrations.

Example 13: Immunostimulatory Capacity of the 18t15-12s Complex

To assess the IL-15 immunostimulatory activity of the 18t15-12s complex, increasing concentrations of 18t15-12s was added to 32Dβ cells (104 cell/well) in 200 IMDM:10% FBS media. The 32Dβ cells were incubated for 3 days at 37° C. On the fourth day, WST-1 proliferation reagent (10 μL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 29, 18t15-12s demonstrated IL-15-dependent cell proliferation of 32Dβ cells. The 18t15-12s complex demonstrated reduced activity compared to human recombinant IL-15, possibly due to the linkage of IL-18 and tissue factor to the IL-15 domain.

In order to assess the individual activities of IL-12 and IL-18 in the 18t15-12s complex, 18t15-12s was added to HEK-Blue IL-12 and HEK-Blue IL-18 reporter cells ($5\times10^4$ cell/well; hkb-il12 and hkb-hmil18, InvivoGen) in 200 μL IMDM:10% heat-inactivated FBS media. Cells were incubated for overnight at 37° C. 20 μl of induced HEK-Blue IL-12 and HEK-Blue IL-18 reporter cell supernatant was added to 180 μl of QUANTI-Blue (InvivoGen), and incubated for 1-3 hours at 37° C. IL-12 or IL-18 activity was assessed by measuring absorbance at 620 nm. Human recombinant IL-12 or IL-18 was assessed as a positive or negative control. As shown in FIG. 30 and FIG. 31, each of the cytokine domains of the 18t15-12s complex retain specific biological activity. The activity of 18t15-12s was reduced compared to that of human recombinant IL-18 or IL-12, possibly due to linkage of IL-15 and tissue factor to the IL-18 domain and linkage of IL-12 to the IL-15Rα sushi domain.

Example 14: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor a (IL-2Ra, CD25), CD69 (and other activation markers), and increased IFN-γ production. To evaluate the ability of 18t15-12s complexes to promote generation of cytokine-induced memory-like NK cells, purified human NK cells (>95% CD56+) were stimulated for 14-18 hours with 0.01 nM to 10000 nM of the 18t15-12s complex or a combination of individual cytokines (recombinant IL-12 (10 ng/ml), IL-18 (50 ng/ml), and IL-15 (50 ng/ml)). Cell-surface CD25 and CD 69 expression and intracellular IFN-γ levels were assessed by antibody-staining and flow cytometry.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-15 (50 ng/mL) (NCI) or with 0.01 nM to 10000 nM of the 18t15-12s at 37° C., 5% $CO_2$ for 14-18 hrs. The cells were then harvested and surface stained for CD56-BV421, CD16-BV510, CD25-PE, CD69-APCFire750 specific antibodies (BioLegend) for 30 minutes. After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACSCelesta™ flow cytometer (Plotted Data-Mean Fluorescence Intensity; FIG. 32A and FIG. 32B).

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37° C., 5% $CO_2$ for 14-18 hrs. The cells were then treated with 10 μg/mL of Brefeldin A (Sigma) and 1× of Monensin (eBioscience) for 4 hrs before harvesting and staining for CD56-BV421, CD16-BV510, CD25-PE, CD69-APCFire750 specific antibodies for 30 minutes. After staining, cells were washed (1500 RPM for 5 minutes in room temperature) in FACS buffer (1×PBS (Hyclone), with 0.5% BSA (EMD Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-γ Positive Cells; FIG. 33).

Example 15: In Vitro Cytotoxicity of NK Cells Against Human Tumor Cells

Human myelogenous leukemia cells, K562 (CellTrace violet labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 34, the 18t15-12s complex induced human NK cytotoxicity against K562, at levels similar or greater than the cytokine mixture, wherein both the 18t15-12s complex and the cytokine mixture induced greater cytotoxicity than the medium control.

Example 16: Creation of IL-12/IL-15RαSu/αCD16scFv and IL-18/TF/IL-15 DNA Constructs In a non-limiting example, IL-12/IL-15RαSu/αCD16scFv and IL-18/TF/IL-15 DNA constructs were created (FIG. 35 and FIG. 36). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of αCD16scFv.

The nucleic acid sequence of the IL-12/IL-15RαSu/αCD16scFv construct is as follows (SEQ ID NO: 226):

```
(Signal peptide)
ATGAAATGGGTGACCTTTATTTCTTTACTGTTCCTCTTTAGCAGCGCCTAC

TCC

(Human IL-12 subunit beta (p40))
ATTTGGGAACTGAAGAAGGACGTCTACGTGGTCGAACTGGACTGGTATCCC

TGCTCCCGGCGAAATGGTGGTGCTCACTTGTGACACCCCCGAAGAAGGAAC

GGCATCACTTGGACCCTCGATCAGAGCAGCGAGGTGCTGGGCTCCGGAAAG

ACCCTCACAATCCAAGTTAAGGAGTTCGGAGACGCTGGCCAATACACATGC

CACAAGGGAGGCGAGGTGCTCAGCCATTCCTTATTATTATTACACAAGAAG
```

-continued

GAAGACGGAATCTGGTCCACCGACATTTTAAAAGATCAGAAGGAGCCCAAG

AATAAGACCTTTTTAAGGTGTGAGGCCAAAAACTACAGCGGTCGTTTCACT

TGTTGGTGGCTGACCACCATTTCCACCGATTTAACCTTCTCCGTGAAAAGC

AGCCGGGGAAGCTCCGACCCTCAAGGTGTGACATGTGGAGCCGCTACCCTC

AGCGCTGAGAGGGTTCGTGGCGATAACAAGGAATACGAGTACAGCGTGGAG

TGCCAAGAAGATAGCGCTTGTCCCGCTGCCGAAGAATCTTTACCCATTGAG

GTGATGGTGGACGCCGTGCACAAACTCAAGTACGAGAACTACACCTCCTCC

TTCTTTATCCGGGACATCATTAAGCCCGATCCTCCTAAGAATTTACAGCTG

AAGCCTCTCAAAAATAGCCGGCAAGTTGAGGTCTCTTGGGAATATCCCGAC

ACTTGGAGCACACCCCACAGCTACTTCTCTTTAACCTTTTGTGTGCAAGTT

CAAGGTAAAAGCAAGCGGGAGAAGAAAGACCGGGTGTTTACCGACAAAACC

AGCGCCACCGTCATCTGTCGGAAGAACGCCTCCATCAGCGTGAGGGCTCAA

GATCGTTATTACTCCAGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTACAC

CACAGCCAGAATTTACTGAGGGCCGTGAGCAACATGCTGCAGAAAGCTAGG

CAGACTTTAGAATTTTACCCTTGCACCAGCGAGGAGATCGACCATGAAGAT

ATCACCAAGGACAAGACATCCACCGTGGAGGCTTGTTTACCTCTGGAGCTG

ACAAAGAACGAGTCTTGTCTCAACTCTCGTGAAACCAGCTTCATCACAAAT

GGCTCTTGTTTAGCTTCCCGGAAGACCTCCTTTATGATGGCTTTATGCCTC

AGCTCCATCTACGAGGATTTAAAGATGTACCAAGTGGAGTTCAAGACCATG

AACGCCAAGCTGCTCATGGACCCTAAACGGCAGATCTTTTTAGACCAGAAC

ATGCTGGCTGTGATTGATGAGCTGATGCAAGCTTTAAACTTCAACTCCGAG

ACCGTCCCTCAGAAGTCCTCCCTCGAGGAGCCCGATTTTTACAAGACAAAG

ATCAAACTGTGCATTTTACTCCACGCCTTTAGGATCCGGGCCGTGACCATT

GACCGGGTCATGAGCTATTTAAACGCCAGC (Human IL-15R α sushi domain)
ATTACATGCCCCCCTCCCATGAGCGTGGAGCACGCCGACATCTGGGTGAAG

GACTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG (anti-Human CD16 light chain variable domain)
TCCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTAC

CAGCAGAAGCCCGGCCAGGCTCCTGTGCTGGTGATCTACGGCAAGAACAAC

AGGCCCTCCGGCATCCCTGACAGGTTCTCCGGATCCTCCTCCGGCAACACC

GCCTCCCTGACCATCACAGGCGCTCAGGCCGAGGACGAGGCTGACTACTAC

TGCAACTCCAGGGACTCCTCCGGCAACCATGTGGTGTTCGGCGGCGGCACC

AAGCTGACCGTGGGCCAT

-continued (Linker)
GGCGGCGGCGGCTCCGGAGGCGGCGGCAGCGGCGGAGGAGGATCC (anti-Human CD16 heavy chain variable domain)
GAGGTGCAGCTGGTGGAGTCCGGAGGAGGAGTGGTGAGGCCTGGAGGCTCC

CTGAGGCTGAGCTGTGCTGCCTCCGGCTTCACCTTCGACGACTACGGCATG

TCCTGGGTGAGGCAGGCTCCTGGAAAGGGCCTGGAGTGGGTGTCCGGCATC

AACTGGAACGGCGGATCCACCGGCTACGCCGATTCCGTGAAGGGCAGGTTC

ACCATCAGCAGGGACAACGCCAAGAACTCCCTGTACCTGCAGATGAACTCC

CTGAGGGCCGAGGACACCGCCGTGTACTACTGCGCCAGGGGCAGGTCCCTG

CTGTTCGACTACTGGGGACAGGGCACCCTGGTGACCGTGTCCAGG

Constructs were also made linking the IL-18 sequence to the N-terminus coding region of tissue factor 219, and linking the IL-18/TF construct with the N-terminus coding region of IL-15 (FIG. 36). The nucleic acid sequence of the IL-18/TF/IL-15 construct (including leader sequence) is as follows (SEQ ID NO: 177):

(Signal peptide)
ATGAAGTGGGTCACATTTATCTCTTTACTGTTCCTCTTCTCCAGCGCCTAC

AGC (Human IL-18)
TACTTCGGCAAACTGGAATCCAAGCTGAGCGTGATCCGGAATTTAAACGAC

CAAGTTCTGTTTATCGATCAAGGTAACCGGCCTCTGTTCGAGGACATGACC

GACTCCGATTGCCGGGACAATGCCCCCCGGACCATCTTCATTATCTCCATG

TACAAGGACAGCCAGCCCCGGGGCATGGCTGTGACAATTAGCGTGAAGTGT

GAGAAAATCAGCACTTTATCTTGTGAGAACAAGATCATCTCCTTTAAGGAA

ATGAACCCCCCCGATAACATCAAGGACACCAAGTCCGATATCATCTTCTTC

CAGCGGTCCGTGCCCGGTCACGATAACAAGATGCAGTTCGAATCCTCCTCC

TACGAGGGCTACTTTTTAGCTTGTGAAAAGGAGAGGGATTTATTCAAGCTG

ATCCTCAAGAAGGAGGACGAGCTGGGCGATCGTTCCATCATGTTCACCGTC

CAAAACGAGGAT (Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

-continued (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

Example 17: Secretion of IL-12/IL-15RαSu/αCD16scFv and IL-18/TF/IL-15 Fusion Proteins The IL-12/IL-15RαSu/αCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/αCD16scFv protein complex (referred to as 18t15-12s/αCD16; FIG. 37 and FIG. 38). Co-expression of the two constructs in CHO-K1 cells resulted in secretion of the soluble IL-18/TF/IL-15:IL-12/IL-15RαSu/αCD16scFv protein complex (referred to as 18t15-12s/αCD16; FIG. 37 and FIG. 38), which can be purified by anti-TF Ab affinity and other chromatography methods. In some cases, the signal peptide is cleaved from the intact polypeptide to generate the mature form.

The amino acid sequence of the IL-12/IL-15RαSu/αCD16scFv fusion protein (including signal peptide sequence) is as follows (SEQ ID NO: 225):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHED

ITKDKTSTVEACLPLELTKNESCLNSRETSFITNGSCLASRKTSFMMALCL

SSIYEDLKMYQVEFKTMNAKLLMDPKRQIFLDQNMLAVIDELMQALNFNSE

TVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKAT

NVAHWTTPSLKCIR

-continued (anti-Human CD16 light chain variable domain)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGH (Linker)
GGGGSGGGGSGGGGS (anti-Human CD16 heavy chain variable domain)
EVQLVESGGGVVRPGGSLRLSCAASGFTFDDYGMSWVRQAPGKGLEWVSGI

NWNGGSTGYADSVKGRFTISRDNAKNSLYLQMNSLRAEDTAVYYCARGRSL

LFDYWGQGTLVTVSR

The amino acid sequence of the IL-18/TF/IL-15 fusion protein (including leader sequence) is as follows (SEQ ID NO: 221):

(Signal peptide)
MKWVTFISLLFLFSSAYS (Human IL-18)
YFGKLESKLSVIRNLNDQVLFIDQGNRPLFEDMTDSDCRDNAPRTIFIISM

YKDSQPRGMAVTISVKCEKISTLSCENKIISFKEMNPPDNIKDTKSDIIFF

QRSVPGHDNKMQFESSSYEGYFLACEKERDLFKLILKKEDELGDRSIMFTV

QNED (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Example 18: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 320):

(Signal peptide)
ATGAAGTGGGTCACATTTATCTCTTTACTGTTCCTCTTCTCCAGCGCCTAC

AGC

-continued

```
(Human IL-18)
TACTTCGGCAAACTGGAATCCAAGCTGAGCGTGATCCGGAATTTAAACGAC

CAAGTTCTGTTTATCGATCAAGGTAACCGGCCTCTGTTCGAGGACATGACC

GACTCCGATTGCCGGGACAATGCCCCCCGGACCATCTTCATTATCTCCATG

TACAAGGACAGCCAGCCCCGGGGCATGGCTGTGACAATTAGCGTGAAGTGT

GAGAAAATCAGCACTTTATCTTGTGAGAACAAGATCATCTCCTTTAAGGAA

ATGAACCCCCCCGATAACATCAAGGACACCAAGTCCGATATCATCTTCTTC

CAGCGGTCCGTGCCCGGTCACGATAACAAGATGCAGTTCGAATCCTCCTCC

TACGAGGGCTACTTTTTAGCTTGTGAAAAGGAGAGGGATTTATTCAAGCTG

ATCCTCAAGAAGGAGGACGAGCTGGGCGATCGTTCCATCATGTTCACCGTC

CAAAACGAGGAT

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG
```

The nucleic acid sequence of the IL-12/TF/IL-15 construct (including leader sequence) is as follows (SEQ ID NO: 321):

```
(Signal peptide)
ATGAAATGGGTGACCTTTATTTCTTTACTGTTCCTCTTTAGCAGCGCCTAC

TCC

(Human IL-12 subunit beta (p40))
ATTTGGGAACTGAAGAAGGACGTCTACGTGGTCGAACTGGACTGGTATCCC

GATGCTCCCGGCGAAATGGTGGTGCTCACTTGTGACACCCCCGAAGAAGAC

GGCATCACTTGGACCCTCGATCAGAGCAGCGAGGTGCTGGGCTCCGGAAAG

ACCCTCACAATCCAAGTTAAGGAGTTCGGAGACGCTGGCCAATACACATGC

CACAAGGGAGGCGAGGTGCTCAGCCATTCCTTATTATTATTACACAAGAAG

GAAGACGGAATCTGGTCCACCGACATTTTAAAAGATCAGAAGGAGCCCAAG

AATAAGACCTTTTTAAGGTGTGAGGCCAAAAACTACAGCGGTCGTTTCACT

TGTTGGTGGCTGACCACCATTTCCACCGATTTAACCTTCTCCGTGAAAAGC

AGCCGGGGAAGCTCCGACCCTCAAGGTGTGACATGTGGAGCCGCTACCCTC

AGCGCTGAGAGGGTTCGTGGCGATAACAAGGAATACGAGTACAGCGTGGAG

TGCCAAGAAGATAGCGCTTGTCCCGCTGCCGAAGAATCTTTACCCATTGAG

GTGATGGTGGACGCCGTGCACAAACTCAAGTACGAGAACTACACCTCCTCC

TTCTTTATCCGGGACATCATTAAGCCCGATCCTCCTAAGAATTTACAGCTG

AAGCCTCTCAAAAATAGCCGGCAAGTTGAGGTCTCTTGGGAATATCCCGAC

ACTTGGAGCACACCCCACAGCTACTTCTCTTTAACCTTTTGTGTGCAAGTT

CAAGGTAAAAGCAAGCGGGAGAAGAAAGACCGGGTGTTTACCGACAAAACC

AGCGCCACCGTCATCTGTCGGAAGAACGCCTCCATCAGCGTGAGGGCTCAA

GATCGTTATTACTCCAGCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTACAC

CACAGCCAGAATTTACTGAGGGCCGTGAGCAACATGCTGCAGAAAGCTAGG

CAGACTTTAGAATTTTACCCTTGCACCAGCGAGGAGATCGACCATGAAGAT

ATCACCAAGGACAAGACATCCACCGTGGAGGCTTGTTTACCTCTGGAGCTG

ACAAAGAACGAGTCTTGTCTCAACTCTCGTGAAACCAGCTTCATCACAAAT

GGCTCTTGTTTAGCTTCCCGGAAGACCTCCTTTATGATGGCTTTATGCCTC

AGCTCCATCTACGAGGATTTAAAGATGTACCAAGTGGAGTTCAAGACCATG

AACGCCAAGCTGCTCATGGACCCTAAACGGCAGATCTTTTTAGACCAGAAC

ATGCTGGCTGTGATTGATGAGCTGATGCAAGCTTTAAACTTCAACTCCGAG

ACCGTCCCTCAGAAGTCCTCCCTCGAGGAGCCCGATTTTTACAAGACAAAG

ATCAAACTGTGCATTTTACTCCACGCCTTTAGGATCCGGGCCGTGACCATT

GACCGGGTCATGAGCTATTTAAACGCCAGC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

Example 19: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/518), which can be purified by anti-TF Ab affinity and other chromatography methods.

The amino acid sequence of the IL-18/IL-15RαSu fusion protein (including signal peptide sequence) is as follows (SEQ ID NO: 322):

```
(Signal peptide)
MKWVTFISLLFLFSSAYS

(Human IL-18)
YFGKLESKLSVIRNLNDQVLFIDQGNRPLFEDMTDSDCRDNAPRTIFIISM

YKDSQPRGMAVTISVKCEKISTLSCENKIISFKEMNPPDNIKDTKSDIIFF

QRSVPGHDNKMQFESSSYEGYFLACEKERDLFKLILKKEDELGDRSIMFTV

QNED

(Human IL-15R α sushi domain)
ITCPPPMSVEHADIWVKSYSLYSRERYICNSGFKRKAGTSSLTECVLNKAT

NVAHWTTPLKCIR
```

The amino acid sequence of the IL-12/TF/IL-15 fusion protein (including leader sequence) is as follows (SEQ ID NO: 323):

```
(Signal peptide)
MKWVTFISLLFLFSSAYS

(Human IL-12 subunit beta (p40))
IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS

(Linker)
GGGGSGGGGSGGGGS

(Human IL-12 subunit alpha (p35))
RNLPVATPDPGMFPCLHHSQNLLRAVSNMLQKARQTLEFYPCTSEEIDHED

ITKDKTSTVEACLPLELTKNESCLNSRETSFITNGSCLASRKTSFMMALCL

SSIYEDLKMYQVEFKTMNAKLLMDPKRQIFLDQNMLAVIDELMQALNFNSE

TVPQKSSLEEPDFYKTKIKLCILLHAFRIRAVTIDRVMSYLNAS

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

In some cases, the leader peptide is cleaved from the intact polypeptide to generate the mature form that may be soluble or secreted.

Example 20: Recombinant Protein Quantitation of the 18t15-12s16 Complex

The 18t15-12s16 complex (comprising IL-12/IL-15RαSu/αCD16scFv; IL-18/TF/IL-15) was detected and quantified using standard sandwich ELISA methods (FIG. 39). Anti-human tissue factor antibody/IL-2 or anti-TF Ab/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (143), and anti-human tissue factor antibody detection.

Example 21: Creation of TGFβRII/IL-15RαSu and IL-21/TF/IL-15 DNA Constructs

In a non-limiting example, a TGFβRII/IL-15RαSu DNA construct was created (FIG. 40). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 196):

```
(Signal peptide)
ATGAAGTGGGTGACCTTCATCAGCCTGCTGTTCCTGTTCTCCAGCGCCTAC

TCC

(Human TGFβRII-1st fragment)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCACGATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

(Linker)
GGAGGTGGCGGATCCGGAGGTGGAGGTTCTGGTGGAGGTGGGAGT

(Human TGFβRII-2nd fragment)
ATTCCTCCCCACGTGCAGAAGAGCGTGAATAATGACATGATCGTGACCGAT

AACAATGGCGCCGTGAAATTTCCCCAGCTGTGCAAATTCTGCGATGTGAGG

TTTTCCACCTGCGACAACCAGAAGTCCTGTATGAGCAACTGCACAATCACC

TCCATCTGTGAGAAGCCTCAGGAGGTGTGCGTGGCTGTCTGGCGGAAGAAT

GACGAGAATATCACCCTGGAAACCGTCTGCCACGATCCCAAGCTGCCCTAC

CACGATTTCATCCTGGAAGACGCCGCCAGCCCTAAGTGCATCATGAAAGAG

AAAAAGAAGCCTGGCGAGACCTTTTTCATGTGCTCCTGCAGCAGCGACGAA

TGCAACGACAATATCATCTTTAGCGAGGAATACAATACCAGCAACCCCGAC
```

-continued (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGTATTAGA

Additionally, an IL-21/TF/IL-15 construct was made linking the IL-21 sequence to the N-terminus coding region of tissue factor 219, and further linking the IL-21/TF construct to the N-terminus coding region of IL-15 (FIG. 41). The nucleic acid sequence of the IL-21/TF/IL-15 construct (including leader sequence) is as follows (SEQ ID NO: 192):

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human Tissue Factor 219)
TCCGGCACCACCAATACCGTGGCCGCTTATAACCTCACATGGAAGAGCACC

AACTTCAAGACAATTCTGGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGATTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

GGCACCAAGGTGAACGTCACCGTCGAGGATGAAAGGACTTTAGTGCGGCGG

AATAACACATTTTTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

-continued

AAGGAGTGCGAAGAGCTGGAGGAGAAGAACATCAAGGAGTTTCTGCAATCC

TTTGTGCACATTGTCCAGATGTTCATCAATACCTCC

Example 22: Secretion of TGFβRII/IL-15RαSu and IL-21/TF/IL-15 Fusion Proteins The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15:TGFβRII/IL-15RαSu protein complex (referred to as 21t15-TGFRs; FIG. 42 and FIG. 43). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 195):

(Signal peptide)
MKWVTFISLLFLFSSAYS (Human TGFβRII-1st fragment)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD (Linker)
GGGGSGGGGSGGGGS (Human TGFβRII-2nd fragment)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR

The amino acid sequence of the mature IL-21/TF/IL-15 fusion protein (including signal peptide sequence) is as follows (SEQ ID NO: 191):

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

-continued (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

In some cases, the leader peptide is cleaved from the intact polypeptide to generate a mature form that may be soluble or secreted.

Example 23: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Cell culture harvest of 21t15-TGFRs was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was then neutralized to pH 7.5-8.0 by adding 1M Tris base. The neutralized sample was then buffer exchanged into PBS using Amicon® centrifugal filters with a 30 KDa molecular weight cutoff. FIG. 44 shows that the 21t15-TGFRs complex binds anti-TF antibody affinity column, wherein TF is a 21t15-TGFRs binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide, and stored at 2-8° C.

Example 24: Size Exclusion Chromatography of 21t15-TGFRs

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 2004, of 1 mg/mL of 21t15-TGFRs complex onto the column. The injection was then chased with 1.25 column volumes of PBS. The SEC chromatograph was shown in FIG. 45. There were two protein peaks, likely representing a monomer and dimer forms of 21t15-TGFRs.

Example 25: SDS-PAGE of 21t15-TGFRs

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 46 shows an example SDS gel of anti-TF antibody affinity purified 21t15-TGFRs, with bands at 39.08 kDa and 53 kDa. Glycosylation of 21t15-TGFRs in CHO cells was confirmed using the Protein Deglycosylation Mix II kit (New England Biolabs) and the manufacturer's instructions. Deglycosylation reduces the molecular weight of 21t15-TGFRs, as seen in lane 4 of FIG. 46.

Example 26: Recombinant Protein Quantitation of 21t15-TGFRs Complexes

The 21t15-TGFRs complex was detected and quantified using standard sandwich ELISA methods (FIGS. 47-50). Anti-human tissue factor antibody served as the capture antibody and biotinylated anti-human IL-21, IL-15, or TGFβRII served as the detection antibody. Tissue factor was also detected using an anti-human tissue factor capture antibody (143), and anti-human tissue factor antibody detection. The 143/anti-TF antibody ELISA was compared to purified tissue factor at similar concentrations.

Example 27: Immunostimulatory Capacity of the 21t15-TGFRs Complex

To assess the IL-15 immunostimulatory activity of the 21t15-TGFRs complexes, increasing concentrations of 21t15-TGFRs was added to 32Dβ cells ($10^4$ cell/well) in 200 μL IMDM:10% FBS media and cells were incubated for 3 days at 37° C. On the fourth day, WST-1 proliferation reagent (10 μL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 51, 21t15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Additionally, HEK-Blue TGFβ reporter cells (hkb-tgfb, InvivoGen) were used to measure the ability of 21t15-TGFRs to block TGFβ1 activity (FIG. 52). Increasing concentrations of 21t15-TGFRs were mixed with 0.1 nM of TGFβ1 and added to HEK-Blue TGFβ reporter cells ($2.5\times10^4$ cell/well) in 200 μL IMDM:10% heat-inactivated FBS media. Cells were incubated overnight at 37° C. The next day, 20 μl of induced HEK-Blue TGFβ reporter cell supernatant was added to 180 μl of QUANTI-Blue (InvivoGen) and incubated for 1-3 hours at 37° C. 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGFβ1. The ability of 21t15-TGFRs to block TGFβ1 activity was reduced compared to that of human recombinant TGFβRII/Fc, possibly due to the linkage of TGFβRII to the IL-15Rα sushi domain.

Example 28: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor a (IL-2Ra, CD25), CD69 (and other activation markers), and increased IFN-γ production. To evaluate the ability of 21t15-TGFRs complexes to promote generation of cytokine-induced memory-like NK cells, purified human NK cells (>95% CD56+) were stimulated for 14-18 hours with 1 nM to 100 nM of the 21t15-TGFRs complex. Cell-surface CD25 and CD 69 expression and intracellular IFN-γ levels were assessed by antibody-staining and flow cytometry.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/ml) (Biolegend) and hIL-15 (50 ng/ml) (NCI) or with 1 nM, 10 nM, or 100 nM 21t15-TGFRs complex overnight at 37° C., 5% $CO_2$ for 14-18 hrs. The cells were then harvested and surface stained for CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer. (Plotted Data-Mean Fluorescence Intensity; FIG. 53 and FIG. 54).

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×106/ml in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/ml) (Biolegend) and hIL-15 (50 ng/ml) (NCI) or with 1 nM, 10 nM, or 100 nM 21t15-TGFRs complex overnight at 37° C., 5% $CO_2$ for 14-18 hrs. The cells were then treated with 10 µg/ml of Brefeldin A (Sigma) and 1× of Monensin (eBioscience) for 4 hrs. Cells were harvested and surface stained for CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE (Biolegend) for 30 minutes at room temperature. Cells were washed once again with 1× permeabilized buffer and then washed with FACS buffer. Cell pellets were resuspended in 300 µls of FACS Buffer and analyzed using a BD FACSCelesta™ flow cytometer. (Plotted % of IFN-γ Positive Cells; FIG. 55).

Example 29: In Vitro Cytotoxicity of NK Cells Against Human Tumor Cells

K562 (CellTrace violet labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 56, the 21t15-TGFRs complex induced human NK cytotoxicity against K562, as compared to control.

Example 30: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 324, shaded nucleotides are mutant and the mutant codons are underlined):

```
(Signal sequence)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTGCC

TGCCCCCGAGGACGTGGAGACCAACTGCGAGTGGTCCGCCTTCTCCTGCTT

TCAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCGG

CAGGAGGCAGAAGCACAGGCTGACCTGCCCCAGCTGTGACTCCTACGAGAA

GAAGCCCCCCAAGGAGTTCCTGGAGAGGTTCAAGTCCCTGCTGCAGAAGAT

GATCCATCAGCACCTGTCCTCCAGGACCCACGGCTCCGAGGACTCC

(Human Tissue Factor 219 mutants)
TCCGGCACCACCAATACCGTGGCCGCTTATAACCTCACATGGAAGAGC

ACCAACTTCGCGACAGCTCTGGAATGGGAACCCAAGCCCGTCAATCAAGTT

TACACCGTGCAGATCTCCACCAAATCCGGAGACTGGAAGAGCAAGTGCTTC

TACACAACAGACACCGAGTGTGCTTTAACCGACGAAATCGTCAAGGACGTC

AAGCAAACCTATCTGGCTCGGGTCTTTTCCTACCCCGCTGGCAATGTCGAG

TCCACCGGCTCCGCTGGCGAGCCTCTCTACGAGAATTCCCCCGAATTCACC

CCTTATTTAGAGACCAATTTAGGCCAGCCTACCATCCAGAGCTTCGAGCAA

GTTGGCACCAAGGTGAACGTCACCGTCGAGGATGAAAGGACTTTAGTGGCG

CGGAATAACACAGCTTTATCCCTCCGGGATGTGTTCGGCAAAGACCTCATC

TACACACTGTACTATTGGAAGTCCAGCTCCTCCGGCAAAAAGACCGCTAAG

ACCAACACCAACGAGTTTTTAATTGACGTGGACAAAGGCGAGAACTACTGC

TTCAGCGTGCAAGCCGTGATCCCTTCTCGTACCGTCAACCGGAAGAGCACA

GATTCCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCACCCC

TCTTGTAAGGTGACCGCCATGAAATGTTTTTTACTGGAGCTGCAAGTTATC

TCTTTAGAGAGCGGAGACGCTAGCATCCACGACACCGTGGAGAATTTAATC
```

-continued

ATTTTAGCCAATAACTCTTTATCCAGCAACGGCAACGTGACAGAGTCCGGC

TGCAAGGAGTGCGAAGAGCTGGAGGAGAAGAACATCAAGGAGTTTCTGCAA

TCCTTTGTGCACATTGTCCAGATGTTCATCAATACCTCC

The amino acid sequence of the IL-21/TF mutant/IL-15 construct (including signal peptide sequence) is as follows (SEQ ID NO: 325, substituted residues are shaded):

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYEK

KPPKEFLERFKSLLQKMIHQHLSSRTHGSEDS (Human Tissue Factor 219)
SGTTNTVAAYNLTWKSTNFATALEWEPKPVNQVYTVQISTKSGDWKSKC

FYTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKDL

IYTLYYWKSSSSGKKTAKTNTNEFLIDVDKGENYCFSVQAVIPSRTVNRK

STDSPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15: TGFβRII/IL-15RαSu complex.

Example 31: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 214):

(Signal sequence)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

-continued

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

The amino acid sequence of the IL-21/IL-15RαSu construct (including signal peptide sequence) is as follows (SEQ ID NO: 213):

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human IL-15R a sushi domain)
ITCPPPMSVEHADIWVKSYSLYSRERYICNSGFKRKAGTSSLTECVLNKAT

NVAHWTTPSLKCIR

In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-15 domain of the TGFβRII/TF/IL-15 fusion protein to create a TGFβRII/TF/IL-15:IL-21/IL-15RαSu complex.

The TGFβRII/TF/IL-15RαSu DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 239):

(Signal peptide)
ATGAAGTGGGTGACCTTCATCAGCCTGCTGTTCCTGTTCTCCAGCGCCTAC

TCC (Human TGFβII-1st fragment)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCACGATCACC

TCCATCTGCGAGAAGCCCCAAGAAGTGTGCGTGGCCGTGTGGCGGAAAAAT

-continued

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT (Linker)
GGAGGTGGCGGATCCGGAGGTGGAGGTTCTGGTGGAGGTGGGAGT (Human TGFβRII-2nd fragment)
ATTCCTCCCCACGTGCAGAAGAGCGTGAATAATGACATGATCGTGACCGAT

AACAATGGCGCCGTGAAATTTCCCCAGCTGTGCAAATTCTGCGATGTGAGG

TTTTCCACCTGCGACAACCAGAAGTCCTGTATGAGCAACTGCACAATCACC

TCCATCTGTGAGAAGCCTCAGGAGGTGTGCGTGGCTGTCTGGCGGAAGAAT

GACGAGAATATCACCCTGGAAACCGTCTGCCACGATCCCAAGCTGCCCTAC

CACGATTTCATCCTGGAAGACGCCGCCAGCCCTAAGTGCATCATGAAAGAG

AAAAAGAAGCCTGGCGAGACCTTTTTCATGTGCTCCTGCAGCAGCGACGAA

TGCAACGACAATATCATCTTTAGCGAGGAATACAATACCAGCAACCCCGAC (Human Tissue Factor 219)
TCCGGCACCACCAATACCGTGGCCGCTTATAACCTCACATGGAAGAGCACC

AACTTCAAGACAATTCTGGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGATTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

GGCACCAAGGTGAACGTCACCGTCGAGGATGAAAGGACTTTAGTGCGGCGG

AATAACACATTTTTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of the TGFβRII/TF/IL-15 fusion protein (including signal peptide) is as follows (SEQ ID NO: 238):

(Signal peptide)
MKWVTFISLLFLFSSAYS (Human TGFβII-1st fragment)
IPPHVQKSVNNDMIVTDNNGAVKFPQLCKFCDVRFSTCDNQKSCMSNCSTI

SICEKPQEVCVAVWRKNDENITLETVCHDPKLPYHDFILEDAASPKCIMKE

KKKPGETFFMCSCSSDECNDNIIFSEEYNTSNPD (Linker)
GGGGSGGGGSGGGGS (Human TGFβRII-2nd fragment)
IPPHVQKSVNNDMIVTDNNGAVKFPQLCKFCDVRFSTCDNQKSCMSNCSTI

SICEKPQEVCVAVWRKNDENITLETVCHDPKLPYHDFILEDAASPKCIMKE

KKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Example 32. Production of an Exemplary Single-Chain Chimeric Polypeptides

An exemplary single-chain chimeric polypeptide including a first target-binding domain that is an anti-CD3 scFv, a soluble human tissue factor domain, and a second target-binding domain that is an anti-CD28 scFv was generated (αCD3scFv/TF/αCD28scFv) (FIG. 57). The nucleic acid and amino acid sequences of this single-chain chimeric polypeptide are shown below.

Nucleic Acid Encoding Exemplary Single-Chain Chimeric Polypeptide (αCD3scFv/TF/αCD28scFv) (SEQ ID NO: 158)

(Signal peptide)
ATGAAGTGGGTGACCTTCATCAGCTTATTATTTTTATTCAGCTCCGCCTAT

TCC (αCD3 light chain variable region)
CAGATCGTGCTGACCCAAAGCCCCGCCATCATGAGCGCTAGCCCCGGTGAG

AAGGTGACCATGACATGCTCCGCTTCCAGCTCCGTGTCCTACATGAACTGG

TATCAGCAGAAAAGCGGAACCAGCCCCAAAAGGTGGATCTACGACACCAGC

AAGCTGGCCTCCGGAGTGCCCGCTCATTTCCGGGGCTCTGGATCCGGCACC

AGCTACTCTTTAACCATTTCCGGCATGGAAGCTGAAGACGCTGCCACCTAC

TATTGCCAGCAATGGAGCAGCAACCCCTTCACATTCGGATCTGGCACCAAG

CTCGAAATCAATCGT

-continued (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGC
CTCCGTCAAGATGAGCTGCAAGGCTTCCGGCTATACATTTACTCGTTACAC
AATGCATTGGGTCAAGCAGAGGCCCGGTCAAGGTTTAGAGTGGATCGGATA
TATCAACCCTTCCCGGGGCTACACCAACTATAACCAAAAGTTCAAGGATAA
AGCCACTTTAACCACTGACAAGAGCTCCTCCACCGCCTACATGCAGCTGTC
CTCTTTAACCAGCGAGGACTCCGCTGTTTACTACTGCGCTAGGTATTACGA
CGACCACTACTGTTTAGACTATTGGGGACAAGGTACCACTTTAACCGTCAG
CAGC (Human tissue factor 219 form)
TCCGGCACCACCAATACCGTGGCCGCTTATAACCTCACATGGAAGAGCACC
AACTTCAAGACAATTCTGGAATGGGAACCCAAGCCCGTCAATCAAGTTTAC
ACCGTGCAGATCTCCACCAAATCCGGAGACTGGAAGAGCAAGTGCTTCTAC
ACAACAGACACCGAGTGTGATTTAACCGACGAAATCGTCAAGGACGTCAAG
CAAACCTATCTGGCTCGGGTCTTTTCCTACCCCGCTGGCAATGTCGAGTCC
ACCGGCTCCGCTGGCGAGCCTCTCTACGAGAATTCCCCCGAATTCACCCCT
TATTTAGAGACCAATTTAGGCCAGCCTACCATCCAGAGCTTCGAGCAAGTT
GGCACCAAGGTGAACGTCACCGTCGAGGATGAAAGGACTTTAGTGCGGCGG
AATAACACATTTTTATCCCTCCGGGATGTGTTCGGCAAAGACCTCATCTAC
ACACTGTACTATTGGAAGTCCAGCTCCTCCGGCAAAAAGACCGCTAAGACC
AACACCAACGAGTTTTTAATTGACGTGGACAAAGGCGAGAACTACTGCTTC
AGCGTGCAAGCCGTGATCCCTTCTCGTACCGTCAACCGGAAGAGCACAGAT
TCCCCCGTTGAGTGCATGGGCCAAGAAAAGGGCGAGTTCCGGGAG (αCD28 light chain variable region)
GTCCAGCTGCAGCAGAGCGGACCCGAACTCGTGAAACCCGGTGCTTCCGTG
AAAATGTCTTGTAAGGCCAGCGGATACACCTTCACCTCCTATGTGATCCAG
TGGGTCAAACAGAAGCCCGGACAAGGTCTCGAGTGGATCGGCAGCATCAAC
CCTTACAACGACTATACCAAATACAACGAGAAGTTTAAGGGAAAGGCTACT
TTAACCTCCGACAAAAGCTCCATCACAGCCTACATGGAGTTCAGCTCTTTA
ACATCCGAGGACAGCGCTCTGTACTATTGCGCCCGGTGGGGCGACGGCAAT
TACTGGGGACGGGGCACAACACTGACCGTGAGCAGC (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCGAG
CGGGTCACAATGACTTGTACAGCCTCCTCCAGCGTCTCCTCCTCCTACTTC
CATTGGTACCAACAGAAACCCGGAAGCTCCCCTAAACTGTGCATCTACAGC
ACCAGCAATCTCGCCAGCGGCGTGCCCCCTAGGTTTTCCGGAAGCGGAAGC
ACCAGCTACTCTTTAACCATCTCCTCCATGGAGGCTGAGGATGCCGCCACC
TACTTTTGTCACCAGTACCACCGGTCCCCCACCTTCGGAGGCGGCACCAAA
CTGGAGACAAAGAGG Exemplary Single-Chain Chimeric Polypeptide (αCD3scFv/TF/αCD28scFv) (SEQ ID NO: 157)

(Signal peptide)
MKWVTFISLLFLFSSAYS (αCD3 light chain variable region)
QIVLTQSPAIMSASPGEKVTMTCSASSSVSYMNWYQQKSGTSPKRWIYDTS
KLASGVPAHFRGSGSGTSYSLTISGMEAEDAATYYCQQWSSNPFTFGSGTK
LEINR (Linker)
GGGGSGGGGSGGGGS (αCD3 heavy chain variable region)
QVQLQQSGAELARPGASVKMSCKASGYTFTRYTMHWVKQRPGQGLEWIGYI
NPSRGYTNYNQKFKDKATLTTDKSSSTAYMQLSSLTSEDSAVYYCARYYDD
HYCLDYWGQGTTLTVSS (Human tissue factor 219)
SGTTNTVAAYNLTWKSTNFKTILEWEPKPVNQVYTVQISTKSGDWKSKCFY
TTDTECDLTDEIVKDVKQTYLARVFSYPAGNVESTGSAGEPLYENSPEFTP
YLETNLGQPTIQSFEQVGTKVNVTVEDERTLVRRNNTFLSLRDVFGKDLIY
TLYYWKSSSSGKKTAKTNTNEFLIDVDKGENYCFSVQAVIPSRTVNRKSTD
SPVECMGQEKGEFRE (αCD28 light chain variable region)
VQLQQSGPELVKPGASVKMSCKASGYTFTSYVIQWVKQKPGQGLEWIGSIN
PYNDYTKYNEKFKGKATLTSDKSSITAYMEFSSLTSEDSALYYCARWGDGN
YWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIYS
TSNLASGVPPRFSGSGSGTSYSLTISSMEAEDAATYFCHQYHRSPTFGGGTK
LETKR A second exemplary single-chain chimeric polypeptide including a first target-binding domain that is an anti-CD28 scFv, a soluble human tissue factor domain, and a second target-binding domain that is an anti-CD3 scFv was generated (αCD28scFv/TF/αCD3scFv) (FIG. 57). The nucleic acid and amino acid sequences of this single-chain chimeric polypeptide are shown below.

Nucleic Acid Encoding Exemplary Single-Chain Chimeric Polypeptide (αCD28scFv/TF/αCD3scFv) (SEQ ID NO: 326)

(Signal peptide)
ATGAAATGGGTCACCTTCATCTCTTTACTGTTTTTATTTAGCAGCGCCTAC
AGC (αCD28 light chain variable region)
GTGCAGCTGCAGCAGTCCGGACCCGAACTGGTCAAGCCCGGTGCCTCCGTG
AAAATGTCTTGTAAGGCTTCTGGCTACACCTTTACCTCCTACGTCATCCAA
TGGGTGAAGCAGAAGCCCGGTCAAGGTCTCGAGTGGATCGGCAGCATCAAT
CCCTACAACGATTACACCAAGTATAACGAAAAGTTTAAGGGCAAGGCCACT
CTGACAAGCGACAAGAGCTCCATTACCGCCTACATGGAGTTTTCCTCTTTA -continued

```
ACTTCTGAGGACTCCGCTTTATACTATTGCGCTCGTTGGGGCGATGGCAAT

TATTGGGGCCGGGGAACTACTTTAACAGTGAGCTCC

(Linker)
GGCGGCGGCGGAAGCGGAGGTGGAGGATCTGGCGGTGGAGGCAGC

(αCD28 heavy chain variable region)
GACATCGAGATGACACAGTCCCCCGCTATCATGAGCGCCTCTTTAGGAGAA

CGTGTGACCATGACTTGTACAGCTTCCTCCAGCGTGAGCAGCTCCTATTTC

CACTGGTACCAGCAGAAACCCGGCTCCTCCCCTAAACTGTGTATCTACTCC

ACAAGCAATTTAGCTAGCGGCGTGCCTCCTCGTTTTAGCGGCTCCGGCAGC

ACCTCTTACTCTTTAACCATTAGCTCTATGGAGGCCGAAGATGCCGCCACA

TACTTTTGCCATCAGTACCACCGGTCCCCTACCTTTGGCGGAGGCACAAAG

CTGGAGACCAAGCGG

(Human tissue factor 219 form)
AGCGGCACCACCAACACAGTGGCCGCCTACAATCTGACTTGGAAATCCACC

AACTTCAAGACCATCCTCGAGTGGGAGCCCAAGCCCGTTAATCAAGTTTAT

ACCGTGCAGATTTCCACCAAGAGCGGCGACTGGAAATCCAAGTGCTTCTAT

ACCACAGACACCGAGTGCGATCTCACCGACGAGATCGTCAAAGACGTGAAG

CAGACATATTTAGCTAGGGTGTTCTCCTACCCCGCTGGAAACGTGGAGAGC

ACCGGATCCGCTGGAGAGCCTTTATACGAGAACTCCCCCGAATTCACCCCC

TATCTGGAAACCAATTTAGGCCAGCCCACCATCCAGAGCTTCGAACAAGTT

GGCACAAAGGTGAACGTCACCGTCGAAGATGAGAGGACTTTAGTGCGGAGG

AACAATACATTTTTATCCTTACGTGACGTCTTCGGCAAGGATTTAATCTAC

ACACTGTATTACTGGAAGTCTAGCTCCTCCGGCAAGAAGACCGCCAAGACC

AATACCAACGAATTTTTAATTGACGTGGACAAGGGCGAGAACTACTGCTTC

TCCGTGCAAGCTGTGATCCCCTCCCGGACAGTGAACCGGAAGTCCACCGAC

TCCCCCGTGGAGTGCATGGGCCAAGAGAAGGGAGAGTTTCGTGAG

(αCD3 light chain variable region)
CAGATCGTGCTGACCCAGTCCCCCGCTATTATGAGCGCTAGCCCCGGTGAA

AAGGTGACTATGACATGCAGCGCCAGCTCTTCCGTGAGCTACATGAACTGG

TATCAGCAGAAGTCCGGCACCAGCCCTAAAAGGTGGATCTACGACACCAGC

AAGCTGGCCAGCGGCGTCCCCGCTCACTTTCGGGGCTCCGGCTCCGGAACA

AGCTACTCTCTGACCATCAGCGGCATGGAAGCCGAGGATGCCGCTACCTAT

TACTGTCAGCAGTGGAGCTCCAACCCCTTCACCTTTGGATCCGGCACCAAG

CTCGAGATTAATCGT

(Linker)
GGAGGCGGAGGTAGCGGAGGAGGCGGATCCGGCGGTGGAGGTAGC

(αCD3 heavy chain variable region)
CAAGTTCAGCTCCAGCAAAGCGGCGCCGAACTCGCTCGGCCCGGCGCTTCC

GTGAAGATGTCTTGTAAGGCCTCCGGCTATACCTTCACCCGGTACACAATG

CACTGGGTCAAGCAACGGCCCGGTCAAGGTTTAGAGTGGATTGGCTATATC

AACCCCTCCCGGGGCTATACCAACTACAACCAGAAGTTCAAGGACAAAGCC

ACCCTCACCACCGACAAGTCCAGCAGCACCGCTTACATGCAGCTGAGCTCT

TTAACATCCGAGGATTCCGCCGTGTACTACTGCGCTCGGTACTACGACGAT

CATTACTGCCTCGATTACTGGGGCCAAGGTACCACCTTAACAGTCTCCTCC
```

Exemplary Single-Chain Chimeric Polypeptide (αCD28scFv/TF/αCD3scFv) (SEQ ID NO: 327)

```
(Signal peptide)
MKWVTFISLLFLFSSAYS

(αCD28 light chain variable region)
VQLQQSGPELVKPGASVKMSCKASGYTFTSYVIQWVKQKPGQGLEWIGSIN

PYNDYTKYNEKFKGKATLTSDKSSITAYMEFSSLTSEDSALYYCARWGDGN

YWGRGTTLTVSS

(Linker)
GGGGSGGGGSGGGGS

(αCD28 heavy chain variable region)
DIEMTQSPAIMSASLGERVTMTCTASSSVSSSYFHWYQQKPGSSPKLCIYS

TSNLASGVPPRFSGSGSTSYSLTISSMEAEDAATYFCHQYHRSPTFGGGTK

LETKR

(Human tissue factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(αCD3 light chain variable region)
QIVLTQSPAIIVISASPGEKVTMTCSASSSVSYMNWYQQKSGTSPKRWIYD

TSKLASGVPAHFRGSGSGTSYSLTISGMEAEDAATYYCQQWSSNPFTFGSG

TKLEINR

(Linker)
GGGGSGGGGSGGGGS

(αCD3 heavy chain variable region)
QVQLQQSGAELARPGASVKMSCKASGYTFTRYTMHWVKQRPGQGLEWIGYI

NPSRGYTNYNQKFKDKATLTTDKSSSTAYMQLSSLTSEDSAVYYCARYYDD

HYCLDYWGQGTTLTVSS
```

The nucleic acid encoding αCD3scFv/TF/αCD28scFv was cloned into a modified retrovirus expression vectors as described previously (Hughes et al., *Hum Gene Ther* 16:457-72, 2005). The expression vector encoding αCD3scFv/TF/αCD28scFv was transfected into CHO-K1 cells. Expression of the expression vector in CHO-K1 cells allowed for secretion of the soluble αCD3scFv/TF/αCD28scFv single-chain chimeric polypeptide (referred to as 3t28), which can be purified by anti-TF Ab affinity and other chromatography methods.

An anti-tissue factor affinity column was used to purify the αCD3scFv/TF/αCD28scFv single-chain chimeric polypeptide. The anti-tissue factor affinity column was connected to a GE Healthcare AKTA Avant system. A flow rate of 4 mL/min was used for all steps except the elution step, which was 2 mL/min.

Cell culture harvest including αCD3scFv/TF/αCD28scFv single-chain chimeric polypeptide was adjusted to pH 7.4 with 1M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff. The data in FIG. 58 show that the anti-tissue factor affinity column can bind the αCD3scFv/TF/αCD28scFv single-chain chimeric polypeptide, which contains a human soluble tissue factor domain. The buffer-exchanged protein sample was stored at 2-8° C. for further biochemical analysis and biological activity testing.

After each elution, the anti-tissue factor affinity column was stripped using 6 column volumes of 0.1 M glycine, pH 2.5. The column was then neutralized using 10 column volumes of PBS, 0.05% $NaN_3$, and stored at 2-8° C.

Analytical size exclusion chromatography (SEC) was performed on the αCD3scFv/TF/αCD28scFv single-chain chimeric polypeptide using a Superdex 200 Increase 10/300 GL gel filtration column (from GE Healthcare) connected to an AKTA Avant system (from GE Healthcare). The column was equilibrated with 2 column volumes of PBS. A flow rate of 0.8 mL/min was used. Two hundred μL of αCD3scFv/TF/αCD28scFv single-chain chimeric polypeptide (1 mg/mL) was injected onto the column using a capillary loop. After injection of the single-chain chimeric polypeptide, 1.25 column volumes of PBS were flowed into the column. The SEC chromatograph is shown in FIG. 59. The data show that there are 3 protein peaks, likely representing a monomer and dimer or other different forms of the αCD3scFv/TF/αCD28scFv single-chain chimeric polypeptide.

To determine the purity and protein molecular weight of the αCD3scFv/TF/αCD28scFv single-chain chimeric polypeptide, the purified αCD3scFv/TF/αCD28scFv protein sample from anti-tissue factor affinity column was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 minutes and destained overnight with purified water. FIG. 60 shows the SDS gel of the αCD3scFv/TF/αCD28scFv single-chain chimeric polypeptide purified using an anti-tissue factor affinity column. The results show that the purified αCD3scFv/TF/αCD28scFv single-chain chimeric polypeptide has the expected molecular weight (72 kDa) in reduced SDS gel.

Example 33. Functional Characterization of αCD3scFv/TF/αCD28scFv Single-Chain Chimeric Polypeptide ELISA-based methods confirmed the formation of the αCD3scFv/TF/αCD28scFv single-chain chimeric polypeptide. The αCD3scFv/TF/αCD28scFv single-chain chimeric polypeptide was detected using an anti-TF antibody (I43)/anti-TF antibody-specific ELISA with a capture antibody, anti-human tissue factor antibody (143), and a detection antibody, anti-TF antibody (FIG. 61). A purified tissue factor protein with a similar concentration was used as a control.

A further in vitro experiment was performed to determine whether the αCD3scFv/TF/αCD28scFv single-chain chimeric polypeptide is capable of activating human peripheral blood mononuclear cells (PBMCs). Fresh human leukocytes were obtained from the blood bank and peripheral blood mononuclear cells (PBMC) were isolated using density gradient Histopaque (Sigma). The cells were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE specific antibodies (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data in FIGS. 62 and 63 show that the αCD3scFv/TF/αCD28scFv single-chain chimeric polypeptide is able to stimulate both $CD8^+$ and $CD4^+$ T-cells. A further experiment was performed, in which PBMCs isolated from blood using Histopaque (Sigma) were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were then stimulated with the αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data again show that the αCD3scFv/TF/αCD28scFv single-chain chimeric polypeptide was able to stimulate activation of $CD4^+$ T cells (FIG. 64).

Example 34: Creation of an IL-7/IL-15RαSu DNA Construct

In a non-limiting example, an IL-7/IL-15RαSu DNA construct was created (see FIG. 65). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 206):

```
(Signal peptide)
ATGGGAGTGAAAGTTCTTTTTGCCCTTATTTGTATTGCTGTGGCCGAGGCC

(Human IL-7)
GATTGTGATATTGAAGGTAAAGATGGCAAACAATATGAGAGTGTTCTAATG

GTCAGCATCGATCAATTATTGGACAGCATGAAAGAAATTGGTAGCAATTGC

CTGAATAATGAATTTAACTTTTTTAAAAGACATATCTGTGATGCTAATAAG

GAAGGTATGTTTTTATTCCGTGCTGCTCGCAAGTTGAGGCAATTTCTTAAA

ATGAATAGCACTGGTGATTTTGATCTCCACTTATTAAAAGTTTCAGAAGGC
```

-continued

```
ACAACAATACTGTTGAACTGCACTGGCCAGGTTAAAGGAAGAAAACCAGCT

GCCCTGGGTGAAGCCCAACCAACAAAGAGTTTGGAAGAAAATAAATCTTTA

AAGGAACAGAAAAAACTGAATGACTTGTGTTTCCTAAAGAGACTATTACAA

GAGATAAAAACTTGTTGGAATAAAATTTTGATGGGCACTAAAGAACAC

(Human IL-15R α sushi domain)
ATCACGTGCCCTCCCCCCATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA
```

The second chimeric polypeptide of IL-7/IL-15RαSu construct (including signal peptide sequence) is as follows (SEQ ID NO: 205):

```
(Signal peptide)
MKWVTFISLLFLFSSAYS

(Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Example 35: Creation of an IL-21/TF/IL-15 DNA Construct

In a non-limiting example, an IL-21/TF/IL-15 construct was made (FIG. 66) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 202):

```
(Signal peptide)
ATGGGAGTGAAAGTTCTTTTTGCCCTTATTTGTATTGCTGTGGCCGAGGCC

(Human IL-21 fragment)
CAAGGTCAAGATCGCCACATGATTAGAATGCGTCAACTTATAGATATTGTT

GATCAGCTGAAAAATTATGTGAATGACTTGGTCCCTGAATTTCTGCCAGCT

CCAGAAGATGTAGAGACAAACTGTGAGTGGTCAGCTTTTTCCTGTTTTCAG
```

-continued

```
AAGGCCCAACTAAAGTCAGCAAATACAGGAAACAATGAAAGGATAATCAAT

GTATCAATTAAAAAGCTGAAGAGGAAACCACCTTCCACAAATGCAGGGAGA

AGACAGAAACACAGACTAACATGCCCTTCATGTGATTCTTATGAGAAAAAA

CCACCCAAAGAATTCCTAGAAAGATTCAAATCACTTCTCCAAAAGATGATT

CATCAGCATCTGTCCTCTAGAACACACGGAAGTGAAGATTCC

(Human Tissue Factor 219)
TCAGGCACTACAAATACTGTGGCAGCATATAATTTAACTTGGAAATCAACT

AATTTCAAGACAATTTTGGAGTGGGAACCCAAACCCGTCAATCAAGTCTAC

ACTGTTCAAATAAGCACTAAGTCAGGAGATTGGAAAAGCAAATGCTTTTAC

ACAACAGACACAGAGTGTGACCTCACCGACGAGATTGTGAAGGATGTGAAG

CAGACGTACTTGGCACGGGTCTTCTCCTACCCGGCAGGGAATGTGGAGAGC

ACCGGTTCTGCTGGGGAGCCTCTGTATGAGAACTCCCCAGAGTTCACACCT

TACCTGGAGACAAACCTCGGACAGCCAACAATTCAGAGTTTTGAACAGGTG

GGAACAAAAGTGAATGTGACCGTAGAAGATGAACGGACTTTAGTCAGAAGG

AACAACACTTTCCTAAGCCTCCGGGATGTTTTTGGCAAGGACTTAATTTAT

ACACTTTATTATTGGAAATCTTCAAGTTCAGGAAAGAAAACAGCCAAAACA

AACACTAATGAGTTTTTGATTGATGTGGATAAAGGAGAAAACTACTGTTTC

AGTGTTCAAGCAGTGATTCCCTCCCGAACAGTTAACCGGAAGAGTACAGAC

AGCCCGGTAGAGTGTATGGGCCAGGAGAAAGGGGAATTCAGAGAA

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The first chimeric polypeptide of IL-21/TF/IL-15 construct including leader sequence is SEQ ID NO: 201:

```
(Signal peptide)
                                     (SEQ ID NO: 328)
MGVKVLFALICIAVAEA

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE
```

-continued

```
(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Example 36: Secretion of IL-7/IL-15RαSu and IL-21/TF/IL-15 Fusion Proteins

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s; FIG. 67 and FIG. 68). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 37: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 38: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 2004, of 1 mg/mL of 7t15-21s complex onto the column. The injection was chased with 1.25 column volumes of PBS.

Example 39: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 40: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 41: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF antibody ELISA will be compared to purified tissue factor at similar concentrations.

Example 42: Creation of an IL-21/IL-15RαSu DNA Construct

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 69.

Example 43: Creation of an IL-7/TF/IL-15 DNA Construct

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 70.

Example 44: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 214):

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

The second chimeric polypeptide of IL-21/IL-15Rα sushi domain (including leader sequence) is as follows (SEQ ID NO: 213):

(Signal Sequence)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human IL-15Ra sushi domain)
ITCPPPMSVEHADIWVKSYSLYSRERYICNSGFKRKAGTSSLTECVLNKAT

NVAHWTTPSLKCIR

Example 45: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 210):

(Signal peptide)
ATGAAGTGGGTGACCTTCATCAGCCTGCTGTTCCTGTTCTCCAGCGCCTAC

TCC (Human IL-7 fragment)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

-continued

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT (Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The first chimeric polypeptide of IL-7/TF/IL-15 (including leader sequence), is as follows (SEQ ID NO: 209):

(Signal peptide)
MKWVTFISLLFLFSSAYS (Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

-continued (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Example 46: Secretion of IL-21/IL-15RαSu and IL-7/TF/IL-15 Fusion Proteins

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See FIG. 71 and FIG. 72.

Example 47: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° and 5% $CO_2$. Cells are maintained at concentration at $0.5\times10^6$/mL not exceeding $2.0\times10^6$/mL by counting every 48-72 hours and media is replenished with fresh stimulator. Cells stimulated with 7t15-21s complex or anti-TF IgG1 antibody or anti-TFIgG4 antibody or anti-TF IgG4+7t15-21s complex are maintained up to day 5. Expansion of primary NK cells upon incubation with 21t15-7s complex+anti-TF IgG1 antibody is observed.

Example 48: Activation of Expanded NK Cells by the 7t15-21s Complex+Anti-TF IgG1 Antibody Primary NK cells are induced ex vivo following overnight stimulation of purified NK cells with 7t15-21s complex+anti-TF IgG1 antibody. Fresh human leukocytes are obtained from a blood bank and CD56+NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° and 5% $CO_2$. Cells are counted every 48-72 hours and maintained at a concentration of $0.5\times10^6$/mL to $2.0\times10^6$/mL until day 14. Media is periodically replenished with fresh stimulator. Cells are harvested and surface stained at day 3 for CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 49: Increase in Glucose Metabolism in NK Cells Using 18t15-12s

A set of experiments was performed to determine the effect of the construct of 18t15-12s on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended in $2\times10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 μg), recombinant human IL-15 (1.25 μg), and recombinant human IL-18 (1.25 μg) overnight at 37° C., 5% $CO_2$. On the next day, the cells were harvested and extracellular flux assays on expanded NK cells were performed using a XFp Analyzer (Seahorse Bioscience). The harvested cells washed and plated $2.0\times10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

The data show that the 18t15-12s results in significantly increased oxygen consumption rate (FIG. 73) and extracellular acidification rate (ECAR) as compared to the same cells activated with a combination of recombinant human IL-12, recombinant human IL-15, and recombinant human IL-18 (FIG. 74).

Example 50: 7t15-16s21 Fusion Protein Generation and Characterization

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

(Signal peptide)
ATGAAGTGGGTGACCTTCATCAGCCTGCTGTTCCTGTTCTCCAGCGCCTAC

TCC (Human IL-7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT (Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of IL-7/TF/IL-15 fusion protein (including the leader sequence) is as follows:

(Signal peptide)
MKWVTFISLLFLFSSAYS (Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of IL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGCCTAC

TCC ((Anti-human CD16scFv)
TCCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTAC

CAGCAGAAGCCCGGCCAGGCTCCTGTGCTGGTGATCTACGGCAAGAACAAC

AGGCCCTCCGGCATCCCTGACAGGTTCTCCGGATCCTCCTCCGGCAACACC

GCCTCCCTGACCATCACAGGCGCTCAGGCCGAGGACGAGGCTGACTACTAC

TGCAACTCCAGGGACTCCTCCGGCAACCATGTGGTGTTCGGCGGCGGCACC

AAGCTGACCGTGGGCCATGGCGGCGGCGGCTCCGGAGGCGGCGGCAGCGGC

GGAGGAGGATCCGAGGTGCAGCTGGTGGAGTCCGGAGGAGGAGTGGTGAGG

CCTGGAGGCTCCCTGAGGCTGAGCTGTGCTGCCTCCGGCTTCACCTTCGAC

GACTACGGCATGTCCTGGGTGAGGCAGGCTCCTGGAAAGGGCCTGGAGTGG

GTGTCCGGCATCAACTGGAACGGCGGATCCACCGGCTACGCCGATTCCGTG

AAGGGCAGGTTCACCATCAGCAGGGACAACGCCAAGAACTCCCTGTACCTG

CAGATGAACTCCCTGAGGGCCGAGGACACCGCCGTGTACTACTGCGCCAGG

GGCAGGTCCCTGCTGTTCGACTACTGGGGACAGGGCACCCTGGTGACCGTG

TCCAGG

-continued (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR (Human IL-15R α sushi domain)
ITCPPPMSVEHADIWVKSYSLYSRERYICNSGFKRKAGTSSLTECVLNKAT

NVAHWTTPSLKCIR (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

In some cases, the leader peptide is cleaved from the intact polypeptide to generate the mature form that may be soluble or secreted.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21; FIG. 75 and FIG. 76), which can be purified by anti-TF IgG1 antibody-based affinity and other chromatography methods.

Binding of 7t15-16s21 to CHO Cells Expressing Human CD16b

CHO cells were transfected with human CD16b in a pMC plasmid and selected with 10 μg/mL of blasticidin for 10 days. The CHO cells stably expressing CD16b were stained with 1.2 μg/mL of 7t15-16s21, containing anti-human CD16 scFv or 18t15-12s, which does not contain anti-human CD16 scFv, as a negative control, and then stained with biotinylated anti-human tissue factor and PE conjugated streptavidin. Only anti-human CD16scFv containing 7t15-16s21 stained the cells as shown in FIG. 77A. 18t15-12s did not stain the CHO cells expressing human CD16b as showed in FIG. 77B.

Detection of IL-15, IL-21, and IL-7 in 7t15-16s21 Using ELISA

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL-15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 pg/mL of HRP-SA (Jackson ImmunoResearch) at 100 μL per well for 30 min at RT, followed by 4 washes and incubation with 1000 of ABTS for 2 mins at RT. Absorbance was read at 405 nm. As shown in FIGS. 78A-78C, the IL-15, IL-21, and IL-7 domains in 7t15-16s21 were detected by the individual antibodies.

The IL-15 in 7t15-16s21 Promotes IL-2R/3 and Common γ Chain Containing 32Dβ Cell Proliferation To analyze the activity of IL-15 in 7t15-16s21, the IL-15 activity of 7t15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 79). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The absorbance at 450 nm was measured by analyzing the amount of formazan dye produced. As shown in FIG. 79, 7t15-16s21 and IL-15 promoted 32Dβ cell proliferation, with the $EC_{50}$ of 7t15-16s21 and IL-15 being 172.2 pM and 16.63 pM, respectively.

Purification Elution Chromatograph of 7t15-16s21 from Anti-TF Antibody Affinity Column 7t15-16s21 harvested from cell culture was loaded onto the anti-TF antibody affinity column equilibrated with 5 column volumes of PBS. The column was then washed with 5 column volumes of PBS, followed by elution with 6 column volumes of 0.1M acetic acid (pH 2.9). A280 elution peak was collected and neutralized to pH 7.5-8.0 with 1M Tris base. The neutralized sample was buffer exchanged into PBS using Amicon centrifugal filters with a 30 KDa molecular weight cutoff. FIG. 80 is a line graph showing the chromatographic profile of 7t15-16s21 protein containing cell culture supernatant following binding and elution on anti-TF antibody resin. As shown in FIG. 80, the anti-TF antibody affinity column bound 7t15-16s21 which contains TF. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 81, the SEC results showed two protein peaks for 7t15-16s21.

Example 51: TGFRt15-16s21 Fusion Protein Generation and Characterization

A fusion protein complex was generated comprising anti-human CD16scFv/IL-15RαSu/IL21 and TGFβ Receptor II/TF/IL-15 fusion proteins (FIGS. 82 and 83). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCCTAC

TCC

(Two Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC
```

-continued

```
ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of TGFβ Receptor II/TF/IL-15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY
```

-continued

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGCCTAC

TCC (Anti-human CD16scFv)
TCCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTAC

CAGCAGAAGCCCGGCCAGGCTCCTGTGCTGGTGATCTACGGCAAGAACAAC

AGGCCCTCCGGCATCCCTGACAGGTTCTCCGGATCCTCCTCCGGCAACACC

GCCTCCCTGACCATCACAGGCGCTCAGGCCGAGGACGAGGCTGACTACTAC

TGCAACTCCAGGGACTCCTCCGGCAACCATGTGGTGTTCGGCGGCGGCACC

AAGCTGACCGTGGGCCATGGCGGCGGCGGCTCCGGAGGCGGCGGCAGCGGC

GGAGGAGGATCCGAGGTGCAGCTGGTGGAGTCCGGAGGAGGAGTGGTGAGG

CCTGGAGGCTCCCTGAGGCTGAGCTGTGCTGCCTCCGGCTTCACCTTCGAC

GACTACGGCATGTCCTGGGTGAGGCAGGCTCCTGGAAAGGGCCTGGAGTGG

GTGTCCGGCATCAACTGGAACGGCGGATCCACCGGCTACGCCGATTCCGTG

AAGGGCAGGTTCACCATCAGCAGGGACAACGCCAAGAACTCCCTGTACCTG

CAGATGAACTCCCTGAGGGCCGAGGACACCGCCGTGTACTACTGCGCCAGG

GGCAGGTCCCTGCTGTTCGACTACTGGGGACAGGGCACCCTGGTGACCGTG

TCCAGG (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

-continued

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR (Human IL-15R α sushi domain)
ITCPPPMSVEHADIWVKSYSLYSRERYICNSGFKRKAGTSSLTECVLNKAT

NVAHWTTPSLKCIR (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF IgG1-based affinity and other chromatography methods.

Interaction Between TGFRt15-16s21 and CHO Cells Expressing Human CD16b

CHO cells were transfected with human CD16b in a pMC plasmid and selected with 10 μg/mL of blasticidin for 10 days. Cells stably expressing CD16b were stained with 1.2 μg/mL of TGFRt15-16s21, containing anti-human CD16 scFv, or 7t15-21s, not containing anti-human CD16 scFv, as a negative control, and with biotinylated anti-human tissue factor antibody and PE conjugated streptavidin. As shown in FIGS. 84A and 84B, TGFRt15-16s21, which contains anti-human CD16scFv, showed positive binding, while 7t15-21s did not show binding.

Effect of TGFRt15-16s21 on TGF/31 Activity in HEK-Blue TGFβ Cells

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, $50_1$1.1 cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells.

The IL-15 in TGFRt15-16s21 Promotes IL-2R/3 and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 86). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. The data are shown in FIG. 85. As shown in FIG. 86, TGFRt15-16s21 and IL-15 promoted 32Dβ cell proliferation, with the $EC_{50}$ of TGFRt15-16s21 and IL-15 being 51298 pM and 10.63 pM, respectively.

Detection of IL-15, IL-21, and TGFβRII in TGFRt15-16s21 Using ELISA

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. As shown in FIGS. 87A-87C, the IL-15, IL-21, and TGFβRII domains in TGFRt15-16s21 were detected by the respective antibodies.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 88, the anti-TF antibody affinity column bound to TGFRt15-16s21, which contains tissue factor as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

To determine the purity and molecular weight of the TGFRt15-16s21 protein, protein sample purified with anti-TF antibody affinity column was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 89 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 104, of SeeBlue Plus2 Prestained Standard.

Example 52: 7t15-7s Fusion Protein Generation and Characterization

A fusion protein complex was generated comprising IL-7/TF/IL-15 and IL-7/IL-15RαSu fusion proteins (FIG. 90 and FIG. 91). The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL 7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG
```

-continued

```
GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAAGT

TTACACCGTGCAGATCAGCACCAAGTCCGGCGACTGGAAGTCCAAATGTTT

CTATACCACCGACACCGAGTGCGATCTCACCGATGAGATCGTGAAAGATGT

GAAACAGACCTACCTCGCCCGGGTGTTTAGCTACCCCGCCGGCAATGTGGA

GAGCACTGGTTCCGCTGGCGAGCCTTTATACGAGAACAGCCCCGAATTTAC

CCCTTACCTCGAGACCAATTTAGGACAGCCCACCATCCAAAGCTTTGAGCA

AGTTGGCACAAAGGTGAATGTGACAGTGGAGGACGAGCGGACTTTAGTGCG

GCGGAACAACACCTTTCTCAGCCTCCGGGATGTGTTCGGCAAAGATTTAAT

CTACACACTGTATTACTGGAAGTCCTCTTCCTCCGGCAAGAAGACAGCTAA

AACCAACACAAACGAGTTTTTAATCGACGTGGATAAAGGCGAAAACTACTG

TTTCAGCGTGCAAGCTGTGATCCCCTCCCGGACCGTGAATAGGAAAAGCAC

CGATAGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQ SFEQVGTKVNVTVEDERTLVRRNNTFLSLRDVFGKDL

IYTLYYWKSSSSGKKTAKTNTNEFLIDVDKGENYCFSVQAVIPSRTVNRKS

TDSPVECMGQEKGEFRE
```

-continued

```
(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Constructs were also made by linking the IL-7 sequence to the N-terminus coding region of IL-15RαSu chain which was synthesized by Genewiz. The nucleic acid and protein sequences of a construct comprising the IL-7 linked to the N-terminus of IL-15RαSu chain are shown below.

The nucleic acid sequence of 7s construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG
```

The amino acid sequence of 7s fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human IL-15R α sushi domain)
ITCPPPMSVEHADIWVKSYSLYSRERYICNSGFKRKAGTSSLTECVLNKAT

NVAHWTTPSLKCIR
```

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:IL-7/IL-15RαSu protein complex referred to as 7t15-7s, which can be purified by anti-TF antibody IgG1 affinity and other chromatography methods.

Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 92, the anti-TF antibody affinity column bound to 7t15-7s which contains tissue factor (TF) as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL/6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

CHO cells were co-transfected with the IL7-TF-IL-15 (7t15) and IL7-IL-15Rαsushi domain (7s) vectors. The 7t15-7s complex was purified from the transfected CHO cell culture supernatant. The IL-7, IL-15 and tissue factor (TF) components were demonstrated in the complex by ELISA as shown in FIG. 93. A humanized anti-TF antibody monoclonal antibody (anti-TF IgG1) was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.).

7t15-7s was subcutaneously injected into C57BL/6 mice at 10 mg/kg to determine the immunostimulatory activity of 7t15-7s in vivo. C57BL/6 mice subcutaneously treated with PBS were used as control. The mouse spleens were collected and weighed day 4 post treatment. Single splenocytes suspensions were prepared, and with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-7s was effective at expanding splenocytes based on spleen weight (FIG. 94A) and specifically, the percentages of $CD8^+$ T cells and NK cells were higher compared to control-treated mice (FIG. 94B).

Example 53: TGFRt15-TGFRs Fusion Protein Generation and Characterization

A fusion protein complex was generated comprising of TGFβ Receptor II/IL-15RαSu and TGFβ Receptor II/TF/IL-15 fusion proteins (FIG. 95 and FIG. 96). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCCACT

TCC

(Two Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC
```

-continued

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATCAGT

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRSTCDNQKSCMSNCSITS

ICEKPQEVCVAVWRKNDENITLETVCHDPKLPYHDFILEDAASPKCIMKEK

KKPGETFFMCSCSSDECNDNIIFSEEYNTSNPDGGGGSGGGGSGGGGSIPP

HVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKK

PGETFFMCSCSSDECNDNIIFSEEYNTSNPD (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(Signal peptide)
ATGAAGTGGGTGACCTTCATCAGCCTGCTGTTCCTGTTCTCCAGCGCCTAC

TCC (Two human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

-continued

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

The amino acid sequence of the two TGFβ Receptor II/IL-15RαSu construct (including signal peptide sequence) is as follows:

(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD (Human IL-15R α sushi domain)
ITCPPPMSVEHADIWVKSYSLYSRERYICNSGFKRKAGTSLTECVLNKAT

NVAHWTTPSLKCIR

In some cases, the leader peptide is cleaved from the intact polypeptide to generate the mature form that may be soluble or secreted.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF IgG1 affinity and other chromatography methods.

Effect of TGFRt15-TGFRs on TGFβ1 Activity in HEK-Blue TGFβ Cells

To evaluate the activity of TGFβRII in TGFRt15-TGFRs, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM (FIG. 97). The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

The IL-15 in TGFRt15-TGFRs Promotes IL-2R/3 and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 98). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 98. TGFRt15-TGFRs and IL-15 promoted 32Dβ cell proliferation, with the $EC_{50}$ of TGFRt15-16s21 and IL-15 being 1901 pM and 10.63 pM, respectively.

Detection of IL-15 and TGFβRII Domains in TGFRt15-TGFRs with Corresponding Antibodies Using ELISA A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAN/247, R&D Systems), or 200 ng/mL of biotinylated-anti-TGFbRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 99A and 99B, the IL-15 and TGFβRII domains in TGFRt15-TGFRs were detected by the individual antibodies.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 100, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 101. The SEC results showed four protein peaks for TGFRt15-TGFRs.

Reduced SDS PAGE Analysis of TGFRt15-TGFRs

To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the TGFRt15-TGFRs protein undergoes glycosylation after translation in CHO cells, a deglycosylation experiment was conducted using the Protein Deglycosylation. Mix II kit from New England Biolabs and the manufacturer's instructions. FIG. 102 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL/6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 103A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 103B, in the spleens of mice treated with TGFRt15-TGFRs, the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular $CD8^+$ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

The mouse splenocytes were prepared in order to evaluate the immunostimulatory activity of TGFRt15-TGFRs over time in mice. As shown in FIG. 104A, the spleen weight in mice treated with TGFRt15-TGFRs increased 48 hours posttreatment and continued to increase over time. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 104B, in the spleens of mice treated with TGFRt15-TGFRs, the percentages of $CD8^+$ T cells and NK cells both increased at 48 hours after treatment and were higher and higher overtime after the single dose treatment. These results further demonstrate that TGFRt15-TGFRs is able to stimulate immune cells in the spleen, in particular $CD8^+$ T cells and NK cells.

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 105A and 105B, in the spleens of mice treated with TGFRt15-TGFRs, the expression of Ki67 and granzyme B by NK cells increased at 24 hours after treatment and its expression of $CD8^+$ T cells and NK cells both increased at 48 hours and later time points after the single dose treatment. These results demonstrate that TGFRt15-TGFRs not only increases the numbers of $CD8^+$ T cells and NK cells but also enhance the cytotoxicity of these cells. The single dose treatment of TGFRt15-TGFRs led $CD8^+$ T cells and NK cells to proliferate for at least 4 days.

The cytotoxicity of the splenocytes from TGFRt15-TGFRs-treated mice against tumor cells was also evaluated. Mouse Moloney leukemia cells (Yac-1) were labeled with CellTrace Violet and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 106, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Pancreatic cancer cells (SW1990, ATCC® CRL-2172) were subcutaneously (s.c.) injected into C57BL/6 scid mice (The Jackson Laboratory, 001913, $2\times10^6$ cells/mouse, in 1004, HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 107).

In Vitro Senescent B16F10 Melanoma Model

Next, in vitro killing of senescent B16F10 melanoma cells by activated mouse NK cells was evaluated. B16F10 senescence cells (B16F10-SNC) cells were labelled with CellTrace violet and incubated for 16 hrs with different E:T ratio of in vitro 2t2-activated mouse NK cells (isolated from spleen of C57BL/6 mice injected with TGFRt15-TGFRs10 mg/kg for 4 days). The cells were trypsinized, washed and resuspended in complete media containing propidium iodide (PI) solution. The cytotoxicity was assessed by flow cytometry (FIG. 108).

Example 54: 7t15-21s137L (Long Version) Fusion Protein Creation and Characterization A fusion protein complex was generated comprising of IL-21/IL-15RαSu/CD137L and IL-7/TF/IL-15 fusion proteins (FIG. 109 and FIG. 110). Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

(Signal peptide)
ATGAAGTGGGTGACCTTCATCAGCCTGCTGTTCCTGTTCTCCAGCGCCTAC
TCC (Human IL7)
GATTGCGACATCGAGGGCAAGGACGGCAAGCAGTACGAGAGCGTGCTGATG
GTGTCCATCGACCAGCTGCTGGACAGCATGAAGGAGATCGGCTCCAACTGC
CTCAACAACGAGTTCAACTTCTTCAAGCGGCACATCTGCGACGCCAACAAG
GAGGGCATGTTCCTGTTCAGGGCCGCCAGGAAACTGCGGCAGTTCCTGAAG
ATGAACTCCACCGGCGACTTCGACCTGCACCTGCTGAAGGTGTCCGAGGGC
ACCACCATCCTGCTGAACTGCACCGGACAGGTGAAGGGCCGGAAACCTGCT
GCTCTGGGAGAGGCCCAACCCACCAAGAGCCTGGAGGAGAACAAGTCCCTG
AAGGAGCAGAAGAAGCTGAACGACCTGTGCTTCCTGAAGAGGCTGCTGCAG
GAGATCAAGACCTGCTGGAACAAGATCCTGATGGGCACCAAGGAGCAT (Human Tissue Factor 219)
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
ACTGGTTCCGCTGGCGAGCCTTTATACGAGAACAGCCCCGAATTTACCCCT
TACCTCGAGACCAATTTAGGACAGCCCACCATCCAAAGCTTTGAGCAAGTT
GGCACAAAGGTGAATGTGACAGTGGAGGACGAGCGGACTTTAGTGCGGCGG
AACAACACCTTTCTCAGCCTCCGGGATGTGTTCGGCAAAGATTTAATCTAC
ACACTGTATTACTGGAAGTCCTCTTCCTCCGGCAAGAAGACAGCTAAAACC
AACACAAACGAGTTTTTAATCGACGTGGATAAAGGCGAAAACTACTGTTTC
AGCGTGCAAGCTGTGATCCCCTCCCGGACCGTGAATAGGAAAAGCACCGAT
AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG
TCCATGCATATCGACGCCACTTTATACACAGAATCCGACGTGCACCCCTCT
TGTAAGGTGACCGCCATGAAATGTTTTTTACTGGAGCTGCAAGTTATCTCT
TTAGAGAGCGGAGACGCTAGCATCCACGACACCGTGGAGAATTTAATCATT
TTAGCCAATAACTCTTTATCCAGCAACGGCAACGTGACAGAGTCCGGCTGC
AAGGAGTGCGAAGAGCTGGAGGAGAAGAACATCAAGGAGTTTCTGCAATCC
TTTGTGCACATTGTCCAGATGTTCATCAATACCTCC The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDANK
EGMFLFRAARKLRQFLKMNSTGDFDLHLLKVSEGTTILLNCTGQVKGRKPA
ALGEAQPTKSLEENKSLKEQKKLNDLCFLKRLLQEIKTCWNKILMGTKEH -continued (Human Tissue Factor 219)
SGTTNTVAAYNLTWKSTNFKTILEWEPKPVNQVYTVQISTKSGDWKSKCFY
TTDTECDLTDEIVKDVKQTYLARVFSYPAGNVESTGSAGEPLYENSPEFTP
YLETNLGQPTIQSFEQVGTKVNVTVEDERTLVRRNNTFLSLRDVFGKDLIY
TLYYWKSSSSGKKTAKTNTNEFLIDVDKGENYCFSVQAVIPSRTVNRKSTD
SPVECMGQEKGEFRE (Human IL-15)
NWVNVISDLKKIEDLIQSMHIDATLYTESDVHPSCKVTAMKCFLLELQVIS
LESGDASIHDTVENLIILANNSLSSNGNVTESGCKECEELEEKNIKEFLQS
FVHIVQMFINTS The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCTAC
TCC (Human IL-21)
CAGGGCCAGGACAGGCACATGATCCGGATGAGGCAGCTCATCGACATCGTC
GACCAGCTGAAGAACTACGTGAACGACCTGGTGCCCGAGTTTCTGCCTGCC
CCCGAGGACGTGGAGACCAACTGCGAGTGGTCCGCCTTCTCCTGCTTTCAG
AAGGCCCAGCTGAAGTCCGCCAACACCGGCAACAACGAGCGGATCATCAAC
GTGAGCATCAAGAAGCTGAAGCGGAAGCCTCCCTCCACAAACGCCGGCAGG
AGGCAGAAGCACAGGCTGACCTGCCCCAGCTGTGACTCCTACGAGAAGAAG
CCCCCCAAGGAGTTCCTGGAGAGGTTCAAGTCCCTGCTGCAGAAGATGATC
CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG
AGCTATAGCCTCTACAGCCGGGAGAGGTATATCTGTAACAGCGGCTTCAAG
AGGAAGGCCGGCACCAGCAGCCTCACCGAGTGCGTGCTGAATAAGGCTACC
AACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCTG
CGGCAGGGCATGTTTGCGCAGCTGGTGGCCCAAAATGTTCTGCTGATCGAT
GGGCCCCTGAGCTGGTACAGTGACCCAGGCCTGGCAGGCGTGTCCCTGACG
GGGGGCCTGAGCTACAAAGAGGACACGAAGGAGCTGGTGGTGGCCAAGGCT
GGAGTCTACTATGTCTTCTTTCAACTAGAGCTGCGGCGCGTGGTGGCCGGC
GAGGGCTCAGGCTCCGTTTCACTTGCGCTGCACCTGCAGCCACTGCGCTCT
GCTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCTG
AGTGCCGGCCAGCGCCTGGGCGTCCATCTTCACACTGAGGCCAGGGCACGC
CATGCCTGGCAGCTTACCCAGGGCGCCACAGTCTTGGGACTCTTCCGGGTG
ACCCCCGAAATCCCAGCCGGACTCCCTTCACCGAGGTCGGAA The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKAT

NVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSLT

GGLSYKEDTKELVVAKAGVYYVFFQLELRRVVAGEGSGSVSLALHLQPLRS

AAGAAALALTVDLPPASSEARNSAFGFQGRLLHLSAGQRLGVHLHTEARAR

HAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF antibody IgG1 affinity and other chromatography methods.

Purification Elution Chromatograph of 7t15-21s137L Using Anti-TF Antibody Affinity Column 7t15-21s137L harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 111, the anti-TF antibody affinity column bound to 7t15-21s137L which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 112 shows the analytical SEC profile of 7t15-21s137L.

Example 55: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

(Signal peptide)
ATGAAGTGGGTGACCTTCATCAGCCTGCTGTTCCTGTTCTCCAGCGCCTAC

TCC (Human IL 7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT (Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

-continued

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

The nucleic acid and protein sequences of the 21s137L (short version) are shown below. The nucleic acid sequence of 21s137L (short version) construct (including signal peptide sequence) is as follows:

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

-continued ((G4S)3 linker)
GGCGGTGGAGGATCCGGAGGAGGTGGCTCCGGCGGCGGAGGATCT (Human CD137 Ligand short version)
GATCCCGCCGGCCTCTTGGACCTGCGGCAGGGCATGTTTGCGCAGCTGGTG

GCCCAAAATGTTCTGCTGATCGATGGGCCCCTGAGCTGGTACAGTGACCCA

GGCCTGGCAGGCGTGTCCCTGACGGGGGGCCTGAGCTACAAAGAGGACACG

AAGGAGCTGGTGGTGGCCAAGGCTGGAGTCTACTATGTCTTCTTTCAACTA

GAGCTGCGGCGCGTGGTGGCCGGCGAGGGCTCAGGCTCCGTTTCACTTGCG

CTGCACCTGCAGCCACTGCGCTCTGCTGCTGGGGCCGCCGCCCTGGCTTTG

ACCGTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTCCAT

CTTCACACTGAGGCCAGGGCACGCCATGCCTGGCAGCTTACCCAGGGCGCC

ACAGTCTTGGGACTCTTCCGGGTGACCCCCGAAATC

The amino acid sequence of the 21s137L (short version) construct (including signal peptide sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKAT

NVAHWTTPSLKCIR ((G4S)3 linker)
GGGGSGGGGSGGGGS (Human CD137 Ligand short version)
DPAGLLDLRQGMFAQLVAQNVLLIDGPLSWYSDPGLAGVSLTGGLSYKEDT

KELVVAKAGVYYVFFQLELRRVVAGEGSGSVSLALHLQPLRSAAGAAALAL

TVDLPPASSEARNSAFGFQGRLLHLSAGQRLGVHLHTEARARHAWQLTQGA

TVLGLFRVTPEI

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF antibody IgG1 affinity and other chromatography methods.

Binding of 7t15-21s137L (Short Version) to CD137 (4.1BB)

On day 1, a 96-well plate was coated with 100 μL (2.5 μg/mL) of GAH IgG Fc (G-102-C, R&D Systems) in R5 (coating buffer) or R5 only and incubated at 4° C., overnight. On day 2, the plates were washed three times and blocked with 300 μL of 1% BSA in PBS at 37° C. for 2 hrs. 10 ng/mL of 4.1BB/Fc (838-4B, R&D Systems) was added at 100

μL/well and incubated for 2 hrs at RT. After three washes, the 7t15-21s137L or 7t15-21s serially diluted at a 1/3 ratio (starting at 10 nM), and incubated at 4° C. overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 113, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

A 96-well plate was coated with 100 μL (8 μg/mL) of anti-TF antibody IgG1 in R5 (coating buffer) and incubated at RT for 2 hrs. The plates were washed 3 times and blocked with 100 μL of 1% BSA in PBS. 7t15-21s137L (short version), serially diluted at a 1:3 ratio was added, and incubated at RT for 60 min. After three washes, 50 ng/mL of biotinylated-anti-IL-15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of HRP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 114A-114C, the IL-15, IL-21, and IL-7 domains in 7t15-21s137L (short version) were detected by the respective antibodies.

The IL-15 in 7t15-1s137L (Short Version) Promotes IL2Rαβγ Containing CTLL2 Cell Proliferation To evaluate the IL-15 activity of 7t15-21s137L (short version), 7t15-21s137L (short version) was compared with recombinant IL-15 in promoting proliferation of IL2Rαβγ expressing CTLL2 cells. IL-15-dependent CTLL2 cells were washed 5 times with IMDM-10% FBS and seeded to the wells at $2\times10^4$ cells/well. Serially diluted 7t15-21s137L (short version) or IL-15 were added to the cells (FIG. 115). Cells were incubated in a $CO_2$ incubator at 37° C. for 3 days. Cell proliferation was detected by adding 10 μL of WST1 to each well on day 3 and incubated for an additional 3 hours in a $CO_2$ incubator at 37° C. The amount of formazan dye produced was analyzed by measuring the absorbance at 450 nm. As shown in FIG. 115, 7t15-21s137L (short version) and IL-15 promoted CTLL2 cell proliferation. The $EC_{50}$ of 7t15-21s137L (short version) and IL-15 was 55.91 pM and 6.22 pM, respectively.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at $1\times10^4$ cells/well. Serially diluted 7t15-21s137L (short version) or IL-21 were added to the cells (FIG. 116). Cells were incubated in a $CO_2$ incubator at 37° C. for 5 days. Cell proliferation was detected by adding 10 μL of WST1 to each well on day 5 and incubated for an additional 4 hours in a $CO_2$ incubator at 37° C. The amount of formazan dye produced was analyzed by measuring the absorbance at 450 inn. As shown in FIG. 116, 7t15-21s137L (short version) and IL-21 promoted B9 cell proliferation. The $EC_{50}$ of 7t15-21s137L (short version) and IL-21 was 1041 nM and 72.55 nM, respectively.

Example 56: 7t15-TGFRs Fusion Protein Generation and Characterization

A fusion protein complex was generated comprising of TGFβ Receptor II/IL-15RαSu and IL-7/TF/IL-15 fusion proteins (FIG. 117 and FIG. 118). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG
```

-continued (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

(Signal peptide)
ATGAAGTGGGTGACCTTCATCAGCCTGCTGTTCCTGTTCTCCAGCGCCTAC

TCC (Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

-continued

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

The amino acid sequence of TGFRs fusion protein (including the leader sequence) is as follows:
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR

Effect of 7t15-TGFRs on TGFβ1 Activity in HEK-Blue TGFβ Cells

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). 7t15-TGFRs or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The data are shown in FIG. 119. The $IC_{50}$ of each protein sample was calculated with GraphPad Prism 7.04. The $IC_{50}$ of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

A 96-well plate was coated with 100 μL (8 μg/mL) of anti-TF antibody IgG1 in R5 (coating buffer) and incubated at room temperature (RT) for 2 hrs. The plates were washed three times and blocked with 100 μL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 μg/mL of HRP-SA (Jackson ImmunoResearch) at 100 μL per well was carried out for 30 min at RT, followed by 4 washes and incubation with 100 μL of ABTS for 2 mins at RT. Absorbance was read at 405 nm. As shown in FIGS. 120A-120C, the IL-15, TGFR, and IL-7 in 7t15-TGFRs were detected by the respective antibodies.

The IL-15 in 7t15-TGFRs Promotes IL-2R/3 and Common γ Chain Containing 32Dβ Cell Proliferation To evaluate the activity of IL-15 in 7t15-TGFRs, 7t15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-TGFRs or IL-15 were added to the cells (FIG. 121). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The amount of formazan dye produced was analyzed by measuring the absorbance at 450 nm. As shown in FIG. 121, 7t15-TGFRs and IL-15 promoted 32Dβ cell proliferation, with the $EC_{50}$ of 7t15-TGFRs and IL-15 being I26 nM and 16.63 pM, respectively.

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 122, the anti-TF antibody affinity column can bind 7t15-TGFRs which contains TF as a fusion partner of 7t15-TGFRs. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 123 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 124. A humanized anti-TF antibody monoclonal antibody (anti-TF antibody IgG1) was used as the capture antibody to determine TF in 7t15-TGFRs, and biotinylated antibodies against human IL-15 (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 124).

In Vivo Characterization of 7t15-TGFRs in C57BL/6 Mice

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-TGFRs was effective at expanding splenocytes based on spleen weight (FIG. 125A), especially at 1-10 mg/kg. The percentages of $CD8^+$ T cells and NK cells were higher compared to control-treated mice (FIG. 125B) at all doses tested.

$CD44$ Expression of $CD4^+$ and $CD8^+$ T Cells

It has been known that IL-15 induces CD44 expression on T cells and development of memory T cells. CD44 expression of $CD4^+$ and $CD8^+$ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of $CD4^+CD44^{high}$ T cells of total CD4+ T cells and $CD8^+CD44^{high}$ T cells of total $CD8^+$ T cells were analyzed by flow cytometry. As shown in FIGS. 126A and 126B, 7t15-TGFRs significantly activated $CD4^+$ and $CD8^+$ T cells to differentiate into memory T cells.

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 127A and 127B, in the spleens of mice treated with 7t15-TGFRs, the expression of Ki67 and granzyme B by $CD8^+$ T cells and NK cells increased compared with PBS control treatment. These results demonstrate that 7t15-TGFRs is not only to increase numbers of $CD8^+$ T cells and NK cells but also enhance potential cytotoxicity of these cells.

Additionally, cytotoxicity of the mouse splenocytes against tumor cells was also evaluated. Mouse Yac-1 cells were labeled with CELLTRAC™ Violet (cell proliferation kit for flow cytometry) and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37° C. for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 128, 7t15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 57: TGFRt15-21s137L Fusion Protein Generation and Characterization

A fusion protein complex was generated comprising IL-21/IL-15RαSu/CD137L and TGFβ Receptor II/TF/IL-15 fusion proteins (FIG. 129 and FIG. 130). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCTAC

TCC

(Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG
```

-continued

```
TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

The nucleic acid and protein sequences of the 21s137L are shown below. The nucleic acid sequence of the 21s137L construct (including signal peptide sequence) is as follows:

```
(Signal peptide)
ATGAAGTGGGTGACCTTCATCAGCCTGCTGTTCCTGTTCTCCAGCGCCTAC

TCC

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG
```

-continued

```
((G4S)3 linker)
GGCGGTGGAGGATCCGGAGGAGGTGGCTCCGGCGGCGGAGGATCT

(Human CD137L)
CGCGAGGGTCCCGAGCTTTCGCCCGACGATCCCGCCGGCCTCTTGGACCTG

CGGCAGGGCATGTTTGCGCAGCTGGTGGCCCAAAATGTTCTGCTGATCGAT

GGGCCCCTGAGCTGGTACAGTGACCCAGGCCTGGCAGGCGTGTCCCTGACG

GGGGGCCTGAGCTACAAAGAGGACACGAAGGAGCTGGTGGTGGCCAAGGCT

GGAGTCTACTATGTCTTCTTTCAACTAGAGCTGCGGCGCGTGGTGGCCGGC

GAGGGCTCAGGCTCCGTTTCACTTGCGCTGCACCTGCAGCCACTGCGCTCT

GCTGCTGGGGCCGCCGCCCTGGCTTTGACCGTGGACCTGCCACCCGCCTCC

TCCGAGGCTCGGAACTCGGCCTTCGGTTTCCAGGGCCGCTTGCTGCACCTG

AGTGCCGGCCAGCGCCTGGGCGTCCATCTTCACACTGAGGCCAGGGCACGC

CATGCCTGGCAGCTTACCCAGGGCGCCACAGTCTTGGGACTCTTCCGGGTG

ACCCCCGAAATCCCAGCCGGACTCCCTTCACCGAGGTCGGAA
```

The amino acid sequence of 21s137L fusion protein (including the leader sequence) is as follows:

```
(Signal peptide)
MKWVTFISLLFLFSSAYS

(Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

(Human IL-15R a sushi domain)
ITCPPPMSVEHADIWVKSYSLYSRERYICNSGFKRKAGTSSLTECVLNKA

TNVAHWTTPSLKCIR

((G4S)3 linker)
GGGGSGGGGSGGGGS

(Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE
```

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF antibody IgG1 affinity and other chromatography methods.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 131, the anti-TF antibody affinity column bound to TGFRt15-21s137L which contains TF as a fusion partner of TGFRt15-21s137L. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 58: TGFRt15-TGFRs21 Fusion Protein Generation and Characterization

A fusion protein complex was generated comprising of TGFβ Receptor II/IL-15RαSu/IL-21 and TGFβ Receptor II/TF/IL-15 fusion proteins (FIG. 132 and FIG. 133). The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC
```

-continued

```
CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

CAAGGAGTTTCTGCAATCCTTTGTGACATTGTCCAGATGTTCATCAAT

ACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD
```

-continued (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human IL-15R a sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

-continued

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG (Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCC

The amino acid sequence of TGFRs21 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDGGGGSGGGGSGGGGSI

PPHVQKSVNNDMIVTDNNGAVKFPQLCKFCDVRFSTCDNQKSCMSNCSITS

ICEKPQEVCVAVWRKNDENITLETVCHDPKLPYHDFILEDAASPKCIMKEK

KKPGETFFMCSCSSDECNDNIIFSEEYNTSNPD (Human IL-15R a sushi domain)
ITCPPPMSVEHADIWVKSYSLYSRERYICNSGFKRKAGTSSLTECVLNKAT

NVAHWTTPSLKCIR (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody IgG1 affinity and other chromatography methods.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 134, the anti-TF antibody affinity column bound to TGFRt15-TGFRs21 which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 135 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL/6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIG. 136. A humanized anti-TF monoclonal antibody (anti-TF IgG1) was used as the capture antibody to determine TF in TGFRt15-TGFRs21, biotinylated anti-human IL-15 antibody (R&D systems), biotinylated anti-human TGFβ receptor antibody (R&D systems, and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 137A, the percentages of $CD4^+$ T cells, $CD8^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of $CD4^+$ T cells, $CD8^+$ T cells, and NK cells and the mean fluorescent intensity (MFI) of Ki67 of corresponding immunocyte subsets were analyzed by flow cytometry (FIGS. 137A and 137B). Furthermore, cytotoxicity potential based on granzyme B expression of the splenocytes induced by TGFRt15-TGFRs21 after the single dose treatment of mouse was also evaluated. As shown in FIG. 138, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 138).

As shown in FIG. 137A, in the spleens of mice treated with TGFRt15-TGFRs21, the percentages of $CD8^+$ T cells and NK cells both increased on day 4 after a single TGFRt15-TGFRs21 treatment. These results demonstrate that TGFRt15-TGFRs21 is able to induce immune cells to proliferate in mouse spleen, in particular $CD8^+$ T cells and NK cells.

Additionally, cytotoxicity of the mouse splenocytes against tumor cells was also evaluated. Mouse Yac-1 cells were labeled with CELLTRACE™ Violet (cell proliferation kit for flow cytometry) and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37° C. for 24 hours. Target Yac-1 cell inhibition was assessed by analysis of viable violet-labeled Yac-1 cells using flow cytometry. Percentage of Yac-1 inhibition was calculated using a formula, (1-[viable Yac-1 cell number in experimental sample]/[viable Yac-1 cell number in the sample without splenocytes])×100. As shown in FIG. 139, TGFRt15-TGFRs21-treated mouse splenocytes had stronger cytotoxicity against Yac-1 cells than the control mouse cells in the presence of TGFRt15-TGFRs21 during cytotoxic assay (FIG. 139).

Example 59: TGFRt15-TGFRs16 Fusion Protein Generation

A fusion protein complex was generated comprising of TGFβ Receptor II/IL-15RαSu/anti-CD16scFv and TGFβ Receptor II/TF/IL-15 fusion proteins (FIG. 140 and FIG. 141). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACTCCATCTGCGAGAAGCCCCAAGAAGTGTGCGTGGCCGTGTGGCGGAAA

AATGACGAGAACATCACCCTGGAGACCGTGTGTCACGACCCCAAGCTCCC

TTATCACGACTTCATTCTGGAGGACGCTGCCTCCCCCAAATGCATCATGA

AGGAGAAGAAGAAGCCCGGAGAGACCTTCTTTATGTGTTCCTGTAGCAGC

GACGAGTGTAACGACAACATCATCTTCAGCGAAGAGTACAACACCAGCAA

CCCTGATGGAGGTGGCGGATCCGGAGGTGGAGGTTCTGGTGGAGGTGGGA

GTATTCCTCCCCACGTGCAGAAGAGCGTGAATAATGACATGATCGTGACC

GATAACAATGGCGCCGTGAAATTTCCCCAGCTGTGCAAATTCTGCGATGT

GAGGTTTTCCACCTGCGACAACCAGAAGTCCTGTATGAGCAACTGCTCCA

TCACCTCCATCTGTGAGAAGCCTCAGGAGGTGTGCGTGGCTGTCTGGCGG

AAGAATGACGAGAATATCACCCTGGAAACCGTCTGCCACGATCCCAAGCT

GCCCTACCACGATTTCATCCTGGAAGACGCCGCCAGCCCTAAGTGCATCA

TGAAAGAGAAAAAGAAGCCTGGCGAGACCTTTTTCATGTGCTCCTGCAGC

AGCGACGAATGCAACGACAATATCATCTTTAGCGAGGAATACAATACCAG

CAACCCCGAC

(Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG
```

-continued

```
(Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE

(Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

```
(Signal peptide)
ATGAAGTGGGTGACCTTCATCAGCCTGCTGTTCCTGTTCTCCAGCGCCTA

CTCC

(Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA
```

-continued

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R a sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Anti-human CD 16scFv)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGG

The amino acid sequence of TGFRs16 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

-continued

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R a sushi domain)
ITCPPPMSVEHADIWVKSYSLYSRERYICNSGFKRKAGTSSLTECVLNKAT

NVAHWTTPSLKCIR (Anti-human CD 16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF IgG1 affinity and other chromatography methods.

Example 60: The TGFRt15-TGFRs137L Fusion Protein Generation

A fusion protein complex was generated comprising of TGFβ Receptor II/IL-15RαSu/CD137L and TGFβ Receptor II/TF/IL-15 fusion proteins (FIG. 142 and FIG. 143). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCTA

CTCC

-continued (Human TGFβ Receptor II fragments)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC (Human Tissue Factor 219)
AGCGGCACAACCAACACAGTCGCTGCCTATAACCTCACTTGGAAGAGCAC
CAACTTCAAAACCATCCTCGAATGGGAACCCAAACCCGTTAACCAAGTTT
ACACCGTGCAGATCAGCACCAAGTCCGGCGACTGGAAGTCCAAATGTTTC
TATACCACCGACACCGAGTGCGATCTCACCGATGAGATCGTGAAAGATGT
GAAACAGACCTACCTCGCCCGGGTGTTTAGCTACCCCGCCGGCAATGTGG
AGAGCACTGGTTCCGCTGGCGAGCCTTTATACGAGAACAGCCCCGAATTT
ACCCCTTACCTCGAGACCAATTTAGGACAGCCCACCATCCAAAGCTTTGA
GCAAGTTGGCACAAAGGTGAATGTGACAGTGGAGGACGAGCGGACTTTAG
TGCGGCGGAACAACACCTTTCTCAGCCTCCGGGATGTGTTCGGCAAAGAT
TTAATCTACACACTGTATTACTGGAAGTCCTCTTCCTCCGGCAAGAAGAC
AGCTAAAACCAACACAAACGAGTTTTTAATCGACGTGGATAAAGGCGAAA
ACTACTGTTTCAGCGTGCAAGCTGTGATCCCCTCCCGGACCGTGAATAGG
AAAAGCACCGATAGCCCCGTTGAGTGCATGGGCCAAGAAAAGGGCGAGTT
CCGGGAG (Human IL-15)
AACTGGGTGAACGTCATCAGCGATTTAAAGAAGATCGAAGATTTAATTCA
GTCCATGCATATCGACGCCACTTTATACACAGAATCCGACGTGCACCCCT
CTTGTAAGGTGACCGCCATGAAATGTTTTTTACTGGAGCTGCAAGTTATC
TCTTTAGAGAGCGGAGACGCTAGCATCCACGACACCGTGGAGAATTTAAT
CATTTTAGCCAATAACTCTTTATCCAGCAACGGCAACGTGACAGAGTCCG
GCTGCAAGGAGTGCGAAGAGCTGGAGGAGAAGAACATCAAGGAGTTTCTG
CAATCCTTTGTGCACATTGTCCAGATGTTCATCAATACCTCC The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF
YTTDTECDLTDEIVKDVKQTYLARVFSYPAGNVESTGSAGEPLYENSPEF
TPYLETNLGQPTIQSFEQVGTKVNVTVEDERTLVRRNNTFLSLRDVFGKD
LIYTLYYWKSSSSGKKTAKTNTNEFLIDVDKGENYCFSVQAVIPSRTVNR
KSTDSPVECMGQEKGEFRE (Human IL-15)
NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTS Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

(Signal peptide)
ATGAAGTGGGTGACCTTCATCAGCCTGCTGTTCCTGTTCTCCAGCGCCTA
CTCC (Human TGFβ Receptor II fragments)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC -continued

```
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC

(Human IL-15R a sushi domain)
ATTACATGCCCCCCTCCCATGAGCGTGGAGCACGCCGACATCTGGGTGAA
GAGCTATAGCCTCTACAGCCGGGAGAGGTATATCTGTAACAGCGGCTTCA
AGAGGAAGGCCGGCACCAGCAGCCTCACCGAGTGCGTGCTGAATAAGGCT
ACCAACGTGGCTCACTGGACAACACCCTCTTTAAAGTGCATCCGG

((G4S)3 linker)
GGCGGTGGAGGATCCGGAGGAGGTGGCTCCGGCGGCGGAGGATCT

(Human CD137L)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG
ACGGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGG
CCGGCGAGGGCTCAGGCTCCGTTTCACTTGCGCTGCACCTGCAGCCACTG
CGCTCTGCTGCTGGGGCCGCCGCCCTGGCTTTGACCGTGGACCTGCCACC
CGCCTCCTCCGAGGCTCGGAACTCGGCCTTCGGTTTCCAGGGCCGCTTGC
TGCACCTGAGTGCCGGCCAGCGCCTGGGCGTCCATCTTCACACTGAGGCC
AGGGCACGCCATGCCTGGCAGCTTACCCAGGGCGCCACAGTCTTGGGACT
CTTCCGGGTGACCCCCGAAATCCCAGCCGGACTCCCTTCACCGAGGTCGG
AA
```

The amino acid sequence of TGFRs137L fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSDECNDNIIFSEEYNTSNPD

(Human IL-15R a sushi domain)
ITCPPPMSVEHADIWVKSYSLYSRERYICNSGFKRKAGTSSLTECVLNKAT
NVAHWTTPSLKCIR

((G4S)3 linker)
GGGGSGGGGSGGGGS
```

-continued

```
(Human CD137L)
REGPELSPDDPAGLLDLRQGMFAQLVAQNVLLIDGPLSWYSDPGLAGVSLT
GGLSYKEDTKELVVAKAGVYYVFFQLELRRVVAGEGSGSVSLALHLQPLRS
AAGAAALALTVDLPPASSEARNSAFGFQGRLLHLSAGQRLGVHLHTEARAR
HAWQLTQGATVLGLFRVTPEIPAGLPSPRSE
```

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF IgG1 affinity and other chromatography methods.

Example 61. Production and Characterization of the Exemplary Single-Chain Chimeric Polypeptide 2t2

An exemplary single-chain chimeric polypeptide including a first target-binding domain that binds to an IL-2 receptor, a soluble human tissue factor domain, and a second target-binding domain that binds to an IL-2 receptor was generated (IL-2/TF/IL-2; referred to as 2t2) (FIG. 144). The nucleic acid and amino acid sequences of this single-chain chimeric polypeptide are shown below.

Nucleic Acid Encoding Exemplary Single-Chain Chimeric Polypeptide (IL-2/TF/IL-2) (SEQ ID NO: 164)

```
(Signal peptide)
ATGAAGTGGGTGACCTTCATCAGCCTGCTGTTCCTGTTCTCCAGCGCCTAC
TCC

(First IL-2 fragment)
GCCCCCACCTCCTCCTCCACCAAGAAGACCCAGCTGCAGCTGGAGCATTTA
CTGCTGGATTTACAGATGATTTTAAACGGCATCAACAACTACAAGAACCCC
AAGCTGACTCGTATGCTGACCTTCAAGTTCTACATGCCCAAGAAGGCCACC
GAGCTGAAGCATTTACAGTGTTTAGAGGAGGAGCTGAAGCCCCTCGAGGAG
GTGCTGAATTTAGCCCAGTCCAAGAATTTCCATTTAAGGCCCCGGGATTTA
ATCAGCAACATCAACGTGATCGTTTTAGAGCTGAAGGGCTCCGAGACCACC
TTCATGTGCGAGTACGCCGACGAGACCGCCACCATCGTGGAGTTTTTAAAT
CGTTGGATCACCTTCTGCCAGTCCATCATCTCCACTTTAACC

(Human tissue factor 219 form)
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
```

-continued

```
ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Second IL-2 fragment)
GCACCTACTTCAAGTTCTACAAAGAAAACACAGCTACAACTGGAGCATTTA

CTGCTGGATTTACAGATGATTTTGAATGGAATTAATAATTACAAGAATCCC

AAACTCACCAGGATGCTCACATTTAAGTTTTACATGCCCAAGAAGGCCACA

GAACTGAAACATCTTCAGTGTCTAGAAGAAGAACTCAAACCTCTGGAGGAA

GTGCTAAATTTAGCTCAAAGCAAAAACTTTCACTTAAGACCCAGGGACTTA

ATCAGCAATATCAACGTAATAGTTCTGGAACTAAAGGGATCTGAAACAACA

TTCATGTGTGAATATGCTGATGAGACAGCAACCATTGTAGAATTTCTGAAC

AGATGGATTACCTTTTGTCAAAGCATCATCTCAACACTAACT
```

Exemplary Single-Chain Chimeric Polypeptide (IL-2/TF/IL-2) (SEQ ID NO: 163)

```
(Signal peptide)
MKWVTFISLLFLFSSAYS

(Human IL-2)
APTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSETT

FMCEYADETATIVEFLNRWITFCQSIISTLT

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-2)
APTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSETT

FMCEYADETATIVEFLNRWITFCQSIISTLT
```

The nucleic acid encoding IL-2/TF/IL-2 was cloned into a modified retrovirus expression vector as described previously (Hughes et al., *Hum Gene Ther* 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

IL-2 and 2t2 Promoted IL-2R/3 and Common γ Chain Containing 32Dβ Cell Proliferation in a Similar Manner To evaluate the IL-2 activity of 2t2, 2t2 was compared with recombinant IL-2 for promoting proliferation of 32Dβ cells that express IL-2R13 and common γ chain. IL-2 dependent 32Dβ cells were washed 5 times with IMDM-10% FBS and seeded to the wells at $2\times10^4$ cells/well. Serial dilutions of 2t2 or IL-2 were added to the cells (FIG. 145). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The amount of formazan dye produced was analyzed by measuring the absorbance at 450 nm. As shown in FIG. 145, 2t2 and IL-2 activated 32Dβ cells in a similar manner. The $EC_{50}$ of 2t2 and IL-2 was 158.1 pM and 140 pM, respectively.

2t2 Showed Improved Ability to Promote IL-2Rαβγ Containing CTLL-2 Cell Proliferation as Compared to IL-2

To evaluate the IL-2 activity of 2t2, 2t2 was compared with recombinant IL-2 for promoting proliferation of CTLL-2 cells that express IL-2Ra, IL-2R13 and common γ chain. IL-2 dependent CTLL-2 cells were washed 5 times with IMDM-10% FBS and seeded to the wells at $2\times10^4$ cells/well. Serial dilutions of 2t2 or IL-2 were added to the cells (FIG. 146). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 146, 2t2 promoted CTLL-2 cell proliferation 4-5-fold stronger than IL-2. The $EC_{50}$ of 2t2 was 123.2 pM and IL-2 was 548.2 pM.

2t2 Suppressed the Increase of the High Fat-Induced Hyperglycemia in $ApoE^{-/-}$ Mice Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with high fat diet were randomly assigned into the control group and treatment group. Mice then received either 2t2 (treatment group) or PBS (chow diet group and control group) per subcutaneous injection at a dosage of 3 mg/kg. Three days post dosing, the mice were fasted overnight, and blood samples were collected through retro-orbital venous plexus puncture. Overnight fasting glucose levels were measured using a OneTouch Glucometer. As shown in FIG. 147, the results showed that 2t2 injection effectively suppresses the increase of glucose levels in $ApoE^{-/-}$ mice.

2t2 Significantly Upregulate the Ratio of $CD4^+CD25^+$ $FoxP3^+$ T Regulatory (Treg) Cells in Blood Lymphocytes Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with the high fat diet were randomly assigned into control group and treatment group. Mice then received either 2t2 (treatment group) or PBS (chow diet group and control group) per subcutaneous injection at a dosage of 3 mg/kg. Three days after the dosing, overnight fasting blood samples were collected through retro-orbital venous plexus puncture and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer followed by centrifugation at 1500 RPM for 5 minutes at room temperature. The cells were analyzed by flow cytometry (Celesta-BD Bioscience). As shown in FIG. 148, 2t2 treatment significantly increased Treg populations in blood lymphocytes (3.5%±0.32) compared to the untreated groups (0.4%±0.16 for chow diet group and 0.46%±0.09 for high fat diet group).

Purification Elution Chromatograph of 2t2 from Anti-TF Antibody Affinity Column

2t2 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 149, the anti-TF antibody affinity column bound to 2t2 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 2t2

To analyze 2t2 using analytical size exclusion chromatography (SEC), a Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing 2t2 in PBS was injected into the Superdex 200 column using a capillary loop, and analyzed by SEC. The SEC chromatograph of the sample is shown in FIG. 150. The SEC results indicated two protein peaks for 2t2.

Reduced SDS PAGE of 2t2

To determine the purity and molecular weight of the protein, 2t2 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 2t2 protein undergoes glycosylation after translation in CHO cells, a deglycosylation experiment was conducted using the Protein Deglycosylation Mix II kit from New England Biolabs according to the manufacturer's instructions. FIGS. 151A and 151B show the reduced SDS-PAGE analysis of the sample in non-deglycosylated (lane 1 in red outline) and deglycosylated (lane 2 in yellow outline) state. The results show that the 2t2 protein is glycosylated when expressed in CHO cells. After deglycosylation, the purified sample ran with expected molecular weights (56 kDa) in reduced SDS gel. Lane M was loaded with 10 μL of SeeBlue Plus2 Prestained Standard.

In Vivo Characterization of 2t2

2t2 was subcutaneously injected into C57BL/6 mice at various doses to determine the immunostimulatory activity of 2t2 in vivo. Mice were subcutaneously treated with control solution (PBS) or 2t2 at 0.1, 0.4, 2 and 10 mg/kg. The treated mice were euthanized day 3 post treatment. The mouse spleens were collected and weighed day 3 post treatment. Single splenocyte suspensions were prepared, and the prepared splenocytes were stained for $CD4^+$ T cells, $CD8^+$ T cells and NK cells (with fluorochrome-conjugated anti-CD4, -CD8, and -NK1.1 antibodies), and analyzed by flow cytometry. The results showed that 2t2 was effective at expanding splenocytes based on spleen weight (FIG. 152A) especially at 0.1-10 mg/kg. The percentage of $CD8^+$ T cells were higher compared to control-treated mice (FIG. 152B) at 2 and 10 mg/kg. The percentage of NK cells were higher compared to control-treated mice (FIG. 152B) at all doses tested.

It has been known that IL-2 upregulates CD25 expression by immunocytes. We therefore accessed CD25 expression of $CD4^+$ T cells, $CD8^+$ T cells and NK cells in the 2t2 treated mice. C57BL/6 mice were subcutaneously treated with 2t2 as described in the paragraph above. The splenocytes were stained with fluorochrome-conjugated anti-CD4, -CD8, CD25 and NK1.1 monoclonal antibodies. The CD25 expression (MFI) of splenocyte subsets was analyzed by flow cytometry. As shown in FIG. 153, at the doses and time points tested, 2t2 significantly upregulated CD25 expression by $CD4^+$ T cells but not CD8+ T cells or NK cells.

The pharmacokinetics of 2t2 in C57BL/6 mice were also investigated. 2t2 was subcutaneously injected into C57BL/6 mice at 1 mg/kg. The mouse blood was drawn from tail vein at various time points as shown in FIG. 154 and the serum was prepared. 2t2 concentrations were determined with ELISA (Capture: anti-tissue factor antibody; Detection: biotinylated anti-human IL-2 antibody followed by SA-HRP and ABTS substrate). The half-life of 2t2 was 1.83 hours calculated with PK Solutions 2.0 (Summit Research Services).

2t2 Attenuated the Formation of High Fat-Induced Atherosclerotic Plaques in $ApoE^{-/-}$ Mice Six-week-old female $ApoE^{-/-}$ mice (The Jackson Laboratory) were fed with standard chow diet or high diet fat (21% fat, 0.15% cholesterol, 34.1% sucrose, 19.5% casein, and 15% starch) (TD88137, Harlan Laboratories) and maintained in the standard conditions. At week 7, mice fed with high fat diet (HFD) were randomly assigned into control group and treatment group. Mice were then administrated either 2t2 (treatment group) or PBS (chow diet group and control group) subcutaneously at a dosage of 3 mg/kg weekly for 4 weeks. At week 12, all mice were euthanized by isoflurane. Aortas were collected, opened longitudinally and stained with Sudan IV solution (0.5%) using en face method. The percentage of plaque area (red color as shown in FIG. 155A) relative to total aorta area was then quantified with Image J software. FIG. 155A shows a representative view of atherosclerotic plaques from each group. FIG. 155B shows the results of quantitative analysis of atherosclerotic plaques of each group. The percentage of plaque areas in control group (HF Diet) was much higher than the treatment group (HFD+2t2), being 10.28% vs 4.68%.

2t2 Suppresses the Progression of Type 2 Diabetes.

Male BKS.Cg-$Dock7^m$+/+$Lepr^{db}$/J (db/db (Jackson Lab)) mice were fed with standard chow diet and received drinking water ad libitum. At the age of six weeks, mice were randomly assigned into control group and treatment group. The treatment group received 2t2 by subcutaneous injection at 3 mg/kg bi-weekly, while control group received vehicle (PBS) only. Overnight fasting glucose levels were measure weekly using a OneTouch Glucometer. The results showed that 2t2 effectively suppressed the increase of glucose levels in BKS.Cg-Dock7$^{m}$+/+Lepr$^{db}$/J mice (FIG. 156).

2t2 Significantly Upregulates the Ratio of CD4+ CD25±FoxP3+T Regulatory Cells in Blood Lymphocytes after the First Injection Male BKS.Cg-Dock7$^{m}$+/+Lepr$^{db}$/J (db/db) (The Jackson Laboratory) mice were fed with standard chow diet and received drinking water ad libitum. At the age of six weeks, mice were randomly assigned into control group and treatment group. The treatment group received 2t2 by subcutaneous injection at 3 mg/kg bi-weekly, while the control group received vehicle (PBS) only. Four days after the first drug injection, overnight fasting blood samples were collected and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer and were analyzed by flow cytometry (Celesta-BD Bioscience). The percentage of $CD4^{+}CD25^{+}$ $FoxP3^{+}$ Tregs in blood lymphocytes were measured. As shown in FIG. 157, the results showed that 2t2 significantly upregulated the ratio of Tregs in blood lymphocytes (* $p<0.05$).

Example 62. Production and Characterization of the Exemplary Single-Chain Chimeric Polypeptide 15t15

A second exemplary single-chain chimeric polypeptide including a first target-binding domain that binds to an IL-15 receptor, a soluble human tissue factor domain, and a second target-binding domain that binds to an IL-15 receptor was generated (IL-15/TF/IL-15; referred to at 15t15) (FIG. 158). The nucleic acid and amino acid sequences of this single-chain chimeric polypeptide are shown below.

Nucleic Acid Encoding Exemplary Single-Chain Chimeric Polypeptide (IL-15/TF/IL-15) (SEQ ID NO: 170)

```
(Signal peptide)
ATGAAGTGGGTGACCTTCATCAGCCTGCTGTTCCTGTTCTCCAGCGCCT

ACTCC

(First IL-15 fragment)
AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC

(Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC
```

-continued

```
TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG

(Second IL-15 fragment)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

Exemplary Single-Chain Chimeric Polypeptide (IL-15/TF/IL-15) (SEQ ID NO: 169)

```
(Signal peptide)
MKWVTFISLLFLFSSAYS

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQNIFINTS
```

The nucleic acid encoding IL-15/TF/IL-15 was cloned into a modified retrovirus expression vector as described previously (Hughes et al., *Hum Gene Ther* 16:457-72, 2005). The expression vector encoding IL-15/TF/IL-15 was transfected into CHO-K1 cells. Expression of the expression vector in CHO-K1 cells allowed for secretion of the soluble IL-15/TF/IL-15 single-chain chimeric polypeptide (referred to as 15t15), which can be purified by anti-TF antibody affinity and other chromatography methods.

15t15 Promotes IL-2R/3 and Common γ Chain Containing 32Dβ Cell Proliferation

IL-15 activity of 15t15 was compared with recombinant IL-15 in IL2Rβ and common γ chain expressed 32Dβ cells. IL-15 dependent 32Dβ cells were washed five times with IMDM-10% FBS and seeded to the wells at $2\times10^4$ cells/well. Serial dilutions of 15t15 or IL-15 were added to the cells (FIG. 159). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 159, 15t15 promoted 32Dβ cell proliferation less efficiently as compared to IL-15. The $EC_{50}$ of 15t15 and IL-15 was 161.4 pM and 1.6 pM, respectively.

Purification Elution Chromatograph of 15t15 from Anti-TF Antibody Affinity Column 15t15 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 160, the anti-TF antibody affinity column bound to 15t15 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of 15t15

To determine the purity and molecular weight of the protein, 15t15 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 15t15 protein undergoes glycosylation after translation in CHO cells, a deglycosylation experiment was conducted using the Protein Deglycosylation Mix II kit from New England Biolabs and the manufacturer's instructions. FIGS. 161A and 161B show the reduced SDS-PAGE analysis of the sample in non-deglycosylated (lane 1 in red outline) and deglycosylated (lane 2 in yellow outline) state. The results showed that the 15t15 protein is glycosylated when expressed in CHO cells. After deglycosylation, the purified sample ran with expected molecular weights (50 kDa) in reduced SDS gel. Lane M was loaded with 10 μL of SeeBlue Plus2 Prestained Standard.

Example 63: Stimulation of NK Cells In Vitro

A set of experiments was performed to assess the changes in surface phenotype of NK cells after stimulation with 18t15-12s, 18t15-12s16, and 7t15-21s+anti-TF antibody. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM); a mixture of single cytokines rhIL-15 (50 ng/mL) (Miltenyi), rhIL18 (50 ng/mL) (Invivogen), and rhIL-12 (10 ng/mL) (Peprotech); 7t15-21s+anti-TF antibody (100 nM-50 nM); 7t15-21s (100 nM); or anti-TF antibody (50 nM) at 37° C. and 5% $CO_2$ for 16 hours. The next day, the cells were harvested and surface stained for 30 minutes with CD56, CD16, CD25, CD69, CD27, CD62L, NKp30, and NKp44 specific antibodies. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIGS. 162A and 162B shows that overnight incubation of purified NK cells with 18t15-12s, 18t15-12s16, and 7t15-21s+ anti-TF antibody resulted in an increase in the percentage of cells expressing CD25, CD69, NKp44, and NKp30 activation markers and a decrease in the percentage of cells expressing CD62L. All activation marker data is from $CD56^+$ gated lymphocytes.

A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL-15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37° C. and 5% $CO_2$ for 16 hours. The next day, the cells were harvested and surface stained for 30 minutes for CD4 or CD8, CD62L, and CD69 specific antibodies. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 163 shows that overnight incubation of purified lymphocyte populations (CD4 and CD8 T cells) with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 163).

A set of experiments was performed to determine the effect of 18t15-12s on the extracellular acidification rate (ECAR) of NK cells purified from human blood. ECAR can be used to measure glycolysis. Glycolysis is the intracellular biochemical conversion of one molecule of glucose into two molecules of pyruvate with the concurrent generation of two molecules of ATP. An increase in glycolysis was indicated by an increase in ECAR measured by a Seahorse XF96 Analyzer. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining for CD56-BV421, CD16-BV510, CD25-PE, and CD69-APCFire750 antibodies (BioLegend). The cells were counted and resuspended in $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either a mixture of single cytokines hIL-12 (10 ng/mL) (Biolegend), hIL-18 (50 ng/mL) (R&D), and hIL-15 (50 ng/mL) (NCI) or 18t15-12s (100 nM) at 37° C. and 5% $CO_2$ for 14-18 hours. The next day, the cells were harvested and washed two times in Seahorse media. The cells ($2\times10^5$ cells/well) were seeded in 96-well flux plates that were coated with 10 μL of poly-L-lysine (Sigma). NK cells were adhered to plates for 30 minutes prior to the assay. Glucose, oligomycin, and 2DG solutions were prepared at 10× concentration in buffered Seahorse medium and injected in port A, B, and C of the calibration plate. ECAR readings were taken every 6.5-7 minutes and ECAR results represent the average readings over 80 minutes or average readings at each timepoint. FIG. 164 shows overnight stimulation of NK cells with 18t15-12s resulted in increased basal ECAR levels. The addition of glucose and oligomycin further showed enhanced glycolysis and glycolytic capacity, respectively, of NK cells stimulated with 18t15-12s overnight (FIG. 164). NK cells treated overnight with media alone or a mixture of IL12, IL18, and IL-15 were used for comparison (FIG. 164).

A set of experiments was performed to determine the increase in phospho-STAT4 and phospho-STAT5 levels in NK cells after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APCFire750 specific antibodies (BioLegend). The cells were counted and resuspended in $0.05\times10^6$/mL in a 96-well flat-bottom plate in 0.1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with hIL-12 (10 ng/mL) (Biolegend) or hIL-15 (50 ng/mL) (NCI) (Single cytokines), or 18t15-12s (100 nM) at 37° C. and 5% $CO_2$ for 90 minutes. Unstimulated NK cells (US) were used as a control. The cells were harvested and fixed in paraformaldehyde (Sigma) to a final concentration of 1.6%. Plates were incubated in the dark at room temperature for 10 minutes. FACS buffer (1×PBS (Hyclone) with 0.5% BSA (EMD Millipore) and 0.001% sodium azide (Sigma)) (100 μL) was added and cells were transferred to 96-well "V" bottom plate. The cells were washed for 1500 RPM for 5 minutes at room temperature. The cell pellet was mixed with 100 μL chilled methanol by gently pipetting up and down, and cells were incubated for 30 minutes at 4° C. The cells were mixed with 100 mL of FACS buffer and washed for 1500 RPM for 5 minutes at room temperature. The cell pellets were mixed with 50 mL of FACS buffer containing 4 mL of pSTAT4 (BD Bioscience) and pSTAT5 antibodies (BD Bioscience) followed by incubation for 30 minutes at room temperature in the dark. The cells were mixed with 100 mL of FACS buffer and washed for 1500 RPM for 5 minutes at room temperature. The cell pellets were mixed with 50 mL of FACS buffer and cells were analyzed by flow cytometry (Celesta-BD Bioscience). FIG. 165 shows that incubation of NK cells with 18t15-12s induced an increase in pSTAT4 and pSTAT5 (plotted data, normalized fold-change).

A set of experiments was performed to determine the effect of 18t15-12s or a mixture of cytokines (e.g., IL12, IL18, and IL-15) on oxygen consumption rate (OCR) and extracellular acidification rate (ECAR) on NK cells purified from human blood. OCR and ECAR were measured by a Seahorse XF96 Analyzer. In these experiments, fresh human NK cells were isolated from human leukocytes via negative selection using the RosetteSep/human NK cell reagent (StemCell Technologies). Freshly purified NK cells were stimulated overnight (16 h) with either 18t15-12s (100 nM) or a mixture of rhIL12 (10 ng/mL), rhIL18 (50 ng/mL), and rhIL-15 (50 ng/mL) cytokines as a control. The next day, the cells were washed, counted, and equal numbers of cells were plated in buffered Seahorse media. Glucose, oligomycin, and 2DG solutions were prepared at 10× concentration in buffered Seahorse medium and injected in port A, B, and C of the calibration plate. FIG. 166 shows OCR (left) and ECAR (right) data from two individual donors. Overnight stimulation of NK cells with 18t15-12s resulted in an increase in basal ECAR and OCR levels. Addition of glucose and oligomycin further showed enhanced glycolysis and glycolytic capacity, respectively, of NK cells stimulated with 18t15-12s overnight. NK cells treated overnight with media alone or a mixture of IL12, IL18, and IL-15 were used for comparison.

Example 64: Stimulation of NK Cells In Vivo by 2t2 and/or TGFRt15-TGFRs

A set of experiments was performed to determine the effect of the 2t2 construct on immune stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. Splenocytes suspensions were stained with conjugated anti-CD4, anti-CD8, and anti-NK1.1 (NK) antibodies. The percentage of $CD4^+$ T cells, $CD8^+$ T cells, and NK cells, and CD25 expression on lymphocyte subsets were analyzed by flow cytometry. FIG. 167A shows that 2t2 was effective at expanding splenocytes based on spleen weight especially at a dose level of 0.1-10 mg/kg. Following treatment, the percentage of $CD8^+$ T cells were higher in 2t2-treated mice compared to control-treated mice at 2 and 10 mg/kg (FIG. 167B). The percentage of NK cells were also higher in 2t2-treated mice compared to control-treated mice at all doses of 2t2 tested (FIG. 167B). Additionally, 2t2 significantly upregulated CD25 expression by $CD4^+$ T cells, but not $CD8^+$ T cells and NK cells following treatment at 0.4 to 10 mg/kg (FIG. 167C).

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.3, 1, 3, and 10 mg/kg. The treated mice were euthanized 4 days post-treatment. Spleen weight was measured and single splenocyte suspensions were prepared. The splenocytes suspensions were stained with conjugated anti-CD4, anti-CD8, and anti-NK1.1 (NK) antibodies. The percentage of $CD4^+$ T cells, $CD8^+$ T cells, and NK cells were analyzed by flow cytometry. FIG. 168A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs were higher as compared to mice treated with the control solution. FIG. 168B shows that the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice.

A set of experiments was performed to determine the effect of the TGFRt15-TGFRs construct or 2t2 construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs or 2t2 at 3 mg/kg. Three days post treatment, mice were fasted for 16 hours and then blood samples were collected through retro-orbital venous plexus puncture. The blood was mixed with 10 μL 0.5 M EDTA, and 20 μL blood was taken for lymphocyte subsets analysis. The red blood cells were lysed with ACK (0.15 M $NH_4Cl$, 1.0 mM $KHCO_3$, 0.1 mM $Na_2EDTA$, pH 7.4) and the lymphocytes were stained with anti-mouse CD8a and anti-mouse NK1.1 antibodies for 30 minutes at 4° C. in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4° C. in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 μL with 1× permeabilization buffer. Anti-Foxp3 antibody was added to the cells, and the cells were incubated for 30 minutes at room temperature. Permeabilization buffer (200 μL) was added to the cells, and the cells were centrifuged at 300-400×g for 5 minutes at room temperature. The cells were resuspended in flow cytometry staining buffer and analyzed on a flow cytometer. FIGS. 169B-169C show that treatment with TGFRt15-TGFRs and 2t2 increased the percentage of NK cells and $CD8^+$ T cells in $ApoE^{-/-}$ mice fed with Western diet. FIG. 169A shows that treatment with 2t2 also increased the percentage of Treg cells.

Example 65: Induction of Proliferation of Immune Cells In Vivo

A set of experiments was performed to determine the effect of the 2t2 construct on immune cell stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. The splenocyte suspensions were stained with conjugated anti-CD4, anti-CD8, and anti-NK1.1 (NK) antibodies. The percentage of $CD4^+$ T cells, $CD8^+$ T cells, and NK cells were analyzed by flow cytometry. FIG. 170A shows that 2t2 treatment was effective at expanding splenocytes based on spleen weight especially at 0.1-10 mg/kg. The percentage of $CD8^+$ T cells was higher compared to control-treated mice at 2 and 10 mg/kg (FIG. 170B). Additionally, the percentage of NK cells was higher compared to control-treated mice at all doses of 2t2 tested (FIG. 170B). These results demonstrate that 2t2 treatment was able to induce proliferation of $CD8^+$ T cells and NK cells in C57BL/6 mice.

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.1, 0.3, 1, 3, and 10 mg/kg. The treated mice were euthanized 4 days post-treatment. Spleen weight was measured and splenocyte suspensions were prepared. The splenocyte suspensions were stained with conjugated anti-CD4, anti-CD8, and anti-NK1.1 (NK) antibodies. The cells were additionally stained for proliferation marker Ki67. FIG. 171A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs was higher as compared to mice treated with just the control solution. The percentages of $CD8^+$ T cells and NK cells both increased with increasing dosage of TGFRt15-TGFRs (FIG. 171B). Finally, TGFRt15-TGFRs significantly upregulated expression of cell proliferation marker Ki67 in both $CD8^+$ T cells and NK cells at all doses of TGFRt15-TGFRs tested. These results demonstrate that TGFRt15-TGFRs treatment induced proliferation of both $CD8^+$ T cells and NK cells in C57BL/6 mice.

A set of experiments was performed to determine the effect of the TGFRt15-TGFRs construct or the 2t2 construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with TGFRt15-TGFRs or 2t2 at 3 mg/kg. Three days post-treatment, the mice were fasted for 16 hours and then blood samples were collected through retro-orbital venous plexus puncture. The blood was mixed with 10 μL 0.5 M EDTA and 20 μL blood was taken for lymphocyte subsets analysis. The red blood cells were lysed with ACK (0.15 M $NH_4Cl$, 1.0 mM $KHCO_3$, 0.1 mM $Na_2EDTA$, pH 7.4) and the lymphocytes were stained with anti-mouse CD8a and anti-mouse NK1.1 antibodies for 30 minutes at 4° C. in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. As described in FIG. 172A, treatment of $ApoE^{-/-}$ mice with TGFRt15-TGFRs induced proliferation (Ki67-positive staining) in NK and $CD8^+$ T cells. Additionally, FIG. 172B shows treatment of $ApoE^{-/-}$ mice with 2t2 also induced proliferation (Ki67-positive staining) in NK and $CD8^+$ T cells.

A set of experiments was performed to determine the effect 7t15-21s+anti-TF antibody-expanded NK cells in NSG mice following treatment with 7t15-21s, TGFRt15-TGFRs, and 2t2. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. The cells were counted using trypan blue to access the fold-expansion. 7t15-21s+anti-TF antibody-expanded NK cells were washed three times in warm HBSS Buffer (Hyclone) at 1000 RPM for 10 minutes at room temperature. The 7t15-21s+anti-TF antibody-expanded-NK cells were resuspended in $10\times10^6$/0.2 mL HBSS buffer and injected intravenously into the tail vein of NSG mice (NOD scid gamma mouse) (Jackson Laboratories). The transferred NK cells were supported every 48 hours with either 7t15-21s (10 ng/dose, i.p.), TGFRt15-TGFRs (10 ng/dose, i.p.) or 2t2 (10 ng/dose, i.p.) for up to 21 days. Engraftment and persistence of the human 7t15-21s+anti-TF antibody-expanded NK cells were measured every week in blood staining for hCD45, mCD45, hCD56, hCD3, and hCD16 antibodies by flow cytometry (Celesta-BD Bioscience) (Data represent 3 mice per group). FIG. 173 indicates that treatment of mice bearing adoptively-transferred 7t15-21s+anti-TF antibody-expanded NK cells with 7t15-21s-, TGFRt15-TGFRs-, or 2t2-induced expansion and persistence of the adoptively transferred NK cells compared to control treated mice.

Example 66: NK-Mediated Cytotoxicity Following Treatment with Single-Chain Constructs or Multi-Chain Constructs A set of experiments was performed to determine if treatment of NK cells with TGFRt15-TGFRs enhanced cytotoxicity of NK cells. In these experiments, Human Daudi B lymphoma cells were labeled with CELLTRACE™ Violet (CTV) (cell proliferation kit for flow cytometry) and used as tumor target cells. Mouse NK effector cells were isolated with NK1.1-positive selection using a magnetic cell sorting method (Miltenyi Biotec) of C57BL/6 female mouse spleens 4 days post TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Human Daudi B lymphoma cells) were mixed with effector cells (either mouse NK effector cells or human NK effector cells) in the presence of 50 nM TGFRt15-TGFRs or in the absence of TGFRt15-TGFRs (control) and incubated at 37° C. for 44 hours for mouse NK cells and for 20 hours for human NK cells. Target cell (Daudi) viability was assessed by analysis of propidium iodide-positive, CTV-labeled cells using flow cytometry. The percentage of Daudi inhibition was calculated using the formula (1-viable tumor cell number in experimental sample/viable tumor cell number in the sample without NK cells)×100. FIG. 174 shows that mouse (FIG. 174A) and human (FIG. 174B) NK cells had significantly stronger cytotoxicity against Daudi B cells following NK cell activation with TGFRt15-TGFRs than in the absence of TGFRt15-TGFRs activation.

A set of experiments was performed to determine antibody-dependent cellular cytotoxicity (ADCC) of mouse and human NK cells following treatment with TGFRt15-TGFRs. In these experiments, human Daudi B lymphoma cells were labeled with CellTrace Violet (CTV) and used as tumor target cells. Mouse NK effector cells were isolated with NK1.1-positive selection using a magnetic cell sorting method (Miltenyi Biotec) of C57BL/6 female mouse spleens 4 days post-TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Daudi B cells) were mixed with effector cells (either mouse NK effector cells or human NK effector cells) in the presence of anti-CD20 antibody (10 nM Rituximab, Genentech) and in the presence of 50 nM TGFRt15-TGFRs, or in the absence of TGFRt15-TGFRs (control) and incubated at 37° C. for 44 hours for mouse NK cells and for 20 hours for human NK cells. The Daudi B cells express the CD20 targets for the anti-CD20 antibody. Target cell viability was assessed after incubation by analysis of propidium iodide-positive, CTV-labeled target cells using flow cytometry. The percentage of Daudi inhibition was calculated using the formula (1-viable tumor cell number in experimental sample/viable tumor cell number in the sample without NK cells)×100. FIG. 175 shows that mouse NK cells (FIG. 175A) and human NK cells (FIG. 175B) had stronger ADCC activity against Daudi B cells following NK cell activation with TGFRt15-TGFRs than in the absence of TGFRt15-TGFRs activation.

A set of experiments was performed to determine cytotoxicity of TGFRt15-TGFRs-activated mouse NK cells towards senescent B16F10 melanoma cells. In these experiments, mouse NK cells were activated in vivo by injecting C57BL/6 mice with 10 mg/kg of TGFRt15-TGFRs for 4 days followed by isolation of splenic NK cells. The NK cells were then expanded in vitro for 7 days in the presence of 100 nM 2t2. The B16F10 senescent target cells (B16F10-SNC) were labelled with CellTrace Violet (CTV) and incubated at different Effector:Target (E:T) ratios with the activated mouse NK effector cells for 16 hours. The cells were trypsinized, washed, and resuspended in complete media containing propidium iodide (PI) solution. The cytotoxicity of the TGFRt15-TGFRs/2t2-activated NK cells against the senescent cell targets was accessed by flow cytometry based on PI staining of the CTV-labeled cells. The findings demonstrate that in vivo activation of NK cells with TGFRt15-TGFRs followed by in vitro expansion and activation with 2t2 resulted in increased killing of senescent melanoma tumor cells by the NK cells (FIG. 176).

Example 67: Treatment of Cancer, Diabetes, and Atherosclerosis

Figure 177A:
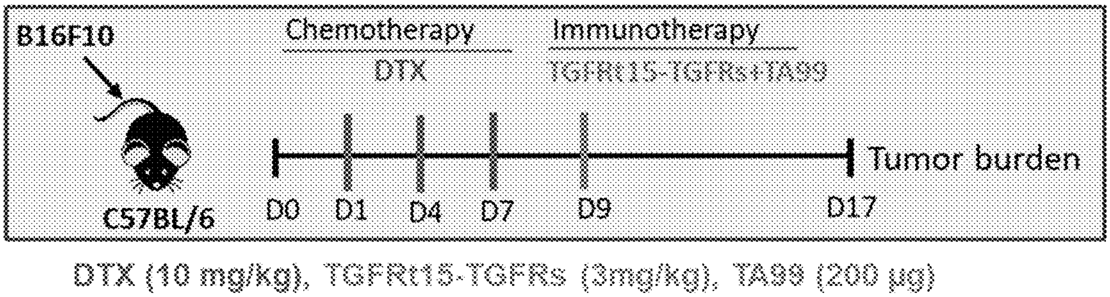
Figure 177B:
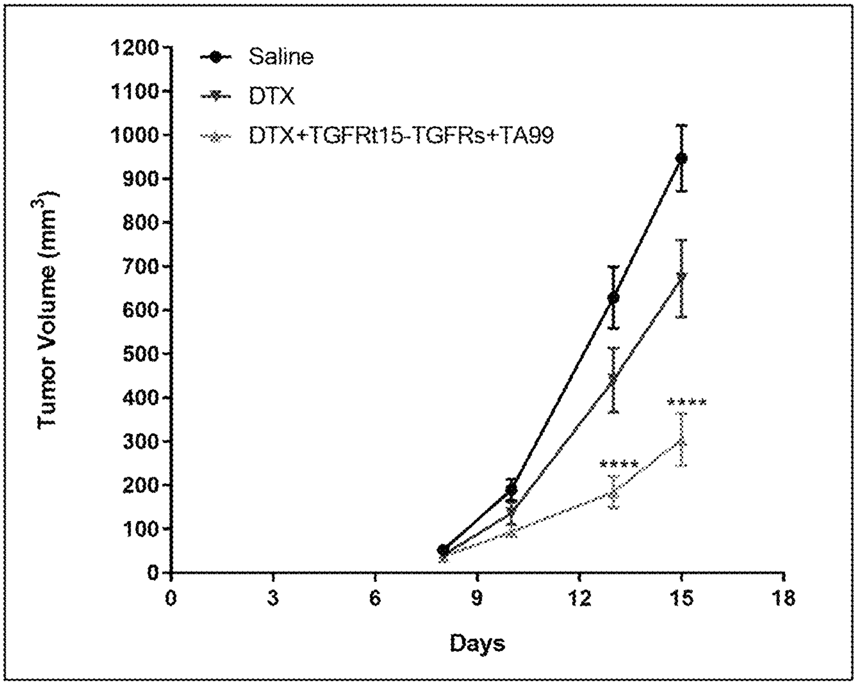

A set of experiments was performed to assess antitumor activity of TGFRt15-TGFRs plus anti-TRP1 antibody (TA99) in combination with chemotherapy in a melanoma mouse model. In these experiments, C57BL/6 mice were subcutaneously injected with $0.5\times10^6$ B16F10 melanoma cells. The mice were treated with three doses of chemotherapy docetaxel (10 mg/kg) (DTX) on day 1, day 4, and day 7, followed by treatment with single dose of combination immunotherapy TGFRt15-TGFRs (3 mg/kg)+anti-TRP1 antibody TA99 (200 μg) on day 9. FIG. 177A shows a schematic of the treatment regimen. Tumor growth was monitored by caliper measurement, and tumor volume was calculated using the formula $V=(L\times W^2)/2$, where L is the largest tumor diameter and W is the perpendicular tumor diameter. FIG. 177B shows that treatment with DTX+TGFRt15-TGFRs+TA99 significantly reduced tumor growth compared to saline control and DTX treatment groups (N=10, ****$p<0.001$, Multiple t test analyses).

Figure 177C:
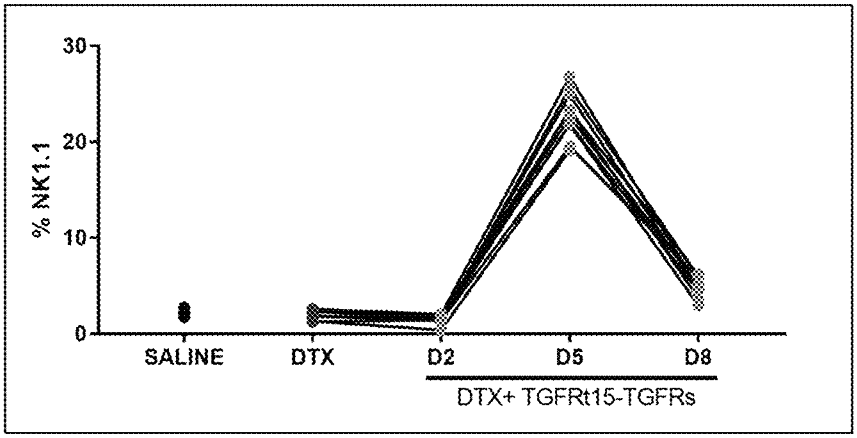
Figure 177D:
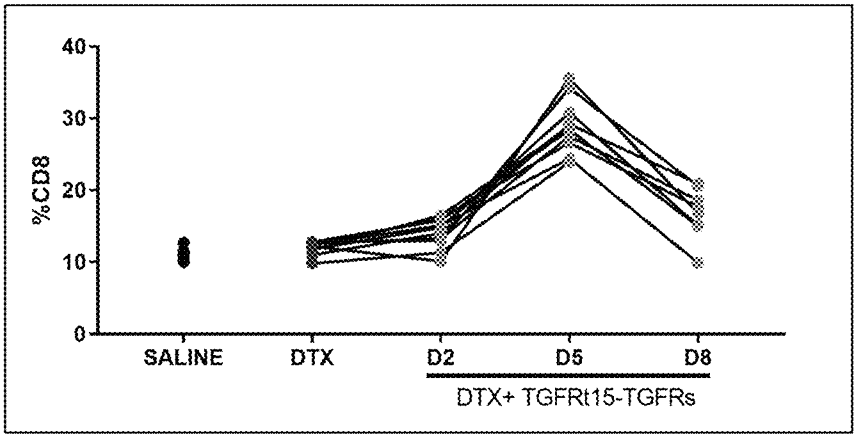
Figure 177E:
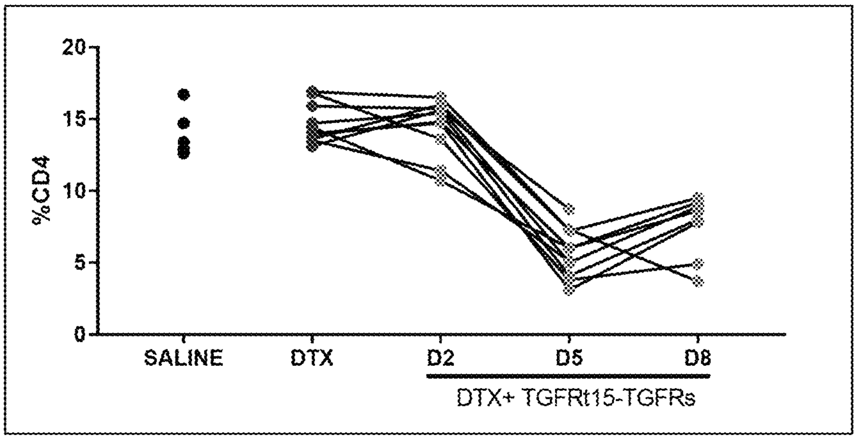

To assess immune cell subsets in the B16F10 tumor model, peripheral blood analysis was performed. In these experiments, C57BL/6 mice were injected with B16F10 cells and treated with DTX, DTX+TGFRt15-TGFRs+TA99, or saline. Blood was drawn from the submandibular vein of B16F10 tumor-bearing mice on days 2, 5, and 8 post-immunotherapy for the DTX+TGFRt15-TGFRs+TA99 group and day 11 post-tumor injection for the DTX and saline groups. RBCs were lysed in ACK lysis buffer and the lymphocytes were washed and stained with anti-NK1.1, anti-CD8, and anti-CD4 antibodies. The cells were analyzed by flow cytometry (Celesta-BD Bioscience). FIGS. 177C-177E show that DTX+TGFRt15-TGFRs+TA99 treatment induced an increase in the percentage of NK cells and $CD8^+$ T cells in the tumors compared to the saline and DTX treatment groups.

Figure 177F:
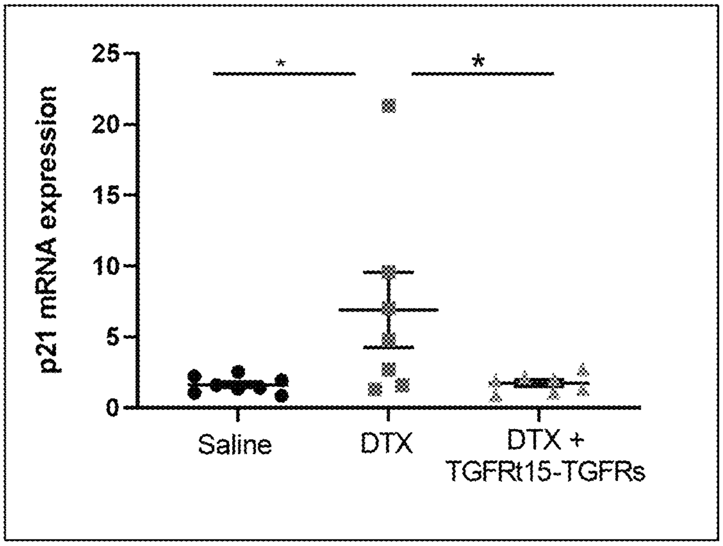
Figure 177G:
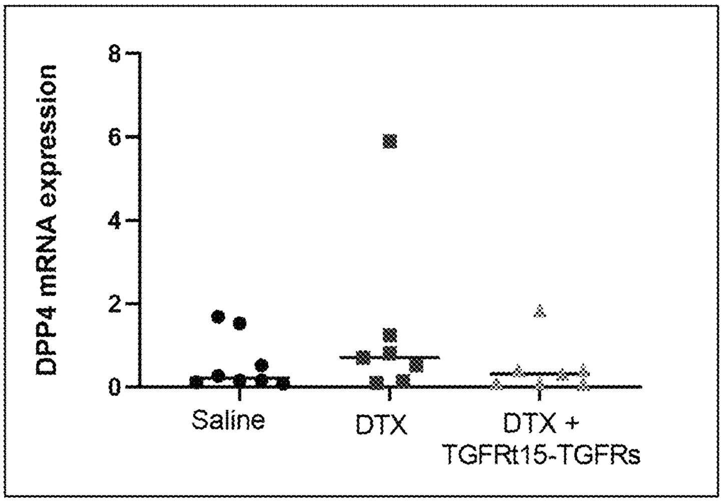
Figure 177H:
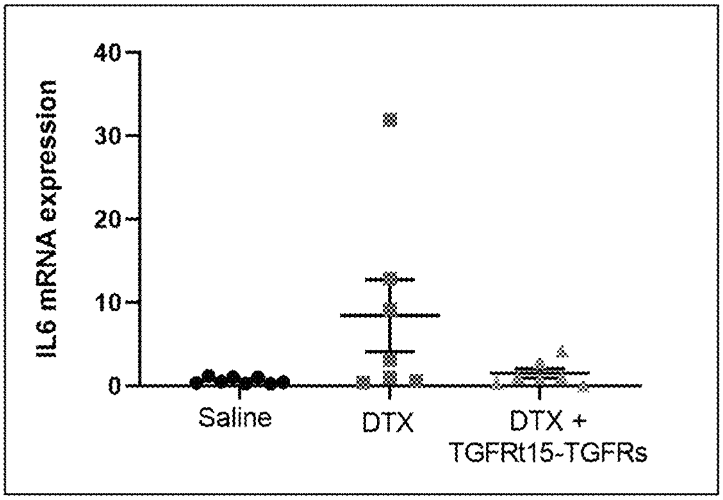

On day 17, total RNA was extracted from tumors of mice treated with saline, DTX or DTX+TGFRt15-TGFRs TA99 using Trizol. Total RNA (1 μg) was used for cDNA synthesis using the QUANTITECT® Reverse Transcription Kit (Qiagen)(kit for cDNA synthesis with integrated removal of genomic DNA contamination). Real-time PCR was carried out with CFX96 Detection System (Bio-Rad) using FAM-labeled predesigned primers for senescence cell markers, (F) p21 (G) DPP4 and (H) IL6. The housekeeping gene 18S ribosomal RNA was used as an internal control to normalize the variability in expression levels. The expression of each target mRNA relative to 18S rRNA was calculated based on Ct as $2^{-\Delta(\Delta Ct)}$, in which $\Delta Ct=Ct_{target}-Ct_{18S}$. The data is presented as fold-change as compared to saline control. FIG. 177F-177H show that DTX treatment induced an increase in senescent tumor cells that were subsequently reduced following treatment with TGFRt15-TGFRs+TA99 immunotherapy.

A set of experiments was performed to investigate amelioration of Western diet-induced hyperglycemia in $ApoE^{-/-}$ mice by 2t2. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs or 2t2 at 3 mg/kg. Three days post-treatment, the mice were fasted for 16 hours and then blood samples were collected through retro-orbital venous plexus puncture. Blood glucose was detected with a glucose meter (OneTouch UltraMini) and GenUltimated test strips using a drop of fresh blood. As shown in FIG. 178A, 2t2 treatment significantly reduced hyperglycemia induced by the Western diet ($p<0.04$). The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 178B, both 2t2 and TGFRt15-TGFRs treatment reduced insulin resistance compared to the untreated group. Both 2t2 ($p<0.02$) and TGFRt15-TGFRs ($p<0.05$) reduced resistin levels significantly compared to the untreated group as shown in FIG. 178C, which may relate to the reduced insulin resistance induced by 2t2 and TGFRt15-TGFRs (FIG. F3B).

Example 68: Induction of Differentiation of NK Cells into Cytokine-Induced Memory Like NK Cells A set of experiments was performed to assess the differentiation of NK cells into cytokine-induced memory like NK Cells (CIMK-NK Cells) after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were unstimulated ("No Spike") or stimulated with 18t15-12s (100 nM) or a mixture of single cytokines including rhIL-15 (50 ng/mL) (Miltenyi), rhIL18 (50 ng/mL) (Invivogen), and rhIL-12 (10 ng/mL) (Peprotech) ("single cytokines") at 37° C. and 5% $CO_2$ for 16 hrs. The next day, the cells were harvested, and washed two times with warm complete media at 1000 RPM for 10 minutes at room temperature. The cells were resuspended at $2\times10^6$/mL in a 24-well flat-bottom plate in 2 mL of complete media with rhIL-15 (1 ng/mL). After every 2 days, half of the medium was replaced with fresh complete media containing rhIL-15.

To assess the change in memory phenotype of NK cells at day 7, the cells were stained with antibodies to cell-surface CD56, CD16, CD27, CD62L, NKp30, and NKp44 (BioLegend). After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 179 shows that incubation of NK cells with 18t15-12s resulted in an increase in the percentage of $CD16^+CD56^+$ NK cells expressing CD27, CD62L, and NKp44, and an increase in the levels (MFI) of NKp30 in $CD16^+CD56^+$ NK cells.

Example 69. Upregulation of CD44 Memory T Cells

C57BL/6 mice were subcutaneously treated with TGFRt15-TGFRs or 2t2. The treated mice were euthanized and the single splenocyte suspensions were prepared 4 days (TGFRt15-TGFRs) or 3 days (2t2) following the treatment. The prepared splenocytes were stained with fluorochrome-conjugated anti-CD4, anti-CD8 and anti-CD44 antibodies and the percentages of $CD44^{high}$ T cells in $CD4^+$ T cells or $CD8^+$ T cells were analyzed by flow cytometry. The results show that TGFRt15-TGFRs and 2t2 upregulated expression of the memory marker CD44 on CD4+ and CD8+ T cells (FIG. 180). These findings indicate that TGFRt15-TGFRs and 2t2 molecules were able to induce mouse T cells to differentiate into memory T cells.

Example 70: Improvement of the Texture and/or Appearance and/or Hair

To examine the effect of 2t2 on hair regrowth, dorsal hair of C57BL6/J mice (Jackson Laboratory) was first shortened with clippers followed by application of depilatory cream (Nair) to the shaved region for a period of 30 seconds before wiping clean. After 4 hours, 2t2 (3 mg/kg, single dose), low dose recombinant IL-2 (25000 IU, 5 consecutive days, 1 dose/day), or PBS were administered subcutaneously. The mice were monitored for skin pigmentation related to hair regrowth and pictures were taken and analyzed using the Image J software. FIG. 181A shows skin pigmentation 10 days after depilation in PBS-, 2t2-, or IL-2-treated mice. FIG. 181B shows the percent pigmentation in each group of mice 10 days post-treatment as analyzed using the Image J software. The results showed that treatment of mice with 2t2 or IL-2 promoted hair regrowth following depilation compared to PBS-treated mice.

Dorsal hair of C57BL6/J mice (Jackson Laboratory) was first shortened with clippers before applying depilatory cream (Nair) to the shaved region for a period of exactly 30 seconds before wiping clean. After 4 hours, 2t2 (3 mg/kg, single dose), low dose recombinant IL-2 (25000 IU, 5 consecutive days, 1 dose/day) or PBS were administered subcutaneously. The mice were monitored for skin pigmentation related to hair regrowth and pictures were taken and analyzed using Image J software. FIG. 182 shows skin pigmentation 14 days after depilation in PBS-, 2t2-, or IL-2-treated mice. The results showed that treatment of mice with 2t2 or IL-2 promoted hair regrowth following depilation compared to the PBS-treated mice.

Example 71: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, Ohio). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain ($TF_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and $TF_{219}$ or a $TF_{219}$-containing multi-chain chimeric polypeptide were mixed at an equal molar concentration (10 nM) in all wells of a 96-well ELISA plate in a total volume of 70 μL. After incubation for 10 minutes at 37° C., 10 μL of 8 mM S-2288 substrate was added to start the reaction. The incubation was then kept at 37° C. for 20 minutes. Finally, color change was monitored by reading absorbance at 405 nm. The OD values of different TF/VIIa complexes are shown in Table 1 and Table 2. Table 1 shows a comparison of $TF_{219}$, 21t15-21s wild-type (WT) and 21t15-21s mutant (Mut). Table 2 shows a comparison of $TF_{219}$, 21t15-TGFRs wild-type (WT), and 21t15-TGFRs mutant (Mut). These data show that $TF_{219}$-containing multi-chain chimeric polypeptides (e.g., 21t15-21s-WT, 21t15-21s-Mut, 21t15-TGFRS-WT, and 21t15-TGFRS-Mut) have lower FVIIa activity than $TF_{219}$ when the chromogenic S-2288 was used as a substrate. Notably, the multi-chain chimeric polypeptides containing $TF_{219}$ mutations showed much lower FVIIa activity when compared to multi-chain chimeric polypeptides containing wild type $TF_{219}$.

TABLE 1

| FVIIa activity | |
|---|---|
| Molecule | OD value at 405 nm |
| $TF_{219}$ | 0.307 |
| 21t15/21S-WT | 0.136 |
| 21t15/21S-Mut | 0.095 |

WT: wild type of $TF_{219}$, Mut: $TF_{219}$ containing mutations.

TABLE 2

| FVIIa activity | |
|---|---|
| Molecule | OD value at 405 nm |
| $TF_{219}$ | 0.345 |
| 21t15/TGFRS-WT | 0.227 |
| 21t15/TGFRS-Mut | 0.100 |

WT: wild type of $TF_{219}$, Mut: $TF_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. $TF_{243}$, which contains the transmembrane domain of TF, has much higher activity in activating FX to FXa than $TF_{219}$, which does not contain the transmembrane domain. TF/VIIa dependent activation of FX is determined by measuring FXa activity using an FXa-specific chromogenic substrate S-2765 (Diapharma, West Chester, Ohio). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or $TF_{219}$. $TF_{219}$ (or $TF_{219}$-containing multi-chain chimeric polypeptides)/FVIIa complexes were mixed at an equal molar concentration (0.1 nM each) in a volume of 50 μL in round bottom wells of a 96-well ELISA plate, after which 10 μL of 180 nM FX was added. After 15 minutes of incubation at 37° C., during which time FX was converted to FXa, 8 μL of 0.5 M EDTA (which chelates calcium and thus terminates FX activation by TF/VIIa) was added to each well to stop FX activation. Next, 10 μL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 183. In this experiment, Innovin, which is a commercial prothrombin reagent containing lipidated recombinant human $TF_{243}$, was used as a positive control for FX activation. Innovin was reconstituted with purified water to about 10 nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37° C. In the PT assay, shorter PT time (clotting time) indicates a higher TF-dependent clotting activity while longer PT (clotting time) means lower TF-dependent clotting activity.

As seen in FIG. 184, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21t15-TGFRs-WT, and 21t15-TGFRs-Mut. FIG. 185 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2\times10^5$ cells/mL) or PBMC (at $1\times10^5$ cells/mL) for 20-30 minutes at room temperature. The PT assay was then conducted as described above. FIGS. 186 and 187 shows that $TF_{219}$ and $TF_{219}$-containing multi-chain chimeric polypeptides mixed with 32Dβ cells (FIG. 186) or PBMC (FIG. 187) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 72: Characterization of 7t15-21s137L (Long Version)

The nucleic acid sequence of the 7t15 construct (including signal peptide sequence) is as follows (SEQ ID NO: 210):

```
(Signal peptide)
ATGAAGTGGGTGACCTTCATCAGCCTGCTGTTCCTGTTCTCCAGCGCCT

ACTCC

(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG
```

-continued (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of 7t15 fusion protein (including the leader sequence) is as follows (SEQ ID NO: 209):

(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

The nucleic acid sequence of the 21s137L construct (including signal peptide sequence) is as follows (SEQ ID NO: 331): (Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human IL-15R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

-continued

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA

The amino acid sequence of 21s137L fusion protein (including the leader sequence) is as follows (SEQ ID NO: 332):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15R a sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37° C. for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with 1/3 dilution, followed by incubation at 4° C. overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 188, both 7t15-21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at 1/3 dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 189A-189D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2\times10^4$ cells/well. Serially diluted 7t15-21s137L (long version), 7t15-21s137L (short version), or IL15 were added to the cells. Cells were incubated in a $CO_2$ incubator at 37° C. for 3 days. Cell proliferation was detected by adding 20 μL of PrestoBlue (A13261, ThermoFisher) to each well on day 3 and incubated for an additional 4 hours in a $CO_2$ incubator at 37° C. Raw absorbance at 570-610 nm was read in a micro-titer plate reader. As shown in FIG. 190, 7t15-21s137L (long version), 7t15-21s137L (short version), and IL15 all promoted CTLL2 cell proliferation. The $EC_{50}$ of 7t15-21s137L (long version), 7t15-21s137L (short version), and IL-15 is 5119 pM, 55.75 pM, and 4.947 pM, respectively.

Example 73: Induction of Treg Cells by 2t2

The peripheral blood mononuclear cells (PBMC) of a healthy donor (Donor 163) were isolated from 5 mL of whole blood buffy coats by Ficoll Paque Plus (GE17144003). The PBMC were then lysed with ACK to remove red blood cells. Cells were washed with IMDM-10% FBS and counted. $1.8\times10^6$ cells (100 μL/tube) were seeded to the flow tubes and incubated with 50 μL of descending 2t2 or IL2 (15000, 1500, 150, 15, 1.5, 0.15, or 0 pM) and 50 μL of pre-staining antibodies (anti-CD8-BV605 and anti-CD127-AF647). Cells were incubated for 30 min at 37° C. in water bath. 200 μL of pre-warmed BD Phosflow Fix Buffer I (Cat #557870, Becton Dickinson Biosciences) was added for 10 min at 37° C. in water bath to stop the stimulation. Cells ($4.5\times10^5$ cells/100 μL) were transferred to a V-shape 96-well plate and were spun down followed by permeabilization with 100 μL of −20° C. pre-cooled BD Phosflow Perm Buffer III (Cat # BD Biosciences) for 30 min on ice. The cells were then extensively washed ×2 with 200 μL of FACS buffer and stained with a panel of fluorescent antibodies (anti-CD25-PE, CD4-PerCP-Cy5.5, CD56-BV421, CD45RA-PE-Cy7 and pSTAT5a-AF488) to distinguish between different lymphocyte subpopulations and evaluate the pSTAT5a status. Cells were spun down and resuspended in 200 μL of FACS buffer for FACSCelesta analysis. As shown in FIG. 191A, 6 pM of 2t2 was sufficient to induce the phosphorylation of Stat5a in $CD4^+CD25^{hi}$ $T_{reg}$ cells while 43.11 pM of IL-2 was required to induce phosphorylation of Stat5a in the same population of lymphocytes. In contrast, 2t2 was less active (FIG. 191B) or equally active (FIG. 191C) as compared to IL2 in inducing phosphorylation of Stat5a in $CD4^+CD25^-T_{con}$ and $CD8^+$ $T_{con}$ cells. These results suggest that 2t2 is superior as compared to IL2 in activating $T_{reg}$ in human PBMC, and that 2t2 demonstrates increased $T_{reg}$ selectivity compared to IL-2 in human blood lymphocyte pStat5a responses.

Example 74. Improvement in Hair Growth Using a Single-Chain Chimeric Polypeptide The dorsal hair of 7-week-old C57BL6/J mice was shaved and depilated using commercial depilatory cream. The mice were injected on the same day subcutaneously with a single dose of 2t2 or low dose commercially available recombinant IL-2, followed by daily dosing for four additional days. Untreated mice served as controls. On day 10, the mice were sacrificed and skin sections of the shaved areas were prepared. Representative H&E staining of skin sections from C57BL6J mice on day 10 following depilation are shown in FIGS. 192A-192E. FIG. 192A shows control mice—only depilation done after hair was shaved, FIG. 192B shows mice where depilation was followed by low dose IL-2 (1 mg/kg) administration, and FIGS. 192C-192E shows mice where depilation was followed by 2t2 administered at 0.3 mg/kg (FIG. 192C), 1 mg/kg (FIG. 192D), and 3 mg/kg (FIG. 192E). Black arrows indicate anagen-phase hair follicles that will later extend into dermis and facilitate hair growth. FIG. 194 shows the total number of anagen phase hair follicles counted per 10 fields for each treatment group. In summary, the data show that the 2t2 molecule resulted in increased numbers of anagen-phase hair follicles compared to depilation alone. This effect was also dose-dependent.

Example 75: Differentiation of the Immune Cell into a Memory-Like Immune Cell Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). The cells were counted and resuspended at a density of $2\times10^6$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). The cells (1 mL) were transferred into a 24-well flat bottom plate, and subjected to either: no treatment, or expanded with 7t15-21s+anti-tissue factor (TF)-antibody (IgG1) (50 nM) for 14 days with medium. The cells were replenished with fresh 7t15-21s+ anti-TF-antibody (IgG1) (50 nM) to keep the cell density at approximately $1\times10^6$ cells/mL.

Unexpanded NK cells to treatment groups were used as positive controls for full DNA methylation levels (Data not shown). NK cells were pelleted ($1\times10^6$), and genomic DNA (nDNA) isolated using the QIAamp UCP DNA Micro Kit (Qiagen). 500 ng of purified nDNA was subjected to sodium bisulfite treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfite-treated nDNA (10-50 ng) was used as template to PCR amplify a 228 bp region of the IFNγ promoter containing two CpG sites (CpG-186 and CpG-54, position relative to the transcription start site, TSS), known to be heavily regulated by DNA methylation in T cells, using the Pyromark PCR kit (Qiagen) with the forward primer IFNG127F (5'-ATGGTATAGGTGGGTATAATGG-3') and the biotinylated reverse primer IFNG355R-bio (biotin-5'-CAATATACTACACCTCCTCTAACTAC-3') (GENEWIZ). The PCR conditions were 15 minutes at 95° C., 48 cycles of 30 seconds at 95° C., 30 seconds at 56° C., 60 seconds at 72° C. followed by 10 minutes at 72° C. The integrity and quality of the PCR amplified products were visualized on a 1.2% TAE agarose gel. The DNA methylation status of these two CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C186-IFNG135F (5'-GGTGGGTATAATGGG-3') (SEQ ID NO: 333) and C54-IFNG261F (5'-ATTATTTTATTTTAAAAAATTTGTG-3') (SEQ ID NO: 334), specific to the CpG sites −186 and −54, respectively. Commercially available non-methylated and methylated DNA (Zymo Research) were used as controls for DNA methylation. The methylation percentages of the two CpG sites (−186 and −54) were pooled for each treatment. The percent difference in DNA methylation was calculated relative to the levels of DNA methylation at the two CpG sites observed in unexposed NK cells.

Analysis of the DNA methylation status of these two IFNγ CpG sites revealed higher levels of DNA demethylation in NK cells supported by 7t15-21s+anti-TF-antibody compared to unexposed NK cells (FIG. 194). These 7t15-21s+ anti-TF-antibody supported NK cells exhibited 47.70%±11.76 difference in DNA methylation (i.e., demethylation) compared to unexposed NK cells. The DNA methylation levels of these two IFNγ CpG sites correlated with increased expression of IFNγ following treatment with 7t15-21s+anti-TF-antibody. These data suggest that long-term exposure of NK cells (14 days expansion in culture) with a combination regimen of 7t15-21s+anti-TF-antibody is able to induce DNA demethylation of the two hypomethylated IFNγCpG sites (−186 and −54) and that 7t15-21s+anti-TF-antibody (IgG1) can epigenetically reprogram gene expression of IFNγ via DNA demethylation of CpG sites leading to interconversion of NK cells into innate immune memory NK cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXEMPLARY EMBODIMENTS

Embodiment A1

A single-chain chimeric polypeptide comprising:
(i) a first target-binding domain;
(ii) a soluble tissue factor domain; and
(iii) a second target-binding domain.

Embodiment A2

The single-chain chimeric polypeptide of embodiment A1, wherein the first target-binding domain and the soluble tissue factor domain directly abut each other.

Embodiment A3

The single-chain chimeric polypeptide of embodiment A1, wherein the single-chain chimeric polypeptide further comprises a linker sequence between the first target-binding domain and the soluble tissue factor domain.

Embodiment A4

The single-chain chimeric polypeptide of any one of embodiments A1-A3, wherein the soluble tissue factor domain and the second target-binding domain directly abut each other.

Embodiment A5

The single-chain chimeric polypeptide of any one of embodiments A1-A3, wherein the single-chain chimeric polypeptide further comprises a linker sequence between the soluble tissue factor domain and the second target-binding domain.

Embodiment A6

The single-chain chimeric polypeptide of embodiment A1, wherein the first target-binding domain and the second target-binding domain directly abut each other.

Embodiment A7

The single-chain chimeric polypeptide of embodiment A1, wherein the single-chain chimeric polypeptide further comprises a linker sequence between the first target-binding domain and the second target-binding domain.

Embodiment A8

The single-chain chimeric polypeptide of embodiment A6 or A7, wherein the second target-binding domain and the soluble tissue factor domain directly abut each other.

Embodiment A9

The single-chain chimeric polypeptide of embodiment A6 or A7, wherein the single-chain chimeric polypeptide further comprises a linker sequence between the second target-binding domain and the soluble tissue factor domain.

Embodiment A10

The single-chain chimeric polypeptide of any one of embodiments A1-A9, wherein the first target-binding domain and the second target-binding domain bind specifically to the same antigen.

Embodiment A11

The single-chain chimeric polypeptide of embodiment A10, wherein the first target-binding domain and the second target-binding domain bind specifically to the same epitope.

Embodiment A12

The single-chain chimeric polypeptide of embodiment A11, wherein the first target-binding domain and the second target-binding domain comprise the same amino acid sequence.

Embodiment A13

The single-chain chimeric polypeptide of any one of embodiments A1-A9, wherein the first target-binding domain and the second target-binding domain bind specifically to different antigens.

Embodiment A14

The single-chain chimeric polypeptide of any one of embodiments A1-A13, wherein one or both of the first target-binding domain and the second target-binding domain is an antigen-binding domain.

Embodiment A15

The single-chain chimeric polypeptide of embodiment A14, wherein the first target-binding domain and the second target-binding domain are each an antigen-binding domain.

Embodiment A16

The single-chain chimeric polypeptide of embodiment A13, wherein antigen-binding domain comprises a scFv or a single domain antibody.

Embodiment A17

The single-chain chimeric polypeptide of any one of embodiments A1-A16, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A18

The single-chain chimeric polypeptide of any one of embodiments A1-A16, wherein one or both of the first target-binding domain and the second target-binding domain is a soluble interleukin or cytokine protein.

Embodiment A19

The single-chain chimeric polypeptide of embodiment A18, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-D, and SCF, FLT3L, MICA, MICB, and a ULP16-binding protein.

Embodiment A20

The single-chain chimeric polypeptide of any one of embodiments A1-A16, wherein one or both of the first target-binding domain and the second target-binding domain is a soluble interleukin or cytokine receptor.

Embodiment A21

The single-chain chimeric polypeptide of embodiment A20, wherein the soluble interleukin or cytokine receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment A22

The single-chain chimeric polypeptide of any one of embodiments A1-A21, wherein the soluble tissue factor domain is a soluble human tissue factor domain.

Embodiment A23

The single-chain chimeric polypeptide of embodiment A22, wherein the soluble human tissue factor domain comprises a sequence that is at least 80% identical to SEQ ID NO: 93.

Embodiment A24

The single-chain chimeric polypeptide of embodiment A23, wherein the soluble human tissue factor domain comprises a sequence that is at least 90% identical to SEQ ID NO: 93.

Embodiment A25

The single-chain chimeric polypeptide of embodiment A24, wherein the soluble human tissue factor domain comprises a sequence that is at least 95% identical to SEQ ID NO: 93.

Embodiment A26

The single-chain chimeric polypeptide of any one of embodiments A22-A25, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A27

The single-chain chimeric polypeptide of embodiment A26, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A28

The single-chain chimeric polypeptide of any one of embodiments A1-A27, wherein the soluble tissue factor domain is not capable of binding Factor VIIa.

Embodiment A29

The single-chain chimeric polypeptide of any one of embodiments A1-A28, wherein the soluble tissue factor domain does not convert inactive Factor X into Factor Xa.

Embodiment A30

The single-chain chimeric polypeptide of any one of embodiments A1-A29, wherein the single-chain chimeric polypeptide does not stimulate blood coagulation in a mammal.

Embodiment A31

The single-chain chimeric polypeptide of any one of embodiments A1-A30, wherein the single-chain chimeric polypeptide further comprises one or more additional target-binding domains at its N- and/or C-terminus.

Embodiment A32

The single-chain chimeric polypeptide of embodiment A31, wherein the single-chain chimeric polypeptide comprises one or more additional target-binding domains at its N-terminus.

Embodiment A33

The single-chain chimeric polypeptide of embodiment A32, wherein one or more additional target-binding domains directly abuts the first target-binding domain, the second target-binding domain, or the soluble tissue factor domain.

Embodiment A34

The single-chain chimeric polypeptide of embodiment A33, wherein the single-chain chimeric polypeptide further comprises a linker sequence between one of the at least one additional target-binding domains and the first target-binding domain, the second target-binding domain, or the soluble tissue factor domain.

Embodiment A35

The single-chain chimeric polypeptide of embodiment A31, wherein the single-chain chimeric polypeptide comprises one or more additional target-binding domains at its C-terminus.

Embodiment A36

The single-chain chimeric polypeptide of embodiment A35, wherein one of the one or more additional target-binding domains directly abuts the first target-binding domain, the second target-binding domain, or the soluble tissue factor domain.

Embodiment A37

The single-chain chimeric polypeptide of embodiment A35, wherein the single-chain chimeric polypeptide further comprises a linker sequence between one of the at least one additional target-binding domains and the first target-binding domain, the second target-binding domain, or the soluble tissue factor domain.

Embodiment A38

The single-chain chimeric polypeptide of embodiment A31, wherein the single-chain chimeric polypeptide comprises one or more additional target binding domains at its N-terminus and the C-terminus.

Embodiment A39

The single-chain chimeric polypeptide of embodiment A38, wherein one of the one or more additional antigen binding domains at the N-terminus directly abuts the first target-binding domain, the second target-binding domain, or the soluble tissue factor domain.

Embodiment A40

The single-chain chimeric polypeptide of embodiment A38, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment A41

The single-chain chimeric polypeptide of embodiment A38, wherein one of the one or more additional antigen binding domains at the C-terminus directly abuts the first target-binding domain, the second target-binding domain, or the soluble tissue factor domain.

Embodiment A42

The single-chain chimeric polypeptide of embodiment A38, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment A43

The single-chain chimeric polypeptide of any one of embodiments A31-A42, wherein two or more of the first target-binding domain, the second target-binding domain, and the one or more additional target-binding domains bind specifically to the same antigen.

Embodiment A44

The single-chain chimeric polypeptide of embodiment A43, wherein two or more of the first target-binding domain, the second target-binding domain, and the one or more additional target-binding domains bind specifically to the same epitope.

Embodiment A45

The single-chain chimeric polypeptide of embodiment A44, wherein two or more of the first target-binding domain, the second target-binding domain, and the one or more additional target-binding domains comprise the same amino acid sequence.

Embodiment A46

The single-chain chimeric polypeptide of embodiment A43, wherein the first target-binding domain, the second target-binding domain, and the one or more additional target-binding domains each bind specifically to the same antigen.

Embodiment A47

The single-chain chimeric polypeptide of embodiment A46, wherein the first target-binding domain, the second target-binding domain, and the one or more additional target-binding domains each bind specifically to the same epitope.

Embodiment A48

The single-chain chimeric polypeptide of embodiment A47, wherein the first target-binding domain, the second target-binding domain, and the one or more additional target-binding domains each comprise the same amino acid sequence.

Embodiment A49

The single-chain chimeric polypeptide of any one of embodiments A31-A42, wherein the first target-binding domain, the second target-binding domain, and the one or more additional target-binding domains bind specifically to different antigens.

Embodiment A50

The single-chain chimeric polypeptide of any one of embodiments A31-A49, wherein one or more of the first target-binding domain, the second target-binding domain, and the one or more target-binding domains is an antigen-binding domain.

Embodiment A51

The single-chain chimeric polypeptide of embodiment A50, wherein the first target-binding domain, the second target-binding domain, and the one or more additional target-binding domains are each an antigen-binding domain.

Embodiment A52

The single-chain chimeric polypeptide of embodiment A51, wherein antigen-binding domain comprises a scFv or a single domain antibody.

Embodiment A53

The single-chain chimeric polypeptide of any one of embodiments A31-A52, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A54

The single-chain chimeric polypeptide of any one of embodiments A31-A52, wherein one or more of the first target-binding domain, the second target-binding domain, and the one or more additional target-binding domains is a soluble interleukin or cytokine protein.

Embodiment A55

The single-chain chimeric polypeptide of embodiment A54, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-D, and SCF, FLT3L, MICA, MICB, and a ULP16-binding protein.

Embodiment A56

The single-chain chimeric polypeptide of any one of embodiments A31-A52, wherein one or more of the first target-binding domain, the second target-binding domain, and the one or more additional target-binding domains is a soluble interleukin or cytokine receptor.

Embodiment A57

The single-chain chimeric polypeptide of embodiment A56, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

Embodiment A58

The single-chain chimeric polypeptide of any one of embodiments A1-A57, wherein the single-chain chimeric polypeptide further comprises a signal sequence at its N-terminal end.

Embodiment A59

The single-chain chimeric polypeptide of any one of embodiments A1-A58, wherein the single-chain chimeric polypeptide further comprises a peptide tag positioned at the N-terminal end or the C-terminal end of the single-chain chimeric polypeptide.

Embodiment A60

A composition comprising any of the single-chain chimeric polypeptides of embodiments A1-A59.

Embodiment A61

The composition of embodiment A60, wherein the composition is a pharmaceutical composition.

Embodiment A62

A kit comprising at least one dose of the composition of embodiment A60 or A61.

Embodiment A63

Nucleic acid encoding any of the single-chain chimeric polypeptides of any one of embodiments A1-A59.

Embodiment A64

A vector comprising the nucleic acid of embodiment A63.

Embodiment A65

The vector of embodiment A64, wherein the vector is an expression vector.

Embodiment A66

A cell comprising the nucleic acid of embodiment A63 or the vector of embodiment A64 or A65.

Embodiment A67

A method of producing a single-chain chimeric polypeptide, the method comprising:

culturing the cell of embodiment A66 in a culture medium under conditions sufficient to result in the production of the single-chain chimeric polypeptide; and recovering the single-chain chimeric polypeptide from the cell and/or the culture medium.

Embodiment A68

A single-chain chimeric polypeptide produced by the method of embodiment A67.

Embodiment A69

The single-chain chimeric polypeptide of embodiment A26, wherein the soluble human tissue factor domain comprises a sequence that is at least 80% identical to SEQ ID NO: 97.

Embodiment A70

The single-chain chimeric polypeptide of embodiment A69, wherein the soluble human tissue factor domain comprises a sequence that is at least 90% identical to SEQ ID NO: 97.

Embodiment A71

The single-chain chimeric polypeptide of embodiment A70, wherein the soluble human tissue factor domain comprises a sequence that is at least 95% identical to SEQ ID NO: 97.

Embodiment A72

The single-chain chimeric polypeptide of embodiment A71, wherein the soluble human tissue factor domain comprises a sequence that is 100% identical to SEQ ID NO: 97.

Embodiment A73

The single-chain chimeric polypeptide of embodiment A26, wherein the soluble human tissue factor domain comprises a sequence that is at least 80% identical to SEQ ID NO: 98.

Embodiment A74

The single-chain chimeric polypeptide of embodiment A73, wherein the soluble human tissue factor domain comprises a sequence that is at least 90% identical to SEQ ID NO: 98.

Embodiment A75

The single-chain chimeric polypeptide of embodiment A74, wherein the soluble human tissue factor domain comprises a sequence that is at least 95% identical to SEQ ID NO: 98.

Embodiment A76

The single-chain chimeric polypeptide of embodiment A75, wherein the soluble human tissue factor domain comprises a sequence that is 100% identical to SEQ ID NO: 98.

Embodiment B1

A single-chain chimeric polypeptide comprising:

(i) a first target-binding domain;

(ii) a soluble tissue factor domain; and (iii) a second target-binding domain, wherein:

the first target-binding domain and the second target-binding domain each specifically bind to an IL-2 receptor; or the first target-binding domain and the second target-binding domain each specifically bind to an IL-15 receptor.

Embodiment B2

The single-chain chimeric polypeptide of embodiment B1, wherein the first target-binding domain and the soluble tissue factor domain directly abut each other.

Embodiment B3

The single-chain chimeric polypeptide of embodiment B1, wherein the single-chain chimeric polypeptide further comprises a linker sequence between the first target-binding domain and the soluble tissue factor domain.

Embodiment B4

The single-chain chimeric polypeptide of any one of embodiments B1-B3, wherein the soluble tissue factor domain and the second target-binding domain directly abut each other.

Embodiment B5

The single-chain chimeric polypeptide of any one of embodiments B1-B3, wherein the single-chain chimeric polypeptide further comprises a linker sequence between the soluble tissue factor domain and the second target-binding domain.

Embodiment B6

The single-chain chimeric polypeptide of embodiment B1, wherein the first target-binding domain and the second target-binding domain directly abut each other.

Embodiment B7

The single-chain chimeric polypeptide of embodiment B1, wherein the single-chain chimeric polypeptide further comprises a linker sequence between the first target-binding domain and the second target-binding domain.

Embodiment B8

The single-chain chimeric polypeptide of embodiment B6 or B7, wherein the second target-binding domain and the soluble tissue factor domain directly abut each other.

Embodiment B9

The single-chain chimeric polypeptide of embodiment B6 or B7, wherein the single-chain chimeric polypeptide further comprises a linker sequence between the second target-binding domain and the soluble tissue factor domain.

Embodiment B10

The single-chain chimeric polypeptide of any one of embodiments B1-B9, wherein both the first target-binding domain and the second target-binding domain is a soluble interleukin protein.

Embodiment B11

The single-chain chimeric polypeptide of embodiment B10, wherein the first target-binding domain and the second target-binding domain is a soluble IL-2 protein.

Embodiment B12

The single-chain chimeric polypeptide of embodiment B11, wherein the soluble IL-2 protein is a soluble human IL-2 protein.

Embodiment B13

The single-chain chimeric polypeptide of embodiment B12, wherein the soluble human IL-2 protein comprises SEQ ID NO: 78.

Embodiment B14

The single-chain chimeric polypeptide of embodiment B10, wherein the first target-binding domain and the second target-binding domain is a soluble IL-15 protein.

Embodiment B15

The single-chain chimeric polypeptide of embodiment B14, wherein the soluble IL-15 protein is a soluble human IL-15 protein.

Embodiment B16

The single-chain chimeric polypeptide of embodiment B15, wherein the soluble human IL-15 protein comprises SEQ ID NO: 82.

Embodiment B17

The single-chain chimeric polypeptide of any one of embodiments B1-B16, wherein the soluble tissue factor domain is a soluble human tissue factor domain.

Embodiment B18

The single-chain chimeric polypeptide of embodiment B17, wherein the soluble human tissue factor domain comprises a sequence that is at least 80% identical to SEQ ID NO: 93.

Embodiment B19

The single-chain chimeric polypeptide of embodiment B18, wherein the soluble human tissue factor domain comprises a sequence that is at least 90% identical to SEQ ID NO: 93.

Embodiment B20

The single-chain chimeric polypeptide of embodiment B19, wherein the soluble human tissue factor domain comprises a sequence that is at least 95% identical to SEQ ID NO: 93.

Embodiment B21

The single-chain chimeric polypeptide of any one of embodiments B17-B20, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B22

The single-chain chimeric polypeptide of embodiment B21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B23

The single-chain chimeric polypeptide of any one of embodiments B1-B22, wherein the soluble tissue factor domain is not capable of binding Factor VIIa.

Embodiment B24

The single-chain chimeric polypeptide of any one of embodiments B1-B23, wherein the soluble tissue factor domain does not convert inactive Factor X into Factor Xa.

Embodiment B25

The single-chain chimeric polypeptide of any one of embodiments B1-B24, wherein the single-chain chimeric polypeptide does not stimulate blood coagulation in a mammal.

Embodiment B26

The single-chain chimeric polypeptide of any one of embodiments B1-B25, wherein the single-chain chimeric polypeptide further comprises one or more additional target-binding domains at its N- and/or C-terminus.

Embodiment B27

The single-chain chimeric polypeptide of embodiment B26, wherein the single-chain chimeric polypeptide comprises one or more additional target-binding domains at its N-terminus.

Embodiment B28

The single-chain chimeric polypeptide of embodiment B27, wherein one or more additional target-binding domains directly abuts the first target-binding domain, the second target-binding domain, or the soluble tissue factor domain.

Embodiment B29

The single-chain chimeric polypeptide of embodiment B28, wherein the single-chain chimeric polypeptide further comprises a linker sequence between one of the at least one additional target-binding domains and the first target-binding domain, the second target-binding domain, or the soluble tissue factor domain.

Embodiment B30

The single-chain chimeric polypeptide of embodiment B26, wherein the single-chain chimeric polypeptide comprises one or more additional target-binding domains at its C-terminus.

Embodiment B31

The single-chain chimeric polypeptide of embodiment B30, wherein one of the one or more additional target-binding domains directly abuts the first target-binding domain, the second target-binding domain, or the soluble tissue factor domain.

Embodiment B32

The single-chain chimeric polypeptide of embodiment B30, wherein the single-chain chimeric polypeptide further comprises a linker sequence between one of the at least one additional target-binding domains and the first target-binding domain, the second target-binding domain, or the soluble tissue factor domain.

Embodiment B33

The single-chain chimeric polypeptide of embodiment B26, wherein the single-chain chimeric polypeptide comprises one or more additional target binding domains at its N-terminus and the C-terminus.

Embodiment B34

The single-chain chimeric polypeptide of embodiment B33, wherein one of the one or more additional antigen binding domains at the N-terminus directly abuts the first target-binding domain, the second target-binding domain, or the soluble tissue factor domain.

Embodiment B35

The single-chain chimeric polypeptide of embodiment B33, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment B36

The single-chain chimeric polypeptide of embodiment B33, wherein one of the one or more additional antigen binding domains at the C-terminus directly abuts the first target-binding domain, the second target-binding domain, or the soluble tissue factor domain.

Embodiment B37

The single-chain chimeric polypeptide of embodiment B33, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment B38

The single-chain chimeric polypeptide of any one of embodiments B26-B37, wherein each of the first target-binding domain, the second target-binding domain, and the one or more additional target-binding domains bind specifically to an IL-2 receptor or an IL-15 receptor.

Embodiment B39

The single-chain chimeric polypeptide of embodiment B38, wherein each of the first target-binding domain, the second target-binding domain, and the one or more additional target-binding domains comprise the same amino acid sequence.

Embodiment B40

The single-chain chimeric polypeptide of any one of embodiments B26-B37, wherein the one or more additional target-binding domains is an antigen-binding domain.

Embodiment B41

The single-chain chimeric polypeptide of embodiment B40, wherein the antigen-binding domain comprises a scFv or a single domain antibody.

Embodiment B42

The single-chain chimeric polypeptide of any one of embodiments B26-B37, B40, and B41, wherein the one or more additional target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment B43

The single-chain chimeric polypeptide of any one of embodiments B6-B37, B40, and B41, wherein the one or more additional target-binding domains is a soluble interleukin or cytokine protein.

Embodiment B44

The single-chain chimeric polypeptide of embodiment B43, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment B45

The single-chain chimeric polypeptide of any one of embodiments B6-B37, B40, and B41, wherein the one or more additional target-binding domains is a soluble interleukin or cytokine receptor.

Embodiment B46

The single-chain chimeric polypeptide of embodiment B45, wherein the soluble receptor is a soluble TGF-β receptor II (TGF-βRII) and a soluble TGF-βRIII.

Embodiment B47

The single-chain chimeric polypeptide of any one of embodiments B1-B46, wherein the single-chain chimeric polypeptide further comprises a signal sequence at its N-terminal end.

Embodiment B48

The single-chain chimeric polypeptide of any one of embodiments B1-B47, wherein the single-chain chimeric polypeptide further comprises a peptide tag positioned at the N-terminal end or the C-terminal end of the single-chain chimeric polypeptide.

Embodiment B49

A composition comprising any of the single-chain chimeric polypeptides of embodiments B1-B48.

Embodiment B50

The composition of embodiment B49, wherein the composition is a pharmaceutical composition.

Embodiment B51

A kit comprising at least one dose of the composition of embodiment B49 or B50.

Embodiment B52

A nucleic acid encoding any of the single-chain chimeric polypeptides of any one of embodiments B1-B48.

Embodiment B53

A vector comprising the nucleic acid of embodiment B52.

Embodiment B54

The vector of embodiment B53, wherein the vector is an expression vector.

Embodiment B55

A cell comprising the nucleic acid of embodiment B52 or the vector of embodiment B53 or B54.

Embodiment B56

A method of producing a single-chain chimeric polypeptide, the method comprising:

culturing the cell of embodiment B55 in a culture medium under conditions sufficient to result in the production of the single-chain chimeric polypeptide; and recovering the single-chain chimeric polypeptide from the cell and/or the culture medium.

Embodiment B57

A single-chain chimeric polypeptide produced by the method of embodiment B56.

Embodiment B58

The single-chain chimeric polypeptide of embodiment B21, wherein the soluble human tissue factor domain comprises a sequence that is at least 80% identical to SEQ ID NO: 97.

Embodiment B59

The single-chain chimeric polypeptide of embodiment B58, wherein the soluble human tissue factor domain comprises a sequence that is at least 90% identical to SEQ ID NO: 97.

Embodiment B60

The single-chain chimeric polypeptide of embodiment B59, wherein the soluble human tissue factor domain comprises a sequence that is at least 95% identical to SEQ ID NO: 97.

Embodiment B61

The single-chain chimeric polypeptide of embodiment B60, wherein the soluble human tissue factor domain comprises a sequence that is 100% identical to SEQ ID NO: 97.

Embodiment B62

The single-chain chimeric polypeptide of embodiment B21, wherein the soluble human tissue factor domain comprises a sequence that is at least 80% identical to SEQ ID NO: 98.

Embodiment B63

The single-chain chimeric polypeptide of embodiment B62, wherein the soluble human tissue factor domain comprises a sequence that is at least 90% identical to SEQ ID NO: 98.

Embodiment B64

The single-chain chimeric polypeptide of embodiment B63, wherein the soluble human tissue factor domain comprises a sequence that is at least 95% identical to SEQ ID NO: 98.

Embodiment B65

The single-chain chimeric polypeptide of embodiment B64, wherein the soluble human tissue factor domain comprises a sequence that is 100% identical to SEQ ID NO: 98.

Embodiment C1

A multi-chain chimeric polypeptide comprising:

(a) a first chimeric polypeptide comprising:

(i) a first target-binding domain;

(ii) a soluble tissue factor domain; and (iii) a first domain of a pair of affinity domains;

(b) a second chimeric polypeptide comprising:

(i) a second domain of a pair of affinity domains; and (ii) a second target-binding domain, wherein the first chimeric polypeptide and the second chimeric polypeptide associate through the binding of the first domain and the second domain of the pair of affinity domains.

Embodiment C2

The multi-chain chimeric polypeptide of embodiment C1, wherein the first target-binding domain and the soluble tissue factor domain directly abut each other in the first chimeric polypeptide.

Embodiment C3

The multi-chain chimeric polypeptide of embodiment C1, wherein the first chimeric polypeptide further comprises a linker sequence between the first target-binding domain and the soluble tissue factor domain in the first chimeric polypeptide.

Embodiment C4

The multi-chain chimeric polypeptide of any one of embodiments C1-C3, wherein the soluble tissue factor domain and the first domain of the pair of affinity domains directly abut each other in the first chimeric polypeptide.

Embodiment C5

The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6

The multi-chain chimeric polypeptide of any one of embodiments C1-05, wherein the second domain of the pair of affinity domains and the second target-binding domain directly abut each other in the second chimeric polypeptide.

Embodiment C7

The multi-chain chimeric polypeptide of any one of embodiments C1-05, wherein second chimeric polypeptide further comprises a linker sequence between the second domain of the pair of affinity domains and the second target-binding domain in the second chimeric polypeptide.

Embodiment C8

The multi-chain chimeric polypeptide of any one of embodiments C1-C7, wherein the first target-binding domain and the second target-binding domain bind specifically to the same antigen.

Embodiment C9

The multi-chain chimeric polypeptide of embodiment C8, wherein the first target-binding domain and the second target-binding domain bind specifically to the same epitope.

Embodiment C10

The multi-chain chimeric polypeptide of embodiment C9, wherein the first target-binding domain and the second target-binding domain comprise the same amino acid sequence.

Embodiment C11

The multi-chain chimeric polypeptide of any one of embodiments C1-C7, wherein the first target-binding domain and the second target-binding domain bind specifically to different antigens.

Embodiment C12

The multi-chain chimeric polypeptide of any one of embodiments C1-C11, wherein one or both of the first target-binding domain and the second target-binding domain is an antigen-binding domain.

Embodiment C13

The multi-chain chimeric polypeptide of embodiment C12, wherein the first target-binding domain and the second target-binding domain are each antigen-binding domains.

Embodiment C14

The multi-chain chimeric polypeptide of embodiment C12 or C13, wherein antigen-binding domain comprises a scFv or a single domain antibody.

Embodiment C15

The multi-chain chimeric polypeptide of any one of embodiments C1-C14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment C16

The multi-chain chimeric polypeptide of any one of embodiments C1-C14, wherein one or both of the first target-binding domain and the second target-binding domain is a soluble interleukin or cytokine protein.

Embodiment C17

The multi-chain chimeric polypeptide of embodiment C16, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C18

The multi-chain chimeric polypeptide of any one of embodiments C1-C14, wherein one or both of the first target-binding domain and the second target-binding domain is a soluble interleukin or cytokine receptor.

Embodiment C19

The multi-chain chimeric polypeptide of embodiment C18, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment C20

The multi-chain chimeric polypeptide of any one of embodiments C1-C19, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment C21

The multi-chain chimeric polypeptide of embodiment C20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment C22

The multi-chain chimeric polypeptide of any one of embodiments C1-C19, wherein the first chimeric polypeptide further comprises one or more additional target-binding domains at the N-terminal and/or C-terminal end of the first chimeric polypeptide.

Embodiment C23

The multi-chain chimeric polypeptide of embodiment C22, wherein at least one of the one or more additional target-binding domains directly abuts the first domain of the pair of affinity domains in the first chimeric polypeptide.

Embodiment C24

The multi-chain chimeric polypeptide of embodiment C22, wherein the first chimeric polypeptide further comprises a linker sequence between the at least one of the one or more additional target-binding domains and the first domain of the pair of affinity domains.

Embodiment C25

The multi-chain chimeric polypeptide of embodiment C22, wherein the at least one of the one or more additional target-binding domains directly abuts the first target-binding domain in the first chimeric polypeptide.

Embodiment C26

The multi-chain chimeric polypeptide of embodiment C22, wherein the first chimeric polypeptide further comprises a linker sequence between the at least one of the one or more additional target-binding domains and the first target-binding domain.

Embodiment C27

The multi-chain chimeric polypeptide of embodiment C22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment C28

The multi-chain chimeric polypeptide of embodiment C27, wherein the at least one additional target-binding domain of the one or more additional target-binding domains disposed at the N-terminus directly abuts the first target-binding domain or the first domain of the pair of affinity domains in the first chimeric polypeptide.

Embodiment C29

The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C30

The multi-chain chimeric polypeptide of embodiment C27, wherein the at least one additional target-binding domain of the one or more additional target-binding domains disposed at the C-terminus directly abuts the first target-binding domain or the first domain of the pair of affinity domains in the first chimeric polypeptide.

Embodiment C31

The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C32

The multi-chain chimeric polypeptide of embodiment C27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C33

The multi-chain chimeric polypeptide of embodiment C27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C34

The multi-chain chimeric polypeptide of any one of embodiments C1-C33, wherein the second chimeric polypeptide further comprises one or more additional target-binding domains at the N-terminal end or the C-terminal end of the second chimeric polypeptide.

Embodiment C35

The multi-chain chimeric polypeptide of embodiment C34, wherein at least one of the one or more additional target-binding domains directly abuts the second domain of the pair of affinity domains in the second chimeric polypeptide.

Embodiment C36

The multi-chain chimeric polypeptide of embodiment C34, wherein the second chimeric polypeptide further comprises a linker sequence between at least one of the one or more additional target-binding domains and the second domain of the pair of affinity domains in the second chimeric polypeptide.

Embodiment C37

The multi-chain chimeric polypeptide of embodiment C34, wherein at least one of the one or more additional target-binding domains directly abuts the second target-binding domain in the second chimeric polypeptide.

Embodiment C38

The multi-chain chimeric polypeptide of embodiment C34, wherein the second chimeric polypeptide further comprises a linker sequence between at least one of the one or more additional target-binding domains and the second target-binding domain in the second chimeric polypeptide.

Embodiment C39

The multi-chain chimeric polypeptide of any one of embodiments C20-C38, wherein two or more of the first target-binding domain, the second target-binding domain, and the one or more additional target-binding domains bind specifically to the same antigen.

Embodiment C40

The multi-chain chimeric polypeptide of embodiment C39, wherein two or more of the first target-binding domain, the second target-binding domain, and the one or more additional target-binding domains bind specifically to the same epitope.

Embodiment C41

The multi-chain chimeric polypeptide of embodiment C40, wherein two or more of the first target-binding domain, the second target-binding domain, and the one or more additional target-binding domains comprise the same amino acid sequence.

Embodiment C42

The multi-chain chimeric polypeptide of embodiment C39, wherein the first target-binding domain, the second target-binding domain, and the one or more additional target-binding domains each bind specifically to the same antigen.

Embodiment C43

The multi-chain chimeric polypeptide of embodiment C42, wherein the first target-binding domain, the second target-binding domain, and the one or more additional target-binding domains each bind specifically to the same epitope.

Embodiment C44

The multi-chain chimeric polypeptide of embodiment C43, wherein the first target-binding domain, the second target-binding domain, and the one or more additional target-binding domains each comprise the same amino acid sequence.

Embodiment C45

The multi-chain chimeric polypeptide of any one of embodiments C20-C38, wherein the first target-binding domain, the second target-binding domain, and the one or more additional target-binding domains bind specifically to different antigens.

Embodiment C46

The multi-chain chimeric polypeptide of any one of embodiments C20-C45, wherein one or more of the first target-binding domain, the second target-binding domain, and the one or more target-binding domains is an antigen-binding domain.

Embodiment C47

The multi-chain chimeric polypeptide of embodiment C46, wherein the first target-binding domain, the second target-binding domain, and the one or more additional target-binding domains are each an antigen-binding domain.

Embodiment C48

The multi-chain chimeric polypeptide of embodiment C47, wherein antigen-binding domain comprises a scFv.

Embodiment C49

The multi-chain chimeric polypeptide of any one of embodiments C20-C48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment C50

The multi-chain chimeric polypeptide of any one of embodiments C20-C48, wherein one or more of the first target-binding domain, the second target-binding domain, and the one or more additional target-binding domains is a soluble interleukin or cytokine protein.

Embodiment C51

The multi-chain chimeric polypeptide of embodiment C50, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, and SCF, FLT3L, MICA, MICB, and a ULP16-binding protein.

Embodiment C52

The multi-chain chimeric polypeptide of any one of embodiments C20-C48, wherein one or more of the first target-binding domain, the second target-binding domain, and the one or more additional target-binding domains is a soluble interleukin or cytokine receptor.

Embodiment C53

The multi-chain chimeric polypeptide of embodiment C52, wherein the soluble receptor is a soluble TGF-β receptor II (TGF-β MI), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

Embodiment C54

The multi-chain chimeric polypeptide of any one of embodiments C1-053, wherein the first chimeric polypeptide further comprises a peptide tag at the N-terminal end or the C-terminal end of the first chimeric polypeptide.

Embodiment C55

The multi-chain chimeric polypeptide of any one of embodiments C1-053, wherein the second chimeric polypeptide further comprises a peptide tag at the N-terminal end or the C-terminal end of the second chimeric polypeptide.

Embodiment C56

The multi-chain chimeric polypeptide of any one of embodiments C1-055, wherein the soluble tissue factor domain is a soluble human tissue factor domain.

Embodiment C57

The multi-chain chimeric polypeptide of embodiment C56, wherein the soluble human tissue factor domain comprises a sequence that is at least 80% identical to SEQ ID NO: 93.

Embodiment C58

The multi-chain chimeric polypeptide of embodiment C57, wherein the soluble human tissue factor domain comprises a sequence that is at least 90% identical to SEQ ID NO: 93.

Embodiment C59

The multi-chain chimeric polypeptide of embodiment C58, wherein the soluble human tissue factor domain comprises a sequence that is at least 95% identical to SEQ ID NO: 93.

Embodiment C60

The multi-chain chimeric polypeptide of any one of embodiments C56-059, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C61

The multi-chain chimeric polypeptide of embodiment C60, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C62

The multi-chain chimeric polypeptide of any one of embodiments C1-C61, wherein the soluble tissue factor domain is not capable of binding to Factor VIIa.

Embodiment C63

The multi-chain chimeric polypeptide of any one of embodiments C1-C62, wherein the soluble tissue factor domain does not convert inactive Factor X into Factor Xa.

Embodiment C64

The multi-chain chimeric polypeptide of any one of embodiments C1-C63, wherein the multi-chain chimeric polypeptide does not stimulate blood coagulation in a mammal.

Embodiment C65

The multi-chain chimeric polypeptide of any one of embodiments C1-C64, wherein the pair of affinity domains is a sushi domain from an alpha chain of human IL-15 receptor (IL-15Rα) and a soluble IL-15.

Embodiment C66

The multi-chain chimeric polypeptide of embodiment C65, wherein the soluble IL-15 has a D8N or D8A amino acid substitution.

Embodiment C67

The multi-chain chimeric polypeptide of embodiment C65 or C66, wherein the human IL-15Rα is a mature full-length IL-15Rα.

Embodiment C68

The multi-chain chimeric polypeptide of any one of embodiments C1-C64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C69

The multi-chain chimeric polypeptide of any one of embodiments C1-C68, wherein the first chimeric polypeptide and/or the second chimeric polypeptide further comprises a signal sequence at its N-terminal end.

Embodiment C70

A composition comprising any of the multi-chain chimeric polypeptides of embodiments C1-C69.

Embodiment C71

The composition of embodiment C70, wherein the composition is a pharmaceutical composition.

Embodiment C72

A kit comprising at least one dose of the composition of embodiment C70 or C71.

Embodiment C73

Nucleic acid encoding any of the multi-chain chimeric polypeptides of any one of embodiments C1-C69.

Embodiment C74

A vector comprising the nucleic acid of embodiment C73.

Embodiment C75

The vector of embodiment C74, wherein the vector is an expression vector.

Embodiment C76

A cell comprising the nucleic acid of embodiment C73 or the vector of embodiment C74 or C75.

Embodiment C77

A method of producing a multi-chain chimeric polypeptide, the method comprising:

culturing the cell of embodiment C76 in a culture medium under conditions sufficient to result in the production of the multi-chain chimeric polypeptide; and recovering the multi-chain chimeric polypeptide from the cell and/or the culture medium.

Embodiment C78

A multi-chain chimeric polypeptide produced by the method of embodiment C77.

Embodiment C79

The multi-chain chimeric polypeptide of embodiment A56, wherein the soluble human tissue factor domain comprises a sequence that is at least 80% identical to SEQ ID NO: 97.

Embodiment C80

The multi-chain chimeric polypeptide of embodiment C79, wherein the soluble human tissue factor domain comprises a sequence that is at least 90% identical to SEQ ID NO: 97.

Embodiment C81

The multi-chain chimeric polypeptide of embodiment C80, wherein the soluble human tissue factor domain comprises a sequence that is at least 95% identical to SEQ ID NO: 97.

Embodiment C82

The multi-chain chimeric polypeptide of embodiment C81, wherein the soluble human tissue factor domain comprises a sequence that is 100% identical to SEQ ID NO: 97.

Embodiment C83

The multi-chain chimeric polypeptide of embodiment C56, wherein the soluble human tissue factor domain comprises a sequence that is at least 80% identical to SEQ ID NO: 98.

Embodiment C84

The multi-chain chimeric polypeptide of embodiment C83, wherein the soluble human tissue factor domain comprises a sequence that is at least 90% identical to SEQ ID NO: 98.

Embodiment C85

The multi-chain chimeric polypeptide of embodiment C84, wherein the soluble human tissue factor domain comprises a sequence that is at least 95% identical to SEQ ID NO: 98.

Embodiment C86

The multi-chain chimeric polypeptide of embodiment C85, wherein the soluble human tissue factor domain comprises a sequence that is 100% identical to SEQ ID NO: 98.

Embodiment D1

A multi-chain chimeric polypeptide comprising:

(a) a first chimeric polypeptide comprising:

(i) a first target-binding domain;

(ii) a soluble tissue factor domain; and (iii) a first domain of a pair of affinity domains;

(b) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-18 or a receptor of IL-12.

Embodiment D2

The multi-chain chimeric polypeptide of embodiment D1, wherein the first target-binding domain and the soluble tissue factor domain directly abut each other in the first chimeric polypeptide.

Embodiment D3

The multi-chain chimeric polypeptide of embodiment D1, wherein the first chimeric polypeptide further comprises a linker sequence between the first target-binding domain and the soluble tissue factor domain in the first chimeric polypeptide.

Embodiment D4

The multi-chain chimeric polypeptide of any one of embodiments D1-D3, wherein the soluble tissue factor domain and the first domain of the pair of affinity domains directly abut each other in the first chimeric polypeptide.

Embodiment D5

The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6

The multi-chain chimeric polypeptide of any one of embodiments D1-D5, wherein the second domain of the pair of affinity domains and the second target-binding domain directly abut each other in the second chimeric polypeptide.

Embodiment D7

The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8

The multi-chain chimeric polypeptide of any one of embodiments D1-D7, wherein the soluble tissue factor domain is a soluble human tissue factor domain.

Embodiment D9

The multi-chain chimeric polypeptide of embodiment D8, wherein the soluble human tissue factor domain comprises a sequence that is at least 80% identical to SEQ ID NO: 93.

Embodiment D10

The multi-chain chimeric polypeptide of embodiment D9, wherein the soluble human tissue factor domain comprises a sequence that is at least 90% identical to SEQ ID NO: 93.

Embodiment D11

The multi-chain chimeric polypeptide of embodiment D10, wherein the soluble human tissue factor domain comprises a sequence that is at least 95% identical to SEQ ID NO: 93.

Embodiment D12

The multi-chain chimeric polypeptide of any one of embodiments D8-D11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D13

The multi-chain chimeric polypeptide of embodiment D12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D14

The multi-chain chimeric polypeptide of any one of embodiments D1-D13, wherein the soluble tissue factor domain is not capable of binding to Factor VIIa.

Embodiment D15

The multi-chain chimeric polypeptide of any one of embodiments D1-D14, wherein the soluble tissue factor domain does not convert inactive Factor X into Factor Xa.

Embodiment D16

The multi-chain chimeric polypeptide of any one of embodiments D1-D15, wherein the multi-chain chimeric polypeptide does not stimulate blood coagulation in a mammal.

Embodiment D17

The multi-chain chimeric polypeptide of any one of embodiments D1-D16, wherein the first chimeric polypeptide further comprises a peptide tag at the N-terminal end or the C-terminal end of the first chimeric polypeptide.

Embodiment D18

The multi-chain chimeric polypeptide of any one of embodiments D1-D17, wherein the second chimeric polypeptide further comprises a peptide tag at the N-terminal end or the C-terminal end of the second chimeric polypeptide.

Embodiment D19

The multi-chain chimeric polypeptide of any one of embodiments D1-D18, wherein the first chimeric polypeptide and/or the second chimeric polypeptide further comprises a signal sequence at its N-terminal end.

Embodiment D20

The multi-chain chimeric polypeptide of embodiment D19, wherein the signal sequence comprises SEQ ID NO: 117.

Embodiment D21

The multi-chain chimeric polypeptide of embodiment D20, wherein the signal sequence is SEQ ID NO: 117.

Embodiment D22

The multi-chain chimeric polypeptide of any one of embodiments D1-D21, wherein the pair of affinity domains is a sushi domain from an alpha chain of human IL-15 receptor (IL-15Rα) and a soluble IL-15.

Embodiment D23

The multi-chain chimeric polypeptide of embodiment D22, wherein the soluble IL-15 has a D8N or D8A amino acid substitution.

Embodiment D24

The multi-chain chimeric polypeptide of embodiment D22, wherein the soluble IL-15 comprises a sequence that is 80% identical to SEQ ID NO: 82.

Embodiment D25

The multi-chain chimeric polypeptide of embodiment D24, wherein the soluble IL-15 comprises a sequence that is 90% identical to SEQ ID NO: 82.

Embodiment D26

The multi-chain chimeric polypeptide of embodiment D25, wherein the soluble IL-15 comprises a sequence that is 95% identical to SEQ ID NO: 82.

Embodiment D27

The multi-chain chimeric polypeptide of embodiment D26, wherein the soluble IL-15 comprises SEQ ID NO: 82.

Embodiment D28

The multi-chain chimeric polypeptide of any one of embodiments D22-D27, wherein the sushi domain of IL-15Rα comprises a sushi domain from human IL-15Rα.

Embodiment D29

The multi-chain chimeric polypeptide of embodiment D28, wherein the sushi domain from human IL-15Rα comprises a sequence that is 80% identical to SEQ ID NO: 113.

Embodiment D30

The multi-chain chimeric polypeptide of embodiment D29, wherein the sushi domain from human IL-15Rα comprises a sequence that is 90% identical to SEQ ID NO: 113.

Embodiment D31

The multi-chain chimeric polypeptide of embodiment D30, wherein the sushi domain from human IL-15Rα comprises a sequence that is 95% identical to SEQ ID NO: 113.

Embodiment D32

The multi-chain chimeric polypeptide of embodiment D31, wherein the sushi domain from human IL-15Rα comprises SEQ ID NO: 113.

Embodiment D33

The multi-chain chimeric polypeptide of embodiment D28, wherein the sushi domain from human IL-15Rα is a mature full-length IL-15Rα.

Embodiment D34

The multi-chain chimeric polypeptide of any one of embodiments D1-D21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D35

The multi-chain chimeric polypeptide of any one of embodiments D1-D34, wherein one or both of the first target-binding domain and the second target-binding domain is an agonistic antigen-binding domain.

Embodiment D36

The multi-chain chimeric polypeptide of embodiment D35, wherein the first target-binding domain and the second target-binding domain are each agonistic antigen-binding domains.

Embodiment D37

The multi-chain chimeric polypeptide of embodiment D35 or D36, wherein antigen-binding domain comprises a scFv or single-domain antibody.

Embodiment D38

The multi-chain chimeric polypeptide of any one of embodiments D1-D34, wherein one or both of the first target-binding domain and the second target-binding domain is a soluble IL-15 or a soluble IL-18.

Embodiment D39

The multi-chain chimeric polypeptide of embodiment D38, wherein the first target-binding domain and the second target-binding domain are each independently a soluble IL-15 or a soluble IL-18.

Embodiment D40

The multi-chain chimeric polypeptide of any one of embodiments D1-D39, wherein the first target-binding domain and the second target-binding domain both bind specifically to a receptor of IL-18 or a receptor of IL-12.

Embodiment D41

The multi-chain chimeric polypeptide of embodiment B40, wherein the first target-binding domain and the second target-binding domain bind specifically to the same epitope.

Embodiment D42

The multi-chain chimeric polypeptide of embodiment D41, wherein the first target-binding domain and the second target-binding domain comprise the same amino acid sequence.

Embodiment D43

The multi-chain chimeric polypeptide of any one of embodiments D1-D39, wherein the first target-binding domain binds specifically to a receptor for IL-12, and the second target-binding domain binds specifically to a receptor for IL-18.

Embodiment D44

The multi-chain chimeric polypeptide of any one of embodiments D1-D39, wherein the first target-binding domain binds specifically to a receptor for IL-18, and the second target-binding domain bind specifically to a receptor for IL-12.

Embodiment D45

The multi-chain chimeric polypeptide of embodiment D44, wherein the first target-binding domain comprises a soluble IL-18.

Embodiment D46

The multi-chain chimeric polypeptide of embodiment D45, wherein the soluble IL-18 is a soluble human IL-18.

Embodiment D47

The multi-chain chimeric polypeptide of embodiment D46, wherein the soluble human IL-18 comprises a sequence at least 80% identical to SEQ ID NO: 109.

Embodiment D48

The multi-chain chimeric polypeptide of embodiment D47, wherein the soluble human IL-18 comprises a sequence at least 90% identical to SEQ ID NO: 109.

Embodiment D49

The multi-chain chimeric polypeptide of embodiment D48, wherein the soluble human IL-18 comprises a sequence at least 95% identical to SEQ ID NO: 109.

Embodiment D50

The multi-chain chimeric polypeptide of embodiment D49, wherein the soluble human IL-18 comprises a sequence of SEQ ID NO: 109.

Embodiment D51

The multi-chain chimeric polypeptide of any one of embodiments D44-D50, wherein the second target-binding domain comprises a soluble IL-12.

Embodiment D52

The multi-chain chimeric polypeptide of embodiment D51, wherein the soluble IL-18 is a soluble human IL-12.

Embodiment D53

The multi-chain chimeric polypeptide of embodiment D52, wherein the soluble human IL-15 comprises a sequence of soluble human IL-12β (p40) and a sequence of soluble human IL-12α (p35).

Embodiment D54

The multi-chain chimeric polypeptide of embodiment D53, wherein the soluble human IL-15 further comprises a linker sequence between the sequence of soluble IL-12β (p40) and the sequence of soluble human IL-12α (p35).

Embodiment D55

The multi-chain chimeric polypeptide of embodiment D54, wherein the linker sequence comprises SEQ ID NO: 102.

Embodiment D56

The multi-chain chimeric polypeptide of any one of embodiments D53-D55, wherein the sequence of soluble human IL-12β (p40) comprises a sequence that is at least 80% identical to SEQ ID NO: 81.

Embodiment D57

The multi-chain chimeric polypeptide of embodiment D56, wherein the sequence of soluble human IL-12β (p40) comprises a sequence that is at least 90% identical to SEQ ID NO: 81.

Embodiment D58

The multi-chain chimeric polypeptide of embodiment D57, wherein the sequence of soluble human IL-12β (p40) comprises a sequence that is at least 95% identical to SEQ ID NO: 81.

Embodiment D59

The multi-chain chimeric polypeptide of embodiment D58, wherein the sequence of soluble human IL-12β (p40) comprises SEQ ID NO: 81.

Embodiment D60

The multi-chain chimeric polypeptide of any one of embodiments D53-D59, wherein the sequence of soluble human IL-12α (p35) comprises a sequence that is at least 80% identical to SEQ ID NO: 80.

Embodiment D61

The multi-chain chimeric polypeptide of embodiment D60, wherein the sequence of soluble human IL-12α (p35) comprises a sequence that is at least 90% identical to SEQ ID NO: 80.

Embodiment D62

The mule-chain chimeric polypeptide of embodiment D61, wherein the sequence of soluble human IL-12α (p35) comprises a sequence that is at least 95% identical to SEQ ID NO: 80.

Embodiment D63

The multi-chain chimeric polypeptide of embodiment D62, wherein the sequence of soluble human IL-12α (p35) comprises SEQ ID NO: 80.

Embodiment D64

The multi-chain chimeric polypeptide of embodiment D1, wherein the first chimeric polypeptide comprises a sequence that is at least 80% identical to SEQ ID NO: 174.

Embodiment D65

The multi-chain chimeric polypeptide of embodiment D64, wherein the first chimeric polypeptide comprises a sequence that is at least 90% identical to SEQ ID NO: 174.

Embodiment D66

The multi-chain chimeric polypeptide of embodiment D65, wherein the first chimeric polypeptide comprises a sequence that is at least 95% identical to SEQ ID NO: 174.

Embodiment D67

The multi-chain chimeric polypeptide of embodiment D66, wherein the first chimeric polypeptide comprises SEQ ID NO: 174.

Embodiment D68

The multi-chain chimeric polypeptide of embodiment D67, wherein the first chimeric polypeptide comprises SEQ ID NO: 176.

Embodiment D69

The multi-chain chimeric polypeptide of any one of embodiments D1 and D64-D68, wherein the second chimeric polypeptide comprises a sequence that is at least 80% identical to SEQ ID NO: 178.

Embodiment D70

The multi-chain chimeric polypeptide of embodiment D69, wherein the second chimeric polypeptide comprises a sequence that is at least 90% identical to SEQ ID NO: 178.

Embodiment D71

The multi-chain chimeric polypeptide of embodiment D70, wherein the second chimeric polypeptide comprises a sequence that is at least 95% identical to SEQ ID NO: 178.

Embodiment D72

The multi-chain chimeric polypeptide of embodiment D71, wherein the second chimeric polypeptide comprises SEQ ID NO: 178.

Embodiment D73

The multi-chain chimeric polypeptide of embodiment D72, wherein the second chimeric polypeptide comprises SEQ ID NO: 180.

Embodiment D74

The multi-chain chimeric polypeptide of any one of embodiments D1-D63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D75

The multi-chain chimeric polypeptide of embodiment D74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D76

The multi-chain chimeric polypeptide of any one of embodiments D1-D63, wherein the first chimeric polypeptide further comprises one or more additional target-binding domains at the N-terminal and/or C-terminal end of the first chimeric polypeptide.

Embodiment D77

The multi-chain chimeric polypeptide of embodiment D76, wherein at least one of the one or more additional target-binding domains directly abuts the first domain of the pair of affinity domains in the first chimeric polypeptide.

Embodiment D78

The multi-chain chimeric polypeptide of embodiment D76, wherein the first chimeric polypeptide further comprises a linker sequence between the at least one of the one or more additional target-binding domains and the first domain of the pair of affinity domains.

Embodiment D79

The multi-chain chimeric polypeptide of embodiment D76, wherein the at least one of the one or more additional target-binding domains directly abuts the first target-binding domain in the first chimeric polypeptide.

Embodiment D80

The multi-chain chimeric polypeptide of embodiment D76, wherein the first chimeric polypeptide further comprises a linker sequence between the at least one of the one or more additional target-binding domains and the first target-binding domain.

Embodiment D81

The multi-chain chimeric polypeptide of embodiment D76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D82

The multi-chain chimeric polypeptide of embodiment D81, wherein the at least one additional target-binding domain of the one or more additional target-binding domains disposed at the N-terminus directly abuts the first target-binding domain or the first domain of the pair of affinity domains in the first chimeric polypeptide.

Embodiment D83

The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D84

The multi-chain chimeric polypeptide of embodiment D81, wherein the at least one additional target-binding domain of the one or more additional target-binding domains disposed at the C-terminus directly abuts the first target-binding domain or the first domain of the pair of affinity domains in the first chimeric polypeptide.

Embodiment D85

The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D86

The multi-chain chimeric polypeptide of embodiment D81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D87

The multi-chain chimeric polypeptide of embodiment D81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D88

The multi-chain chimeric polypeptide of any one of embodiments D1-D63 and D74-D87, wherein the second chimeric polypeptide further comprises one or more additional target-binding domains at the N-terminal end or the C-terminal end of the second chimeric polypeptide.

Embodiment D89

The multi-chain chimeric polypeptide of embodiment D88, wherein at least one of the one or more additional target-binding domains directly abuts the second domain of the pair of affinity domains in the second chimeric polypeptide.

Embodiment D90

The multi-chain chimeric polypeptide of embodiment D88, wherein the second chimeric polypeptide further comprises a linker sequence between at least one of the one or more additional target-binding domains and the second domain of the pair of affinity domains in the second chimeric polypeptide.

Embodiment D91

The multi-chain chimeric polypeptide of embodiment D88, wherein at least one of the one or more additional target-binding domains directly abuts the second target-binding domain in the second chimeric polypeptide.

Embodiment D92

The multi-chain chimeric polypeptide of embodiment D88, wherein the second chimeric polypeptide further comprises a linker sequence between at least one of the one or more additional target-binding domains and the second target-binding domain in the second chimeric polypeptide.

Embodiment D93

The multi-chain chimeric polypeptide of any one of embodiments D74-D92, wherein two or more of the first target-binding domain, the second target-binding domain, and the one or more additional target-binding domains bind specifically to the same antigen.

Embodiment D94

The multi-chain chimeric polypeptide of embodiment B93, wherein two or more of the first target-binding domain, the second target-binding domain, and the one or more additional target-binding domains bind specifically to the same epitope.

Embodiment D95

The multi-chain chimeric polypeptide of embodiment B94, wherein two or more of the first target-binding domain, the second target-binding domain, and the one or more additional target-binding domains comprise the same amino acid sequence.

Embodiment D96

The multi-chain chimeric polypeptide of any one of embodiments D74-D92, wherein the first target-binding domain, the second target-binding domain, and the one or more additional target-binding domains bind specifically to different antigens.

Embodiment D97

The multi-chain chimeric polypeptide of any one of embodiments D74-D96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D98

The multi-chain chimeric polypeptide of any one of embodiments D74-D96, wherein the one or more additional target-binding domains is a soluble interleukin or cytokine protein.

Embodiment D99

The multi-chain chimeric polypeptide of embodiment B98, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment D100

The multi-chain chimeric polypeptide of any one of embodiments D74-D96, wherein the one or more additional target-binding domains is a soluble interleukin or cytokine receptor.

Embodiment D101

The multi-chain chimeric polypeptide of embodiment B100, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, or a soluble CD28.

Embodiment D102

A composition comprising any of the multi-chain chimeric polypeptides of embodiments D1-D101.

Embodiment D103

The composition of embodiment D102, wherein the composition is a pharmaceutical composition.

Embodiment D104

A kit comprising at least one dose of the composition of embodiment D102 or D103.

Embodiment D105

Nucleic acid encoding any of the multi-chain chimeric polypeptides of any one of embodiments D1-D101.

Embodiment D106

A vector comprising the nucleic acid of embodiment D105.

Embodiment D107

The vector of embodiment D106, wherein the vector is an expression vector.

Embodiment D108

A cell comprising the nucleic acid of embodiment D105 or the vector of embodiment D106 or D107.

Embodiment D109

A method of producing a multi-chain chimeric polypeptide, the method comprising:

culturing the cell of embodiment D108 in a culture medium under conditions sufficient to result in the production of the multi-chain chimeric polypeptide; and recovering the multi-chain chimeric polypeptide from the cell and/or the culture medium.

Embodiment D110

A multi-chain chimeric polypeptide produced by the method of embodiment D109.

Embodiment D111

The multi-chain chimeric polypeptide of embodiment D8, wherein the soluble human tissue factor domain comprises a sequence that is at least 80% identical to SEQ ID NO: 97.

Embodiment D112

The multi-chain chimeric polypeptide of embodiment D111, wherein the soluble human tissue factor domain comprises a sequence that is at least 90% identical to SEQ ID NO: 97.

Embodiment D113

The multi-chain chimeric polypeptide of embodiment D112, wherein the soluble human tissue factor domain comprises a sequence that is at least 95% identical to SEQ ID NO: 97.

Embodiment D114

The multi-chain chimeric polypeptide of embodiment D113, wherein the soluble human tissue factor domain comprises a sequence that is 100% identical to SEQ ID NO: 97.

Embodiment D115

The multi-chain chimeric polypeptide of embodiment D8, wherein the soluble human tissue factor domain comprises a sequence that is at least 80% identical to SEQ ID NO: 98.

Embodiment D116

The multi-chain chimeric polypeptide of embodiment D115, wherein the soluble human tissue factor domain comprises a sequence that is at least 90% identical to SEQ ID NO: 98.

Embodiment D117

The multi-chain chimeric polypeptide of embodiment D116, wherein the soluble human tissue factor domain comprises a sequence that is at least 95% identical to SEQ ID NO: 98.

Embodiment D118

The multi-chain chimeric polypeptide of embodiment D117, wherein the soluble human tissue factor domain comprises a sequence that is 100% identical to SEQ ID NO: 98.

Embodiment E1

A multi-chain chimeric polypeptide comprising:

(a) a first chimeric polypeptide comprising:

(i) a first target-binding domain;

(ii) a soluble tissue factor domain; and (iii) a first domain of a pair of affinity domains;

(b) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to a receptor of IL-21 or a ligand of tumor growth factor receptor 0 II (TGFβRII).

Embodiment E2

The multi-chain chimeric polypeptide of embodiment E1, wherein the first target-binding domain and the soluble tissue factor domain directly abut each other in the first chimeric polypeptide.

Embodiment E3

The multi-chain chimeric polypeptide of embodiments E1, wherein the first chimeric polypeptide further comprises a linker sequence between the first target-binding domain and the soluble tissue factor domain in the first chimeric polypeptide.

Embodiment E4

The multi-chain chimeric polypeptide of any one of embodiments E1-E3, wherein the soluble tissue factor domain and the first domain of the pair of affinity domains directly abut each other in the first chimeric polypeptide.

Embodiment E5

The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6

The multi-chain chimeric polypeptide of any one of embodiments E1-E5, wherein the second domain of the pair of affinity domains and the second target-binding domain directly abut each other in the second chimeric polypeptide.

Embodiment E7

The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8

The multi-chain chimeric polypeptide of any one of embodiments E1-E7, wherein the soluble tissue factor domain is a soluble human tissue factor domain.

Embodiment E9

The multi-chain chimeric polypeptide of embodiment E8, wherein the soluble human tissue factor domain comprises a sequence that is at least 80% identical to SEQ ID NO: 93.

Embodiment E10

The multi-chain chimeric polypeptide of embodiment E9, wherein the soluble human tissue factor domain comprises a sequence that is at least 90% identical to SEQ ID NO: 93.

Embodiment E11

The multi-chain chimeric polypeptide of embodiment E10, wherein the soluble human tissue factor domain comprises a sequence that is at least 95% identical to SEQ ID NO: 93.

Embodiment E12

The multi-chain chimeric polypeptide of any one of embodiments E8-E11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E13

The multi-chain chimeric polypeptide of embodiment E12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E14

The multi-chain chimeric polypeptide of any one of embodiments E1-E13, wherein the soluble tissue factor domain is not capable of binding to Factor VIIa.

Embodiment E15

The multi-chain chimeric polypeptide of any one of embodiments E1-E14, wherein the soluble tissue factor domain does not convert inactive Factor X into Factor Xa.

Embodiment E16

The multi-chain chimeric polypeptide of any one of embodiments E1-E15, wherein the multi-chain chimeric polypeptide does not stimulate blood coagulation in a mammal.

Embodiment E17

The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18

The multi-chain chimeric polypeptide of any one of embodiments E1-E17, wherein the second chimeric polypeptide further comprises a peptide tag at the N-terminal end or the C-terminal end of the second chimeric polypeptide.

Embodiment E19

The multi-chain chimeric polypeptide of any one of embodiments E1-E18, wherein the first chimeric polypeptide and/or the second chimeric polypeptide further comprises a signal sequence at its N-terminal end.

Embodiment E20

The multi-chain chimeric polypeptide of embodiment E19, wherein the signal sequence comprises SEQ ID NO: 117.

Embodiment E21

The multi-chain chimeric polypeptide of embodiment E20, wherein the signal sequence is SEQ ID NO: 117.

Embodiment E22

The multi-chain chimeric polypeptide of any one of embodiments E1-E21, wherein the pair of affinity domains is a sushi domain from an alpha chain of human IL-15 receptor (IL-15Rα and a soluble IL-15.

Embodiment E23

The multi-chain chimeric polypeptide of embodiment E22, wherein the soluble IL-15 has a D8N or D8A amino acid substitution.

Embodiment E24

The multi-chain chimeric polypeptide of embodiment E22, wherein the soluble IL-15 comprises a sequence that is 80% identical to SEQ ID NO: 82.

Embodiment E25

The multi-chain chimeric polypeptide of embodiment E24, wherein the soluble IL-15 comprises a sequence that is 90% identical to SEQ ID NO: 82.

Embodiment E26

The multi-chain chimeric polypeptide of embodiment E25, wherein the soluble IL-15 comprises a sequence that is 95% identical to SEQ ID NO: 82.

Embodiment E27

The multi-chain chimeric polypeptide of embodiment E26, wherein the soluble IL-15 comprises SEQ ID NO: 82.

Embodiment E28

The multi-chain chimeric polypeptide of any one of embodiments E22-E27, wherein the sushi domain of IL-15Rα comprises a sushi domain from human IL-15Rα.

Embodiment E29

The multi-chain chimeric polypeptide of embodiment E28, wherein the sushi domain from human IL-15Rα comprises a sequence that is 80% identical to SEQ ID NO: 113.

Embodiment E30

The multi-chain chimeric polypeptide of embodiment E29, wherein the sushi domain from human IL-15Rα comprises a sequence that is 90% identical to SEQ ID NO: 113.

Embodiment E31

The multi-chain chimeric polypeptide of embodiment E30, wherein the sushi domain from human IL-15Rα comprises a sequence that is 95% identical to SEQ ID NO: 113.

Embodiment E32

The multi-chain chimeric polypeptide of embodiment E31, wherein the sushi domain from human IL-15Rα comprises SEQ ID NO: 113.

Embodiment E33

The multi-chain chimeric polypeptide of embodiment E28, wherein the sushi domain from human IL-15Rα is a mature full-length IL-15Rα.

Embodiment E34

The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35

The multi-chain chimeric polypeptide of any one of embodiments E1-E34, wherein one or both of the first target-binding domain and the second target-binding domain is an antigen-binding domain.

Embodiment E36

The multi-chain chimeric polypeptide of embodiment E35, wherein the first target-binding domain and the second target-binding domain are antigen-binding domains.

Embodiment E37

The multi-chain chimeric polypeptide of embodiment E35 or E36, wherein antigen-binding domain comprises a scFv or single-domain antibody.

Embodiment E38

The multi-chain chimeric polypeptide of any one of embodiments E1-E34, wherein one or both of the first target-binding domain and the second target-binding domain is a soluble IL-21 or a soluble TGFβRII.

Embodiment E39

The multi-chain chimeric polypeptide of any one of embodiments E1-E38, wherein the first target-binding domain and the second target-binding domain both bind specifically to a receptor of IL-21 or a ligand of TGFβRII.

Embodiment E40

The multi-chain chimeric polypeptide of embodiment E39, wherein the first target-binding domain and the second target-binding domain bind specifically to the same epitope.

Embodiment E41

The multi-chain chimeric polypeptide of embodiment E40, wherein the first target-binding domain and the second target-binding domain comprise the same amino acid sequence.

Embodiment E42

The multi-chain chimeric polypeptide of any one of embodiments E1-E38, wherein the first target-binding domain binds specifically to a ligand of TGFβRII, and the second target-binding domain binds specifically to a receptor for IL-21.

Embodiment E43

The multi-chain chimeric polypeptide of any one of embodiments E1-E38, wherein the first target-binding domain binds specifically to a receptor for IL-21, and the second target-binding domain bind specifically to a ligand of TGFβRII.

Embodiment E44

The multi-chain chimeric polypeptide of embodiment E43, wherein the first target-binding domain comprises a soluble IL-21.

Embodiment E45

The multi-chain chimeric polypeptide of embodiment E44, wherein the soluble IL-21 is a soluble human IL-21.

Embodiment E46

The multi-chain chimeric polypeptide of embodiment E45, wherein the soluble human IL-21 comprises a sequence at least 80% identical to SEQ ID NO: 83.

Embodiment E47

The multi-chain chimeric polypeptide of embodiment E46, wherein the soluble human IL-21 comprises a sequence at least 90% identical to SEQ ID NO: 83.

Embodiment E48

The multi-chain chimeric polypeptide of embodiment E47, wherein the soluble human IL-21 comprises a sequence at least 95% identical to SEQ ID NO: 83.

Embodiment E49

The multi-chain chimeric polypeptide of embodiment E48, wherein the soluble human IL-21 comprises a sequence of SEQ ID NO: 83.

Embodiment E50

The multi-chain chimeric polypeptide of any one of embodiments E43-E49, wherein the second target-binding domain comprises a soluble TGFβRII.

Embodiment E51

The multi-chain chimeric polypeptide of embodiment E50, wherein the soluble TGFβRII is a soluble human TGFβRII.

Embodiment E52

The multi-chain chimeric polypeptide of embodiment E51, wherein the soluble human TGFβRII comprises a first sequence of soluble human TGFβRII and a second sequence of soluble human TGFβRII.

Embodiment E53

The multi-chain chimeric polypeptide of embodiment E52, wherein the soluble human TGFβRII further comprises a linker sequence between the first sequence of soluble human TGFβRII and the second sequence of soluble human TGFβRII.

Embodiment E54

The multi-chain chimeric polypeptide of embodiment E53, wherein the linker sequence comprises SEQ ID NO: 102.

Embodiment E55

The multi-chain chimeric polypeptide of any one of embodiments E52-E54, wherein the first sequence of soluble human TGFβRII comprises a sequence that is at least 80% identical to SEQ ID NO: 183.

Embodiment E56

The multi-chain chimeric polypeptide of embodiment E55, wherein the first sequence of soluble human TGFβRII comprises a sequence that is at least 90% identical to SEQ ID NO: 183.

Embodiment E57

The multi-chain chimeric polypeptide of embodiment E56, wherein the first sequence of soluble human TGFβRII comprises a sequence that is at least 95% identical to SEQ ID NO: 183.

Embodiment E58

The multi-chain chimeric polypeptide of embodiment E57, wherein the first sequence of soluble human TGFβRII comprises SEQ ID NO: 183.

Embodiment E59

The multi-chain chimeric polypeptide of any one of embodiments E52-E58, wherein the second sequence of soluble human TGFβRII comprises a sequence that is at least 80% identical to SEQ ID NO: 184.

Embodiment E60

The multi-chain chimeric polypeptide of embodiment E59, wherein the second sequence of soluble human TGFβRII comprises a sequence that is at least 90% identical to SEQ ID NO: 184.

Embodiment E61

The mule-chain chimeric polypeptide of embodiment E60, wherein the second sequence of soluble human TGFβRII comprises a sequence that is at least 95% identical to SEQ ID NO: 184.

Embodiment E62

The multi-chain chimeric polypeptide of embodiment E61, wherein the second sequence of soluble human TGFβRII comprises SEQ ID NO: 184.

Embodiment E63

The multi-chain chimeric polypeptide of embodiment E1, wherein the first chimeric polypeptide comprises a sequence that is at least 80% identical to SEQ ID NO: 189.

Embodiment E64

The multi-chain chimeric polypeptide of embodiment E63, wherein the first chimeric polypeptide comprises a sequence that is at least 90% identical to SEQ ID NO: 189.

Embodiment E65

The multi-chain chimeric polypeptide of embodiment E64, wherein the first chimeric polypeptide comprises a sequence that is at least 95% identical to SEQ ID NO: 189.

Embodiment E66

The multi-chain chimeric polypeptide of embodiment E65, wherein the first chimeric polypeptide comprises SEQ ID NO: 189.

Embodiment E67

The multi-chain chimeric polypeptide of embodiment E66, wherein the first chimeric polypeptide comprises SEQ ID NO: 191.

Embodiment E68

The multi-chain chimeric polypeptide of any one of embodiments E1 and E63-E67, wherein the second chimeric polypeptide comprises a sequence that is at least 80% identical to SEQ ID NO: 193.

Embodiment E69

The multi-chain chimeric polypeptide of embodiment E68, wherein the second chimeric polypeptide comprises a sequence that is at least 90% identical to SEQ ID NO: 193.

Embodiment E70

The multi-chain chimeric polypeptide of embodiment E69, wherein the second chimeric polypeptide comprises a sequence that is at least 95% identical to SEQ ID NO: 193.

Embodiment E71

The multi-chain chimeric polypeptide of embodiment E70, wherein the second chimeric polypeptide comprises SEQ ID NO: 193.

Embodiment E72

The multi-chain chimeric polypeptide of embodiment E71, wherein the second chimeric polypeptide comprises SEQ ID NO: 195.

Embodiment E73

The multi-chain chimeric polypeptide of any one of embodiments E1-E62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E74

The multi-chain chimeric polypeptide of embodiment E73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E75

The multi-chain chimeric polypeptide of any one of embodiments E1-E62, wherein the first chimeric polypeptide further comprises one or more additional target-binding domains at the N-terminal and/or C-terminal end of the first chimeric polypeptide.

Embodiment E76

The multi-chain chimeric polypeptide of embodiment E75, wherein at least one of the one or more additional target-binding domains directly abuts the first domain of the pair of affinity domains in the first chimeric polypeptide.

Embodiment E77

The multi-chain chimeric polypeptide of embodiment E75, wherein the first chimeric polypeptide further comprises a linker sequence between the at least one of the one or more additional target-binding domains and the first domain of the pair of affinity domains.

Embodiment E78

The multi-chain chimeric polypeptide of embodiment E75, wherein the at least one of the one or more additional target-binding domains directly abuts the first target-binding domain in the first chimeric polypeptide.

Embodiment E79

The multi-chain chimeric polypeptide of embodiment E75, wherein the first chimeric polypeptide further comprises a linker sequence between the at least one of the one or more additional target-binding domains and the first target-binding domain.

Embodiment E80

The multi-chain chimeric polypeptide of embodiment E75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E81

The multi-chain chimeric polypeptide of embodiment E80, wherein the at least one additional target-binding domain of the one or more additional target-binding domains disposed at the N-terminus directly abuts the first target-binding domain or the first domain of the pair of affinity domains in the first chimeric polypeptide.

Embodiment E82

The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E83

The multi-chain chimeric polypeptide of embodiment E80, wherein the at least one additional target-binding domain of the one or more additional target-binding domains disposed at the C-terminus directly abuts the first target-binding domain or the first domain of the pair of affinity domains in the first chimeric polypeptide.

Embodiment E84

The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E85

The multi-chain chimeric polypeptide of embodiment E80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E86

The multi-chain chimeric polypeptide of embodiment E80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E87

The multi-chain chimeric polypeptide of any one of embodiments E1-E62 and E73-E86, wherein the second chimeric polypeptide further comprises one or more additional target-binding domains at the N-terminal end or the C-terminal end of the second chimeric polypeptide.

Embodiment E88

The multi-chain chimeric polypeptide of embodiment E87, wherein at least one of the one or more additional target-binding domains directly abuts the second domain of the pair of affinity domains in the second chimeric polypeptide.

Embodiment E89

The multi-chain chimeric polypeptide of embodiment E87, wherein the second chimeric polypeptide further comprises a linker sequence between at least one of the one or more additional target-binding domains and the second domain of the pair of affinity domains in the second chimeric polypeptide.

Embodiment E90

The multi-chain chimeric polypeptide of embodiment E87, wherein at least one of the one or more additional target-binding domains directly abuts the second target-binding domain in the second chimeric polypeptide.

Embodiment E91

The multi-chain chimeric polypeptide of embodiment E87, wherein the second chimeric polypeptide further comprises a linker sequence between at least one of the one or more additional target-binding domains and the second target-binding domain in the second chimeric polypeptide.

Embodiment E92

The multi-chain chimeric polypeptide of any one of embodiments E73-E91, wherein two or more of the first target-binding domain, the second target-binding domain, and the one or more additional target-binding domains bind specifically to the same antigen.

Embodiment E93

The multi-chain chimeric polypeptide of embodiment E92, wherein two or more of the first target-binding domain, the second target-binding domain, and the one or more additional target-binding domains bind specifically to the same epitope.

Embodiment E94

The multi-chain chimeric polypeptide of embodiment E93, wherein two or more of the first target-binding domain, the second target-binding domain, and the one or more additional target-binding domains comprise the same amino acid sequence.

Embodiment E95

The multi-chain chimeric polypeptide of any one of embodiments E73-E91, wherein the first target-binding domain, the second target-binding domain, and the one or more additional target-binding domains bind specifically to different antigens.

Embodiment E96

The multi-chain chimeric polypeptide of any one of embodiments E73-E95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment E97

The multi-chain chimeric polypeptide of any one of embodiments E73-E95, wherein the one or more additional target-binding domains is a soluble interleukin or cytokine protein.

Embodiment E98

The multi-chain chimeric polypeptide of embodiment E97, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment E99

The multi-chain chimeric polypeptide of any one of embodiments E73-E95, wherein the one or more additional target-binding domains is a soluble interleukin or cytokine receptor.

Embodiment E100

The multi-chain chimeric polypeptide of embodiment E99, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment E101

A composition comprising any of the multi-chain chimeric polypeptides of embodiments E1-E100.

Embodiment E102

The composition of embodiment E101, wherein the composition is a pharmaceutical composition.

Embodiment E103

A kit comprising at least one dose of the composition of embodiment E101 or E102.

Embodiment E104

Nucleic acid encoding any of the multi-chain chimeric polypeptides of any one of embodiments E1-E100.

Embodiment E105

A vector comprising the nucleic acid of embodiment E104.

Embodiment E106

The vector of embodiment E105, wherein the vector is an expression vector.

Embodiment E107

A cell comprising the nucleic acid of embodiment C104 or the vector of embodiment E105 or E106.

Embodiment E108

A method of producing a multi-chain chimeric polypeptide, the method comprising:

culturing the cell of embodiment E107 in a culture medium under conditions sufficient to result in the production of the multi-chain chimeric polypeptide; and recovering the multi-chain chimeric polypeptide from the cell and/or the culture medium.

Embodiment E109

A multi-chain chimeric polypeptide produced by the method of embodiment E108.

Embodiment E110

The multi-chain chimeric polypeptide of embodiment E12, wherein the soluble human tissue factor domain comprises a sequence that is at least 80% identical to SEQ ID NO: 97.

Embodiment E111

The multi-chain chimeric polypeptide of embodiment E110, wherein the soluble human tissue factor domain comprises a sequence that is at least 90% identical to SEQ ID NO: 97.

Embodiment E112

The multi-chain chimeric polypeptide of embodiment E111, wherein the soluble human tissue factor domain comprises a sequence that is at least 95% identical to SEQ ID NO: 97.

Embodiment E113

The multi-chain chimeric polypeptide of embodiment E112, wherein the soluble human tissue factor domain comprises a sequence that is 100% identical to SEQ ID NO: 97.

Embodiment E114

The multi-chain chimeric polypeptide of embodiment E12, wherein the soluble human tissue factor domain comprises a sequence that is at least 80% identical to SEQ ID NO: 98.

Embodiment E115

The multi-chain chimeric polypeptide of embodiment E114, wherein the soluble human tissue factor domain comprises a sequence that is at least 90% identical to SEQ ID NO: 98.

Embodiment E116

The multi-chain chimeric polypeptide of embodiment E115, wherein the soluble human tissue factor domain comprises a sequence that is at least 95% identical to SEQ ID NO: 98.

Embodiment E117

The multi-chain chimeric polypeptide of embodiment E116, wherein the soluble human tissue factor domain comprises a sequence that is 100% identical to SEQ ID NO: 98.

Embodiment F1

A multi-chain chimeric polypeptide comprising:

(c) a first chimeric polypeptide comprising:

(i) a first target-binding domain;

(ii) a soluble tissue factor domain; and (iii) a first domain of a pair of affinity domains;

(d) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-21 or a receptor of IL-7.

Embodiment F2

The multi-chain chimeric polypeptide of embodiment F1, wherein the first target-binding domain and the soluble tissue factor domain directly abut each other in the first chimeric polypeptide.

Embodiment F3

The multi-chain chimeric polypeptide of embodiment F1, wherein the first chimeric polypeptide further comprises a linker sequence between the first target-binding domain and the soluble tissue factor domain in the first chimeric polypeptide.

Embodiment F4

The multi-chain chimeric polypeptide of any one of embodiments F1-F3, wherein the soluble tissue factor domain and the first domain of the pair of affinity domains directly abut each other in the first chimeric polypeptide.

Embodiment F5

The multi-chain chimeric polypeptide of any one of embodiments F1-F3, wherein the first chimeric polypeptide further comprises a linker sequence between the soluble tissue factor domain and the first domain of the pair of affinity domains in the first chimeric polypeptide.

Embodiment F6

The multi-chain chimeric polypeptide of any one of embodiments F1-F5, wherein the second domain of the pair of affinity domains and the second target-binding domain directly abut each other in the second chimeric polypeptide.

Embodiment F7

The multi-chain chimeric polypeptide of any one of embodiments F1-F5, wherein second chimeric polypeptide further comprises a linker sequence between the second domain of the pair of affinity domains and the second target-binding domain in the second chimeric polypeptide.

Embodiment F8

The multi-chain chimeric polypeptide of any one of embodiments F1-F7, wherein the soluble tissue factor domain is a soluble human tissue factor domain.

Embodiment F9

The multi-chain chimeric polypeptide of embodiment F8, wherein the soluble human tissue factor domain comprises a sequence that is at least 80% identical to SEQ ID NO: 93.

Embodiment F10

The multi-chain chimeric polypeptide of embodiment F9, wherein the soluble human tissue factor domain comprises a sequence that is at least 90% identical to SEQ ID NO: 93.

Embodiment F11

The multi-chain chimeric polypeptide of embodiment F10, wherein the soluble human tissue factor domain comprises a sequence that is at least 95% identical to SEQ ID NO: 93.

Embodiment F12

The multi-chain chimeric polypeptide of embodiment F11, wherein the soluble human tissue factor domain comprises SEQ ID NO: 93.

Embodiment F13

The multi-chain chimeric polypeptide of embodiment F8, wherein the soluble human tissue factor domain comprises a sequence that is at least 80% identical to SEQ ID NO: 97.

Embodiment F14

The multi-chain chimeric polypeptide of embodiment F13, wherein the soluble human tissue factor domain comprises a sequence that is at least 90% identical to SEQ ID NO: 97.

Embodiment F15

The multi-chain chimeric polypeptide of embodiment F14, wherein the soluble human tissue factor domain comprises a sequence that is at least 95% identical to SEQ ID NO: 97.

Embodiment F16

The multi-chain chimeric polypeptide of embodiment F15, wherein the soluble human tissue factor domain comprises SEQ ID NO: 97.

Embodiment F17

The multi-chain chimeric polypeptide of embodiment F8, wherein the soluble human tissue factor domain comprises a sequence that is at least 80% identical to SEQ ID NO: 98.

Embodiment F18

The multi-chain chimeric polypeptide of embodiment F17, wherein the soluble human tissue factor domain comprises a sequence that is at least 90% identical to SEQ ID NO: 98.

Embodiment F19

The multi-chain chimeric polypeptide of embodiment F18, wherein the soluble human tissue factor domain comprises a sequence that is at least 95% identical to SEQ ID NO: 98.

Embodiment F20

The multi-chain chimeric polypeptide of embodiment F19, wherein the soluble human tissue factor domain comprises SEQ ID NO: 98.

Embodiment F21

The multi-chain chimeric polypeptide of any one of embodiments F8-F11, F13-F15, and F17-F19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F22

The multi-chain chimeric polypeptide of embodiment F21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F23

The multi-chain chimeric polypeptide of any one of embodiments F1-F22, wherein the soluble tissue factor domain is not capable of binding to Factor VIIa.

Embodiment F24

The multi-chain chimeric polypeptide of any one of embodiments F1-F23, wherein the soluble tissue factor domain does not convert inactive Factor X into Factor Xa.

Embodiment F25

The multi-chain chimeric polypeptide of any one of embodiments F1-F24, wherein the multi-chain chimeric polypeptide does not stimulate blood coagulation in a mammal.

Embodiment F26

The multi-chain chimeric polypeptide of any one of embodiments F1-F25, wherein the first chimeric polypeptide further comprises a peptide tag at the N-terminal end or the C-terminal end of the first chimeric polypeptide.

Embodiment F27

The multi-chain chimeric polypeptide of any one of embodiments F1-F26, wherein the second chimeric polypeptide further comprises a peptide tag at the N-terminal end or the C-terminal end of the second chimeric polypeptide.

Embodiment F28

The multi-chain chimeric polypeptide of any one of embodiments F1-F27, wherein the first chimeric polypeptide and/or the second chimeric polypeptide further comprises a signal sequence at its N-terminal end.

Embodiment F29

The multi-chain chimeric polypeptide of embodiment F28, wherein the signal sequence comprises SEQ ID NO: 117.

Embodiment F30

The multi-chain chimeric polypeptide of embodiment F28, wherein the signal sequence is SEQ ID NO: 328.

Embodiment F31

The multi-chain chimeric polypeptide of any one of embodiments F1-F30, wherein the pair of affinity domains is a sushi domain from an alpha chain of human IL-15 receptor (IL-15Rα) and a soluble IL-15.

Embodiment F32

The multi-chain chimeric polypeptide of embodiment F31, wherein the soluble IL-15 has a D8N or D8A amino acid substitution.

Embodiment F33

The multi-chain chimeric polypeptide of embodiment F31, wherein the soluble IL-15 comprises a sequence that is at least 80% identical to SEQ ID NO: 82.

Embodiment F34

The multi-chain chimeric polypeptide of embodiment F33, wherein the soluble IL-15 comprises a sequence that is at least 90% identical to SEQ ID NO: 82.

Embodiment F35

The multi-chain chimeric polypeptide of embodiment F34, wherein the soluble IL-15 comprises a sequence that is at least 95% identical to SEQ ID NO: 82.

Embodiment F36

The multi-chain chimeric polypeptide of embodiment F35, wherein the soluble IL-15 comprises SEQ ID NO: 82.

Embodiment F37

The multi-chain chimeric polypeptide of any one of embodiments F31-F36, wherein the sushi domain of IL-15Rα comprises a sushi domain from human IL-15Rα.

Embodiment F38

The multi-chain chimeric polypeptide of embodiment F37, wherein the sushi domain from human IL-15Rα comprises a sequence that is at least 80% identical to SEQ ID NO: 113.

Embodiment F39

The multi-chain chimeric polypeptide of embodiment F38, wherein the sushi domain from human IL-15Rα comprises a sequence that is at least 90% identical to SEQ ID NO: 113.

Embodiment F40

The multi-chain chimeric polypeptide of embodiment F39, wherein the sushi domain from human IL-15Rα comprises a sequence that is at least 95% identical to SEQ ID NO: 113.

Embodiment F41

The multi-chain chimeric polypeptide of embodiment F40, wherein the sushi domain from human IL-15Rα comprises SEQ ID NO: 113.

Embodiment F42

The multi-chain chimeric polypeptide of embodiment F37, wherein the sushi domain from human IL-15Rα is a mature full-length IL-15Rα.

Embodiment F43

The multi-chain chimeric polypeptide of any one of embodiments F1-F30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F44

The multi-chain chimeric polypeptide of any one of embodiments F1-F43, wherein one or both of the first target-binding domain and the second target-binding domain is an agonistic antigen-binding domain.

Embodiment F45

The multi-chain chimeric polypeptide of embodiment F44, wherein the first target-binding domain and the second target-binding domain are each agonistic antigen-binding domains.

Embodiment F46

The multi-chain chimeric polypeptide of embodiment F44 or F45, wherein antigen-binding domain comprises a scFv or single-domain antibody.

Embodiment F47

The multi-chain chimeric polypeptide of any one of embodiments F1-F43, wherein one or both of the first target-binding domain and the second target-binding domain is a soluble IL-21 or a soluble IL-7.

Embodiment F48

The multi-chain chimeric polypeptide of embodiment F47, wherein the first target-binding domain and the second target-binding domain are each independently a soluble IL-21 or a soluble IL-7.

Embodiment F49

The multi-chain chimeric polypeptide of any one of embodiments F1-F48, wherein the first target-binding domain and the second target-binding domain both bind specifically to a receptor of IL-21 or a receptor of IL-7.

Embodiment F50

The multi-chain chimeric polypeptide of embodiment F49, wherein the first target-binding domain and the second target-binding domain bind specifically to the same epitope.

Embodiment F51

The multi-chain chimeric polypeptide of embodiment F50, wherein the first target-binding domain and the second target-binding domain comprise the same amino acid sequence.

Embodiment F52

The multi-chain chimeric polypeptide of any one of embodiments F1-F48, wherein the first target-binding domain binds specifically to a receptor for IL-21, and the second target-binding domain binds specifically to a receptor for IL-7.

Embodiment F53

The multi-chain chimeric polypeptide of any one of embodiments F1-F48, wherein the first target-binding domain binds specifically to a receptor for IL-7, and the second target-binding domain bind specifically to a receptor for IL-21.

Embodiment F54

The multi-chain chimeric polypeptide of embodiment F53, wherein the first target-binding domain comprises a soluble IL-21.

Embodiment F55

The multi-chain chimeric polypeptide of embodiment F54, wherein the soluble IL-21 is a soluble human IL-21.

Embodiment F56

The multi-chain chimeric polypeptide of embodiment F55, wherein the soluble human IL-21 comprises a sequence at least 80% identical to SEQ ID NO: 83.

Embodiment F57

The multi-chain chimeric polypeptide of embodiment F56, wherein the soluble human IL-21 comprises a sequence at least 90% identical to SEQ ID NO: 83.

Embodiment F58

The multi-chain chimeric polypeptide of embodiment F57, wherein the soluble human IL-21 comprises a sequence at least 95% identical to SEQ ID NO: 83.

Embodiment F59

The multi-chain chimeric polypeptide of embodiment F58, wherein the soluble human IL-21 comprises a sequence of SEQ ID NO: 83.

Embodiment F60

The multi-chain chimeric polypeptide of any one of embodiments F53-F59, wherein the second target-binding domain comprises a soluble IL-7.

Embodiment F61

The multi-chain chimeric polypeptide of embodiment F60, wherein the soluble IL-7 is a soluble human IL-7.

Embodiment F62

The multi-chain chimeric polypeptide of embodiment F61, wherein the soluble human IL-7 comprises a sequence at least 80% identical to SEQ ID NO: 79.

Embodiment F63

The multi-chain chimeric polypeptide of embodiment F62, wherein the soluble human IL-7 comprises a sequence at least 90% identical to SEQ ID NO: 79.

Embodiment F64

The multi-chain chimeric polypeptide of embodiment F63, wherein the soluble human IL-7 comprises a sequence at least 95% identical to SEQ ID NO: 79.

Embodiment F65

The multi-chain chimeric polypeptide of embodiment F64, wherein the soluble human IL-7 comprises a sequence of SEQ ID NO: 79.

Embodiment F66

The multi-chain chimeric polypeptide of embodiment F1, wherein the first chimeric polypeptide comprises a sequence that is at least 80% identical to SEQ ID NO: 207.

Embodiment F67

The multi-chain chimeric polypeptide of embodiment F66, wherein the first chimeric polypeptide comprises a sequence that is at least 90% identical to SEQ ID NO: 207.

Embodiment F68

The multi-chain chimeric polypeptide of embodiment F67, wherein the first chimeric polypeptide comprises a sequence that is at least 95% identical to SEQ ID NO: 207.

Embodiment F69

The multi-chain chimeric polypeptide of embodiment F68, wherein the first chimeric polypeptide comprises SEQ ID NO: 207.

Embodiment F70

The multi-chain chimeric polypeptide of embodiment F69, wherein the first chimeric polypeptide comprises SEQ ID NO: 209.

Embodiment F71

The multi-chain chimeric polypeptide of any one of embodiments F1 and F66-F70, wherein the second chimeric polypeptide comprises a sequence that is at least 80% identical to SEQ ID NO: 211.

Embodiment F72

The multi-chain chimeric polypeptide of embodiment F71, wherein the second chimeric polypeptide comprises a sequence that is at least 90% identical to SEQ ID NO: 211.

Embodiment F73

The multi-chain chimeric polypeptide of embodiment F72, wherein the second chimeric polypeptide comprises a sequence that is at least 95% identical to SEQ ID NO: 211.

Embodiment F74

The multi-chain chimeric polypeptide of embodiment F73, wherein the second chimeric polypeptide comprises SEQ ID NO: 211.

Embodiment F75

The multi-chain chimeric polypeptide of embodiment F74, wherein the second chimeric polypeptide comprises SEQ ID NO: 213.

Embodiment F76

The multi-chain chimeric polypeptide of embodiment F1, wherein the first chimeric polypeptide comprises a sequence that is at least 80% identical to SEQ ID NO: 199.

Embodiment F77

The multi-chain chimeric polypeptide of embodiment F76, wherein the first chimeric polypeptide comprises a sequence that is at least 90% identical to SEQ ID NO: 199.

Embodiment F78

The multi-chain chimeric polypeptide of embodiment F77, wherein the first chimeric polypeptide comprises a sequence that is at least 95% identical to SEQ ID NO: 199.

Embodiment F79

The multi-chain chimeric polypeptide of embodiment F68, wherein the first chimeric polypeptide comprises SEQ ID NO: 199.

Embodiment F80

The multi-chain chimeric polypeptide of embodiment F69, wherein the first chimeric polypeptide comprises SEQ ID NO: 201.

Embodiment F81

The multi-chain chimeric polypeptide of any one of embodiments F1 and F76-F80, wherein the second chimeric polypeptide comprises a sequence that is at least 80% identical to SEQ ID NO: 203.

Embodiment F82

The multi-chain chimeric polypeptide of embodiment F81, wherein the second chimeric polypeptide comprises a sequence that is at least 90% identical to SEQ ID NO: 203.

Embodiment F83

The multi-chain chimeric polypeptide of embodiment F82, wherein the second chimeric polypeptide comprises a sequence that is at least 95% identical to SEQ ID NO: 203.

Embodiment F84

The multi-chain chimeric polypeptide of embodiment F83, wherein the second chimeric polypeptide comprises SEQ ID NO: 203.

Embodiment F85

The multi-chain chimeric polypeptide of embodiment F84, wherein the second chimeric polypeptide comprises SEQ ID NO: 209.

Embodiment F86

The multi-chain chimeric polypeptide of any one of embodiments F1-F65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment F87

The multi-chain chimeric polypeptide of embodiment F86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment F88

The multi-chain chimeric polypeptide of any one of embodiments F1-F65, wherein the first chimeric polypeptide further comprises one or more additional target-binding domains at the N-terminal and/or C-terminal end of the first chimeric polypeptide.

Embodiment F89

The multi-chain chimeric polypeptide of embodiment F88, wherein at least one of the one or more additional target-binding domains directly abuts the first domain of the pair of affinity domains in the first chimeric polypeptide.

Embodiment F90

The multi-chain chimeric polypeptide of embodiment F88, wherein the first chimeric polypeptide further comprises a linker sequence between the at least one of the one or more additional target-binding domains and the first domain of the pair of affinity domains.

Embodiment F91

The multi-chain chimeric polypeptide of embodiment F88, wherein the at least one of the one or more additional target-binding domains directly abuts the first target-binding domain in the first chimeric polypeptide.

Embodiment F92

The multi-chain chimeric polypeptide of embodiment F88, wherein the first chimeric polypeptide further comprises a linker sequence between the at least one of the one or more additional target-binding domains and the first target-binding domain.

Embodiment F93

The multi-chain chimeric polypeptide of embodiment F88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment F94

The multi-chain chimeric polypeptide of embodiment F93, wherein the at least one additional target-binding domain of the one or more additional target-binding domains disposed at the N-terminus directly abuts the first target-binding domain or the first domain of the pair of affinity domains in the first chimeric polypeptide.

Embodiment F95

The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F96

The multi-chain chimeric polypeptide of embodiment F93, wherein the at least one additional target-binding domain of the one or more additional target-binding domains disposed at the C-terminus directly abuts the first target-binding domain or the first domain of the pair of affinity domains in the first chimeric polypeptide.

Embodiment F97

The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F98

The multi-chain chimeric polypeptide of embodiment F93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment F99

The multi-chain chimeric polypeptide of embodiment F93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment F100

The multi-chain chimeric polypeptide of any one of embodiments F1-F65 and F86-F99, wherein the second chimeric polypeptide further comprises one or more additional target-binding domains at the N-terminal end or the C-terminal end of the second chimeric polypeptide.

Embodiment F101

The multi-chain chimeric polypeptide of embodiment F100, wherein at least one of the one or more additional target-binding domains directly abuts the second domain of the pair of affinity domains in the second chimeric polypeptide.

Embodiment F102

The multi-chain chimeric polypeptide of embodiment F100, wherein the second chimeric polypeptide further comprises a linker sequence between at least one of the one or more additional target-binding domains and the second domain of the pair of affinity domains in the second chimeric polypeptide.

Embodiment F103

The multi-chain chimeric polypeptide of embodiment F100, wherein at least one of the one or more additional target-binding domains directly abuts the second target-binding domain in the second chimeric polypeptide.

Embodiment F104

The multi-chain chimeric polypeptide of embodiment F100, wherein the second chimeric polypeptide further comprises a linker sequence between at least one of the one or more additional target-binding domains and the second target-binding domain in the second chimeric polypeptide.

Embodiment F105

The multi-chain chimeric polypeptide of any one of embodiments F86-F104, wherein two or more of the first target-binding domain, the second target-binding domain, and the one or more additional target-binding domains bind specifically to the same antigen.

Embodiment F106

The multi-chain chimeric polypeptide of embodiment F105, wherein two or more of the first target-binding domain, the second target-binding domain, and the one or more additional target-binding domains bind specifically to the same epitope.

Embodiment F107

The multi-chain chimeric polypeptide of embodiment F106, wherein two or more of the first target-binding domain, the second target-binding domain, and the one or more additional target-binding domains comprise the same amino acid sequence.

Embodiment F108

The multi-chain chimeric polypeptide of any one of embodiments F86-F104, wherein the first target-binding domain, the second target-binding domain, and the one or more additional target-binding domains bind specifically to different antigens.

Embodiment F109

The multi-chain chimeric polypeptide of any one of embodiments F86-F108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment F110

The multi-chain chimeric polypeptide of any one of embodiments F86-F108, wherein the one or more additional target-binding domains is a soluble interleukin or cytokine protein.

Embodiment F111

The multi-chain chimeric polypeptide of embodiment F110, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment F112

The multi-chain chimeric polypeptide of any one of embodiments F86-F108, wherein the one or more additional target-binding domains is a soluble interleukin or cytokine receptor.

Embodiment F113

The multi-chain chimeric polypeptide of embodiment F112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, or a soluble CD28.

Embodiment F114

A composition comprising any of the multi-chain chimeric polypeptides of embodiments F1-F113.

Embodiment F115

The composition of embodiment F114, wherein the composition is a pharmaceutical composition.

Embodiment F116

A kit comprising at least one dose of the composition of embodiment F114 or F115.

Embodiment F117

Nucleic acid encoding any of the multi-chain chimeric polypeptides of any one of embodiments F1-F113.

Embodiment F118

A vector comprising the nucleic acid of embodiment F117.

Embodiment F119

The vector of embodiment F118, wherein the vector is an expression vector.

Embodiment F120

A cell comprising the nucleic acid of embodiment F117 or the vector of embodiment F118 or F119.

Embodiment F121

A method of producing a multi-chain chimeric polypeptide, the method comprising:

culturing the cell of embodiment F120 in a culture medium under conditions sufficient to result in the production of the multi-chain chimeric polypeptide; and recovering the multi-chain chimeric polypeptide from the cell and/or the culture medium.

Embodiment F122

A multi-chain chimeric polypeptide produced by the method of embodiment F121.

Embodiment G1

A multi-chain chimeric polypeptide comprising:

(e) a first chimeric polypeptide comprising:

(i) a first target-binding domain;

(ii) a soluble tissue factor domain; and (iii) a first domain of a pair of affinity domains;

(f) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to: a receptor for IL-7, CD16, a receptor for IL-21, TGF-β, or a receptor for CD137L.

Embodiment G2

The multi-chain chimeric polypeptide of embodiment G1, wherein the first target-binding domain and the soluble tissue factor domain directly abut each other in the first chimeric polypeptide.

Embodiment G3

The multi-chain chimeric polypeptide of embodiment G1, wherein the first chimeric polypeptide further comprises a linker sequence between the first target-binding domain and the soluble tissue factor domain in the first chimeric polypeptide.

Embodiment G4

The multi-chain chimeric polypeptide of any one of embodiments G1-G3, wherein the soluble tissue factor domain and the first domain of the pair of affinity domains directly abut each other in the first chimeric polypeptide.

Embodiment G5

The multi-chain chimeric polypeptide of any one of embodiments G1-G3, wherein the first chimeric polypeptide further comprises a linker sequence between the soluble tissue factor domain and the first domain of the pair of affinity domains in the first chimeric polypeptide.

Embodiment G6

The multi-chain chimeric polypeptide of any one of embodiments G1-G5, wherein the second domain of the pair of affinity domains and the second target-binding domain directly abut each other in the second chimeric polypeptide.

Embodiment G7

The multi-chain chimeric polypeptide of any one of embodiments G1-G5, wherein second chimeric polypeptide further comprises a linker sequence between the second domain of the pair of affinity domains and the second target-binding domain in the second chimeric polypeptide.

Embodiment G8

The multi-chain chimeric polypeptide of any one of embodiments G1-G7, wherein the soluble tissue factor domain is a soluble human tissue factor domain.

Embodiment G9

The multi-chain chimeric polypeptide of embodiment G8, wherein the soluble human tissue factor domain comprises a sequence that is at least 80% identical to SEQ ID NO: 93.

Embodiment G10

The multi-chain chimeric polypeptide of embodiment G9, wherein the soluble human tissue factor domain comprises a sequence that is at least 90% identical to SEQ ID NO: 93.

Embodiment G11

The multi-chain chimeric polypeptide of embodiment G10, wherein the soluble human tissue factor domain comprises a sequence that is at least 95% identical to SEQ ID NO: 93.

Embodiment G12

The multi-chain chimeric polypeptide of any one of embodiments G8-G11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G13

The multi-chain chimeric polypeptide of embodiment G12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G14

The multi-chain chimeric polypeptide of any one of embodiments G1-G13, wherein the soluble tissue factor domain is not capable of binding to Factor VIIa.

Embodiment G15

The multi-chain chimeric polypeptide of any one of embodiments G1-G14, wherein the soluble tissue factor domain does not convert inactive Factor X into Factor Xa.

Embodiment G16

The multi-chain chimeric polypeptide of any one of embodiments G1-G15, wherein the multi-chain chimeric polypeptide does not stimulate blood coagulation in a mammal.

Embodiment G17

The multi-chain chimeric polypeptide of any one of embodiments G1-G16, wherein the first chimeric polypeptide further comprises a peptide tag at the N-terminal end or the C-terminal end of the first chimeric polypeptide.

Embodiment G18

The multi-chain chimeric polypeptide of any one of embodiments G1-G17, wherein the second chimeric polypeptide further comprises a peptide tag at the N-terminal end or the C-terminal end of the second chimeric polypeptide.

Embodiment G19

The multi-chain chimeric polypeptide of any one of embodiments G1-G18, wherein the first chimeric polypeptide and/or the second chimeric polypeptide further comprises a signal sequence at its N-terminal end.

Embodiment G20

The multi-chain chimeric polypeptide of embodiment G19, wherein the signal sequence comprises SEQ ID NO: 117.

Embodiment G21

The multi-chain chimeric polypeptide of embodiment G20, wherein the signal sequence is SEQ ID NO: 117.

Embodiment G22

The multi-chain chimeric polypeptide of any one of embodiments G1-G21, wherein the pair of affinity domains is a sushi domain from an alpha chain of human IL-15 receptor (IL-15Rα) and a soluble IL-15.

Embodiment G23

The multi-chain chimeric polypeptide of embodiment G22, wherein the soluble IL-15 has a D8N or D8A amino acid substitution.

Embodiment G24

The multi-chain chimeric polypeptide of embodiment G22, wherein the soluble IL-15 comprises a sequence that is 80% identical to SEQ ID NO: 82.

Embodiment G25

The multi-chain chimeric polypeptide of embodiment G24, wherein the soluble IL-15 comprises a sequence that is 90% identical to SEQ ID NO: 82.

Embodiment G26

The multi-chain chimeric polypeptide of embodiment G25, wherein the soluble IL-15 comprises a sequence that is 95% identical to SEQ ID NO: 82.

Embodiment G27

The multi-chain chimeric polypeptide of embodiment G26, wherein the soluble IL-15 comprises SEQ ID NO: 82.

Embodiment G28

The multi-chain chimeric polypeptide of any one of embodiments G22-G27, wherein the sushi domain of IL-15Rα comprises a sushi domain from human IL-15Rα.

Embodiment G29

The multi-chain chimeric polypeptide of embodiment G28, wherein the sushi domain from human IL-15Rα comprises a sequence that is 80% identical to SEQ ID NO: 113.

Embodiment G30

The multi-chain chimeric polypeptide of embodiment G29, wherein the sushi domain from human IL-15Rα comprises a sequence that is 90% identical to SEQ ID NO: 113.

Embodiment G31

The multi-chain chimeric polypeptide of embodiment G30, wherein the sushi domain from human IL-15Rα comprises a sequence that is 95% identical to SEQ ID NO: 113.

Embodiment G32

The multi-chain chimeric polypeptide of embodiment G31, wherein the sushi domain from human IL-15Rα comprises SEQ ID NO: 113.

Embodiment G33

The multi-chain chimeric polypeptide of embodiment G28, wherein the sushi domain from human IL-15Rα is a mature full-length IL-15Rα.

Embodiment G34

The multi-chain chimeric polypeptide of any one of embodiments G1-G21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment G35

The multi-chain chimeric polypeptide of any one of embodiments G1-G34, wherein the first target-binding domain and the second targeting-binding domain each independently bind specifically to a receptor for IL-7, CD16, or a receptor for IL-21.

Embodiment G36

The multi-chain chimeric polypeptide of embodiment G35, wherein the first target-binding domain binds specifically to a receptor IL-7 and the second target-binding domain binds specifically to CD16 or a receptor for IL-21.

Embodiment G37

The multi-chain chimeric polypeptide of embodiment G36, wherein the first target-binding domain comprises a soluble IL-7 protein.

Embodiment G38

The multi-chain chimeric polypeptide of embodiment G37, wherein the soluble IL-7 protein is a soluble human IL-7.

Embodiment G39

The multi-chain chimeric polypeptide of any one of embodiments G36-G38, wherein the second antigen-binding domain comprises an antigen-binding domain that binds specifically to CD16.

Embodiment G40

The multi-chain chimeric polypeptide of embodiment G39, wherein the second antigen-binding domain comprises an scFv that binds specifically to CD16.

Embodiment G41

The multi-chain chimeric polypeptide of any one of embodiments G36-G38, wherein the second antigen-binding domain bind specifically to a receptor for IL-21.

Embodiment G42

The multi-chain chimeric polypeptide of embodiment G41, wherein the second antigen-binding domain comprises a soluble IL-21.

Embodiment G43

The multi-chain chimeric polypeptide of embodiment G42, wherein the soluble IL-21 is a soluble human IL-21.

Embodiment G44

The multi-chain chimeric polypeptide of any one of embodiments G36-G40, wherein the second chimeric polypeptide further comprises an additional target-binding domain that binds specifically to a receptor for IL-21.

Embodiment G45

The multi-chain chimeric polypeptide of embodiment G44, wherein the additional target-binding domain comprises a soluble IL-21.

Embodiment G46

The multi-chain chimeric polypeptide of embodiment G45, wherein the soluble IL-21 is a soluble human IL-12.

Embodiment G47

The multi-chain chimeric polypeptide of any one of embodiments G1-G34, wherein the first target-binding domain and the second targeting-binding domain each independently bind specifically to TGF-β, CD16, or a receptor for IL-21.

Embodiment G48

The multi-chain chimeric polypeptide of embodiment G47, wherein the first target-binding domain binds specifically to a TGF-β and the second target-binding domain binds specifically to CD16 or a receptor of IL-21.

Embodiment G49

The multi-specific chimeric polypeptide of embodiment G48, wherein the first target-binding domain is a soluble TGF-β receptor.

Embodiment G50

The multi-specific chimeric polypeptide of embodiment G49, wherein soluble TGF-β receptor is a soluble TGFβRII receptor.

Embodiment G51

The multi-specific chimeric polypeptide of any one of embodiments G48-G50, wherein the second target-binding domain binds specifically to CD16.

Embodiment G52

The multi-specific chimeric polypeptide of embodiment G51, wherein the second antigen-binding domain comprises an antigen-binding domain that binds specifically to CD16.

Embodiment G53

The multi-chain chimeric polypeptide of embodiment G52, wherein the second antigen-binding domain comprises an scFv that binds specifically to CD16.

Embodiment G54

The multi-chain chimeric polypeptide of any one of embodiments G48-G50, wherein the second target-binding domain binds specifically to a receptor for IL-21.

Embodiment G55

The multi-chain chimeric polypeptide of embodiment G54, wherein the second target-binding domain comprises a soluble IL-21.

Embodiment G56

The multi-chain chimeric polypeptide of embodiment G55, wherein the second target-binding domain comprises a soluble human IL-21.

Embodiment G57

The multi-chain chimeric polypeptide of any one of embodiments G48-G53, wherein the second chimeric polypeptide further comprises an additional target-binding domain that binds specifically to a receptor for IL-21.

Embodiment G58

The multi-chain chimeric polypeptide of embodiment G57, wherein the additional target-binding domain comprises a soluble IL-21.

Embodiment G59

The multi-chain chimeric polypeptide of embodiment G58, wherein the soluble IL-21 is a soluble human IL-21.

Embodiment G60

The multi-chain chimeric polypeptide of any one of embodiments G1-G34, wherein the first target-binding domain and the second target-binding domain each independently bind specifically to a receptor for IL-7.

Embodiment G61

The multi-chain chimeric polypeptide of embodiment G60, wherein the first target-binding domain and the second target-binding domain include a soluble IL-7.

Embodiment G62

The multi-chain chimeric polypeptide of embodiment G61, wherein the soluble IL-7 is a soluble human IL-7.

Embodiment G63

The multi-chain chimeric polypeptide of any one of embodiments G1-G34, wherein the first target-binding domain and the second target-binding domain each independently bind specifically to TGF-0.

Embodiment G64

The multi-specific chimeric polypeptide of embodiment G63, wherein the first target-binding domain and the second target-binding domain is a soluble TGF-β receptor.

Embodiment G65

The multi-specific chimeric polypeptide of embodiment G64, wherein the soluble TGF-β receptor is a soluble TGFβRII receptor.

Embodiment G66

The multi-specific chimeric polypeptide of any one of embodiments G1-G34, wherein the first target-binding domain and the second targeting-binding domain each independently bind specifically to a receptor for IL-7, a receptor for IL-21, or a receptor for CD137L.

Embodiment G67

The multi-chain chimeric polypeptide of embodiment G66, wherein the first target-binding domain binds specifically to a receptor for IL-7 and the second target-binding domain binds specifically to a receptor for IL-21 or a receptor for CD137L.

Embodiment G68

The multi-specific chimeric polypeptide of embodiment G67, wherein the first target-binding domain is a soluble IL-7.

Embodiment G69

The multi-specific chimeric polypeptide of embodiment G68, wherein the soluble IL-7 is a soluble human IL-7.

Embodiment G70

The multi-chain chimeric polypeptide of any one of embodiments G67-G69, wherein the second target-binding domain binds specifically to a receptor for IL-21.

Embodiment G71

The multi-chain chimeric polypeptide of embodiment G70, wherein the second target-binding domain is a soluble IL-21.

Embodiment G72

The multi-chain chimeric polypeptide of embodiment G71, wherein the soluble IL-21 is a soluble human IL-21.

Embodiment G73

The multi-chain chimeric polypeptide of any one of embodiments G67-G69, wherein the second antigen-binding domain binds specifically to a receptor for CD137L.

Embodiment G74

The multi-chain chimeric polypeptide of embodiment G73, wherein the second antigen-binding domain is a soluble CD137L.

Embodiment G75

The multi-chain chimeric polypeptide of embodiment G74, wherein the soluble CD137L is a soluble human CD137L.

Embodiment G76

The multi-chain chimeric polypeptide of any one of embodiments G67-G72, wherein the second chimeric polypeptide further comprises an additional target-binding domain that binds specifically to a receptor for CD137L.

Embodiment G77

The multi-chain chimeric polypeptide of embodiment G76, wherein the additional target-binding domain comprises a soluble CD137L.

Embodiment G78

The multi-chain chimeric polypeptide of embodiment G77, wherein the soluble CD137L is a soluble human CD137L.

Embodiment G79

The multi-chain chimeric polypeptide of any one of embodiments G1-G34, wherein the first target-binding domain and the second targeting-binding domain each independently bind specifically to a receptor for IL-7 or TGF-0.

Embodiment G80

The multi-chain chimeric polypeptide of embodiment G79, wherein the first target-binding domain binds specifically to a receptor IL-7 and the second target-binding domain binds specifically to TGF-0.

Embodiment G81

The multi-chain chimeric polypeptide of embodiment G80, wherein the first target-binding domain comprises a soluble IL-7 protein.

Embodiment G82

The multi-chain chimeric polypeptide of embodiment G81, wherein the soluble IL-7 protein is a soluble human IL-7.

Embodiment G83

The multi-chain chimeric polypeptide of any one of embodiments G80-G82, wherein the second antigen-binding domain comprises an antigen-binding domain that binds specifically to TGF-β.

Embodiment G84

The multi-specific chimeric polypeptide of embodiment G83, wherein the second target-binding domain is a soluble TGF-β receptor.

Embodiment G85

The multi-specific chimeric polypeptide of embodiment G84, wherein the soluble TGF-β receptor is a soluble TGFβRII receptor.

Embodiment G86

The multi-chain chimeric polypeptide of any one of embodiments G1-G34, wherein the first target-binding domain and the second targeting-binding domain each independently bind specifically to TGF-β, a receptor for IL-21, or a receptor for CD137L.

Embodiment G87

The multi-chain chimeric polypeptide of embodiment G86, wherein the first target-binding domain binds specifically to a TGF-β and the second target-binding domain binds specifically to a receptor for IL-21 or a receptor for CD137L.

Embodiment G88

The multi-specific chimeric polypeptide of embodiment G87, wherein the first target-binding domain is a soluble TGF-β receptor.

Embodiment G89

The multi-specific chimeric polypeptide of embodiment G88, wherein the soluble TGF-β receptor is a soluble TGFβRII receptor.

Embodiment G90

The multi-specific chimeric polypeptide of any one of embodiments G87-G89, wherein the second target-binding domain binds specifically to a receptor for IL-21.

Embodiment G91

The multi-chain chimeric polypeptide of embodiment G90, wherein the second target-binding domain comprises a soluble IL-21.

Embodiment G92

The multi-chain chimeric polypeptide of embodiment G91, wherein the second target-binding domain comprises a soluble human IL-21.

Embodiment G93

The multi-specific chimeric polypeptide of any one of embodiments G87-G89, wherein the second target-binding domain binds specifically to a receptor for CD137L.

Embodiment G94

The multi-chain chimeric polypeptide of embodiment G93, wherein the second target-binding domain comprises a soluble CD137L.

Embodiment G95

The multi-chain chimeric polypeptide of embodiment G94, wherein the second target-binding domain comprises a soluble human CD137L.

Embodiment G96

The multi-chain chimeric polypeptide of any one of embodiments G87-G92, wherein the second chimeric polypeptide further comprises an additional target-binding domain that binds specifically to a receptor for CD137L.

Embodiment G97

The multi-chain chimeric polypeptide of embodiment G96, wherein the additional target-binding domain comprises a soluble CD137L.

Embodiment G98

The multi-chain chimeric polypeptide of embodiment G97, wherein the soluble CD137L is a soluble human CD137L.

Embodiment G99

The multi-chain chimeric polypeptide of any one of embodiments G1-G34, wherein the first target-binding domain and the second targeting-binding domain each independently bind specifically to TGF-β or a receptor for IL-21.

Embodiment G100

The multi-chain chimeric polypeptide of embodiment G99, wherein the first target-binding domain binds specifically to a TGF-β and the second target-binding domain binds specifically to TGF-β or a receptor for IL-21.

Embodiment G101

The multi-specific chimeric polypeptide of embodiment G100, wherein the first target-binding domain is a soluble TGF-β receptor.

Embodiment G102

The multi-specific chimeric polypeptide of embodiment G101, wherein the soluble TGF-β receptor is a soluble TGFβRII receptor.

Embodiment G103

The multi-specific chimeric polypeptide of any one of embodiments G100-G102, wherein the second target-binding domain binds specifically to a receptor for IL-21.

Embodiment G104

The multi-chain chimeric polypeptide of embodiment G103, wherein the second target-binding domain comprises a soluble IL-21.

Embodiment G105

The multi-chain chimeric polypeptide of embodiment G104, wherein the second target-binding domain comprises a soluble human IL-21.

Embodiment G106

The multi-specific chimeric polypeptide of any one of embodiments G100-G102, wherein the second target-binding domain binds specifically to TGF-0.

Embodiment G107

The multi-specific chimeric polypeptide of embodiment G106, wherein the first target-binding domain is a soluble TGF-β receptor.

Embodiment G108

The multi-specific chimeric polypeptide of embodiment G107, wherein the soluble TGF-β receptor is a soluble TGFβRII receptor.

Embodiment G109

The multi-specific chimeric polypeptide of any one of embodiments G100-G105, wherein the second polypeptide further comprises an additional target-binding domain that binds specifically to TGF-β.

Embodiment G110

The multi-specific chimeric polypeptide of embodiment G109, wherein the first target-binding domain is a soluble TGF-β receptor.

Embodiment G111

The multi-specific chimeric polypeptide of embodiment G110, wherein the soluble TGF-β receptor is a soluble TGFβRII receptor.

Embodiment G112

The multi-chain chimeric polypeptide of any one of embodiments G1-G34, wherein the first target-binding domain and the second targeting-binding domain each independently bind specifically to TGF-β or IL-16.

Embodiment G113

The multi-chain chimeric polypeptide of embodiment G112, wherein the first target-binding domain binds specifically to a TGF-β and the second target-binding domain binds specifically to TGF-β or IL-16.

Embodiment G114

The multi-specific chimeric polypeptide of embodiment G113, wherein the first target-binding domain is a soluble TGF-β receptor.

Embodiment G115

The multi-specific chimeric polypeptide of embodiment G114, wherein the soluble TGF-β receptor is a soluble TGFβRII receptor.

Embodiment G116

The multi-specific chimeric polypeptide of any one of embodiments G113-G115, wherein the second target-binding domain binds specifically to IL-16.

Embodiment G117

The multi-specific chimeric polypeptide of embodiment G116, wherein the second antigen-binding domain comprises an antigen-binding domain that binds specifically to CD16.

Embodiment G118

The multi-chain chimeric polypeptide of embodiment G117, wherein the second antigen-binding domain comprises an scFv that binds specifically to CD16.

Embodiment G119

The multi-specific chimeric polypeptide of any one of embodiments G113-G115, wherein the second target-binding domain binds specifically to TGF-0.

Embodiment G120

The multi-specific chimeric polypeptide of embodiment G119, wherein the first target-binding domain is a soluble TGF-β receptor.

Embodiment G121

The multi-specific chimeric polypeptide of embodiment G120, wherein the soluble TGF-β receptor is a soluble TGFβRII receptor.

Embodiment G122

The multi-specific chimeric polypeptide of any one of embodiments G113-G118, wherein the second chimeric polypeptide further comprises an additional target-binding domain that binds specifically to TGF-β.

Embodiment G123

The multi-specific chimeric polypeptide of embodiment G122, wherein the first target-binding domain is a soluble TGF-β receptor.

Embodiment G124

The multi-specific chimeric polypeptide of embodiment G123, wherein the soluble TGF-β receptor is a soluble TGFβRII receptor.

Embodiment G125

The multi-chain chimeric polypeptide of any one of embodiments G1-G34, wherein the first target-binding domain and the second targeting-binding domain each independently bind specifically to a TGF-β or a receptor for CD137L.

Embodiment G126

The multi-chain chimeric polypeptide of embodiment G125, wherein the first target-binding domain binds specifically to TGF-β and the second target-binding domain binds specifically to a receptor for CD137L.

Embodiment G127

The multi-specific chimeric polypeptide of embodiment G126, wherein the first target-binding domain is a soluble TGF-β receptor.

Embodiment G128

The multi-specific chimeric polypeptide of embodiment G127, wherein the soluble TGF-β receptor is a soluble TGFβRII receptor.

Embodiment G129

The multi-chain chimeric polypeptide of embodiment G128, wherein the second target-binding domain comprises a soluble CD137L protein.

Embodiment G130

The multi-chain chimeric polypeptide of embodiment G129, wherein the soluble CD137L protein is a soluble human CD137L.

Embodiment G131

The multi-chain chimeric polypeptide of any one of embodiments G126-G130, wherein the second chimeric polypeptide further comprises an additional target-binding domain that binds specifically to TGF-β.

Embodiment G132

The multi-specific chimeric polypeptide of embodiment G131, wherein the additional target-binding domain is a soluble TGF-β receptor.

Embodiment G133

The multi-specific chimeric polypeptide of embodiment G132, wherein the soluble TGF-β receptor is a soluble TGFβRII receptor.

Embodiment G134

The multi-chain chimeric polypeptide of embodiment G1, wherein the first chimeric polypeptide comprises a sequence that is at least 80% identical to SEQ ID NO: 207.

Embodiment G135

The multi-chain chimeric polypeptide of embodiment G134, wherein the first chimeric polypeptide comprises a sequence that is at least 90% identical to SEQ ID NO: 207.

Embodiment G136

The multi-chain chimeric polypeptide of embodiment G135, wherein the first chimeric polypeptide comprises a sequence that is at least 95% identical to SEQ ID NO: 207.

Embodiment G137

The multi-chain chimeric polypeptide of embodiment G136, wherein the first chimeric polypeptide comprises SEQ ID NO: 207.

Embodiment G138

The multi-chain chimeric polypeptide of embodiment G137, wherein the first chimeric polypeptide comprises SEQ ID NO: 209.

Embodiment G139

The multi-chain chimeric polypeptide of any one of embodiments G1 and G134-G138, wherein the second chimeric polypeptide comprises a sequence that is at least 80% identical to SEQ ID NO: 232.

Embodiment G140

The multi-chain chimeric polypeptide of embodiment G139, wherein the second chimeric polypeptide comprises a sequence that is at least 90% identical to SEQ ID NO: 232.

Embodiment G141

The multi-chain chimeric polypeptide of embodiment G140, wherein the second chimeric polypeptide comprises a sequence that is at least 95% identical to SEQ ID NO: 232.

Embodiment G142

The multi-chain chimeric polypeptide of embodiment G141, wherein the second chimeric polypeptide comprises SEQ ID NO: 232.

Embodiment G143

The multi-chain chimeric polypeptide of embodiment G142, wherein the second chimeric polypeptide comprises SEQ ID NO: 234.

Embodiment G144

The multi-chain chimeric polypeptide of embodiment G1, wherein the first chimeric polypeptide comprises a sequence that is at least 80% identical to SEQ ID NO: 236.

Embodiment G145

The multi-chain chimeric polypeptide of embodiment G144, wherein the first chimeric polypeptide comprises a sequence that is at least 90% identical to SEQ ID NO: 236.

Embodiment G146

The multi-chain chimeric polypeptide of embodiment G145, wherein the first chimeric polypeptide comprises a sequence that is at least 95% identical to SEQ ID NO: 236.

Embodiment G147

The multi-chain chimeric polypeptide of embodiment G146, wherein the first chimeric polypeptide comprises SEQ ID NO: 236.

Embodiment G148

The multi-chain chimeric polypeptide of embodiment G147, wherein the first chimeric polypeptide comprises SEQ ID NO: 238.

Embodiment G149

The multi-chain chimeric polypeptide of any one of embodiments G1 and G144-G148, wherein the second chimeric polypeptide comprises a sequence that is at least 80% identical to SEQ ID NO: 232.

Embodiment G150

The multi-chain chimeric polypeptide of embodiment G149, wherein the second chimeric polypeptide comprises a sequence that is at least 90% identical to SEQ ID NO: 232.

Embodiment G151

The multi-chain chimeric polypeptide of embodiment G150, wherein the second chimeric polypeptide comprises a sequence that is at least 95% identical to SEQ ID NO: 232.

Embodiment G152

The multi-chain chimeric polypeptide of embodiment G151, wherein the second chimeric polypeptide comprises SEQ ID NO: 232.

Embodiment G153

The multi-chain chimeric polypeptide of embodiment G152, wherein the second chimeric polypeptide comprises SEQ ID NO: 234.

Embodiment G154

The multi-chain chimeric polypeptide of embodiment G1, wherein the first chimeric polypeptide comprises a sequence that is at least 80% identical to SEQ ID NO: 207.

Embodiment G155

The multi-chain chimeric polypeptide of embodiment G154, wherein the first chimeric polypeptide comprises a sequence that is at least 90% identical to SEQ ID NO: 207.

Embodiment G156

The multi-chain chimeric polypeptide of embodiment G155, wherein the first chimeric polypeptide comprises a sequence that is at least 95% identical to SEQ ID NO: 207.

Embodiment G157

The multi-chain chimeric polypeptide of embodiment G156, wherein the first chimeric polypeptide comprises SEQ ID NO: 207.

Embodiment G158

The multi-chain chimeric polypeptide of embodiment G157, wherein the first chimeric polypeptide comprises SEQ ID NO: 209.

Embodiment G159

The multi-chain chimeric polypeptide of any one of embodiments G1 and G154-G158, wherein the second chimeric polypeptide comprises a sequence that is at least 80% identical to SEQ ID NO: 203.

Embodiment G160

The multi-chain chimeric polypeptide of embodiment G159, wherein the second chimeric polypeptide comprises a sequence that is at least 90% identical to SEQ ID NO: 203.

Embodiment G161

The multi-chain chimeric polypeptide of embodiment G160, wherein the second chimeric polypeptide comprises a sequence that is at least 95% identical to SEQ ID NO: 203.

Embodiment G162

The multi-chain chimeric polypeptide of embodiment G161, wherein the second chimeric polypeptide comprises SEQ ID NO: 203.

Embodiment G163

The multi-chain chimeric polypeptide of embodiment G162, wherein the second chimeric polypeptide comprises SEQ ID NO: 250.

Embodiment G164

The multi-chain chimeric polypeptide of embodiment G1, wherein the first chimeric polypeptide comprises a sequence that is at least 80% identical to SEQ ID NO: 236.

Embodiment G165

The multi-chain chimeric polypeptide of embodiment G164, wherein the first chimeric polypeptide comprises a sequence that is at least 90% identical to SEQ ID NO: 236.

Embodiment G166

The multi-chain chimeric polypeptide of embodiment G165, wherein the first chimeric polypeptide comprises a sequence that is at least 95% identical to SEQ ID NO: 236.

Embodiment G167

The multi-chain chimeric polypeptide of embodiment G166, wherein the first chimeric polypeptide comprises SEQ ID NO: 236.

Embodiment G168

The multi-chain chimeric polypeptide of embodiment G167, wherein the first chimeric polypeptide comprises SEQ ID NO: 238.

Embodiment G169

The multi-chain chimeric polypeptide of any one of embodiments G1 and G164-G168, wherein the second chimeric polypeptide comprises a sequence that is at least 80% identical to SEQ ID NO: 193.

Embodiment G170

The multi-chain chimeric polypeptide of embodiment G169, wherein the second chimeric polypeptide comprises a sequence that is at least 90% identical to SEQ ID NO: 193.

Embodiment G171

The multi-chain chimeric polypeptide of embodiment G170, wherein the second chimeric polypeptide comprises a sequence that is at least 95% identical to SEQ ID NO: 193.

Embodiment G172

The multi-chain chimeric polypeptide of embodiment G171, wherein the second chimeric polypeptide comprises SEQ ID NO: 193.

Embodiment G173

The multi-chain chimeric polypeptide of embodiment G172, wherein the second chimeric polypeptide comprises SEQ ID NO: 195.

Embodiment G174

The multi-chain chimeric polypeptide of embodiment G1, wherein the first chimeric polypeptide comprises a sequence that is at least 80% identical to SEQ ID NO: 207.

Embodiment G175

The multi-chain chimeric polypeptide of embodiment G174, wherein the first chimeric polypeptide comprises a sequence that is at least 90% identical to SEQ ID NO: 207.

Embodiment G176

The multi-chain chimeric polypeptide of embodiment G175, wherein the first chimeric polypeptide comprises a sequence that is at least 95% identical to SEQ ID NO: 207.

Embodiment G177

The multi-chain chimeric polypeptide of embodiment G176, wherein the first chimeric polypeptide comprises SEQ ID NO: 207.

Embodiment G178

The multi-chain chimeric polypeptide of embodiment G177, wherein the first chimeric polypeptide comprises SEQ ID NO: 209.

Embodiment G179

The multi-chain chimeric polypeptide of any one of embodiments G1 and G174-G178, wherein the second chimeric polypeptide comprises a sequence that is at least 80% identical to SEQ ID NO: 268.

Embodiment G180

The multi-chain chimeric polypeptide of embodiment G179, wherein the second chimeric polypeptide comprises a sequence that is at least 90% identical to SEQ ID NO: 268.

Embodiment G181

The multi-chain chimeric polypeptide of embodiment G180, wherein the second chimeric polypeptide comprises a sequence that is at least 95% identical to SEQ ID NO: 268.

Embodiment G182

The multi-chain chimeric polypeptide of embodiment G181, wherein the second chimeric polypeptide comprises SEQ ID NO: 268.

Embodiment G183

The multi-chain chimeric polypeptide of embodiment G182, wherein the second chimeric polypeptide comprises SEQ ID NO: 270.

Embodiment G184

The multi-chain chimeric polypeptide of embodiment G1, wherein the first chimeric polypeptide comprises a sequence that is at least 80% identical to SEQ ID NO: 207.

Embodiment G185

The multi-chain chimeric polypeptide of embodiment G184, wherein the first chimeric polypeptide comprises a sequence that is at least 90% identical to SEQ ID NO: 207.

Embodiment G186

The multi-chain chimeric polypeptide of embodiment G185, wherein the first chimeric polypeptide comprises a sequence that is at least 95% identical to SEQ ID NO: 207.

Embodiment G187

The multi-chain chimeric polypeptide of embodiment G186, wherein the first chimeric polypeptide comprises SEQ ID NO: 207.

Embodiment G188

The multi-chain chimeric polypeptide of embodiment G187, wherein the first chimeric polypeptide comprises SEQ ID NO: 209.

Embodiment G189

The multi-chain chimeric polypeptide of any one of embodiments G1 and G184-G188, wherein the second chimeric polypeptide comprises a sequence that is at least 80% identical to SEQ ID NO: 272.

Embodiment G190

The multi-chain chimeric polypeptide of embodiment G189, wherein the second chimeric polypeptide comprises a sequence that is at least 90% identical to SEQ ID NO: 272.

Embodiment G191

The multi-chain chimeric polypeptide of embodiment G190, wherein the second chimeric polypeptide comprises a sequence that is at least 95% identical to SEQ ID NO: 272.

Embodiment G192

The multi-chain chimeric polypeptide of embodiment G191, wherein the second chimeric polypeptide comprises SEQ ID NO: 272.

Embodiment G193

The multi-chain chimeric polypeptide of embodiment G192, wherein the second chimeric polypeptide comprises SEQ ID NO: 272.

Embodiment G194

The multi-chain chimeric polypeptide of embodiment G1, wherein the first chimeric polypeptide comprises a sequence that is at least 80% identical to SEQ ID NO: 207.

Embodiment G195

The multi-chain chimeric polypeptide of embodiment G194, wherein the first chimeric polypeptide comprises a sequence that is at least 90% identical to SEQ ID NO: 207.

Embodiment G196

The multi-chain chimeric polypeptide of embodiment G195, wherein the first chimeric polypeptide comprises a sequence that is at least 95% identical to SEQ ID NO: 207.

Embodiment G197

The multi-chain chimeric polypeptide of embodiment G196, wherein the first chimeric polypeptide comprises SEQ ID NO: 207.

Embodiment G198

The multi-chain chimeric polypeptide of embodiment G197, wherein the first chimeric polypeptide comprises SEQ ID NO: 209.

Embodiment G199

The multi-chain chimeric polypeptide of any one of embodiments G1 and G194-G198, wherein the second chimeric polypeptide comprises a sequence that is at least 80% identical to SEQ ID NO: 193.

Embodiment G200

The multi-chain chimeric polypeptide of embodiment G199, wherein the second chimeric polypeptide comprises a sequence that is at least 90% identical to SEQ ID NO: 193.

Embodiment G201

The multi-chain chimeric polypeptide of embodiment G200, wherein the second chimeric polypeptide comprises a sequence that is at least 95% identical to SEQ ID NO: 193.

Embodiment G202

The multi-chain chimeric polypeptide of embodiment G201, wherein the second chimeric polypeptide comprises SEQ ID NO: 193.

Embodiment G203

The multi-chain chimeric polypeptide of embodiment G202, wherein the second chimeric polypeptide comprises SEQ ID NO: 195.

Embodiment G204

The multi-chain chimeric polypeptide of embodiment G1, wherein the first chimeric polypeptide comprises a sequence that is at least 80% identical to SEQ ID NO: 236.

Embodiment G205

The multi-chain chimeric polypeptide of embodiment G204, wherein the first chimeric polypeptide comprises a sequence that is at least 90% identical to SEQ ID NO: 236.

Embodiment G206

The multi-chain chimeric polypeptide of embodiment G205, wherein the first chimeric polypeptide comprises a sequence that is at least 95% identical to SEQ ID NO: 236.

Embodiment G207

The multi-chain chimeric polypeptide of embodiment G206, wherein the first chimeric polypeptide comprises SEQ ID NO: 236.

Embodiment G208

The multi-chain chimeric polypeptide of embodiment G207, wherein the first chimeric polypeptide comprises SEQ ID NO: 238.

Embodiment G209

The multi-chain chimeric polypeptide of any one of embodiments G1 and G204-G208, wherein the second chimeric polypeptide comprises a sequence that is at least 80% identical to SEQ ID NO: 268.

Embodiment G210

The multi-chain chimeric polypeptide of embodiment G209, wherein the second chimeric polypeptide comprises a sequence that is at least 90% identical to SEQ ID NO: 268.

Embodiment G211

The multi-chain chimeric polypeptide of embodiment G210, wherein the second chimeric polypeptide comprises a sequence that is at least 95% identical to SEQ ID NO: 268.

Embodiment G212

The multi-chain chimeric polypeptide of embodiment G211, wherein the second chimeric polypeptide comprises SEQ ID NO: 268.

Embodiment G213

The multi-chain chimeric polypeptide of embodiment G212, wherein the second chimeric polypeptide comprises SEQ ID NO: 270.

Embodiment G214

The multi-chain chimeric polypeptide of embodiment G1, wherein the first chimeric polypeptide comprises a sequence that is at least 80% identical to SEQ ID NO: 236.

Embodiment G215

The multi-chain chimeric polypeptide of embodiment G214, wherein the first chimeric polypeptide comprises a sequence that is at least 90% identical to SEQ ID NO: 236.

Embodiment G216

The multi-chain chimeric polypeptide of embodiment G215, wherein the first chimeric polypeptide comprises a sequence that is at least 95% identical to SEQ ID NO: 236.

Embodiment G217

The multi-chain chimeric polypeptide of embodiment G216, wherein the first chimeric polypeptide comprises SEQ ID NO: 236.

Embodiment G218

The multi-chain chimeric polypeptide of embodiment G217, wherein the first chimeric polypeptide comprises SEQ ID NO: 238.

Embodiment G219

The multi-chain chimeric polypeptide of any one of embodiments G1 and G214-G218, wherein the second chimeric polypeptide comprises a sequence that is at least 80% identical to SEQ ID NO: 300.

Embodiment G220

The multi-chain chimeric polypeptide of embodiment G219, wherein the second chimeric polypeptide comprises a sequence that is at least 90% identical to SEQ ID NO: 300.

Embodiment G221

The multi-chain chimeric polypeptide of embodiment G220, wherein the second chimeric polypeptide comprises a sequence that is at least 95% identical to SEQ ID NO: 300.

Embodiment G222

The multi-chain chimeric polypeptide of embodiment G221, wherein the second chimeric polypeptide comprises SEQ ID NO: 300.

Embodiment G223

The multi-chain chimeric polypeptide of embodiment G222, wherein the second chimeric polypeptide comprises SEQ ID NO: 302.

Embodiment G224

The multi-chain chimeric polypeptide of embodiment G1, wherein the first chimeric polypeptide comprises a sequence that is at least 80% identical to SEQ ID NO: 236.

Embodiment G225

The multi-chain chimeric polypeptide of embodiment G224, wherein the first chimeric polypeptide comprises a sequence that is at least 90% identical to SEQ ID NO: 236.

Embodiment G226

The multi-chain chimeric polypeptide of embodiment G225, wherein the first chimeric polypeptide comprises a sequence that is at least 95% identical to SEQ ID NO: 236.

Embodiment G227

The multi-chain chimeric polypeptide of embodiment G226, wherein the first chimeric polypeptide comprises SEQ ID NO: 236.

Embodiment G228

The multi-chain chimeric polypeptide of embodiment G227, wherein the first chimeric polypeptide comprises SEQ ID NO: 238.

Embodiment G229

The multi-chain chimeric polypeptide of any one of embodiments G1 and G224-G228, wherein the second chimeric polypeptide comprises a sequence that is at least 80% identical to SEQ ID NO: 308.

Embodiment G230

The multi-chain chimeric polypeptide of embodiment G229, wherein the second chimeric polypeptide comprises a sequence that is at least 90% identical to SEQ ID NO: 308.

Embodiment G231

The multi-chain chimeric polypeptide of embodiment G230, wherein the second chimeric polypeptide comprises a sequence that is at least 95% identical to SEQ ID NO: 308.

Embodiment G232

The multi-chain chimeric polypeptide of embodiment G231, wherein the second chimeric polypeptide comprises SEQ ID NO: 308.

Embodiment G233

The multi-chain chimeric polypeptide of embodiment G232, wherein the second chimeric polypeptide comprises SEQ ID NO: 310.

Embodiment G234

The multi-chain chimeric polypeptide of embodiment G1, wherein the first chimeric polypeptide comprises a sequence that is at least 80% identical to SEQ ID NO: 236.

Embodiment G235

The multi-chain chimeric polypeptide of embodiment G234, wherein the first chimeric polypeptide comprises a sequence that is at least 90% identical to SEQ ID NO: 236.

Embodiment G236

The multi-chain chimeric polypeptide of embodiment G235, wherein the first chimeric polypeptide comprises a sequence that is at least 95% identical to SEQ ID NO: 236.

Embodiment G237

The multi-chain chimeric polypeptide of embodiment G236, wherein the first chimeric polypeptide comprises SEQ ID NO: 236.

Embodiment G238

The multi-chain chimeric polypeptide of embodiment G237, wherein the first chimeric polypeptide comprises SEQ ID NO: 238.

Embodiment G239

The multi-chain chimeric polypeptide of any one of embodiments G1 and G234-G238, wherein the second chimeric polypeptide comprises a sequence that is at least 80% identical to SEQ ID NO: 316.

Embodiment G240

The multi-chain chimeric polypeptide of embodiment G239, wherein the second chimeric polypeptide comprises a sequence that is at least 90% identical to SEQ ID NO: 316.

Embodiment G241

The multi-chain chimeric polypeptide of embodiment G240, wherein the second chimeric polypeptide comprises a sequence that is at least 95% identical to SEQ ID NO: 316.

Embodiment G242

The multi-chain chimeric polypeptide of embodiment G241, wherein the second chimeric polypeptide comprises SEQ ID NO: 316.

Embodiment G243

The multi-chain chimeric polypeptide of embodiment G242, wherein the second chimeric polypeptide comprises SEQ ID NO: 318.

Embodiment G244

The multi-chain chimeric polypeptide of any one of embodiments G1-G133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment G245

The multi-chain chimeric polypeptide of embodiment G244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment G246

The multi-chain chimeric polypeptide of any one of embodiments G1-G133, wherein the first chimeric polypeptide further comprises one or more additional target-binding domains at the N-terminal and/or C-terminal end of the first chimeric polypeptide.

Embodiment G247

The multi-chain chimeric polypeptide of embodiment G246, wherein at least one of the one or more additional target-binding domains directly abuts the first domain of the pair of affinity domains in the first chimeric polypeptide.

Embodiment G248

The multi-chain chimeric polypeptide of embodiment G246, wherein the first chimeric polypeptide further comprises a linker sequence between the at least one of the one or more additional target-binding domains and the first domain of the pair of affinity domains.

Embodiment G249

The multi-chain chimeric polypeptide of embodiment G246, wherein the at least one of the one or more additional target-binding domains directly abuts the first target-binding domain in the first chimeric polypeptide.

Embodiment G250

The multi-chain chimeric polypeptide of embodiment G246, wherein the first chimeric polypeptide further comprises a linker sequence between the at least one of the one or more additional target-binding domains and the first target-binding domain.

Embodiment G251

The multi-chain chimeric polypeptide of embodiment G246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment G252

The multi-chain chimeric polypeptide of embodiment G251, wherein the at least one additional target-binding domain of the one or more additional target-binding domains disposed at the N-terminus directly abuts the first target-binding domain or the first domain of the pair of affinity domains in the first chimeric polypeptide.

Embodiment G253

The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G254

The multi-chain chimeric polypeptide of embodiment G251, wherein the at least one additional target-binding domain of the one or more additional target-binding domains disposed at the C-terminus directly abuts the first target-binding domain or the first domain of the pair of affinity domains in the first chimeric polypeptide.

Embodiment G255

The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G256

The multi-chain chimeric polypeptide of embodiment G251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment G257

The multi-chain chimeric polypeptide of embodiment G251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment G258

The multi-chain chimeric polypeptide of any one of embodiments G44-G46, G57-G59, G76-G78, G96-G98, G109-G111, G122-G124, and G131-G133, wherein the second chimeric polypeptide further comprises the additional target-binding domain at the N-terminal end or the C-terminal end of the second chimeric polypeptide.

Embodiment G259

The multi-chain chimeric polypeptide of embodiment G258, wherein the additional target-binding domain directly abuts the second domain of the pair of affinity domains in the second chimeric polypeptide.

Embodiment G260

The multi-chain chimeric polypeptide of embodiment G258, wherein the second chimeric polypeptide further comprises a linker sequence between the additional target-binding domain and the second domain of the pair of affinity domains in the second chimeric polypeptide.

Embodiment G261

The multi-chain chimeric polypeptide of embodiment G258, wherein the additional target-binding domain directly abuts the second target-binding domain in the second chimeric polypeptide.

Embodiment G262

The multi-chain chimeric polypeptide of embodiment G258, wherein the second chimeric polypeptide further comprises a linker sequence between the additional target-binding domain and the second target-binding domain in the second chimeric polypeptide.

Embodiment G263

A composition comprising any of the multi-chain chimeric polypeptides of embodiments G1-G262.

Embodiment G264

The composition of embodiment G263, wherein the composition is a pharmaceutical composition.

Embodiment G265

A kit comprising at least one dose of the composition of embodiment G263 or G264.

Embodiment G266

Nucleic acid encoding any of the multi-chain chimeric polypeptides of any one of embodiments G1-G262.

Embodiment G267

A vector comprising the nucleic acid of embodiment G266.

Embodiment G268

The vector of embodiment G267, wherein the vector is an expression vector.

Embodiment G269

A cell comprising the nucleic acid of embodiment G323 or the vector of embodiment G267 or G268.

Embodiment G270

A method of producing a multi-chain chimeric polypeptide, the method comprising:

culturing the cell of embodiment G269 in a culture medium under conditions sufficient to result in the production of the multi-chain chimeric polypeptide; and recovering the multi-chain chimeric polypeptide from the cell and/or the culture medium.

Embodiment G271

A multi-chain chimeric polypeptide produced by the method of embodiment G270.

Embodiment G272

The multi-chain chimeric polypeptide of embodiment G8, wherein the soluble human tissue factor domain comprises a sequence that is at least 80% identical to SEQ ID NO: 97.

Embodiment G273

The multi-chain chimeric polypeptide of embodiment G272, wherein the soluble human tissue factor domain comprises a sequence that is at least 90% identical to SEQ ID NO: 97.

Embodiment G274

The multi-chain chimeric polypeptide of embodiment G273, wherein the soluble human tissue factor domain comprises a sequence that is at least 95% identical to SEQ ID NO: 97.

Embodiment G275

The multi-chain chimeric polypeptide of embodiment G274, wherein the soluble human tissue factor domain comprises a sequence that is 100% identical to SEQ ID NO: 97.

Embodiment G276

The multi-chain chimeric polypeptide of embodiment G8, wherein the soluble human tissue factor domain comprises a sequence that is at least 80% identical to SEQ ID NO: 98.

Embodiment G277

The multi-chain chimeric polypeptide of embodiment G276, wherein the soluble human tissue factor domain comprises a sequence that is at least 90% identical to SEQ ID NO: 98.

Embodiment G278

The multi-chain chimeric polypeptide of embodiment G277, wherein the soluble human tissue factor domain comprises a sequence that is at least 95% identical to SEQ ID NO: 98.

Embodiment G279

The multi-chain chimeric polypeptide of embodiment G278, wherein the soluble human tissue factor domain comprises a sequence that is 100% identical to SEQ ID NO: 98.

Embodiment H1

A method of treating an aging-related disease or condition in a subject in need thereof, the method comprising administering to a subject identified as having an aging-related disease or condition a therapeutically effective amount of one or more natural killer (NK) cell activating agent(s).

Embodiment H2

A method of killing or reducing the number of senescent cells in a subject in need thereof, the method comprising administering to the subject a therapeutically effective amount of one or more NK cell activating agent(s).

Embodiment H3

The method of embodiment H2, wherein the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells.

Embodiment H4

The method of embodiment H3, wherein the senescent cancer cells are chemotherapy-induced senescent cells or radiation-induced senescent cells.

Embodiment H5

The method of embodiment H2, wherein the subject has been identified or diagnosed as having an aging-related disease or condition.

Embodiment H6

The method of embodiment H1 or H5, wherein the aging-related disease or condition is selected from the group consisting of: a cancer, an autoimmune disease, a metabolic disease, a neurodegenerative disease, a cardiovascular disease, a skin disease, a progeria disease, and a fragility disease.

Embodiment H7

The method of embodiment H6, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H8

The method of embodiment H6, wherein the autoimmune disease is type-1 diabetes.

Embodiment H9

The method of embodiment H6, wherein the metabolic disease is selected from the group consisting of: obesity, a lipodystrophy, and type 2 diabetes mellitus.

Embodiment H10

The method of embodiment H6, wherein the neurodegenerative disease is selected from the group consisting of: Alzheimer's disease, Parkinson's disease, and dementia.

Embodiment H11

The method of embodiment H6, wherein the cardiovascular disease is selected from the group consisting of: coronary artery disease, atherosclerosis, and pulmonary arterial hypertension.

Embodiment H12

The method of embodiment H6, wherein the skin disease is selected from the group consisting of: wound healing, alopecia, wrinkles, senile lentigo, skin thinning, xeroderma pigmentosum, and dyskeratosis congenita.

Embodiment H13

The method of embodiment H6, wherein the progeria disease is selected from the group consisting of: progeria and Hutchinson-Gilford Progeria Syndrome.

Embodiment H14

The method of embodiment H6, wherein the fragility disease is selected from the group consisting of: frailty, responsiveness to vaccination, osteoporosis, and sarcopenia.

Embodiment H15

The method of embodiment H1 or H5, wherein the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Embodiment H16

The method of embodiment H1 or H5, wherein the aging-related disease or condition is type 2 diabetes or atherosclerosis.

Embodiment H17

The method of any one of embodiments H1-H16, wherein the administering results in a decrease in the number of senescent cells in a target tissue in the subject.

Embodiment H18

The method of embodiment H17, wherein the target tissue is selected from the group consisting of: adipose tissue, pancreatic tissue, liver tissue, lung tissue, vasculature, bone tissue, central nervous system (CNS) tissue, eye tissue, skin tissue, muscle tissue, and secondary lympho-organ tissue.

Embodiment H19

The method of any one of embodiments H1-H18, wherein the administering results in an increase in the expression levels of CD25, CD69, MTOR-C1, SREBP1, IFN-$\gamma$, and granzyme B in activated NK cells.

Embodiment H20

A method of treating an aging-related disease or condition in a subject in need thereof, the method comprising administering to a subject identified as having an aging-related disease or condition a therapeutically effective number of activated NK cells.

Embodiment H21

A method of killing or reducing the number of senescent cells in a subject in need thereof, the method comprising administering to the subject a therapeutically effective number of activated NK cells.

Embodiment H22

The method of embodiment H21, wherein the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells.

Embodiment H23

The method of embodiment H22, wherein the senescent cancer cells are chemotherapy-induced senescent cells or radiation-induced senescent cells.

Embodiment H24

The method of embodiment H21, wherein the subject has been identified or diagnosed as having an aging-related disease or condition.

Embodiment H25

The method of embodiment H20 or H24, wherein the aging-related disease or condition is selected from the group consisting of: a cancer, an autoimmune disease, a metabolic disease, a neurodegenerative disease, a cardiovascular disease, a skin disease, a progeria disease, and a fragility disease.

Embodiment H26

The method of embodiment H25, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H27

The method of embodiment H25, wherein the autoimmune disease is type-1 diabetes.

Embodiment H28

The method of embodiment H25, wherein the metabolic disease is selected from the group consisting of: obesity, a lipodystrophy, and type 2 diabetes mellitus.

Embodiment H29

The method of embodiment H25, wherein the neurodegenerative disease is selected from the group consisting of: Alzheimer's disease, Parkinson's disease, and dementia.

Embodiment H30

The method of embodiment H25, wherein the cardiovascular disease is selected from the group consisting of: coronary artery disease, atherosclerosis, and pulmonary arterial hypertension.

Embodiment H31

The method of embodiment H25, wherein the skin disease is selected from the group consisting of: wound healing, alopecia, wrinkles, senile lentigo, skin thinning, xeroderma pigmentosum, and dyskeratosis congenita.

Embodiment H32

The method of embodiment H25, wherein the progeria disease is selected from the group consisting of: progeria and Hutchinson-Gilford Progeria Syndrome.

Embodiment H33

The method of embodiment H25, wherein the fragility disease is selected from the group consisting of: frailty, responsiveness to vaccination, osteoporosis, and sarcopenia.

Embodiment H34

The method of embodiment H20 or H24, wherein the aging-related disease or condition is selected from the group consisting of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Embodiment H35

The method of any one of embodiments H20-H34, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H36

The method of embodiment H35, wherein the resting NK cell is an autologous NK cell obtained from the subject.

Embodiment H37

The method of embodiment H35, wherein the resting NK cell is an allogeneic resting NK cell.

Embodiment H38

The method of embodiment H35, wherein the resting NK cell is an artificial NK cell.

Embodiment H39

The method of embodiment H35, wherein the resting NK cell is a haploidentical resting NK cell.

Embodiment H40

The method of any one of embodiments H35-H39, wherein the resting NK cell is a genetically-engineered NK cell carrying a chimeric antigen receptor or recombinant T cell receptor.

Embodiment H41

The method of any one of embodiments H35-H40, wherein the method further comprises isolating the activated NK cells before the activated NK cells are administered to the subject.

Embodiment H42

A method of improving the texture and/or appearance of skin and/or hair in a subject in need thereof over a period of time, the method comprising administering to the subject a therapeutically effective amount of one or more natural killer (NK) cell activating agent(s).

Embodiment H43

A method of improving the texture and/or appearance of skin and/or hair in a subject in need thereof over a period of time, the method comprising administering to the subject a therapeutically effective number of activated NK cells.

Embodiment H44

The method of embodiment H43, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H45

The method of embodiment H44, wherein the resting NK cell is an autologous NK cell obtained from the subject.

Embodiment H46

The method of embodiment H44, wherein the resting NK cell is an allogeneic resting NK cell.

Embodiment H47

The method of embodiment H44, wherein the resting NK cell is an artificial NK cell.

Embodiment H48

The method of embodiment H44, wherein the resting NK cell is a haploidentical resting NK cell.

Embodiment H49

The method of any one of embodiments H44-H48, wherein the resting NK cell is a genetically-engineered NK cell carrying a chimeric antigen receptor or recombinant T cell receptor.

Embodiment H50

The method of any one of embodiments H44-H49, wherein the method further comprises isolating the activated NK cells before the activated NK cells are administered to the subject.

Embodiment H51

The method of any one of embodiments H42-H50, wherein the method provides for an improvement in the texture and/or appearance of skin of the subject over the period of time.

Embodiment H52

The method of embodiment H51, wherein the method results in a decrease in the rate of formation of wrinkles in the skin of the subject over the period of time.

Embodiment H53

The method of embodiment H51 or H52, wherein the method results in an improvement in the coloration of skin of the subject over the period of time.

Embodiment H54

The method of any one of embodiments H51-H53, wherein the method results in an improvement in the texture of skin of the subject over the period of time.

Embodiment H55

The method of any one of embodiments H42-H50, wherein the method provides for an improvement in the texture and/or appearance of hair of the subject over the period of time.

Embodiment H56

The method of embodiment H55, wherein the method results in a decrease in the rate of formation of gray hair in the subject over the period of time.

Embodiment H57

The method of embodiment H55 or H56, wherein the method results in a decrease in the number of gray hairs of the subject over the period of time.

Embodiment H58

The method of any one of embodiments H55-H57, wherein the method results in a decrease in the rate of hair loss in the subject over time.

Embodiment H59

The method of any one of embodiments H55-H58, wherein the method results in an improvement in the texture of hair of the subject over the period of time.

Embodiment H60

The method of any one of embodiments H42-H59, wherein the period of time is between about one month and about 10 years.

Embodiment H61

The method of any one of embodiments H42-H60, wherein the method results in a decrease in the number of senescent dermal fibroblasts in the skin of the subject over the period of time.

Embodiment H62

A method of assisting in the treatment of obesity in a subject in need thereof over a period of time, the method comprising administering to the subject a therapeutically effective amount of one or more natural killer (NK) cell activating agent(s).

Embodiment H63

A method of assisting in the treatment of obesity in a subject in need thereof over a period of time, the method comprising administering to the subject a therapeutically effective number of activated NK cells.

Embodiment H64

The method of embodiment H63, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H65

The method of embodiment H64, wherein the resting NK cell is an autologous NK cell obtained from the subject.

Embodiment H66

The method of embodiment H64, wherein the resting NK cell is an allogeneic resting NK cell.

Embodiment H67

The method of embodiment H64, wherein the resting NK cell is an artificial NK cell.

Embodiment H68

The method of embodiment H64, wherein the resting NK cell is a haploidentical resting NK cell.

Embodiment H69

The method of any one of embodiments H64-H68, wherein the resting NK cell is a genetically-engineered NK cell carrying a chimeric antigen receptor or recombinant T cell receptor.

Embodiment H70

The method of any one of embodiments H64-H69, wherein the method further comprises isolating the activated NK cells before the activated NK cells are administered to the subject.

Embodiment H71

The method of any one of embodiments H62-H70, wherein the method results in a decrease in the mass of the subject over the period of time.

Embodiment H72

The method of any one of embodiments H62-H71, wherein the method results in a decrease in the body mass index (BMI) of the subject over the period of time.

Embodiment H73

The method of any one of embodiments H62-H70, wherein the method results in a decrease in the rate of progression from pre-diabetes to type 2 diabetes in the subject.

Embodiment H74

The method of any one of embodiments H62-H70, wherein the method results in a decrease in fasting serum glucose level in the subject.

Embodiment H75

The method of any one of embodiments H62-H70, wherein the method results in an increase in insulin sensitivity in the subject.

Embodiment H76

The method of any one of embodiments H62-H70, wherein the method results in a decrease in the severity of atherosclerosis in the subject.

Embodiment H77

The method of any one of embodiments H62-H76, wherein the period of time is between about two weeks and about 10 years.

Embodiment H78

The method of any one of embodiments H1-H19, H35-H42, H44-H62, and H64-H77, wherein at least one of the one or more NK cell activating agent(s) results in activation of one or more of: a receptor for IL-2, a receptor for IL-7, a receptor for IL-12, a receptor for IL-15, a receptor for IL-18, a receptor for IL-21, a receptor for IL-33, CD16, CD69, CD25, CD36, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1.

Embodiment H79

The method of embodiment H78, wherein the at least one of the one or more NK cell activating agent(s) that results in activation of a receptor for IL-2 is a soluble IL-2 or an agonistic antibody that binds specifically to an IL-2 receptor.

Embodiment H80

The method of embodiment H78, wherein the at least one of the one or more NK cell activating agent(s) that results in activation of a receptor for IL-7 is a soluble IL-7 or an agonistic antibody that binds specifically to an IL-7 receptor.

Embodiment H81

The method of embodiment H78, wherein the at least one of the one or more NK cell activating agent(s) that results in activation of a receptor for IL-12 is a soluble IL-12 or an agonistic antibody that binds specifically to an IL-12 receptor.

Embodiment H82

The method of embodiment H78, wherein the at least one of the one or more NK cell activating agent(s) that results in activation of a receptor for IL-15 is a soluble IL-15 or an agonistic antibody that binds specifically to an IL-15 receptor.

Embodiment H83

The method of embodiment H78, wherein the at least one of the one or more NK cell activating agent(s) that results in activation of a receptor for IL-21 is a soluble IL-21 or an agonistic antibody that binds specifically to an IL-21 receptor.

Embodiment H84

The method of embodiment H78, wherein the at least one of the one or more NK cell activating agent(s) that results in activation of a receptor for IL-33 is a soluble IL-33 or an agonistic antibody that binds specifically to an IL-33 receptor.

Embodiment H85

The method of embodiment H78, wherein the at least one of the one or more NK cell activating agent(s) that results in activation of a receptor for CD16 is an agonistic antibody that binds specifically to a CD16.

Embodiment H86

The method of embodiment H78, wherein the at least one of the one or more NK cell activating agent(s) that results in activation of a receptor for CD69 is an agonistic antibody that binds specifically to a CD69.

Embodiment H87

The method of embodiment H78, wherein the at least one of the one or more NK cell activating agent(s) that results in activation of a receptor for CD25, CD36, CD59 is an agonistic antibody that binds specifically to a CD25, CD6, CD59.

Embodiment H88

The method of embodiment H78, wherein the at least one of the one or more NK cell activating agent(s) that results in activation of a receptor for CD352 is an agonistic antibody that binds specifically to a CD352.

Embodiment H89

The method of embodiment H78, wherein the at least one of the one or more NK cell activating agent(s) that results in activation of a receptor for NKp80 is an agonistic antibody that binds specifically to an NKp80.

Embodiment H90

The method of embodiment H78, wherein the at least one of the one or more NK cell activating agent(s) that results in activation of a receptor for DNAM-1 is an agonistic antibody that binds specifically to a DNAM-1.

Embodiment H91

The method of embodiment H78, wherein the at least one of the one or more NK cell activating agent(s) that results in activation of a receptor for 2B4 is an agonistic antibody that binds specifically to a 2B4.

Embodiment H92

The method of embodiment H78, wherein the at least one of the one or more NK cell activating agent(s) that results in activation of a receptor for NKp30 is an agonistic antibody that binds specifically to an NKp30.

Embodiment H93

The method of embodiment H78, wherein the at least one of the one or more NK cell activating agent(s) that results in activation of a receptor for NKp44 is an agonistic antibody that binds specifically to an NKp44.

Embodiment H94

The method of embodiment H78, wherein the at least one of the one or more NK cell activating agent(s) that results in activation of a receptor for NKp46 is an agonistic antibody that binds specifically to an NKp46.

Embodiment H95

The method of embodiment H78, wherein the at least one of the one or more NK cell activating agent(s) that results in activation of a receptor for NKG2D is an agonistic antibody that binds specifically to an NKG2D.

Embodiment H96

The method of embodiment H78, wherein the at least one of the one or more NK cell activating agent(s) that results in activation of a receptor for KIR2DS1 is an agonistic antibody that binds specifically to a KIR2DS1.

Embodiment H97

The method of embodiment H78, wherein the at least one of the one or more NK cell activating agent(s) that results in activation of a receptor for KIR2DS2/3 is an agonistic antibody that binds specifically to a KIR2DS2/3.

Embodiment H98

The method of embodiment H78, wherein the at least one of the one or more NK cell activating agent(s) that results in activation of a receptor for KIR2DL4 is an agonistic antibody that binds specifically to a KIR2DL4.

Embodiment H99

The method of embodiment H78, wherein the at least one of the one or more NK cell activating agent(s) that results in activation of a receptor for KIR2DS4 is an agonistic antibody that binds specifically to a KIR2DS4.

Embodiment H100

The method of embodiment H78, wherein the at least one of the one or more NK cell activating agent(s) that results in activation of a receptor for KIR2DS5 is an agonistic antibody that binds specifically to a KIR2DS5.

Embodiment H101

The method of embodiment H78, wherein the at least one of the one or more NK cell activating agent(s) that results in activation of a receptor for KIR3DS1 is an agonistic antibody that binds specifically to a KIR3DS1.

Embodiment H102

The method of any one of embodiments H1-H19, H35-H42, H44-H62, and H64-H101, wherein at least one of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2.

Embodiment H103

The method of embodiment H102, wherein the at least one of the one or more NK cell activating agent(s) that results in a decrease in the activation of PD-1 is an antagonistic antibody that binds specifically to PD-1, a soluble PD-1, a soluble PD-L1, or an antibody that binds specifically to PD-L1.

Embodiment H104

The method of embodiment H102, wherein at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

Embodiment H105

The method of embodiment H102, wherein at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

Embodiment H106

The method of embodiment H102, wherein at least one of the one or more NK cell activating agent(s) that results in a decrease in the activation of CD1 is an antagonistic antibody that binds specifically to CD1, a soluble CD1, or an antibody that binds specifically to a ligand of CD1.

Embodiment H107

The method of embodiment H102, wherein at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

Embodiment H108

The method of embodiment H102, wherein at least one of the one or more NK cell activating agent(s) that results in a decrease in the activation of Siglec-7 is an antagonistic antibody that binds specifically to Siglec-7 or an antibody that binds specifically to a ligand of Siglec-7.

Embodiment H109

The method of embodiment H102, wherein at least one of the one or more NK cell activating agent(s) that results in a decrease in the activation of IRP60 is an antagonistic antibody that binds specifically to IRP60 or an antibody that binds specifically to a ligand of IRP60.

Embodiment H110

The method of embodiment H102, wherein at least one of the one or more NK cell activating agent(s) that results in a decrease in the activation of Tactile is an antagonistic antibody that binds specifically to Tactile or an antibody that binds specifically to a ligand of Tactile.

Embodiment H111

The method of embodiment H102, wherein at least one of the one or more NK cell activating agent(s) that results in a decrease in the activation of IL1R8 is an antagonistic antibody that binds specifically to IL1R8 or an antibody that binds specifically to a ligand of IL1R8.

Embodiment H112

The method of embodiment H102, wherein at least one of the one or more NK cell activating agent(s) that results in a decrease in the activation of NKG2A/KLRD1 is an antagonistic antibody that binds specifically to NKG2A/KLRD1 or an antibody that binds specifically to a ligand of NKG2A/KLRD1.

Embodiment H113

The method of embodiment H102, wherein at least one of the one or more NK cell activating agent(s) that results in a decrease in the activation of KIR2DL1 is an antagonistic antibody that binds specifically to KIR2DL1 or an antibody that binds specifically to a ligand of KIR2DL1.

Embodiment H114

The method of embodiment H102, wherein at least one of the one or more NK cell activating agent(s) that results in a decrease in the activation of KIR2DL2/3 is an antagonistic antibody that binds specifically to KIR2DL2/3 or an antibody that binds specifically to a ligand of KIR2DL2/3.

Embodiment H115

The method of embodiment H102, wherein at least one of the one or more NK cell activating agent(s) that results in a decrease in the activation of KIR2DL5 is an antagonistic antibody that binds specifically to KIR2DL5 or an antibody that binds specifically to a ligand of KIR2DL5.

Embodiment H116

The method of embodiment H102, wherein at least one of the one or more NK cell activating agent(s) that results in a decrease in the activation of KIR3DL1 is an antagonistic antibody that binds specifically to KIR3DL1 or an antibody that binds specifically to a ligand of KIR3DL1.

Embodiment H117

The method of embodiment H102, wherein at least one of the one or more NK cell activating agent(s) that results in a decrease in the activation of KIR3DL2 is an antagonistic antibody that binds specifically to KIR3DL2 or an antibody that binds specifically to a ligand of KIR3DL2.

Embodiment H118

The method of embodiment H102, wherein at least one of the one or more NK cell activating agent(s) that results in a decrease in the activation of ILT2/LIR-1 is an antagonistic antibody that binds specifically to ILT2/LIR-1 or an antibody that binds specifically to a ligand of ILT2/LIR-1.

Embodiment H119

The method of embodiment H102, wherein at least one of the one or more NK cell activating agent(s) that results in a decrease in the activation of LAG-2 is an antagonistic antibody that binds specifically to LAG-2 or an antibody that binds specifically to a ligand of LAG-2.

Embodiment H120

The method of any one of embodiments H1-H19, H35-H42, H44-H62, and H64-H77, wherein at least one of the one or more NK cell activating agent(s) is a single-chain chimeric polypeptide comprising:

(i) a first target-binding domain;

(ii) a soluble tissue factor domain; and (iii) a second target-binding domain.

Embodiment H121

The method of embodiment H120, wherein the first target-binding domain and the soluble tissue factor domain directly abut each other.

Embodiment H122

The method of embodiment H120, wherein the single-chain chimeric polypeptide further comprises a linker sequence between the first target-binding domain and the soluble tissue factor domain.

Embodiment H123

The method of any one of embodiments H120-H122, wherein the soluble tissue factor domain and the second target-binding domain directly abut each other.

Embodiment H124

The method of any one of embodiments H120-H122, wherein the single-chain chimeric polypeptide further comprises a linker sequence between the soluble tissue factor domain and the second target-binding domain.

Embodiment H125

The method of embodiment H120, wherein the first target-binding domain and the second target-binding domain directly abut each other.

Embodiment H126

The method of embodiment H120, wherein the single-chain chimeric polypeptide further comprises a linker sequence between the first target-binding domain and the second target-binding domain.

Embodiment H127

The method of embodiment H125 or H126, wherein the second target-binding domain and the soluble tissue factor domain directly abut each other.

Embodiment H128

The method of embodiment H125 or H126, wherein the single-chain chimeric polypeptide further comprises a linker sequence between the second target-binding domain and the soluble tissue factor domain.

Embodiment H129

The method of any one of embodiments H120-H128, wherein the first target-binding domain and the second target-binding domain bind specifically to the same antigen.

Embodiment H130

The method of embodiment H129, wherein the first target-binding domain and the second target-binding domain bind specifically to the same epitope.

Embodiment H131

The method of embodiment H130, wherein the first target-binding domain and the second target-binding domain comprise the same amino acid sequence.

Embodiment H132

The method of any one of embodiments H120-H128, wherein the first target-binding domain and the second target-binding domain bind specifically to different antigens.

Embodiment H133

The method of any one of embodiments H120-H132, wherein one or both of the first target-binding domain and the second target-binding domain is an antigen-binding domain.

Embodiment H134

The method of embodiment H133, wherein the first target-binding domain and the second target-binding domain are each an antigen-binding domain.

Embodiment H135

The method of embodiment H134, wherein antigen-binding domain comprises a scFv or a single domain antibody.

Embodiment H136

The method of any one of embodiments H120-H135, wherein one or both of the first target-binding domain and the second target-binding domain bind to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H137

The method of any one of embodiments H120-H128, wherein one or both of the first target-binding domain and the second target-binding domain is a soluble interleukin or cytokine protein.

Embodiment H138

The method of embodiment H137, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H139

The method of any one of embodiments H120-H128, wherein one or both of the first target-binding domain and the second target-binding domain is a soluble interleukin or cytokine receptor.

Embodiment H140

The method of embodiment H139, wherein the soluble interleukin or cytokine receptor is a soluble TGF-β receptor II (TGF-βRII) a soluble TGF-βRIII, a soluble receptor for TNFα, a soluble receptor for IL-4, or a soluble receptor for IL-10.

Embodiment H141

The method of any one of embodiments H120-H140, wherein the soluble tissue factor domain is a soluble human tissue factor domain.

Embodiment H142

The method of embodiment H141, wherein the soluble human tissue factor domain comprises a sequence that is at least 80% identical to SEQ ID NO: 93.

Embodiment H143

The method of embodiment H142, wherein the soluble human tissue factor domain comprises a sequence that is at least 90% identical to SEQ ID NO: 93.

Embodiment H144

The method of embodiment H143, wherein the soluble human tissue factor domain comprises a sequence that is at least 95% identical to SEQ ID NO: 93.

Embodiment H145

The method of any one of embodiments H141-H144, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H146

The method of embodiment H145, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H147

The method of any one of embodiments H120-H146, wherein the soluble tissue factor domain is not capable of binding Factor VIIa.

Embodiment H148

The method of any one of embodiments H120-H147, wherein the soluble tissue factor domain does not convert inactive Factor X into Factor Xa.

Embodiment H149

The method of any one of embodiments H120-H148, wherein the single-chain chimeric polypeptide does not stimulate blood coagulation in a mammal.

Embodiment H150

The method of any one of embodiments H120-H149, wherein the single-chain chimeric polypeptide further comprises one or more additional target-binding domains at its N- and/or C-terminus.

Embodiment H151

The method of embodiment H150, wherein the single-chain chimeric polypeptide comprises one or more additional target-binding domains at its N-terminus.

Embodiment H152

The method of embodiment H151, wherein one or more additional target-binding domains directly abuts the first target-binding domain, the second target-binding domain, or the soluble tissue factor domain.

Embodiment H153

The method of embodiment H152, wherein the single-chain chimeric polypeptide further comprises a linker sequence between one of the at least one additional target-binding domains and the first target-binding domain, the second target-binding domain, or the soluble tissue factor domain.

Embodiment H154

The method of embodiment H150, wherein the single-chain chimeric polypeptide comprises one or more additional target-binding domains at its C-terminus.

Embodiment H155

The method of embodiment H154, wherein one of the one or more additional target-binding domains directly abuts the first target-binding domain, the second target-binding domain, or the soluble tissue factor domain.

Embodiment H156

The method of embodiment H154, wherein the single-chain chimeric polypeptide further comprises a linker sequence between one of the at least one additional target-binding domains and the first target-binding domain, the second target-binding domain, or the soluble tissue factor domain.

Embodiment H157

The method of embodiment H150, wherein the single-chain chimeric polypeptide comprises one or more additional target binding domains at its N-terminus and the C-terminus.

Embodiment H158

The method of embodiment H157, wherein one of the one or more additional antigen binding domains at the N-terminus directly abuts the first target-binding domain, the second target-binding domain, or the soluble tissue factor domain.

Embodiment H159

The method of embodiment H157, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment H160

The method of embodiment H157, wherein one of the one or more additional antigen binding domains at the C-terminus directly abuts the first target-binding domain, the second target-binding domain, or the soluble tissue factor domain.

Embodiment H161

The method of embodiment H157, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment H162

The method of any one of embodiments H150-H161, wherein two or more of the first target-binding domain, the second target-binding domain, and the one or more additional target-binding domains bind specifically to the same antigen.

Embodiment H163

The method of embodiment H162, wherein two or more of the first target-binding domain, the second target-binding domain, and the one or more additional target-binding domains bind specifically to the same epitope.

Embodiment H164

The method of embodiment H163, wherein two or more of the first target-binding domain, the second target-binding domain, and the one or more additional target-binding domains comprise the same amino acid sequence.

Embodiment H165

The method of embodiment H162, wherein the first target-binding domain, the second target-binding domain, and the one or more additional target-binding domains each bind specifically to the same antigen.

Embodiment H166

The method of embodiment H165, wherein the first target-binding domain, the second target-binding domain, and the one or more additional target-binding domains each bind specifically to the same epitope.

Embodiment H167

The method of embodiment H166, wherein the first target-binding domain, the second target-binding domain, and the one or more additional target-binding domains each comprise the same amino acid sequence.

Embodiment H168

The method of any one of embodiments H150-H161, wherein the first target-binding domain, the second target-binding domain, and the one or more additional target-binding domains bind specifically to different antigens.

Embodiment H169

The method of any one of embodiments H150-H168, wherein one or more of the first target-binding domain, the second target-binding domain, and the one or more target-binding domains is an antigen-binding domain.

Embodiment H170

The method of embodiment H169, wherein the first target-binding domain, the second target-binding domain, and the one or more additional target-binding domains are each an antigen-binding domain.

Embodiment H171

The method of embodiment H170, wherein antigen-binding domain comprises a scFv or a single domain antibody.

Embodiment H172

The method of any one of embodiments H150-H171, wherein one or more of the first target-binding domain, the second target-binding domain, and the one or more target-binding domains bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H173

The method of any one of embodiments H150-H161, wherein one or more of the first target-binding domain, the second target-binding domain, and the one or more additional target-binding domains is a soluble interleukin or cytokine protein.

Embodiment H174

The method of embodiment H173, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H175

The method of any one of embodiments H150-H161, wherein one or more of the first target-binding domain, the second target-binding domain, and the one or more additional target-binding domains is a soluble interleukin or cytokine receptor.

Embodiment H176

The method of embodiment H175, wherein the soluble receptor is a soluble TGF-β receptor II (TGF-βRII) a soluble TGF-βRIII, a soluble receptor for TNFα, a soluble receptor for IL-4, or a soluble receptor for IL-10.

Embodiment H177

The method of any one of embodiments H1-H19, H35-H42, H44-H62, and H64-H77, wherein at least one of the one or more NK cell activating agent(s) is a multi-chain chimeric polypeptide comprising:

(c) a first chimeric polypeptide comprising:

(i) a first target-binding domain;

(ii) a soluble tissue factor domain; and (iii) a first domain of a pair of affinity domains;

(d) a second chimeric polypeptide comprising:

(i) a second domain of a pair of affinity domains; and (ii) a second target-binding domain, wherein the first chimeric polypeptide and the second chimeric polypeptide associate through the binding of the first domain and the second domain of the pair of affinity domains.

Embodiment H178

The method of embodiment H177, wherein the first target-binding domain and the soluble tissue factor domain directly abut each other in the first chimeric polypeptide.

Embodiment H179

The method of embodiment H177, wherein the first chimeric polypeptide further comprises a linker sequence between the first target-binding domain and the soluble tissue factor domain in the first chimeric polypeptide.

Embodiment H180

The method of any one of embodiments H177-H179, wherein the soluble tissue factor domain and the first domain of the pair of affinity domains directly abut each other in the first chimeric polypeptide.

Embodiment H181

The method of any one of embodiments H177-H179, wherein the first chimeric polypeptide further comprises a linker sequence between the soluble tissue factor domain and the first domain of the pair of affinity domains in the first chimeric polypeptide.

Embodiment H182

The method of any one of embodiments H177-H181, wherein the second domain of the pair of affinity domains and the second target-binding domain directly abut each other in the second chimeric polypeptide.

Embodiment H183

The method of any one of embodiments H177-H181, wherein second chimeric polypeptide further comprises a linker sequence between the second domain of the pair of affinity domains and the second target-binding domain in the second chimeric polypeptide.

Embodiment H184

The method of any one of embodiments H177-H183, wherein the first target-binding domain and the second target-binding domain bind specifically to the same antigen.

Embodiment H185

The method of embodiment H184, wherein the first target-binding domain and the second target-binding domain bind specifically to the same epitope.

Embodiment H186

The method of embodiment H185, wherein the first target-binding domain and the second target-binding domain comprise the same amino acid sequence.

Embodiment H187

The method of any one of embodiments H177-H183, wherein the first target-binding domain and the second target-binding domain bind specifically to different antigens.

Embodiment H188

The method of any one of embodiments H177-H187, wherein one or both of the first target-binding domain and the second target-binding domain is an antigen-binding domain.

Embodiment H189

The method of embodiment H188, wherein the first target-binding domain and the second target-binding domain are each antigen-binding domains.

Embodiment H190

The method of embodiment H188 or H189, wherein antigen-binding domain comprises a scFv or a single domain antibody.

Embodiment H191

The method of any one of embodiments H177-H190, wherein one or both of the first target-binding domain and the second target-binding domain bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H192

The method of any one of embodiments H177-H183, wherein one or both of the first target-binding domain and the second target-binding domain is a soluble interleukin or cytokine protein.

Embodiment H193

The method of embodiment H192, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H194

The method of any one of embodiments H177-H183, wherein one or both of the first target-binding domain and the second target-binding domain is a soluble interleukin or cytokine receptor.

Embodiment H195

The method of embodiment H194, wherein the soluble receptor is a soluble TGF-β receptor II (TGF-βRII) a soluble TGF-βRIII, a soluble receptor for TNFα, a soluble receptor for IL-4, or a soluble receptor for IL-10.

Embodiment H196

The method of any one of embodiments H177-H195, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment H197

The method of embodiment H196, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment H198

The method of any one of embodiments H177-H195, wherein the first chimeric polypeptide further comprises one or more additional target-binding domains at the N-terminal and/or C-terminal end of the first chimeric polypeptide.

Embodiment H199

The method of embodiment H198, wherein at least one of the one or more additional target-binding domains directly abuts the first domain of the pair of affinity domains in the first chimeric polypeptide.

Embodiment H200

The method of embodiment H198, wherein the first chimeric polypeptide further comprises a linker sequence between the at least one of the one or more additional target-binding domains and the first domain of the pair of affinity domains.

Embodiment H201

The method of embodiment H198, wherein the at least one of the one or more additional target-binding domains directly abuts the first target-binding domain in the first chimeric polypeptide.

Embodiment H202

The method of embodiment H198, wherein the first chimeric polypeptide further comprises a linker sequence between the at least one of the one or more additional target-binding domains and the first target-binding domain.

Embodiment H203

The method of embodiment H198, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment H204

The method of embodiment H203, wherein the at least one additional target-binding domain of the one or more additional target-binding domains disposed at the N-terminus directly abuts the first target-binding domain or the first domain of the pair of affinity domains in the first chimeric polypeptide.

Embodiment H205

The method of embodiment H203, wherein the first chimeric polypeptide further comprises a linker sequence disposed between the at least one additional target-binding domain and the first target-binding domain or the first domain of the pair of affinity domains in the first chimeric polypeptide.

Embodiment H206

The method of embodiment H203, wherein the at least one additional target-binding domain of the one or more additional target-binding domains disposed at the C-terminus directly abuts the first target-binding domain or the first domain of the pair of affinity domains in the first chimeric polypeptide.

Embodiment H207

The method of embodiment H203, wherein the first chimeric polypeptide further comprises a linker sequence disposed between the at least one additional target-binding domain and the first target-binding domain or the first domain of the pair of affinity domains in the first chimeric polypeptide.

Embodiment H208

The method of embodiment H203, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment H209

The method of embodiment H203, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment H210

The method of any one of embodiments H177-H209, wherein the second chimeric polypeptide further comprises one or more additional target-binding domains at the N-terminal end or the C-terminal end of the second chimeric polypeptide.

Embodiment H211

The method of embodiment H210, wherein at least one of the one or more additional target-binding domains directly abuts the second domain of the pair of affinity domains in the second chimeric polypeptide.

Embodiment H212

The method of embodiment H210, wherein the second chimeric polypeptide further comprises a linker sequence between at least one of the one or more additional target-binding domains and the second domain of the pair of affinity domains in the second chimeric polypeptide.

Embodiment H213

The method of embodiment H210, wherein at least one of the one or more additional target-binding domains directly abuts the second target-binding domain in the second chimeric polypeptide.

Embodiment H214

The method of embodiment H210, wherein the second chimeric polypeptide further comprises a linker sequence between at least one of the one or more additional target-binding domains and the second target-binding domain in the second chimeric polypeptide.

Embodiment H215

The method of any one of embodiments H196-H214, wherein two or more of the first target-binding domain, the second target-binding domain, and the one or more additional target-binding domains bind specifically to the same antigen.

Embodiment H216

The method of embodiment H215, wherein two or more of the first target-binding domain, the second target-binding domain, and the one or more additional target-binding domains bind specifically to the same epitope.

Embodiment H217

The method of embodiment H216, wherein two or more of the first target-binding domain, the second target-binding domain, and the one or more additional target-binding domains comprise the same amino acid sequence.

Embodiment H218

The method of embodiment H215, wherein the first target-binding domain, the second target-binding domain, and the one or more additional target-binding domains each bind specifically to the same antigen.

Embodiment H219

The method of embodiment H218, wherein the first target-binding domain, the second target-binding domain, and the one or more additional target-binding domains each bind specifically to the same epitope.

Embodiment H220

The method of embodiment H219, wherein the first target-binding domain, the second target-binding domain, and the one or more additional target-binding domains each comprise the same amino acid sequence.

Embodiment H221

The method of any one of embodiments H196-H214, wherein the first target-binding domain, the second target-binding domain, and the one or more additional target-binding domains bind specifically to different antigens.

Embodiment H222

The method of any one of embodiments H196-H221, wherein one or more of the first target-binding domain, the second target-binding domain, and the one or more target-binding domains is an antigen-binding domain.

Embodiment H223

The method of embodiment H222, wherein the first target-binding domain, the second target-binding domain, and the one or more additional target-binding domains are each an antigen-binding domain.

Embodiment H224

The method of embodiment H223, wherein antigen-binding domain comprises a scFv.

Embodiment H225

The method of any one of embodiments H196-H224, wherein one or more of the first target-binding domain, the second target-binding domain, and the one or more target-binding domains bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H226

The method of any one of embodiments H196-H214, wherein one or more of the first target-binding domain, the second target-binding domain, and the one or more additional target-binding domains is a soluble interleukin or cytokine protein.

Embodiment H227

The method of embodiment H226, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H228

The method of any one of embodiments H196-H214, wherein one or more of the first target-binding domain, the second target-binding domain, and the one or more additional target-binding domains is a soluble interleukin or cytokine receptor.

Embodiment H229

The method of embodiment H228, wherein the soluble receptor a soluble TGF-β receptor II (TGF-βRII) a soluble TGF-βRIII, a soluble receptor for TNFα, a soluble receptor for IL-4, or a soluble receptor for IL-10.

Embodiment H230

The method of any one of embodiments H196-H229, wherein the soluble tissue factor domain is a soluble human tissue factor domain.

Embodiment H231

The method of embodiment H230, wherein the soluble human tissue factor domain comprises a sequence that is at least 80% identical to SEQ ID NO: 93.

Embodiment H232

The method of embodiment H231, wherein the soluble human tissue factor domain comprises a sequence that is at least 90% identical to SEQ ID NO: 93.

Embodiment H233

The method of embodiment H232, wherein the soluble human tissue factor domain comprises a sequence that is at least 95% identical to SEQ ID NO: 93.

Embodiment H234

The method of any one of embodiments H230-H233, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H235

The method of embodiment H234, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H236

The method of any one of embodiments H196-H235, wherein the soluble tissue factor domain is not capable of binding to Factor VIIa.

Embodiment H237

The method of any one of embodiments H196-H236, wherein the soluble tissue factor domain does not convert inactive Factor X into Factor Xa.

Embodiment H238

The method of any one of embodiments H196-H237, wherein the multi-chain chimeric polypeptide does not stimulate blood coagulation in a mammal.

Embodiment H239

The method of any one of embodiments H196-H238, wherein the pair of affinity domains is a sushi domain from an alpha chain of human IL-15 receptor (IL-15Rα) and a soluble IL-15.

Embodiment H240

The method of embodiment H239, wherein the soluble IL-15 has a D8N or D8A amino acid substitution.

Embodiment H241

The method of embodiment H239 or H240, wherein the human IL-15Rα is a mature full-length IL-15Rα.

Embodiment H242

The method of any one of embodiments H196-H238, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H243

The method of any one of embodiments H1-H19, H35-H42, H44-H62, and H64-H77, wherein at least one of the one or more NK cell activating agent(s) is a multi-chain chimeric polypeptide comprising:

(a) a first and second chimeric polypeptides, wherein each comprises:

(i) a first target-binding domain;

(ii) a Fc domain; and (iii) a first domain of a pair of affinity domains;

(b) a third and fourth chimeric polypeptide, wherein each comprises:

(i) a second domain of a pair of affinity domains; and (ii) a second target-binding domain, wherein the first and second chimeric polypeptides and the third and fourth chimeric polypeptides associate through the binding of the first domain and the second domain of the pair of affinity domains, and the first and second chimeric polypeptides associate through their Fc domains.

Embodiment H244

The method of embodiment H243, wherein the first target-binding domain and the Fc domain directly abut each other in the first and second chimeric polypeptides.

Embodiment H245

The method of embodiment H243, wherein the first and second chimeric polypeptides further comprise a linker sequence between the first target-binding domain and the Fc domain in the first and second chimeric polypeptides.

Embodiment H246

The method of any one of embodiments H243-H245, wherein the Fc domain and the first domain of the pair of affinity domains directly abut each other in the first and second chimeric polypeptides.

Embodiment H247

The method of any one of embodiments H243-H245, wherein the first chimeric polypeptide further comprises a linker sequence between the Fc domain and the first domain of the pair of affinity domains in the first and second chimeric polypeptides.

Embodiment H248

The method of any one of embodiments H243-H247, wherein the second domain of the pair of affinity domains and the second target-binding domain directly abut each other in the third and fourth chimeric polypeptides.

Embodiment H249

The method of any one of embodiments H243-H247, wherein third and fourth chimeric polypeptides further comprise a linker sequence between the second domain of the pair of affinity domains and the second target-binding domain in the third and fourth chimeric polypeptides.

Embodiment H250

The method of any one of embodiments H243-H249, wherein the first target-binding domain and the second target-binding domain bind specifically to the same antigen.

Embodiment H251

The method of embodiment H250, wherein the first target-binding domain and the second target-binding domain bind specifically to the same epitope.

Embodiment H252

The method of embodiment H251, wherein the first target-binding domain and the second target-binding domain comprise the same amino acid sequence.

Embodiment H253

The method of any one of embodiments H243-H249, wherein the first target-binding domain and the second target-binding domain bind specifically to different antigens.

Embodiment H254

The method of any one of embodiments H243-H253, wherein one or both of the first target-binding domain and the second target-binding domain is an antigen-binding domain.

Embodiment H255

The method of embodiment H254, wherein the first target-binding domain and the second target-binding domain are each antigen-binding domains.

Embodiment H256

The method of embodiment H254 or H255, wherein antigen-binding domain comprises a scFv or a single domain antibody.

Embodiment H257

The method of any one of embodiments H243-H256, wherein one or both of the first target-binding domain and the second target-binding domain bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H258

The method of any one of embodiments H243-H256, wherein one or both of the first target-binding domain and the second target-binding domain is a soluble interleukin or cytokine protein.

Embodiment H259

The method of embodiment H258, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H260

The method of any one of embodiments H243-H256, wherein one or both of the first target-binding domain and the second target-binding domain is a soluble interleukin or cytokine receptor.

Embodiment H261

The method of embodiment H260, wherein the soluble receptor is a soluble TGF-β receptor II (TGF-βRII) a soluble TGF-βRIII, a soluble receptor for TNFα, a soluble receptor for IL-4, or a soluble receptor for IL-10.

What is claimed is:

1. A method of treating a cancer in a subject, the method comprising administering to the subject a therapeutically effective amount of a multi-chain chimeric polypeptide comprising:

(a) a first chimeric polypeptide comprising:
  (i) a first target-binding domain comprising a sequence that is at least 90% identical to SEQ ID NO: 188;
  (ii) a soluble tissue factor domain comprising a sequence that is at least 90% identical to SEQ ID NO: 93; and
  (iii) a first domain of a pair of affinity domains, wherein the first domain of the pair of the affinity domains comprises a sequence that is at least 90% identical to SEQ ID NO: 115; and (b) a second chimeric polypeptide comprising:
  (i) a second domain of the pair of affinity domains, wherein the second domain of the pair of affinity domains comprises a sequence that is at least 90% identical to SEQ ID NO: 113; and
  (ii) a second target-binding domain comprising a sequence that is at least 90% identical to SEQ ID NO: 188, wherein the first chimeric polypeptide and the second chimeric polypeptide associate through the binding of the first domain and the second domain of the pair of affinity domains.

2. A method of killing or reducing the number of senescent cells in a subject having a cancer, the method comprising administering to the subject a therapeutically effective amount of a multi-chain chimeric polypeptide comprising:

(a) a first chimeric polypeptide comprising:
  (i) a first target-binding domain comprising a sequence that is at least 90% identical to SEQ ID NO: 188;
  (ii) a soluble tissue factor domain comprising a sequence that is at least 90% identical to SEQ ID NO: 93; and
  (iii) a first domain of a pair of affinity domains, wherein the first domain of the pair of the affinity domains comprises a sequence that is at least 90% identical to SEQ ID NO: 115; and (b) a second chimeric polypeptide comprising:
  (i) a second domain of the pair of affinity domains, wherein the second domain of the pair of affinity domains comprises a sequence that is at least 90% identical to SEQ ID NO: 113; and
  (ii) a second target-binding domain comprising a sequence that is at least 90% identical to SEQ ID NO: 188, wherein the first chimeric polypeptide and the second chimeric polypeptide associate through the binding of the first domain and the second domain of the pair of affinity domains.

3. The method of claim 1, wherein the multi-chain chimeric polypeptide results in a decrease in the activation of a TGF-β receptor.

4. The method of claim 1, wherein the first target-binding domain and the soluble tissue factor domain directly abut each other in the first chimeric polypeptide.

5. The method of claim 1, wherein the first chimeric polypeptide further comprises a linker sequence between the first target-binding domain and the soluble tissue factor domain in the first chimeric polypeptide.

6. The method of claim 1, wherein the soluble tissue factor domain and the first domain of the pair of affinity domains directly abut each other in the first chimeric polypeptide.

7. The method of claim 1, wherein the first chimeric polypeptide further comprises a linker sequence between the soluble tissue factor domain and the first domain of the pair of affinity domains in the first chimeric polypeptide.

8. The method of claim 1, wherein the second domain of the pair of affinity domains and the second target-binding domain directly abut each other in the second chimeric polypeptide.

9. The method of claim 1, wherein second chimeric polypeptide further comprises a linker sequence between the second domain of the pair of affinity domains and the second target-binding domain in the second chimeric polypeptide.

10. The method of claim 1, wherein the soluble tissue factor domain does not stimulate blood coagulation.

11. The method of claim 1, wherein the soluble tissue factor domain comprises or consists of a sequence from a wildtype soluble human tissue factor.

12. The method of claim 1, wherein the cancer is pancreatic cancer.

13. The method of claim 1, wherein:
  the first target-binding domain comprises a sequence that is at least 95% identical to SEQ ID NO: 188;
  the soluble tissue factor domain comprises a sequence that is at least 95% identical to SEQ ID NO: 93;
  the first domain of the pair of affinity domains comprises a sequence that is at least 95% identical to SEQ ID NO: 115;
  the second domain of the pair of affinity domains comprises a sequence that is at least 95% identical to SEQ ID NO: 113; and
  the second target-binding domain comprises a sequence that is at least 95% identical to SEQ ID NO: 188.

14. The method of claim 1, wherein:
  the first target-binding domain comprises SEQ ID NO: 188;
  the soluble tissue factor domain comprises SEQ ID NO: 93;
  the first domain of the pair of affinity domains comprises SEQ ID NO: 115;
  the second domain of the pair of affinity domains comprises SEQ ID NO: 113; and
  the second target-binding domain comprises SEQ ID NO: 188.

15. The method of claim 1, wherein:
the first chimeric polypeptide comprises a sequence that is at least 90% identical to SEQ ID NO: 236; and
the second chimeric polypeptide comprises a sequence that is at least 90% identical to SEQ ID NO: 193.

16. The method of claim 1, wherein:
the first chimeric polypeptide comprises a sequence that is at least 95% identical to SEQ ID NO: 236; and
the second chimeric polypeptide comprises a sequence that is at least 95% identical to SEQ ID NO: 193.

17. The method of claim 1, wherein:
the first chimeric polypeptide comprises SEQ ID NO: 236; and
the second chimeric polypeptide comprises SEQ ID NO: 193.

18. The method of claim 2, wherein the cancer is pancreatic cancer.

19. The method of claim 2, wherein:
the first target-binding domain comprises a sequence that is at least 95% identical to SEQ ID NO: 188;
the soluble tissue factor domain comprises a sequence that is at least 95% identical to SEQ ID NO: 93;
the first domain of the pair of affinity domains comprises a sequence that is at least 95% identical to SEQ ID NO: 115;
the second domain of the pair of affinity domains comprises a sequence that is at least 95% identical to SEQ ID NO: 113; and
the second target-binding domain comprises a sequence that is at least 95% identical to SEQ ID NO: 188.

20. The method of claim 2, wherein:
the first target-binding domain comprises SEQ ID NO: 188;
the soluble tissue factor domain comprises SEQ ID NO: 93;
the first domain of the pair of affinity domains comprises SEQ ID NO: 115;
the second domain of the pair of affinity domains comprises SEQ ID NO: 113; and
the second target-binding domain comprises SEQ ID NO: 188.

21. The method of claim 2, wherein:
the first chimeric polypeptide comprises a sequence that is at least 90% identical to SEQ ID NO: 236; and
the second chimeric polypeptide comprises a sequence that is at least 90% identical to SEQ ID NO: 193.

22. The method of claim 2, wherein:
the first chimeric polypeptide comprises a sequence that is at least 95% identical to SEQ ID NO: 236; and
the second chimeric polypeptide comprises a sequence that is at least 95% identical to SEQ ID NO: 193.

23. The method of claim 2, wherein:
the first chimeric polypeptide comprises SEQ ID NO: 236; and
the second chimeric polypeptide comprises SEQ ID NO: 193.

24. The method of claim 2, wherein the multi-chain chimeric polypeptide results in a decrease in the activation of a TGF-β receptor.

25. The method of claim 2, wherein the first target-binding domain and the soluble tissue factor domain directly abut each other in the first chimeric polypeptide.

26. The method of claim 2, wherein the first chimeric polypeptide further comprises a linker sequence between the first target-binding domain and the soluble tissue factor domain in the first chimeric polypeptide.

27. The method of claim 2, wherein the soluble tissue factor domain and the first domain of the pair of affinity domains directly abut each other in the first chimeric polypeptide.

28. The method of claim 2, wherein the first chimeric polypeptide further comprises a linker sequence between the soluble tissue factor domain and the first domain of the pair of affinity domains in the first chimeric polypeptide.

29. The method of claim 2, wherein the second domain of the pair of affinity domains and the second target-binding domain directly abut each other in the second chimeric polypeptide.

30. The method of claim 2, wherein second chimeric polypeptide further comprises a linker sequence between the second domain of the pair of affinity domains and the second target-binding domain in the second chimeric polypeptide.

31. The method of claim 2, wherein the soluble tissue factor domain does not stimulate blood coagulation.

32. The method of claim 2, wherein the soluble tissue factor domain comprises or consists of a sequence from a wildtype soluble human tissue factor.

33. The method of claim 1, wherein the cancer is ovarian cancer.

34. The method of claim 1, wherein the cancer is colorectal cancer.

35. The method of claim 1, wherein the cancer is breast cancer.

36. The method of claim 2, wherein the cancer is ovarian cancer.

37. The method of claim 2, wherein the cancer is colorectal cancer.

38. The method of claim 2, wherein the cancer is breast cancer.

39. The method of claim 1, wherein the cancer is hepatocellular carcinoma.

40. The method of claim 2, wherein the cancer is hepatocellular carcinoma.

41. The method of claim 1, wherein the cancer is melanoma.

42. The method of claim 2, wherein the cancer is melanoma.

43. The method of claim 1, wherein the cancer is gastric cancer.

44. The method of claim 2, wherein the cancer is gastric cancer.

45. The method of claim 1, wherein the cancer is urothelial carcinoma.

46. The method of claim 2, wherein the cancer is urothelial carcinoma.

* * * * *

UNITED STATES PATENT AND TRADEMARK OFFICE

CERTIFICATE OF CORRECTION

PATENT NO. : 11,672,826 B2
APPLICATION NO. : 16/557875
DATED : June 13, 2023
INVENTOR(S) : Hing Wong It is certified that error appears in the above-identified patent and that said Letters Patent is hereby corrected as shown below:

On the Title Page

Item (71), Line 1, delete “Biologies,” and insert -- Biologics, --.

Item (56), In “References Cited” in Line 8 of “Other Publications”, delete “Immunogentics” and insert -- Immunogenetics --.

Signed and Sealed this
Twenty-eighth Day of November, 2023

Katherine Kelly Vidal

Katherine Kelly Vidal
*Director of the United States Patent and Trademark Office*